United States Patent
Bryan et al.

(10) Patent No.: US 10,988,478 B1
(45) Date of Patent: Apr. 27, 2021

(54) PYRAZOLO[1,5A]PYRIMIDINE DERIVATIVES AS IRAK4 MODULATORS

(71) Applicant: Genentech, Inc., South San Francisco, CA (US)

(72) Inventors: Marian C. Bryan, San Francisco, CA (US); Alberto Gobbi, San Francisco, CA (US); James Richard Kiefer, Jr., Belmont, CA (US); Aleksandr Kolesnikov, San Francisco, CA (US); Alan G. Olivero, Half Moon Bay, CA (US); Joy Drobnick, Daly City, CA (US); Jun Liang, Los Altos Hills, CA (US); Naomi Rajapaksa, San Mateo, CA (US); Chudi Ndubaku, Oakland, CA (US); Jianwen Feng, Millbrae, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/775,650

(22) Filed: Jan. 29, 2020

Related U.S. Application Data

(63) Continuation of application No. 16/014,231, filed on Jun. 21, 2018, now abandoned, which is a continuation of application No. PCT/EP2016/081810, filed on Dec. 19, 2016.

(60) Provisional application No. 62/271,171, filed on Dec. 22, 2015, provisional application No. 62/279,459, filed on Jan. 15, 2016, provisional application No. 62/398,341, filed on Sep. 22, 2016.

(51) Int. Cl.
| | | |
|---|---|---|
| *C07D 487/04* | (2006.01) | |
| *C07D 519/00* | (2006.01) | |
| *A61P 35/00* | (2006.01) | |
| *A61P 37/02* | (2006.01) | |
| *A61P 29/00* | (2006.01) | |

(52) U.S. Cl.
CPC ............ *C07D 487/04* (2013.01); *A61P 29/00* (2018.01); *A61P 35/00* (2018.01); *A61P 37/02* (2018.01); *C07D 519/00* (2013.01)

(58) Field of Classification Search
CPC ............................ C07D 487/04; C07D 519/00
See application file for complete search history.

(56) References Cited

U.S. PATENT DOCUMENTS

| | | | | |
|---|---|---|---|---|
| 2009/0163545 A1* | 6/2009 | Goldfarb | ........... | A61K 31/47 514/312 |
| 2012/0015962 A1 | 1/2012 | Arora et al. | | |

FOREIGN PATENT DOCUMENTS

| | | |
|---|---|---|
| WO | 2005/058837 A1 | 6/2005 |
| WO | 2012/007375 A1 | 1/2012 |
| WO | 2015/193846 A1 | 12/2015 |
| WO | 2016/073895 A1 | 5/2016 |
| WO | 2017/009798 A1 | 1/2017 |

OTHER PUBLICATIONS

CAS Registry Database, 1214541-80-6, (Compound with the Registry No. 1214541-80-6) pp. 1, Creation Date Mar. 25, 2010.
CAS Registry Database, 1214554-03-6, (Compound with the Registry No. 1214554-03-6), pp. 1, Creation Date Mar. 25, 2010.
CAS Registry Database, 1214562-99-8, (Compound with the Registry No. 1214562-99-8), pp. 1, Creation Date Mar. 25, 2010.
CAS Registry Database, 1214582-23-6, (Compound with the Registry No. 1214582-23-6), pp. 1, Creation Date Mar. 25, 2010.
CAS Registry Database, 1214608-12-4, (Compound with the Registry No. 1214608-12-4), pp. 1-3, Creation Date Mar. 25, 2010.
CAS Registry Database, 1311711-91-7, (Compound with the Registry No. 1311711-91-7), pp. 1-3 ,Creation Date Jul. 7, 2011.
!Cas Registry Database, 1332092-83-7, (Compound with the Registry Number: 1332092-83-7), pp. 1-3, Creation Date Sep. 14, 2011.
CAS Registry Database, 1356058-08-6, (Compound with the Registry No. 1356058-08-6), pp. 1-3, Creation Date Feb. 8, 2012.
CAS Registry Database, 1581653-89-5, (Compound with the Registry No. 1581653-89-5), pp. 1, Creation Date Apr. 8, 2014.
CAS Registry Database, 1582010-99-8, (Compound with the Registry No. 1582010-99-8), pp. 1-3, Creation Date Apr. 8, 2014.
CAS Registry Database, 1585025-45-1, (Compound with the Registry No. 1585025-45-1), pp. 1, Creation Date Apr. 16, 2014.
CAS Registry Database, 1585340-91-5, (Compound with the Registry No. 1585340-91-5), pp. 1-3, Creation Date Apr. 16, 2014.
CAS Registry Database, 1844896-04-3, (Compound with the Registry No. 1844896-04-3), pp. 1-4, Creation Date Jan. 11, 2016.
International Search Report for International Application No. PCT/EP2016/081810, pp. 1-8 (dated Jun. 19, 2017).
Database CA [Online] Chemical Abstracts Service, Columbus, Ohio, US; 2009, Goldfarb, David Scott: "Method using lifespan-altering compounds for altering the lifespan of eukaryotic organisms, and screening for such compounds", Database accession No. 2009:846108 Compound with the registry No. 717829-94-2.
Database Registry [Online] Chemical Abstracts Service, Columbus, Ohio, US; Mar. 28, 2014 (Mar. 28, 2014), Database accession No. 1575662-27-9 Compounds with the Registry No. 1575662-27-9 and 1574985-62-8.
Database Registry [Online] Chemical Abstracts Service, Columbus, Ohio, US; Jun. 14, 2011 (Jun. 14, 2011), Database accession No. 1309337-74-3 abstract Compound with the Registry No. 1309337-74-3.
Database Registry [Online] Chemical Abstracts Service, Columbus, Ohio, US; Sep. 14, 2011 (Sep. 14, 2011), Database accession No. 1332167-51-7 Compound with the Registry No. 1332167-51-7.
Database Registry [Online] Chemical Abstracts Service, Columbus, Ohio, US; Feb. 27, 2005 (Feb. 27, 2005), Database accession No. 838811-58-8 abstract Compound with the Registry No. 838811-58-8.

(Continued)

*Primary Examiner* — Erich A Leeser

(57) ABSTRACT

Compounds of Formula 0, Formula I, and Formula II and methods of use as Interleukin-1 Receptor Associated Kinase (IRAK4) inhibitors are described herein.

22 Claims, No Drawings

(56) References Cited

OTHER PUBLICATIONS

Database Registry [Online] Chemical Abstracts Service, Columbus, Ohio, US; Dec. 14, 2015 (Dec. 14, 2015), Database accession No. 1829481-02-8 Compounds with the Registry No. 1829481-02-8 and 1829481-01-7.
Database Registry [Online] Chemical Abstracts Service, Columbus, Ohio, US; Jan. 7, 2011 (Jan. 7, 2011), Database accession No. 1258739-95-5 abstract Compound with the Registry No. 1258739-95-5.

* cited by examiner

PYRAZOLO[1,5A]PYRIMIDINE DERIVATIVES AS IRAK4 MODULATORS

CROSS REFERENCE TO RELATED APPLICATIONS

This application is a continuation of U.S. application Ser. No. 16/014,321, filed Jun. 21, 2018 which is a continuation of International Application No. PCT/EP2016/081810, filed Dec. 19, 2016, which claims priority to U.S. provisional application Ser. No. 62/271,171, filed Dec. 22, 2015; U.S. provisional application Ser. No. 62/279,459, filed Jan. 15, 2016; and U.S. provisional application Ser. No. 62/398,341, filed Sep. 22, 2016, each of which is incorporated herein by reference in its entirety.

FIELD OF THE INVENTION

This invention pertains to compounds useful for inhibition of Interleukin-1 Receptor Associated Kinase 4 (IRAK4).

BACKGROUND OF THE INVENTION

TIR-domain (Toll-Interleukin 1 Receptor-domain) containing cell surface receptors such as the Toll-like receptors (TLR) and the IL-1 and IL-18 receptors play critical roles in innate immunity and have been implicated in the pathogenesis of autoimmunity. TLRs, for example, recognize pathogenic or endogenous ligands and provide a requisite signal for dendritic cell maturation and antigen presentation to T cell. Similarly, proteins that mediate signaling from these receptors have also been shown to play important roles in the pathogenesis of autoimmune disorders. For example mice deficient in MyD88, an adaptor protein that directly interacts with the TIR domain, are more susceptible to bacterial, fungal and parasitic infections. In addition, MyD88 deficient mice are resistant to experimental autoimmune encephalomyelitis (EAE) and streptococcal cell wall-induced arthritis.

The Interleukin-1 Receptor Associated Kinase (IRAK) family is comprised of four family members IRAK1, IRAK2, IRAK3 (also termed IRAK-M), and IRAK4. These proteins are characterized by a typical N-terminal death domain that mediates interaction with MyD88-family adaptor proteins and a centrally located kinase domain. Whereas IRAK1 and IRAK4 have kinase activity, IRAK2 and IRAK3 are catalytically inactive. Upon activation of their upstream cognate receptors, IRAK4 is thought to phosphorylate IRAK1, resulting in the activation and autophosphorylation of IRAK1 and subsequent phosphorylation of downstream substrates. The hyperphosphorylation of IRAK1 directs its dissociation from the receptor complex and its eventual ubiquitylation and proteasomal degradation. Phosphorylation of downstream substrates such as Pellino-2 ultimately leads to the activation of the MAPKs such as p38 and c-Jun N-terminal kinase (JNK) and NF-kB followed by production of pro-inflammatory cytokines, chemokines, and destructive enzyme.

The role of IRAK4 in innate immunity and in the pathogenesis of autoimmune diseases is emerging. See, e.g., Li et al., "IRAK-4: A novel member of the IRAK family with the properties of an IRAK-kinase," PNAS 2002, 99(8), 5567-5572; Flannery et al., "The interleukin-1 receptor-associated kinases: Critical regulators of innate immune signaling," Biochem Pharm 2010, 80(12), 1981-1991. Patients with destabilizing or null mutations in IRAK4 demonstrate defects in TLR signaling and the production of pro-inflammatory cytokines such as IL-1 and TNF as well as antiviral cytokines such as IFNα and IFNβ. These patients demonstrate an increased susceptibility to gram-positive bacterial infections although they are generally resistant to gram-negative bacterial, viral, and fungal infections. Similarly, IRAK4 deficient mice have defects in TLR- and IL-1-mediated cytokine production and exhibit an increased susceptibility to infection. IRAK1 deficient mice demonstrate a loss of responsiveness to lipopolysaccharides (LPS), IL-1, and IL-18 as well as impaired Th1 development. These mice were resistant to experimental autoimmune encephalomyelitis, exhibiting little or no CNS inflammation.

Accordingly, compounds that modulate the function of IRAK4 represent an attractive approach to the development of therapeutic agents for the treatment of diseases such as inflammatory, cell proliferative and immune-related conditions and diseases associated with IRAK-mediated signal transduction, such as rheumatoid arthritis, inflammatory bowel disease, multiple sclerosis, lupus, diabetes, obesity, allergic disease, psoriasis, asthma, graft rejection, cancer and sepsis.

SUMMARY OF THE INVENTION

One aspect of the invention includes a compound of Formula 0:

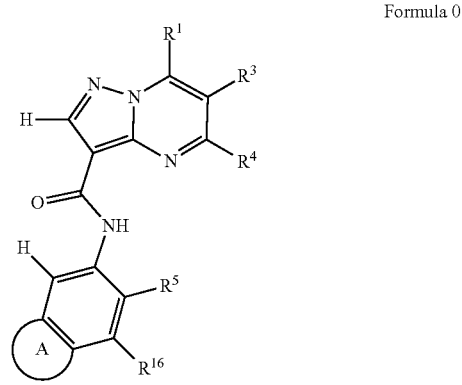

Formula 0 or a stereoisomer or pharmaceutically acceptable salt thereof,
wherein:
$R^1$ is hydrogen or halogen;
$R^3$ is hydrogen, halogen, CN, OH, $C_{1-3}$alkyl, $C_{2-3}$alkenyl, $C_{3-7}$cycloalkyl group, $C_1$-$C_3$alkanoyl, —($C_0$-$C_3$alkyl)C(O)NR$^6$R$^7$, —($C_{2-3}$alkenyl)C(O)NR$^6$R$^7$, —S(O)$_{1,2}$NR$^6$R$^7$, —NR$^8$R$^9$, —O—$C_{1-3}$alkyl, a 3-7 membered monocyclic saturated or partially saturated heterocyclic group, a 5-6 membered monocyclic heteroaryl ring, or a 5-6 membered monocyclic aryl ring,
wherein any alkyl, alkanoyl, or alkenyl is independently optionally substituted by halogen, oxo, CN, OH, $C_{1-3}$alkoxy, or $C_{1-3}$haloalkoxy, and
wherein any cycloalkyl group, heterocyclic group, heteroaryl ring, or aryl ring is independently optionally substituted by halogen, oxo, CN, OH, $C_{1-3}$alkyl, or $C_{1-3}$haloalkyl;
$R^4$ is hydrogen, halogen, $C_{1-3}$alkyl, $C_{2-3}$alkenyl, —($C_0$-$C_3$alkyl)C(O)R$^{13}$—($C_{2-3}$alkenyl)C(O)NR$^{10}$R$^{11}$, —S(O)$_{1-2}$NR$^{10}$R$^{11}$, a 3-7 membered monocyclic saturated or partially saturated heterocyclic group, —C(O)NR$^8$R$^9$, or —NR$^8$R$^9$, wherein any alkyl, alkenyl, or heterocyclic group is independently optionally substituted by halogen, oxo, CN, OH, $C_{1-3}$alkoxy, $C_{1-3}$haloalkoxy, or a 3-7 membered monocyclic saturated or partially saturated heterocyclic group that may be optionally substituted with oxo;

$R^5$ is hydrogen, —CN, $C_{1-6}$alkyl, $C_{1-6}$alkoxy, $C_{3-10}$cycloalkyl group, —$NR^8R^9$, —$C(O)NR^8R^9$, —$O(C_{3-7}$cycloalkyl group), —$O(C_{1-3}$alkyl)-3-8 membered cycloalkyl group, —$O(C_{0-3}$alkyl)-3-8 membered saturated or partially saturated heterocyclic group, —$O(C_{1-3}$alkyl)-phenyl, a —$O(C_{1-3}$ alkyl)-5-6 membered heteroaryl ring, a 3-11 membered saturated or partially saturated heterocyclic group, or a 5-6 membered monocyclic heteroaryl ring, wherein any alkyl or alkoxy is independently optionally substituted by halogen, oxo, CN, OH, $C_{1-3}$alkoxy, $C_{1-3}$haloalkoxy, or a 3-11 membered saturated or partially saturated heterocyclic group that may be optionally substituted with (i) —$C(O)(C_{1-3}$alkyl) optionally substituted with halogen or (ii) with $C_{1-3}$alkyl optionally substituted with halogen, and wherein any cycloalkyl group, heterocyclic group, phenyl, or heteroaryl ring is optionally substituted by halogen; oxo; CN; OH; $C_{1-6}$alkoxy; —$NR^8R^9$; —$C(O)(C_{1-3}$alkyl); —$(C_{0-3}$alkyl)$C(O)NR^{10}R^{11}$; —$S(O)_{1-2}NR^8R^9$; —$OP(O)(OC_{1-3}$alkyl)$_2$; $C_{3-10}$cycloalkyl group optionally substituted with OH or halogen; a 3-11 membered saturated or partially saturated heterocyclic group optionally substituted with oxo or $C_{1-3}$alkyl; a 5-6 membered monocyclic heteroaryl ring optionally substituted by halogen, oxo, CN, OH, $C_{1-3}$alkyl, or $C_{1-3}$haloalkyl; or $C_{1-4}$alkyl optionally substituted by halogen, oxo, CN, OH, —O—$C_{1-3}$ alkyl, —S—$C_{1-3}$alkyl, —$SO_2$—$C_{1-3}$alkyl, —$NR^8R^9$, —$C(O)NR^8R^9$, phenyl, $C_{3-10}$cycloalkyl, a 3-11 membered saturated or partially saturated heterocyclic group optionally substituted with oxo or $C_{1-3}$ alkyl, or a 5-6 membered monocyclic heteroaryl ring optionally substituted with oxo, halogen, or $C_{1-3}$alkyl;

A is a 3-11 membered heterocyclic group optionally substituted by halogen, oxo, CN, OH, $C_{1-6}$alkyl, —$(C_{0-3}$alkyl)-$C_{3-6}$cycloalkyl group, a —$(C_{0-3}$alkyl)-3-11 membered heterocyclic group, —$NR^8R^9$, —$NR^{12}C(O)R^{13}$, —$NR^{12}S(O)_{1-2}R^{13}$, —$C(O)(C_{1-3}$alkyl), —$C(O)NR^{10}R^{11}$, —$C(O)OR^{13}$, —$S(O)_{1-2}NR^{10}R^{11}$, or —$(C_{0-3}$alkyl)-$OP(O)(OC_{1-3}$alkyl)$_2$, wherein any alkyl, cycloalkyl group, or heterocyclic group is independently optionally substituted by halogen; oxo; CN; $OR^{13}$; $C_{1-3}$haloalkoxy; —$C(O)(C_{1-3}$alkyl); —S—$C_{1-3}$alkyl; or $C_{1-3}$alkyl optionally substituted with OH, halogen, $C_{1-3}$haloalkyl, $C_{1-3}$alkoxy, $C_{1-3}$haloalkoxy, or a 3-8 membered heterocyclic group, and wherein when A is a 5-membered nitrogen containing heterocyclic group, the nitrogen atom is substituted;

$R^6$ and $R^7$ are, independently at each occurrence, hydrogen, $C_{1-3}$alkyl, or $C_{3-6}$cycloalkyl group, wherein any alkyl or cycloalkyl group is independently optionally substituted by halogen, oxo, CN, OH, $C_{1-3}$alkyl, $C_{1-3}$haloalkyl, $C_{1-3}$alkoxy, or $C_{1-3}$haloalkoxy;

$R^8$, $R^9$, $R^{10}$ and $R^{11}$ are, independently at each occurrence, hydrogen, $C_{1-6}$alkyl, $C_{3-6}$cycloalkyl group, —$(C_{0-3}$alkyl)-phenyl, a 3-11 membered saturated heterocyclic group, a 5-6 membered monocyclic heteroaryl ring, —$C(O)R^{13}$, —$C(O)R^{13}$, —$C(O)NR^6R^7$, or —$S(O)_{1-2}R^{13}$, or $R^{10}$ and $R^{11}$ are taken together to form a 5-8 membered heterocyclic group, wherein any alkyl, cycloalkyl group, phenyl, heterocyclic group, or heteroaryl ring is independently optionally substituted by halogen, oxo, CN, $C_{1-3}$alkyl, $C_{1-3}$haloalkyl, $C_{1-3}$alkoxy, $C_{1-3}$haloalkoxy, —$OR^{13}$, —$NR^6R^7$, or a 5-6 membered monocyclic heteroaryl ring;

$R^{12}$ is, independently at each occurrence, hydrogen, $C_{1-6}$alkyl or $C_{3-6}$cycloalkyl group, wherein any alkyl or cycloalkyl group is independently optionally substituted by halogen, oxo, CN, OH, $C_{1-3}$alkyl, $C_{1-3}$haloalkyl, $C_{1-3}$alkoxy, or $C_{1-3}$haloalkoxy;

$R^{13}$ is, independently at each occurrence, hydrogen, $C_{1-6}$alkyl, $C_{3-10}$cycloalkyl group, or a 3-11 membered saturated heterocyclic group, wherein any alkyl, cycloalkyl group, or heterocyclic group is independently optionally substituted by halogen, oxo, CN, OH, $C_{1-3}$alkyl, $C_{1-3}$haloalkyl, $C_{1-3}$alkoxy, $C_{1-3}$haloalkoxy, —$OR^{12}$, or —$NR^6R^7$; and $R^{16}$ is hydrogen, halogen, CN, or $C_{1-3}$alkyl optionally substituted with —$NH_2$, halogen, or CN.

Another aspect of the invention includes a compound of Formula I:

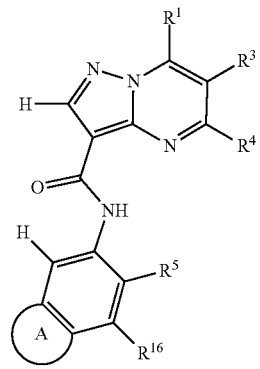

Formula I or a stereoisomer or pharmaceutically acceptable salt thereof,
wherein:

$R^1$ is hydrogen or halogen;

$R^3$ is hydrogen, halogen, CN, OH, $C_{1-3}$alkyl, $C_{2-3}$alkenyl, $C_{3-7}$cycloalkyl group, $C_1$-$C_3$alkanoyl, —$(C_0$-$C_3$alkyl)$C(O)NR^6R^7$, —$(C_{2-3}$alkenyl)$C(O)NR^6R^7$, —$S(O)_{12}NR^6R^7$, —$NR^8R^9$, a 3-7 membered monocyclic saturated or partially saturated heterocyclic group, a 5-6 membered monocyclic heteroaryl ring, or a 5-6 membered monocyclic aryl ring, wherein any alkyl, alkanoyl, or alkenyl is independently optionally substituted by halogen, oxo, CN, OH, $C_{1-3}$alkoxy, or $C_{1-3}$haloalkoxy, and any cycloalkyl group or other ring is independently optionally substituted by halogen, oxo, CN, OH, $C_{1-3}$alkyl, or $C_{1-3}$haloalkyl;

$R^4$ is hydrogen, halogen, $C_{1-3}$alkyl, $C_{2-3}$alkenyl, —$(C_0$-$C_3$alkyl)$C(O)R^{13}$—$(C_2$-3alkenyl)$C(O)NR^{10}R^{11}$, —$S(O)_{1-2}NR^{10}R^{11}$, or —$NR^8R^9$;

wherein any alkyl or alkenyl is independently optionally substituted by halogen, oxo, CN, OH, $C_{1-3}$alkoxy, or $C_{1-3}$haloalkoxy;

$R^5$ is hydrogen, $C_{1-6}$alkyl, $C_{1-6}$alkoxy, $C_{3-10}$cycloalkyl group, —$NR^8R^9$, —$O(C_{3-7}$cycloalkyl group), —$O(C_{1-3}$alkyl)-3-8 membered cycloalkyl group, —$O(C_{1-3}$alkyl)-3-8 membered saturated or partially saturated heterocyclic group, —$O(C_{1-3}$alkyl)-phenyl, a —$O(C_{1-3}$alkyl)-5-6 membered heteroaryl ring, a 3-11 membered saturated or partially saturated heterocyclic group, or a 5-6 membered monocyclic heteroaryl ring, wherein any alkyl or alkoxy is independently optionally substituted by halogen, oxo, CN, OH, $C_{1-3}$alkoxy, or $C_{1-3}$haloalkoxy, and any cycloalkyl group or other ring is optionally substituted by halogen, oxo, CN, OH, $C_{1-6}$ alkoxy, —C(O)($C_{1-3}$alkyl), —($C_{0-3}$alkyl)C(O)NR$^{10}$R$^{11}$, —S(O)$_{1-2}$NR$^8$R$^9$, —OP(O)(O$C_{1-3}$alkyl)$_2$, a 5-6 membered monocyclic heteroaryl ring optionally substituted by halogen, oxo, CN, OH, $C_{1-3}$alkyl, or $C_{1-3}$haloalkyl, or $C_{1-3}$alkyl optionally substituted by halogen, oxo, CN, OH, phenyl, a 3-8 membered saturated heterocyclic group, a 5-6 membered monocyclic heteroaryl ring, or —NR$^8$R$^9$;

A is a 3-11 membered heterocyclic group optionally substituted by halogen, oxo, CN, OH, $C_{1-6}$alkyl, —($C_{0-3}$alkyl)-$C_{3-6}$cycloalkyl group, a —($C_{1-3}$alkyl)-3-11 membered heterocyclic group optionally substituted by halogen, oxo, CN, OH, $C_{1-3}$alkyl, or $C_{1-3}$haloalkyl, —NR$^8$R$^9$, —NR$^{12}$C(O)R$^{13}$, —NR$^{12}$S(O)$_{12}$R$^{13}$, —C(O)($C_{1-3}$alkyl), —C(O)NR$^{10}$R$^{11}$, —C(O)OR$^{13}$, —S(O)$_{1-2}$NR$^{10}$R$^{11}$ or —OP(O)(O$C_{1-3}$alkyl)$_2$, wherein any alkyl, cycloalkyl group, or heterocyclic group is independently optionally substituted by halogen, oxo, CN, OH, $C_{1-3}$alkyl, $C_{1-3}$haloalkyl, $C_{1-3}$alkoxy, $C_{1-3}$haloalkoxy, or a 3-8 membered heterocyclic group;

wherein when A is a 5-membered nitrogen containing heterocyclic group, the nitrogen atom is substituted;

R$^6$ and R$^7$ are, independently at each occurrence, hydrogen, $C_{1-3}$alkyl, or $C_{3-6}$cycloalkyl group, wherein any alkyl or cycloalkyl group is independently optionally substituted by halogen, oxo, CN, OH, $C_{1-3}$alkyl, $C_{1-3}$haloalkyl, $C_{1-3}$alkoxy, or $C_{1-3}$haloalkoxy;

R$^8$, R$^9$, R$^{10}$ and R$^{11}$ are, independently at each occurrence, hydrogen, $C_{1-6}$alkyl, $C_{3-6}$cycloalkyl group, —($C_{0-3}$alkyl)-phenyl, a 3-11 membered saturated heterocyclic group, —C(O)R$^{13}$, —C(O)OR$^{13}$, —C(O)NR$^6$R$^7$, or —S(O)$_{1-2}$R$^{13}$, or R$^{10}$ and R$^{11}$ are taken together to form a 5-8 membered heterocyclic group optionally substituted by halogen, oxo, CN, OH, $C_{1-3}$alkyl, $C_1$-3haloalkyl, $C_{1-3}$alkoxy, or $C_{1-3}$haloalkoxy;

wherein any alkyl, cycloalkyl group, or other ring is independently optionally substituted by halogen, oxo, CN, $C_{1-3}$alkyl, $C_{1-3}$haloalkyl, $C_{1-3}$alkoxy, $C_{1-3}$haloalkoxy, —OR$^{13}$, or —NR$^6$R$^7$;

R$^{12}$ is, independently at each occurrence, hydrogen, $C_{1-6}$alkyl or $C_{3-6}$cycloalkyl group, wherein any alkyl or cycloalkyl group is independently optionally substituted by halogen, oxo, CN, OH, $C_{1-3}$alkyl, $C_{1-3}$haloalkyl, $C_{1-3}$alkoxy, or $C_{1-3}$haloalkoxy;

R$^{13}$ is, independently at each occurrence, hydrogen, $C_{1-6}$alkyl, $C_{3-10}$cycloalkyl group, or a 3-11 membered saturated heterocyclic group, wherein any alkyl, cycloalkyl group, or other ring is independently optionally substituted by halogen, oxo, CN, OH, $C_{1-3}$alkyl, $C_{1-3}$haloalkyl, $C_{1-3}$alkoxy, $C_{1-3}$haloalkoxy, —OR$^{12}$, or —NR$^6$R$^7$; and R$^{16}$ is H, —Cl, —CN, or —CH$_3$.

Yet another aspect of the invention includes a compound of Formula II:

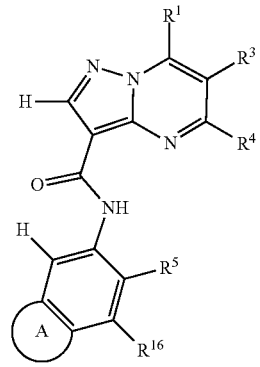

Formula II or a stereoisomer or pharmaceutically acceptable salt thereof, wherein:

R$^1$ is hydrogen or halogen;

R$^3$ is hydrogen, halogen, CN, OH, $C_{1-3}$alkyl, $C_{2-3}$alkenyl, $C_{3-7}$cycloalkyl group, $C_1$-$C_3$alkanoyl, —($C_0$-$C_3$alkyl)C(O)NR$^6$R$^7$, —($C_{2-3}$alkenyl)C(O)NR$^6$R$^7$, —S(O)$_{12}$NR$^6$R$^7$, —NR$^8$R$^9$, a 3-7 membered monocyclic saturated or partially saturated heterocyclic group, a 5-6 membered monocyclic heteroaryl ring, or a 5-6 membered monocyclic aryl ring, wherein any alkyl, alkanoyl, or alkenyl is independently optionally substituted by halogen, oxo, CN, OH, $C_{1-3}$alkoxy, or $C_{1-3}$haloalkoxy, and any cycloalkyl group or other ring is independently optionally substituted by halogen, oxo, CN, OH, $C_{1-3}$alkyl, or $C_{1-3}$haloalkyl;

R$^4$ is hydrogen, halogen, $C_{1-3}$alkyl, $C_{2-3}$alkenyl, —($C_0$-$C_3$alkyl)C(O)R$^{13}$—($C_{2-3}$alkenyl)C(O)NR$^{10}$R$^{11}$, —S(O)$_{1-2}$NR$^{10}$R$^{11}$, or —NR$^8$R$^9$;

wherein any alkyl or alkenyl is independently optionally substituted by halogen, oxo, CN, OH, $C_{1-3}$alkoxy, or $C_{1-3}$haloalkoxy;

R$^5$ is hydrogen, $C_{1-6}$alkyl, $C_{1-6}$alkoxy, $C_{3-10}$cycloalkyl group, —NR$^8$R$^9$, —O($C_{3-7}$cycloalkyl group), a 3-11 membered saturated or partially saturated heterocyclic group, or a 5-6 membered monocyclic heteroaryl ring, wherein any alkyl or alkoxy is independently optionally substituted by halogen, oxo, CN, OH, $C_{1-3}$alkoxy, or $C_{1-3}$haloalkoxy, and any cycloalkyl group or other ring is optionally substituted by halogen, oxo, CN, OH, —($C_{0-3}$alkyl)C(O)NR$^{10}$R$^{11}$, —OP(O)(O$C_{1-3}$alkyl)$_2$, or $C_{1-3}$alkyl optionally substituted by halogen, oxo, CN, OH, or —NR$^8$R$^9$;

A is a 3-11 membered heterocyclic group optionally substituted by halogen, oxo, CN, OH, $C_{1-6}$alkyl, $C_{3-6}$cycloalkyl group, —NR$^8$R$^9$, —NR$^{12}$C(O)R$^{13}$, —NR$^{12}$S(O)$_{1-2}$R$^{13}$, —C(O)NR$^{10}$R$^{11}$, —C(O)OR$^{13}$, or —S(O)$_{1-2}$NR$^{10}$R$^{11}$, wherein any alkyl or cycloalkyl group is independently optionally substituted by halogen, oxo, CN, OH, $C_{1-3}$alkyl, $C_{1-3}$haloalkyl, $C_{1-3}$alkoxy, or $C_{1-3}$haloalkoxy; wherein when A is a 5-membered nitrogen containing heterocyclic group, the nitrogen atom is substituted;

R$^6$ and R$^7$ are, independently at each occurrence, hydrogen, $C_{1-3}$alkyl, or $C_{3-6}$cycloalkyl group, wherein any alkyl or cycloalkyl group is independently optionally substituted by halogen, oxo, CN, OH, $C_{1-3}$alkyl, $C_{1-3}$haloalkyl, $C_{1-3}$alkoxy, or $C_{1-3}$haloalkoxy;

R$^8$, R$^9$, R$^{10}$ and R$^{11}$ are, independently at each occurrence, hydrogen, $C_{1-6}$alkyl, $C_{3-6}$cycloalkyl group, a 3-11 membered saturated heterocyclic group, —C(O)R$^{13}$, —C(O)OR$^{13}$, —C(O)NR$^6$R$^7$, or —S(O)$_{1-2}$R$^{13}$, wherein any alkyl, cycloalkyl group or other ring is independently optionally substituted by halogen, oxo, CN, C$_{1-3}$alkyl, C$_{1-3}$haloalkyl, C$_{1-3}$alkoxy, C$_{1-3}$haloalkoxy, —OR$^{13}$, or —NR$^6$R$^7$;

R$^{12}$ is, independently at each occurrence, hydrogen, C$_{1-6}$alkyl or C$_{3-6}$cycloalkyl group, wherein any alkyl or cycloalkyl group is independently optionally substituted by halogen, oxo, CN, OH, C$_{1-3}$alkyl, C$_{1-3}$haloalkyl, C$_{1-3}$alkoxy, or C$_{1-3}$haloalkoxy;

R$^{12}$ is, independently at each occurrence, hydrogen, C$_{1-6}$alkyl, C$_{3-10}$cycloalkyl group, or a 3-11 membered saturated heterocyclic group, wherein any alkyl, cycloalkyl group, or other ring is independently optionally substituted by halogen, oxo, CN, OH, C$_{1-3}$alkyl, C$_{1-3}$haloalkyl, C$_{1-3}$alkoxy, C$_{1-3}$haloalkoxy, —OR$^{12}$, or —NR$^6$R$^7$; and R$^{16}$ is H, —Cl, —CN, or —CH$_3$.

Also provided is a pharmaceutical composition that comprises a compound of the invention and a pharmaceutically acceptable carrier, diluent or excipient.

Another aspect includes a compound of the invention for use in therapy, such as the treatment of an inflammatory disease, an autoimmune disease or cancer.

Another aspect includes a method of preventing, treating or lessening the severity of a disease or condition responsive to the inhibition of IRAK4, in a patient. The method can comprise administering to the patient a therapeutically effective amount of a compound of the invention.

Another aspect includes the use of a compound of the invention in the manufacture of a medicament for the treatment of a disease responsive to the inhibition of IRAK4.

Another aspect includes a kit for treating a disease or disorder responsive to the inhibition of IRAK4. The kit can comprise a first pharmaceutical composition comprising a compound of the invention, and instructions for use.

DETAILED DESCRIPTION OF THE INVENTION

Definitions

"Halogen" or "halo" refers to F, Cl, Br or I. Additionally, terms such as "haloalkyl," are meant to include monohaloalkyl and polyhaloalkyl.

The term "alkyl" refers to a saturated linear or branched-chain monovalent hydrocarbon radical, wherein the alkyl radical may be optionally substituted. In one example, the alkyl radical is one to eighteen carbon atoms (C-Cis). In other examples, the alkyl radical is C$_0$-C$_6$, C$_0$-C$_5$, C$_0$-C$_3$, C$_1$-C$_{12}$, C$_1$-C$_{10}$, C$_1$-C$_8$, C$_1$-C$_6$, C$_1$-C$_5$, C$_1$-C$_4$, or C$_1$-C$_3$. C$_0$ alkyl refers to a bond. Examples of alkyl groups include methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 1-heptyl and 1-octyl. In some embodiments, substituents for "optionally substituted alkyls" include one to four instances of F, Cl, Br, I, OH, SH, CN, NH$_2$, NHCH$_3$, N(CH$_3$)$_2$, NO$_2$, N$_3$, C(O)CH$_3$, COOH, CO$_2$CH$_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, SO$_2$, phenyl, piperidinyl, piperizinyl, and pyrimidinyl, wherein the alkyl, phenyl and heterocyclic portions thereof may be optionally substituted, such as by one to four instances of substituents selected from this same list.

"Aryl" refers to a carbocyclic aromatic group, whether or not fused to one or more groups, having the number of carbon atoms designated, or if no number is designated, up to 14 carbon atoms. One example includes aryl groups having 6-14 carbon atoms. Another example includes aryl groups having 6-10 carbon atoms. Examples of aryl groups include phenyl, naphthyl, biphenyl, phenanthrenyl, naphthacenyl, 1,2,3,4-tetrahydronaphthalenyl, 1H-indenyl, 2,3-dihydro-1H-indenyl, and the like (see, e.g., Lang's Handbook of Chemistry (Dean, J. A., ed.) 13$^{th}$ ed. Table 7-2 [1985]). A particular aryl is phenyl. Substituted phenyl or substituted aryl means a phenyl group or aryl group substituted with one, two, three, four or five substituents, for example, 1-2, 1-3 or 1-4 substituents, such as chosen from groups specified herein (see "optionally substituted" definition), such as F, Cl, Br, I, OH, SH, CN, NH$_2$, NHCH$_3$, N(CH$_3$)$_2$, NO$_2$, N$_3$, C(O)CH$_3$, COOH, CO$_2$CH$_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, SO$_2$, phenyl, piperidinyl, piperizinyl, and pyrimidinyl, wherein the alkyl, phenyl and heterocyclic portions thereof may be optionally substituted, such as by one to four instances of substituents selected from this same list. Examples of the term "substituted phenyl" include a mono- or di(halo)phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl, 2,4-difluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(alkyl)phenyl group such as 4-methylphenyl, 2,4-dimethylphenyl, 2-methylphenyl, 4-(isopropyl)phenyl, 4-ethylphenyl, 3-(n-propyl)phenyl and the like; a mono or di(alkoxy)phenyl group, for example, 3,4-dimethoxyphenyl, 3-methoxy-4-benzyloxyphenyl, 3-ethoxyphenyl, 4-(isopropoxy)phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl, a mono- or di(hydroxymethyl) phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, 2-chloro-5-difluoromethoxy and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino.

The terms "compound(s) of the invention," and "compound(s) of the present invention" and the like, unless otherwise indicated, include compounds of Formula 0, Formula I, Formula II, and the compounds of Tables 1, 2 and 3 herein, including stereoisomers (including atropisomers), geometric isomers, tautomers, solvates, metabolites, isotopes, salts (e.g., pharmaceutically acceptable salts), and prodrugs thereof. In some embodiments, solvates, metabolites, isotopes or prodrugs are excluded, or any combination thereof.

"Cycloalkyl" refers to a non-aromatic, saturated or partially unsaturated hydrocarbon ring group wherein the cycloalkyl group may be optionally substituted independently with one or more substituents described herein. In one example, the cycloalkyl group is 3 to 12 carbon atoms ($C_3$-$C_2$). In other examples, cycloalkyl is $C_3$-$C_8$, $C_3$-$C_{10}$ or $C_5$-$C_{10}$. In other examples, the cycloalkyl group, as a monocycle, is $C_3$-$C_8$, $C_3$-$C_6$ or $C_5$-$C_6$. In another example, the cycloalkyl group, as a bicycle, is $C_7$-$C_{12}$. In another example, the cycloalkyl group, as a spiro system, is $C_5$-$C_{12}$. Examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[2.2.1]heptane, bicyclo[2.2.2]octane and bicyclo[3.2.2]nonane. Examples of spiro cycloalkyl include, spiro[2.2]pentane, spiro[2.3] hexane, spiro[2.4]heptane, spiro[2.5]octane and spiro[4.5] decane. In some embodiments, substituents for "optionally substituted cycloalkyls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, isopropyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, aryl and heterocyclic portions thereof may be optionally substituted, such as by one to four instances of substituents selected from this same list.

"Heterocyclic group", "heterocyclic", "heterocycle", "heterocyclyl", or "heterocyclo" are used interchangeably and refer to any mono-, bi-, tricyclic or spiro, saturated, partially saturated or unsaturated, aromatic (heteroaryl) or non-aromatic (e.g., heterocycloalkyl), ring system, having 3 to 20 ring atoms, where the ring atoms are carbon, and at least one atom in the ring or ring system is a heteroatom selected from nitrogen, sulfur or oxygen. If any ring atom of a cyclic system is a heteroatom, that system is a heterocycle, regardless of the point of attachment of the cyclic system to the rest of the molecule. In one example, heterocyclyl includes 3-11 ring atoms ("members") and includes monocycles, bicycles, tricycles and spiro ring systems, wherein the ring atoms are carbon, where at least one atom in the ring or ring system is a heteroatom selected from nitrogen, sulfur or oxygen. In one example, heterocyclyl includes 1 to 4 heteroatoms. In one example, heterocyclyl includes 1 to 3 heteroatoms. In another example, heterocyclyl includes 3- to 7-membered monocycles having 1-2, 1-3 or 1-4 heteroatoms selected from nitrogen, sulfur or oxygen. In another example, heterocyclyl includes 4- to 6-membered monocycles having 1-2, 1-3 or 1-4 heteroatoms selected from nitrogen, sulfur or oxygen. In another example, heterocyclyl includes 3-membered monocycles. In another example, heterocyclyl includes 4-membered monocycles. In another example, heterocyclyl includes 5-6 membered monocycles, e.g., 5-6 membered heteroaryl. In another example, heterocyclyl includes 3-11 membered heterocycloyalkyls, such as 4-11 membered heterocycloalkyls. In some embodiments, a heterocycloalkyl includes at least one nitrogen. In one example, the heterocyclyl group includes 0 to 3 double bonds. Any nitrogen or sulfur heteroatom may optionally be oxidized (e.g., NO, SO, $SO_2$), and any nitrogen heteroatom may optionally be quaternized (e.g., $[NR_4]^+Cl^-$, $[NR_4]^+$ $OH^-$). Example heterocycles are oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, isoquinolinyl, tetrahydroisoquinolinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5] decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocycles containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocycles containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Example benzo-fused 5-membered heterocycles are benzoxazol-2-yl, benzthiazol-2-yl and benzimidazol-2-yl. Example 6-membered heterocycles contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are other example heterocycle groups. Heterocycles may be optionally substituted. For example, substituents for "optionally substituted heterocycles" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, oxo, trifluoromethyl, difluoromethyl, sulfonylamino, methanesulfonylamino, SO, $SO_2$, phenyl, piperidinyl, piperizinyl, and pyrimidinyl, wherein the alkyl, aryl and heterocyclic portions thereof may be optionally substituted, such as by one to four instances of substituents selected from this same list.

"Heteroaryl" refers to any mono-, bi-, or tricyclic ring system where at least one ring is a 5- or 6-membered aromatic ring containing from 1 to 4 heteroatoms selected from nitrogen, oxygen, and sulfur, and in an example embodiment, at least one heteroatom is nitrogen. See, for example, Lang's Handbook of Chemistry (Dean, J. A., ed.) $13^{th}$ ed. Table 7-2 [1985]. Included in the definition are any bicyclic groups where any of the above heteroaryl rings are fused to an aryl ring, wherein the aryl ring or the heteroaryl ring is joined to the remainder of the molecule. In one embodiment, heteroaryl includes 5-6 membered monocyclic aromatic groups where one or more ring atoms is nitrogen, sulfur or oxygen. Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, imidazol[1,2-a]pyrimidinyl and purinyl, as well as benzo-fused derivatives, for example benzoxazolyl, benzofuryl, benzothiazolyl, benzothiadiazolyl, benzotriazolyl, benzoimidazolyl and indolyl. Heteroaryl groups can be optionally substituted. In some embodiments, substituents for "optionally substituted heteroaryls" include one to four instances of F, Cl, Br, I, OH, SH, CN, $NH_2$, $NHCH_3$, $N(CH_3)_2$, $NO_2$, $N_3$, $C(O)CH_3$, COOH, $CO_2CH_3$, methyl, ethyl, propyl, iso-propyl, butyl, isobutyl, cyclopropyl, methoxy, ethoxy, propoxy, trifluoromethyl, difluoromethyl, sulfonylamino, methanesulfonylamino, SO, $SO_2$, phenyl, piperidinyl, piperizinyl, and pyrimidinyl, wherein the alkyl, phenyl and heterocyclic portions thereof may be optionally substituted, such as by one to four instances of substituents selected from this same list.

In particular embodiments, a heterocyclyl group is attached at a carbon atom of the heterocyclyl group. By way of example, carbon bonded heterocyclyl groups include bonding arrangements at position 2, 3, 4, 5, or 6 of a pyridine ring, position 3, 4, 5, or 6 of a pyridazine ring, position 2, 4, 5, or 6 of a pyrimidine ring, position 2, 3, 5, or 6 of a pyrazine ring, position 2, 3, 4, or 5 of a furan, tetrahydrofuran, thiofuran, thiophene, pyrrole or tetrahydropyrrole ring, position 2, 4, or 5 of an oxazole, imidazole or thiazole ring, position 3, 4, or 5 of an isoxazole, pyrazole, or isothiazole ring, position 2 or 3 of an aziridine ring, position 2, 3, or 4 of an azetidine ring, position 2, 3, 4, 5, 6, 7, or 8 of a quinoline ring or position 1, 3, 4, 5, 6, 7, or 8 of an isoquinoline ring.

In certain embodiments, the heterocyclyl group is N-attached. By way of example, nitrogen bonded heterocyclyl or heteroaryl groups include bonding arrangements at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "alkoxy" refers to a linear or branched monovalent radical represented by the formula —OR in which R is alkyl, as defined herein. Alkoxy groups include methoxy, ethoxy, propoxy, isopropoxy, mono-, di- and tri-fluoromethoxy and cyclopropoxy. "Haloalkoxy" refers to a haloalkyl group, as that term is defined herein, as R.

The term "alkanoyl" refers to group (alkyl)-C(=O)—, wherein alkyl is as defined herein. For example, $C_1$-$C_6$alkanoyl refers to a group of formula ($C_1$-$C_5$alkyl)-C(=O)—. Alkanoyl groups include, formyl, acetyl, propanoyl, isopropanoyl, butanoyl, isobutanoyl, pentanoyl, 3-methylpentanoyl, and hexanoyl.

"Optionally substituted" unless otherwise specified means that a group may be unsubstituted or substituted by one or more (e.g., 0, 1, 2, 3, 4, or 5 or more, or any range derivable therein) of the substituents listed for that group in which said substituents may be the same or different. In an embodiment, an optionally substituted group has 1 substituent. In another embodiment an optionally substituted group has 2 substituents. In another embodiment an optionally substituted group has 3 substituents. In another embodiment an optionally substituted group has 4 substituents. In another embodiment an optionally substituted group has 5 substituents.

As used herein a wavy line "〜" that intersects a bond in a chemical structure indicate the point of attachment of the atom to which the wavy bond is connected in the chemical structure to the remainder of a molecule, or to the remainder of a fragment of a molecule. In some embodiments, an arrow together with an asterisk is used in the manner of a wavy line to indicate a point of attachment.

In certain embodiments, divalent groups are described generically without specific bonding configurations. It is understood that the generic description is meant to include both bonding configurations, unless specified otherwise. For example, in the group $R^1$—$R^2$—$R^3$, if the group $R^2$ is described as —$CH_2C(O)$—, then it is understood that this group can be bonded both as $R^1$—$CH_2C(O)$—$R^3$, and as $R^1$—$C(O)CH_2$—$R^3$, unless specified otherwise.

The phrase "pharmaceutically acceptable" refers to molecular entities and compositions that do not produce an adverse, allergic or other untoward reaction when administered to an animal, such as, for example, a human, as appropriate.

Compounds of the invention may be in the form of a salt, such as a pharmaceutically acceptable salt. "Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particular base addition salts are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particular organic non-toxic bases include isopropylamine, diethylamine, ethanolamine, tromethamine, dicyclohexylamine, choline, and caffeine.

In some embodiments, a salt is selected from a hydrochloride, hydrobromide, trifluoroacetate, sulphate, phosphate, acetate, fumarate, maleate, tartrate, lactate, citrate, pyruvate, succinate, oxalate, methanesulphonate, p-toluenesulphonate, bisulphate, benzenesulphonate, ethanesulphonate, malonate, xinafoate, ascorbate, oleate, nicotinate, saccharinate, adipate, formate, glycolate, palmitate, L-lactate, D-lactate, aspartate, malate, L-tartrate, D-tartrate, stearate, furoate (e.g., 2-furoate or 3-furoate), napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isothionate (2-hydroxyethylsulfonate), 2-mesitylenesulphonate, 2-naphthalenesulphonate, 2,5-dichlorobenzenesulphonate, D-mandelate, L-mandelate, cinnamate, benzoate, adipate, esylate, malonate, mesitylate (2-mesitylenesulphonate), napsylate (2-naphthalenesulfonate), camsylate (camphor-O-sulphonate, for example (1S)-(+)-10-camphorsulfonic acid salt), glutamate, glutarate, hippurate (2-(benzoylamino)acetate), orotate, xylate (p-xylene-2-sulphonate), and pamoic (2,2'-dihydroxy-1,1'-dinaphthylmethane-3,3'-dicarboxylate).

A "sterile" formulation is aseptic or free from all living microorganisms and their spores.

"Stereoisomers" refer to compounds that have identical chemical constitution, but differ with regard to the arrangement of the atoms or groups in space. Stereoisomers include diastereomers, enantiomers, conformers and the like.

"Chiral" refers to molecules which have the property of non-superimposability of the mirror image partner, while the term "achiral" refers to molecules which are superimposable on their mirror image partner.

"Diastereomer" refers to a stereoisomer with two or more centers of chirality and whose molecules are not mirror images of one another. Diastereomers have different physical properties, e.g., melting points, boiling points, spectral properties or biological activities. Mixtures of diastereomers may separate under high resolution analytical procedures such as electrophoresis and chromatography such as HPLC.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Certain compounds of the invention can exist in unsolvated forms as well as solvated forms, including hydrated forms. A "solvate" refers to an association or complex of one or more solvent molecules and a compound of the present invention. Examples of solvents that form solvates include water, isopropanol, ethanol, methanol, DMSO, ethyl acetate, acetic acid, and ethanolamine. Certain compounds of the invention can exist in multiple crystalline or amorphous forms. In general, all physical forms are intended to be within the scope of the present invention. The term "hydrate" refers to the complex where the solvent molecule is water.

A "metabolite" refers to a product produced through metabolism in the body of a specified compound or salt thereof. Such products can result, for example, from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it in a detectable dose (e.g., greater than about 0.5 mg/kg) to an animal such as rat, mouse, guinea pig, monkey, or to a human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

"Amino-protecting group" as used herein refers to a derivative of the groups commonly employed to block or protect an amino group while reactions are carried out on other functional groups on the compound. Examples of such protecting groups include carbamates, amides, alkyl and aryl groups, and imines, as well as many N-heteroatom derivatives which can be removed to regenerate the desired amine group. Particular amino protecting groups are Pmb (p-Methoxybenzyl), Boc (tert-Butyloxycarbonyl), Fmoc (9-Fluorenylmethyloxycarbonyl) and Cbz (Carbobenzyloxy). Further examples of these groups are found in T. W. Greene and P. G. M. Wuts, "Protecting Groups in Organic Synthesis, $3^{rd}$ ed., John Wiley & Sons, Inc., 1999. The term "protected amino" refers to an amino group substituted with one of the above amino-protecting groups.

"Carboxy-protecting group" as used herein refers to those groups that are stable to the conditions of subsequent reaction(s) at other positions of the molecule, which may be removed at the appropriate point without disrupting the remainder of the molecule, to give the unprotected carboxy-group. Examples of carboxy protecting groups include, ester groups and heterocyclyl groups. Ester derivatives of the carboxylic acid group may be employed to block or protect the carboxylic acid group while reactions are carried out on other functional groups on the compound. Examples of such ester groups include substituted arylalkyl, including substituted benzyls, such as 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl or substituted alkyl esters such as methyl, ethyl, t-butyl allyl or t-amyl, triphenylmethyl (trityl), 4-methoxytrityl, 4,4'-dimethoxytrityl, 4,4',4"-trimethoxytrityl, 2-phenylprop-2-yl, thioesters such as t-butyl thioester, silyl esters such as trimethylsilyl, t-butyldimethylsilyl esters, phenacyl, 2,2,2-trichloroethyl, beta-(trimethylsilyl)ethyl, beta-(di(n-butyl) methylsilyl)ethyl, p-toluenesulfonylethyl, 4-nitrobenzylsulfonylethyl, allyl, cinnamyl, 1-(trimethylsilylmethyl) prop-1-en-3-yl, and like moieties. Another example of carboxy-protecting groups are heterocyclyl groups such as 1,3-oxazolinyl. Further examples of these groups are found in T. W. Greene and P. G. M. Wuts, "Protecting Groups in Organic Synthesis, 3d ed., John Wiley & Sons, Inc., 1999. The term "protected carboxy" refers to a carboxy group substituted with one of the above carboxy-protecting groups.

"Hydroxy-protecting group" as used herein refers to a derivative of the hydroxy group commonly employed to block or protect the hydroxy group while reactions are carried out on other functional groups on the compound. Examples of such protecting groups include tetrahydropyranyloxy, benzoyl, acetoxy, carbamoyloxy, benzyl, and silylethers (e.g., TBS, TBDPS) groups. Further examples of these groups are found in T. W. Greene and P. G. M. Wuts, "Protecting Groups in Organic Synthesis, $3^{rd}$ ed., John Wiley & Sons, Inc., 1999. The term "protected hydroxy" refers to a hydroxy group substituted with one of the above hydroxy-protecting groups.

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Mixtures of particular diastereomeric compounds may be separated, or enriched in one or more particular diastereomers, by chromatographic or crystallization methods. Similarly, enantiomeric mixtures may be separated, or enantiomerically enriched, using the same techniques or others known in the art. Each of the asymmetric carbon or nitrogen atoms may be in the R or S configuration and both of these configurations are within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined. Unless otherwise specified, if solid wedges or dashed lines are used, relative stereochemistry is intended.

Another aspect includes prodrugs of the compounds of the invention including known amino-protecting and carboxy-protecting groups which are released, for example hydrolyzed, to yield the compound of the present invention under physiologic conditions.

The term "prodrug" refers to a precursor or derivative form of a pharmaceutically active substance that is less efficacious to the patient compared to the parent drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, and 5-fluorocytosine and 5-fluorouridine prodrugs.

A particular class of prodrugs are compounds in which a nitrogen atom in an amino, amidino, aminoalkyleneamino, iminoalkyleneamino or guanidino group is substituted with a hydroxy group, an alkylcarbonyl (—CO—R) group, an alkoxycarbonyl (—CO—OR), or an acyloxyalkyl-alkoxycarbonyl (—CO—R—CO—R) group where R is a monovalent or divalent group, for example alkyl, alkylene or aryl, or a group having the Formula —C(O)—O—CP1P2-haloalkyl, where P1 and P2 are the same or different and are hydrogen, alkyl, alkoxy, cyano, halogen, alkyl or aryl. In a particular embodiment, the nitrogen atom is one of the nitrogen atoms of the amidino group of the compounds of the invention. Prodrugs may be prepared by reacting a compound of the present invention with an activated group, such as acyl groups, to bond, for example, a nitrogen atom in the compound to the exemplary carbonyl of the activated acyl group. Examples of activated carbonyl compounds are those containing a leaving group bonded to the carbonyl group, and include, for example, acyl halides, acyl amines, acyl pyridinium salts, acyl alkoxides, acyl phenoxides such as p-nitrophenoxy acyl, dinitrophenoxy acyl, fluorophenoxy acyl, and difluorophenoxy acyl. The reactions are generally carried out in inert solvents at reduced temperatures such as −78 to about 50° C. The reactions may also be carried out in the presence of an inorganic base, for example potassium carbonate or sodium bicarbonate, or an organic base such as an amine, including pyridine, trimethylamine, triethylamine, triethanolamine, or the like.

Additional types of prodrugs are also encompassed. For instance, a free carboxyl group of a compound of the invention can be derivatized as an amide or alkyl ester. As another example, compounds of the invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_1-C_6)$alkanoyloxymethyl, $1-((C_1-C_6)$alkanoyloxy)ethyl, 1-methyl-$((C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, alpha-amino $(C_1-C_4)$alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate).

"Leaving group" refers to a portion of a first reactant in a chemical reaction that is displaced from the first reactant in the chemical reaction. Examples of leaving groups include, but are not limited to, halogen atoms, alkoxy and sulfonyloxy groups. Example sulfonyloxy groups include, but are not limited to, alkylsulfonyloxy groups (for example methyl sulfonyloxy (mesylate group) and trifluoromethylsulfonyloxy (triflate group)) and arylsulfonyloxy groups (for example p-toluenesulfonyloxy (tosylate group) and p-nitrosulfonyloxy (nosylate group)).

A "subject," "individual," or "patient" is a vertebrate. In certain embodiments, the vertebrate is a mammal. Mammals include, but are not limited to, farm animals (such as cows), sport animals, pets (such as guinea pigs, cats, dogs, rabbits and horses), primates, mice and rats. In certain embodiments, a mammal is a human. In embodiments comprising administration of a compound of to a patient, the patient is typically in need thereof.

The terms "inhibiting" and "reducing," or any variation of these terms, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity (e.g., IRAK4 activity) compared to normal.

In some embodiments, a compound of Formula 0, Formula I, or Formula II, such as a compound of Tables 1, 2 or 3, is selective for inhibition of IRAK4 over IRAK1. By "selective for inhibition" it is meant that the compound is at least a 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, better inhibitor of IRAK4 activity compared to IRAK1 activity, or is at least a 2-, 3-, 4-, 5-, 10-, 25-, 50-, 100-, 250-, or 500-fold better inhibitor of IRAK4 activity compared to IRAK1 activity.

A "therapeutically effective amount" means an amount of a compound of the present invention, such as a compound of Formula 0, Formula I, or Formula II (e.g., a compound of Tables 1, 2 or 3), that (i) treats or prevents the particular disease, condition or disorder, or (ii) attenuates, ameliorates or eliminates one or more symptoms of the particular disease, condition, or disorder, and optionally (iii) prevents or delays the onset of one or more symptoms of the particular disease, condition or disorder described herein. In some embodiments, the therapeutically effective amount is an amount sufficient to decrease or alleviate the symptoms of an autoimmune or inflammatory disease (e.g., lupus). In some embodiments, a therapeutically effective amount is an amount of a chemical entity described herein sufficient to significantly decrease the activity or number of B-cells. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; or relieve to some extent one or more of the symptoms associated with the cancer. To the extent the drug may prevent growth or kill existing cancer cells, it may be cytostatic or cytotoxic. For cancer therapy, efficacy can, for example, be measured by assessing the time to disease progression (TTP) or determining the response rate (RR).

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, stabilized (i.e., not worsening) state of disease, decreasing the rate of disease progression, amelioration or palliation of the disease state, prolonging survival as compared to expected survival if not receiving treatment and remission or improved prognosis. In some embodiments, compounds of the invention, are used to delay development of a disease or disorder or to slow the progression of a disease or disorder. Those in need of treatment include those already with the condition or disorder as well as those prone to have the condition or disorder, (for example, through a genetic mutation) or those in which the condition or disorder is to be prevented.

"Inflammatory disorder" refers to any disease, disorder or syndrome in which an excessive or unregulated inflammatory response leads to excessive inflammatory symptoms, host tissue damage, or loss of tissue function. "Inflammatory disorder" also refers to a pathological state mediated by influx of leukocytes or neutrophil chemotaxis.

"Inflammation" refers to a localized, protective response elicited by injury or destruction of tissues, which serves to destroy, dilute, or wall off (sequester) both the injurious agent and the injured tissue. Inflammation is notably associated with influx of leukocytes or neutrophil chemotaxis. Inflammation can result from infection with pathogenic organisms and viruses and from noninfectious means such as trauma or reperfusion following myocardial infarction or stroke, immune responses to foreign antigens, and autoimmune responses. Accordingly, inflammatory disorders amenable to treatment with a compound of the present invention, such as a compound of Formula 0, Formula I, or Formula II (e.g., a compound of Tables 1, 2 or 3), encompass disorders associated with reactions of the specific defense system as well as with reactions of the nonspecific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity responses mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" refers to any group of disorders in which tissue injury is associated with humoral or cell-mediated responses to the body's own constituents. Non-limiting examples of autoimmune diseases include rheumatoid arthritis, lupus and multiple sclerosis.

"Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

"Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

In some embodiments, inflammatory disorders which can be treated according to the methods of this invention include, but are not limited to, asthma, rhinitis (e.g., allergic rhinitis), allergic airway syndrome, atopic dermatitis, bronchitis, rheumatoid arthritis, psoriasis, lupus, chronic obstructive pulmonary disease (COPD), contact dermatitis, chronic obstructive pulmonary disease and delayed hypersensitivity reactions.

The terms "cancer" and "cancerous", "neoplasm", and "tumor" and related terms refer to or describe the physiological condition in mammals that is typically characterized by unregulated cell growth. A "tumor" comprises one or more cancerous cells. Examples of cancer include carcinoma, blastoma, sarcoma, seminoma, glioblastoma, melanoma, leukemia, and myeloid or lymphoid malignancies. More particular examples of such cancers include squamous cell cancer (e.g., epithelial squamous cell cancer) and lung cancer including small-cell lung cancer, non-small cell lung cancer ("NSCLC"), adenocarcinoma of the lung and squamous carcinoma of the lung. Other cancers include skin, keratoacanthoma, follicular carcinoma, hairy cell leukemia, buccal cavity, pharynx (oral), lip, tongue, mouth, salivary gland, esophageal, larynx, hepatocellular, gastric, stomach, gastrointestinal, small intestine, large intestine, pancreatic, cervical, ovarian, liver, bladder, hepatoma, breast, colon, rectal, colorectal, genitourinary, biliary passage, thyroid, papillary, hepatic, endometrial, uterine, salivary gland, kidney or renal, prostate, testis, vulval, peritoneum, anal, penile, bone, multiple myeloma, B-cell lymphoma, diffuse large B-Cell lymphoma (DLBCL), central nervous system, brain, head and neck, Hodgkin's, and associated metastases. Examples of neoplastic disorders include myeloproliferative disorders, such as polycythemia vera, essential thrombocytosis, myelofibrosis, such as primary myelofibrosis, and chronic myelogenous leukemia (CML).

A "chemotherapeutic agent" is an agent useful in the treatment of a given disorder, for example, cancer or inflammatory disorders. Examples of chemotherapeutic agents are well-known in the art and include examples such as those disclosed in U.S. Publ. Appl. No. 2010/0048557, incorporated herein by reference. Additionally, chemotherapeutic agents include pharmaceutically acceptable salts, acids or derivatives of any of chemotherapeutic agents, as well as combinations of two or more of them.

Unless otherwise stated, structures depicted herein are also meant to include compounds that differ only in the presence of one or more isotopically enriched atoms. Exemplary isotopes that can be incorporated into compounds of the invention, include isotopes of hydrogen, carbon, nitrogen, oxygen, phosphorus, sulfur, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I, and $^{125}$I, respectively. Isotopically-labeled compounds (e.g., those labeled with $^3$H and $^{14}$C) can be useful in compound or substrate tissue distribution assays. Tritiated (i.e., $^3$H) and carbon-14 (i.e., $^{14}$C) isotopes can be useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements). In some embodiments, in compounds of the invention, one or more carbon atoms are replaced by $^{13}$C- or $^{14}$C-enriched carbon. Positron emitting isotopes such as $^{15}$O, $^{13}$N, $^{11}$C, and $^{18}$F are useful for positron emission tomography (PET) studies to examine substrate receptor occupancy. Isotopically labeled compounds can generally be prepared by following procedures analogous to those disclosed in the Schemes or in the Examples herein, by substituting an isotopically labeled reagent for a non-isotopically labeled reagent.

It is specifically contemplated that any limitation discussed with respect to one embodiment of the invention may apply to any other embodiment of the invention. Furthermore, any compound or composition of the invention may be used in any method of the invention, and any method of the invention may be used to produce or to utilize any compound or composition of the invention.

If any discrepancy exists between a structure and its name, the structure prevails.

The use of the term "or" is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device or method being employed to determine the value.

As used herein, "a" or "an" means one or more, unless clearly indicated otherwise. As used herein, "another" means at least a second or more.

Headings used herein are intended only for organizational purposes.

IRAK4 Inhibitors

As noted, one aspect of the invention includes a compound of Formula 0:

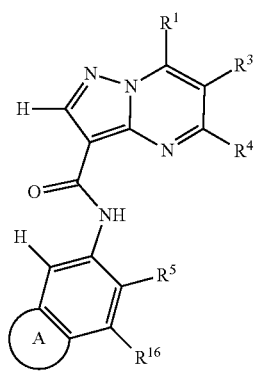

Formula 0 or a stereoisomer or pharmaceutically acceptable salt thereof, wherein:

$R^1$ is hydrogen or halogen;

$R^3$ is hydrogen, halogen, CN, OH, $C_{1-3}$alkyl, $C_{2-3}$alkenyl, $C_{3-7}$cycloalkyl group, $C_1$-$C_3$alkanoyl, —($C_0$-$C_3$alkyl)C(O)NR$^6$R$^7$, —($C_{2-3}$alkenyl)C(O)NR$^6$R$^7$, —S(O)$_{1,2}$NR$^6$R$^7$, —NR$^8$R$^9$, —O—$C_{1-3}$alkyl, a 3-7 membered monocyclic saturated or partially saturated heterocyclic group, a 5-6 membered monocyclic heteroaryl ring, or a 5-6 membered monocyclic aryl ring, wherein any alkyl, alkanoyl, or alkenyl is independently optionally substituted by halogen, oxo, CN, OH, $C_{1-3}$alkoxy, or $C_{1-3}$haloalkoxy, and wherein any cycloalkyl group, heterocyclic group, heteroaryl ring, or aryl ring is independently optionally substituted by halogen, oxo, CN, OH, $C_{1-3}$alkyl, or $C_{1-3}$haloalkyl;

$R^4$ is hydrogen, halogen, $C_{1-3}$alkyl, $C_{2-3}$alkenyl, —($C_0$-$C_3$alkyl)C(O)R$^{13}$—($C_{2-3}$alkenyl)C(O)NR$^{10}$R$^{11}$, —S(O)$_{1-2}$NR$^{10}$R$^{11}$, a 3-7 membered monocyclic saturated or partially saturated heterocyclic group, —C(O)NR$^8$R$^9$, or —NR$^8$R$^9$, wherein any alkyl, alkenyl, or heterocyclic group is independently optionally substituted by halogen, oxo, CN, OH, $C_{1-3}$alkoxy, $C_{1-3}$haloalkoxy, or a 3-7 membered monocyclic saturated or partially saturated heterocyclic group that may be optionally substituted with oxo;

$R^5$ is hydrogen, —CN, $C_{1-6}$alkyl, $C_{1-6}$alkoxy, $C_{3-10}$cycloalkyl group, —NR$^8$R$^9$, —C(O)NR$^8$R$^9$, —O($C_{3-7}$cycloalkyl group), —O($C_{1-3}$alkyl)-3-8 membered cycloalkyl group, —O($C_{0-3}$alkyl)-3-8 membered saturated or partially saturated heterocyclic group, —O($C_{1-3}$alkyl)-phenyl, a —O($C_{1-3}$ alkyl)-5-6 membered heteroaryl ring, a 3-11 membered saturated or partially saturated heterocyclic group, or a 5-6 membered monocyclic heteroaryl ring, wherein any alkyl or alkoxy is independently optionally substituted by halogen, oxo, CN, OH, $C_{1-3}$alkoxy, $C_{1-3}$haloalkoxy, or a 3-11 membered saturated or partially saturated heterocyclic group that may be optionally substituted with (i) —C(O)($C_{1-3}$alkyl) optionally substituted with halogen or (ii) with $C_{1-3}$alkyl optionally substituted with halogen, and wherein any cycloalkyl group, heterocyclic group, phenyl, or heteroaryl ring is optionally substituted by halogen; oxo; CN; OH; $C_{1-6}$alkoxy; —NR$^8$R$^9$; —C(O)($C_{1-3}$alkyl); —($C_{0-3}$alkyl)C(O)NR$^{10}$R$^{11}$; —S(O)$_{1-2}$NR$^8$R$^9$; —OP(O) (OC$_{1-3}$alkyl)$_2$; $C_{3-10}$cycloalkyl group optionally substituted with OH or halogen; a 3-11 membered saturated or partially saturated heterocyclic group optionally substituted with oxo or $C_{1-3}$alkyl; a 5-6 membered monocyclic heteroaryl ring optionally substituted by halogen, oxo, CN, OH, $C_{1-3}$alkyl, or $C_{1-3}$haloalkyl; or $C_{1-4}$alkyl optionally substituted by halogen, oxo, CN, OH, —$C_{1-3}$ alkyl, —S—$C_{1-3}$alkyl, —SO$_2$—$C_{1-3}$alkyl, —NR$^8$R$^9$, —C(O)NR$^8$R$^9$, phenyl, $C_{3-10}$cycloalkyl, a 3-11 membered saturated or partially saturated heterocyclic group optionally substituted with oxo or $C_{1-3}$ alkyl, or a 5-6 membered monocyclic heteroaryl ring optionally substituted with oxo, halogen, or $C_{1-3}$alkyl;

A is a 3-11 membered heterocyclic group optionally substituted by halogen, oxo, CN, OH, $C_{1-6}$alkyl, —($C_{0-3}$alkyl)-$C_{3-6}$cycloalkyl group, a —($C_{0-3}$alkyl)-3-11 membered heterocyclic group, —NR$^8$R$^9$, —NR$^2$C(O)R$^{13}$, —NR$^{12}$S(O)$_{1-2}$R$^{13}$, —C(O)($C_{1-3}$alkyl), —C(O)NR$^{10}$R$^{11}$, —C(O)OR$^{13}$, —S(O)$_{1-2}$NR$^{10}$R$^{11}$, or —($C_{0-3}$alkyl)-OP(O) (OC$_{1-3}$alkyl)$_2$, wherein any alkyl, cycloalkyl group, or heterocyclic group is independently optionally substituted by halogen; oxo; CN; OR$^{13}$; $C_{1-3}$haloalkoxy; —C(O)($C_{1-3}$alkyl); —S—$C_{1-3}$alkyl; or $C_{1-3}$alkyl optionally substituted with OH, halogen, $C_{1-3}$haloalkyl, $C_{1-3}$alkoxy, $C_{1-3}$haloalkoxy, or a 3-8 membered heterocyclic group, and wherein when A is a 5-membered nitrogen containing heterocyclic group, the nitrogen atom is substituted;

$R^6$ and $R^7$ are, independently at each occurrence, hydrogen, $C_{1-3}$alkyl, or $C_{3-6}$cycloalkyl group, wherein any alkyl or cycloalkyl group is independently optionally substituted by halogen, oxo, CN, OH, $C_{1-3}$alkyl, $C_{1-3}$haloalkyl, $C_{1-3}$alkoxy, or $C_{1-3}$haloalkoxy;

$R^8$, $R^9$, $R^{10}$ and $R^{11}$ are, independently at each occurrence, hydrogen, $C_{1-6}$alkyl, $C_{3-6}$cycloalkyl group, —($C_{0-3}$alkyl)-phenyl, a 3-11 membered saturated heterocyclic group, a 5-6 membered monocyclic heteroaryl ring, —C(O)R$^{13}$, —C(O) OR$^{13}$, —C(O)NR$^6$R$^7$, or —S(O)$_{1-2}$R$^{13}$, or $R^{10}$ and $R^{11}$ are taken together to form a 5-8 membered heterocyclic group, wherein any alkyl, cycloalkyl group, phenyl, heterocyclic group, or heteroaryl ring is independently optionally substituted by halogen, oxo, CN, $C_{1-3}$alkyl, $C_{1-3}$haloalkyl, $C_{1-3}$alkoxy, $C_{1-3}$haloalkoxy, —OR$^{13}$, —NR$^6$R$^7$, or a 5-6 membered monocyclic heteroaryl ring;

$R^{12}$ is, independently at each occurrence, hydrogen, $C_{1-6}$alkyl or $C_{3-6}$cycloalkyl group, wherein any alkyl or cycloalkyl group is independently optionally substituted by halogen, oxo, CN, OH, $C_{1-3}$alkyl, $C_{1-3}$haloalkyl, $C_{1-3}$alkoxy, or $C_{1-3}$haloalkoxy;

$R^{13}$ is, independently at each occurrence, hydrogen, $C_{1-6}$alkyl, $C_{3-10}$cycloalkyl group, or a 3-11 membered saturated heterocyclic group, wherein any alkyl, cycloalkyl group, or heterocyclic group is independently optionally substituted by halogen, oxo, CN, OH, $C_{1-3}$alkyl, $C_{1-3}$haloalkyl, $C_{1-3}$alkoxy, $C_{1-3}$haloalkoxy, —$OR^{12}$, or —$NR^6R^7$; and $R^{16}$ is hydrogen, halogen, CN, or $C_{1-3}$alkyl optionally substituted with —$NH_2$, halogen, or CN.

Another aspect of the invention includes a compound of Formula I:

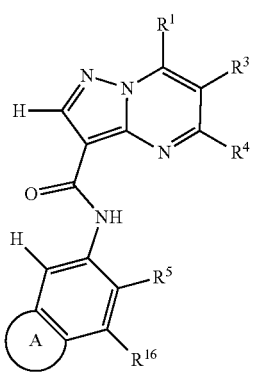

I or a stereoisomer or pharmaceutically acceptable salt thereof, wherein:

$R^1$ is hydrogen or halogen;

$R^3$ is hydrogen, halogen, CN, OH, $C_{1-3}$alkyl, $C_{2-3}$alkenyl, $C_{3-7}$cycloalkyl group, $C_1$-$C_3$alkanoyl, —($C_0$-$C_3$alkyl)C(O)NR$^6$R$^7$, —($C_{2-3}$alkenyl)C(O)NR$^6$R$^7$, —$S(O)_{12}NR^6R^7$, —$NR^8R^9$, a 3-7 membered monocyclic saturated or partially saturated heterocyclic group, a 5-6 membered monocyclic heteroaryl ring, or a 5-6 membered monocyclic aryl ring, wherein any alkyl, alkanoyl, or alkenyl is independently optionally substituted by halogen, oxo, CN, OH, $C_{1-3}$alkoxy, or $C_{1-3}$haloalkoxy, and any cycloalkyl group or other ring is independently optionally substituted by halogen, oxo, CN, OH, $C_{1-3}$alkyl, or $C_{1-3}$haloalkyl;

$R^4$ is hydrogen, halogen, $C_{1-3}$alkyl, $C_{2-3}$alkenyl, —($C_0$-$C_3$alkyl)C(O)R$^{13}$—($C_2$-3alkenyl)C(O)NR$^{10}$R$^{11}$, —$S(O)_{1-2}NR^{10}R^{11}$, or —$NR^8R^9$;

wherein any alkyl or alkenyl is independently optionally substituted by halogen, oxo, CN, OH, $C_{1-3}$alkoxy, or $C_{1-3}$haloalkoxy;

$R^5$ is hydrogen, $C_{1-6}$alkyl, $C_{1-6}$alkoxy, $C_{3-10}$cycloalkyl group, —$NR^8R^9$, —$O(C_{3-7}$cycloalkyl group), —$O(C_{1-3}$alkyl)-3-8 membered cycloalkyl group, —$O(C_{1-3}$alkyl)-3-8 membered saturated or partially saturated heterocyclic group, —$O(C_{1-3}$alkyl)-phenyl, a —$O(C_{1-3}$alkyl)-5-6 membered heteroaryl ring, a 3-11 membered saturated or partially saturated heterocyclic group, or a 5-6 membered monocyclic heteroaryl ring, wherein any alkyl or alkoxy is independently optionally substituted by halogen, oxo, CN, OH, $C_{1-3}$alkoxy, or $C_{1-3}$haloalkoxy, and any cycloalkyl group or other ring is optionally substituted by halogen, oxo, CN, OH, $C_{1-6}$ alkoxy, —C(O)($C_{1-3}$alkyl), —($C_{0-3}$alkyl)C(O)NR$^{10}$R$^{11}$, —$S(O)_{1-2}NR^8R^9$, —$OP(O)(OC_{1-3}$alkyl)$_2$, a 5-6 membered monocyclic heteroaryl ring optionally substituted by halo-gen, oxo, CN, OH, $C_{1-3}$alkyl, or $C_{1-3}$haloalkyl, or $C_{1-3}$alkyl optionally substituted by halogen, oxo, CN, OH, phenyl, a 3-8 membered saturated heterocyclic group, a 5-6 membered monocyclic heteroaryl ring, or —$NR^8R^9$;

A is a 3-11 membered heterocyclic group optionally substituted by halogen, oxo, CN, OH, $C_{1-6}$alkyl, —($C_{0-3}$alkyl)-$C_{3-6}$cycloalkyl group, a —($C_{0-3}$alkyl)-3-11 membered heterocyclic group optionally substituted by halogen, oxo, CN, OH, $C_{1-3}$alkyl, or $C_{1-3}$haloalkyl, —$NR^8R^9$, —$NR^{12}C(O)R^{13}$, —$NR^{12}S(O)_{12}R^{13}$, —C(O)($C_{1-3}$alkyl), —C(O)NR$^{10}$R$^{11}$, —C(O)OR$^{13}$, —$S(O)_{1-2}NR^{10}R^{11}$, or —$OP(O)(OC_{1-3}$alkyl)$_2$, wherein any alkyl, cycloalkyl group, or heterocyclic group is independently optionally substituted by halogen, oxo, CN, OH, $C_{1-3}$alkyl, $C_{1-3}$haloalkyl, $C_{1-3}$alkoxy, $C_{1-3}$haloalkoxy, or a 3-8 membered heterocyclic group;

wherein when A is a 5-membered nitrogen containing heterocyclic group, the nitrogen atom is substituted;

$R^6$ and $R^7$ are, independently at each occurrence, hydrogen, $C_{1-3}$alkyl, or $C_{3-6}$cycloalkyl group, wherein any alkyl or cycloalkyl group is independently optionally substituted by halogen, oxo, CN, OH, $C_{1-3}$alkyl, $C_{1-3}$haloalkyl, $C_{1-3}$alkoxy, or $C_{1-3}$haloalkoxy;

$R^8$, $R^9$, $R^{10}$ and $R^{11}$ are, independently at each occurrence, hydrogen, $C_{1-6}$alkyl, $C_{3-6}$cycloalkyl group, —($C_{0-3}$alkyl)-phenyl, a 3-11 membered saturated heterocyclic group, —C(O)R$^{13}$, —C(O)OR$^{13}$, —C(O)NR$^6$R$^7$, or —$S(O)_{1-2}R^{13}$, or $R^{10}$ and $R^{11}$ are taken together to form a 5-8 membered heterocyclic group optionally substituted by halogen, oxo, CN, OH, $C_{1-3}$alkyl, $C_1$-3haloalkyl, $C_{1-3}$alkoxy, or $C_{1-3}$haloalkoxy;

wherein any alkyl, cycloalkyl group, or other ring is independently optionally substituted by halogen, oxo, CN, $C_{1-3}$alkyl, $C_{1-3}$haloalkyl, $C_{1-3}$alkoxy, $C_{1-3}$haloalkoxy, —$OR^{13}$, or —$NR^6R^7$;

$R^{12}$ is, independently at each occurrence, hydrogen, $C_{1-6}$alkyl or $C_{3-6}$cycloalkyl group, wherein any alkyl or cycloalkyl group is independently optionally substituted by halogen, oxo, CN, OH, $C_{1-3}$alkyl, $C_{1-3}$haloalkyl, $C_{1-3}$alkoxy, or $C_{1-3}$haloalkoxy;

$R^{13}$ is, independently at each occurrence, hydrogen, $C_{1-6}$alkyl, $C_{3-10}$cycloalkyl group, or a 3-11 membered saturated heterocyclic group, wherein any alkyl, cycloalkyl group, or other ring is independently optionally substituted by halogen, oxo, CN, OH, $C_{1-3}$alkyl, $C_{1-3}$haloalkyl, $C_{1-3}$alkoxy, $C_{1-3}$haloalkoxy, —$OR^{12}$, or —$NR^6R^7$; and $R^{16}$ is H, —Cl, —CN, or —$CH_3$.

Another aspect of the invention includes a compound of Formula II:

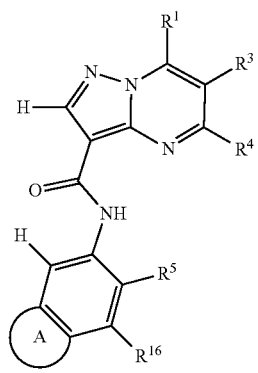

II or a stereoisomer or pharmaceutically acceptable salt thereof,
wherein:
$R^1$ is hydrogen or halogen;
$R^3$ is hydrogen, halogen, CN, OH, $C_{1-3}$alkyl, $C_{2-3}$alkenyl, $C_{3-7}$cycloalkyl group, $C_1$-$C_3$alkanoyl, —($C_0$-$C_3$alkyl)C(O)NR$^6$R$^7$, —($C_{2-3}$alkenyl)C(O)NR$^6$R$^7$, —S(O)$_{12}$NR$^6$R$^7$, —NR$^8$R$^9$, a 3-7 membered monocyclic saturated or partially saturated heterocyclic group, a 5-6 membered monocyclic heteroaryl ring, or a 5-6 membered monocyclic aryl ring,
wherein any alkyl, alkanoyl, or alkenyl is independently optionally substituted by halogen, oxo, CN, OH, $C_{1-3}$alkoxy, or $C_{1-3}$haloalkoxy, and
any cycloalkyl group or other ring is independently optionally substituted by halogen, oxo, CN, OH, $C_{1-3}$alkyl, or $C_{1-3}$haloalkyl;
$R^4$ is hydrogen, halogen, $C_{1-3}$alkyl, $C_{2-3}$alkenyl, —($C_0$-$C_3$alkyl)C(O)R$^{13}$—($C_2$-3alkenyl)C(O)NR$^{10}$R$^{11}$, —S(O)$_{1-2}$NR$^{10}$R$^{11}$, or —NR$^8$R$^9$;
wherein any alkyl or alkenyl is independently optionally substituted by halogen, oxo, CN, OH, $C_{1-3}$alkoxy, or $C_{1-3}$haloalkoxy;
$R^5$ is hydrogen, $C_{1-6}$alkyl, $C_{1-6}$alkoxy, $C_{3-10}$cycloalkyl group, —NR$^8$R$^9$, —O($C_{3-7}$cycloalkyl group), a 3-11 membered saturated or partially saturated heterocyclic group, or a 5-6 membered monocyclic heteroaryl ring,
wherein any alkyl or alkoxy is independently optionally substituted by halogen, oxo, CN, OH, $C_{1-3}$alkoxy, or $C_{1-3}$haloalkoxy, and
any cycloalkyl group or other ring is optionally substituted by halogen, oxo, CN, OH, —($C_{0-3}$alkyl)C(O)NR$^{10}$R$^{11}$, —OP(O)(OC$_{1-3}$alkyl)$_2$, or $C_{1-3}$alkyl optionally substituted by halogen, oxo, CN, OH, or —NR$^8$R$^9$;
A is a 3-11 membered heterocyclic group optionally substituted by halogen, oxo, CN, OH, $C_{1-6}$alkyl, $C_{3-6}$cycloalkyl group, —NR$^8$R$^9$, —NR$^{12}$C(O)R$^{13}$, —NR$^{12}$S(O)$_{1-2}$R$^{13}$, —C(O)NR$^{10}$R$^{11}$, —C(O)OR$^{13}$, or —S(O)$_{1-2}$NR$^{10}$R$^{11}$,
wherein any alkyl or cycloalkyl group is independently optionally substituted by halogen, oxo, CN, OH, $C_{1-3}$alkyl, $C_{1-3}$haloalkyl, $C_{1-3}$alkoxy, or $C_{1-3}$haloalkoxy; wherein when A is a 5-membered nitrogen containing heterocyclic group, the nitrogen atom is substituted;
$R^6$ and $R^7$ are, independently at each occurrence, hydrogen, $C_{1-3}$alkyl, or $C_{3-6}$cycloalkyl group,
wherein any alkyl or cycloalkyl group is independently optionally substituted by halogen, oxo, CN, OH, $C_{1-3}$alkyl, $C_{1-3}$haloalkyl, $C_{1-3}$alkoxy, or $C_{1-3}$haloalkoxy;
$R^8$, $R^9$, $R^{10}$ and $R^{11}$ are, independently at each occurrence, hydrogen, $C_{1-6}$alkyl, $C_{3-6}$cycloalkyl group, a 3-11 membered saturated heterocyclic group, —C(O)R$^{13}$, —C(O)OR$^{13}$, —C(O)NR$^6$R$^7$, or —S(O)$_{1-2}$R$^{13}$,
wherein any alkyl, cycloalkyl group or other ring is independently optionally substituted by halogen, oxo, CN, $C_{1-3}$alkyl, $C_{1-3}$haloalkyl, $C_{1-3}$alkoxy, $C_{1-3}$haloalkoxy, —OR$^{13}$, or —NR$^6$R$^7$;
$R^{12}$ is, independently at each occurrence, hydrogen, $C_{1-6}$alkyl or $C_{3-6}$cycloalkyl group,
wherein any alkyl or cycloalkyl group is independently optionally substituted by halogen, oxo, CN, OH, $C_{1-3}$alkyl, $C_{1-3}$haloalkyl, $C_{1-3}$alkoxy, or $C_{1-3}$haloalkoxy;
$R^{12}$ is, independently at each occurrence, hydrogen, $C_{1-6}$alkyl, $C_{3-10}$cycloalkyl group, or a 3-11 membered saturated heterocyclic group, wherein any alkyl, cycloalkyl group, or other ring is independently optionally substituted by halogen, oxo, CN, OH, $C_{1-3}$alkyl, $C_{1-3}$haloalkyl, $C_{1-3}$alkoxy, $C_{1-3}$haloalkoxy, —OR$^{12}$, or —NR$^6$R$^7$; and
$R^{16}$ is H, —Cl, —CN, or —CH$_3$.
In some embodiments, $R^1$ and $R^4$ are each hydrogen, and $R^3$ is hydrogen, OH, halogen, CH$_3$, CH$_2$OH, CH$_2$F, OCHF$_2$, CHF$_2$, CF$_3$, cyclopropyl, azetidinyl, CN, —C(O)CH$_3$, —C(O)NH$_2$, —C(O)NHCH$_3$, —NHCH$_3$, —SO$_2$—NH$_2$, or —SO$_2$—NHCH$_3$.
In some embodiments, $R^1$ and $R^4$ are each hydrogen, and $R^3$ is hydrogen, halogen, CH$_3$, CH$_2$F, CHF$_2$, CF$_3$, cyclopropyl, or —C(O)CH$_3$.
In some embodiments, $R^1$ and $R^4$ are each hydrogen, and $R^3$ is hydrogen, OH, CH$_3$, or CH$_2$OH.
In some embodiments, $R^1$ and $R^4$ are each hydrogen, and $R^3$ is Br, Cl, F, OCHF$_2$, CHF$_2$, or CF$_3$.
In some embodiments, $R^1$ and $R^4$ are each hydrogen, and $R^3$ is cyclopropyl, azetidinyl, CN, —C(O)CH$_3$, —C(O)NH$_2$, —C(O)NHCH$_3$, —NHCH$_3$, —SO$_2$—NH$_2$, or —SO$_2$—NHCH$_3$.
In some embodiments, $R^1$ and $R^3$ are each hydrogen, and $R^4$ is Cl, CHF$_2$, or a stereoisomer thereof.
In some embodiments, $R^1$ and $R^3$ are each hydrogen, and $R^4$ is hydrogen or CH$_3$.
In some embodiments, $R^1$, $R^4$ and $R^3$ are each hydrogen.
In some embodiments, $R^{16}$ is H. In some embodiments, $R^{16}$ is —Cl, —CN, or —CH$_3$.
In some embodiments, $R^5$ is a 3-11 membered saturated or partially saturated heterocyclic group optionally substituted by halogen; oxo; CN; OH; $C_{1-6}$alkoxy; —NR$^8$R$^9$; —C(O)(C$_{1-3}$alkyl); —(C$_{0-3}$alkyl)C(O)NR$^{10}$R$^{11}$; —S(O)$_{1-2}$NR$^8$R$^9$; —OP(O)(OC$_{1-3}$alkyl)$_2$; $C_{3-10}$cycloalkyl group optionally substituted with OH or halogen; a 3-11 membered saturated or partially saturated heterocyclic group optionally substituted with oxo or $C_{1-3}$alkyl; a 5-6 membered monocyclic heteroaryl ring optionally substituted by halogen, oxo, CN, OH, $C_{1-3}$alkyl, or $C_{1-3}$haloalkyl; or $C_{1-4}$alkyl optionally substituted by halogen, oxo, CN, OH, —O—$C_{1-3}$ alkyl, —S—$C_{1-3}$alkyl, —SO$_2$—$C_{1-3}$alkyl, —NR$^8$R$^9$, —C(O)NR$^8$R$^9$, phenyl, $C_{3-10}$cycloalkyl, a 3-11 membered saturated or partially saturated heterocyclic group optionally substituted with oxo or $C_{1-3}$ alkyl, or a 5-6 membered monocyclic heteroaryl ring optionally substituted with oxo, halogen, or $C_{1-3}$alkyl.

In some embodiments, $R^5$ is a 3-11 membered saturated or partially saturated heterocyclic group optionally substituted by halogen, oxo, CN, OH, —($C_{0-3}$alkyl)C(O)NR$^{10}$R$^{11}$, —OP(O)(O$C_{1-3}$alkyl)$_2$, or $C_{1-3}$alkyl optionally substituted by halogen, oxo, CN, OH, or —NR$^8$R$^9$. In some embodiments, $R^5$ is an N-linked 3-11 membered saturated heterocyclic group optionally substituted by halogen, oxo, CN, OH, —($C_{0-3}$alkyl)C(O)NR$^{10}$R$^{11}$, —OP(O)(O$C_{1-3}$alkyl)$_2$, or $C_{1-3}$alkyl optionally substituted by halogen, oxo, CN, OH, or —NR$^8$R$^9$.

In some embodiments, the ring heteroatoms of the 3-11 membered saturated or partially saturated heterocyclic group of $R^5$ are selected from nitrogen and oxygen.

In some embodiments, $R^5$ is piperidinyl, piperazinyl, or morpholinyl, wherein any $R^5$ is optionally substituted by halogen; oxo; CN; OH; $C_{1-6}$alkoxy; —NR$^8$R$^9$; —C(O)(C$_{1-3}$alkyl); —(C$_{0-3}$alkyl)C(O)NR$^{10}$R$^{11}$; —S(O)$_{1-2}$NR$^8$R$^9$; —OP(O)(OC$_{1-3}$alkyl)$_2$; $C_{3-10}$cycloalkyl group optionally substituted with OH or halogen; a 3-11 membered saturated or partially saturated heterocyclic group optionally substituted with oxo or $C_{1-3}$alkyl; a 5-6 membered monocyclic heteroaryl ring optionally substituted by halogen, oxo, CN, OH, $C_{1-3}$alkyl, or $C_{1-3}$haloalkyl; or $C_{1-4}$alkyl optionally substituted by halogen, oxo, CN, OH, —O—$C_{1-3}$ alkyl, —S—$C_{1-3}$alkyl, —SO$_2$—$C_{1-3}$alkyl, —NR$^8$R$^9$, —C(O)NR$^8$R$^9$, phenyl, $C_{3-10}$cycloalkyl, a 3-11 membered saturated or partially saturated heterocyclic group optionally substituted with oxo or $C_{1-3}$ alkyl, or a 5-6 membered monocyclic heteroaryl ring optionally substituted with oxo, halogen, or $C_{1-3}$alkyl.

In some embodiments, $R^5$ is N-linked piperidinyl, N-linked piperazinyl, or N-linked morpholinyl, wherein any $R^5$ is optionally substituted by halogen, oxo, CN, OH, or $C_{1-3}$alkyl optionally substituted by halogen, oxo, CN, or OH.

In some embodiments, $R^5$ is:
—CH$_2$CH$_3$, —C(CH$_3$)$_2$, Cl, CN, cyclopropyl, —C(O)NH$_2$, —OCH$_3$, —OCH$_2$CF$_3$, —OCH$_2$CHF$_2$, —CF$_3$, —CHF$_2$, —OCF$_3$, —OCHF$_2$, —NHCH$_3$, —N(CH$_3$)$_2$,

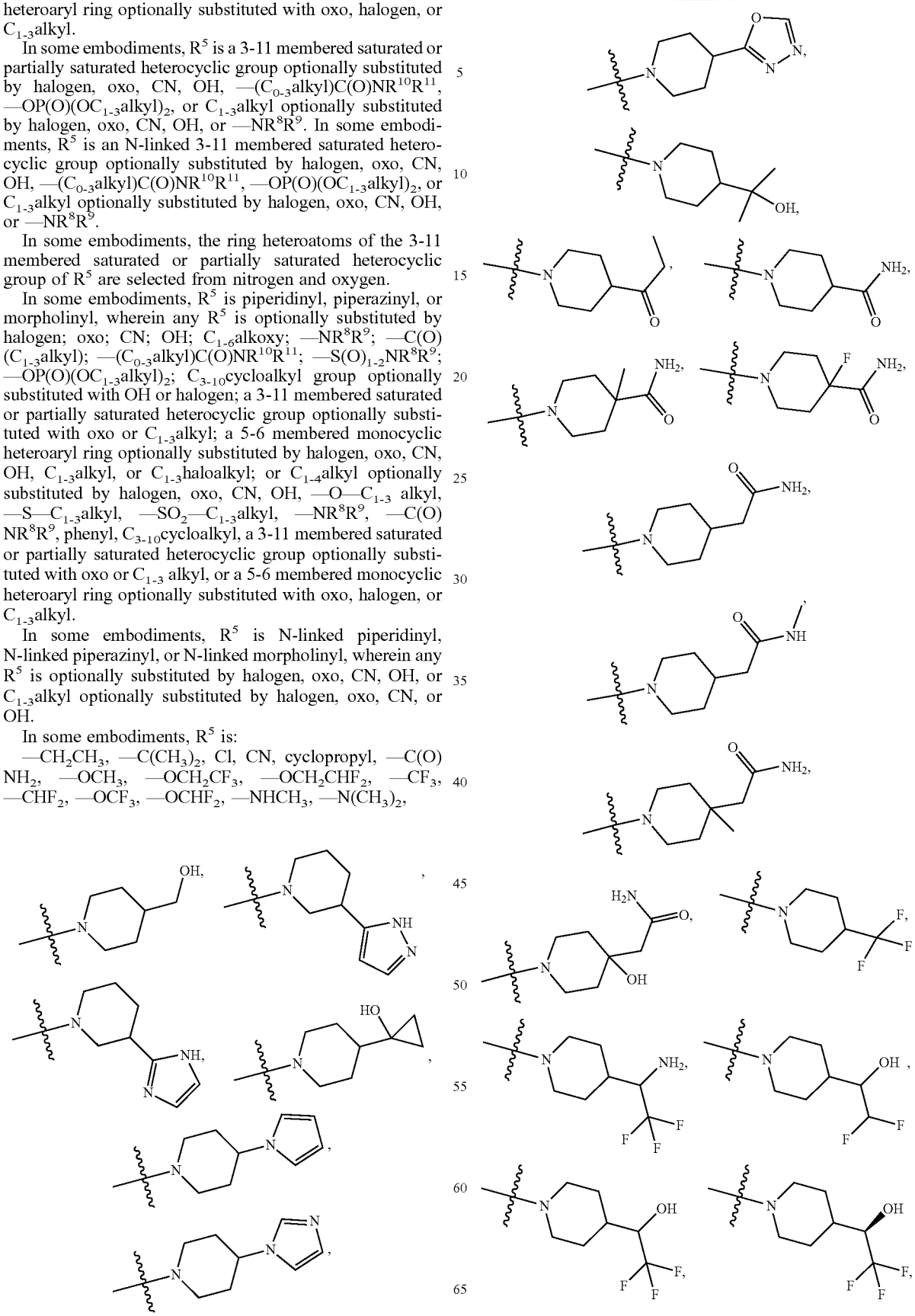

29
-continued
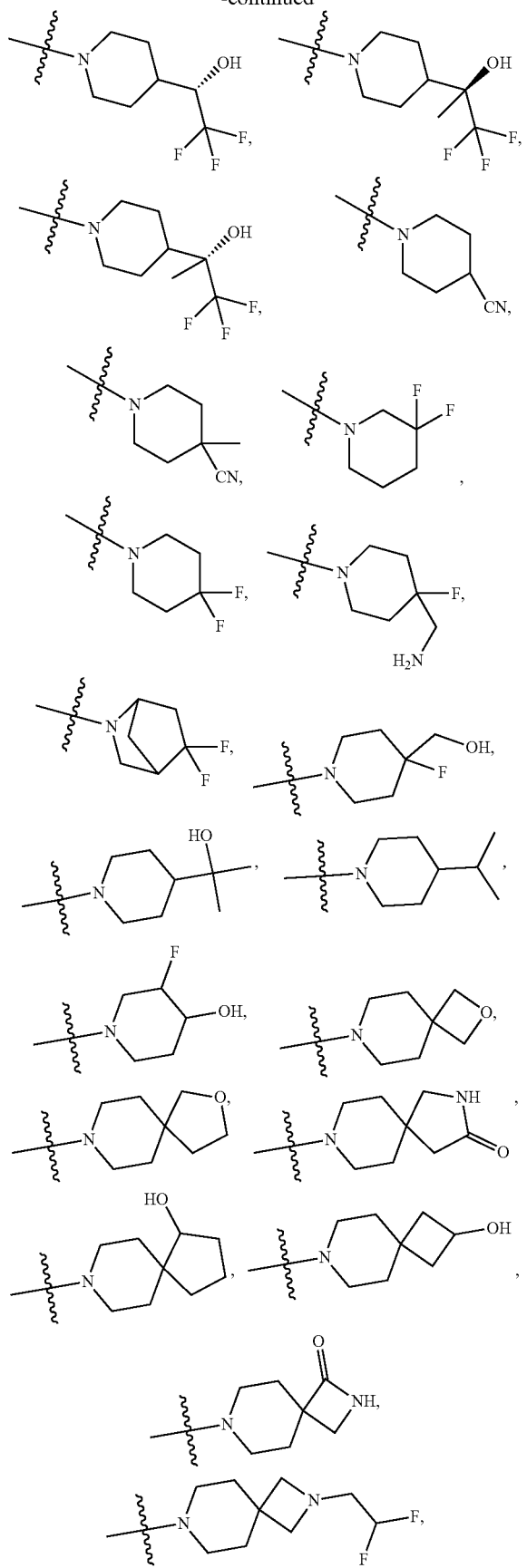
30
-continued
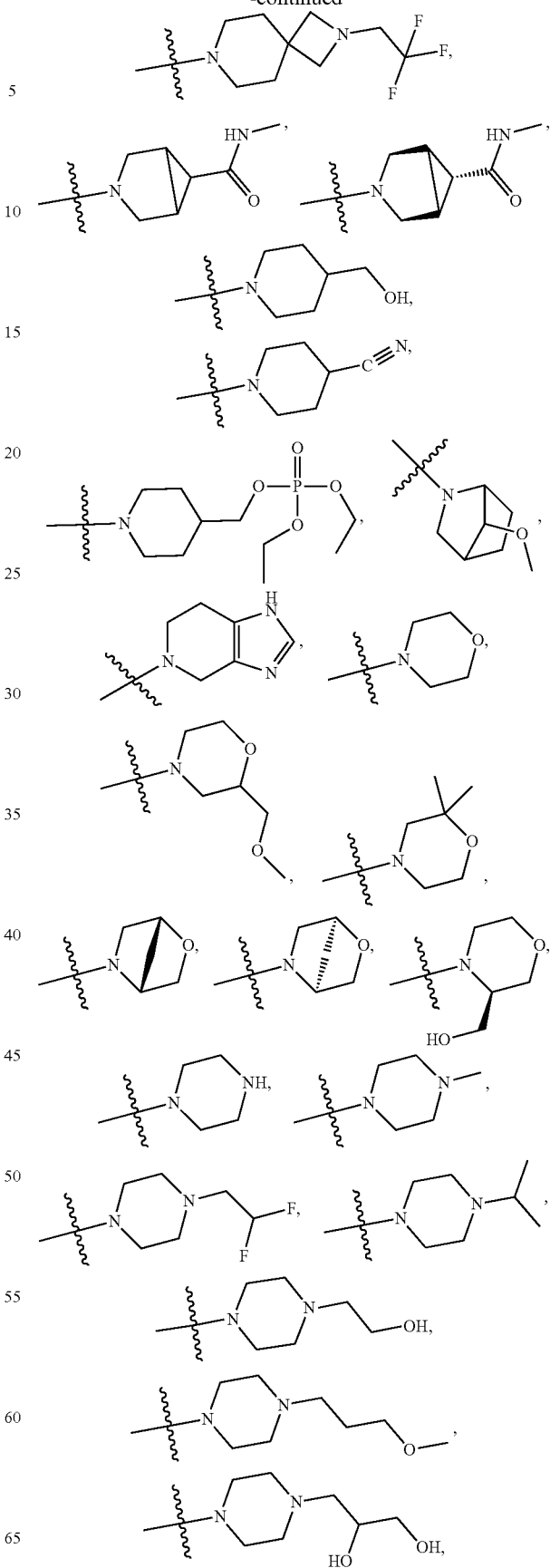

-continued
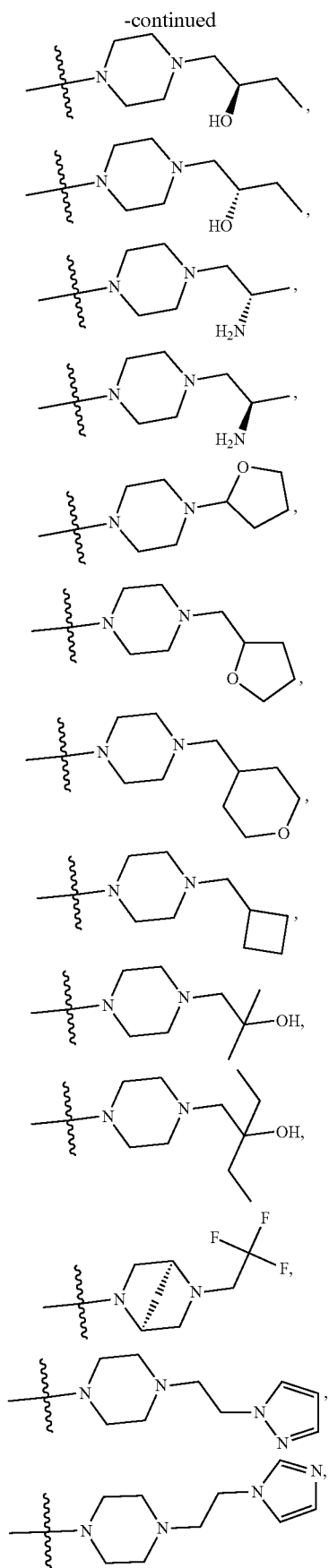
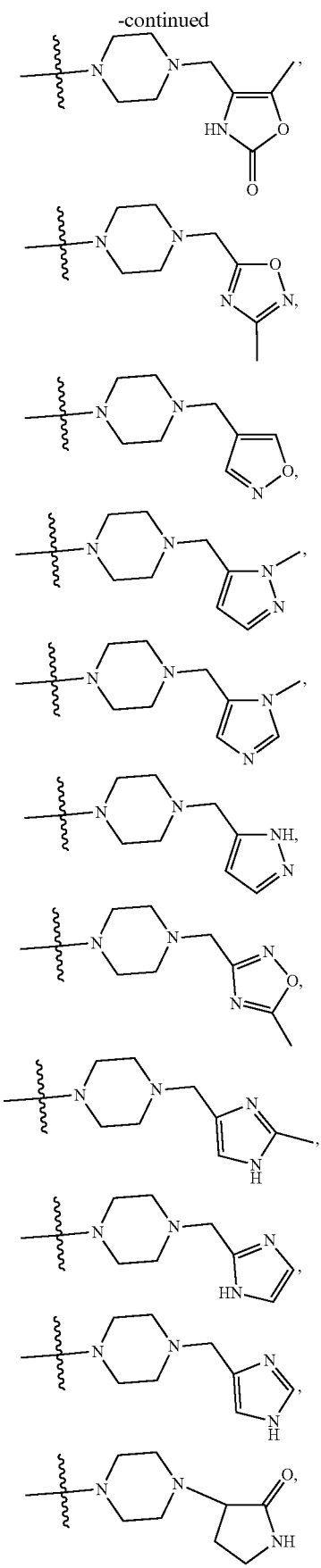

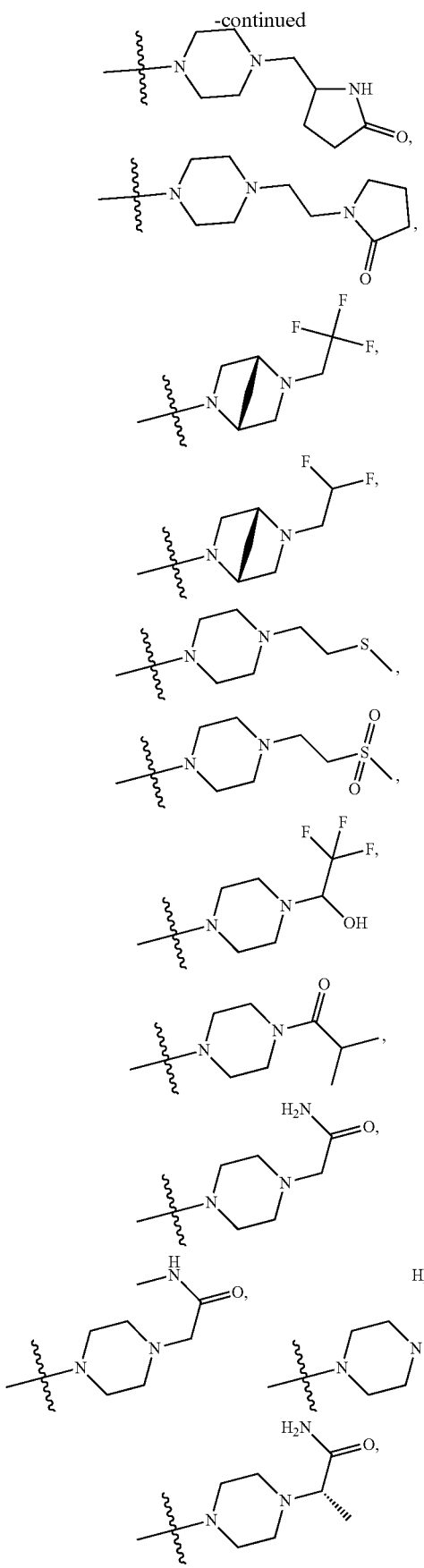
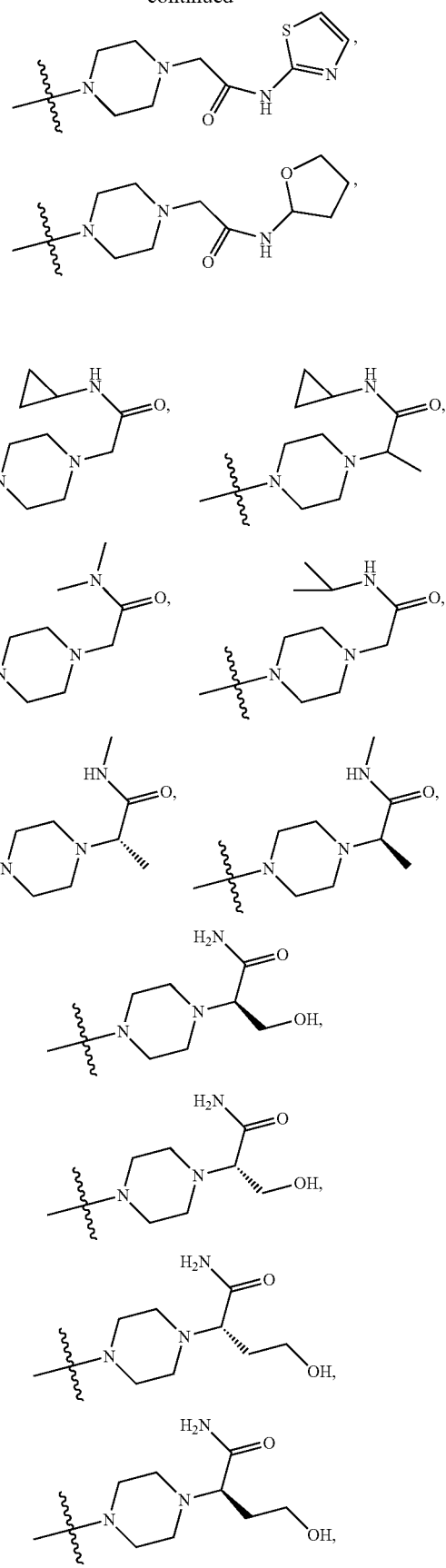

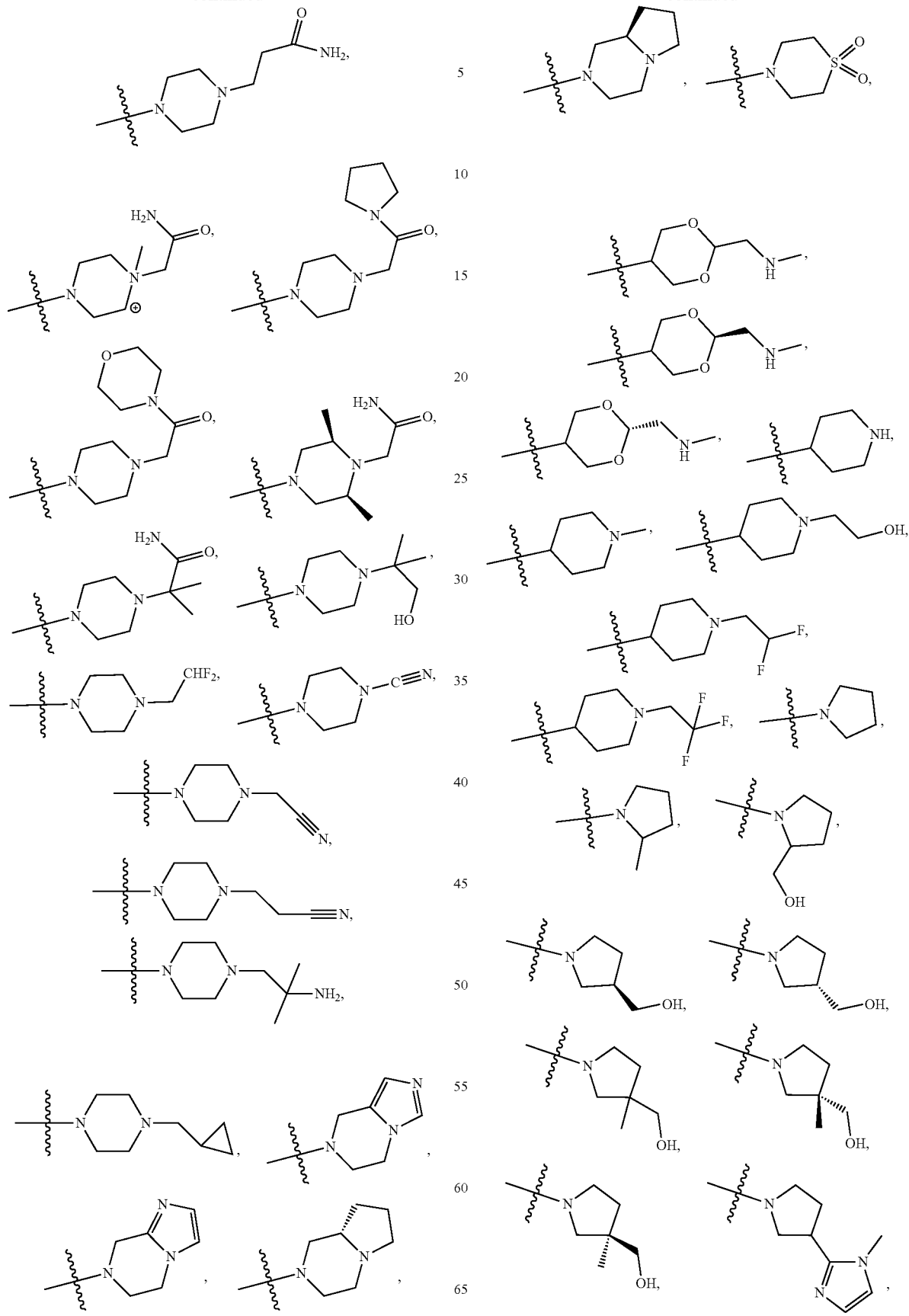

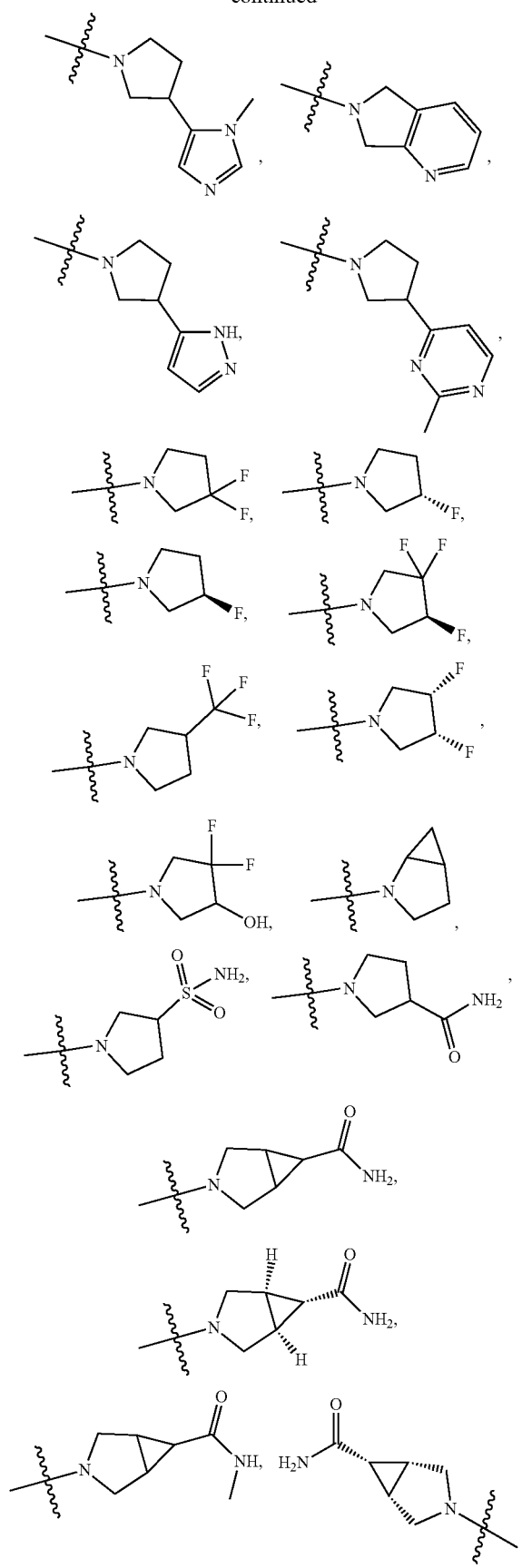
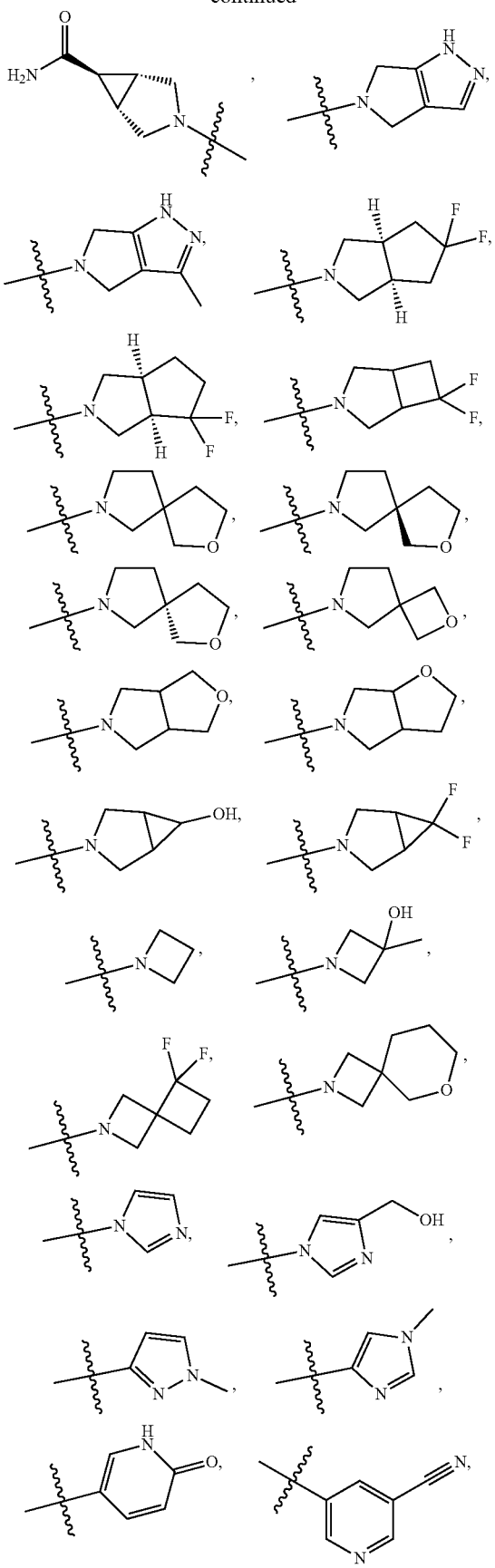

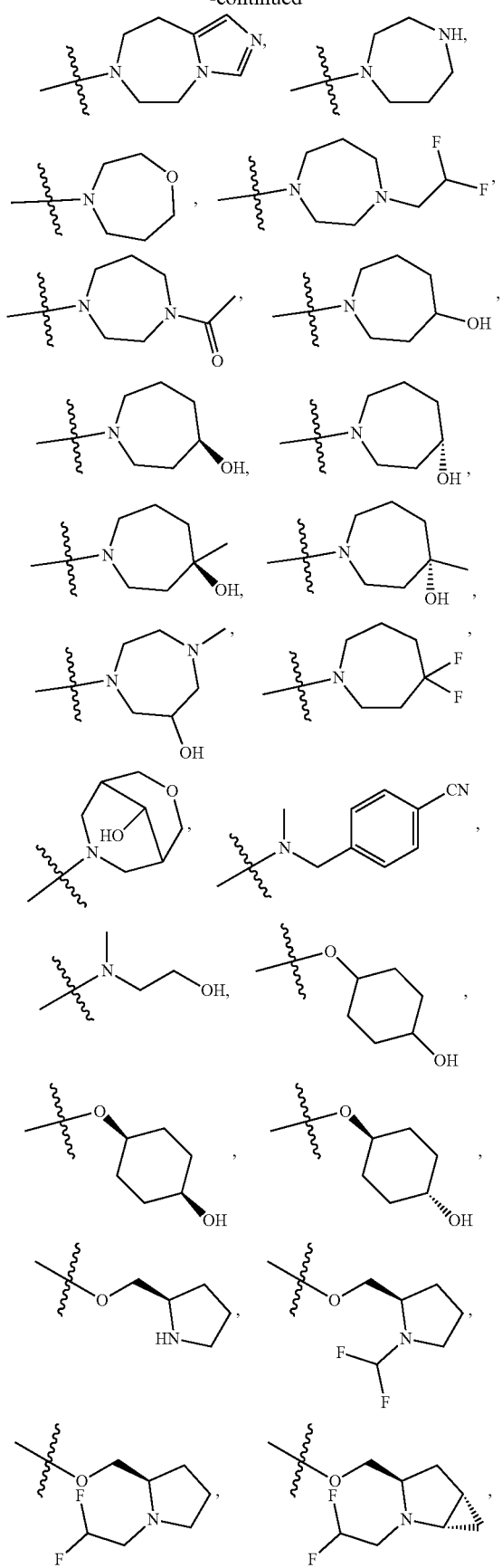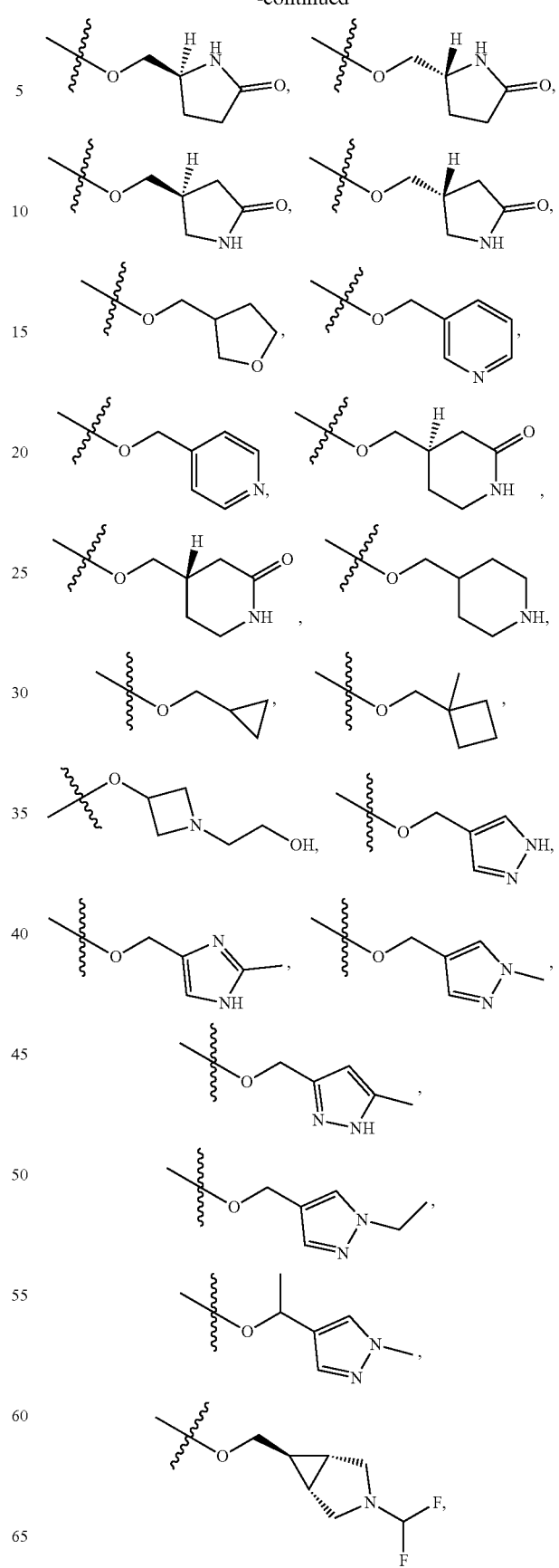

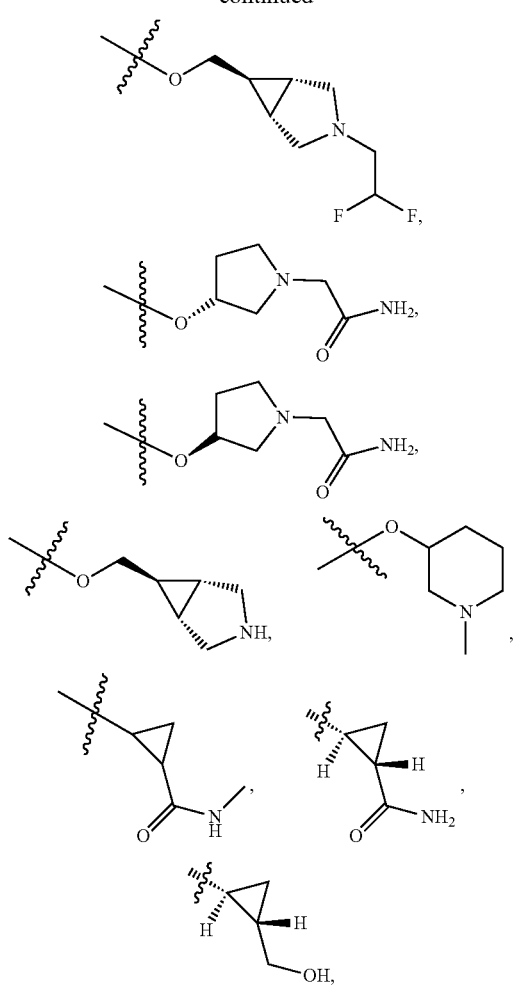
or a stereoisomer thereof.
In some embodiments, $R^5$ is:
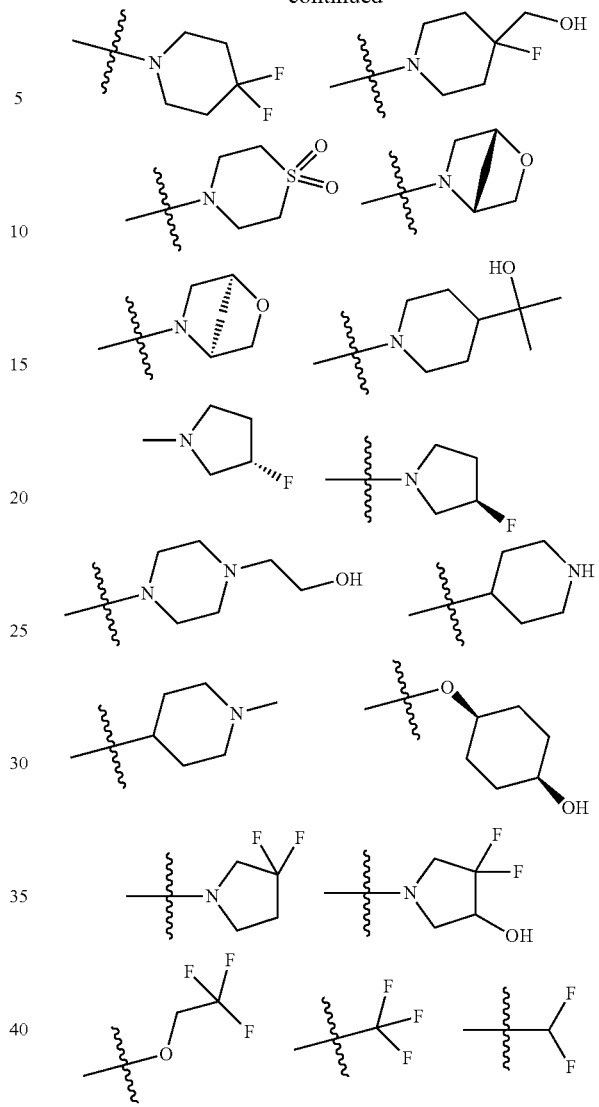
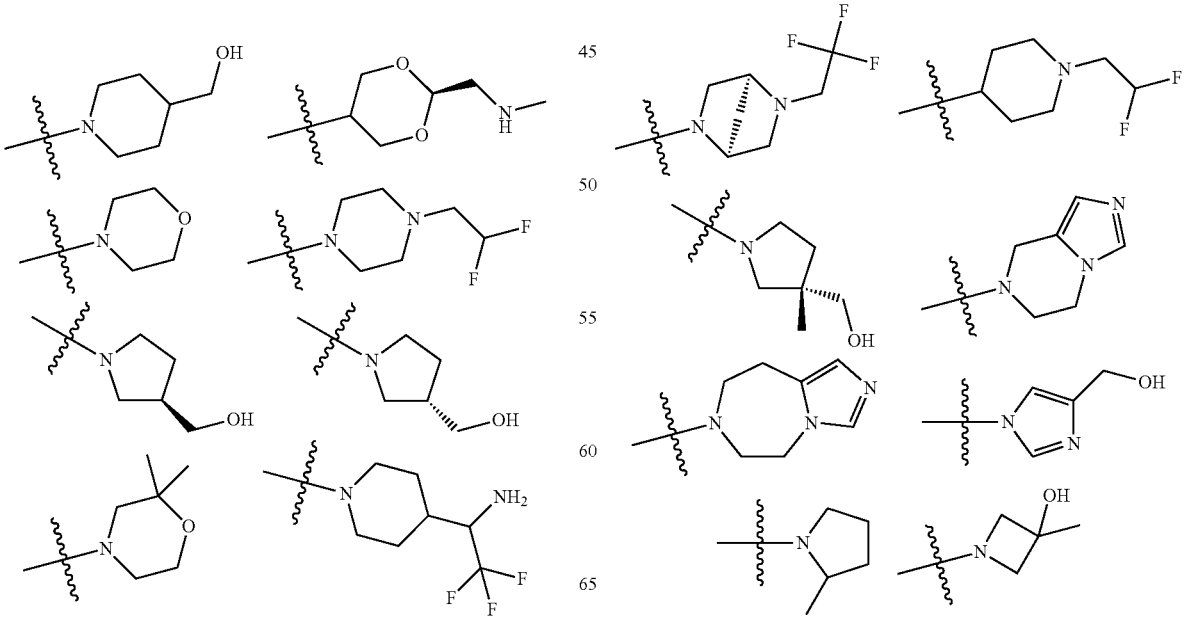

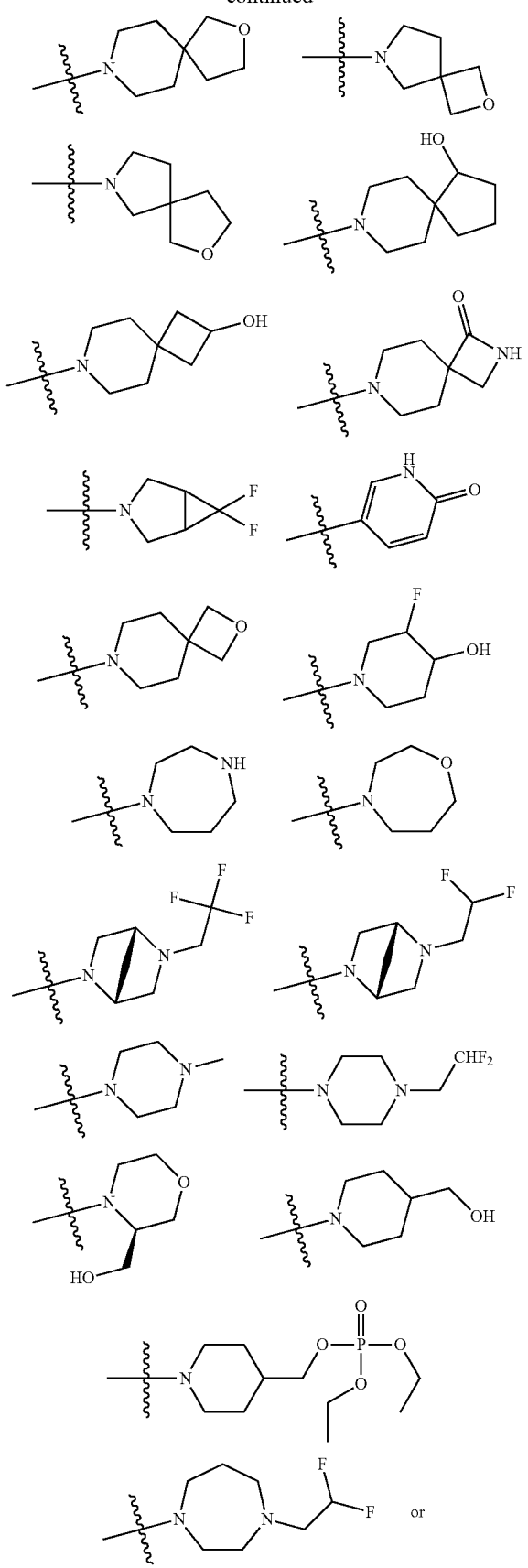
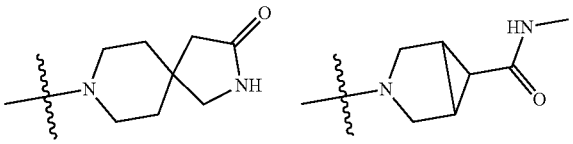
or a stereoisomer thereof.
In some embodiments, R⁵ is
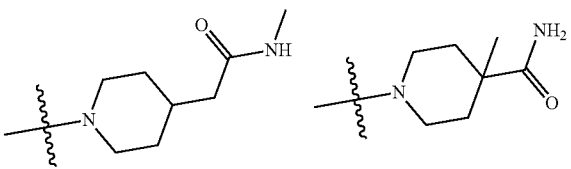
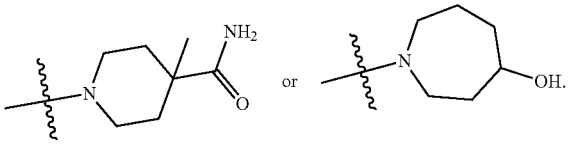
As previously noted, when A is a 5-membered nitrogen containing heterocyclic ring, the nitrogen atom is substituted. In embodiments wherein A comprises one or more nitrogen atoms, e.g., 2, 3, or more nitrogen atoms, each nitrogen atom is substituted. More particularly, in some embodiments, the compound is not
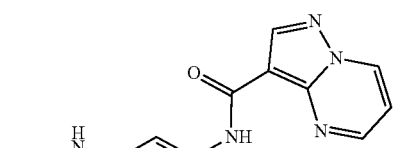
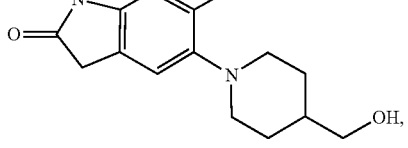
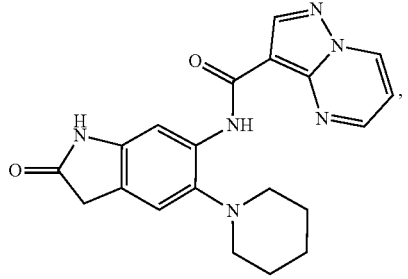

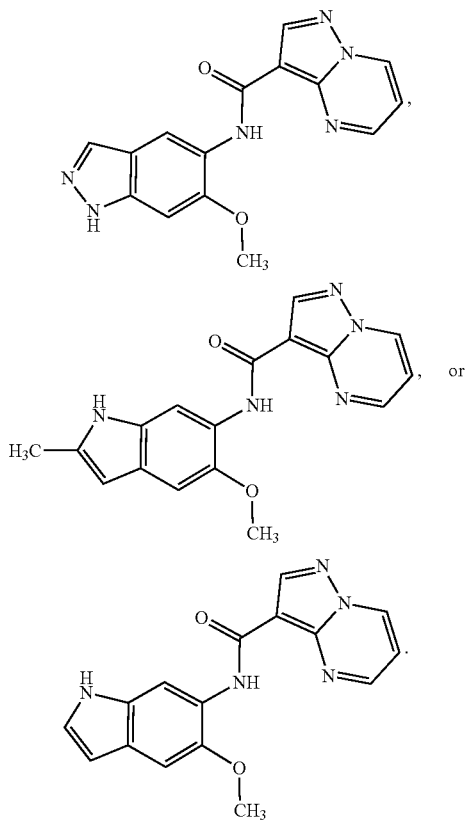

In some embodiments, A is a 3-11 membered, non-aromatic heterocyclic group.

In some embodiments, A is a 3-11 membered heterocyclic group comprising at least one oxygen as a ring atom and is optionally substituted by halogen, oxo, CN, OH, C$_{1-6}$alkyl, C$_{3-6}$cycloalkyl group, —NR$^8$R$^9$, —NR$^{12}$C(O)R$^{13}$, —NR$^{12}$S(O)$_{1-2}$R$^{13}$, —C(O)NR$^{10}$R$^{11}$, —C(O)OR$^{13}$, or —S(O)$_{1-2}$NR$^{10}$R$^{11}$, wherein any alkyl or cycloalkyl group is independently optionally substituted by halogen, oxo, CN, OH, C$_{1-3}$alkyl, C$_{1-3}$haloalkyl, C$_{1-3}$alkoxy, or C$_{1-3}$haloalkoxy.

In some embodiments, the following portion of Formula 0, Formula I, or Formula II,

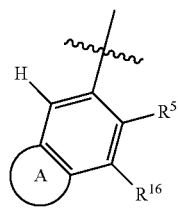

is further defined as 0-A, I-A, or II-A:

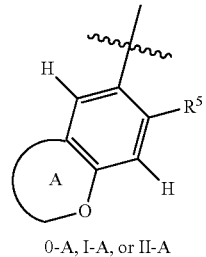

0-A, I-A, or II-A wherein A is a 5 or 6 membered ring optionally containing an additional ring heteroatom and wherein A is optionally substituted by halogen, oxo, CN, OH, C$_{1-6}$alkyl, C$_{3-6}$cycloalkyl group, —NR$^8$R$^9$, —NR$^{12}$C(O)R$^{13}$, —NR$^{12}$S(O)$_{12}$R$^{13}$, —C(O)NR$^{10}$R$^{11}$, —C(O)OR$^{13}$, or —S(O)$_{1-2}$NR$^{10}$R$^{11}$, wherein any alkyl or cycloalkyl group is independently optionally substituted by halogen, oxo, CN, OH, C$_{1-3}$alkyl, C$_{1-3}$haloalkyl, C$_{1-3}$alkoxy, or C$_{1-3}$haloalkoxy.

In some embodiments, 0-A, I-A, or II-A is further defined as 0-B, I—B, or II-B:

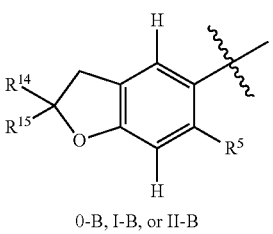

0-B, I-B, or II-B wherein R$^{10}$ and R$^{11}$ are each selected from halogen, oxo, CN, OH, C$_{1-6}$alkyl, C$_{3-6}$cycloalkyl group, —NR$^8$R$^9$, —NR$^{12}$C(O)R$^{13}$, —NR$^{12}$S(O)$_{1-2}$R$^{13}$, —C(O)NR$^{10}$R$^{11}$, —C(O)OR$^{13}$, and —S(O)$_{1-2}$NR$_{10}$R$^{11}$, wherein any alkyl or cycloalkyl group is independently optionally substituted by halogen, oxo, CN, OH, C$_{1-3}$alkyl, C$_{1-3}$haloalkyl, C$_{1-3}$alkoxy, or C$_{1-3}$haloalkoxy; or R$^{10}$ and R$^{11}$ together form a C$_{3-6}$cycloalkyl group or saturated or partially saturated 3-6 membered heterocyclic group, wherein any cycloalkyl group or other ring is independently optionally substituted by halogen, oxo, CN, OH, C$_{1-3}$alkyl, C$_{1-3}$haloalkyl, C$_{1-3}$alkoxy, or C$_{1-3}$haloalkoxy.

In some embodiments, A does not contain oxygen as a ring atom and is optionally substituted by halogen, oxo, CN, OH, C$_{1-6}$alkyl, C$_{3-6}$cycloalkyl group, —NR$^8$R$^9$, —NR$^{12}$C(O)R$^{13}$, —NR$^{12}$S(O)$_{1-2}$R$^{13}$, —C(O)NR$^{10}$R$^{11}$, —C(O)OR$^{13}$, or —S(O)$_{1-2}$NR$^{10}$R$^{11}$, wherein any alkyl or cycloalkyl group is independently optionally substituted by halogen, oxo, CN, OH, C$_{1-3}$alkyl, C$_{1-3}$haloalkyl, C$_{1-3}$alkoxy, or C$_{1-3}$haloalkoxy.

In some embodiments, the following portion of Formula 0, Formula I, or Formula II,

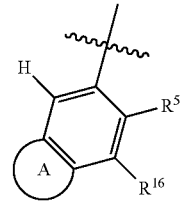

is further defined as 0-C, I—C, or II-C:

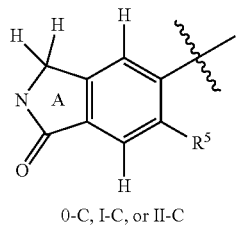

0-C, I-C, or II-C wherein the nitrogen comprises a substituent as defined herein.

In some embodiments, the following portion of Formula 0, Formula I, or Formula II,

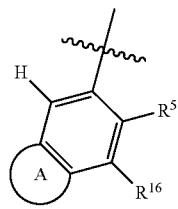

is further defined as 0-C, I—C, or II-C:

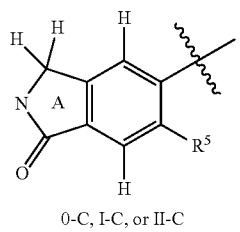

0-C, I-C, or II-C wherein the nitrogen of A is substituted by $C_{1-6}$alkyl or $C_{3-6}$cycloalkyl group, wherein any alkyl or cycloalkyl group is independently optionally substituted by halogen, oxo, CN, OH, $C_{1-3}$alkyl, $C_{1-3}$haloalkyl, $C_{1-3}$alkoxy, or $C_{1-3}$haloalkoxy.

In some embodiments, the following portion of Formula 0, Formula I, or Formula II,

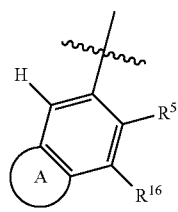

is selected from

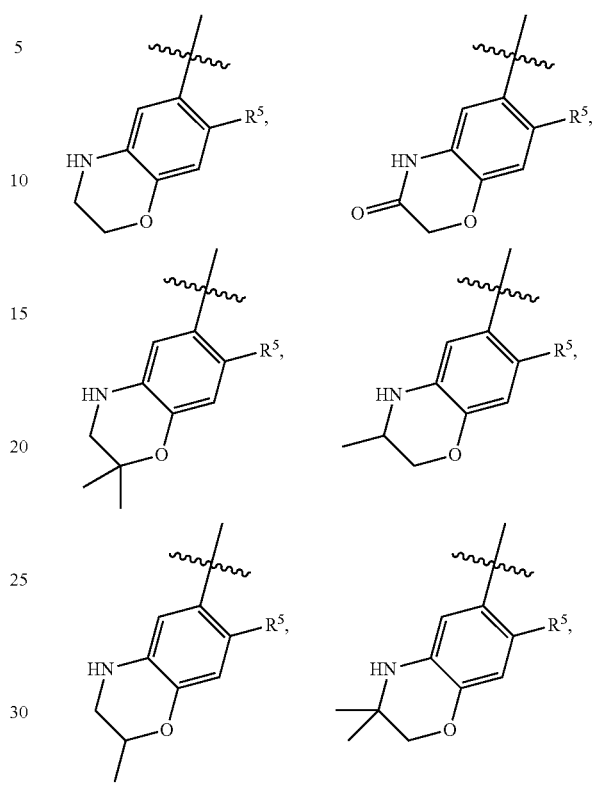

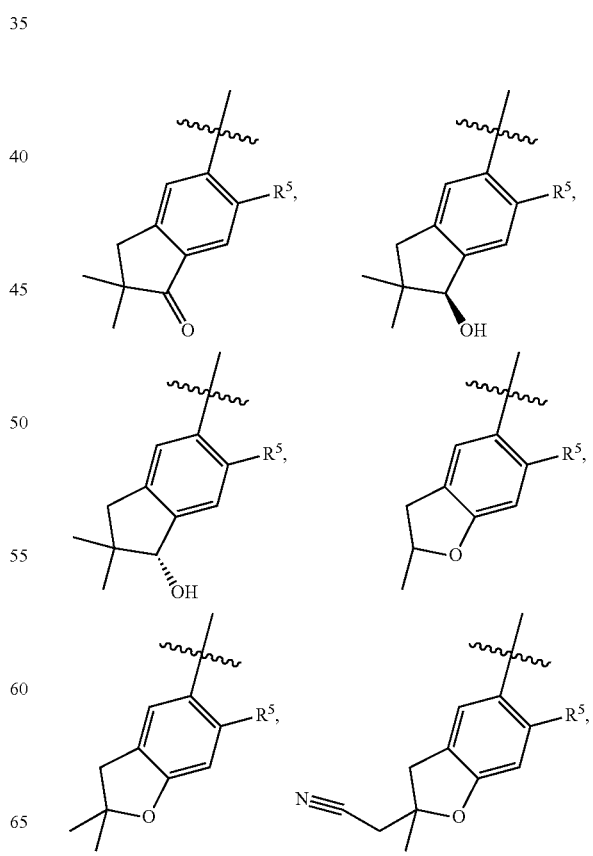

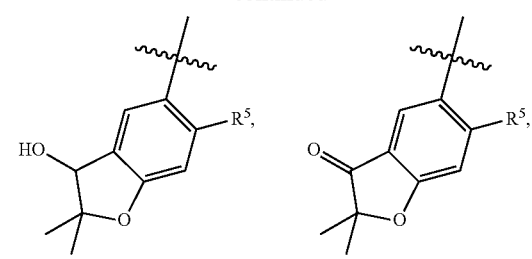
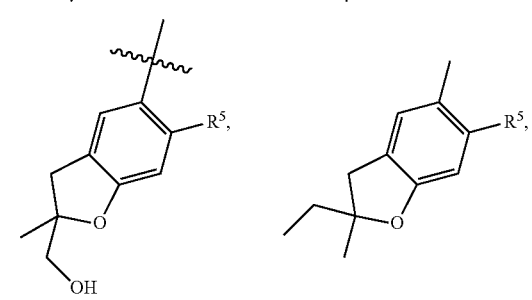
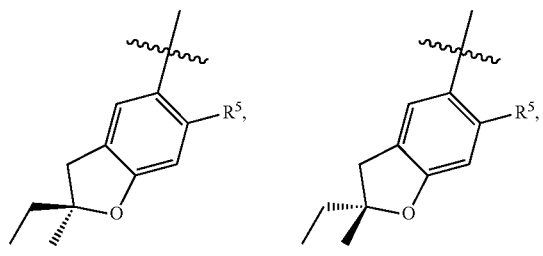
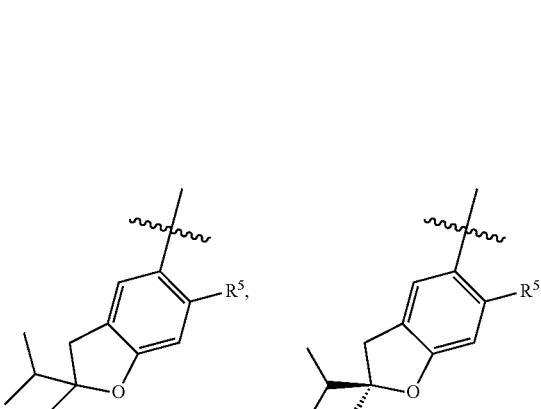
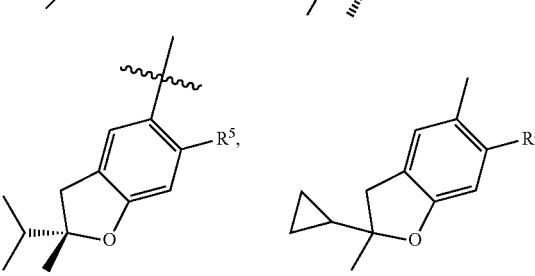
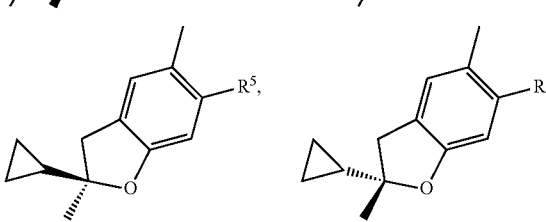
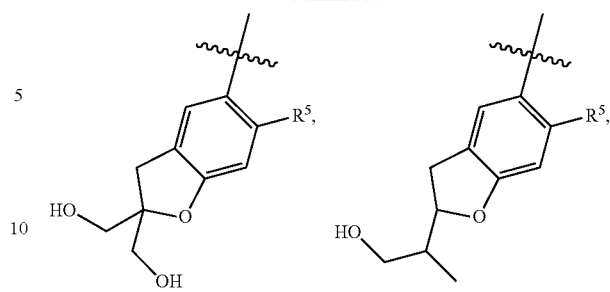
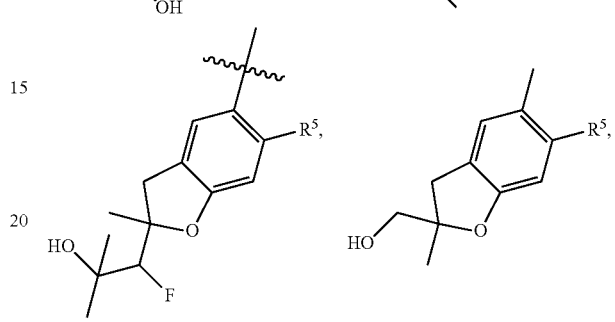
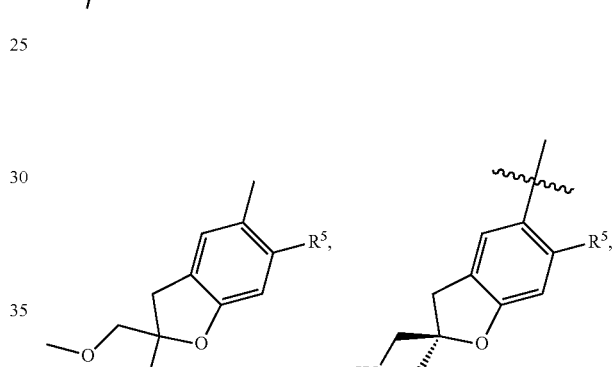
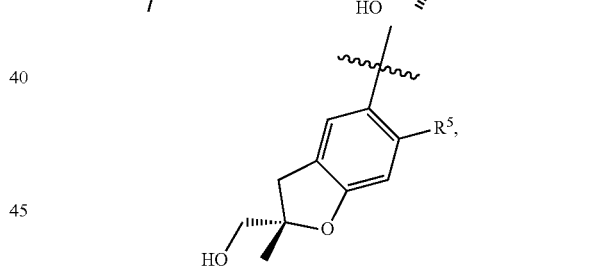
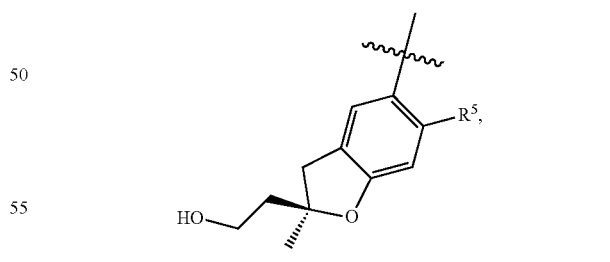
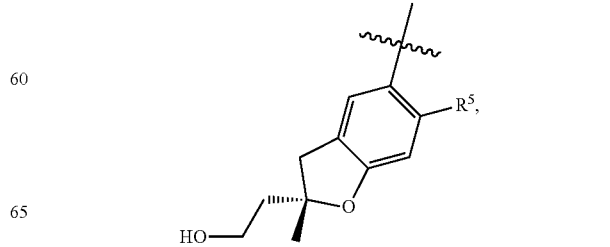

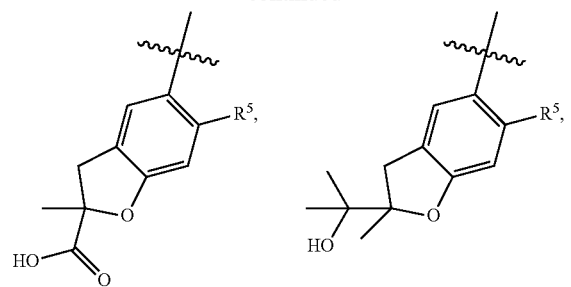
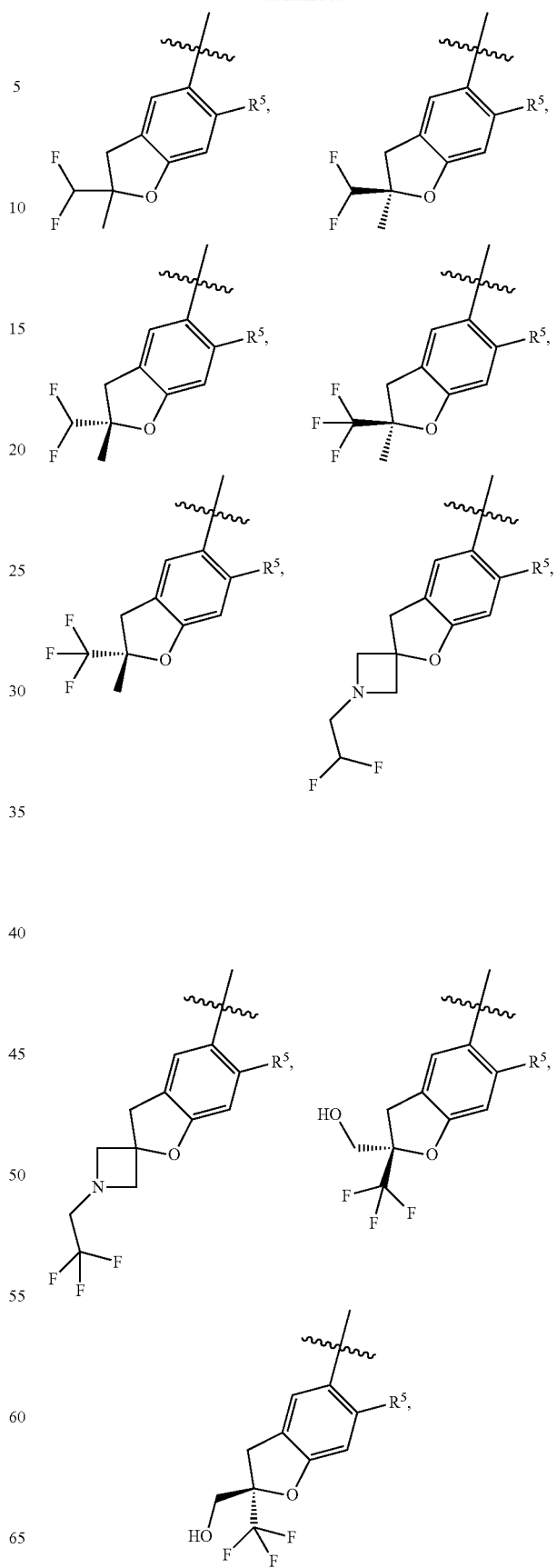

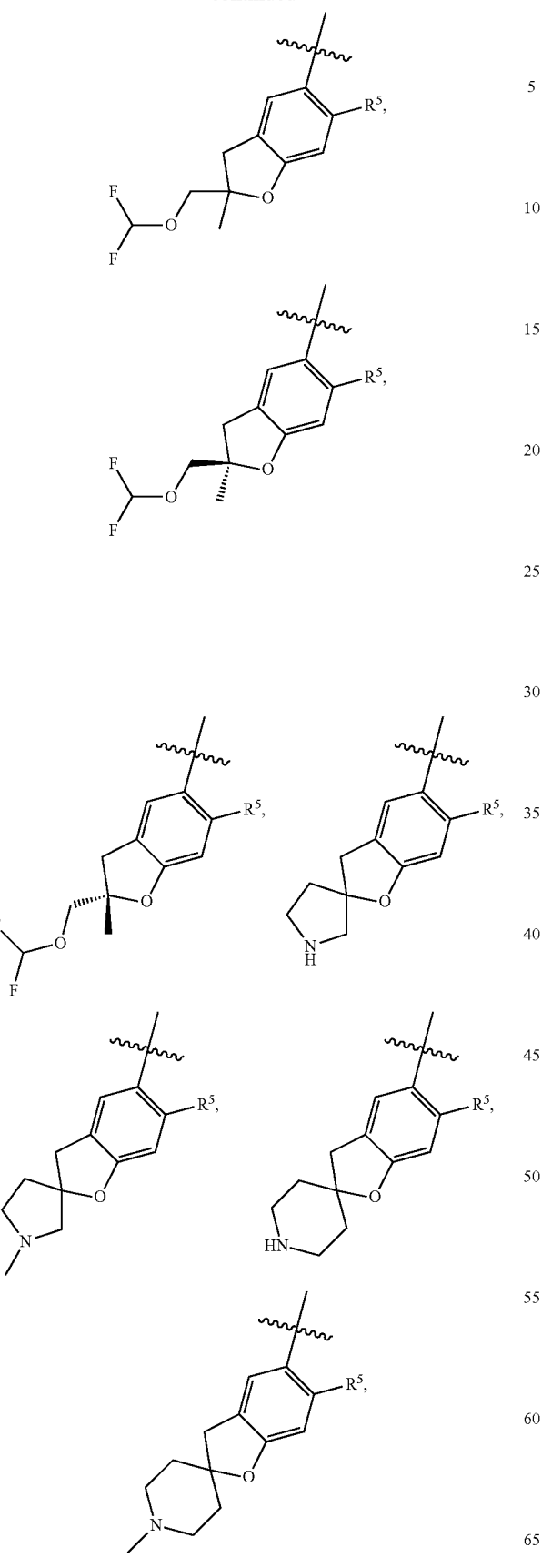
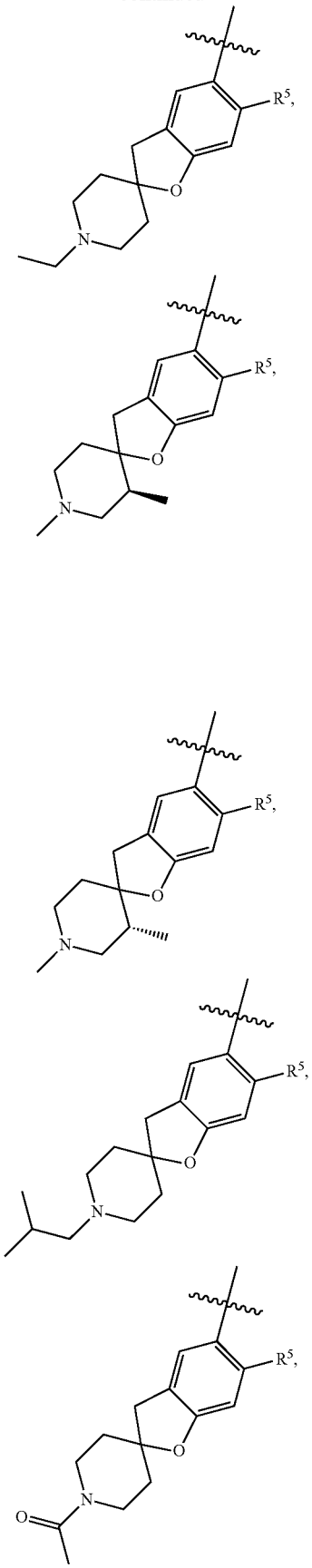

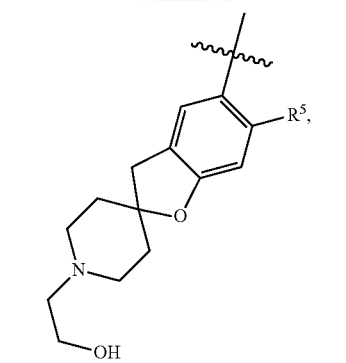
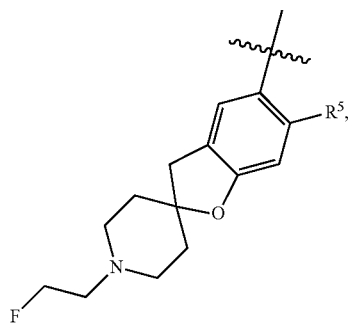
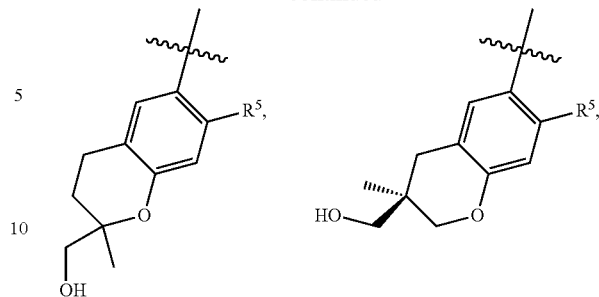
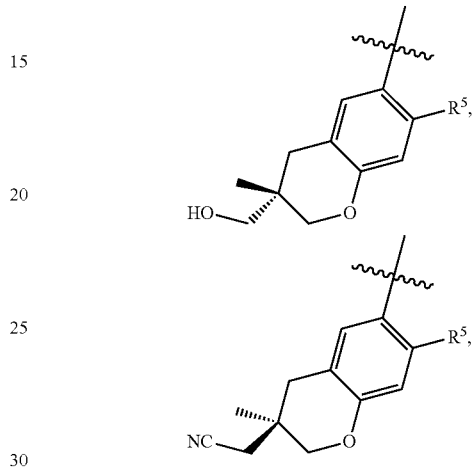
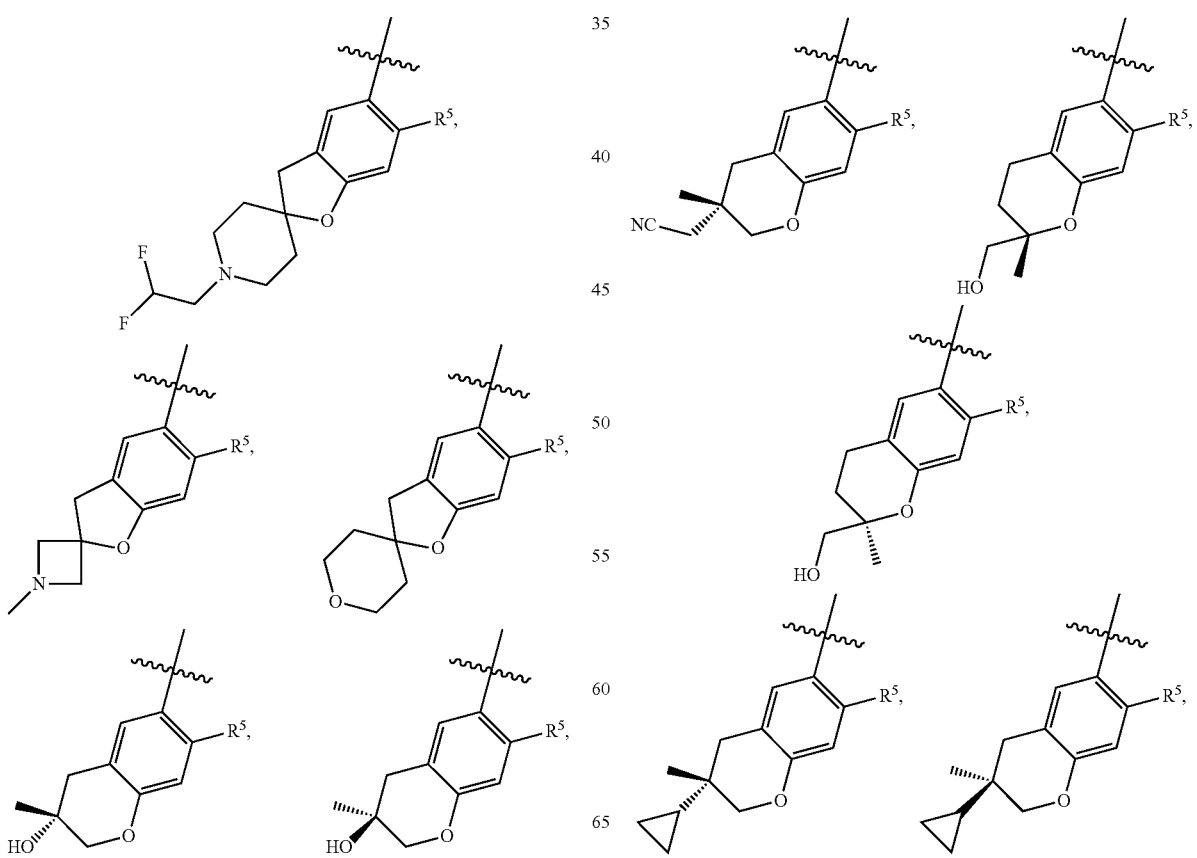

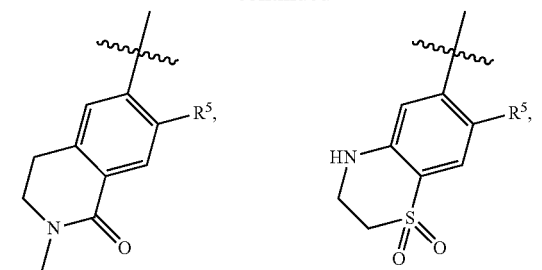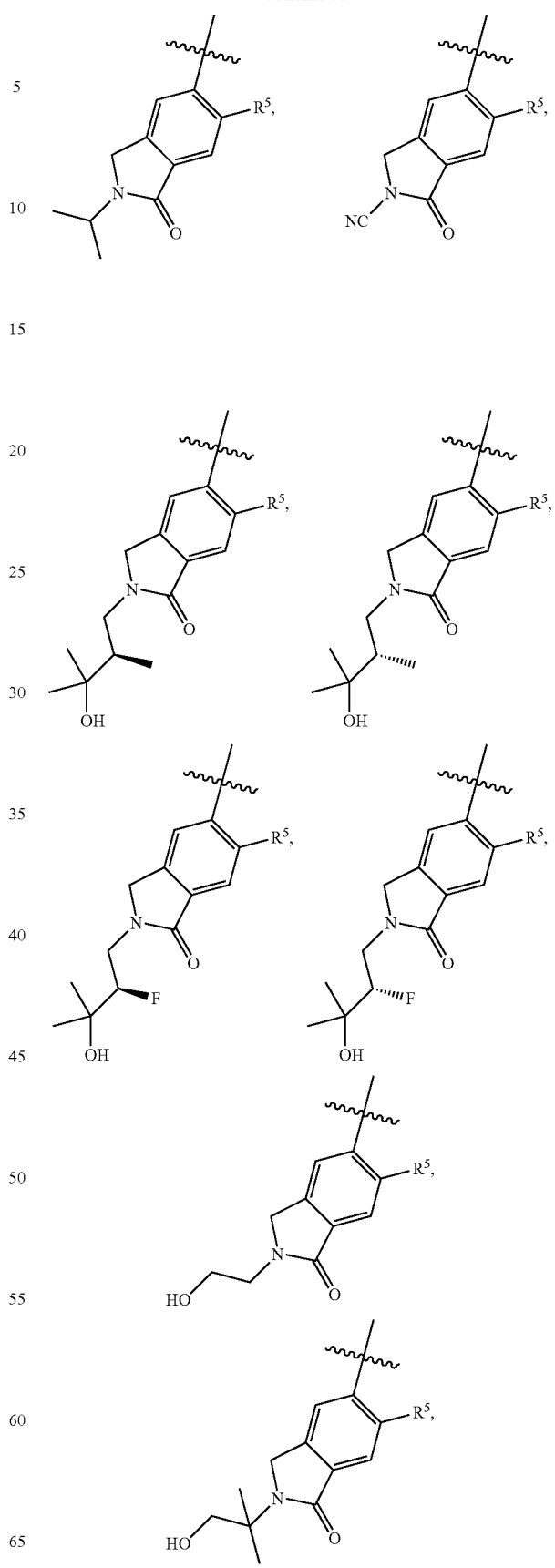

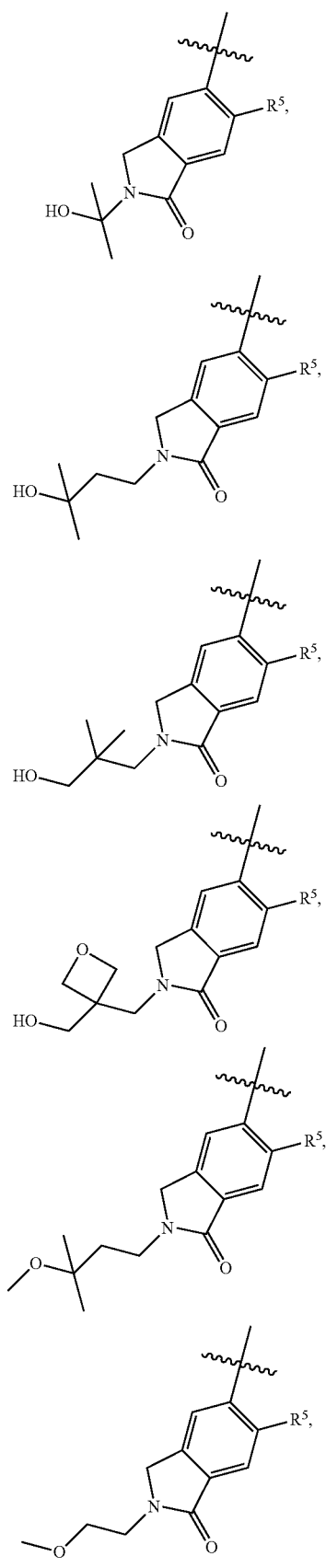
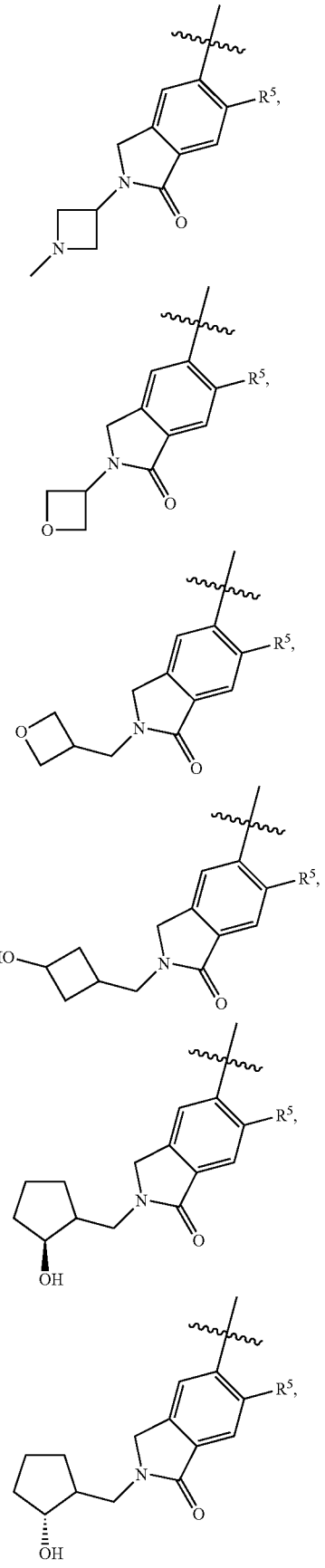

61
-continued
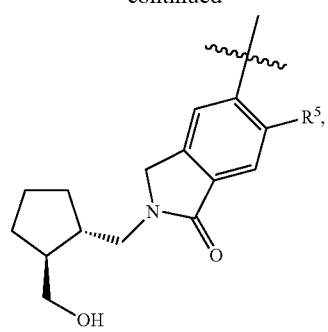
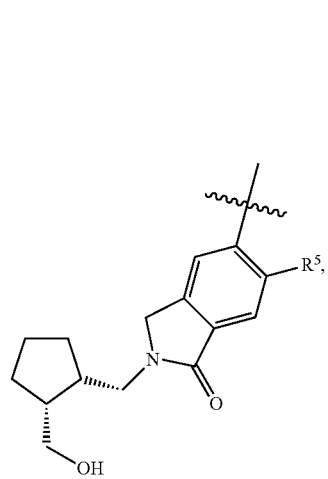
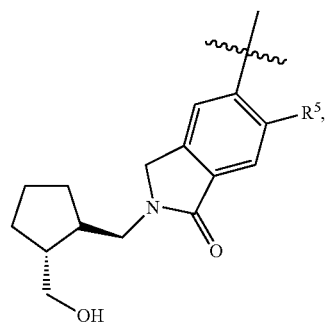
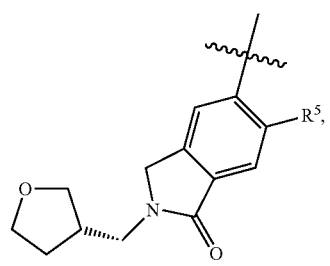
62
-continued
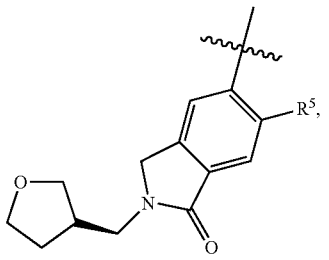
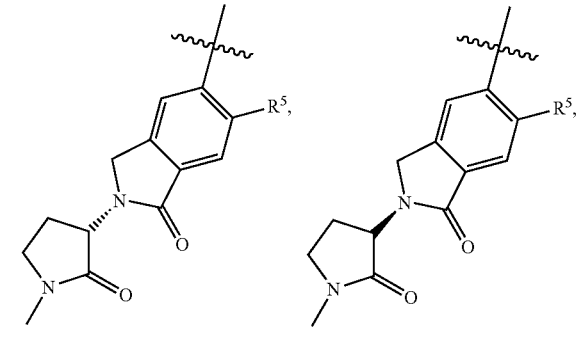
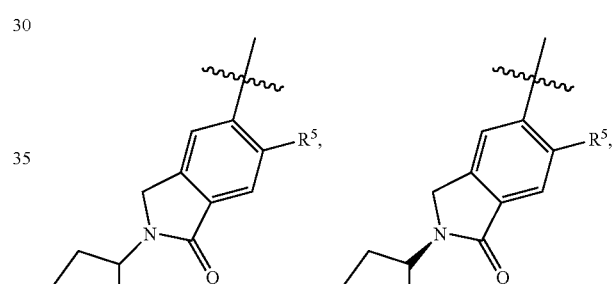
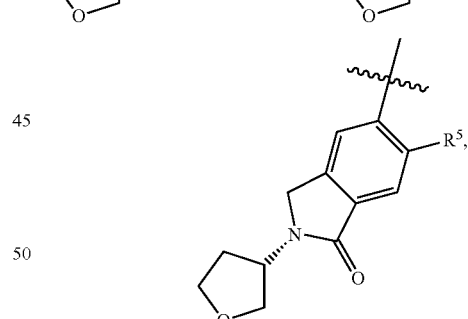
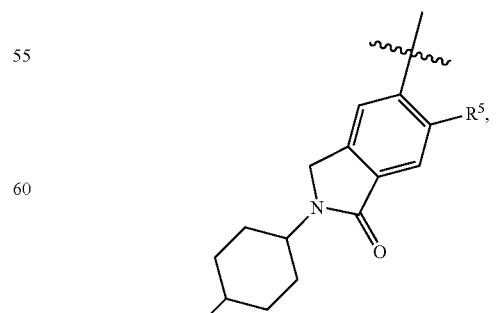

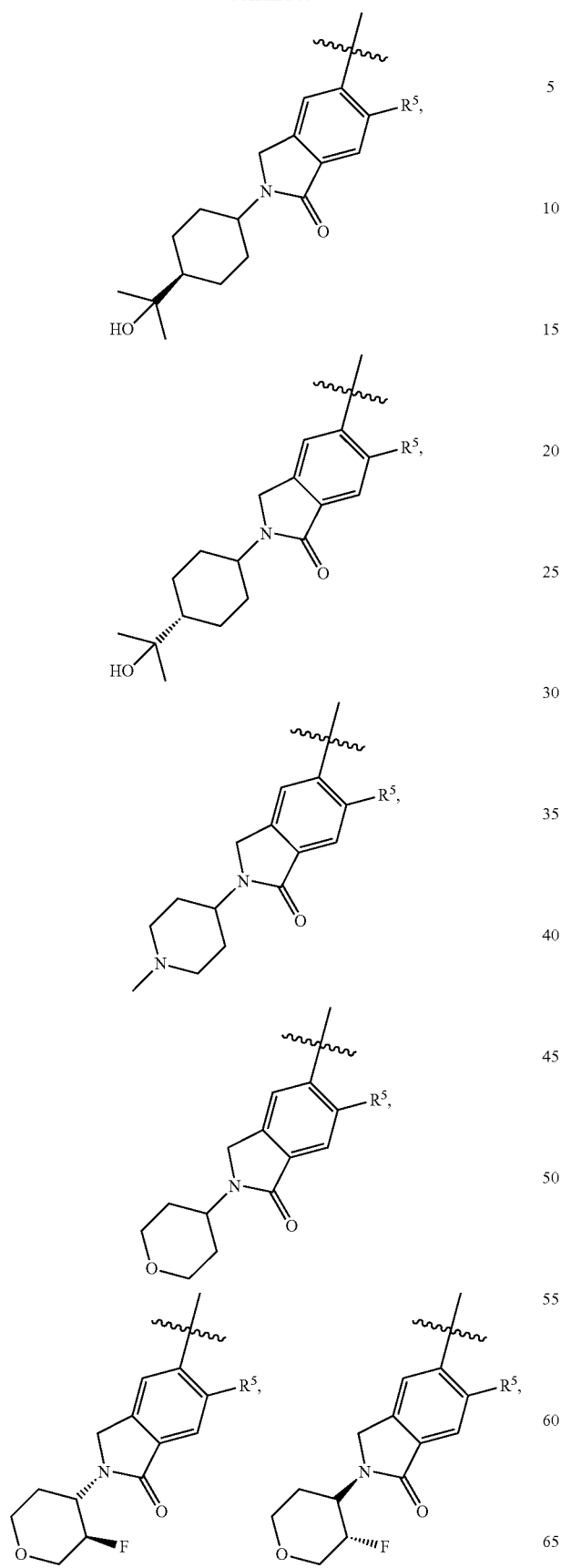
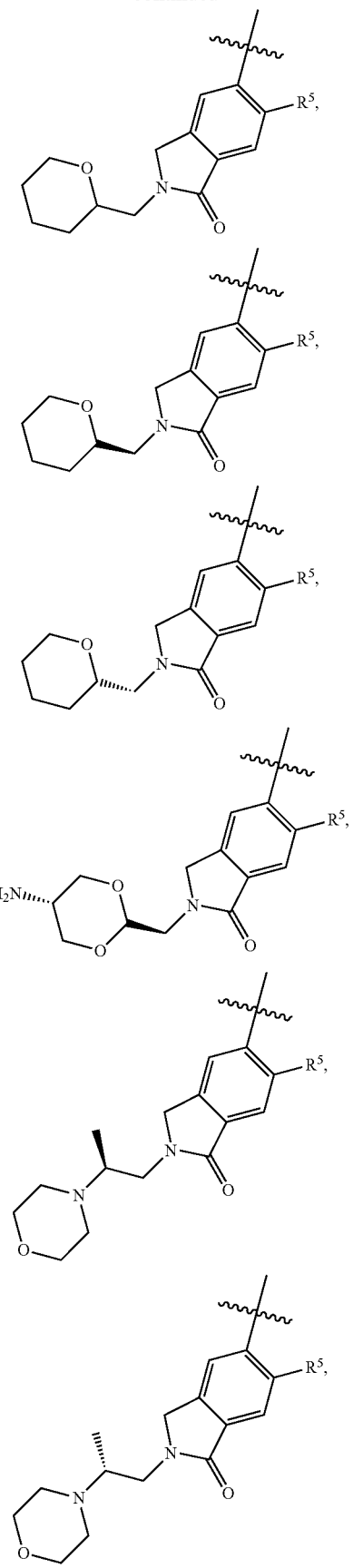

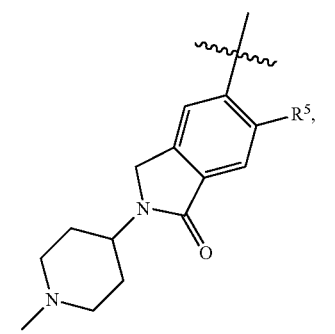
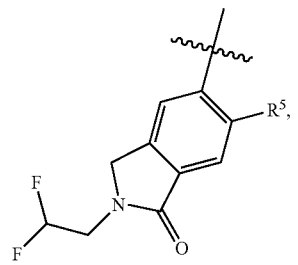
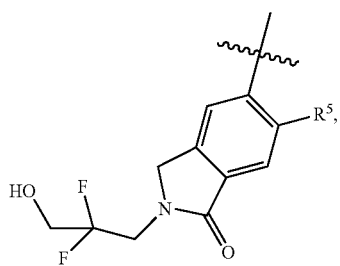
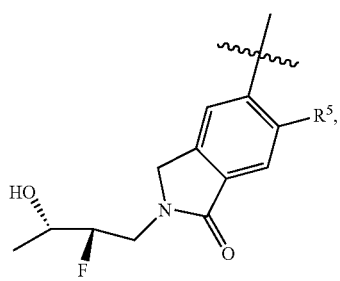

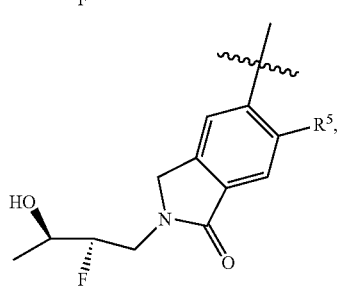
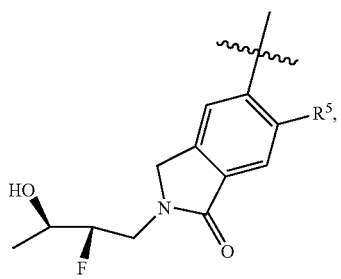
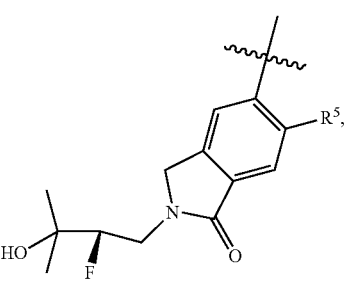
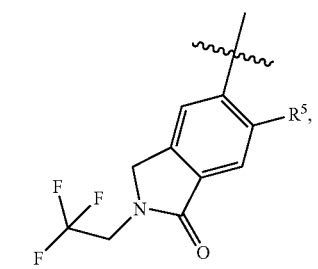
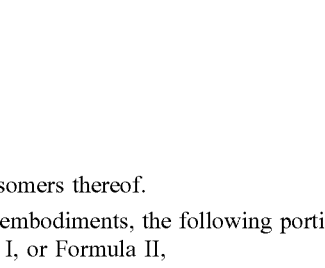
and stereoisomers thereof.
In some embodiments, the following portion of Formula 0, Formula I, or Formula II,
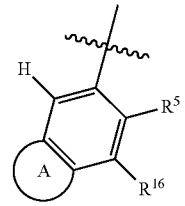
is selected from
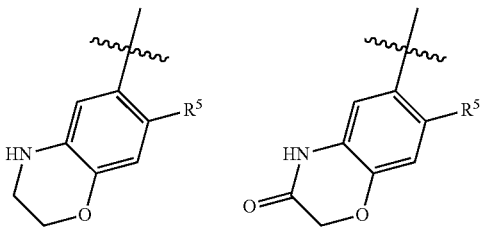

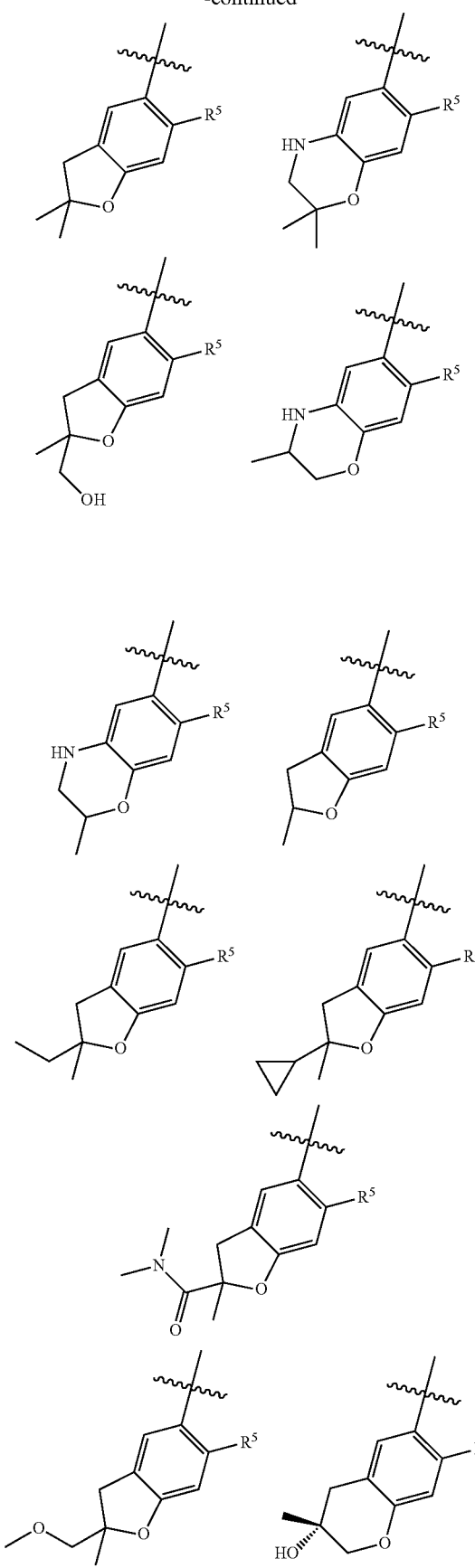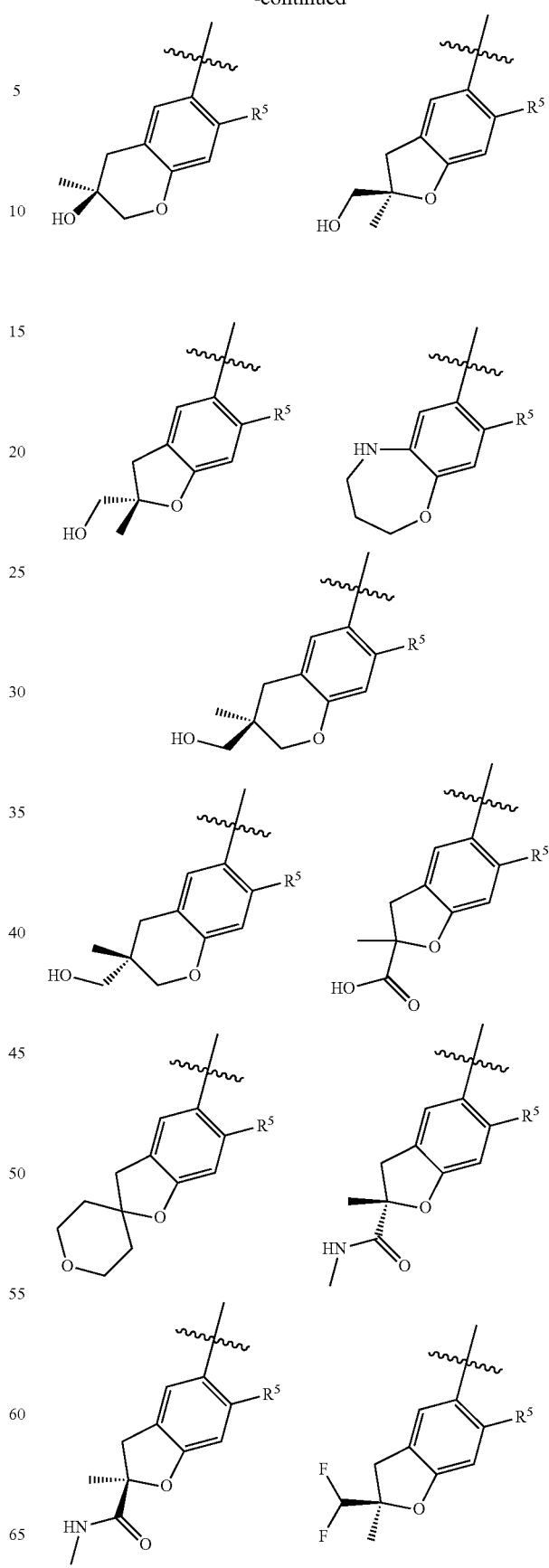

-continued
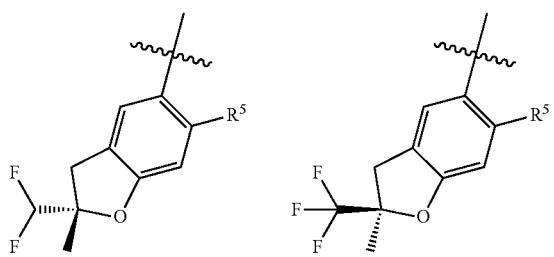
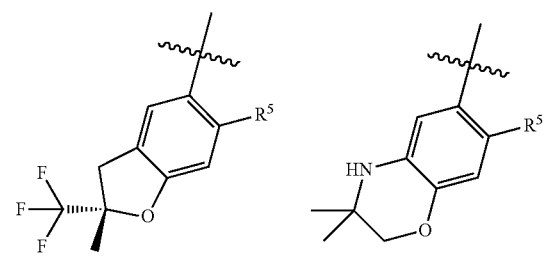
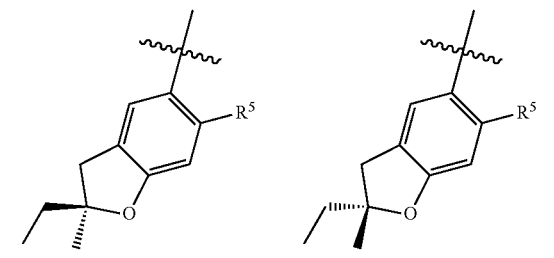
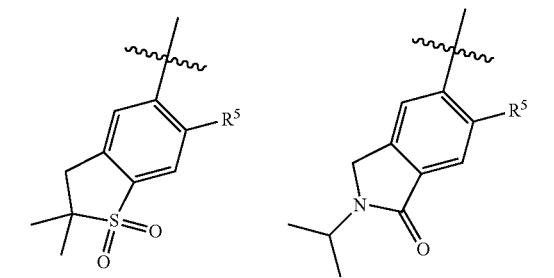
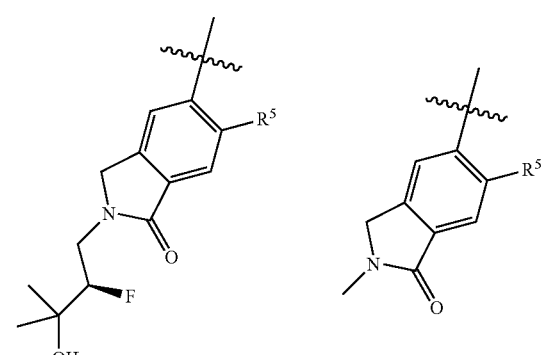
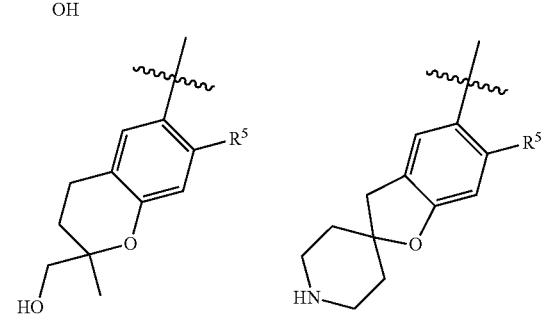
-continued
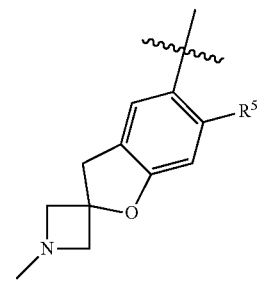
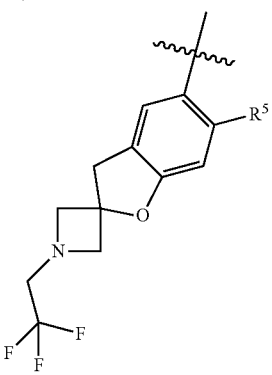
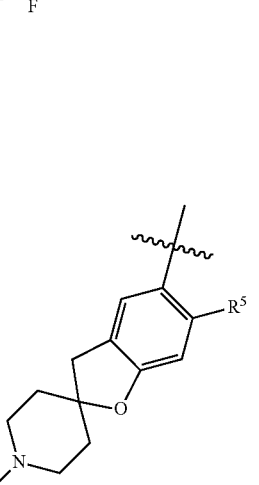
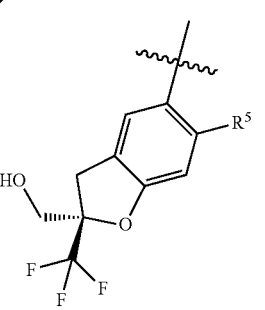
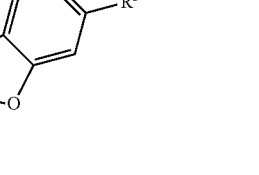

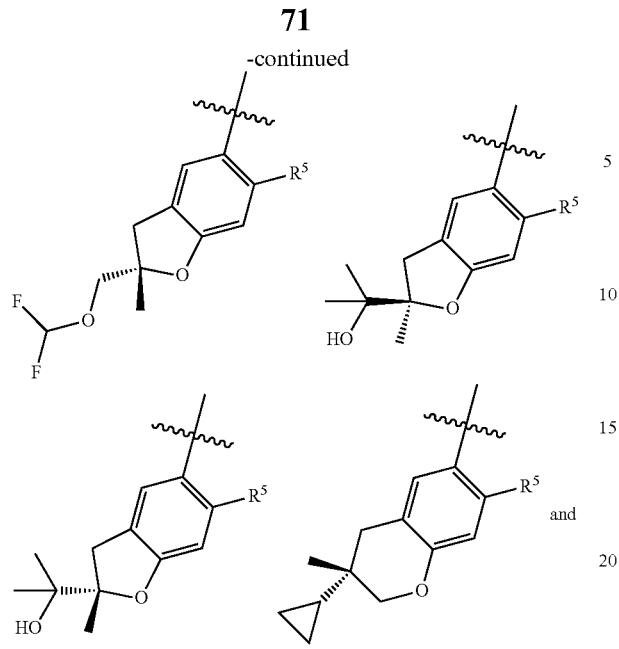

and stereoisomers thereof.

In some embodiments, a compound is selected from the group consisting of the compounds of Tables 1, 2 and 3, shown below, or a stereoisomer or pharmaceutically acceptable salt thereof.

TABLE 1

Exemplary compounds of the present invention. Salts of such compounds are also contemplated. See the Examples section for preparation of such compounds.

| Ex. | Structure | Name |
|---|---|---|
| 1 | 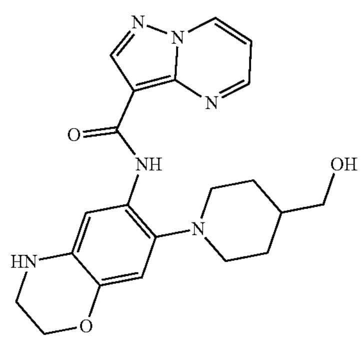 [SMILES: O=C(Nc1cc2c(cc1N1CCC(CO)CC1)OCCN2)c1cnn2cccnc12] | N-[7-[4-(hydroxymethyl)-1-piperidyl]-3,4-dihydro-2H-1,4-benzoxazin-6-yl]pyrazolo[1,5-a]pyrimidine-3-carboxamide |
| 2 | 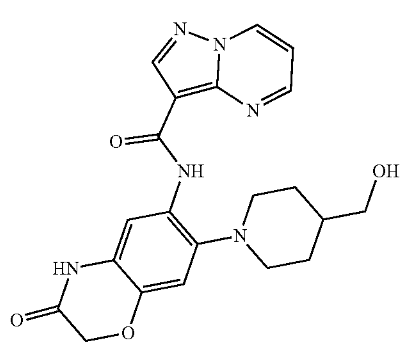 [SMILES: O=C1COc2cc(N3CCC(CO)CC3)c(NC(=O)c3cnn4cccnc34)cc2N1] | N-[7-[4-(hydroxymethyl)-1-piperidyl]-3-oxo-4H-1,4-benzoxazin-6-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 3 | 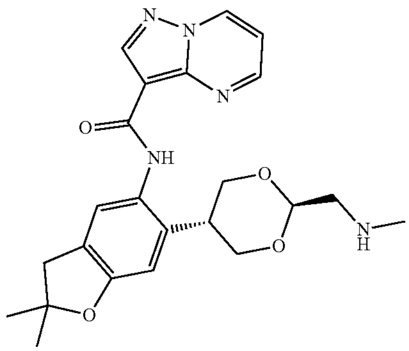 | N-[2,2-dimethyl-6-[2-(methylaminomethyl)-1,3-dioxan-5-yl]-3H-benzofuran-5-yl]pyrazolo[1,5-a]pyrimidine-3-carboxamide |
| 4 | 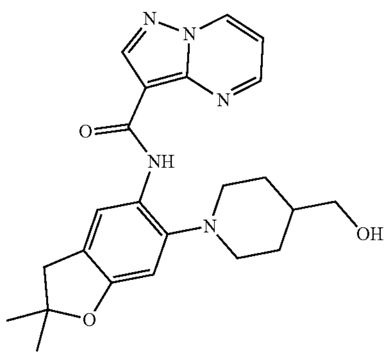 [SMILES: CC1(C)Cc2cc(NC(=O)c3cnn4cccnc34)c(N3CCC(CO)CC3)cc2O1] | N-[6-[4-(hydroxymethyl)-1-piperidyl]-2,2-dimethyl-3H-benzofuran-5-yl]pyrazolo[1,5-a]pyrimidine-3-carboxamide |
| 5 | 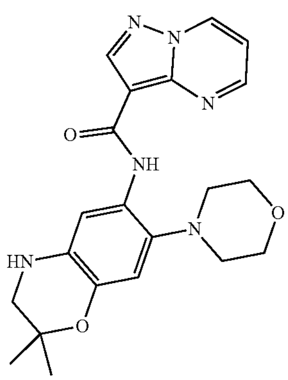 [SMILES: CC1(C)CNc2cc(NC(=O)c3cnn4cccnc34)c(N3CCOCC3)cc2O1] | N-(2,2-dimethyl-7-morpholino-3,4-dihydro-1,4-benzoxazin-6-yl)pyrazolo[1,5-a]pyrimidine-3-carboxamide |
| 6 | 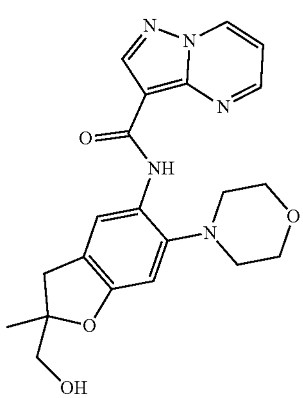 [SMILES: CC1(CO)Cc2cc(NC(=O)c3cnn4cccnc34)c(N3CCOCC3)cc2O1] | N-[2-(hydroxymethyl)-2-methyl-6-morpholino-3H-benzofuran-5-yl]pyrazolo[1,5-a]pyrimidine-3-carboxamide |

TABLE 1-continued

*Exemplary compounds of the present invention. Salts of such compounds are also contemplated. See the Examples section for preparation of such compounds.*

| Ex. | Structure | Name |
|---|---|---|
| 7 | 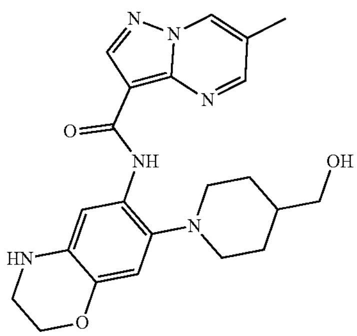 [SMILES: Cc1cnc2c(C(=O)Nc3cc4c(cc3N3CCC(CO)CC3)OCCN4)cnn2c1] | N-[7-[4-(hydroxymethyl)-1-piperidyl]-3,4-dihydro-2H-1,4-benzoxazin-6-yl]-6-methyl-pyrazolo[1,5-a]pyrimidine-3-carboxamide |
| 8 | 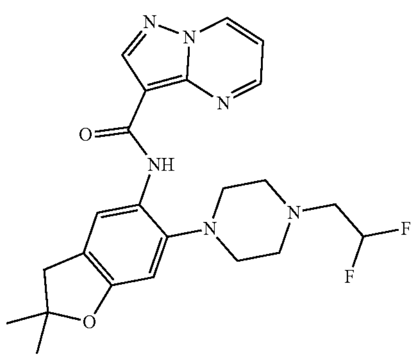 [SMILES: CC1(C)Cc2cc(NC(=O)c3cnn4cccnc34)c(N3CCN(CC(F)F)CC3)cc2O1] | N-[6-[4-(2,2-difluoroethyl)piperazin-1-yl]-2,2-dimethyl-3H-benzofuran-5-yl]pyrazolo[1,5-a]pyrimidine-3-carboxamide |
| 9 | 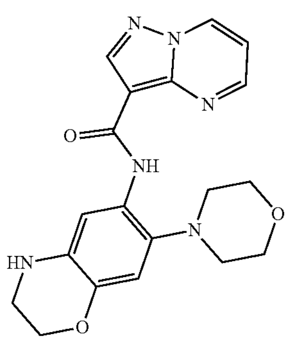 [SMILES: O=C(Nc1cc2c(cc1N1CCOCC1)OCCN2)c1cnn2cccnc12] | N-(7-morpholino-3,4-dihydro-2H-1,4-benzoxazin-6-yl)pyrazolo[1,5-a]pyrimidine-3-carboxamide |
| 10 | 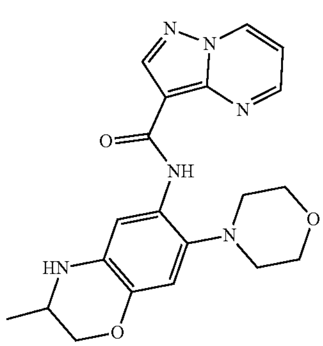 [SMILES: CC1COc2cc(N3CCOCC3)c(NC(=O)c3cnn4cccnc34)cc2N1] | N-(3-methyl-7-morpholino-3,4-dihydro-2H-1,4-benzoxazin-6-yl)pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
| --- | --- | --- |
| 11 | 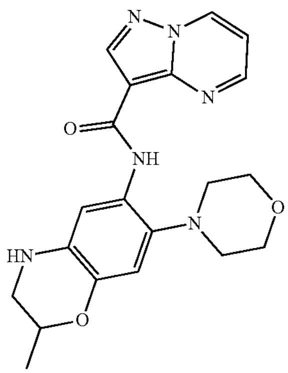 [SMILES: CC1CNc2cc(NC(=O)c3cnn4cccnc34)c(N3CCOCC3)cc2O1] | N-(2-methyl-7-morpholino-3,4-dihydro-2H-1,4-benzoxazin-6-yl)pyrazolo[1,5-a]pyrimidine-3-carboxamide |
| 12 | 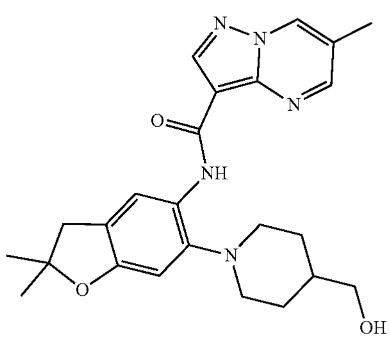 | N-[6-[4-(hydroxymethyl)-1-piperidyl]-2,2-dimethyl-3H-benzofuran-5-yl]-6-methyl-pyrazolo[1,5-a]pyrimidine-3-carboxamide |
| 13 | 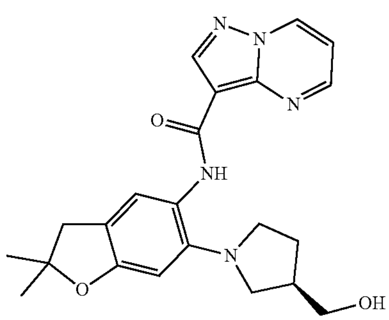 [SMILES: CC1(C)Cc2cc(NC(=O)c3cnn4cccnc34)c(N3CC[C@@H](CO)C3)cc2O1] | N-[6-[(3S)-3-(hydroxymethyl)pyrrolidin-1-yl]-2,2-dimethyl-3H-benzofuran-5-yl]pyrazolo[1,5-a]pyrimidine-3-carboxamide |
| 14 | 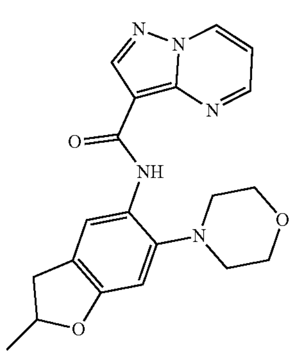 [SMILES: CC1Cc2cc(NC(=O)c3cnn4cccnc34)c(N3CCOCC3)cc2O1] | N-(2-methyl-6-morpholino-2,3-dihydrobenzofuran-5-yl)pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 15 | 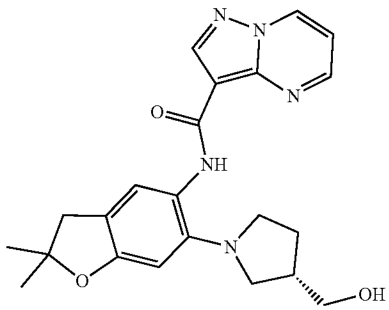 [SMILES: CC1(C)Cc2cc(NC(=O)c3cnn4cccnc34)c(N3CC[C@H](CO)C3)cc2O1] | N-[6-[(3R)-3-(hydroxymethyl)pyrrolidin-1-yl]-2,2-dimethyl-3H-benzofuran-5-yl]pyrazolo[1,5-a]pyrimidine-3-carboxamide |
| 16 | 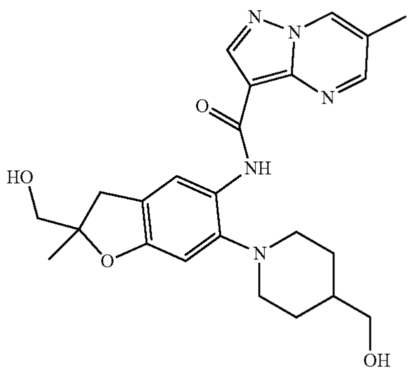 [SMILES: Cc1cnc2c(C(=O)Nc3cc4c(cc3N3CCC(CO)CC3)OC(C)(CO)C4)cnn2c1] | N-[2-(hydroxymethyl)-6-[4-(hydroxymethyl)-1-piperidyl]-2-methyl-3H-benzofuran-5-yl]-6-methyl-pyrazolo[1,5-a]pyrimidine-3-carboxamide |
| 17 | 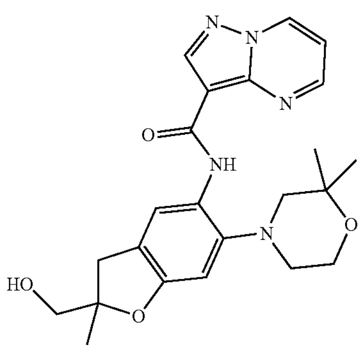 [SMILES: CC1(C)CN(c2cc3c(cc2NC(=O)c2cnn4cccnc24)CC(C)(CO)O3)CCO1] | N-[6-(2,2-dimethylmorpholin-4-yl)-2-(hydroxymethyl)-2-methyl-3H-benzofuran-5-yl]pyrazolo[1,5-a]pyrimidine-3-carboxamide |
| 18 | 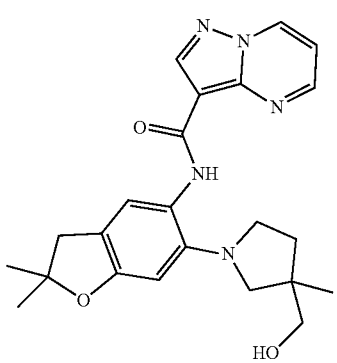 | N-[6-[3-(hydroxymethyl)-3-methyl-pyrrolidin-1-yl]-2,2-dimethyl-3H-benzofuran-5-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 19 | 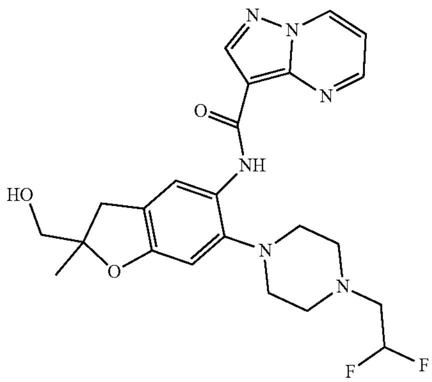 [SMILES: CC1(CO)Cc2cc(NC(=O)c3cnn4cccnc34)c(N3CCN(CC(F)F)CC3)cc2O1] | N-[6-[4-(2,2-difluoroethyl)piperazin-1-yl]-2-(hydroxymethyl)-2-methyl-3H-benzofuran-5-yl]pyrazolo[1,5-a]pyrimidine-3-carboxamide |
| 20 | 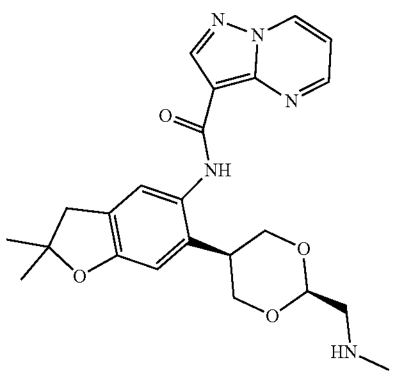 | N-[2,2-dimethyl-6-[2-(methylaminomethyl)-1,3-dioxan-5-yl]-3H-benzofuran-5-yl]pyrazolo[1,5-a]pyrimidine-3-carboxamide |
| 21 | 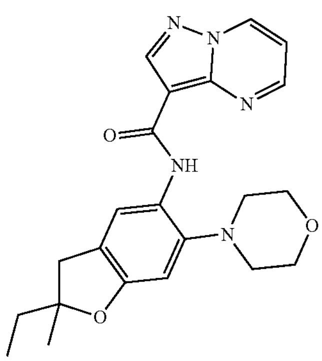 [SMILES: CCC1(C)Cc2cc(NC(=O)c3cnn4cccnc34)c(N3CCOCC3)cc2O1] | N-(2-ethyl-2-methyl-6-morpholino-3H-benzofuran-5-yl)pyrazolo[1,5-a]pyrimidine-3-carboxamide |
| 22 | 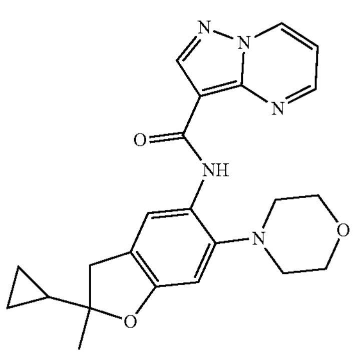 [SMILES: CC1(C2CC2)Cc2cc(NC(=O)c3cnn4cccnc34)c(N3CCOCC3)cc2O1] | N-(2-cyclopropyl-2-methyl-6-morpholino-3H-benzofuran-5-yl)pyrazolo[1,5-a]pyrimidine-3-carboxamide |

TABLE 1-continued

*Exemplary compounds of the present invention. Salts of such compounds are also contemplated. See the Examples section for preparation of such compounds.*

| Ex. | Structure | Name |
|---|---|---|
| 23 | 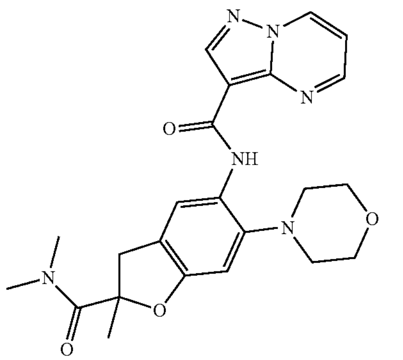 [SMILES: CN(C)C(=O)C1(C)Cc2cc(NC(=O)c3cnn4cccnc34)c(N3CCOCC3)cc2O1] | N-[2-(dimethylcarbamoyl)-2-methyl-6-morpholino-3H-benzofuran-5-yl]pyrazolo[1,5-a]pyrimidine-3-carboxamide |
| 24 | 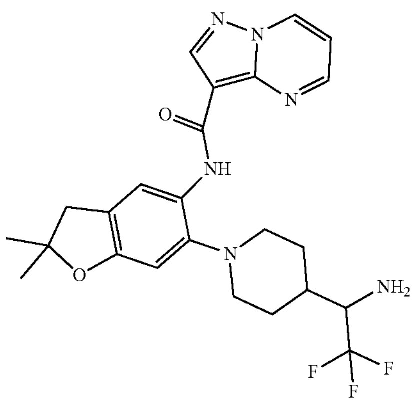 [SMILES: CC1(C)Cc2cc(NC(=O)c3cnn4cccnc34)c(N3CCC(C(N)C(F)(F)F)CC3)cc2O1] | N-[6-[4-(1-amino-2,2,2-trifluoro-ethyl)-1-piperidyl]-2,2-dimethyl-3H-benzofuran-5-yl]pyrazolo[1,5-a]pyrimidine-3-carboxamide |
| 25 | 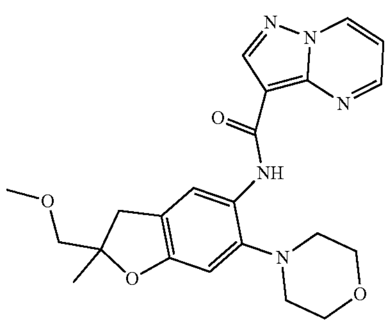 [SMILES: COCC1(C)Cc2cc(NC(=O)c3cnn4cccnc34)c(N3CCOCC3)cc2O1] | N-[2-(methoxymethyl)-2-methyl-6-morpholino-3H-benzofuran-5-yl]pyrazolo[1,5-a]pyrimidine-3-carboxamide |
| 26 | 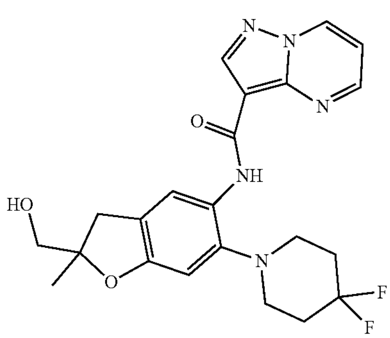 [SMILES: CC1(CO)Cc2cc(NC(=O)c3cnn4cccnc34)c(N3CCC(F)(F)CC3)cc2O1] | N-[6-(4,4-difluoro-1-piperidyl)-2-(hydroxymethyl)-2-methyl-3H-benzofuran-5-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 27 and 28 | 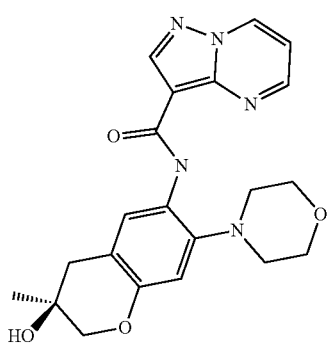 | N-(3-hydroxy-3-methyl-7-morpholino-chroman-6-yl)pyrazolo[1,5-a]pyrimidine-3-carboxamide and N-(3-hydroxy-3-methyl-7-morpholino-chroman-6-yl)pyrazolo[1,5-a]pyrimidine-3-carboxamide |
| 29 and 30 | 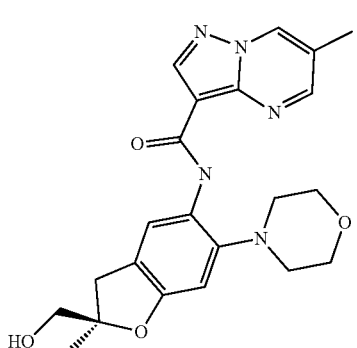 | N-[2-(hydroxymethyl)-2-methyl-6-morpholino-3H-benzofuran-5-yl]-6-methyl-pyrazolo[1,5-a]pyrimidine-3-carboxamide and N-[2-(hydroxymethyl)-2-methyl-6-morpholino-3H-benzofuran-5-yl]-6-methyl-pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 31 and 32 | 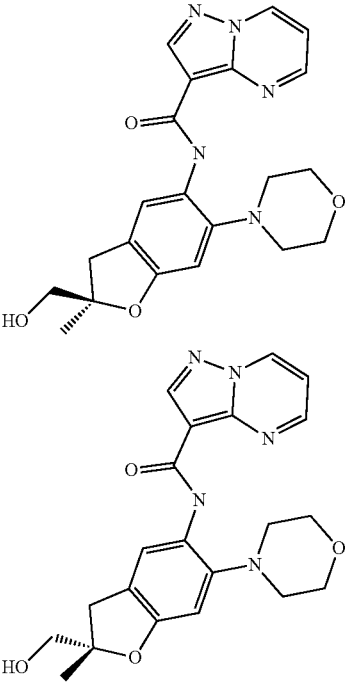 | N-[(2R)-2-(hydroxymethyl)-2-methyl-6-morpholino-3H-benzofuran-5-yl]pyrazolo[1,5-a]pyrimidine-3-carboxamide and N-[(2S)-2-(hydroxymethyl)-2-methyl-6-morpholino-3H-benzofuran-5-yl]pyrazolo[1,5-a]pyrimidine-3-carboxamide |
| 33 | 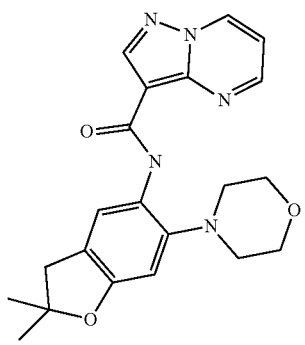 [SMILES: CC1(C)Cc2cc(NC(=O)c3cnn4cccnc34)c(N3CCOCC3)cc2O1] | N-(2,2-dimethyl-6-morpholino-3H-benzofuran-5-yl)pyrazolo[1,5-a]pyrimidine-3-carboxamide |
| 34 | 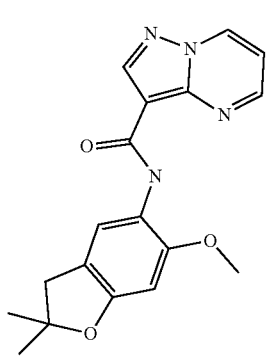 [SMILES: COc1cc2c(cc1NC(=O)c1cnn3cccnc13)CC(C)(C)O2] | N-(6-methoxy-2,2-dimethyl-3H-benzofuran-5-yl)pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
| --- | --- | --- |
| 35 | 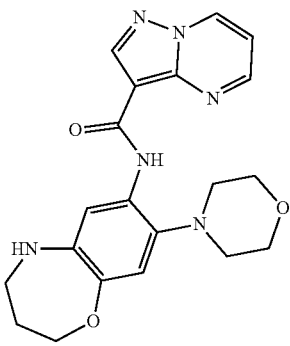 [SMILES: O=C(Nc1cc2c(cc1N1CCOCC1)OCCCN2)c1cnn2cccnc12] | N-(8-morpholino-2,3,4,5-tetrahydro-1,5-benzoxazepin-7-yl)pyrazolo[1,5-a]pyrimidine-3-carboxamide |
| 36 and 37 | 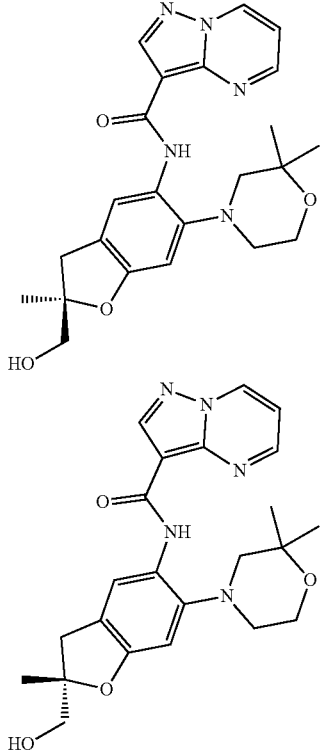 | N-[(2R)-6-(2,2-dimethylmorpholin-4-yl)-2-(hydroxymethyl)-2-methyl-3H-benzofuran-5-yl]pyrazolo[1,5-a]pyrimidine-3-carboxamide and N-[(2S)-6-(2,2-dimethylmorpholin-4-yl)-2-(hydroxymethyl)-2-methyl-3H-benzofuran-5-yl]pyrazolo[1,5-a]pyrimidine-3-carboxamide |
| 38 | 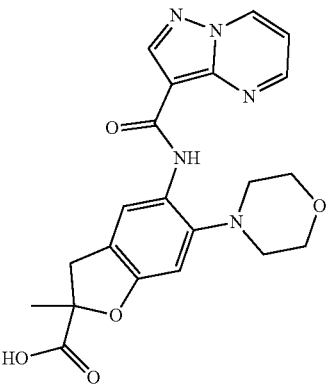 [SMILES: CC1(C(=O)O)Cc2cc(NC(=O)c3cnn4cccnc34)c(N3CCOCC3)cc2O1] | 2-methyl-6-morpholino-5-(pyrazolo[1,5-a]pyrimidine-3-carbonylamino)-3H-benzofuran-2-carboxylic acid |

TABLE 1-continued

Exemplary compounds of the present invention. Salts of such compounds are also contemplated. See the Examples section for preparation of such compounds.

| Ex. | Structure | Name |
|---|---|---|
| 39 | 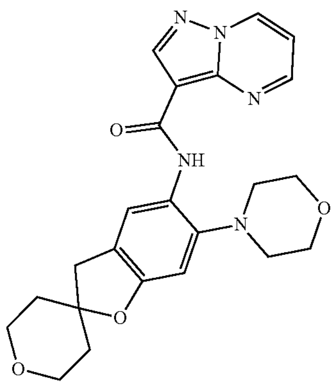 [SMILES: O=C(Nc1cc2c(cc1N1CCOCC1)OC1(CCOCC1)C2)c1cnn2cccnc12] | N-(6-morpholinospiro[3H-benzofuran-2,4'-tetrahydropyran]-5-yl)pyrazolo[1,5-a]pyrimidine-3-carboxamide |
| 40 | 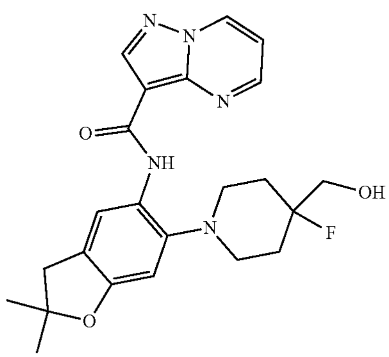 [SMILES: CC1(C)Cc2cc(NC(=O)c3cnn4cccnc34)c(N3CCC(F)(CO)CC3)cc2O1] | N-[6-[4-fluoro-4-(hydroxymethyl)-1-piperidyl]-2,2-dimethyl-3H-benzofuran-5-yl]pyrazolo[1,5-a]pyrimidine-3-carboxamide |
| 41 | 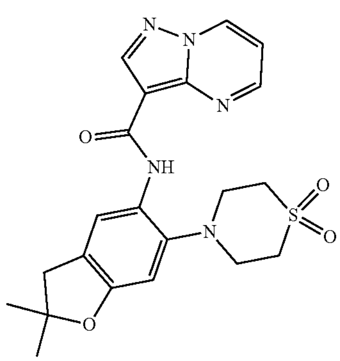 [SMILES: CC1(C)Cc2cc(NC(=O)c3cnn4cccnc34)c(N3CCS(=O)(=O)CC3)cc2O1] | N-[6-(1,1-dioxo-1,4-thiazinan-4-yl)-2,2-dimethyl-3H-benzofuran-5-yl]pyrazolo[1,5-a]pyrimidine-3-carboxamide |
| 42 and 43 | 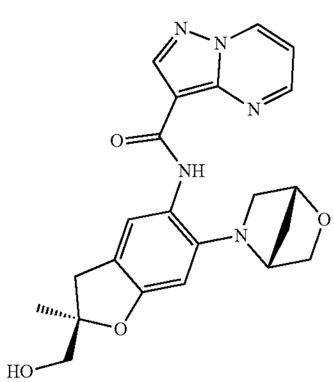 | N-[(2S)-2-(hydroxymethyl)-2-methyl-6-[(1R,4R)-2-oxa-5-azabicyclo[2.2.1]heptan-5-yl]-3H-benzofuran-5-yl]pyrazolo[1,5-a]pyrimidine-3-carboxamide and N-[(2R)-2-(hydroxymethyl)-2-methyl-6-[(1R,4R)-2-oxa-5-azabicyclo[2.2.1]heptan-5-yl]-3H-benzofuran-5-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 44 and 45 | | N-[(2R)-6-[4-fluoro-4-(hydroxymethyl)-1-piperidyl]-2-(hydroxymethyl)-2-methyl-3H-benzofuran-5-yl]pyrazolo[1,5-a]pyrimidine-3-carboxamide and N-[(2S)-6-[4-fluoro-4-(hydroxymethyl)-1-piperidyl]-2-(hydroxymethyl)-2-methyl-3H-benzofuran-5-yl]pyrazolo[1,5-a]pyrimidine-3-carboxamide |
| 46 and 47 | 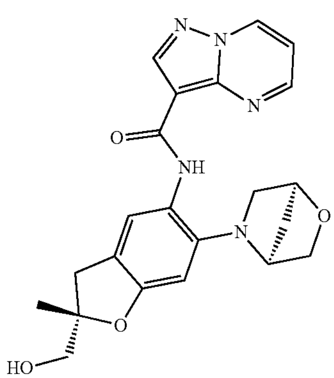 | N-[(2S)-2-(hydroxymethyl)-2-methyl-6-[(1S,4S)-2-oxa-5-azabicyclo[2.2.1]heptan-5-yl]-3H-benzofuran-5-yl]pyrazolo[1,5-a]pyrimidine-3-carboxamide and N-[(2R)-2-(hydroxymethyl)-2-methyl-6-[(1S,4S)-2-oxa-5-azabicyclo[2.2.1]heptan-5-yl]-3H-benzofuran-5-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 48 and 49 | | N-[(2S)-2-methyl-2-(methylcarbamoyl)-6-morpholino-3H-benzofuran-5-yl]pyrazolo[1,5-a]pyrimidine-3-carboxamide and N-[(2R)-2-methyl-2-(methylcarbamoyl)-6-morpholino-3H-benzofuran-5-yl]pyrazolo[1,5-a]pyrimidine-3-carboxamide |
| 50 and 51 | 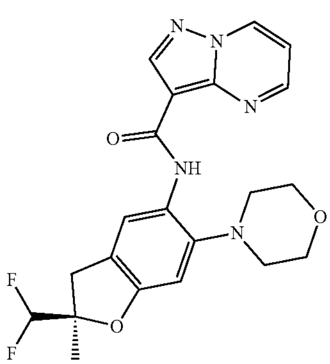 | N-[(2R)-2-(difluoromethyl)-2-methyl-6-morpholino-3H-benzofuran-5-yl]pyrazolo[1,5-a]pyrimidine-3-carboxamide and N-[(2S)-2-(difluoromethyl)-2-methyl-6-morpholino-3H-benzofuran-5-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 52 and 53 | | N-[(2R)-2-(hydroxymethyl)-6-[4-(1-hydroxy-1-methyl-ethyl)-1-piperidyl]-2-methyl-3H-benzofuran-5-yl]-6-methyl-pyrazolo[1,5-a]pyrimidine-3-carboxamide<br>and<br>N-[(2S)-2-(hydroxymethyl)-6-[4-(1-hydroxy-1-methyl-ethyl)-1-piperidyl]-2-methyl-3H-benzofuran-5-yl]-6-methyl-pyrazolo[1,5-a]pyrimidine-3-carboxamide |
| 54 and 55 | 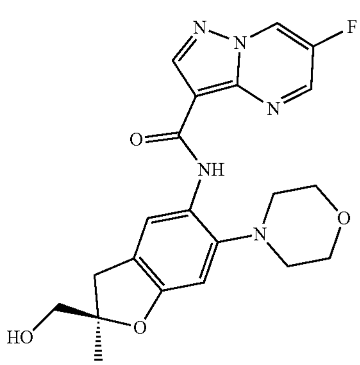 | 6-fluoro-N-[(2R)-2-(hydroxymethyl)-2-methyl-6-morpholino-3H-benzofuran-5-yl]pyrazolo[1,5-a]pyrimidine-3-carboxamide<br>and<br>6-fluoro-N-[(2S)-2-(hydroxymethyl)-2-methyl-6-morpholino-3H-benzofuran-5-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| | | |
| 56 and 57 | | N-[(2S)-6-[(3S)-3-fluoropyrrolidin-1-yl]-2-(hydroxymethyl)-2-methyl-3H-benzofuran-5-yl]pyrazolo[1,5-a]pyrimidine-3-carboxamide and N-[(2R)-6-[(3S)-3-fluoropyrrolidin-1-yl]-2-(hydroxymethyl)-2-methyl-3H-benzofuran-5-yl]pyrazolo[1,5-a]pyrimidine-3-carboxamide |
| 58 and 59 | 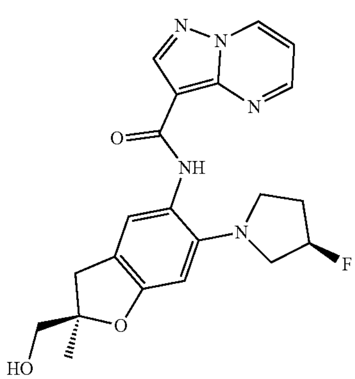 [SMILES: C[C@]1(CO)Cc2cc(NC(=O)c3cnn4cccnc34)c(N3CC[C@H](F)C3)cc2O1] | N-[(2R)-6-[(3R)-3-fluoropyrrolidin-1-yl]-2-(hydroxymethyl)-2-methyl-3H-benzofuran-5-yl]pyrazolo[1,5-a]pyrimidine-3-carboxamide and N-[(2S)-6-[(3R)-3-fluoropyrrolidin-1-yl]-2-(hydroxymethyl)-2-methyl-3H-benzofuran-5-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| | (structure) | |
| 60 | (structure) | N-[6-[4-(2-hydroxyethyl)piperazin-1-yl]-2,2-dimethyl-3H-benzofuran-5-yl]pyrazolo[1,5-a]pyrimidine-3-carboxamide |
| 61 | (structure) | 6-cyclopropyl-N-(2,2-dimethyl-6-morpholino-3H-benzofuran-5-yl)pyrazolo[1,5-a]pyrimidine-3-carboxamide |
| 62 | (structure) | N-[2,2-dimethyl-6-(4-piperidyl)-3H-benzofuran-5-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 63 | 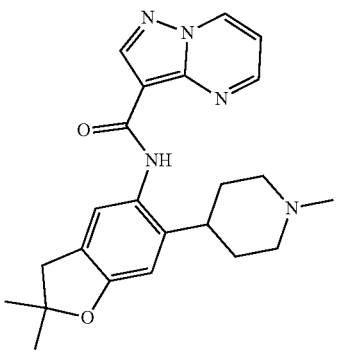 | N-[2,2-dimethyl-6-(1-methyl-4-piperidyl)-3H-benzofuran-5-yl]pyrazolo[1,5-a]pyrimidine-3-carboxamide |
| 64 and 65 |  | N-[6-(4-hydroxycyclohexoxy)-2,2-dimethyl-3H-benzofuran-5-yl]pyrazolo[1,5-a]pyrimidine-3-carboxamide and N-[6-(4-hydroxycyclohexoxy)-2,2-dimethyl-3H-benzofuran-5-yl]pyrazolo[1,5-a]pyrimidine-3-carboxamide |
| 66 and 67 | 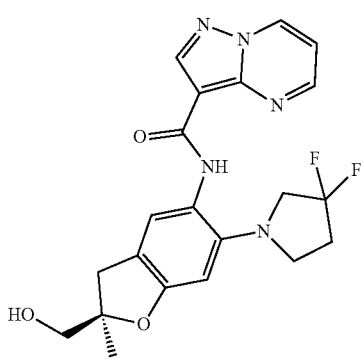 | N-[(2R)-6-(3,3-difluoropyrrolidin-1-yl)-2-(hydroxymethyl)-2-methyl-3H-benzofuran-5-yl]pyrazolo[1,5-a]pyrimidine-3-carboxamide and N-[(2S)-6-(3,3-difluoropyrrolidin-1-yl)-2-(hydroxymethyl)-2-methyl-3H-benzofuran-5-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 68 | 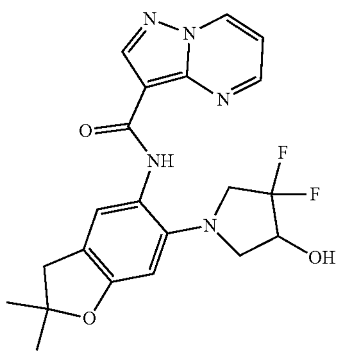 [SMILES: CC1(C)Cc2cc(NC(=O)c3cnn4cccnc34)c(N3CC(O)C(F)(F)C3)cc2O1] | N-[6-(3,3-difluoro-4-hydroxy-pyrrolidin-1-yl)-2,2-dimethyl-3H-benzofuran-5-yl]pyrazolo[1,5-a]pyrimidine-3-carboxamide |
| 69 | 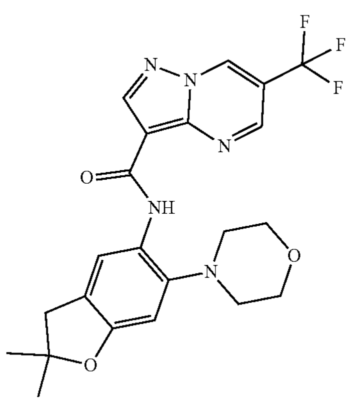 [SMILES: CC1(C)Cc2cc(NC(=O)c3cnn4cc(C(F)(F)F)cnc34)c(N3CCOCC3)cc2O1] | N-(2,2-dimethyl-6-morpholino-3H-benzofuran-5-yl)-6-(trifluoromethyl)pyrazolo[1,5-a]pyrimidine-3-carboxamide |
| 70 | 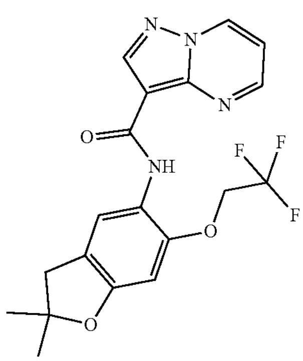 [SMILES: CC1(C)Cc2cc(NC(=O)c3cnn4cccnc34)c(OCC(F)(F)F)cc2O1] | N-[2,2-dimethyl-6-(2,2,2-trifluoroethoxy)-3H-benzofuran-5-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 71 and 72 | | N-[(2R)-2-(hydroxymethyl)-2-methyl-6-(trifluoromethyl)-3H-benzofuran-5-yl]pyrazolo[1,5-a]pyrimidine-3-carboxamide and N-[(2S)-2-(hydroxymethyl)-2-methyl-6-(trifluoromethyl)-3H-benzofuran-5-yl]pyrazolo[1,5-a]pyrimidine-3-carboxamide |
| 73 and 74 | | N-[(2R)-6-(difluoromethyl)-2-(hydroxymethyl)-2-methyl-3H-benzofuran-5-yl]pyrazolo[1,5-a]pyrimidine-3-carboxamide and N-[(2S)-6-(difluoromethyl)-2-(hydroxymethyl)-2-methyl-3H-benzofuran-5-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 75 | 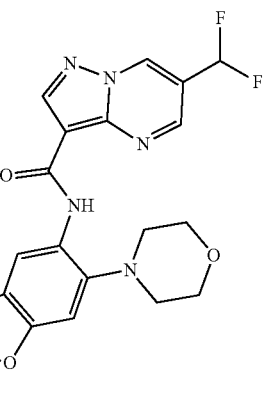 | 6-(difluoromethyl)-N-[2-(hydroxymethyl)-2-methyl-6-morpholino-3H-benzofuran-5-yl]pyrazolo[1,5-a]pyrimidine-3-carboxamide |
| 76 and 77 | 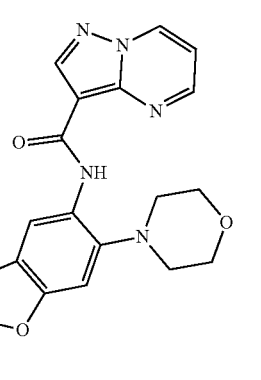 | N-[(2R)-2-methyl-6-morpholino-2-(trifluoromethyl)-3H-benzofuran-5-yl]pyrazolo[1,5-a]pyrimidine-3-carboxamide and N-[(2S)-2-methyl-6-morpholino-2-(trifluoromethyl)-3H-benzofuran-5-yl]pyrazolo[1,5-a]pyrimidine-3-carboxamide |
| 78 and 79 | 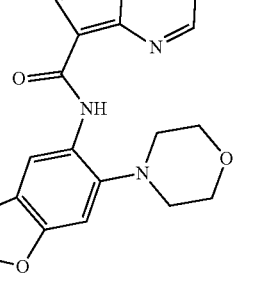 | N-[(2R)-2-(hydroxymethyl)-2-methyl-6-[(1S,4S)-5-(2,2,2-trifluoroethyl)-2,5-diazabicyclo[2.2.1]heptan-2-yl]-3H-benzofuran-5-yl]pyrazolo[1,5-a]pyrimidine-3-carboxamide and N-[(2S)-2-(hydroxymethyl)-2-methyl-6-[(1S,4S)-5-(2,2,2-trifluoroethyl)-2,5-diazabicyclo[2.2.1]heptan-2-yl]-3H-benzofuran-5-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 80 and 81 | | N-[(2R)-7-chloro-2-(hydroxymethyl)-2-methyl-6-morpholino-3H-benzofuran-5-yl]pyrazolo[1,5-a]pyrimidine-3-carboxamide and N-[(2S)-7-chloro-2-(hydroxymethyl)-2-methyl-6-morpholino-3H-benzofuran-5-yl]pyrazolo[1,5-a]pyrimidine-3-carboxamide |
| 82 | 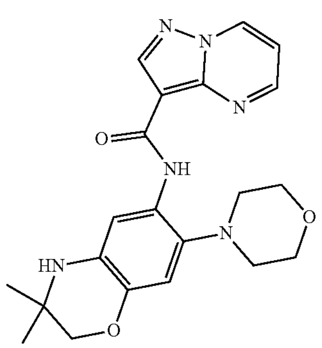 [SMILES: CC1(C)COc2cc(N3CCOCC3)c(NC(=O)c3cnn4cccnc34)cc2N1] | N-(3,3-dimethyl-7-morpholino-2,4-dihydro-1,4-benzoxazin-6-yl)pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 83 and 84 | 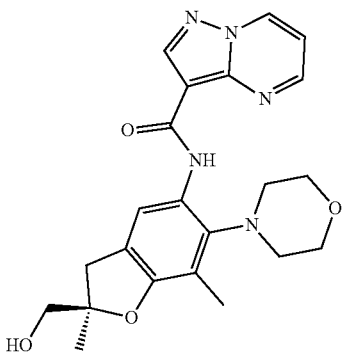 [SMILES: Cc1c2c(cc(NC(=O)c3cnn4cccnc34)c1N1CCOCC1)C[C@](C)(CO)O2] | N-[(2R)-2-(hydroxymethyl)-2,7-dimethyl-6-morpholino-3H-benzofuran-5-yl]pyrazolo[1,5-a]pyrimidine-3-carboxamide and N-[(2S)-2-(hydroxymethyl)-2,7-dimethyl-6-morpholino-3H-benzofuran-5-yl]pyrazolo[1,5-a]pyrimidine-3-carboxamide |
| 85 and 86 | 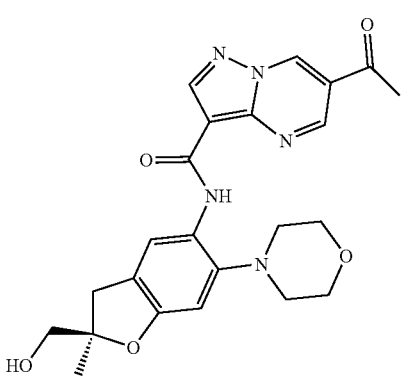 | 6-acetyl-N-[(2R)-2-(hydroxymethyl)-2-methyl-6-morpholino-3H-benzofuran-5-yl]pyrazolo[1,5-a]pyrimidine-3-carboxamide and 6-acetyl-N-[(2S)-2-(hydroxymethyl)-2-methyl-6-morpholino-3H-benzofuran-5-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 87 and 88 | 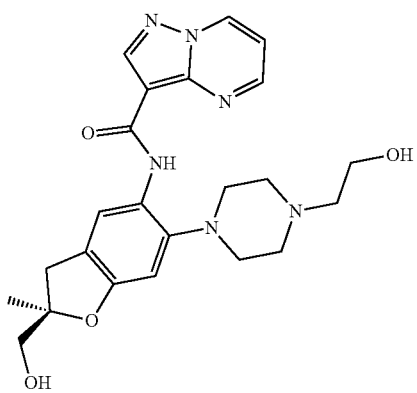 [SMILES: C[C@]1(CO)Cc2cc(NC(=O)c3cnn4cccnc34)c(N3CCN(CCO)CC3)cc2O1] | N-[(2R)-6-[4-(2-hydroxyethyl)piperazin-1-yl]-2-(hydroxymethyl)-2-methyl-3H-benzofuran-5-yl]pyrazolo[1,5-a]pyrimidine-3-carboxamide and N-[(2S)-6-[4-(2-hydroxyethyl)piperazin-1-yl]-2-(hydroxymethyl)-2-methyl-3H-benzofuran-5-yl]pyrazolo[1,5-a]pyrimidine-3-carboxamide |
| 89 | 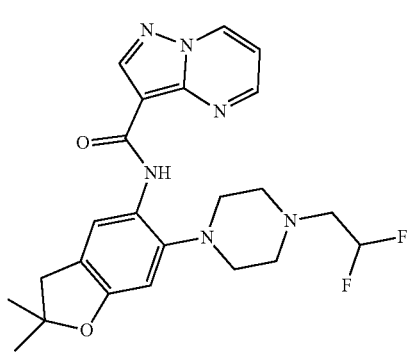 [SMILES: CC1(C)Cc2cc(NC(=O)c3cnn4cccnc34)c(N3CCN(CC(F)F)CC3)cc2O1] | N-[6-[1-(2,2-difluoroethyl)-4-piperidyl]-2,2-dimethyl-3H-benzofuran-5-yl]pyrazolo[1,5-a]pyrimidine-3-carboxamide |
| 90 | 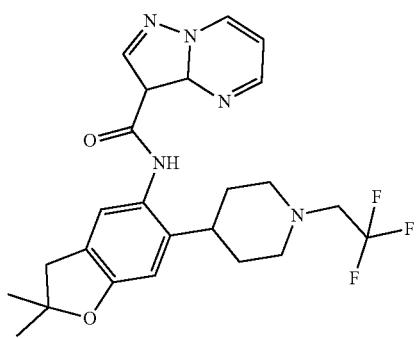 [SMILES: CC1(C)Cc2cc(NC(=O)C3C=NN4C=CC=NC34)c(C3CCN(CC(F)(F)F)CC3)cc2O1] | N-[2,2-dimethyl-6-[1-(2,2,2-trifluoroethyl)-4-piperidyl]-3H-benzofuran-5-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 91 | 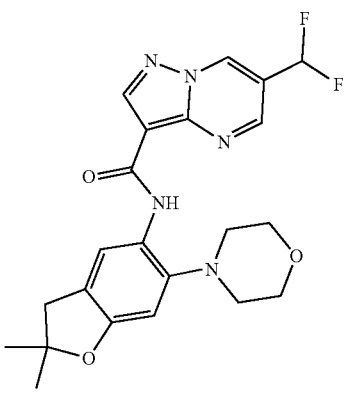 [SMILES: CC1(C)Cc2cc(NC(=O)c3cnn4cc(C(F)F)cnc34)c(N3CCOCC3)cc2O1] | 6-(difluoromethyl)-N-(2,2-dimethyl-6-morpholino-3H-benzofuran-5-yl)pyrazolo[1,5-a]pyrimidine-3-carboxamide |
| 92 and 93 | 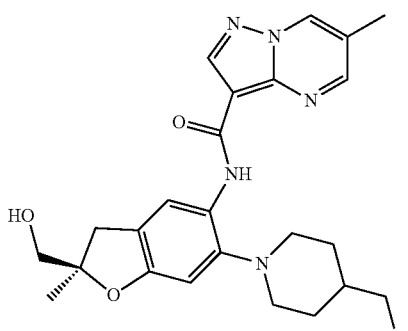 | N-[(2S)-2-(hydroxymethyl)-6-[4-(hydroxymethyl)-1-piperidyl]-2-methyl-3H-benzofuran-5-yl]-6-methyl-pyrazolo[1,5-a]pyrimidine-3-carboxamide and N-[(2R)-2-(hydroxymethyl)-6-[4-(hydroxymethyl)-1-piperidyl]-2-methyl-3H-benzofuran-5-yl]-6-methyl-pyrazolo[1,5-a]pyrimidine-3-carboxamide |
| 94 and 95 | 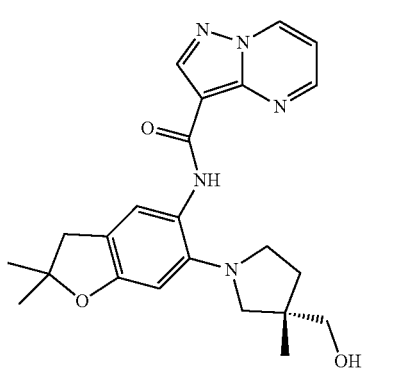 | N-[6-[(3S)-3-(hydroxymethyl)-3-methyl-pyrrolidin-1-yl]-2,2-dimethyl-3H-benzofuran-5-yl]pyrazolo[1,5-a]pyrimidine-3-carboxamide and N-[6-[(3R)-3-(hydroxymethyl)-3-methyl-pyrrolidin-1-yl]-2,2-dimethyl-3H-benzofuran-5-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 96 and 97 | | N-(2-ethyl-2-methyl-6-morpholino-3H-benzofuran-5-yl)pyrazolo[1,5-a]pyrimidine-3-carboxamide and N-(2-ethyl-2-methyl-6-morpholino-3H-benzofuran-5-yl)pyrazolo[1,5-a]pyrimidine-3-carboxamide |
| 98 and 99 | 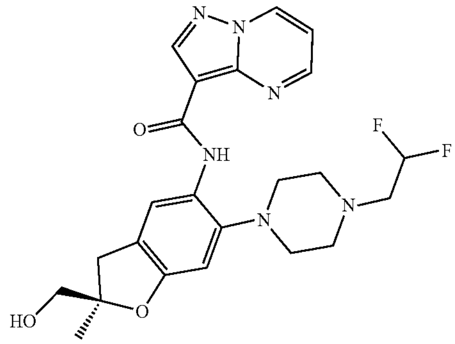 | N-[6-[4-(2,2-difluoroethyl)piperazin-1-yl]-2-(hydroxymethyl)-2-methyl-3H-benzofuran-5-yl]pyrazolo[1,5-a]pyrimidine-3-carboxamide and N-[6-[4-(2,2-difluoroethyl)piperazin-1-yl]-2-(hydroxymethyl)-2-methyl-3H-benzofuran-5-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 100 | 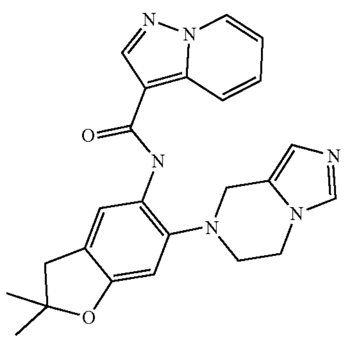 [SMILES: CC1(C)Cc2cc(NC(=O)c3cnn4ccccc34)c(N3CCn4cncc4C3)cc2O1] | N-[6-(6,8-dihydro-5H-imidazo[1,5-a]pyrazin-7-yl)-2,2-dimethyl-3H-benzofuran-5-yl]pyrazolo[1,5-a]pyridine-3-carboxamide |
| 101 | 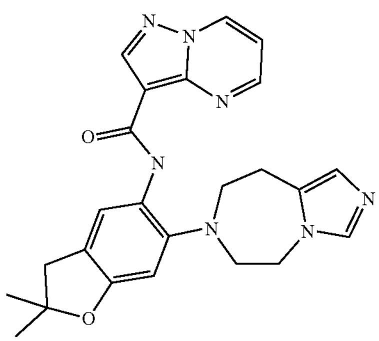 [SMILES: CC1(C)Cc2cc(NC(=O)c3cnn4cccnc34)c(N3CCc4cncn4CC3)cc2O1] | N-[2,2-dimethyl-6-(5,6,8,9-tetrahydroimidazo[1,5-d][1,4]diazepin-7-yl)-3H-benzofuran-5-yl]pyrazolo[1,5-a]pyrimidine-3-carboxamide |
| 102 | 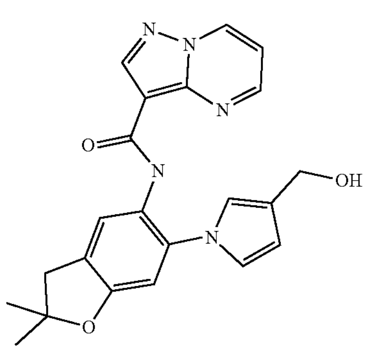 [SMILES: CC1(C)Cc2cc(NC(=O)c3cnn4cccnc34)c(-n3ccc(CO)c3)cc2O1] | N-[6-[4-(hydroxymethyl)imidazol-1-yl]-2,2-dimethyl-3H-benzofuran-5-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 103 | 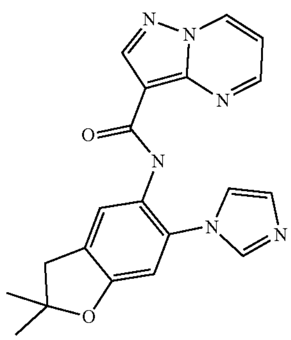 [SMILES: CC1(C)Cc2cc(NC(=O)c3cnn4cccnc34)c(-n3ccnc3)cc2O1] | N-(6-imidazol-1-yl-2,2-dimethyl-3H-benzofuran-5-yl)pyrazolo[1,5-a]pyrimidine-3-carboxamide |
| 104 | 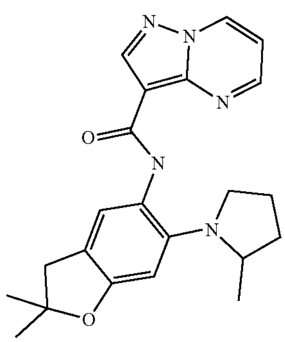 [SMILES: CC1CCCN1c1cc2c(cc1NC(=O)c1cnn3cccnc13)CC(C)(C)O2] | N-[2,2-dimethyl-6-(2-methylpyrrolidin-1-yl)-3H-benzofuran-5-yl]pyrazolo[1,5-a]pyrimidine-3-carboxamide |
| 105 | 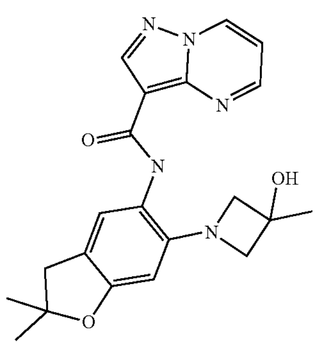 | N-[6-(3-hydroxy-3-methyl-azetidin-1-yl)-2,2-dimethyl-3H-benzofuran-5-yl]pyrazolo[1,5-a]pyrimidine-3-carboxamide |
| 106 | 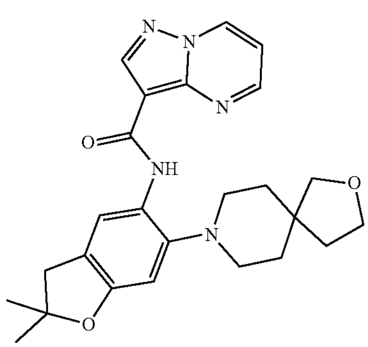 [SMILES: CC1(C)Cc2cc(NC(=O)c3cnn4cccnc34)c(N3CCC4(CCOC4)CC3)cc2O1] | N-[2,2-dimethyl-6-(2-oxa-8-azaspiro[4.5]decan-8-yl)-3H-benzofuran-5-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 107 | 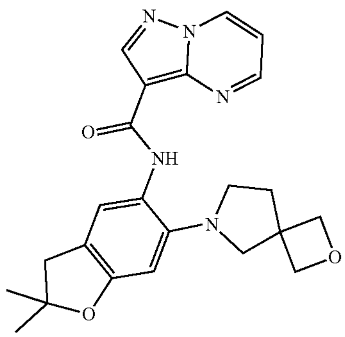 [SMILES: CC1(C)Cc2cc(NC(=O)c3cnn4cccnc34)c(N3CCC4(COC4)C3)cc2O1] | N-[2,2-dimethyl-6-(2-oxa-7-azaspiro[3.4]octan-7-yl)-3H-benzofuran-5-yl]pyrazolo[1,5-a]pyrimidine-3-carboxamide |
| 108 | 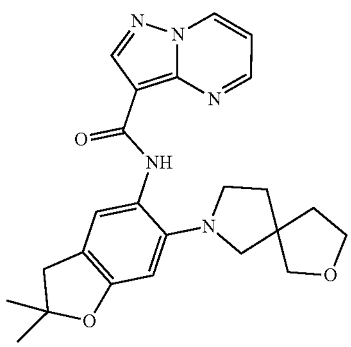 [SMILES: CC1(C)Cc2cc(NC(=O)c3cnn4cccnc34)c(N3CCC4(CCOC4)C3)cc2O1] | N-[2,2-dimethyl-6-(2-oxa-7-azaspiro[4.4]nonan-7-yl)-3H-benzofuran-5-yl]pyrazolo[1,5-a]pyrimidine-3-carboxamide |
| 109 | 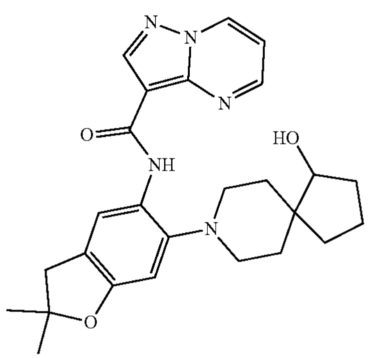 [SMILES: CC1(C)Cc2cc(NC(=O)c3cnn4cccnc34)c(N3CCC4(CCCC4O)CC3)cc2O1] | N-[6-(4-hydroxy-8-azaspiro[4.5]decan-8-yl)-2,2-dimethyl-3H-benzofuran-5-yl]pyrazolo[1,5-a]pyrimidine-3-carboxamide |
| 110 | 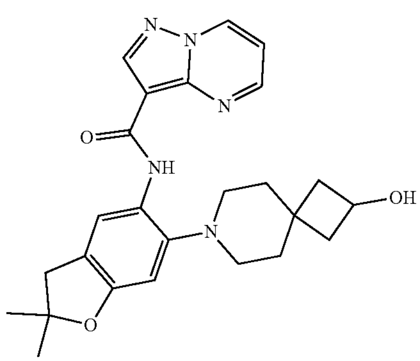 [SMILES: CC1(C)Cc2cc(NC(=O)c3cnn4cccnc34)c(N3CCC4(CC3)CC(O)C4)cc2O1] | N-[6-(2-hydroxy-7-azaspiro[3.5]nonan-7-yl)-2,2-dimethyl-3H-benzofuran-5-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
| --- | --- | --- |
| 111 | 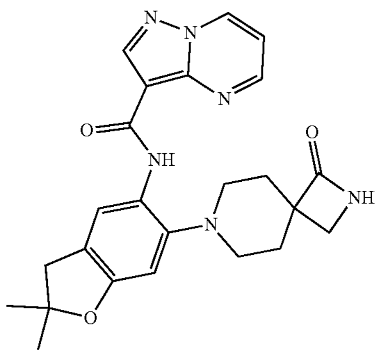 [SMILES: CC1(C)Cc2cc(NC(=O)c3cnn4cccnc34)c(N3CCC4(CC3)CNC4=O)cc2O1] | N-[2,2-dimethyl-6-(3-oxo-2,7-diazaspiro[3.5]nonan-7-yl)-3H-benzofuran-5-yl]pyrazolo[1,5-a]pyrimidine-3-carboxamide |
| 112 | 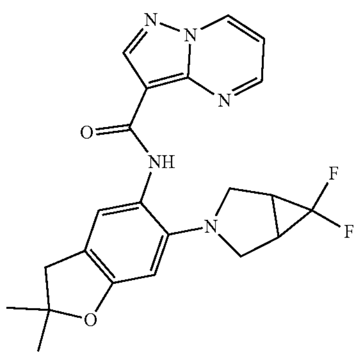 [SMILES: CC1(C)Cc2cc(NC(=O)c3cnn4cccnc34)c(N3CC4C(C3)C4(F)F)cc2O1] | N-[6-(6,6-difluoro-3-azabicyclo[3.1.0]hexan-3-yl)-2,2-dimethyl-3H-benzofuran-5-yl]pyrazolo[1,5-a]pyrimidine-3-carboxamide |
| 113 | 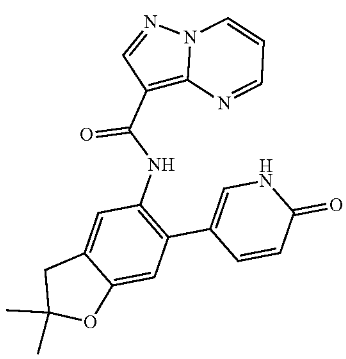 [SMILES: CC1(C)Cc2cc(NC(=O)c3cnn4cccnc34)c(-c3ccc(=O)[nH]c3)cc2O1] | N-[2,2-dimethyl-6-(6-oxo-1H-pyridin-3-yl)-3H-benzofuran-5-yl]pyrazolo[1,5-a]pyrimidine-3-carboxamide |
| 114 | 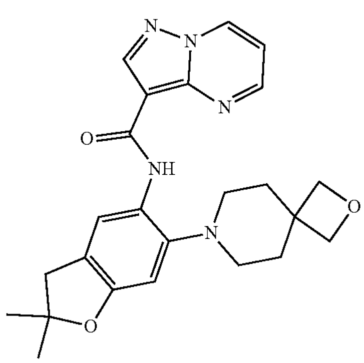 [SMILES: CC1(C)Cc2cc(NC(=O)c3cnn4cccnc34)c(N3CCC4(CC3)COC4)cc2O1] | N-[2,2-dimethyl-6-(2-oxa-7-azaspiro[3.5]nonan-7-yl)-3H-benzofuran-5-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 115 | 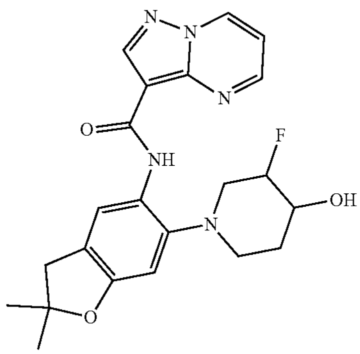 [SMILES: CC1(C)Cc2cc(NC(=O)c3cnn4cccnc34)c(N3CCC(O)C(F)C3)cc2O1] | N-[6-(3-fluoro-4-hydroxy-1-piperidyl)-2,2-dimethyl-3H-benzofuran-5-yl]pyrazolo[1,5-a]pyrimidine-3-carboxamide |
| 116 | 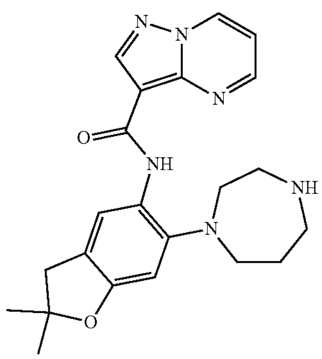 [SMILES: CC1(C)Cc2cc(NC(=O)c3cnn4cccnc34)c(N3CCCNCC3)cc2O1] | N-[6-(1,4-diazepan-1-yl)-2,2-dimethyl-3H-benzofuran-5-yl]pyrazolo[1,5-a]pyrimidine-3-carboxamide |
| 117 | 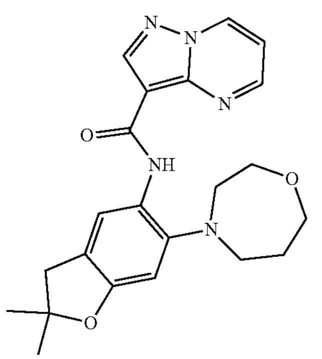 [SMILES: CC1(C)Cc2cc(NC(=O)c3cnn4cccnc34)c(N3CCCOCC3)cc2O1] | N-[2,2-dimethyl-6-(1,4-oxazepan-4-yl)-3H-benzofuran-5-yl]pyrazolo[1,5-a]pyrimidine-3-carboxamide |
| 118 | 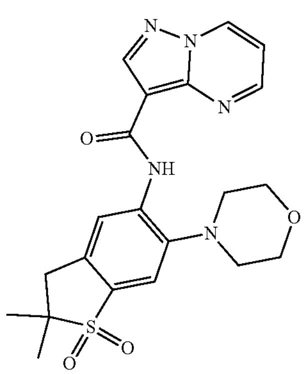 [SMILES: CC1(C)Cc2cc(NC(=O)c3cnn4cccnc34)c(N3CCOCC3)cc2S1(=O)=O] | N-(2,2-dimethyl-6-morpholino-1,1-dioxo-3H-benzothiophen-5-yl)pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 119 and 120 | 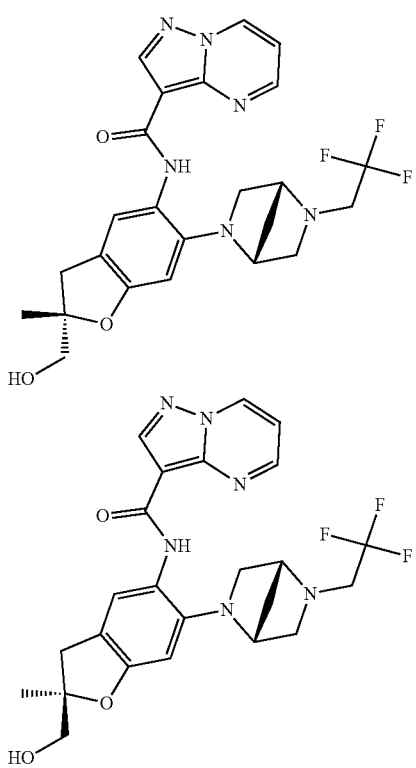 | N-[(2S)-2-(hydroxymethyl)-2-methyl-6-[(1R,4R)-5-(2,2,2-trifluoroethyl)-2,5-diazabicyclo[2.2.1]heptan-2-yl]-3H-benzofuran-5-yl]pyrazolo[1,5-a]pyrimidine-3-carboxamide and N-[3-[3-(2-hydroxyethyl)-2-oxo-imidazolidin-1-yl]-1-methyl-pyrazol-4-yl]-2-[2-(2,2,2-trifluoroethylamino)-4-pyridyl]oxazole-4-carboxamide |
| 121 and 122 | 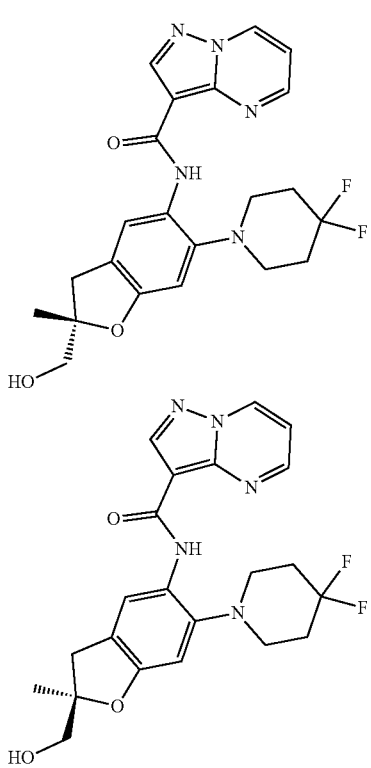 | N-[(2R)-6-(4,4-difluoro-1-piperidyl)-2-(hydroxymethyl)-2-methyl-3H-benzofuran-5-yl]pyrazolo[1,5-a]pyrimidine-3-carboxamide and N-[(2S)-6-(4,4-difluoro-1-piperidyl)-2-(hydroxymethyl)-2-methyl-3H-benzofuran-5-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 123 and 124 | 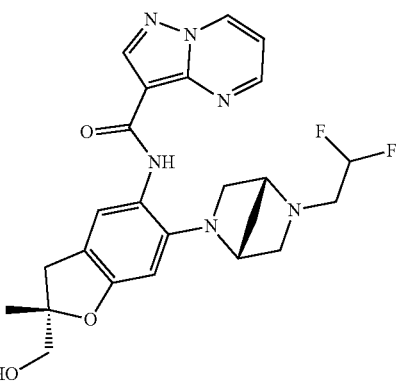 | N-[(2R)-6-[(1R,4R)-5-(2,2-difluoroethyl)-2,5-diazabicyclo[2.2.1]heptan-2-yl]-2-(hydroxymethyl)-2-methyl-3H-benzofuran-5-yl]pyrazolo[1,5-a]pyrimidine-3-carboxamide and N-[(2S)-6-[(1R,4R)-5-(2,2-difluoroethyl)-2,5-diazabicyclo[2.2.1]heptan-2-yl]-2-(hydroxymethyl)-2-methyl-3H-benzofuran-5-yl]pyrazolo[1,5-a]pyrimidine-3-carboxamide |
| 125 and 126 | 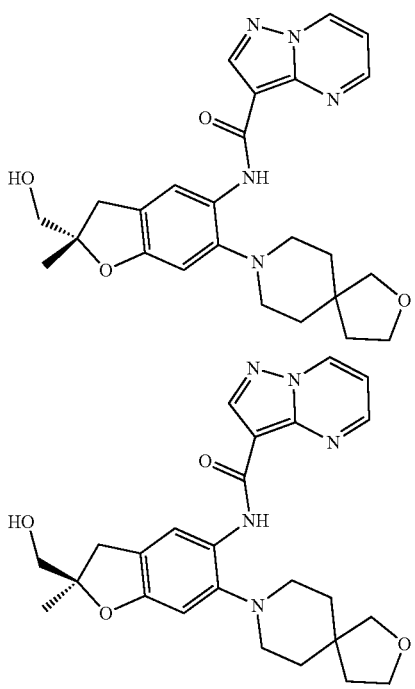 | N-[(2S)-2-(hydroxymethyl)-2-methyl-6-(2-oxa-8-azaspiro[4.5]decan-8-yl)-3H-benzofuran-5-yl]pyrazolo[1,5-a]pyrimidine-3-carboxamide and N-[(2R)-2-(hydroxymethyl)-2-methyl-6-(2-oxa-8-azaspiro[4.5]decan-8-yl)-3H-benzofuran-5-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 127 and 128 | | N-[(2R)-2-(hydroxymethyl)-2-methyl-6-(4-methylpiperazin-1-yl)-3H-benzofuran-5-yl]pyrazolo[1,5-a]pyrimidine-3-carboxamide and N-[(2S)-2-(hydroxymethyl)-2-methyl-6-(4-methylpiperazin-1-yl)-3H-benzofuran-5-yl]pyrazolo[1,5-a]pyrimidine-3-carboxamide |
| 129 and 130 | | N-[(2S)-2-(hydroxymethyl)-6-[4-(hydroxymethyl)-1-piperidyl]-2-methyl-3H-benzofuran-5-yl]pyrazolo[1,5-a]pyrimidine-3-carboxamide and N-[(2R)-2-(hydroxymethyl)-6-[4-(hydroxymethyl)-1-piperidyl]-2-methyl-3H-benzofuran-5-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 131 | 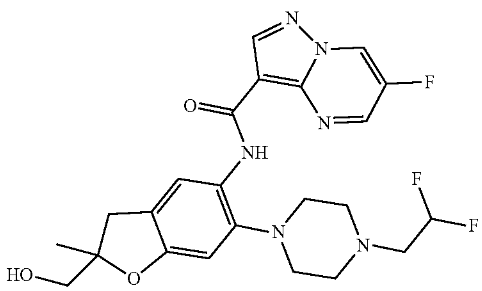 [SMILES: CC1(CO)Cc2cc(NC(=O)c3cnn4cc(F)cnc34)c(N3CCN(CC(F)F)CC3)cc2O1] | N-(6-(4-(2,2-difluoroethyl)piperazin-1-yl)-2-(hydroxymethyl)-2-methyl-2,3-dihydrobenzofuran-5-yl)-6-fluoropyrazolo[1,5-a]pyrimidine-3-carboxamide |
| 132 and 133 | | (S)-N-(6-(4-(2,2-Difluoroethyl)piperazin-1-yl)-2-(hydroxymethyl)-2-methyl-2,3-dihydrobenzofuran-5-yl)-6-fluoropyrazolo[1,5-a]pyrimidine-3-carboxamide<br>and<br>(R)-N-(6-(4-(2,2-Difluoroethyl)piperazin-1-yl)-2-(hydroxymethyl)-2-methyl-2,3-dihydrobenzofuran-5-yl)-6-fluoropyrazolo[1,5-a]pyrimidine-3-carboxamide |
| 134 and 135 | | (R)-N-(2-isopropyl-2-methyl-6-morpholino-2,3-dihydrobenzofuran-5-yl)pyrazolo[1,5-a]pyrimidine-3-carboxamide<br>and<br>(S)-N-(2-isopropyl-2-methyl-6-morpholino-2,3-dihydrobenzofuran-5-yl)pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 136 | 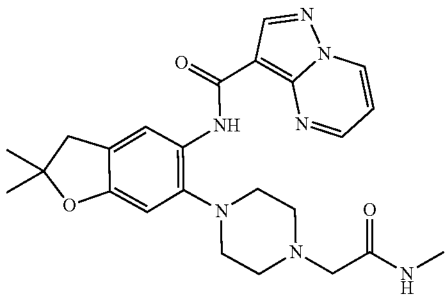 | N-(6-Methyl-2-morpholino-7-oxo-6,7-dihydro-5H-pyrrolo[3,4-b]pyridin-3-yl)pyrazolo[1,5-a]pyrimidine-3-carboxamide |
| 137 | 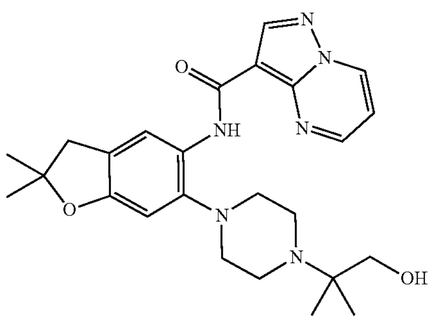 [SMILES: CC1(C)Cc2cc(NC(=O)c3cnn4cccnc34)c(N3CCN(C(C)(C)CO)CC3)cc2O1] | N-[6-[4-(2-Hydroxy-1,1-dimethyl-ethyl)piperazin-1-yl]-2,2-dimethyl-3H-benzofuran-5-yl]pyrazolo[1,5-a]pyrimidine-3-carboxamide |
| 138 | 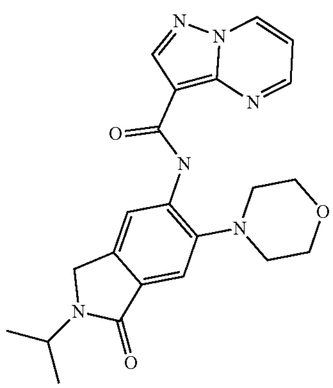 [SMILES: CC(C)N1Cc2cc(NC(=O)c3cnn4cccnc34)c(N3CCOCC3)cc2C1=O] | N-(2-isopropyl-6-morpholino-1-oxo-isoindolin-5-yl)pyrazolo[1,5-a]pyrimidine-3-carboxamide |
| 139 | 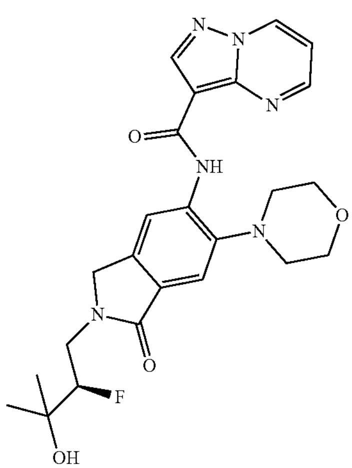 [SMILES: CC(C)(O)[C@H](F)CN1Cc2cc(NC(=O)c3cnn4cccnc34)c(N3CCOCC3)cc2C1=O] | N-[2-[(2R)-2-fluoro-3-hydroxy-3-methyl-butyl]-6-morpholino-1-oxo-isoindolin-5-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 140 | 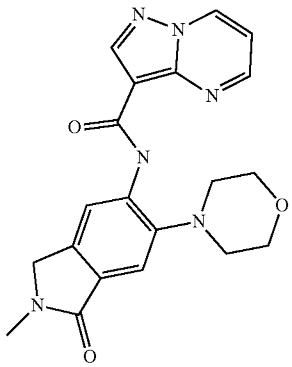 [SMILES: CN1Cc2cc(NC(=O)c3cnn4cccnc34)c(N3CCOCC3)cc2C1=O] | N-(2-methyl-6-morpholino-1-oxo-isoindolin-5-yl)pyrazolo[1,5-a]pyrimidine-3-carboxamide |
| 141 | 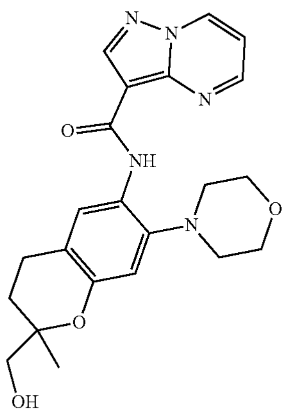 [SMILES: CC1(CO)CCc2cc(NC(=O)c3cnn4cccnc34)c(N3CCOCC3)cc2O1] | N-[2-(hydroxymethyl)-2-methyl-7-morpholino-chroman-6-yl]pyrazolo[1,5-a]pyrimidine-3-carboxamide |
| 142 | 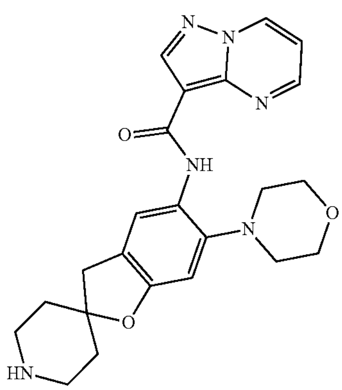 [SMILES: O=C(Nc1cc2c(cc1N1CCOCC1)OC1(CCNCC1)C2)c1cnn2cccnc12] | N-(6-morpholinospiro[3H-benzofuran-2,4'-piperidine]-5-yl)pyrazolo[1,5-a]pyrimidine-3-carboxamide |
| 143 | 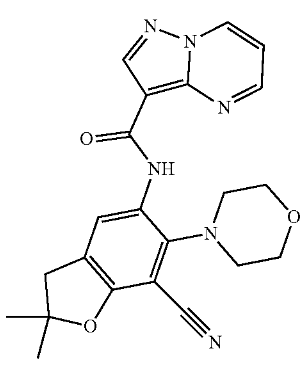 [SMILES: CC1(C)Cc2cc(NC(=O)c3cnn4cccnc34)c(N3CCOCC3)c(C#N)c2O1] | N-(7-cyano-2,2-dimethyl-6-morpholino-3H-benzofuran-5-yl)pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
| --- | --- | --- |
| 144 | 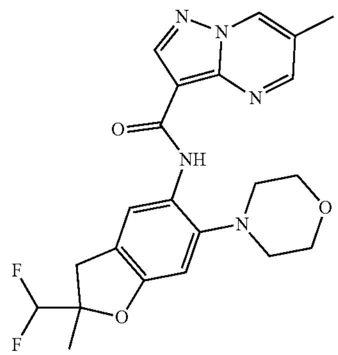 [SMILES: Cc1cnc2c(C(=O)Nc3cc4c(cc3N3CCOCC3)OC(C)(C(F)F)C4)cnn2c1] | N-[2-(difluoromethyl)-2-methyl-6-morpholino-3H-benzofuran-5-yl]-6-methyl-pyrazolo[1,5-a]pyrimidine-3-carboxamide |
| 145 | 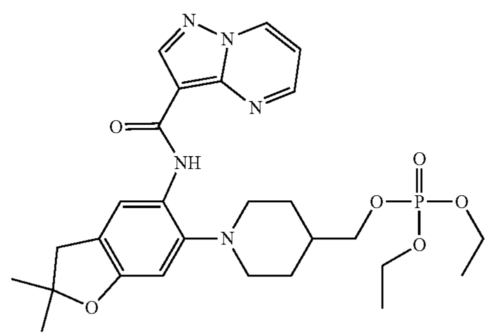 [SMILES: CCOP(=O)(OCC)OCC1CCN(c2cc3c(cc2NC(=O)c2cnn4cccnc24)CC(C)(C)O3)CC1] | [1-[2,2-dimethyl-5-(pyrazolo[1,5-a]pyrimidine-3-carbonylamino)-3H-benzofuran-6-yl]-4-piperidyl]methyl diethyl phosphate |
| 146 | 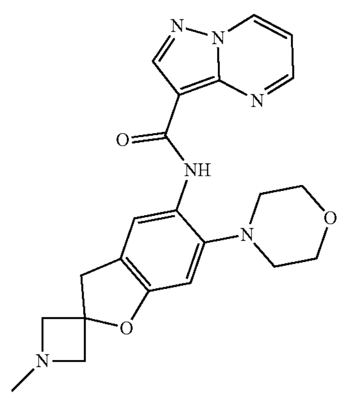 [SMILES: CN1CC2(Cc3cc(NC(=O)c4cnn5cccnc45)c(N4CCOCC4)cc3O2)C1] | N-(1-methyl-6'-morpholino-3'H-spiro[azetidine-3,2'-benzofuran]-5'-yl)pyrazolo[1,5-a]pyrimidine-3-carboxamide |
| 147 | 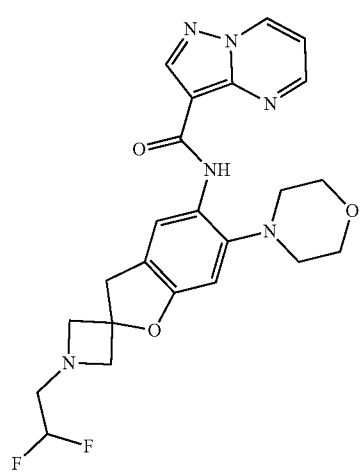 [SMILES: O=C(Nc1cc2c(cc1N1CCOCC1)OC1(C2)CN(CC(F)F)C1)c1cnn2cccnc12] | N-[1'-(2,2-difluoroethyl)-6-morpholino-spiro[3H-benzofuran-2,3'-azetidine]-5-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 148 | 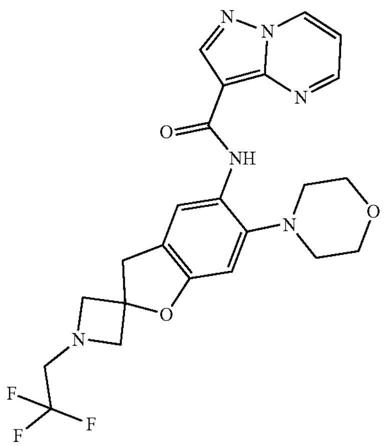 [SMILES: O=C(Nc1cc2c(cc1N1CCOCC1)OC1(C2)CN(CC(F)(F)F)C1)c1cnn2cccnc12] | N-[6-morpholino-1'-(2,2,2-trifluoroethyl)spiro[3H-benzofuran-2,3'-azetidine]-5-yl]pyrazolo[1,5-a]pyrimidine-3-carboxamide |
| 149 | 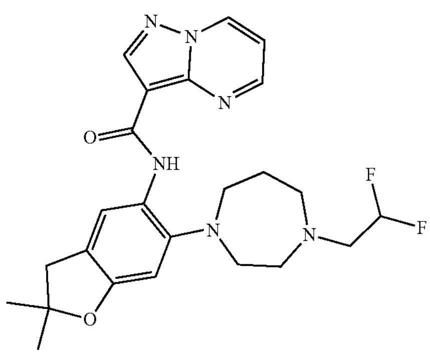 [SMILES: CC1(C)Cc2cc(NC(=O)c3cnn4cccnc34)c(N3CCCN(CC(F)F)CC3)cc2O1] | N-[6-[4-(2,2-difluoroethyl)-1,4-diazepan-1-yl]-2,2-dimethyl-3H-benzofuran-5-yl]pyrazolo[1,5-a]pyrimidine-3-carboxamide |
| 150 | 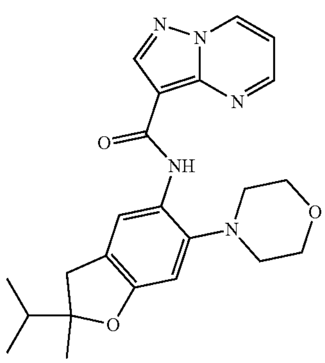 [SMILES: CC(C)C1(C)Cc2cc(NC(=O)c3cnn4cccnc34)c(N3CCOCC3)cc2O1] | N-(2-isopropyl-2-methyl-6-morpholino-3H-benzofuran-5-yl)pyrazolo[1,5-a]pyrimidine-3-carboxamide |
| 151 | 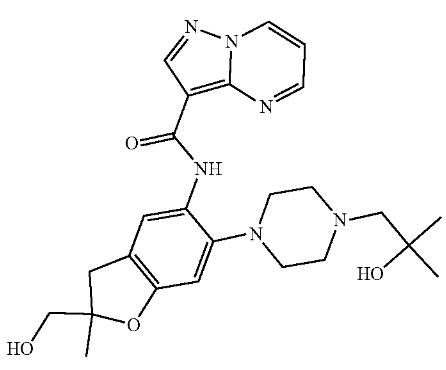 [SMILES: CC(C)(O)CN1CCN(c2cc3c(cc2NC(=O)c2cnn4cccnc24)CC(C)(CO)O3)CC1] | N-[2-(hydroxymethyl)-6-[4-(2-hydroxy-2-methyl-propyl)piperazin-1-yl]-2-methyl-3H-benzofuran-5-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 152 | 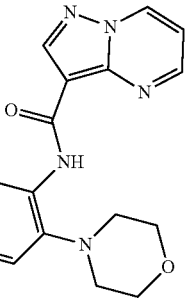 | N-(1'-methyl-6-morpholino-spiro[3H-benzofuran-2,4'-piperidine]-5-yl)pyrazolo[1,5-a]pyrimidine-3-carboxamide |
| 153 and 154 | 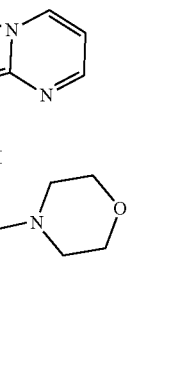 | N-[(2R)-2-(hydroxymethyl)-6-morpholino-2-(trifluoromethyl)-3H-benzofuran-5-yl]pyrazolo[1,5-a]pyrimidine-3-carboxamide and N-[(2S)-2-(hydroxymethyl)-6-morpholino-2-(trifluoromethyl)-3H-benzofuran-5-yl]pyrazolo[1,5-a]pyrimidine-3-carboxamide |
| 155 and 156 | 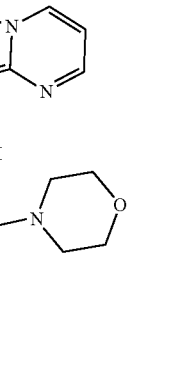 | N-[(2S)-2-(difluoromethoxymethyl)-2-methyl-6-morpholino-3H-benzofuran-5-yl]pyrazolo[1,5-a]pyrimidine-3-carboxamide and N-[(2R)-2-(difluoromethoxymethyl)-2-methyl-6-morpholino-3H-benzofuran-5-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 157 and 158 | 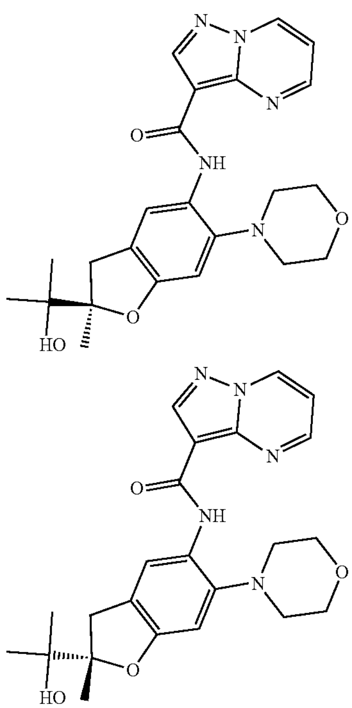 | N-[(2R)-2-(1-hydroxy-1-methyl-ethyl)-2-methyl-6-morpholino-3H-benzofuran-5-yl]pyrazolo[1,5-a]pyrimidine-3-carboxamide and N-[(2S)-2-(1-hydroxy-1-methyl-ethyl)-2-methyl-6-morpholino-3H-benzofuran-5-yl]pyrazolo[1,5-a]pyrimidine-3-carboxamide |
| 159 and 160 | 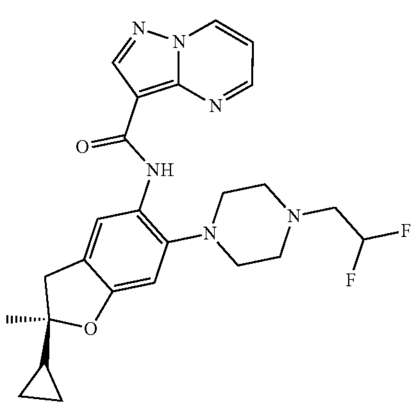 | N-[(2R)-2-cyclopropyl-6-[4-(2,2-difluoroethyl)piperazin-1-yl]-2-methyl-3H-benzofuran-5-yl]pyrazolo[1,5-a]pyrimidine-3-carboxamide and N-[(2S)-2-cyclopropyl-6-[4-(2,2-difluoroethyl)piperazin-1-yl]-2-methyl-3H-benzofuran-5-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 161 and 162 | | N-[(2R)-2-cyclopropyl-6-[4-fluoro-4-(hydroxymethyl)-1-piperidyl]-2-methyl-3H-benzofuran-5-yl]pyrazolo[1,5-a]pyrimidine-3-carboxamide and N-[(2S)-2-cyclopropyl-6-[4-fluoro-4-(hydroxymethyl)-1-piperidyl]-2-methyl-3H-benzofuran-5-yl]pyrazolo[1,5-a]pyrimidine-3-carboxamide |
| 163 and 164 | 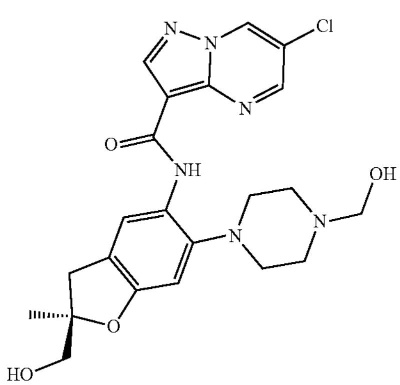 | 6-chloro-N-[(2S)-2-(hydroxymethyl)-6-[4-(hydroxymethyl)-1-piperidyl]-2-methyl-3H-benzofuran-5-yl]pyrazolo[1,5-a]pyrimidine-3-carboxamide and 6-chloro-N-[(2R)-2-(hydroxymethyl)-6-[4-(hydroxymethyl)-1-piperidyl]-2-methyl-3H-benzofuran-5-yl]pyrazolo[1,5-a]pyrimidine-3-carboxamide |

TABLE 1-continued

Exemplary compounds of the present invention. Salts of such compounds are also contemplated. See the Examples section for preparation of such compounds.

| Ex. | Structure | Name |
|---|---|---|
| 165 and 166 | | 6-chloro-N-[(2S)-2-(hydroxymethyl)-2-methyl-6-morpholino-3H-benzofuran-5-yl]pyrazolo[1,5-a]pyrimidine-3-carboxamide and 6-chloro-N-[(2R)-2-(hydroxymethyl)-2-methyl-6-morpholino-3H-benzofuran-5-yl]pyrazolo[1,5-a]pyrimidine-3-carboxamide |
| 167 | 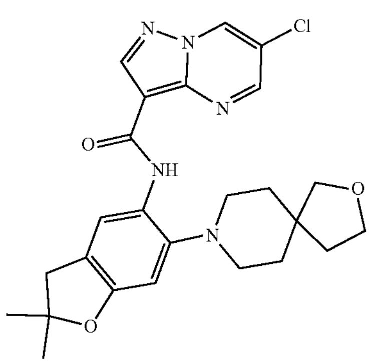 [SMILES: CC1(C)Cc2cc(NC(=O)c3cnn4cc(Cl)cnc34)c(N3CCC4(CCOC4)CC3)cc2O1] | 6-chloro-N-[2,2-dimethyl-6-(2-oxa-8-azaspiro[4.5]decan-8-yl)-3H-benzofuran-5-yl]pyrazolo[1,5-a]pyrimidine-3-carboxamide |

TABLE 2

*Additional exemplary compounds of the present invention. Salts of such compounds are also contemplated. See the Examples section for preparation of such compounds.*

| | | |
|---|---|---|
| 168 | 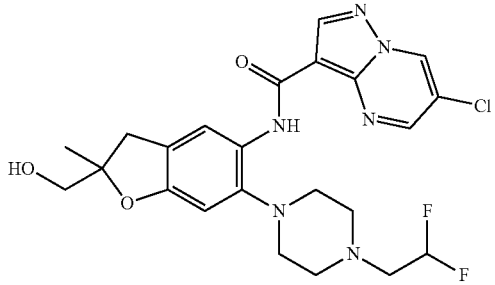 [SMILES: CC1(CO)Cc2cc(NC(=O)c3cnn4cc(Cl)cnc34)c(N3CCN(CC(F)F)CC3)cc2O1] | N-(6-(4-(2,2-Difluoroethyl)piperazin-1-yl)-2-(hydroxymethyl)-2-methyl-2,3-dihydrobenzofuran-5-yl)-6-methylpyrazolo[1,5-a]pyrimidine-3-carboxamide |
| 169 and 170 | 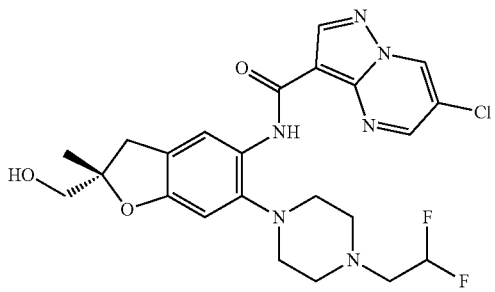<br>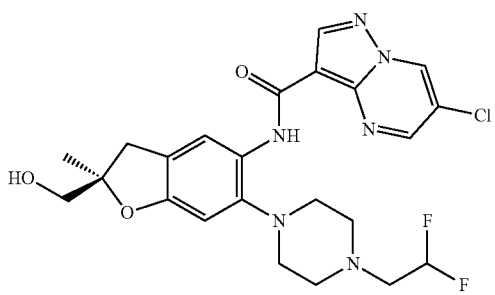 | (S)-6-Chloro-N-(6-(4-(2,2-difluoroethyl)piperazin-1-yl)-2-(hydroxymethyl)-2-methyl-2,3-dihydrobenzofuran-5-yl)pyrazolo[1,5-a]pyrimidine-3-carboxamide<br>and<br>(R)-6-Chloro-N-(6-(4-(2,2-difluoroethyl)piperazin-1-yl)-2-(hydroxymethyl)-2-methyl-2,3-dihydrobenzofuran-5-yl)pyrazolo[1,5-a]pyrimidine-3-carboxamide (absolute stereochemistry assigned arbitrarily) |
| 171 and 172 | 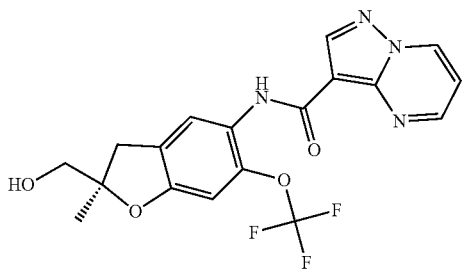<br>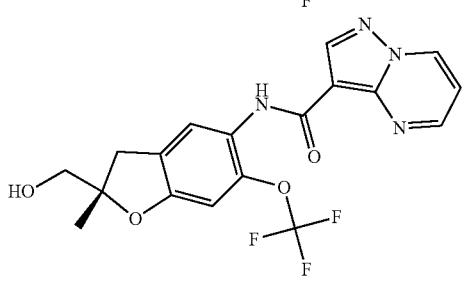 | (R)-N-(2-(Hydroxymethyl)-2-methyl-6-(trifluoromethoxy)-2,3-dihydrobenzofuran-5-yl)pyrazolo[1,5-a]pyrimidine-3-carboxamide<br>and<br>(S)-N-(2-(hydroxymethyl)-2-methyl-6-(trifluoromethoxy)-2,3-dihydrobenzofuran-5-yl)pyrazolo[1,5-a]pyrimidine-3-carboxamide |

TABLE 2-continued

*Additional exemplary compounds of the present invention. Salts of such compounds are also contemplated. See the Examples section for preparation of such compounds.*

| 173 | 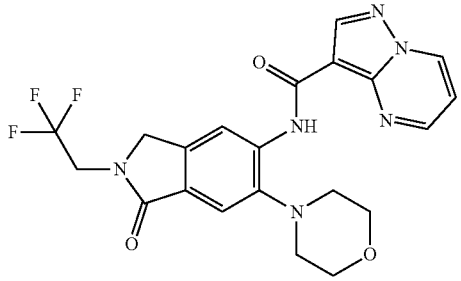 [SMILES: O=C(Nc1cc2c(cc1N1CCOCC1)C(=O)N(CC(F)(F)F)C2)c1cnn2cccnc12] | N-[6-Morpholino-1-oxo-2-(2,2,2-trifluoroethyl)isoindolin-5-yl]pyrazolo[1,5-a]pyrimidine-3-carboxamide |
| 174 | 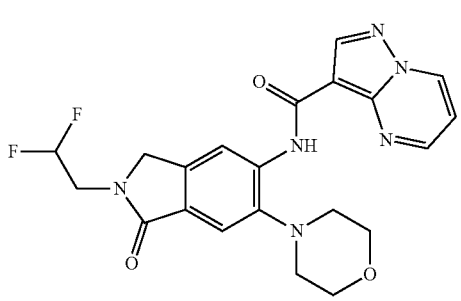 [SMILES: O=C(Nc1cc2c(cc1N1CCOCC1)C(=O)N(CC(F)F)C2)c1cnn2cccnc12] | N-[2-(2,2-difluoroethyl)-6-morpholino-1-oxo-isoindolin-5-yl]pyrazolo[1,5-a]pyrimidine-3-carboxamide |
| 175 | 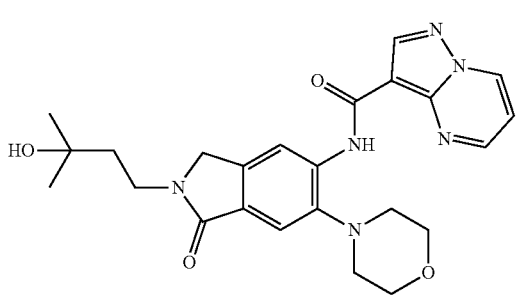 [SMILES: CC(C)(O)CCN1Cc2cc(NC(=O)c3cnn4cccnc34)c(N3CCOCC3)cc2C1=O] | N-[2-(3-hydroxy-3-methyl-butyl)-6-morpholino-1-oxo-isoindolin-5-yl]pyrazolo[1,5-a]pyrimidine-3-carboxamide |
| 176 | 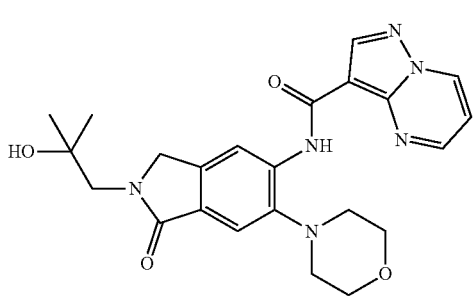 [SMILES: CC(C)(O)CN1Cc2cc(NC(=O)c3cnn4cccnc34)c(N3CCOCC3)cc2C1=O] | N-[2-(2-hydroxy-2-methyl-propyl)-6-morpholino-1-oxo-isoindolin-5-yl]pyrazolo[1,5-a]pyrimidine-3-carboxamide |
| 177 | 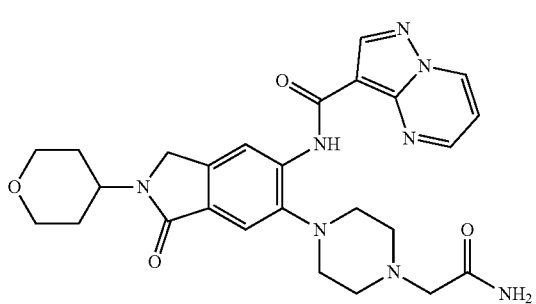 [SMILES: NC(=O)CN1CCN(c2cc3c(cc2NC(=O)c2cnn4cccnc24)CN(C2CCOCC2)C3=O)CC1] | N-[6-[4-(2-amino-2-oxo-ethyl)piperazin-1-yl]-1-oxo-2-tetrahydropyran-4-yl-isoindolin-5-yl]pyrazolo[1,5-a]pyrimidine-3-carboxamide |

TABLE 2-continued

*Additional exemplary compounds of the present invention. Salts of such compounds are also contemplated. See the Examples section for preparation of such compounds.*

| | | |
|---|---|---|
| 178 | 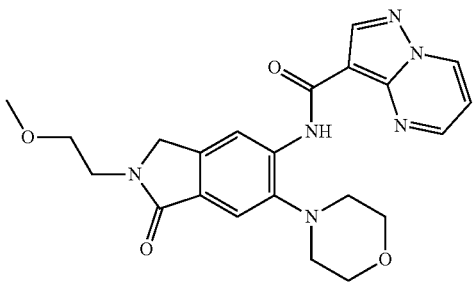 [SMILES: COCCN1Cc2cc(NC(=O)c3cnn4cccnc34)c(N3CCOCC3)cc2C1=O] | N-[2-(2-methoxyethyl)-6-morpholino-1-oxo-isoindolin-5-yl]pyrazolo[1,5-a]pyrimidine-3-carboxamide |
| 179 | 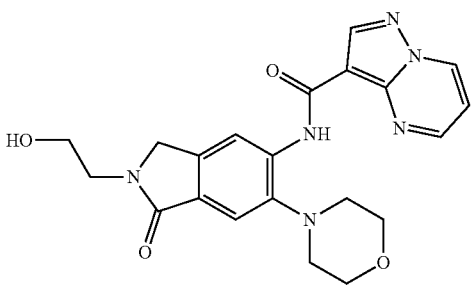 [SMILES: O=C(Nc1cc2c(cc1N1CCOCC1)C(=O)N(CCO)C2)c1cnn2cccnc12] | N-[2-(2-hydroxyethyl)-6-morpholino-1-oxo-isoindolin-5-yl]pyrazolo[1,5-a]pyrimidine-3-carboxamide |
| 180 | 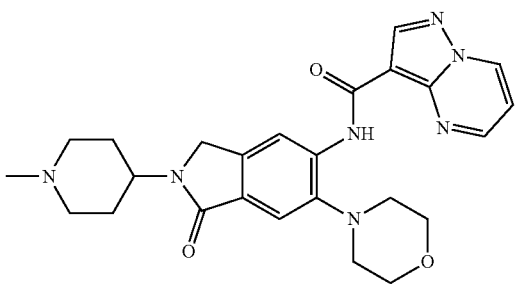 [SMILES: CN1CCC(N2Cc3cc(NC(=O)c4cnn5cccnc45)c(N4CCOCC4)cc3C2=O)CC1] | N-[2-(1-methyl-4-piperidyl)-6-morpholino-1-oxo-isoindolin-5-yl]pyrazolo[1,5-a]pyrimidine-3-carboxamide |
| 181 | 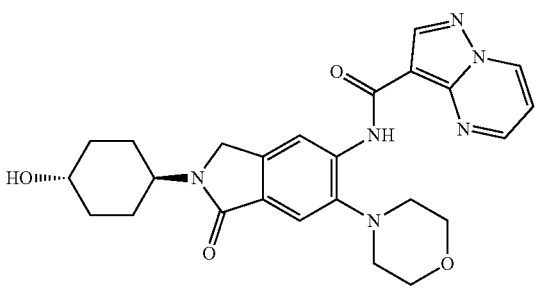 [SMILES: O=C(Nc1cc2c(cc1N1CCOCC1)C(=O)N([C@H]1CC[C@H](O)CC1)C2)c1cnn2cccnc12] | N-[2-(4-hydroxycyclohexyl)-6-morpholino-1-oxo-isoindolin-5-yl]pyrazolo[1,5-a]pyrimidine-3-carboxamide |
| 182 | 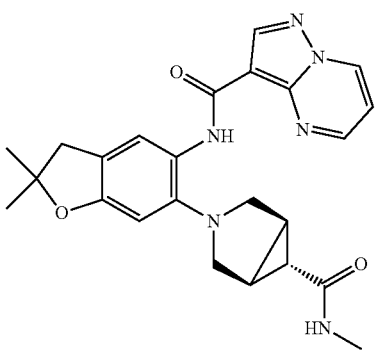 [SMILES: CNC(=O)[C@H]1[C@@H]2CN(c3cc4c(cc3NC(=O)c3cnn5cccnc35)CC(C)(C)O4)C[C@@H]21] | N-[2,2-dimethyl-6-[(1S,5R)-6-(methylcarbamoyl)-3-azabicyclo[3.1.0]hexan-3-yl]-3H-benzofuran-5-yl]pyrazolo[1,5-a]pyrimidine-3-carboxamide |

TABLE 2-continued

*Additional exemplary compounds of the present invention. Salts of such compounds are also contemplated. See the Examples section for preparation of such compounds.*

| | | |
|---|---|---|
| 183 | 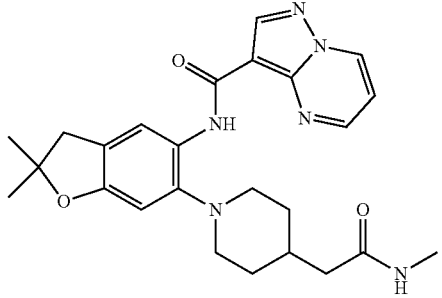 | N-[2,2-dimethyl-6-[4-[2-(methylamino)-2-oxo-ethyl]-1-piperidyl]-3H-benzofuran-5-yl]pyrazolo[1,5-a]pyrimidine-3-carboxamide |
| 184 | 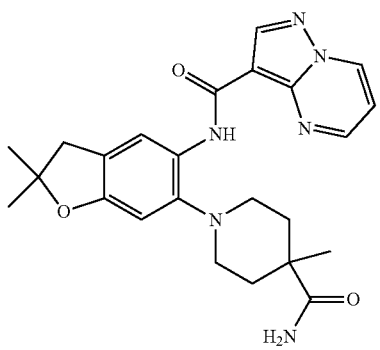 [SMILES: CC1(C)Cc2cc(NC(=O)c3cnn4cccnc34)c(N3CCC(C)(C(N)=O)CC3)cc2O1] | N-[6-(4-carbamoyl-4-methyl-1-piperidyl)-2,2-dimethyl-3H-benzofuran-5-yl]pyrazolo[1,5-a]pyrimidine-3-carboxamide |
| 185 | 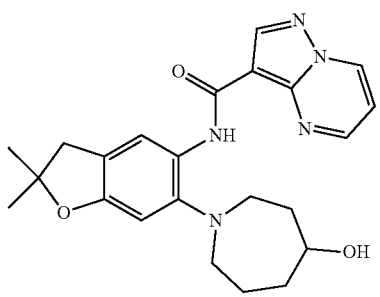 [SMILES: CC1(C)Cc2cc(NC(=O)c3cnn4cccnc34)c(N3CCCC(O)CC3)cc2O1] | N-[6-(4-hydroxyazepan-1-yl)-2,2-dimethyl-3H-benzofuran-5-yl]pyrazolo[1,5-a]pyrimidine-3-carboxamide |
| 186 | 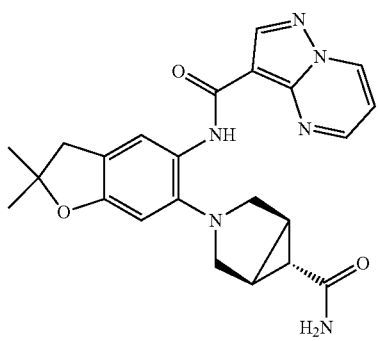 [SMILES: CC1(C)Cc2cc(NC(=O)c3cnn4cccnc34)c(N3C[C@@H]4[C@H](C3)[C@H]4C(N)=O)cc2O1] | N[6-[(1S,5R)-6-carbamoyl-3-azabicyclo[3.1.0]hexan-3-yl]-2,2-dimethyl-3H-benzofuran-5-yl]pyrazolo[1,5-a]pyrimidine-3-carboxamide |
| 187 | 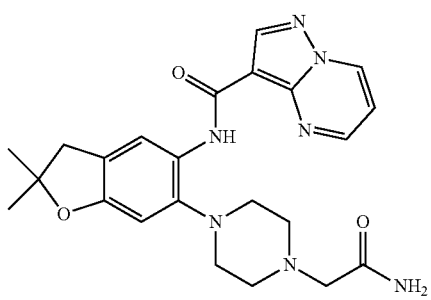 [SMILES: CC1(C)Cc2cc(NC(=O)c3cnn4cccnc34)c(N3CCN(CC(N)=O)CC3)cc2O1] | N-[6-[4-(2-amino-2-oxo-ethyl)piperazin-1-yl]-2,2-dimethyl-3H-benzofuran-5-yl]pyrazolo[1,5-a]pyrimidine-3-carboxamide |

TABLE 2-continued

*Additional exemplary compounds of the present invention. Salts of such compounds are also contemplated. See the Examples section for preparation of such compounds.*

| 188 | 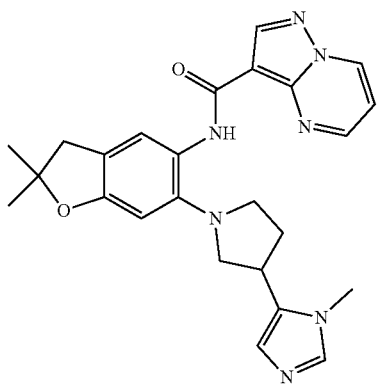 [SMILES: Cn1cncc1C1CCN(c2cc3c(cc2NC(=O)c2cnn4cccnc24)CC(C)(C)O3)C1] | N-[2,2-dimethyl-6-[3-(3-methylimidazol-4-yl)pyrrolidin-1-yl]-3H-benzofuran-5-yl]pyrazolo[1,5-a]pyrimidine-3-carboxamide |
| 189 | 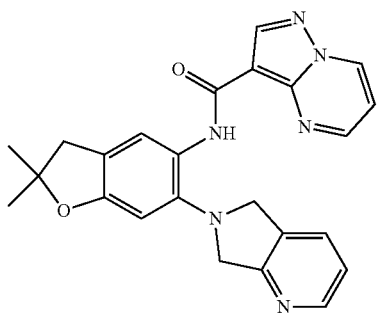 [SMILES: CC1(C)Cc2cc(NC(=O)c3cnn4cccnc34)c(N3Cc4cccnc4C3)cc2O1] | N-[6-(5,7-dihydropyrrolo[3,4-b]pyridin-6-yl)-2,2-dimethyl-3H-benzofuran-5-yl]pyrazolo[1,5-a]pyrimidine-3-carboxamide |
| 190 | 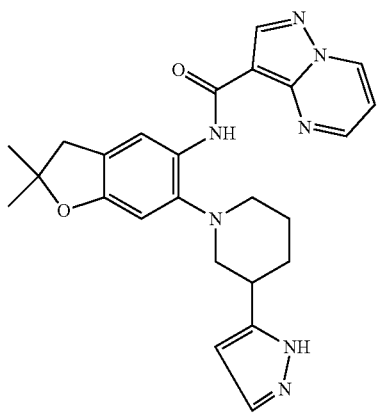 [SMILES: CC1(C)Cc2cc(NC(=O)c3cnn4cccnc34)c(N3CCCC(c4ccn[nH]4)C3)cc2O1] | N-[2,2-dimethyl-6-[3-(1H-pyrazol-5-yl)-1-piperidyl]-3H-benzofuran-5-yl]pyrazolo[1,5-a]pyrimidine-3-carboxamide |
| 191 | 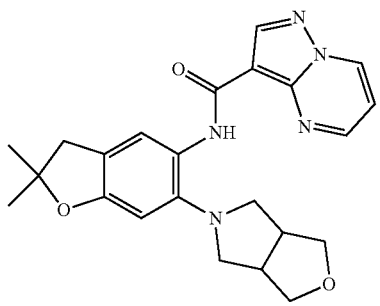 [SMILES: CC1(C)Cc2cc(NC(=O)c3cnn4cccnc34)c(N3CC4COCC4C3)cc2O1] | N-[6-(1,3,3a,4,6,6a-hexahydrofuro[3,4-c]pyrrol-5-yl)-2,2-dimethyl-3H-benzofuran-5-yl]pyrazolo[1,5-a]pyrimidine-3-carboxamide |

TABLE 2-continued

*Additional exemplary compounds of the present invention. Salts of such compounds are also contemplated. See the Examples section for preparation of such compounds.*

| | | |
|---|---|---|
| 192 | 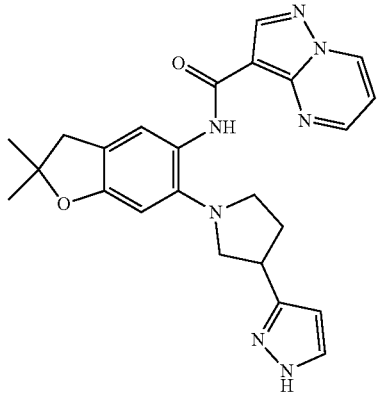 [SMILES: CC1(C)Cc2cc(NC(=O)c3cnn4cccnc34)c(N3CCC(c4cc[nH]n4)C3)cc2O1] | N-[2,2-dimethyl-6-[3-(1H-pyrazol-3-yl)pyrrolidin-1-yl]-3H-benzofuran-5-yl]pyrazolo[1,5-a]pyrimidine-3-carboxamide |
| 193 | 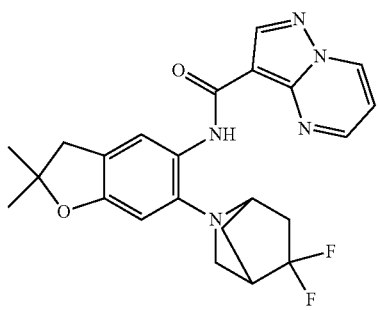 [SMILES: CC1(C)Cc2cc(NC(=O)c3cnn4cccnc34)c(N3CC4CC3CC4(F)F)cc2O1] | N-[6-(5,5-difluoro-2-azabicyclo[2.2.1]heptan-2-yl)-2,2-dimethyl-3H-benzofuran-5-yl]pyrazolo[1,5-a]pyrimidine-3-carboxamide |
| 194 | 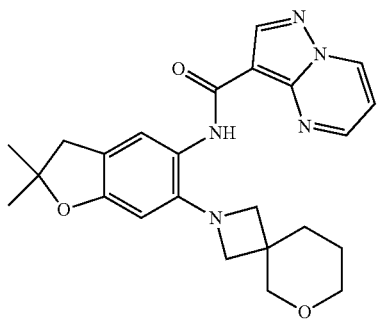 [SMILES: CC1(C)Cc2cc(NC(=O)c3cnn4cccnc34)c(N3CC4(CCCOC4)C3)cc2O1] | N-[2,2-dimethyl-6-(6-oxa-2-azaspiro[3.5]nonan-2-yl)-3H-benzofuran-5-yl]pyrazolo[1,5-a]pyrimidine-3-carboxamide |
| 195 | 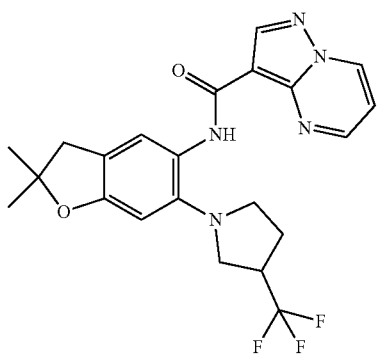 [SMILES: CC1(C)Cc2cc(NC(=O)c3cnn4cccnc34)c(N3CCC(C(F)(F)F)C3)cc2O1] | N-[2,2-dimethyl-6-[3-(trifluoromethyl)pyrrolidin-1-yl]-3H-benzofuran-5-yl]pyrazolo[1,5-a]pyrimidine-3-carboxamide |

TABLE 2-continued

*Additional exemplary compounds of the present invention. Salts of such compounds are also contemplated. See the Examples section for preparation of such compounds.*

| | | |
|---|---|---|
| 196 | 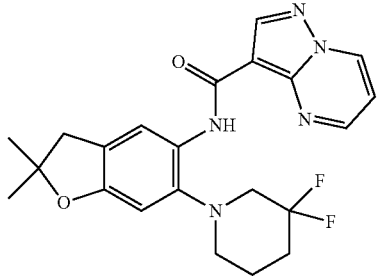 [SMILES: CC1(C)Cc2cc(NC(=O)c3cnn4cccnc34)c(N3CCCC(F)(F)C3)cc2O1] | N-(6-(3,3-difluoropiperidin-1-yl)-2,2-dimethyl-2,3-dihydrobenzofuran-5-yl)pyrazolo[1,5-a]pyrimidine-3-carboxamide |
| 197 |  | N-(6-((3aR,6aS)-5,5-difluorohexahydrocyclopenta[c]pyrrol-2(1H)-yl)-2,2-dimethyl-2,3-dihydrobenzofuran-5-yl)pyrazolo[1,5-a]pyrimidine-3-carboxamide |
| 198 | 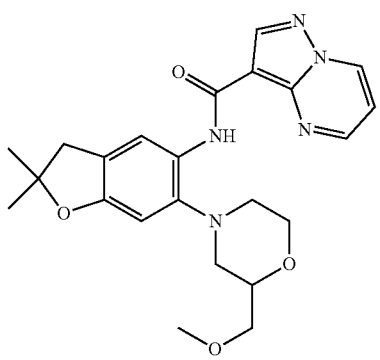 [SMILES: COCC1CN(c2cc3c(cc2NC(=O)c2cnn4cccnc24)CC(C)(C)O3)CCO1] | N-(6-(2-(methoxymethyl)morpholino)-2,2-dimethyl-2,3-dihydrobenzofuran-5-yl)pyrazolo[1,5-a]pyrimidine-3-carboxamide |
| 199 | 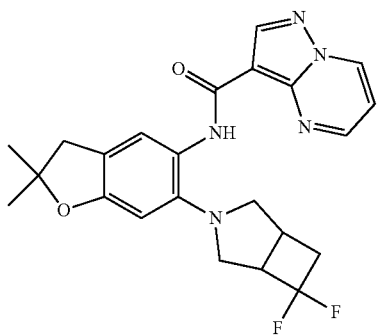 [SMILES: CC1(C)Cc2cc(NC(=O)c3cnn4cccnc34)c(N3CC4CC(F)(F)C4C3)cc2O1] | N-(6-(6,6-difluoro-3-azabicyclo[3.2.0]heptan-3-yl)-2,2-dimethyl-2,3-dihydrobenzofuran-5-yl)pyrazolo[1,5-a]pyrimidine-3-carboxamide |

TABLE 2-continued

*Additional exemplary compounds of the present invention. Salts of such compounds are also contemplated. See the Examples section for preparation of such compounds.*

| 200 | 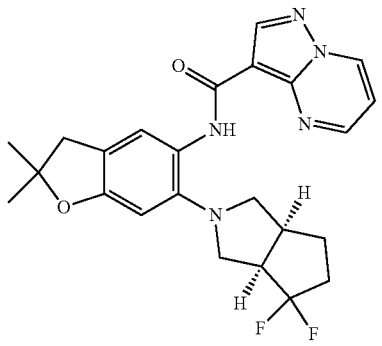 [SMILES: CC1(C)Cc2cc(NC(=O)c3cnn4cccnc34)c(N3C[C@H]4CCC(F)(F)[C@H]4C3)cc2O1] | N-(6-[((3aR,6aS)-4,4-difluorohexahydrocyclopenta[c]pyrrol-2(1H)-yl)-2,2-dimethyl-2,3-dihydrobenzofuran-5-yl)pyrazolo[1,5-a]pyrimidine-3-carboxamide |
| 201 | 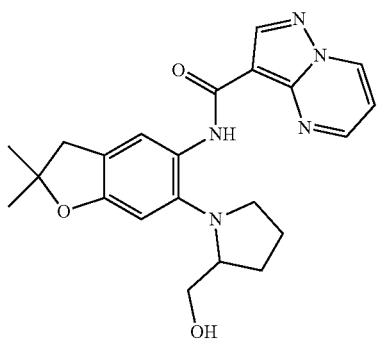 [SMILES: CC1(C)Cc2cc(NC(=O)c3cnn4cccnc34)c(N3CCCC3CO)cc2O1] | N-(6-(2-(hydroxymethyl)pyrrolidin-1-yl)-2,2-dimethyl-2,3-dihydrobenzofuran-5-yl)pyrazolo[1,5-a]pyrimidine-3-carboxamide |
| 202 | 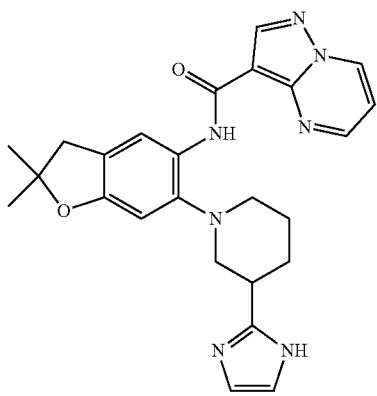 [SMILES: CC1(C)Cc2cc(NC(=O)c3cnn4cccnc34)c(N3CCCC(c4ncc[nH]4)C3)cc2O1] | N-(6-(3-(1H-imidazol-2-yl)piperidin-1-yl)-2,2-dimethyl-2,3-dihydrobenzofuran-5-yl)pyrazolo[1,5-a]pyrimidine-3-carboxamide |
| 203 | 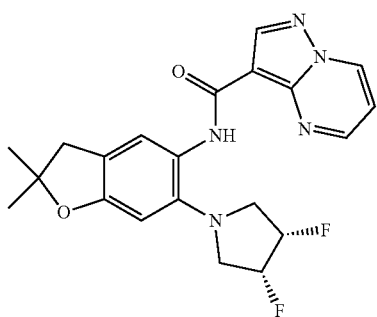 [SMILES: CC1(C)Cc2cc(NC(=O)c3cnn4cccnc34)c(N3C[C@@H](F)[C@@H](F)C3)cc2O1] | N-(6-[((3R,4S)-3,4-difluoropyrrolidin-1-yl)-2,2-dimethyl-2,3-dihydrobenzofuran-5-yl)pyrazolo[1,5-a]pyrimidine-3-carboxamide |

TABLE 2-continued

*Additional exemplary compounds of the present invention. Salts of such compounds are also contemplated. See the Examples section for preparation of such compounds.*

| | | |
|---|---|---|
| 204 | 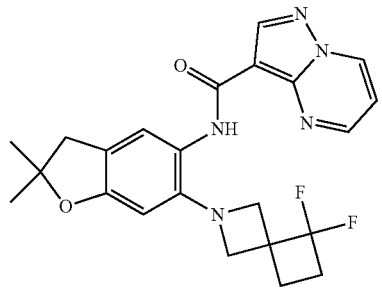 [SMILES: CC1(C)Cc2cc(NC(=O)c3cnn4cccnc34)c(N3CC4(CCC4(F)F)C3)cc2O1] | N-(6-(5,5-difluoro-2-azaspiro[3.3]heptan-2-yl)-2,2-dimethyl-2,3-dihydrobenzofuran-5-yl)pyrazolo[1,5-a]pyrimidine-3-carboxamide |
| 205 | 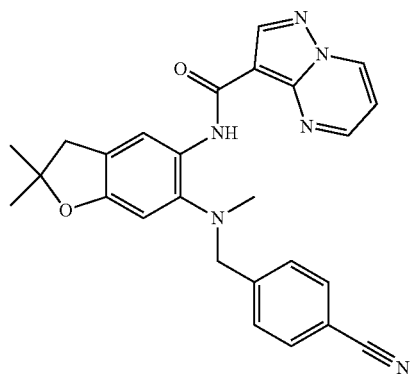 [SMILES: CN(Cc1ccc(C#N)cc1)c1cc2c(cc1NC(=O)c1cnn3cccnc13)CC(C)(C)O2] | N-(6-((4-cyanobenzyl)(methyl)amino)-2,2-dimethyl-2,3-dihydrobenzofuran-5-yl)pyrazolo[1,5-a]pyrimidine-3-carboxamide |
| 206 | 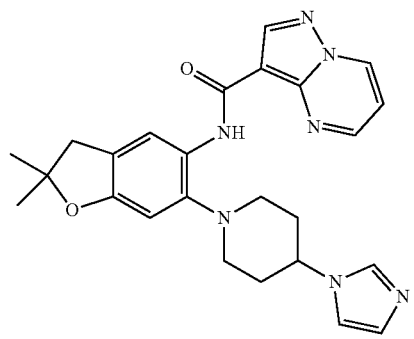 [SMILES: CC1(C)Cc2cc(NC(=O)c3cnn4cccnc34)c(N3CCC(n4ccnc4)CC3)cc2O1] | N-(6-(4-(1H-imidazol-1-yl)piperidin-1-yl)-2,2-dimethyl-2,3-dihydrobenzofuran-5-yl)pyrazolo[1,5-a]pyrimidine-3-carboxamide |
| 207 | 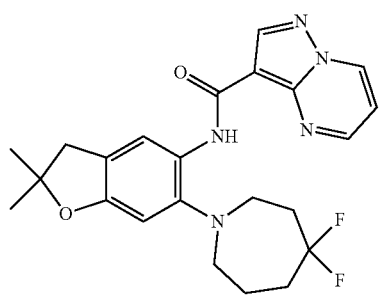 [SMILES: CC1(C)Cc2cc(NC(=O)c3cnn4cccnc34)c(N3CCCC(F)(F)CC3)cc2O1] | N-(6-(4,4-difluoroazepan-1-yl)-2,2-dimethyl-2,3-dihydrobenzofuran-5-yl)pyrazolo[1,5-a]pyrimidine-3-carboxamide |

TABLE 2-continued

*Additional exemplary compounds of the present invention. Salts of such compounds are also contemplated. See the Examples section for preparation of such compounds.*

| | | |
|---|---|---|
| 208 | 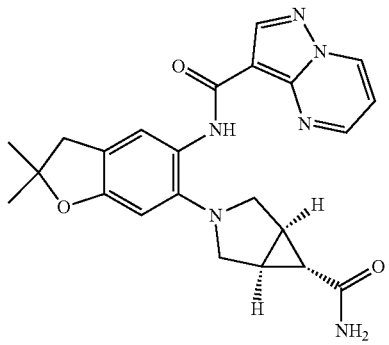 [SMILES: CC1(C)Cc2cc(NC(=O)c3cnn4cccnc34)c(N3C[C@@H]4[C@H](C3)[C@H]4C(N)=O)cc2O1] | N-(6-((1R,5S,6r)-6-carbamoyl-3-azabicyclo[3.1.0]hexan-3-yl)-2,2-dimethyl-2,3-dihydrobenzofuran-5-yl)pyrazolo[1,5-a]pyrimidine-3-carboxamide |
| 209 | 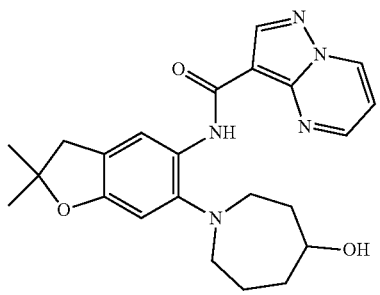 [SMILES: CC1(C)Cc2cc(NC(=O)c3cnn4cccnc34)c(N3CCCC(O)CC3)cc2O1] | N-(6-(4-hydroxyazepan-1-yl)-2,2-dimethyl-2,3-dihydrobenzofuran-5-yl)pyrazolo[1,5-a]pyrimidine-3-carboxamide |
| 210 | 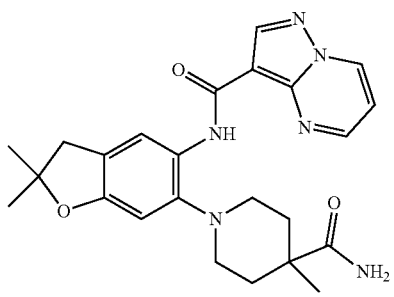 [SMILES: CC1(C)Cc2cc(NC(=O)c3cnn4cccnc34)c(N3CCC(C)(C(N)=O)CC3)cc2O1] | N-(6-(4-carbamoyl-4-methylpiperidin-1-yl)-2,2-dimethyl-2,3-dihydrobenzofuran-5-yl)pyrazolo[1,5-a]pyrimidine-3-carboxamide |
| 211 | 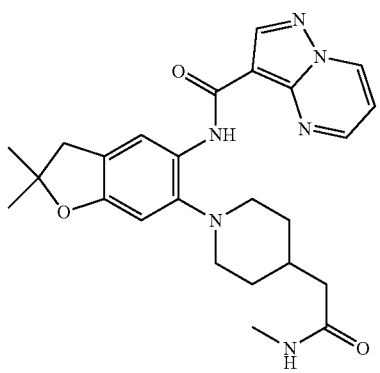 [SMILES: CNC(=O)CC1CCN(c2cc3c(cc2NC(=O)c2cnn4cccnc24)CC(C)(C)O3)CC1] | N-(2,2-dimethyl-6-(4-(2-(methylamino)-2-oxoethyl)piperidin-1-yl)-2,3-dihydrobenzofuran-5-yl)pyrazolo[1,5-a]pyrimidine-3-carboxamide |

TABLE 2-continued

*Additional exemplary compounds of the present invention. Salts of such compounds are also contemplated. See the Examples section for preparation of such compounds.*

| | | |
|---|---|---|
| 212 | 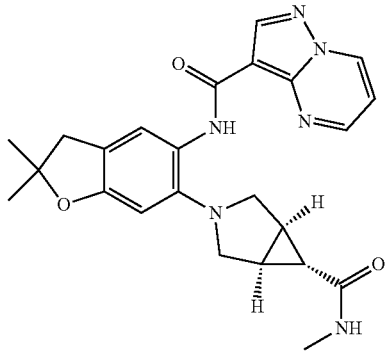 [SMILES: CNC(=O)[C@H]1[C@@H]2CN(c3cc4c(cc3NC(=O)c3cnn5cccnc35)CC(C)(C)O4)C[C@@H]21] | N-(2,2-dimethyl-6-((1R,5S,6r)-6-(methylcarbamoyl)-3-azabicyclo[3.1.0]hexan-3-yl)-2,3-dihydrobenzofuran-5-yl)pyrazolo[1,5-a]pyrimidine-3-carboxamide |
| 213 | 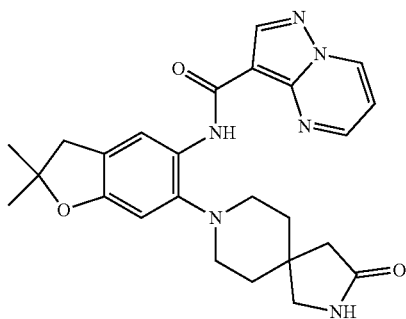 [SMILES: CC1(C)Cc2cc(NC(=O)c3cnn4cccnc34)c(N3CCC4(CC3)CNC(=O)C4)cc2O1] | N-(2,2-dimethyl-6-(3-oxo-2,8-diazaspiro[4.5]decan-8-yl)-2,3-dihydrobenzofuran-5-yl)pyrazolo[1,5-a]pyrimidine-3-carboxamide |
| 214 | 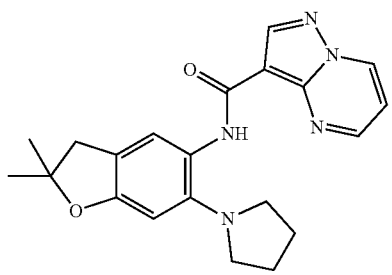 [SMILES: CC1(C)Cc2cc(NC(=O)c3cnn4cccnc34)c(N3CCCC3)cc2O1] | N-(2,2-dimethyl-6-(pyrrolidin-1-yl)-2,3-dihydrobenzofuran-5-yl)pyrazolo[1,5-a]pyrimidine-3-carboxamide |
| 215 | 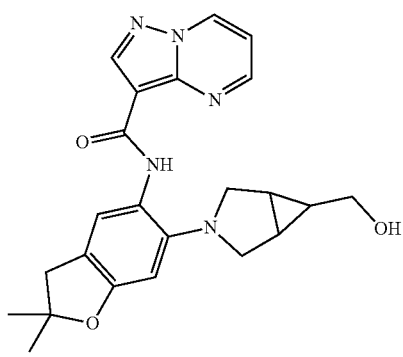 [SMILES: CC1(C)Cc2cc(NC(=O)c3cnn4cccnc34)c(N3CC4C(CO)C4C3)cc2O1] | N-(6-(6-(hydroxymethyl)-3-azabicyclo[3.1.0]hexan-3-yl)-2,2-dimethyl-2,3-dihydrobenzofuran-5-yl)pyrazolo[1,5-a]pyrimidine-3-carboxamide |

TABLE 2-continued

Additional exemplary compounds of the present invention. Salts of such compounds are also contemplated. See the Examples section for preparation of such compounds.

| | | |
|---|---|---|
| 216 | 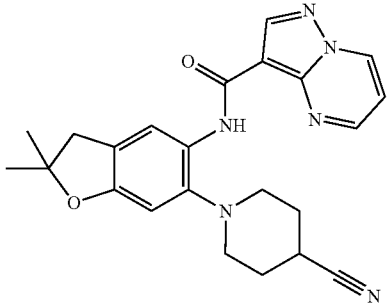 [SMILES: CC1(C)Cc2cc(NC(=O)c3cnn4cccnc34)c(N3CCC(C#N)CC3)cc2O1] | N-(6-(4-cyanopiperidin-1-yl)-2,2-dimethyl-2,3-dihydrobenzofuran-5-yl)pyrazolo[1,5-a]pyrimidine-3-carboxamide |
| 217 | 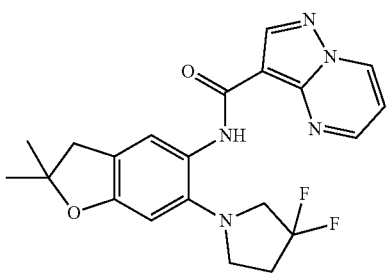 [SMILES: CC1(C)Cc2cc(NC(=O)c3cnn4cccnc34)c(N3CCC(F)(F)C3)cc2O1] | N-(6-(3,3-difluoropyrrolidin-1-yl)-2,2-dimethyl-2,3-dihydrobenzofuran-5-yl)pyrazolo[1,5-a]pyrimidine-3-carboxamide |
| 218 | 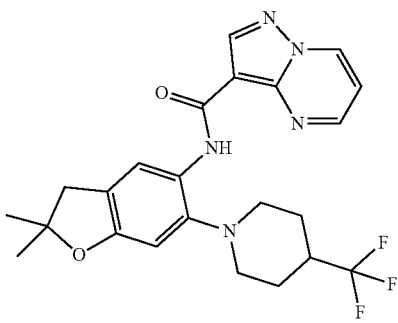 [SMILES: CC1(C)Cc2cc(NC(=O)c3cnn4cccnc34)c(N3CCC(C(F)(F)F)CC3)cc2O1] | N-(2,2-dimethyl-6-(4-(trifluoromethyl)piperidin-1-yl)-2,3-dihydrobenzofuran-5-yl)pyrazolo[1,5-a]pyrimidine-3-carboxamide |
| 219 | 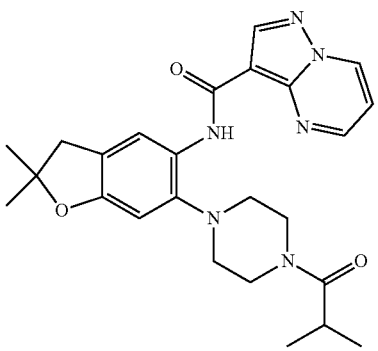 [SMILES: CC(C)C(=O)N1CCN(c2cc3c(cc2NC(=O)c2cnn4cccnc24)CC(C)(C)O3)CC1] | N-(6-(4-isobutyrylpiperazin-1-yl)-2,2-dimethyl-2,3-dihydrobenzofuran-5-yl)pyrazolo[1,5-a]pyrimidine-3-carboxamide |
| 220 | 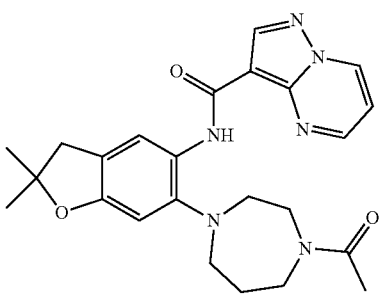 [SMILES: CC(=O)N1CCCN(c2cc3c(cc2NC(=O)c2cnn4cccnc24)CC(C)(C)O3)CC1] | N-(6-(4-acetyl-1,4-diazepan-1-yl)-2,2-dimethyl-2,3-dihydrobenzofuran-5-yl)pyrazolo[1,5-a]pyrimidine-3-carboxamide |

TABLE 2-continued

*Additional exemplary compounds of the present invention. Salts of such compounds are also contemplated. See the Examples section for preparation of such compounds.*

| | | |
|---|---|---|
| 221 | 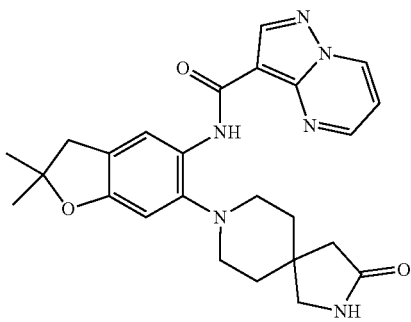 [SMILES: CC1(C)Cc2cc(NC(=O)c3cnn4cccnc34)c(N3CCC4(CC3)CNC(=O)C4)cc2O1] | N-(2,2-dimethyl-6-(3-oxo-2,8-diazaspiro[4.5]decan-8-yl)-2,3-dihydrobenzofuran-5-yl)pyrazolo[1,5-a]pyrimidine-3-carboxamide |
| 222 and 223 | 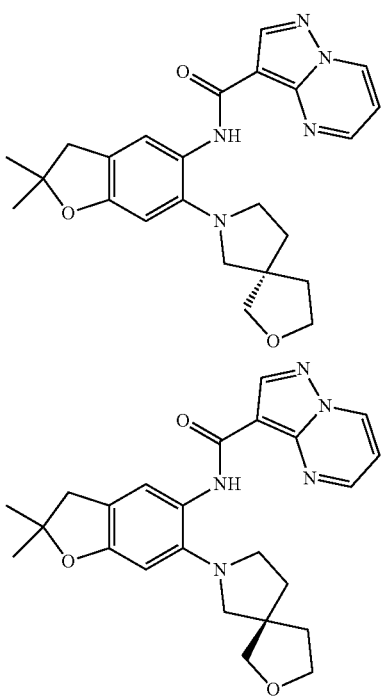 | (R)-N-(2,2-dimethyl-6-(2-oxa-7-azaspiro[4.4]nonan-7-yl)-2,3-dihydrobenzofuran-5-yl)pyrazolo[1,5-a]pyrimidine-3-carboxamide and (S)-N-(2,2-dimethyl-6-(2-oxa-7-azaspiro[4.4]nonan-7-yl)-2,3-dihydrobenzofuran-5-yl)pyrazolo[1,5-a]pyrimidine-3-carboxamide (stereochemistry assigned arbitrarily) |
| 224 | 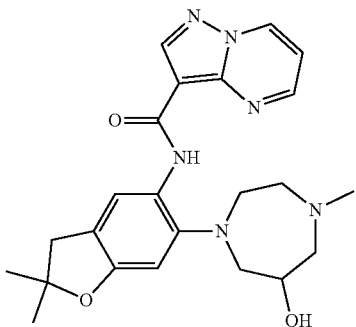 | N-[6-(6-hydroxy-4-methyl-1,4-diazepan-1-yl)-2,2-dimethyl-3H-benzofuran-5-yl]pyrazolo[1,5-a]pyrimidine-3-carboxamide |

TABLE 2-continued

*Additional exemplary compounds of the present invention. Salts of such compounds are also contemplated. See the Examples section for preparation of such compounds.*

| | | |
|---|---|---|
| 225 | 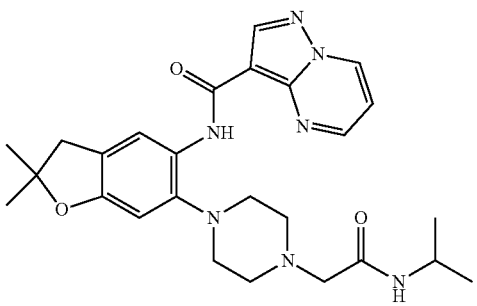 [SMILES: CC(C)NC(=O)CN1CCN(c2cc3c(cc2NC(=O)c2cnn4cccnc24)CC(C)(C)O3)CC1] | N-(6-(4-(2-(Isopropylamino)-2-oxoethyl)piperazin-1-yl)-2,2-dimethyl-2,3-dihydrobenzofuran-5-yl)pyrazolo[1,5-a]pyrimidine-3-carboxamide |
| 226 | 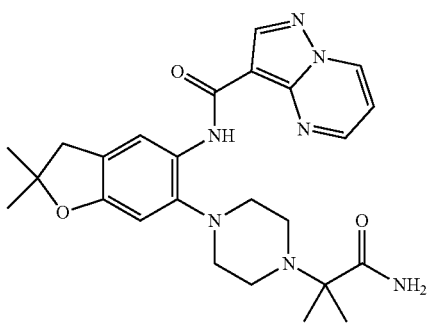 [SMILES: CC1(C)Cc2cc(NC(=O)c3cnn4cccnc34)c(N3CCN(C(C)(C)C(N)=O)CC3)cc2O1] | N-(6-(4-(1-Amino-2-methyl-1-oxopropan-2-yl)piperazin-1-yl)-2,2-dimethyl-2,3-dihydrobenzofuran-5-yl)pyrazolo[1,5-a]pyrimidine-3-carboxamide |
| 227 | 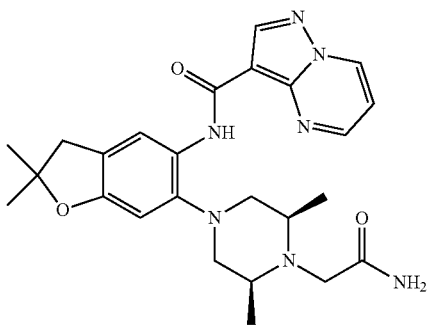 [SMILES: C[C@@H]1CN(c2cc3c(cc2NC(=O)c2cnn4cccnc24)CC(C)(C)O3)C[C@H](C)N1CC(N)=O] | N-(6-((3R,5S)-4-(2-Amino-2-oxoethyl)-3,5-dimethylpiperazin-1-yl)-2,2-dimethyl-2,3-dihydrobenzofuran-5-yl)pyrazolo[1,5-a]pyrimidine-3-carboxamide |
| 228 | 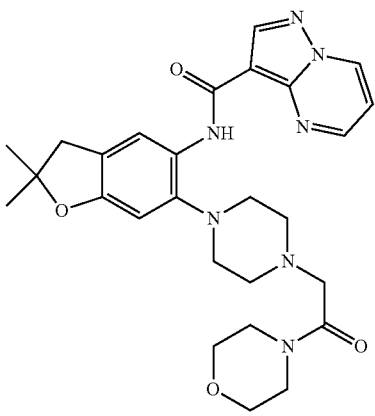 [SMILES: CC1(C)Cc2cc(NC(=O)c3cnn4cccnc34)c(N3CCN(CC(=O)N4CCOCC4)CC3)cc2O1] | N-(2,2-Dimethyl-6-(4-(2-morpholino-2-oxoethyl)piperazin-1-yl)-2,3-dihydrobenzofuran-5-yl)pyrazolo[1,5-a]pyrimidine-3-carboxamide |

TABLE 2-continued

Additional exemplary compounds of the present invention. Salts of such compounds are also contemplated. See the Examples section for preparation of such compounds.

| 229 | 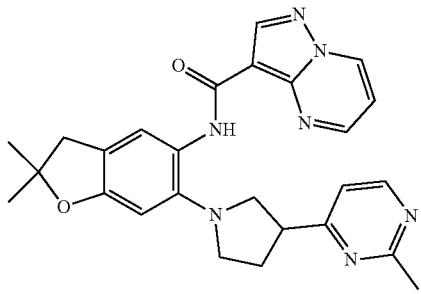 | N-(2,2-Dimethyl-6-(3-(2-methylpyrimidin-4-yl)pyrrolidin-1-yl)-2,3-dihydrobenzofuran-5-yl)pyrazolo[1,5-a]pyrimidine-3-carboxamide |
| --- | --- | --- |
| 230 | 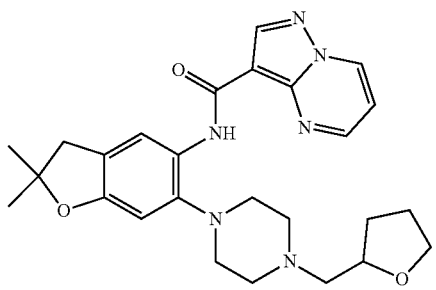 [SMILES: CC1(C)Cc2cc(NC(=O)c3cnn4cccnc34)c(N3CCN(CC4CCCO4)CC3)cc2O1] | N-(2,2-Dimethyl-6-(4-((tetrahydrofuran-2-yl)methyl)piperazin-1-yl)-2,3-dihydrobenzofuran-5-yl)pyrazolo[1,5-a]pyrimidine-3-carboxamide |
| 231 | 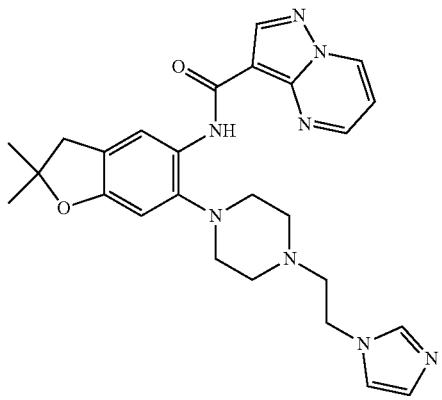 [SMILES: CC1(C)Cc2cc(NC(=O)c3cnn4cccnc34)c(N3CCN(CCn4ccnc4)CC3)cc2O1] | N-(6-(4-(2-(1H-Imidazol-1-yl)ethyl)piperazin-1-yl)-2,2-dimethyl-2,3-dihydrobenzofuran-5-yl)pyrazolo[1,5-a]pyrimidine-3-carboxamide |
| 232 | 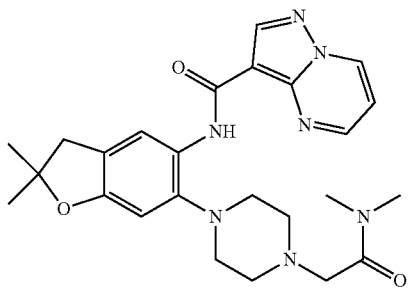 | N-(6-(4-(2-(Dimethylamino)-2-oxoethyl)piperazin-1-yl)-2,2-dimethyl-2,3-dihydrobenzofuran-5-yl)pyrazolo[1,5-a]pyrimidine-3-carboxamide |
| 233 | 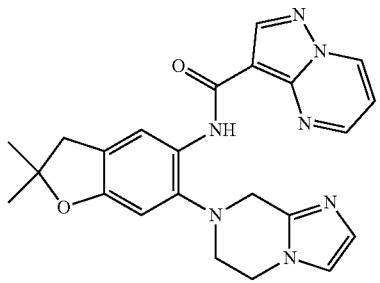 [SMILES: CC1(C)Cc2cc(NC(=O)c3cnn4cccnc34)c(N3CCn4ccnc4C3)cc2O1] | N-(6-(5,6-Dihydroimidazo[1,2-a]pyrazin-7(8H)-yl)-2,2-dimethyl-2,3-dihydrobenzofuran-5-yl)pyrazolo[1,5-a]pyrimidine-3-carboxamide |

TABLE 2-continued

*Additional exemplary compounds of the present invention. Salts of such compounds are also contemplated. See the Examples section for preparation of such compounds.*

| | | |
|---|---|---|
| 234 | 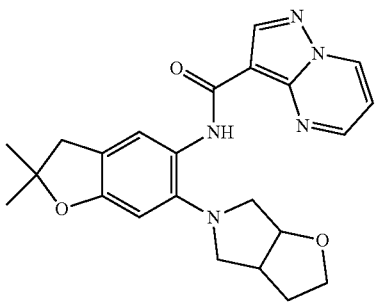 [SMILES: CC1(C)Cc2cc(NC(=O)c3cnn4cccnc34)c(N3CC4CCOC4C3)cc2O1] | N-(6-(Hexahydro-5H-furo[2,3-c]pyrrol-5-yl)-2,2-dimethyl-2,3-dihydrobenzofuran-5-yl)pyrazolo[1,5-a]pyrimidine-3-carboxamide |
| 235 | 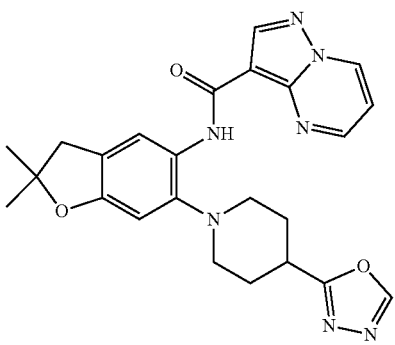 [SMILES: CC1(C)Cc2cc(NC(=O)c3cnn4cccnc34)c(N3CCC(c4nnco4)CC3)cc2O1] | N-(6-(4-(1,3,4-Oxadiazol-2-yl)piperidin-1-yl)-2,2-dimethyl-2,3-dihydrobenzofuran-5-yl)pyrazolo[1,5-a]pyrimidine-3-carboxamide |
| 236 | 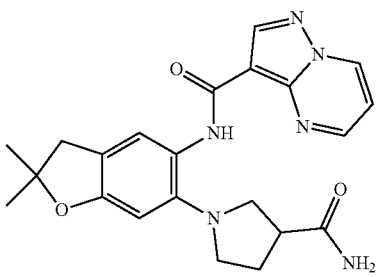 | N-(6-(3-Carbamoylpyrrolidin-1-yl)-2,2-dimethyl-2,3-dihydrobenzofuran-5-yl)pyrazolo[1,5-a]pyrimidine-3-carboxamide |
| 237 | 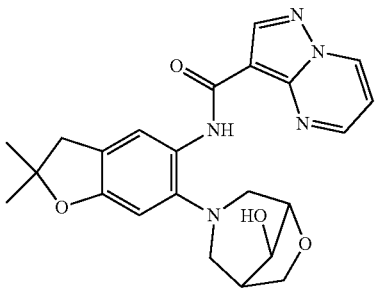 [SMILES: CC1(C)Cc2cc(NC(=O)c3cnn4cccnc34)c(N3CC4COC(C3)C4O)cc2O1] | N-(6-(9-Hydroxy-3-oxa-7-azabicyclo[3.3.1]nonan-7-yl)-2,2-dimethyl-2,3-dihydrobenzofuran-5-yl)pyrazolo[1,5-a]pyrimidine-3-carboxamide |
| 238 | 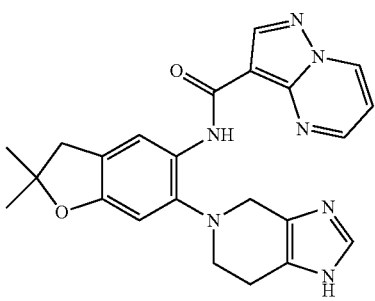 [SMILES: CC1(C)Cc2cc(NC(=O)c3cnn4cccnc34)c(N3CCc4[nH]cnc4C3)cc2O1] | N-(2,2-Dimethyl-6-(1,4,6,7-tetrahydro-5H-imidazo[4,5-c]pyridin-5-yl)-2,3-dihydrobenzofuran-5-yl)pyrazolo[1,5-a]pyrimidine-3-carboxamide |

TABLE 2-continued

Additional exemplary compounds of the present invention. Salts of such compounds are also contemplated. See the Examples section for preparation of such compounds.

| | | |
|---|---|---|
| 239 | 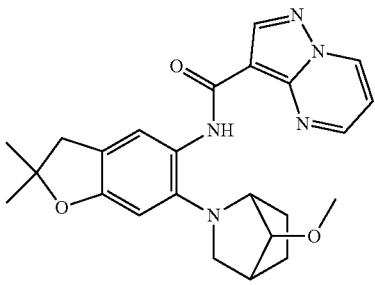 [SMILES: COC1C2CCC1N(c1cc3c(cc1NC(=O)c1cnn4cccnc14)CC(C)(C)O3)C2] | N-(6-(7-Methoxy-2-azabicyclo[2.2.1]heptan-2-yl)-2,2-dimethyl-2,3-dihydrobenzofuran-5-yl)pyrazolo[1,5-a]pyrimidine-3-carboxamide |
| 240 | 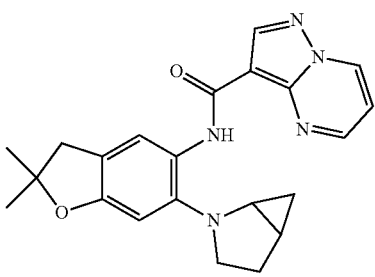 [SMILES: CC1(C)Cc2cc(NC(=O)c3cnn4cccnc34)c(N3CCC4CC43)cc2O1] | N-(6-(2-Azabicyclo[3.1.0]hexan-2-yl)-2,2-dimethyl-2,3-dihydrobenzofuran-5-yl)pyrazolo[1,5-a]pyrimidine-3-carboxamide |
| 241 | 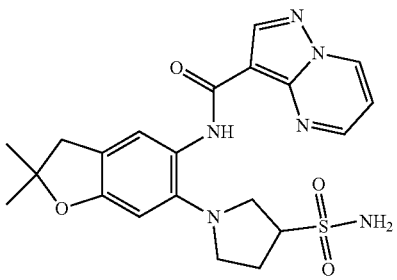 [SMILES: CC1(C)Cc2cc(NC(=O)c3cnn4cccnc34)c(N3CCC(S(N)(=O)=O)C3)cc2O1] | N-(2,2-Dimethyl-6-(3-sulfamoylpyrrolidin-1-yl)-2,3-dihydrobenzofuran-5-yl)pyrazolo[1,5-a]pyrimidine-3-carboxamide |
| 242 | 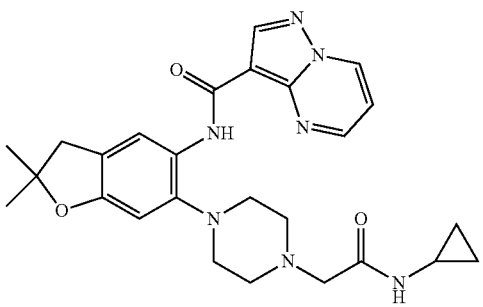 [SMILES: CC1(C)Cc2cc(NC(=O)c3cnn4cccnc34)c(N3CCN(CC(=O)NC4CC4)CC3)cc2O1] | N-(6-(4-(2-(Cyclopropylamino)-2-oxoethyl)piperazin-1-yl)-2,2-dimethyl-2,3-dihydrobenzofuran-5-yl)pyrazolo[1,5-a]pyrimidine-3-carboxamide |
| 243 | 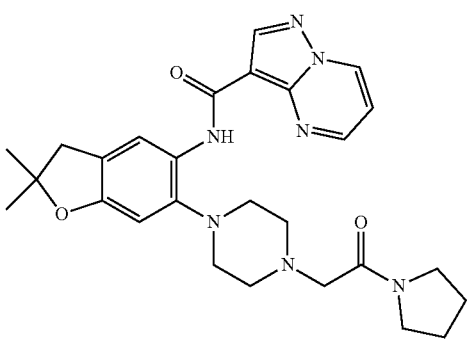 [SMILES: CC1(C)Cc2cc(NC(=O)c3cnn4cccnc34)c(N3CCN(CC(=O)N4CCCC4)CC3)cc2O1] | N-(2,2-Dimethyl-6-(4-(2-oxo-2-(pyrrolidin-1-yl)ethyl)piperazin-1-yl)-2,3-dihydrobenzofuran-5-yl)pyrazolo[1,5-a]pyrimidine-carboxamide |

TABLE 2-continued

*Additional exemplary compounds of the present invention. Salts of such compounds are also contemplated. See the Examples section for preparation of such compounds.*

| | | |
|---|---|---|
| 244 | 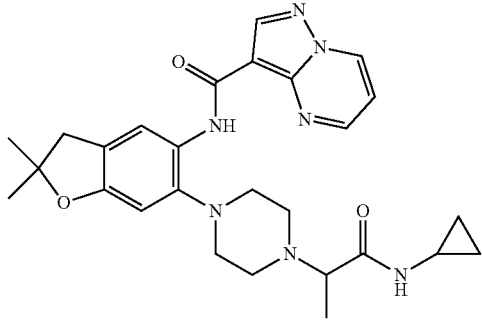 [SMILES: CC(C(=O)NC1CC1)N1CCN(c2cc3c(cc2NC(=O)c2cnn4cccnc24)CC(C)(C)O3)CC1] | N-(6-(4-(1-(Cyclopropylamino)-1-oxopropan-2-yl)piperazin-1-yl)-2,2-dimethyl-2,3-dihydrobenzofuran-5-yl)pyrazolo[1,5-a]pyrimidine-3-carboxamide |
| 245 | 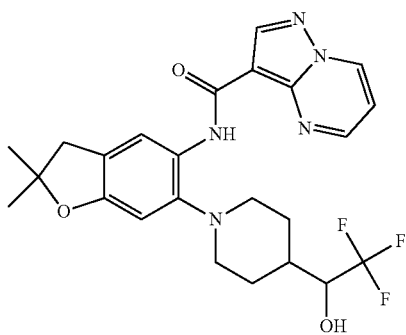 [SMILES: CC1(C)Cc2cc(NC(=O)c3cnn4cccnc34)c(N3CCC(C(O)C(F)(F)F)CC3)cc2O1] | N-(2,2-Dimethyl-6-(4-(2,2,2-trifluoro-1-hydroxyethyl)piperidin-1-yl)-2,3-dihydrobenzofuran-5-yl)pyrazolo[1,5-a]pyrimidine-3-carboxamide |
| 246 | 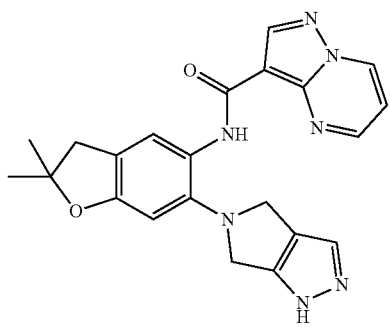 [SMILES: CC1(C)Cc2cc(NC(=O)c3cnn4cccnc34)c(N3Cc4cn[nH]c4C3)cc2O1] | N-(6-(4,6-dihydropyrrolo[3,4-c]pyrazol-5(1H)-yl)-2,2-dimethyl-2,3-dihydrobenzofuran-5-yl)pyrazolo[1,5-a]pyrimidine-3-carboxamide |
| 247 | 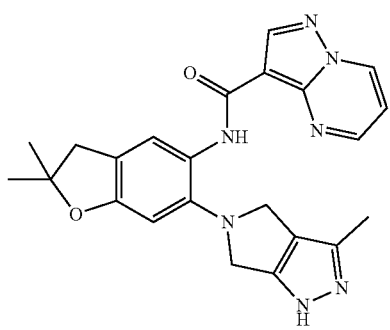 [SMILES: Cc1n[nH]c2c1CN(c1cc3c(cc1NC(=O)c1cnn4cccnc14)CC(C)(C)O3)C2] | N-(2,2-dimethyl-6-(3-methyl-4,6-dihydropyrrolo[3,4-c]pyrazol-5(1H)-yl)-2,3-dihydrobenzofuran-5-yl)pyrazolo[1,5-a]pyrimidine-3-carboxamide |

TABLE 2-continued

*Additional exemplary compounds of the present invention. Salts of such compounds are also contemplated. See the Examples section for preparation of such compounds.*

| | | |
|---|---|---|
| 248 | 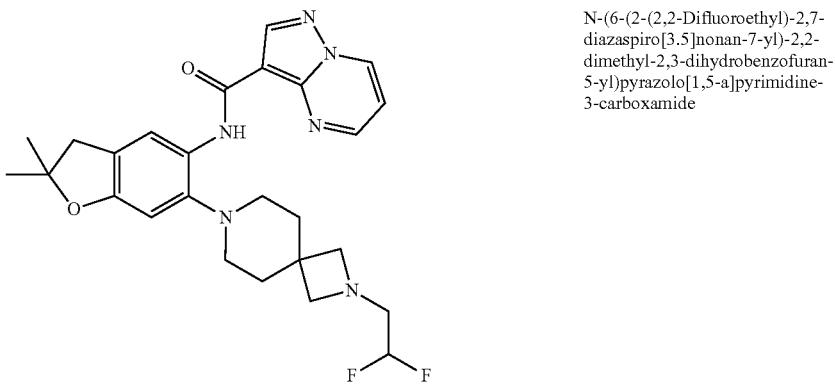 | N-(6-(2-(2,2-Difluoroethyl)-2,7-diazaspiro[3.5]nonan-7-yl)-2,2-dimethyl-2,3-dihydrobenzofuran-5-yl)pyrazolo[1,5-a]pyrimidine-3-carboxamide |
| 249 | 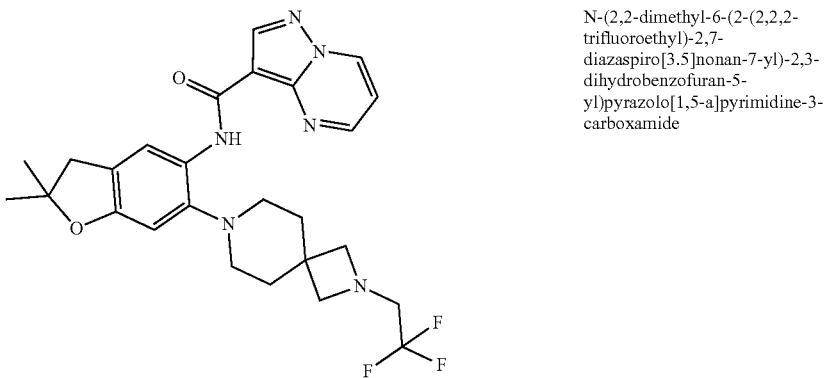 | N-(2,2-dimethyl-6-(2-(2,2,2-trifluoroethyl)-2,7-diazaspiro[3.5]nonan-7-yl)-2,3-dihydrobenzofuran-5-yl)pyrazolo[1,5-a]pyrimidine-3-carboxamide |
| 250 | 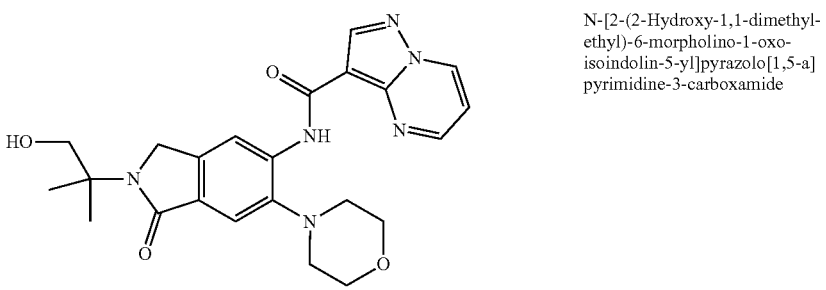 | N-[2-(2-Hydroxy-1,1-dimethyl-ethyl)-6-morpholino-1-oxo-isoindolin-5-yl]pyrazolo[1,5-a]pyrimidine-3-carboxamide |
| 251 | 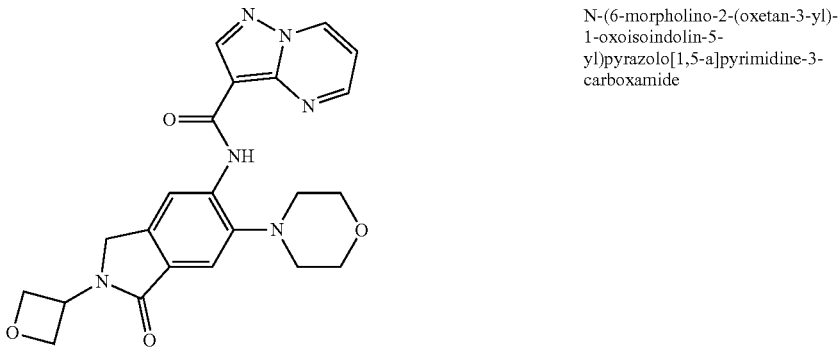 | N-(6-morpholino-2-(oxetan-3-yl)-1-oxoisoindolin-5-yl)pyrazolo[1,5-a]pyrimidine-3-carboxamide |

TABLE 2-continued

*Additional exemplary compounds of the present invention. Salts of such compounds are also contemplated. See the Examples section for preparation of such compounds.*

| | | |
|---|---|---|
| 252 | 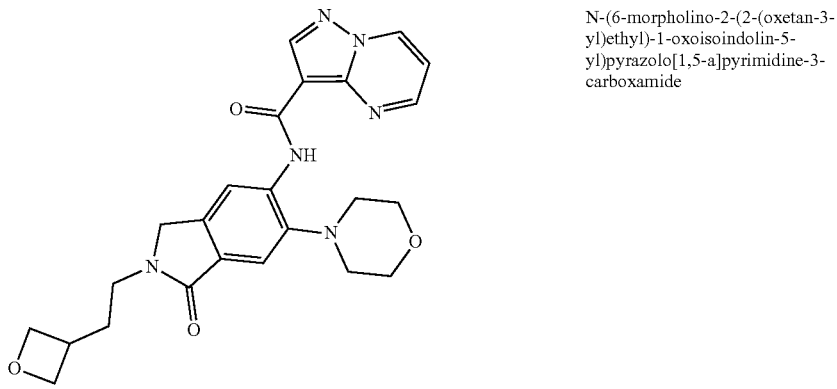 | N-(6-morpholino-2-(2-(oxetan-3-yl)ethyl)-1-oxoisoindolin-5-yl)pyrazolo[1,5-a]pyrimidine-3-carboxamide |
| 253 | 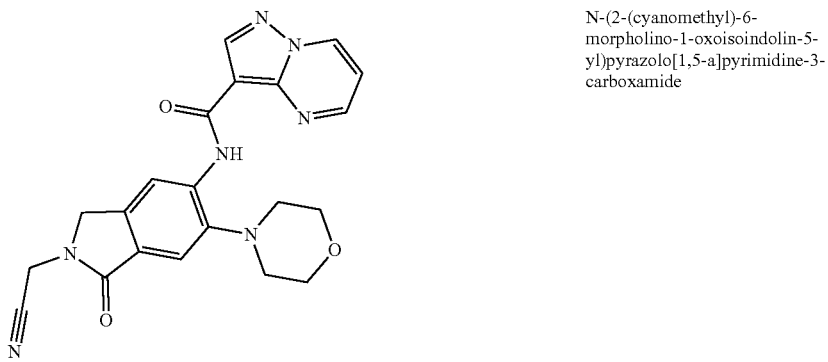 | N-(2-(cyanomethyl)-6-morpholino-1-oxoisoindolin-5-yl)pyrazolo[1,5-a]pyrimidine-3-carboxamide |
| 254 | 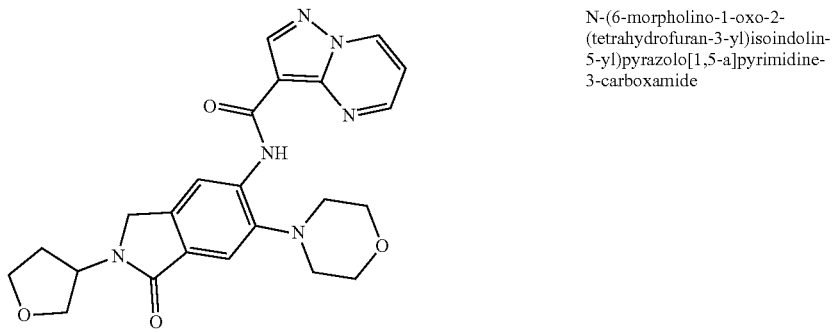 | N-(6-morpholino-1-oxo-2-(tetrahydrofuran-3-yl)isoindolin-5-yl)pyrazolo[1,5-a]pyrimidine-3-carboxamide |
| 255 | 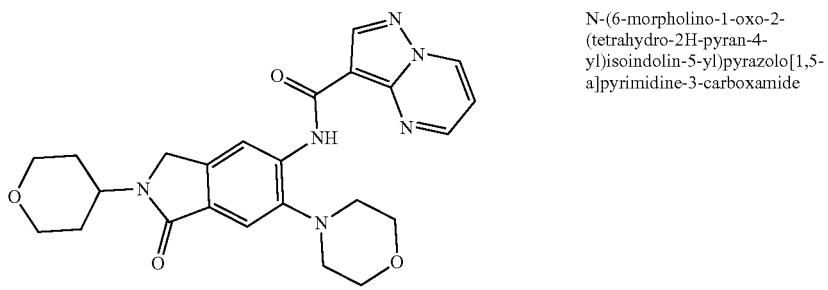 | N-(6-morpholino-1-oxo-2-(tetrahydro-2H-pyran-4-yl)isoindolin-5-yl)pyrazolo[1,5-a]pyrimidine-3-carboxamide |

TABLE 2-continued

*Additional exemplary compounds of the present invention. Salts of such compounds are also contemplated. See the Examples section for preparation of such compounds.*

| | | |
|---|---|---|
| 256 | 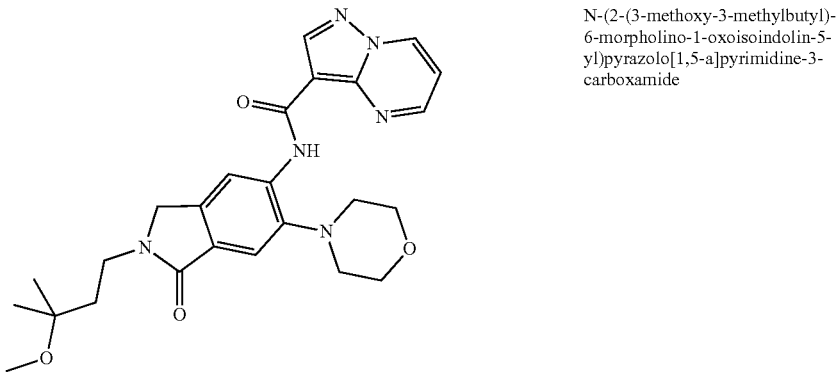 | N-(2-(3-methoxy-3-methylbutyl)-6-morpholino-1-oxoisoindolin-5-yl)pyrazolo[1,5-a]pyrimidine-3-carboxamide |
| 257 | 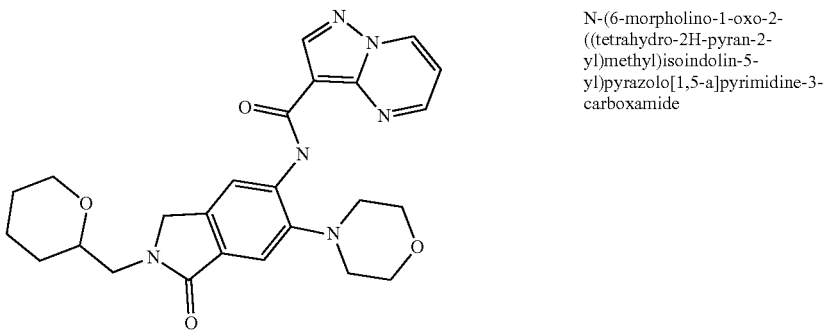 | N-(6-morpholino-1-oxo-2-((tetrahydro-2H-pyran-2-yl)methyl)isoindolin-5-yl)pyrazolo[1,5-a]pyrimidine-3-carboxamide |
| 258 | 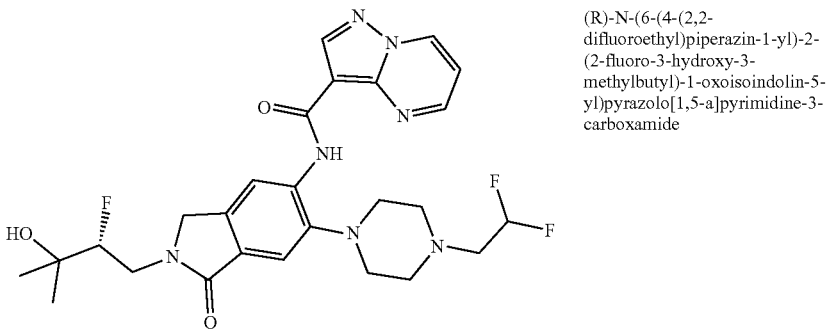 | (R)-N-(6-(4-(2,2-difluoroethyl)piperazin-1-yl)-2-(2-fluoro-3-hydroxy-3-methylbutyl)-1-oxoisoindolin-5-yl)pyrazolo[1,5-a]pyrimidine-3-carboxamide |
| 259 and 260 | 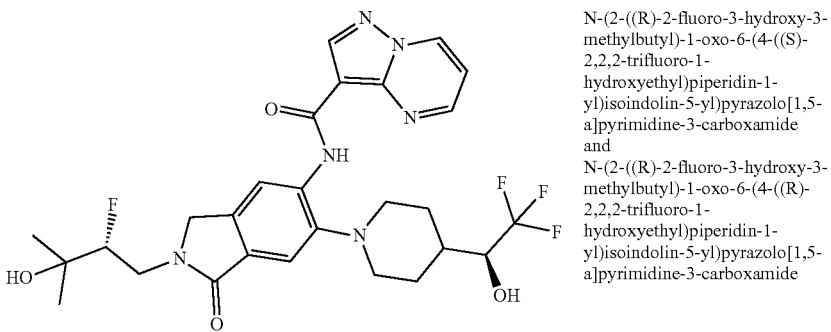 | N-(2-((R)-2-fluoro-3-hydroxy-3-methylbutyl)-1-oxo-6-(4-((S)-2,2,2-trifluoro-1-hydroxyethyl)piperidin-1-yl)isoindolin-5-yl)pyrazolo[1,5-a]pyrimidine-3-carboxamide and N-(2-((R)-2-fluoro-3-hydroxy-3-methylbutyl)-1-oxo-6-(4-((R)-2,2,2-trifluoro-1-hydroxyethyl)piperidin-1-yl)isoindolin-5-yl)pyrazolo[1,5-a]pyrimidine-3-carboxamide |

TABLE 2-continued

*Additional exemplary compounds of the present invention. Salts of such compounds are also contemplated. See the Examples section for preparation of such compounds.*

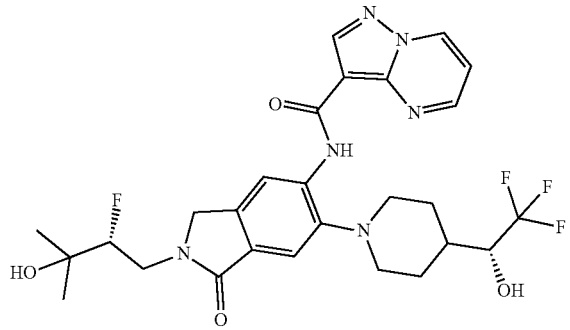

| 261 | 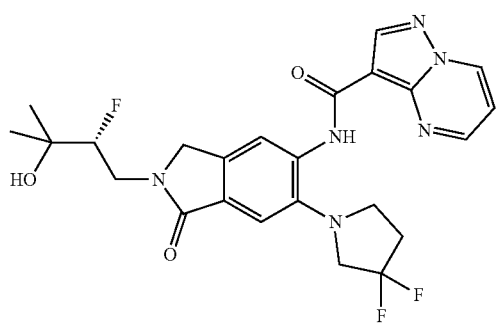 [SMILES: CC(C)(O)[C@H](F)CN1Cc2cc(NC(=O)c3cnn4cccnc34)c(N3CCC(F)(F)C3)cc2C1=O] | (R)-N-(6-(3,3-difluoropyrrolidin-1-yl)-2-(2-fluoro-3-hydroxy-3-methylbutyl)-1-oxoisoindolin-5-yl)pyrazolo[1,5-a]pyrimidine-3-carboxamide |
|---|---|---|
| 262 | 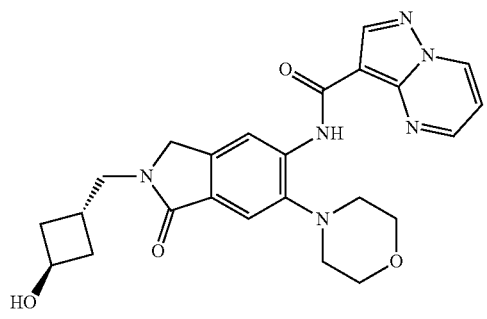 [SMILES: O=C(Nc1cc2c(cc1N1CCOCC1)C(=O)N(C[C@H]1C[C@H](O)C1)C2)c1cnn2cccnc12] | N-(2-(((1r,3r)-3-hydroxycyclobutyl)methyl)-6-morpholino-1-oxoisoindolin-5-yl)pyrazolo[1,5-a]pyrimidine-3-carboxamide |
| 263 | 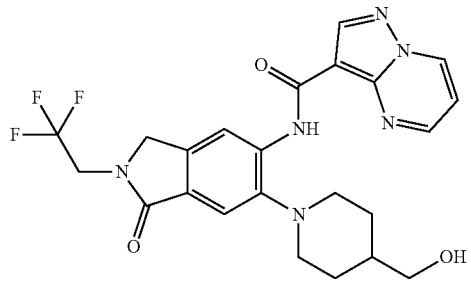 [SMILES: O=C(Nc1cc2c(cc1N1CCC(CO)CC1)C(=O)N(CC(F)(F)F)C2)c1cnn2cccnc12] | N-(6-(4-(hydroxymethyl)piperidin-1-yl)-1-oxo-2-(2,2,2-trifluoroethyl)isoindolin-5-yl)pyrazolo[1,5-a]pyrimidine-3-carboxamide |
| 264 | 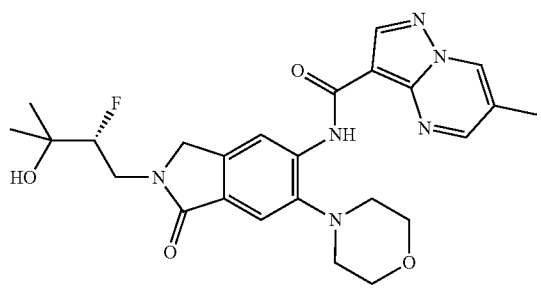 [SMILES: Cc1cnc2c(C(=O)Nc3cc4c(cc3N3CCOCC3)C(=O)N(C[C@@H](F)C(C)(C)O)C4)cnn2c1] | (R)-N-(2-(2-fluoro-3-hydroxy-3-methylbutyl)-6-morpholino-1-oxoisoindolin-5-yl)-6-methylpyrazolo[1,5-a]pyrimidine-3-carboxamide |

TABLE 2-continued

*Additional exemplary compounds of the present invention. Salts of such compounds are also contemplated. See the Examples section for preparation of such compounds.*

265 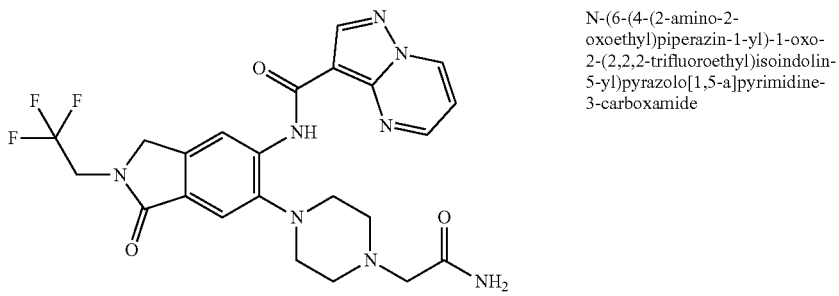 N-(6-(4-(2-amino-2-oxoethyl)piperazin-1-yl)-1-oxo-2-(2,2,2-trifluoroethyl)isoindolin-5-yl)pyrazolo[1,5-a]pyrimidine-3-carboxamide 266 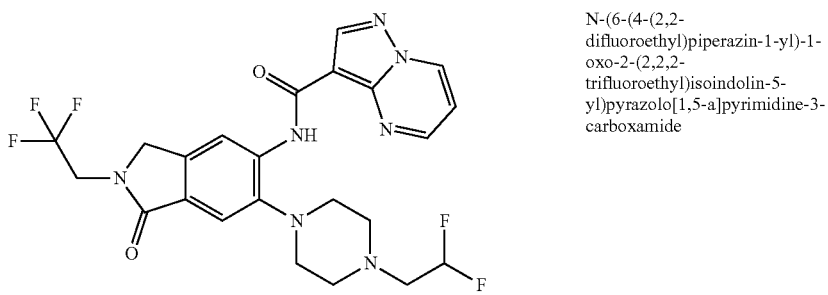 N-(6-(4-(2,2-difluoroethyl)piperazin-1-yl)-1-oxo-2-(2,2,2-trifluoroethyl)isoindolin-5-yl)pyrazolo[1,5-a]pyrimidine-3-carboxamide 267 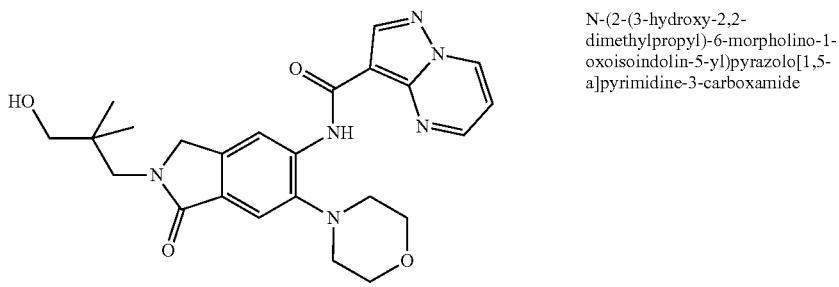 N-(2-(3-hydroxy-2,2-dimethylpropyl)-6-morpholino-1-oxoisoindolin-5-yl)pyrazolo[1,5-a]pyrimidine-3-carboxamide 268 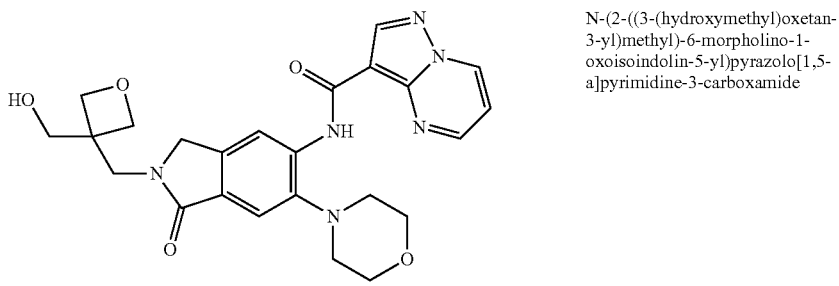 N-(2-((3-(hydroxymethyl)oxetan-3-yl)methyl)-6-morpholino-1-oxoisoindolin-5-yl)pyrazolo[1,5-a]pyrimidine-3-carboxamide 269 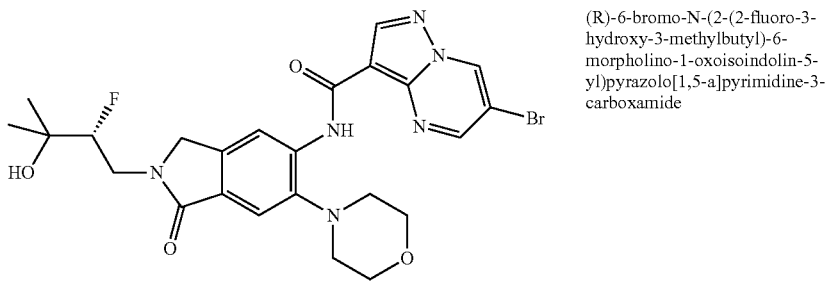 (R)-6-bromo-N-(2-(2-fluoro-3-hydroxy-3-methylbutyl)-6-morpholino-1-oxoisoindolin-5-yl)pyrazolo[1,5-a]pyrimidine-3-carboxamide TABLE 2-continued

*Additional exemplary compounds of the present invention. Salts of such compounds are also contemplated. See the Examples section for preparation of such compounds.*

| 270 | 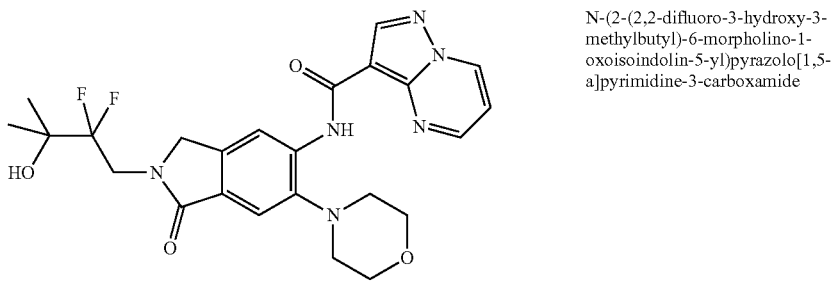 | N-(2-(2,2-difluoro-3-hydroxy-3-methylbutyl)-6-morpholino-1-oxoisoindolin-5-yl)pyrazolo[1,5-a]pyrimidine-3-carboxamide |
| 271 | 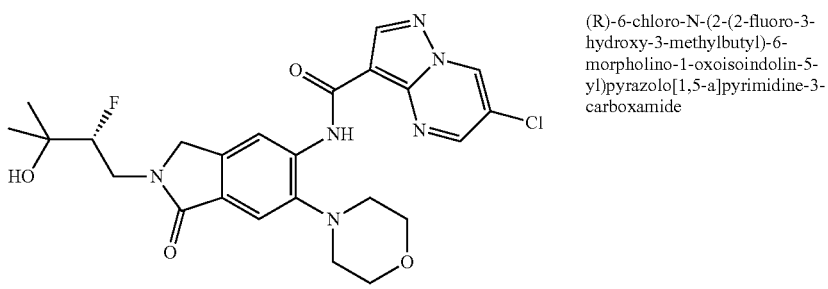 | (R)-6-chloro-N-(2-(2-fluoro-3-hydroxy-3-methylbutyl)-6-morpholino-1-oxoisoindolin-5-yl)pyrazolo[1,5-a]pyrimidine-3-carboxamide |
| 272 | 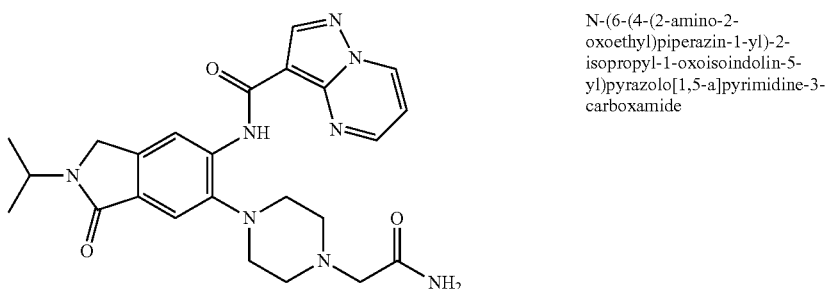 | N-(6-(4-(2-amino-2-oxoethyl)piperazin-1-yl)-2-isopropyl-1-oxoisoindolin-5-yl)pyrazolo[1,5-a]pyrimidine-3-carboxamide |
| 273 | 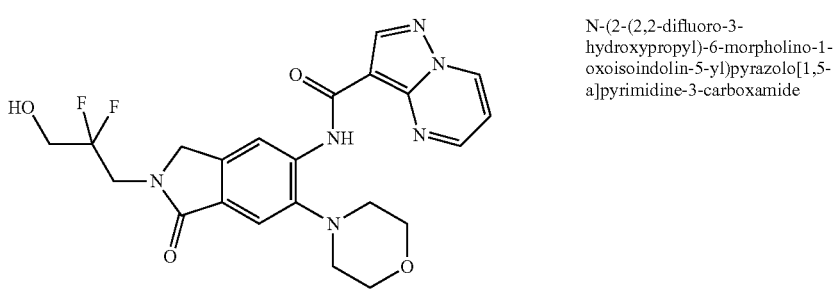 | N-(2-(2,2-difluoro-3-hydroxypropyl)-6-morpholino-1-oxoisoindolin-5-yl)pyrazolo[1,5-a]pyrimidine-3-carboxamide |
| 274 | 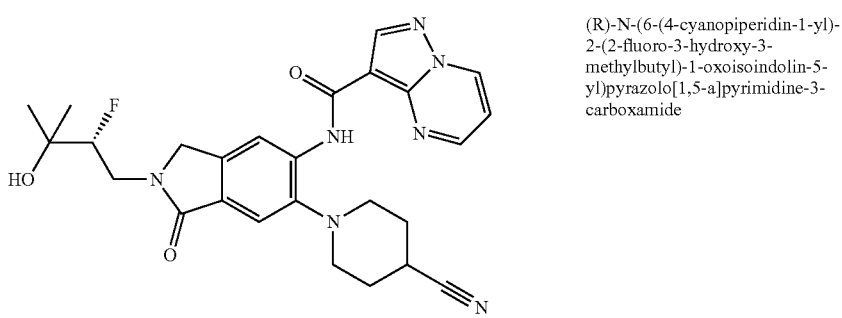 | (R)-N-(6-(4-cyanopiperidin-1-yl)-2-(2-fluoro-3-hydroxy-3-methylbutyl)-1-oxoisoindolin-5-yl)pyrazolo[1,5-a]pyrimidine-3-carboxamide |

TABLE 2-continued

*Additional exemplary compounds of the present invention. Salts of such compounds are also contemplated. See the Examples section for preparation of such compounds.*

275 and 276

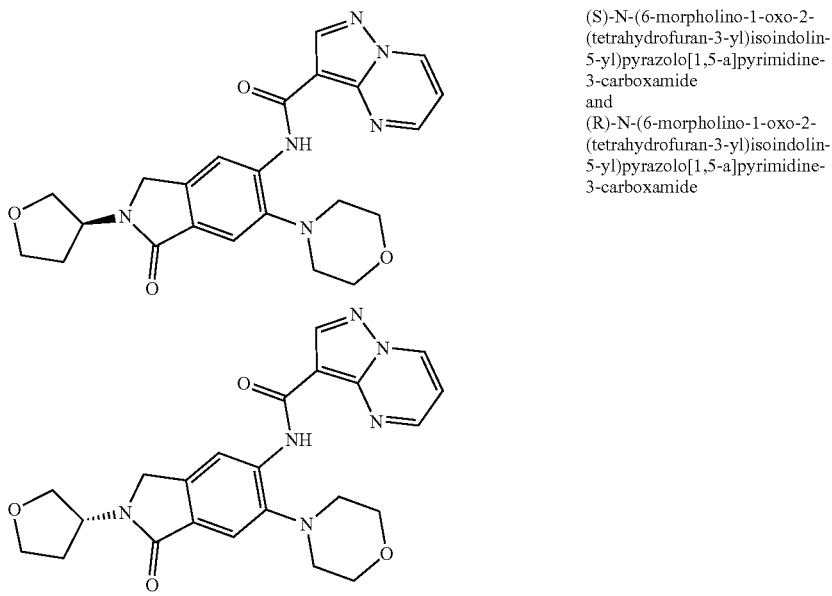

(S)-N-(6-morpholino-1-oxo-2-(tetrahydrofuran-3-yl)isoindolin-5-yl)pyrazolo[1,5-a]pyrimidine-3-carboxamide
and
(R)-N-(6-morpholino-1-oxo-2-(tetrahydrofuran-3-yl)isoindolin-5-yl)pyrazolo[1,5-a]pyrimidine-3-carboxamide 277 and 278

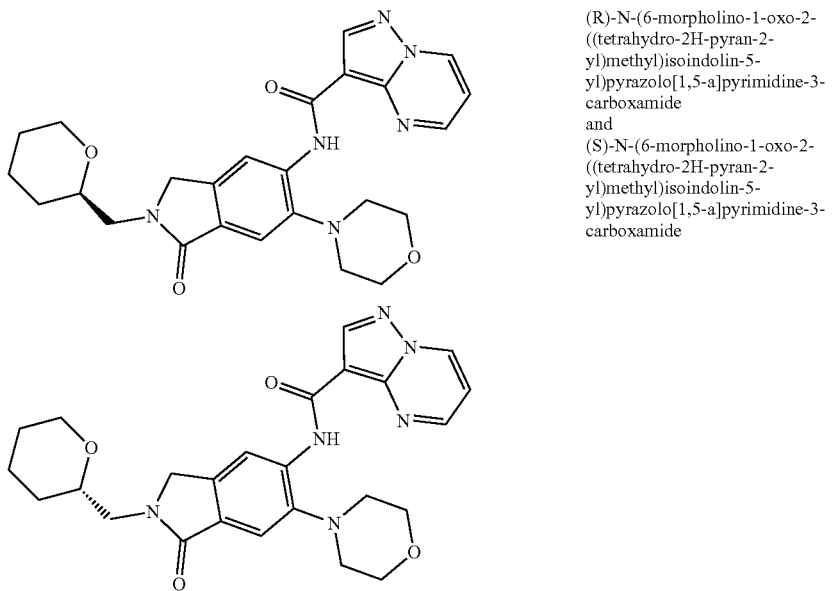

(R)-N-(6-morpholino-1-oxo-2-((tetrahydro-2H-pyran-2-yl)methyl)isoindolin-5-yl)pyrazolo[1,5-a]pyrimidine-3-carboxamide
and
(S)-N-(6-morpholino-1-oxo-2-((tetrahydro-2H-pyran-2-yl)methyl)isoindolin-5-yl)pyrazolo[1,5-a]pyrimidine-3-carboxamide

279

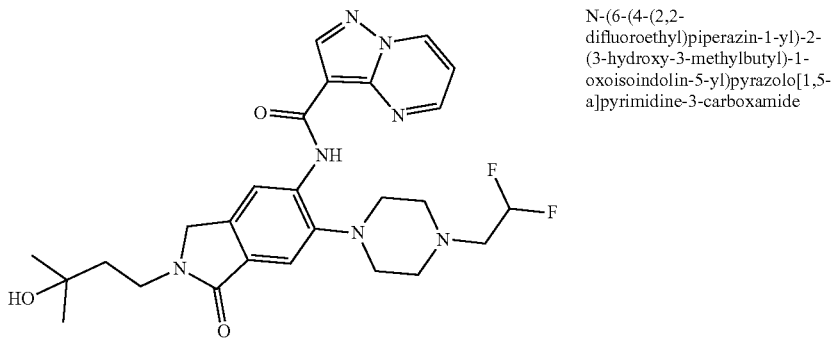

N-(6-(4-(2,2-difluoroethyl)piperazin-1-yl)-2-(3-hydroxy-3-methylbutyl)-1-oxoisoindolin-5-yl)pyrazolo[1,5-a]pyrimidine-3-carboxamide

TABLE 2-continued

*Additional exemplary compounds of the present invention. Salts of such compounds are also contemplated. See the Examples section for preparation of such compounds.*

280 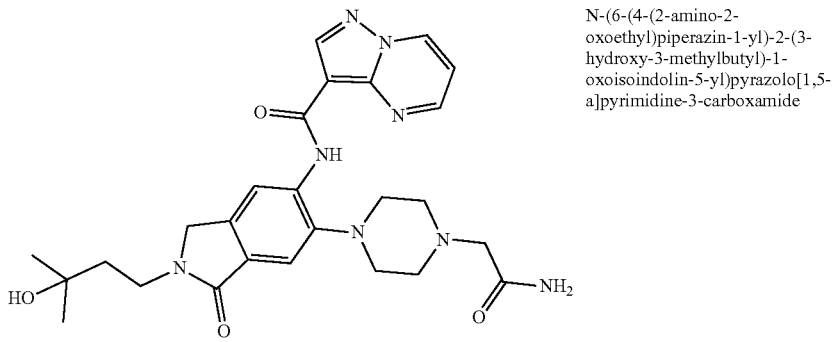 N-(6-(4-(2-amino-2-oxoethyl)piperazin-1-yl)-2-(3-hydroxy-3-methylbutyl)-1-oxoisoindolin-5-yl)pyrazolo[1,5-a]pyrimidine-3-carboxamide 281 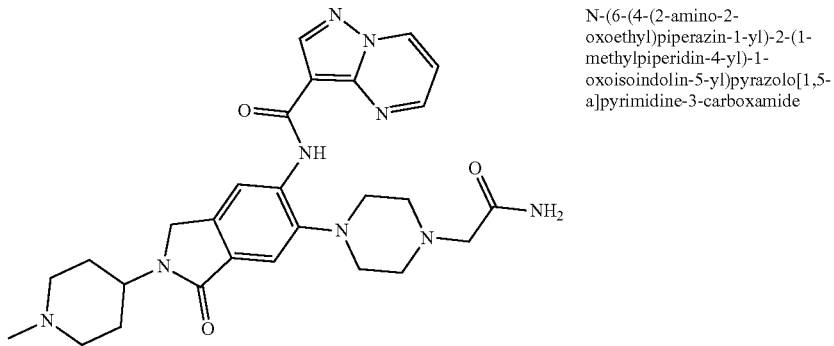 N-(6-(4-(2-amino-2-oxoethyl)piperazin-1-yl)-2-(1-methylpiperidin-4-yl)-1-oxoisoindolin-5-yl)pyrazolo[1,5-a]pyrimidine-3-carboxamide 282 and 283 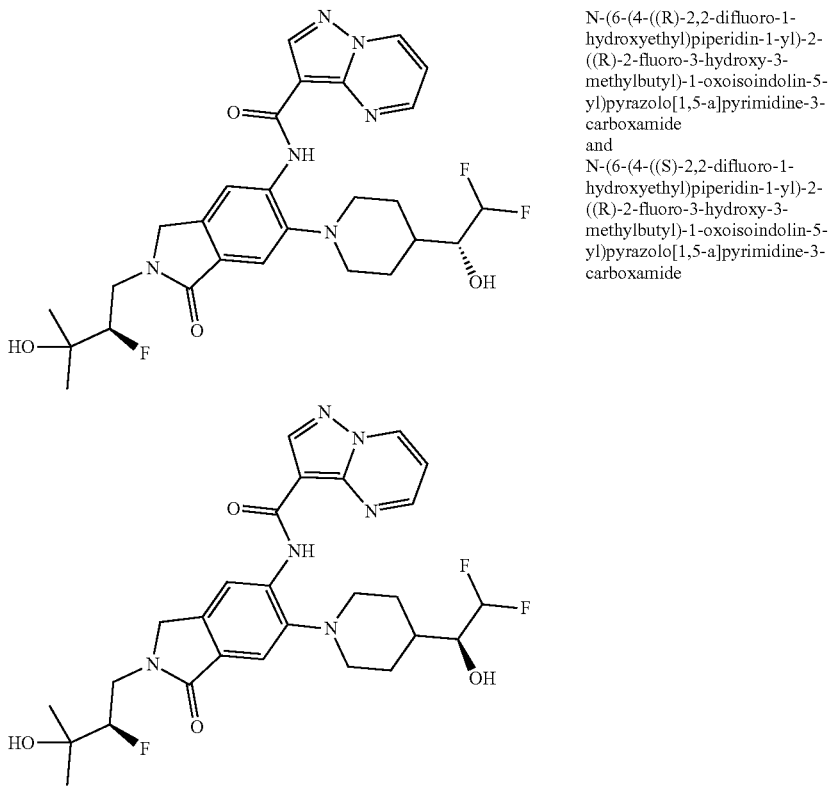 N-(6-(4-((R)-2,2-difluoro-1-hydroxyethyl)piperidin-1-yl)-2-((R)-2-fluoro-3-hydroxy-3-methylbutyl)-1-oxoisoindolin-5-yl)pyrazolo[1,5-a]pyrimidine-3-carboxamide
and
N-(6-(4-((S)-2,2-difluoro-1-hydroxyethyl)piperidin-1-yl)-2-((R)-2-fluoro-3-hydroxy-3-methylbutyl)-1-oxoisoindolin-5-yl)pyrazolo[1,5-a]pyrimidine-3-carboxamide TABLE 2-continued

*Additional exemplary compounds of the present invention. Salts of such compounds are also contemplated. See the Examples section for preparation of such compounds.*

| | | |
|---|---|---|
| 284 | 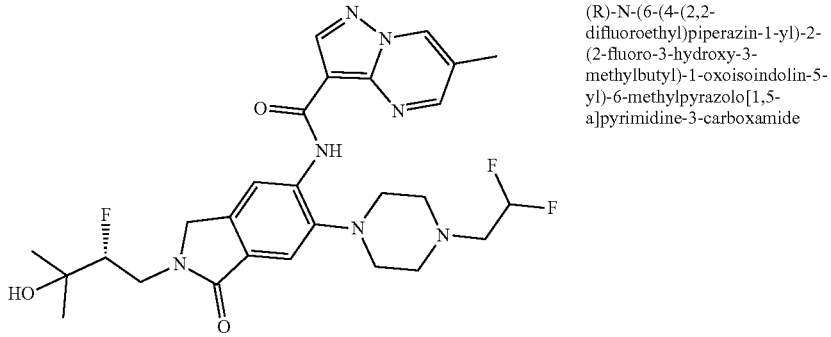 | (R)-N-(6-(4-(2,2-difluoroethyl)piperazin-1-yl)-2-(2-fluoro-3-hydroxy-3-methylbutyl)-1-oxoisoindolin-5-yl)-6-methylpyrazolo[1,5-a]pyrimidine-3-carboxamide |
| 285 | 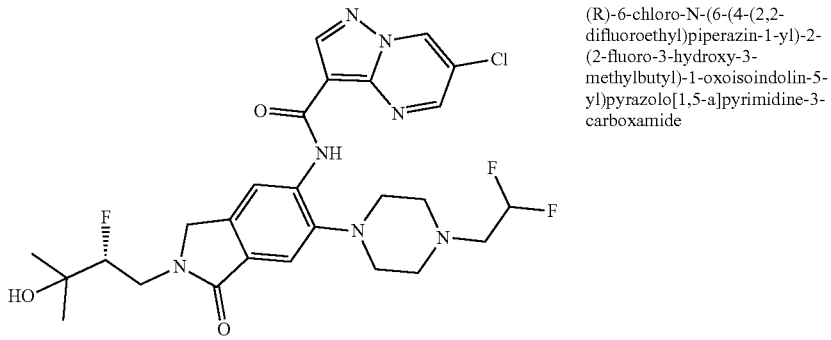 | (R)-6-chloro-N-(6-(4-(2,2-difluoroethyl)piperazin-1-yl)-2-(2-fluoro-3-hydroxy-3-methylbutyl)-1-oxoisoindolin-5-yl)pyrazolo[1,5-a]pyrimidine-3-carboxamide |
| 286 | 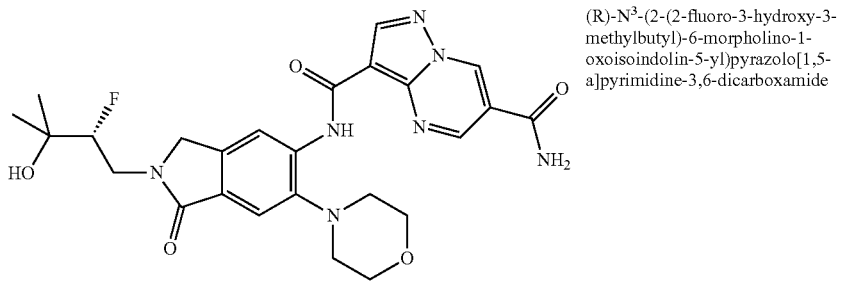 | (R)-N³-(2-(2-fluoro-3-hydroxy-3-methylbutyl)-6-morpholino-1-oxoisoindolin-5-yl)pyrazolo[1,5-a]pyrimidine-3,6-dicarboxamide |
| 287 | 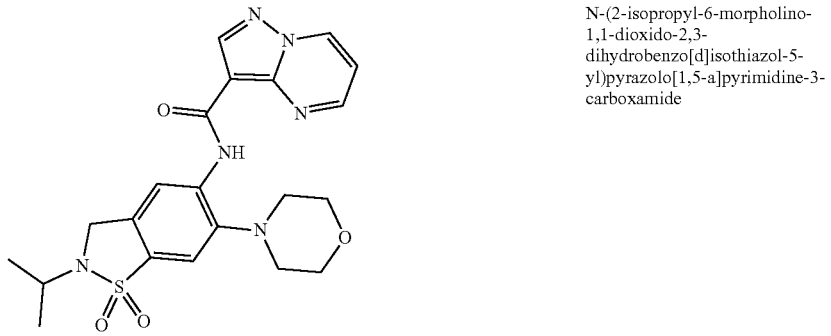 | N-(2-isopropyl-6-morpholino-1,1-dioxido-2,3-dihydrobenzo[d]isothiazol-5-yl)pyrazolo[1,5-a]pyrimidine-3-carboxamide |

| | | |
|---|---|---|
| 288 | 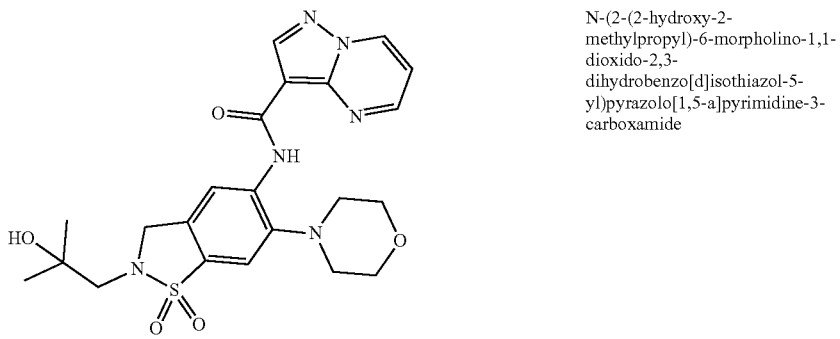 | N-(2-(2-hydroxy-2-methylpropyl)-6-morpholino-1,1-dioxido-2,3-dihydrobenzo[d]isothiazol-5-yl)pyrazolo[1,5-a]pyrimidine-3-carboxamide |
| 289 | 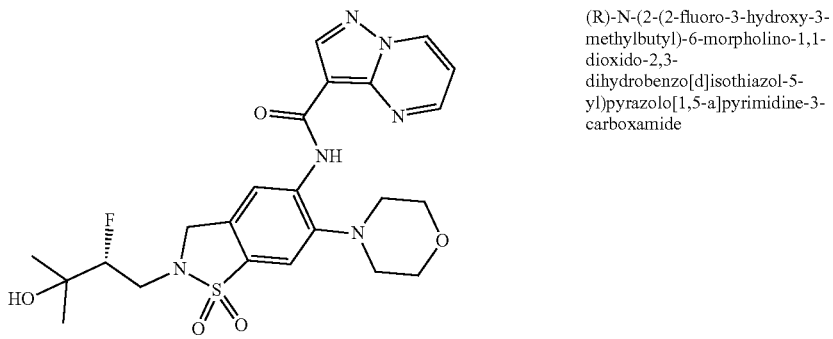 | (R)-N-(2-(2-fluoro-3-hydroxy-3-methylbutyl)-6-morpholino-1,1-dioxido-2,3-dihydrobenzo[d]isothiazol-5-yl)pyrazolo[1,5-a]pyrimidine-3-carboxamide |
| 290 | 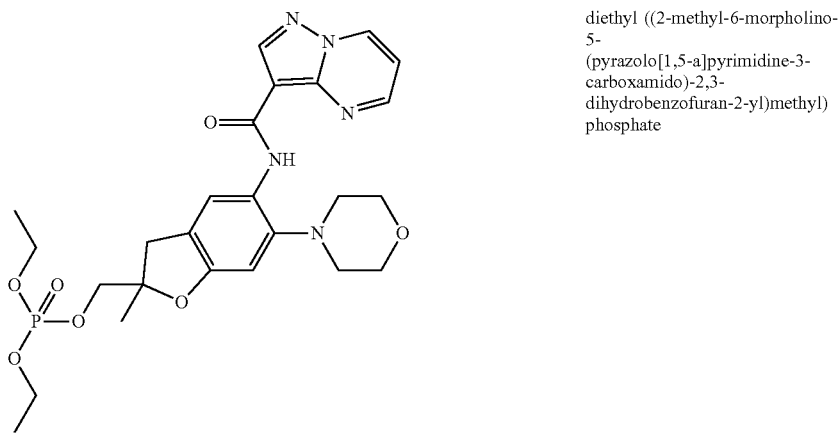 | diethyl ((2-methyl-6-morpholino-5-(pyrazolo[1,5-a]pyrimidine-3-carboxamido)-2,3-dihydrobenzofuran-2-yl)methyl) phosphate |
| 291 | 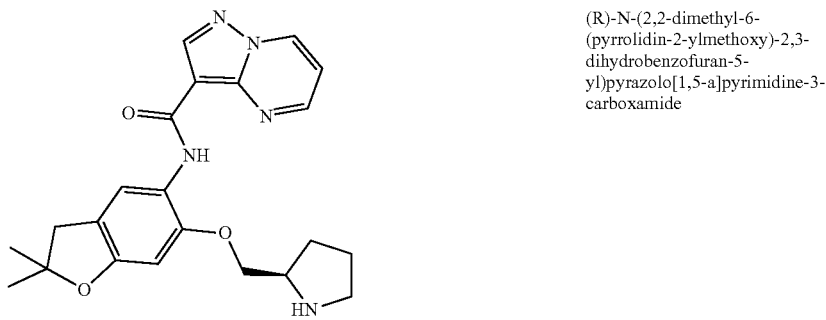 | (R)-N-(2,2-dimethyl-6-(pyrrolidin-2-ylmethoxy)-2,3-dihydrobenzofuran-5-yl)pyrazolo[1,5-a]pyrimidine-3-carboxamide |

TABLE 2-continued

*Additional exemplary compounds of the present invention. Salts of such compounds are also contemplated. See the Examples section for preparation of such compounds.*

292 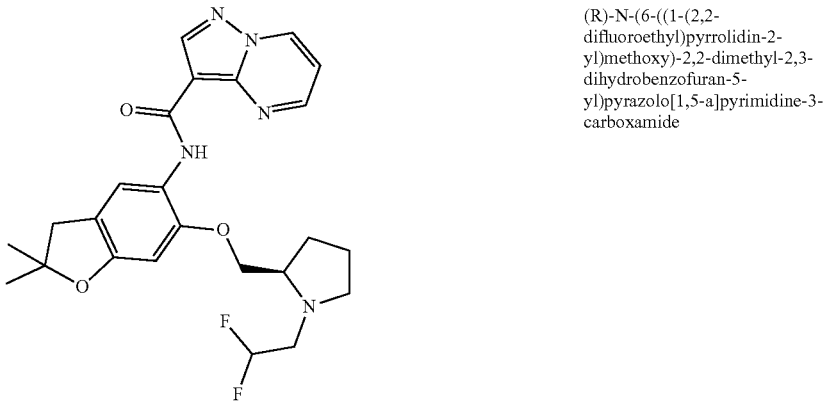

(R)-N-(6-((1-(2,2-difluoroethyl)pyrrolidin-2-yl)methoxy)-2,2-dimethyl-2,3-dihydrobenzofuran-5-yl)pyrazolo[1,5-a]pyrimidine-3-carboxamide 293 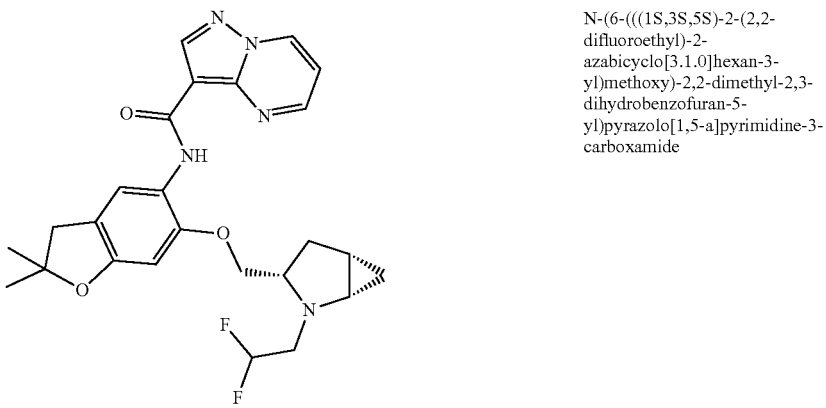

N-(6-((((1S,3S,5S)-2-(2,2-difluoroethyl)-2-azabicyclo[3.1.0]hexan-3-yl)methoxy)-2,2-dimethyl-2,3-dihydrobenzofuran-5-yl)pyrazolo[1,5-a]pyrimidine-3-carboxamide 294 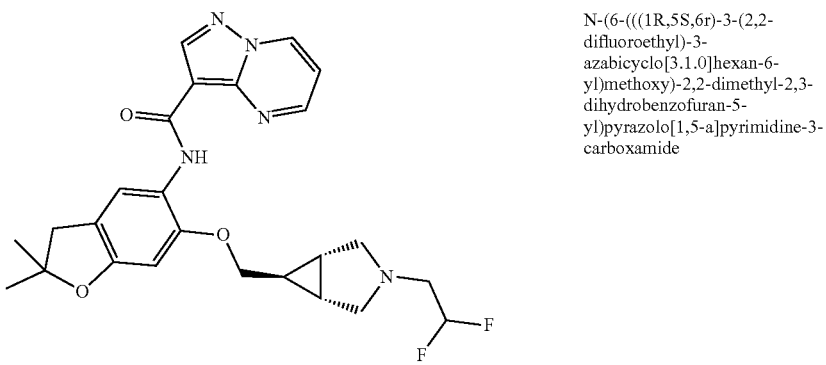

N-(6-((((1R,5S,6r)-3-(2,2-difluoroethyl)-3-azabicyclo[3.1.0]hexan-6-yl)methoxy)-2,2-dimethyl-2,3-dihydrobenzofuran-5-yl)pyrazolo[1,5-a]pyrimidine-3-carboxamide 295 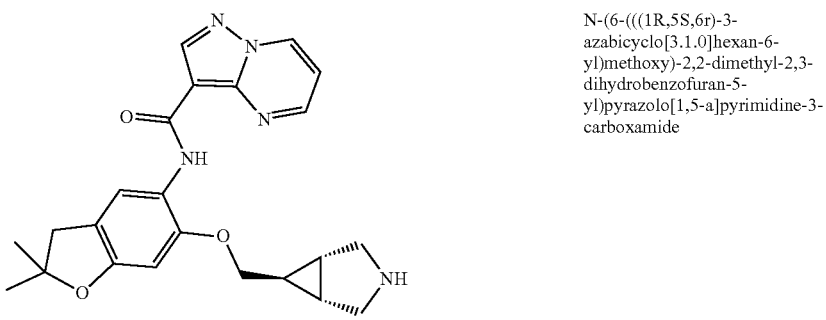

N-(6-((((1R,5S,6r)-3-azabicyclo[3.1.0]hexan-6-yl)methoxy)-2,2-dimethyl-2,3-dihydrobenzofuran-5-yl)pyrazolo[1,5-a]pyrimidine-3-carboxamide TABLE 2-continued

*Additional exemplary compounds of the present invention. Salts of such compounds are also contemplated. See the Examples section for preparation of such compounds.*

296 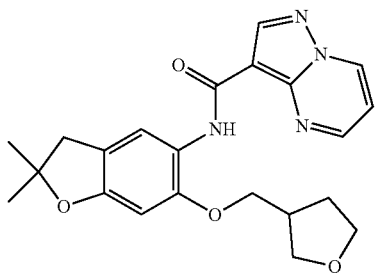 [SMILES: CC1(C)Cc2cc(NC(=O)c3cnn4cccnc34)c(OCC3CCOC3)cc2O1] N-(2,2-dimethyl-6-((tetrahydrofuran-3-yl)methoxy)-2,3-dihydrobenzofuran-5-yl)pyrazolo[1,5-a]pyrimidine-3-carboxamide 297 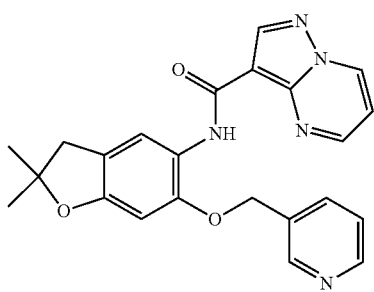 [SMILES: CC1(C)Cc2cc(NC(=O)c3cnn4cccnc34)c(OCc3cccnc3)cc2O1] N-(2,2-dimethyl-6-(pyridin-3-ylmethoxy)-2,3-dihydrobenzofuran-5-yl)pyrazolo[1,5-a]pyrimidine-3-carboxamide 298 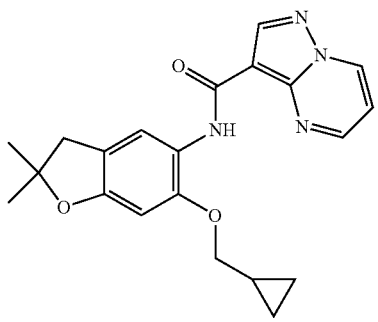 [SMILES: CC1(C)Cc2cc(NC(=O)c3cnn4cccnc34)c(OCC3CC3)cc2O1] N-(6-(cyclopropylmethoxy)-2,2-dimethyl-2,3-dihydrobenzofuran-5-yl)pyrazolo[1,5-a]pyrimidine-3-carboxamide 299 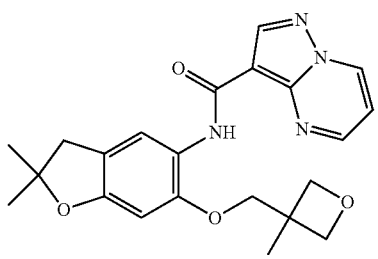 [SMILES: CC1(COc2cc3c(cc2NC(=O)c2cnn4cccnc24)CC(C)(C)O3)COC1] N-(2,2-dimethyl-6-((3-methyloxetan-3-yl)methoxy)-2,3-dihydrobenzofuran-5-yl)pyrazolo[1,5-a]pyrimidine-3-carboxamide 300 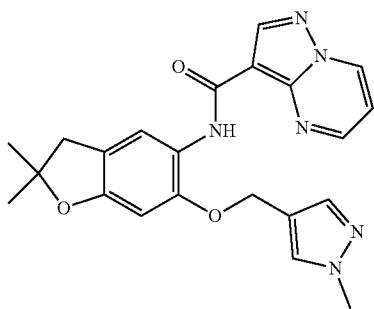 [SMILES: Cn1cc(COc2cc3c(cc2NC(=O)c2cnn4cccnc24)CC(C)(C)O3)cn1] N-(2,2-dimethyl-6-((1-methyl-1H-pyrazol-4-yl)methoxy)-2,3-dihydrobenzofuran-5-yl)pyrazolo[1,5-a]pyrimidine-3-carboxamide TABLE 2-continued Additional exemplary compounds of the present invention. Salts of such compounds are also contemplated. See the Examples section for preparation of such compounds.

| 301 | 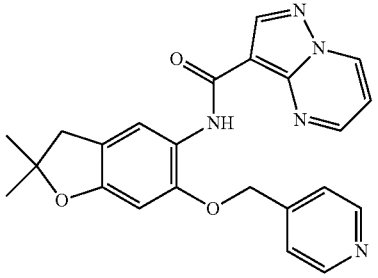 [SMILES: CC1(C)Cc2cc(NC(=O)c3cnn4cccnc34)c(OCc3ccncc3)cc2O1] | N-(2,2-dimethyl-6-(pyridin-4-ylmethoxy)-2,3-dihydrobenzofuran-5-yl)pyrazolo[1,5-a]pyrimidine-3-carboxamide |
| --- | --- | --- |
| 302 | 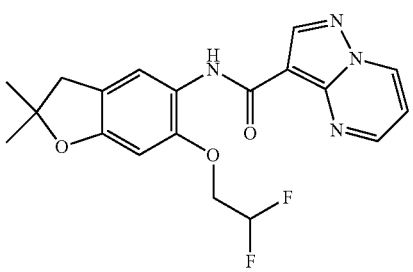 [SMILES: CC1(C)Cc2cc(NC(=O)c3cnn4cccnc34)c(OCC(F)F)cc2O1] | N-(6-(2,2-difluoroethoxy)-2,2-dimethyl-2,3-dihydrobenzofuran-5-yl)pyrazolo[1,5-a]pyrimidine-3-carboxamide |
| 303 | 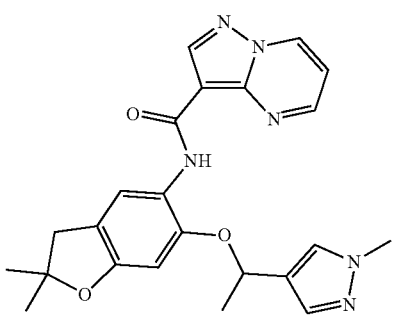 | N-(2,2-dimethyl-6-(1-(1-methyl-1H-pyrazol-4-yl)ethoxy)-2,3-dihydrobenzofuran-5-yl)pyrazolo[1,5-a]pyrimidine-3-carboxamide |
| 304 | 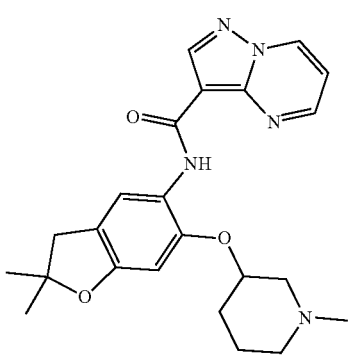 | N-(2,2-dimethyl-6-((1-methylpiperidin-3-yl)oxy)-2,3-dihydrobenzofuran-5-yl)pyrazolo[1,5-a]pyrimidine-3-carboxamide |
| 305 and 306 | 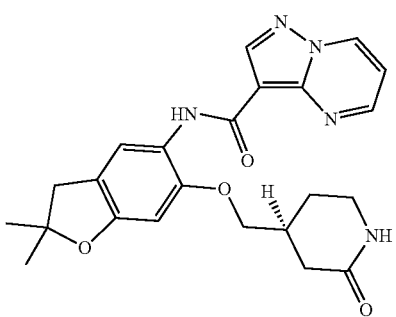 | (S)-N-(2,2-dimethyl-6-((2-oxopiperidin-4-yl)methoxy)-2,3-dihydrobenzofuran-5-yl)pyrazolo[1,5-a]pyrimidine-3-carboxamide and (R)-N-(2,2-dimethyl-6-((2-oxopiperidin-4-yl)methoxy)-2,3-dihydrobenzofuran-5-yl)pyrazolo[1,5-a]pyrimidine-3-carboxamide |

TABLE 2-continued

*Additional exemplary compounds of the present invention. Salts of such compounds are also contemplated. See the Examples section for preparation of such compounds.*

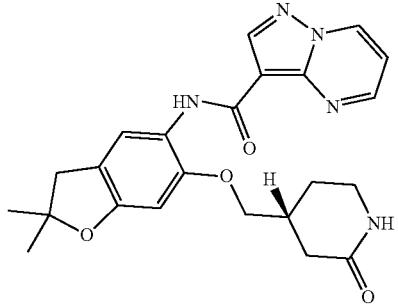

| | | |
|---|---|---|
| 307 and 308 | 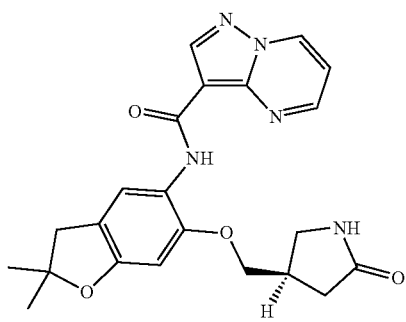 | (R)-N-(2,2-dimethyl-6-((5-oxopyrrolidin-3-yl)methoxy)-2,3-dihydrobenzofuran-5-yl)pyrazolo[1,5-a]pyrimidine-3-carboxamide and (S)-N-(2,2-dimethyl-6-((5-oxopyrrolidin-3-yl)methoxy)-2,3-dihydrobenzofuran-5-yl)pyrazolo[1,5-a]pyrimidine-3-carboxamide |
| | 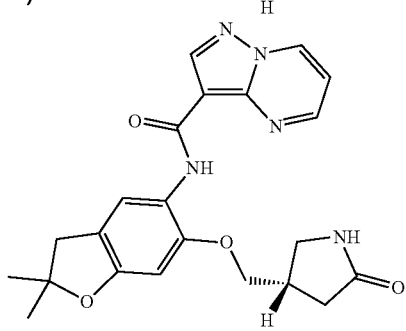 | |
| 309 | 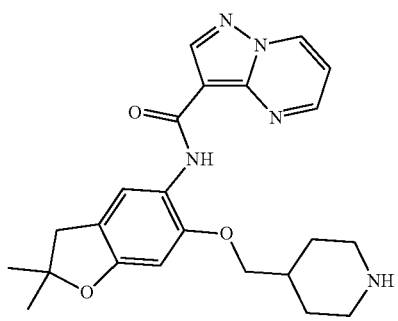 [SMILES: CC1(C)Cc2cc(NC(=O)c3cnn4cccnc34)c(OCC3CCNCC3)cc2O1] | N-(2,2-dimethyl-6-(piperidin-4-ylmethoxy)-2,3-dihydrobenzofuran-5-yl)pyrazolo[1,5-a]pyrimidine-3-carboxamide |
| 310 and 311 | 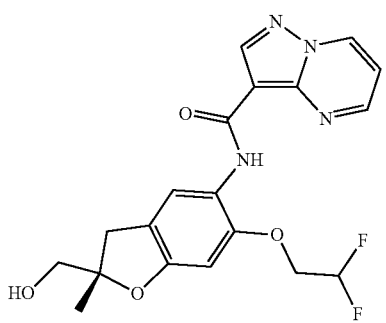 | (S)-N-(6-(2,2-difluoroethoxy)-2-(hydroxymethyl)-2-methyl-2,3-dihydrobenzofuran-5-yl)pyrazolo[1,5-a]pyrimidine-3-carboxamide and (R)-N-(6-(2,2-difluoroethoxy)-2-(hydroxymethyl)-2-methyl-2,3-dihydrobenzofuran-5-yl)pyrazolo[1,5-a]pyrimidine-3-carboxamide |

TABLE 2-continued

*Additional exemplary compounds of the present invention. Salts of such compounds are also contemplated. See the Examples section for preparation of such compounds.*

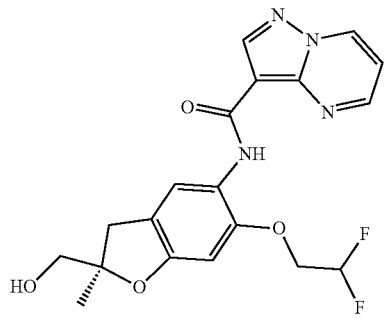

312 and 313

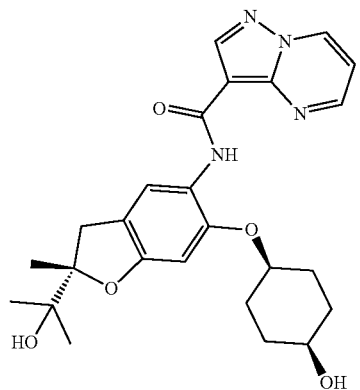

N-((S)-6-(((1S,4R)-4-hydroxycyclohexyl)oxy)-2-(2-hydroxypropan-2-yl)-2-methyl-2,3-dihydrobenzofuran-5-yl)pyrazolo[1,5-a]pyrimidine-3-carboxamide
and
N-((R)-6-(((1S,4S)-4-hydroxycyclohexyl)oxy)-2-(2-hydroxypropan-2-yl)-2-methyl-2,3-dihydrobenzofuran-5-yl)pyrazolo[1,5-a]pyrimidine-3-carboxamide

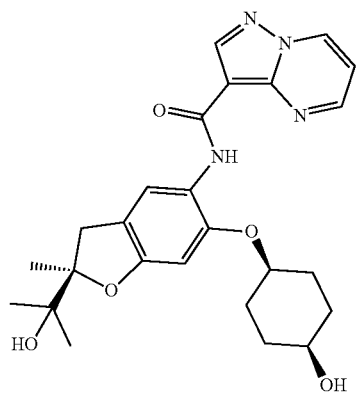

314 and 315

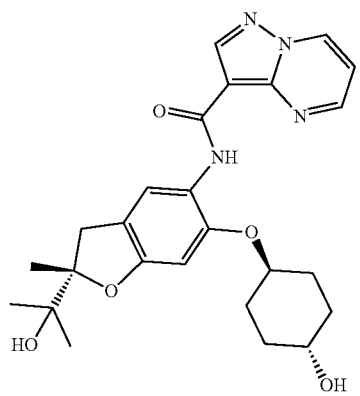

N-((S)-6-(((1r,4S)-4-hydroxycyclohexyl)oxy)-2-(2-hydroxypropan-2-yl)-2-methyl-2,3-dihydrobenzofuran-5-yl)pyrazolo[1,5-a]pyrimidine-3-carboxamide
and
N-((R)-6-(((1r,4R)-4-hydroxycyclohexyl)oxy)-2-(2-hydroxypropan-2-yl)-2-methyl-2,3-dihydrobenzofuran-5-yl)pyrazolo[1,5-a]pyrimidine-3-carboxamide TABLE 2-continued

*Additional exemplary compounds of the present invention. Salts of such compounds are also contemplated. See the Examples section for preparation of such compounds.*

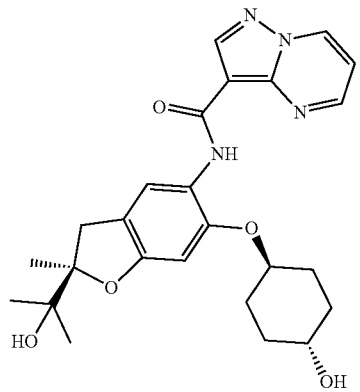

| | | |
|---|---|---|
| 316 and 317 | 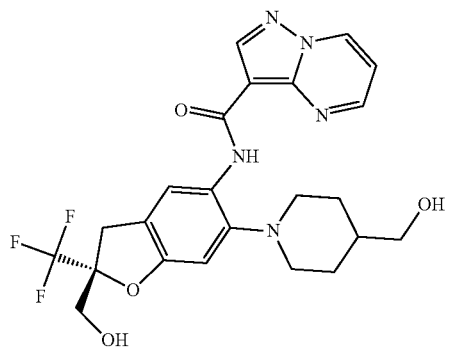 | (R)-N-(2-(hydroxymethyl)-6-(4-(hydroxymethyl)piperidin-1-yl)-2-(trifluoromethyl)-2,3-dihydrobenzofuran-5-yl)pyrazolo[1,5-a]pyrimidine-3-carboxamide and (S)-N-(2-(hydroxymethyl)-6-(4-(hydroxymethyl)piperidin-1-yl)-2-(trifluoromethyl)-2,3-dihydrobenzofuran-5-yl)pyrazolo[1,5-a]pyrimidine-3-carboxamide |
| 318 and 319 | 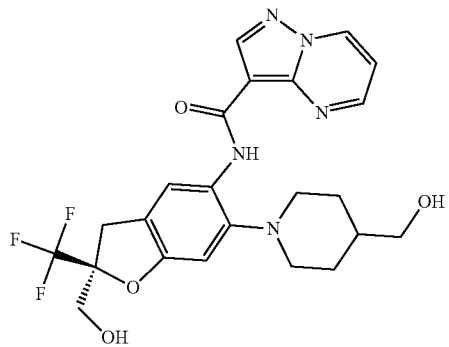 | (S)-N-(6-(4-fluoro-4-(hydroxymethyl)piperidin-1-yl)-2-(hydroxymethyl)-2-(trifluoromethyl)-2,3-dihydrobenzofuran-5-yl)pyrazolo[1,5-a]pyrimidine-3-carboxamide and (R)-N-(6-(4-fluoro-4-(hydroxymethyl)piperidin-1-yl)-2-(hydroxymethyl)-2-(trifluoromethyl)-2,3-dihydrobenzofuran-5-yl)pyrazolo[1,5-a]pyrimidine-3-carboxamide |

TABLE 2-continued

*Additional exemplary compounds of the present invention. Salts of such compounds are also contemplated. See the Examples section for preparation of such compounds.*

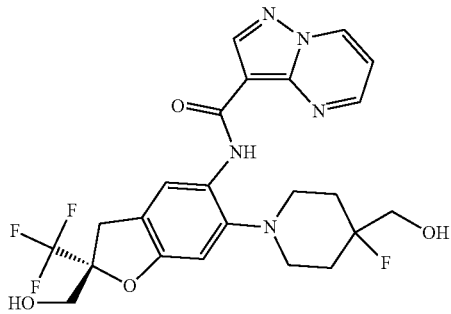

| | | |
|---|---|---|
| 320 and 321 | 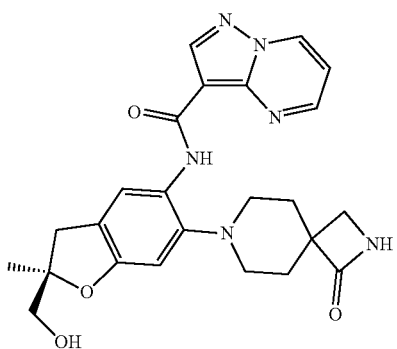 | (R)-N-(2-(hydroxymethyl)-2-methyl-6-(1-oxo-2,7-diazaspiro[3.5]nonan-7-yl)-2,3-dihydrobenzofuran-5-yl)pyrazolo[1,5-a]pyrimidine-3-carboxamide and (S)-N-(2-(hydroxymethyl)-2-methyl-6-(1-oxo-2,7-diazaspiro[3.5]nonan-7-yl)-2,3-dihydrobenzofuran-5-yl)pyrazolo[1,5-a]pyrimidine-3-carboxamide |
| | 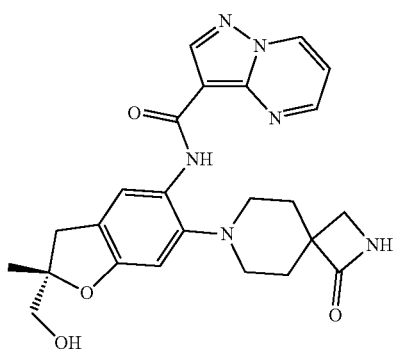 | |
| 322 | 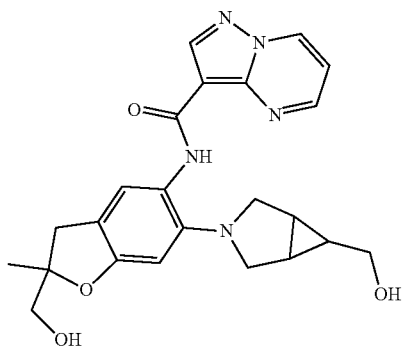 [SMILES: CC1(CO)Cc2cc(NC(=O)c3cnn4cccnc34)c(N3CC4C(CO)C4C3)cc2O1] | N-(2-(hydroxymethyl)-6-(6-(hydroxymethyl)-3-azabicyclo[3.1.0]hexan-3-yl)-2-methyl-2,3-dihydrobenzofuran-5-yl)pyrazolo[1,5-a]pyrimidine-3-carboxamide |

TABLE 2-continued

*Additional exemplary compounds of the present invention. Salts of such compounds are also contemplated. See the Examples section for preparation of such compounds.*

| | | |
|---|---|---|
| 323 and 324 | 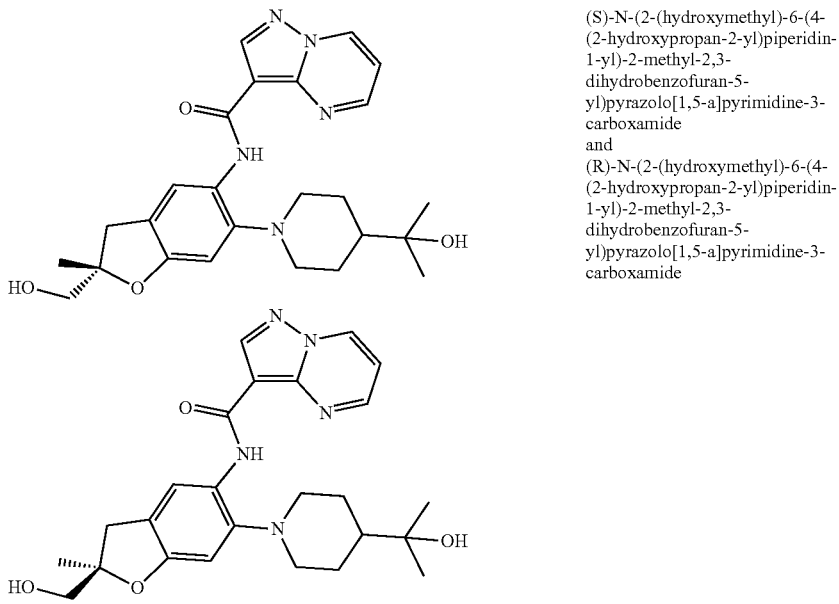 | (S)-N-(2-(hydroxymethyl)-6-(4-(2-hydroxypropan-2-yl)piperidin-1-yl)-2-methyl-2,3-dihydrobenzofuran-5-yl)pyrazolo[1,5-a]pyrimidine-3-carboxamide and (R)-N-(2-(hydroxymethyl)-6-(4-(2-hydroxypropan-2-yl)piperidin-1-yl)-2-methyl-2,3-dihydrobenzofuran-5-yl)pyrazolo[1,5-a]pyrimidine-3-carboxamide |
| 325 | 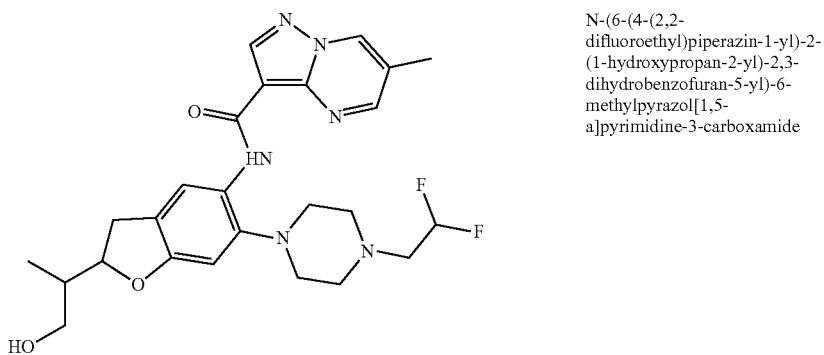 | N-(6-(4-(2,2-difluoroethyl)piperazin-1-yl)-2-(1-hydroxypropan-2-yl)-2,3-dihydrobenzofuran-5-yl)-6-methylpyrazol[1,5-a]pyrimidine-3-carboxamide |
| 326 and 327 | 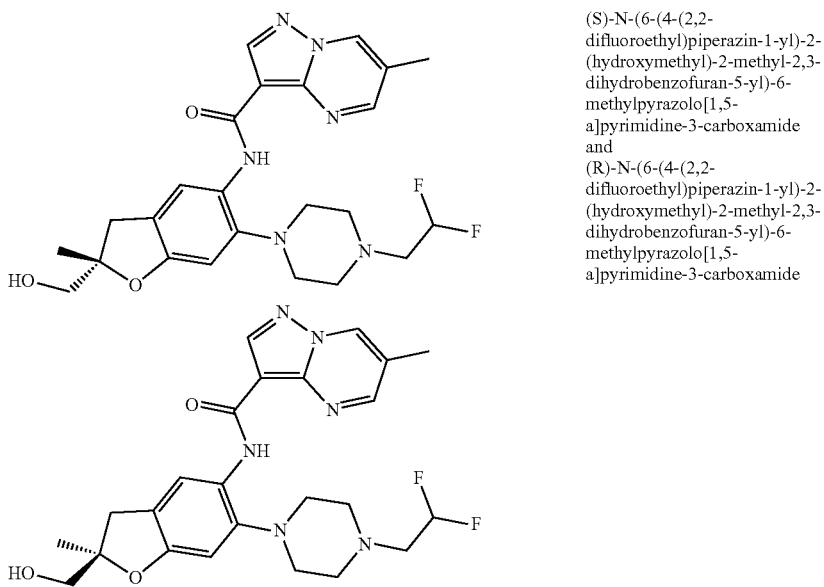 | (S)-N-(6-(4-(2,2-difluoroethyl)piperazin-1-yl)-2-(hydroxymethyl)-2-methyl-2,3-dihydrobenzofuran-5-yl)-6-methylpyrazolo[1,5-a]pyrimidine-3-carboxamide and (R)-N-(6-(4-(2,2-difluoroethyl)piperazin-1-yl)-2-(hydroxymethyl)-2-methyl-2,3-dihydrobenzofuran-5-yl)-6-methylpyrazolo[1,5-a]pyrimidine-3-carboxamide |

TABLE 2-continued

Additional exemplary compounds of the present invention. Salts of such compounds are also contemplated. See the Examples section for preparation of such compounds.

| | | |
|---|---|---|
| 328 | 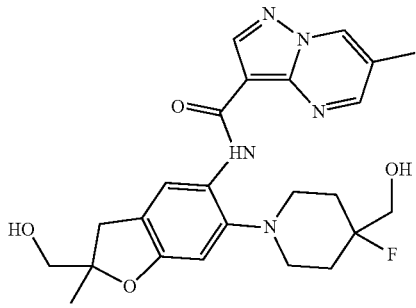 [SMILES: Cc1cnc2c(C(=O)Nc3cc4c(cc3N3CCC(F)(CO)CC3)OC(C)(CO)C4)cnn2c1] | N-(6-(4-fluoro-4-(hydroxymethyl)piperidin-1-yl)-2-(hydroxymethyl)-2-methyl-2,3-dihydrobenzofuran-5-yl)-6-methylpyrazolo[1,5-a]pyrimidine-3-carboxamide |
| 329, 330, 331, and 332 | 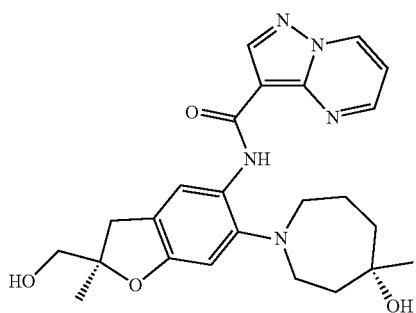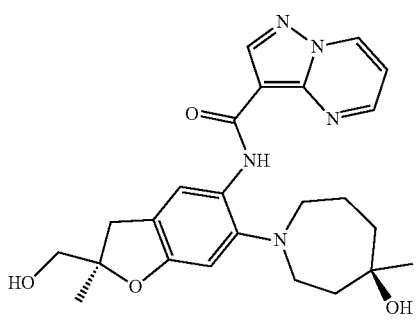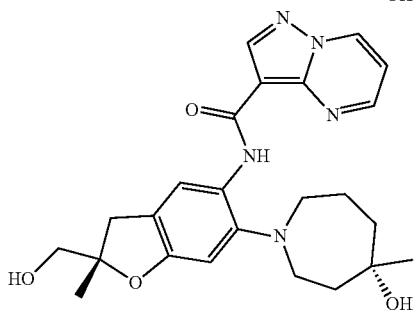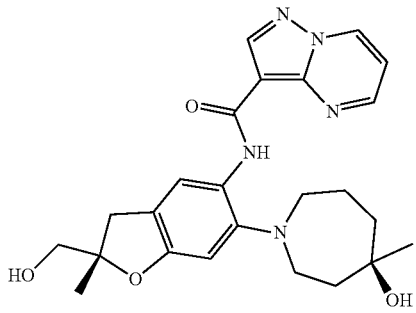 | N-((R)-6-((S)-4-hydroxy-4-methylazepan-1-yl)-2-(hydroxymethyl)-2-methyl-2,3-dihydrobenzofuran-5-yl)pyrazolo[1,5-a]pyrimidine-3-carboxamide;<br>N-((R)-6-((R)-4-hydroxy-4-methylazepan-1-yl)-2-(hydroxymethyl)-2-methyl-2,3-dihydrobenzofuran-5-yl)pyrazolo[1,5-a]pyrimidine-3-carboxamide;<br>N-((4S)-6-((S)-4-hydroxy-4-methylazepan-1-yl)-2-(hydroxymethyl)-2-methyl-2,3-dihydrobenzofuran-5-yl)pyrazolo[1,5-a]pyrimidine-3-carboxamide;<br>N-((S)-6-((R)-4-hydroxy-4-methylazepan-1-yl)-2-(hydroxymethyl)-2-methyl-2,3-dihydrobenzofuran-5-yl)pyrazolo[1,5-a]pyrimidine-3-carboxamide |

TABLE 2-continued

*Additional exemplary compounds of the present invention. Salts of such compounds are also contemplated. See the Examples section for preparation of such compounds.*

| | | |
|---|---|---|
| 333 and 334 | 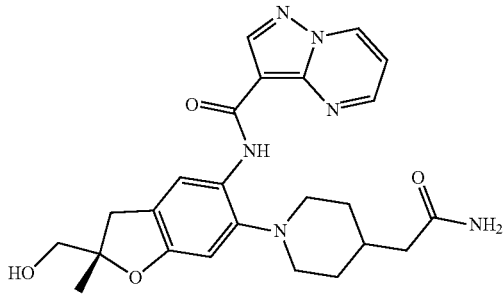 | (S)-N-(6-(4-(2-amino-2-oxoethyl)piperidin-1-yl)-2-(hydroxymethyl)-2-methyl-2,3-dihydrobenzofuran-5-yl)pyrazolo[1,5-a]pyrimidine-3-carboxamide and (R)-N-(6-(4-(2-amino-2-oxoethyl)piperidin-1-yl)-2-(hydroxymethyl)-2-methyl-2,3-dihydrobenzofuran-5-yl)pyrazolo[1,5-a]pyrimidine-3-carboxamide |
| | 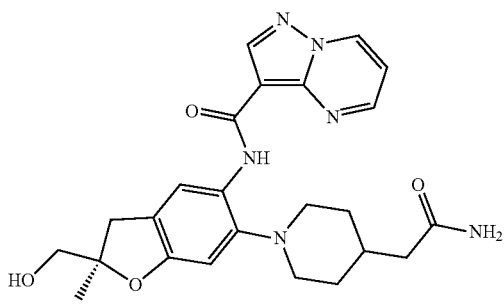 | |
| 335 and 336 | 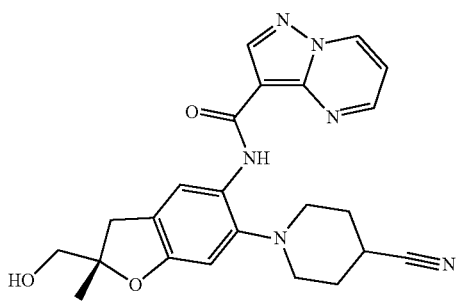 | (S)-N-(6-(4-cyanopiperidin-1-yl)-2-(hydroxymethyl)-2-methyl-2,3-dihydrobenzofuran-5-yl)pyrazolo[1,5-a]pyrimidine-3-carboxamide and (R)-N-(6-(4-cyanopiperidin-1-yl)-2-(hydroxymethyl)-2-methyl-2,3-dihydrobenzofuran-5-yl)pyrazolo[1,5-a]pyrimidine-3-carboxamide |
| | 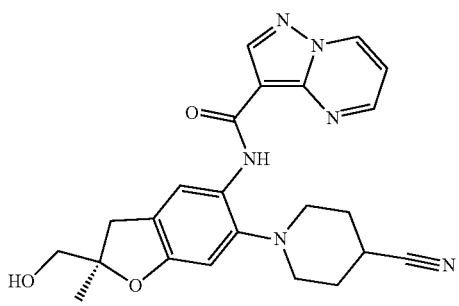 | |

TABLE 2-continued

*Additional exemplary compounds of the present invention. Salts of such compounds are also contemplated. See the Examples section for preparation of such compounds.*

| 337, 338, 339, and 340 | 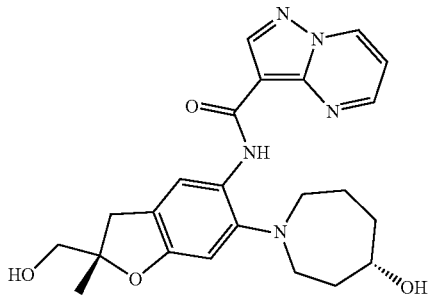<br>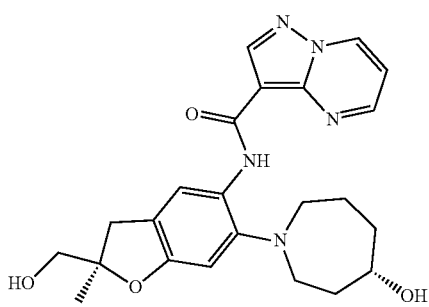<br>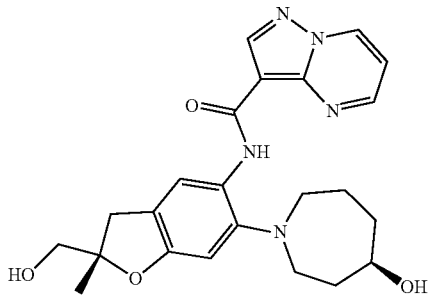<br>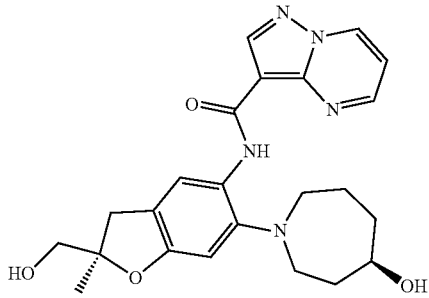 | N-((S)-6-((S)-4-hydroxyazepan-1-yl)-2-(hydroxymethyl)-2-methyl-2,3-dihydrobenzofuran-5-yl)pyrazolo[1,5-a]pyrimidine-3-carboxamide;<br>N-((R)-6-((S)-4-hydroxyazepan-1-yl)-2-(hydroxymethyl)-2-methyl-2,3-dihydrobenzofuran-5-yl)pyrazolo[1,5-a]pyrimidine-3-carboxamide;<br>N-((S)-6-((R)-4-hydroxyazepan-1-yl)-2-(hydroxymethyl)-2-methyl-2,3-dihydrobenzofuran-5-yl)pyrazolo[1,5-a]pyrimidine-3-carboxamide;<br>N-((R)-6-((R)-4-hydroxyazepan-1-yl)-2-(hydroxymethyl)-2-methyl-2,3-dihydrobenzofuran-5-yl)pyrazolo[1,5-a]pyrimidine-3-carboxamide |
| 341 and 342 | 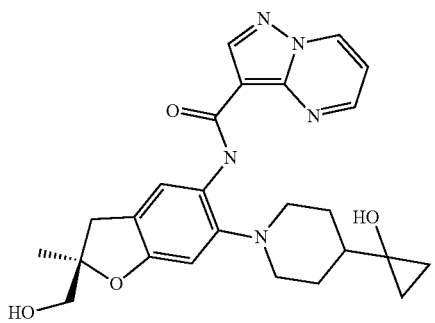 | (R)-N-(6-(4-(1-hydroxycyclopropyl)piperidin-1-yl)-2-(hydroxymethyl)-2-methyl-2,3-dihydrobenzofuran-5-yl)pyrazolo[1,5-a]pyrimidine-3-carboxamide<br>and<br>(S)-N-(6-(4-(1-hydroxycyclopropyl)piperidin-1-yl)-2-(hydroxymethyl)-2-methyl-2,3-dihydrobenzofuran-5-yl)pyrazolo[1,5-a]pyrimidine-3-carboxamide |

US 10,988,478 B1

TABLE 2-continued

Additional exemplary compounds of the present invention. Salts of such compounds are also contemplated. See the Examples section for preparation of such compounds.

| | | |
|---|---|---|
| 343 | 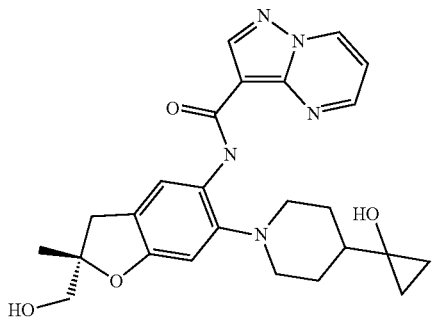 | |
| | 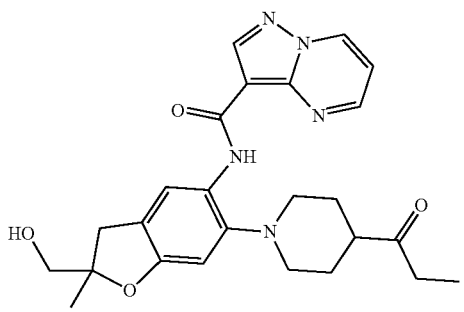 [SMILES: CCC(=O)C1CCN(c2cc3c(cc2NC(=O)c2cnn4cccnc24)CC(C)(CO)O3)CC1] | N-(2-(hydroxymethyl)-2-methyl-6-(4-propionylpiperidin-1-yl)-2,3-dihydrobenzofuran-5-yl)pyrazolo[1,5-a]pyrimidine-3-carboxamide |
| 344 and 345 | 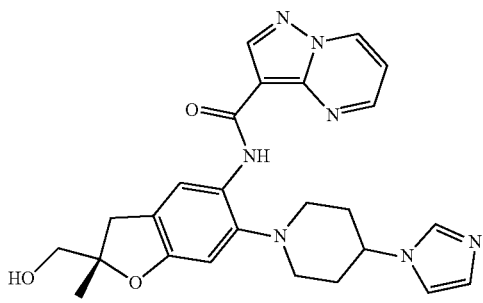 | (S)-N-(6-(4-(1H-imidazol-1-yl)piperidin-1-yl)-2-(hydroxymethyl)-2-methyl-2,3-dihydrobenzofuran-5-yl)pyrazolo[1,5-a]pyrimidine-3-carboxamide and (R)-N-(6-(4-(1H-imidazol-1-yl)piperidin-1-yl)-2-(hydroxymethyl)-2-methyl-2,3-dihydrobenzofuran-5-yl)pyrazolo[1,5-a]pyrimidine-3-carboxamide |
| | 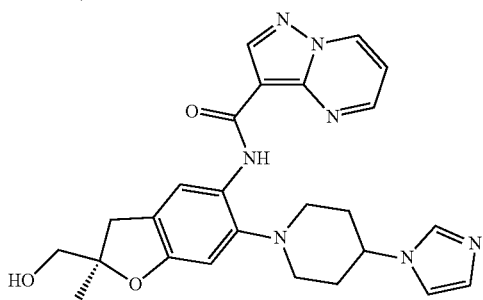 | |
| 346 an 347 | 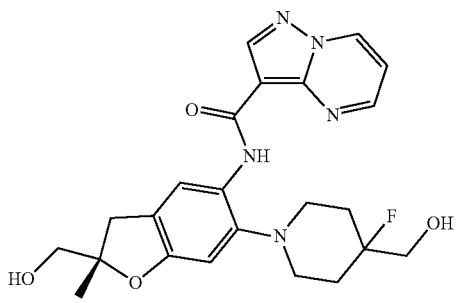 | (S)-N-(6-(4-fluoro-4-(hydroxymethyl)piperidin-1-yl)-2-(hydroxymethyl)-2-methyl-2,3-dihydrobenzofuran-5-yl)pyrazolo[1,5-a]pyrimidine-3-carboxamide and (R)-N-(6-(4-fluoro-4-(hydroxymethyl)piperidin-1-yl)-2-(hydroxymethyl)-2-methyl-2,3-dihydrobenzofuran-5-yl)pyrazolo[1,5-a]pyrimidine-3-carboxamide |

US 10,988,478 B1

235                                                                                                                   236

TABLE 2-continued

Additional exemplary compounds of the present invention. Salts of such compounds are also contemplated. See the Examples section for preparation of such compounds.

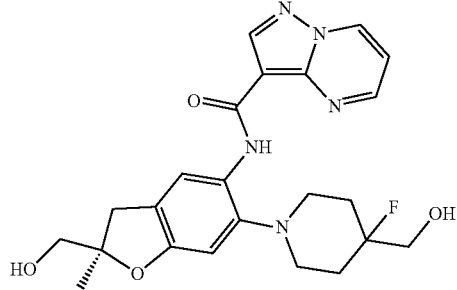

348 and 349

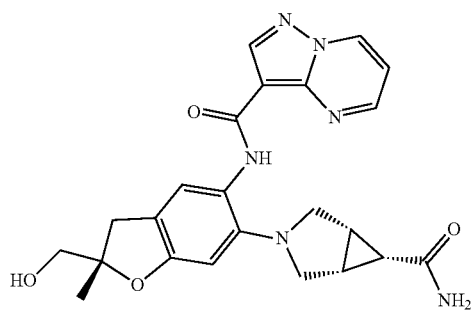

N-((S)-6-((1R,5S,6R)-6-carbamoyl-3-azabicyclo[3.1.0]hexan-3-yl)-2-(hydroxymethyl)-2-methyl-2,3-dihydrobenzofuran-5-yl)pyrazolo[1,5-a]pyrimidine-3-carboxamide
and
N-((R)-6-((1R,5S,6S)-6-carbamoyl-3-azabicyclo[3.1.0]hexan-3-yl)-2-(hydroxymethyl)-2-methyl-2,3-dihydrobenzofuran-5-yl)pyrazolo[1,5-a]pyrimidine-3-carboxamide

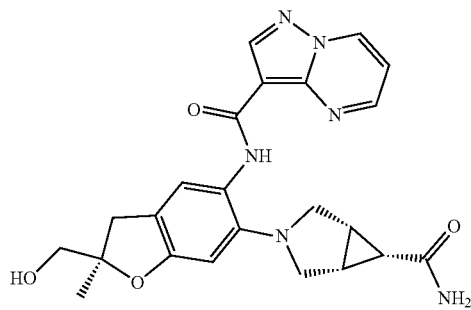

350 and 351

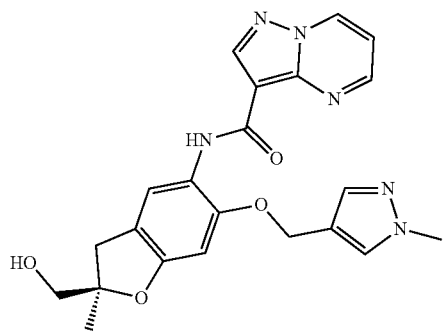

(R)-N-(2-(hydroxymethyl)-2-methyl-6-((1-methyl-1H-pyrazol-4-yl)methoxy)-2,3-dihydrobenzofuran-5-yl)pyrazolo[1,5-a]pyrimidine-3-carboxamide
and
(S)-N-(2-(hydroxymethyl)-2-methyl-6-((1-methyl-1H-pyrazol-4-yl)methoxy)-2,3-dihydrobenzofuran-5-yl)pyrazolo[1,5-a]pyrimidine-3-carboxamide

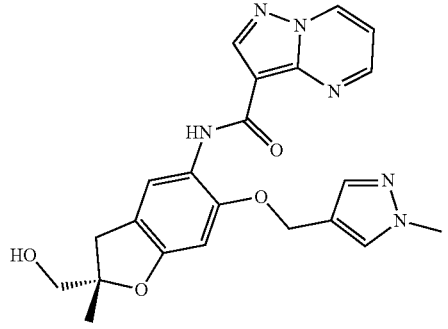

TABLE 2-continued

*Additional exemplary compounds of the present invention. Salts of such compounds are also contemplated. See the Examples section for preparation of such compounds.*

| | | |
|---|---|---|
| 352 | 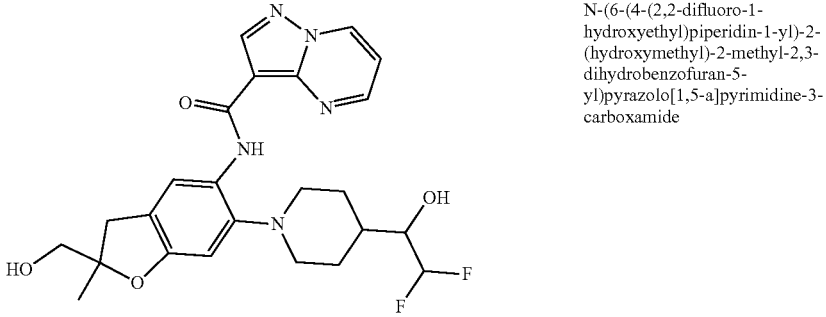 | N-(6-(4-(2,2-difluoro-1-hydroxyethyl)piperidin-1-yl)-2-(hydroxymethyl)-2-methyl-2,3-dihydrobenzofuran-5-yl)pyrazolo[1,5-a]pyrimidine-3-carboxamide |
| 353 | 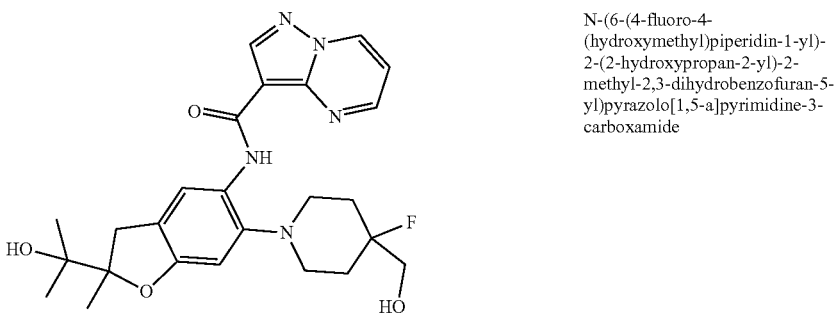 | N-(6-(4-fluoro-4-(hydroxymethyl)piperidin-1-yl)-2-(2-hydroxypropan-2-yl)-2-methyl-2,3-dihydrobenzofuran-5-yl)pyrazolo[1,5-a]pyrimidine-3-carboxamide |
| 354 and 355 | 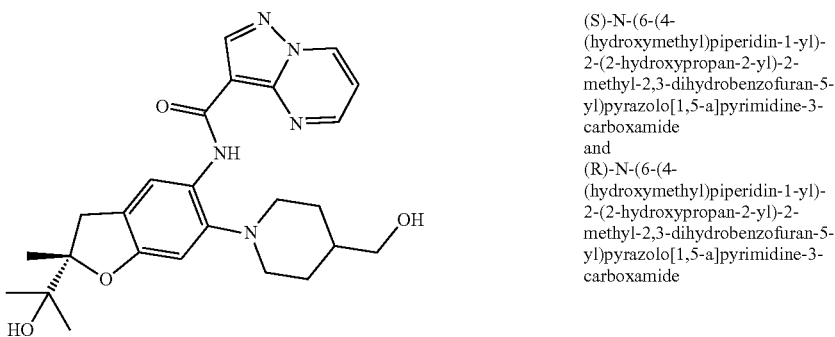<br>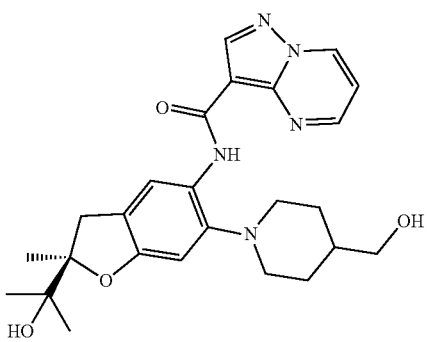 | (S)-N-(6-(4-(hydroxymethyl)piperidin-1-yl)-2-(2-hydroxypropan-2-yl)-2-methyl-2,3-dihydrobenzofuran-5-yl)pyrazolo[1,5-a]pyrimidine-3-carboxamide and (R)-N-(6-(4-(hydroxymethyl)piperidin-1-yl)-2-(2-hydroxypropan-2-yl)-2-methyl-2,3-dihydrobenzofuran-5-yl)pyrazolo[1,5-a]pyrimidine-3-carboxamide |

TABLE 2-continued

*Additional exemplary compounds of the present invention. Salts of such compounds are also contemplated. See the Examples section for preparation of such compounds.*

356 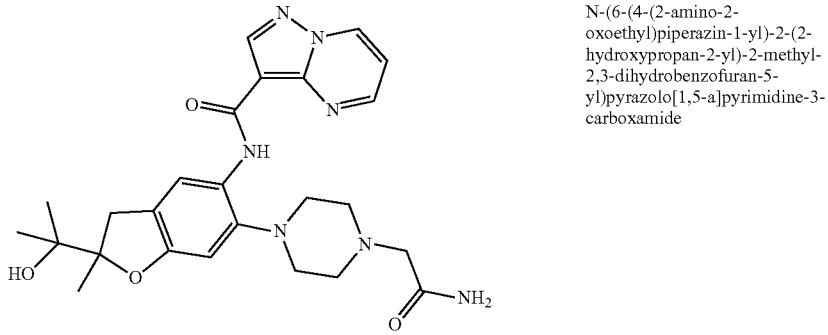 N-(6-(4-(2-amino-2-oxoethyl)piperazin-1-yl)-2-(2-hydroxypropan-2-yl)-2-methyl-2,3-dihydrobenzofuran-5-yl)pyrazolo[1,5-a]pyrimidine-3-carboxamide 357 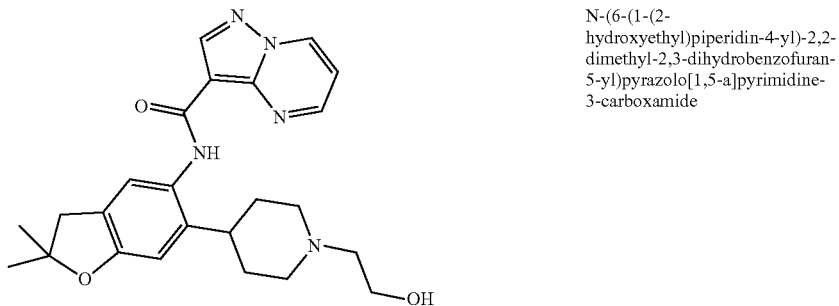 N-(6-(1-(2-hydroxyethyl)piperidin-4-yl)-2,2-dimethyl-2,3-dihydrobenzofuran-5-yl)pyrazolo[1,5-a]pyrimidine-3-carboxamide 358 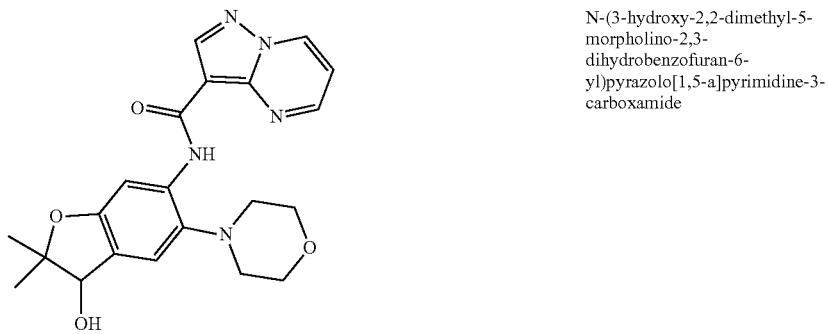 N-(3-hydroxy-2,2-dimethyl-5-morpholino-2,3-dihydrobenzofuran-6-yl)pyrazolo[1,5-a]pyrimidine-3-carboxamide 359 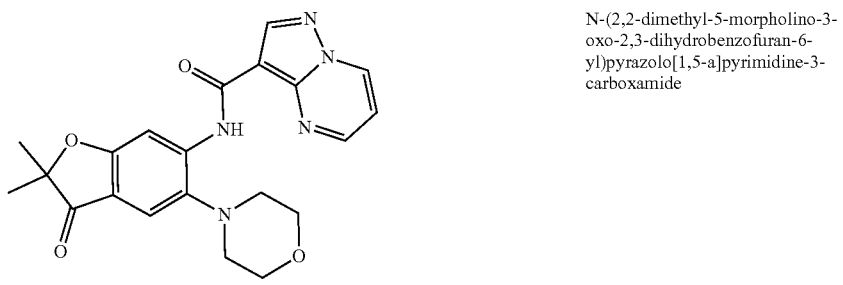 N-(2,2-dimethyl-5-morpholino-3-oxo-2,3-dihydrobenzofuran-6-yl)pyrazolo[1,5-a]pyrimidine-3-carboxamide 360 and 361 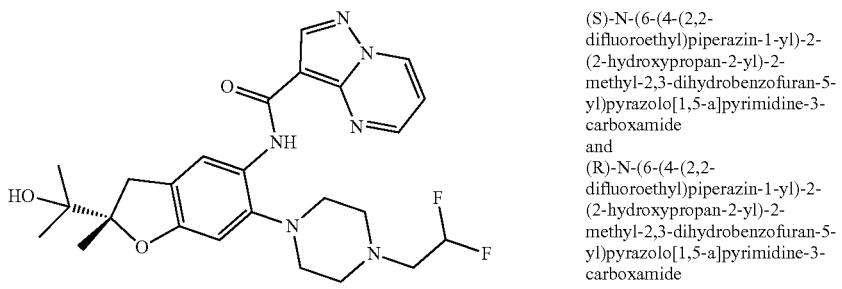 (S)-N-(6-(4-(2,2-difluoroethyl)piperazin-1-yl)-2-(2-hydroxypropan-2-yl)-2-methyl-2,3-dihydrobenzofuran-5-yl)pyrazolo[1,5-a]pyrimidine-3-carboxamide
and
(R)-N-(6-(4-(2,2-difluoroethyl)piperazin-1-yl)-2-(2-hydroxypropan-2-yl)-2-methyl-2,3-dihydrobenzofuran-5-yl)pyrazolo[1,5-a]pyrimidine-3-carboxamide TABLE 2-continued Additional exemplary compounds of the present invention. Salts of such compounds are also contemplated. See the Examples section for preparation of such compounds.

| 362 | 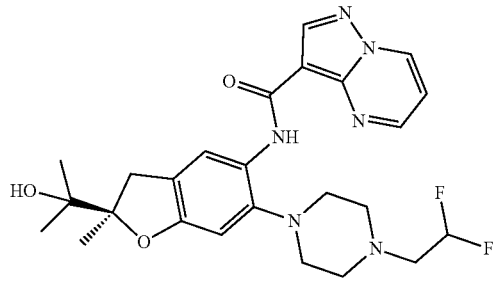 | N-(6-(4-(2,2-difluoroethyl)piperazin-1-yl)-2-((difluoromethoxy)methyl)-2-methyl-2,3-dihydrobenzofuran-5-yl)pyrazolo[1,5-a]pyrimidine-3-carboxamide |
| --- | --- | --- |
| 363 | 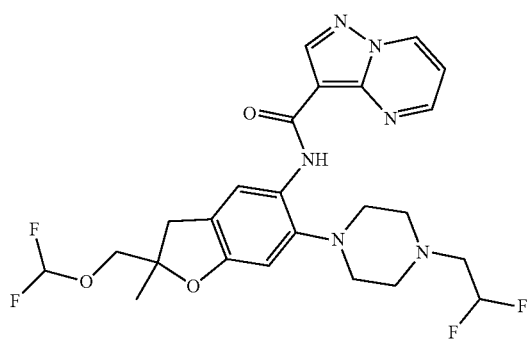 [SMILES: CC1(COC(F)F)Cc2cc(NC(=O)c3cnn4cccnc34)c(N3CCN(CC(F)F)CC3)cc2O1] | N-(6-(4-(hydroxymethyl)piperidin-1-yl)-2-(2-hydroxypropan-2-yl)-2-methyl-2,3-dihydrobenzofuran-5-yl)pyrazolo[1,5-a]pyrimidine-3-carboxamide |
| 364 | 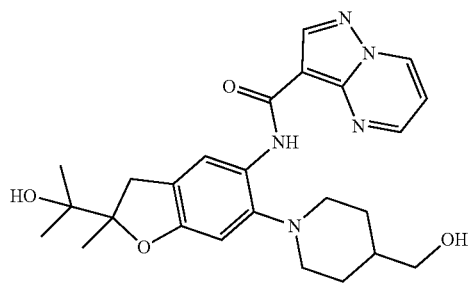 [SMILES: CC(C)(O)C1(C)Cc2cc(NC(=O)c3cnn4cccnc34)c(N3CCC(CO)CC3)cc2O1] | N-(6-(4-(2,2-difluoroethyl)piperazin-1-yl)-2-(difluoromethyl)-2-methyl-2,3-dihydrobenzofuran-5-yl)pyrazolo[1,5-a]pyrimidine-3-carboxamide |
| 365 and 366 | 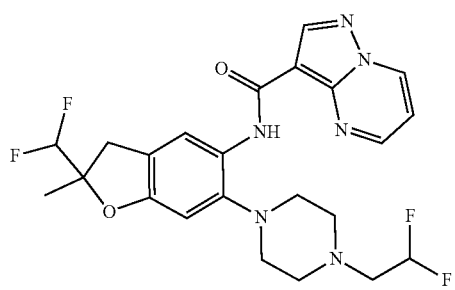 [SMILES: CC1(C(F)F)Cc2cc(NC(=O)c3cnn4cccnc34)c(N3CCN(CC(F)F)CC3)cc2O1] | (R)-N-(6-(4-(2,2-difluoroethyl)piperazin-1-yl)-2-(hydroxymethyl)-2-(trifluoromethyl)-2,3-dihydrobenzofuran-5-yl)pyrazolo[1,5-a]pyrimidine-3-carboxamide and (S)-N-(6-(4-(2,2-difluoroethyl)piperazin-1-yl)-2-(hydroxymethyl)-2-(trifluoromethyl)-2,3-dihydrobenzofuran-5-yl)pyrazolo[1,5-a]pyrimidine-3-carboxamide |

TABLE 2-continued

*Additional exemplary compounds of the present invention. Salts of such compounds are also contemplated. See the Examples section for preparation of such compounds.*

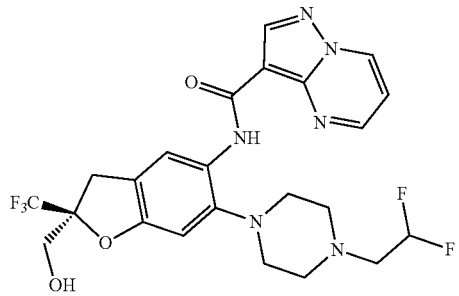

367 and 368

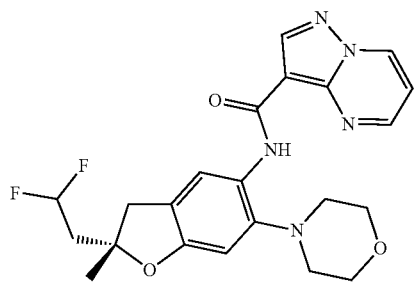

(S)-N-(2-(2,2-difluoroethyl)-2-methyl-6-morpholino-2,3-dihydrobenzofuran-5-yl)pyrazolo[1,5-a]pyrimidine-3-carboxamide
and
(R)-N-(2-(2,2-difluoroethyl)-2-methyl-6-morpholino-2,3-dihydrobenzofuran-5-yl)pyrazolo[1,5-a]pyrimidine-3-carboxamide

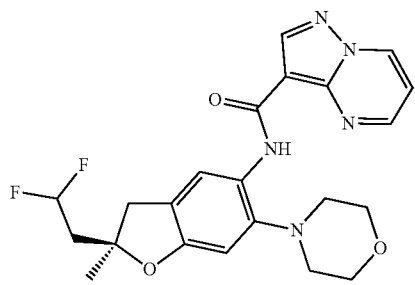

369

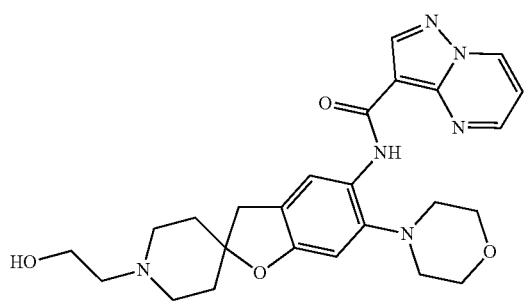 [SMILES: O=C(Nc1cc2c(cc1N1CCOCC1)OC1(CCN(CCO)CC1)C2)c1cnn2cccnc12]

N-(1'-(2-hydroxyethyl)-6-morpholino-3H-spiro[benzofuran-2,4'-piperidin]-5-yl)pyrazolo[1,5-a]pyrimidine-3-carboxamide

370

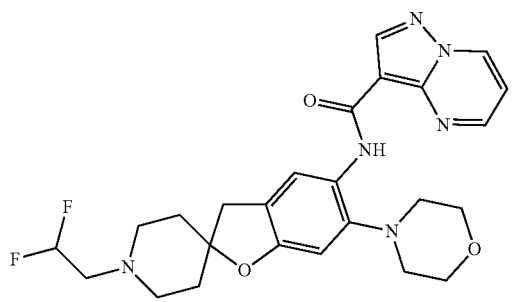 [SMILES: O=C(Nc1cc2c(cc1N1CCOCC1)OC1(CCN(CC(F)F)CC1)C2)c1cnn2cccnc12]

N-(1'-(2,2-difluoroethyl)-6-morpholino-3H-spiro[benzofuran-2,4'-piperidin]-5-yl)pyrazolo[1,5-a]pyrimidine-3-carboxamide TABLE 2-continued Additional exemplary compounds of the present invention. Salts of such compounds are also contemplated. See the Examples section for preparation of such compounds.

| 371 | 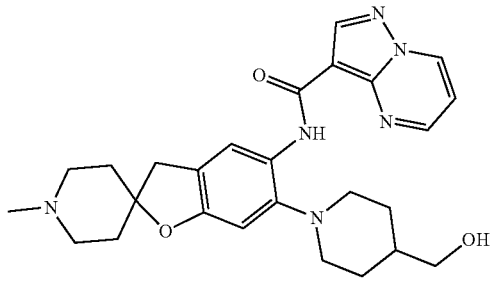 [SMILES: CN1CCC2(CC1)Cc1cc(NC(=O)c3cnn4cccnc34)c(N3CCC(CO)CC3)cc1O2] | N-(6-(4-(hydroxymethyl)piperidin-1-yl)-1'-methyl-3H-spiro[benzofuran-2,4'-piperidin]-5-yl)pyrazolo[1,5-a]pyrimidine-3-carboxamide |
| --- | --- | --- |
| 372 | 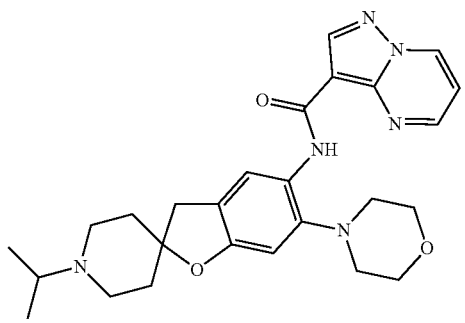 [SMILES: CC(C)N1CCC2(CC1)Cc1cc(NC(=O)c3cnn4cccnc34)c(N3CCOCC3)cc1O2] | N-(1'-isopropyl-6-morpholino-3H-spiro[benzofuran-2,4'-piperidin]-5-yl)pyrazolo[1,5-a]pyrimidine-3-carboxamide |
| 373 | 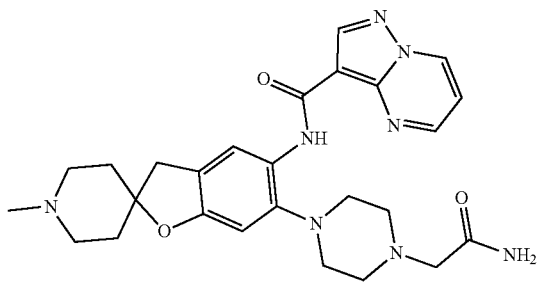 [SMILES: CN1CCC2(CC1)Cc1cc(NC(=O)c3cnn4cccnc34)c(N3CCN(CC(N)=O)CC3)cc1O2] | N-(6-(4-(2-amino-2-oxoethyl)piperazin-1-yl)-1'-methyl-3H-spiro[benzofuran-2,4'-piperidin]-5-yl)pyrazolo[1,5-a]pyrimidine-3-carboxamide |
| 374 | 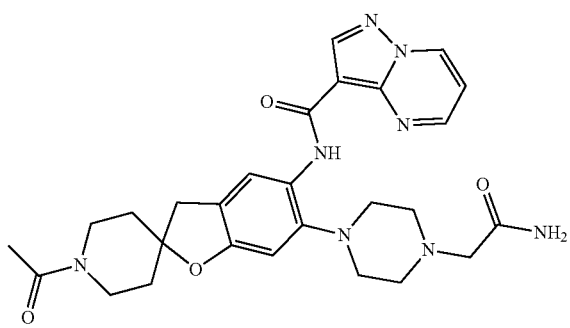 [SMILES: CC(=O)N1CCC2(CC1)Cc1cc(NC(=O)c3cnn4cccnc34)c(N3CCN(CC(N)=O)CC3)cc1O2] | N-(1'-acetyl-6-(4-(2-amino-2-oxoethyl)piperazin-1-yl)-3H-spiro[benzofuran-2,4'-piperidin]-5-yl)pyrazolo[1,5-a]pyrimidine-3-carboxamide |
| 375 | 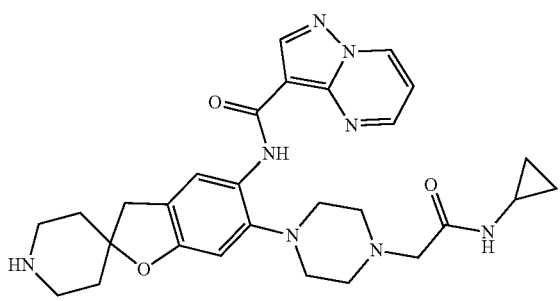 [SMILES: O=C(CN1CCN(c2cc3c(cc2NC(=O)c2cnn4cccnc24)CC2(CCNCC2)O3)CC1)NC1CC1] | N-(6-(4-(2-(cyclopropylamino)-2-oxoethyl)piperazin-1-yl)-3H-spiro[benzofuran-2,4'-piperidin]-5-yl)pyrazolo[1,5-a]pyrimidine-3-carboxamide |

TABLE 2-continued

*Additional exemplary compounds of the present invention. Salts of such compounds are also contemplated. See the Examples section for preparation of such compounds.*

376 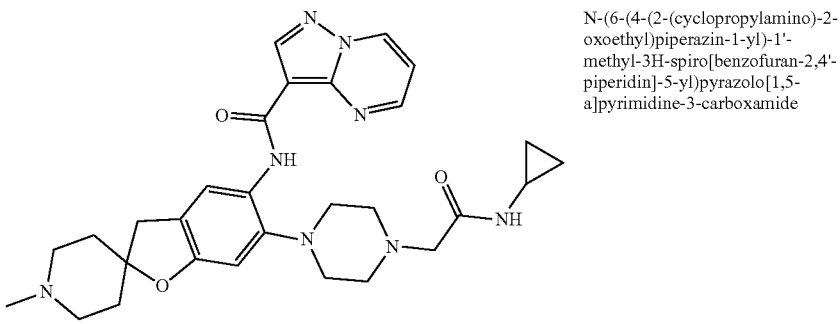 N-(6-(4-(2-(cyclopropylamino)-2-oxoethyl)piperazin-1-yl)-1'-methyl-3H-spiro[benzofuran-2,4'-piperidin]-5-yl)pyrazolo[1,5-a]pyrimidine-3-carboxamide 377 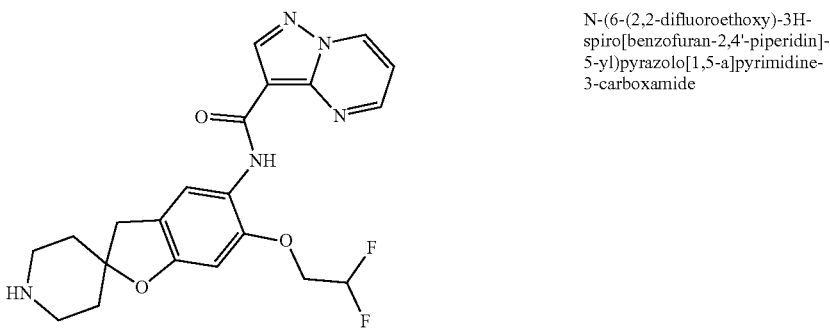 N-(6-(2,2-difluoroethoxy)-3H-spiro[benzofuran-2,4'-piperidin]-5-yl)pyrazolo[1,5-a]pyrimidine-3-carboxamide 378 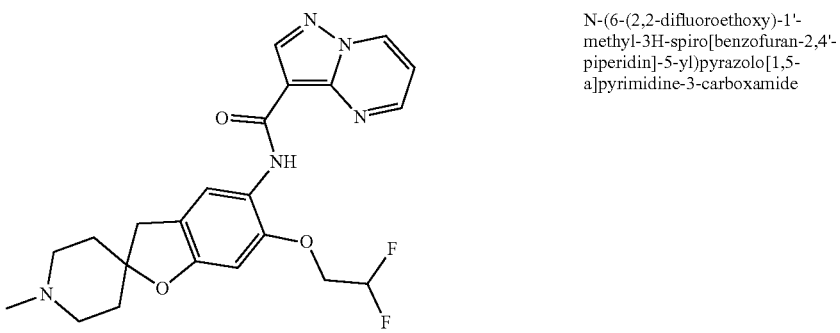 N-(6-(2,2-difluoroethoxy)-1'-methyl-3H-spiro[benzofuran-2,4'-piperidin]-5-yl)pyrazolo[1,5-a]pyrimidine-3-carboxamide 379 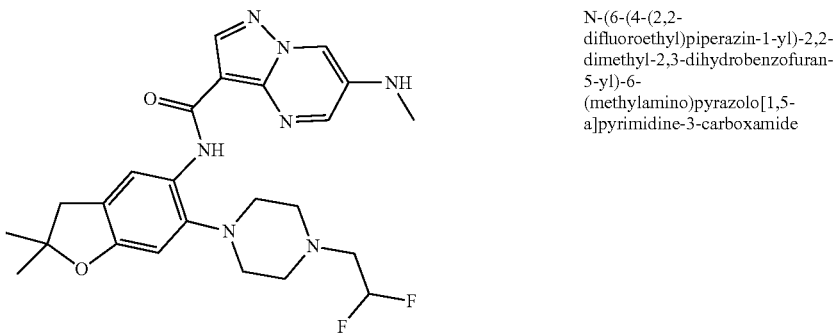 N-(6-(4-(2,2-difluoroethyl)piperazin-1-yl)-2,2-dimethyl-2,3-dihydrobenzofuran-5-yl)-6-(methylamino)pyrazolo[1,5-a]pyrimidine-3-carboxamide TABLE 2-continued

*Additional exemplary compounds of the present invention. Salts of such compounds are also contemplated. See the Examples section for preparation of such compounds.*

| | | |
|---|---|---|
| 380 | 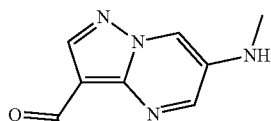 | N-(1'-methyl-6-morpholino-3H-spiro[benzofuran-2,4'-piperidin]-5-yl)-6-(methylamino)pyrazolo[1,5-a]pyrimidine-3-carboxamide |
| 381 and 382 | 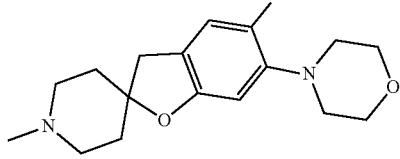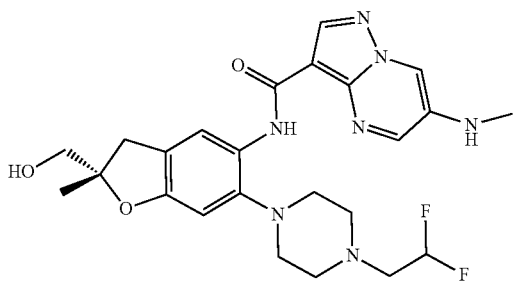 | (S)-N-(6-(4-(2,2-difluoroethyl)piperazin-1-yl)-2-(hydroxymethyl)-2-methyl-2,3-dihydrobenzofuran-5-yl)-6-(methylamino)pyrazolo[1,5-a]pyrimidine-3-carboxamide and (R)-N-(6-(4-(2,2-difluoroethyl)piperazin-1-yl)-2-(hydroxymethyl)-2-methyl-2,3-dihydrobenzofuran-5-yl)-6-(methylamino)pyrazolo[1,5-a]pyrimidine-3-carboxamide |
| 383 | 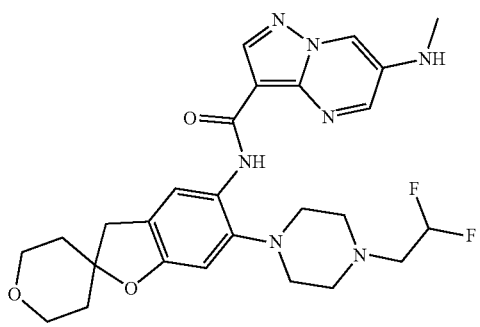 [SMILES: CNc1cnc2c(C(=O)Nc3cc4c(cc3N3CCN(CC(F)F)CC3)OC3(CCOCC3)C4)cnn2c1] | N-(6-(4-(2,2-difluoroethyl)piperazin-1-yl)-2',3',5',6'-tetrahydro-3H-spiro[benzofuran-2,4'-pyran]-5-yl)-6-(methylamino)pyrazolo[1,5-a]pyrimidine-3-carboxamide |
| 384 | 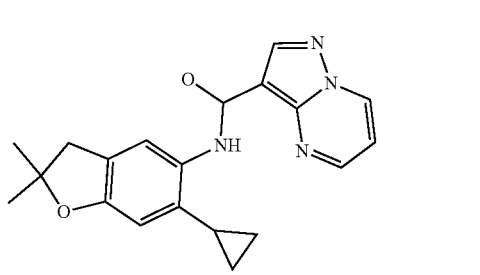 [SMILES: CC1(C)Cc2cc(NC(O)c3cnn4cccnc34)c(C3CC3)cc2O1] | N-(6-cyclopropyl-2,2-dimethyl-2,3-dihydrobenzofuran-5-yl)pyrazolo[1,5-a]pyrimidine-3-carboxamide |

TABLE 2-continued

*Additional exemplary compounds of the present invention. Salts of such compounds are also contemplated. See the Examples section for preparation of such compounds.*

| | | |
|---|---|---|
| 385 | 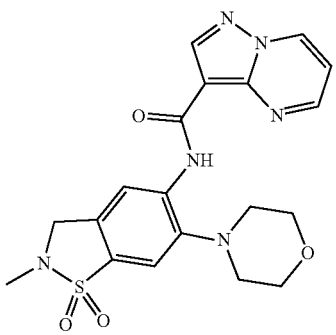 [SMILES: CN1Cc2cc(NC(=O)c3cnn4cccnc34)c(N3CCOCC3)cc2S1(=O)=O] | N-(2-methyl-6-morpholino-1,1-dioxido-2,3-dihydrobenzo[d]isothiazol-5-yl)pyrazolo[1,5-a]pyrimidine-3-carboxamide |
| 386 | 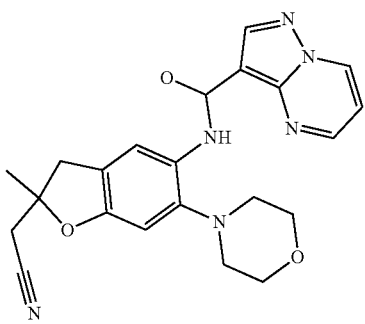 [SMILES: CC1(CC#N)Cc2cc(NC(O)c3cnn4cccnc34)c(N3CCOCC3)cc2O1] | N-(2-(cyanomethyl)-2-methyl-6-morpholino-2,3-dihydrobenzofuran-5-yl)pyrazolo[1,5-a]pyrimidine-3-carboxamide |
| 387 and 388 | 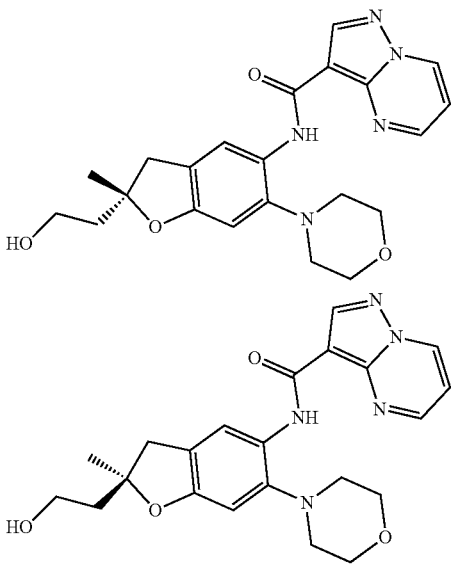 | (S)-N-(2-(2-hydroxyethyl)-2-methyl-6-morpholino-2,3-dihydrobenzofuran-5-yl)pyrazolo[1,5-a]pyrimidine-3-carboxamide and (R)-N-(2-(2-hydroxyethyl)-2-methyl-6-morpholino-2,3-dihydrobenzofuran-5-yl)pyrazolo[1,5-a]pyrimidine-3-carboxamide |
| 389 | 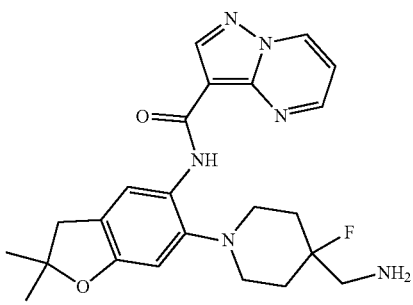 [SMILES: CC1(C)Cc2cc(NC(=O)c3cnn4cccnc34)c(N3CCC(F)(CN)CC3)cc2O1] | N-(6-(4-(aminomethyl)-4-fluoropiperidin-1-yl)-2,2-dimethyl-2,3-dihydrobenzofuran-5-yl)pyrazolo[1,5-a]pyrimidine-3-carboxamide |

TABLE 2-continued

*Additional exemplary compounds of the present invention. Salts of such compounds are also contemplated. See the Examples section for preparation of such compounds.*

| | | |
|---|---|---|
| 390 and 391 | 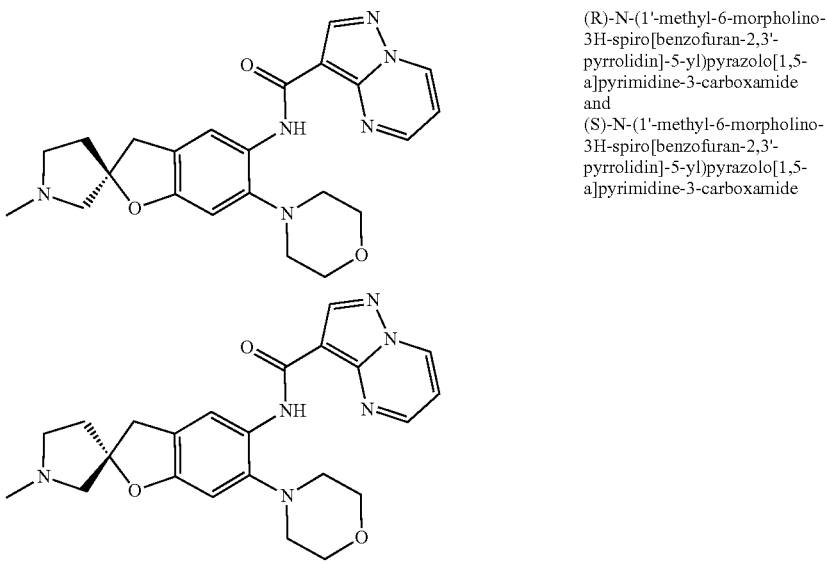 | (R)-N-(1'-methyl-6-morpholino-3H-spiro[benzofuran-2,3'-pyrrolidin]-5-yl)pyrazolo[1,5-a]pyrimidine-3-carboxamide and (S)-N-(1'-methyl-6-morpholino-3H-spiro[benzofuran-2,3'-pyrrolidin]-5-yl)pyrazolo[1,5-a]pyrimidine-3-carboxamide |
| 392 | 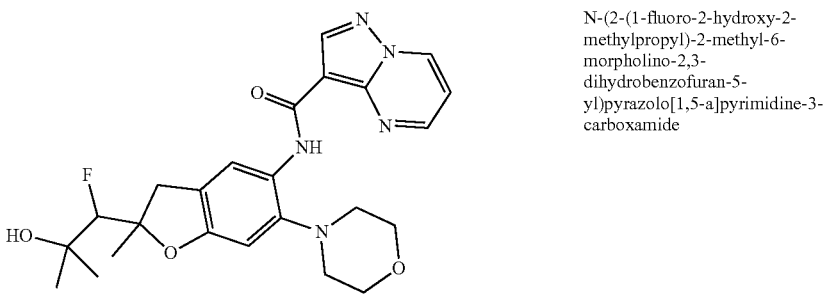 | N-(2-(1-fluoro-2-hydroxy-2-methylpropyl)-2-methyl-6-morpholino-2,3-dihydrobenzofuran-5-yl)pyrazolo[1,5-a]pyrimidine-3-carboxamide |
| 393 | 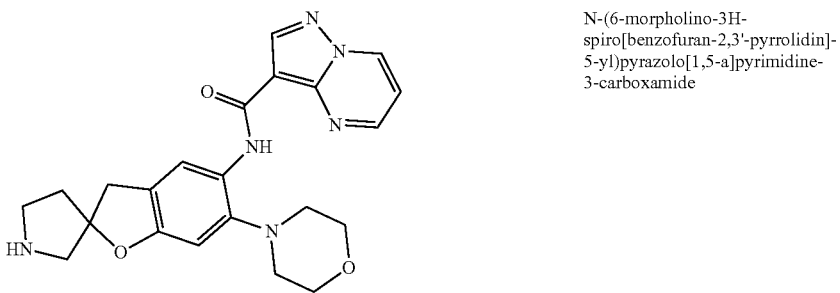 | N-(6-morpholino-3H-spiro[benzofuran-2,3'-pyrrolidin]-5-yl)pyrazolo[1,5-a]pyrimidine-3-carboxamide |
| 394 | 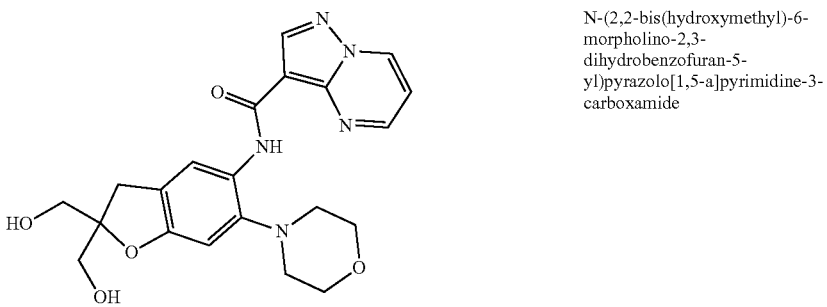 | N-(2,2-bis(hydroxymethyl)-6-morpholino-2,3-dihydrobenzofuran-5-yl)pyrazolo[1,5-a]pyrimidine-3-carboxamide |

TABLE 2-continued

*Additional exemplary compounds of the present invention. Salts of such compounds are also contemplated. See the Examples section for preparation of such compounds.*

| | | |
|---|---|---|
| 395 | 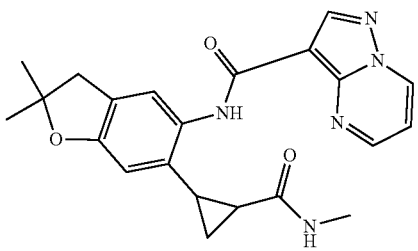 [SMILES: CNC(=O)C1CC1c1cc2c(cc1NC(=O)c1cnn3cccnc13)CC(C)(C)O2] | N-(2,2-dimethyl-6-(2-(methylcarbamoyl)cyclopropyl)-2,3-dihydrobenzofuran-5-yl)pyrazolo[1,5-a]pyrimidine-3-carboxamide |
| 396 | 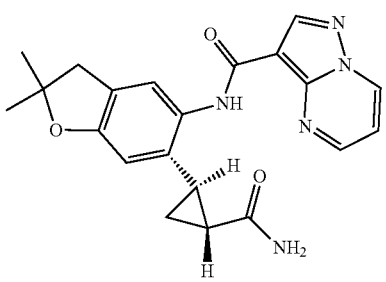 | N-(6-((1R,2R)-2-carbamoylcyclopropyl)-2,2-dimethyl-2,3-dihydrobenzofuran-5-yl)pyrazolo[1,5-a]pyrimidine-3-carboxamide |
| 397 | 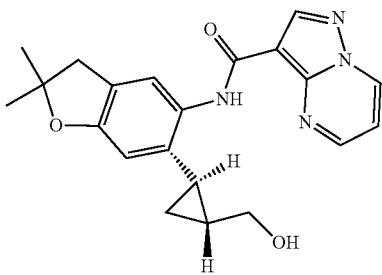 | N-(6-((1R,2R)-2-(hydroxymethyl)cyclopropyl)-2,2-dimethyl-2,3-dihydrobenzofuran-5-yl)pyrazolo[1,5-a]pyrimidine-3-carboxamide |
| 398 | 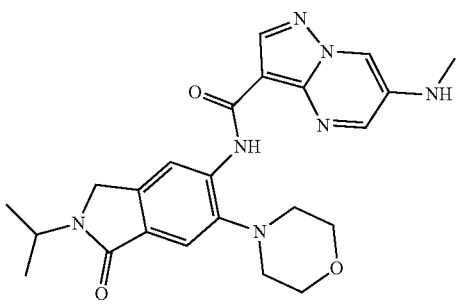 [SMILES: CNc1cnc2c(C(=O)Nc3cc4c(cc3N3CCOCC3)C(=O)N(C(C)C)C4)cnn2c1] | N-(2-isopropyl-6-morpholino-1-oxoisoindolin-5-yl)-6-(methylamino)pyrazolo[1,5-a]pyrimidine-3-carboxamide |
| 399 and 400 | 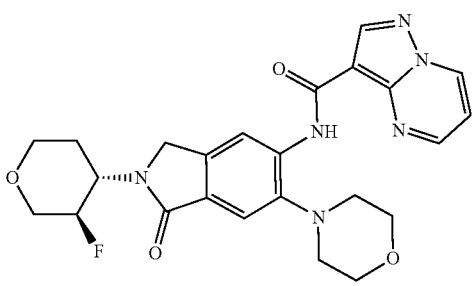 | N-(2-((3R,4S)-3-fluorotetrahydro-2H-pyran-4-yl)-6-morpholino-1-oxoisoindolin-5-yl)pyrazolo[1,5-a]pyrimidine-3-carboxamide and N-(2-(3S,4R)-3-fluorotetrahydro-2H-pyran-4-yl)-6-morpholino-1-oxoisoindolin-5-yl)pyrazolo[1,5-a]pyrimidine-3-carboxamide |

TABLE 2-continued

*Additional exemplary compounds of the present invention. Salts of such compounds are also contemplated. See the Examples section for preparation of such compounds.*

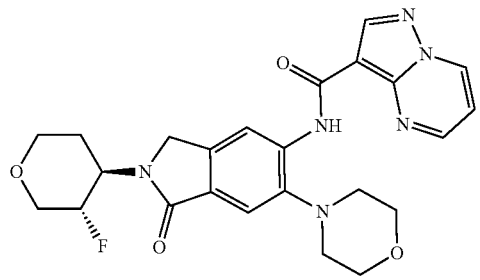

| 401 | 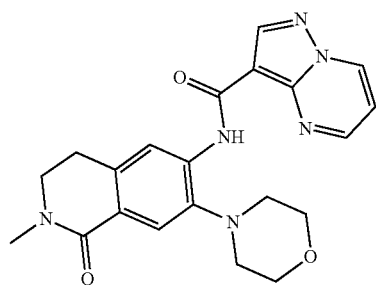 [SMILES: CN1CCc2cc(NC(=O)c3cnn4cccnc34)c(N3CCOCC3)cc2C1=O] | N-(2-methyl-7-morpholino-1-oxo-1,2,3,4-tetrahydroisoquinolin-6-yl)pyrazolo[1,5-a]pyrimidine-3-carboxamide |
|---|---|---|
| 402 | 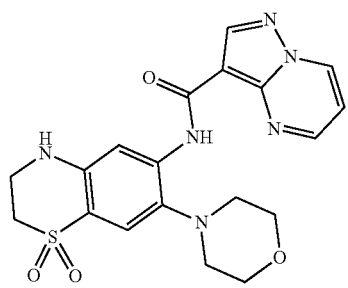 [SMILES: O=C(Nc1cc2c(cc1N1CCOCC1)S(=O)(=O)CCN2)c1cnn2cccnc12] | N-(7-morpholino-1,1-dioxido-3,4-dihydro-2H-benzo[b][1,4]thiazin-6-yl)pyrazolo[1,5-a]pyrimidine-3-carboxamide |
| 403 | 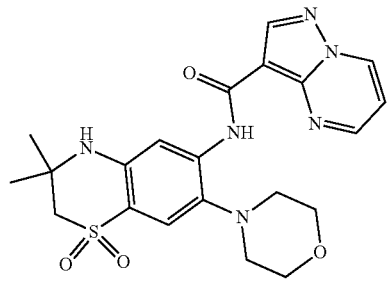 [SMILES: CC1(C)CS(=O)(=O)c2cc(N3CCOCC3)c(NC(=O)c3cnn4cccnc34)cc2N1] | N-(3,3-dimethyl-7-morpholino-1,1-dioxido-3,4-dihydro-2H-benzo[b][1,4]thiazin-6-yl)pyrazolo[1,5-a]pyrimidine-3-carboxamide |
| 404 | 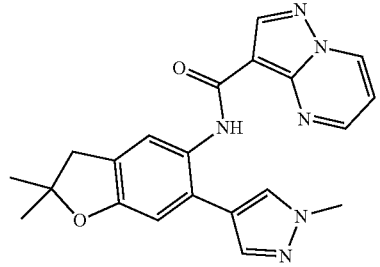 [SMILES: Cn1cc(-c2cc3c(cc2NC(=O)c2cnn4cccnc24)CC(C)(C)O3)cn1] | N-(2,2-dimethyl-6-(1-methyl-1H-pyrazol-4-yl)-2,3-dihydrobenzofuran-5-yl)pyrazolo[1,5-a]pyrimidine-3-carboxamide |

TABLE 2-continued

*Additional exemplary compounds of the present invention. Salts of such compounds are also contemplated. See the Examples section for preparation of such compounds.*

| | | |
|---|---|---|
| 405 | 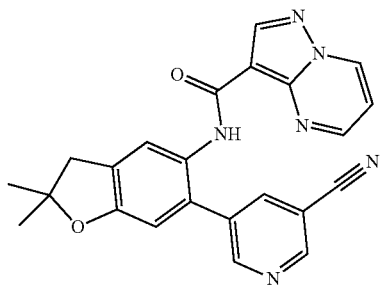 [SMILES: CC1(C)Cc2cc(NC(=O)c3cnn4cccnc34)c(-c3cncc(C#N)c3)cc2O1] | N-(6-(5-cyanopyridin-3-yl)-2,2-dimethyl-2,3-dihydrobenzofuran-5-yl)pyrazolo[1,5-a]pyrimidine-3-carboxamide |
| 406 | 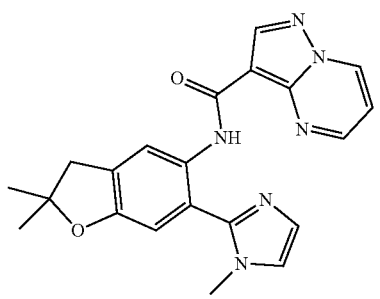 [SMILES: Cn1ccnc1-c1cc2c(cc1NC(=O)c1cnn3cccnc13)CC(C)(C)O2] | N-(2,2-dimethyl-6-(1-methyl-1H-imidazol-2-yl)-2,3-dihydrobenzofuran-5-yl)pyrazolo[1,5-a]pyrimidine-3-carboxamide |
| 407 | 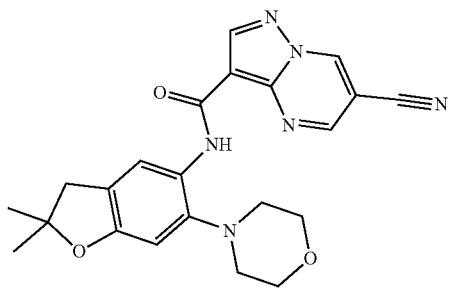 [SMILES: CC1(C)Cc2cc(NC(=O)c3cnn4cc(C#N)cnc34)c(N3CCOCC3)cc2O1] | 6-cyano-N-(2,2-dimethyl-6-morpholino-2,3-dihydrobenzofuran-5-yl)pyrazolo[1,5-a]pyrimidine-3-carboxamide |
| 408 | 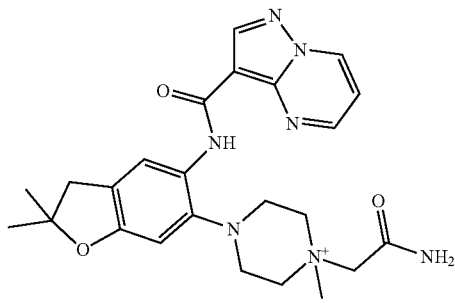 [SMILES: CC1(C)Cc2cc(NC(=O)c3cnn4cccnc34)c(N3CC[N+](C)(CC(N)=O)CC3)cc2O1] | 1-(2-amino-2-oxoethyl)-4-(2,2-dimethyl-5-(pyrazolo[1,5-a]pyrimidine-3-carboxamido)-2,3-dihydrobenzofuran-6-yl)-1-methylpiperazin-1-ium |

TABLE 2-continued

*Additional exemplary compounds of the present invention. Salts of such compounds are also contemplated. See the Examples section for preparation of such compounds.*

409, 410, 411, and 412

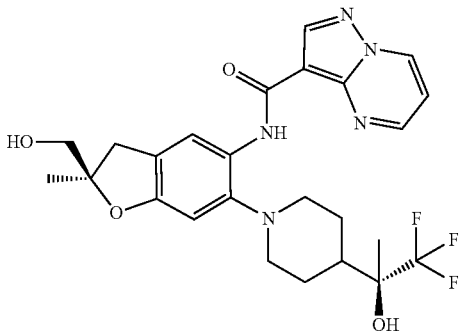

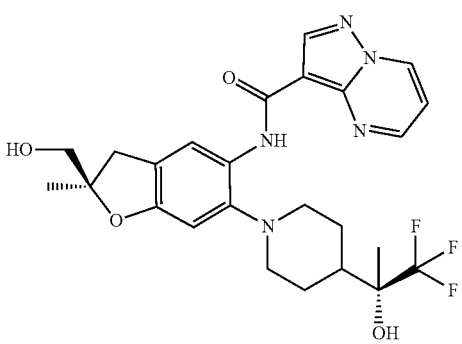

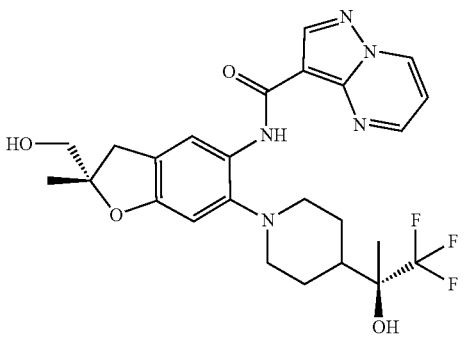

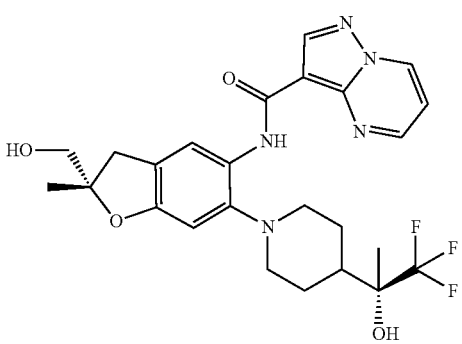

N-((R)-2-(hydroxymethyl)-2-methyl-6-(4-((R)-1,1,1-trifluoro-2-hydroxypropan-2-yl)piperidin-1-yl)-2,3-dihydrobenzofuran-5-yl)pyrazolo[1,5-a]pyrimidine-3-carboxamide;
N-((R)-2-(hydroxymethyl)-2-methyl-6-(4-((S)-1,1,1-trifluoro-2-hydroxypropan-2-yl)piperidin-1-yl)-2,3-dihydrobenzofuran-5-yl)pyrazolo[1,5-a]pyrimidine-3-carboxamide;
N-((S)-2-(hydroxymethyl)-2-methyl-6-(4-((R)-1,1,1-trifluoro-2-hydroxypropan-2-yl)piperidin-1-yl)-2,3-dihydrobenzofuran-5-yl)pyrazolo[1,5-a]pyrimidine-3-carboxamide;
N-((S)-2-(hydroxymethyl)-2-methyl-6-(4-((S)-1,1,1-trifluoro-2-hydroxypropan-2-yl)piperidin-1-yl)-2,3-dihydrobenzofuran-5-yl)pyrazolo[1,5-a]pyrimidine-3-carboxamide

TABLE 2-continued

*Additional exemplary compounds of the present invention. Salts of such compounds are also contemplated. See the Examples section for preparation of such compounds.*

| | | |
|---|---|---|
| 413 and 414 | 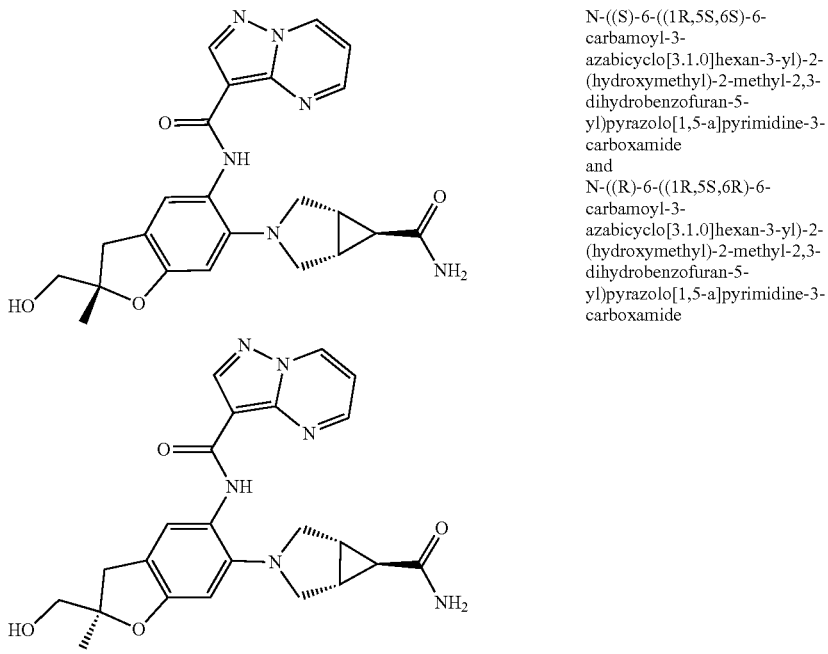 | N-((S)-6-((1R,5S,6S)-6-carbamoyl-3-azabicyclo[3.1.0]hexan-3-yl)-2-(hydroxymethyl)-2-methyl-2,3-dihydrobenzofuran-5-yl)pyrazolo[1,5-a]pyrimidine-3-carboxamide and N-((R)-6-((1R,5S,6R)-6-carbamoyl-3-azabicyclo[3.1.0]hexan-3-yl)-2-(hydroxymethyl)-2-methyl-2,3-dihydrobenzofuran-5-yl)pyrazolo[1,5-a]pyrimidine-3-carboxamide |
| 415 and 416 | 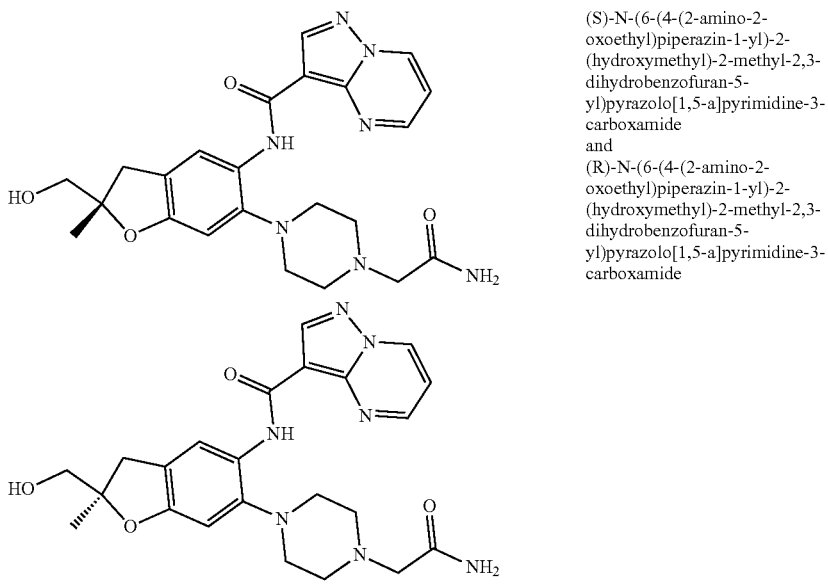 | (S)-N-(6-(4-(2-amino-2-oxoethyl)piperazin-1-yl)-2-(hydroxymethyl)-2-methyl-2,3-dihydrobenzofuran-5-yl)pyrazolo[1,5-a]pyrimidine-3-carboxamide and (R)-N-(6-(4-(2-amino-2-oxoethyl)piperazin-1-yl)-2-(hydroxymethyl)-2-methyl-2,3-dihydrobenzofuran-5-yl)pyrazolo[1,5-a]pyrimidine-3-carboxamide |
| 417 and 418 | 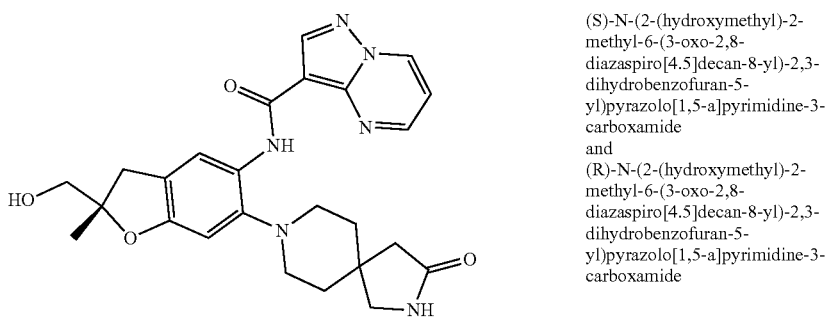 | (S)-N-(2-(hydroxymethyl)-2-methyl-6-(3-oxo-2,8-diazaspiro[4.5]decan-8-yl)-2,3-dihydrobenzofuran-5-yl)pyrazolo[1,5-a]pyrimidine-3-carboxamide and (R)-N-(2-(hydroxymethyl)-2-methyl-6-(3-oxo-2,8-diazaspiro[4.5]decan-8-yl)-2,3-dihydrobenzofuran-5-yl)pyrazolo[1,5-a]pyrimidine-3-carboxamide |

TABLE 2-continued

Additional exemplary compounds of the present invention. Salts of such compounds are also contemplated. See the Examples section for preparation of such compounds.

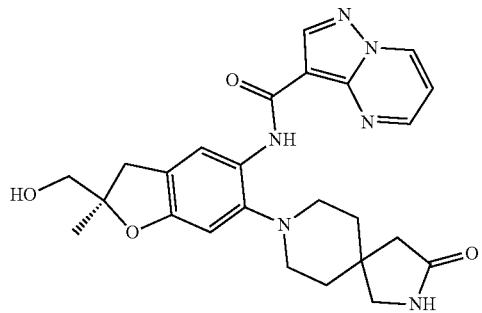

419 and 420

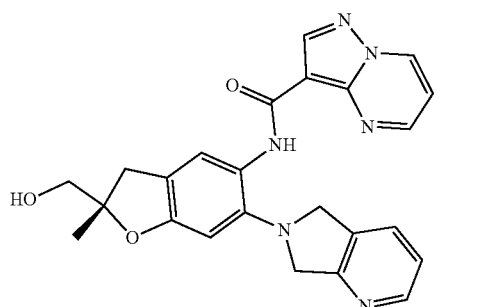

(S)-N-(6-(5,7-dihydro-6H-pyrrolo[3,4-b]pyridin-6-yl)-2-(hydroxymethyl)-2-methyl-2,3-dihydrobenzofuran-5-yl)pyrazolo[1,5-a]pyrimidine-3-carboxamide
and
(R)-N-(6-(5,7-dihydro-6H-pyrrolo[3,4-b]pyridin-6-yl)-2-(hydroxymethyl)-2-methyl-2,3-dihydrobenzofuran-5-yl)pyrazolo[1,5-a]pyrimidine-3-carboxamide

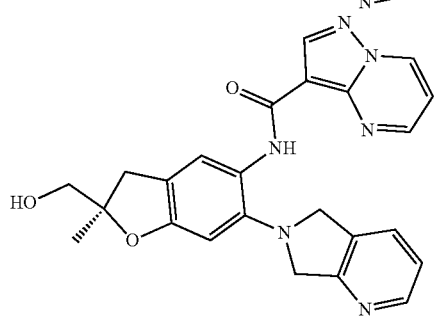

421, 422, and 423

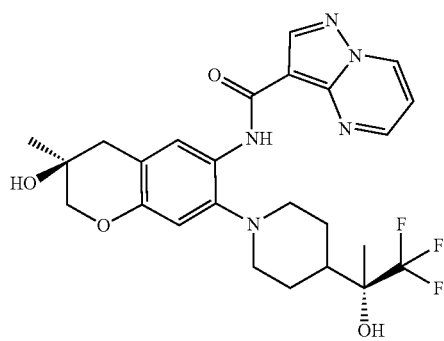

N-((S)-3-hydroxy-3-methyl-7-(4-((S)-1,1,1-trifluoro-2-hydroxypropan-2-yl)piperidin-1-yl)chroman-6-yl)pyrazolo[1,5-a]pyrimidine-3-carboxamide;
N-((R)-3-hydroxy-3-methyl-7-(4-((S)-1,1,1-trifluoro-2-hydroxypropan-2-yl)piperidin-1-yl)chroman-6-yl)pyrazolo[1,5-a]pyrimidine-3-carboxamide;
N-(3-hydroxy-3-methyl-7-(4-((R)-1,1,1-trifluoro-2-hydroxypropan-2-yl)piperidin-1-yl)chroman-6-yl)pyrazolo[1,5-a]pyrimidine-3-carboxamide

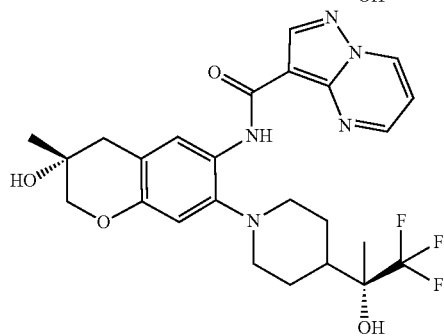

TABLE 2-continued

Additional exemplary compounds of the present invention. Salts of such compounds are also contemplated. See the Examples section for preparation of such compounds.

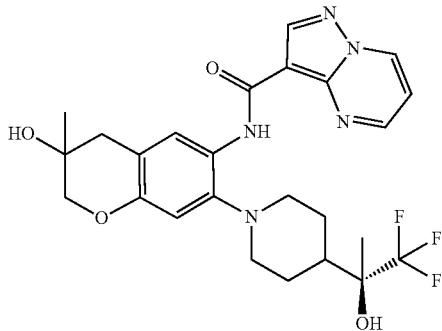

424 and 425

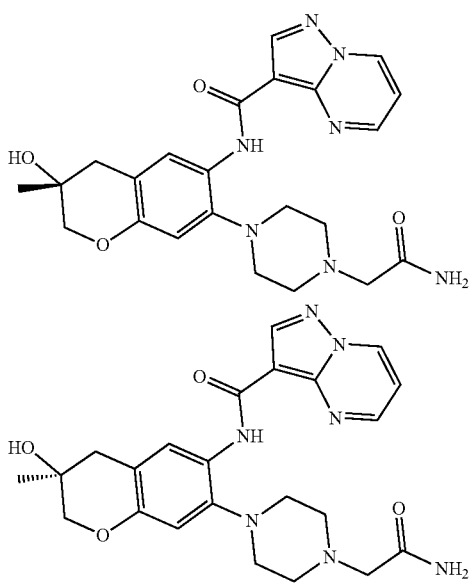

(R)-N-(7-(4-(2-amino-2-oxoethyl)piperazin-1-yl)-3-hydroxy-3-methylchroman-6-yl)pyrazolo[1,5-a]pyrimidine-3-carboxamide
and
(S)-N-(7-(4-(2-amino-2-oxoethyl)piperazin-1-yl)-3-hydroxy-3-methylchroman-6-yl)pyrazolo[1,5-a]pyrimidine-3-carboxamide 426 and 427

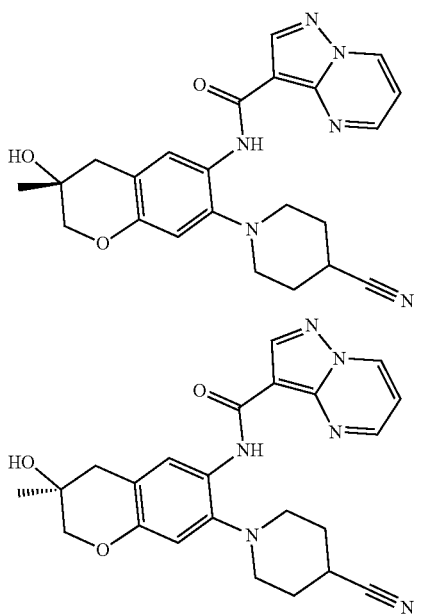

(R)-N-(7-(4-cyanopiperidin-1-yl)-3-hydroxy-3-methylchroman-6-yl)pyrazolo[1,5-a]pyrimidine-3-carboxamide
and
(S)-N-(7-(4-cyanopiperidin-1-yl)-3-hydroxy-3-methylchroman-6-yl)pyrazolo[1,5-a]pyrimidine-3-carboxamide TABLE 2-continued

*Additional exemplary compounds of the present invention. Salts of such compounds are also contemplated. See the Examples section for preparation of such compounds.*

| | | |
|---|---|---|
| 428 and 429 | 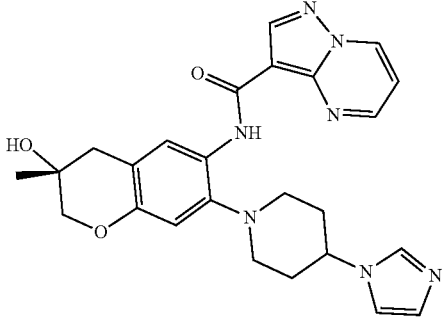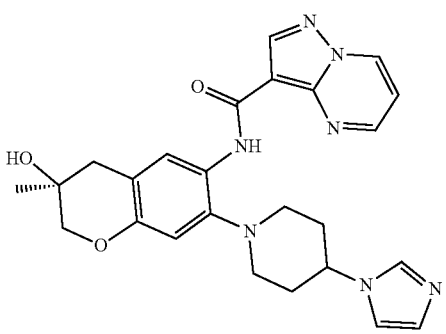 | (R)-N-(7-(4-(1H-imidazol-1-yl)piperidin-1-yl)-3-hydroxy-3-methylchroman-6-yl)pyrazolo[1,5-a]pyrimidine-3-carboxamide and (S)-N-(7-(4-(1H-imidazol-1-yl)piperidin-1-yl)-3-hydroxy-3-methylchroman-6-yl)pyrazolo[1,5-a]pyrimidine-3-carboxamide |
| 430 and 431 | 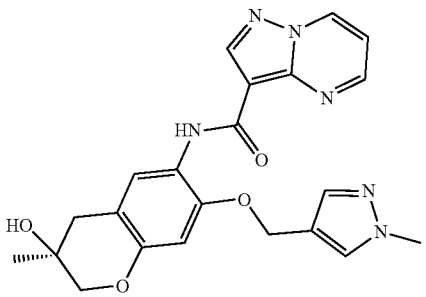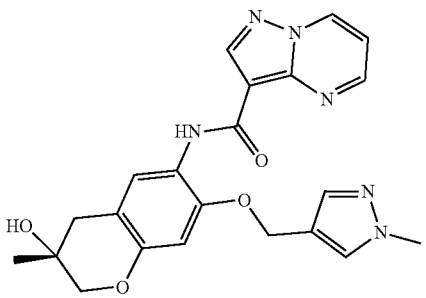 | (S)-N-(3-hydroxy-3-methyl-7-((1-methyl-1H-pyrazol-4-yl)methoxy)chroman-6-yl)pyrazolo[1,5-a]pyrimidine-3-carboxamide and (R)-N-(3-hydroxy-3-methyl-7-((1-methyl-1H-pyrazol-4-yl)methoxy)chroman-6-yl)pyrazolo[1,5-a]pyrimidine-3-carboxamide |
| 432 and 433 | 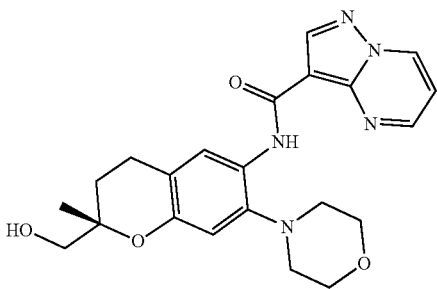 | (S)-N-(2-(hydroxymethyl)-2-methyl-7-morpholinochroman-6-yl)pyrazolo[1,5-a]pyrimidine-3-carboxamide and (R)-N-(2-(hydroxymethyl)-2-methyl-7-morpholinochroman-6-yl)pyrazolo[1,5-a]pyrimidine-3-carboxamide |

TABLE 2-continued

Additional exemplary compounds of the present invention. Salts of such compounds are also contemplated. See the Examples section for preparation of such compounds.

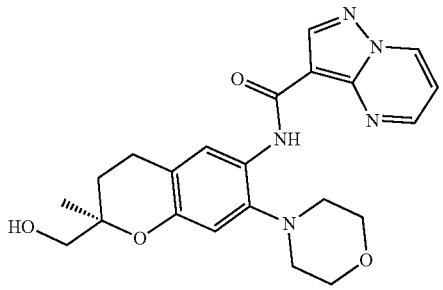

| 434 | 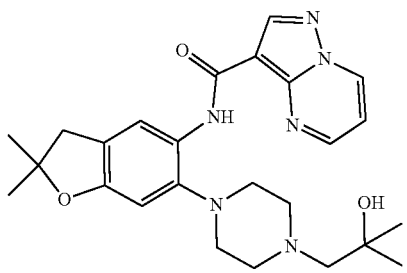 [SMILES: CC(C)(O)CN1CCN(c2cc3c(cc2NC(=O)c2cnn4cccnc24)CC(C)(C)O3)CC1] | N-(6-(4-(2-hydroxy-2-methylpropyl)piperazin-1-yl)-2,2-dimethyl-2,3-dihydrobenzofuran-5-yl)pyrazolo[1,5-a]pyrimidine-3-carboxamide |

| 435 | 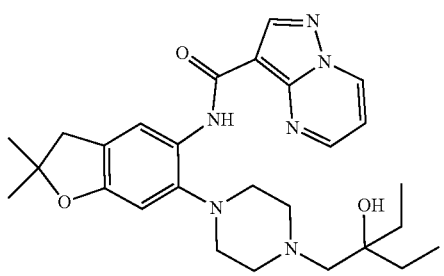 [SMILES: CCC(O)(CC)CN1CCN(c2cc3c(cc2NC(=O)c2cnn4cccnc24)CC(C)(C)O3)CC1] | N-(6-(4-(2-ethyl-2-hydroxybutyl)piperazin-1-yl)-2,2-dimethyl-2,3-dihydrobenzofuran-5-yl)pyrazolo[1,5-a]pyrimidine-3-carboxamide |

TABLE 3

Additional exemplary compounds of the present invention. Salts of such compounds are also contemplated. See the Examples section for preparation of such compounds.

| Ex. | Structure | Name |
|---|---|---|
| 436 | 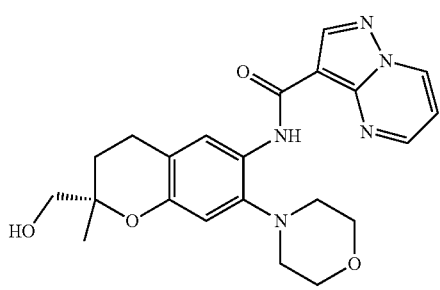 [SMILES: C[C@@]1(CO)CCc2cc(NC(=O)c3cnn4cccnc34)c(N3CCOCC3)cc2O1] | (S)-N-(2-(hydroxymethyl)-2-methyl-7-morpholinochroman-6-yl)pyrazolo[1,5-a]pyrimidine-3-carboxamide |

TABLE 3-continued

*Additional exemplary compounds of the present invention. Salts of such compounds are also contemplated. See the Examples section for preparation of such compounds.*

| Ex. | Structure | Name |
|---|---|---|
| 437 | 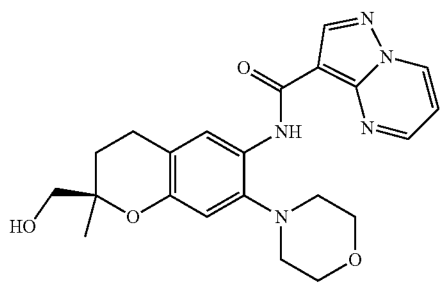 [SMILES: C[C@]1(CO)CCc2cc(NC(=O)c3cnn4cccnc34)c(N3CCOCC3)cc2O1] | (R)-N-(2-(hydroxymethyl)-2-methyl-7-morpholinochroman-6-yl)pyrazolo[1,5-a]pyrimidine-3-arboxamide |
| 438 | 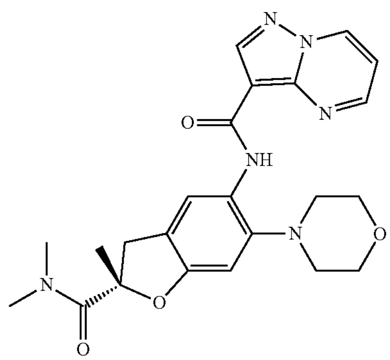 [SMILES: CN(C)C(=O)[C@]1(C)Cc2cc(NC(=O)c3cnn4cccnc34)c(N3CCOCC3)cc2O1] | (S)-N-(2-(dimethylcarbamoyl)-2-methyl-6-morpholino-2,3-dihydrobenzofuran-5-yl)pyrazolo[1,5-a]pyrimidine-3-carboxamide |
| 439 | 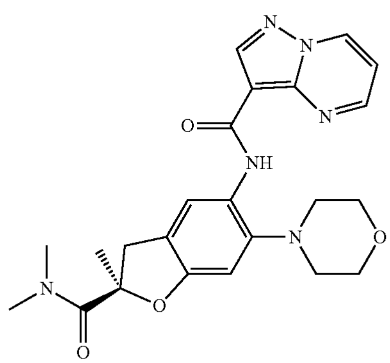 [SMILES: CN(C)C(=O)[C@@]1(C)Cc2cc(NC(=O)c3cnn4cccnc34)c(N3CCOCC3)cc2O1] | (R)-N-(2-(dimethylcarbamoyl)-2-methyl-6-morpholino-2,3-dihydrobenzofuran-5-yl)pyrazolo[1,5-a]pyrimidine-3-carboxamide |
| 440 | 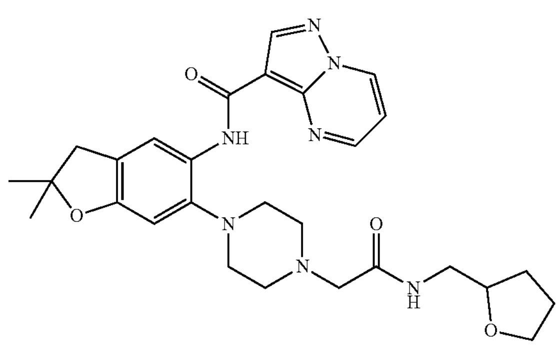 [SMILES: CC1(C)Cc2cc(NC(=O)c3cnn4cccnc34)c(N3CCN(CC(=O)NCC4CCCO4)CC3)cc2O1] | N-(2,2-dimethyl-6-(4-(2-oxo-2-(((tetrahydrofuran-2-yl)methyl)amino)ethyl)piperazin-1-yl)-2,3-dihydrobenzofuran-5-yl)pyrazolo[1,5-a]pyrimidine-3-carboxamide |

TABLE 3-continued

*Additional exemplary compounds of the present invention. Salts of such compounds are also contemplated. See the Examples section for preparation of such compounds.*

| Ex. | Structure | Name |
|---|---|---|
| 441 | 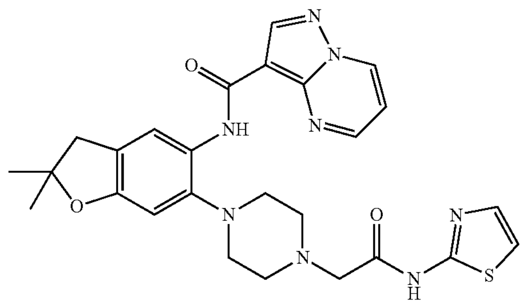 [SMILES: CC1(C)Cc2cc(NC(=O)c3cnn4cccnc34)c(N3CCN(CC(=O)Nc4nccs4)CC3)cc2O1] | N-(2,2-dimethyl-6-(4-(2-oxo-2-(thiazol-2-ylamino)ethyl)piperazin-dihydrobenzofuran-5-yl)pyrazolo[1,5-a]pyrimidine-3-carboxamide |
| 442 | 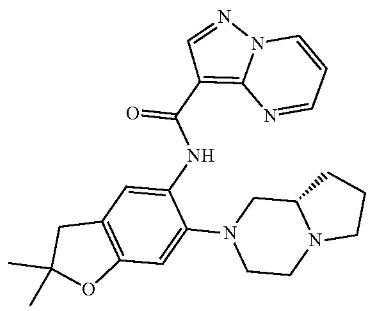 [SMILES: CC1(C)Cc2cc(NC(=O)c3cnn4cccnc34)c(N3CCN4CCC[C@H]4C3)cc2O1] | (S)-N-(6-(hexahydropyrrolo[1,2-a]pyrazin-2(1H)-yl)-2,2-dimethyl-2,3-dihydrobenzofuran-5-yl)pyrazolo[1,5-a]pyrimidine-3-carboxamide |
| 443 | 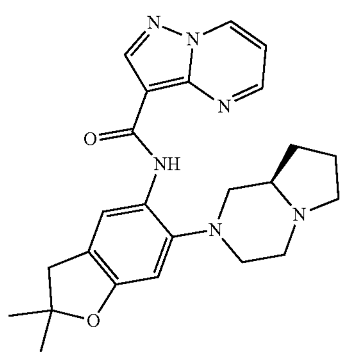 [SMILES: CC1(C)Cc2cc(NC(=O)c3cnn4cccnc34)c(N3CCN4CCC[C@@H]4C3)cc2O1] | (R)-N-(6-(hexahydropyrrolo[1,2-a]pyrazin-2(1H)-yl)-2,2-dimethyl-2,3-dihydrobenzofuran-5-yl)pyrazolo[1,5-a]pyrimidine-3-carboxamide |
| 444 | 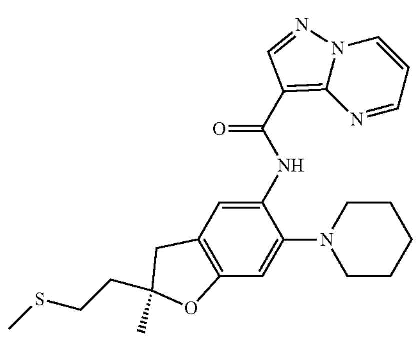 [SMILES: CSCC[C@@]1(C)Cc2cc(NC(=O)c3cnn4cccnc34)c(N3CCCCC3)cc2O1] | (R)-N-(2-methyl-2-(2-(methylthio)ethyl)-6-morpholino-2,3-dihydrobenzofuran-5-yl)pyrazolo[1,5-a]pyrimidine-3-carboxamide |

TABLE 3-continued

*Additional exemplary compounds of the present invention. Salts of such compounds are also contemplated. See the Examples section for preparation of such compounds.*

| Ex. | Structure | Name |
|---|---|---|
| 445 | 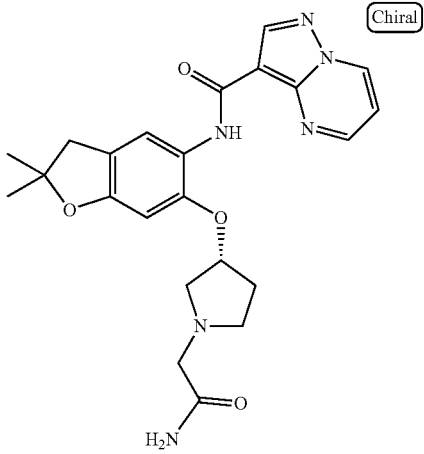 [SMILES: CC1(C)Cc2cc(NC(=O)c3cnn4cccnc34)c(O[C@@H]3CCN(CC(N)=O)C3)cc2O1] | (R)-N-(6-((1-(2-amino-2-oxoethyl)pyrrolidin-3-yl)oxy)-2,2-dimethyl-2,3-dihydrobenzofuran-5-yl)pyrazolo[1,5-a]pyrimidine-3-carboxamide |
| 446 | 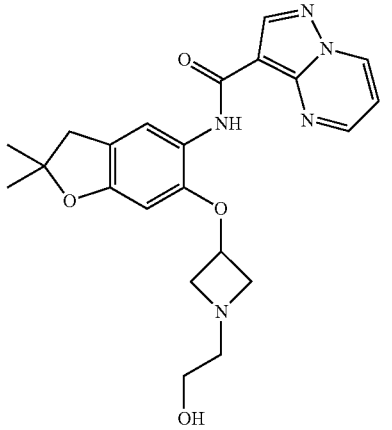 [SMILES: CC1(C)Cc2cc(NC(=O)c3cnn4cccnc34)c(OC3CN(CCO)C3)cc2O1] | N-(6-((1-ethyl-1H-hydroxyethyl)azetidin-3-yl)oxy-2,2-dimethyl-2,3-dihydrobenzofuran-5-yl)pyrazolo[1,5-a]pyrimidine-3-carboxamide |
| 447 | 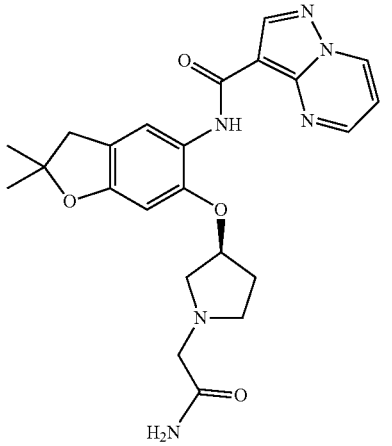 [SMILES: CC1(C)Cc2cc(NC(=O)c3cnn4cccnc34)c(O[C@H]3CCN(CC(N)=O)C3)cc2O1] | (S)-N-(6-((1-(2-amino-2-oxoethyl)pyrrolidin-3-yl)oxy)-2,2-dimethyl-2,3-dihydrobenzofuran-5-yl)pyrazolo[1,5-a]pyrimidine-3-carboxamide |

TABLE 3-continued

*Additional exemplary compounds of the present invention. Salts of such compounds are also contemplated. See the Examples section for preparation of such compounds.*

| Ex. | Structure | Name |
|---|---|---|
| 448 | 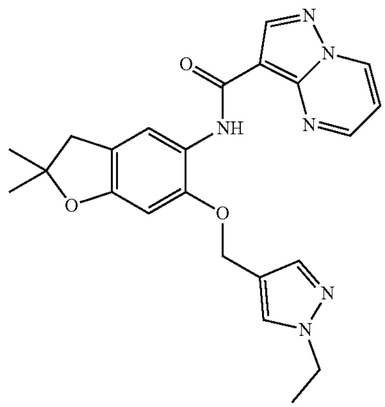 [SMILES: CCn1cc(COc2cc3c(cc2NC(=O)c2cnn4cccnc24)CC(C)(C)O3)cn1] | N-(6-((1-ethyl-1H-pyrazol-4-yl)methoxy)-2,2-dimethyl-2,3-dihydrobenzofuran-5-yl)pyrazolo[1,5-a]pyrimidine-3-carboxamide |
| 449 | 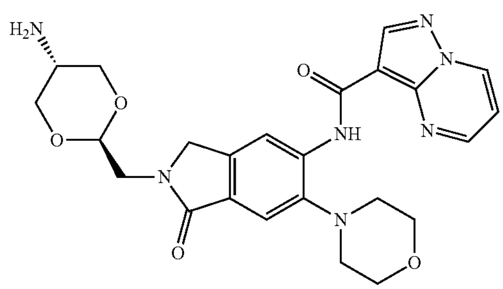 [SMILES: N[C@H]1CO[C@H](CN2Cc3cc(NC(=O)c4cnn5cccnc45)c(N4CCOCC4)cc3C2=O)OC1] | N-(2-(((2R,5R)-5-amino-1,3-dioxan-2-yl)methyl)-6-morpholino-1-oxoisoindolin-5-yl)pyrazolo[1,5-a]pyrimidine-3-carboxamide |
| 450 | 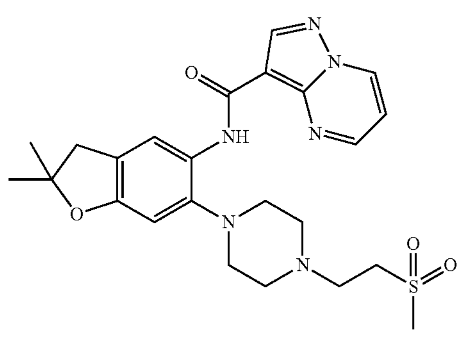 [SMILES: CC1(C)Cc2cc(NC(=O)c3cnn4cccnc34)c(N3CCN(CCS(C)(=O)=O)CC3)cc2O1] | N-(2,2-dimethyl-6-(4-(2-(methylsulfonyl)ethyl)piperazin-1-yl)-2,3-dihydrobenzofuran-5-yl)pyrazolo[1,5-a]pyrimidine-3-carboxamide |
| 451 | 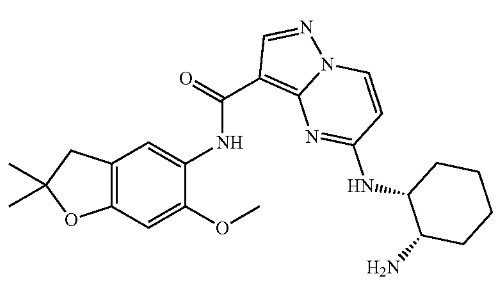 [SMILES: COc1cc2c(cc1NC(=O)c1cnn3ccc(N[C@@H]4CCCC[C@@H]4N)nc13)CC(C)(C)O2] | 5-(((1R,2S)-2-aminocyclohexyl)amino)-N-(6-methoxy-2,2-dimethyl-2,3-dihydrobenzofuran-5-yl)pyrazolo[1,5-a]pyrimidine-3-carboxamide |

TABLE 3-continued

*Additional exemplary compounds of the present invention. Salts of such compounds are also contemplated. See the Examples section for preparation of such compounds.*

| Ex. | Structure | Name |
|---|---|---|
| 452 | 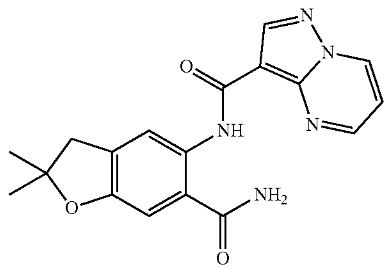 [SMILES: CC1(C)Cc2cc(NC(=O)c3cnn4cccnc34)c(C(N)=O)cc2O1] | N-(6-carbamoyl-2,2-dimethyl-2,3-dihydrobenzofuran-5-yl)pyrazolo[1,5-a]pyrimidine-3-carboxamide |
| 453 | 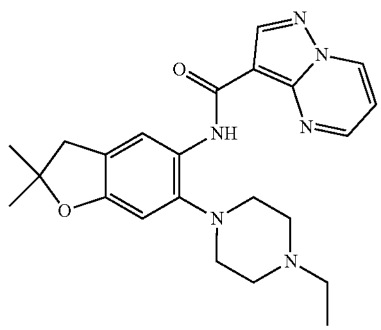 [SMILES: CCN1CCN(c2cc3c(cc2NC(=O)c2cnn4cccnc24)CC(C)(C)O3)CC1] | N-(6-(4-ethylpiperazin-1-yl)-2,2-dimethyl-2,3-dihydrobenzofuran-5-yl)pyrazolo[1,5-a]pyrimidine-3-carboxamide |
| 454 | 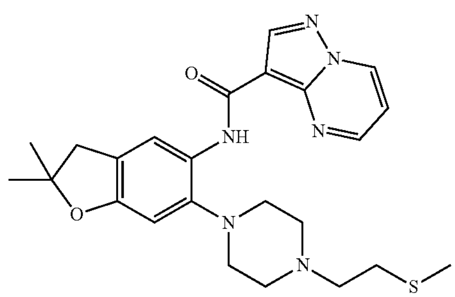 | N-(2,2-dimethyl-6-(4-(2-(methylthio)ethyl)piperazin-1-yl)-2,3-dihydrobenzofuran-5-yl)pyrazolo[1,5-a]pyrimidine-3-carboxamide |
| 455 | 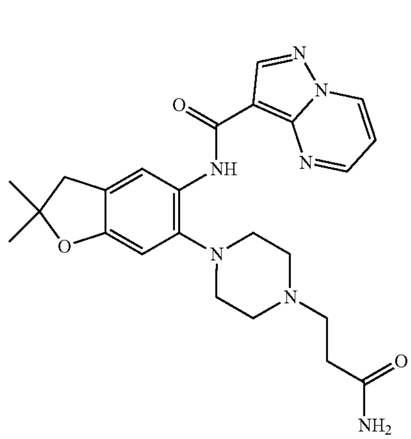 [SMILES: CC1(C)Cc2cc(NC(=O)c3cnn4cccnc34)c(N3CCN(CCC(N)=O)CC3)cc2O1] | N-(6-(4-(3-amino-3-oxopropyl)piperazin-1-yl)-2,2-dimethyl-2,3-dihydrobenzofuran-5-yl)pyrazolo[1,5-a]pyrimidine-3-carboxamide |

TABLE 3-continued

Additional exemplary compounds of the present invention. Salts of such compounds are also contemplated. See the Examples section for preparation of such compounds.

| Ex. | Structure | Name |
|---|---|---|
| 456 | 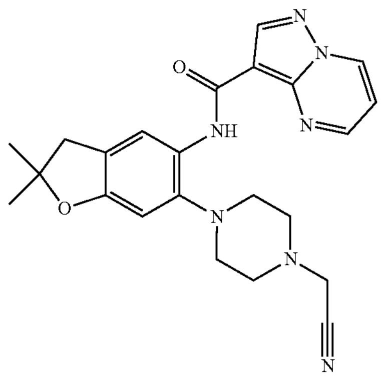 [SMILES: CC1(C)Cc2cc(NC(=O)c3cnn4cccnc34)c(N3CCN(CC#N)CC3)cc2O1] | N-(6-(4-(cyanomethyl)piperazin-1-yl)-2,2-dimethyl-2,3-dihydrobenzofuran-5-yl)pyrazolo[1,5-a]pyrimidine-3-carboxamide |
| 457 | 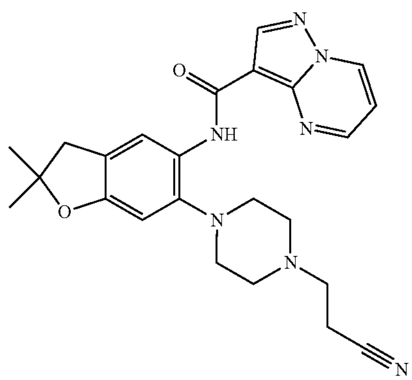 [SMILES: CC1(C)Cc2cc(NC(=O)c3cnn4cccnc34)c(N3CCN(CCC#N)CC3)cc2O1] | N-(6-(4-(2-cyanoethyl)piperazin-1-yl)-2,2-dimethyl-2,3-dihydrobenzofuran-5-yl)pyrazolo[1,5-a]pyrimidine-3-carboxamide |
| 458 | 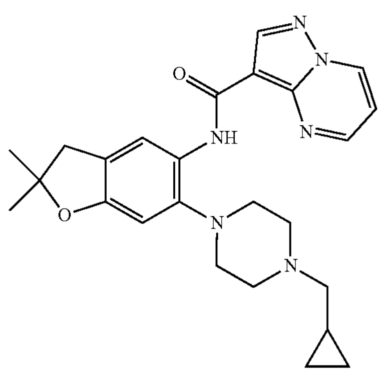 [SMILES: CC1(C)Cc2cc(NC(=O)c3cnn4cccnc34)c(N3CCN(CC4CC4)CC3)cc2O1] | N-(6-(4-(cyclopropylmethyl)piperazin-1-yl)-2,2-dimethyl-2,3-dihydrobenzofuran-5-yl)pyrazolo[1,5-a]pyrimidine-3-carboxamide |
| 459 | 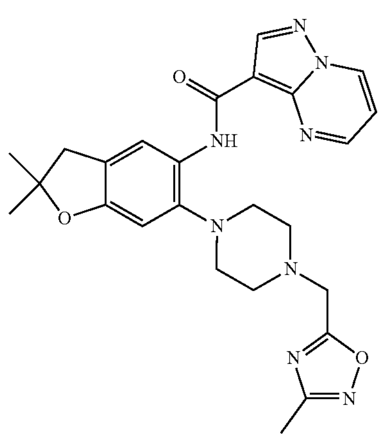 [SMILES: Cc1noc(CN2CCN(c3cc4c(cc3NC(=O)c3cnn5cccnc35)CC(C)(C)O4)CC2)n1] | N-(2,2-dimethyl-6-(4-((3-methyl-1,2,4-oxadiazol-5-yl)methyl)piperazin-1-yl)-2,3-dihydrobenzofuran-5-yl)pyrazolo[1,5-a]pyrimidine-3-carboxamide |

TABLE 3-continued

Additional exemplary compounds of the present invention. Salts of such compounds are also contemplated. See the Examples section for preparation of such compounds.

| Ex. | Structure | Name |
|---|---|---|
| 460 | 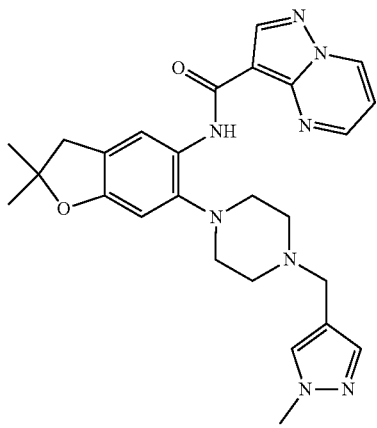 [SMILES: Cn1cc(CN2CCN(c3cc4c(cc3NC(=O)c3cnn5cccnc35)CC(C)(C)O4)CC2)cn1] | N-(2,2-dimethyl-6-(4-((1-methyl-1H-pyrazol-4-yl)methyl)piperazin-1-yl)-2,3-dihydrobenzofuran-5-yl)pyrazolo[1,5-a]pyrimidine-3-carboxamide |
| 461 | 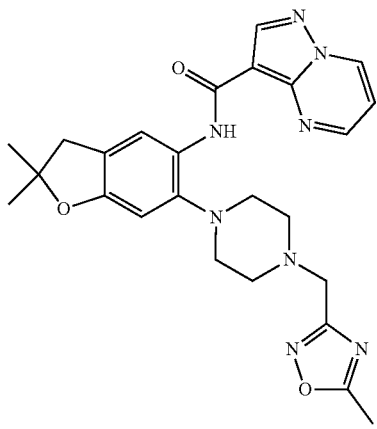 [SMILES: Cc1nc(CN2CCN(c3cc4c(cc3NC(=O)c3cnn5cccnc35)CC(C)(C)O4)CC2)no1] | N-(2,2-dimethyl-6-(4-((5-methyl-1,2,4-oxadiazol-3-yl)methyl)piperazin-1-yl)-2,3-dihydrobenzofuran-5-yl)pyrazolo[1,5-a]pyrimidine-3-carboxamide |
| 462 | 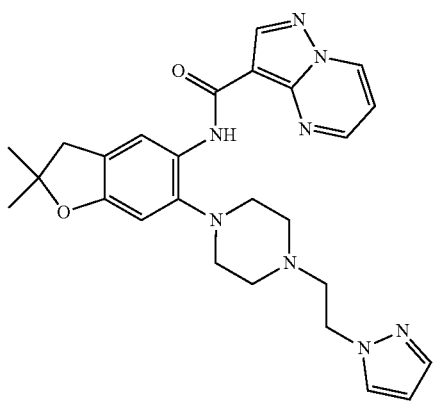 [SMILES: CC1(C)Cc2cc(NC(=O)c3cnn4cccnc34)c(N3CCN(CCn4cccn4)CC3)cc2O1] | N-(6-(4-(2-(1H-pyrazol-1-yl)ethyl)piperazin-1-yl)-2,2-dimethyl-2,3-dihydrobenzofuran-5-yl)pyrazolo[1,5-a]pyrimidine-3-carboxamide |

TABLE 3-continued

*Additional exemplary compounds of the present invention. Salts of such compounds are also contemplated. See the Examples section for preparation of such compounds.*

| Ex. | Structure | Name |
|---|---|---|
| 463 | 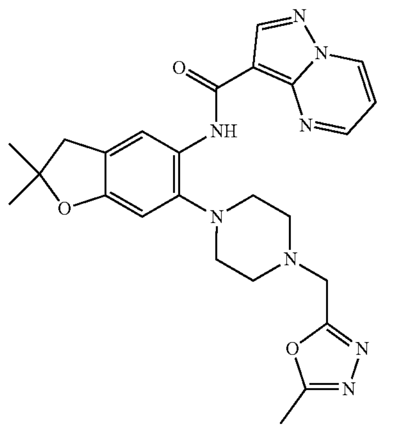 [SMILES: Cc1nnc(CN2CCN(c3cc4c(cc3NC(=O)c3cnn5cccnc35)CC(C)(C)O4)CC2)o1] | N-(2,2-dimethyl-6-(4-((5-methyl-1,3,4-oxadiazol-2-yl)methyl)piperazin-1-yl)-2,3-dihydrobenzofuran-5-yl)pyrazolo[1,5-a]pyrimidine-3-carboxamide |
| 464 | 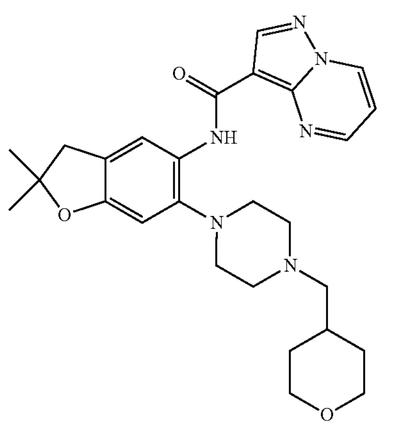 [SMILES: CC1(C)Cc2cc(NC(=O)c3cnn4cccnc34)c(N3CCN(CC4CCOCC4)CC3)cc2O1] | N-(2,2-dimethyl-6-(4-((tetrahydro-2H-pyran-4-yl)methyl)piperazin-1-yl)-2,3-dihydrobenzofuran-5-yl)pyrazolo[1,5-a]pyrimidine-3-carboxamide |
| 465 | 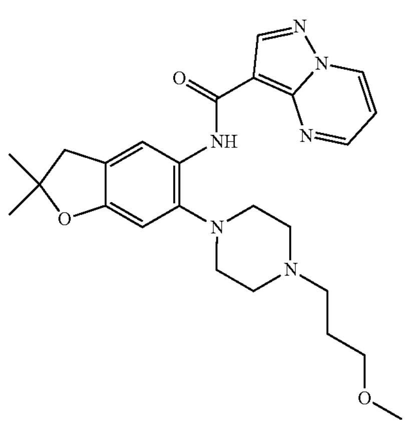 | N-(6-(4-(3-methoxypropyl)piperazin-1-yl)-2,2-dimethyl-2,3-dihydrobenzofuran-5-yl)pyrazolo[1,5-a]pyrimidine-3-carboxamide |

TABLE 3-continued

Additional exemplary compounds of the present invention. Salts of such compounds are also contemplated. See the Examples section for preparation of such compounds.

| Ex. | Structure | Name |
|---|---|---|
| 466 | 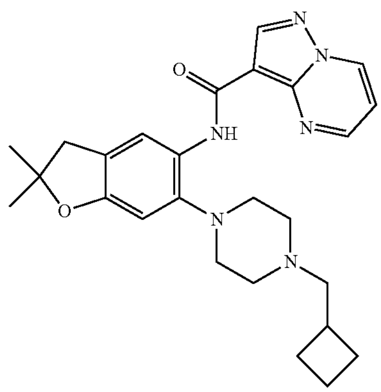 [SMILES: CC1(C)Cc2cc(NC(=O)c3cnn4cccnc34)c(N3CCN(CC4CCC4)CC3)cc2O1] | N-(6-(4-(cyclobutylmethyl)piperazin-1-yl)-2,2-dimethyl-2,3-dihydrobenzofuran-5-yl)pyrazolo[1,5-a]pyrimidine-3-carboxamide |
| 467 | 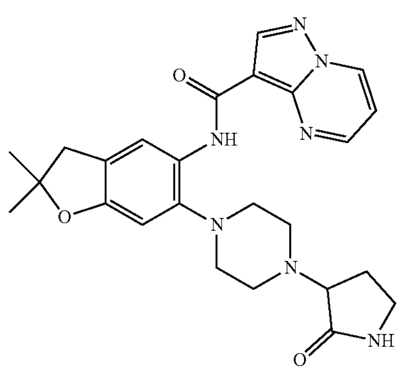 [SMILES: CC1(C)Cc2cc(NC(=O)c3cnn4cccnc34)c(N3CCN(C4CCNC4=O)CC3)cc2O1] | N-(2,2-dimethyl-6-(4-(2-oxopyrrolidin-3-yl)piperazin-1-yl)-2,3-dihydrobenzofuran-5-yl)pyrazolo[1,5-a]pyrimidine-3-carboxamide |
| 468 | 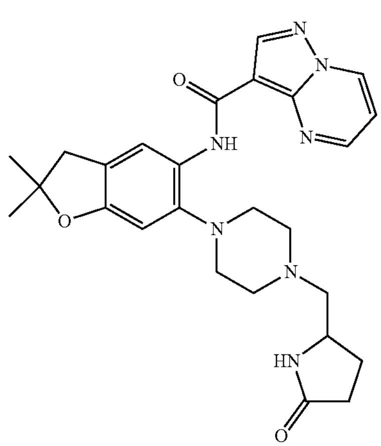 [SMILES: CC1(C)Cc2cc(NC(=O)c3cnn4cccnc34)c(N3CCN(CC4CCC(=O)N4)CC3)cc2O1] | N-(2,2-dimethyl-6-(4-((5-oxopyrrolidin-2-yl)methyl)piperazin-1-yl)-2,3-dihydrobenzofuran-5-yl)pyrazolo[1,5-a]pyrimidine-3-carboxamide |

TABLE 3-continued

*Additional exemplary compounds of the present invention. Salts of such compounds are also contemplated. See the Examples section for preparation of such compounds.*

| Ex. | Structure | Name |
|---|---|---|
| 469 | 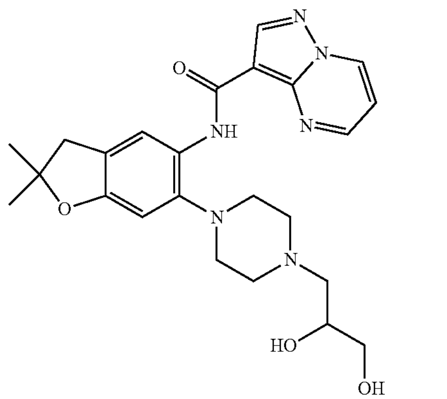 [SMILES: CC1(C)Cc2cc(NC(=O)c3cnn4cccnc34)c(N3CCN(CC(O)CO)CC3)cc2O1] | N-(6-(4-(2,3-dihydroxypropyl)piperazin-1-yl)-2,2-dimethyl-2,3-dihydrobenzofuran-5-yl)pyrazolo[1,5-a]pyrimidine-3-carboxamide |
| 470 | 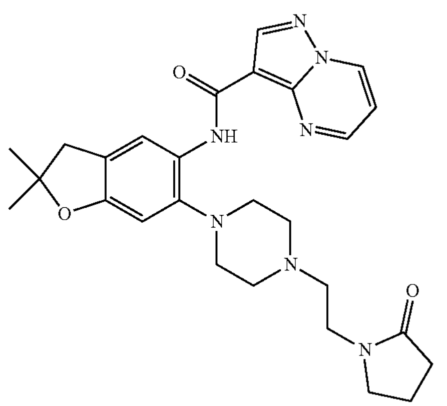 [SMILES: CC1(C)Cc2cc(NC(=O)c3cnn4cccnc34)c(N3CCN(CCN4CCCC4=O)CC3)cc2O1] | N-(2,2-dimethyl-6-(4-(2-(2-oxopyrrolidin-1-yl)ethyl)piperazin-1-yl)-2,3-dihydrobenzofuran-5-yl)pyrazolo[1,5-a]pyrimidine-3-carboxamide |
| 471 | 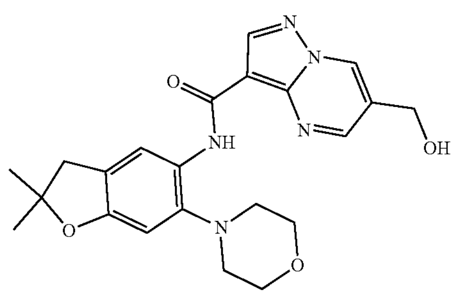 [SMILES: CC1(C)Cc2cc(NC(=O)c3cnn4cc(CO)cnc34)c(N3CCOCC3)cc2O1] | N-(2,2-dimethyl-6-morpholino-2,3-dihydrobenzofuran-5-yl)-6-(hydroxymethyl)pyrazolo[1,5-a]pyrimidine-3-carboxamide |
| 472 | 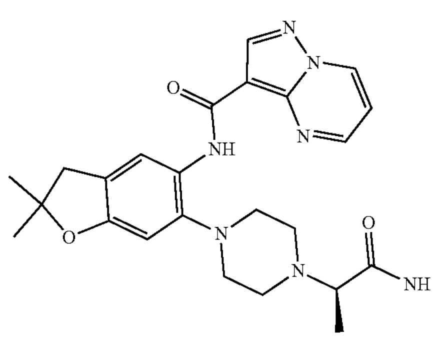 [SMILES: C[C@H](C(N)=O)N1CCN(c2cc3c(cc2NC(=O)c2cnn4cccnc24)CC(C)(C)O3)CC1] | (R)-N-(6-(4-(1-amino-1-oxopropan-2-yl)piperazin-1-yl)-2,2-dimethyl-2,3-dihydrobenzofuran-5-yl)pyrazolo[1,5-a]pyrimidine-3-carboxamide |

TABLE 3-continued

Additional exemplary compounds of the present invention. Salts of such compounds are also contemplated. See the Examples section for preparation of such compounds.

| Ex. | Structure | Name |
|---|---|---|
| 473 | 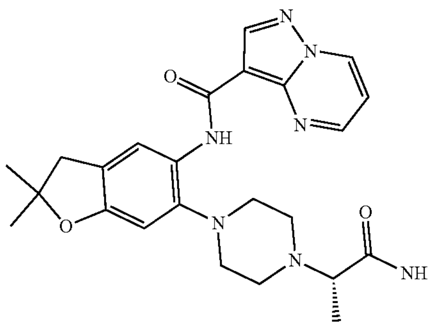 [SMILES: C[C@@H](C(N)=O)N1CCN(c2cc3c(cc2NC(=O)c2cnn4cccnc24)CC(C)(C)O3)CC1] | (S)-N-(6-(4-(1-amino-1-oxopropan-2-yl)piperazin-1-yl)-2,2-dimethyl-2,3-dihydrobenzofuran-5-yl)pyrazolo[1,5-a]pyrimidine-3-carboxamide |
| 474 | 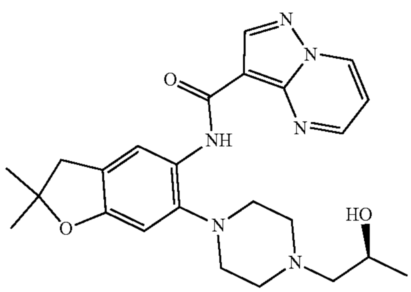 [SMILES: C[C@H](O)CN1CCN(c2cc3c(cc2NC(=O)c2cnn4cccnc24)CC(C)(C)O3)CC1] | (S)-N-(6-(4-(2-hydroxypropyl)piperazin-1-yl)-2,2-dimethyl-2,3-dihydrobenzofuran-5-yl)pyrazolo[1,5-a]pyrimidine-3-carboxamide |
| 475 | 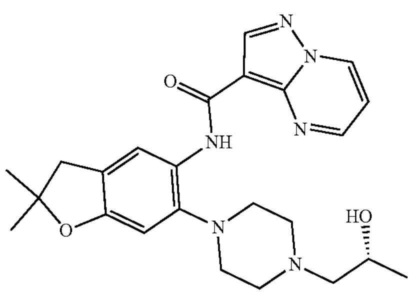 [SMILES: C[C@@H](O)CN1CCN(c2cc3c(cc2NC(=O)c2cnn4cccnc24)CC(C)(C)O3)CC1] | (R)-N-(6-(4-(2-hydroxypropyl)piperazin-1-yl)-2,2-dimethyl-2,3-dihydrobenzofuran-5-yl)pyrazolo[1,5-a]pyrimidine-3-carboxamide |
| 476 | 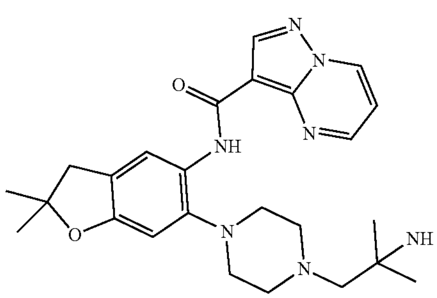 [SMILES: CC(C)(N)CN1CCN(c2cc3c(cc2NC(=O)c2cnn4cccnc24)CC(C)(C)O3)CC1] | N-(6-(4-(2-amino-2-methylpropyl)piperazin-1-yl)-2,2-dimethyl-2,3-dihydrobenzofuran-5-yl)pyrazolo[1,5-a]pyrimidine-3-carboxamide |
| 477 | 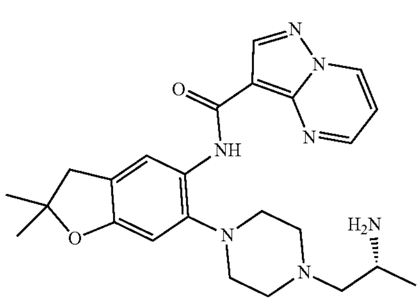 [SMILES: C[C@@H](N)CN1CCN(c2cc3c(cc2NC(=O)c2cnn4cccnc24)CC(C)(C)O3)CC1] | (R)-N-(6-(4-(2-aminopropyl)piperazin-1-yl)-2,2-dimethyl-2,3-dihydrobenzofuran-5-yl)pyrazolo[1,5-a]pyrimidine-3-carboxamide |

TABLE 3-continued

Additional exemplary compounds of the present invention. Salts of such compounds are also contemplated. See the Examples section for preparation of such compounds.

| Ex. | Structure | Name |
|---|---|---|
| 478 | 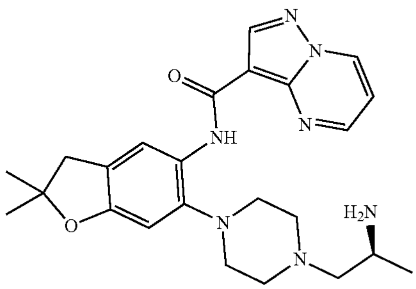 [SMILES: C[C@H](N)CN1CCN(c2cc3c(cc2NC(=O)c2cnn4cccnc24)CC(C)(C)O3)CC1] | (S)-N-(6-(4-(2-aminopropyl)piperazin-1-yl)-2,2-dimethyl-2,3-dihydrobenzofuran-5-yl)pyrazolo[1,5-a]pyrimidine-3-carboxamide |
| 479 | 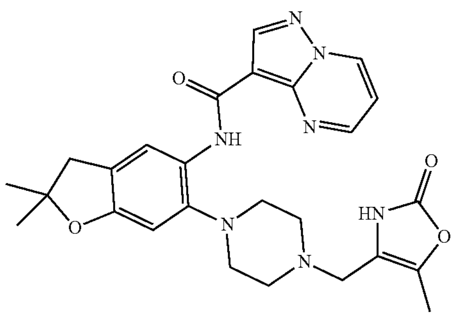 [SMILES: Cc1oc(=O)[nH]c1CN1CCN(c2cc3c(cc2NC(=O)c2cnn4cccnc24)CC(C)(C)O3)CC1] | N-(2,2-dimethyl-6-(4-((5-methyl-2-oxo-2,3-dihydrooxazol-4-yl)methyl)piperazin-1-yl)-2,3-dihydrobenzofuran-5-yl)pyrazolo[1,5-a]pyrimidine-3-carboxamide |
| 480 | 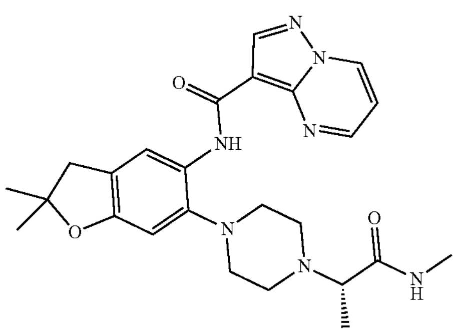 | (S)-N-(2,2-dimethyl-6-(4-(1-(methylamino)-1-oxopropan-2-yl)piperazin-1-yl)-2,3-dihydrobenzofuran-5-yl)pyrazolo[1,5-a]pyrimidine-3-carboxamide |
| 481 | 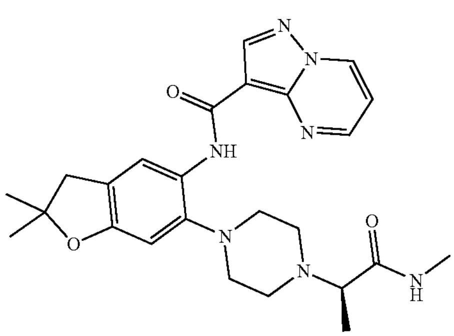 | (R)-N-(2,2-dimethyl-6-(4-(1-(methylamino)-1-oxopropan-2-yl)piperazin-1-yl)-2,3-dihydrobenzofuran-5-yl)pyrazolo[1,5-a]pyrimidine-3-carboxamide |

TABLE 3-continued

*Additional exemplary compounds of the present invention. Salts of such compounds are also contemplated. See the Examples section for preparation of such compounds.*

| Ex. | Structure | Name |
|---|---|---|
| 482 | 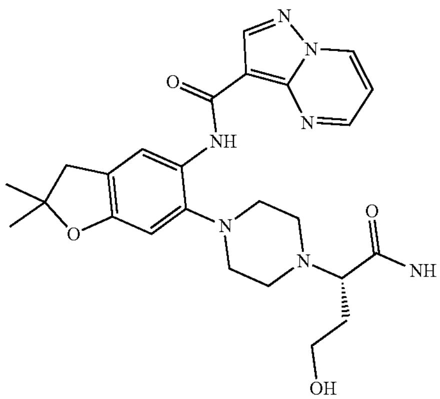 [SMILES: CC1(C)Cc2cc(NC(=O)c3cnn4cccnc34)c(N3CCN([C@@H](CCO)C(N)=O)CC3)cc2O1] | (S)-N-(6-(4-(1-amino-4-hydroxy-1-oxobutan-2-yl)piperazin-1-yl)-2,2-dimethyl-2,3-dihydrobenzofuran-5-yl)pyrazolo[1,5-a]pyrimidine-3-carboxamide |
| 483 | 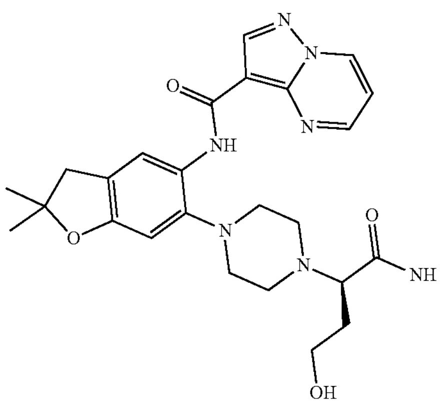 [SMILES: CC1(C)Cc2cc(NC(=O)c3cnn4cccnc34)c(N3CCN([C@H](CCO)C(N)=O)CC3)cc2O1] | (R)-N-(6-(4-(1-amino-4-hydroxy-1-oxobutan-2-yl)piperazin-1-yl)-2,2-dimethyl-2,3-dihydrobenzofuran-5-yl)pyrazolo[1,5-a]pyrimidine-3-carboxamide |
| 484 | 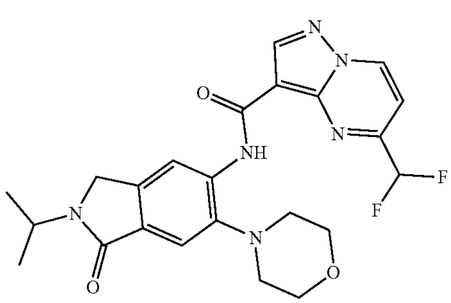 [SMILES: CC(C)N1Cc2cc(NC(=O)c3cnn4ccc(C(F)F)nc34)c(N3CCOCC3)cc2C1=O] | 5-(difluoromethyl)-N-(2-isopropyl-6-morpholino-1-oxoisoindolin-5-yl)pyrazolo[1,5-a]pyrimidine-3-carboxamide |
| 485 | 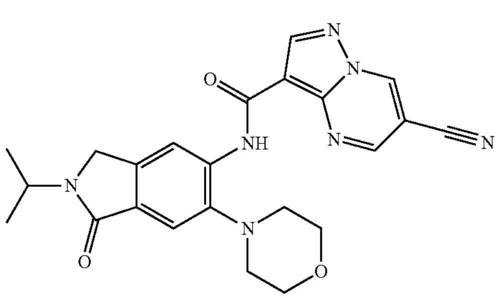 [SMILES: CC(C)N1Cc2cc(NC(=O)c3cnn4cc(C#N)cnc34)c(N3CCOCC3)cc2C1=O] | 6-cyano-N-(2-isopropyl-6-morpholino-1-oxoisoindolin-5-yl)pyrazolo[1,5-a]pyrimidine-3-carboxamide |

TABLE 3-continued

Additional exemplary compounds of the present invention. Salts of such compounds are also contemplated. See the Examples section for preparation of such compounds.

| Ex. | Structure | Name |
|---|---|---|
| 486 | 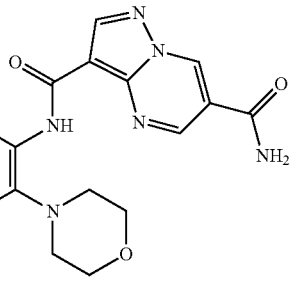 | $N^3$-(2-isopropyl-6-morpholino-1-oxoisoindolin-5-yl)pyrazolo[1,5-a]pyrimidine-3,6-dicarboxamide |
| 487 | 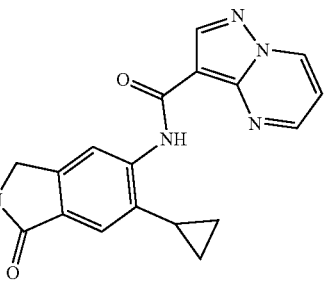 | (R)-N-(6-cyclopropyl-2-(2-fluoro-3-hydroxy-3-methylbutyl)-1-oxoisoindolin-5-yl)pyrazolo[1,5-a]pyrimidine-3-carboxamide |
| 488 | 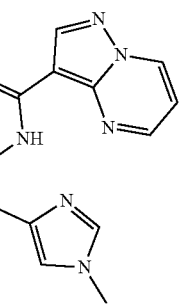 | N-(2,2-dimethyl-6-(1-methyl-1H-imidazol-4-yl)-2,3-dihydrobenzofuran-5-yl)pyrazolo[1,5-a]pyrimidine-3-carboxamide |
| 489 | 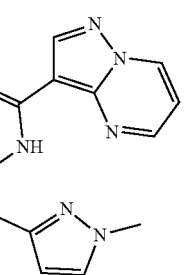 | N-(2,2-dimethyl-6-(1-methyl-1H-pyrazol-3-yl)-2,3-dihydrobenzofuran-5-yl)pyrazolo[1,5-a]pyrimidine-3-carboxamide |
| 490 | 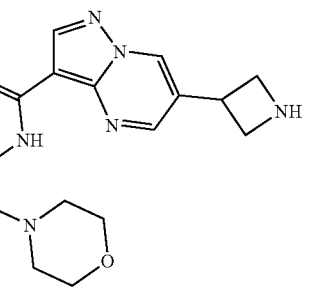 | 6-(azetidin-3-yl)-N-(2,2-dimethyl-6-morpholino-2,3-dihydrobenzofuran-5-yl)pyrazolo[1,5-a]pyrimidine-3-carboxamide hydrochloride |

TABLE 3-continued

*Additional exemplary compounds of the present invention. Salts of such compounds are also contemplated. See the Examples section for preparation of such compounds.*

| Ex. | Structure | Name |
|---|---|---|
| 491 | 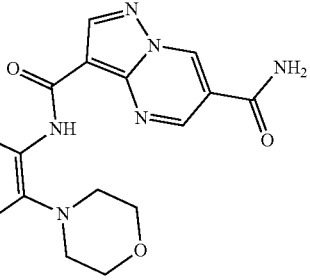 | $N^3$-(2,2-dimethyl-6-morpholino-2,3-dihydrobenzofuran-5-yl)pyrazolo[1,5-a]pyrimidine-3,6-dicarboxamide |
| 492 | 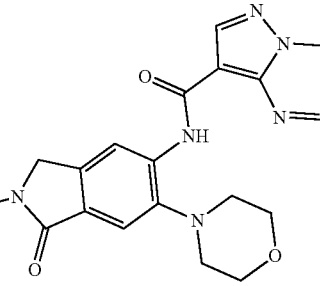 | (R)-$N^3$-(2-(2-fluoro-3-hydroxy-3-methylbutyl)-6-morpholino-1-oxoisoindolin-5-yl)-$N^6$-methylpyrazolo[1,5-a]pyrimidine-3,6-dicarboxamide |
| 493 | 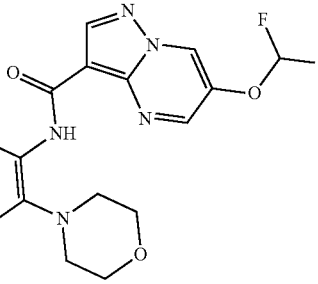 | 6-(difluoromethoxy)-N-(2,2-dimethyl-6-morpholino-2,3-dihydrobenzofuran-5-yl)pyrazolo[1,5-a]pyrimidine-3-carboxamide |
| 494 | 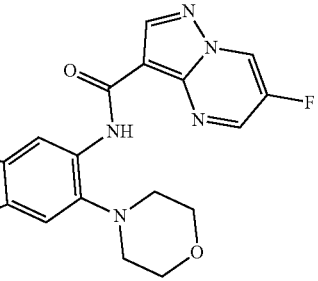 | (R)-6-fluoro-N-(2-(hydroxymethyl)-2-methyl-6-morpholino-2,3-dihydrobenzofuran-5-yl)pyrazolo[1,5-a]pyrimidine-3-carboxamide |
| 495 | 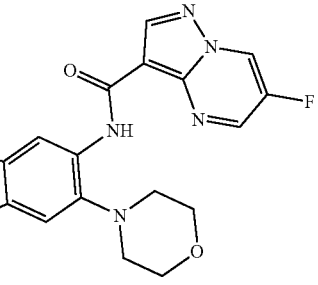 | (S)-6-fluoro-N-(2-(hydroxymethyl)-2-methyl-6-morpholino-2,3-dihydrobenzofuran-5-yl)pyrazolo[1,5-a]pyrimidine-3-carboxamide |

TABLE 3-continued

Additional exemplary compounds of the present invention. Salts of such compounds are also contemplated. See the Examples section for preparation of such compounds.

| Ex. | Structure | Name |
|---|---|---|
| 496 | 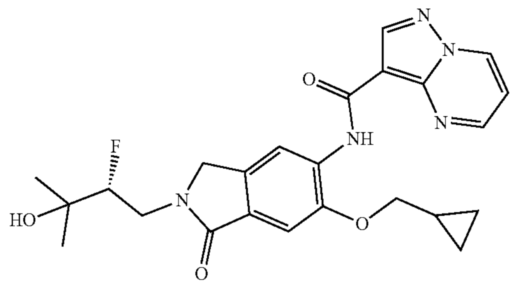 [SMILES: CC(C)(O)[C@H](F)CN1Cc2cc(NC(=O)c3cnn4cccnc34)c(OCC3CC3)cc2C1=O] | (R)-N-(6-(cyclopropylmethoxy)-2-(2-fluoro-3-hydroxy-3-methylbutyl)-1-oxoisoindolin-5-yl)pyrazolo[1,5-a]pyrimidine-3-carboxamide |
| 497 | 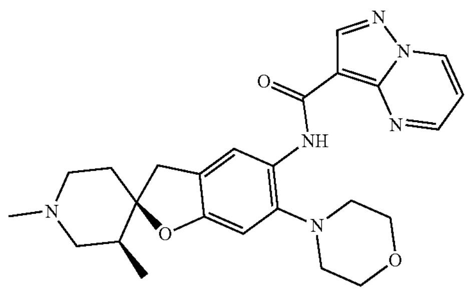 [SMILES: C[C@H]1CN(C)CC[C@]12Cc1cc(NC(=O)c3cnn4cccnc34)c(N3CCOCC3)cc1O2] | N-((2R,3'S)-1',3'-dimethyl-6-morpholino-3H-spiro[benzofuran-2,4'-piperidin]-5-yl)pyrazolo[1,5-a]pyrimidine-3-carboxamide |
| 498 | 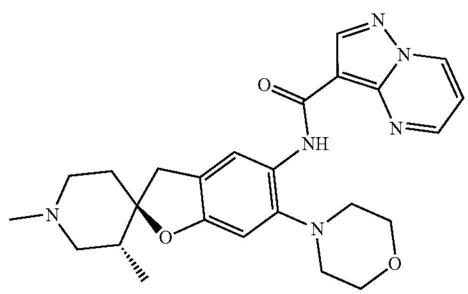 [SMILES: C[C@@H]1CN(C)CC[C@]12Cc1cc(NC(=O)c3cnn4cccnc34)c(N3CCOCC3)cc1O2] | N-((2R,3'R)-1',3'-dimethyl-6-morpholino-3H-spiro[benzofuran-2,4'-piperidin]-5-yl)pyrazolo[1,5-a]pyrimidine-3-carboxamide |
| 499 | 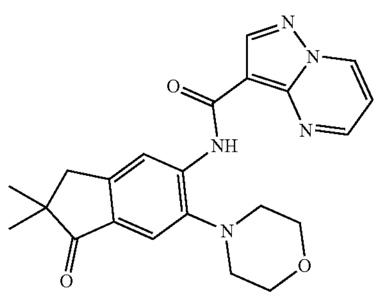 [SMILES: CC1(C)Cc2cc(NC(=O)c3cnn4cccnc34)c(N3CCOCC3)cc2C1=O] | N-(2,2-dimethyl-6-morpholino-1-oxo-2,3-dihydro-1H-inden-5-yl)pyrazolo[1,5-a]pyrimidine-3-carboxamide |
| 500 | 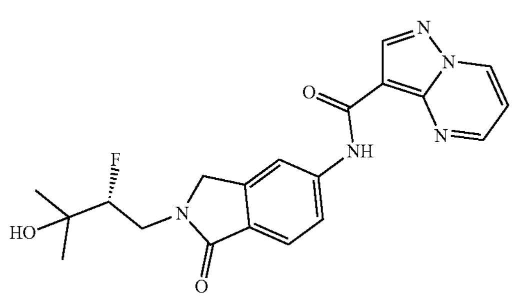 [SMILES: CC(C)(O)[C@H](F)CN1Cc2cc(NC(=O)c3cnn4cccnc34)ccc2C1=O] | (R)-N-(2-(2-fluoro-3-hydroxy-3-methylbutyl)-1-oxoisoindolin-5-yl)pyrazolo[1,5-a]pyrimidine-3-carboxamide |

TABLE 3-continued

Additional exemplary compounds of the present invention. Salts of such compounds are also contemplated. See the Examples section for preparation of such compounds.

| Ex. | Structure | Name |
|---|---|---|
| 501 | 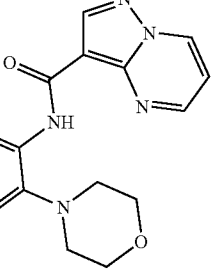 | N-(1'-(2-fluoroethyl)-6-morpholino-3H-spiro[benzofuran-2,4'-piperidin]-5-yl)pyrazolo[1,5-a]pyrimidine-3-carboxamide |
| 502 | 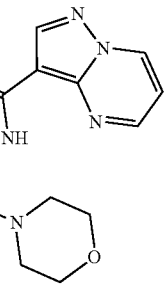 | N-(1'-ethyl-6-morpholino-3H-spiro[benzofuran-2,4'-piperidin]-5-yl)pyrazolo[1,5-a]pyrimidine-3-carboxamide |
| 503 | 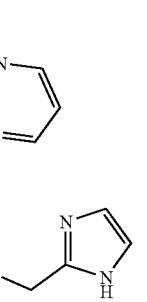 | N-(6-(4-((1H-imidazol-2-yl)methyl)piperazin-1-yl)-2,2-dimethyl-2,3-dihydrobenzofuran-5-yl)pyrazolo[1,5-a]pyrimidine-3-carboxamide |
| 504 | 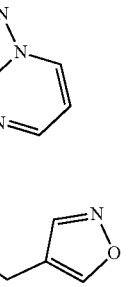 | N-(6-(4-(isoxazol-4-ylmethyl)piperazin-1-yl)-2,2-dimethyl-2,3-dihydrobenzofuran-5-yl)pyrazolo[1,5-a]pyrimidine-3-carboxamide |
| 505 | 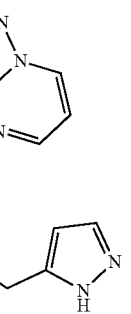 | N-(6-(4-((1H-pyrazol-5-yl)methyl)piperazin-1-yl)-2,2-dimethyl-2,3-dihydrobenzofuran-5-yl)pyrazolo[1,5-a]pyrimidine-3 carboxamide |

TABLE 3-continued

Additional exemplary compounds of the present invention. Salts of such compounds are also contemplated. See the Examples section for preparation of such compounds.

| Ex. | Structure | Name |
|---|---|---|
| 506 | 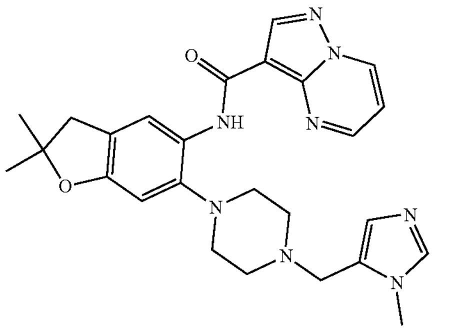 [SMILES: Cn1cncc1CN1CCN(c2cc3c(cc2NC(=O)c2cnn4cccnc24)CC(C)(C)O3)CC1] | N-(2,2-dimethyl-6-(4-((1-methyl-1H-imidazol-5-yl)methyl)piperazin-1-yl)-2,3-dihydrobenzofuran-5-yl)pyrazolo[1,5-a]pyrimidine-3-carboxamide |
| 507 | 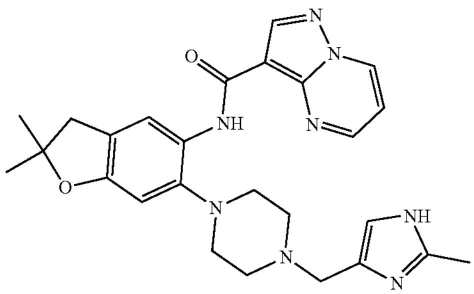 | N-(2,2-dimethyl-6-(4-((2-methyl-1H-imidazol-4-yl)methyl)piperazin-1-yl)-2,3-dihydrobenzofuran-5-yl)pyrazolo[1,5-a]pyrimidine-3-carboxamide |
| 508 | 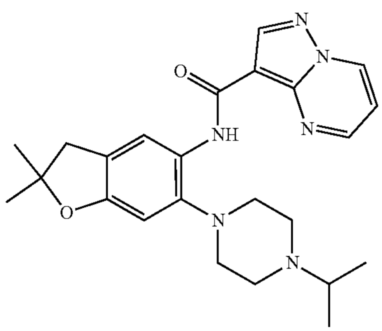 [SMILES: CC(C)N1CCN(c2cc3c(cc2NC(=O)c2cnn4cccnc24)CC(C)(C)O3)CC1] | N-(6-(4-isopropylpiperazin-1-yl)-2,2-dimethyl-2,3-dihydrobenzofuran-5-yl)pyrazolo[1,5-a]pyrimidine-3-carboxamide |
| 509 | 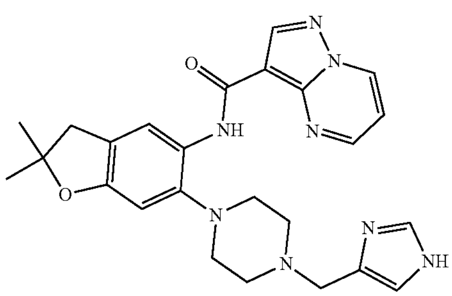 [SMILES: CC1(C)Cc2cc(NC(=O)c3cnn4cccnc34)c(N3CCN(Cc4c[nH]cn4)CC3)cc2O1] | N-(6-(4-((1H-imidazol-4-yl)-2,2-dimethyl-2,3-yl)methyl)piperazin-1-dihydrobenzofuran-5-yl)pyrazolo[1,5-a]pyrimidine-3-carboxamide |
| 510 | 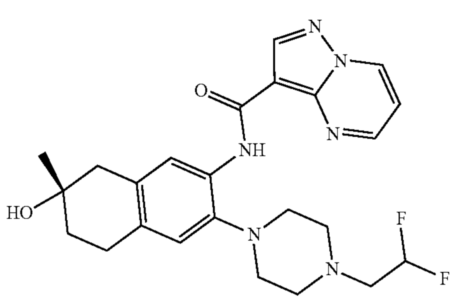 [SMILES: C[C@]1(O)CCc2cc(N3CCN(CC(F)F)CC3)c(NC(=O)c3cnn4cccnc34)cc2C1] | (R)-N-(7-(4-(2,2-difluoroethyl)piperazin-1-yl)-3-hydroxy-3-methylchroman-6-yl)pyrazolo[1,5-a]pyrimidine-3-carboxamide |

TABLE 3-continued

*Additional exemplary compounds of the present invention. Salts of such compounds are also contemplated. See the Examples section for preparation of such compounds.*

| Ex. | Structure | Name |
|---|---|---|
| 511 | 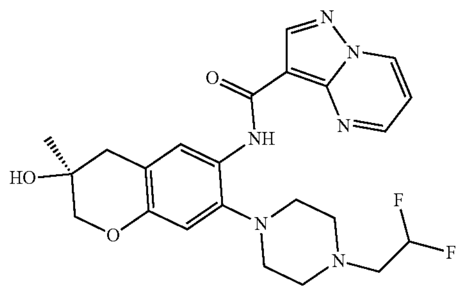 [SMILES: C[C@@]1(O)COc2cc(N3CCN(CC(F)F)CC3)c(NC(=O)c3cnn4cccnc34)cc2C1] | (S)-N-(7-(4-(2,2-difluoroethyl)piperazin-1-yl)-3-hydroxy-3-methylchroman-6-yl)pyrazolo[1,5-a]pyrimidine-3-carboxamide |
| 512 | 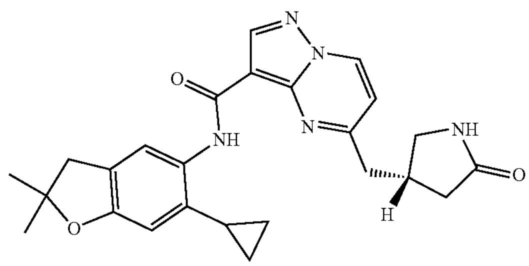 [SMILES: CC1(C)Cc2cc(NC(=O)c3cnn4ccc(C[C@@H]5CNC(=O)C5)nc34)c(C3CC3)cc2O1] | (S)-N-(6-cyclopropyl-2,2-dimethyl-2,3-dihydrobenzofuran-5-yl)-5-((5-oxopyrrolidin-3-yl)methyl)pyrazolo[1,5-a]pyrimidine-3-carboxamide |
| 513 | 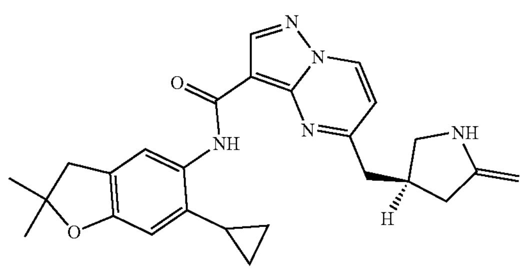 | (R)-N-(6-cyclopropyl-2,2-dimethyl-2,3-dihydrobenzofuran-5-yl)-5-((5-oxopyrrolidin-3-yl)methyl)pyrazolo[1,5-a]pyrimidine-3-carboxamide |
| 514 | 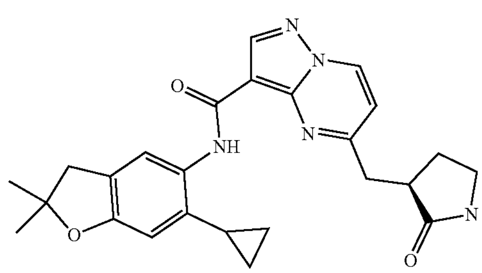 [SMILES: CC1(C)Cc2cc(NC(=O)c3cnn4ccc(C[C@H]5CCNC5=O)nc34)c(C3CC3)cc2O1] | (R)-N-(6-cyclopropyl-2,2-dimethyl-2,3-dihydrobenzofuran-5-yl)-5-((2-oxopyrrolidin-3-yl)methyl)pyrazolo[1,5-a]pyrimidine-3-carboxamide |
| 515 | 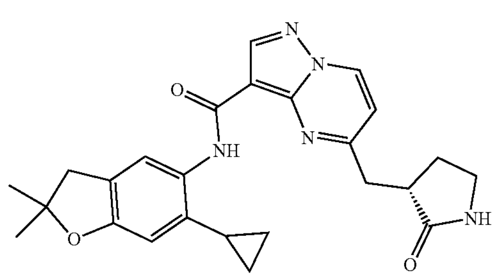 [SMILES: CC1(C)Cc2cc(NC(=O)c3cnn4ccc(C[C@@H]5CCNC5=O)nc34)c(C3CC3)cc2O1] | (S)-N-(6-cyclopropyl-2,2-dimethyl-2,3-dihydrobenzofuran-5-yl)-5-((2-oxopyrrolidin-3-yl)methyl)pyrazolo[1,5-a]pyrimidine-3-carboxamide |

TABLE 3-continued

*Additional exemplary compounds of the present invention. Salts of such compounds are also contemplated. See the Examples section for preparation of such compounds.*

| Ex. | Structure | Name |
|---|---|---|
| 516 | 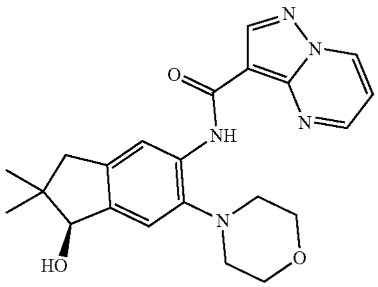 [SMILES: CC1(C)Cc2cc(NC(=O)c3cnn4cccnc34)c(N3CCOCC3)cc2[C@H]1O] | (S)-N-(1-hydroxy-2,2-dimethyl-6-morpholino-2,3-dihydro-1H-inden-5-yl)pyrazolo[1,5-a]pyrimidine-3-carboxamide |
| 517 | 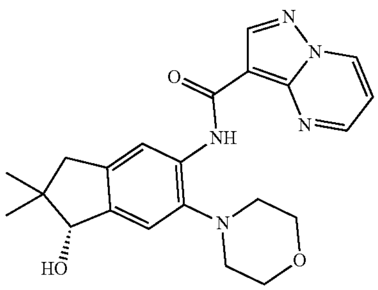 [SMILES: CC1(C)Cc2cc(NC(=O)c3cnn4cccnc34)c(N3CCOCC3)cc2[C@@H]1O] | (R)-N-(1-hydroxy-2,2-dimethyl-6-morpholino-2,3-dihydro-1H-inden-5-yl)pyrazolo[1,5-a]pyrimidine-3-carboxamide |
| 518 | 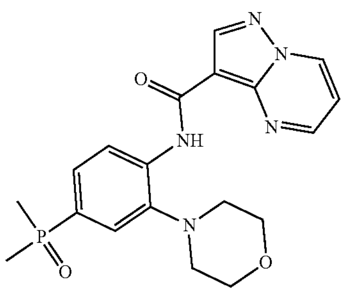 [SMILES: CP(C)(=O)c1ccc(NC(=O)c2cnn3cccnc23)c(N2CCOCC2)c1] | N-(4-(dimethylphosphoryl)-2-morpholinophenyl)pyrazolo[1,5-a]pyrimidine-3-carboxamide |
| 519 | 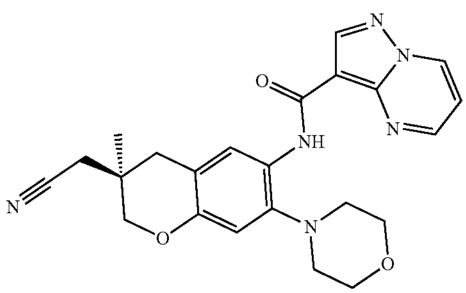 [SMILES: C[C@@]1(CC#N)COc2cc(N3CCOCC3)c(NC(=O)c3cnn4cccnc34)cc2C1] | (R)-N-(6-(4-((1H-3-methyl-7-morpholinochroman-6-yl)pyrazolo[1,5-a]pyrimidine-3-carboxamide |
| 520 | 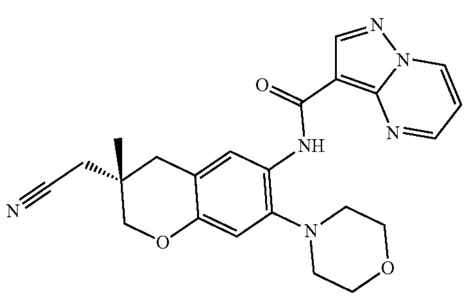 [SMILES: C[C@]1(CC#N)COc2cc(N3CCOCC3)c(NC(=O)c3cnn4cccnc34)cc2C1] | (S)-N-(3-(cyanomethyl)-3-methyl-7-morpholinochroman-6-yl)pyrazolo[1,5-a]pyrimidine-3-carboxamide |

TABLE 3-continued

*Additional exemplary compounds of the present invention. Salts of such compounds are also contemplated. See the Examples section for preparation of such compounds.*

| Ex. | Structure | Name |
|---|---|---|
| 521 | 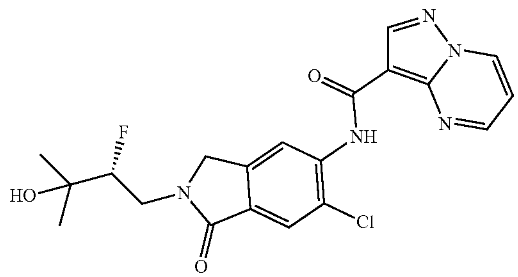 [SMILES: CC(C)(O)[C@H](F)CN1Cc2cc(NC(=O)c3cnn4cccnc34)c(Cl)cc2C1=O] | (R)-N-(6-chloro-2-(2-fluoro-3-hydroxy-3-methylbutyl)-1-oxoisoindolin-5-yl)pyrazolo[1,5-a]pyrimidine-3-carboxamide |
| 522 | 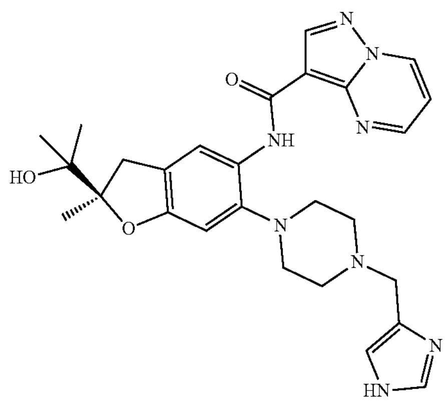 [SMILES: CC(C)(O)[C@@]1(C)Cc2cc(NC(=O)c3cnn4cccnc34)c(N3CCN(Cc4c[nH]cn4)CC3)cc2O1] | (R)-N-(6-4-((1H-imidazol-4-yl)methyl)piperazin-1-yl)-2-(2-hydroxypropan-2-yl)-2-methyl-2,3-dihydrobenzofuran-5-yl)pyrazolo[1,5-a]pyrimidine-3-carboxamide |
| 523 | 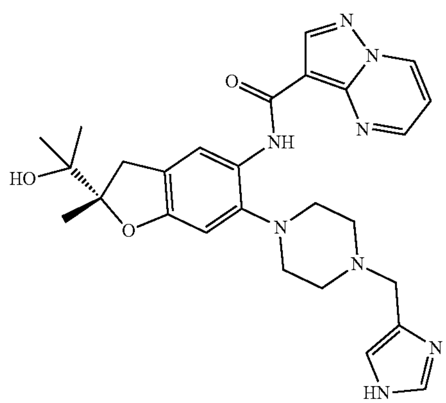 [SMILES: CC(C)(O)[C@]1(C)Cc2cc(NC(=O)c3cnn4cccnc34)c(N3CCN(Cc4c[nH]cn4)CC3)cc2O1] | (S)-N-(6-(4-((1H-imidazol-4-yl)methyl)piperazin-1-yl)-2-(2-hydroxypropan-2-yl)-2-methyl-2,3-dihydrobenzofuran-5-yl)pyrazolo[1,5-a]pyrimidine-3-carboxamide |
| 524 | 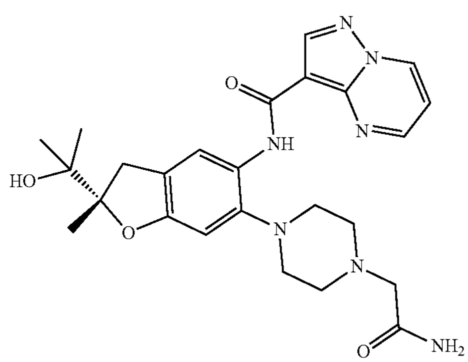 [SMILES: CC(C)(O)[C@]1(C)Cc2cc(NC(=O)c3cnn4cccnc34)c(N3CCN(CC(N)=O)CC3)cc2O1] | (S)-N-(6-(4-(2-amino-2-oxoethyl)piperazin-1-yl)-2-(2-hydroxypropan-2-yl)-2-methyl-2,3-dihydrobenzofuran-5-yl)pyrazolo[1,5-a]pyrimidine-3-carboxamide |

TABLE 3-continued

Additional exemplary compounds of the present invention. Salts of such compounds are also contemplated. See the Examples section for preparation of such compounds.

| Ex. | Structure | Name |
|---|---|---|
| 525 | 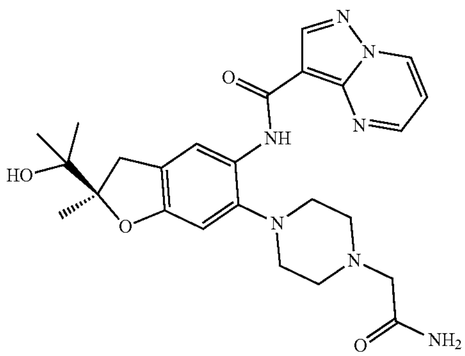 [SMILES: CC(C)(O)[C@@]1(C)Cc2cc(NC(=O)c3cnn4cccnc34)c(N3CCN(CC(N)=O)CC3)cc2O1] | (R)-N-(6-(4-(2-amino-2-oxoethyl)piperazin-1-yl)-2-(2-hydroxypropan-2-yl)-2-methyl-2,3-dihydrobenzofuran-5-yl)pyrazolo[1,5-a]pyrimidine-3-carboxamide |
| 526 | 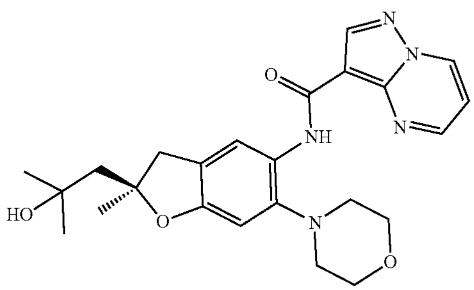 [SMILES: CC(C)(O)C[C@@]1(C)Cc2cc(NC(=O)c3cnn4cccnc34)c(N3CCOCC3)cc2O1] | (R)-N-(2-(2-hydroxy-2-methylpropyl)-2-methyl-6-morpholino-2,3-dihydrobenzofuran-5-yl)pyrazolo[1,5-a]pyrimidine-3-carboxamide |
| 527 | 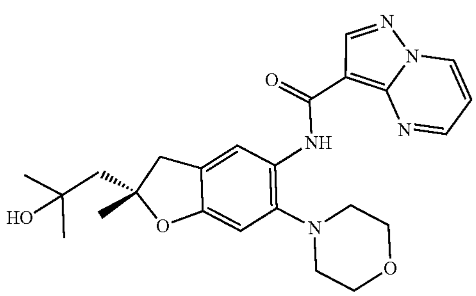 [SMILES: CC(C)(O)C[C@]1(C)Cc2cc(NC(=O)c3cnn4cccnc34)c(N3CCOCC3)cc2O1] | (S)-N-(2-(2-hydroxy-2-methylpropyl)-2-methyl-6-morpholino-2,3-dihydrobenzofuran-5-yl)pyrazolo[1,5-a]pyrimidine-3-carboxamide |
| 528 | 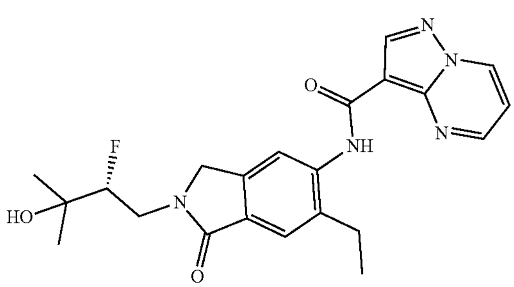 [SMILES: CCc1cc2c(cc1NC(=O)c1cnn3cccnc13)CN(C[C@@H](F)C(C)(C)O)C2=O] | (R)-N-(6-ethyl-2-(2-fluoro-3-hydroxy-3-methylbutyl)-1-oxoisoindolin-5-yl)pyrazolo[1,5-a]pyrimidine-3-carboxamide |
| 529 | 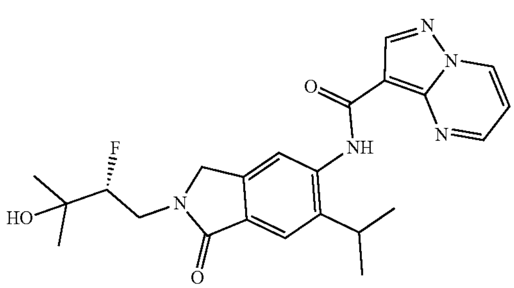 [SMILES: CC(C)c1cc2c(cc1NC(=O)c1cnn3cccnc13)CN(C[C@@H](F)C(C)(C)O)C2=O] | (R)-N-(2-(2-fluoro-3-hydroxy-3-methylbutyl)-6-isopropyl-1-oxoisoindolin-5-yl)pyrazolo[1,5-a]pyrimidine-3-carboxamide |

TABLE 3-continued

*Additional exemplary compounds of the present invention. Salts of such compounds are also contemplated. See the Examples section for preparation of such compounds.*

| Ex. | Structure | Name |
|---|---|---|
| 530 | 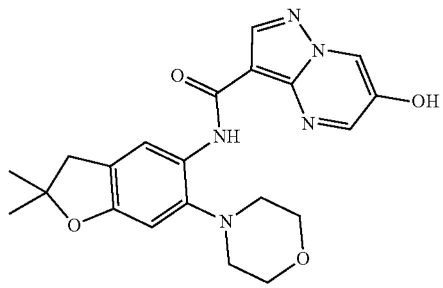 [SMILES: CC1(C)Cc2cc(NC(=O)c3cnn4cc(O)cnc34)c(N3CCOCC3)cc2O1] | N-(2,2-dimethyl-6-morpholino-2,3-dihydrobenzofuran-5-yl)-6-hydroxypyrazolo[1,5-a]pyrimidine-3-carboxamide |
| 531 | 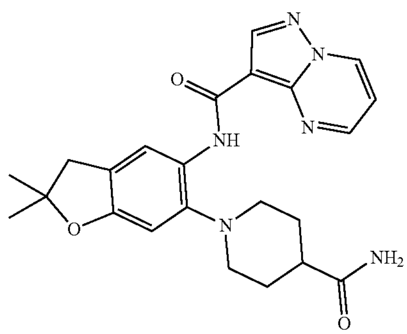 [SMILES: CC1(C)Cc2cc(NC(=O)c3cnn4cccnc34)c(N3CCC(C(N)=O)CC3)cc2O1] | N-(6-(4-carbamoylpiperidin-1-yl)-2,2-dimethyl-2,3-dihydrobenzofuran-5-yl)pyrazolo[1,5-a]pyrimidine-3-carboxamide |
| 532 | 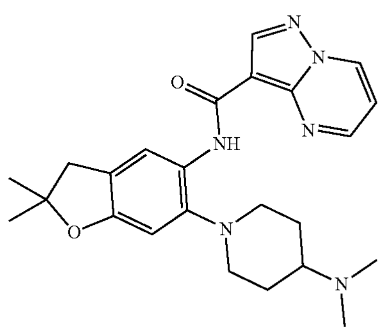 | N-(6-(4-(dimethylamino)piperidin-1-yl)-2,2-dimethyl-2,3-dihydrobenzofuran-5-yl)pyrazolo[1,5-a]pyrimidine-3-carboxamide |
| 533 | 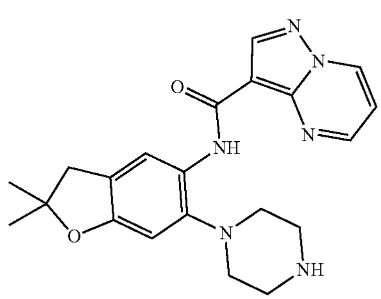 [SMILES: CC1(C)Cc2cc(NC(=O)c3cnn4cccnc34)c(N3CCNCC3)cc2O1] | N-(2,2-dimethyl-6-(piperazin-1-yl)-2,3-dihydrobenzofuran-5-yl)pyrazolo[1,5-a]pyrimidine-3-carboxamide |

TABLE 3-continued

*Additional exemplary compounds of the present invention. Salts of such compounds are also contemplated. See the Examples section for preparation of such compounds.*

| Ex. | Structure | Name |
|---|---|---|
| 534 | 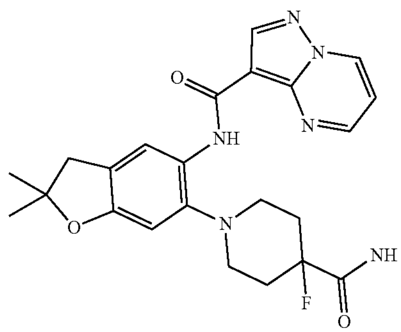 [SMILES: CC1(C)Cc2cc(NC(=O)c3cnn4cccnc34)c(N3CCC(F)(C(N)=O)CC3)cc2O1] | N-(6-(4-carbamoyl-4-fluoropiperidin-1-yl)-2,2-dimethyl-2,3-dihydrobenzofuran-5-yl)pyrazolo[1,5-a]pyrimidine-3-carboxamide |
| 535 | 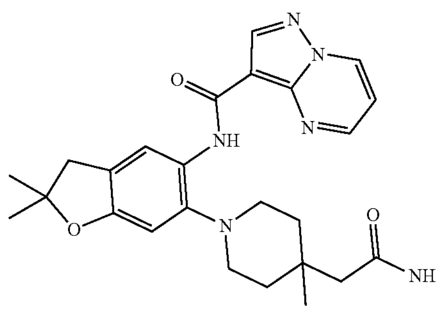 [SMILES: CC1(CC(N)=O)CCN(c2cc3c(cc2NC(=O)c2cnn4cccnc24)CC(C)(C)O3)CC1] | N-(6-(4-(2-amino-2-oxoethyl)-4-methylpiperidin-1-yl)-2,2-dimethyl-2,3-dihydrobenzofuran-5-yl)pyrazolo[1,5-a]pyrimidine-3-carboxamide |
| 536 | 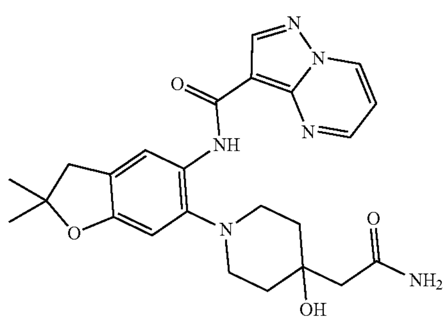 [SMILES: CC1(C)Cc2cc(NC(=O)c3cnn4cccnc34)c(N3CCC(O)(CC(N)=O)CC3)cc2O1] | N-(6-(4-(2-amino-2-oxoethyl)-4-hydroxypiperidin-1-yl)-2,2-dimethyl-2,3-dihydrobenzofuran-5-yl)pyrazolo[1,5-a]pyrimidine-3-carboxamide |
| 537 | 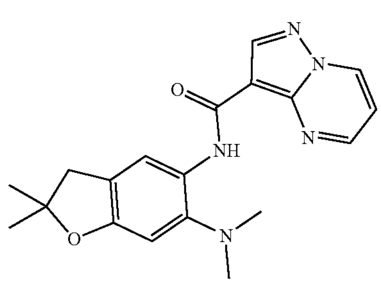 [SMILES: CN(C)c1cc2c(cc1NC(=O)c1cnn3cccnc13)CC(C)(C)O2] | N-(6-(dimethylamino)-2,2-dimethyl-2,3-dihydrobenzofuran-5-yl)pyrazolo[1,5-a]pyrimidine-3-carboxamide |

TABLE 3-continued

Additional exemplary compounds of the present invention. Salts of such compounds are also contemplated. See the Examples section for preparation of such compounds.

| Ex. | Structure | Name |
|---|---|---|
| 538 | 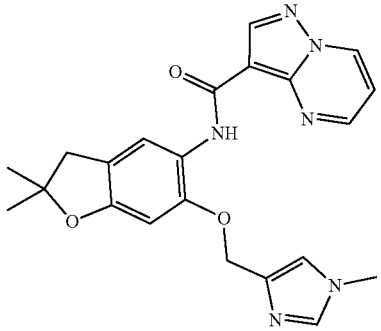 | N-(2,2-dimethyl-6-((1-methyl-1H-imidazol-4-yl)methoxy)-2,3-dihydrobenzofuran-5-yl)pyrazolo[1,5-a]pyrimidine-3-carboxamide |
| 539 | 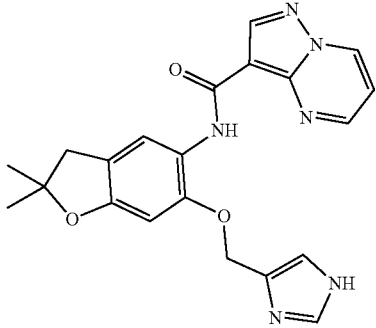 [SMILES: CC1(C)Cc2cc(NC(=O)c3cnn4cccnc34)c(OCc3c[nH]cn3)cc2O1] | N-(6-((1H-imidazol-4-yl)methoxy)-2,2-dimethyl-2,3-dihydrobenzofuran-5-yl)pyrazolo[1,5-a]pyrimidine-3-carboxamide |
| 540 | 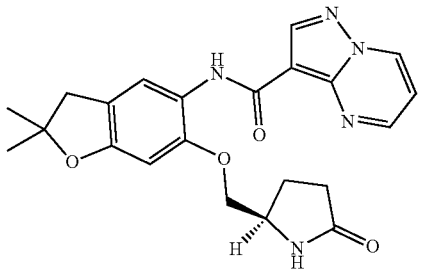 [SMILES: CC1(C)Cc2cc(NC(=O)c3cnn4cccnc34)c(OC[C@H]3CCC(=O)N3)cc2O1] | (R)-N-(2,2-dimethyl-6-((5-oxopyrrolidin-2-yl)methoxy)-2,3-dihydrobenzofuran-5-yl)pyrazolo[1,5-a]pyrimidine-3-carboxamide |
| 541 | 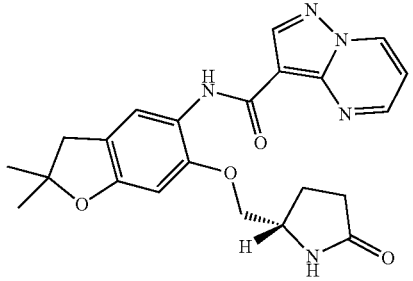 [SMILES: CC1(C)Cc2cc(NC(=O)c3cnn4cccnc34)c(OC[C@@H]3CCC(=O)N3)cc2O1] | (S)-N-(2,2-dimethyl-6-((5-oxopyrrolidin-2-yl)methoxy)-2,3-dihydrobenzofuran-5-yl)pyrazolo[1,5-a]pyrimidine-3-carboxamide |
| 542 | 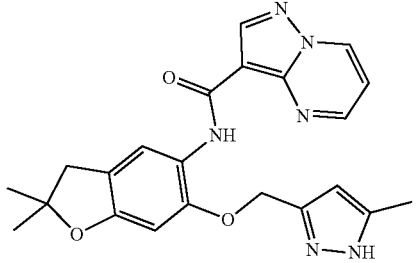 | N-(2,2-dimethyl-6-((5-methyl-1H-pyrazol-3-yl)methoxy)-2,3-dihydrobenzofuran-5-yl)pyrazolo[1,5-a]pyrimidine-3-carboxamide |

TABLE 3-continued

Additional exemplary compounds of the present invention. Salts of such compounds are also contemplated. See the Examples section for preparation of such compounds.

| Ex. | Structure | Name |
|---|---|---|
| 543 | 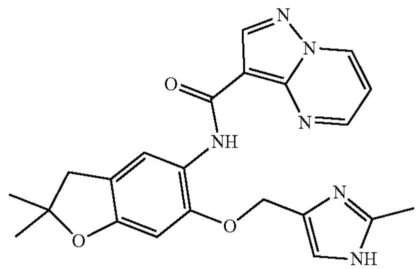 | N-(2,2-dimethyl-6-((2-methyl-1H-imidazol-4-yl)methoxy)-2,3-dihydrobenzofuran-5-yl)pyrazolo[1,5-a]pyrimidine-3-carboxamide |
| 544 | 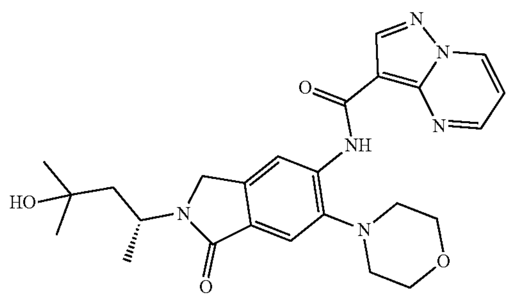 [SMILES: C[C@H](CC(C)(C)O)N1Cc2cc(NC(=O)c3cnn4cccnc34)c(N3CCOCC3)cc2C1=O] | (R)-N-(2-(4-hydroxy-4-methylpentan-2-yl)-6-morpholino-1-oxoisoindolin-5-yl)pyrazolo[1,5-a]pyrimidine-3-carboxamide |
| 545 | 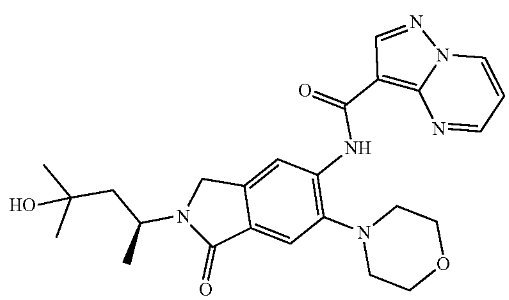 [SMILES: C[C@@H](CC(C)(C)O)N1Cc2cc(NC(=O)c3cnn4cccnc34)c(N3CCOCC3)cc2C1=O] | (S)-N-(2-(4-hydroxy-4-methylpentan-2-yl)-6-morpholino-1-oxoisoindolin-5-yl)pyrazolo[1,5-a]pyrimidine-3-carboxamide |
| 546 | 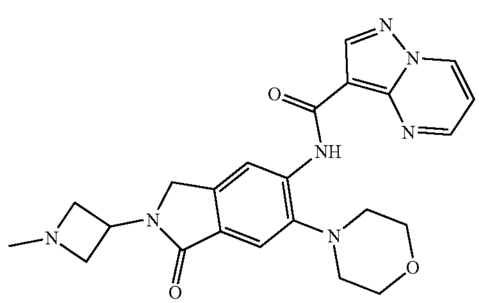 [SMILES: CN1CC(N2Cc3cc(NC(=O)c4cnn5cccnc45)c(N4CCOCC4)cc3C2=O)C1] | N-(2-(1-methylazetidin-3-yl)-6-morpholino-1-oxoisoindolin-5-yl)pyrazolo[1,5-a]pyrimidine-3-carboxamide |
| 547 | 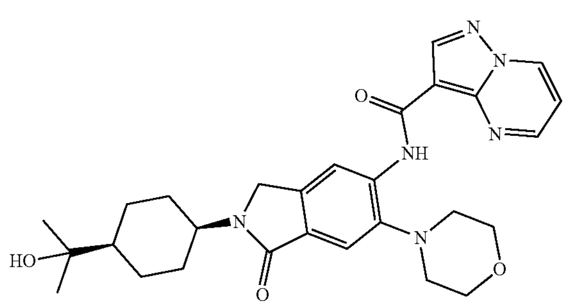 [SMILES: CC(C)(O)[C@H]1CC[C@@H](N2Cc3cc(NC(=O)c4cnn5cccnc45)c(N4CCOCC4)cc3C2=O)CC1] | N-(2-((1S,4S)-4-(2-hydroxypropan-2-yl)cyclohexyl)-6-morpholino-1-oxoisoindolin-5-yl)pyrazolo[1,5-a]pyrimidine-3-carboxamide |

TABLE 3-continued

Additional exemplary compounds of the present invention. Salts of such compounds are also contemplated. See the Examples section for preparation of such compounds.

| Ex. | Structure | Name |
|---|---|---|
| 548 | 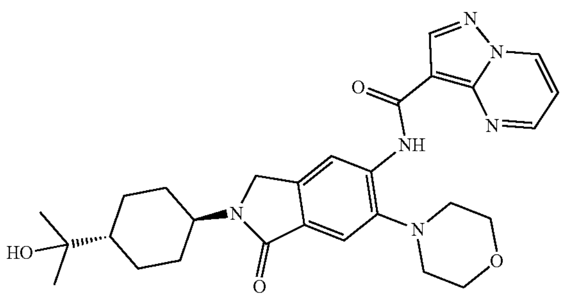 [SMILES: CC(C)(O)[C@H]1CC[C@H](N2Cc3cc(NC(=O)c4cnn5cccnc45)c(N4CCOCC4)cc3C2=O)CC1] | N-(2-((1R,4R)-4-(2-hydroxypropan-2-yl)cyclohexyl)-6-morpholino-1-oxoisoindolin-5-yl)pyrazolo[1,5-a]pyrimidine-3-carboxamide |
| 549 | 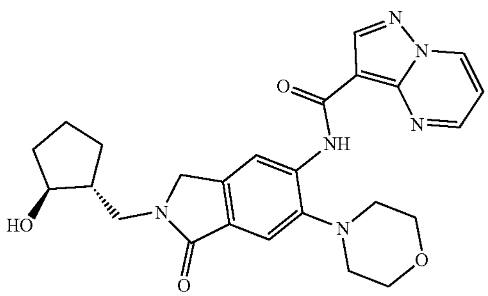 [SMILES: O=C(Nc1cc2c(cc1N1CCOCC1)C(=O)N(C[C@H]1CCC[C@@H]1O)C2)c1cnn2cccnc12] | N-(2-(((1R,2S)-2-hydroxycyclopentyl)methyl)-6-morpholino-1-oxoisoindolin-5-yl)pyrazolo[1,5-a]pyrimidine-3-carboxamide |
| 550 | 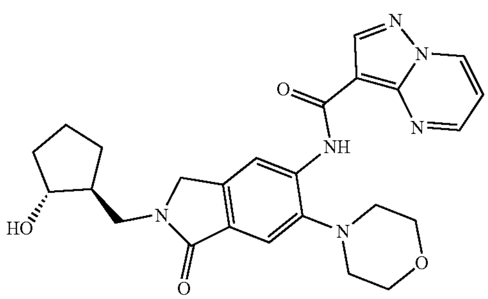 [SMILES: O=C(Nc1cc2c(cc1N1CCOCC1)C(=O)N(C[C@@H]1CCC[C@H]1O)C2)c1cnn2cccnc12] | N-(2-(((1S,2R)-2-hydroxycyclopentyl)methyl)-6-morpholino-1-oxoisoindolin-5-yl)pyrazolo[1,5-a]pyrimidine-3-carboxamide |
| 551 | 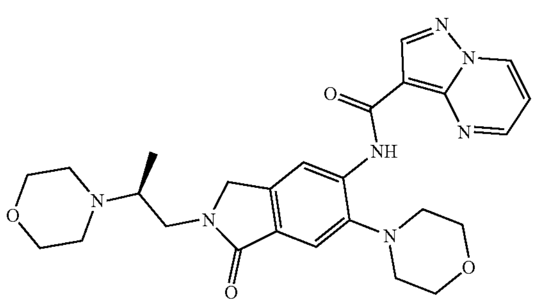 [SMILES: C[C@@H](CN1Cc2cc(NC(=O)c3cnn4cccnc34)c(N3CCOCC3)cc2C1=O)N1CCOCC1] | (S)-N-(6-morpholino-2-(2-morpholinopropyl)-1-oxoisoindolin-5-yl)pyrazolo[1,5-a]pyrimidine-3-carboxamide |
| 552 | 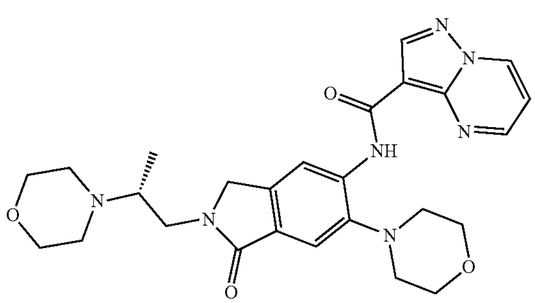 [SMILES: C[C@H](CN1Cc2cc(NC(=O)c3cnn4cccnc34)c(N3CCOCC3)cc2C1=O)N1CCOCC1] | (R)-N-(6-morpholino-2-(2-morpholinopropyl)-1-oxoisoindolin-5-yl)pyrazolo[1,5-a]pyrimidine-3-carboxamide |

TABLE 3-continued

Additional exemplary compounds of the present invention. Salts of such compounds are also contemplated. See the Examples section for preparation of such compounds.

| Ex. | Structure | Name |
|---|---|---|
| 553 | 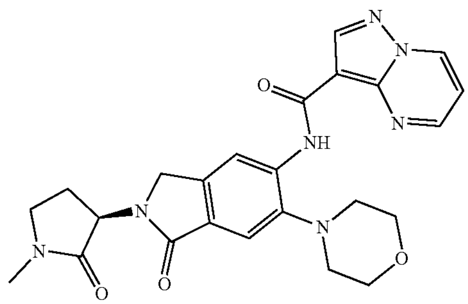 [SMILES: CN1CC[C@@H](N2Cc3cc(NC(=O)c4cnn5cccnc45)c(N4CCOCC4)cc3C2=O)C1=O] | (R)-N-(2-(1-methyl-2-oxopyrrolidin-3-yl)-6-morpholino-1-oxoisoindolin-5-yl)pyrazolo[1,5-a]pyrimidine-3-carboxamide |
| 554 | 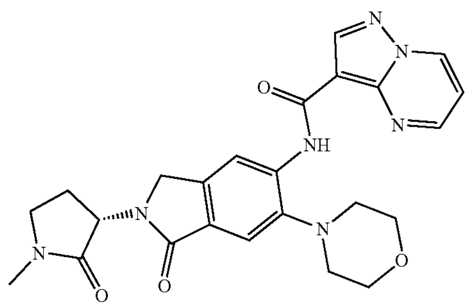 [SMILES: CN1CC[C@H](N2Cc3cc(NC(=O)c4cnn5cccnc45)c(N4CCOCC4)cc3C2=O)C1=O] | (S)-N-(2-(1-methyl-2-oxopyrrolidin-3-yl)-6-morpholino-1-oxoisoindolin-5-yl)pyrazolo[1,5-a]pyrimidine-3-carboxamide |
| 555 | 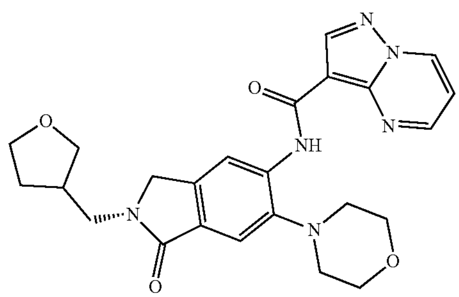 | (S)-N-(6-morpholino-1-oxo-2-((tetrahydrofuran-3-yl)methyl)isoindolin-5-yl)pyrazolo[1,5-a]pyrimidine-3-carboxamide |
| 556 | 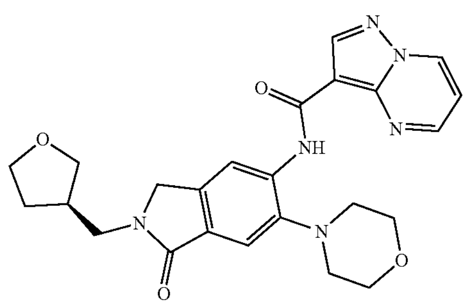 [SMILES: O=C(Nc1cc2c(cc1N1CCOCC1)C(=O)N(C[C@H]1CCOC1)C2)c1cnn2cccnc12] | (R)-N-(6-morpholino-1-oxo-2-((tetrahydrofuran-3-yl)methyl)isoindolin-5-yl)pyrazolo[1,5-a]pyrimidine-3-carboxamide |
| 557 | 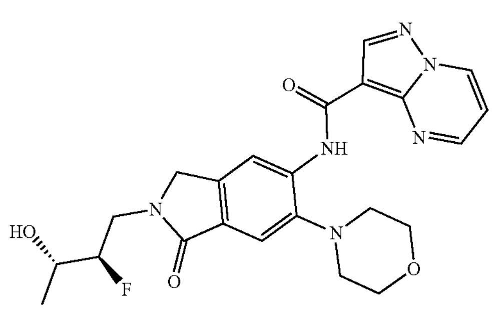 [SMILES: C[C@H](O)[C@H](F)CN1Cc2cc(NC(=O)c3cnn4cccnc34)c(N3CCOCC3)cc2C1=O] | N-(2-((2R,3S)-2-fluoro-3-hydroxybutyl)-6-morpholino-1-oxoisoindolin-5-yl)pyrazolo[1,5-a]pyrimidine-3-carboxamide |

TABLE 3-continued

Additional exemplary compounds of the present invention. Salts of such compounds are also contemplated. See the Examples section for preparation of such compounds.

| Ex. | Structure | Name |
|---|---|---|
| 558 | 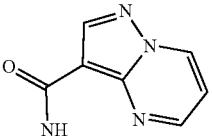 | N-(2-((2S,3R)-2-fluoro-3-hydroxybutyl)-6-morpholino-1-oxoisoindolin-5-yl)pyrazolo[1,5-a]pyrimidine-3-carboxamide |
| 559 | 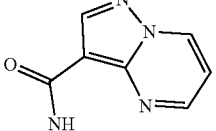 | N-(2-(((1S,2S)-2-hydroxycyclopentyl)methyl)-6-morpholino-1-oxoisoindolin-5-yl)pyrazolo[1,5-a]pyrimidine-3-carboxamide |
| 560 | 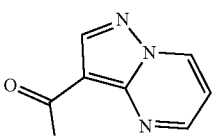 | N-(2-(((1R,2R)-2-hydroxycyclopentyl)methyl)-6-morpholino-1-oxoisoindolin-5-yl)pyrazolo[1,5-a]pyrimidine-3-carboxamide |
| 561 | 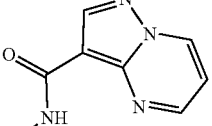 | N-(2-((2S,3S)-2-fluoro-3-hydroxybutyl)-6-morpholino-1-oxoisoindolin-5-yl)pyrazolo[1,5-a]pyrimidine-3-carboxamide |
| 562 | 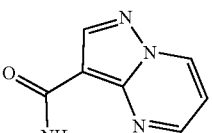 | N-(2-((2R,3R)-2-fluoro-3-hydroxybutyl)-6-morpholino-1-oxoisoindolin-5-yl)pyrazolo[1,5-a]pyrimidine-3-carboxamide |

TABLE 3-continued

*Additional exemplary compounds of the present invention. Salts of such compounds are also contemplated. See the Examples section for preparation of such compounds.*

| Ex. | Structure | Name |
|---|---|---|
| 563 | 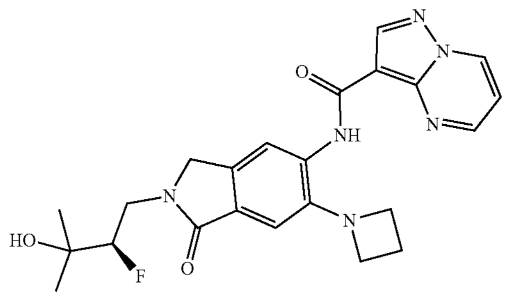 [SMILES: CC(C)(O)[C@H](F)CN1Cc2cc(NC(=O)c3cnn4cccnc34)c(N3CCC3)cc2C1=O] | (R)-N-(6-(azetidin-1-yl)-2-(2-fluoro-3-hydroxy-3-methylbutyl)-1-oxoisoindolin-5-yl)pyrazolo[1,5-a]pyrimidine-3-carboxamide |
| 564 | 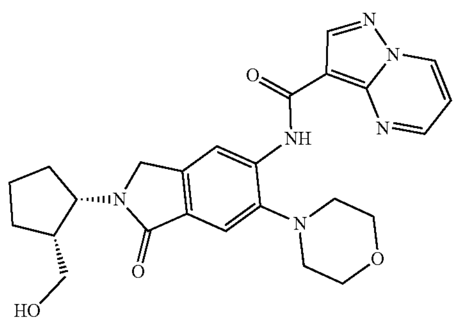 [SMILES: O=C(Nc1cc2c(cc1N1CCOCC1)C(=O)N([C@H]1CCC[C@H]1CO)C2)c1cnn2cccnc12] | N-(2-((1S,2R)-2-(hydroxymethyl)cyclopentyl)-6-morpholino-1-oxoisoindolin-5-yl)pyrazolo[1,5-a]pyrimidine-3-carboxamide |
| 565 | 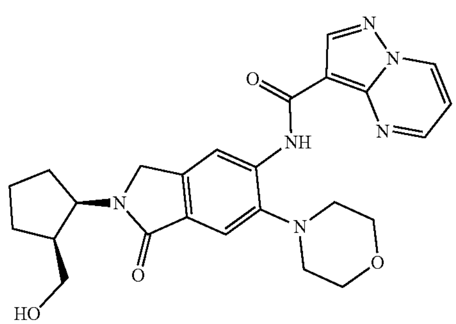 [SMILES: O=C(Nc1cc2c(cc1N1CCOCC1)C(=O)N([C@@H]1CCC[C@@H]1CO)C2)c1cnn2cccnc12] | N-(2-((1R,2S)-2-(hydroxymethyl)cyclopentyl)-6-morpholino-1-oxoisoindolin-5-yl)pyrazolo[1,5-a]pyrimidine-3-carboxamide |
| 566 | 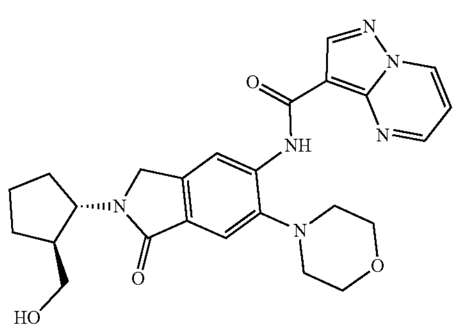 [SMILES: O=C(Nc1cc2c(cc1N1CCOCC1)C(=O)N([C@H]1CCC[C@@H]1CO)C2)c1cnn2cccnc12] | N-(2-((1S,2S)-2-(hydroxymethyl)cyclopentyl)-6-morpholino-1-oxoisoindolin-5-yl)pyrazolo[1,5-a]pyrimidine-3-carboxamide |

TABLE 3-continued

Additional exemplary compounds of the present invention. Salts of such compounds are also contemplated. See the Examples section for preparation of such compounds.

| Ex. | Structure | Name |
|---|---|---|
| 567 | 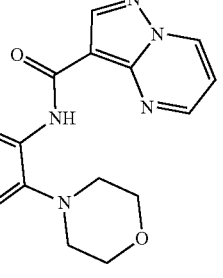 | N-(2-((1R,2R)-2-(hydroxymethyl)cyclopentyl)-6-morpholino-1-oxoisoindolin-5-yl)pyrazolo[1,5-a]pyrimidine-3-carboxamide |
| 568 | 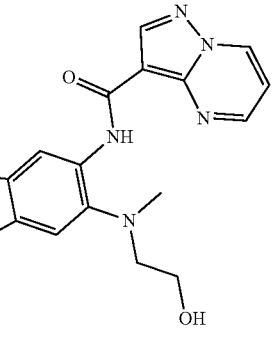 | (R)-N-(2-(2-fluoro-3 hydroxy-3-methylbutyl)-6-((2-hydroxyethyl)(methyl)amino-1-oxoisoindolin-5-yl)pyrazolo[1,5-a]pyrimidine-3-carboxamide |
| 569 | 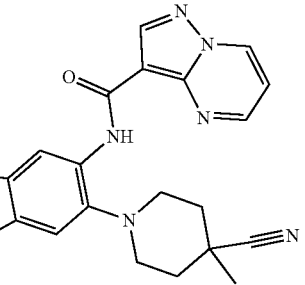 | (R)-N-(6-(4-cyano-4-methylpiperidin-1-yl)-2-(2-fluoro-3-hydroxy-3-methylbutyl)-1-oxoisoindolin-5-yl)pyrazolo[1,5-a]pyrimidine-3-carboxamide |
| 570 | 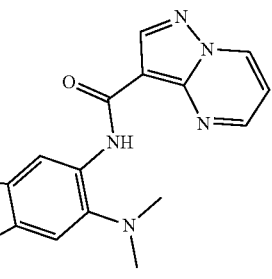 | (R)-N-(6-(dimethylamino)-2-(2-fluoro-3-hydroxy-3-methylbutyl)-1-oxoisoindolin-5-yl)pyrazolo[1,5-a]pyrimidine-3-carboxamide |

Synthesis of IRAK4 Inhibitors

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, vol. 1-21; R. C. LaRock, *Comprehensive Organic Transformations*, 2nd edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds.) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, vol. 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

For illustrative purposes, reaction Schemes below provide routes for synthesizing the compounds of the invention as well as key intermediates. For a more detailed description of the individual reaction steps, see the Examples section below. Those skilled in the art will appreciate that other synthetic routes may be used. Although some specific starting materials and reagents are depicted in the Schemes and discussed below, other starting materials and reagents can be substituted to provide a variety of derivatives or reaction conditions. In addition, many of the compounds prepared by the methods described below can be further modified in light of this disclosure using conventional chemistry well known to those skilled in the art.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, or, about 20° C.

Some compounds in following schemes are depicted with generalized substituents; however, one skilled in the art will immediately appreciate that the nature of the R groups can varied to afford the various compounds contemplated in this invention. Moreover, the reaction conditions are exemplary and alternative conditions are well known. The reaction sequences in the following examples are not meant to limit the scope of the invention as set forth in the claims.

Some compounds in following schemes are depicted with generalized substituents; however, one skilled in the art will immediately appreciate that the nature of the R groups can varied to afford the various compounds contemplated in this invention. Moreover, the reaction conditions are exemplary and alternative conditions are well known. The reaction sequences in the following examples are not meant to limit the scope of the invention as set forth in the claims.

SCHEME I

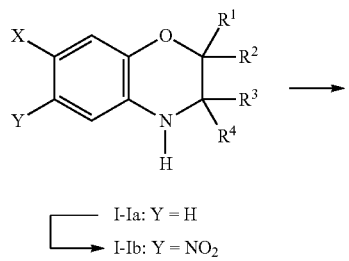

I-1a: Y = H
I-1b: Y = NO$_2$

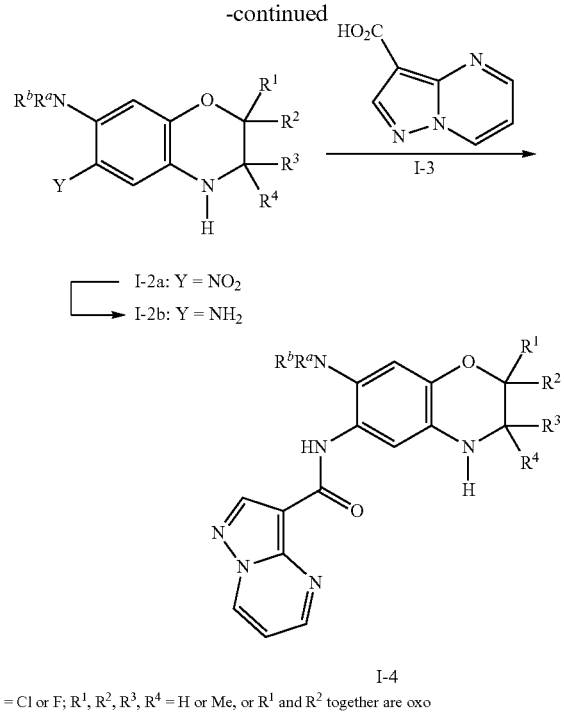

I-2a: Y = NO$_2$
I-2b: Y = NH$_2$

I-4

X = Cl or F; R$^1$, R$^2$, R$^3$, R$^4$ = H or Me, or R$^1$ and R$^2$ together are oxo Regarding Scheme I, requisite 3,4-dihydro-2H-benzo[b][1,4]oxazin-6-yl derivatives can be prepared by nitration of 7-halo-3,4-dihydro-2H-benzo[b][1,4]oxazin-6-yl derivatives I-1a to afford I-1b followed by displacement of the halogen with an amine to afford I-2a. Typical amines include morpholine and 3-hydroxymethyl piperidine. Reduction of the nitro group and condensation with pyrazolo[1,5-a]pyrimidine-3-carboxylic acid (I-3), or an activated derivative thereof, affords the desired amides. The requisite precursors are commercially available or are prepared as described herein.

Aromatic nitration is well known and can be conducted under a variety of conditions known in the art. Nitration can be carried out, for example, by exposing an aromatic compound to concentrated nitric acid and sulfuric acid. Active substrates can be nitrated with HNO$_3$ alone or in H$_2$O, HOAc and acetic anhydride and active compounds may be oxidized by mixtures of HNO$_3$ and H$_2$SO$_4$. Other nitrating reagents include NaNO$_3$/TFA, Cu(NO$_3$)$_2$/HOAc/Ac$_2$O, N$_2$O$_4$, NO$_2$$^+$BF$_4$$^-$, NO$_2$PF$_6$$^-$ and NO$_2$CF$_3$SO$^{4-}$. See, e.g., J. March, Advanced Organic Chemistry, John Wiley & Sons: New York, N.Y., 1992, pp. 522-23.

Reduction of the nitro group can be carried out with a variety of well-known reducing agents. For example, the nitro can be reduced under a hydrogen atmosphere in the presence of an inert solvent and in the presence of a metal effective to catalyze hydrogenation reactions such as platinum or palladium. The reduction can also be carried out with an activated metal such as activated iron, zinc or tin (produced for example by washing iron powder with a dilute acid solution such as dilute hydrochloric acid).

Coupling of the amine 2b intermediate with 3 is achieved with commonly used coupling reagents or, alternatively, 3 can be converted to the corresponding acid chloride and condensed with 2b.

Acylation of a primary amine with an acid chloride is typically carried out in an inert solvent such as DMF, DCM, THF, pyridine with or without water as a co-solvent, at temperatures between 0° C. and 60° C. generally in the presence of a base such as Na₂CO₃, NaHC₃, K₂CO₃, DIPEA, TEA or pyridine and the like to afford the corresponding amide. Carboxylic acids can be converted into their acid chlorides using standard reagents well known to someone skilled in the art, such as thionyl chloride, oxalyl chloride, phosphoryl chloride and the like. Those reagents can be used in presence of bases such as DIPEA, TEA or pyridine.

Alternatively a carboxylic acid can be converted in situ into activated derivatives by utilizing reagents developed for peptide synthesis which are well known to those skilled in the art. These activated acids were reacted directly with the amines as described to afford the corresponding amide. Common coupling reagents include EDC, DCC, benzotriazol-1-yloxy-tris(dimethylamino)-phosphonium hexafluorophosphate (BOP), bromo-tris-pyrrolidinophosphonium hexafluorophosphate (PyBrOP), 2-fluoro-1-methylpyridinium p-toluenesulphonate (Mukaiyama's reagent), O-(7-azabenzotriazol-1-yl)-N,N,N',N'-tetramethyluronium hexafluorophosphate (HATU), 1-hydroxy-7-azabenzotriazole (HOAt) or (3-hydroxy-3H-1,2,3-triazolo[4,5-b]pyridinato-O)tri-1-pyrrolidinylphosphonium hexafluorophosphate (PyAOP) optionally in the presence of modifiers such as HOBt, with or without a base such NMM, TEA or DIPEA in an inert solvent such as DMF or DCM at temperatures between 0° C. and 60° C. Acylation of amines (see, e.g., J. March, supra pp. 417-425; H. G. Benz, *Synthesis of Amides and Related Compounds* in *Comprehensive Organic Synthesis*, E. Winterfeldt, ed., vol. 6, Pergamon Press, Oxford 1991 pp. 381-411; R. C. Larock, *Comprehensive Organic Transformations—A Guide to Functional Group Preparations*, 1989, VCH Publishers Inc., New York; pp. 972-976) has been reviewed.

SCHEME II

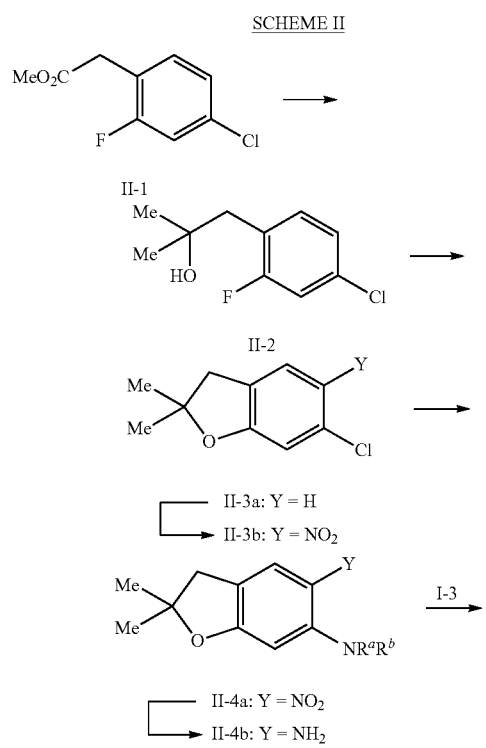

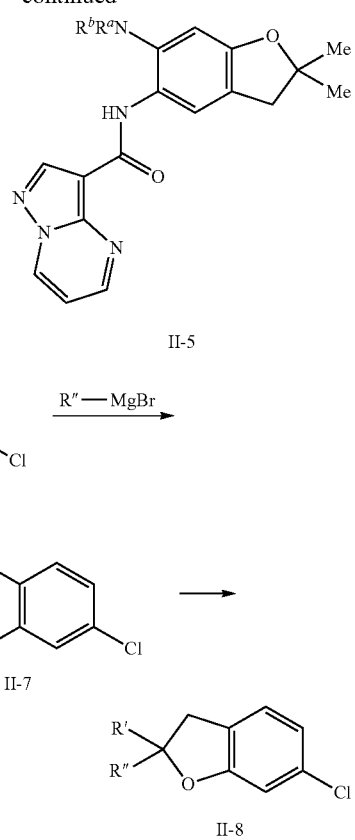

5,6-Diamino-2,2-dimethyl-3H-benzofuran derivatives exemplified herein can be prepared utilizing a 2,2-dimethyl-5-nitro-6-halo-3H-benzofuran II-3b as the key intermediate as depicted in Scheme II. Addition of a methyl Grignard to methyl 5-chloro-2-fluoro-phenylacetate affords the tertiary alcohol II-2 which undergoes an intra-molecular cyclization to afford the II-3a. Nitration and displacement of the chloride with an amine followed by reduction of the nitro and acylation with I-3 is carried out in analogy with Scheme I. One skilled in the art will appreciate that the corresponding 5-fluoro and 5-bromo derivatives are readily available from methyl 2,5-difluorophenylacetate and methyl 5-bromo-2-fluorophenylacetate, respectively.

SCHEME III

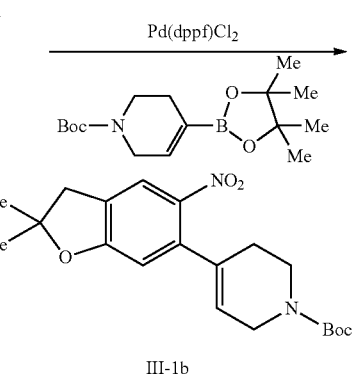

-continued

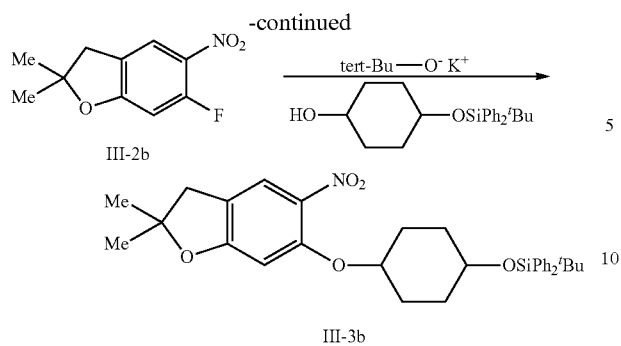

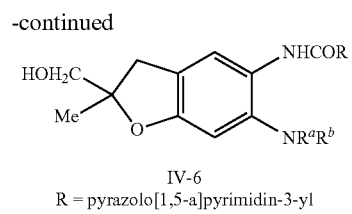

IV-6
R = pyrazolo[1,5-a]pyrimidin-3-yl

With respect to Scheme III, introduction of substituents other than amines at the 2-position can be easily accomplished by addition of an organometallic to 1-(4-chloro-2-fluorophenyl)propan-2-one, or a derivative thereof, and carry on further transformations as described herein. Compounds wherein the 5-amino-2,2-dimethyl-3H-benzofuran-6-yl moiety is linked to a substituent by a carbon-carbon bond were prepared by a palladium-catalyzed coupling of II-3b with a boric acid derivative or a boronic ester. Similarly ether substituents can be readily prepared by reacting 5-amino-2,2-dimethyl-6-fluoro-3H-benzofuran (III-2b) with a alcohol in the presence of potassium tert-butoxide or other suitable strong base. Subsequent reduction of the nitro group, acylation of the resulting amine and any subsequent deprotection which may be required are carried out using standard methodology.

Compounds with a hydroxymethyl substituent attached to the dihydrofuran ring are accessible by condensation of 5-chloro-2-fluorobenzyl magnesium bromide with methyl pyruvate which afforded IV-2. (Scheme IV) Intramolecular cyclization and reduction of the pendant carboxylic acid affords IV-b which is transformed to the final compounds using protocols analogous to those previously described.

SCHEME V

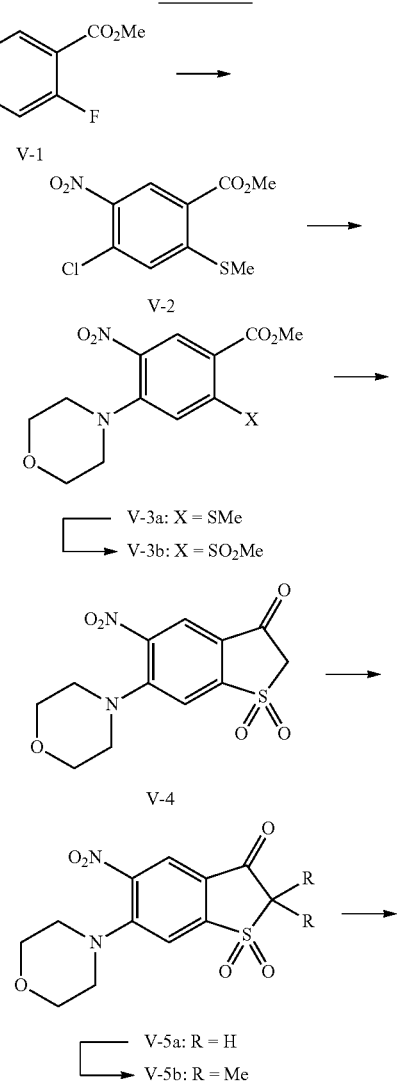

SCHEME IV

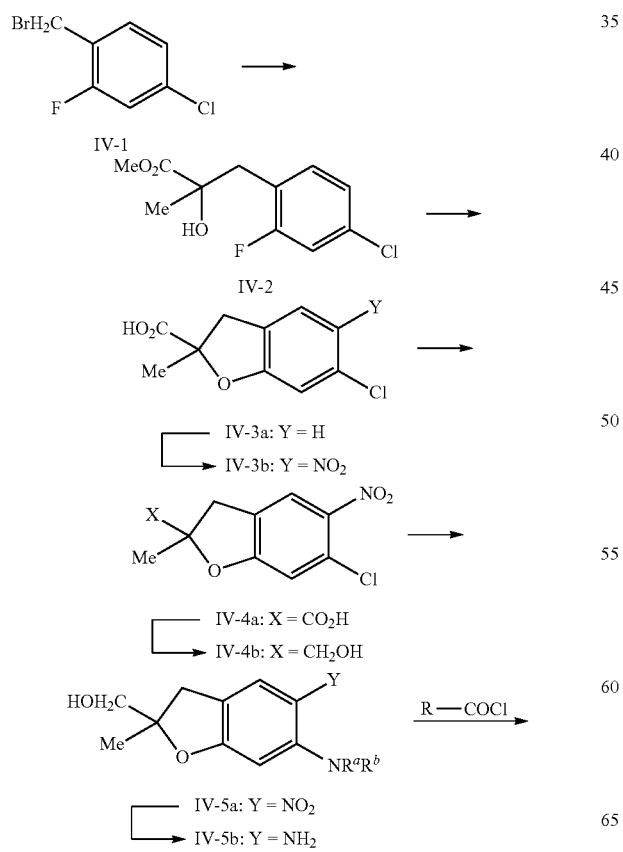

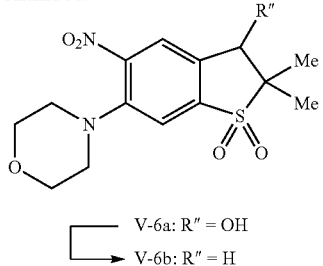

V-6a: R″ = OH
V-6b: R″ = H

With respect to Scheme V, 3H-benzothiophene-1,1-dioxide derivatives can be prepared by intramolecular cyclization methyl 2-methylsulfonyl-4-morpholino-5-nitro-benzoate (V-3b) to afford morpholino-5-nitro-1,1-dioxobenzothiophen-3-one (V-4) which is subsequently reduced to V-6b utilizing a two-step sequence comprising sodium borohydride reduction followed by triethylsilane/TFA reduction that is carried on as previously described. Reduction of the nitro group and acylation of the resulting amine is carried out as described previously.

Methods of Treatment with and Uses of Irak 4 Inhibitors

Compounds of the present invention are useful as IRAK4 inhibitors. Accordingly, in one embodiment is provided a method of contacting a cell, such as an ex vivo cell, with a compound of the present invention to inhibit IRAK4 activity in the cell.

Also provided is a pharmaceutical composition comprising a compound of Formula 0, Formula I, or Formula II, or a stereoisomer or pharmaceutically acceptable salt thereof, and a pharmaceutically acceptable excipient, carrier or diluent. Compounds of the invention, including pharmaceutical compositions comprising such compounds, may be used in the methods described herein.

Further provided is a method of preventing, treating, or lessening the severity of a disease or condition responsive to the inhibition of IRAK4 in a patient, comprising administering to the patient a therapeutically effective amount of a compound of the present invention, or a stereoisomer or pharmaceutically acceptable salt thereof.

Also provided is a method for treating cancer in a patient, comprising administering to the patient a therapeutically effective amount of a compound of the present invention, or a stereoisomer or pharmaceutically acceptable salt thereof.

Further provided is a method for treating an inflammatory or autoimmune disease in a patient, comprising administering to the patient a therapeutically effective amount of a compound of the present invention, or a stereoisomer or pharmaceutically acceptable salt thereof.

In some embodiments, the disease is selected from the group consisting of Crohn's disease, ulcerative colitis, Irritable Bowel Disorder (IBD), asthma, graft versus host disease, allograft rejection, chronic obstructive pulmonary disease (COPD), rheumatoid arthritis, systemic lupus erythematosus, lupus nephritis, cutaneous lupus, psoriasis, systemic onset juvenile idiopathic arthritis, multiple sclerosis, neuropathic pain, gout, and gouty arthritis.

In some embodiments, other diseases and conditions responsive to the inhibition of IRAK4 that can be treated using a compound of the present invention include metabolic syndromes, atherosclerosis, and neurodegeneration.

Further provided is the use of a compound of the present invention, or a stereoisomer or pharmaceutically acceptable salt thereof, in therapy. In some embodiments, use of a compound of the present invention, or a stereoisomer or pharmaceutically acceptable salt thereof, is provided in the treatment of an inflammatory disease. In some embodiments, use of a compound of the present invention, or a stereoisomer or pharmaceutically acceptable salt thereof, is provided for the preparation of a medicament for the treatment of an inflammatory disease. Furthermore, in some embodiments, a compound of the present invention, or a stereoisomer or pharmaceutically acceptable salt thereof, is provided for use in the treatment of an inflammatory disease.

Also provided is a method of inhibiting IRAK4 in a patient in need of therapy, comprising administering to the patient a compound of the present invention.

Dosage & Administration

The present invention provides pharmaceutical compositions or medicaments containing the compounds of the invention and at least one therapeutically inert carrier, diluent or excipient, as well as methods of using the compounds of the invention to prepare such compositions and medicaments. In one example, compounds of Formula 0, Formula I, or Formula II, or a stereoisomer or pharmaceutically acceptable salt thereof, with the desired degree of purity may be formulated by mixing with physiologically acceptable carriers, i.e., carriers that are non-toxic to recipients at the dosages and concentrations employed into a dosage form at ambient temperature and at the appropriate pH. The pH of the formulation depends mainly on the particular use and the concentration of compound, but typically ranges anywhere from about 3 to about 8. In one example, a compound of Formula 0, Formula I, or Formula II is formulated in an acetate buffer, at pH 5. In another embodiment, the compounds of Formula 0, Formula I, or Formula II are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the severity of the disorder, the particular patient being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit IRAK4 activity. Typically such amount may be below the amount that is toxic to normal cells, or the patient as a whole.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Sustained-release preparations may be prepared. Suitable examples of sustained-release preparations include semipermeable matrices of solid hydrophobic polymers containing a compound of Formula 0, Formula I, or Formula II, or a stereoisomer or pharmaceutically acceptable salt thereof, which matrices are in the form of shaped articles, e.g. films, or microcapsules. Examples of sustained-release matrices include polyesters, hydrogels (for example, poly(2-hydroxy-ethyl-methacrylate), or poly(vinylalcohol)), polylactides, copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid.

A dose to treat human patients may range from about 0.1 mg to about 1000 mg of a compound of Formula 0, Formula I, or Formula II, or a stereoisomer or pharmaceutically acceptable salt thereof. A typical dose may be about 1 mg to about 300 mg of the compound. A dose may be administered once a day (QD), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal, epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, H. C., et al., Ansel's *PharmaceuticalDosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, R. C., *Handbook of Pharmaceutical Excipients*, Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

For oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

An example of a suitable oral dosage form is a tablet containing about 25 mg, 50 mg, 100 mg, 250 mg or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such as sodium chloride, if desired. The solution may be filtered, e.g., using a 0.2 micron filter, to remove impurities and contaminants.

In one embodiment, the pharmaceutical composition also includes at least one additional anti-proliferative agent.

An embodiment, therefore, includes a pharmaceutical composition comprising a compound of Formula 0, Formula I, or Formula II, or a stereoisomer or pharmaceutically acceptable salt thereof. A further embodiment includes a pharmaceutical composition comprising a compound of Formula 0, Formula I, or Formula II, or a stereoisomer or pharmaceutically acceptable salt thereof, together with a pharmaceutically acceptable carrier or excipient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula 0, Formula I, or Formula II may be employed alone or in combination with other therapeutic agents for the treatment of a disease or disorder described herein. The second compound of the pharmaceutical combination formulation or dosing regimen preferably has complementary activities to the compound of Formula 0, Formula I, or Formula II such that they do not adversely affect each other. The combination therapy may provide "synergy" and prove "synergistic", i.e., the effect achieved when the active ingredients used together is greater than the sum of the effects that results from using the compounds separately.

The combination therapy may be administered as a simultaneous or sequential regimen. When administered sequentially, the combination may be administered in two or more administrations. The combined administration includes co-administration, using separate formulations or a single pharmaceutical formulation, and consecutive administration in either order, wherein preferably there is a time period while both (or all) active agents simultaneously exert their biological activities.

Combination therapies according to the present invention thus comprise the administration of at least one compound of Formula 0, Formula I, or Formula II, or a stereoisomer or pharmaceutically acceptable salt thereof, and the use of at least one other treatment method. The amounts of the compound(s) of Formula 0, Formula I, or Formula II and the other pharmaceutically active agent(s) and the relative timings of administration will be selected in order to achieve the desired combined therapeutic effect.

Articles of Manufacture

In another embodiment of the invention, an article of manufacture, or "kit", containing materials useful for the treatment of the diseases and disorders described above is provided. In one embodiment, the kit comprises a container comprising a compound of Formula 0, Formula I, or Formula II, or a stereoisomer or pharmaceutically acceptable salt thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula 0, Formula I, or Formula II or a formulation thereof which is effective for treating the condition and may have a sterile access port (for example, the container may be an intravenous solution bag or a vial having a stopper pierceable by a hypodermic injection needle). At least one active agent in the composition is a compound of Formula 0, Formula I, or Formula II. Alternatively, or additionally, the article of manufacture may further comprise a second container comprising a pharmaceutical diluent, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In another embodiment, the kits are suitable for the delivery of solid oral forms of a compound of Formula 0, Formula I, or Formula II, such as tablets or capsules. Such a kit can include a number of unit dosages. An example of such a kit is a "blister pack". Blister packs are well known in the packaging industry and are widely used for packaging pharmaceutical unit dosage forms.

EXAMPLES

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

Intermediate 1.
6-Chloro-2,2-dimethyl-5-nitro-3H-benzofuran

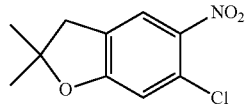

Step A. Methyl 2-(4-chloro-2-fluoro-phenyl)acetate

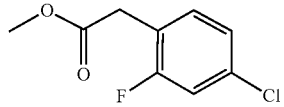

A mixture of 2-(4-chloro-2-fluoro-phenyl)acetic acid (8.4 g, 44.5 mmol) and concentrated sulfuric acid (3.0 mL) in methanol (50 mL) was stirred at reflux for 18h. After concentration under reduced pressure, the residue was dissolved in DCM (200 ml). The organic phase was washed with sodium bicarbonate saturated solution, brine and dried over sodium sulfate. After concentration under reduced pressure, it was afforded crude methyl 2-(4-chloro-2-fluoro-phenyl)acetate (7.6 g) as a yellow oil, which was used without further purification. MS (ESI): m/z=203.1 [M+1]$^+$.

Step B. 1-(4-Chloro-2-fluoro-phenyl)-2-methyl-propan-2-ol

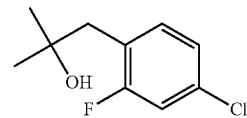

To a solution of methyl 2-(4-chloro-2-fluoro-phenyl)acetate (7.6 g, 37.51 mmol) in anhydrous THF (70 mL) was added methyl magnesium bromide (3 m in ethyl ether, 37.5 mL, 112.5 mmol) drop wise at −78° C. The reaction was warmed to room temperature and stirred for 30 min. Saturated ammonium chloride solution was added. The aqueous phase was extracted with ethyl acetate (2×200 mL). The combined organic phases were washed with brine and dried over sodium sulfate. The crude was concentrated under reduced pressure to afford 1-(4-chloro-2-fluoro-phenyl)-2-methyl-propan-2-ol (6.9 g) as a yellow oil, which was used without further purification. MS (ESI): z=185.1 [M-OH]$^+$.

Step C. 6-Chloro-2,2-dimethyl-3H-benzofuran

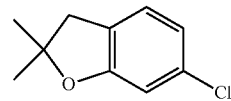

A mixture of 1-(4-chloro-2-fluoro-phenyl)-2-methyl-propan-2-ol (6.9 g, 34.05 mmol) and potassium tert-butanolate (9.55 g, 85.12 mmol) in THF (170 mL) was stirred at 65° C. for 18h. 1N hydrogen chloride solution was added until pH=3.0. Ethyl acetate (200 mL) was added. The organic phase was separated and dried over sodium sulfate. After concentration under reduced pressure, the residue was purified by silica gel chromatography using ethyl acetate:petroleum ether (from 1:20 to 1:10) as eluting solvents to afford 6-chloro-2,2-dimethyl-3H-benzofuran (4.3 g, 69%) as a colorless oil. $^1$H NMR (400 MHz, CDCl$_3$): δ 6.99 (d, J=8.0 Hz, 1H), 6.75 (d, J=8.0 Hz, 1H), 6.88 (s, 1H), 2.93 (s, 2H), 1.44 (s, 3H).

Step D.
6-Chloro-2,2-dimethyl-5-nitro-3H-benzofuran

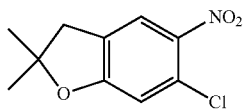

To a solution of 6-chloro-2,2-dimethyl-3H-benzofuran (4.3 g, 23.54 mmol) in DCM (45 mL) at 25° C. was slowly added fuming nitric acid (4.5 mL) until starting material was disappeared. Water and ethyl acetate (100 mL) were added. The organic phase was separated and dried over sodium sulfate. After concentration under reduced pressure, it was afforded 6-chloro-2,2-dimethyl-5-nitro-3H-benzofuran (5.0 g) as orange solid, which was used without further purification. H NMR (400 MHz, CDCl$_3$): δ 7.84 (s, 1H), 6.83 (s, 1H), 3.04 (s, 2H), 1.52 (s, 3H).

Intermediate 2. (6-Chloro-2-methyl-5-nitro-2,3-dihydrobenzofuran-2-yl)methanol

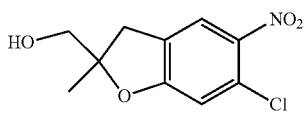 [SMILES: CC1(CO)Cc2cc([N+](=O)[O-])c(Cl)cc2O1]

Step A. Methyl 3-(4-chloro-2-fluoro-phenyl)-2-hydroxy-2-methyl-propanoate

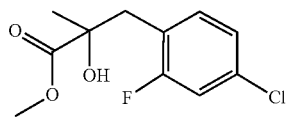 [SMILES: COC(=O)C(C)(O)Cc1ccc(Cl)cc1F]

To a solution of magnesium (1350.0 mg, 56.25 mmol) and iodine (100.0 mg, 0.39 mmol) in diethyl ether (50 mL) at reflux was added 1-(bromomethyl)-4-chloro-2-fluoro-benzene (5.0 g, 22.4 mmol) drop wise. The reaction was stirred for 30 min. This solution was then added to a solution of methyl pyruvate (2.3 g, 22.5 mmol) in diethyl ether (50 mL) at −78° C. and stirred for 30 min followed by warming to room temperature for 2h. Saturated ammonium chloride solution and ethyl acetate (200 mL) was added. The organic phase was separated and dried over sodium sulfate. After concentration, the residue was purified by silica gel chromatography using ethyl acetate:petroleum ether (from 1:20 to 1:10) as eluting solvents to afford methyl 3-(4-chloro-2-fluoro-phenyl)-2-hydroxy-2-methyl-propanoate (2.8 g, 51%) as a yellow oil. $^1$H NMR (400 MHz, CDCl$_3$): δ 7.33-7.25 (m, 1H), 7.18-7.09 (m, 2H), 3.73 (s, 3H), 3.03 (s, 2H), 1.39 (s, 3H).

Step B.
6-Chloro-2-methyl-3H-benzofuran-2-carboxylic acid

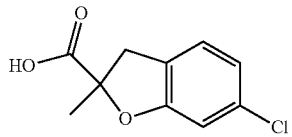

The mixture of methyl 3-(4-chloro-2-fluoro-phenyl)-2-hydroxy-2-methyl-propanoate (493.0 mg, 2 mmol) and potassium tert-butanolate (561.0 mg, 5 mmol) in THF (10 mL) was stirred at 60° C. for 18h. After cooling to room temperature, water and 1N hydrogen chloride solution was added until pH=3.0. Ethyl acetate (20 mL) was added. The organic phase was separated and dried over sodium sulfate. After concentration, the residue was purified by silica gel chromatography using ethyl acetate:petroleum ether (from 1:1 to 2:1) as eluting solvents to afford 6-chloro-2-methyl-3H-benzofuran-2-carboxylic acid (271 mg, 64%) as a yellow solid. $^1$H NMR (400 MHz, CDCl$_3$) δ 10.95-10.24 (m, 1H), 7.04 (d, J=8.0 Hz, 1H), 6.87 (dd, J=1.6, 9.2 Hz, 1H), 6.85 (s, 1H), 3.59 (d, J=16 Hz, 1H), 3.13 (d, J=16 Hz, 1H), 1.73, (s, 3H).

Step C. 6-Chloro-2-methyl-5-nitro-3H-benzofuran-2-carboxylicacid

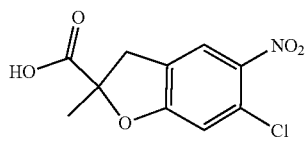 [SMILES: CC1(C(=O)O)Cc2cc([N+](=O)[O-])c(Cl)cc2O1]

To a solution of 6-chloro-2-methyl-3H-benzofuran-2-carboxylic acid (230.0 mg, 1.08 mmol) in DCM (10 mL) at 25° C. was slowly added fuming nitric acid (0.5 mL) and stirred for 5 min. Water and ethyl acetate (20 mL) were added. The organic phase was separated and dried over sodium sulfate. After concentration, the residue was purified by silica gel chromatography using ethyl acetate:petroleum ether (from 1:4 to 1:3) as eluting solvents to afford 6-chloro-2-methyl-5-nitro-3H-benzofuran-2-carboxylic acid (150 mg, 54%) as orange solid. $^1$H NMR (400 MHz, CDCl$_3$) δ 7.84 (s, 1H), 6.99 (s, 1H), 3.68 (d, J=16.8 Hz, 1H), 3.23 (d, J=16.8 Hz, 1H), 1.80 (s, 3H).

Step D. (6-Chloro-2-methyl-5-nitro-3H-benzofuran-2-yl)methanol

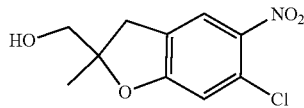 [SMILES: CC1(CO)Cc2cc([N+](=O)[O-])c(Cl)cc2O1]

The mixture of 6-chloro-2-methyl-5-nitro-3H-benzofuran-2-carboxylic acid (1.93 g, 7.5 mmol) and borane (1 M in THF, 14.0 mL, 14 mmol) in THF (75 mL) was stirred at 25° C. for 2h. After slowly adding methanol (10 mL) and then concentration, the residue was purified by silica gel chromatography using ethyl acetate:petroleum ether (1:1) as eluting solvents to afford (6-chloro-2-methyl-5-nitro-3H-benzofuran-2-yl)methanol (580 mg, 32%) as a yellow oil. $^1$H NMR (400 MHz, DMSO-$d_6$): δ 7.84 (s, 1H), 6.99 (s, 1H), 6.60-5.80 (m, 1H), 3.68 (d, J=16.8 Hz, 1H), 3.23 (d, J=16.8 Hz, 1H), 1.80 (s, 3H). MS (ESI): m/z=244.1 [M+1]$^+$.

Intermediate 3. (6-Fluoro-2-methyl-5-nitro-2,3-dihydrobenzofuran-2-yl)methanol

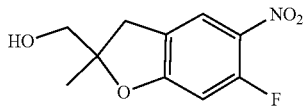 [SMILES: CC1(CO)Cc2cc([N+](=O)[O-])c(F)cc2O1]

Step A. Methyl 3-(2,4-difluorophenyl)-2-hydroxy-2-methyl-propanoate

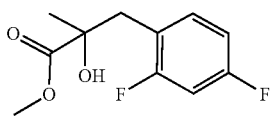 [SMILES: COC(=O)C(C)(O)Cc1ccc(F)cc1F]

To a solution of magnesium (3290.81 mg, 137.12 mmol) and iodine (243.76 mg, 0.96 mmol) in diethyl ether (50 mL) at reflux was added 2,4-difluorobenzyl bromide (11291.0 mg, 54.54 mmol) drop wise and stirred for 30 min. This solution was then added to a solution of methyl pyruvate (5606.57 mg, 54.92 mmol) in diethyl ether (50 mL) at −78° C. and stirred for 30 min followed by room temperature for 2h. Saturated ammonium chloride solution and ethyl acetate (200 mL) was added. The organic phase was separated and dried over sodium sulfate. After concentration, the residue was purified by silica gel chromatography using ethyl acetate:petroleum ether from 1:20 to 1:10 as eluting solvents to afford methyl 3-(2,4-difluorophenyl)-2-hydroxy-2-methyl-propanoate (8.9 g, 71%) as a yellow oil. MS (ESI): m/z=231.1 [M+1]$^+$.

Step B. 6-Fluoro-2-methyl-2,3-dihydrobenzofuran-2-carboxylicacid

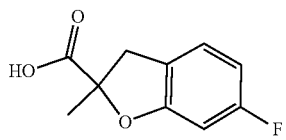

A mixture of methyl 3-(2,4-difluorophenyl)-2-hydroxy-2-methyl-propanoate (8.0 g, 34.75 mmol) and potassium tert-butanolate (9.73 g, 86.9 mmol) in THF (200 mL) was stirred at room temperature for 18h. Another portion of potassium tert-butanolate (9.73 g, 86.9 mmol) was added. The mixture was stirred at 50° C. for 10h. After cooling to room temperature, the mixture was brought to pH 3 with 2N HCl. The organic phase was separated and concentrated under reduced pressure to afford 6-fluoro-2-methyl-3H-benzofuran-2-carboxylic acid (8.0 g) as a yellow solid, which was used directly to next step without further purification. MS (ESI): m/z=197.1 [M+1]$^+$.

Step C. Methyl 6-fluoro-2-methyl-2,3-dihydrobenzofuran-2-carboxylate

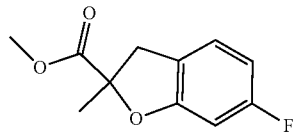

A mixture of 6-fluoro-2-methyl-3H-benzofuran-2-carboxylic acid (8 g, 40.81 mmol) and cesium carbonate (19.8 g, 60.7 mmol) in DMF (150 mL) was added methyl iodide (6.92 g, 48.7 mmol). The mixture was stirred at room temperature for 18h. The mixture was extracted with ethyl acetate (200 mL). The organic phase was washed with brine, dried over sodium sulfate and concentrated under reduced pressure. The residue was purified by silica gel chromatography using petroleum ether to afford methyl 6-fluoro-2-methyl-2,3-dihydrobenzofuran-2-carboxylate (5 g) as a brown oil, which was used directly to next step without further purification. MS (ESI): m/z=211.1 [M+1]$^+$.

Step D. Methyl 6-fluoro-2-methyl-5-nitro-2,3-dihydrobenzofuran-2-carboxylate

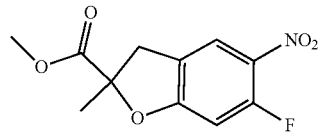 [SMILES: COC(=O)C1(C)Cc2cc([N+](=O)[O-])c(F)cc2O1]

A mixture of methyl 6-fluoro-2-methyl-2,3-dihydrobenzofuran-2-carboxylate (5 g, 23.7 mmol) in DCM (70 mL) was added drop wise fuming nitric acid (5 mL) at room temperature. The mixture was stirred at room temperature for 30 min, poured into ice water and extracted with ethyl acetate (150 mL). The organic phase was concentrated to afford methyl 6-fluoro-2-methyl-5-nitro-2,3-dihydrobenzofuran-2-carboxylate as a brown oil (5 g) as orange oil, which was used directly to next step without further purification. MS (ESI): m/z=256.1 [M+1]$^+$.

Step E. (6-fluoro-2-methyl-5-nitro-2,3-dihydrobenzofuran-2-yl)methanol

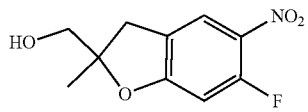

To a mixture of methyl 6-fluoro-2-methyl-5-nitro-2,3-dihydrobenzofuran-2-carboxylate (5 g, 19.53 mmol) in THF (100 mL) and ethanol (25 mL) was added sodium borohydride (2.22 g, 58.6 mmol) followed by lithium chloride (2.5 g, 58.6 mmol) at 0° C. The mixture was stirred at room temperature for 3h, quenched with saturated ammonium chloride and extracted with DCM. The organic phase was dried over sodium sulfate and concentrated under reduced pressure. The residue was purified by silica gel chromatography using ethyl acetate:petroleum ether (1:1) as eluting solvents to afford (6-fluoro-2-methyl-5-nitro-2,3-dihydrobenzofuran-2-yl)methanol (3.0 g, 98%) as a brown oil. $^1$H NMR (400 MHz, DMSO-$d_6$): δ 7.94 (d, J=8.0 Hz, 1H), 6.60 (d, J=11.6 Hz, 1H), 3.78 (dd, J=5.6, 12.0 Hz, 1H), 3.66 (dd, J=7.2, 12.0 Hz, 1H), 3.34 (d, J=15.6 Hz, 1H), 2.93 (d, J=15.6 Hz, 1H), 1.84 (t, J=6.4 Hz, 1H), 1.49 (s, 3H). MS (ESI): m/z=228.1 [M+1]$^+$.

Intermediate 4.
6-Bromo-2,2-dimethyl-5-nitro-2,3-dihydrobenzofuran

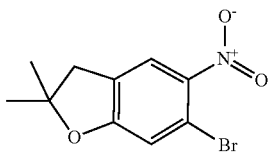

Step A. Methyl 2-(4-bromo-2-fluorophenyl)acetate

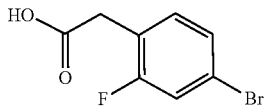

A mixture of 2-(4-bromo-2-fluorophenyl)acetic acid (20.2 g, 86.6 mmol) and concentrated sulfuric acid (7 mL) in methanol (200 mL) was heated to reflux for 18h. After removal of solvent, the residue was diluted with DCM (200 mL) and washed with saturated sodium bicarbonate, brine and dried over sodium sulfate. After concentration, it was afforded methyl 2-(4-bromo-2-fluorophenyl)acetate (21.1 g, 99%) as a brown oil. MS (ESI): m/z=280.1 [M+1]$^+$.

Step B.
1-(4-Bromo-2-fluorophenyl)-2-methylpropan-2-ol

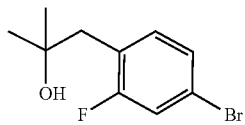

To a solution of methyl 2-(4-bromo-2-fluorophenyl)acetate (16.0 g, 64.8 mmol) in THF (160 mL) at −78° C. was added methyl magnesium bromide (3 M in diethyl ether, 225 mmol, 75 mL) drop-wise under nitrogen atmosphere. The reaction was stirred at −78° C. for 30 min followed by room temperature for 2h. The reaction was quenched with saturated ammonium chloride solution. The aqueous phase was extracted with ethyl acetate (3×100 mL). The combined organic phases were dried over sodium sulfate. After filtration and removal of solvent, the residue was purified by silica gel chromatography using ethyl acetate:hexane (from 0 to 1:20) as eluting solvents to afford 1-(4-bromo-2-fluorophenyl)-2-methylpropan-2-ol as a colorless oil (15.5 g), which was used directly to next step without further purification. MS (ESI): m/z=263.1 [M+1]$^+$.

Step C.
1-(4-Bromo-2-fluorophenyl)-2-methylpropan-2-ol

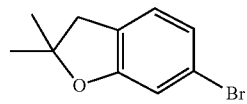

To a solution of 1-(4-bromo-2-fluorophenyl)-2-methylpropan-2-ol (15.5 g, 52.7 mmol) in anhydrous THF (300 mL) was added potassium tert-butanolate (17.6 g, 156.8 mmol). The mixture was heated at 65° C. for 18h. The reaction was brought to pH 3 with 2N HCl. The aqueous phase was extracted with ethyl acetate (100 mL). The organic phase was dried over sodium sulfate. After filtration and removal of solvent, the residue was purified by silica gel chromatography using ethyl acetate:hexane (from 0 to 1:20) as eluting solvents to afford 1-(4-bromo-2-fluorophenyl)-2-methylpropan-2-ol (8.9 g, 63%) as a white solid. $^1$H NMR (400 MHz, CDCl$_3$): δ 6.98 (d, J=8.0 Hz, 1H), 6.93 (dd, J=1.6, 8.0 Hz, 1H), 6.87 (d, J=1.6 Hz, 1H), 2.94 (s, 2H), 1.46 (s, 6H).

Step D.
6-Bromo-2,2-dimethyl-5-nitro-2,3-dihydrobenzofuran

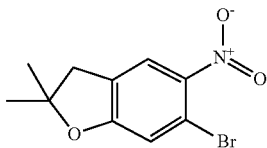

To a solution of 1-(4-bromo-2-fluorophenyl)-2-methylpropan-2-ol (2.88 g, 12.7 mmol) in DCM (60 mL) was added concentrated nitric acid (60 mL) slowly. The mixture was stirred at room temperature for 30 min. The reaction was quenched with water (100 mL) and the aqueous phase was extracted with ethyl acetate (100 mL). The organic solution was dried over sodium sulfate. After filtration and removal of solvent, the residue was purified by silica gel chromatography using ethyl acetate:hexane (3:50) as eluting solvents to afford 6-bromo-2,2-dimethyl-5-nitro-2,3-dihydrobenzofuran (2.83 g, 78%) as a yellowish solid. $^1$H NMR (400 MHz, CDCl$_3$): δ 7.83 (s, 1H), 7.03 (s, 1H), 3.03 (d, J=1.6, 1.2 Hz, 2H), 1.53 (s, 6H). MS (ESI): m/z=274.0 [M+1]$^+$.

Example 1. N-(7-(4-(Hydroxymethyl)piperidin-1-yl)-3,4-dihydro-2H-benzo[b][1,4]oxazin-6-yl)pyrazolo[1,5-a]pyrimidine-3-carboxamide

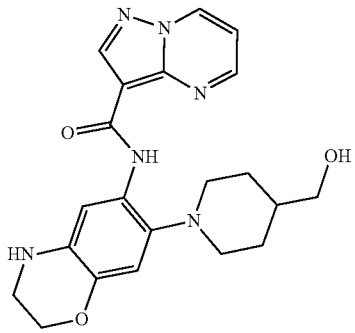 [SMILES: O=C(Nc1cc2c(cc1N1CCC(CO)CC1)OCCN2)c1cnn2cccnc12]

Step A. (1-(6-Nitro-3,4-dihydro-2H-benzo[b][1,4]oxazin-7-yl)piperidin-4-yl)methanol

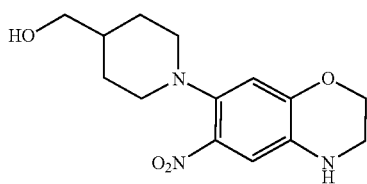 [SMILES: O=[N+]([O-])c1cc2c(cc1N1CCC(CO)CC1)OCCN2]

A mixture of commercial available 7-fluoro-6-nitro-3,4-dihydro-2H-benzo[b][1,4]oxazine (300 mg, 1.51 mmol), piperidin-4-ylmethanol (183 mg, 1.59 mmol) and N-ethyl-N-isopropylpropan-2-amine (391 mg, 3.03 mmol) in N-methyl-2-pyrrolidone (5 mL) was stirred at 120° C. for 18h. After cooling to room temperature, the mixture was poured into water and the aqueous phase was extracted with ethyl acetate (2×50 mL). The organic phases were combined and washed with water and brine. After concentration under reduced pressure, the residue was purified by silica gel chromatography using ethyl acetate:petroleum ether (1:1) as eluting solvents to afford (1-(6-nitro-3,4-dihydro-2H-benzo[b][1,4]oxazin-7-yl)piperidin-4-yl)methanol (300 mg, 67%) as a yellow solid. MS (ESI): m/z=294.1 [M+1]$^+$.

Step B. (1-(6-Amino-3,4-dihydro-2H-benzo[b][1,4]oxazin-7-yl)piperidin-4-yl)methanol

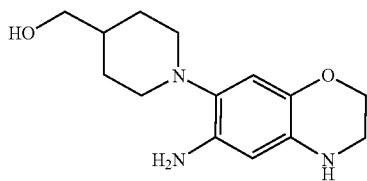

A mixture of (1-(6-nitro-3,4-dihydro-2H-benzo[b][1,4]oxazin-7-yl)piperidin-4-yl)methanol (300 mg, 1.02 mmol) and 10% palladium on carbon (30 mg) in 2-methylpropan-2-ol (10 mL) was stirred at 50° C. for 18h under an atmosphere of hydrogen. After the mixture was cooled to room temperature and filtered, the filtrate was concentrated under reduced pressure to afford (1-(6-amino-3,4-dihydro-2H-benzo[b][1,4]oxazin-7-yl)piperidin-4-yl)methanol as a white solid (260 mg), which was used directly in the next step without purification. MS (ESI): m/z=264.1 [M+1]$^+$.

Step C. N-(7-(4-(Hydroxymethyl)piperidin-1-yl)-3,4-dihydro-2H-benzo[b][1,4]oxazin-6-yl)pyrazolo[1,5-a]pyrimidine-3-carboxamide

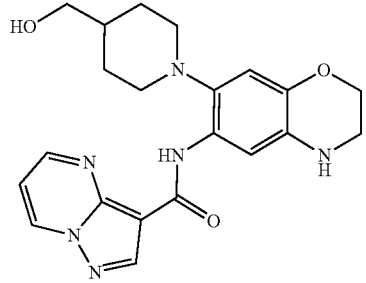

A mixture of pyrazolo[1,5-a]pyrimidine-3-carboxylic acid (322 mg, 1.97 mmol), (7-Azabenzotriazol-1-yloxy)tripyrrolidinophosphoniumhexafluorophosphate (1.03 g, 1.97 mmol) and N-ethyl-N-isopropylpropan-2-amine (510 mg, 3.95 mmol) in DMF (10 mL) was stirred at room temperature for 30 min. (1-(6-amino-3,4-dihydro-2H-benzo[b][1,4]oxazin-7-yl)piperidin-4-yl)methanol (260 mg, 0.99 mmol) was added. The resulting mixture was stirred at room temperature for 18h. After concentration, the residue was purified by preparative HPLC ((Xbridge 21.2*250 mm c18, 10 um; A: acetonitrile 10-20%; B: 10 mM ammonium bicarbonate in water) to afford N-(7-(4-(hydroxymethyl)piperidin-1-yl)-3,4-dihydro-2H-benzo[b][1,4]oxazin-6-yl)pyrazolo[1,5-a]pyrimidine-3-carboxamide as a white solid (165 mg, 41%). $^1$H NMR (400 MHz, DMSO-d$_6$): δ 10.58 (s, 1H), 9.36 (d, J=7.2 Hz, 1H), 8.89 (d, J=4.0 Hz, 1H), 8.66 (s, 1H), 7.89 (s, 1H), 7.33 (dd, J=4.0, 6.8 Hz, 1H), 6.62 (s, 1H), 5.71 (s, 1H), 4.58 (t, J=5.2 Hz, 1H), 4.21-3.95 (m, 2H), 3.41 (t, J=4.5 Hz, 2H), 3.29-3.15 (m, 2H), 2.95-2.74 (m, 2H), 2.71-2.54 (m, 2H), 1.85-1.29 (m, 5H). MS (ESI): m/z=409.1 [M+1]$^+$.

Example 2. N-(7-(4-(Hydroxymethyl)piperidin-1-yl)-3-oxo-3,4-dihydro-2H-benzo[b][1,4]oxazin-6-yl)pyrazolo[1,5-a]pyrimidine-3-carboxamide

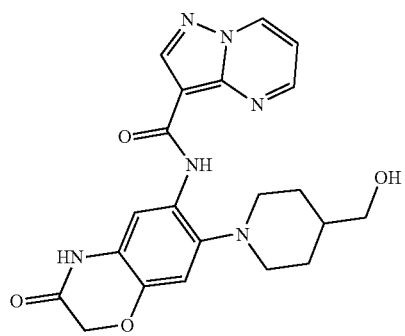 [SMILES: O=C1COc2cc(N3CCC(CO)CC3)c(NC(=O)c3cnn4cccnc34)cc2N1]

Step A. 7-(4-(Hydroxymethyl)piperidin-1-yl)-6-nitro-2H-benzo[b][1,4]oxazin-3(4H)-one

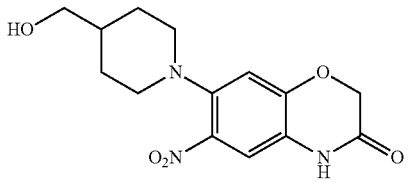 [SMILES: O=C1COc2cc(N3CCC(CO)CC3)c([N+](=O)[O-])cc2N1]

A mixture of 7-fluoro-6-nitro-4H-1,4-benzoxazin-3-one (300 mg, 1.41 mmol), 4-piperidinylmethanol (162 mg, 1.41 mmol) and N,N-diisopropylethylamine (342 mg, 2.82 mmol) in 4-methyl-2-pentanone (5 mL) was stirred at 30° C. for 16h in a sealed tube. Water and ethyl acetate (2×30 mL) were added. The organic phases were combined and washed with water, dried over sodium sulfate and concentrated in vacuo. The residue was purified by silica gel chromatography using ethyl acetate:petroleum ether (1:5) as eluting solvents to afford 7-(4-(hydroxymethyl)piperidin-1-yl)-6-nitro-2H-benzo[b][1,4]oxazin-3(4H)-one (400 mg, 92%) as a yellow solid. MS (ESI): m/z=308.2 [M+1]$^+$.

Step B. 6-Amino-7-(4-(hydroxymethyl)piperidin-1-yl)-2H-benzo[b][1,4]oxazin-3(4H)-one

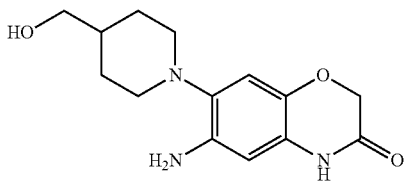 [SMILES: Nc1cc2c(cc1N1CCC(CO)CC1)OCC(=O)N2]

A mixture of 7-(4-(hydroxymethyl)piperidin-1-yl)-6-nitro-2H-benzo[b][1,4]oxazin-3(4H)-one (350 mg, 1.14 mmol) and 10% palladium on carbon (35 mg) in methanol (10 mL) was stirred at room temperature under an atmosphere of hydrogen for 1h. The solid was filtered off and the filtrate was concentrated under reduced pressure to afford 6-amino-7-(4-(hydroxymethyl)piperidin-1-yl)-2H-benzo[b][1,4]oxazin-3(4H)-one (300 mg) as a colorless oil, which was used directly to next step without further purification. MS (ESI): m/z=278.2 [M+1]$^+$.

Step C. N-(7-(4-(Hydroxymethyl)piperidin-1-yl)-3-oxo-3,4-dihydro-2H-benzo[b][1,4]oxazin-6-yl)pyrazolo[1,5-a]pyrimidine-3-carboxamide

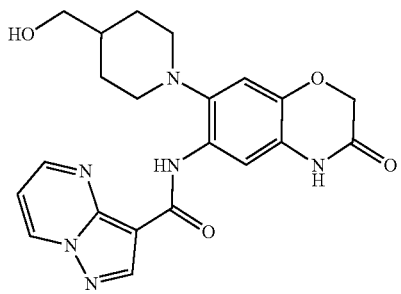

A mixture of 6-amino-7-[4-(hydroxymethyl)-1-piperidyl]-4H-1,4-benzoxazin-3-one (250 mg, 0.90 mmol), (3-hydroxy-3H-1,2,3-triazolo[4,5-b]pyridinato-O)tri-1-pyrrolidinylphosphonium hexafluorophosphate (100 mg, 0.19 mmol), pyrazolo[1,5-a]pyrimidine-3-carboxylic acid (145 mg, 0.89 mmol) and N,N-diisopropylethylamine (23 mg, 0.19 mmol) in DMF (5 mL) was stirred at room temperature for 18h. The crude reaction was purified by preparative HPLC ((Xbridge 21.2*250 mm c18, 10 um; A: acetonitrile 15-30%; B: 10 mM ammonium bicarbonate in water)) to afford N-(7-(4-(hydroxymethyl)piperidin-1-yl)-3-oxo-3,4-dihydro-2H-benzo[b][1,4]oxazin-6-yl)pyrazolo[1,5-a]pyrimidine-3-carboxamide (68 mg, 18%) as a white solid. $^1$H NMR (400 MHz, DMSO-d$_6$): δ 10.72 (s, 1H), 10.62 (s, 1H), 9.38 (d, J=6.0 Hz, 1H), 8.91 (d, J=4.0 Hz, 1H), 8.70 (s, 1H), 8.25 (s, 1H), 7.53 (dd, J=4.0, 6.8 Hz, 1H), 6.93 (s, 1H), 4.59 (t, J=5.6 Hz, 1H), 4.53 (s, 2H), 3.41 (d, J=5.2 Hz, 2H), 2.92-2.89 (m, 2H), 2.67-2.61 (m, 2H), 1.73-1.51 (m, 5H). MS (ESI): m/z=423.2 [M+1]$^+$.

Example 3. Trans-N-[2, 2-dimethyl-6-[2-(methylaminomethyl)-1,3-dioxan-5-yl]-3H-benzofuran-5-yl]pyrazolo[1,5-a]pyrimidine-3-carboxamide

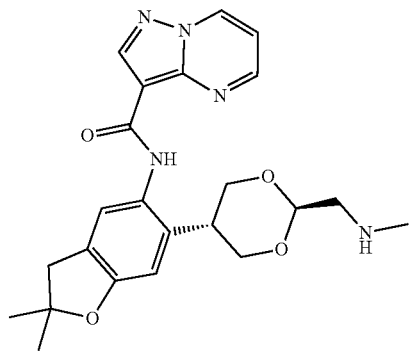

Step A. 2-Trimethylsilylethyl N-(2, 2-dimethoxyethyl)carbamate

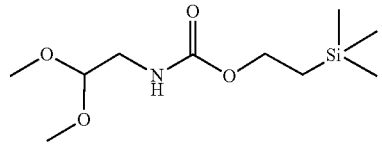

To the mixture of 2,2-dimethoxyethanamine (608.0 mg, 5.78 mmol) and triethylamine (1.07 mL, 7.71 mmol) in THF (10 mL) was added 1-[2-(trimethylsilyl)ethoxycarbonyloxy]pyrrolidin-2,5-dione (1.0 g, 3.86 mmol) at 0° C. and the mixture was stirred at room temperature for 1h. The reaction was concentrated to dryness under reduced pressure. The residue was dissolved in DCM (150 mL) and the organic phase was washed with water and brine, dried over sodium sulfate and concentrated to afford 2-trimethylsilylethyl N-(2, 2-dimethoxyethyl)carbamate (945 mg) as a colorless oil, which was used directly in the next step without further purification. $^1$HNMR (400 MHz, CDCl$_3$) δ 4.76 (brs, 1H), 4.33 (t, J=5.6 Hz, 1H), 4.12 (t, J=8.4 Hz, 2H), 3.36 (s, 6H), 3.27 (t, J=5.6 Hz, 2H), 0.94 (t, J=8.4 Hz, 2H), 0.00 (s, 9H).

Step B. Pyrazolo[1,5-a]pyrimidine-3-carbonyl chloride

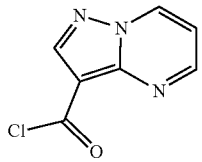 [SMILES: O=C(Cl)c1cnn2cccnc12]

To the mixture of pyrazolo[1,5-a]pyrimidine-3-carboxylic acid (500.0 mg, 3.07 mmol) in DCM (12 mL) was added oxalyl chloride (0.65 mL, 7.64 mmol) and DMF (100.0 mg, 1.37 mmol) at 0° C. followed by room temperature for 2h. The mixture was concentrated to dryness to afford pyrazolo[1,5-a]pyrimidine-3-carbonyl chloride (550 mg) as brown solid, which was used directly to the next step without further purification. MS (ESI): m/z=178.1 [M-Cl+MeO]$^+$.

Step C. Methyl 2-(2, 4-difluorophenyl)acetate

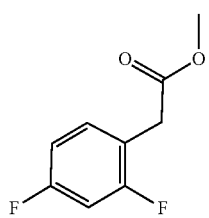

The mixture of 2-(2,4-difluorophenyl)acetic acid (2.0 g, 11.62 mmol) and concentrated sulfuric acid (2 mL) in methanol (40 mL) was stirred at 70° C. for 16h. After concentration, the residue was dissolved in ethyl acetate (300 mL). The organic phase was washed with saturated sodium bicarbonate, water and brine, dried over sodium sulfate and concentrated to afford methyl 2-(2, 4-difluorophenyl)acetate (2.1 g) as a colorless oil, which was used directly to the next step without further purification. MS (ESI): m/z=187.1 [M+1]$^+$.

Step D. 1-(2,4-Difluorophenyl)-2-methyl-propan-2-ol

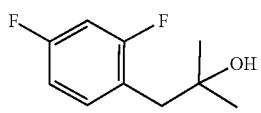

To a mixture of methyl 2-(2,4-difluorophenyl)acetate (1.8 g, 9.67 mmol) in THF (20 mL) was drop-wise added methyl magnesium bromide (3.0 m in diethyl ether, 9.67 mL, 29.01 mmol) under an atmosphere of nitrogen at −78° C. The mixture was warmed and stirred at room temperature for 1h. The reaction was quenched by saturated ammonium chloride solution. The aqueous phase was extracted with ethyl acetate (2×200 mL). The combined organic phases were washed with water and brine, dried over sodium sulfate and concentrated under reduced pressure to afford 1-(2,4-difluorophenyl)-2-methyl-propan-2-ol (1.8 g) as a yellow oil, which was used directly to the next step without further purification. MS (ESI): m/z=169.1 [M-OH]$^+$.

Step E. 6-Fluoro-2,2-dimethyl-3H-benzofuran

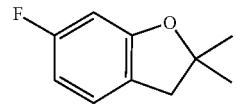

A mixture of 1-(2,4-difluorophenyl)-2-methyl-propan-2-ol (1.8 g, 9.67 mmol) and potassium tert-butanolate (2720.0 mg, 24.24 mmol) in THF (50 mL) was stirred at 65° C. for 90 min. After concentration, the residue was dissolved in ethyl acetate (150 mL). The organic phase was washed with water and brine, dried over sodium sulfate and concentrated under reduced pressure. The residue was purified by silica gel chromatography using ethyl acetate:petroleum ether (1:100) as eluting solvents to afford 6-fluoro-2,2-dimethyl-3H-benzofuran (1.14 g, 71%) as a colorless oil. MS (ESI): m/z=167.1 [M+1]$^+$.

Step F. 6-Fluoro-2,2-dimethyl-5-nitro-3H-benzofuran

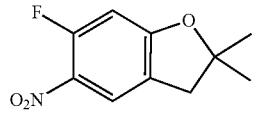

To a solution of 6-fluoro-2,2-dimethyl-3H-benzofuran (1.1 g, 6.9 mmol) in DCM (20 mL) was added into nitric acid (1.0 mL) drop-wise over 10 min at 25° C. and stirred for 20 min. The mixture was poured into ice water. The aqueous phase was extracted with ethyl acetate (150 mL). The organic phase was washed with saturated sodium bicarbonate solution, water and brine and dried over sodium sulfate before concentration under reduced pressure. The residue was purified by silica gel chromatography eluting using ethyl acetate:petroleum ether (1:10) as eluting solvents to afford 6-fluoro-2,2-dimethyl-5-nitro-3H-benzofuran (1.04 g, 72%) as gray solid. $^1$HNMR (400 MHz, CDCl$_3$) δ 7.92 (d, J=7.6 Hz, 1.2 Hz, 1H), 6.55 (d, J=11.6 Hz, 1H), 3.03 (s, 2H), 1.56 (s, 6H). MS (ESI): m/z=212.1 [M+1]$^+$.

Step G. Dimethyl 2-(2,2-dimethyl-5-nitro-3H-benzofuran-6-yl)propanedioate

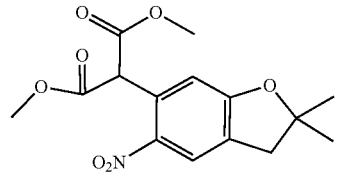

To the mixture of 6-fluoro-2,2-dimethyl-5-nitro-3H-benzofuran (420.0 mg, 1.99 mmol) and dimethyl malonate (0.68 mL, 5.96 mmol) in DMF (8 mL) was added cesium carbonate (1296.0 mg, 3.98 mmol) and stirred at 20° C. for 16h.

The mixture was poured into water (30 mL) and extracted with ethyl acetate (200 mL). The organic phase was washed with water and brine and dried over sodium sulfate before concentration to dryness. The residue was purified by silica gel chromatography using ethyl acetate:petroleum ether (1:5) as eluting solvents to afford dimethyl 2-(2,2-dimethyl-5-nitro-3H-benzofuran-6-yl)propanedioate (280 mg, 44%) as a yellow oil. MS (ESI): m/z=324.1 [M+1]$^+$.

Step H. 2-(2, 2-Dimethyl-5-nitro-3H-benzofuran-6-yl)propane-1,3-diol

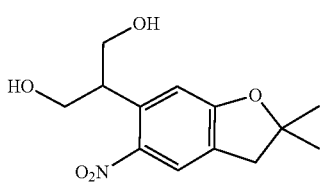 [SMILES: CC1(C)Cc2cc([N+](=O)[O-])c(C(CO)CO)cc2O1]

To a solution of diisobutylaluminium hydride (1 M in toluene, 5.2 mL, 5.2 mmol) in THF (2.5 mL) was drop-wise added the solution of dimethyl 2-(2,2-dimethyl-5-nitro-3H-benzofuran-6-yl)propanedioate (280.0 mg, 0.87 mmol) in THF (10 mL) under an atmosphere of nitrogen at 0° C. and maintained there for 1h followed by 1h at room temperature. To the mixture was added sodium sulfate decahydrate and the mixture was stirred for 1h. After filtration and concentration, the residue was purified by silica gel chromatography using ethyl acetate:petroleum ether (1:3) as eluting solvents to afford 2-(2, 2-dimethyl-5-nitro-3H-benzofuran-6-yl)propane-1,3-diol (75 mg, 32%) as yellow oil. $^1$HNMR (400 MHz, CDCl$_3$) δ 7.78 (s, 1H), 6.81 (s, 1H), 4.02 (d, J=1.2 Hz, 2H), 4.00 (s, 2H), 3.83-3.75 (m, 1H), 3.04 (s, 2H), 1.51 (s, 6H). MS (ESI): m/z=290.0 [M+Na]$^+$.

Step I. Trans-2-trimethylsilylethyl N-[[5-(2, 2-dimethyl-5-nitro-3H-benzofuran-6-yl)-1,3-dioxan-2-yl]methyl]carbamate

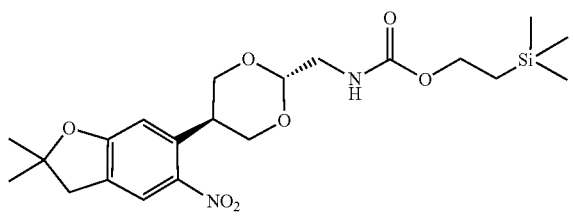

The mixture of 2-(2,2-dimethyl-5-nitro-3H-benzofuran-6-yl)propane-1,3-diol (80.0 mg, 0.30 mmol), 2-trimethylsilylethyl N-(2,2-dimethoxyethyl)carbamate (223.99 mg, 0.90 mmol) and 4-toluene sulfonic acid (3.0 mg, 0.02 mmol) in toluene (5 mL) was stirred at 110° C. in a sealed tube for 72h. The mixture was neutralized with triethylamine then concentrated to dryness. The residue was purified by silica gel chromatography using ethyl acetate:petroleum ether (1:5) as eluting solvents to afford trans-2-trimethylsilylethyl N-[[5-(2,2-dimethyl-5-nitro-3H-benzofuran-6-yl)-1,3-dioxan-2-yl]methyl]carbamate (61 mg, 45%) as a yellow oil.

$^1$HNMR (400 MHz, CDCl$_3$) δ 7.72 (s, 1H), 6.53 (s, 1H), 4.92 (brs, 1H), 4.65 (t, J=4.0 Hz, 1H), 4.26-4.17 (m, 2H), 4.18-4.07 (m, 2H), 3.84-3.68 (m, 3H), 3.35 (t, J=4.8 Hz, 2H), 3.00 (s, 2H), 1.47 (s, 6H), 0.95 (t, J=8.4 Hz, 2H), 0.00 (s, 9H).

Step J. Trans-2-trimethylsilylethyl N-[[5-(2,2-dimethyl-5-nitro-3H-benzofuran-6-yl)-1,3-dioxan-2-yl]methyl]-N-methyl-carbamate

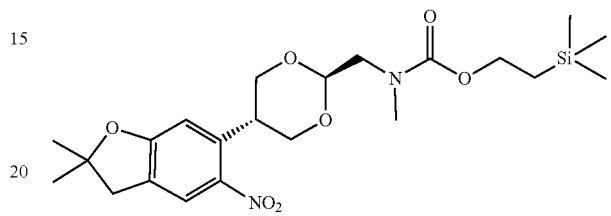

To the mixture of trans-2-trimethylsilylethyl N-[[5-(2,2-dimethyl-5-nitro-3H-benzofuran-6-yl)-1, 3-dioxan-2-yl]methyl]carbamate (61.0 mg, 0.13 mmol) in DMF (2.5 mL) was added sodium hydride (35.0 mg, 0.88 mmol) in ice water bath and stirred for 10 min. To the mixture was added methyl iodide (0.02 mL, 0.35 mmol) and stirred at 20° C. for 1h. The mixture was poured into water and the aqueous phase was extracted with ethyl acetate (50 mL). The organics was washed with water and brine and dried over sodium sulfate before concentration under reduced pressure. The residue was purified by silica gel chromatography using ethyl acetate:petroleum ether (1:5) as eluting solvents to afford trans-2-trimethylsilylethyl N-[[5-(2,2-dimethyl-5-nitro-3H-benzofuran-6-yl)-1,3-dioxan-2-yl]methyl]-N-methyl-carbamate (47 mg, 75%) as a yellow solid. MS (ESI): m/z=489.2 [M+Na]$^+$.

Step K. Trans-2-trimethylsilylethyl N-[[5-(5-amino-2,2-dimethyl-3H-benzofuran-6-yl)-1,3-dioxan-2-yl]methyl]-N-methyl-carbamate

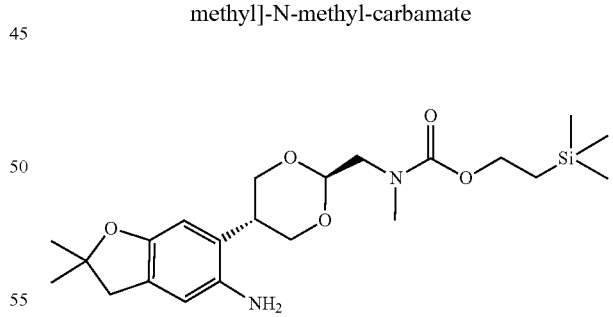

A mixture of trans-2-trimethylsilylethyl N-[[5-(2,2-dimethyl-5-nitro-3H-benzofuran-6-yl)-1,3-dioxan-2-yl]methyl]-N-methyl-carbamate (47.0 mg, 0.10 mmol) and 10% palladium on carbon (20.0 mg) in methanol (8 mL) was stirred under a hydrogen atmosphere at 20° C. for 1h. After filtration and concentration, it was afforded trans-2-trimethylsilylethyl N-[[5-(5-amino-2,2-dimethyl-3H-benzofuran-6-yl)-1,3-dioxan-2-yl]methyl]-N-methyl-carbamate (42 mg) as a colorless oil, which was used directly to the next step without further purification. MS (ESI): m/z=437.2 [M+1]$^+$.

Step L. Trans-2-trimethylsilylethyl N-[[5-[2,2-dimethyl-5-(pyrazolo[1, 5-a]pyrimidine-3-carbonylamino)-3H-benzofuran-6-yl]-1,3-dioxan-2-yl]methyl]-N-methyl-carbamate

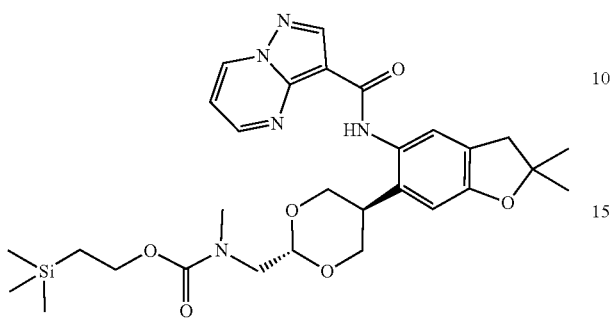

To the mixture of trans-2-trimethylsilylethyl N-[[5-(5-amino-2,2-dimethyl-3H-benzofuran-6-yl)-1, 3-dioxan-2-yl]methyl]-N-methyl-carbamate (42.0 mg, 0.10 mmol), triethylamine (0.04 mL, 0.30 mmol) and 4-dimethylaminopyridine (3.0 mg, 0.02 mmol) in THF (5 mL) was added pyrazolo[1,5-a]pyrimidine-3-carbonyl chloride (25.0 mg, 0.14 mmol) and stirred for 1h. To the mixture was added methanol (2 mL). After concentration, the residue was purified by silica gel chromatography using ethyl acetate:petroleum ether (1:1) as eluting solvents to afford trans-2-trimethylsilylethyl N-[[5-[2,2-dimethyl-5-(pyrazolo[1,5-a]pyrimidine-3-carbonylamino)-3H-benzofuran-6-yl]-1,3-dioxan-2-yl]methyl]-N-methyl-carbamate (31 mg, 55%) as a yellow oil. MS (ESI): m/z=604.2 [M+Na]+.

Step M. Trans-N-[2,2-dimethyl-6-[2-(methylaminomethyl)-1,3-dioxan-5-yl]-3H-benzofuran-5-yl]pyrazolo[1, 5-a]pyrimidine-3-carboxamide

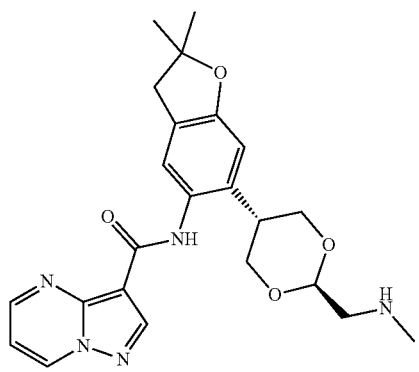 [SMILES: CNC[C@H]1OC[C@H](c2cc3c(cc2NC(=O)c2cnn4cccnc24)CC(C)(C)O3)CO1]

To the mixture of trans-2-trimethylsilylethyl N-[[5-[2,2-dimethyl-5-(pyrazolo[1,5-a]pyrimidine-3-carbonylamino)-3H-benzofuran-6-yl]-1,3-dioxan-2-yl]methyl]-N-methyl-carbamate (31.0 mg, 0.05 mmol) in DCM (0.50 mL) was added trifluoroacetic acid (250 μL) at 0° C. and stirred for 1h. The mixture was neutralized with triethylamine. After concentration, the residue was purified by preparative HPLC (Xbridge 21.2*250 mm c18, 10 μm; A: acetonitrile 25-55%; B: 10 mM ammonium bicarbonatein water) to afford trans-N-[2,2-dimethyl-6-[2-(methylaminomethyl)-1,3-dioxan-5-yl]-3H-benzofuran-5-yl]pyrazolo[1,5-a]pyrimidine-3-carboxamide (17.8 mg, 76%) as a yellow solid. 1H NMR (400 MHz, CDCl3) δ 9.73 (s, 1H), 8.84 (dd, J=1.6, 6.8 Hz, 1H), 8.75 (s, 1H), 8.74 (dd, J=1.6, 4.0 Hz, 1H), 7.72 (s, 1H), 7.06 (dd, J=3.6, 7.2 Hz, 1H), 6.55 (s, 1H), 4.75 (t, J=4.8 Hz, 1H), 4.28 (dd, J=4.4, 11.2 Hz, 2H), 3.84 (t, J=7.2 Hz, 2H), 3.65-3.55 (m, 1H), 3.03 (s, 2H), 2.76 (d, J=4.8 Hz, 2H), 2.46 (s, 3H), 1.48 (s, 6H). MS (ESI): m/z=438.2 [M+1]+.

Example 4. N-(6-(4-(Hydroxymethyl)piperidin-1-yl)-2,2-dimethyl-2,3-dihydrobenzofuran-5-yl)pyrazolo[1,5-a]pyrimidine-3-carboxamide

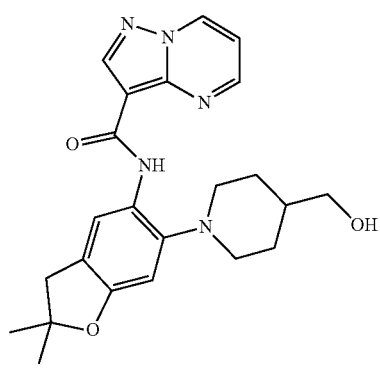 [SMILES: CC1(C)Cc2cc(NC(=O)c3cnn4cccnc34)c(N3CCC(CO)CC3)cc2O1]

Step A. (1-(2,2-Dimethyl-5-nitro-2,3-dihydrobenzofuran-6-yl)piperidin-4-yl)methanol

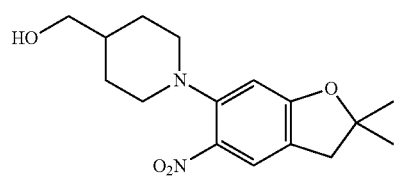

A mixture of 6-chloro-2,2-dimethyl-5-nitro-3H-benzofuran (Intermediate 1) (1.14 g, 5.01 mmol) and 4-piperidinylmethanol (5.77 g, 50.08 mmol) was stirred at 110° C. for 18h. The reaction was concentrated to dryness. The residue was purified by silica gel chromatography using ethyl acetate:petroleum ether (from 1:4 to 2:3) to afford [1-(2,2-dimethyl-5-nitro-3H-benzofuran-6-yl)-4-piperidyl]methanol (1.53 g, 97%) as orange oil. MS (ESI): m/z=307.2 [M+1]+.

Step B. (1-(5-Amino-2,2-dimethyl-2,3-dihydrobenzofuran-6-yl)piperidin-4-yl)methanol

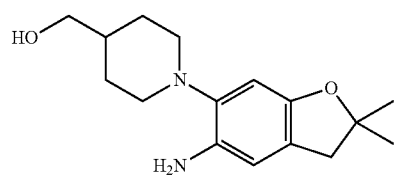 [SMILES: CC1(C)Cc2cc(N)c(N3CCC(CO)CC3)cc2O1]

A mixture of [1-(2,2-dimethyl-5-nitro-3H-benzofuran-6-yl)-4-piperidyl]methanol (1.16 g, 3.75 mmol) and 10%

363 palladium on carbon (116 mg) in methanol (30 mL) was stirred at 25° C. under hydrogen atmosphere for 2h. After filtration and concentration under reduced pressure, [1-(5-amino-2,2-dimethyl-3H-benzofuran-6-yl)-4-piperidyl]methanol was afforded (1.29 g) as an orange oil, which was used directly to next step without further purification. MS (ESI): m/z=277.2 [M+1]$^+$.

Step C. N-(6-(4-(Hydroxymethyl)piperidin-1-yl)-2,2-dimethyl-2,3-dihydrobenzofuran-5-yl)pyrazolo[1,5-a]pyrimidine-3-carboxamide

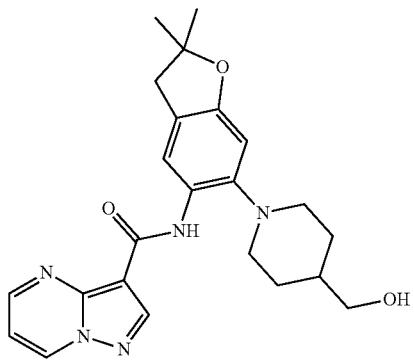 [SMILES: CC1(C)Cc2cc(NC(=O)c3cnn4cccnc34)c(N3CCC(CO)CC3)cc2O1]

A mixture of [1-(5-amino-2,2-dimethyl-3H-benzofuran-6-yl)-4-piperidyl]methanol (990.0 mg, 3.58 mmol) and triethylamine (1087.4 mg, 10.75 mmol) in DCM (10 mL) was stirred at 0° C. To the mixture was a added solution of pyrazolo[1,5-a]pyrimidine-3-carbonyl chloride (Example 3, Step B) (975.67 mg, 5.37 mmol) in DCM (10 mL) and the reaction was stirred at 25° C. for 1h. After concentration, the residue was purified by preparative HPLC (Xbridge 21.2*250 mm c18, 10 um; A: acetonitrile 45-55%; B: 10 mM ammonium bicarbonate in water) to afford N-[6-[4-(hydroxymethyl)-1-piperidyl]-2,2-dimethyl-3H-benzofuran-5-yl]pyrazolo[1,5-a]pyrimidine-3-carboxamide (916 mg, 61%) as a yellow solid. $^1$H NMR (400 MHz, CDCl$_3$): δ 10.50 (s, 1H), 8.82-8.72 (m, 3H), 8.43 (s, 1H), 7.01 (dd, J=4, 6.8 Hz, 1H), 6.65 (s, 1H), 3.67-3.57 (m, 2H), 3.14-3.06 (m, 2H), 3.03 (s, 2H), 2.72-2.61 (m, 2H), 1.82-1.61 (m, 5H), 1.48 (s, 6H). MS (ESI): m/z=422.1 [M+1]$^+$.

Example 5. N-(2,2-Dimethyl-7-morpholino-3,4-dihydro-2H-benzo[b][1,4]oxazin-6-yl)pyrazolo[1,5-a]pyrimidine-3-carboxamide

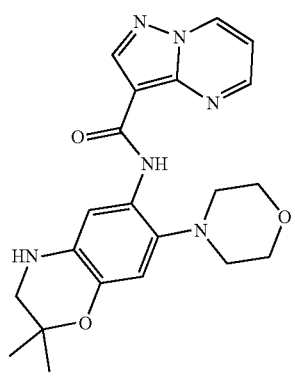 [SMILES: CC1(C)CNc2cc(NC(=O)c3cnn4cccnc34)c(N3CCOCC3)cc2O1]

364

Step A. 7-Fluoro-2,2-dimethyl-2H-benzo[b][1,4]oxazin-3(4H)-one

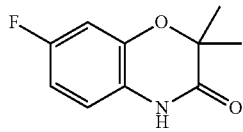

A mixture of 2-amino-5-fluorophenol (150 mg, 1.18 mmol), ethyl 2-bromo-2-methylpropanoate (345 mg, 1.77 mmol), cesium carbonate (1.1 g, 3.54 mmol) in 1,4-dioxane (8 mL) was stirred at 110° C. for 4h. The reaction was filtered, concentrated under reduced pressure and purified by silica gel chromatography using ethyl acetate:petroleum ether (1:4) to afford 7-fluoro-2,2-dimethyl-2H-benzo[b][1,4]oxazin-3(4H)-one (95 mg, 39%) as grey solid. MS (ESI): m/z=196.1 [M+1]$^+$.

Step B. 7-Fluoro-2,2-dimethyl-6-nitro-2H-benzo[b][1,4]oxazin-3(4H)-one

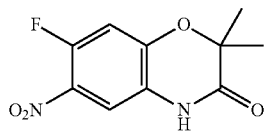 [SMILES: CC1(C)Oc2cc(F)c([N+](=O)[O-])cc2NC1=O]

To a solution of 7-fluoro-2,2-dimethyl-2H-benzo[b][1,4]oxazin-3(4H)-one (95 mg, 0.49 mmol) in sulfuric acid (4 mL) was added guanidine nitrate (59 mg, 0.49 mmol) drop-wise at 0° C. and stirred for 30 min. The mixture was poured into ice water and the aqueous was extracted with ethyl acetate (30 mL). The organic phase was dried over sodium sulfate and concentrated to afford 7-fluoro-2,2-dimethyl-6-nitro-2H-benzo[b][1,4]oxazin-3(4H)-one as grey solid (108 mg), which was used directly to next step without further purification. MS (ESI): m/z=241.1 [M+1]$^+$.

Step C. 2,2-Dimethyl-7-morpholino-6-nitro-2H-benzo[b][1,4]oxazin-3(4H)-one

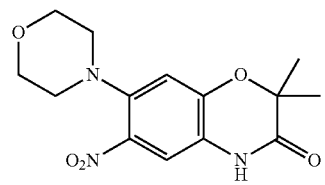 [SMILES: CC1(C)Oc2cc(N3CCOCC3)c([N+](=O)[O-])cc2NC1=O]

A mixture of 7-fluoro-2,2-dimethyl-6-nitro-2H-benzo[b][1,4]oxazin-3(4H)-one (100 mg, 0.41 mmol), morpholine (43 mg, 0.50 mmol) and N,N-diisopropylethylamine (86 mg, 0.67 mmol) in acetonitrile (10 mL) was stirred at room temperature for 18h. After concentration, the residue was purified by silica gel chromatography using ethyl acetate:petroleum ether (1:1) as eluting solvents to afford 2,2-dimethyl-7-morpholino-6-nitro-2H-benzo[b][1,4]oxazin-3(4H)-one (122 mg, 97%) as grey oil. MS (ESI): m/z=308.1 [M+1]$^+$.

Step D. 2,2-Dimethyl-7-morpholino-6-nitro-3,4-dihydro-2H-benzo[b][1,4]oxazine

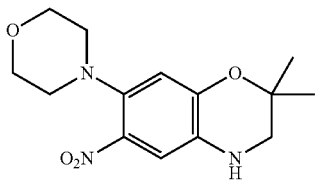 [SMILES: CC1(C)CNc2cc([N+](=O)[O-])c(N3CCOCC3)cc2O1]

To a solution of 2,2-dimethyl-7-morpholino-6-nitro-2H-benzo[b][1,4]oxazin-3(4H)-one (122 mg, 0.40 mmol) in THF (4 mL) was added borane (1M in THF, 1.59 mL, 1.59 mmol) at room temperature. Then the mixture was stirred at 65° C. for 2h. The mixture was cooled to 0° C. Methanol (10 mL) was added drop wise. The mixture was stirred at reflux for 1h. After concentration, it was afforded 2-methyl-7-morpholino-6-nitro-3,4-dihydro-2H-benzo[b][1,4]oxazine (120 mg) as red oil, which was used to next step without further purification. MS (ESI): m/z=294.2 [M+1]$^+$.

Step E. 2,2-Dimethyl-7-morpholino-3,4-dihydro-2H-benzo[b][1,4]oxazin-6-amine

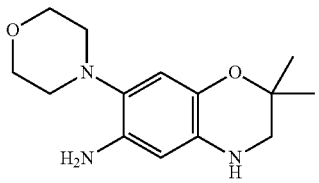 [SMILES: CC1(C)CNc2cc(N)c(N3CCOCC3)cc2O1]

A mixture of 2-methyl-7-morpholino-6-nitro-3,4-dihydro-2H-benzo[b][1,4]oxazine (120 mg, 0.41 mmol) and 10% palladium on carbon (30.0 mg) in ethyl acetate (30 mL) was stirred at 40° C. under hydrogen atmosphere for 2h. The solid was filtered off and the filtrate was concentrated under reduced pressure to afford 2,2-dimethyl-7-morpholino-3,4-dihydro-2H-benzo[b][1,4]oxazin-6-amine (110 mg) as black oil, which was used to next step without further purification. MS (ESI): m/z=264.1 [M+1]$^+$.

Step F. N-(2,2-Dimethyl-7-morpholino-3,4-dihydro-2H-benzo[b][1,4]oxazin-6-yl)pyrazolo[1,5-a]pyrimidine-3-carboxamide

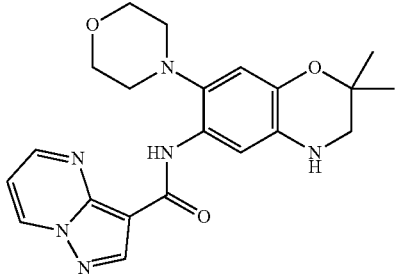

A mixture of 2,2-dimethyl-7-morpholino-3,4-dihydro-2H-benzo[b][1,4]oxazin-6-amine as black oil (110 mg, 0.42 mmol), pyrazolo[1,5-a]pyrimidine-3-carboxylic acid (82 mg, 0.50 mmol), (3-hydroxy-3H-1,2,3-triazolo[4,5-b]pyridinato-O)tri-1-pyrrolidinylphosphonium hexafluorophosphate (327 mg, 0.63 mmol) and diisopropylethylamine (152 mg, 1.25 mmol) in DMF (10 mL) was stirred at 25° C. for 4h. The mixture was purified by preparative HPLC (phenomenex, Gemini C18, 21.2×100 mm. 5 um, 110A, A: acetonitrile 30-40%; B: 0.05% formic acid in water) to afford N-(2,2-dimethyl-7-morpholino-3,4-dihydro-2H-benzo[b][1,4]oxazin-6-yl)pyrazolo[1,5-a]pyrimidine-3-carboxamide (70 mg, 41%) as a yellow solid. $^1$HNMR (400 MHz, DMSO-d6): δ 10.51 (s, 1H), 9.36 (dd, J=1.6, 7.2 Hz, 1H), 8.92 (dd, J=1.6, 4.4 Hz, 1H), 8.66 (s, 1H), 7.89 (s, 1H), 7.33 (dd, J=4.4, 7.2 Hz, 1H), 6.61 (s, 1H), 5.82 (s, 1H), 3.89-3.73 (m, 4H), 2.95 (s, 2H), 2.82-2.69 (m, 4.0 Hz, 4H), 1.24 (s, 6H). MS (ESI): m/z=409.1 [M+1]$^+$.

Example 6. N-(2-(Hydroxymethyl)-2-methyl-6-morpholino-2,3-dihydrobenzofuran-5-yl)pyrazolo[1,5-a]pyrimidine-3-carboxamide

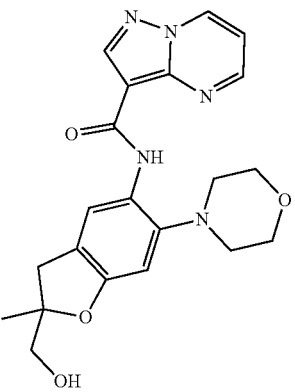 [SMILES: CC1(CO)Cc2cc(NC(=O)c3cnn4cccnc34)c(N3CCOCC3)cc2O1]

Step A. (2-Methyl-6-morpholino-5-nitro-2,3-dihydrobenzofuran-2-yl)methanol

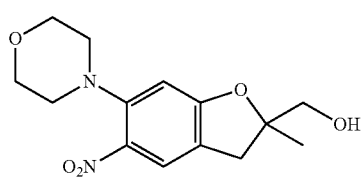 [SMILES: CC1(CO)Cc2cc([N+](=O)[O-])c(N3CCOCC3)cc2O1]

A mixture of (6-chloro-2-methyl-5-nitro-2,3-dihydrobenzofuran-2-yl)methanol (900 mg, 3.70 mmol) in morpholine (5 mL) was stirred at 120° C. for 18h. The mixture was concentrated under reduced pressure and the residue purified by silica gel chromatography using ethyl acetate:petroleum ether (1:1) as eluting solvents to afford (2-methyl-6-morpholino-5-nitro-2,3-dihydrobenzofuran-2-yl)methanol (780 mg, 72%) as a yellow oil. MS (ESI): m/z=295.1 [M+1]$^+$.

Step B. (5-Amino-2-methyl-6-morpholino-2,3-dihydrobenzofuran-2-yl)methanol

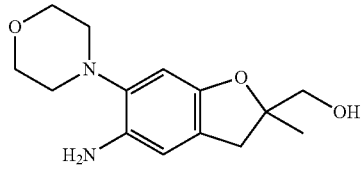

A mixture of (2-methyl-6-morpholino-5-nitro-3H-benzofuran-2-yl)methanol (780 mg, 2.65 mmol) and 10% palladium on carbon (200 mg) in methanol (30 mL) was stirred at 25° C. under hydrogen atmosphere for 1h. The reaction was filtered and the filtrate was concentrated under reduced pressure to afford (5-amino-2-methyl-6-morpholino-2,3-dihydrobenzofuran-2-yl)methanol (550 mg) as light green oil, which was used directly to next step without further purification. MS (ESI): m/z=265.1 [M+1]$^+$.

Step C. N-(2-(Hydroxymethyl)-2-methyl-6-morpholino-2,3-dihydrobenzofuran-5-yl)pyrazolo[1,5-a]pyrimidine-3-carboxamide

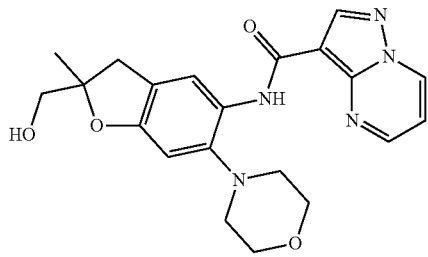 [SMILES: CC1(CO)Cc2cc(NC(=O)c3cnn4cccnc34)c(N3CCOCC3)cc2O1]

A mixture of (5-amino-2-methyl-6-morpholino-2,3-dihydrobenzofuran-2-yl)methanol (550 mg, 2.08 mmol), pyrazolo[1,5-a]pyrimidine-3-carboxylic acid (407 mg, 2.5 mmol), (3-hydroxy-3H-1,2,3-triazolo[4,5-b]pyridinato-O) tri-1-pyrrolidinylphosphonium hexafluorophosphate (1.63 g, 3.12 mmol) and diisopropyethylamine (756 mg, 6.24 mmol) in DMF (10 mL) was stirred at 25° C. for 3h. Water was added. The aqueous phase was extracted with ethyl acetate (2×50 mL). The combined organic phases were washed with brine, dried over sodium sulfate and concentrated under reduced pressure. The residue was purified by silica gel chromatography using methanol: DCM (3:100) as eluting solvents to afford N-[2-(hydroxymethyl)-2-methyl-6-morpholino-3H-benzofuran-5-yl]pyrazolo[1,5-a]pyrimidine-3-carboxamide (490 mg, 58%) as a yellow solid. $^1$H NMR (400 MHz, CDCl$_3$) δ 10.47 (s, 1H), 8.83 (dd, J=1.5, 7.2 Hz, 1H), 8.78 (s, 1H), 8.77 (dd, J=1.6, 4.0 Hz, 1H), 7.07 (dd, J=4.0, 7.2 Hz, 1H), 6.67 (s, 1H), 3.94-3.96 (m, 4H), 3.67 (d, J=5.6 Hz, 2H), 3.25 (d, J=15.6 Hz, 1H), 2.95 (d, J=15.6 Hz, 1H), 2.91-2.93 (m, 4H), 1.46 (s, 3H). MS (ESI): m/z=410.1 [M+1]$^+$.

Example 7. N-(7-(4-(Hydroxymethyl)piperidin-1-yl)-3,4-dihydro-2H-benzo[b][1,4]oxazin-6-yl)-6-methylpyrazolo[1,5-a]pyrimidine-3-carboxamide

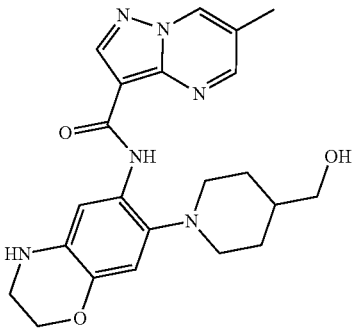 [SMILES: Cc1cnc2c(C(=O)Nc3cc4c(cc3N3CCC(CO)CC3)OCCN4)cnn2c1]

Step A. 6-Methylpyrazolo[1,5-a]pyrimidine-3-carboxylic acid

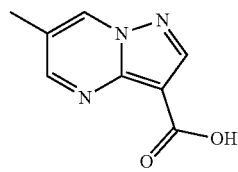

A solution of 5-amino-1H-pyrazole-4-carboxylic acid (2000 mg, 15.74 mmol) and (E)-3-(dimethylamino)-2-methylacrylaldehyde (1780 mg, 15.74 mmol) in acetic acid (3 mL) and ethanol (1 mL) was heated at 70° C. for 1h. The resulting mixture was cooled to room temperature and the solid was collected by filtration, washed with water and dried in vacuum to afford 6-methylpyrazolo[1,5-a]pyrimidine-3-carboxylic acid (1610 mg, 58%) as a white solid. MS (ESI): m/z=178.1 [M+1]$^+$.

Step B. (1-(6-Nitro-3,4-dihydro-2H-benzo[b][1,4]oxazin-7-yl)piperidin-4-yl)methanol

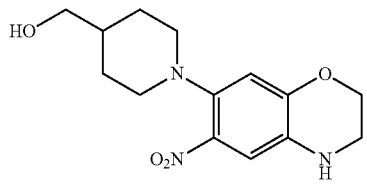

A mixture of 7-fluoro-6-nitro-3,4-dihydro-2H-benzo[b][1,4]oxazine (300 mg, 1.51 mmol), piperidin-4-ylmethanol (183 mg, 1.59 mmol) and N-ethyl-N-isopropylpropan-2-amine (391 mg, 3.03 mmol) in N-methyl-2-pyrrolidone (5 mL) was stirred at 120° C. for 18h. After cooling to room temperature, the mixture was poured into water and the aqueous phase was extracted with ethyl acetate (2×50 mL). The organic phases were combined and washed with water, brine and dried over sodium sulfate. After concentration under reduced pressure, the residue was purified by silica gel chromatography using ethyl acetate:petroleum ether (1:1) as eluting solvents to afford (1-(6-nitro-3,4-dihydro-2H-benzo[b][1,4]oxazin-7-yl)piperidin-4-yl)methanol (300 mg, 67%) as a yellow solid. MS (ESI): m/z=294.1 [M+1]⁺.

Step C. (1-(6-Amino-3,4-dihydro-2H-benzo[b][1,4]oxazin-7-yl)piperidin-4-yl)methanol

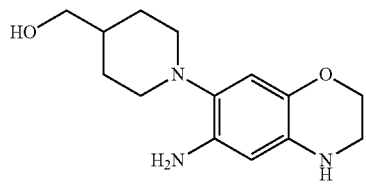 [SMILES: O=[N+]([O-])c1cc2c(cc1N1CCC(CO)CC1)OCCN2]

A mixture of (1-(6-nitro-3,4-dihydro-2H-benzo[b][1,4]oxazin-7-yl)piperidin-4-yl)methanol (300 mg, 1.02 mmol) and 10% palladium on carbon (30 mg) in 2-methylpropan-2-ol (10 mL) was stirred at 50° C. for 18h under hydrogen atmosphere. After the mixture was cooled down to room temperature, the reaction was filtered and the filtrate was concentrated under reduced pressure to afford (1-(6-amino-3,4-dihydro-2H-benzo[b][1,4]oxazin-7-yl)piperidin-4-yl)methanol (260 mg) as a white solid, which was used directly to the next step without purification. MS (ESI): m/z=264.1 [M+1]⁺.

Step D. N-(7-(4-(Hydroxymethyl)piperidin-1-yl)-3,4-dihydro-2H-benzo[b][1,4]oxazin-6-yl)-6-methylpyrazolo[1,5-a]pyrimidine-3-carboxamide

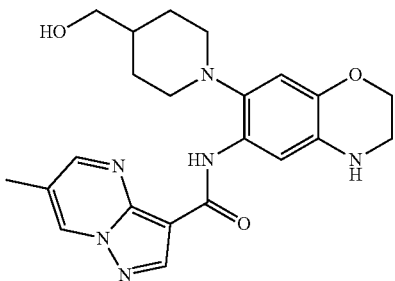

A mixture of 6-methylpyrazolo[1,5-a]pyrimidine-3-carboxylic acid (58 mg, 0.33 mmol), (7-azabenzotriazol-1-yloxy)tripyrrolidinophosphoniumhexafluorophosphate (215 mg, 0.41 mmol), (1-(6-amino-3,4-dihydro-2H-benzo[b][1,4]oxazin-7-yl)piperidin-4-yl)methanol (85 mg, 0.27 mmol) and N-ethyl-N-isopropylpropan-2-amine (71 mg, 0.55 mmol) in DMF (5 mL) was stirred at room temperature for 18h. After filtration and concentration, the residue was purified by preparative HPLC (Xbridge 21.2*250 mm c18, 10 um; A: acetonitrile 25-55%; B: 10 mM ammonium bicarbonate in water) to afford N-(7-(4-(hydroxymethyl)piperidin-1-yl)-3,4-dihydro-2H-benzo[b][1,4]oxazin-6-yl)-6-methylpyrazolo[1,5-a]pyrimidine-3-carboxamide (35 mg, 30%) as a yellow solid. ¹H NMR (400 MHz, DMSO-d₆): δ 10.55 (s, 1H), 9.21 (s, 1H), 8.83 (d, J=2.8 Hz, 1H), 8.57 (s, 1H), 7.88 (s, 1H), 6.61 (s, 1H), 5.68 (s, 1H), 4.6 (t, J=2.8 Hz, 2H), 4.08 (t, J=4.4 Hz, 2H), 3.43 (t, J=5.2 Hz, 2H), 3.25-3.22 (m, 2H), 2.86-2.83 (m, 2H), 2.62-2.56 (m, 2H), 2.42 (s, 3H), 1.73-1.63 (m, 4H), 1.51-1.47 (m, 1H). MS (ESI): m/z=423.1 [M+1]⁺.

Example 8. N-[6-[4-(2, 2-Difluoroethyl)piperazin-1-yl]-2, 2-dimethyl-3H-benzofuran-5-yl]pyrazolo[1,5-a]pyrimidine-3-carboxamide

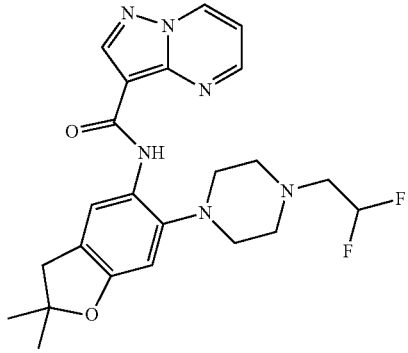 [SMILES: CC1(C)Cc2cc(NC(=O)c3cnn4cccnc34)c(N3CCN(CC(F)F)CC3)cc2O1]

Step A. 1-(2,2-Difluoroethyl)-4-(2,2-dimethyl-5-nitro-3H-benzofuran-6-yl)piperazine

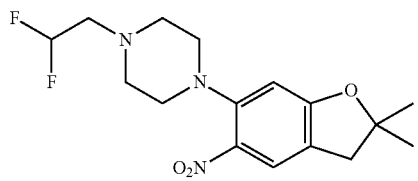

A mixture of 6-fluoro-2,2-dimethyl-5-nitro-3H-benzofuran (80.0 mg, 0.38 mmol), 1-(2,2-difluoroethyl)piperazine hydrochloride (212.0 mg, 1.14 mmol) and cesium carbonate (556.0 mg, 1.71 mmol) in DMF (4 mL) was stirred at 20° C. for 5h. The mixture was poured into water (20 mL) and the aqueous phase was extracted with ethyl acetate (50 mL). The organic phase was washed with water and brine and dried over sodium sulfate before concentration to dryness. The residue was purified by silica gel chromatography using ethyl acetate:petroleum ether (1:6) as eluting solvents to afford 1-(2,2-difluoroethyl)-4-(2,2-dimethyl-5-nitro-3H-benzofuran-6-yl)piperazine (88 mg, 68%) as yellow oil. MS (ESI): m/z=342.1 [M+1]⁺.

Step B. 6-[4-(2,2-Difluoroethyl)piperazin-1-yl]-2,2-dimethyl-3H-benzofuran-5-amine

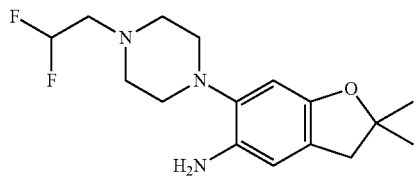 [SMILES: CC1(C)Cc2cc(N)c(N3CCN(CC(F)F)CC3)cc2O1]

A mixture of 1-(2,2-difluoroethyl)-4-(2,2-dimethyl-5-nitro-3H-benzofuran-6-yl)piperazine (84.0 mg, 0.25 mmol) and 10% palladium on carbon (50.0 mg) in methanol (12 mL) was stirred at 25° C. under hydrogen atmosphere for 1h. After filtration and concentration under reduced pressure, it was afforded 6-[4-(2,2-difluoroethyl)piperazin-1-yl]-2,2-dimethyl-3H-benzofuran-5-amine (75 mg) as a yellow oil, which was used directly in the next step without further purification. MS (ESI): m/z=312.2 [M+1]$^+$.

Step C. N-[6-[4-(2, 2-Difluoroethyl)piperazin-1-yl]-2, 2-dimethyl-3H-benzofuran-5-yl]pyrazolo[1, 5-a]pyrimidine-3-carboxamide

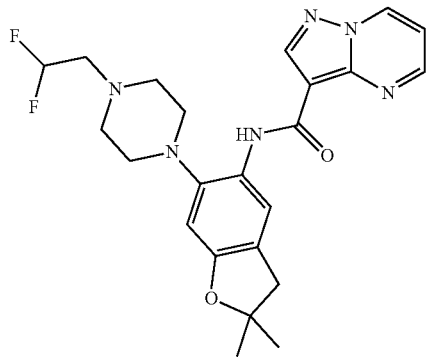 [SMILES: CC1(C)Cc2cc(NC(=O)c3cnn4cccnc34)c(N3CCN(CC(F)F)CC3)cc2O1]

To the mixture of pyrazolo[1,5-a]pyrimidine-3-carbonyl chloride (63.0 mg, 0.35 mmol), triethylamine (0.1 mL, 0.69 mmol) and 4-dimethylaminopyridine (7.0 mg, 0.06 mmol) in THF (10 mL) was added 6-[4-(2,2-difluoroethyl)piperazin-yl]-2,2-dimethyl-3H-benzofuran-5-amine (70.0 mg, 0.22 mmol) and the mixture was stirred at 25° C. for 1h. To the mixture was added methanol (4 mL) and stirred for 30 min. After concentration, the residue was purified by silica gel chromatography using ethyl acetate:petroleum ether: DCM (2:1:1) as eluting solvents to afford N-[6-[4-(2,2-difluoroethyl)piperazin-1-yl]-2,2-dimethyl-3H-benzofuran-5-yl]pyrazolo[1,5-a]pyrimidine-3-carboxamide (84.1 mg, 82%) as a yellow solid. $^1$H NMR (400 MHz, DMSO-d$_6$) δ 10.40 (brs, 1H), 9.37 (dd, J=1.6, 7.2 Hz, 1H), 8.95 (dd, J=1.2, 4.4 Hz, 1H), 8.68 (s, 1H), 8.32 (s, 1H), 7.35 (dd, J=4.0, 6.8 Hz, 1H), 6.71 (s, 1H), 6.20 (tt, J=4.4, 55.6 Hz, 1H), 3.00 (s, 2H), 2.94-2.73 (m, 10H), 1.41 (s, 6H). MS (ESI): m/z=457.2 [M+1]$^+$.

Example 9. N-(7-Morpholino-3,4-dihydro-2H-benzo[b][1,4]oxazin-6-yl)pyrazolo[1,5-a]pyrimidine-3-carboxamide

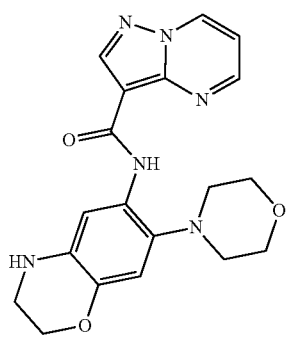 [SMILES: O=C(Nc1cc2c(cc1N1CCOCC1)OCCN2)c1cnn2cccnc12]

Step A. 7-Morpholino-6-nitro-3,4-dihydro-2H-benzo[b][1,4]oxazine

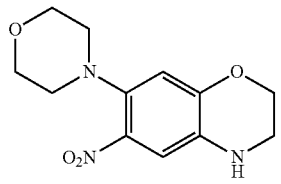

A mixture of morpholine (176 mg, 2.02 mmol), 7-fluoro-6-nitro-3,4-dihydro-2H-1,4-benzoxazine (200 mg, 1.01 mmol), potassium carbonate (488 mg, 3.53 mmol) and sodium iodide (530 mg, 3.53 mmol) in acetonitrile (20 mL) was stirred at 85° C. for 16h. After filtration and concentration under reduced pressure, the residue was purified by silica gel chromatography using ethyl acetate:petroleum ether (1:1) as eluting solvents to afford 7-morpholino-6-nitro-3,4-dihydro-2H-benzo[b][1,4]oxazine as red-brown oil (250 mg, 93%). MS (ESI): m/z=266.2 [M+1]$^+$.

Step B. 7-Morpholino-3,4-dihydro-2H-benzo[b][1,4]oxazin-6-amine

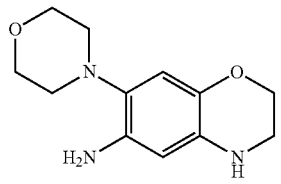 [SMILES: Nc1cc2c(cc1N1CCOCC1)OCCN2]

A mixture of 7-morpholino-6-nitro-3,4-dihydro-2H-1,4-benzoxazine (125 mg, 0.47 mmol) and 10% palladium on carbon (50.0 mg) in ethyl acetate (20 mL) was stirred at 45° C. under an atmosphere of hydrogen for 3h. After filtration and concentration, it was afforded 7-morpholino-3,4-dihydro-2H-benzo[b][1,4]oxazin-6-amine as a brown solid (100 mg), which was used directly to next step without further purification. MS (ESI): m/z=236.2 [M+1]$^+$.

Step C. N-(7-Morpholino-3,4-dihydro-2H-benzo[b][1,4]oxazin-6-yl)pyrazolo[1,5-a]pyrimidine-3-carboxamide

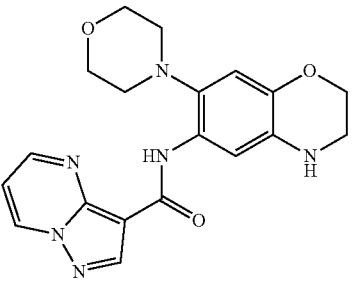 [SMILES: O=C(Nc1cc2c(cc1N1CCOCC1)OCCN2)c1cnn2cccnc12]

A mixture of 7-morpholino-3,4-dihydro-2H-1,4-benzoxazin-6-amine (95.0 mg, 0.40 mmol), pyrazolo[1,5-a]pyrimidine-3-carboxylic acid (79.0 mg, 0.48 mmol), and 2-(7- aza-1H-benzotriazole-1-yl)-1,1,3,3-tetramethyluronium hexafluorophosphate (307 mg, 0.810 mmol) in DMF (5 mL) and diisopropyethylamine (260 mg, 2.02 mmol) was stirred at 25° C. for 16h. After concentration, the residue was purified by preparative HPLC (Boston ODS 40 g flash, A: MeCN25-35%; B: 0.5% ammonium bicarbonate in H$_2$O) to afford N-(7-morpholino-3,4-dihydro-2H-benzo[b][1,4] oxazin-6-yl)pyrazolo[1,5-a]pyrimidine-3-carboxamide (22.9 mg, 15%) as pale yellow solid. $^1$H NMR (400 MHz, DMSO-d$_6$): δ 10.52 (s, 1H), 9.36 (dd, J=1.6, 6.8 Hz, 1H), 8.93 (dd, J=1.2, 4.0 Hz, 1H), 8.66 (s, 1H), 7.87 (s, 1H), 7.33 (dd, J=4.0, 6.8 Hz, 1H), 6.64 (s, 1H), 5.76 (s, 1H), 4.10-4.08 (m, 2H), 3.89-3.74 (m, 4H), 3.28-3.22 (m, 2H), 2.79-2.69 (m, 4H). MS (ESI): m/z=381.2 [M+1]$^+$.

Example 10. N-(3-Methyl-7-morpholino-3,4-dihydro-2H-benzo[b][1,4]oxazin-6-yl)pyrazolo[1,5-a]pyrimidine-3-carboxamide

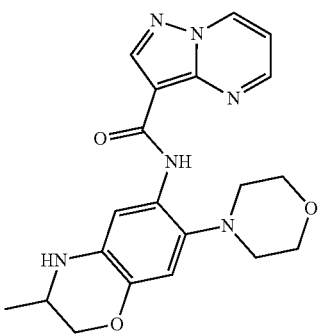 [SMILES: CC1COc2cc(N3CCOCC3)c(NC(=O)c3cnn4cccnc34)cc2N1]

Step A. 4-Benzyl-7-fluoro-2H-benzo[b][1,4]oxazin-3(4H)-one

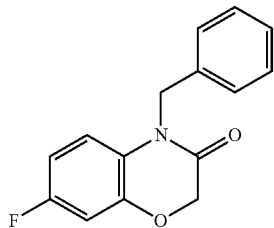 [SMILES: O=C1COc2cc(F)ccc2N1Cc1ccccc1]

A mixture of 7-fluoro-4H-1,4-benzoxazin-3-one (200 mg, 1.2 mmol), (chloromethyl)benzene (159 mg, 1.26 mmol) and cesium carbonate (1.95 g, 5.98 mmol) in 1,4-dioxane (10 mL) was stirred at 110° C. for 4h. After filtration, the filtrate was concentrated and purified by silica gel chromatography using ethyl acetate:petroleum ether (1:4) as eluting solvents to afford 4-benzyl-7-fluoro-2H-benzo[b][1,4] oxazin-3(4H)-one (250 mg, 75%) as a white solid. MS (ESI): m/z=258.1 [M+1]$^+$.

Step B. 4-Benzyl-7-fluoro-3-methyl-3,4-dihydro-2H-benzo[b][1,4]oxazine

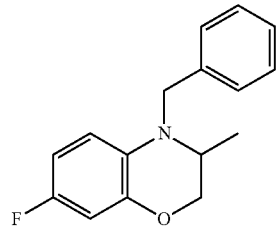 [SMILES: CC1COc2cc(F)ccc2N1Cc1ccccc1]

To a mixture of 4-benzyl-7-fluoro-2H-benzo[b][1,4] oxazin-3(4H)-one (250 mg, 0.97 mmol) in THF (10 mL) was added methyl magnesium bromide (3M in diethyl ether, 1.3 mL, 3.89 mmol) drop-wise at 0° C. The mixture was stirred at room temperature for 2h. The reaction mixture was cooled to 0° C. and acetic acid (2 mL) was added followed by addition of sodium borohydride (92 mg, 2.43 mmol). The reaction mixture was stirred at room temperature for 12h and then poured into ice water. The aqueous phase was extracted with ethyl acetate (10 mL). The organic phase was dried over sodium sulfate and concentrated under reduced pressure. The residue was purified by silica gel chromatography using ethyl acetate:petroleum ether (1:4) as eluting solvents to afford 4-benzyl-7-fluoro-3-methyl-3,4-dihydro-2H-benzo [b][1,4]oxazine (220 mg, 67%) as a white solid. MS (ESI): m/z=258.2 [M+1]$^+$.

Step C. 7-Fluoro-3-methyl-3,4-dihydro-2H-benzo[b][1,4]oxazine

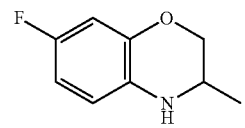

A mixture of 4-benzyl-7-fluoro-3-methyl-3,4-dihydro-2H-benzo[b][1,4]oxazine (220 mg, 0.86 mmol) and 10% palladium on carbon (40 mg) in ethanol (20 mL) was stirred at 40° C. under hydrogen atmosphere for 4h. The solid was filtered off and the filtrate was concentrated under reduced pressure to afford 7-fluoro-3-methyl-3,4-dihydro-2H-benzo [b][1,4]oxazine (100 mg) as a light oil, which was used directly in the next step without purification. MS (ESI): m/z=168.2 [M+1]$^+$.

Step D. 7-Fluoro-3-methyl-6-nitro-3,4-dihydro-2H-benzo[b][1,4]oxazine

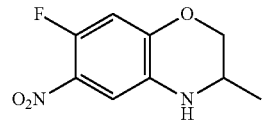

To a solution of 7-fluoro-3-methyl-3,4-dihydro-2H-benzo [b][1,4]oxazine (100 mg, 0.60 mmol) in concentrated sulfuric acid (4 mL) was added guanidine nitrate (73 mg, 0.60 mmol) at 0° C. Then the mixture was stirred at 0° C. for 30 min and poured into ice water. The aqueous phase was extracted with ethyl acetate (30 mL). The organic phase was dried over sodium sulfate and concentrated to afford 7-fluoro-3-methyl-6-nitro-3,4-dihydro-2H-benzo[b][1,4] oxazine (80 mg) as red solid, which was used directly in the next step without purification. MS (ESI): m/z=213.2 [M+1]⁺.

Step E. 3-Methyl-7-morpholino-6-nitro-3,4-dihydro-2H-benzo[b][1,4]oxazine

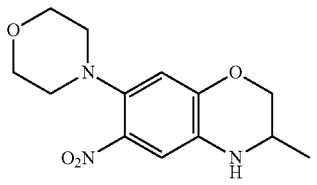 [SMILES: CC1COc2cc(N3CCOCC3)c([N+](=O)[O-])cc2N1]

A mixture of 7-fluoro-3-methyl-6-nitro-3,4-dihydro-2H-benzo[b][1,4]oxazine (80 mg, 0.38 mmol), morpholine (49 mg, 0.57 mmol) and cesium carbonate (246 mg, 0.75 mmol) in acetonitrile (5 mL) was stirred at 85° C. for 18h. The mixture was purified by silica gel chromatography using ethyl acetate:petroleum ether (1:4) as eluting solvents to afford 3-methyl-7-morpholino-6-nitro-3,4-dihydro-2H-benzo[b][1,4]oxazine (80 mg, 61%) as a red oil. MS (ESI): m/z=280.1 [M+1]⁺.

Step F. N-(3-Methyl-7-morpholino-3,4-dihydro-2H-benzo[b][1,4]oxazin-6-yl)pyrazolo[1,5-a]pyrimidine-3-carboxamide

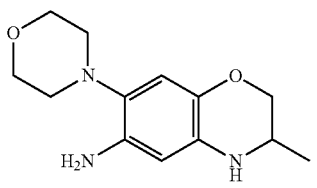

A mixture of 3-methyl-7-morpholino-3,4-dihydro-2H-1,4-benzoxazin-6-amine (43 mg, 0.17 mmol), pyrazolo[1,5-a]pyrimidine-3-carboxylic acid (33 mg, 0.21 mmol), (3-hydroxy-3H-1,2,3-triazolo[4,5-b]pyridinato-O)tri-1-pyrrolidinylphosphonium hexafluorophosphate (107 mg, 0.21 mmol) and diisopropylethylamine (44 mg, 0.34 mmol) in DMF (5 mL) was stirred at 20° C. for 16h. The crude was purified by preparative HPLC (Xbridge 21.2*250 mm c18, 10 um; A: acetonitrile 25-55%; B: 10 mM ammonium bicarbonate in water) to afford N-(3-methyl-7-morpholino-3,4-dihydro-2H-benzo[b][1,4]oxazin-6-yl)pyrazolo[1,5-a]pyrimidine-3-carboxamide (15 mg, 22%) as a white solid. ¹H NMR (400 MHz, DMSO-d₆): δ 10.52 (s, 1H), 9.36 (dd, J=1.2, 6.8 Hz, 1H), 8.93 (dd, J=1.6, 4 Hz, 1H), 8.67 (s, 1H), 7.78 (s, 1H), 7.33 (dd, J=4.4, 7.2 Hz, 1H), 6.66 (s, 1H), 5.81 (s, 1H), 4.13-4.08 (m, 1H), 3.87-3.80 (m, 4H), 3.61 (dd, J=8, 10 Hz, 1H), 3.41-3.33 (m, 1H), 2.78-2.71 (m, 4H), 1.08 (d, J=6.4 Hz, 3H). MS (ESI): m/z=395.2 [M+1]⁺.

Example 11. N-(2-Methyl-7-morpholino-3,4-dihydro-2H-benzo[b][1,4]oxazin-6-yl)pyrazolo[1,5-a]pyrimidine-3-carboxamide

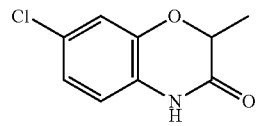

Step A. 7-Chloro-2-methyl-2H-benzo[b][1,4]oxazin-3(4H)-one

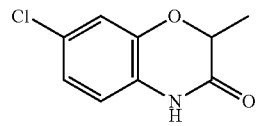

A mixture of 2-amino-5-chlorophenol (2.26 g, 15.73 mmol), ethyl 2-bromopropanoate (4.27 g, 23.6 mmol) and cesium carbonate (15.39 g, 47.2 mmol) in 1,4-dioxane (20 mL) was stirred at 20° C. for 18h. After filtration and concentration, the residue was purified by silica gel chromatography using ethyl acetate:petroleum ether (1:4) as eluting solvents to afford 7-chloro-2-methyl-2H-benzo[b][1,4]oxazin-3(4H)-one as grey solid (1.4 g, 42%). MS (ESI): m/z=198.1 [M+1]⁺.

Step B. 7-Chloro-2-methyl-6-nitro-2H-benzo[b][1,4]oxazin-3(4H)-one

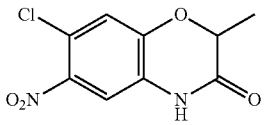 [SMILES: CC1Oc2cc(Cl)c([N+](=O)[O-])cc2NC1=O]

To a solution of 7-chloro-2-methyl-2H-benzo[b][1,4]oxazin-3(4H)-one (664 mg, 3.36 mmol) in concentrated sulfuric acid (10 mL) was added guanidine nitrate (410 mg, 3.36 mmol) at 0° C. The mixture was stirred for 30 min then poured to ice water. The aqueous phase was extracted with ethyl acetate (100 mL). The organic phase was dried over sodium sulfate and concentrated under reduced pressure to afford 7-chloro-2-methyl-6-nitro-2H-benzo[b][1,4]oxazin-3 (4H)-one (660 mg) as a grey solid, which was used directly to next step without further purification. MS (ESI): m/z=243.1 [M+1]⁺.

Step C. 2-Methyl-7-morpholino-6-nitro-2H-benzo[b][1,4]oxazin-3(4H)-one

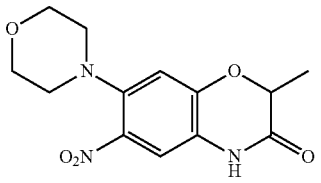 [SMILES: CC1Oc2cc(N3CCOCC3)c([N+](=O)[O-])cc2NC1=O]

A mixture of 7-chloro-2-methyl-6-nitro-4H-1,4-benzoxazin-3-one (151 mg, 0.62 mmol) in morpholine (2 mL) was stirred at 120° C. in a sealed tube for 16h. The mixture was concentrated and the residue was purified by silica gel chromatography using ethyl acetate:petroleum ether (1:1) as eluting solvents to afford 2-methyl-7-morpholino-6-nitro-4H-1,4-benzoxazin-3-one (180 mg, 78%) as red oil. MS (ESI): m/z=294.2 [M+1]$^+$.

Step D. 2-Methyl-7-morpholino-6-nitro-3,4-dihydro-2H-benzo[b][1,4]oxazine

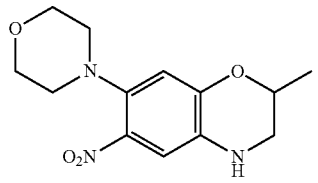 [SMILES: CC1CNc2cc([N+](=O)[O-])c(N3CCOCC3)cc2O1]

To a solution of 2-methyl-7-morpholino-6-nitro-4H-1,4-benzoxazin-3-one (183.0 mg, 0.62 mmol) in THF (4 mL) was added borane (1M in THF, 2.5 mL, 2.5 mmol). The mixture was stirred at 65° C. for 2h. The mixture was cooled to 0° C. and methanol (10 mL) was added drop wise. The mixture was stirred at reflux for 1h. After concentration, it was afforded 2-methyl-7-morpholino-6-nitro-3,4-dihydro-2H-benzo[b][1,4]oxazine (180 mg) as red oil, which was used directly to next step without further purification. MS (ESI): m/z=280.2 [M+1]$^+$.

Step E. 2-Methyl-7-morpholino-3,4-dihydro-2H-benzo[b][1,4]oxazin-6-amine

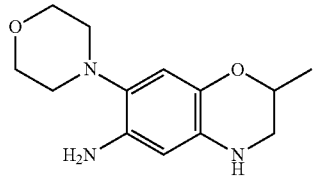

A mixture of 2-methyl-7-morpholino-6-nitro-3,4-dihydro-2H-benzo[b][1,4]oxazine (180 mg, 0.64 mmol) and 10% palladium on carbon (40.0 mg) in ethyl acetate (30 mL) was stirred at 40° C. under hydrogen atmosphere for 2h. After filtration, the filtrate was concentrated under reduced pressure to afford 2-methyl-7-morpholino-3,4-dihydro-2H-benzo[b][1,4]oxazin-6-amine as dark grey oil (162 mg), which was used directly to next step without further purification. MS (ESI): m/z=250.2 [M+1]$^+$.

Step F. N-(2-Methyl-7-morpholino-3,4-dihydro-2H-benzo[b][1,4]oxazin-6-yl)pyrazolo[1,5-a]pyrimidine-3-carboxamide

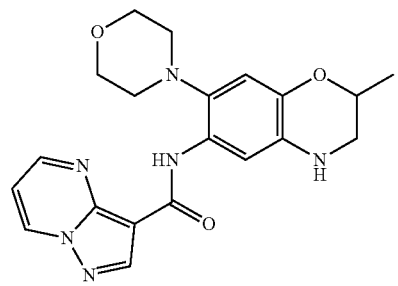

A mixture of 2-methyl-7-morpholino-3,4-dihydro-2H-benzo[b][1,4]oxazin-6-amine (162 mg, 0.65 mmol), pyrazolo[1,5-a]pyrimidine-3-carboxylic acid (127 mg, 0.78 mmol), diisopropyethylamine (236 mg, 1.95 mmol) and (3-hydroxy-3H-1,2,3-triazolo[4,5-b]pyridinato-O)tri-1-pyrrolidinylphosphonium hexafluorophosphate (508 mg, 0.97 mmol) in DMF (10 mL) was stirred at 25° C. for 4h. The residue was purified by preparative HPLC (phenomenex, Gemini C18, 21.2×100 mm. 5 um, 110A; A: acetonitrile 25-35%; B: 0.05% TFA in water) to afford N-(2-methyl-7-morpholino-3,4-dihydro-2H-benzo[b][1,4]oxazin-6-yl)pyrazolo[1,5-a]pyrimidine-3-carboxamide (100 mg, 39%) as a yellow solid. $^1$H NMR (400 MHz, DMSO-d$_6$) δ 10.51 (s, 1H), 9.35 (dd, J=1.6, 6.8 Hz, 1H), 8.92 (dd, J=1.6, 4.0 Hz, 1H), 8.66 (s, 1H), 7.87 (s, 1H), 7.33 (dd, J=4.0, 6.8 Hz, 1H), 6.65 (s, 1H), 5.76 (s, 1H), 4.05-4.08 (m, 1H), 3.82-3.84 (m, 4H), 3.26-3.29 (m, 1H), 2.87-2.92 (m, 1H), 2.74-2.76 (m, 4H), 1.26 (d, J=5.6 Hz, 3H). MS (ESI): m/z=395.1 [M+1]$^+$.

Example 12. N-(6-(4-(Hydroxymethyl)piperidin-1-yl)-2,2-dimethyl-2,3-dihydrobenzofuran-5-yl)-6-methylpyrazolo[1,5-a]pyrimidine-3-carboxamide

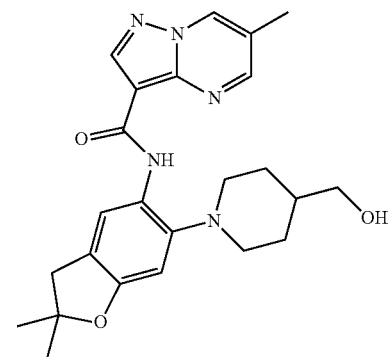 [SMILES: Cc1cnc2c(C(=O)Nc3cc4c(cc3N3CCC(CO)CC3)OC(C)(C)C4)cnn2c1]

A flask equipped with astir bar was charged with the 6-methylpyrazolo[1,5-a]pyrimidine-3-carboxylic acid (Example 7, Step A) (127.53 mg, 0.72 mmol) and charged with nitrogen atmosphere. DMF (10 mL) was added and the mixture was cooled 0° C. (7-Azabenzotriazol-1-yloxy)tripyrrolidinophosphonium hexafluorophosphate (359.01 mg, 0.69 mmol) was added followed by addition of 2,4,6-trimethylpyridine (83.44 mg, 0.69 mmol). [1-(5-Amino-2,2-dimethyl-3H-benzofuran-6-yl)-4-piperidyl]methanol (Example 4, Step B) (173.0 mg, 0.63 mmol) was added and the ice bath was removed allowing the reaction to stir at room temperature for 3h. After concentration, the residue was purified by preparative HPLC (Xbridge Prep C18 10 um OBD, 19*250 mm, A: acetonitrile 45-75% and 0.01% NH$_3$; B: 10 mM ammonium bicarbonate in water) to afford N-(6-(4-(hydroxymethyl)piperidin-1-yl)-2,2-dimethyl-2,3-dihydrobenzofuran-5-yl)-6-methylpyrazolo[1,5-a]pyrimidine-3-carboxamide (173.0 mg, 63%) as a yellow solid. $^1$H NMR (400 MHz, CDCl$_3$): δ 10.45 (s, 1H), 8.69 (s, 1H), 8.63 (d, J=2 Hz, 1H), 8.59-8.56 (m, 1H), 8.42 (s, 1H), 6.64 (s, 1H), 3.64 (s, 2H), 3.14-3.06 (m, 2H), 3.03 (s, 2H), 2.72-2.63 (m, 2H), 2.46 (s, 2H), 1.83-1.62 (m, 5H), 1.48 (s, 6H). MS (ESI): m/z=436.3 [M+1]$^+$.

Example 13. (S)—N-(6-(3-(hydroxymethyl)pyrrolidin-1-yl)-2,2-dimethyl-2,3-dihydrobenzofuran-5-yl)pyrazolo[1,5-a]pyrimidine-3-carboxamide

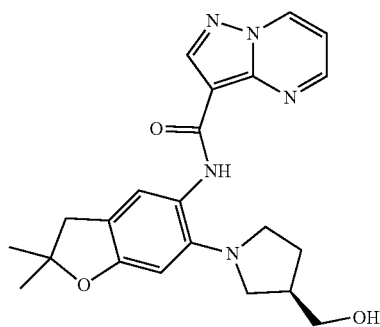 [SMILES: CC1(C)Cc2cc(NC(=O)c3cnn4cccnc34)c(N3CC[C@@H](CO)C3)cc2O1]

Step A. (S)-(1-(2,2-Dimethyl-5-nitro-2,3-dihydrobenzofuran-6-yl)pyrrolidin-3-yl)methanol

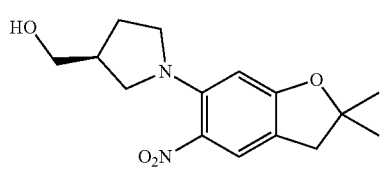 [SMILES: CC1(C)Cc2cc([N+](=O)[O-])c(N3CC[C@H](CO)C3)cc2O1]

A mixture of 6-fluoro-2,2-dimethyl-5-nitro-3H-benzofuran (Example 3, Step F) (133.0 mg, 0.62 mmol), (S)-pyrrolidin-3-ylmethanol (94.83 mg, 0.94 mmol) and potassium carbonate (215.5 mg, 3.15 mmol) in acetonitrile (30 mL) was stirred at 25° C. for 18h. After filtration and concentration under reduced pressure, it was afforded [(3S)-1-(2,2-dimethyl-5-nitro-3H-benzofuran-6-yl)pyrrolidin-3-yl]methanol (254 mg) as a yellow oil, which was used directly to next step without further purification. MS (ESI): m/z=293.2 [M+1]$^+$.

Step B. (S)-(1-(5-Amino-2,2-dimethyl-2,3-dihydrobenzofuran-6-yl)pyrrolidin-3-yl)methanol

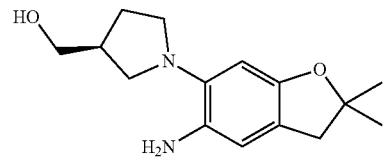

A mixture of [(3S)-1-(2,2-dimethyl-5-nitro-3H-benzofuran-6-yl)pyrrolidin-3-yl]methanol (254.0 mg, 0.87 mmol) and 10% palladium on carbon (25 mg) in methanol (10 mL) was stirred at 25° C. under hydrogen atmosphere for 1h. After filtration and concentration, the residue was purified on silica gel chromatography using ethyl acetate:petroleum ether (2:1) as eluting solvents to afford [(3S)-1-(5-amino-2,2-dimethyl-3H-benzofuran-6-yl)pyrrolidin-3-yl]methanol (102 mg, 44%) as red oil. MS (ESI): m/z=263.2 [M+1]$^+$.

Step C. (S)—N-(6-(3-(Hydroxymethyl)pyrrolidin-1-yl)-2,2-dimethyl-2,3-dihydrobenzofuran-5-yl)pyrazolo[1,5-a]pyrimidine-3-carboxamide

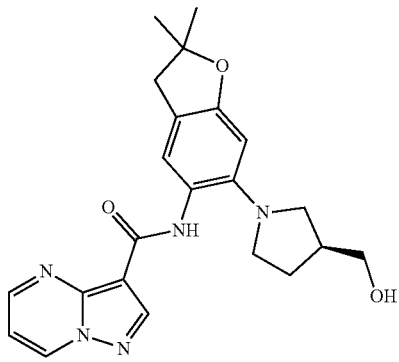 [SMILES: CC1(C)Cc2cc(NC(=O)c3cnn4cccnc34)c(N3CC[C@H](CO)C3)cc2O1]

A mixture of [(3 S)-1-(5-amino-2,2-dimethyl-3H-benzofuran-6-yl)pyrrolidin-3-yl]methanol (78.0 mg, 0.30 mmol) and trimethylamine (90.26 mg, 0.89 mmol) in DCM (15 mL) was stirred at 0° C. To the mixture was added the solution of pyrazolo[1,5-a]pyrimidine-3-carbonyl chloride (Example 3, Step B) (80.98 mg, 0.45 mmol) in DCM (10 mL). The reaction was stirred at 25° C. for 1h. The residue was purified by preparative HPLC (Xbridge Prep C18 10 um OBD, 19*250 mm, A: acetonitrile 45-75% and 0.01% ammonia; B: 10 mM ammonium bicarbonate in water) to afford (S)—N-(6-(3-(hydroxymethyl)pyrrolidin-1-yl)-2,2-dimethyl-2,3-dihydrobenzofuran-5-yl)pyrazolo[1,5-a]pyrimidine-3-carboxamide (78.5 mg, 68%) as a yellow solid. $^1$H NMR (400 MHz, CDCl$_3$): δ 9.97 (s, 1H), 8.04 (dd, J=2.0, 7.2 Hz, 1H), 8.78 (s, 1H), 8.75 (dd, J=1.6, 4.0 Hz, 1H), 8.20 (s, 1H), 7.02 (dd, J=4.0, 6.8 Hz, 1H), 6.58 (s, 1H), 3.74 (d, J=6.4 Hz, 2H), 3.56-3.22 (m, 2H), 3.02 (s, 2H), 2.97-2.82 (m, 2H), 2.61-2.48 (m, 1H), 2.16-2.05 (m, 1H), 1.84-1.68 (m, 2H), 1.48 (s, 6H). MS (ESI): m/z=408.3 [M+1]$^+$.

Example 14. N-(2-Methyl-6-morpholino-2,3-dihydrobenzofuran-5-yl)pyrazolo[1,5-a]pyrimidine-3-carboxamide

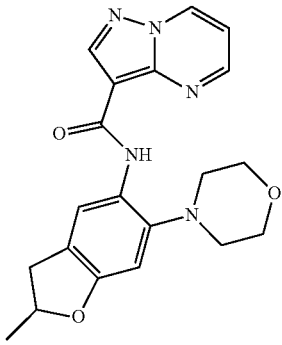 [SMILES: CC1Cc2cc(NC(=O)c3cnn4cccnc34)c(N3CCOCC3)cc2O1]

Step A. 2-(4-Chloro-2-fluorophenyl)-N-methoxy-N-methylacetamide

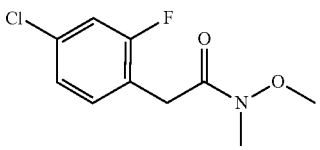

A mixture of 2-(4-chloro-2-fluoro-phenyl)acetic acid (5.00 g, 26.51 mmol), N, O-dimethylhydroxylamine hydrochloride (7.76 g, 79.54 mmol), 1-ethyl-3-(3-dimethylaminopropyl)carbodiimide hydrochloride (7.62 g, 39.77 mmol) and 4-dimethylaminopyridine (4.85 g, 39.77 mmol) in DCM (100 mL) was stirred at 20° C. for 16h. The reaction mixture was concentrated in vacuo and the residue was purified by silica gel chromatography using ethyl acetate:petroleum ether (1:5) as eluting solvents to afford 2-(4-chloro-2-fluoro-phenyl)-N-methoxy-N-methyl-acetamide (4.65 g, 73%) as a colorless oil. MS (ESI): m/z=232.1 [M+1]$^+$.

Step B. 1-(4-Chloro-2-fluorophenyl)propan-2-one

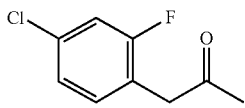

To a mixture of 2-(4-chloro-2-fluoro-phenyl)-N-methoxy-N-methyl-acetamide (4.65 g, 20.07 mmol) in DCM (50 mL) at −78° C. under nitrogen gas, was added methyl magnesium bromide (3.0 m in diethyl ether, 8.03 mL, 24.09 mmol) drop-wise. The reaction mixture was stirred at 25° C. for 30 min. The reaction was quenched by addition of 50 mL of water. The aqueous phase was extracted with ethyl acetate (2×50 mL). The combined organic phases were washed with water, dried over sodium sulfate and concentrated in vacuo. The residue was purified on silica gel chromatography using ethyl acetate:petroleum ether (1:3) as eluting solvents to afford 1-(4-chloro-2-fluoro-phenyl)propan-2-one (2.65 g, 67.2%) as light yellow foam. MS (ESI): m/z=187.1 [M+1]$^+$.

Step C. 1-(4-Chloro-2-fluoro-5-nitrophenyl)propan-2-one

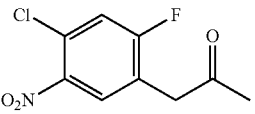

To a solution of 1-(4-chloro-2-fluoro-phenyl)propan-2-one (373.22 mg, 2 mmol) in sulfuric acid (1 mL) at 0° C. was added 2-oxohydrazinecarboximidamide 2-oxide (229.0 mg, 2.20 mmol). The resultant mixture was stirred at 0° C. for 2h. The mixture was poured into ice water and ethyl acetate (50 mL) was added. The organic phase was separated, dried over sodium sulfate and concentrated in vacuo to afford 1-(4-chloro-2-fluoro-5-nitro-phenyl)propan-2-one (400 mg, 78%) as a yellow solid. MS (ESI): m/z=232.1 [M+1]$^+$.

Step D. 1-(4-Chloro-2-fluoro-5-nitrophenyl)propan-2-ol

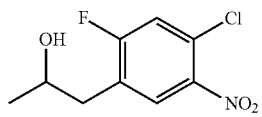

To a solution of 1-(4-chloro-2-fluoro-5-nitro-phenyl)propan-2-one (200 mg, 0.86 mmol) in methanol (4 mL) at 0° C. was added sodium borohydride (65 mg, 1.72 mmol). The resultant mixture was stirred at 0° C. for 1h. The reaction was quenched by addition of saturated ammonium chloride solution. The aqueous phase was extracted with ethyl acetate (2×50 mL). The combined organic phases were washed with water, dried over sodium sulfate and concentrated in vacuo to afford 1-(4-chloro-2-fluoro-5-nitrophenyl)propan-2-ol (160 mg) as light yellow solid, which was used directly to next step without further purification. MS (ESI): m/z=234.2 [M+1]$^+$.

Step E. 6-Chloro-2-methyl-5-nitro-2,3-dihydrobenzofuran

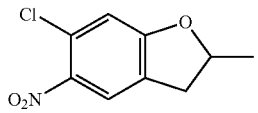

A mixture of 1-(4-chloro-2-fluoro-5-nitro-phenyl)propan-2-ol (105 mg, 0.45 mmol) and potassium tert-butanolate (100 mg, 0.90 mmol) in THF (5 mL) was stirred at 60° C. for 16h. After cooling to room temperature, the reaction was concentrated in vacuo and the residue was purified by silica gel chromatography using ethyl acetate:petroleum ether (1:5) as eluting solvents to afford 6-chloro-2-methyl-5-nitro-2,3-dihydrobenzofuran (50 mg, 52.1%) as light yellow foam. MS (ESI): m/z=214.2 [M+1]$^+$.

Step F. 4-(2-Methyl-5-nitro-2,3-dihydrobenzofuran-6-yl)morpholine

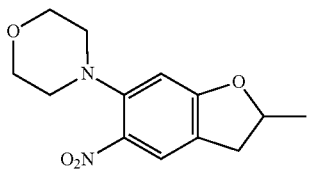 [SMILES: CC1Cc2cc([N+](=O)[O-])c(N3CCOCC3)cc2O1]

A mixture of 6-chloro-2-methyl-5-nitro-2,3-dihydrobenzofuran (100.0 mg, 0.47 mmol) in morpholine (2 mL) was stirred at 110° C. for 16h in a sealed tube. After cooling to room temperature, the reaction was concentrated in vacuo and the residue was purified by silica gel chromatography using ethyl acetate:petroleum ether (5:1) as eluting solvents to afford 4-(2-methyl-5-nitro-2,3-dihydrobenzofuran-6-yl) morpholine (85 mg, 65%) as light yellow solid. MS (ESI): m/z=265.2 [M+1]$^+$.

Step G. 2-Methyl-6-morpholino-2,3-dihydrobenzofuran-5-amine

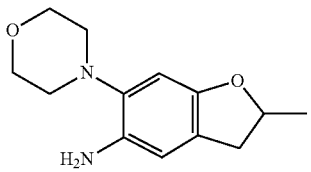

A mixture of 4-(2-methyl-5-nitro-2,3-dihydrobenzofuran-6-yl)morpholine (85 mg, 0.32 mmol) and 10% palladium on carbon (8.5 mg) in methanol (5 mL) was stirred at room temperature under hydrogen atmosphere for 1h. The solid was filtered off and the filtrate was concentrated under reduced pressure to afford 2-methyl-6-morpholino-2,3-dihydrobenzofuran-5-amine (55 mg) as a colorless foam, which was used directly to next step without further purification. MS (ESI): m/z=235.2 [M+1]$^+$.

Step H. N-(2-Methyl-6-morpholino-2,3-dihydrobenzofuran-5-yl)pyrazolo[1,5-a]pyrimidine-3-carboxamide

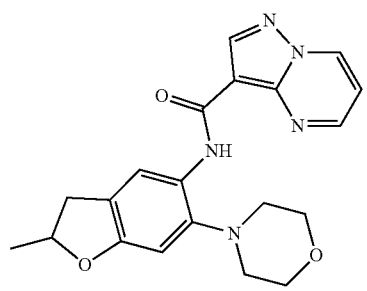 [SMILES: CC1Cc2cc(NC(=O)c3cnn4cccnc34)c(N3CCOCC3)cc2O1]

To a solution of 2-methyl-6-morpholino-2,3-dihydrobenzofuran-5-amine (55 mg, 0.23 mmol) and triethylamine (23 mg, 0.23 mmol) in DCM (4 mL) was stirred at 0° C. A solution of pyrazolo[1,5-a]pyrimidine-3-carbonyl chloride (Example 3, Step B) (42 mg, 0.23 mmol) in DCM (2 mL) was added. The resultant mixture was stirred at 20° C. for 1h. Methanol (2 mL) was added. After concentration, the residue was purified by preparative HPLC ((Xbridge Prep C18 10 um OBD, 19*250 mm, A: acetonitrile 45-75% and 0.01% NH$_3$; B: 10 mM ammonium bicarbonate in water) to afford N-(2-methyl-6-morpholino-2,3-dihydrobenzofuran-5-yl)pyrazolo[1,5-a]pyrimidine-3-carboxamide (45 mg, 51%) as a yellow solid. $^1$H NMR (400 MHz, CDCl$_3$): δ 10.47 (s, 1H), 8.83 (dd, J=1.6, 6.8 Hz, 1H), 8.78 (s, 1H), 8.77 (dd, J=2, 4.4 Hz, 1H), 8.45 (s, 1H), 7.07 (dd, J=4.0, 6.8 Hz, 1H), 6.67 (s, 1H), 4.97-4.92 (m, 1H), 3.96-3.94 (m, 4H), 3.34 (dd, J=8.8, 15.6 Hz, 1H), 2.93-2.91 (m, 4H), 2.84 (dd, J=7.6, 15.6 Hz, 1H), 1.47 (d, J=6.4 Hz, 3H). MS (ESI): m/z=380.2 [M+1]$^+$.

Example 15. (R)—N-(6-(3-(Hydroxymethyl)pyrrolidin-1-yl)-2,2-dimethyl-2,3-dihydrobenzofuran-5-yl) pyrazolo[1,5-a]pyrimidine-3-carboxamide

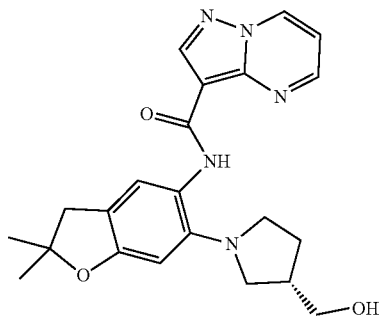 [SMILES: CC1(C)Cc2cc(NC(=O)c3cnn4cccnc34)c(N3CC[C@H](CO)C3)cc2O1]

Step A. (R)-(1-(2,2-Dimethyl-5-nitro-2,3-dihydrobenzofuran-6-yl)pyrrolidin-3-yl)methanol

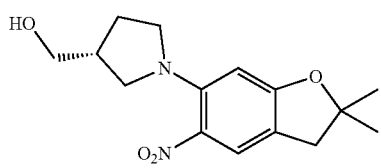 [SMILES: CC1(C)Cc2cc([N+](=O)[O-])c(N3CC[C@@H](CO)C3)cc2O1]

A mixture of 6-fluoro-2,2-dimethyl-5-nitro-3H-benzofuran (141.0 mg, 0.67 mmol), (R)-pyrrolidin-3-ylmethanol (101.3 mg, 1 mmol) and potassium carbonate (230.19 mg, 1.67 mmol) in acetonitrile (30 mL) was stirred at 25° C. for 18h. After filtration and concentration under reduced pressure, it was afforded [(3R)-1-(2,2-dimethyl-5-nitro-3H-benzofuran-6-yl)pyrrolidin-3-yl]methanol (272 mg) as a yellow oil, which was used directly to next step without further purification. MS (ESI): m/z=293.2 [M+1]$^+$.

Step B. (R)-(1-(5-Amino-2,2-dimethyl-2,3-dihydrobenzofuran-6-yl)pyrrolidin-3-yl)methanol

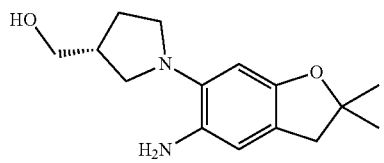

A mixture of [(3R)-1-(2,2-dimethyl-5-nitro-3H-benzofuran-6-yl)pyrrolidin-3-yl]methanol (272.0 mg, 0.93 mmol) and 10% palladium on carbon (27 mg) in methanol (10 mL) was stirred at 25° C. under hydrogen atmosphere for 1h. After filtration and concentration under reduced pressure, the residue was purified on silica gel column eluted ethyl acetate/petroleum ether (2:1) to afford [(3R)-1-(5-amino-2,2-dimethyl-3H-benzofuran-6-yl)pyrrolidin-3-yl]methanol (108 mg, 43%) as red oil. MS (ESI): m/z=263.2 [M+1]$^+$.

Step C. (R)—N-(6-(3-(Hydroxymethyl)pyrrolidin-1-yl)-2,2-dimethyl-2,3-dihydrobenzofuran-5-yl)pyrazolo[1,5-a]pyrimidine-3-carboxamide

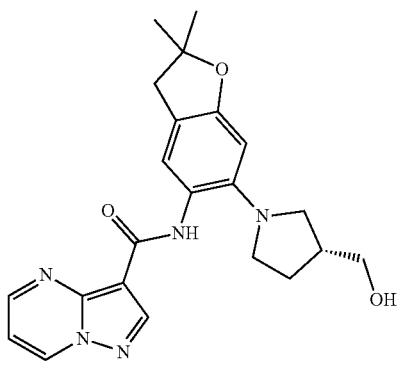 [SMILES: CC1(C)Cc2cc(NC(=O)c3cnn4cccnc34)c(N3CC[C@@H](CO)C3)cc2O1]

A mixture of [(3R)-1-(5-amino-2,2-dimethyl-3H-benzofuran-6-yl)pyrrolidin-3-yl]methanol (108.0 mg, 0.41 mmol) and trimethylamine (124.97 mg, 1.23 mmol) in DCM (15 mL) was stirred at 0° C. To the mixture was added a solution of pyrazolo[1,5-a]pyrimidine-3-carbonyl chloride (Example 3, Step B) (112.12 mg, 0.62 mmol) in DCM (10 mL). The reaction was stirred at 25° C. for 1h. The residue was purified by preparative HPLC (Xbridge Prep C18 10 um OBD, 19*250 mm, A: acetonitrile 45-75% and 0.01% NH$_3$; B: 10 mM ammonium bicarbonate in water) to afford (R)—N-(6-(3-(hydroxymethyl)pyrrolidin-1-yl)-2,2-dimethyl-2,3-dihydrobenzofuran-5-yl)pyrazolo[1,5-a]pyrimidine-3-carboxamide (101.3 mg 60%) as a yellow solid. $^1$H NMR (400 MHz, CDCl$_3$): δ 9.90 (s, 1H), 8.73 (dd, J=1.2, 6.7 Hz, 1H), 8.70 (s, 1H), 8.68 (dd, J=1.6, 4.4 Hz, 1H), 8.12 (s, 1H), 6.95 (dd, J=4.0, 6.8 Hz, 1H), 6.51 (s, 1H), 3.67 (d, J=6.4 Hz, 2H), 3.28-3.16 (m, 2H), 2.95 (s, 2H), 2.91-2.75 (m, 2H), 2.53-2.42 (m, 1H), 2.08-1.98 (m, 1H), 1.78-1.63 (m, 2H), 1.41 (s, 6H). MS (ESI): m/z=408.2 [M+1]$^+$.

Example 16. N-(2-(Hydroxymethyl)-6-(4-(hydroxymethyl)piperidin-1-yl)-2-methyl-2,3-dihydrobenzofuran-5-yl)-6-methylpyrazolo[1,5-a]pyrimidine-3-carboxamide

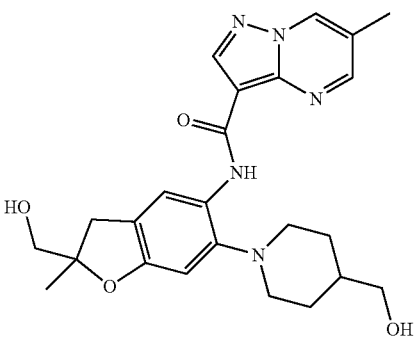 [SMILES: Cc1cnc2c(C(=O)Nc3cc4c(cc3N3CCC(CO)CC3)OC(C)(CO)C4)cnn2c1]

Step A. (1-(2-(Hydroxymethyl)-2-methyl-5-nitro-2,3-dihydrobenzofuran-6-yl)piperidin-4-yl)methanol

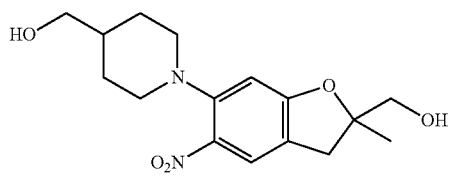

A mixture of (6-chloro-2-methyl-5-nitro-2,3-dihydrobenzofuran-2-yl)methanol, piperidin-4-ylmethanol (Intermediate 2) (150 mg, 0.62 mmol) in piperidin-4-ylmethanol (1.42 g, 12.31 mmol) was stirred at 110° C. for 18h. The mixture was concentrated and the residue was purified by silica gel chromatography using ethyl acetate:petroleum ether (1:1) as eluting solvents to afford (1-(2-(hydroxymethyl)-2-methyl-5-nitro-2,3-dihydrobenzofuran-6-yl)piperidin-4-yl)methanol (100 mg, 50%) as a yellow oil. MS (ESI): m/z=323.1 [M+1]$^+$.

Step B. (1-(5-Amino-2-(hydroxymethyl)-2-methyl-2,3-dihydrobenzofuran-6-yl)piperidin-4-yl)methanol

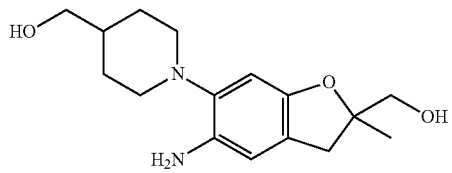 [SMILES: CC1(CO)Cc2cc([N+](=O)[O-])c(N3CCC(CO)CC3)cc2O1]

A mixture of (1-(2-(hydroxymethyl)-2-methyl-5-nitro-2,3-dihydrobenzofuran-6-yl)piperidin-4-yl)methanol (100 mg, 0.31 mmol) and 10% palladium on carbon (25 mg) in methanol (10 mL) was stirred at 25° C. under hydrogen atmosphere for 1h. The solid was filtered. The filtrate was concentrated under reduced pressure to afford (1-(5-amino-2-(hydroxymethyl)-2-methyl-2,3-dihydrobenzofuran-6-yl)piperidin-4-yl)methanol (80 mg) as light green oil, which was used directly to next step without further purification. MS (ESI): m/z=293.2 [M+1]⁺.

Step C. N-(2-(Hydroxymethyl)-6-(4-(hydroxymethyl)piperidin-1-yl)-2-methyl-2,3-dihydrobenzofuran-5-yl)-6-methylpyrazolo[1,5-a]pyrimidine-3-carboxamide

A mixture of (1-(5-amino-2-(hydroxymethyl)-2-methyl-2,3-dihydrobenzofuran-6-yl)piperidin-4-yl)methanol (80 mg, 0.27 mmol), 6-methylpyrazolo[1,5-a]pyrimidine-3-carboxylic acid (69 mg, 0.39 mmol), (3-hydroxy-3H-1,2,3-triazolo[4,5-b]pyridinato-O)tri-1-pyrrolidinylphosphonium hexafluorophosphate (255 mg, 0.49 mmol) and diisopropylethylamine (118 mg, 0.98 mmol) in DMF (10 mL) was stirred at 25° C. for 3h. The mixture was purified by preparative HPLC (Xbridge 21.2*250 mm c18, 10 um; A: acetonitrile 25-55%; B: 10 mM ammonium bicarbonate in water) to afford N-(2-(hydroxymethyl)-6-(4-(hydroxymethyl)piperidin-1-yl)-2-methyl-2,3-dihydrobenzofuran-5-yl)-6-methylpyrazolo[1,5-a]pyrimidine-3-carboxamide (65 mg, 53%) as a yellow solid. ¹H NMR (400 MHz, DMSO-d6) δ 10.45 (s, 1H), 8.69 (s, 1H), 8.63 (d, J=2.0 Hz, 1H), 8.57-8.58 (m, 1H), 8.43 (s, 1H), 6.65 (s, 1H), 3.64-3.66 (m, 4H), 3.23 (d, J=16.0 Hz, 1H), 3.07-3.10 (m, 2H), 2.93 (d, J=15.6 Hz, 1H), 2.63-2.69 (m, 2H), 2.45 (s, 3H), 2.00-2.02 (m, 1H), 1.64-1.80 (m, 5H), 1.54 (s, 1H), 1.46 (s, 3H). MS (ESI): m/z=452.2 [M+1]⁺.

Example 17. N-(6-(2,2-Dimethylmorpholino)-2-(hydroxymethyl)-2-methyl-2,3-dihydrobenzofuran-5-yl)pyrazolo[1,5-a]pyrimidine-3-carboxamide

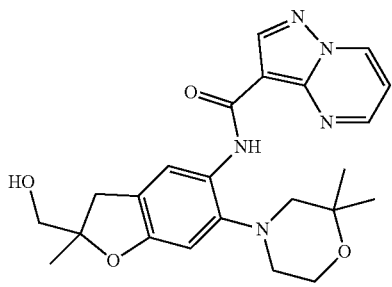 [SMILES: CC1(C)CN(c2cc3c(cc2NC(=O)c2cnn4cccnc24)CC(C)(CO)O3)CCO1]

Step A. (6-(2,2-Dimethylmorpholino)-2-methyl-5-nitro-2,3-dihydrobenzofuran-2-yl)methanol

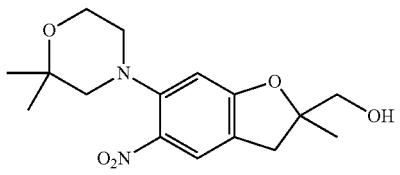 [SMILES: CC1(C)CN(c2cc3c(cc2N)CC(C)(CO)O3)CCO1]

A mixture of (6-chloro-2-methyl-5-nitro-2,3-dihydrobenzofuran-2-yl)methanol (Intermediate 2) (130 mg, 0.53 mmol) in 2,2-dimethylmorpholine (1 mL) was stirred at 100° C. for 18h in a sealed tube. After cooling to room temperature and concentration under reduced pressure, the residue was purified by silica gel chromatography using ethyl acetate:petroleum ether (2:1) as eluting solvents to afford (6-(2,2-dimethylmorpholino)-2-methyl-5-nitro-2,3-dihydrobenzofuran-2-yl)methanol (95 mg, 55%) as a yellow solid. MS (ESI): m/z=323.2 [M+1]⁺.

Step B. (5-Amino-6-(2,2-dimethylmorpholino)-2-methyl-2,3-dihydrobenzofuran-2-yl)methanol

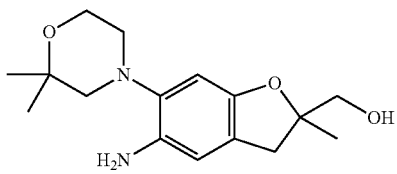

A mixture of (6-(2,2-dimethylmorpholino)-2-methyl-5-nitro-2,3-dihydrobenzofuran-2-yl)methanol (95 mg, 0.29 mmol) and 10% palladium on carbon (9.5 mg) in methanol (10 mL) was stirred at room temperature under hydrogen atmosphere for 1h. The solid was filtered off and the filtrate was concentrated under reduced pressure to afford (5-amino-6-(2,2-dimethylmorpholino)-2-methyl-2,3-dihydrobenzofuran-2-yl)methanol (55 mg) as a colorless foam, which was used directly to the next step without purification. MS (ESI): m/z=293.2 [M+1]⁺.

Step C. N-(6-(2,2-Dimethylmorpholino)-2-(hydroxymethyl)-2-methyl-2,3-dihydrobenzofuran-5-yl)pyrazolo[1,5-a]pyrimidine-3-carboxamide

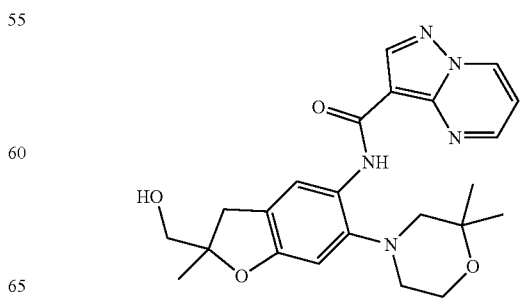

A mixture of pyrazolo[1,5-a]pyrimidine-3-carboxylic acid (34 mg, 0.21 mmol), (3-hydroxy-3H-1,2,3-triazolo[4,5-b]pyridinato-O)tri-1-pyrrolidinylphosphonium hexafluorophosphate (109 mg, 0.21 mmol) and 2,3,4-trimethylpyridine (46 mg, 0.38 mmol) in DMF (5 mL) was stirred at room temperature for 30 min. (5-Amino-6-(2,2-dimethylmorpholino)-2-methyl-2,3-dihydrobenzofuran-2-yl)methanol (55 mg, 0.19 mmol) was added and stirred for 18h. To the reaction was added water. The aqueous phase was extracted with ethyl acetate (2×30 mL). The combined phases were washed with brine, dried over sulfate and concentrated in vacuo. The residue was purified by silica gel chromatography using ethyl acetate:petroleum ether (20:1) as eluting solvents to afford desired product. The product was further purified by preparative HPLC ((Xbridge 21.2*250 mm c18, 10 um; A: acetonitrile 15-30%; B:10 mM ammonium bicarbonate in water)) to afford N-(6-(2,2-dimethylmorpholino)-2-(hydroxymethyl)-2-methyl-2,3-dihydrobenzofuran-5-yl)pyrazolo[1,5-a]pyrimidine-3-carboxamide (48 mg, 58%) as a yellow solid. $^1$H NMR (400 MHz, DMSO-$d_6$): δ 9.97 (s, 1H), 9.37 (dd, J=1.6, 7.2 Hz, 1H), 8.84 (dd, J=1.6, 4.4 Hz, 1H), 8.70 (s, 1H), 8.20 (s, 1H), 7.33 (dd, J=4.4, 6.8 Hz, 1H), 6.61 (s, 1H), 5.05 (t, J=6.0 Hz, 1H), 3.82-3.74 (m, 2H), 3.48-3.40 (m, 2H), 3.20 (d, J=16 Hz, 1H), 2.83 (d, J=15.6 Hz, 1H), 2.73-2.69 (m, 2H), 2.67-2.62 (m, 2H), 1.35 (s, 6H), 1.34 (s, 3H). MS (ESI): m/z=438.3 [M+1]$^+$.

Example 18. N-(6-(3-(Hydroxymethyl)-3-methylpyrrolidin-1-yl)-2,2-dimethyl-2,3-dihydrobenzofuran-5-yl)pyrazolo[1,5-a]pyrimidine-3-carboxamide

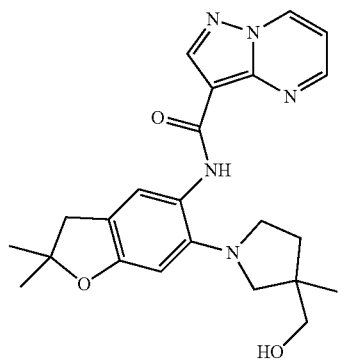

Step A. (1-(2,2-Dimethyl-5-nitro-2,3-dihydrobenzofuran-6-yl)-3-methylpyrrolidin-3-yl)methanol

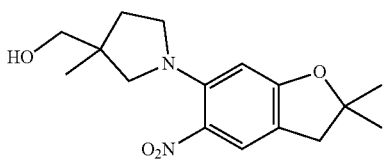

A mixture of 6-fluoro-2,2-dimethyl-5-nitro-3H-benzofuran (100 mg, 0.47 mmol), (3-methylpyrrolidin-3-yl)methanol hydrochloride (144 mg, 0.95 mmol) and cesium carbonate (308 mg, 0.94 mmol) in DMF (6 mL) was stirred at 25° C. for 18h. Water was added. The aqueous phase was extracted with ethyl acetate (30 mL). The organic phase was washed with brine, dried over sodium sulfate and concentrated under reduced pressure. The residue was purified by silica gel chromatography using ethyl acetate:petroleum ether (1:1) to afford (1-(2,2-dimethyl-5-nitro-2,3-dihydrobenzofuran-6-yl)-3-methylpyrrolidin-3-yl)methanol (149 mg, 95%) as a yellow oil. MS (ESI): m/z=307.1 [M+1]$^+$.

Step B. (1-(5-Amino-2,2-dimethyl-2,3-dihydrobenzofuran-6-yl)-3-methylpyrrolidin-3-yl)methanol

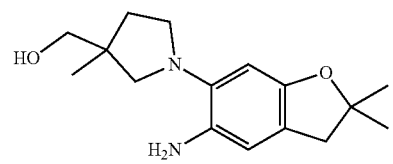 [SMILES: CC1(CO)CCN(c2cc3c(cc2N)CC(C)(C)O3)C1]

A mixture of (1-(2,2-dimethyl-5-nitro-2,3-dihydrobenzofuran-6-yl)-3-methylpyrrolidin-3-yl)methanol (100 mg, 0.33 mmol) and 10% palladium on carbon (40 mg) in methanol (10 mL) was stirred at 25° C. under hydrogen atmosphere for 1h. The reaction was filtered and the filtrate was concentrated under reduced pressure to afford (1-(5-amino-2,2-dimethyl-2,3-dihydrobenzofuran-6-yl)-3-methylpyrrolidin-3-yl)methanol (90 mg, 49%) as a light green oil. MS (ESI): m/z=277.1 [M+1]$^+$.

Step C. N-(6-(3-(Hydroxymethyl)-3-methylpyrrolidin-1-yl)-2,2-dimethyl-2,3-dihydrobenzofuran-5-yl)pyrazolo[1,5-a]pyrimidine-3-carboxamide

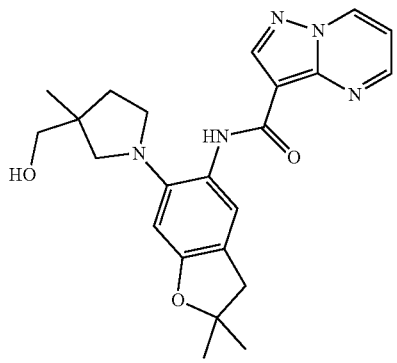 [SMILES: CC1(CO)CCN(c2cc3c(cc2NC(=O)c2cnn4cccnc24)CC(C)(C)O3)C1]

A mixture of (1-(5-amino-2,2-dimethyl-2,3-dihydrobenzofuran-6-yl)-3-methylpyrrolidin-3-yl)methanol (90 mg, 0.32 mmol), pyrazolo[1,5-a]pyrimidine-3-carboxylic acid (64 mg, 0.39 mmol) and (3-hydroxy-3H-1,2,3-triazolo[4,5-b]pyridinato-O)tri-1-pyrrolidinylphosphonium hexafluorophosphate (118 mg, 0.98 mmol) in DMF (10 mL) was stirred at 25° C. for 2h. After concentration under reduced pressure, the residue was purified by preparative HPLC (Xbridge Prep C18 10 um, 19*250 mm, A: acetonitrile 25-55%; B: 10 mM ammonium bicarbonatein water) to afford N-(6-(3-(hydroxymethyl)-3-methylpyrrolidin-1-yl)-2,2-dimethyl-2,3-dihydrobenzofuran-5-yl)pyrazolo[1,5-a]pyrimidine-3-carboxamide (50 mg, 36%) as a yellow solid. 1H NMR (400 MHz, DMSO-$d_6$) δ 9.82 (s, 1H), 8.76-8.80 (m, 3H), 8.12 (s, 1H), 7.01 (dd, J=4.0, 6.8 Hz, 1H), 6.55 (s, 1H), 3.63-3.66 (m, 2H), 3.34-3.39 (m, 1H), 3.10 (d, J=9.2 Hz, 1H), 3.00 (s, 2H), 2.86-2.93 (m, 2H), 2.39 (s, 1H), 1.94-2.01 (m, 1H), 1.60-1.66 (m, 1H), 1.47 (s, 6H), 1.20 (s, 3H). MS (ESI): m/z=422.2 [M+1]⁺.

Example 19. N-[6-[4-(2, 2-Difluoroethyl)piperazin-1-yl]-2-(hydroxymethyl)-2-methyl-3H-benzofuran-5-yl]pyrazolo[1, 5-a]pyrimidine-3-carboxamide

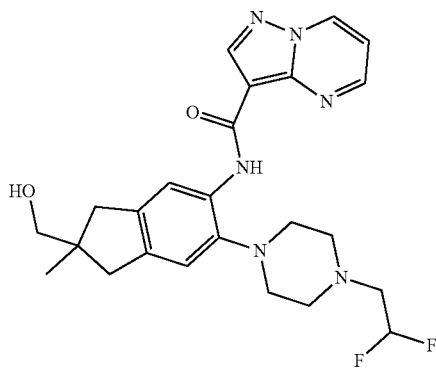 [SMILES: CC1(CO)Cc2cc(NC(=O)c3cnn4cccnc34)c(N3CCN(CC(F)F)CC3)cc2C1]

Step A. [6-[4-(2,2-Difluoroethyl)piperazin-1-yl]-2-methyl-5-nitro-3H-benzofuran-2-yl]methanol

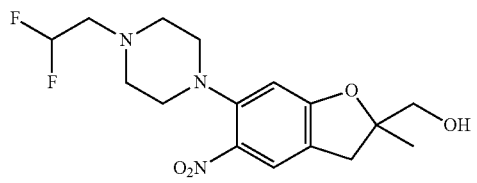

The mixture of (6-chloro-2-methyl-5-nitro-3H-benzofuran-2-yl)methanol (120.0 mg, 0.49 mmol), 1-(2, 2-difluoroethyl)piperazine hydrochloride (720.0 mg, 3.86 mmol) and cesium carbonate (820.0 mg, 2.52 mmol) in DMSO (5 mL) was stirred at 90° C. for 5 d. The reaction mixture was diluted with ethyl acetate (30 mL) and water. The organic phase was isolated and dried over sodium sulfate and concentrated in vacuo. The residue was purified by silica gel chromatography using ethyl acetate:petroleum ether (1:1) as eluting solvents to afford [6-[4-(2, 2-difluoroethyl)piperazin-1-yl]-2-methyl-5-nitro-3H-benzofuran-2-yl]methanol (65 mg, 37%) as a yellow oil. MS (ESI): m/z=358.2 [M+1]⁺.

Step B. [5-Amino-6-[4-(2, 2-difluoroethyl)piperazin-1-yl]-2-methyl-3H-benzofuran-2-yl]methanol

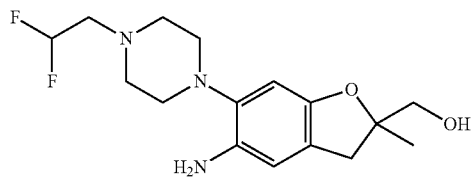

A mixture of [6-[4-(2, 2-difluoroethyl)piperazin-1-yl]-2-methyl-5-nitro-3H-benzofuran-2-yl]methanol (65.0 mg, 0.18 mmol) and 10% palladium on carbon (25.0 mg) in methanol (8 mL) was stirred under hydrogen atmosphere at 25° C. for 1h. After filtration and concentration, it was afforded [5-amino-6-[4-(2, 2-difluoroethyl)piperazin-1-yl]-2-methyl-3H-benzofuran-2-yl]methanol (55 mg, 92%) as a brown oil, which was used directly to the next step without purification. MS (ESI): m/z=328.1 [M+1]⁺.

Step C. N-[6-[4-(2, 2-Difluoroethyl)piperazin-1-yl]-2-(hydroxymethyl)-2-methyl-3H-benzofuran-5-yl]pyrazolo[1, 5-a]pyrimidine-3-carboxamide

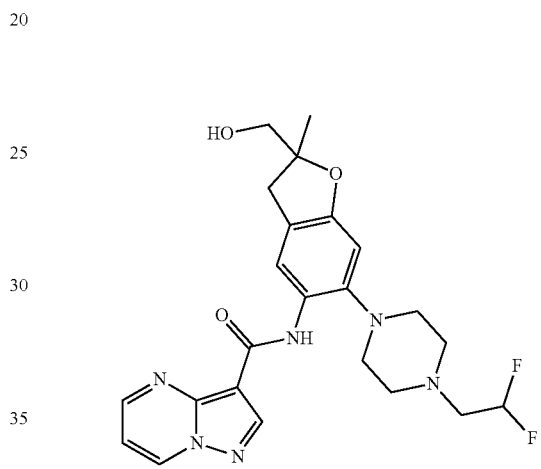

To the mixture of pyrazolo[1, 5-a]pyrimidine-3-carboxylic acid (44.0 mg, 0.27 mmol) and diisopropyethylamine (0.08 mL, 0.51 mmol) in DMF (2 mL) was added 2-(7-aza-1H-benzotriazole-1-yl)-1,1,3,3-tetramethyluronium hexafluorophosphate (130.0 mg, 0.34 mmol). The mixture was stirred at 25° C. for 30 min. To the mixture was added a solution of [5-amino-6-[4-(2, 2-difluoroethyl)piperazin-1-yl]-2-methyl-3H-benzofuran-2-yl]methanol (55.0 mg, 0.17 mmol) in DMF (2 mL) and the mixture was stirred at 25° C. for 3h. After concentration, the residue was purified by preparative HPLC (Xbridge 21.2*250 mm c18, 10 um; A: acetonitrile 25-55%; B: 10 mM ammonium bicarbonate in water) to afford N-[6-[4-(2, 2-difluoroethyl)piperazin-1-yl]-2-(hydroxymethyl)-2-methyl-3H-benzofuran-5-yl]pyrazolo[1,5-a]pyrimidine-3-carboxamide (36.4 mg, 46%) as a yellow solid. ¹H NMR (400 MHz, DMSO-d₆) δ 10.41 (s, 1H), 9.37 (dd, J=2.0, 7.2 Hz, 1H), 8.95 (dd, J=1.6, 4.0 Hz, 1H), 8.68 (s, 1H), 8.31 (s, 1H), 7.35 (dd, J=4, 6.8 Hz, 1H), 6.70 (s, 1H), 6.20 (tt, J=4.4, 14 Hz, 1H), 5.05 (t, J=5.6 Hz, 1H), 3.49-3.37 (m, 2H), 3.19 (d, J=16 Hz, 1H), 2.94-2.72 (m, 11H), 1.34 (s, 3H). MS (ESI): m/z=473.2 [M+1]⁺.

Example 20. Cis-N-[2,2-dimethyl-6-[2-(methylaminomethyl)-1, 3-dioxan-5-yl]-3H-benzofuran-5-yl]pyrazolo[1,5-a]pyrimidine-3-carboxamide

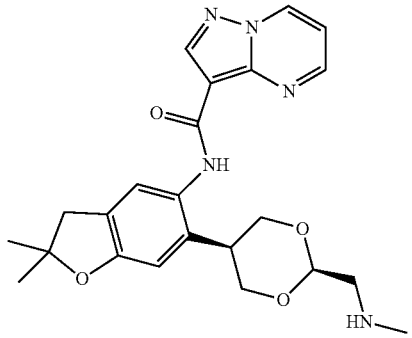

Step A. Cis-2-trimethylsilylethyl N-[[5-(2, 2-dimethyl-5-nitro-3H-benzofuran-6-yl)-1, 3-dioxan-2-yl]methyl]carbamate

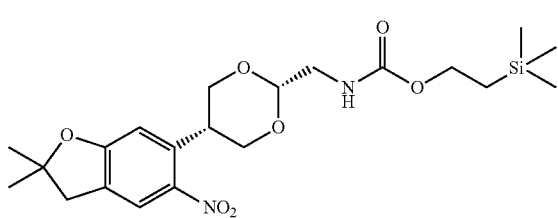

The mixture of 2-(2, 2-dimethyl-5-nitro-3H-benzofuran-6-yl)propane-1, 3-diol (80.0 mg, 0.30 mmol), 2-trimethylsilylethyl N-(2, 2-dimethoxyethyl)carbamate (223.99 mg, 0.90 mmol) and 4-toluene sulfonic acid (3.0 mg, 0.02 mmol) in toluene (5 mL) was stirred at 110° C. in a sealed tube for 72h. The mixture was neutralized with triethylamine. After concentration, the residue was purified by silica gel chromatography using ethyl acetate:petroleum ether (1:5) as eluting solvents to afford cis-2-trimethylsilylethyl N-[[5-(2, 2-dimethyl-5-nitro-3H-benzofuran-6-yl)-1, 3-dioxan-2-yl]methyl]carbamate (40 mg, 30%) as a yellow oil. $^1$HNMR (400 MHz, CDCl$_3$) δ 7.83 (s, 1H), 7.57 (s, 1H), 4.90 (brs, 1H), 4.70 (t, J=4.4 Hz, 1H), 4.24-4.06 (m, 6H), 3.40-3.37 (m, 1H), 3.33-3.29 (m, 2H), 3.01 (s, 2H), 1.49 (s, 6H), 0.94 (t, J=8.4 Hz, 2H), 0.00 (s, 9H). MS (ESI): m/z=475.1 [M+Na]$^+$.

Step B. Cis-2-trimethylsilylethyl-N-[[5-(2, 2-dimethyl-5-nitro-3H-benzofuran-6-yl)-1,3-dioxan-2-yl]methyl]-N-methyl-carbamate

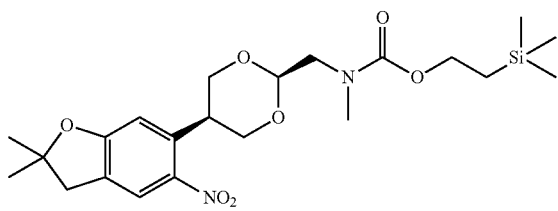

To the mixture of cis-2-trimethylsilylethyl N-[[5-(2, 2-dimethyl-5-nitro-3H-benzofuran-6-yl)-1, 3-dioxan-2-yl]methyl]carbamate (45.0 mg, 0.10 mmol) in DMF (2 mL) was added sodium hydride (30.0 mg, 0.75 mmol) at 0° C. and stirred for 10 min. To the mixture was added methyl iodide (0.02 mL, 0.28 mmol) and reaction was stirred at 20° C. for 1h. The mixture was poured into water. The aqueous phase was extracted with ethyl acetate (50 mL). The organics washed with water, brine and dried over sodium sulfate before concentration under reduced pressure. The residue was purified by silica gel chromatography using ethyl acetate:petroleum ether (1:5) as eluting solvents to afford cis-2-trimethylsilylethyl N-[[5-(2, 2-dimethyl-5-nitro-3H-benzofuran-6-yl)-1,3-dioxan-2-yl]methyl]-N-methyl-carbamate (37 mg, 80%) as a yellow oil. MS (ESI): m/z=489.1 [M+Na]$^+$.

Step C. Cis-2-trimethylsilylethyl N-[[5-(5-amino-2, 2-dimethyl-3H-benzofuran-6-yl)-1, 3-dioxan-2-yl]methyl]-N-methyl-carbamate

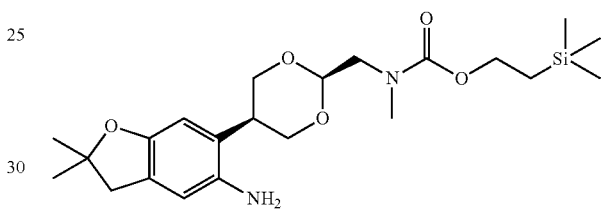

The mixture of cis-2-trimethylsilylethyl N-[[5-(2, 2-dimethyl-5-nitro-3H-benzofuran-6-yl)-1,3-dioxan-2-yl]methyl]-N-methyl-carbamate (37.0 mg, 0.08 mmol) and 10% palladium on carbon (15.0 mg) in methanol (8 mL) was stirred under hydrogen atmosphere at 20° C. for 1h. After filtration and concentration, it was afforded cis-2-trimethylsilylethyl-N-[[5-(5-amino-2, 2-dimethyl-3H-benzofuran-6-yl)-1,3-dioxan-2-yl]methyl]-N-methyl-carbamate (33 mg, 95%) as a colorless oil, which was used directly to next step without further purification. MS (ESI): m/z=437.2 [M+1]$^+$.

Step D. Cis-2-trimethylsilylethyl-N-[[5-[2,2-dimethyl-5-(pyrazolo[1,5-a]pyrimidine-3-carbonylamino)-3H-benzofuran-6-yl]-1,3-dioxan-2-yl]methyl]-N-methyl-carbamate

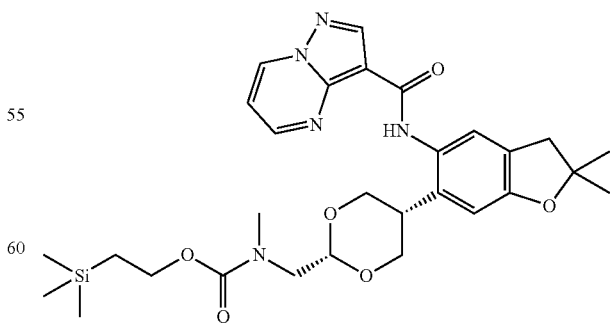

To the mixture of cis-2-trimethylsilylethyl-N-[[5-(5-amino-2,2-dimethyl-3H-benzofuran-6-yl)-1,3-dioxan-2-yl]methyl]-N-methyl-carbamate (32.0 mg, 0.07 mmol), triethylamine (25.0 mg, 0.25 mmol) and 4-dimethylaminopyridine (2.0 mg, 0.02 mmol) in THF (5 mL) was added pyrazolo[1,5-a]pyrimidine-3-carbonyl chloride (20.0 mg, 0.11 mmol) and stirred at 20° C. for 1h. To the mixture was added methanol (2 mL) then the mixture was concentrated to dryness. The residue was purified by silica gel chromatography using methanol: DCM (1:20) as eluting solvents to afford cis-2-trimethylsilylethyl-N-[[5-[2,2-dimethyl-5-(pyrazolo[1,5-a]pyrimidine-3-carbonylamino)-3H-benzofuran-6-yl]-1,3-dioxan-2-yl]methyl]-N-methyl-carbamate (17 mg, 40%) as a yellow oil. MS (ESI): m/z=604.2 [M+Na]+.

Step E. Cis-N-[2,2-dimethyl-6-[2-(methylaminomethyl)-1,3-dioxan-5-yl]-3H-benzofuran-5-yl]pyrazolo[1,5-a]pyrimidine-3-carboxamide

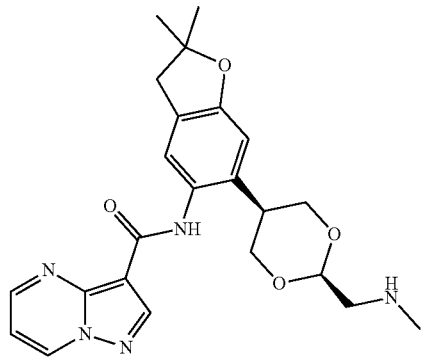 [SMILES: CNC[C@H]1OC[C@@H](c2cc3c(cc2NC(=O)c2cnn4cccnc24)CC(C)(C)O3)CO1]

To the mixture of cis-2-trimethylsilylethyl N-[[5-[2,2-dimethyl-5-(pyrazolo[1,5-a]pyrimidine-3-carbonylamino)-3H-benzofuran-6-yl]-1,3-dioxan-2-yl]methyl]-N-methyl-carbamate (17.0 mg, 0.03 mmol) in DCM (0.40 mL) was added trifluoroacetic acid (200.0 uL) at 0° C. and stirred for 1h. The mixture was neutralized with triethylamine. After concentration, the residue was purified by preparative HPLC (Xbridge 21.2*250 mm c18, 10 um, A: acetonitrile 25-55%; B: 10 mM ammonium bicarbonate in water) to afford cis-N-[2,2-dimethyl-6-[2-(methylaminomethyl)-1,3-dioxan-5-yl]-3H-benzofuran-5-yl]pyrazolo[1,5-a]pyrimidine-3-carboxamide (7.9 mg, 62%) as a yellow solid. $^1$H NMR (400 MHz, CDCl$_3$) δ 9.31 (s, 1H), 8.84 (dd, J=1.6, 6.8 Hz, 1H), 8.74 (s, 1H), 8.65 (dd, J=1.6, 4.0 Hz, 1H), 7.53 (s, 1H), 7.50 (s, 1H), 7.05 (dd, J=4.4, 7.2 Hz, 1H), 4.81 (t, J=5.2 Hz, 1H), 4.31 (d, J=11.6 Hz, 2H), 4.18 (dd, J=3.2, 11.6 Hz, 2H), 3.04 (s, 2H), 2.98-2.93 (m, 1H), 2.81 (d, J=4.8 Hz, 2H), 2.46 (s, 3H), 1.50 (s, 6H). MS (ESI): m/z=438.3 [M+1]+.

Example 21. N-(2-Ethyl-2-methyl-6-morpholino-2,3-dihydrobenzofuran-5-yl)pyrazolo[1,5-a]pyrimidine-3-carboxamide

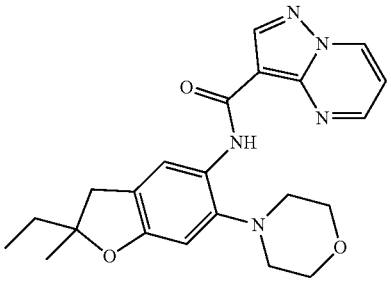 [SMILES: CCC1(C)Cc2cc(NC(=O)c3cnn4cccnc34)c(N3CCOCC3)cc2O1]

Step A.
1-(4-Chloro-2-fluorophenyl)-2-methylbutan-2-ol

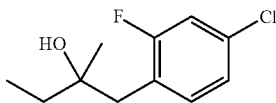

To a solution of 1-(4-chloro-2-fluoro-phenyl)propan-2-one (300 mg, 1.61 mmol) in THF (10 mL) was added ethyl magnesium bromide (1 m in THF, 1.93 mL, 1.93 mmol) drop-wise at −78° C. under nitrogen atmosphere. The mixture was stirred at room temperature for 1h. The reaction was quenched with saturated ammonium chloride solution. The aqueous phase was extracted with ethyl acetate (30 mL). The organic phase was dried over sodium sulfate and concentrated to afford 1-(4-chloro-2-fluoro-phenyl)-2-methyl-butan-2-ol (300 mg) as a colorless oil, which was used directly to next step without further purification. MS (ESI): m/z=199.1 [M-OH]+.

Step B.
6-Chloro-2-ethyl-2-methyl-2,3-dihydrobenzofuran

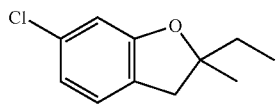

A mixture of 1-(4-chloro-2-fluoro-phenyl)-2-methyl-butan-2-ol (300 mg, 1.38 mmol) and potassium tert-butanolate (387 mg, 3.46 mmol) in THF (20 mL) was stirred at 65° C. for 3h. Water was added and the aqueous was extracted with ethyl acetate (20 mL). The organic phase was washed with brine, dried over sodium sulfate and concentrated under reduced pressure. The residue was purified by silica chromatography using ethyl acetate:petroleum ether (1:100) to afford 6-chloro-2-ethyl-2-methyl-3H-benzofuran (132 mg, 49%) as a colorless oil. HH NMR (400 MHz, CDCl$_3$) δ 7.01 (d, J=8.0 Hz, 1H), 6.77 (dd, J=1.6, 7.6 Hz, 1H), 6.71 (d, J=1.6 Hz, 1H), 3.02 (d, J=15.6 Hz, 1H), 2.86 (d, J=15.6 Hz, 1H), 1.74 (t, J=7.2 Hz, 2H), 1.41 (s, 3H), 0.95 (q, J=7.2 Hz, 3H).

Step C. 4-(2-Ethyl-2-methyl-5-nitro-2,3-dihydrobenzofuran-6-yl)morpholine

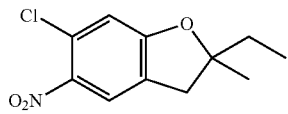 [SMILES: CCC1(C)Cc2cc([N+](=O)[O-])c(Cl)cc2O1]

A mixture of 6-chloro-2-ethyl-2-methyl-3H-benzofuran (132 mg, 0.67 mmol) in DCM (10 mL) was added nitric acid (0.5 mL) drop-wise and the mixture was stirred for 30 min. The mixture was poured into ice water. The aqueous phase was extracted with ethyl acetate (30 mL). The organic phase was washed with saturated sodium bicarbonate solution, dried over sodium sulfate and concentrated under reduced pressure to afford 6-chloro-2-ethyl-2-methyl-5-nitro-3H-benzofuran (126 mg, 67%) as black solid. MS (ESI): m/z=242.1 [M+1]+.

Step D. 4-(2-Ethyl-2-methyl-5-nitro-2,3-dihydrobenzofuran-6-yl)morpholine

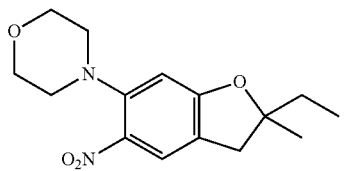 [SMILES: CCC1(C)Cc2cc(N)c(N3CCOCC3)cc2O1]

A mixture of 6-chloro-2-ethyl-2-methyl-5-nitro-3H-benzofuran (132 mg, 0.55 mmol) in morpholine (2 mL) was stirred at 120° C. for 18h. After concentration, the residue was purified by silica gel chromatography using ethyl acetate:petroleum ether (15:100) to afford 4-(2-ethyl-2-methyl-5-nitro-2,3-dihydrobenzofuran-6-yl)morpholine (106 mg, 42%) as a yellow oil. MS (ESI): m/z=293.2 [M+1]+.

Step E. 2-Ethyl-2-methyl-6-morpholino-2,3-dihydrobenzofuran-5-amine

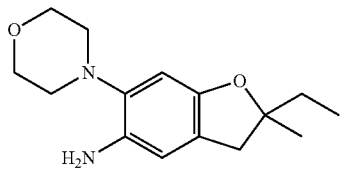

A mixture of 4-(2-ethyl-2-methyl-5-nitro-2,3-dihydrobenzofuran-6-yl)morpholine (106 mg, 0.35 mmol) and 10% palladium on carbon (40 mg) in methanol (10 mL) was stirred at 25° C. under hydrogen atmosphere for 1h. The reaction was filtered and the filtrate was concentrated under reduced pressure to afford (2-ethyl-2-methyl-6-morpholino-2,3-dihydrobenzofuran-5-amine (77 mg, 68%) as light green oil. MS (ESI): m/z=263.3 [M+1]+.

Step F. N-(2-Ethyl-2-methyl-6-morpholino-2,3-dihydrobenzofuran-5-yl)pyrazolo[1,5-a]pyrimidine-3-carboxamide

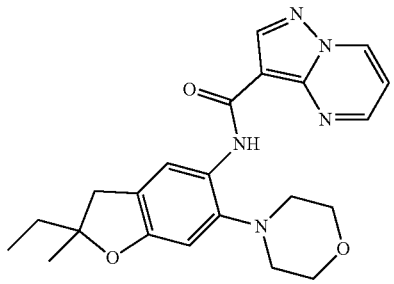 [SMILES: CCC1(C)Cc2cc(NC(=O)c3cnn4cccnc34)c(N3CCOCC3)cc2O1]

To a mixture of 2-ethyl-2-methyl-6-morpholino-3H-benzofuran-5-amine (80 mg, 0.30 mmol) and triethylamine (92 mg, 0.91 mmol) in DCM (15 mL) was added pyrazolo[1,5-a]pyrimidine-3-carbonyl chloride (Example 3, Step B) (83 mg, 0.46 mmol). The mixture was stirred at room temperature for 3h, concentrated and purified by preparative HPLC (Xbridge Prep C18 10 um OBD, 19*250 mm, A: acetonitrile 45-75% and 0.01% ammonia; B: 10 mM ammonium bicarbonate in water) to yield N-(2-ethyl-2-methyl-6-morpholino-3H-benzofuran-5-yl)pyrazolo[1,5-a]pyrimidine-3-carboxamide as a yellow solid (70 mg, 56%). ¹HNMR (400 MHz, CDCl₃): δ 10.46 (s, 1H), 8.83 (dd, J=1.6, 6.8 Hz, 1H), 8.78 (s, 1H), 8.75 (dd, J=2.0, 4.0 Hz, 1H), 8.42 (s, 1H), 7.06 (dd, J=1.6, 6.8 Hz, 1H), 3.94-3.96 (m, 4H), 3.09 (d, J=15.2 Hz, 1H), 2.94 (d, J=15.2 Hz, 1H) 2.91-2.93 (m, 4H), 1.78 (q, J=7.6 Hz, 2H), 0.98 (t, J=7.2 Hz, 3H). MS (ESI): m/z=408.2 [M+1]+.

Example 22. N-(2-Cyclopropyl-2-methyl-6-morpholino-2,3-dihydrobenzofuran-5-yl)pyrazolo[1,5-a]pyrimidine-3-carboxamide

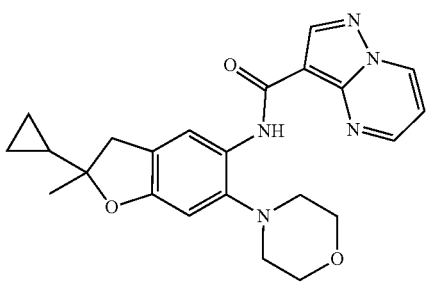

Step A. 1-(4-Chloro-2-fluorophenyl)-2-cyclopropylpropan-2-ol

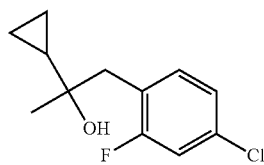

A mixture of 1-(4-chloro-2-fluoro-phenyl)propan-2-one (300 mg, 1.61 mmol) in THF (10 mL) was added drop-wise cyclopropyl magnesium bromide (0.5 M in THF, 3.86 mL, 1.93 mmol) at −78° C. under nitrogen atmosphere. The mixture was stirred at room temperature for 1h. The mixture was quenched with saturated ammonium chloride solution (20 mL) and extracted with ethyl acetate (30 mL). The organic phase was dried over sodium sulfate and concentrated to afford 1-(4-chloro-2-fluorophenyl)-2-cyclopropyl-propan-2-ol as light oil (350 mg), which was used directly to next step without further purification. MS (ESI): m/z=211.1 [M-OH]+

Step B. 6-Chloro-2-cyclopropyl-2-methyl-2,3-dihydrobenzofuran

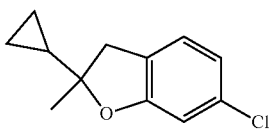

A mixture of 1-(4-chloro-2-fluorophenyl)-2-cyclopropyl-propan-2-ol (317 mg, 1.38 mmol) and potassium tert-butanolate (387 mg, 3.46 mmol) in THF (20 mL) was stirred at 65° C. for 3h. Water was added and the aqueous phase was extracted with ethyl acetate (20 mL). The organic phase was washed with brine, dried over sodium sulfate and concentrated under reduced pressure. The residue was purified by silica gel chromatography using ethyl acetate:petroleum ether (1:100) to afford 6-chloro-2-cyclopropyl-2-methyl-2,3-dihydrobenzofuran (82 mg, 28%) as light oil. ¹H NMR (400 MHz, CDCl₃) δ 7.00 (d, J=7.6 Hz, 1H), 6.77 (dd, J=1.6, 8.0 Hz, 1H), 6.69 (d, J=1.6 Hz, 1H), 3.02 (d, J=15.6 Hz, 1H), 2.90 (d, J=15.6 Hz, 1H), 1.42 (s, 3H), 1.11-1.16 (m, 1H), 0.44-0.49 (m, 3H), 0.33-0.37 (m, 1H).

Step C. 6-Chloro-2-cyclopropyl-2-methyl-5-nitro-2,3-dihydrobenzofuran

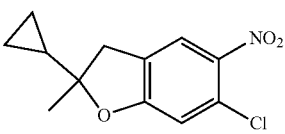 [SMILES: CC1(C2CC2)Cc2cc([N+](=O)[O-])c(Cl)cc2O1]

To a solution of 6-chloro-2-cyclopropyl-2-methyl-2,3-dihydrobenzofuran (82 mg, 0.38 mmol) in DCM (10 mL) was added drop-wise nitric acid (0.5 mL) at 25° C. and the mixture was stirred for 30 min. The mixture was poured into ice water and extracted with ethyl acetate (30 mL). The organic phase was washed with saturated sodium bicarbonate solution, dried over sodium sulfate and concentrated under reduced pressure to afford 6-chloro-2-cyclopropyl-2-methyl-5-nitro-2,3-dihydrobenzofuran as black solid (100 mg, crude). MS (ESI): m/z=254.1 [M+1]⁺.

Step D. 4-(2-Cyclopropyl-2-methyl-5-nitro-2,3-dihydrobenzofuran-6-yl)morpholine

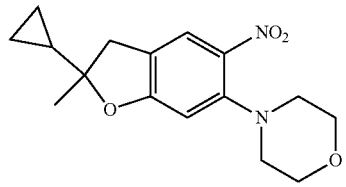

A mixture of 6-chloro-2-cyclopropyl-2-methyl-5-nitro-2,3-dihydrobenzofuran (100 mg, 0.39 mmol) in morpholine (2 mL) was stirred at 120° C. for 18h. The mixture was concentrated and the residue was purified by silica gel chromatography using ethyl acetate:petroleum ether (15:100) as eluting solvents to afford 4-(2-cyclopropyl-2-methyl-5-nitro-2,3-dihydrobenzofuran-6-yl)morpholine (130 mg, 49%) as a yellow oil. MS (ESI): m/z=305.1 [M+1]⁺.

Step E. 2-Cyclopropyl-2-methyl-6-morpholino-2,3-dihydrobenzofuran-5-amine

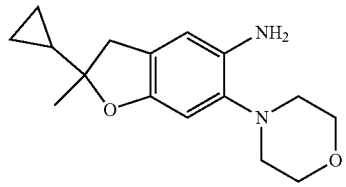 [SMILES: CC1(C2CC2)Cc2cc([N+](=O)[O-])c(N3CCOCC3)cc2O1]

A mixture of 4-(2-cyclopropyl-2-methyl-5-nitro-2,3-dihydrobenzofuran-6-yl)morpholine (130 mg, 0.35 mmol) and 10% palladium on carbon (40 mg) in methanol (10 mL) was stirred at 25° C. under H₂ atmosphere for 1h. The reaction was filtered and the filtrate was concentrated under reduced pressure to afford 2-cyclopropyl-2-methyl-6-morpholino-2,3-dihydrobenzofuran-5-amine (63 mg) as light green oil, which was used directly to next step without further purification. MS (ESI): m/z=275.2 [M+1]⁺.

Step F. N-(2-Cyclopropyl-2-methyl-6-morpholino-2,3-dihydrobenzofuran-5-yl)pyrazolo[1,5-a]pyrimidine-3-carboxamide

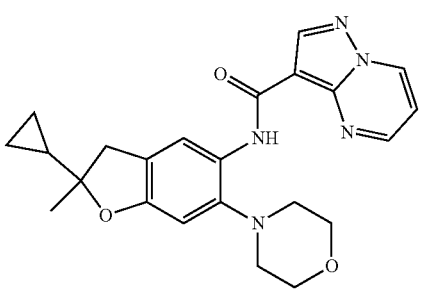 [SMILES: CC1(C2CC2)Cc2cc(NC(=O)c3cnn4cccnc34)c(N3CCOCC3)cc2O1]

A mixture of 2-cyclopropyl-2-methyl-6-morpholino-2,3-dihydrobenzofuran-5-amine (63 mg, 0.23 mmol) and triethylamine (70 mg, 0.69 mmol) in DCM (15 mL) was added pyrazolo[1,5-a]pyrimidine-3-carbonyl chloride (Example 3, Step B) (63 mg, 0.34 mmol). The mixture was stirred at 25° C. for 3h. After concentration, the residue was purified by preparative HPLC (Xbridge Prep C18 10 um OBD, 19*250 mm, A: acetonitrile 45-75% and 0.01% NH$_3$; B:10 mM ammonium bicarbonate in water) to afford N-(2-cyclopropyl-2-methyl-6-morpholino-2,3-dihydrobenzofuran-5-yl)pyrazolo[1,5-a]pyrimidine-3-carboxamide as a yellow solid (30 mg, 31%). $^1$HNMR (400 MHz, CDCl$_3$): δ 10.45 (s, 1H), 8.82 (dd, J=2.0, 7.2 Hz, 1H), 8.78 (s, 1H), 8.76 (dd, J=2.0, 4.0 Hz, 1H), 8.40 (s, 1H), 7.06 (d, J=4.0, 6.8 Hz), 6.63 (s, 1H), 3.93-3.95 (m, 4H), 3.12 (d, J=16.4 Hz, 1H), 2.96 (d, J=16.4 Hz, 1H), 2.89-2.92 (m, 4H), 1.43 (s, 3H), 1.15-1.19 (m, 1H), 0.40-0.49 (m, 4H). MS (ESI): m/z=420.2 [M+1]$^+$.

Example 23. N-(2-(Dimethylcarbamoyl)-2-methyl-6-morpholino-2,3-dihydrobenzofuran-5-yl)pyrazolo[1,5-a]pyrimidine-3-carboxamide

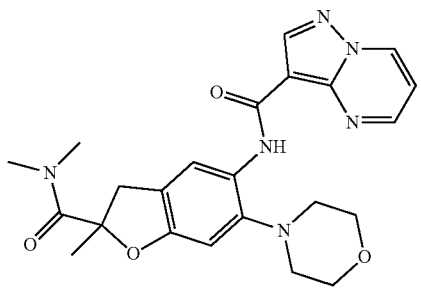 [SMILES: CN(C)C(=O)C1(C)Cc2cc(NC(=O)c3cnn4cccnc34)c(N3CCOCC3)cc2O1]

Step A. 3-(2,4-Difluorophenyl)-2-hydroxy-2-methyl-propanoate

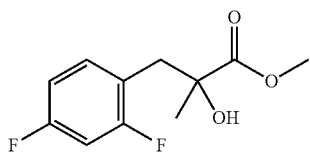

To a solution of magnesium (1206.62 mg, 50.28 mmol) and iodine (89.38 mg, 0.35 mmol) in diethyl ether (50 mL) at reflux was added 2,4-difluorobenzyl bromide (4140.0 mg, 20 mmol) drop-wise and the resulting mixture was stirred for 30 min. This solution was then added to a solution of methyl pyruvate (2055.73 mg, 20.14 mmol) in diethyl ether (50 mL) at −78° C. followed by 2h at room temperature. Saturated ammonium chloride and ethyl acetate (200 mL) were added. The organic phase was separated and dried over ethyl acetate. After concentration, the residue was purified by silica gel chromatography using ethyl acetate:petroleum ether (1:20 to 1:10) as eluting solvent to afford methyl 3-(2,4-difluorophenyl)-2-hydroxy-2-methyl-propanoate (4000 mg, 87%) as a yellow oil. $^1$H NMR (400 MHz, CDCl$_3$): δ 7.25-7.10 (m, 1H) 6.84-6.70 (m, 2H), 3.75 (s, 3H), 3.09 (d, J=14 Hz, 1H), 2.92 (d, d, J=13.6 Hz, 1H), 1.47 (s, 3H).

Step B. 6-Fluoro-2-methyl-2,3-dihydrobenzofuran-2-carboxylicacid

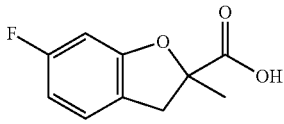

A mixture of methyl 3-(2,4-difluorophenyl)-2-hydroxy-2-methyl-propanoate (4000.0 mg, 17.38 mmol) and potassium tert-butanolate (4874.2 mg, 43.44 mmol) was stirred in THF (180 mL) at 65° C. for 18h. After cooling to room temperature, the reaction was acidified to pH 3 with 1N HCl. Ethyl acetate (200 mL) was added and the organic phase was separated, dried over sodium sulfate and concentration. The residue was purified by silica gel chromatography using ethyl acetate:petroleum ether (3:2) to afford 6-fluoro-2-methyl-2,3-dihydrobenzofuran-2-carboxylic acid (650 mg, 18%) as a yellow solid. $^1$H NMR (400 MHz, CDCl$_3$): δ7.11-6.98 (m, 1H), 6.66-6.50 (m, 2H), 3.60 (d, J=16 Hz, 1H), 3.14 (d, J=16 Hz), 1.77 (s, 3H).

Step C. 6-Fluoro-2-methyl-5-nitro-2,3-dihydrobenzofuran-2-carboxylic acid

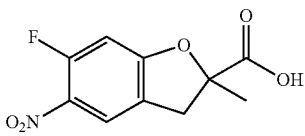 [SMILES: CC1(C(=O)O)Cc2cc([N+](=O)[O-])c(F)cc2O1]

To a solution of 6-fluoro-2-methyl-3H-benzofuran-2-carboxylic acid (500.0 mg, 2.55 mmol) in DCM (20 mL) was added fuming nitric acid (845.23 mg, 12.74 mmol) drop-wise at 20° C. The mixture was stirred for 30 min. The mixture was poured into ice water. The aqueous phase was extracted with ethyl acetate (2×100 mL). The combined organic phases were washed with water, dried over sodium sulfate and concentrated in vacuo to afford 6-fluoro-2-methyl-5-nitro-3H-benzofuran-2-carboxylic acid (580 mg) as light yellow foam, which was used directly to next step without further purification. MS (ESI): m/z=242.0 [M+1]$^+$.

Step D. 2-Methyl-6-morpholino-5-nitro-2,3-dihydrobenzofuran-2-carboxylic acid

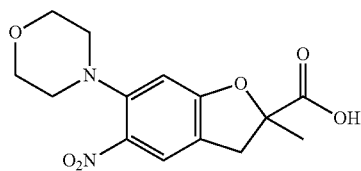 [SMILES: CC1(C(=O)O)Cc2cc([N+](=O)[O-])c(N3CCOCC3)cc2O1]

A mixture of 6-fluoro-2-methyl-5-nitro-3H-benzofuran-2-carboxylic acid (280.00 mg, 1.16 mmol), morpholine (202.29 mg, 2.32 mmol) and cesium carbonate (1513.12 mg, 4.64 mmol) in acetonitrile (5 mL) was stirred at 20° C. for 16h. The mixture was filtered and the filtrate was concentrated in vacuo to obtain 2-methyl-6-morpholino-5-nitro- 3H-benzofuran-2-carboxylic acid (300 mg) as a brown oil, which was used directly to next step without further purification. MS (ESI): m/z=309.1 [M+1]+.

Step E. N,N, 2-Trimethyl-6-morpholino-5-nitro-2,3-dihydrobenzofuran-2-carboxamide

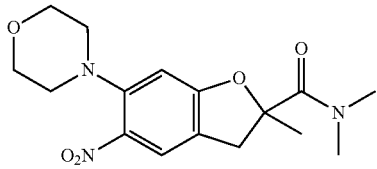

A mixture of 2-methyl-6-morpholino-5-nitro-3H-benzofuran-2-carboxylic acid (120.0 mg, 0.39 mmol), N,N-dimethylamine hydrochloride (63.48 mg, 0.78 mmol), 2-(7-aza-1H-benzotriazole-1-yl)-1,1,3,3-tetramethyluronium hexafluorophosphate (296.0 mg, 0.78 mmol) and diisopropyethylamine (201.10 mg, 1.56 mmol) in DMF (5 mL) was stirred at 20° C. for 2h. Water was added and the aqueous phase was extracted with ethyl acetate (2×50 mL). The combined organic phases were washed with water, dried over sodium sulfate and concentrated in vacuo. The residue was purified by silica gel chromatography using ethyl acetate:petroleum ether (1:1) to afford N,N, 2-trimethyl-6-morpholino-5-nitro-3H-benzofuran-2-carboxamide (100 mg, 69%) as light yellow solid. MS (ESI): m/z=336.2 [M+1]+.

Step F. 5-Amino-N,N, 2-trimethyl-6-morpholino-2,3-dihydrobenzofuran-2-carboxamide

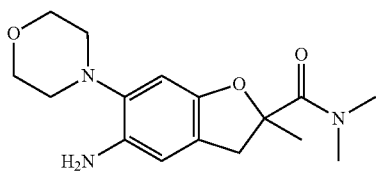 [SMILES: CN(C)C(=O)C1(C)Cc2cc(N)c(N3CCOCC3)cc2O1]

A mixture of N,N, 2-trimethyl-6-morpholino-5-nitro-3H-benzofuran-2-carboxamide (100.00 mg, 0.30 mmol) and 10% palladium on carbon (10 mg) in methanol (10 mL) was stirred at room temperature under hydrogen atmosphere for 1h. The reaction was filtered and the filtrate was concentrated under reduced pressure to afford 5-amino-N,N, 2-trimethyl-6-morpholino-3H-benzofuran-2-carboxamide (100 mg, crude) as a colorless oil, which was used directly to next step without further purification. MS (ESI): m/z=306.2 [M+1]+.

Step G. N-(2-(Dimethylcarbamoyl)-2-methyl-6-morpholino-2,3-dihydrobenzofuran-5-yl)pyrazolo[1,5-a]pyrimidine-3-carboxamide

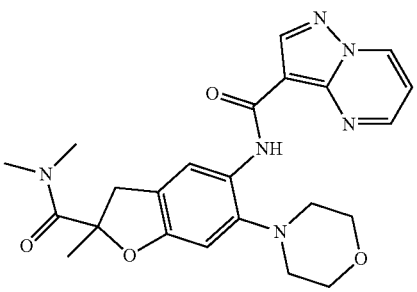 [SMILES: CN(C)C(=O)C1(C)Cc2cc(NC(=O)c3cnn4cccnc34)c(N3CCOCC3)cc2O1]

A mixture of 5-amino-N,N, 2-trimethyl-6-morpholino-3H-benzofuran-2-carboxamide (100.00 mg, 0.33 mmol) and triethylamine (66.27 mg, 0.65 mmol) in DCM (5 mL) was stirred at 0° C. The solution of pyrazolo[1,5-a]pyrimidine-3-carbonyl chloride (Example 3, Step B) (71.36 mg, 0.39 mmol) in DCM (5 mL) was added drop-wise. The mixture was stirred at 20° C. for 1h.

Methanol (3 mL) was added. After concentration, the residue was purified by preparative HPLC ((Xbridge Prep C18 10 um OBD, 19*250 mm, A: acetonitrile 50-70% and 0.01% NH$_3$; B:10 mM ammonium bicarbonate in water) to afford N-[2-(dimethylcarbamoyl)-2-methyl-6-morpholino-3H-benzofuran-5-yl]pyrazolo[1,5-a]pyrimidine-3-carboxamide (60 mg, 41%) as an off-white solid. $^1$H NMR (400 MHz, DMSO-d$_6$): δ 10.46 (s, 1H), 9.38 (d, J=6.8 Hz, 1H), 8.95 (d, J=1.6, 4 Hz, 1H), 8.69 (s, 1H), 8.35 (s, 1H), 7.35 (dd, J=4.4, 6.8 Hz, 1H), 6.85 (s, 1H), 3.90 (d, J=16 Hz, 1H), 3.86-3.83 (m, 4H), 3.16 (s, 3H), 3.05 (d, J=16.4 Hz, 1H), 2.88 (s, 3H), 2.84-2.81 (m, 4H), 1.58 (s, 3H). MS (ESI): m/z=451.2 [M+1]+.

Example 24. N-[6-[4-(1-Amino-2,2,2-trifluoroethyl)-1-piperidyl]-2,2-dimethyl-3H-benzofuran-5-yl]pyrazolo[1,5-a]pyrimidine-3-carboxamide

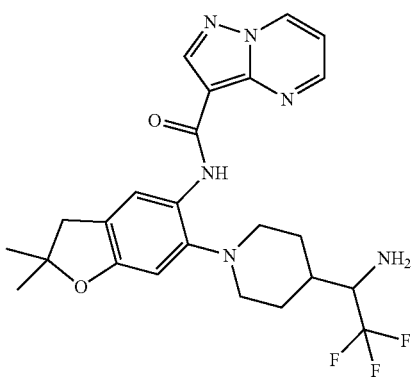 [SMILES: CC1(C)Cc2cc(NC(=O)c3cnn4cccnc34)c(N3CCC(C(N)C(F)(F)F)CC3)cc2O1]

Step A. tert-Butyl 4-((4-methoxybenzylimino)methyl)piperidine-1-carboxylate

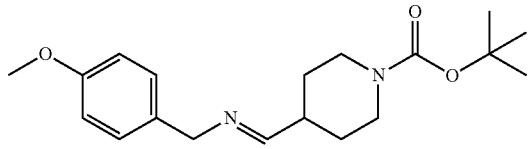 [SMILES: COc1ccc(C/N=C/C2CCN(C(=O)OC(C)(C)C)CC2)cc1]

The mixture of tert-butyl 4-formyl-1-piperidinecarboxylate (1.07 g, 5 mmol) 4-methoxybenzylamine (685.9 mg, 5 mmol) 4A molecular sieves (1.00 g, 5 mmol) in methanol (10 mL) was stirred for 18h. After filtration and concentration, it was afforded tert-butyl 4-((4-methoxybenzylimino)methyl)piperidine-1-carboxylate (1.66 g) as a colorless oil, which used directly to next step without further purification. MS (ESI): m/z=333.3 [M+1]$^+$.

Step B. tert-Butyl 4-(2,2,2-trifluoro-1-(4-methoxybenzylamino)ethyl)piperidine-1-carboxylate

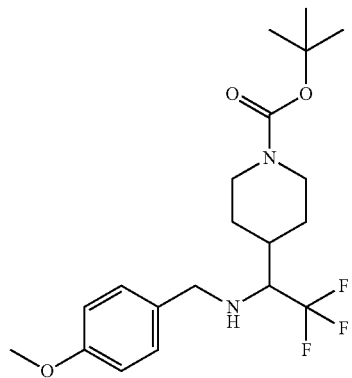 [SMILES: COc1ccc(CNC(C2CCN(C(=O)OC(C)(C)C)CC2)C(F)(F)F)cc1]

To the mixture of tert-butyl 4-[(Z)-(4-methoxyphenyl)methyliminomethyl]piperidine-1-carboxylate (1.66 g, 5 mmol), (trifluoromethyl)trimethylsilane (1.07 g, 7.5 mmol) and potassium hydrogen fluoride (585.0 mg, 7.5 mmol) in acetonitrile (10 mL) was added trifluoroacetic acid (427.5 mg, 3.75 mmol) drop-wise at room temperature. The mixture was stirred at room temperature for 18h. Water was added and the aqueous phase was extracted by ethyl acetate (3×20 mL). The combined organic phases were dried over sodium sulfate and concentrated under reduced pressure. The residue was purified by silica gel chromatography using ethyl acetate: petroleum ether (from 1:10 to 1:6) as eluting solvents to afford tert-butyl 4-[2,2,2-trifluoro-1-[(4-methoxyphenyl)methylamino]ethyl]piperidine-1-carboxylate (1.08 g, 50%) as a colorless oil. MS (ESI): m/z=303.2 [M-100]$^+$

Step C. 2,2,2-Trifluoro-N-[(4-methoxyphenyl)methyl]-1-(4-piperidyl)ethanamine trifluoroacetic acid salt

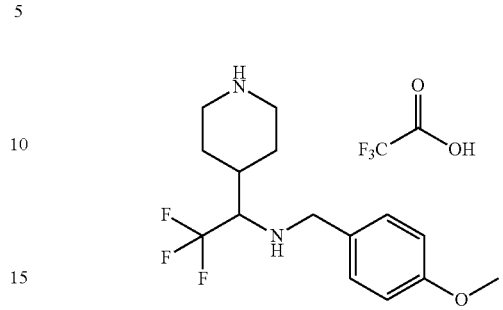

To a solution of tert-butyl 4-[2,2,2-trifluoro-1-[(4-methoxyphenyl)methylamino]ethyl]piperidine-1-carboxylate (150 mg, 0.37 mmol) in DCM (5 mL) was added 2,2,2-trifluoroacetic acid (0.3 mL) and the resulting mixture was stirred at 25° C. for 2h. The reaction mixture was concentrated to dryness to afford 2,2-trifluoro-N-[(4-methoxyphenyl)methyl]-1-(4-piperidyl)ethanamine (100 mg) as the trifluoroacetic acid salt, which was used directly to the next step without further purification. MS (ESI): m/z=303.1 [M+1]$^+$.

Step D. 1-[1-(2,2-Dimethyl-5-nitro-3H-benzofuran-6-yl)-4-piperidyl]-2,2,2-trifluoro-N-[(4-methoxyphenyl)methyl]ethanamine

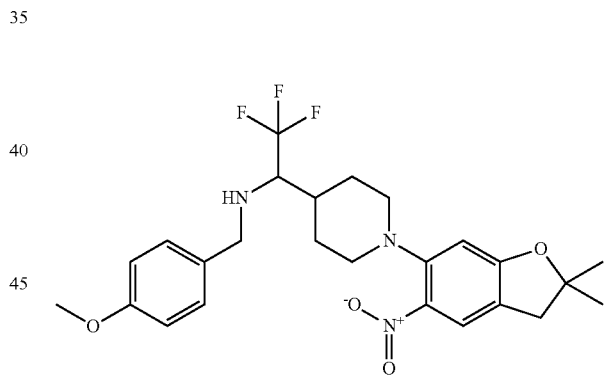

A mixture of 6-fluoro-2,2-dimethyl-5-nitro-3H-benzofuran (100 mg, 0.47 mmol), 2,2,2-trifluoro-N-[(4-methoxyphenyl)methyl]-1-(4-piperidyl)ethanamine trifluoroacetic acid salt (170 mg, 0.56 mmol) and cesium carbonate (490 mg, 1.5 mmol) in DMF (5 mL) was stirred at 25° C. for 18h. Then water was added and the aqueous phase was extracted with ethyl acetate (3×20 mL). The combined organic phases were washed with brine, dried over sodium sulfate and concentrated under reduced pressure. The residue was purified by silica gel column chromatography using ethyl acetate:petroleum ether (0-25%) as eluting solvents to afford 1-[1-(2,2-dimethyl-5-nitro-3H-benzofuran-6-yl)-4-piperidyl]-2,2,2-trifluoro-N-[(4-methoxyphenyl)methyl]ethanamine (190 mg, 74%) as a yellow oil. MS (ESI): m/z=494.3 [M+1]$^+$.

Step E. tert-Butyl 4-[(4-amino-3-pyridyl)oxy]piperidine-1-carboxylate

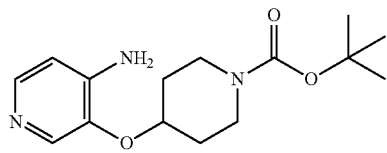 [SMILES: CC(C)(C)OC(=O)N1CCC(Oc2cnccc2N)CC1]

A mixture of 1-[1-(2,2-dimethyl-5-nitro-3H-benzofuran-6-yl)-4-piperidyl]-2,2,2-trifluoro-N-[(4-methoxyphenyl)methyl]ethanamine (180 mg, 0.36 mmol), iron powder (420 mg, 7.52 mmol) and ammonium chloride (396 mg, 7.4 mmol) in ethanol (10 mL) and water (2 mL) was stirred at 80° C. for 2h. After filtration and concentration, the residue was purified by silica gel column chromatography using ethyl acetate:petroleum ether (20%-50%) to afford tert-butyl 4-[(4-amino-3-pyridyl)oxy]piperidine-1-carboxylate as a yellow solid (110 mg, 97%). MS (ESI): m/z=464.3 [M+1]$^+$.

Step F. N-(2,2-Dimethyl-6-(4-(2,2,2-trifluoro-1-((4-methoxybenzyl)amino)ethyl)piperidin-1-yl)-2,3-dihydrobenzofuran-5-yl)pyrazolo[1,5-a]pyrimidine-3-carboxamide

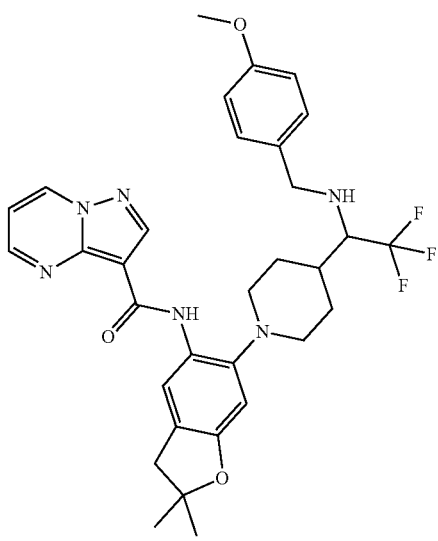 [SMILES: COc1ccc(CNC(C2CCN(c3cc4c(cc3NC(=O)c3cnn5cccnc35)CC(C)(C)O4)CC2)C(F)(F)F)cc1]

A mixture of 2,2-dimethyl-6-[4-[2,2,2-trifluoro-1-[(4-methoxyphenyl)methylamino]ethyl]-1-piperidyl]-3H-benzofuran-5-amine (105 mg, 0.23 mmol), pyrazolo[1,5-a]pyrimidine-3-carboxylic acid (60 mg, 0.37 mmol), 2-(7-aza-1H-benzotriazole-1-yl)-1,1,3,3-tetramethyluronium hexafluorophosphate (140 mg, 0.37 mmol) and diisopropylethylamine (165 mg, 1.28 mmol) in DMF (5 mL) was stirred at 25° C. for 3h. The mixture was purified by preparative HPLC to afford N-[2,2-dimethyl-6-[4-[2,2,2-trifluoro-1-[(4-methoxyphenyl)methylamino] ethyl]-1-piperidyl]-3H-benzofuran-5-yl]pyrazolo[1,5-a]pyrimidine-3-carboxamide (95 mg, 66%) as a yellow solid. MS (ESI): m/z=609.3 [M+1]$^+$.

Step G. N-[6-[4-(1-Amino-2,2,2-trifluoro-ethyl)-1-piperidyl]-2,2-dimethyl-3H-benzofuran-5-yl]pyrazolo[1,5-a]pyrimidine-3-carboxamide

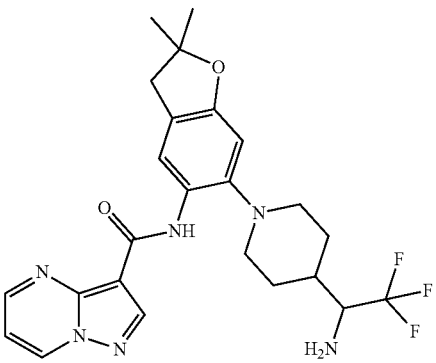 [SMILES: CC1(C)Cc2cc(NC(=O)c3cnn4cccnc34)c(N3CCC(C(N)C(F)(F)F)CC3)cc2O1]

A mixture of N-[2,2-dimethyl-6-[4-[2,2,2-trifluoro-1-[(4-methoxyphenyl) methylamino]ethyl]-1-piperidyl]-3H-benzofuran-5-yl]pyrazolo[1,5-a]pyrimidine-3-carboxamide (90 mg, 0.15 mmol) and 2,2,2-trifluoroacetic acid (1.5 mL) was stirred at 85° C. for 1h. The reaction was basified to pH 8 with 2N ammonia in methanol. Upon concentration, the residue was purified by preparative HPLC (Xbridge 21.2*250 mm c18, 10 um; A: acetonitrile 25-55%; B: 10 mM ammonium bicarbonate in water) to afford N-[6-[4-(1-amino-2,2,2-trifluoro-ethyl)-1-piperidyl]-2,2-dimethyl-3H-benzofuran-5-yl]pyrazolo[1,5-a]pyrimidine-3-carboxamide (29.4 mg, 41%) as a yellow solid. $^1$H NMR (400 MHz, DMSO-d$_6$) δ 10.47 (s, 1H), 9.35 (dd, J=1.6, 7.2 Hz, 1H), 9.13 (dd, J=1.6, 4.4 Hz, 1H), 8.67 (s, 1H), 8.33 (s, 1H), 7.30 (dd, J=4.4, 7.2 Hz, 1H), 6.69 (s, 1H), 3.24-3.12 (m, 1H), 3.03-2.90 (m, 4H), 2.74-2.56 (m, 2H), 2.10-1.87 (m, 3H), 1.84-1.55 (m, 4H), 1.408 (s, 6H). MS (ESI): m/z=489.3 [M+1]$^+$.

Example 25. N-(2-(Methoxymethyl)-2-methyl-6-morpholino-2,3-dihydrobenzofuran-5-yl)pyrazolo[1,5-a]pyrimidine-3-carboxamide

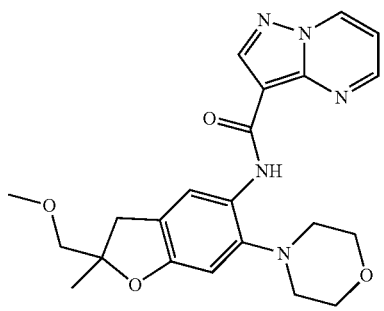 [SMILES: COCC1(C)Cc2cc(NC(=O)c3cnn4cccnc34)c(N3CCOCC3)cc2O1]

Step A. (2-Methyl-6-morpholino-5-nitro-2,3-dihydrobenzofuran-2-yl)methanol

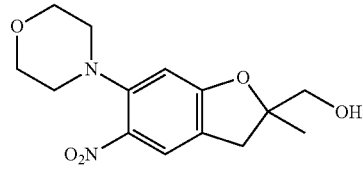

A mixture of (6-chloro-2-methyl-5-nitro-3H-benzofuran-2-yl)methanol (Intermediate 2) (310.0 mg, 1.27 mmol) and morpholine (10 mL) was stirred at 120° C. for 18h. The reaction was concentrated to dryness. The residue was purified by silica gel chromatography using ethyl acetate: petroleum ether (1:4 to 2:3) to afford (2-methyl-6-morpholino-5-nitro-3H-benzofuran-2-yl)methanol (239 mg, 64%) as an orange oil. MS (ESI): m/z=295.1 [M+1]$^+$.

Step B. 4-(2-(Methoxymethyl)-2-methyl-5-nitro-2,3-dihydrobenzofuran-6-yl)morpholine

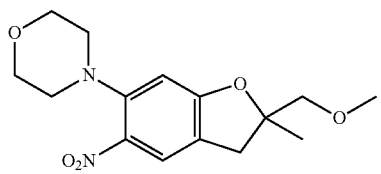 [SMILES: COCC1(C)Cc2cc([N+](=O)[O-])c(N3CCOCC3)cc2O1]

To a solution of (2-methyl-6-morpholino-5-nitro-3H-benzofuran-2-yl)methanol (81.0 mg, 0.28 mmol) in THF (3 mL) was added sodium hydride (9.91 mg, 0.41 mmol) at 0° C. The mixture was stirred for 20 min. Methyl iodide (87.9 mg, 0.62 mmol) was added and the mixture was warmed to room temperature while stirring for 18h. Ethyl acetate (10 mL) and saturated ammonium chloride were added. The organic phase was separated and dried over sodium sulfate before concentration to afford 4-[2-(methoxymethyl)-2-methyl-5-nitro-3H-benzofuran-6-yl]morpholine (121 mg), which was used directly to next step without further purification. MS (ESI): m/z=309.1 [M+1]$^+$.

Step C. 2-(Methoxymethyl)-2-methyl-6-morpholino-2,3-dihydrobenzofuran-5-amine

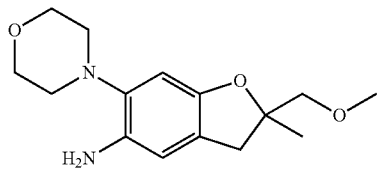 [SMILES: COCC1(C)Cc2cc(N)c(N3CCOCC3)cc2O1]

A mixture of [1-(2,2-dimethyl-5-nitro-3H-benzofuran-6-yl)-4-piperidyl]methanol (121.0 mg, 0.39 mmol) and 10% palladium on carbon (10 mg) in methanol (30 mL) was stirred at 25° C. under hydrogen atmosphere for 2h. The reaction was filtered and the filtrate was concentrated in vacuo to afford [1-(5-amino-2,2-dimethyl-3H-benzofuran-6-yl)-4-piperidyl]methanol (106 mg) as a red oil, which was used directly to next step without further purification. MS (ESI): m/z=279.3[M+1]$^+$.

Step D. N-(2-(Methoxymethyl)-2-methyl-6-morpholino-2,3-dihydrobenzofuran-5-yl)pyrazolo[1,5-a]pyrimidine-3-carboxamide

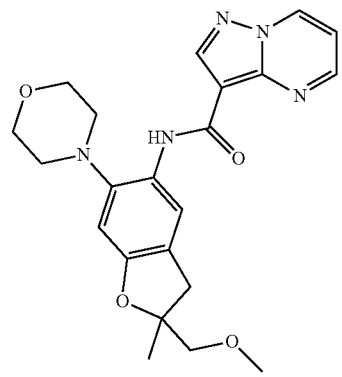 [SMILES: COCC1(C)Cc2cc(NC(=O)c3cnn4cccnc34)c(N3CCOCC3)cc2O1]

To a solution of 2-(methoxymethyl)-2-methyl-6-morpholino-3H-benzofuran-5-amine (106.0 mg, 0.38 mmol) in DMF (10 mL) under nitrogen atmosphere at 0° C. was added (3-hydroxy-3H-1,2,3-triazolo[4,5-b]pyridinato-O)tri-1-pyrrolidinylphosphonium hexafluorophosphate (218.4 mg, 0.42 mmol) followed by 2,4,6-trimethylpyridine (50.76 mg, 0.42 mmol). Pyrazolo[1,5-a]pyrimidine-3-carboxylic acid (71.44 mg, 0.44 mmol) was then introduced and the ice bath was removed allowing the reaction to stir at room temperature for 18h. After concentration, the residue was purified by preparative HPLC (Xbridge Prep C18 10 um OBD, 19*250 mm, A: acetonitrile 45-75% and 0.01% NH$_3$; B: 10 mM ammonium bicarbonate in water) to afford [1-(5-amino-2,2-dimethyl-3H-benzofuran-6-yl)-4-piperidyl]methanol (34.9 mg, 22%) as a yellow solid. $^1$H NMR (400 MHz, CDCl$_3$): δ 10.47 (s, 1H), 8.61 (dd, J=1.6, 5.6 Hz, 1H), 8.78 (s, 1H), 8.75 (dd, J=1.6, 3.6 Hz, 1H), 8.42 (s, 1H), 7.07 (dd, J=3.6, 5.6 Hz, 1H), 6.69 (s, 1H), 3.98-3.90 (m, 4H), 3.47 (s, 2H), 3.43 (s, 3H), 3.22 (d, J=12.8 Hz, 1H), 2.95-2.88 (m, 5H), 1.48 (s, 3H). MS (ESI): m/z=424.1 [M+1]$^+$.

Example 26. N-[6-(4,4-Difluoro-1-piperidyl)-2-(hydroxymethyl)-2-methyl-3H-benzofuran-5-yl]pyrazolo[1,5-a]pyrimidine-3-carboxamide

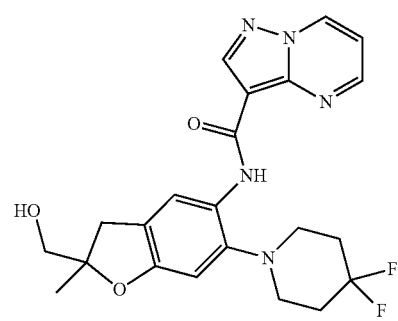 [SMILES: CC1(CO)Cc2cc(NC(=O)c3cnn4cccnc34)c(N3CCC(F)(F)CC3)cc2O1]

411

Step A. [6-(4,4-Difluoro-1-piperidyl)-2-methyl-5-nitro-3H-benzofuran-2-yl]methanol

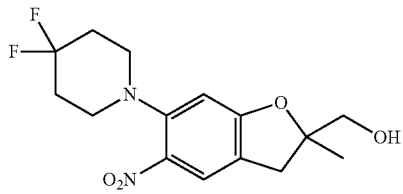 [SMILES: CC1(CO)Cc2cc([N+](=O)[O-])c(N3CCC(F)(F)CC3)cc2O1]

The mixture of (6-chloro-2-methyl-5-nitro-3H-benzofuran-2-yl)methanol (Intermediate 2) (104.0 mg, 0.43 mmol), 4,4-difluoropiperidine hydrochloride (670.0 mg, 4.25 mmol) and cesium carbonate (920.0 mg, 2.82 mmol) in DMSO (5 mL) was stirred at 90° C. for 16h. The mixture was poured into water and the aqueous phase was extracted with ethyl acetate (150 mL). The organic phase was washed with water and brine and dried over sodium sulfate before concentration to dryness. The residue was purified by silica gel chromatography using ethyl acetate:petroleum ether (1:3) as eluting solvents to afford [6-(4, 4-difluoro-1-piperidyl)-2-methyl-5-nitro-3H-benzofuran-2-yl]methanol (100 mg, 71%) as a brown oil. MS (ESI): m/z=329.1 [M+1]$^+$.

Step B. [5-Amino-6-(4,4-difluoro-1-piperidyl)-2-methyl-3H-benzofuran-2-yl]methanol

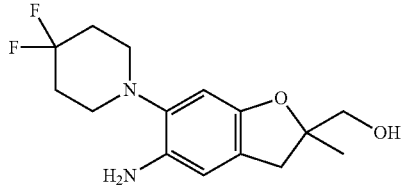

The mixture of [6-(4, 4-difluoro-1-piperidyl)-2-methyl-5-nitro-3H-benzofuran-2-yl]methanol (63.0 mg, 0.19 mmol) and 10% palladium on carbon (28.0 mg) in methanol (8 mL) was stirred under hydrogen atmosphere at 20° C. for 1h. After filtration and concentration, it was afforded [5-amino-6-(4, 4-difluoro-1-piperidyl)-2-methyl-3H-benzofuran-2-yl]methanol (55 mg) as a brown oil, which was used directly in the next step without purification. MS (ESI): m/z=299.1 [M+1]$^+$.

412

Step C. N-[6-(4,4-Difluoro-1-piperidyl)-2-(hydroxymethyl)-2-methyl-3H-benzofuran-5-yl]pyrazolo[1,5-a]pyrimidine-3-carboxamide

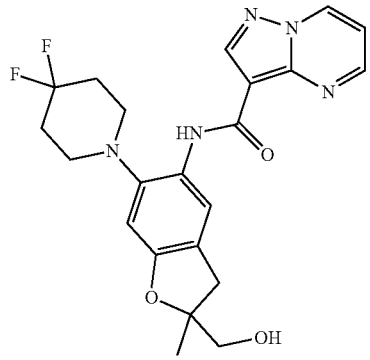 [SMILES: CC1(CO)Cc2cc(NC(=O)c3cnn4cccnc34)c(N3CCC(F)(F)CC3)cc2O1]

To the mixture of pyrazolo[1,5-a]pyrimidine-3-carboxylic acid (45.0 mg, 0.28 mmol) and diisopropyethylamine (0.09 mL, 0.56 mmol) in DMF (2 mL) was added 2-(7-aza-1H-benzotriazole-1-yl)-1,1,3,3-tetramethyluronium hexafluorophosphate (141.0 mg, 0.37 mmol) and the mixture was stirred at 20° C. for 30 min. To the mixture was added the solution of [5-amino-6-(4, 4-difluoro-1-piperidyl)-2-methyl-3H-benzofuran-2-yl]methanol (55.0 mg, 0.18 mmol) in DMF (2 mL) and the mixture was stirred at 20° C. for 16h. After concentration, the residue was purified by preparative HPLC (Xbridge 21.2*250 mm c18, 10 um; A: acetonitrile 5-75%; B: 10 mM ammonium bicarbonate in water) to afford N-[6-(4, 4-difluoro-1-piperidyl)-2-(hydroxymethyl)-2-methyl-3H-benzofuran-5-yl]pyrazolo[1,5-a]pyrimidine-3-carboxamide (35 mg, 43%) as a yellow solid. $^1$H NMR (400 MHz, DMSO-d$_6$) δ 10.43 (s, 1H), 9.39 (dd, J=2.0, 6.8 Hz, 1H), 8.75 (dd, J=2.0, 4.4 Hz, 1H), 8.70 (s, 1H), 8.32 (s, 1H), 7.37 (dd, J=4.0, 6.8 Hz, 1H), 6.73 (s, 1H), 5.05 (t, J=6.0 Hz, 1H), 3.49-3.37 (m, 2H), 3.20 (d, J=16.0 Hz, 1H), 2.98-2.90 (m, 4H), 2.83 (d, J=16.0 Hz, 1H), 2.34-2.14 (m, 4H), 1.34 (s, 3H). MS (ESI): m/z=444.1 [M+1]$^+$.

Examples 27 and 28. (R)—N-(3-hydroxy-3-methyl-7-morpholinochroman-6-yl)pyrazolo[1,5-a]pyrimidine-3-carboxamide and (S)—N-(3-hydroxy-3-methyl-7-morpholinochroman-6-yl)pyrazolo[1,5-a]pyrimidine-3-carboxamide

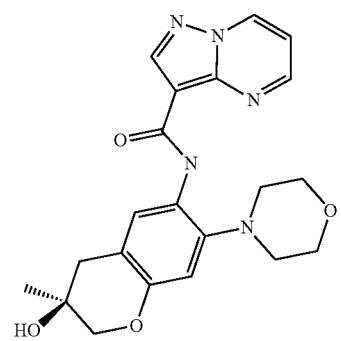

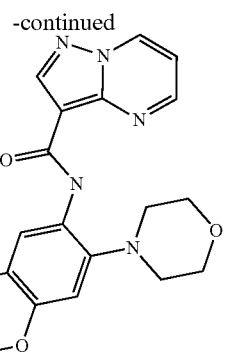

Step A.
2-Chloro-4-((2-methylallyl)oxy)-1-nitrobenzene

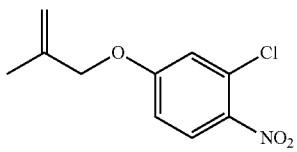

To a solution of 3-chloro-4-nitrophenol (25.2 g, 145 mmol) in acetonitrile (184 mL) was added 3-bromo-2-methylpropene (16.1 mL, 159 mmol) and potassium carbonate (28.0 g, 203 mmol). The reaction mixture was stirred at 55° C. for 18h. The mixture was diluted with isopropyl acetate, filtered and the precipitate was washed with isopropyl acetate and dichloromethane. The combined filtrates were concentrated under reduced pressure and purified by silica gel chromatography eluting using (3:1) isopropyl acetate/MeOH in heptanes (0-40%) as eluting solvents to afford the title compound as a light yellow oil (32.712 g, 99%). $^1$H NMR (400 MHz, DMSO-d6) δ 8.10 (d, J=9.1 Hz, 1H), 7.34 (d, J=2.7 Hz, 1H), 7.14 (dd, J=9.2, 2.7 Hz, 1H), 5.13-5.03 (m, 1H), 5.05-4.97 (m, 1H), 4.66 (s, 2H), 1.83-1.68 (m, 3H).

Step B. 4-(5-((2-Methylallyl)oxy)-2-nitrophenyl)morpholine

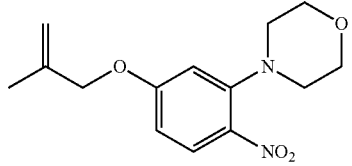 [SMILES: C=C(C)COc1ccc([N+](=O)[O-])c(N2CCOCC2)c1]

To a mixture of 2-chloro-4-((2-methylallyl)oxy)-1-nitrobenzene (3.01 g, 13.2 mmol), and potassium carbonate (6.03 g, 43.7 mmol) in dimethyl sulfoxide (20.1 mL, 280 mmol) was added morpholine (1.15 g, 13.2 mmol) and the mixture was heated to 100° C. in a sealed tube for 1h. The mixture was cooled to room temperature and diluted with water and ethyl acetate. The organic phase was washed with saturated sodium bicarbonate solution, water and brine and dried over sodium sulfate before concentration under reduced pressure. The crude residue was purified by silica gel chromatography using 0-50% isopropyl acetate in heptane as the eluting solvents to afford the title compound as a bright yellow solid (3.22 g, 11.6 mmol, 88%). $^1$H NMR (400 MHz, DMSO-d6) δ 7.90 (d, J=9.0 Hz, 1H), 6.71 (d, J=2.6 Hz, 1H), 6.68 (dd, J=9.0, 2.6 Hz, 1H), 5.08 (d, J=0.8 Hz, 1H), 4.99 (s, 1H), 4.59 (s, 2H), 3.76-3.63 (m, 4H), 3.06-2.95 (m, 4H), 1.82-1.72 (m, 3H).

Step C.
2-(2-methylallyl)-5-morpholino-4-nitrophenol

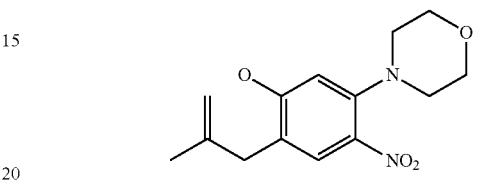

4-(5-((2-Methylallyl)oxy)-2-nitrophenyl)morpholine (5.0 g, 18 mmol) was dissolved in DMF (15 mL, 190 mmol) and heated at 220° C. in the microwave for 60 min in quintuplicate. The reaction mixtures were combined, concentrated under reduced pressure and brought up in isopropyl acetate and washed with water and brine. The aqueous layer was extracted with isopropyl acetate. The combined organic phases were dried over sodium sulfate before concentration under reduced pressure. The crude residue was purified by silica gel chromatography using 0-50% isopropyl acetate in heptane to afford the title compound as a dark orange oil (3.53 g, 12.7 mmol, 12%). $^1$H NMR (400 MHz, DMSO-d6) δ 10.72 (s, 1H), 7.74 (s, 1H), 6.59 (s, 1H), 4.80-4.74 (m, 1H), 4.67-4.60 (m, 1H), 3.71 (q, J=4.0, 3.6 Hz, 4H), 3.20 (s, 2H), 2.95-2.90 (m, 4H), 1.66 (s, 3H). $^1$H NMR (400 MHz, Chloroform-d) δ 7.82 (s, 1H), 6.54 (s, 1H), 6.02 (s, 1H), 5.03-4.96 (m, 1H), 4.94-4.92 (m, 1H), 3.92-3.83 (m, 4H), 3.36 (s, 2H), 3.04 (dd, J=5.5, 3.7 Hz, 4H), 1.75 (s, 3H).

Step D. 1-(2-Hydroxy-4-morpholino-5-nitrophenyl)propan-2-one

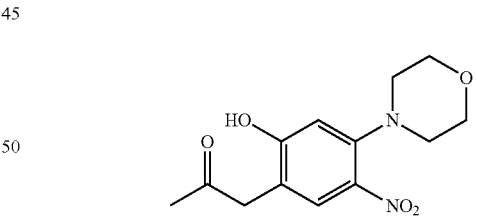

To a solution of 2-(2-methylallyl)-5-morpholino-4-nitrophenol (3.77 g, 13.5 mmol) in water (169 mL, 9.40 mol) and dioxane (521 mL, 6.1 mol) was first added osmium tetroxide (0.08 mol/L, catalytic) in tert-butyl alcohol (700 mg, 0.677 mml) followed by sodium periodate (5.79 g, 27.1 mmol). The suspension formed was stirred overnight at room temperature and poured onto water. The aqueous layer was acidified to neutral pH with 1M HCl and extracted into DCM. The organic phase was dried over sodium sulfate before concentration under reduced pressure. The crude residue was purified by silica gel chromatography using 0-100% isopropyl acetate in heptane to afford the title compound (1.95 g, 6.94 mmol, 51%). $^1$H NMR (400 MHz, Chloroform-d) δ 8.26 (s, 1H), 7.78 (s, 1H), 6.61 (s, 1H), 3.89-3.79 (m, 4H), 3.73 (s, 2H), 3.08-2.99 (m, 4H), 2.36 (s, 3H).

Step E. 1-(2-Methoxy-4-morpholino-5-nitrophenyl)propan-2-one

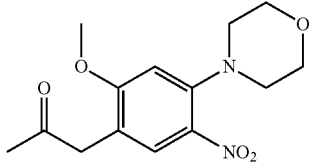 [SMILES: COc1cc(N2CCOCC2)c([N+](=O)[O-])cc1CC(C)=O]

A suspension of sodium hydride (60% in oil, 319 mg, 7.98 mmol) in anhydrous tetrahydrofuran (19.8 mL, 243 mmol) was heated to reflux. Dimethylsulfoxide (19.8 mL, 280 mmol) was slowly added and the reaction was continued for 15 min at reflux. The mixture was then cooled to ambient temperature and trimethylsulfoxonium iodide (1.70 g, 243 mmol) was added. Stirring was continued for 30 min at room temperature. A solution of 1-(2-Hydroxy-4-morpholino-5-nitrophenyl)propan-2-one (1.44 g, 5.15 mmol) dissolved in tetrahydrofuran (5.48 mL) was added and the reaction mixture was stirred at room temperature for 30 min followed by heating at 50° C. for 18h. Water was then added and the mixture was extracted with DCM (6×). The combined organic phases were washed water (3×), and dried over sodium sulfate before concentration under reduced pressure. The crude residue was purified by silica gel chromatography using 0-100% isopropyl acetate in heptane to afford the crude product as a yellow foam/oil residue.

Step F. 1-(5-Amino-2-methoxy-4-morpholinophenyl)propan-2-one

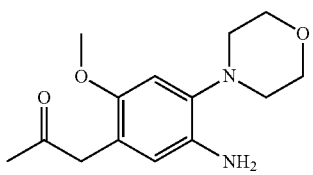

1-(2-Methoxy-4-morpholino-5-nitrophenyl)propan-2-one (1.03 g, 3.51 mmol) was dissolved in ethanol (17.2 mL, 295 mmol) and treated with 10% palladium activated carbon (373 mg, 0.3509 mmol) and the flask was put under a hydrogen atmosphere. After 4h the reaction mixture was filtered through celite and concentrated under reduced pressure. The crude material was carried on without further purification.

Step G. (R)—N-(3-hydroxy-3-methyl-7-morpholinochroman-6-yl)pyrazolo[1,5-a]pyrimidine-3-carboxamide and (S)—N-(3-hydroxy-3-methyl-7-morpholinochroman-6-yl)pyrazolo[1,5-a]pyrimidine-3-carboxamide

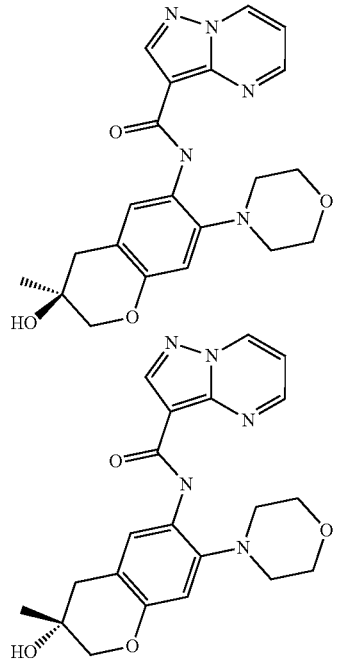

A 100 mL RBF equipped with a stir bar was charged with pyrazolo[1,5-a]pyrimidine-3-carboxylic acid (745 mg, 4.335 mmol) and purged with nitrogen. DMF (12.4 mL, 161 mmol) was added and the mixture was cooled 0° C. (7-Azabenzotriazol-1-yloxy)tripyrrolidinophosphonium hexafluorophosphate (2.28 g, 4.146 mmol) was then added, followed by 2,4,6-trimethylpyridine (0.55 mL, 4.146 mmol). Crude 1-(5-amino-2-methoxy-4-morpholinophenyl)propan-2-one (1.000 g, 3.77 mmol) was then introduced and the reaction was allowed to stir at room temperature for 18h. The reaction mixture was filtered through a plug of silica and concentrated under reduced pressure. The crude material was purified and resolved via Chiral SFC to afford the title compounds as yellow solids. Stereochemistry was arbitrarily assigned based on peak elution.

Example 27, Peak 1 (37 mg, 2.5%): Purified via Chiral SFC (Thar 350 SFC (Lux Cellulose-1, 30×250 mm, 5 um), 40% MeOH isocratic (0.1% $NH_{40}H$) in $C_{02}$). $^1$H NMR (400 MHz, DMSO-d6) δ 10.37 (s, 1H), 9.37 (dd, J=7.0, 1.6 Hz, 1H), 8.95 (dd, J=4.2, 1.6 Hz, 1H), 8.67 (s, 1H), 8.16 (s, 1H), 7.34 (dd, J=7.0, 4.2 Hz, 1H), 6.70 (s, 1H), 4.83 (s, 1H), 3.90-3.80 (m, 4H), 3.76 (s, 2H), 2.87-2.79 (m, 4H), 2.76-2.60 (m, 2H), 1.20 (s, 3H). MS (ESI): m/z=410.2 [M+1]$^+$.

Example 28, Peak 2 (41 mg, 2.7%): Purified via Chiral SFC (Thar 350 SFC (Chiral Technologies AD-H, 50×250 mm, 5 um), 40% MeOH isocratic (0.1% $NH_{40}H$) in $C_{02}$) $^1$H NMR (400 MHz, DMSO-d6) δ 10.37 (s, 1H), 9.37 (dd, J=7.0, 1.6 Hz, 1H), 8.95 (dd, J=4.2, 1.6 Hz, 1H), 8.67 (s, 1H), 8.16 (s, 1H), 7.34 (dd, J=7.0, 4.2 Hz, 1H), 6.70 (s, 1H), 4.83 (s, 1H), 3.88-3.79 (m, 4H), 3.76 (s, 2H), 2.89-2.76 (m, 4H), 2.76-2.58 (m, 2H), 1.20 (s, 3H). MS (ESI): m/z=410.2 [M+1]$^+$.

Examples 29 and 30. (R)—N-(2-(hydroxymethyl)-2-methyl-6-morpholino-2,3-dihydrobenzofuran-5-yl)-6-methylpyrazolo[1,5-a]pyrimidine-3-carboxamide and (S)—N-(2-(hydroxymethyl)-2-methyl-6-morpholino-2,3-dihydrobenzofuran-5-yl)-6-methylpyrazolo[1,5-a]pyrimidine-3-carboxamide

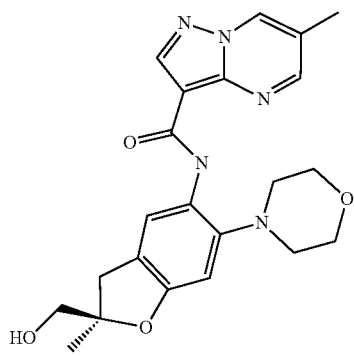

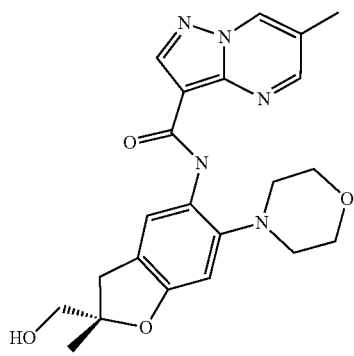

A solution of 6-methylpyrazolo[1,5-a]pyrimidine-3-carboxylic acid (58 mg, 0.33 mmol) in DMF (1.0 mL) was purged with nitrogen and cooled to 0° C. (7-Azabenzotriazol-1-yloxy)tripyrrolidinophosphonium hexafluorophosphate (170 mg, 0.31 mmol) was then added followed by 2,4,6-trimethylpyridine (0.04 mL, 0.31 mmol). (5-amino-2-methyl-6-morpholino-2,3-dihydrobenzofuran-2-yl)methanol (75 mg, 0.28 mmol) was then introduced and the reaction was allowed to warm to ambient temperature and stirred for 18h. The reaction mixture was filtered through a plug of silica, washed with a solution of 20% methanol in DCM. The filtrate was then concentrated and purified and resolved via chiral SFC (PIC 100 SFC (Lux Cellulose-3, 21.1*150 mm, 5 um), 25% MeOH isocratic (0.1% NH4OH) in $CO_2$) to afford the title compounds as solids. Stereochemistry was arbitrarily assigned based on peak elution.

Example 29, Peak 1: (23 mg, 20%): $^1$H NMR (400 MHz, DMSO-d6) δ 10.37 (s, 1H), 9.23 (dd, J=2.0, 1.1 Hz, 1H), 8.86 (d, J=2.0 Hz, 1H), 8.59 (s, 1H), 8.29 (s, 1H), 6.69 (s, 1H), 5.03 (t, J=5.8 Hz, 1H), 3.89-3.80 (m, 4H), 3.42 (q, J=5.5 Hz, 2H), 3.20 (d, J=16.5 Hz, 1H), 2.88-2.77 (m, 5H), 2.47-2.41 (m, 3H), 1.34 (s, 3H). MS (ESI): m/z=424.2[M+1]$^+$.

Example 30, Peak 2: (23 mg, 20%): $^1$H NMR (400 MHz, DMSO-d6) δ 10.37 (s, 1H), 9.23 (dd, J=2.0, 1.1 Hz, 1H), 8.86 (d, J=2.0 Hz, 1H), 8.59 (s, 1H), 8.29 (s, 1H), 6.69 (s, 1H), 5.03 (t, J=5.8 Hz, 1H), 3.89-3.80 (m, 4H), 3.42 (q, J=5.5 Hz, 2H), 3.20 (d, J=16.5 Hz, 1H), 2.88-2.77 (m, 5H), 2.47-2.41 (m, 3H), 1.34 (s, 3H). MS (ESI): m/z=424.2[M+1]$^+$.

Examples 31 and 32. (R)—N-(2-(hydroxymethyl)-2-methyl-6-morpholino-2,3-dihydrobenzofuran-5-yl)pyrazolo[1,5-a]pyrimidine-3-carboxamide and (S)—N-(2-(hydroxymethyl)-2-methyl-6-morpholino-2,3-dihydrobenzofuran-5-yl)pyrazolo[1,5-a]pyrimidine-3-carboxamide

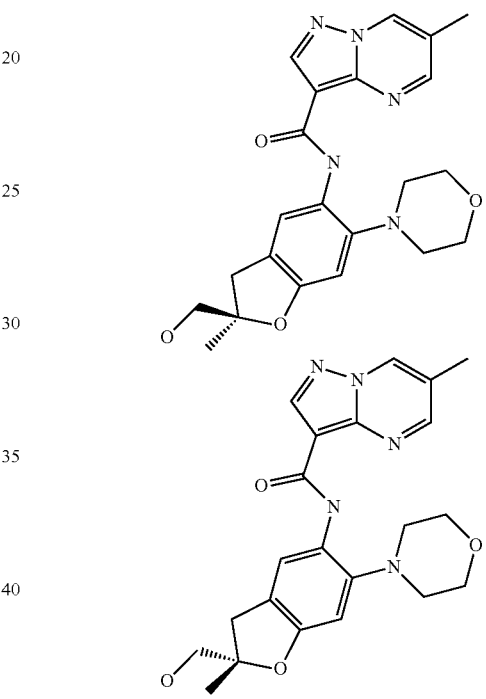

N-(2-(hydroxymethyl)-2-methyl-6-morpholino-2,3-dihydrobenzofuran-5-yl)pyrazolo[1,5-a]pyrimidine-3-carboxamide (Example 6) was resolved via chiral SFC (PIC 100 SFC (Lux Cellulose-3, 21.1*150 mm, Sum), 25% MeOH isocratic (0.1% NH$_{40}$H) in $CO_2$) to afford the title compounds as solids. Stereochemistry was arbitrarily assigned based on peak elution.

Example 31, Peak 1: $^1$H NMR (400 MHz, DMSO-d6) δ 10.43 (s, 1H), 9.37 (dd, J=7.0, 1.6 Hz, 1H), 8.94 (dd, J=4.2, 1.6 Hz, 1H), 8.68 (s, 1H), 8.29 (s, 1H), 7.34 (dd, J=7.0, 4.2 Hz, 1H), 6.70 (s, 1H), 5.10-4.98 (m, 1H), 3.91-3.74 (m, 4H), 3.43 (t, J=5.7 Hz, 2H), 3.20 (dd, J=15.9, 0.7 Hz, 1H), 2.90-2.73 (m, 5H), 1.34 (s, 3H). MS (ESI): m/z=410.2 [M+1]$^+$.

Example 32, Peak 2: $^1$H NMR (400 MHz, DMSO-d6) δ 10.43 (s, 1H), 9.37 (dd, J=7.0, 1.6 Hz, 1H), 8.94 (dd, J=4.2, 1.6 Hz, 1H), 8.68 (s, 1H), 8.29 (s, 1H), 7.34 (dd, J=7.0, 4.2 Hz, 1H), 6.70 (s, 1H), 5.10-4.98 (m, 1H), 3.91-3.74 (m, 4H), 3.43 (t, J=5.7 Hz, 2H), 3.20 (dd, J=15.9, 0.7 Hz, 1H), 2.90-2.73 (m, 5H), 1.34 (s, 3H). MS (ESI): m/z=410.2 [M+1]$^+$.

Example 33. N-(2,2-dimethyl-6-morpholino-2,3-dihydrobenzofuran-5-yl)pyrazolo[1,5-a]pyrimidine-3-carboxamide

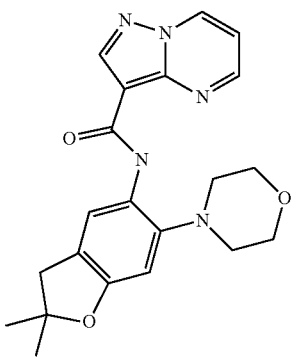

Step A. 4-(2,2-Dimethyl-5-nitro-2,3-dihydrobenzofuran-6-yl)morpholine

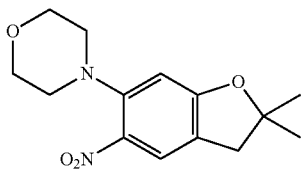 [SMILES: CC1(C)Cc2cc([N+](=O)[O-])c(N3CCOCC3)cc2O1]

2-(2-Methylallyl)-5-morpholino-4-nitrophenol (1.0 g, 3.6 mmol) was dissolved in MeOH (12 mL) and cooled to 0° C. A solution of 35% aqueous HCl (12 mL) was added and the reaction mixture was allowed to warm to ambient temperature and then heated at reflux for 60h. The reaction was cooled to room temperature, neutralized with saturated sodium bicarbonate and extracted with isopropyl acetate. The organic phase was dried over sodium sulfate, filtered, and absorbed onto celite under reduced pressure. The crude residue was purified by silica gel chromatography using (0-30%) isopropyl acetate in heptane to afford the title compound as a yellow foam/oil residue (520 mg, 1.87 mmol, 52%). $^1$H NMR (400 MHz, DMSO-d6) δ 7.85 (t, J=1.2 Hz, 1H), 6.60 (s, 1H), 3.76-3.61 (m, 4H), 3.01 (d, J=1.1 Hz, 2H), 2.98-2.90 (m, 4H), 1.44 (s, 6H). $^1$H NMR (400 MHz, Chloroform-d) δ 7.85 (t, J=1.2 Hz, 1H), 6.44 (s, 1H), 3.90-3.79 (m, 4H), 3.05-3.01 (m, 4H), 3.00 (d, J=1.1 Hz, 2H), 1.51 (s, 6H).

Step B. 2,2-Dimethyl-6-morpholino-3H-benzofuran-5-amine

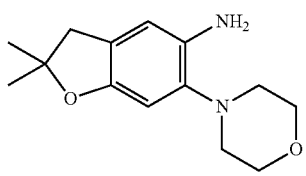 [SMILES: CC1(C)Cc2cc(N)c(N3CCOCC3)cc2O1]

The mixture of 4-(2,2-dimethyl-5-nitro-3H-benzofuran-6-yl)morpholine (60 mg, 0.22 mmol) and 10% palladium on carbon (30 mg) in methanol (8 mL) was stirred under hydrogen atmosphere at 25° C. for 1h. After filtration through a plug of celite and concentration, it was afforded 2,2-dimethyl-6-morpholino-3H-benzofuran-5-amine (50 mg) as a yellow oil, which was directly used in the next step without purification. MS (ESI): m/z=249.2[M+1]$^+$.

Step C. N-(2,2-dimethyl-6-morpholino-2,3-dihydrobenzofuran-5-yl)pyrazolo[1,5-a]pyrimidine-3-carboxamide

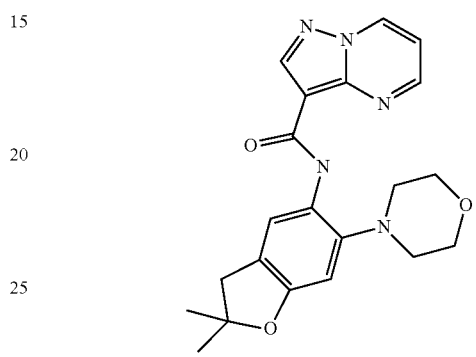

A solution of pyrazolo[1,5-a]pyrimidine-3-carboxylic acid (370 mg, 2.1 mmol) in DMF (6.2 mL) was purged with nitrogen and cooled to 0° C. (7-Azabenzotriazol-1-yloxy)tripyrrolidinophosphonium hexafluorophosphate (1.1 g, 2.1 mmol) was then added followed by 2,4,6-trimethylpyridine (0.27 mL, 2.1 mmol). 2,2-Dimethyl-6-morpholino-2,3-dihydrobenzofuran-5-amine (460 mg, 1.9 mmol) was then introduced and the reaction was allowed to warm to ambient temperature and stirred for 18h. The reaction mixture was filtered through a plug of silica, washed with 20% methanol in DCM and the filtrate was then concentrated and purified via Prep-HPLC ((Gemini-NX 50*30 mm c18, 5um, 110A), acetonitrile 20-60% (0.1% NH$_{40}$H) in water) to afford 330 mg of the title compound as a solid. $^1$H NMR (400 MHz, DMSO-d6) δ 10.43 (s, 1H), 9.41-9.32 (m, 1H), 8.98-8.91 (m, 1H), 8.68 (s, 1H), 8.31 (s, 1H), 7.34 (dd, J=7.0, 4.2 Hz, 1H), 6.71 (s, 1H), 3.89-3.77 (m, 4H), 3.04-2.96 (m, 2H), 2.86-2.78 (m, 4H), 1.42 (s, 6H). MS (ESI): m/z=394.2 [M+1]$^+$.

Example 34. N-(6-Methoxy-2,2-dimethyl-2,3-dihydrobenzofuran-5-yl)pyrazolo[1,5-a]pyrimidine-3-carboxamide

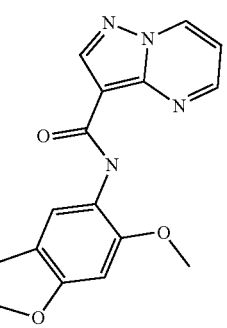

Step A. 6-Methoxy-2,2-dimethyl-5-nitro-2,3-dihydrobenzofuran

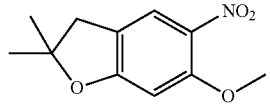

The mixture of cesium carbonate (300.0 mg, 0.92 mmol), palladium diacetate (12.8 mg, 0.06 mmol), 6-bromo-2,2-dimethyl-5-nitro-3H-benzofuran (Intermediate 1) (156.0 mg, 0.57 mmol) and racemic-2-(di-tert-butylphosphino)-1,1'-binaphthyl (228.2 mg, 0.57 mmol) in methanol (0.50 mL) and toluene (5.0 mL) was heated in a sealed tube at 80° C. under microwave condition for 3h. The reaction was concentrated to dryness under reduced pressure and then purified by silica gel chromatography using ethyl acetate:petroleum ether (1:10) to afford 6-methoxy-2,2-dimethyl-5-nitro-3H-benzofuran (155 mg, 97%) as red solid. MS (ESI): m/z=224.2 [M+1]$^+$.

Step B. 6-Methoxy-2,2-dimethyl-2,3-dihydrobenzofuran-5-amine

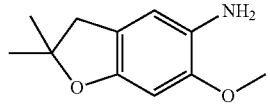

A mixture of 10% palladium on carbon (31.0 mg) and 6-methoxy-2,2-dimethyl-5-nitro-3H-benzofuran (155.0 mg, 0.69 mmol) in methanol (15 mL) was stirred at 25° C. under hydrogen atmosphere for 2h. After filtration over a plug of celite and concentration under reduced pressure, 6-methoxy-2,2-dimethyl-3H-benzofuran-5-amine (111 mg, 62%) was afforded as a yellow oil. MS (ESI): m/z=194.2 [M+1]$^+$.

Step C. N-(6-Methoxy-2,2-dimethyl-2,3-dihydrobenzofuran-5-yl)pyrazolo[1,5-a]pyrimidine-3-carboxamide

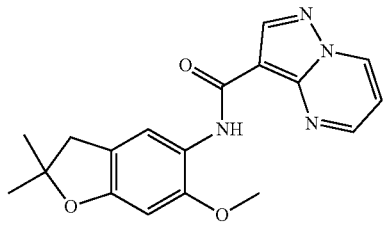 [SMILES: COc1cc2c(cc1NC(=O)c1cnn3cccnc13)CC(C)(C)O2]

A mixture of pyrazolo[1,5-a]pyrimidine-3-carboxylic acid (107.76 mg, 0.66 mmol), (7-azabenzotriazol-1-yloxy)tripyrrolidinophosphoniumhexafluorophosphate (329.44 mg, 0.63 mmol), N-ethyl-N-isopropylpropan-2-amine (222.72 mg, 1.72 mmol) and 6-methoxy-2,2-dimethyl-3H-benzofuran-5-amine (111.0 mg, 0.57 mmol) in DMF (10 mL) was stirred at room temperature for 18h. After filtration and concentration, the residue was purified by preparative HPLC reverse phase chromatography (phenomenex, Gemini C18, 21.2×100 mm. 5 um, 110A, A: acetonitrile 25-45%; B: 0.05% formic acid in water) to afford N-(6-methoxy-2,2-dimethyl-3H-benzofuran-5-yl)pyrazolo[1,5-a]pyrimidine-3-carboxamide (110 mg, 57%) as a yellow solid. $^1$H NMR (400 MHz, CDCl$_3$): δ 10.04 (s, 1H), 8.80 (dd, J=1.6, 7.2 Hz, 1H), 8.75 (s, 1H), 8.71 (dd, J=1.6, 4.0 Hz, 1H), 8.29 (s, 1H), 7.02 (dd, J=4.0, 7.2 Hz, 1H), 6.43 (s, 2H), 3.91 (s, 3H), 3.02 (s, 2H), 1.49 (s, 6H). MS (ESI): m/z=339.2 [M+1]$^+$.

Example 35. N-(8-Morpholino-2,3,4,5-tetrahydrobenzo[b][1,4]oxazepin-7-yl)pyrazolo[1,5-a]pyrimidine-3-carboxamide

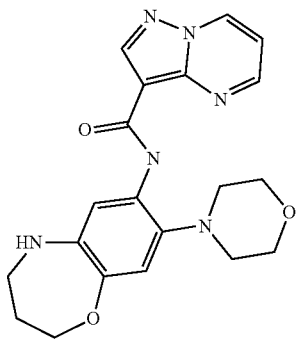 [SMILES: O=C(Nc1cc2c(cc1N1CCOCC1)OCCCN2)c1cnn2cccnc12]

Step A. N-(4-Chloro-2-hydroxyphenyl)benzamide

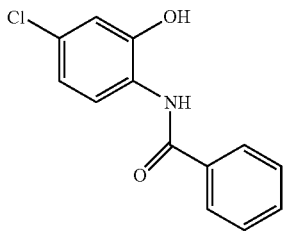 [SMILES: O=C(Nc1ccc(Cl)cc1O)c1ccccc1]

To a solution of 2-amino-5-chlorophenol (1.45 g, 10.1 mmol) in ethyl acetate (30 mL) and water (30 mL) was added sodium bicarbonate (1.27 g, 15.15 mmol) and benzoyl chloride (1.42 g, 10.1 mmol). The mixture was stirred at room temperature for 1h. The organic phase was washed with brine, dried over sodium sulfate and concentrated in vacuo. The residue was washed with petroleum ether to afford N-(4-chloro-2-hydroxy-phenyl)benzamide (2.34 g, 94%) as a brown solid. MS (ESI): m/z=248.1 [M+1]$^+$.

Step B. (8-Chloro-3,4-dihydrobenzo[b][1,4]oxazepin-5(2H)-yl)(phenyl)methanone

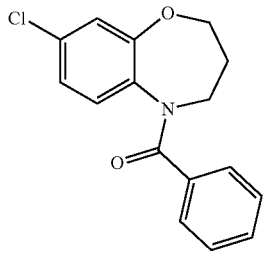 [SMILES: O=C(c1ccccc1)N1CCCOc2cc(Cl)ccc21]

To a solution of N-(4-chloro-2-hydroxy-phenyl)benzamide (2.08 g, 8.4 mmol) in acetonitrile (16 mL) and DCM (24 mL) was added 1,3-dibromopropane (6781.83 mg, 33.59 mmol) and aliquot 336 (tri-n-octylmethylammonium chloride) (339.41 mg, 0.84 mmol). Then sodium hydride (1343.67 mg, 33.59 mmol, 60% wt with mineral oil) were added. The mixture was heated at 60° C. for 3h. Saturated ammonium chloride solution was added. The aqueous phase was extracted with ethyl acetate (2×200 mL). The combined organic phases were washed with brine and dried over sodium sulfate. After filtration and concentration, the residue was purified by silica gel column eluted ethyl acetate: petroleum ether (1:1) to afford (8-chloro-3,4-dihydro-2H-1,5-benzoxazepin-5-yl)-phenyl-methanone (1.3 g, 54%) as off-white solid. MS (ESI): m/z=288.1 [M+1]$^+$.

Step C. 8-Chloro-2,3,4,5-tetrahydrobenzo[b][1,4]oxazepine

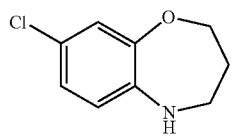 [SMILES: Clc1ccc2c(c1)OCCCN2]

(8-Chloro-3,4-dihydro-2H-1,5-benzoxazepin-5-yl)-phenyl-methanone (1.0 g, 3.48 mmol) was dissolved in 1,4-dioxane (20 mL) and 6 m hydrogen chloride solution (87.11 mL, 522.66 mmol) was added. The mixture was heated at reflux for 20h. Saturated ammonium chloride solution was added and the aqueous phase was extracted with ethyl acetate (100 mL). The organic extract was washed with brine and dried over sodium sulfate. After filtration and concentration under reduced pressure, the residue was purified by silica gel chromatography using ethyl acetate:petroleum ether (1:3) as eluting solvents to afford (8-chloro-3,4-dihydro-2H-1,5-benzoxazepin-5-yl)-phenyl-methanone (808 mg, 100%) as a brown solid. MS (ESI): m/z=184.1 [M+1]$^+$.

Step D. 8-Chloro-7-nitro-2,3,4,5-tetrahydrobenzo[b][1,4]oxazepine

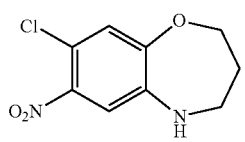 [SMILES: O=[N+]([O-])c1cc2c(cc1Cl)OCCCN2]

To a solution of 8-chloro-2,3,4,5-tetrahydro-1,5-benzoxazepine (183.0 mg, 1 mmol) in concentrated sulfuric acid (4 mL) was slowly added guanidine nitrate (121.58 mg, 1 mmol) at 0° C. The reaction was stirred for 30 min. The mixture was poured into ice water. The solution was adjusted to pH=7.0 by saturated aqueous sodium carbonate. The aqueous phase was extracted with ethyl acetate (30 mL). The organic phase wash was concentrated under reduced pressure to afford 8-chloro-7-nitro-2,3,4,5-tetrahydro-1,5-benzoxazepine (185 mg) as a red solid, which was used directly to next step without further purification. MS (ESI): m/z=229.0 [M+1]$^+$.

Step E. 8-Morpholino-7-nitro-2,3,4,5-tetrahydrobenzo[b][1,4]oxazepine

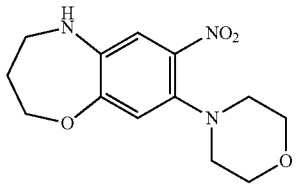 [SMILES: O=[N+]([O-])c1cc2c(cc1N1CCOCC1)OCCCN2]

A mixture of 8-chloro-7-nitro-2,3,4,5-tetrahydro-1,5-benzoxazepine (185.0 mg, 0.81 mmol) and morpholine (10 mL) was stirred at 120° C. for 18h. After concentration, the residue was purified by silica gel chromatography using ethyl acetate:petroleum ether (1:5 to 1:3) to afford 8-morpholino-7-nitro-2,3,4,5-tetrahydro-1,5-benzoxazepine (193 mg, 64.1%) as orange solid. MS (ESI): m/z=280.1 [M+1]$^+$.

Step F. 8-Morpholino-2,3,4,5-tetrahydrobenzo[b][1,4]oxazepin-7-amine

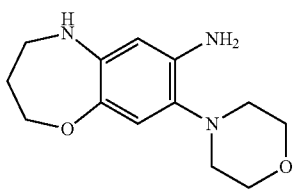 [SMILES: Nc1cc2c(cc1N1CCOCC1)OCCCN2]

A mixture of 10% palladium on carbon (40.0 mg) and 8-morpholino-7-nitro-2,3,4,5-tetrahydro-1,5-benzoxazepine (193.0 mg, 0.69 mmol) in methanol (15 mL) was stirred at 25° C. under hydrogen atmosphere for 2h. After filtration and concentration in vacuo, it was afforded 8-morpholino-2,3,4,5-tetrahydro-1,5-benzoxazepin-7-amine (154 mg, 89%) as a red oil. MS (ESI): m/z=20.1 [M+1]$^+$.

425

Step G. N-(8-Morpholino-2,3,4,5-tetrahydrobenzo[b][1,4]oxazepin-7-yl)pyrazolo[1,5-a]pyrimidine-3-carboxamide

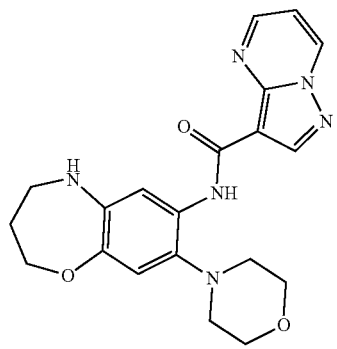 [SMILES: O=C(Nc1cc2c(cc1N1CCOCC1)OCCCN2)c1cnn2cccnc12]

A mixture of 8-morpholino-2,3,4,5-tetrahydro-1,5-benzoxazepin-7-amine (193.0 mg, 0.77 mmol) and triethylamine (235.0 mg, 2.32 mmol) in DCM (10 mL) was stirred at 0° C. To this mixture was added pyrazolo[1,5-a]pyrimidine-3-carbonyl chloride (Example 3, Step B) (210.85 mg, 1.16 mmol) and then the reaction was stirred at 25° C. for 1h. After concentration under reduced pressure, the residue was purified by preparative HPLC (Phenomenex, Gemini C18, 21.2×100 mm. 5 um, 110A, A: acetonitrile 25-45%; B: 0.05% formic acid in water) to afford N-(8-morpholino-2,3,4,5-tetrahydro-1,5-benzoxazepin-7-yl)pyrazolo[1,5-a]pyrimidine-3-carboxamide (35 mg, 12%) as dark yellow solid. $^1$H NMR (400 MHz, CDCl$_3$): δ 10.60 (s, 1H), 8.83 (dd, J=1.6, 7.2 Hz, 1H), 8.79-8.76 (m, 1H), 8.20 (s, 1H), 7.07 (dd, J=4.0, 7.2 Hz, 1H), 6.88 (s, 1H), 4.07 (t, J=5.6 Hz, 2H), 3.98-3.93 (m, 4H), 3.22 (t, J=5.6 Hz, 2H), 2.92-2.85 (m, 4H), 2.04-1.96 (m, 2H). m/z=395.1 [M+1]$^+$.

Example 36 and 37. (R)—N-(6-(2,2-dimethylmorpholino)-2-(hydroxymethyl)-2-methyl-2,3-dihydrobenzofuran-5-yl)pyrazolo[1,5-a]pyrimidine-3-carboxamide and (S)—N-(6-(2,2-dimethylmorpholino)-2-(hydroxymethyl)-2-methyl-2,3-dihydrobenzofuran-5-yl)pyrazolo[1,5-a]pyrimidine-3-carboxamide

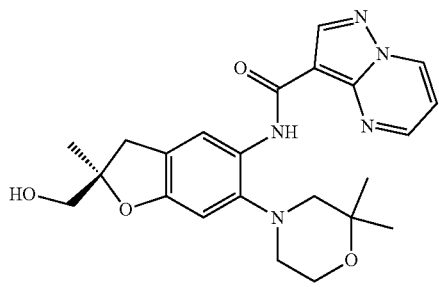

426

-continued

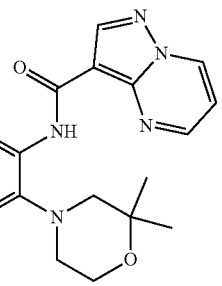

Step A. (6-(2,2-Dimethylmorpholino)-2-methyl-5-nitro-2,3-dihydrobenzofuran-2-yl)methanol

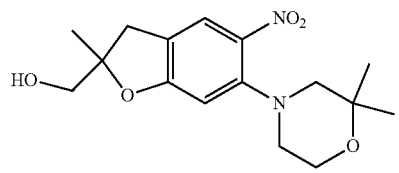

A mixture of (6-chloro-2-methyl-5-nitro-2,3-dihydrobenzofuran-2-yl)methanol (Intermediate 2) (130 mg, 0.53 mmol) in 2,2-dimethylmorpholine (0.5 mL) was stirred at 100° C. for 18h in a sealed tube. After concentration, the residue was purified by silica gel chromatography using ethyl acetate:petroleum ether (1:1) as eluting solvents to afford (6-(2,2-dimethylmorpholino)-2-methyl-5-nitro-2,3-dihydrobenzofuran-2-yl)methanol (95 mg, 55%) as a yellow solid. MS (ESI): m/z=323.3 [M+1]$^+$.

Step B. (5-Amino-6-(2,2-dimethylmorpholino)-2-methyl-2,3-dihydrobenzofuran-2-yl)methanol

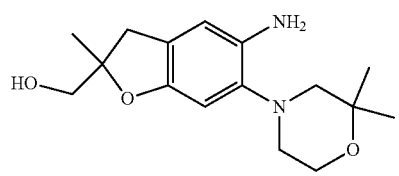 [SMILES: CC1(C)CN(c2cc3c(cc2[N+](=O)[O-])CC(C)(CO)O3)CCO1]

A mixture of (6-(2,2-dimethylmorpholino)-2-methyl-5-nitro-2,3-dihydrobenzofuran-2-yl)methanol (95 mg, 0.29 mmol) and 10% palladium on carbon (10 mg) in methanol (5 mL) was stirred at room temperature for 1h under an atmosphere of hydrogen. The reaction was then filtered over a plug of celite and the filtrate was concentrated under reduced pressure to afford (5-amino-6-(2,2-dimethylmorpholino)-2-methyl-2,3-dihydrobenzofuran-2-yl)methanol (55 mg), which was used directly in the next step without purification. MS (ESI): m/z=293.1 [M+1]$^+$.

Step C. (R)—N-(6-(2,2-dimethylmorpholino)-2-(hydroxymethyl)-2-methyl-2,3-dihydrobenzofuran-5-yl)pyrazolo[1,5-a]pyrimidine-3-carboxamide and (S)—N-(6-(2,2-dimethylmorpholino)-2-(hydroxymethyl)-2-methyl-2,3-dihydrobenzofuran-5-yl)pyrazolo[1,5-a]pyrimidine-3-carboxamide

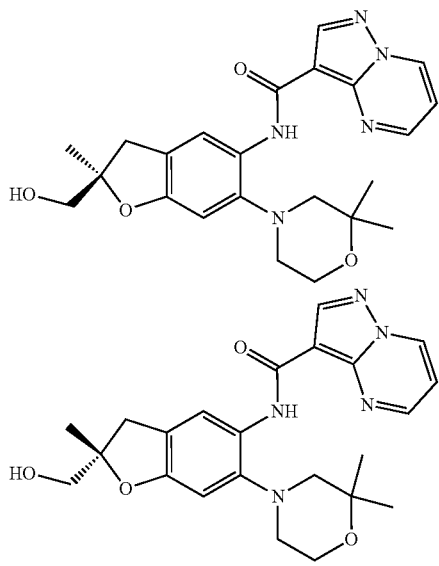

A mixture of pyrazolo[1,5-a]pyrimidine-3-carboxylic acid (31 mg, 0.19 mmol), (7-azabenzotriazol-1-yloxy)tripyrrolidinophosphoniumhexafluorophosphate (98 mg, 0.19 mmol) and collidine (68 mg, 0.57 mmol) in DMF (5 mL) was stirred at room temperature for 30 min. (5-amino-6-(2,2-dimethylmorpholino)-2-methyl-2,3-dihydrobenzofuran-2-yl)methanol (55 mg, 0.19 mmol) was added. The resulting mixture was stirred at room temperature for 18h. After concentration, the residue was purified by preparative HPLC (Xbridge Prep Cis 10 um OBD, 19*250 mm, 10 um; A: acetonitrile 45-75% and 0.01% NH$_3$; B: 10 mM ammonium bicarbonate in water) to afford N-(6-(2,2-dimethylmorpholino)-2-(hydroxymethyl)-2-methyl-2,3-dihydrobenzofuran-5-yl)pyrazolo[1,5-a]pyrimidine-3-carboxamide as a yellow solid (50 mg, 0.11 mmol, 61%). The enantiomers were then resolved by chiral SFC to give (R)—N-(6-(2,2-dimethylmorpholino)-2-(hydroxymethyl)-2-methyl-2,3-dihydrobenzofuran-5-yl)pyrazolo[1,5-a]pyrimidine-3-carboxamide and (S)—N-(6-(2,2-dimethylmorpholino)-2-(hydroxymethyl)-2-methyl-2,3-dihydrobenzofuran-5-yl)pyrazolo[1,5-a]pyrimidine-3-carboxamide with absolute stereochemistry assigned arbitrarily.

Example 36, Peak 1: $^1$H NMR (400 MHz, DMSO-d$_6$) δ 9.97 (s, 1H), 9.37 (dd, J=7.0, 1.6 Hz, 1H), 8.84 (dd, J=4.2, 1.7 Hz, 1H), 8.69 (s, 1H), 8.19 (d, J=0.9 Hz, 1H), 7.33 (dd, J=7.0, 4.2 Hz, 1H), 6.60 (s, 1H), 5.07-4.99 (m, 1H), 3.79 (d, J=4.6 Hz, 2H), 3.43 (t, J=5.8 Hz, 2H), 3.23-3.16 (m, 1H), 2.82 (dd, J=15.6, 1.1 Hz, 1H), 2.71 (s, 2H), 2.65 (s, 2H), 1.38-1.32 (m, 9H). MS (ESI): m/z=438.2 [M+1]$^+$.

Example 37, Peak 2: $^1$H NMR (400 MHz, DMSO-d$_6$) δ 9.97 (s, 1H), 9.37 (dd, J=7.0, 1.6 Hz, 1H), 8.84 (dd, J=4.2, 1.7 Hz, 1H), 8.69 (s, 1H), 8.19 (d, J=0.9 Hz, 1H), 7.33 (dd, J=7.0, 4.2 Hz, 1H), 6.60 (s, 1H), 5.03 (t, J=5.8 Hz, 1H), 3.79 (d, J=5.8 Hz, 2H), 3.48-3.38 (m, 2H), 3.20 (ddt, J=15.6, 0.9, 0.5 Hz, 1H), 2.86-2.77 (m, 1H), 2.71 (s, 2H), 2.65 (d, J=5.3 Hz, 2H), 1.35 (d, J=4.4 Hz, 9H). MS (ESI): m/z=438.2 [M+1]$^+$.

Example 38. 2-Methyl-6-morpholino-5-(pyrazolo[1,5-a]pyrimidine-3-carboxamido)-2,3-dihydrobenzofuran-2-carboxylicacid

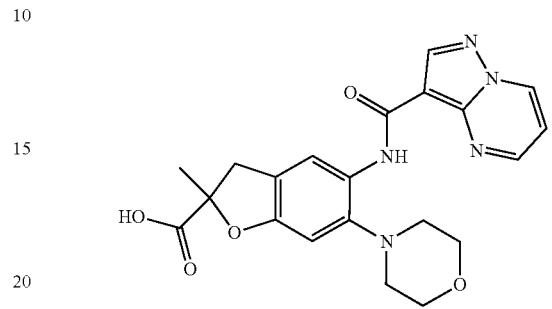

Step A. Methyl 6-chloro-2-methyl-5-nitro-2,3-dihydrobenzofuran-2-carboxylate

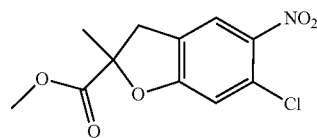 [SMILES: COC(=O)C1(C)Cc2cc([N+](=O)[O-])c(Cl)cc2O1]

A mixture of 6-chloro-2-methyl-5-nitro-2,3-dihydrobenzofuran-2-carboxylic acid (Intermediate 2, Step C) (1.60 g, 6.21 mol), methyl iodide (1.76 g, 12.42 mmol) and potassium carbonate (1.72 g, 12.42 mmol) in DMF (10 mL) was stirred at room temperature. Water and ethyl acetate (50 mL) was added upon consumption of starting material. The organic phase was separated and dried over sodium sulfate. After filtration and concentration, the residue was purified by silica gel chromatography using ethyl acetate:petroleum ether (from 1:6 to 1:4) as eluting solvents to afford methyl 6-chloro-2-methyl-5-nitro-2,3-dihydrobenzofuran-2-carboxylate (550 mg, 33%) as orange solid. MS (ESI): m/z=272.1 [M+1]$^+$.

Step B. 2-Methyl-6-morpholino-5-nitro-2,3-dihydrobenzofuran-2-carboxylicacid

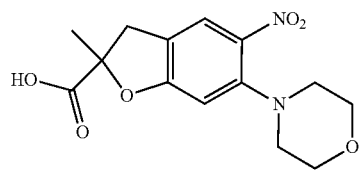

A mixture of methyl 6-chloro-2-methyl-5-nitro-2,3-dihydrobenzofuran-2-carboxylate (550 mg, 2.02 mmol) in morpholine (3 mL) was stirred at 110° C. for 18h in a sealed tube. The mixture was concentrated under reduced pressure to afford 2-methyl-6-morpholino-5-nitro-2,3-dihydrobenzofuran-2-carboxylic acid (260 mg) as a yellow oil, which was used directly in the next step without purification. MS (ESI): m/z=309.1 [M+1]⁺.

Step C. Methyl 2-methyl-6-morpholino-5-nitro-2,3-dihydrobenzofuran-2-carboxylate

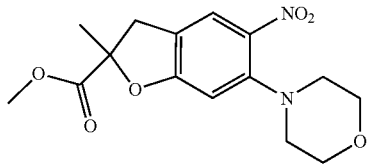

A mixture of 2-methyl-6-morpholino-5-nitro-2,3-dihydrobenzofuran-2-carboxylic acid (260 mg, 0.84 mol), iodomethane (239 mg, 1.69 mmol) and potassium carbonate (233 mg, 1.69 mmol) in DMF (10 mL) was stirred at room temperature. Upon consumption of starting material, water and ethyl acetate (50 mL) were added. The organic phase was separated and dried over sodium sulfate. After concentration, the residue was purified by silica gel chromatography using ethyl acetate:petroleum ether (from 1:4 to 1:2) as eluting solvents to afford methyl 2-methyl-6-morpholino-5-nitro-2,3-dihydrobenzofuran-2-carboxylate (200 mg, 74%) as orange solid. MS (ESI): m/z=323.2 [M+1]⁺.

Step D. Methyl 5-amino-2-methyl-6-morpholino-2,3-dihydrobenzofuran-2-carboxylate

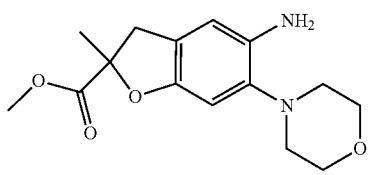 [SMILES: COC(=O)C1(C)Cc2cc(N)c(N3CCOCC3)cc2O1]

A mixture of methyl 2-methyl-6-morpholino-5-nitro-2,3-dihydrobenzofuran-2-carboxylate (200 mg, 0.62 mmol) and 10% palladium on carbon (20 mg) in methanol (10 mL) was stirred at room temperature for 1h under an atmosphere of hydrogen. The reaction was then filtered over a plug of celite and the filtrate was concentrated under reduced pressure to afford methyl 5-amino-2-methyl-6-morpholino-2,3-dihydrobenzofuran-2-carboxylate as a white solid (150 mg), which was used directly to the next step without purification. MS (ESI): m/z=292.3 [M+1]⁺.

Step E. Methyl 2-methyl-6-morpholino-5-(pyrazolo[1,5-a]pyrimidine-3-carboxamido)-2,3-dihydrobenzofuran-2-carboxylate

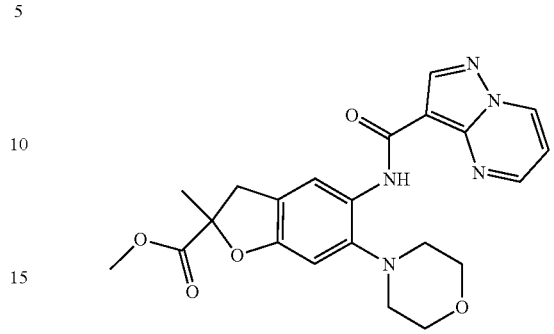

A mixture of methyl 5-amino-2-methyl-6-morpholino-2,3-dihydrobenzofuran-2-carboxylate (150 mg, 0.51 mmol) and triethylamine (103 mg, 1.02 mmol) in DCM (10 mL) was stirred at 0° C. To the mixture was added a solution of pyrazolo[1,5-a]pyrimidine-3-carbonyl chloride (Example 3, Step B) (93 mg, 0.51 mmol) in DCM (10 mL) and then the reaction was stirred at 25° C. for 1h. After concentration, the residue was purified by silica gel chromatography using ethyl acetate:petroleum ether (from 1:1 to 10:1) as eluting solvents to afford methyl 2-methyl-6-morpholino-5-(pyrazolo[1,5-a]pyrimidine-3-carboxamido)-2,3-dihydrobenzofuran-2-carboxylate as a white solid (160 mg, 71%). MS (ESI): m/z=438.1 [M+1]⁺.

Step F. 2-Methyl-6-morpholino-5-(pyrazolo[1,5-a]pyrimidine-3-carboxamido)-2,3-dihydrobenzofuran-2-carboxylic acid

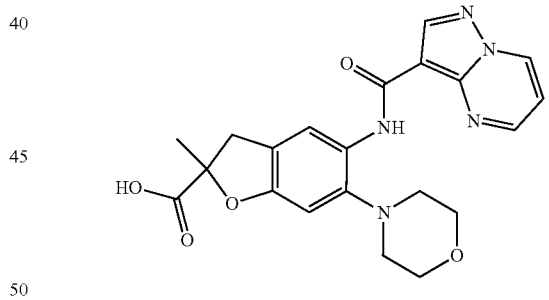

A mixture of methyl 2-methyl-6-morpholino-5-(pyrazolo[1,5-a]pyrimidine-3-carboxamido)-2,3-dihydrobenzofuran-2-carboxylate (70 mg, 0.16 mmol) and sodium hydroxide (13 mg, 0.32 mmol) in THF (5 mL) and water (1 mL) was stirred at 25° C. for 1h. The reaction was then purified by preparative HPLC (Xbridge Prep C18 10 um OBD, 19*250 mm, 10 um; A: acetonitrile 35-65% and 0.01% NH₃; B: 10 mM ammonium bicarbonate in water) to afford 2-methyl-6-morpholino-5-(pyrazolo[1,5-a]pyrimidine-3-carboxamido)-2,3-dihydrobenzofuran-2-carboxylic acid (10 mg, 15%) as a yellow solid. ¹HNMR (400 MHz, DMSO-d₆): δ 10.45 (s, 1H), 9.37 (dd, J=1.6, 7.2 Hz, 1H), 8.95 (dd, J=1.6, 4.0 Hz, 1H), 8.68 (s, 1H), 8.30 (s, 1H), 7.34 (dd, J=4.0, 7.2 Hz, 1H), 6.80 (s, 1H), 3.89-3.78 (m, 4H), 3.54-3.48 (m, 1H), 3.13-3.07 (m, 1H), 2.88-2.75 (m, 4H), 1.57 (s, 3H). MS (ESI): m/z=424.2 [M+1]⁺.

Example 39. N-(6-Morpholino-2',3',5',6'-tetrahydro-3H-spiro[benzofuran-2,4'-pyran]-5-yl)pyrazolo[1,5-a]pyrimidine-3-carboxamide

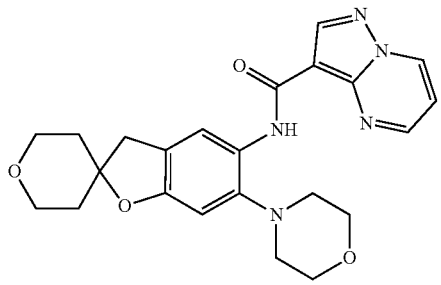 [SMILES: O=C(Nc1cc2c(cc1N1CCOCC1)OC1(CCOCC1)C2)c1cnn2cccnc12]

Step A.
4-(2,4-Difluorobenzyl)tetrahydro-2H-pyran-4-ol

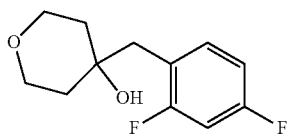 [SMILES: OC1(Cc2ccc(F)cc2F)CCOCC1]

To a solution of magnesium (1.20 g, 45.59 mmol) and iodine (90.0 mg, 0.35 mmol) in diethyl ether (20 mL) at 40° C. was slowly added 1-(bromomethyl)-2,4-difluorobenzene (4.10 g, 19.8 mmol). The solution was then cooled to room temperature and added to dihydro-2H-pyran-4(3H)-one (3.00 g, 29.96 mmol) in diethyl ether (50 mL) at −78° C. and the reaction was stirred at room temperature for 18h. After quenching with saturated ammonium chloride solution, ethyl acetate (100 mL) was added. The organic phase was separated and dried over sodium sulfate. After concentration, the residue was purified by silica gel chromatography using ethyl acetate:petroleum ether (1:10) as eluting solvents to afford 4-(2,4-difluorobenzyl)tetrahydro-2H-pyran-4-ol (1.80 g, 40%) as a colorless oil. MS (ESI): m/z=229.1 [M+1]$^+$.

Step B. 6-Fluoro-2',3',5',6'-tetrahydro-3H-spiro[benzofuran-2,4'-pyran]

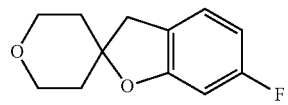

A mixture of methyl 4-(2,4-difluorobenzyl)tetrahydro-2H-pyran-4-ol (1.81 g, 7.93 mmol) and potassium tert-butoxide (2.67 g, 23.79 mmol) in THF (50 mL) was stirred at 60° C. for 18h. After cooling to room temperature, 1N hydrogen chloride solution was added to reach pH=3.0. Ethyl acetate (100 mL) was added and the organic phase was separated and dried over sodium sulfate. After concentration, the residue was purified by silica gel chromatography using ethyl acetate:petroleum ether (from 1:3 to 1:2) as eluting solvents to afford 6-fluoro-2',3',5',6'-tetrahydro-3H-spiro[benzofuran-2,4'-pyran] (1.53 g, 93%) as a yellow solid. MS (ESI): m/z=209.1 [M+1]$^+$.

Step C. 6-Fluoro-5-nitro-2',3',5',6'-tetrahydro-3H-spiro[benzofuran-2,4'-pyran]

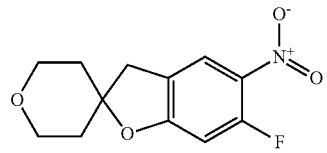 [SMILES: O=[N+]([O-])c1cc2c(cc1F)OC1(CCOCC1)C2]

To a solution of 6-fluoro-2',3',5',6'-tetrahydro-3H-spiro[benzofuran-2,4'-pyran] (1.53 g, 7.35 mmol) in DCM (50 mL) at 25° C. was slowly added fuming nitric acid (2 mL) and the reaction was stirred for 15 min. Water and ethyl acetate (100 mL) was added. The organic phase was separated and dried over sodium sulfate. After concentration, the residue was purified by silica gel chromatography using ethyl acetate:petroleum ether (from 1:6 to 1:4) as eluting solvents to afford 6-fluoro-5-nitro-2',3',5',6'-tetrahydro-3H-spiro[benzofuran-2,4'-pyran] (1.29 g, 69%) as orange solid. MS (ESI): m/z=254.3 [M+1]$^+$.

Step D. 4-(5-Nitro-2',3',5',6'-tetrahydro-3H-spiro[benzofuran-2,4'-pyran]-6-yl)morpholine

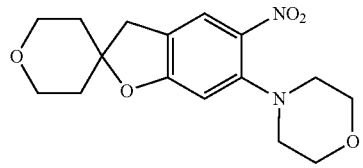 [SMILES: O=[N+]([O-])c1cc2c(cc1N1CCOCC1)OC1(CCOCC1)C2]

A mixture of 6-fluoro-5-nitro-2',3',5',6'-tetrahydro-3H-spiro[benzofuran-2,4'-pyran] (150 mg, 0.59 mmol), morpholine (103 mg, 1.18 mmol) and cesium carbonate (579 mg, 1.78 mmol) in acetonitrile (5 mL) was stirred at room temperature for 18h. Upon consumption of starting material, the mixture was poured into water and the aqueous phase was extracted with ethyl acetate (2×50 mL). The organic phases were combined and washed with water and brine. After concentration under reduced pressure, the residue was purified by silica gel chromatography using ethyl acetate:petroleum ether (1:2) as eluting solvents to afford (4-(5-nitro-2',3',5',6'-tetrahydro-3H-spiro[benzofuran-2,4'-pyran]-6-yl)morpholine (180 mg, 95%) as a yellow solid. MS (ESI): m/z=321.1 [M+1]$^+$.

Step E. 6-Morpholino-2',3',5',6'-tetrahydro-3H-spiro[benzofuran-2,4'-pyran]-5-amine

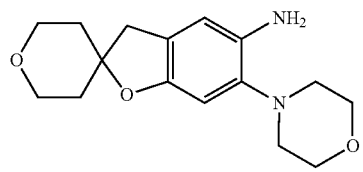

A mixture of 4-(5-nitro-2',3',5',6'-tetrahydro-3H-spiro[benzofuran-2,4'-pyran]-6-yl)morpholine (180 mg, 0.56 mmol) and 10% palladium on carbon (18 mg) in methanol (10 mL) was stirred at room temperature for 1 h under an atmosphere of hydrogen. Upon filtration through a plug of celite, the filtrate was concentrated under reduced pressure to afford (6-morpholino-2',3',5',6'-tetrahydro-3H-spiro[benzofuran-2,4'-pyran]-5-amine as a white solid (150 mg), which was used directly in the next step without purification. MS (ESI): m/z=291.1 [M+1]+.

Step F. N-(6-Morpholino-2',3',5',6'-tetrahydro-3H-spiro[benzofuran-2,4'-pyran]-5-yl)pyrazolo[1,5-a]pyrimidine-3-carboxamide

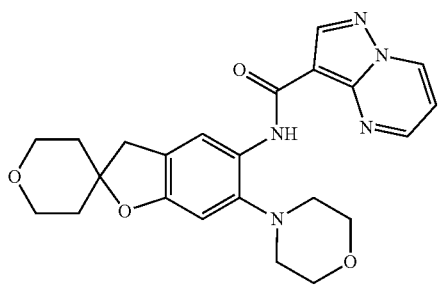 [SMILES: O=C(Nc1cc2c(cc1N1CCOCC1)OC1(CCOCC1)C2)c1cnn2cccnc12]

A mixture of 6-morpholino-2',3',5',6'-tetrahydro-3H-spiro[benzofuran-2,4'-pyran]-5-amine (150 mg, 0.52 mmol) and triethylamine (157 mg, 1.55 mmol) in DCM (5 mL) was stirred at 0° C. To the mixture was added a solution of pyrazolo[1,5-a]pyrimidine-3-carbonyl chloride (Example 3, Step B) (113 mg, 0.62 mmol) in DCM (5 mL) and the reaction was stirred at 25° C. for 1h. After filtration, the residue was purified by preparative HPLC(Xbridge 21.2*250 mm c18, 10 um; A: acetonitrile 25-55%; B: 10 mM ammonium bicarbonate in water) to afford N-(6-morpholino-2',3',5',6'-tetrahydro-3H-spiro[benzofuran-2,4'-pyran]-5-yl)pyrazolo[1,5-a]pyrimidine-3-carboxamide (60 mg, 27%) as a white solid. $^1$H NMR (400 MHz, DMSO-d$_6$): δ 10.45 (s, 1H), 9.37 (dd, J=2.0, 7.2 Hz, 1H), 8.94 (dd, J=1.6, 4.0 Hz, 1H), 8.68 (s, 1H), 8.33 (s, 1H), 7.35 (dd, J=4.0, 7.2 Hz, 1H), 6.79 (s, 1H), 3.83-3.85 (m, 4H), 3.74-3.80 (m, 2H), 3.61-3.66 (m, 2H), 3.06 (s, 2H), 2.81-2.82 (m, 4H), 1.79-1.81 (m, 4H). MS (ESI): m/z=436.2 [M+1]+.

Example 40. N-(6-(4-Fluoro-4-(hydroxymethyl)piperidin-1-yl)-2,2-dimethyl-2,3-dihydrobenzofuran-5-yl)pyrazolo[1,5-a]pyrimidine-3-carboxamide

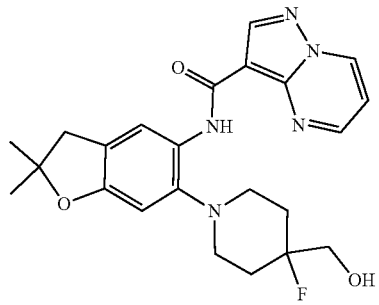 [SMILES: CC1(C)Cc2cc(NC(=O)c3cnn4cccnc34)c(N3CCC(F)(CO)CC3)cc2O1]

Step A. 4-Fluoropiperidin-4-yl)methanol 2,2,2-trifluoroacetate

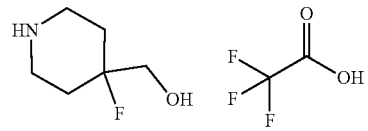

A mixture of tert-butyl 4-fluoro-4-(hydroxymethyl)piperidine-1-carboxylate (300 mg, 1.29 mmol) in trifluoroacetic acid (1 mL) and DCM (2 mL) was stirred at 20° C. for 1h. The mixture was concentrated under reduced pressure to afford (4-fluoropiperidin-4-yl)methanol trifluoroacetic acid salt (300 mg) as a colorless oil, which was used directly without purification. MS (ESI): m/z=134.1 [M+1]+.

Step B. (1-(2,2-Dimethyl-5-nitro-2,3-dihydrobenzofuran-6-yl)-4-fluoropiperidin-4-yl)methanol

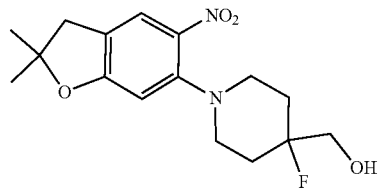 [SMILES: CC1(C)Cc2cc([N+](=O)[O-])c(N3CCC(F)(CO)CC3)cc2O1]

A mixture of 6-chloro-2,2-dimethyl-5-nitro-2,3-dihydrobenzofuran (Intermediate 2) (107 mg, 0.47 mmol), (4-fluoropiperidin-4-yl)methanol 2,2,2-trifluoroacetate (232 mg, 0.94 mmol) and cesium carbonate (459 mg, 1.41 mmol) in acetonitrile (1 mL) was stirred at 100° C. for 18h in a sealed tube. The mixture was poured into water and the aqueous phase was extracted with ethyl acetate (2×50 mL). The organic phases were combined, washed with water and brine, concentrated under reduced pressure and purified by silica gel chromatography using ethyl acetate:petroleum ether (1:1) as eluting solvents to afford (1-(2,2-dimethyl-5-nitro-2,3-dihydrobenzofuran-6-yl)-4-fluoropiperidin-4-yl)methanol (95 mg, 62%) as a yellow solid. MS (ESI): m/z=325.3 [M+1]+.

Step C. (1-(5-Amino-2,2-dimethyl-2,3-dihydrobenzofuran-6-yl)-4-fluoropiperidin-4-yl)methanol

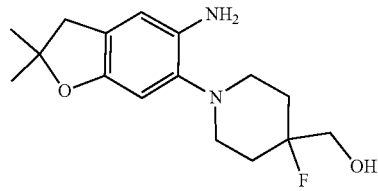 [SMILES: CC1(C)Cc2cc(N)c(N3CCC(F)(CO)CC3)cc2O1]

A mixture of (1-(2,2-dimethyl-5-nitro-2,3-dihydrobenzofuran-6-yl)-4-fluoropiperidin-4-yl)methanol (95 mg, 0.29 mmol) and 10% palladium on carbon (10 mg) in methanol (5 mL) was stirred at room temperature for 1h under an atmosphere of hydrogen. Upon filtration over a plug of celite, the filtrate was concentrated under reduced pressure to afford (1-(5-amino-2,2-dimethyl-2,3-dihydrobenzofuran-6-yl)-4-fluoropiperidin-4-yl)methanol (60 mg), which was used directly in the next step without purification. MS (ESI): m/z=295.1 [M+1]$^+$.

Step D. N-(6-(4-Fluoro-4-(hydroxymethyl)piperidin-1-yl)-2,2-dimethyl-2,3-dihydrobenzofuran-5-yl)pyrazolo[1,5-a]pyrimidine-3-carboxamide

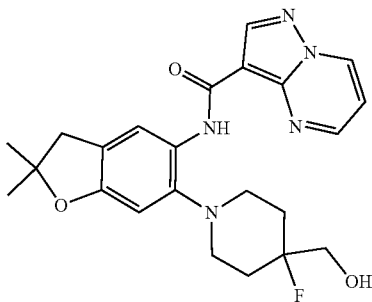 [SMILES: CC1(C)Cc2cc(NC(=O)c3cnn4cccnc34)c(N3CCC(F)(CO)CC3)cc2O1]

A mixture of (1-(5-amino-2,2-dimethyl-2,3-dihydrobenzofuran-6-yl)-4-fluoropiperidin-4-yl)methanol (60 mg, 0.20 mmol) and triethylamine (61 mg, 0.60 mmol) in DCM (10 mL) was stirred at 0° C. To the mixture was added a solution of pyrazolo[1,5-a]pyrimidine-3-carbonyl chloride (Example 3, Step B) (54 mg, 0.30 mmol) in DCM (10 mL) and the reaction was stirred at 25° C. for 1h. The crude reaction was purified by preparative HPLC (Xbridge 21.2*250 mm c18, 10 um; A: acetonitrile 35-55%; B: 10 mM ammonium bicarbonate in water) to afford N-(6-(4-fluoro-4-(hydroxymethyl)piperidin-1-yl)-2,2-dimethyl-2,3-dihydrobenzofuran-5-yl)pyrazolo[1,5-a]pyrimidine-3-carboxamide (55 mg, 65%) as a white solid. $^1$H NMR (400 MHz, DMSO-d$_6$): δ 10.43 (s, 1H), 9.36 (dd, J=1.6, 7.21 Hz, 1H), 8.89 (dd, J=1.6, 4.0 Hz, 1H), 8.68 (s, 1H), 8.34 (s, 1H), 7.53 (dd, J=4.0, 7.2 Hz, 1H), 6.71 (s, 1H), 5.18 (br, 1H), 3.53 (d, J=17.6 Hz, 2H), 3.37 (s, 2H), 2.81-2.91 (m, 4H), 1.98-2.10 (m, 2H). 1.83-1.88 (m, 2H). 1.42 (s, 6H). MS (ESI): m/z=440.2 [M+1]$^+$.

Example 41. N-[6-(1,1-Dioxo-thiomorpholin-4-yl)-2,2-dimethyl-2,3-dihydro-1-benzofuran-5-yl]pyrazolo[1,5-a]pyrimidine-3-carboxamide

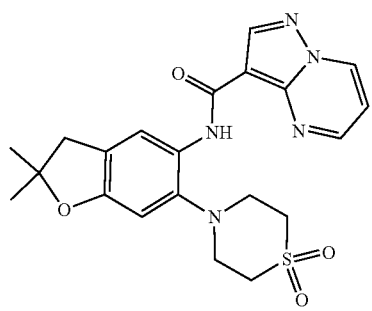 [SMILES: CC1(C)Cc2cc(NC(=O)c3cnn4cccnc34)c(N3CCS(=O)(=O)CC3)cc2O1]

Step A. 4-(2,2-Dimethyl-5-nitro-2,3-dihydro-1-benzofuran-6-yl)-thiomorpholine-1,1-dione

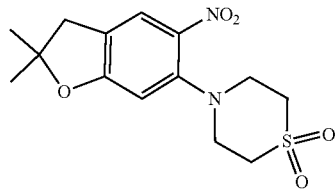 [SMILES: CC1(C)Cc2cc([N+](=O)[O-])c(N3CCS(=O)(=O)CC3)cc2O1]

A mixture of 6-chloro-2,2-dimethyl-5-nitro-2,3-dihydrobenzofuran (Intermediate 1) (100 mg, 0.44 mmol), thiomorpholine-1,1-dione (119 mg, 0.88 mmol) and cesium carbonate (429 mg, 1.32 mmol) in acetonitrile (5 mL) was stirred 100° C. for 18h. Upon consumption of starting material, the mixture was poured into water and the aqueous phase was extracted with ethyl acetate (2×50 mL). The organic phases were combined and washed with water and brine. After concentration under reduced pressure, the residue was purified by silica gel chromatography using ethyl acetate:petroleum ether (1:2) as eluting solvents to afford 4-(2,2-dimethyl-5-nitro-2,3-dihydro-1-benzofuran-6-yl)-thiomorpholine-1,1-dione (70 mg, 49%) as a yellow solid. MS (ESI): m/z=327.1 [M+1]$^+$.

Step B. 4-(5-Amino-2,2-dimethyl-2,3-dihydro-1-benzofuran-6-yl)-thiomorpholine-1,1-dione

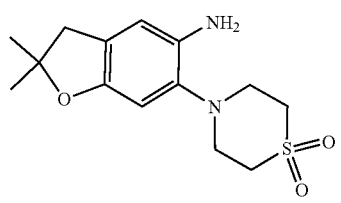 [SMILES: CC1(C)Cc2cc(N)c(N3CCS(=O)(=O)CC3)cc2O1]

A mixture of 4-(2,2-dimethyl-5-nitro-2,3-dihydro-1-benzofuran-6-yl)-thiomorpholine-1,1-dione (70 mg, 0.21 mmol) and 15% palladium on carbon (10 mg) in methanol (10 mL) was stirred at room temperature for 1h under an atmosphere of hydrogen. Upon filtration over a plug of celite, the filtrate was concentrated under reduced pressure to afford 4-(5-amino-2,2-dimethyl-2,3-dihydro-1-benzofuran-6-yl)-thiomorpholine-1,1-dione (50 mg, 81%), which was used directly to the next step without purification. MS (ESI): m/z=297.1 [M+1]$^+$.

437

Step C. N-[6-(1,1-Dioxo-thiomorpholin-4-yl)-2,2-dimethyl-2,3-dihydro-1-benzofuran-5-yl]pyrazolo[1,5-a]pyrimidine-3-carboxamide

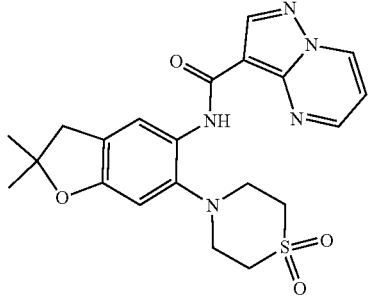 [SMILES: CC1(C)Cc2cc(NC(=O)c3cnn4cccnc34)c(N3CCS(=O)(=O)CC3)cc2O1]

A mixture of pyrazolo[1,5-a]pyrimidine-3-carboxylic acid (28 mg, 0.17 mmol), (7-azabenzotriazol-1-yloxy)tripyrrolidinophosphoniumhexafluorophosphate (88 mg, 0.17 mmol) and N-ethyl-N-isopropylpropan-2-amine (65 mg, 0.51 mmol) in DMF (5 mL) was stirred at room temperature for 30 min. 4-(5-Amino-2,2-dimethyl-2,3-dihydro-1-benzofuran-6-yl)-thiomorpholine-1,1-dione (50 mg, 0.17 mmol) was added and the resulting mixture was stirred at room temperature for 18h. The residue was purified by preparative HPLC(Xbridge 21.2*250 mm c18, 10 um; A: acetonitrile 25-55%; B:10 mM ammonium bicarbonate in water) to afford N-[6-(1,1-dioxo-thiomorpholin-4-yl)-2,2-dimethyl-2,3-dihydro-1-benzofuran-5-yl]pyrazolo[1,5-a]pyrimidine-3-carboxamide as a white solid (25 mg, 34%). $^1$H NMR (400 MHz, DMSO-$d_6$): δ 10.43 (s, 1H), 9.39 (dd, J=1.2, 6.8 Hz, 1H), 8.84 (dd, J=1.6, 4.4 Hz, 1H), 8.69 (s, 1H), 8.36 (s, 1H), 7.42 (dd, J=4.4, 7.2 Hz, 1H), 6.83 (s, 1H), 3.46-3.47 (m, 4H), 3.34-3.35 (m, 4H), 3.01 (s, 2H), 1.41 (s, 6H). MS (ESI): m/z=442.2 [M+1]$^+$.

Examples 42 and 43. N—((R)-6-((1R,4R)-2-Oxa-5-azabicyclo[2.2.1]heptan-5-yl)-2-(hydroxymethyl)-2-methyl-2,3-dihydrobenzofuran-5-yl)pyrazolo[1,5-a]pyrimidine-3-carboxamide and N—((S)-6-((1R,4R)-2-Oxa-5-azabicyclo[2.2.1]heptan-5-yl)-2-(hydroxymethyl)-2-methyl-2,3-dihydrobenzofuran-5-yl)pyrazolo[1,5-a]pyrimidine-3-carboxamide

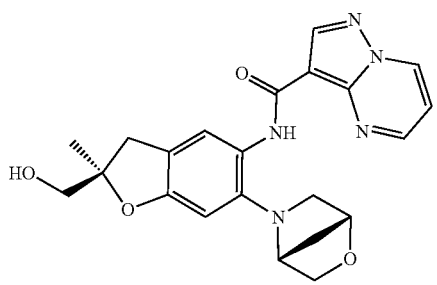

438

-continued

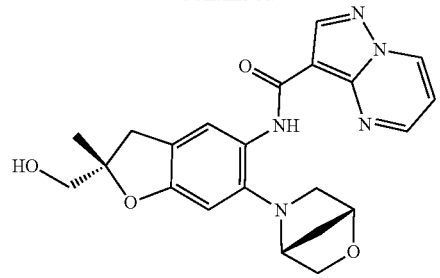

Step A. (6-((1R,4R)-2-Oxa-5-azabicyclo[2.2.1]heptan-5-yl)-2-methyl-5-nitro-2,3-dihydrobenzofuran-2-yl)methanol

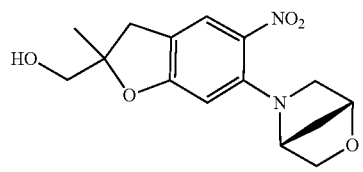 [SMILES: CC1(CO)Cc2cc([N+](=O)[O-])c(N3C[C@H]4C[C@@H]3CO4)cc2O1]

A mixture of (6-chloro-2-methyl-5-nitro-2,3-dihydrobenzofuran-2-yl)methanol (Intermediate 2) (85 mg, 0.35 mmol), (1R,4R)-2-oxa-5-azabicyclo[2.2.1]heptane hydrochloride (95 mg, 0.70 mmol) and cesium carbonate (455 mg, 1.40 mmol) in acetonitrile (1 mL) was stirred 100° C. for 18h in sealed tube. After filtered and concentrated, the residue was purified by silica gel chromatography using ethyl acetate: petroleum ether (1:2) as eluting solvents to afford (6-((1R,4R)-2-oxa-5-azabicyclo[2.2.1]heptan-5-yl)-2-methyl-5-nitro-2,3-dihydrobenzofuran-2-yl)methanol (60 mg, 56%) as a yellow solid. MS (ESI): m/z=307.3 [M+1]$^+$.

Step B. (5-Amino-6-((1R,4R)-2-oxa-5-azabicyclo[2.2.1]heptan-5-yl)-2-methyl-2,3-dihydrobenzofuran-2-yl)methanol

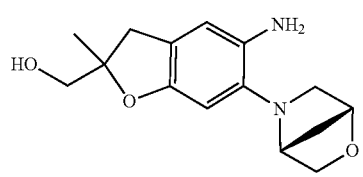

A mixture of (6-((1R,4R)-2-oxa-5-azabicyclo[2.2.1]heptan-5-yl)-2-methyl-5-nitro-2,3-dihydrobenzofuran-2-yl)methanol (60 mg, 0.20 mmol) and 10% palladium on carbon (12 mg) in methanol (5 mL) was stirred at room temperature for 1h under an atmosphere of hydrogen. Upon filtration over a plug of celite, the filtrate was concentrated under reduced pressure to afford (5-amino-6-((1R,4R)-2-oxa-5-azabicyclo[2.2.1]heptan-5-yl)-2-methyl-2,3-dihydrobenzofuran-2-yl)methanol (50 mg) as a yellow oil, which was used directly to the next step without purification. MS (ESI): m/z=277.1 [M+1]$^+$.

Step C. N—((R)-6-((1R,4R)-2-Oxa-5-azabicyclo[2.2.1]heptan-5-yl)-2-(hydroxymethyl)-2-methyl-2,3-dihydrobenzofuran-5-yl)pyrazolo[1,5-a]pyrimidine-3-carboxamide and N—((S)-6-((1R,4R)-2-Oxa-5-azabicyclo[2.2.1]heptan-5-yl)-2-(hydroxymethyl)-2-methyl-2,3-dihydrobenzofuran-5-yl)pyrazolo[1,5-a]pyrimidine-3-carboxamide

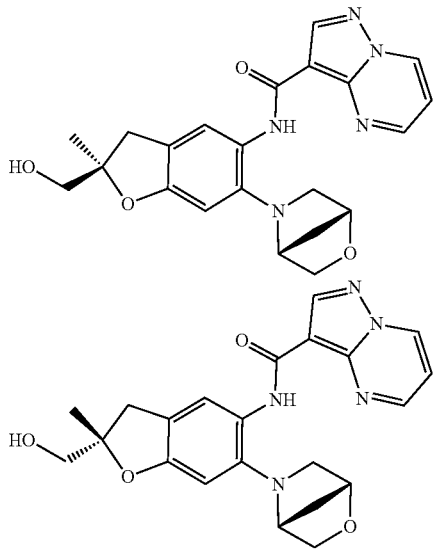

A mixture of (5-amino-6-((1R,4R)-2-oxa-5-azabicyclo[2.2.1]heptan-5-yl)-2-methyl-2,3-dihydrobenzofuran-2-yl)methanol (50 mg, 0.18 mmol) and triethylamine (55 mg, 0.54 mmol) in DCM (5 mL) was stirred at 0° C. To the mixture was added a solution of pyrazolo[1,5-a]pyrimidine-3-carbonyl chloride (Example 3, Step B) (49 mg, 0.27 mmol) in DCM (5 mL) and then the reaction was stirred at 25° C. for 1h. After concentration under reduced pressure the residue was purified by silica gel chromatography using ethyl acetate:petroleum ether (15:1) as eluting solvents to afford the desired product and then it was separated by preparative HPLC (Xbridge 21.2*250 mm c18, 10 um; A: acetonitrile 25-55%; B:10 mM ammonium bicarbonate in water) to obtain N—((R)-6-((1R,4R)-2-oxa-5-azabicyclo[2.2.1]heptan-5-yl)-2-(hydroxymethyl)-2-methyl-2,3-dihydrobenzofuran-5-yl)pyrazolo[1,5-a]pyrimidine-3-carboxamide and N—((S)-6-((1R,4R)-2-oxa-5-azabicyclo[2.2.1]heptan-5-yl)-2-(hydroxymethyl)-2-methyl-2,3-dihydrobenzofuran-5-yl)pyrazolo[1,5-a]pyrimidine-3-carboxamide (10 mg each, 12% each) as a yellow solids with absolute stereochemistry assigned arbitrarily.

Example 42, Peak 1: $^1$H NMR (400 MHz, CDCl$_3$): δ 10.10 (s, 1H), 8.82 (dd, J=1.6, 7.2 Hz, 1H), 8.77 (s, 1H), 8.71 (dd, J=1.6, 4.0 Hz, 1H), 8.14 (s, 1H), 7.04 (dd, J=4.0, 7.2 Hz, 1H), 6.57 (s, 1H), 4.57 (s, 1H), 4.13 (d, J=7.2 Hz, 1H), 4.04 (s, 1H), 3.78 (dd, J=1.6 7.2 Hz, 1H), 3.67 (d, J=4.0 Hz, 2H), 3.60 (d, J=9.6 Hz, 1H), 3.22 (d, J=15.2 Hz, 1H), 3.08 (dd, J=1.6, 9.6 Hz, 1H), 2.93 (d, J=15.6 Hz, 1H), 2.10 (dd, J=1.6, 9.6 Hz, 1H), 1.96-1.89 (m, 2H), 1.47 (s, 3H). MS (ESI): m/z=422.2[M+1]$^+$.

Example 43, Peak 2. $^1$H NMR (400 MHz, CDCl$_3$): δ 10.09 (s, 1H), 8.82 (dd, J=1.6, 7.2 Hz, 1H), 8.77 (s, 1H), 8.72 (dd, J=1.6, 4.0 Hz, 1H), 8.14 (s, 1H), 7.04 (dd, J=4.0, 7.2 Hz, 1H), 6.57 (s, 1H), 4.57 (s, 1H), 4.13 (d, J=7.6 Hz, 1H), 4.05 (s, 1H), 3.78 (dd, J=2.0, 7.2 Hz, 1H), 3.67 (d, J=5.6 Hz, 2H), 3.59 (d, J=9.6 Hz, 1H), 3.22 (d, J=16.0 Hz, 1H), 3.10 (dd, J=1.6, 9.6 Hz, 1H), 2.92 (d, J=16.0 Hz, 1H), 2.10 (dd, J=1.6, 9.6 Hz, 1H), 1.96-1.89 (m, 2H), 1.46 (s, 3H). MS (ESI): m/z=422.1 [M+1]$^+$.

Examples 44 and 45. (R)—N-(6-(4-Fluoro-4-(hydroxymethyl)piperidin-1-yl)-2-(hydroxymethyl)-2-methyl-2,3-dihydrobenzofuran-5-yl)pyrazolo[1,5-a]pyrimidine-3-carboxamide and (S)—N-(6-(4-Fluoro-4-(hydroxymethyl)piperidin-1-yl)-2-(hydroxymethyl)-2-methyl-2,3-dihydrobenzofuran-5-yl)pyrazolo[1,5-a]pyrimidine-3-carboxamide

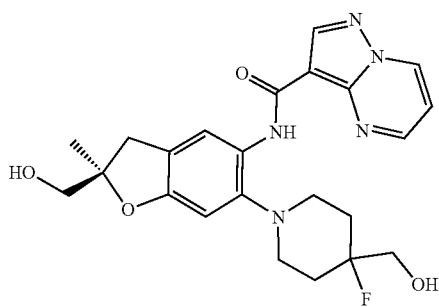

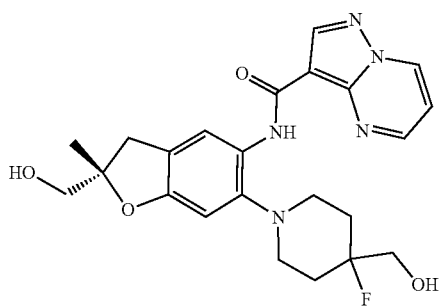

Step A. (4-Fluoropiperidin-4-yl)methanol 2,2,2-trifluoroacetate

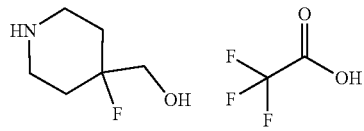 [SMILES: OCC1(F)CCNCC1 ; O=C(O)C(F)(F)F]

A mixture of tert-butyl 4-fluoro-4-(hydroxymethyl)piperidine-1-carboxylate (300 mg, 1.29 mmol in trifluoroacetic acid (1 mL) and DCM (2 mL) was stirred 20° C. for 1h. Upon consumption of starting material, the mixture was concentrated under reduced pressure to afford (4-fluoropiperidin-4-yl)methanol trifluoroacetic acid salt (300 mg) as a colorless oil, which was used directly to next step without further purification MS (ESI): m/z=134.1 [M+1]$^+$.

Step B. (4-Fluoro-1-(2-(hydroxymethyl)-2-methyl-5-nitro-2,3-dihydrobenzofuran-6-yl)piperidin-4-yl)methanol

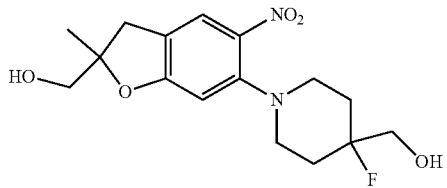

A mixture of (6-chloro-2-methyl-5-nitro-2,3-dihydrobenzofuran-2-yl)methanol (80 mg, 0.33 mmol), (4-fluoropiperidin-4-yl)methanol 2,2,2-trifluoroacetate (162 mg, 0.66 mmol) and cesium carbonate (428 mg, 1.32 mmol) in acetonitrile (1 mL) was stirred 100° C. for 18h in sealed tube. Upon filtration and concentration, the residue was purified by silica gel chromatography using ethyl acetate: petroleum ether (1:2) as eluting solvents to afford (4-fluoro-1-(2-(hydroxymethyl)-2-methyl-5-nitro-2,3-dihydrobenzofuran-6-yl)piperidin-4-yl)methanol (100 mg, 90%) as a yellow solid. MS (ESI): m/z=341.1 [M+1]$^+$.

Step C. (1-(5-Amino-2-(hydroxymethyl)-2-methyl-2,3-dihydrobenzofuran-6-yl)-4-fluoropiperidin-4-yl)methanol

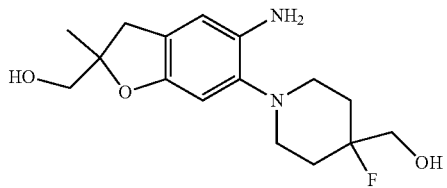 [SMILES: CC1(CO)Cc2cc(N)c(N3CCC(F)(CO)CC3)cc2O1]

A mixture of (4-fluoro-1-(2-(hydroxymethyl)-2-methyl-5-nitro-2,3-dihydrobenzofuran-6-yl)piperidin-4-yl)methanol (100 mg, 0.29 mmol) and 10% palladium on carbon (10 mg) in methanol (5 mL) was stirred at room temperature for 1h under an atmosphere of hydrogen. Upon filtration over a plug of celite, the filtrate was concentrated under reduced pressure to afford (1-(5-amino-2-(hydroxymethyl)-2-methyl-2,3-dihydrobenzofuran-6-yl)-4-fluoropiperidin-4-yl)methanol (90 mg) as a yellow oil, which was used directly in the next step without purification. MS (ESI): m/z=311.1 [M+1]$^+$.

Step D. (R)—N-(6-(4-Fluoro-4-(hydroxymethyl)piperidin-1-yl)-2-(hydroxymethyl)-2-methyl-2,3-dihydrobenzofuran-5-yl)pyrazolo[1,5-a]pyrimidine-3-carboxamide and (S)—N-(6-(4-Fluoro-4-(hydroxymethyl)piperidin-1-yl)-2-(hydroxymethyl)-2-methyl-2,3-dihydrobenzofuran-5-yl)pyrazolo[1,5-a]pyrimidine-3-carboxamide

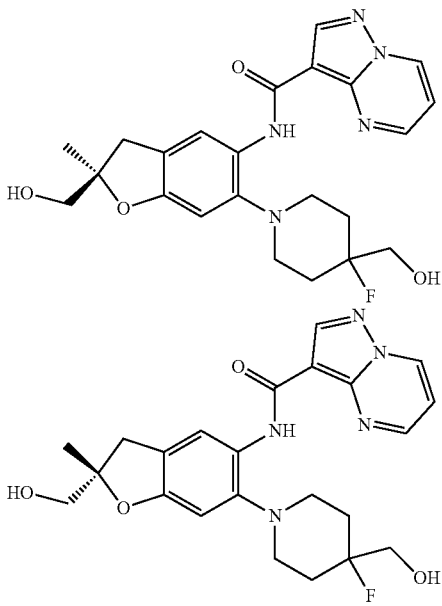

A mixture of (1-(5-amino-2-(hydroxymethyl)-2-methyl-2,3-dihydrobenzofuran-6-yl)-4-fluoropiperidin-4-yl)methanol (90 mg, 0.29 mmol) and triethylamine (88 mg, 0.87 mmol) in DCM (5 mL) was stirred at 0° C. To the mixture was added a solution of pyrazolo[1,5-a]pyrimidine-3-carbonyl chloride (Example 3, Step B) (105 mg, 0.58 mmol) in DCM (5 mL) and the reaction was stirred at 25° C. for 1h. After concentration under reduced pressure, the residue was purified by silica gel chromatography using ethyl acetate: petroleum ether (15:1) as eluting solvents to afford the desired product then it was separated by chiral HPLC (OJ 20*250 mm, 5u at CO$_2$/methanol{0.2% Ammonia (7 m methanol)}=80/20, 80 g/min, 100 bar, 35° C.) to obtain (R)—N-(6-(4-fluoro-4-(hydroxymethyl)piperidin-1-yl)-2-(hydroxymethyl)-2-methyl-2,3-dihydrobenzofuran-5-yl)pyrazolo[1,5-a]pyrimidine-3-carboxamide and (S)—N-(6-(4-fluoro-4-(hydroxymethyl)piperidin-1-yl)-2-(hydroxymethyl)-2-methyl-2,3-dihydrobenzofuran-5-yl)pyrazolo[1,5-a]pyrimidine-3-carboxamide (15 mg, 11%) (10 mg, 8%) as a yellow solids with absolute stereochemistry assigned arbitrarily.

Example 44, Peak 1: $^1$HNMR (400 MHz, DMSO-d$_6$): δ 10.42 (s, 1H), 9.36 (dd, J=1.6, 7.2 Hz, 1H), 8.89 (dd, J=1.6, 4.4 Hz, 1H), 8.68 (s, 1H), 8.32 (s, 1H), 7.33 (dd, J=4.4, 7.2 Hz, 1H), 6.69 (s, 1H), 5.16 (t, J=6.0 Hz, 1H), 5.05 (t, J=5.6 Hz, 1H), 3.57-3.49 (m, 2H), 3.43 (t, J=6.0 Hz, 2H), 3.23-3.16 (m, 1H), 2.93-2.77 (m, 5H), 2.15-1.95 (m, 2H), 1.90-1.79 (m, 2H), 1.34 (s, 3H). MS (ESI): m/z=456.2 [M+1]$^+$.

Example 45, Peak 2: $^1$H NMR (400 MHz, DMSO-d$_6$): δ 10.43 (s, 1H), 9.36 (dd, J=1.6, 6.8 Hz, 1H), 8.89 (dd, J=1.6, 4.0 Hz, 1H), 8.68 (s, 1H), 8.32 (s, 1H), 7.32 (dd, J=4.0, 6.8 Hz, 1H), 6.69 (s, 1H), 5.16 (t, J=6.0 Hz, 1H), 5.05 (t, J=5.6 Hz, 1H), 3.57-3.49 (m, 2H), 3.43 (t, J=6.0 Hz, 2H), 3.23-

3.16 (m, 1H), 2.93-2.77 (m, 5H), 2.15-1.94 (m, 2H), 1.91-1.79 (m, 2H), 1.34 (s, 3H). MS (ESI): m/z=456.2 [M+1]⁺.

Examples 46 and 47. N—((S)-6-((1S,4S)-2-Oxa-5-azabicyclo[2.2.1]heptan-5-yl)-2-(hydroxymethyl)-2-methyl-2,3-dihydrobenzofuran-5-yl)pyrazolo[1,5-a]pyrimidine-3-carboxamide and N—((R)-6-((1S,4S)-2-Oxa-5-azabicyclo[2.2.1]heptan-5-yl)-2-(hydroxymethyl)-2-methyl-2,3-dihydrobenzofuran-5-yl)pyrazolo[1,5-a]pyrimidine-3-carboxamide

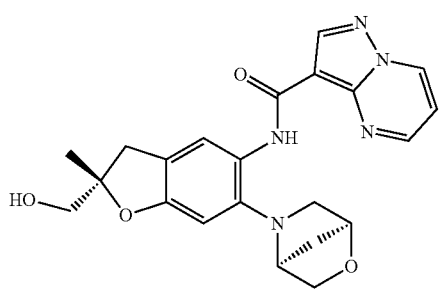

Step A. (6-((1S,4S)-2-Oxa-5-azabicyclo[2.2.1]heptan-5-yl)-2-methyl-5-nitro-2,3-dihydrobenzofuran-2-yl)methanol

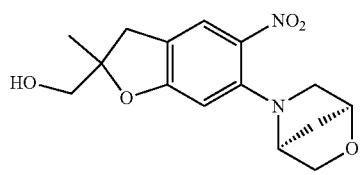

A mixture of (6-chloro-2-methyl-5-nitro-2,3-dihydrobenzofuran-2-yl)methanol (Intermediate 2) (126 mg, 0.52 mmol), (1S,4S)-2-oxa-5-azabicyclo[2.2.1]heptane hydrochloride (140 mg, 1.03 mmol) and cesium carbonate (674 mg, 2.07 mmol) in acetonitrile (2 mL) was stirred 100° C. for 18h in a sealed tube. After filtered and concentrated, the residue was purified by silica gel chromatography using ethyl acetate:petroleum ether (1:2) as eluting solvents to afford (6-((1S,4S)-2-oxa-5-azabicyclo[2.2.1]heptan-5-yl)-2-methyl-5-nitro-2,3-dihydrobenzofuran-2-yl)methanol (120 mg, 76%) as a yellow solid. MS (ESI): m/z=307.3 [M+1]⁺.

Step B. (5-Amino-6-((1S,4S)-2-oxa-5-azabicyclo[2.2.1]heptan-5-yl)-2-methyl-2,3-dihydrobenzofuran-2-yl)methanol

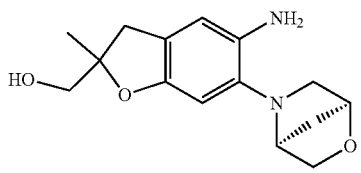

A mixture of (6-((1S,4S)-2-oxa-5-azabicyclo[2.2.1]heptan-5-yl)-2-methyl-5-nitro-2,3-dihydrobenzofuran-2-yl)methanol (120 mg, 0.39 mmol) and 10% palladium on carbon (12 mg) in methanol (5 mL) was stirred at room temperature for 1h under an atmosphere of hydrogen. Upon filtration over a plug of celite, the filtrate was concentrated under reduced pressure to afford (5-amino-6-((1S,4S)-2-oxa-5-azabicyclo[2.2.1]heptan-5-yl)-2-methyl-2,3-dihydrobenzofuran-2-yl)methanol (100 mg) as a yellow oil, which was used directly to the next step without purification. MS (ESI): m/z=277.1 [M+1]⁺.

Step C. N—((S)-6-((1S,4S)-2-Oxa-5-azabicyclo[2.2.1]heptan-5-yl)-2-(hydroxymethyl)-2-methyl-2,3-dihydrobenzofuran-5-yl)pyrazolo[1,5-a]pyrimidine-3-carboxamide and N—((R)-6-((1S,4S)-2-Oxa-5-azabicyclo[2.2.1]heptan-5-yl)-2-(hydroxymethyl)-2-methyl-2,3-dihydrobenzofuran-5-yl)pyrazolo[1,5-a]pyrimidine-3-carboxamide

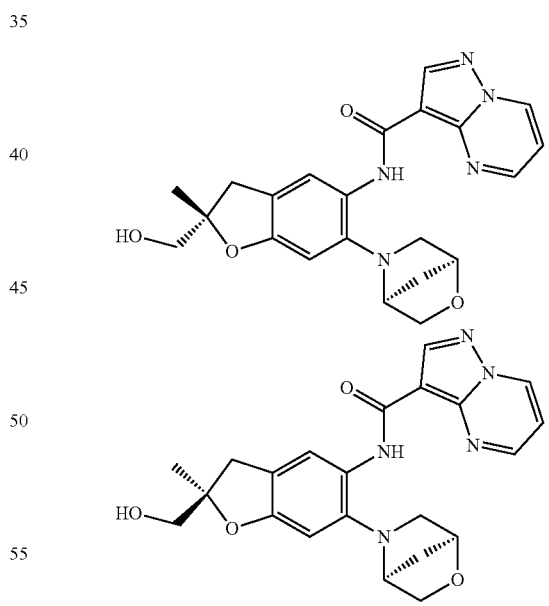

A mixture of (5-amino-6-((1S,4S)-2-oxa-5-azabicyclo[2.2.1]heptan-5-yl)-2-methyl-2,3-dihydrobenzofuran-2-yl)methanol (100 mg, 0.36 mmol) and triethylamine (109 mg, 1.08 mmol) in DCM (5 mL) was stirred at 0° C. To the mixture was added a solution of pyrazolo[1,5-a]pyrimidine-3-carbonyl chloride (Example 3, Step B) (98 mg, 0.54 mmol) in DCM (5 mL) and the reaction was stirred at 25° C. for 1h. After filtration, the residue was purified by preparative HPLC(Xbridge 21.2*250 mm c18, 10 um, acenitrile 25-55% (10 mM ammonium bicarbonate) in water) to afford N-(6-morpholino-2',3',5',6'-tetrahydro-3H-spiro[benzofuran-2,4'-pyran]-5-yl)pyrazolo[1,5-a]pyrimidine-3-carboxamide (120 mg, 0.24 mmol, 79%) as a yellow solid and it was separated by chiral pre-SFC(Column: AD 20*250 mm, Sum (Dacel), Mobile phase: CO2/methanol{0.5% Ammonia (7 m methanol)}=60/40) to obtain N—((S)-6-((1S,4S)-2-oxa-5-azabicyclo[2.2.1]heptan-5-yl)-2-(hydroxymethyl)-2-methyl-2,3-dihydrobenzofuran-5-yl)pyrazolo[1,5-a]pyrimidine-3-carboxamide and N—((R)-6-((1S,4S)-2-oxa-5-azabicyclo[2.2.1]heptan-5-yl)-2-(hydroxymethyl)-2-methyl-2,3-dihydrobenzofuran-5-yl)pyrazolo[1,5-a]pyrimidine-3-carboxamide (42 mg, 28%) (45 mg, 31%) as a yellow solids with absolute stereochemistry assigned arbitrarily.

Example 46, Peak 1: $^1$HNMR (400 MHz, DMSO-d$_6$): 9.89 (s, 1H), 9.37 (dd, J=1.6, 7.2 Hz, 1H), 8.85 (dd, J=1.6, 4.0 Hz, 1H), 8.67 (s, 1H), 7.88 (s, 1H), 7.32 (dd, J=4.0, 7.2 Hz, 1H), 6.52 (s, 1H), 5.04 (t, J=6.0 Hz, 1H), 4.49 (s, 1H), 4.10 (s, 1H), 3.90 (d, J=7.6 Hz, 1H), 3.66 (d, J=6.0 Hz, 1H), 3.48-3.38 (m, 2H), 3.30 (d, J=8.8 Hz, 1H), 3.20-3.07 (m, 2H), 2.79 (d, J=15.6 Hz, 1H), 2.00 (d, J=9.6 Hz, 1H), 1.80 (d, J=8.8 Hz, 1H), 1.34 (s, 3H). MS (ESI): m/z=422.1 [M+1]$^+$.

Example 47, Peak 2: $^1$H NMR (400 MHz, DMSO-d$_6$): 9.87 (s, 1H), 9.37 (dd, J=1.6, 7.2 Hz, 1H), 8.85 (dd, J=1.6, 4.0 Hz, 1H), 8.67 (s, 1H), 7.86 (s, 1H), 7.32 (dd, J=4.0, 7.2 Hz, 1H), 6.51 (s, 1H), 5.05 (t, J=6.0 Hz, 1H), 4.49 (s, 1H), 4.10 (s, 1H), 3.93 (d, J=7.6 Hz, 1H), 3.67 (d, J=7.2 Hz, 1H), 3.48-3.38 (m, 2H), 3.25 (d, J=9.2 Hz, 1H), 3.20-3.10 (m, 2H), 2.79 (d, J=16.0 Hz, 1H), 2.00 (d, J=8.0 Hz, 1H), 1.80 (d, J=9.2 Hz, 1H), 1.34 (s, 3H). MS (ESI): m/z=422.1 [M+1]$^+$.

Examples 48 and 49. (S)—N-(2-Methyl-2-(methylcarbamoyl)-6-morpholino-2,3-dihydrobenzofuran-5-yl)pyrazolo[1,5-a]pyrimidine-3-carboxamide and (R)—N-(2-Methyl-2-(methylcarbamoyl)-6-morpholino-2,3-dihydrobenzofuran-5-yl)pyrazolo[1,5-a]pyrimidine-3-carboxamide

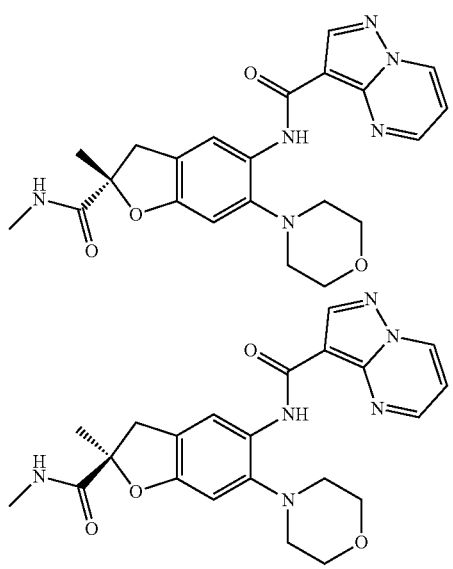

Step A. N, 2-Dimethyl-6-morpholino-5-nitro-2,3-dihydrobenzofuran-2-carboxamide

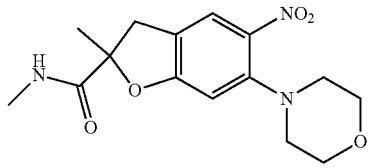

A mixture of 2-methyl-6-morpholino-5-nitro-2,3-dihydrobenzofuran-2-carboxylic acid (100 mg, 0.32 mmol), (7-azabenzotriazol-1-yloxy)tripyrrolidinophosphoniumhexafluorophosphate (338 mg, 0.65 mmol) and N-ethyl-N-isopropylpropan-2-amine (168 mg, 1.30 mmol) in DMF (10 mL) was stirred at room temperature for 30 min. Then methyl amine hydrochloride (44 mg, 0.65 mmol) was added. The resulting mixture was stirred at room temperature for 18h. Water and ethyl acetate (50 mL) was added. The organic phase was separated and dried over sodium sulfate. After concentration, the residue was purified by silica gel chromatography using ethyl acetate:petroleum ether (from 1:3 to 1:1) as eluting solvents to afford N, 2-dimethyl-6-morpholino-5-nitro-2,3-dihydrobenzofuran-2-carboxamide (80 mg, 77%) as orange solid. MS (ESI): m/z=322.1 [M+1]$^+$.

Step B. 5-Amino-N, 2-dimethyl-6-morpholino-2,3-dihydrobenzofuran-2-carboxamide

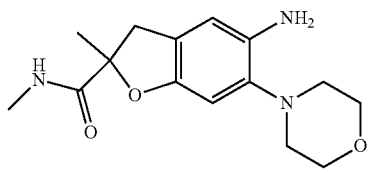 [SMILES: CNC(=O)C1(C)Cc2cc([N+](=O)[O-])c(N3CCOCC3)cc2O1]

A mixture of N, 2-dimethyl-6-morpholino-5-nitro-2,3-dihydrobenzofuran-2-carboxamide (80 mg, 0.25 mmol) and 10% palladium on carbon (8 mg) in methanol (10 mL) was stirred at room temperature for 1h under an atmosphere of hydrogen. Upon filtration over a plug of celite, the filtrate was concentrated under reduced pressure to afford 5-amino-N, 2-dimethyl-6-morpholino-2,3-dihydrobenzofuran-2-carboxamide as a white solid (60 mg), which was used directly in the next step without purification. MS (ESI): m/z=292.1 [M+1]$^+$.

Step C. (S)—N-(2-Methyl-2-(methylcarbamoyl)-6-morpholino-2,3-dihydrobenzofuran-5-yl)pyrazolo[1,5-a]pyrimidine-3-carboxamide and (R)—N-(2-Methyl-2-(methylcarbamoyl)-6-morpholino-2,3-dihydrobenzofuran-5-yl)pyrazolo[1,5-a]pyrimidine-3-carboxamide

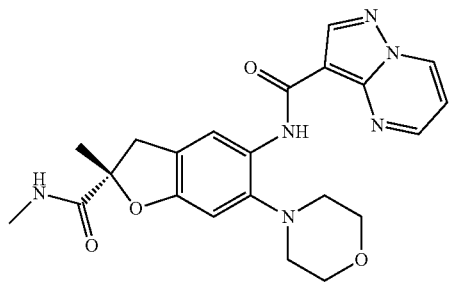

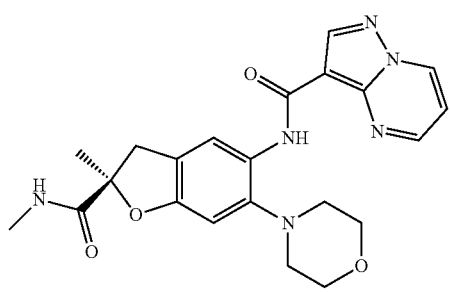

A mixture of pyrazolo[1,5-a]pyrimidine-3-carboxylic acid (34 mg, 0.21 mmol), (7-azabenzotriazol-1-yloxy)tripyrrolidinophosphoniumhexafluorophosphate (107 mg, 0.21 mmol) and N-ethyl-N-isopropylpropan-2-amine (53 mg, 0.42 mmol) in DMF (5 mL) was stirred at room temperature for 30 min. 5-Amino-N, 2-dimethyl-6-morpholino-2,3-dihydrobenzofuran-2-carboxamide (The absolute structure was assigned arbitrarily) (60 mg, 0.21 mmol) was then added and the resulting mixture was stirred at room temperature for 18h. After concentration, the residue was purified by silica gel chromatography using ethyl acetate:petroleum ether (15:1) as eluting solvents to afford the desired product separated by chiral SFC (AS 20*250 mm, Sum (Dacel), CO2/methanol{0.2% Ammonia (7 m methanol)}=70/30) to obtain (S)—N-(2-methyl-2-(methylcarbamoyl)-6-morpholino-2,3-dihydrobenzofuran-5-yl)pyrazolo[1,5-a]pyrimidine-3-carboxamide and (R)—N-(2-methyl-2-(methylcarbamoyl)-6-morpholino-2,3-dihydrobenzofuran-5-yl)pyrazolo[1,5-a]pyrimidine-3-carboxamide (12 mg, 13%) (10 mg, 11%) as a yellow solid with absolute stereochemistry assigned arbitrarily.

Example 48, Peak 1: $^1$HNMR (400 MHz, MeOD-d$_4$):δ 9.14 (dd, J=1.6, 6.8 Hz, 1H), 8.94 (dd, J=1.6, 4.4 Hz, 1H), 8.67 (s, 1H), 8.27 (s, 1H), 7.30 (dd, J=4.4, 7.2 Hz, 1H), 6.90 (s, 1H), 3.95-3.97 (m, 4H), 3.55 (d, J=16.0 Hz, 1H), 3.19 (d, J=16.0 Hz, 1H), 2.92-2.94 (m, 4H), 2.78 (s, 3H), 1.65 (s, 3H). MS (ESI): m/z=437.2 [M+1]$^+$.

Example 49, Peak 2: $^1$H NMR (400 MHz, MeOD-d$_4$):δ 9.03 (dd, J=1.5, 7.2 Hz, 1H), 8.81 (dd, J=1.6, 4.4 Hz, 1H), 8.56 (s, 1H), 8.15 (s, 1H), 7.18 (dd, J=4.4, 7.2 Hz, 1H), 6.78 (s, 1H), 3.83-3.86 (m, 4H), 3.43 (d, J=16.4 Hz, 1H), 3.06 (d, J=16.4 Hz, 1H), 2.80-2.82 (m, 4H), 2.62 (s, 3H), 1.20 (s, 3H). MS (ESI): m/z=437.1 [M+1]$^+$.

Examples 50 and 51. (R)—N-(2-(Difluoromethyl)-2-methyl-6-morpholino-2,3-dihydrobenzofuran-5-yl)pyrazolo[1,5-a]pyrimidine-3-carboxamide and (S)—N-(2-(Difluoromethyl)-2-methyl-6-morpholino-2,3-dihydrobenzofuran-5-yl)pyrazolo[1,5-a]pyrimidine-3-carboxamide

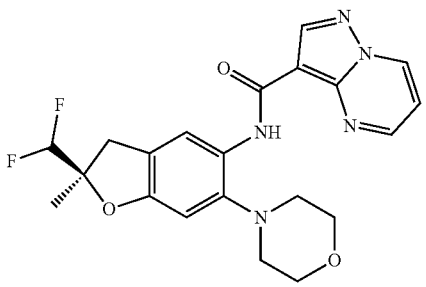

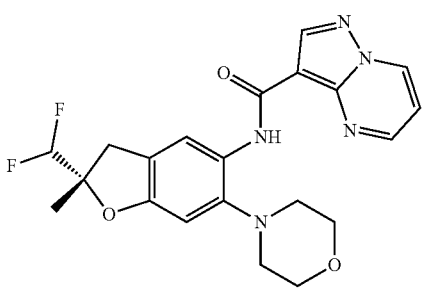

Step A. Methyl 2-methyl-6-morpholino-5-nitro-2,3-dihydrobenzofuran-2-carboxylate

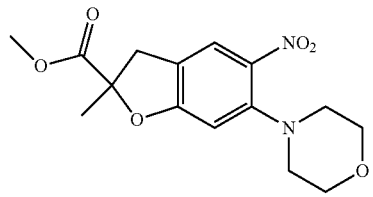 [SMILES: COC(=O)C1(C)Cc2cc([N+](=O)[O-])c(N3CCOCC3)cc2O1]

A mixture of morpholine (270 mg, 3.1 mmol), methyl 6-fluoro-2-methyl-5-nitro-3H-benzofuran-2-carboxylate (Intermediate 3, Step D) (500 mg, 1.55 mmol) and potassium carbonate (427 mg, 3.1 mmol) in acetonitrile (10 mL) was stirred at 25° C. for 18h. Water was added. The aqueous phase was extracted with ethyl acetate (50 mL). The organic phase was dried over sodium sulfate and concentrated to afford methyl 2-methyl-6-morpholino-5-nitro-3H-benzofuran-2-carboxylate (382 mg) as a yellow oil, which was used directly to next step without further purification. MS (ESI): m/z=323.1 [M+1]$^+$.

Step B. 2-Methyl-6-morpholino-5-nitro-2,3-dihydrobenzofuran-2-carbaldehyde

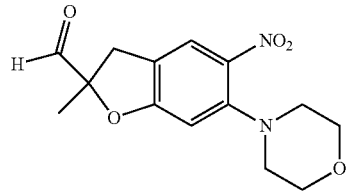

To a mixture of methyl 2-methyl-6-morpholino-5-nitro-3H-benzofuran-2-carboxylate (382 mg, 1.08 mmol) in DCM (10 mL) was added diisobutylaluminium hydride (1.62 mL, 1 m in hexane, 1.62 mmol) drop wise at −78° C. over 5 min and the reaction was maintained at −78° C. for 2h with stirring. The mixture was quenched with sodium sulfate decahydrate and filtered. The filtrate was concentrated under reduced pressure and the residue was purified by silica gel chromatography eluting with using ethyl acetate:petroleum ether (1:1) as eluting solvents to afford 2-methyl-6-morpholino-5-nitro-3H-benzofuran-2-carbaldehyde (230 mg, 73%) as a yellow solid. MS (ESI): m/z=325.1 [M+methanol]$^+$.

Step C. 4-(2-(Difluoromethyl)-2-methyl-5-nitro-2,3-dihydrobenzofuran-6-yl)morpholine

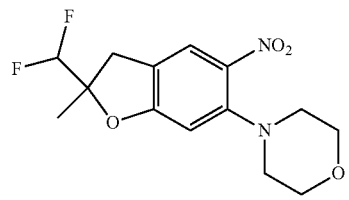 [SMILES: CC1(C(F)F)Cc2cc(N)c(N3CCOCC3)cc2O1]

To a mixture of 2-methyl-6-morpholino-5-nitro-3H-benzofuran-2-carbaldehyde (180 mg, 0.62 mmol) in DCM (30 mL) was added drop wise diethylaminosulfur trifluoride (620 mg, 80%, 3.08 mmol) at −78° C. The mixture was stirred at 25° C. for 18h. The mixture was concentrated and purified by silica gel chromatography using ethyl acetate:petroleum ether (from 1:3 to 2:3) as eluting solvents to afford 4-[2-(difluoromethyl)-2-methyl-5-nitro-3H-benzofuran-6-yl]morpholine (110 mg, 53% yield) as a yellow solid. MS (ESI): m/z=323.1 [M+1]$^+$.

Step D. 2-(Difluoromethyl)-2-methyl-6-morpholino-2,3-dihydrobenzofuran-5-amine

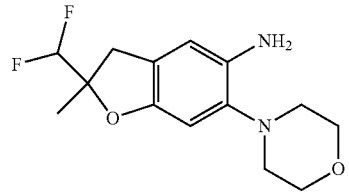

A mixture of 4-[2-(difluoromethyl)-2-methyl-5-nitro-3H-benzofuran-6-yl]morpholine (110 mg, 0.35 mmol) and 10% palladium on carbon (40 mg) in methanol (20 mL) was stirred at 25° C. under an atmosphere of hydrogen for 1h. Upon filtration over a plug of celite, the filtrate was concentrated under reduced pressure to afford 2-(difluoromethyl)-2-methyl-6-morpholino-3H-benzofuran-5-amine (140 mg) as light green oil, which was used directly to next step without further purification. MS (ESI): m/z=285.1 [M+1]$^+$.

Step E. N-(2-(Difluoromethyl)-2-methyl-6-morpholino-2,3-dihydrobenzofuran-5-yl)pyrazolo[1,5-a]pyrimidine-3-carboxamide

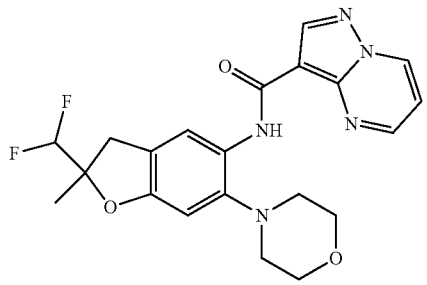 [SMILES: CC1(C(F)F)Cc2cc(NC(=O)c3cnn4cccnc34)c(N3CCOCC3)cc2O1]

A mixture of 2-(difluoromethyl)-2-methyl-6-morpholino-3H-benzofuran-5-amine (90 mg, 0.32 mmol), pyrazolo[1,5-a]pyrimidine-3-carboxylic acid (62 mg, 0.38 mmol) (3-Hydroxy-3H-1,2,3-triazolo[4,5-b]pyridinato-O)tri-1-pyrrolidinylphosphonium hexafluorophosphate (247 mg, 0.47 mmol) and diisopropylethylamine (115 mg, 0.95 mmol) in DMF (5 mL) was stirred at 25° C. for 2h. Water was added. The aqueous was extracted with ethyl acetate (70 mL). The organic phase was washed with brine, dried over sodium sulfate and concentrated under reduced pressure. The residue was purified by silica gel chromatography using ethyl acetate:petroleum ether (9:1) as eluting solvents to afford N-(2-(difluoromethyl)-2-methyl-6-morpholino-2,3-dihydrobenzofuran-5-yl)pyrazolo[1,5-a]pyrimidine-3-carboxamide (100 mg, 73%) as a yellow solid. MS (ESI): m/z=430.1 [M+1]$^+$.

Step F. (R)—N-(2-(Difluoromethyl)-2-methyl-6-morpholino-2,3-dihydrobenzofuran-5-yl)pyrazolo[1,5-a]pyrimidine-3-carboxamide and (S)—N-(2-(Difluoromethyl)-2-methyl-6-morpholino-2,3-dihydrobenzofuran-5-yl)pyrazolo[1,5-a]pyrimidine-3-carboxamide

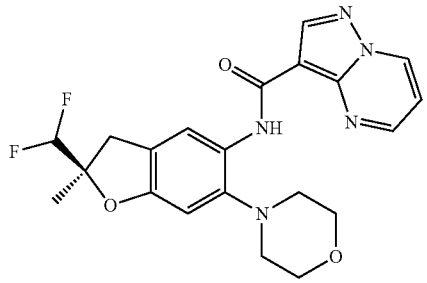

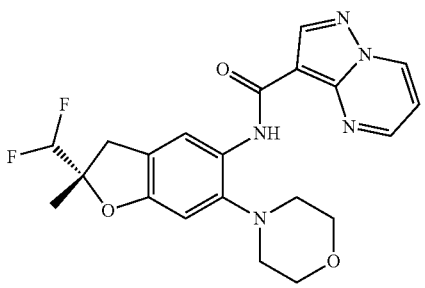

The N-(2-(difluoromethyl)-2-methyl-6-morpholino-2,3-dihydrobenzofuran-5-yl)pyrazolo[1,5-a]pyrimidine-3-carboxamide (100 mg, 0.23 mmol) was purified by chiral separation (OJ 20*250 mm, 5u at CO$_2$/methanol{0.2% Ammonia (7 m methanol)}=80/20, 80 g/min, 100 bar, 35° C.) to afford (R)—N-(2-(difluoromethyl)-2-methyl-6-morpholino-2,3-dihydrobenzofuran-5-yl)pyrazolo[1,5-a]pyrimidine-3-carboxamide and (S)—N-(2-(difluoromethyl)-2-methyl-6-morpholino-2,3-dihydrobenzofuran-5-yl)pyrazolo[1,5-a]pyrimidine-3-carboxamide (30 mg, 30%) (40 mg, 40%) as a yellow solids with absolute stereochemistry assigned arbitrarily.

Example 50, Peak 1: $^1$H NMR (400 MHz, CDCl3) δ 10.47 (s, 1H), 8.84 (dd, J=1.6, 6.8 Hz, 1H), 8.78 (s, 1H), 8.77 (dd, J=1.6, 4.0 Hz, 1H), 8.46 (s, 1H), 7.07 (dd, J=4.0, 6.8 Hz, 1H), 5.75 (t, J=56.0 Hz, 1H), 3.94-3.96 (m, 4H), 3.43 (d, J=16.0 Hz, 1H), 3.03 (d, J=16.0 Hz, 1H), 2.90-2.93 (m, 4H), 1.54 (s, 3H). MS (ESI): m/z=430.1 [M+1]$^+$.

Example 51, Peak 2: $^1$H NMR (400 MHz, CDCl3) δ 10.48 (s, 1H), 8.84 (dd, J=1.6, 6.8 Hz, 1H), 8.78 (s, 1H), 8.77 (dd, J=1.6, 4.0 Hz, 1H), 8.46 (s, 1H), 7.07 (dd, J=4.0, 6.8 Hz, 1H), 5.75 (t, J=56.0 Hz, 1H), 3.94-3.96 (m, 4H), 3.43 (d, J=16.0 Hz, 1H), 3.03 (d, J=16.0 Hz, 1H), 2.90-2.93 (m, 4H), 1.54 (s, 3H). MS (ESI): m/z=430.1 [M+1]$^+$.

Examples 52 and 53. (R)—N-(2-(Hydroxymethyl)-6-(4-(2-hydroxypropan-2-yl)piperidin-1-yl)-2-methyl-2,3-dihydrobenzofuran-5-yl)-6-methylpyrazolo[1,5-a]pyrimidine-3-carboxamide and (S)—N-(2-(Hydroxymethyl)-6-(4-(2-hydroxypropan-2-yl)piperidin-1-yl)-2-methyl-2,3-dihydrobenzofuran-5-yl)-6-methylpyrazolo[1,5-a]pyrimidine-3-carboxamide

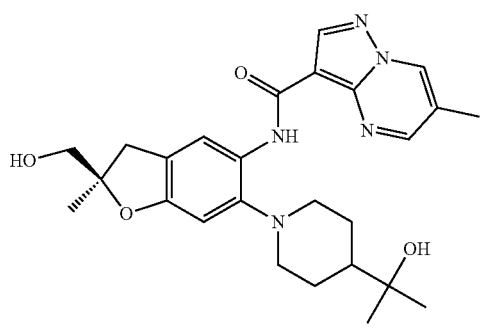

Step A. (2-(1-(2-(Hydroxymethyl)-2-methyl-5-nitro-2,3-dihydrobenzofuran-6-yl)piperidin-4-yl)propan-2-ol

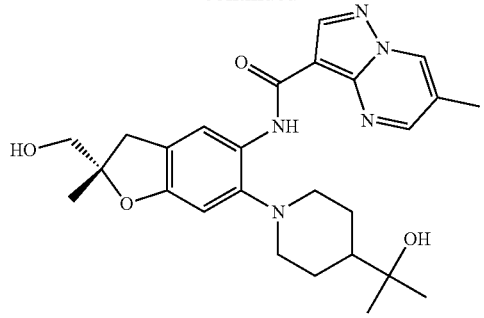

A mixture of 2-(4-piperidyl)-2-propanol (76 mg, 0.53 mmol) (6-fluoro-2-methyl-5-nitro-3H-benzofuran-2-yl)methanol (100 mg, 0.44 mmol) and potassium (91 mg, 0.66 mmol) in acetonitrile (10 mL) was stirred at 25° C. for 18h. Water was added. The aqueous phase was extracted with ethyl acetate (30 mL). The organic phase dried over sodium sulfate and concentrated to afford 2-[1-[2-(hydroxymethyl)-2-methyl-5-nitro-3H-benzofuran-6-yl]-4-piperidyl]propan-2-ol (150 mg) as a yellow oil, which was used directly to next step without further purification. MS (ESI): m/z=351.1 [M+1]$^+$.

Step B. 2-(1-(5-Amino-2-(hydroxymethyl)-2-methyl-2,3-dihydrobenzofuran-6-yl)piperidin-4-yl)propan-2-ol

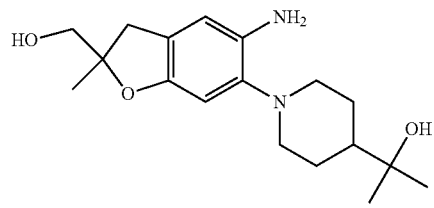 [SMILES: CC1(CO)Cc2cc(N)c(N3CCC(C(C)(C)O)CC3)cc2O1]

A mixture of 2-[1-[2-(hydroxymethyl)-2-methyl-5-nitro-3H-benzofuran-6-yl]-4-piperidyl]propan-2-ol (150 mg, 0.43 mmol) and 10% palladium on carbon (40 mg, 0.43 mmol) in methanol (30 mL) was stirred at 25° C. under hydrogen atmosphere for 1h. After filtration, the filtrate was concentrated under reduced pressure to afford 2-[1-[5-amino-2-(hydroxymethyl)-2-methyl-3H-benzofuran-6-yl]-4-piperidyl]propan-2-ol (160 mg, 82%) as a brown oil. MS (ESI): m/z=321.1 [M+1]$^+$.

Step C. N-(2-(Hydroxymethyl)-6-(4-(2-hydroxypropan-2-yl)piperidin-1-yl)-2-methyl-2,3-dihydrobenzofuran-5-yl)-6-methylpyrazolo[1,5-a]pyrimidine-3-carboxamide

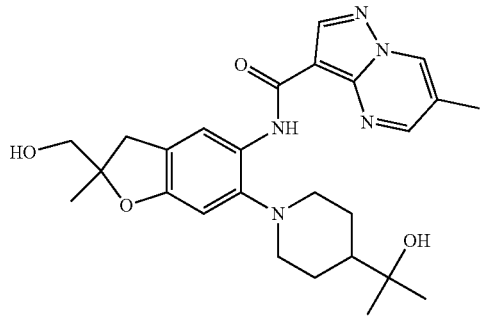 [SMILES: Cc1cnc2c(C(=O)Nc3cc4c(cc3N3CCC(C(C)(C)O)CC3)OC(C)(CO)C4)cnn2c1]

A mixture of 2-[1-[5-amino-2-(hydroxymethyl)-2-methyl-3H-benzofuran-6-yl]-4-piperidyl]propan-2-ol (160 mg, 0.50 mmol), 6-methylpyrazolo[1,5-a]pyrimidine-3-carboxylic acid (106 mg, 0.60 mmol), (3-hydroxy-3H-1,2,3-triazolo[4,5-b]pyridinato-O)tri-1-pyrrolidinylphosphonium hexafluorophosphate (390 mg, 0.75 mmol) and diisopropylethylamine (181 mg, 1.50 mmol) in DMF (5 mL) was stirred at 25° C. for 2h. Water was added. The aqueous phase was extracted with ethyl acetate (70 mL). The organic phase was washed with brine, dried over sodiumsulfate and concentrated under reduced pressure. The residue was purified by silica gel chromatography using ethyl acetate:petroleum ether (9:1) as eluting solvents to afford N-(2-(hydroxymethyl)-6-(4-(2-hydroxypropan-2-yl)piperidin-1-yl)-2-methyl-2,3-dihydrobenzofuran-5-yl)-6-methylpyrazolo[1,5-a]pyrimidine-3-carboxamide (100 mg, 42%) as a yellow solid. MS (ESI): m/z=480.1 [M+1]$^+$.

Step D. (R)—N-(2-(Hydroxymethyl)-6-(4-(2-hydroxypropan-2-yl)piperidin-1-yl)-2-methyl-2,3-dihydrobenzofuran-5-yl)-6-methylpyrazolo[1,5-a]pyrimidine-3-carboxamide and (S)—N-(2-(Hydroxymethyl)-6-(4-(2-hydroxypropan-2-yl)piperidin-1-yl)-2-methyl-2,3-dihydrobenzofuran-5-yl)-6-methylpyrazolo[1,5-a]pyrimidine-3-carboxamide

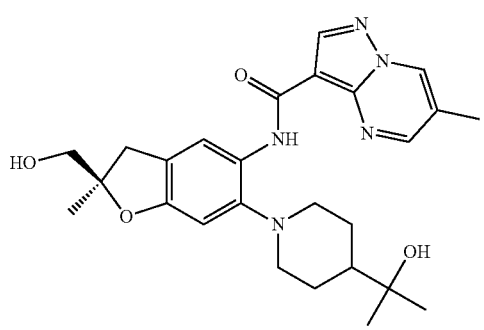

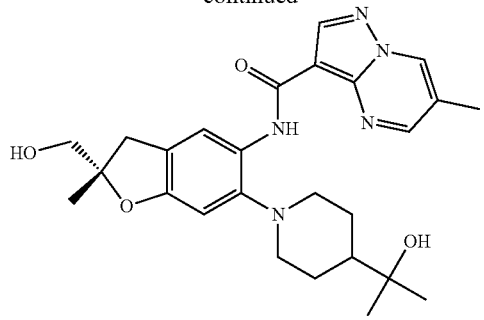

The N-(2-(hydroxymethyl)-6-(4-(2-hydroxypropan-2-yl)piperidin-1-yl)-2-methyl-2,3-dihydrobenzofuran-5-yl)-6-methylpyrazolo[1,5-a]pyrimidine-3-carboxamide was purified by chiral separation (OJ 20*250 mm, 5u at CO$_2$/methanol{0.2% Ammonia (7 m methanol)}=80/20, 80 g/min, 100 bar, 35° C.) to afford (R)—N-(2-(hydroxymethyl)-6-(4-(2-hydroxypropan-2-yl)piperidin-1-yl)-2-methyl-2,3-dihydrobenzofuran-5-yl)-6-methylpyrazolo[1,5-a]pyrimidine-3-carboxamide and (S)—N-(2-(hydroxymethyl)-6-(4-(2-hydroxypropan-2-yl)piperidin-1-yl)-2-methyl-2,3-dihydrobenzofuran-5-yl)-6-methylpyrazolo[1,5-a]pyrimidine-3-carboxamide (40 mg, 40%) (50 mg, 50%) as a yellow solids with absolute stereochemistry assigned arbitrarily.

Example 52, Peak 1: $^1$H NMR (400 MHz, CDCl$_3$) δ 10.42 (s, 1H), 8.69 (d, J=2.0 Hz, 1H), 8.68 (s, 1H), 8.57-8.58 (m, 1H), 8.39 (s, 1H), 6.64 (s, 1H), 3.65-3.67 (m, 2H), 3.23 (d, J=16.0 Hz, 1H), 3.12-3.15 (m, 2H), 2.94 (d, J=16.0 Hz, 1H), 2.58-2.64 (m, 2H), 2.42 (s, 3H), 2.02-2.06 (m, 2H), 1.71-1.84 (m, 4H), 1.46 (s, 3H), 1.25 (s, 6H). MS (ESI): m/z=480.2 [M+1]$^+$.

Example 53, Peak 2: $^1$H NMR (400 MHz, CDCl$_3$) δ 10.43 (s, 1H), 8.69 (d, J=2.0 Hz, 1H), 8.68 (s, 1H), 8.57-8.58 (m, 1H), 8.39 (s, 1H), 6.64 (s, 1H), 3.65-3.67 (m, 2H), 3.23 (d, J=16.0 Hz, 1H), 3.12-3.15 (m, 2H), 2.94 (d, J=16.0 Hz, 1H), 2.58-2.64 (m, 2H), 2.42 (s, 3H), 2.02-2.06 (m, 2H), 1.71-1.84 (m, 4H), 1.46 (s, 3H), 1.25 (s, 6H). MS (ESI): m/z=480.2 [M+1]$^+$.

Examples 54 and 55. (R)-6-Fluoro-N-(2-(hydroxymethyl)-2-methyl-6-morpholino-2,3-dihydrobenzofuran-5-yl)pyrazolo[1,5-a]pyrimidine-3-carboxamide and (S)-6-Fluoro-N-(2-(hydroxymethyl)-2-methyl-6-morpholino-2,3-dihydrobenzofuran-5-yl)pyrazolo[1,5-a]pyrimidine-3-carboxamide

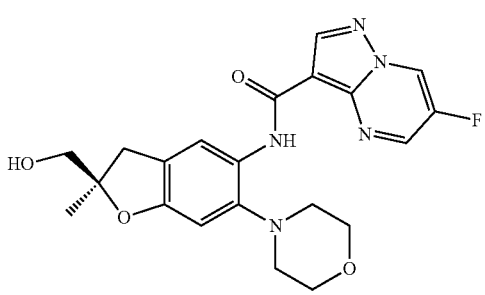

-continued

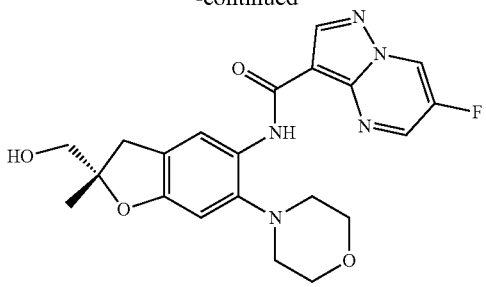

Step A. (Z)-2,3,3-Trifluoroprop-1-enyl 4-methylbenzenesulfonate

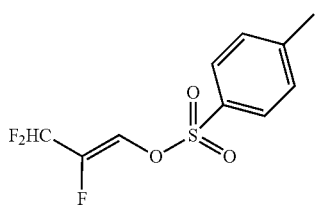 [SMILES: Cc1ccc(S(=O)(=O)O/C=C(\F)C(F)F)cc1]

A mixture of 2,2,3,3-tetrafluoropropyl 4-methylbenzenesulfonate (3.0 g, 10.49 mmol) in THF (30 mL), was cooled to −78° C. n-butyllithium (9.23 mL, 23.08 mmol, 2.5 M in hexane) was added drop wise and the reaction was stirred at −78° C. for 10 min. The reaction was quenched with water and allowed to warm to room temperature. The aqueous phase was extracted with DCM (2×50 mL). The organic phases were dried over sodium sulfate and concentrated in vacuo to afford (Z)-2,3,3-trifluoroprop-1-enyl 4-methylbenzenesulfonate (1.96 g, 70%) as a yellow oil, which was used directly to next step without further purification. MS (ESI): m/z=267.0 [M+1]$^+$

Step B. (Z)-3-(Diethylamino)-2-fluoroacrylaldehyde

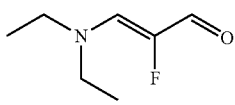

To a solution of diethylamine (362 mg, 1.96 mmol), triethylamine (456 mg, 4.51 mmol), and a catalytic amount of tetrabutylammonium fluoride (0.45 mmol, 0.45 mL, 1 m in THF) in acetonitrile (3 mL), was added a solution of (Z)-2,3,3-trifluoroprop-1-enyl 4-methylbenzenesulfonate (1200 mg, 4.51 mmol) in acetonitrile (6 mL) at 0° C. The mixture was stirred at room temperature for 3h and quenched with brine. The aqueous phase was extracted with DCM (2×30 mL), dried over sodium sulfate and concentrated in vacuo. The residue was purified by silica gel chromatography using ethyl acetate:petroleum ether (1:4 to 1:1) as eluting solvents to afford (Z)-3-(diethylamino)-2-fluoroacrylaldehyde (558 mg, 85%) as a yellow oil. MS (ESI): m/z=146.1 [M+1]$^+$

Step C. Ethyl 6-fluoropyrazolo[1,5-a]pyrimidine-3-carboxylate

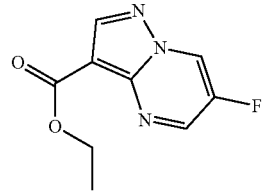

A mixture of (Z)-3-(diethylamino)-2-fluoroacrylaldehyde (400 mg, 2.76 mmol) and ethyl 5-amino-1H-pyrazole-4-carboxylate (428 mg, 2.76 mmol) in acetic acid (5 mL) was stirred at 80° C. for 1h. After concentration in vacuo, the residue was purified by silica gel chromatography using ethyl acetate:petroleum ether (1:5) as eluting solvents to afford ethyl 6-fluoropyrazolo[1,5-a]pyrimidine-3-carboxylate (180 mg, 26%) as a yellow solid. MS (ESI): m/z=210.1 [M+1]$^+$.

Step D. 6-Fluoropyrazolo[1,5-a]pyrimidine-3-carboxylic acid

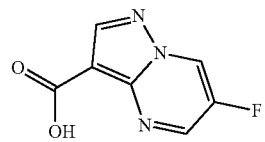

A mixture of ethyl 6-fluoropyrazolo[1,5-a]pyrimidine-3-carboxylate (70 mg, 0.33 mmol) and hydroxyl lithium hydrate (13 mg, 0.33 mmol) in methanol (1 mL), THF (1 mL) and water (1 mL), was stirred at 100° C. under microwave for 10 min. After concentration in vacuo, it was afforded 6-fluoropyrazolo[1,5-a]pyrimidine-3-carboxylic acid (47 mg) as a yellow solid, which as used directly to next step without further purification. MS (ESI): m/z=204.0 [M+1]$^+$.

Step E. (5-Amino-2-methyl-6-morpholino-2,3-dihydrobenzofuran-2-yl)methanol

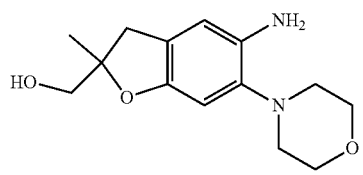 [SMILES: CC1(CO)Cc2cc(N)c(N3CCOCC3)cc2O1]

A mixture of (2-methyl-6-morpholino-5-nitro-2,3-dihydrobenzofuran-2-yl)methanol (Example 6, Step B) (128 mg, 0.44 mmol) and 10% palladium on carbon (30 mg) in methanol (5 mL) was stirred at 20° C. under hydrogen atmosphere for 2h. Upon filtration through a plug of celite, the filtrate was concentrated under reduced pressure to afford (5-amino-2-methyl-6-morpholino-2,3-dihydrobenzofuran-2-yl)methanol (102 mg, 89%) as a brown solid. MS (ESI): m/z=265.1 [M+1]$^+$.

Step F. 6-Fluoro-N-(2-(hydroxymethyl)-2-methyl-6-morpholino-2,3-dihydrobenzofuran-5-yl)pyrazolo[1,5-a]pyrimidine-3-carboxamide

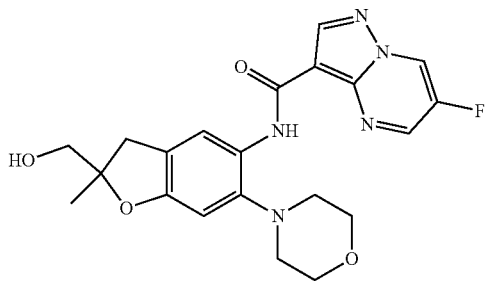 [SMILES: CC1(CO)Cc2cc(NC(=O)c3cnn4cc(F)cnc34)c(N3CCOCC3)cc2O1]

A mixture of 6-fluoropyrazolo[1,5-a]pyrimidine-3-carboxylic acid (47 mg, 0.26 mmol), (5-amino-2-methyl-6-morpholino-2,3-dihydrobenzofuran-2-yl)methanol (82 mg, 0.31 mmol), 2-(7-aza-1H-benzotriazole-1-yl)-1,1,3,3-tetramethyluronium hexafluorophosphate (148 mg, 0.39 mmol) and diisopropylethylamine (101 mg, 0.78 mmol) in DMF (5 mL) was stirred at 20° C. for 2h. The crude reaction was purified by preparative HPLC(Xbridge 21.2*250 mm c18, 10 um, A: acetonitrile 15-40%; B: 10 mM ammonium bicarbonate in water) to afford 6-fluoro-N-(2-(hydroxymethyl)-2-methyl-6-morpholino-2,3-dihydrobenzofuran-5-yl)pyrazolo[1,5-a]pyrimidine-3-carboxamide (46 mg, 42%) as a yellow solid.

Step G. (R)-6-Fluoro-N-(2-(hydroxymethyl)-2-methyl-6-morpholino-2,3-dihydrobenzofuran-5-yl)pyrazolo[1,5-a]pyrimidine-3-carboxamide and (S)-6-Fluoro-N-(2-(hydroxymethyl)-2-methyl-6-morpholino-2,3-dihydrobenzofuran-5-yl)pyrazolo[1,5-a]pyrimidine-3-carboxamide

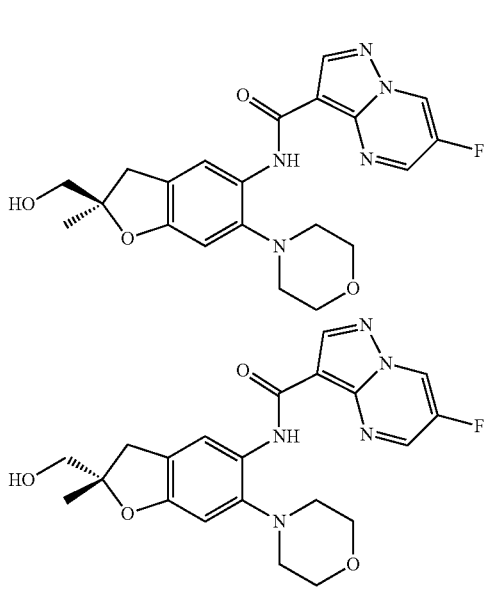

6-Fluoro-N-(2-(hydroxymethyl)-2-methyl-6-morpholino-2,3-dihydrobenzofuran-5-yl)pyrazolo[1,5-a]pyrimidine-3-carboxamide (46 mg, 0.11 mmol) was separated by chiral separation (SFC-80 (Thar, Waters), OJ 20*250 mm, 5 um (Dacel), C Mobile phase: CO2/methanol{0.5% Ammonia (7 m methanol)}=70/30) to afford (R)-6-fluoro-N-(2-(hydroxymethyl)-2-methyl-6-morpholino-2,3-dihydrobenzofuran-5-yl)pyrazolo[1,5-a]pyrimidine-3-carboxamide and (S)-6-fluoro-N-(2-(hydroxymethyl)-2-methyl-6-morpholino-2,3-dihydrobenzofuran-5-yl)pyrazolo[1,5-a]pyrimidine-3-carboxamide (8.4 mg each, 37% each) as a yellow solids with absolute stereochemistry assigned arbitrarily.

Example 54, Peak 1: $^1$H NMR (400 MHz, DMSO-d$_6$): δ 10.28 (s, 1H), 9.82 (dd, J=2.4, 4.4 Hz, 1H), 9.20 (d, J=2.4 Hz, 1H), 8.70 (s, 1H), 8.26 (s, 1H), 6.70 (s, 1H), 5.04 (t, J=6.0 Hz, 1H), 3.83-3.81 (m, 4H), 3.47-3.38 (m, 2H), 3.22-3.18 (m, 1H), 2.84-2.79 (m, 5H), 1.34 (s, 3H). MS (ESI): m/z=428.2 [M+1]$^+$.

Example 55, Peak 2: $^1$H NMR (400 MHz, DMSO-d$_6$): δ 10.28 (s, 1H), 9.82 (dd, J=2.4, 4.4 Hz, 1H), 9.20 (d, J=2.4 Hz, 1H), 8.70 (s, 1H), 8.26 (s, 1H), 6.70 (s, 1H), 5.04 (t, J=6.0 Hz, 1H), 3.83-3.81 (m, 4H), 3.47-3.38 (m, 2H), 3.22-3.18 (m, 1H), 2.84-2.79 (m, 5H), 1.34 (s, 3H). MS (ESI): m/z=428.2 [M+1]$^+$.

Examples 56 and 57. N-[(2S)-6-[(3S)-3-Fluoropyrrolidin-1-yl]-2-(hydroxymethyl)-2-methyl-3H-benzofuran-5-yl]pyrazolo[1,5-a]pyrimidine-3-carboxamide and N-[(2R)-6-[(3S)-3-Fluoropyrrolidin-1-yl]-2-(hydroxymethyl)-2-methyl-3H-benzofuran-5-yl]pyrazolo[1,5-a]pyrimidine-3-carboxamide

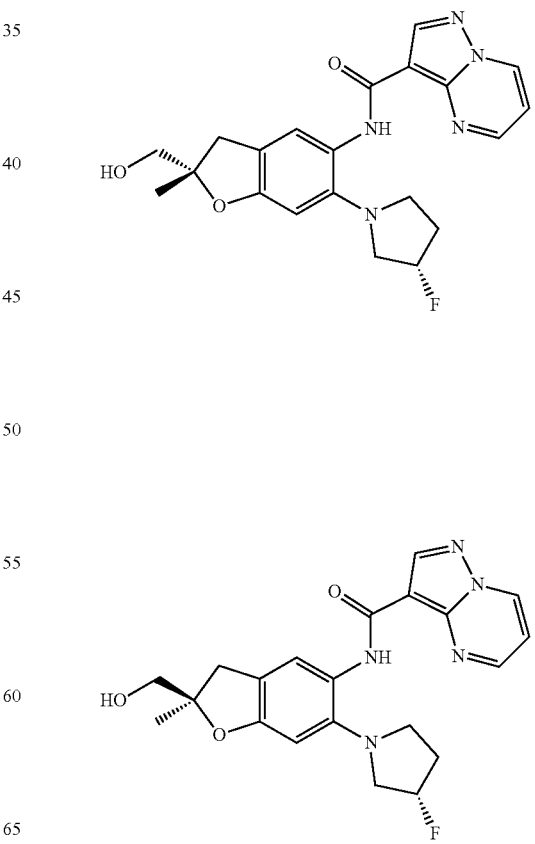

Step A. [6-[(3S)-3-Fluoropyrrolidin-1-yl]-2-methyl-5-nitro-3H-benzofuran-2-yl]methanol

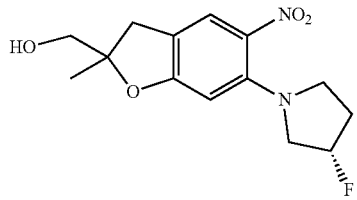

A mixture of (6-chloro-2-methyl-5-nitro-3H-benzofuran-2-yl)methanol (Intermediate 2) (150 mg, 0.62 mmol), (S)-3-fluoropyrrolidine hydrochloride (110 mg, 1.23 mmol) and cesium carbonate (600 mg, 1.84 mmol) in DMSO (2 mL) was stirred at 90° C. for 3h. The mixture was then poured into water and the aqueous phase was extracted with ethyl acetate (2×30 mL). The organic phases were combined and washed with water, brine and dried over sodium sulfate before concentration to dryness. The residue was purified by preparative TLC using ethyl acetate:petroleum ether (1:3) as eluting solvents to afford [6-[(3S)-3-fluoropyrrolidin-1-yl]-2-methyl-5-nitro-3H-benzofuran-2-yl]methanol (102 mg, 55%) as a yellow oil. MS (ESI): m/z=297.1 [M+1].

Step B. [5-Amino-6-[(3S)-3-Fluoropyrrolidin-1-yl]-2-methyl-3H-benzofuran-2-yl]methanol

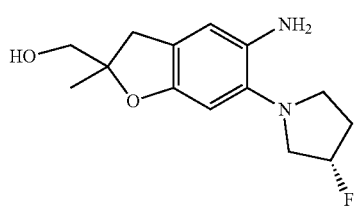 [SMILES: CC1(CO)Cc2cc([N+](=O)[O-])c(N3CC[C@H](F)C3)cc2O1]

A mixture of [6-[(3S)-3-fluoropyrrolidin-1-yl]-2-methyl-5-nitro-3H-benzofuran-2-yl]methanol (102 mg, 0.34 mmol) and 10% palladium on carbon (10 mg) in methanol (10 mL) was stirred at room temperature under hydrogen atmosphere for 1h. The reaction was filtered through a plug of celite and the filtrate was concentrated under reduced pressure to afford[5-amino-6-[(3R)-3-fluoropyrrolidin-1-yl]-2-methyl-3H-benzofuran-2-yl]methanol (96 mg) as a brown oil, which was used directly to next step without further purification. MS (ESI): m/z=297.1 [M+1].

Step C. N-[(2S)-6-[(3S)-3-Fluoropyrrolidin-1-yl]-2-(hydroxymethyl)-2-methyl-3H-benzofuran-5-yl]pyrazolo[1,5-a]pyrimidine-3-carboxamide and N-[(2R)-6-[(3S)-3-Fluoropyrrolidin-1-yl]-2-(hydroxymethyl)-2-methyl-3H-benzofuran-5-yl]pyrazolo[1,5-a]pyrimidine-3-carboxamide

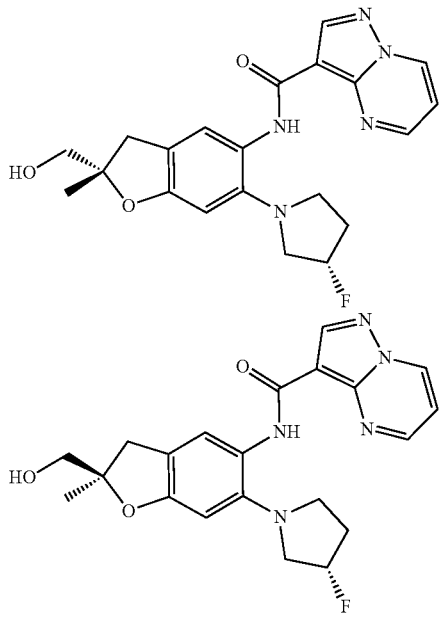

A solution of pyrazolo[1,5-a]pyrimidine-3-carboxylic acid (118 mg, 0.72 mmol), 2-(7-aza-1H-benzotriazole-1-yl)-1,1,3,3-tetramethyluronium hexafluorophosphate (340 mg, 0.89 mmol) and diisopropylethylamine (0.24 mL, 1.45 mmol) was stirred in DMF (3 mL) at room temperature for 10 min. To this mixture was added [5-amino-6-[(3S)-3-fluoropyrrolidin-1-yl]-2-methyl-3H-benzofuran-2-yl]methanol (96 mg, 0.36 mmol) in DMF (2 mL) and stirred for 16h. The final products was purified by preparative HPLC (Xbridge 21.2*250 mm c18, 10 um, A: acetonitrile 25-70%; B:10 mM ammonium bicarbonate in water) and then the product was resolved by chiral separation (SFC (AD-H 20*250 mm, 5um, CO$_2$/methanol (0.5% Ammonia (7 m methanol))=50/50, 35° C.) to afford N-[(2S)-6-[(3S)-3-fluoropyrrolidin-1-yl]-2-(hydroxymethyl)-2-methyl-3H-benzofuran-5-yl]pyrazolo[1,5-a]pyrimidine-3-carboxamide and N-[(2R)-6-[(3S)-3-fluoropyrrolidin-1-yl]-2-(hydroxymethyl)-2-methyl-3H-benzofuran-5-yl]pyrazolo[1,5-a]pyrimidine-3-carboxamide (16 mg, 11%) (19 mg, 13%) as a yellow solids with absolute stereochemistry assigned arbitrarily.

Example 56, Peak 1: $^1$H NMR (400 MHz, CDCl$_3$) δ 10.25 (s, 1H), 8.81 (dd, J=1.6, 6.8 Hz, 1H), 8.77 (s, 1H), 8.69 (dd, J=2.0, 4.0, Hz, 1H), 8.26 (s, 1H), 7.02 (dd, J=4.4, 7.2, Hz, 1H), 6.59 (s, 1H), 5.42-5.25 (m, 1H), 3.67 (s, 2H), 355-3.44 (m, 1H), 3.43-3.40 (m, 1H), 3.36-3.32 (m, 1H), 3.24 (d, J=15.5 Hz, 1H), 2.95-2.86 (m, 2H), 2.34-2.21 (m, 2H), 2.08-1.89 (m, 1H), 1.46 (s, 3H). MS (ESI): m/z=412.1 [M+1]

Example 57, Peak 2: $^1$H NMR (400 MHz, CDCl$_3$) δ 10.24 (s, 1H), 8.81 (dd, J=2.0, 7.2 Hz, 1H), 8.76 (s, 1H), 8.67 (dd, J=1.6, 4.0 Hz, 1H), 8.25 (s, 1H), 7.02 (dd, J=4.0, 7.2 Hz, 1H), 6.59 (s, 1H), 5.46-5.23 (m, 1H), 3.67 (s, 2H), 3.54-3.46

(m, 1H), 3.44-3.39 (m, 1H), 3.36-3.32 (m, 1H), 3.23 (d, J=16.0 Hz, 1H), 2.94 (d, J=16.0 Hz, 1H), 2.93-2.85 (m, 1H), 2.40-2.13 (m, 2H), 2.08-1.85 (m, 1H), 1.46 (s, 3H). MS (ESI): m/z=412.2 [M+1]

Examples 58 and 59. N-[(2R)-6-[(3R)-3-Fluoropyrrolidin-1-yl]-2-(hydroxymethyl)-2-methyl-3H-benzofuran-5-yl]pyrazolo[1,5-a]pyrimidine-3-carboxamide and N-[(2S)-6-[(3R)-3-Fluoropyrrolidin-1-yl]-2-(hydroxymethyl)-2-methyl-3H-benzofuran-5-yl]pyrazolo[1,5-a]pyrimidine-3-carboxamide

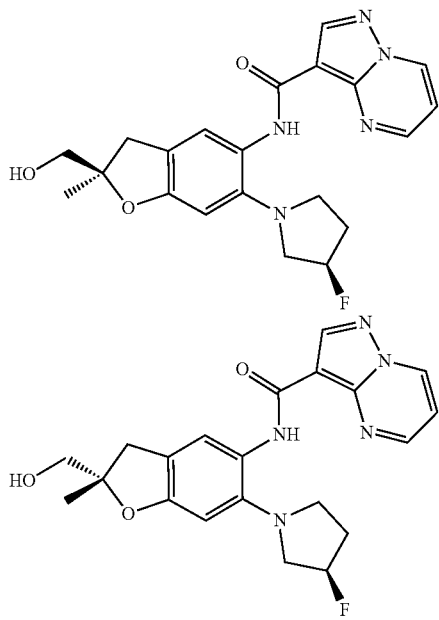

Step A. [6-[(3R)-3-Fluoropyrrolidin-1-yl]-2-methyl-5-nitro-3H-benzofuran-2-yl]methanol

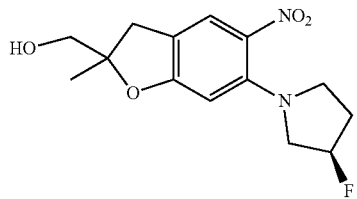

A mixture of (6-chloro-2-methyl-5-nitro-3H-benzofuran-2-yl)methanol (Intermediate 1) (150 mg, 0.62 mmol), (3R)-3-fluoropyrrolidine hydrochloride (440 mg, 3.5 mmol) and cesium carbonate (780 mg, 2.4 mmol) in DMSO (2 mL) was stirred at 90° C. for 7h. The mixture was poured into water and extracted ethyl acetate (100 mL) and the organics washed with water brine and dried over sodium sulfate before concentration to dryness. The residue was then purified by preparative TLC using ethyl acetate:petroleum ether (1:3) as eluting solvents to afford [6-[(3R)-3-fluoropyrrolidin-1-yl]-2-methyl-5-nitro-3H-benzofuran-2-yl]methanol (135 mg, 74%) as a yellow oil. MS (ESI): m/z=297.1 [M+1]$^+$.

Step B. [5-Amino-6-[(3R)-3-fluoropyrrolidin-1-yl]-2-methyl-3H-benzofuran-2-yl]methanol

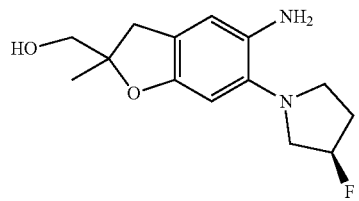 [SMILES: CC1(CO)Cc2cc([N+](=O)[O-])c(N3CC[C@@H](F)C3)cc2O1]

A mixture of [6-[(3R)-3-Fluoropyrrolidin-1-yl]-2-methyl-5-nitro-3H-benzofuran-2-yl]methanol (135 mg, 0.46 mmol) and 10% palladium on carbon (50 mg) in methanol (12 mL) was stirred under hydrogen atmosphere at 25° C. for 1h. After filtration through a plug of celite and concentration, it was afforded [5-amino-6-[(3R)-3-fluoropyrrolidin-1-yl]-2-methyl-3H-benzofuran-2-yl]methanol (110 mg) as a brown oil which was directly used to the next step without further purification. MS (ESI): m/z=267.1 [M+1]$^+$.

Step C. N-[(2R)-6-[(3R)-3-Fluoropyrrolidin-1-yl]-2-(hydroxymethyl)-2-methyl-3H-benzofuran-5-yl]pyrazolo[1,5-a]pyrimidine-3-carboxamide and N-[(2S)-6-[(3R)-3-Fluoropyrrolidin-1-yl]-2-(hydroxymethyl)-2-methyl-3H-benzofuran-5-yl]pyrazolo[1,5-a]pyrimidine-3-carboxamide

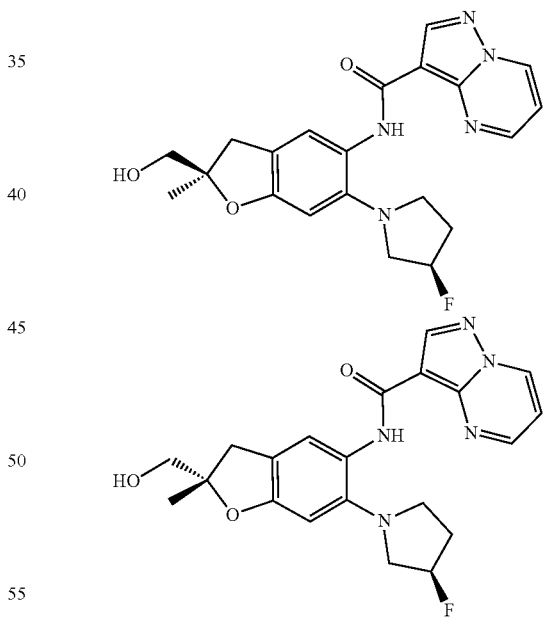

To a solution of diisopropylethylamine (0.2 mL, 1.24 mmol) and pyrazolo[1,5-a]pyrimidine-3-carboxylic acid (102 mg, 0.63 mmol) was added 2-(7-aza-H-benzotriazole-1-yl)-1,1,3,3-tetramethyluronium hexafluorophosphate (314 mg, 0.83 mmol) then was stirred at 25° C. for 20 min. To the mixture was added the solution of [5-amino-6-[(3R)-3-fluoropyrrolidin-1-yl]-2-methyl-3H-benzofuran-2-yl]methanol (110 mg, 0.41 mmol) in DMF (3 mL) and the mixture was stirred at 25° C. for 16h. The crude was purified by preparative HPLC (Xbridge 21.2*250 mm c18, 10 um, A:

acetonitrile 25-55%; B: 10 mM ammonium bicarbonate in water) and resolved by chiral separation (SFC-80 (Thar, Waters), AD 20*250 mm, Sum (Dacel), CO₂/methanol{0.5% Ammonia (7 m methanol)}=50/50) to afford N-[(2R)-6-[(3R)-3-fluoropyrrolidin-1-yl]-2-(hydroxymethyl)-2-methyl-3H-benzofuran-5-yl]pyrazolo[1,5-a]pyrimidine-3-carboxamide and N-[(2S)-6-[(3R)-3-fluoropyrrolidin-1-yl]-2-(hydroxymethyl)-2-methyl-3H-benzofuran-5-yl]pyrazolo[1,5-a]pyrimidine-3-carboxamide (24 mg, 14%) (29 mg, 17%) as a yellowsolids with absolute stereochemistry assigned arbitrarily.

Example 58, Peak 1: ¹HNMR (400 MHz, DMSO-$d_6$) δ 10.11 (s, 1H), 9.36 (dd, J=1.6, 7.2 Hz, 1H), 8.81 (dd, J=1.6, 4.0 Hz, 1H), 8.68 (s, 1H), 8.05 (s, 1H), 7.31 (dd, J=4.0, 7.2 Hz, 1H), 6.59 (s, 1H), 5.39 (td, J=4.4, 55.2 Hz, 1H), 5.04 (t, J=5.6 Hz, 1H), 3.56-3.34 (m, 4H), 3.22-3.07 (m, 2H), 2.93-2.85 (m, 1H), 2.81 (d, J=16.0 Hz, 1H), 2.36-2.05 (m, 2H), 1.34 (s, 3H). MS (ESI): m/z=412.1 [M+1]⁺.

Example 59, Peak 1: ¹H NMR (400 MHz, DMSO-$d_6$) δ 10.11 (s, 1H), 9.36 (dd, J=1.6, 7.2 Hz, 1H), 8.81 (dd, J=1.6, 4.0 Hz, 1H), 8.68 (s, 1H), 8.05 (s, 1H), 7.31 (dd, J=4.0, 7.2 Hz, 1H), 6.60 (s, 1H), 5.39 (td, J=4.4, 54.4 Hz, 1H), 5.04 (t, J=5.6 Hz, 1H), 3.56-3.34 (m, 4H), 3.22-3.07 (m, 2H), 2.93-2.85 (m, 1H), 2.81 (d, J=16.0 Hz, 1H), 2.36-2.07 (m, 2H), 1.34 (s, 3H). MS (ESI): m/z=412.2 [M+1]⁺.

Example 60. N-[6-[4-(2-Hydroxyethyl)piperazin-1-yl]-2,2-dimethyl-3H-benzofuran-5-yl]pyrazolo[1,5-a]pyrimidine-3-carboxamide

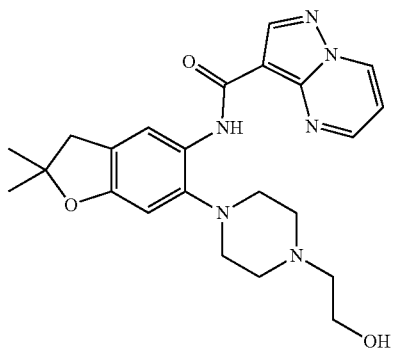

Step A. 2-[4-(2,2-Dimethyl-5-nitro-3H-benzofuran-6-yl)piperazin-1-yl]ethanol

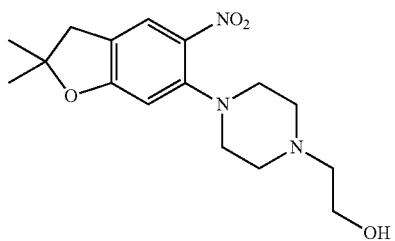 [SMILES: CC1(C)Cc2cc([N+](=O)[O-])c(N3CCN(CCO)CC3)cc2O1]

A mixture of 6-chloro-2,2-dimethyl-5-nitro-3H-benzofuran (Intermediate 1) (100 mg, 0.44 mmol) and 1-piperazineethanol (572 mg, 4.39 mmol) in DMSO (1 mL) was stirred at 110° C. for 16h. The mixture was poured into water and the aqueous phase was extracted by ethyl acetate (100 mL). The organic phase was washed with water, brine and dried over sodium sulfate before concentration to dryness. The residue was purified by preparative TLC using methanol:DCM=1:20 as eluting solvents to afford 2-[4-(2,2-dimethyl-5-nitro-3H-benzofuran-6-yl)piperazin-1-yl]ethanol (110 mg, 78%) as a brown oil. MS (ESI): m/z=322.1 [M+1]⁺.

Step B. 2-[4-(5-Amino-2,2-dimethyl-3H-benzofuran-6-yl)piperazin-1-yl]ethanol

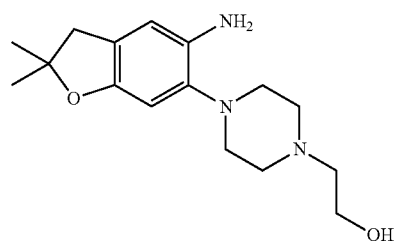

A mixture of 2-[4-(2,2-dimethyl-5-nitro-3H-benzofuran-6-yl)piperazin-1-yl]ethanol (59 mg, 0.18 mmol) and 10% palladium on carbon (29 mg) in methanol (8 mL) was stirred under hydrogen atmosphere at 20° C. for 1h. After filtration and concentration, 2-[4-(5-amino-2,2-dimethyl-3H-benzofuran-6-yl)piperazin-1-yl]ethanol (50 mg) was afforded as a brown oil, which was used to the next step without further purification. MS (ESI): m/z=392.2 [M+1].

Step C. N-[6-[4-(2-Hydroxyethyl)piperazin-1-yl]-2,2-dimethyl-3H-benzofuran-5-yl]pyrazolo[1,5-a]pyrimidine-3-carboxamide

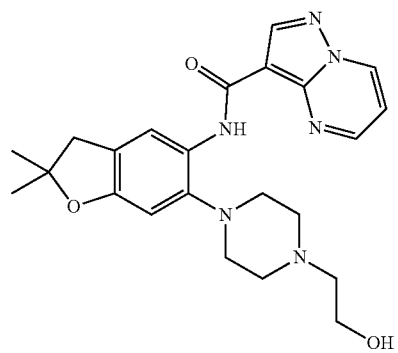

To the mixture of pyrazolo[1,5-a]pyrimidine-3-carboxylic acid (42 mg, 0.26 mmol) and diisopropylethylamine (0.09 mL, 0.52 mmol) in DMF (2 mL) was added 2-(7-aza-1H-benzotriazole-1-yl)-1,1,3,3-tetramethyluronium hexafluorophosphate (131 mg, 0.34 mmol) then the mixture was stirred at 25° C. for 15 min. To the mixture was added a solution of 2-[4-(5-amino-2,2-dimethyl-3H-benzofuran-6-yl)piperazin-1-yl]ethanol (50 mg, 0.17 mmol) in DMF (2 mL) and the resulting mixture was stirred at 25° C. for 16h. The mixture was purified by preparative HPLC(Xbridge 21.2*250 mm c18, 10 um, A: acetonitrile 10-70%; B:10 mM ammonium bicarbonate in water) to afford N-[6-[4-(2-hydroxyethyl)piperazin-1-yl]-2,2-dimethyl-3H-benzofuran-5-yl]pyrazolo

[1,5-a]pyrimidine-3-carboxamide (45 mg, 60%) as a yellow solid. H NMR (400 MHz, DMSO-$d_6$) δ 10.42 (s, 1H), 9.37 (dd, J=1.6, 7.2 Hz, 1H), 8.92 (dd, J=1.6, 4.4 Hz, 1H), 8.68 (s, 1H), 8.31 (s, 1H), 7.36 (dd, J=4.4, 7.2 Hz, 1H), 6.69 (s, 1H), 4.45 (t, J=5.2 Hz, 1H), 3.54 (q, J=5.6 Hz, 2H), 3.00 (s, 2H), 2.84-2.78 (m, 4H), 2.74-2.61 (m, 4H), 2.50 (t, J=5.6 Hz, 2H), 1.41 (s, 6H). MS (ESI): m/z=437.3 [M+1]$^+$.

Example 61. 6-Cyclopropyl-N-(2,2-dimethyl-6-morpholino-3H-benzofuran-5-yl)pyrazolo[1,5-a]pyrimidine-3-carboxamide

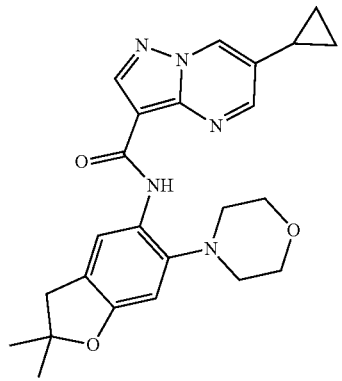 [SMILES: CC1(C)Cc2cc(NC(=O)c3cnn4cc(C5CC5)cnc34)c(N3CCOCC3)cc2O1]

Step A. Ethyl 6-bromopyrazolo[1,5-a]pyrimidine-3-carboxylate

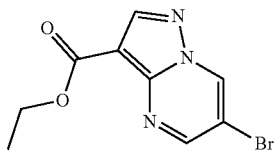

To a mixture of ethyl 3-amino-1H-pyrazole-4-carboxylate (3.0 g, 19.34 mmol) and 2-bromomalonaldehyde (3.21 g, 21.26 mmol) in ethanol (10 mL) was added acetic acid (30 mL). The mixture was stirred for 2h at 70° C. The reaction was concentrated to dryness. The residue was dissolved in ethyl acetate and saturated sodium bicarbonate solution was added. The organic phase was extracted and dried over sodium sulfate before concentration to dryness. The residue was then purified by silica gel chromatography using ethyl acetate:petroleum ether (1:3) as eluting solvents to afford ethyl 6-bromopyrazolo[1,5-a]pyrimidine-3-carboxylate (3.3 g, 63%) as a white solid. MS (ESI): m/z=270.0 [M+1]$^+$.

Step B. Ethyl 6-cyclopropylpyrazolo[1,5-a]pyrimidine-3-carboxylate

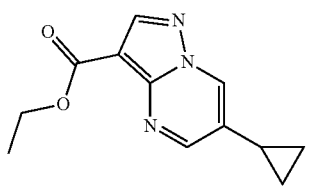 [SMILES: CCOC(=O)c1cnn2cc(C3CC3)cnc12]

A mixture of ethyl 6-bromopyrazolo[1,5-a]pyrimidine-3-carboxylate (400 mg, 1.48 mmol), cyclopropylboronicacid (200 mg, 2.33 mmol), palladium diacetate (56 mg, 0.25 mmol), triphenylphosphine (168 mg, 0.60 mmol) and potassium phosphate (1260 mg, 5.94 mmol) in toluene (6 mL) and water (1 mL) in a sealed tube was stirred under $N_2$ atmosphere at 120° C. for 2h. The mixture was poured onto water (30 mL) and the aqueous phase was extracted with ethyl acetate (100 mL). The organic phase was washed with water and brine and dried over sodium sulfate before concentration to dryness. The residue was purified by preparative TLC using ethyl acetate:petroleum ether (1:3) to afford ethyl 6-cyclopropylpyrazolo[1,5-a]pyrimidine-3-carboxylate (205 mg, 60%) as a yellow solid. MS(ESI): m/z=232.1 [M+1]$^+$.

Step C. 6-Cyclopropylpyrazolo[1,5-a]pyrimidine-3-carboxylic acid

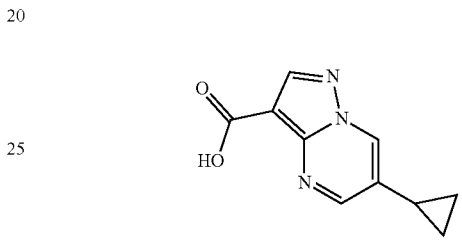

The mixture of ethyl 6-cyclopropylpyrazolo[1,5-a]pyrimidine-3-carboxylate (60 mg, 0.26 mmol) and lithium hydroxide (12 mg, 0.29 mmol) in THF (3 mL), methanol (3 mL) and water (3 mL) was stirred at 100° C. for 10 min. The mixture was neutralized with 1N hydrogen chloride solution. The aqueous phase was extracted with EtOAc (20 mL). The organic phase was separated, dried over sodium sulfate and concentrated under reduced pressure to afford 6-cyclopropylpyrazolo[1,5-a]pyrimidine-3-carboxylic acid (52 mg) as a yellow solid, which was directly used in the next step without further purification. MS (ESI): m/z=204.1[M+1]$^+$.

Step E. 6-Cyclopropyl-N-(2,2-dimethyl-6-morpholino-3H-benzofuran-5-yl)pyrazolo[1,5-a]pyrimidine-3-carboxamide

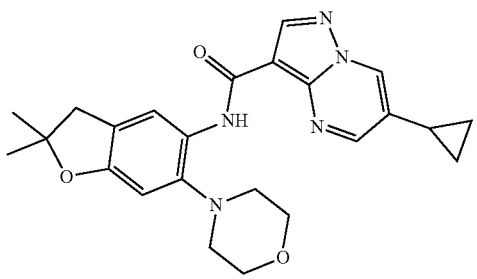 [SMILES: CC1(C)Cc2cc(NC(=O)c3cnn4cc(C5CC5)cnc34)c(N3CCOCC3)cc2O1]

To a mixture of 6-cyclopropylpyrazolo[1,5-a]pyrimidine-3-carboxylic acid (61 mg, 0.30 mmol) and diisopropylethylamine (0.11 mL, 0.66 mmol) in DMF (2 mL) was added 2-(7-aza-1H-benzotriazole-1-yl)-1,1,3,3-tetramethyluronium hexafluorophosphate (154 mg, 0.41 mmol) and the mixture was stirred at 25° C. for 20 min. To the mixture was added a solution of 2,2-dimethyl-6-morpholino-3H-benzofuran-5-amine (50 mg, 0.20 mmol) in DMF (2 mL) and the mixture was stirred at 25° C. for 16h. The product was crushed out. After filtration, the solid was collected and washed with methanol to afford 6-cyclopropyl-N-(2,2-dimethyl-6-morpholino-3H-benzofuran-5-yl)pyrazolo[1,5-a]pyrimidine-3-carboxamide (61 mg, 70%) as a yellow solid. ¹H NMR (400 MHz, CDCl₃) δ 10.41 (s, 1H), 8.70 (s, 1H), 8.65 (d, J=2.0 Hz, 1H), 8.50 (dd, J=0.8 Hz, 2.0 Hz, 1H), 8.43 (s, 1H), 6.65 (s, 1H), 3.97 (t, J=4.4 Hz, 4H), 3.04 (s, 2H), 2.92 (t, J=4.4 Hz, 4H), 2.09-2.00 (m, 1H), 1.49 (s, 6H), 1.20-1.13 (m, 2H), 0.86-0.79 (m, 2H). MS (ESI): m/z=434.1 [M+1]⁺.

Example 62. N-[2, 2-Dimethyl-6-(4-piperidyl)-3H-benzofuran-5-yl]pyrazolo[1,5-a]pyrimidine-3-carboxamide

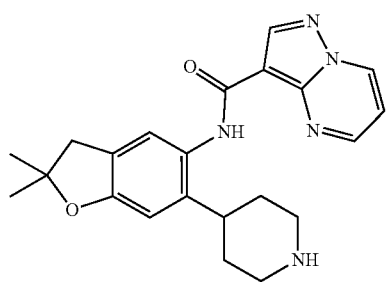 [SMILES: CC1(C)Cc2cc(NC(=O)c3cnn4cccnc34)c(C3CCNCC3)cc2O1]

Step A. tert-Butyl 4-(2, 2-dimethyl-5-nitro-3H-benzofuran-6-yl)-3,6-dihydro-2H-pyridine-1-carboxylate

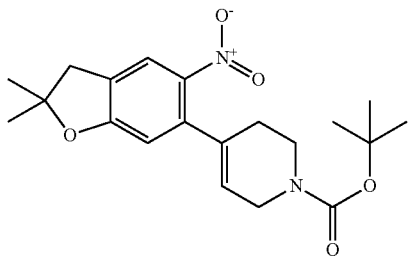 [SMILES: CC(C)(C)OC(=O)N1CC=C(c2cc3c(cc2[N+](=O)[O-])CC(C)(C)O3)CC1]

A mixture of N-Boc-1,2,5,6-tetrahydropyridine-4-boronicacidpinacolester (1350 mg, 4.37 mmol) 6-chloro-2,2-dimethyl-5-nitro-3H-benzofuran (Intermediate 1) (345 mg, 1.52 mmol), [1,1'-bis(diphenylphosphino)ferrocene]dichloropalladium (II) (99 mg, 0.14 mmol) and cesium carbonate (1120 mg, 3.44 mmol) in 1,4-dioxane (10 mL) and water (1 mL) in a sealed tube was stirred at 90° C. under microwave conditions for 2h. The mixture was poured into water (30 mL) and extracted with ethyl acetate (200 mL). The organic phase was washed with water and brine and dried over sodium sulfate before concentration to dryness. The residue was then purified by preparative TLC using ethyl acetate:petroleum ether (1:5) to afford tert-butyl 4-(2,2-dimethyl-5-nitro-3H-benzofuran-6-yl)-3,6-dihydro-2H-pyridine-1-carboxylate (550 mg, 87%) as a yellow oil. MS (ESI): m/z=397.2[M+Na]⁺.

Step B. tert-Butyl 4-(5-amino-2,2-dimethyl-3H-benzofuran-6-yl)piperidine-1-carboxylate

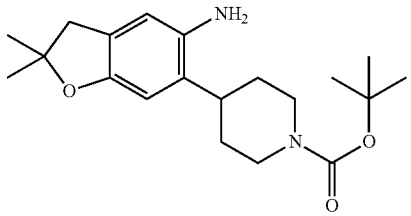 [SMILES: CC(C)(C)OC(=O)N1CCC(c2cc3c(cc2N)CC(C)(C)O3)CC1]

A mixture of tert-butyl 4-(2,2-dimethyl-5-nitro-3H-benzofuran-6-yl)-3,6-dihydro-2H-pyridine-1-carboxylate (100 mg, 0.27 mmol) and 10% palladium on carbon (50 mg) in methanol (10 mL) was stirred under hydrogen atmosphere at 20° C. for 2h. After filtration through a plug of celite and concentration under reduced pressure, it was afforded tert-butyl 4-(5-amino-2, 2-dimethyl-3H-benzofuran-6-yl)piperidine-1-carboxylate (85 mg) as a brown oil, which was directly used in the next step without further purification. MS (ESI): m/z=291.1[M-tBu]⁺.

Step C. tert-Butyl4-[2,2-dimethyl-5-(pyrazolo[1,5-a]pyrimidine-3-carbonylamino)-3H-benzofuran-6-yl]piperidine-1-carboxylate

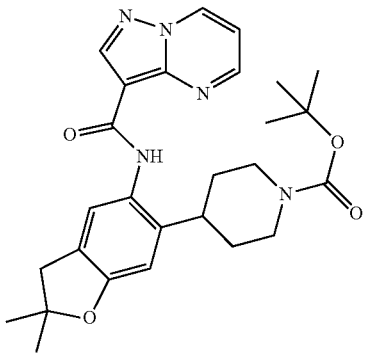 [SMILES: CC(C)(C)OC(=O)N1CCC(c2cc3c(cc2NC(=O)c2cnn4cccnc24)CC(C)(C)O3)CC1]

To a mixture of pyrazolo[1,5-a]pyrimidine-3-carboxylic acid (60 mg, 0.37 mmol) and diisopropylethylamine (0.12 mL, 0.74 mmol) in DMF (2 mL) was added 2-(7-aza-1H-benzotriazole-1-yl)-1,1,3,3-tetramethyluronium hexafluorophosphate and stirred for 20 min at 25° C. To the mixture was added a solution of tert-butyl 4-(5-amino-2,2-dimethyl-3H-benzofuran-6-yl)piperidine-1-carboxylate (85 mg, 0.25 mmol) in DMF (2 mL) and stirred at 25° C. for 16h. The mixture was poured into water and the aqueous phase was extracted with ethyl acetate (100 mL). The organic phase was washed with water and brine and dried over sodium sulfate before concentration to dryness. The residue was purified by preparative TLC using ethyl acetate:petroleum ether (3:2) as eluting solvents to afford tert-butyl 4-[2,2-dimethyl-5-(pyrazolo[1,5-a]pyrimidine-3-carbonylamino)-3H-benzofuran-6-yl]piperidine-1-carboxylate (63 mg, 52%) as a yellow solid. MS (ESI): m/z=492.2[M+1]⁺.

Step D. N-[2,2-Dimethyl-6-(4-piperidyl)-3H-benzofuran-5-yl]pyrazolo[1,5-a]pyrimidine-3-carboxamide

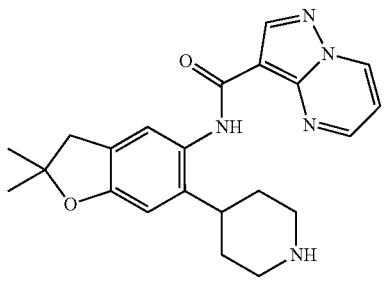

To a solution of tert-butyl 4-[2,2-dimethyl-5-(pyrazolo[1,5-a]pyrimidine-3-carbonylamino)-3H-benzofuran-6-yl]piperidine-carboxylate (63 mg, 0.13 mmol) in DCM (4 mL) was added trifluoroacetic acid (0.29 mL, 3.95 mmol) and the mixture was stirred at 25° C. for 2h. The mixture was neutralized by triethylamine. After concentration, the residue was purified by preparative HPLC (Xbridge 21.2*250 mm c18, 10 um; A: acetonitrile 25-55%; B: 10 mM ammonium bicarbonate in water) to afford N-[2,2-dimethyl-6-(4-piperidyl)-3H-benzofuran-5-yl]pyrazolo[1,5-a]pyrimidine-3-carboxamide (33 mg, 66%) as a yellow solid. $^1$H NMR (400 MHz, DMSO-$d_6$) δ 9.64 (s, 1H), 9.40 (dd, J=1.6, 6.8 Hz, 1H), 8.87 (dd, J=1.6, 4.4 Hz, 1H), 8.69 (s, 1H), 7.74 (s, 1H), 7.34 (dd, J=4.4, 6.8 Hz, 1H), 6.63 (s, 1H), 3.02 (t, J=12.0 Hz, 2H), 3.00 (s, 2H), 2.97-2.87 (m, 1H), 2.59 (t, J=12.0 Hz, 2H), 1.69 (d, J=11.2 Hz, 2H), 1.59-1.45 (m, 2H), 1.42 (s, 6H). MS (ESI): m/z=392.2[M+1]$^+$.

Example 63. N-[2,2-Dimethyl-6-(1-methyl-4-piperidyl)-3H-benzofuran-5-yl]pyrazolo[1,5-a]pyrimidine-3-carboxamide

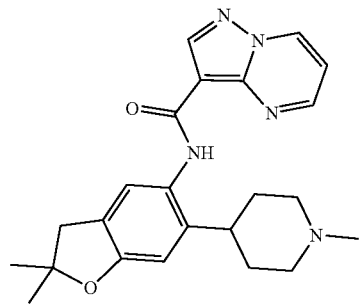

Step A. N-[2,2-Dimethyl-6-(1-methyl-4-piperidyl)-3H-benzofuran-5-yl]pyrazolo[1,5-a]pyrimidine-3-carboxamide

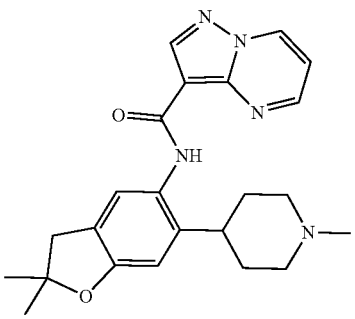

To a solution of N-[2,2-dimethyl-6-(4-piperidyl)-3H-benzofuran-5-yl]pyrazolo[1,5-a]pyrimidine-3-carboxamide (Example 62) (39 mg, 0.10 mmol) in methanol (4 mL) was added formaldehyde (200 mg, 2.46 mmol, 30 wt %) and the mixture was stirred at 25° C. for 30 min. To the mixture was added sodium cyanoborohydride (30 mg, 0.5 mmol) the reaction was stirred at 25° C. for 1h. Water was added and the mixture was purified by preparative HPLC (Xbridge 21.2*250 mm c18, 10 um; A: acetonitrile 25-55%; B: 10 mM ammonium bicarbonate in water) to afford N-[2,2-dimethyl-6-(1-methyl-4-piperidyl)-3H-benzofuran-5-yl]pyrazolo[1,5-a]pyrimidine-3-carboxamide (23 mg, 57%) as a yellow solid. $^1$H NMR (400 MHz, DMSO-$d_6$) δ 9.61 (s, 1H), 9.40 (dd, J=1.6, 6.8 Hz, 1H), 8.87 (dd, J=1.6, 4.4 Hz, 1H), 8.69 (s, 1H), 7.73 (s, 1H), 7.35 (dd, J=4.4, 6.8 Hz, 1H), 6.65 (s, 1H), 3.00 (s, 2H), 2.88 (d, J=11.6 Hz, 2H), 2.83-2.73 (m, 1H), 2.18 (s, 3H), 1.96 (t, J=9.6 Hz, 2H), 1.77-1.59 (m, 4H), 1.42 (s, 6H). MS (ESI): m/z=406.2[M+1]$^+$.

Examples 64 and 65. Cis-N-[6-(4-hydroxycyclohexoxy)-2,2-dimethyl-3H-benzofuran-5-yl]pyrazolo[1,5-a]pyrimidine-3-carboxamide and Trans-N-[6-(4-hydroxycyclohexoxy)-2,2-dimethyl-3H-benzofuran-5-yl]pyrazolo[1,5-a]pyrimidine-3-carboxamide

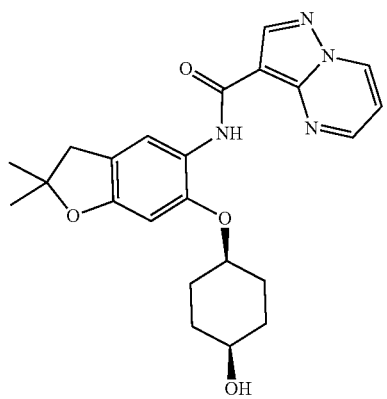

-continued

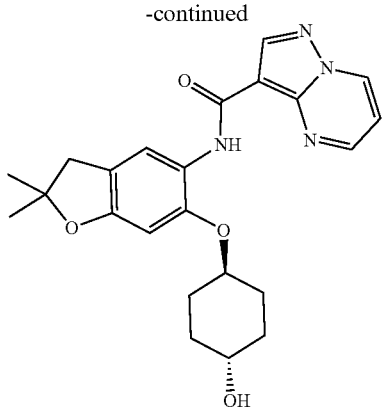

Step B. 4-[(2,2-Dimethyl-5-nitro-3H-benzofuran-6-yl)oxy]cyclohexanol

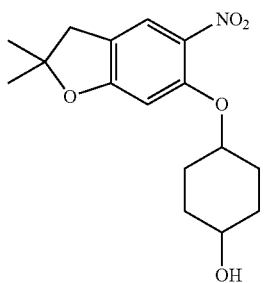

The mixture of tert-butyl-[4-[(2,2-dimethyl-5-nitro-3H-benzofuran-6-yl)oxy]cyclohexoxy]-diphenyl-silane (100.0 mg, 0.18 mmol) in methanol (10 mL) was added 12N hydrogen chloride solution (0.3 mL, 3.6 mmol) and the mixture was stirred at 25° C. for 5h. The mixture was neutralized by triethylamine to pH=8.0 and concentrated under reduced pressure. The residue was purified by preparative TLC using ethyl acetate:petroleum ether (1:3) to afford 4-[(2,2-dimethyl-5-nitro-3H-benzofuran-6-yl)oxy]cyclohexanol (53 mg, 94%) as a yellow oil. MS (ESI): m/z=330.1[M+Na]$^+$.

Step A. tert-Butyl-[4-[(2,2-dimethyl-5-nitro-3H-benzofuran-6-yl)oxy]cyclohexoxy]-diphenyl-silane

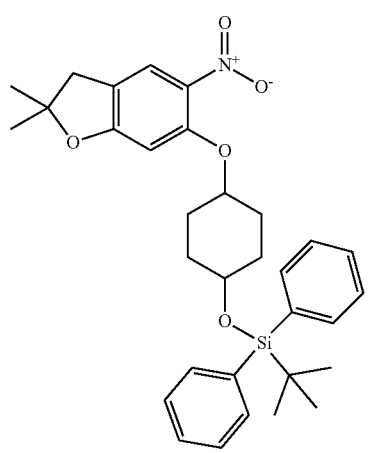 [SMILES: CC1(C)Cc2cc([N+](=O)[O-])c(OC3CCC(O[Si](c4ccccc4)(c4ccccc4)C(C)(C)C)CC3)cc2O1]

Step C. 4-[(5-Amino-2,2-dimethyl-3H-benzofuran-6-yl)oxy]cyclohexanol

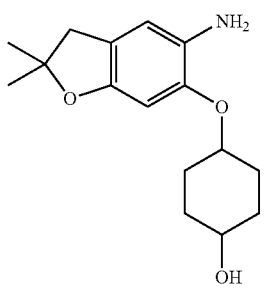 [SMILES: CC1(C)Cc2cc([N+](=O)[O-])c(OC3CCC(O)CC3)cc2O1]

To a mixture of 4-[tert-butyl(diphenyl)silyl]oxycyclohexanol (255 mg, 0.72 mmol), potassium tert-butanolate (130 mg, 1.16 mmol) and 6-fluoro-2,2-dimethyl-5-nitro-3H-benzofuran (Example 3, Step F) (265 mg, 1.25 mmol) in 1,4-dioxane (7 mL) was stirred at 40° C. for 36h. The mixture was purified by reverse phase chromatography (C18, 80 g, 40-60 um, 10 um; A: acetonitrile 0.1% to 100%; 10 mM in water) to afford tert-butyl-[4-[(2,2-dimethyl-5-nitro-3H-benzofuran-6-yl)oxy]cyclohexoxy]-diphenyl-silane (110 mg, 28%) as a yellow oil. MS (ESI): m/z=568.2 [M+Na]$^+$.

A mixture of 4-[(2,2-dimethyl-5-nitro-3H-benzofuran-6-yl)oxy]cyclohexanol (53 mg, 0.17 mmol) and 10% palladium on carbon (25 mg) in methanol (6 mL) was stirred under a hydrogen atmosphere at 25° C. for 1h. After filtration through a plug of celite and concentration, it was afforded 4-[(5-amino-2,2-dimethyl-3H-benzofuran-6-yl)oxy]cyclohexanol (45 mg) as a brown oil which was directly used in the next step without further purification. MS (ESI): m/z=278.1[M+1]$^+$.

Step D. Cis-N-[6-(4-hydroxycyclohexoxy)-2,2-dimethyl-3H-benzofuran-5-yl]pyrazolo[1,5-a]pyrimidine-3-carboxamide and Trans-N-[6-(4-hydroxycyclohexoxy)-2,2-dimethyl-3H-benzofuran-5-yl]pyrazolo[1,5-a]pyrimidine-3-carboxamide

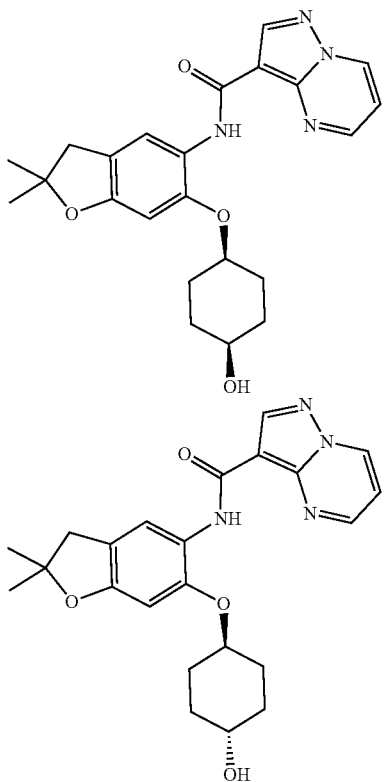

To the mixture of pyrazolo[1,5-a]pyrimidine-3-carboxylic acid (40 mg, 0.25 mmol) and diisopropylethylamine (0.08 mL, 0.50 mmol) in DMF (2 mL) was added 2-(7-aza-1H-benzotriazole-1-yl)-1,1,3,3-tetramethyluronium hexafluorophosphate (123 mg, 0.32 mmol) then the mixture was stirred at 25° C. for 20 min. To the mixture was added the solution of 4-[(5-amino-2,2-dimethyl-3H-benzofuran-6-yl)oxy]cyclohexanol (45 mg, 0.16 mmol) in DMF (2 mL) and the mixture was stirred at 25° C. for 16h. The crude was purified by preparative HPLC (Xbridge 21.2*250 mm c18, 10 um; A: acetonitrile 25-55%; B: 10 mM ammonium bicarbonate in water) to afford Cis-N-[6-(4-hydroxycyclohexoxy)-2,2-dimethyl-3H-benzofuran-5-yl]pyrazolo[1,5-a]pyrimidine-3-carboxamide (26 mg, 38%) and Trans-N-[6-(4-hydroxycyclohexoxy)-2,2-dimethyl-3H-benzofuran-5-yl]pyrazolo[1,5-a]pyrimidine-3-carboxamide (10 mg, 15%) as a yellow solids.

Cis-N-[6-(4-hydroxycyclohexoxy)-2,2-dimethyl-3H-benzofuran-5-yl]pyrazolo[1,5-a]pyrimidine-3-carboxamide: $^1$H NMR (400 MHz, DMSO-d$_6$) δ 10.18 (s, 1H), 9.36 (dd, J=1.6, 7.2 Hz, 1H), 8.83 (dd, J=1.6, 4.4 Hz, 1H), 8.66 (s, 1H), 8.28 (s, 1H), 7.31 (dd, J=4.4, 7.2 Hz, 1H), 6.63 (s, 1H), 4.57 (d, J=4.4 Hz, 1H), 4.42-4.34 (m, 1H), 3.62-3.51 (m, 1H), 2.97 (s, 2H), 2.12-2.01 (m, 2H), 1.95-1.85 (m, 2H), 1.65-1.52 (m, 2H), 1.41 (s, 6H), 1.39-1.28 (m, 2H). MS (ESI): m/z=423.2[M+1]$^+$.

Trans-N-[6-(4-hydroxycyclohexoxy)-2,2-dimethyl-3H-benzofuran-5-yl]pyrazolo[1,5-a]pyrimidine-3-carboxamide: $^1$H NMR (400 MHz, DMSO-d$_6$) δ 10.11 (s, 1H), 9.37 (dd, J=1.6, 7.2 Hz, 1H), 8.98 (dd, J=1.6, 4.4 Hz, 1H), 8.67 (s, 1H), 8.26 (s, 1H), 7.35 (dd, J=4.4, 7.2 Hz, 1H), 6.60 (s, 1H), 4.61 (d, J=3.2 Hz, 1H), 4.54-4.47 (m, 1H), 3.69-3.61 (m, 1H), 2.97 (s, 2H), 2.04-1.94 (m, 2H), 1.82-1.72 (m, 2H), 1.72-1.65 (m, 2H), 1.64-1.55 (m, 2H), 1.41 (s, 6H). MS (ESI): m/z=423.2[M+1]$^+$.

Examples 66 and 67. N-[(2R)-6-(3,3-Difluoropyrrolidin-1-yl)-2-(hydroxymethyl)-2-methyl-3H-benzofuran-5-yl]pyrazolo[1,5-a]pyrimidine-3-carboxamide and N-[(2S)-6-(3,3-Difluoropyrrolidin-1-yl)-2-(hydroxymethyl)-2-methyl-3H-benzofuran-5-yl]pyrazolo[1,5-a]pyrimidine-3-carboxamide

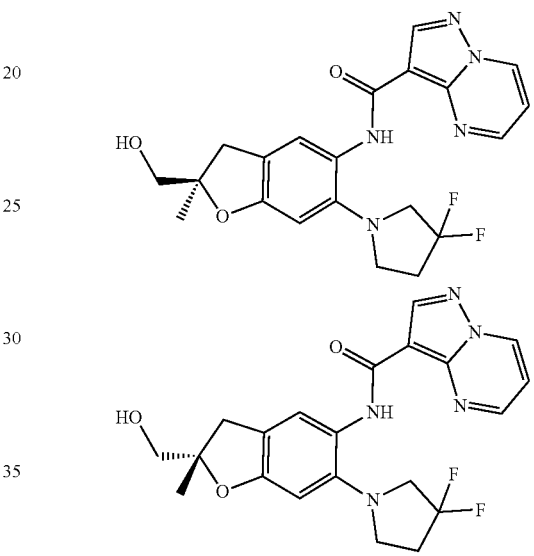

Step A. [6-(3,3-Difluoropyrrolidin-1-yl)-2-methyl-5-nitro-3H-benzofuran-2-yl]methanol

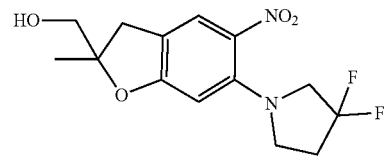 [SMILES: CC1(CO)Cc2cc([N+](=O)[O-])c(N3CCC(F)(F)C3)cc2O1]

To a solution of (6-fluoro-2-methyl-5-nitro-3H-benzofuran-2-yl)methanol (Intermediate 3) (150.0 mg, 0.66 mmol) and potassium carbonate (228.0 mg, 1.65 mmol) in acetonitrile (5 mL) was added 3,3-difluoropyrrolidine hydrochloride (114.0 mg, 0.79 mmol) and the mixture was stirred for 16 h. Water (10 mL) was added to the mixture. The aqueous phase was extracted with DCM (3×20 mL). The organic phases were combined and washed with water, dried over sodium sulfate and concentrated in vacuo to afford the [6-(3,3-difluoropyrrolidin-1-yl)-2-methyl-5-nitro-3H-benzofuran-2-yl]methanol (208 mg) as a yellow solid, which was used directly to next step without further purification. MS (ESI): m/z=315.1 [M+1]$^+$.

Step B. [5-Amino-6-(3,3-difluoropyrrolidin-1-yl)-2-methyl-3H-benzofuran-2-yl]methanol

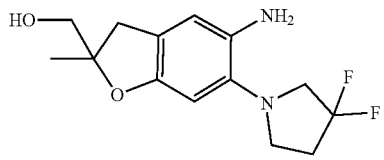

A mixture of [6-(3,3-difluoropyrrolidin-1-yl)-2-methyl-5-nitro-3H-benzofuran-2-yl]methanol (208.0 mg, 0.66 mmol) and 10% palladium on carbon (20.0 mg, 0.66 mmol) in methanol (5 mL) was stirred at room temperature under hydrogen atmosphere for 1h. The reaction was filtered through a plug of celite and the filtrate was concentrated under reduced pressure to afford [5-amino-6-(3,3-difluoropyrrolidin-1-yl)-2-methyl-3H-benzofuran-2-yl]methanol (188 mg) as a colorless oil, which was used directly to next step without further purification. MS (ESI): m/z=285.1 [M+1]$^+$.

Step C. N-[(2R)-6-(3,3-Difluoropyrrolidin-1-yl)-2-(hydroxymethyl)-2-methyl-3H-benzofuran-5-yl]pyrazolo[1,5-a]pyrimidine-3-carboxamide and N-[(2S)-6-(3,3-Difluoropyrrolidin-1-yl)-2-(hydroxymethyl)-2-methyl-3H-benzofuran-5-yl]pyrazolo[1,5-a]pyrimidine-3-carboxamide

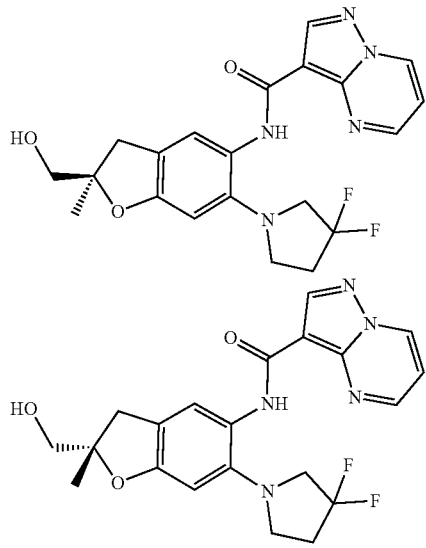

A mixture of [5-amino-6-(3,3-difluoropyrrolidin-1-yl)-2-methyl-3H-benzofuran-2-yl]methanol (181.0 mg, 0.64 mmol), pyrazolo[1,5-a]pyrimidine-3-carboxylic acid (104.0 mg, 0.64 mmol) and diisopropylethylamine (0.22 mL, 1.33 mmol) in DMF (5 mL) was added 2-(7-aza-1H-benzotriazole-1-yl)-1,1,3,3-tetramethyluronium hexafluorophosphate (364.0 mg, 0.90 mmol) at 25° C. The mixture was stirred at 25° C. for 16 h. The mixture was purified by preparative HPLC (Xbridge 21.2*250 mm c18, 10 um; A: acetonitrile 25-55%; B:10 mM ammonium bicarbonate in water) and followed chiral resolution by SFC(SFC-80 (Thar, Waters), OD 20*250 mm, Sum (Dacel), CO$_2$/methanol{0.2% Ammonia (7 m methanol)}=65/35) to afford N-[(2R)-6-(3,3-difluoropyrrolidin-1-yl)-2-(hydroxymethyl)-2-methyl-3H-benzofuran-5-yl]pyrazolo[1,5-a]pyrimidine-3-carboxamide and N-[(2S)-6-(3,3-difluoropyrrolidin-1-yl)-2-(hydroxymethyl)-2-methyl-3H-benzofuran-5-yl]pyrazolo[1,5-a]pyrimidine-3-carboxamide (32.3 mg, 12%) (38.6 mg, 14%) as a yellow solids with absolute stereochemistry assigned arbitrarily.

Example 66, Peak 1: $^1$H NMR (400 MHz, DMSO-d$_6$): δ:10.25 (s, 1H), 9.37 (dd, J=1.6, 6.8 Hz, 1H), 8.79 (dd, J=1.6, 4.0 Hz, 1H), 8.68 (s, 1H), 8.21 (s, 1H), 7.33 (dd, J=4.0, 6.8 Hz, 1H), 6.72 (s, 1H), 5.05 (t, J=5.6 Hz, 1H), 3.52-3.39 (m, 4H), 3.24-3.15 (m, 3H), 2.83 (d, J=15.6 Hz, 1H), 1.34 (s, 3H). MS (ESI): m/z=430.2 [M+1]$^+$.

Example 67, Peak 1: $^1$H NMR (400 MHz, DMSO-d$_6$): δ:10.24 (s, 1H), 9.37 (dd, J=1.6, 6.8 Hz, 1H), 8.79 (dd, J=1.6, 4.0 Hz, 1H), 8.68 (s 1H), 8.21 (s, 1H), 7.34 (dd, J=4.0, 7.2 Hz, 1H), 6.72 (s, 1H), 5.05 (t, J=5.6 Hz, 1H), 3.53-3.39 (m, 4H), 3.24-3.15 (m, 3H), 2.83 (d, J=15.6 Hz, 1H), 1.34 (s, 3H). MS (ESI): m/z=430.1 [M+1]$^+$.

Example 68. N-(6-(3,3-Difluoro-4-hydroxypyrrolidin-1-yl)-2,2-dimethyl-2,3-dihydrobenzofuran-5-yl)pyrazolo[1,5-a]pyrimidine-3-carboxamide

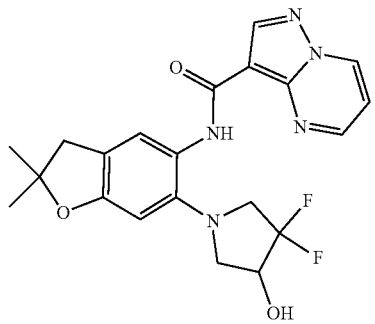 [SMILES: CC1(C)Cc2cc(NC(=O)c3cnn4cccnc34)c(N3CC(O)C(F)(F)C3)cc2O1]

Step A. 4,4-Difluoropyrrolidin-3-ol trifluoroacetic acid salt

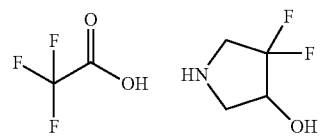

A mixture of tert-butyl 3,3-difluoro-4-hydroxypyrrolidine-1-carboxylate (100 mg, 0.45 mmol) and trifluoroacetic acid (1 mL) in DCM (5 mL), was stirred at 20° C. for 2h. After removal of solvents under reduced pressure, it was afforded 4,4-difluoropyrrolidin-3-ol trifluoroacetic acid salt (46 mg) as a brown oil, which was used directly to next step without further purification. MS (ESI): m/z=124.1 [M+1]$^+$.

Step B. 1-(2,2-Dimethyl-5-nitro-2,3-dihydrobenzofuran-6-yl)-4,4-difluoropyrrolidin-3-ol

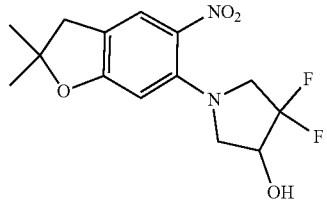 [SMILES: CC1(C)Cc2cc([N+](=O)[O-])c(N3CC(O)C(F)(F)C3)cc2O1]

A mixture of 4,4-difluoropyrrolidin-3-ol trifluoroacetic acid salt (46 mg, 0.35 mmol), 6-fluoro-2,2-dimethyl-5-nitro-3H-benzofuran (Example 3, Step F) (75 mg, 0.35 mmol) and potassium carbonate (145 mg, 1.05 mmol) in acetonitrile (5 mL) was stirred at 90° C. for 20h. After removal of the solvents under reduced pressure, the residue was purified by silica gel chromatography using ethyl acetate:petroleum ether (1:4 to 1:1) to afford 1-(2,2-dimethyl-5-nitro-2,3-dihydrobenzofuran-6-yl)-4,4-difluoropyrrolidin-3-ol (62 mg, 53%) as a yellow solid. MS (ESI): m/z=315.1 [M+1]$^+$.

Step C. 1-(5-Amino-2,2-dimethyl-2,3-dihydrobenzofuran-6-yl)-4,4-difluoropyrrolidin-3-ol

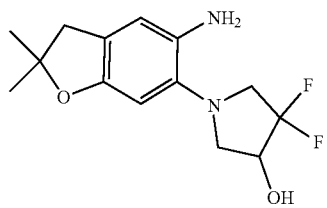

A mixture of 1-(2,2-dimethyl-5-nitro-2,3-dihydrobenzofuran-6-yl)-4,4-difluoropyrrolidin-3-ol (62 mg, 0.20 mmol) and 10% palladium on carbon (15 mg) in methanol (5 mL) was stirred at 20° C. under hydrogen atmosphere for 2h. After filtration and careful concentration (product is volatile), it was afforded 1-(5-amino-2,2-dimethyl-2,3-dihydrobenzofuran-6-yl)-4,4-difluoropyrrolidin-3-ol (52 mg, 80%) as a yellow solid. MS (ESI): m/z=285.0 [M+1]$^+$.

Step D. N-(6-(3,3-Difluoro-4-hydroxypyrrolidin-1-yl)-2,2-dimethyl-2,3-dihydrobenzofuran-5-yl)pyrazolo[1,5-a]pyrimidine-3-carboxamide

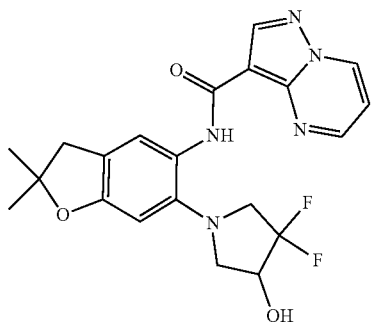 [SMILES: CC1(C)Cc2cc(NC(=O)c3cnn4cccnc34)c(N3CC(O)C(F)(F)C3)cc2O1]

A mixture of 1-(5-amino-2,2-dimethyl-2,3-dihydrobenzofuran-6-yl)-4,4-difluoropyrrolidin-3-ol (52 mg, 0.15 mmol), pyrazolo[1,5-a]pyrimidine-3-carboxylic acid (30 mg, 0.18 mmol), (7-azabenzotriazol-1-yloxy)tripyrrolidinophosphoniumhexafluorophosphate (119 mg, 0.23 mmol) and diisopropylethylamine (59 mg, 0.46 mmol) in DMF (3 mL) was stirred at 20° C. for 16h. The crude was purified by preparative HPLC (Xbridge 21.2*250 mm c18, 10 um; A: acetonitrile 15-40%; B: 10 mM ammonium bicarbonate in water) to afford N-(6-(3,3-difluoro-4-hydroxypyrrolidin-1-yl)-2,2-dimethyl-2,3-dihydrobenzofuran-5-yl)pyrazolo[1,5-a]pyrimidine-3-carboxamide (51.2 mg, 78%) as a yellow solid. $^1$H NMR (400 MHz, DMSO-d$_6$): δ 10.07 (s, 1H), 9.37 (dd, J=1.6, 6.8 Hz, 1H), 8.77 (dd, J=2.0, 4.4 Hz, 1H), 8.68 (s, 1H), 8.10 (s, 1H), 7.35 (dd, J=4.0, 6.8 Hz, 1H), 6.65 (s, 1H), 5.92 (d, J=5.6 Hz, 1H), 4.37-4.32 (m, 1H), 3.60-3.45 (m, 3H), 2.99 (s, 2H), 2.91-2.87 (m, 1H), 1.42 (s, 3H), 1.41 (s, 3H). MS (ESI): m/z=430.1 [M+1]$^+$.

Example 69. N-(2,2-Dimethyl-6-morpholino-2,3-dihydrobenzofuran-5-yl)-6-(trifluoromethyl)pyrazolo[1,5-a]pyrimidine-3-carboxamide

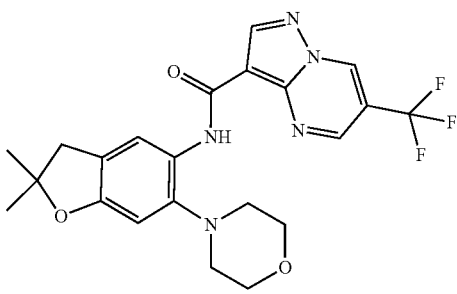 [SMILES: CC1(C)Cc2cc(NC(=O)c3cnn4cc(C(F)(F)F)cnc34)c(N3CCOCC3)cc2O1]

Step A. Methylpyrazolo[1,5-a]pyrimidine-3-carboxylate

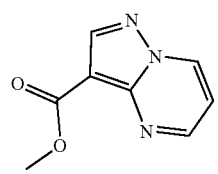

To a solution of pyrrolo[1,2-a]pyrimidine-8-carboxylic acid (4.97 g, 30.7 mmol) in methanol (120 mL) was added concentrated sulfuric acid (5 mL). The reaction mixture was stirred for 18h at reflux. After concentration, saturated sodium bicarbonate solution was added slowly. The aqueous phase was extracted with ethyl acetate (3×50 mL). The combined organic phases were washed with brine and dried over sodium sulfate. After filtration and concentration, methyl pyrrolo[1,2-a]pyrimidine-8-carboxylate (4.50 g, 83%) was afforded as a yellow solid. MS (ESI): m/z=200.0 [M+Na].

Step B. Methyl 6-iodopyrazolo[1,5-a]pyrimidine-3-carboxylate

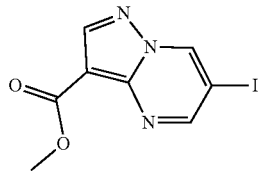

To a mixture of methyl pyrrolo[1,2-a]pyrimidine-8-carboxylate (3.43 g, 19.47 mmol) and sodium acetate (15.97 g, 194.74 mmol) in acetic acid (80 mL) was added iodine monochloride (3.79 g, 23.37 mmol). The reaction mixture was stirred for 18h at 25° C. After concentration, saturated sodium bicarbonate solution was added. The aqueous phase was extracted with ethyl acetate (3×100 mL). The combined organic phases were washed with brine and dried over sodium sulfate. After concentration under reduced pressure, the residue was purified by silica gel chromatography using ethyl acetate:petroleum ether (1:4) as eluting solvents to afford methyl 6-iodopyrazolo[1,5-a]pyrimidine-3-carboxylate (2.97 g, 51%) as a yellow solid. MS (ESI): m/z=325.9 [M+Na].

Step C. Methyl 6-(trifluoromethyl)pyrazolo[1,5-a]pyrimidine-3-carboxylate

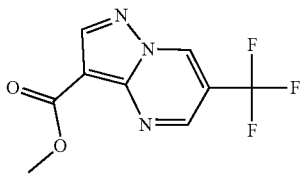 [SMILES: COC(=O)c1cnn2cc(C(F)(F)F)cnc12]

A mixture of methyl 6-iodopyrazolo[1,5-a]pyrimidine-3-carboxylate (400.0 mg, 1.32 mmol) and (1,10-phenanthroline)(trifluoromethyl)copper(I) (619.2 mg, 1.98 mmol) in DMF (0.5 mL) was heated to 50° C. and stirred for 18h in glove box. Water and ethyl acetate (50 mL) was added and the organic phase was washed with water, brine and dried over sodium sulfate. After concentration under reduced pressure, the residue was purified by silica gel chromatography using ethyl acetate:petroleum ether (1:4) as eluting solvents to afford methyl 6-(trifluoromethyl)pyrazolo[1,5-a]pyrimidine-3-carboxylate (100 mg, 31%) as a yellow solid. MS (ESI): m/z=246.0 [M+1]$^+$.

Step D. 6-(Trifluoromethyl)pyrazolo[1,5-a]pyrimidine-3-carboxylic acid

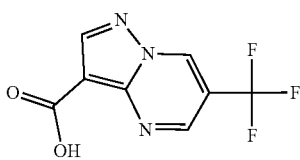 [SMILES: O=C(O)c1cnn2cc(C(F)(F)F)cnc12]

A mixture of methyl 6-(trifluoromethyl)pyrazolo[1,5-a]pyrimidine-3-carboxylate (50.0 mg, 0.20 mmol) in concentrated hydrochloric acid (2 mL) was stirred for 4 h at 100° C. The reaction was concentrated to dryness and the residue was purified by preparative HPLC (A: acetonitrile 25-37%; B: 0.05% formic acid in water) to afford 6-(trifluoromethyl)pyrazolo[1,5-a]pyrimidine-3-carboxylic acid (25 mg, 53%) as a white solid. MS (ESI): m/z=232.0 [M+1]$^+$.

Step E. N-(2,2-Dimethyl-6-morpholino-2,3-dihydrobenzofuran-5-yl)-6-(trifluoromethyl)pyrazolo[1,5-a]pyrimidine-3-carboxamide

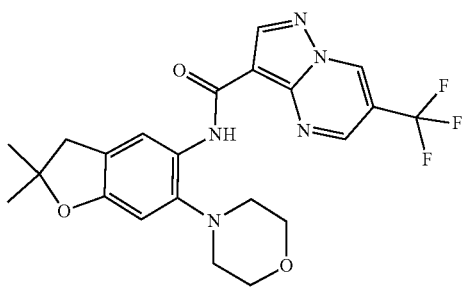 [SMILES: CC1(C)Cc2cc(NC(=O)c3cnn4cc(C(F)(F)F)cnc34)c(N3CCOCC3)cc2O1]

A mixture of 2,2-dimethyl-6-morpholino-3H-benzofuran-5-amine (Example 33, step B) (34.0 mg, 0.14 mmol), 6-(trifluoromethyl)pyrazolo[1,5-a]pyrimidine-3-carboxylic acid (25 mg, 0.11 mmol), 2-(7-aza-1H-benzotriazole-1-yl)-1,1,3,3-tetramethyluronium hexafluorophosphate (78.09 mg, 0.21 mmol) and diisopropylethylamine (52.99 mg, 0.41 mmol) in DMF (5 mL) was stirred for 18h at 25° C. The crude was purified by preparative HPLC (Xbridge 21.2*250 mm c18, 10 um; A: acetonitrile 25-55%; B:10 mmol/L ammonium bicarbonate in water) to afford N-(2,2-dimethyl-6-morpholino-3H-benzofuran-5-yl)-6-(trifluoromethyl)pyrazolo[1,5-a]pyrimidine-3-carboxamide (34 mg, 67%) as a yellow solid.

$^1$H NMR (400 MHz, DMSO-d$_6$): δ 10.26 (s, 1H), 10.12 (d, J=0.8 Hz, 1H), 9.23 (d, J=2.0 Hz, 1H), 8.88 (s, 1H), 8.27 (s, 1H), 6.72 (s, 1H), 3.83-8.10 (m, 4H), 3.01 (s, 2H), 2.83-2.79 (m, 4H), 1.42 (s, 6H). MS (ESI): m/z=462.1 [M+1]$^+$.

Example 70. N-[2,2-Dimethyl-6-(2,2,2-trifluoroethoxy)-3H-benzofuran-5-yl]pyrazolo[1,5-a]pyrimidine-3-carboxamide

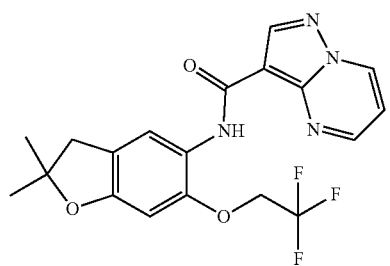

Step A. 2,2-Dimethyl-5-nitro-6-(2,2,2-trifluoroethoxy)-3H-benzofuran

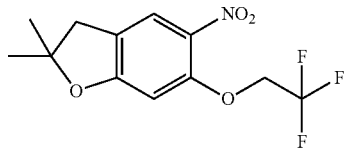 [SMILES: CC1(C)Cc2cc([N+](=O)[O-])c(OCC(F)(F)F)cc2O1]

The mixture of cesium carbonate (125.0 mg, 0.38 mmol), palladium diacetate (5.0 mg, 0.02 mmol), 6-bromo-2,2-dimethyl-5-nitro-3H-benzofuran (Intermediate 4) (52.0 mg, 0.19 mmol) and racemic-2-(di-tert-butylphosphino)-1,1'-binaphthyl (77.0 mg, 0.19 mmol) in 2,2,2-trifluoroethanol (0.30 mL) and toluene (3.0 mL) was heated in a sealed tube at 80° C. under microwave condition and the reaction was stirred for 3h. The reaction was concentrated to dryness under reduced pressure and then purified by silica gel chromatography using ethyl acetate:petroleum ether (1:10) as eluting solvents to afford 2,2-dimethyl-5-nitro-6-(2,2,2-trifluoroethoxy)-3H-benzofuran (37 mg, 56%) as a colorless oil. MS (ESI): m/z=292.0 [M+1]$^+$.

Step B. 2,2-Dimethyl-6-(2,2,2-trifluoroethoxy)-3H-benzofuran-5-amine

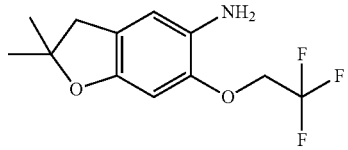

A mixture of 10% palladium on carbon (5.0 mg) and 2,2-dimethyl-5-nitro-6-(2,2,2-trifluoroethoxy)-3H-benzofuran (37.0 mg, 0.13 mmol) in methanol (2 mL) was stirred at 25° C. under hydrogen atmosphere for 2h. After filtration and concentration under reduced pressure, it was afforded 2,2-dimethyl-6-(2,2,2-trifluoroethoxy)-3H-benzofuran-5-amine (33 mg) as a colorless oil, which was used to next step without further purification. MS (ESI): m/z=262.1 [M+1]$^+$.

Step C. N-[2,2-Dimethyl-6-(2,2,2-trifluoroethoxy)-3H-benzofuran-5-yl]pyrazolo[1,5-a]pyrimidine-3-carboxamide

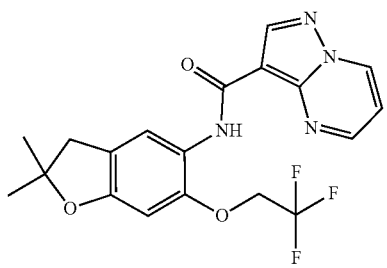 [SMILES: CC1(C)Cc2cc(NC(=O)c3cnn4cccnc34)c(OCC(F)(F)F)cc2O1]

A mixture of pyrazolo[1,5-a]pyrimidine-3-carboxylic acid (21.0 mg, 0.13 mmol), (7-azabenzotriazol-1-yloxy)tripyrrolidinophosphoniumhexafluorophosphate (99.0 mg, 0.19 mmol), N-ethyl-N-isopropylpropan-2-amine (0.04 mL, 0.25 mmol) and 2,2-dimethyl-6-(2,2,2-trifluoroethoxy)-3H-benzofuran-5-amine (33.0 mg, 0.13 mmol) in DMF (5 mL) was stirred at room temperature for 18h. After filtration and concentration, the residue was purified by preparative HPLC (Xbridge 21.2*250 mm c18, 10 um; A: acetonitrile 25-55%; B:10 mM ammonium bicarbonate in water) to afford N-[2,2-dimethyl-6-(2,2,2-trifluoroethoxy)-3H-benzofuran-5-yl]pyrazolo[1,5-a]pyrimidine-3-carboxamide (9.1 mg, 17%) as a yellow solid. $^1$H NMR (400 MHz, CDCl$_3$): δ 10.27 (s, 1H), 8.80 (dd, J=1.6, 6.8 Hz, 1H), 8.74 (s, 1H), 8.68 (dd, J=1.6, 4.0 Hz, 1H), 8.46 (s, 1H), 7.03 (dd, J=4.0, 7.2 Hz, 1H), 6.35 (s, 1H), 4.41 (q, J=8.0 Hz, 2H), 3.03 (s, 2H), 1.48 (s, 6H). MS (ESI): m/z=407.1 [M+1]$^+$.

Examples 71 and 72. N-[(2R)-2-(Hydroxymethyl)-2-methyl-6-(trifluoromethyl)-3H-benzofuran-5-yl]pyrazolo[1,5-a]pyrimidine-3-carboxamide and N-[(2S)-2-(hydroxymethyl)-2-methyl-6-(trifluoromethyl)-3H-benzofuran-5-yl]pyrazolo[1,5-a]pyrimidine-3-carboxamide

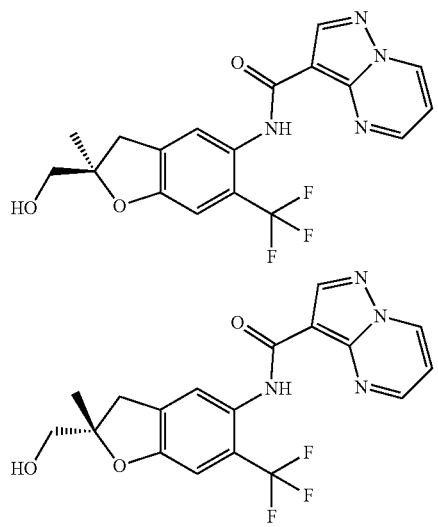

Step A. 4-(2-Methylallyloxy)-1-nitro-2-(trifluoromethyl)benzene

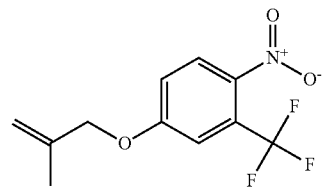 [SMILES: C=C(C)COc1ccc([N+](=O)[O-])c(C(F)(F)F)c1]

A mixture of 4-nitro-3-(trifluoromethyl)phenol (1000 mg, 4.83 mmol), 3-bromo-2-methylpropene (0.65 mL, 6.5 mmol), cesium carbonate (3080 mg, 9.45 mmol) in DMF (12 mL) was stirred at 50° C. for 2h. The mixture was poured into water (50 mL) and extracted by ethyl acetate (150 ml) and the organics washed with water and brine. The organic phases were then separated and dried over anhydrous sodium sulfate then was concentration to dryness to afford 4-(2-methylallyloxy)-1-nitro-2-(trifluoromethyl)benzene (1.2 g) as a yellow oil, which was directly used to the next step without purification. MS (ESI): m/z=262.0 [M+1]$^+$.

Step B. 2-(2-Methylallyl)-4-nitro-5-(trifluoromethyl)phenol

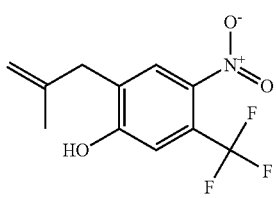 [SMILES: C=C(C)Cc1cc([N+](=O)[O-])c(C(F)(F)F)cc1O]

A mixture of 4-(2-methylallyloxy)-1-nitro-2-(trifluoromethyl)benzene (1200 mg, 4.59 mmol) in DMF (14 mL) was stirred at 200° C. in a sealed tube under microwave condition for 3h. The mixture was purified by reverse phase chromatography (C18, 120 g, acetonitrile 18-22%; B: 0.1% ammonium bicarbonate in water) to afford 2-(2-methylallyl)-4-nitro-5-(trifluoromethyl)phenol (222 mg, 19%) as a yellow oil. MS (ESI): m/z=262.0 [M+1]$^+$ Step C. [2-Methyl-5-nitro-6-(trifluoromethyl)-3H-benzofuran-2-yl]methanol

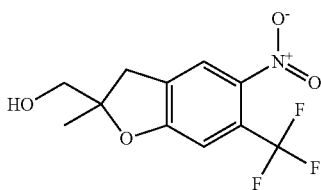 [SMILES: CC1(CO)Cc2cc([N+](=O)[O-])c(C(F)(F)F)cc2O1]

A mixture of 2-(2-methylallyl)-4-nitro-5-(trifluoromethyl)phenol (222 mg, 0.85 mmol) in DCM (15 mL) was added 3-chloroperbenzoic acid (222 mg, 1.13 mmol) at 0° C. then was stirred at 25° C. for 18h. The reaction mixture was diluted with DCM (30 mL) then was washed with sodium sulfite solution, sodium bicarbonate solution and water, dried over anhydrous sodium sulfate, and concentrated in vacuo. The residue was purified by reverse phase chromatography (C18, 60 g, acetonitrile 25-27%; B: 0.1% ammonium bicarbonate in water) to afford [2-methyl-5-nitro-6-(trifluoromethyl)-3H-benzofuran-2-yl]methanol (66 mg, 28%) as a yellow oil. MS (ESI): m/z=278.0 [M+1]$^+$.

Step D. [5-Amino-2-methyl-6-(trifluoromethyl)-3H-benzofuran-2-yl]methanol

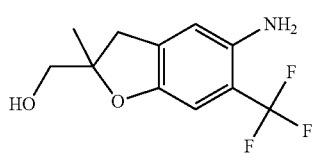 [SMILES: CC1(CO)Cc2cc(N)c(C(F)(F)F)cc2O1]

The mixture of [2-methyl-5-nitro-6-(trifluoromethyl)-3H-benzofuran-2-yl]methanol (66 mg, 0.24 mmol) and 10% palladium on carbon (20 mg) in methanol (10 mL) was stirred at 25° C. under hydrogen atmosphere for 1h. After filtration and concentration under reduced pressure, it was afforded [5-amino-2-methyl-6-(trifluoromethyl)-3H-benzofuran-2-yl]methanol (55 mg, 93%) as a brown oil. MS (ESI): m/z=248.1 [M+1]$^+$.

Step E. N-[(2S)-2-(hydroxymethyl)-2-methyl-6-(trifluoromethyl)-3H-benzofuran-5-yl]pyrazolo[1,5-a]pyrimidine-3-carboxamide and N-[(2R)-2-(hydroxymethyl)-2-methyl-6-(trifluoromethyl)-3H-benzofuran-5-yl]pyrazolo[1,5-a]pyrimidine-3-carboxamide

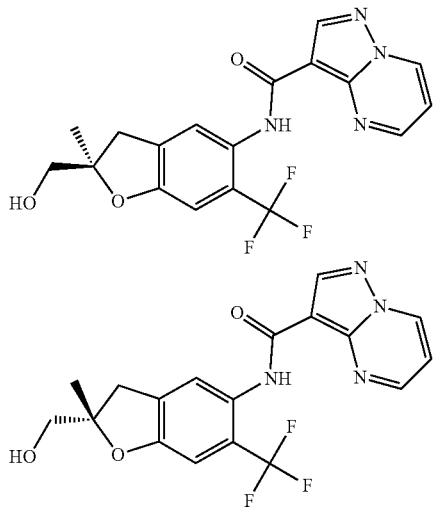

The mixture of pyrazolo[1,5-a]pyrimidine-3-carboxylic acid (55 mg, 0.34 mmol) and 2-(7-aza-1H-benzotriazole-1-yl)-1,1,3,3-tetramethyluronium hexafluorophosphate (170 mg, 0.45 mmol), N,N-diisopropylethylamine (0.11 mL, 0.68 mmol) and [5-amino-2-methyl-6-(trifluoromethyl)-3H-benzofuran-2-yl]methanol (55 mg, 0.22 mmol) in DMF (4 mL) was stirred at 75° C. for 24h. After cooling room temperature, the mixture was purified by preparative HPLC(Xbridge 21.2*250 mm c18, 10 um, A: acetonitrile 25-55%; B:10 mM ammonium bicarbonate) in water) and then the product was resolved by chiral-HPLC [SFC-80 (Thar, Waters), AD 20*250 mm, Sum (Dacel), carbon dioxide/methanol {0.5% ammonia (7 m methanol)}=65/35] to afford N-[(2R)-2-(hydroxymethyl)-2-methyl-6-(trifluoromethyl)-3H-benzofuran-5-yl]pyrazol [1,5-a]pyrimidine-3-carboxamide and N-[(2S)-2-(hydroxymethyl)-2-methyl-6-(trifluoromethyl)-3H-benzofuran-5-yl]pyrazol [1,5-a]pyrimidine-3-carboxamide (5.6 mg, 6%) (8.1 mg, 9%) as a white solids with absolute stereochemistry assigned arbitrarily.

Example 70, Peak 1: $^1$H NMR (400 MHz, CDCl$_3$) δ 9.94 (s, 1H), 8.82 (dd, J=1.6, 7.2 Hz, 1H), 8.76 (s, 1H), 8.70 (dd, J=1.6, 4.0 Hz, 1H), 8.00 (s, 1H), 7.05 (dd, J=4.0, 7.2 Hz, 1H), 7.03 (s, 1H), 3.76-3.61 (m, 2H), 3.36 (d, J=16.4 Hz, 1H), 3.00 (d, J=16.4 Hz, 1H), 1.89 (t, J=6.0 Hz, 1H), 1.47 (s, 3H). MS (ESI): m/z=393.1 [M+1]$^+$.

Example 71, Peak 2: $^1$H NMR (400 MHz, CDCl$_3$) δ 9.94 (s, 1H), 8.82 (dd, J=1.6, 7.2 Hz, 1H), 8.76 (s, 1H), 8.70 (dd, J=1.6, 4.0 Hz, 1H), 8.00 (s, 1H), 7.05 (dd, J=4.0, 7.2 Hz, 1H), 7.03 (s, 1H), 3.76-3.61 (m, 2H), 3.36 (d, J=16.4 Hz, 1H), 3.00 (d, J=16.4 Hz, 1H), 1.89 (t, J=6.0 Hz, 1H), 1.47 (s, 3H). MS (ESI): m/z=393.1 [M+1]⁺.

Examples 73 and 74. N-[(2S)-6-(Difluoromethyl)-2-(hydroxymethyl)-2-methyl-3H-benzofuran-5-yl]pyrazolo[1,5-a]pyrimidine-3-carboxamide and N-[(2R)-6-(difluoromethyl)-2-(hydroxymethyl)-2-methyl-3H-benzofuran-5-yl]pyrazolo[1,5-a]pyrimidine-3-carboxamide

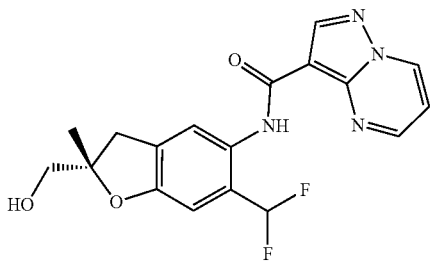

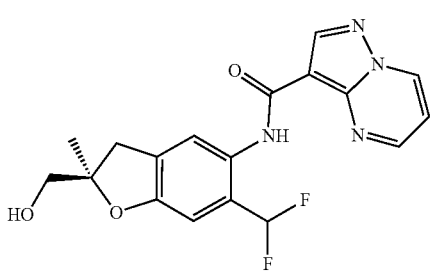

Step A. 5-(2-Methylallyloxy)-2-nitro-benzaldehyde

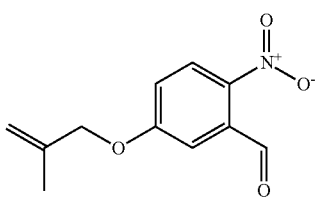 [SMILES: C=C(C)COc1ccc([N+](=O)[O-])c(C=O)c1]

A mixture of 5-hydroxy-2-nitrobenzaldehyde (1000 mg, 5.98 mmol), 3-bromo-2-methylpropene (0.81 mL, 8.0 mmol), cesium carbonate (4000 mg, 12.28 mmol) in DMF (10 mL) was stirred at 50° C. for 2h. The mixture was poured into water (50 mL). The aqueous phase was extracted by ethyl acetate (150 mL) and the organic phase was washed with water and brine and dried over anhydrous sodium sulfate. The organic phase was concentration to dryness to afford 5-(2-methylallyloxy)-2-nitro-benzaldehyde (1.25 g) as a yellow oil, which was directly used to the next step without purification. MS (ESI): m/z=222.1 [M+1]⁺.

Step B. 2-(Difluoromethyl)-4-(2-methylallyloxy)-1-nitro-benzene

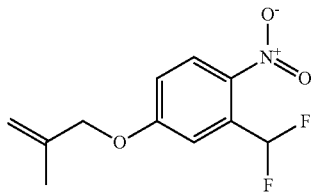 [SMILES: C=C(C)COc1ccc([N+](=O)[O-])c(C(F)F)c1]

The mixture of 5-(2-methylallyloxy)-2-nitro-benzaldehyde (1250 mg, 5.65 mmol) in DCM (25 mL) was added diethylaminosulfurtrifluoride (1.88 mL, 14.13 mmol) at 0° C. then was stirred at 25° C. for 8h. The mixture was diluted with DCM (200 mL) then was washed with water, dried over anhydrous sodium sulfate and concentrated in vacuo. The residue was purified by silica gel chromatography using ethyl acetate:petroleum ether (1:20) as eluting solvents to afford 2-(difluoromethyl)-4-(2-methylallyloxy)-nitro-benzene (1310 mg, 95%) as a yellow oil. MS (ESI): m/z=244.1 [M+1]⁺.

Step C. 5-(Difluoromethyl)-2-(2-methylallyl)-4-nitro-phenol

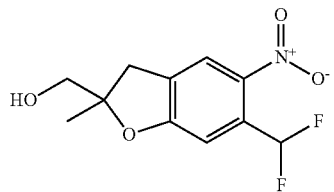 [SMILES: CC1(CO)Cc2cc([N+](=O)[O-])c(C(F)F)cc2O1]

The mixture of 2-(difluoromethyl)-4-(2-methylallyloxy)-1-nitro-benzene (1300 mg, 5.35 mmol) in DMF (16 mL) was stirred at 200° C. in a sealed tube under microwave condition for 3h. The mixture was purified by reverse phase chromatography (C18, 120 g, A: acetonitrile 22-25%; B: 0.1% ammonium bicarbonate in water) to afford 5-(difluoromethyl)-2-(2-methylallyl)-4-nitro-phenol (310 mg, 24%) as a yellow oil. MS (ESI): m/z=244.1 [M+1]⁺.

Step D. [6-(Difluoromethyl)-2-methyl-5-nitro-3H-benzofuran-2-yl]methanol

A mixture of 5-(difluoromethyl)-2-(2-methylallyl)-4-nitro-phenol (310 mg, 1.27 mmol) in DCM (15 mL) was added 3-chloroperbenzoic acid (375 mg, 1.91 mmol) at 0° C. then was stirred at 25° C. for 18h. The reaction mixture was diluted with DCM (50 mL). The organic phase was washed with sodium bicarbonate solution, water, dried over anhydrous sodium sulfate and concentrated in vacuo. The residue was purified by reverse phase chromatography (C18, 80 g, A: acetonitrile 20-27%; B: 0.1% ammonium bicarbonate in water) to afford [6-(difluoromethyl)-2-methyl-5-nitro-3H-benzofuran-2-yl]methanol (156 mg, 47%) as a yellow oil. MS (ESI): m/z=260.1 [M+1]$^+$.

Step E. [5-Amino-6-(difluoromethyl)-2-methyl-3H-benzofuran-2-yl]methanol

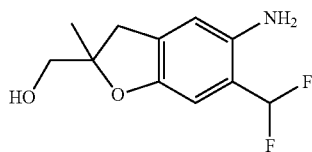 [SMILES: CC1(CO)Cc2cc(N)c(C(F)F)cc2O1]

The mixture of [6-(difluoromethyl)-2-methyl-5-nitro-3H-benzofuran-2-yl]methanol (140 mg, 0.54 mmol) and 10% palladium on carbon (50 mg) in methanol (15 mL) was stirred at 25° C. under hydrogen atmosphere for 1h. After filtration and concentration under reduced pressure, it was afforded [5-amino-6-(difluoromethyl)-2-methyl-3H-benzofuran-2-yl]methanol (115 mg) as a brown oil, which was used directly to next step without further purification. MS (ESI): m/z=230.1 [M+1]$^+$.

Step F. N-[(2S)-6-(difluoromethyl)-2-(hydroxymethyl)-2-methyl-3H-benzofuran-5-yl]pyrazolo[1,5-a]pyrimidine-3-carboxamide and N-[(2R)-6-(difluoromethyl)-2-(hydroxymethyl)-2-methyl-3H-benzofuran-5-yl]pyrazolo[1,5-a]pyrimidine-3-carboxamide

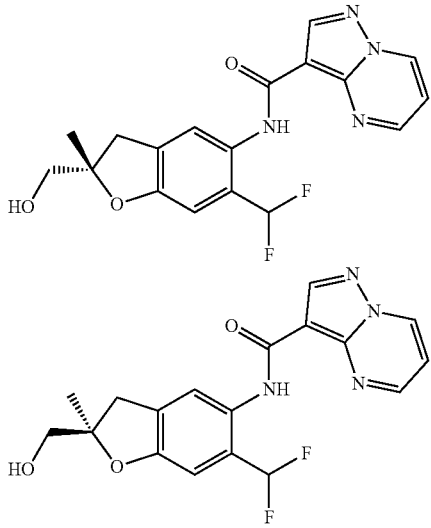

The mixture of pyrazolo[1,5-a]pyrimidine-3-carboxylic acid (120 mg, 0.74 mmol), N,N-diisopropylethylamine (0.26 mL, 1.56 mmol), 2-(7-aza-1H-benzotriazole-1-yl)-1,1,3,3-tetramethyluronium hexafluorophosphate (395 mg, 1.04 mmol) and [5-amino-6-(difluoromethyl)-2-methyl-3H-benzofuran-2-yl]methanol (115 mg, 0.50 mmol) in DMF (6 mL) was stirred at 65° C. for 16h. After cooling room temperature, the mixture was purified by preparative HPLC (Xbridge 21.2*250 mm c18, 10 um; A: acetonitrile 25-55%; B: 10 mM ammonium bicarbonate in water) and Chiral-HPLC [SFC-80 (Thar, Waters), AY 20*250 mm, 5um (Dacel), carbon dioxide/methanol {0.5% ammonia (7 m methanol)}=60/40] to afford N-[(2R)-6-(difluoromethyl)-2-(hydroxymethyl)-2-methyl-3H-benzofuran-5-yl]pyrazolo[1,5-a]pyrimidine-3-carboxamide and N-[(2S)-6-(difluoromethyl)-2-(hydroxymethyl)-2-methyl-3H-benzofuran-5-yl]pyrazolo[1,5-a]pyrimidine-3-carboxamide (44.4 mg, 24%) (32.7 mg, 17%) as yellow solids with absolute stereochemistry assigned arbitrarily.

Example 73, Peak 1: $^1$H NMR (400 MHz, DMSO-d$_6$) δ 9.77 (s, 1H), 9.38 (dd, J=1.6, 7.2 Hz, 1H), 8.87 (dd, J=1.6, 4.4 Hz, 1H), 8.70 (s, 1H), 7.67 (s, 1H), 7.33 (dd, J=4.4, 7.2 Hz, 1H), 7.042 (t, J=55.2 Hz, 1H), 6.90 (s, 1H), 5.11 (t, J=6.0 Hz, 1H), 3.53-3.40 (m, 2H), 3.29 (d, J=16.0 Hz, 1H), 2.92 (d, J=16.0 Hz, 1H), 1.37 (s, 3H). MS (ESI): m/z=375.1 [M+1]$^+$.

Example 74, Peak 2: $^1$H NMR (400 MHz, DMSO-d$_6$) δ 9.77 (s, 1H), 9.38 (dd, J=1.6, 7.2 Hz, 1H), 8.87 (dd, J=1.6, 4.4 Hz, 1H), 8.70 (s, 1H), 7.67 (s, 1H), 7.33 (dd, J=4.4, 7.2 Hz, 1H), 7.042 (t, J=55.2 Hz, 1H), 6.90 (s, 1H), 5.11 (t, J=6.0 Hz, 1H), 3.53-3.40 (m, 2H), 3.29 (d, J=16.0 Hz, 1H), 2.92 (d, J=16.0 Hz, 1H), 1.37 (s, 3H). MS (ESI): m/z=375.1 [M+1]$^+$.

Example 75. 6-(Difluoromethyl)-N-[2-(hydroxymethyl)-2-methyl-6-morpholino-3H-benzofuran-5-yl]pyrazolo[1,5-a]pyrimidine-3-carboxamide

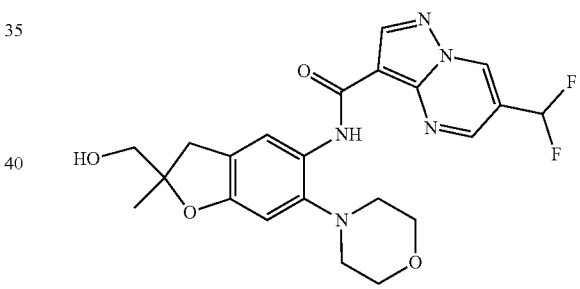

Step A. 6-Formylpyrazolo[1,5-a]pyrimidine-3-carboxylic acid

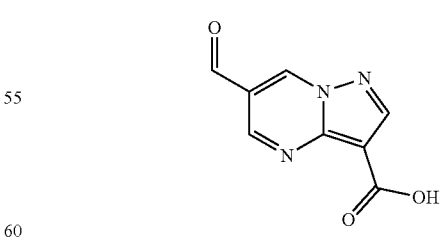

The mixture of 5-amino-1H-pyrazole-4-carboxylic acid (270 mg, 2.12 mmol) and methanetricarbaldehyde (205 mg, 2.05 mmol) in ethanol (1.5 mL) and acetic acid (0.50 mL) was stirred at 25° C. for 1h and at 70° C. for 1h. After cooling to room temperature, the mixture was filtered, the solid was washed with ethanol and dryness in vacuo to afford 6-formylpyrazolo[1,5-a]pyrimidine-3-carboxylic acid (135 mg, 33.2%) as a yellow solid. $^1$H NMR (400 MHz, DMSO-$d_6$) δ 12.04 (brs, 1H), 10.06 (s, 1H), 9.93 (d, J=2.0 Hz, 1H), 9.11 (d, J=2.0 Hz, 1H), 8.79 (s, 1H). MS (ESI): m/z=192.1 [M+1]$^+$.

Step B. 6-Formyl-N-[2-(hydroxymethyl)-2-methyl-6-morpholino-3H-benzofuran-5-yl]pyrazolo[1,5-a]pyrimidine-3-carboxamide

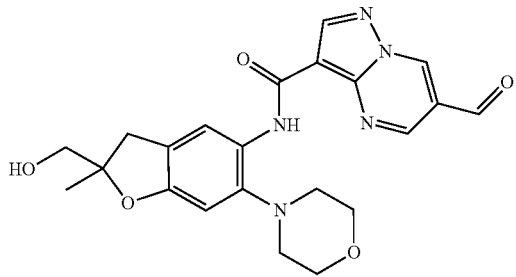 [SMILES: CC1(CO)Cc2cc(NC(=O)c3cnn4cc(C=O)cnc34)c(N3CCOCC3)cc2O1]

The mixture of 6-formylpyrazolo[1,5-a]pyrimidine-3-carboxylic acid (110 mg, 0.58 mmol), N,N-diisopropylethylamine (0.22 mL, 1.35 mmol), 2-(7-aza-1H-benzotriazole-1-yl)-1,1,3,3-tetramethyluronium hexafluorophosphate (330 mg, 0.87 mmol) and (5-amino-2-methyl-6-morpholino-3H-benzofuran-2-yl)methanol (Example 6, Step B) (115 mg, 0.44 mmol) in DMF (6 mL) was stirred at 25° C. for 3h. Water and ethyl acetate (150 mL) was added. The organic phase was washed with water, brine, dried over anhydrous sodium sulfate and concentrated in vacuo. Methyl alcohol (1 mL) was added then the solid was collected after filtration to afford 6-formyl-N-[2-(hydroxymethyl)-2-methyl-6-morpholino-3H-benzofuran-5-yl]pyrazolo[1,5-a]pyrimidine-3-carboxamide (115 mg) and as a yellow solid, which was used directly to next step without further purification. MS (ESI): m/z=438.1 [M+1]$^+$.

Step C. 6-(Difluoromethyl)-N-[2-(hydroxymethyl)-2-methyl-6-morpholino-3H-benzofuran-5-yl]pyrazolo[1,5-a]pyrimidine-3-carboxamide

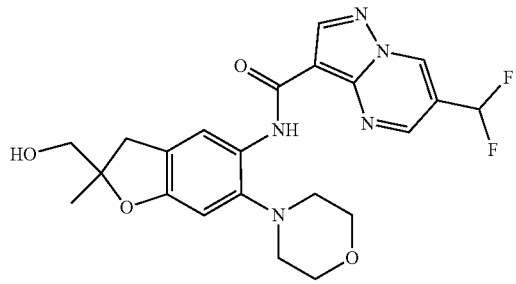

To the mixture of 6-formyl-N-[2-(hydroxymethyl)-2-methyl-6-morpholino-3H-benzofuran-5-yl]pyrazolo[1,5-a]pyrimidine-3-carboxamide (70 mg, 0.16 mmol) in DCM (10 mL) was added diethylaminosulfurtrifluoride (0.21 mL, 1.55 mmol) under at 0° C. and the mixture was stirred for 2h. The reaction mixture was diluted with DCM (10 mL) and water. The organic phase was dried over anhydrous sodium sulfate and concentrated in vacuo. The residue was purified by preparative HPLC (A: acetonitrile 25-45%; B: 0.05% formic acid in water) to afford 6-(difluoromethyl)-N-[2-(hydroxymethyl)-2-methyl-6-morpholino-3H-benzofuran-5-yl]pyrazolo[1,5-a]pyrimidine-3-carboxamide (10.9 mg, 15%) as a yellow solid. $^1$H NMR (400 MHz, MeOD-$d_4$) δ 9.46 (d, J=1.6 Hz, 1H), 9.07 (d, J=1.6 Hz, 1H), 8.78 (s, 1H), 8.26 (s, 1H), 7.15 (t, J=55.2 Hz, 1H), 6.73 (s, 1H), 4.01-3.90 (m, 4H), 3.65-3.56 (m, 2H), 3.27 (d, J=15.2 Hz, 1H), 2.99-2.90 (m, 5H), 1.44 (s, 3H). MS (ESI): m/z=460.1 [M+1]$^+$.

Examples 76 and 77. (R)—N-(2-Methyl-6-morpholino-2-(trifluoromethyl)-2,3-dihydrobenzofuran-5-yl)pyrazolo[1,5-a]pyrimidine-3-carboxamide and (S)—N-(2-methyl-6-morpholino-2-(trifluoromethyl)-2,3-dihydrobenzofuran-5-yl)pyrazolo[1,5-a]pyrimidine-3-carboxamide

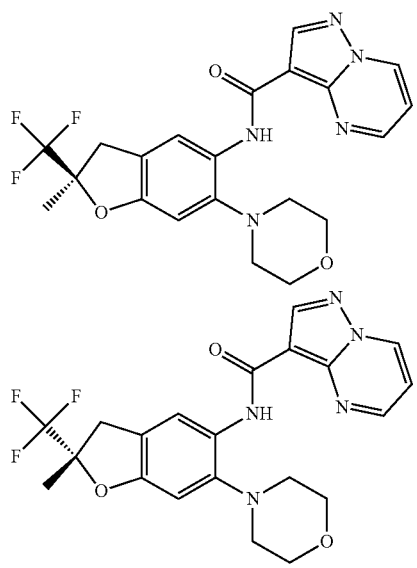

Step A. 6-Chloro-2-methyl-2-(trifluoromethyl)-2,3-dihydrobenzofuran

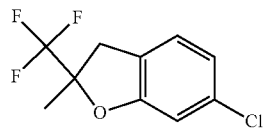

The mixture of 3-(4-chloro-2-fluorophenyl)-1,1,1-trifluoro-2-methylpropan-2-ol (500 mg, 1.95 mmol) and tert-butoxypotassium (875 mg, 7.80 mmol) in THF (20 mL) was stirred at 65° C. for 18h. After cooling to room temperature, water was added. The organic phase was separated and dried over sodium sulfate. After concentration under reduced pressure, the residue was purified by silica gel chromatography using ethyl acetate:petroleum ether (from 1:4 to 1:3) as eluting solvents to afford 6-chloro-2-methyl-2-(trifluoromethyl)-2,3-dihydrobenzofuran (200 mg, 22%) as a colorless oil. MS (ESI): m/z=237.1 [M+1]$^+$.

Step B. 6-Chloro-2-methyl-5-nitro-2-(trifluoromethyl)-2,3-dihydrobenzofuran

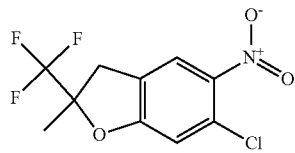 [SMILES: CC1(C(F)(F)F)Cc2cc([N+](=O)[O-])c(Cl)cc2O1]

To a solution of 6-chloro-2-methyl-2-(trifluoromethyl)-2,3-dihydrobenzofuran (250 mg, 1.06 mmol) in DCM (20 mL) at 25° C. was slowly added fuming nitric acid (0.5 mL) and stirred for 15 min. Water and ethyl acetate (30 mL) was added. The organic phase was separated and dried over sodium sulfate. After concentration under reduced pressure, the residue was purified by silica gel chromatography using ethyl acetate:petroleum ether (from 1:6 to 1:4) as eluting solvents to afford 6-chloro-2-methyl-5-nitro-2-(trifluoromethyl)-2,3-dihydrobenzofuran (250 mg, 82%) as orange solid. MS (ESI): m/z=282.2 [M+1]$^+$.

Step C. 4-(2-Methyl-5-nitro-2-(trifluoromethyl)-2,3-dihydrobenzofuran-6-yl)morpholine

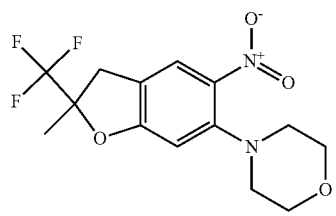

A mixture of 6-chloro-2-methyl-5-nitro-2-(trifluoromethyl)-2,3-dihydrobenzofuran (250 mg, 0.89 mmol) in morpholine (1 mL) in a sealed vial was stirred at 65° C. for 18h. The mixture was concentrated under reduced pressure. The residue was purified by silica gel chromatography using ethyl acetate:petroleum ether (1:3) as eluting solvents to afford 4-(2-methyl-5-nitro-2-(trifluoromethyl)-2,3-dihydrobenzofuran-6-yl)morpholine (150 mg, 84%) as a yellow solid. MS (ESI): m/z=333.1 [M+1]$^+$.

Step D. 2-Methyl-6-morpholino-2-(trifluoromethyl)-2,3-dihydrobenzofuran-5-amine

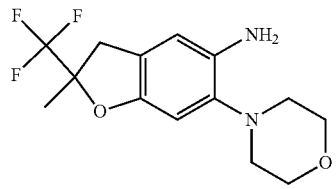 [SMILES: CC1(C(F)(F)F)Cc2cc(N)c(N3CCOCC3)cc2O1]

A mixture of 4-(2-methyl-5-nitro-2-(trifluoromethyl)-2,3-dihydrobenzofuran-6-yl)morpholine (150 mg, 0.45 mmol) and 10% palladium on carbon (15 mg) in methanol (6 mL) was stirred at room temperature for 1h under an atmosphere of hydrogen. The catalyst was filtered off. The filtrate was concentrated under reduced pressure to afford 2-methyl-6-morpholino-2-(trifluoromethyl)-2,3-dihydrobenzofuran-5-amine (100 mg) as a colorless oil, which was used directly in the next step without purification. MS (ESI): m/z=303.1 [M+1]$^+$.

Step E. (R)—N-(2-Methyl-6-morpholino-2-(trifluoromethyl)-2,3-dihydrobenzofuran-5-yl)pyrazolo[1,5-a]pyrimidine-3-carboxamide and (S)—N-(2-Methyl-6-morpholino-2-(trifluoromethyl)-2,3-dihydrobenzofuran-5-yl)pyrazolo[1,5-a]pyrimidine-3-carboxamide

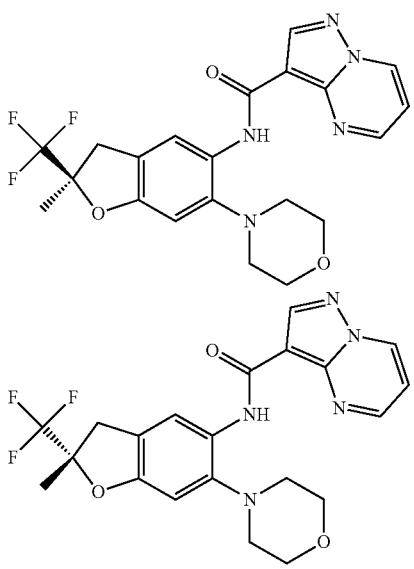

A mixture of pyrazolo[1,5-a]pyrimidine-3-carboxylic acid (54 mg, 0.33 mmol), (7-azabenzotriazol-1-yloxy)tripyrrolidinophosphoniumhexafluorophosphate (172 mg, 0.33 mmol) and N-ethyl-N-isopropylpropan-2-amine (85 mg, 0.66 mmol) in DMF (5 mL) was stirred at room temperature for 30 min. 2-Methyl-6-morpholino-2-(trifluoromethyl)-2,3-dihydrobenzofuran-5-amine (100 mg, 0.33 mmol) was added. The resulting mixture was stirred at room temperature for 18h. Water and ethyl acetate (30 mL) was added. The organic phase was separated and dried over sodium sulfate. After concentration, the residue was purified by silica gel chromatography using ethyl acetate:petroleum ether (10:1) as eluting solvents to afford the desired product and then it was resolved by chiral HPLC (Column: CE-4, Mobile Phase: Hexane/ethanol/DEA=70/30/0.1) to afford (R)—N-(2-methyl-6-morpholino-2-(trifluoromethyl)-2,3-dihydrobenzofuran-5-yl)pyrazolo[1,5-a]pyrimidine-3-carboxamide and (S)—N-(2-methyl-6-morpholino-2-(trifluoromethyl)-2,3-dihydrobenzofuran-5-yl)pyrazolo[1,5-a]pyrimidine-3-carboxamide (48 mg each, 33.3% each) as a yellow solids with absolute stereochemistry assigned arbitrarily.

Example 76, Peak 1: $^1$H NMR (400 MHz, DMSO-d$_6$): δ 10.48 (s, 1H), 9.38 (dd, J=1.6, 6.8 Hz, 1H), 8.96 (dd, J=1.6, 4.4 Hz, 1H), 8.69 (s, 1H), 8.40 (s, 1H), 7.35 (dd, J=4.0, 6.8 Hz, 1H), 6.93 (s, 1H), 3.85-3.83 (m, 4H), 3.52 (d, J=16.8 Hz, 1H), 3.30 (d, J=16.8 Hz, 1H), 2.85-2.83 (m, 4H), 1.62 (s, 3H). MS (ESI): m/z=448.2 [M+1]$^+$.

Example 77, Peak 2: ¹H NMR (400 MHz, DMSO-d₆): δ 10.48 (s, 1H), 9.38 (dd, J=1.6, 6.8 Hz, 1H), 8.95 (dd, J=1.6, 4.0 Hz, 1H), 8.69 (s, 1H), 8.40 (s, 1H), 7.35 (dd, J=4.0, 6.8 Hz, 1H), 6.93 (s, 1H), 3.85-3.83 (m, 4H), 3.52 (d, J=16.8 Hz, 1H), 3.30 (d, J=16.8 Hz, 1H), 2.90-2.80 (m, 4H), 1.62 (s, 3H). MS (ESI): m/z=448.2 [M+1]⁺.

Examples 78 and 79. N—((S)-2-(Hydroxymethyl)-2-methyl-6-((1S,4S)-5-(2,2,2-trifluoroethyl)-2,5-diazabicyclo[2.2.1]heptan-2-yl)-2,3-dihydrobenzofuran-5-yl)pyrazolo[1,5-a]pyrimidine-3-carboxamide and N—((R)-2-(hydroxymethyl)-2-methyl-6-((1S,4S)-5-(2,2,2-trifluoroethyl)-2,5-diazabicyclo[2.2.1]heptan-2-yl)-2,3-dihydrobenzofuran-5-yl)pyrazolo[1,5-a]pyrimidine-3-carboxamide

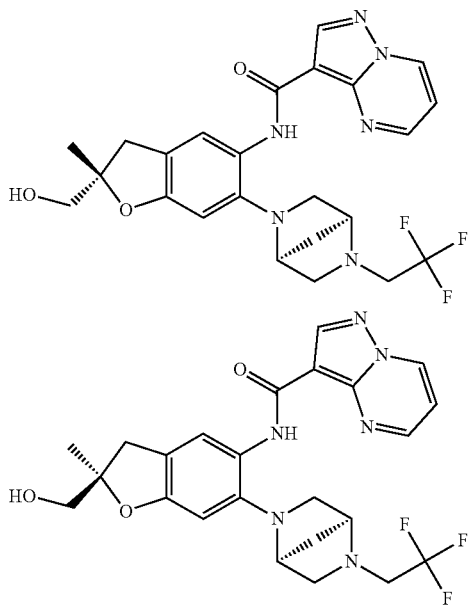

Step A. (1S,4S)-tert-Butyl5-(2,2,2-trifluoroethyl)-2,5-diazabicyclo[2.2.1]heptane-2-carboxylate

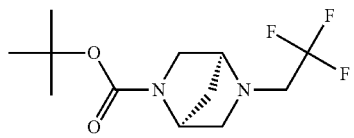 [SMILES: CC(C)(C)OC(=O)N1C[C@@H]2C[C@H]1CN2CC(F)(F)F]

The mixture of (1S,4S)-tert-butyl 2,5-diazabicyclo[2.2.1]heptane-2-carboxylate (70 mg, 0.35 mmol), 2,2,2-trifluoroethyl trifluoromethanesulfonate (81 mg, 0.35 mmol) and potassium carbonate (97 mg, 0.70 mmol) in acetonitrile (5 mL) was stirred at room temperature for 18h. After filtration, the filtrate was concentrated in vacuo to afford (1S,4S)-tert-butyl 5-(2,2,2-trifluoroethyl)-2,5-diazabicyclo[2.2.1]heptane-2-carboxylate (95 mg) as a colorless oil, which was used directly to the next step without purification. MS (ESI): m/z=281.1 [M+1]⁺.

Step B. (1S,4S)-2-(2,2,2-Trifluoroethyl)-2,5-diazabicyclo[2.2.1]heptane

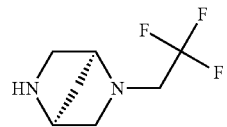 [SMILES: FC(F)(F)CN1C[C@@H]2C[C@H]1CN2]

A mixture of (1S,4S)-tert-butyl 5-(2,2,2-trifluoroethyl)-2,5-diazabicyclo[2.2.1]heptane-2-carboxylate (95 mg, 0.34 mmol) in 2,2,2-trifluoroacetic acid (1 mL) and DCM (2 mL) was stirred at room temperature for anh. The mixture was concentrated in vacuo to afford ((1S,4S)-2-(2,2,2-trifluoroethyl)-2,5-diazabicyclo[2.2.1]heptane 2,2,2-trifluoroacetic acid salt (55 mg) as a colorless oil, which was used directly to the next step without purification. MS (ESI): m/z=181.1 [M+1]⁺.

Step C. (2-Methyl-5-nitro-6-((1S,4S)-5-(2,2,2-trifluoroethyl)-2,5-diazabicyclo[2.2.1]heptan-2-yl)-2,3-dihydrobenzofuran-2-yl)methanol

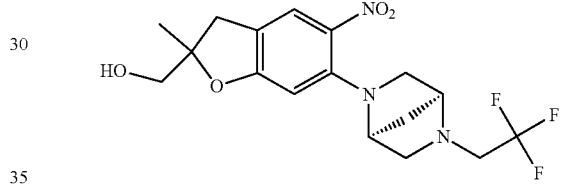

A mixture of (6-fluoro-2-methyl-5-nitro-2,3-dihydrobenzofuran-2-yl)methanol (70 mg, 0.31 mmol), (1S,4S)-2-(2,2,2-trifluoroethyl)-2,5-diazabicyclo[2.2.1]heptane (55 mg, 0.31 mmol) and cesium carbonate (303 mg, 0.93 mmol) in acetonitrile (5 mL) was stirred at room temperature for 18h. The mixture was poured into water and the aqueous phase was extracted with ethyl acetate (2×30 mL). The organic phases were combined, washed with water and brine. After concentration under reduced pressure, the residue was purified by silica gel chromatography using ethyl acetate:petroleum ether (1:3) as eluting solvents to afford (2-methyl-5-nitro-6-((1S,4S)-5-(2,2,2-trifluoroethyl)-2,5-diazabicyclo[2.2.1]heptan-2-yl)-2,3-dihydrobenzofuran-2-yl)methanol (110 mg, 92%) as a yellow solid. MS (ESI): m/z=388.1 [M+1]⁺.

Step D. (5-Amino-2-methyl-6-((1S,4S)-5-(2,2,2-trifluoroethyl)-2,5-diazabicyclo[2.2.1]heptan-2-yl)-2,3-dihydrobenzofuran-2-yl)methanol

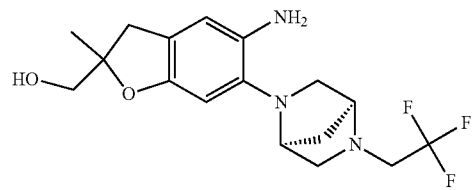 [SMILES: CC1(CO)Cc2cc(N)c(N3C[C@@H]4C[C@H]3CN4CC(F)(F)F)cc2O1]

A mixture of (2-methyl-5-nitro-6-((1S,4S)-5-(2,2,2-trifluoroethyl)-2,5-diazabicyclo[2.2.1]heptan-2-yl)-2,3-dihydrobenzofuran-2-yl)methanol (110 mg, 0.28 mmol) and 10% palladium on carbon (11 mg) in methanol (5 mL) was stirred at room temperature for 1h under an atmosphere of hydrogen. After filtration and concentration under reduced pressure, it was afforded (5-amino-2-methyl-6-((1S,4S)-5-(2,2,2-trifluoroethyl)-2,5-diazabicyclo[2.2.1]heptan-2-yl)-2,3-dihydrobenzofuran-2-yl)methanol (80 mg, 79%) as a colorless oil, which was used directly to the next step without purification. MS (ESI): m/z=358.1 [M+1]$^+$.

Step E. N—((S)-2-(Hydroxymethyl)-2-methyl-6-((1S,4S)-5-(2,2,2-trifluoroethyl)-2,5-diazabicyclo[2.2.1]heptan-2-yl)-2,3-dihydrobenzofuran-5-yl)pyrazolo[1,5-a]pyrimidine-3-carboxamide and N—((R)-2-(Hydroxymethyl)-2-methyl-6-((1S,4S)-5-(2,2,2-trifluoroethyl)-2,5-diazabicyclo[2.2.1]heptan-2-yl)-2,3-dihydrobenzofuran-5-yl)pyrazolo[1,5-a]pyrimidine-3-carboxamide

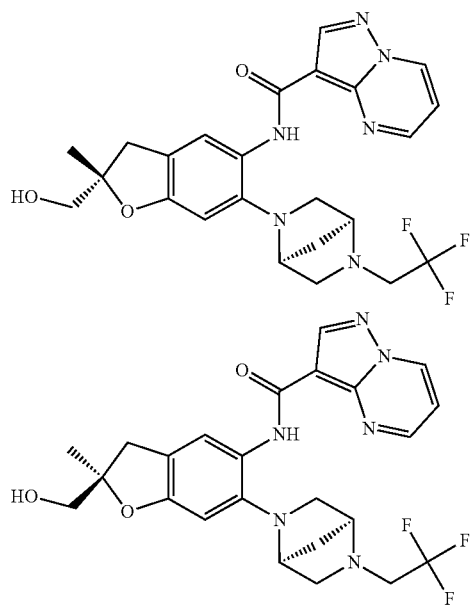

A mixture of pyrazolo[1,5-a]pyrimidine-3-carboxylic acid (36 mg, 0.22 mmol), (7-azabenzotriazol-1-yloxy)tripyrrolidinophosphoniumhexafluorophosphate (115 mg, 0.22 mmol) and N-ethyl-N-isopropylpropan-2-amine (85 mg, 0.66 mmol) in DMF (5 mL) was stirred at room temperature for 30 min. (5-Amino-2-methyl-6-((1S,4S)-5-(2,2,2-trifluoroethyl)-2,5-diazabicyclo[2.2.1]heptan-2-yl)-2,3-dihydrobenzofuran-2-yl)methanol (80 mg, 0.22 mmol) was added. The resulting mixture was stirred at room temperature for 18h. Water and ethyl acetate (30 mL) was added. The organic phase was separated and dried over sodium sulfate. After concentration under reduced pressure, the residue was purified by silica gel chromatography using ethyl acetate: petroleum ether (10:1) as eluting solvents to afford the desired product and then it was resolved by chiral pre-SFC (Column: OD 4.6*250 mm, Sum (Decial), Column temperature: 35° C., Mobile phase: CO2/Methanol (0.2% Methanol Ammonia)=70/30) to afford N—((S)-2-(hydroxymethyl)-2-methyl-6-((1S,4S)-5-(2,2,2-trifluoroethyl)-2,5-diazabicyclo[2.2.1]heptan-2-yl)-2,3-dihydrobenzofuran-5-yl)pyrazolo[1,5-a]pyrimidine-3-carboxamide and N—((R)-2-(hydroxymethyl)-2-methyl-6-((1S,4S)-5-(2,2,2-trifluoroethyl)-2,5-diazabicyclo[2.2.1]heptan-2-yl)-2,3-dihydrobenzofuran-5-yl)pyrazolo[1,5-a]pyrimidine-3-carboxamide (8 mg each, 7% each) as yellow solids with absolute stereochemistry assigned arbitrarily.

Example 78, Peak 1: $^1$H NMR (400 MHz, DMSO-d$_6$): δ9.74 (s, 1H), 9.37 (dd, J=1.6, 6.8 Hz, 1H), 8.85 (dd, J=1.6, 4.0 Hz, 1H), 8.69 (s, 1H), 7.80 (s, 1H), 7.33 (dd, J=4.0, 6.8 Hz, 1H), 6.48 (s, 1H), 5.04 (t, J=6.0 Hz, 1H), 3.93 (s, 1H), 3.51 (s, 1H), 3.45-3.41 (m, 2H), 3.32-3.25 (m, 3H), 3.16 (d, J=16.0 Hz, 1H), 3.07-3.04 (m, 1H), 2.92-2.88 (m, 2H), 2.78 (d, J=15.6 Hz, 1H), 1.89-1.76 (m, 2H), 1.34 (s, 3H). MS (ESI): m/z=503.3 [M+1]$^+$.

Example 79, Peak 2: $^1$H NMR (400 MHz, DMSO-d$_6$): δ 9.72 (s, 1H), 9.37 (dd, J=1.6, 6.8 Hz, 1H), 8.85 (dd, J=1.6, 4.0 Hz, 1H), 8.68 (s, 1H), 7.78 (s, 1H), 7.33 (dd, J=4.0, 6.8 Hz, 1H), 6.47 (s, 1H), 5.04 (t, J=6.0 Hz, 1H), 3.93 (s, 1H), 3.50 (s, 1H), 3.45-3.41 (m, 2H), 3.32-3.25 (m, 3H), 3.16 (d, J=16.0 Hz, 1H), 3.07-3.04 (m, 1H), 2.92-2.88 (m, 2H), 2.78 (d, J=15.6 Hz, 1H), 1.89-1.76 (m, 2H), 1.34 (s, 3H). MS (ESI): m/z=503.3 [M+1]$^+$.

Examples 80 and 81. (R)—N-(7-Chloro-2-(hydroxymethyl)-2-methyl-6-morpholino-2,3-dihydrobenzofuran-5-yl)pyrazolo[1,5-a]pyrimidine-3-carboxamide and (S)—N-(7-chloro-2-(hydroxymethyl)-2-methyl-6-morpholino-2,3-dihydrobenzofuran-5-yl)pyrazolo[1,5-a]pyrimidine-3-carboxamide

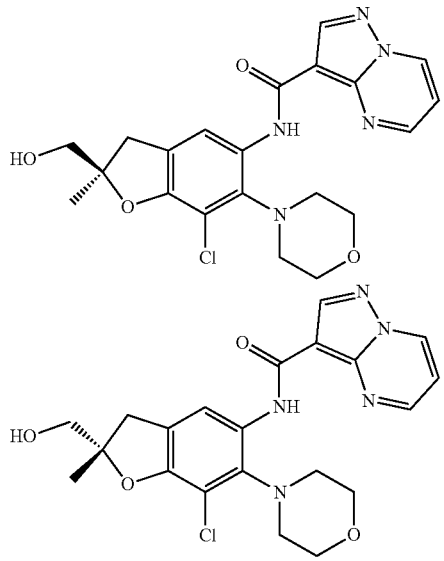

Step A. 1,2-Dichloro-3-(2-methylallyloxy)benzene

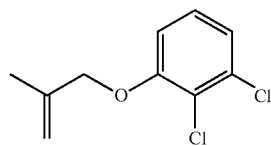

A mixture of 2,3-dichlorophenol (500 mg, 3.07 mmol), 3-bromo-2-methylpropene (497 mg, 3.68 mmol) and potassium carbonate (848 mg, 6.14 mmol) in acetonitrile (10 mL) was stirred at 25° C. for 18h. The reaction was then filtered, concentrated and purified by silica gel chromatography using petroleum ether to afford 1,2-dichloro-3-(2-methylallyloxy)benzene (659 mg, 99%) as a colorless oil. MS (ESI): m/z=218.1 [M+1]⁺.

Step B. 2,3-Dichloro-6-(2-methylallyl)phenol

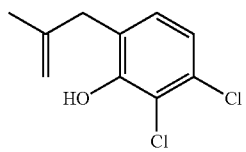

A mixture of 1,2-dichloro-3-(2-methylallyloxy)benzene (600 mg, 2.76 mmol) in DMF (3 mL) was stirred at 220° C. under microwave for 2h. Water was added and the mixture was extracted with ethyl acetate (10 mL). The organic phase was washed with brine, dried over sodium sulfate and concentrated to afford 2,3-dichloro-6-(2-methylallyl)phenol (400 mg) as light yellow oil, which was used directly to next step without further purification.

Step C. (6,7-Dichloro-2-methyl-2,3-dihydrobenzofuran-2-yl)methanol

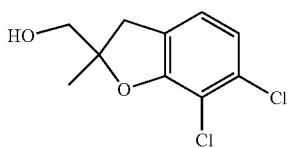

A mixture of 3-chloro-2-methyl-6-(2-methylallyl)phenol (400 mg, 1.84 mmol) in DCM (10 mL) was added 3-chloroperoxybenzoic acid (558 mg, 2.76 mmol) under ice-cooling. The mixture was stirred at 25° C. for 18h. The reaction was filtered and the filtrate was concentrated to afford (6,7-dichloro-2-methyl-2,3-dihydrobenzofuran-2-yl)methanol (300 mg, 70%) as a yellow oil, which was used directly to next step without purification further. MS (ESI): m/z=233.1 [M+1]⁺.

Step D. (6,7-Dichloro-2-methyl-5-nitro-2,3-dihydrobenzofuran-2-yl)methanol

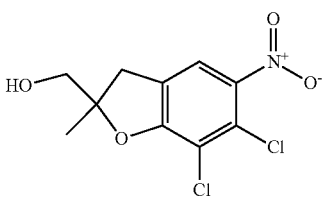 [SMILES: CC1(CO)Cc2cc([N+](=O)[O-])c(Cl)c(Cl)c2O1]

To a mixture of (6,7-dichloro-2-methyl-2,3-dihydrobenzofuran-2-yl)methanol (300 mg, 1.29 mmol) in DCM (10 mL) was added drop-wise fuming nitric acid (0.5 mL) at 25° C. The mixture was stirred at 25° C. for 30 min and poured into ice water. The aqueous phase was extracted with ethyl acetate (30 mL). The organic phase was dried over sodium sulfate. After concentration under reduced pressure, the residue was purified by silica gel chromatography using ethyl acetate:petroleum ether (1:4) as eluting solvents to afford (6,7-dichloro-2-methyl-5-nitro-2,3-dihydrobenzofuran-2-yl)methanol (220 mg, 61%) as light grey solid. MS (ESI): m/z=279.1 [M+1]⁺.

Step E. (7-Chloro-2-methyl-6-morpholino-5-nitro-2,3-dihydrobenzofuran-2-yl)methanol

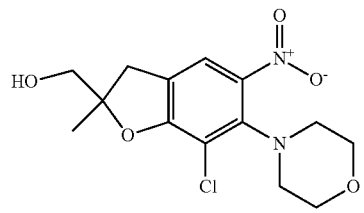 [SMILES: CC1(CO)Cc2cc([N+](=O)[O-])c(N3CCOCC3)c(Cl)c2O1]

A mixture of (6,7-dichloro-2-methyl-5-nitro-2,3-dihydrobenzofuran-2-yl)methanol (220 mg, 0.79 mmol) in morpholine (2 mL) in a sealed tube was stirred at 110° C. for 18h. The mixture was concentrated and purified by silica gel chromatography using ethyl acetate:petroleum ether (1:1) as eluting solvents to afford (7-chloro-2-methyl-6-morpholino-5-nitro-2,3-dihydrobenzofuran-2-yl)methanol (200 mg, 77%) as a yellow oil. MS (ESI): m/z=329.1 [M+1]⁺.

Step F. (5-Amino-7-chloro-2-methyl-6-morpholino-2,3-dihydrobenzofuran-2-yl)methanol

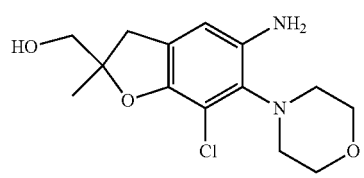 [SMILES: CC1(CO)Cc2cc(N)c(N3CCOCC3)c(Cl)c2O1]

A mixture of (7-chloro-2-methyl-6-morpholino-5-nitro-2,3-dihydrobenzofuran-2-yl)methanol (100 mg, 0.30 mmol) and 10% palladium on carbon (10 mg) in methanol (10 mL) was stirred at 25° C. under hydrogen atmosphere for 1h. After filtration and concentration under reduced pressure, it was afforded (5-amino-7-chloro-2-methyl-6-morpholino-2,3-dihydrobenzofuran-2-yl)methanol (60 mg) as a green oil, which was used directly to next step without further purification. MS (ESI): m/z=299.1[M+1]⁺.

Step G. (R)—N-(7-Chloro-2-(hydroxymethyl)-2-methyl-6-morpholino-2,3-dihydrobenzofuran-5-yl)pyrazolo[1,5-a]pyrimidine-3-carboxamide and (S)—N-(7-chloro-2-(hydroxymethyl)-2-methyl-6-morpholino-2,3-dihydrobenzofuran-5-yl)pyrazolo[1,5-a]pyrimidine-3-carboxamide

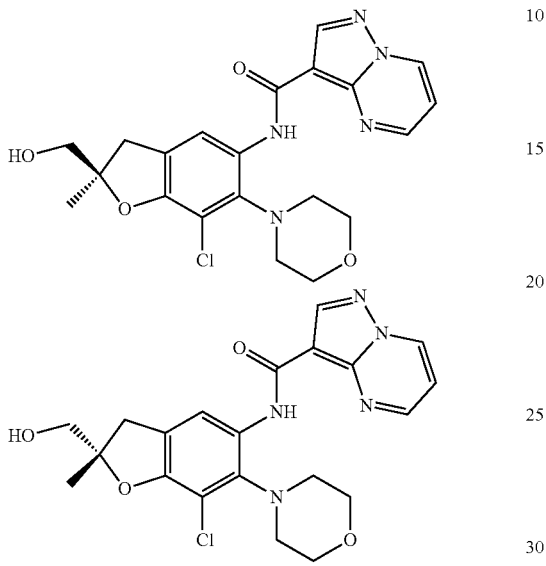

A mixture of pyrazolo[1,5-a]pyrimidine-3-carboxylic acid (33 mg, 0.20 mmol), (7-azabenzotriazol-1-yloxy)tripyrrolidinophosphoniumhexafluorophosphate (104 mg, 0.69 mmol), N-ethyl-N-isopropylpropan-2-amine (78 mg, 0.60 mmol) and (5-amino-7-chloro-2-methyl-6-morpholino-2,3-dihydrobenzofuran-2-yl)methanol (60 mg, 0.20 mmol) in DMF (5 mL) was stirred at room temperature for 18h. Water was added and the mixture was extracted with ethyl acetate (10 mL). The organic phase was washed with brine and dried over sodium sulfate. After concentration under reduced pressure and the residue was purified by silica gel chromatography using ethyl acetate:petroleum ether (10:1) as eluting solvents to afford N-(7-chloro-2-(hydroxymethyl)-2-methyl-6-morpholino-2,3-dihydrobenzofuran-5-yl)pyrazolo[1,5-a]pyrimidine-3-carboxamide (40 mg, 45%) as a yellow solid. Then the desired product was resolved by chiral pre-SFC(Column: AD 20*250 mm, Sum (Dacel), Column temperature: 35° C., Mobile phase: CO₂/Ethanol{0.5% Ammonia (7 m methanol)}=70/30) to obtain (R)—N-(7-chloro-2-(hydroxymethyl)-2-methyl-6-morpholino-2,3-dihydrobenzofuran-5-yl)pyrazolo[1,5-a]pyrimidine-3-carboxamide and (S)—N-(7-chloro-2-(hydroxymethyl)-2-methyl-6-morpholino-2,3-dihydrobenzofuran-5-yl)pyrazolo[1,5-a]pyrimidine-3-carboxamide (15 mg each, 17% each) as a yellow solids with absolute stereochemistry assigned arbitrarily.

Example 80, Peak 1: ¹HNMR (400 MHz, DMSO-d₆): δ 10.73 (s, 1H), 9.39 (dd, J=1.6, 7.2 Hz, 1H), 8.91 (dd, J=1.6, 4.0 Hz, 1H), 8.70 (s, 1H), 8.44 (s, 1H), 7.37 (dd, J=4.0, 7.2 Hz, 1H), 5.13 (t, J=5.6 Hz, 1H), 4.02-3.93 (m, 2H), 3.89-3.83 (m, 2H), 3.70 (t, J=10.8 Hz, 2H), 3.54-3.41 (m, 2H), 3.38-3.34 (m, 1H), 2.96 (d, J=16.4 Hz, 1H), 2.69 (d, J=11.6 Hz, 2H), 1.38 (s, 3H). MS (ESI): m/z=444.1 [M+1]⁺.

Example 81, Peak 2: ¹H NMR (400 MHz, DMSO-d₆): δ 10.73 (s, 1H), 9.39 (dd, J=1.6, 7.2 Hz, 1H), 8.91 (dd, J=1.6, 4.4 Hz, 1H), 8.70 (s, 1H), 8.44 (s, 1H), 7.37 (dd, J=4.4, 6.8 Hz, 1H), 5.13 (t, J=5.6 Hz, 1H), 4.02-3.93 (m, 2H), 3.89-3.82 (m, 2H), 3.70 (t, J=10.0 Hz, 2H), 3.55-3.41 (m, 2H), 3.38-3.34 (m, 1H), 2.96 (d, J=16.4 Hz, 1H), 2.69 (d, J=12.0 Hz, 2H), 1.38 (s, 3H). MS (ESI): m/z=444.1 [M+1]⁺.

Example 82. N-(3,3-Dimethyl-7-morpholino-3,4-dihydro-2H-benzo[b][1,4]oxazin-6-yl)pyrazolo[1,5-a]pyrimidine-3-carboxamide

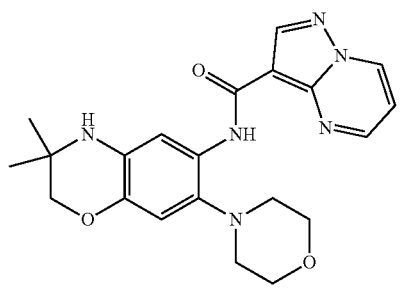 [SMILES: CC1(C)COc2cc(N3CCOCC3)c(NC(=O)c3cnn4cccnc34)cc2N1]

Step A.
4-Fluoro-2-(2-methylallyloxy)-1-nitrobenzene

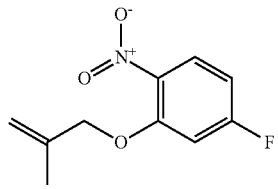

A mixture of 5-fluoro-2-nitrophenol (2.0 g, 12.73 mmol), 3-bromo-2-methylpropene (1.54 mL, 15.3 mmol) and potassium carbonate (3.5 g, 25.46 mmol) in acetonitrile (50 mL) was stirred at 50° C. for 18h. The reaction was filtered and the filtrate was concentrated and purified by silica gel chromatography using petroleum ether to afford 4-fluoro-2-(2-methylallyloxy)-1-nitro-benzene (780 mg, 29%) as light oil. MS (ESI): m/z=230.2 [M+H₂O]⁺.

Step B. 4-Fluoro-2-(2-methylallyloxy)aniline

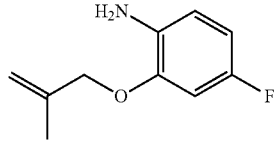

A mixture of 4-fluoro-2-(2-methylallyloxy)-1-nitro-benzene (780 mg, 3.69 mmol), iron powder (1.0 g, 18.47 mmol) and ammonium chloride (978 mg, 18.47 mmol) in ethanol (30 mL) and water (4 mL) was stirred at 70° C. for 2h. The reaction was filtered and the filtrate was dried over sodium sulfate and concentrated. The residue was purified by silica gel chromatography using ethyl acetate:petroleum ether (1:30) to afford 4-fluoro-2-(2-methylallyloxy)aniline (560 mg, 84%) as light oil. MS (ESI): m/z=182.1 [M+1]⁺.

Step C.
1-Azido-4-fluoro-2-(2-methylallyloxy)benzene

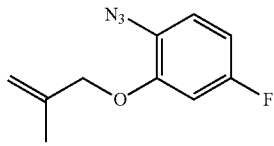

To a mixture of 4-fluoro-2-(2-methylallyloxy)aniline (100 mg, 0.55 mmol) in acetonitrile (10 mL) was added tert-butyl nitrite (85 mg, 0.83 mmol) followed by trimethylsilylazid (95 mg, 0.83 mmol) at 0° C. The mixture was stirred at 25° C. for 1h. Water was added and the aqueous phase was extracted with ethyl acetate (20 mL). The organic phase was separated, dried over sodium sulfate. The filtrate was concentrated under reduced pressure to afford 1-azido-4-fluoro-2-(2-methylallyloxy)benzene (99 mg) as a yellow oil, which was used directly to next step without further purification. MS (ESI): m/z=208.0 [M+1]$^+$.

Step D. 5-Fluoro-1a-methyl-1a, 2-dihydro-1H-azirino[1,2-d]benzo[b][1,4]oxazine

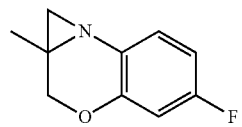

A mixture of 1-azido-4-fluoro-2-(2-methylallyloxy)benzene (99 mg, 0.48 mmol) in toluene (5 mL) was stirred at 110° C. for 18h. The solvent was removed under reduced pressure. The residue was purified by silica gel chromatography using ethyl acetate:petroleum ether (1:15) as eluting solvents to afford 5-fluoro-1a-methyl-1,2-dihydroazirino[2,1-c][1,4]benzoxazine (38 mg, 44%) as a colorless oil. $^1$HNMR (400 MHz, CDCl$_3$): 7.00-7.03 (m, 1H), 6.75-6.79 (m, 1H), 6.66-6.71 (m, 1H), 4.13 (d, J=11.2 Hz, 1H), 3.95 (d, J=11.2 Hz, 1H), 2.30 (s, 2H), 1.37 (s, 3H).

Step E. 7-Fluoro-3,3-dimethyl-3,4-dihydro-2H-benzo[b][1,4]oxazine

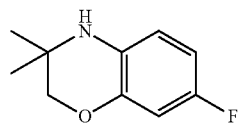

A mixture of 10% palladium on carbon (60 mg) and 5-fluoro-1a-methyl-1,2-dihydroazirino[2,1-c][1,4]benzoxazine (300 mg, 1.67 mmol) in ethanol (20 mL) was stirred at 25° C. under hydrogen atmosphere for 2h. After filtration and concentration under reduced pressure, it was afforded 7-fluoro-3,3-dimethyl-2,4-dihydro-1,4-benzoxazine (200 mg) as a brown solid, which was used directly to next step without further purification. MS (ESI): m/z=182.1 [M+1]$^+$.

Step F. 7-Fluoro-3,3-dimethyl-6-nitro-3,4-dihydro-2H-benzo[b][1,4]oxazine

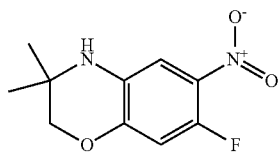 [SMILES: CC1(C)COc2cc(F)c([N+](=O)[O-])cc2N1]

To a mixture of 7-fluoro-3,3-dimethyl-2,4-dihydro-1,4-benzoxazine (160 mg, 0.88 mmol) in sulfuric acid (4 mL) was added slowly guanidine nitrate (108 mg, 0.88 mmol) at 0° C. The mixture was stirred at 0° C. for 3h. The mixture was poured into ice water and neutralized with sodium carbonate. The aqueous phase was extracted with ethyl acetate (20 mL). The organic phase was dried over sodium sulfate and concentrated. The residue was purified by silica gel chromatography using ethyl acetate:petroleum ether (1:4) as eluting solvents to afford 7-fluoro-3,3-dimethyl-6-nitro-2,4-dihydro-1,4-benzoxazine (70 mg, 35%) as a brown solid. MS (ESI): m/z=227.1 [M+1]$^+$.

Step G. 3,3-Dimethyl-7-morpholino-6-nitro-3,4-dihydro-2H-benzo[b][1,4]oxazine

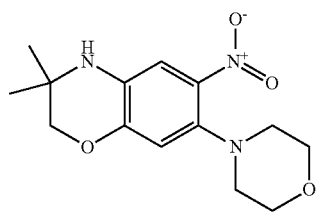 [SMILES: CC1(C)COc2cc(N3CCOCC3)c([N+](=O)[O-])cc2N1]

A mixture of 7-fluoro-3,3-dimethyl-6-nitro-2,4-dihydro-1,4-benzoxazine (70 mg, 0.31 mmol), morpholine (40 mg, 0.46 mmol) and cesium carbonate (202 mg, 0.62 mmol) in acetonitrile (10 mL) was stirred at 85° C. for 18h. The reaction was filtered and the filtrate was purified by silica gel chromatography using ethyl acetate:petroleum ether (1:1) as eluting solvents to afford 3,3-dimethyl-7-morpholino-6-nitro-2,4-dihydro-1,4-benzoxazine (69 mg, 56%) as a yellow oil. MS (ESI): m/z=294.1 [M+1]$^+$.

Step H. 3,3-Dimethyl-7-morpholino-3,4-dihydro-2H-benzo[b][1,4]oxazin-6-amine

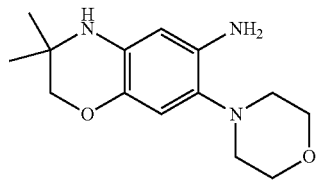 [SMILES: CC1(C)COc2cc(N3CCOCC3)c(N)cc2N1]

A mixture of 10% palladium on carbon (15 mg) and 3-dimethyl-7-morpholino-6-nitro-2,4-dihydro-1,4-benzoxazine (69 mg, 0.24 mmol) in ethyl acetate (15 mL) was stirred at 40° C. under hydrogen atmosphere for 2h. After filtration and concentration under reduced pressure, it was afforded 3,3-dimethyl-7-morpholino-3,4-dihydro-2H-benzo[b][1,4]oxazin-6-amine (50 mg, 76%) as dark solid. MS (ESI): m/z=264.1 [M+1]⁺.

Step I. N-(3,3-Dimethyl-7-morpholino-3,4-dihydro-2H-benzo[b][1,4]oxazin-6-yl)pyrazolo[1,5-a]pyrimidine-3-carboxamide

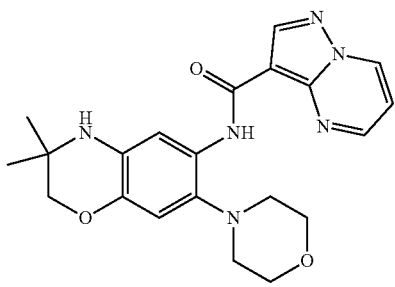 [SMILES: CC1(C)COc2cc(N3CCOCC3)c(NC(=O)c3cnn4cccnc34)cc2N1]

A mixture of pyrazolo[1,5-a]pyrimidine-3-carboxylic acid (37 mg, 0.23 mmol), (7-azabenzotriazol-1-yloxy)tripyrrolidinophosphoniumhexafluorophosphate (148 mg, 0.28 mmol), N-ethyl-N-isopropylpropan-2-amine (69 mg, 0.57 mmol) and 3,3-dimethyl-7-morpholino-3,4-dihydro-2H-benzo[b][1,4]oxazin-6-amine (50 mg, 0.19 mmol) in DMF (10 mL) was stirred at room temperature for 18h. Water was added. The aqueous phase was extracted with ethyl acetate (10 mL). The organic phase was washed with brine and dried over sodium sulfate. After concentration under reduced pressure, the residue was purified by silica gel chromatography using ethyl acetate:petroleum ether (9:1) as eluting solvents to afford N-(6-methoxy-2,2-dimethyl-3H-benzofuran-5-yl)pyrazolo[1,5-a]pyrimidine-3-carboxamide (10 mg, 13%) as a yellow solid. ¹HNMR (400 MHz, CDCl₃): 10.48 (s, 1H), 8.82 (dd, J=1.6, 7.2 Hz, 1H), 8.79 (s, 1H), 8.75 (dd, J=1.6, 4.0 Hz, 1H), 8.18 (s, 1H), 7.05 (dd, J=4.0, 7.2 Hz, 1H), 6.47 (s, 1H), 5.36 (brs, 1H), 3.93-3.95 (m, 4H), 3.83 (s, 2H), 2.88-2.89 (m, 4H), 1.24 (s, 6H). MS (ESI): m/z=409.2 [M+1]⁺.

Examples 83 and 84. (R)—N-(2-(Hydroxymethyl)-2,7-dimethyl-6-morpholino-2,3-dihydrobenzofuran-5-yl)pyrazolo[1,5-a]pyrimidine-3-carboxamide and (S)—N-(2-(hydroxymethyl)-2,7-dimethyl-6-morpholino-2,3-dihydrobenzofuran-5-yl)pyrazolo[1,5-a]pyrimidine-3-carboxamide

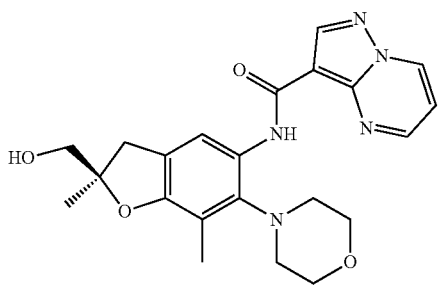

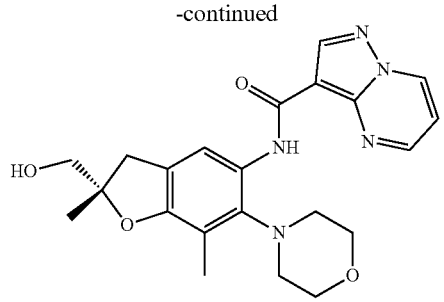

Step A.
1-Chloro-2-methyl-3-(2-methylallyloxy)benzene

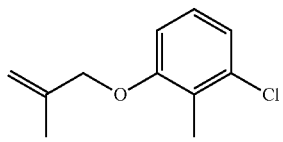

A mixture of 3-chloro-2-methylphenol (2.0 g, 14.03 mmol), 3-bromo-2-methylpropene (1.7 mL, 16.86 mmol) and potassium carbonate (3.87 g, 28.05 mmol) in acetonitrile (50 mL) was stirred at 25° C. for 18h. The reaction was filtered and the filtrate was concentrated under reduced pressure and the residue was purified by silica gel chromatography using petroleum ether to afford 1-chloro-2-methyl-3-(2-methylallyloxy)benzene (2.3 g, 83%) as a colorless oil. ¹HNMR (400 MHz, CDCl₃): 7.03-7.07 (m, 1H), 6.96-6.98 (m, 1H), 6.72 (d, J=8.0 Hz, 1H), 5.10 (s, 1H), 4.99 (s, 1H), 4.42 (s, 1H), 2.31 (s, 3H), 1.84 (s, 3H).

Step B. 3-Chloro-2-methyl-6-(2-methylallyl)phenol

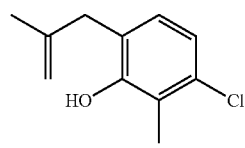

A mixture of 1-chloro-2-methyl-3-(2-methylallyloxy)benzene (300 mg, 1.53 mmol) in DMF (4.5 mL) was stirred at 220° C. under microwave condition for 2h. Water was added and the mixture was extracted with ethyl acetate (10 mL). The organic phase was washed with brine and dried over sodium sulfate. The reaction was filtered and the filtrate was concentrated to afford 3-chloro-2-methyl-6-(2-methylallyl)phenol (322 mg, 86%) as a colorless oil. ¹H NMR (400 MHz, CDCl₃) δ 6.90 (d, J=8.4 Hz, 1H), 6.85 (d, J=8.0 Hz, 1H), 5.42 (s, 1H), 4.96 (s, 1H), 4.91 (s, 1H), 3.34 (s, 1H), 2.28 (s, 3H), 1.57 (s, 3H).

Step C. (6-Chloro-2,7-dimethyl-2,3-dihydrobenzofuran-2-yl)methanol

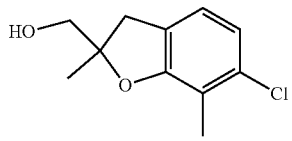

A mixture of 3-chloro-2-methyl-6-(2-methylallyl)phenol (300 mg, 1.53 mmol) in DCM (10 mL) was added 3-chloroperoxybenzoic acid (306 mg, 1.83 mmol) at 0° C. The mixture was stirred at 25° C. for 18h. The reaction was filtered and the filtrate was concentrated to afford (6-chloro-2,7-dimethyl-3H-benzofuran-2-yl)methanol (500 mg) as a yellow oil, which was used directly to next step without further purification. MS (ESI): m/z=213.1 [M+1]$^+$.

Step D. (6-Chloro-2,7-dimethyl-5-nitro-2,3-dihydrobenzofuran-2-yl)methanol

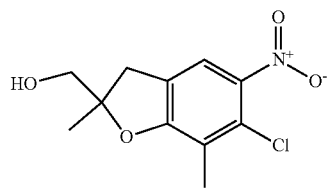 [SMILES: Cc1c(Cl)c([N+](=O)[O-])cc2c1OC(C)(CO)C2]

A mixture of (6-chloro-2,7-dimethyl-3H-benzofuran-2-yl)methanol (500 mg, 2.35 mmol) in DCM (10 mL) was added drop wise fuming nitric acid (0.3 mL) at 25° C. The mixture was stirred at 25° C. for 30 min. The mixture was poured into ice water and extracted with ethyl acetate (30 mL). The organic phase was dried over sodium sulfate and concentrated. The residue was purified by silica gel chromatography using ethyl acetate:petroleum ether (1:4) as eluting solvents to afford (6-chloro-2,7-dimethyl-5-nitro-3H-benzofuran-2-yl)methanol (182 mg, 50%) as light grey solid. MS (ESI): m/z=258.1 [M+1]$^+$.

Step E. (2,7-Dimethyl-6-morpholino-5-nitro-2,3-dihydrobenzofuran-2-yl)methanol

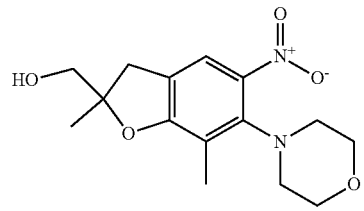 [SMILES: Cc1c2c(cc([N+](=O)[O-])c1N1CCOCC1)CC(C)(CO)O2]

A mixture of (6-chloro-2,7-dimethyl-5-nitro-3H-benzofuran-2-yl)methanol (182 mg, 0.71 mmol) in morpholine (4 mL) was stirred at 110° C. for 18h. After concentration under reduced pressure, the residue was purified by silica gel chromatography using ethyl acetate:petroleum ether (1:1) as eluting solvents to afford (2,7-dimethyl-6-morpholino-5-nitro-3H-benzofuran-2-yl)methanol (200 mg, 79%) as a yellow oil. MS (ESI): m/z=309.1 [M+1]$^+$.

Step F. (5-Amino-2,7-dimethyl-6-morpholino-2,3-dihydrobenzofuran-2-yl)methanol

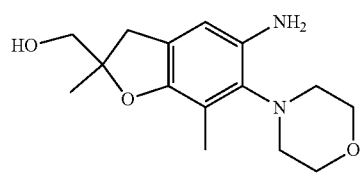 [SMILES: Cc1c2c(cc(N)c1N1CCOCC1)CC(C)(CO)O2]

A mixture of 10% palladium on carbon (60 mg) and (2,7-dimethyl-6-morpholino-5-nitro-3H-benzofuran-2-yl) methanol (200 mg, 0.65 mmol) in methanol (20 mL) was stirred at 25° C. under hydrogen atmosphere for 1h. After filtration and concentration under reduced pressure, it was afforded (5-amino-2,7-dimethyl-6-morpholino-2,3-dihydrobenzofuran-2-yl)methanol (183 mg) as a green oil, which was used directly to next step without further purification. MS (ESI): m/z=279.1[M+1]$^+$.

Step G. (R)—N-(2-(Hydroxymethyl)-2,7-dimethyl-6-morpholino-2,3-dihydrobenzofuran-5-yl)pyrazolo [1,5-a]pyrimidine-3-carboxamide and (S)—N-(2-(Hydroxymethyl)-2,7-dimethyl-6-morpholino-2,3-dihydrobenzofuran-5-yl)pyrazolo[1,5-a]pyrimidine-3-carboxamide

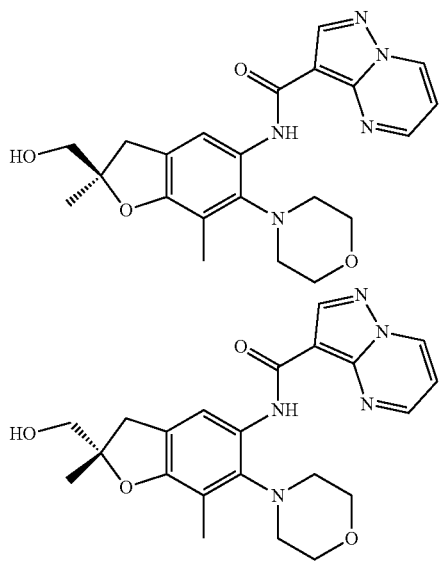

A mixture of pyrazolo[1,5-a]pyrimidine-3-carboxylic acid (90 mg, 0.55 mmol), (7-azabenzotriazol-1-yloxy)tripyrrolidinophosphoniumhexafluorophosphate (360 mg, 0.69 mmol), N-ethyl-N-isopropylpropan-2-amine (167 mg, 1.38 mmol) and (5-amino-2,7-dimethyl-6-morpholino-2,3-dihydrobenzofuran-2-yl)methanol (183 mg, 0.46 mmol) in DMF (10 mL) was stirred at room temperature for 18h. Water was added and the mixture was extracted with ethyl acetate (20 mL). The organic phase was washed with brine and dried over sodium sulfate and concentration under reduced pressure. The residue was purified by silica gel chromatography using ethyl acetate:petroleum ether (9:1) as eluting solvents to afford N-(2-(hydroxymethyl)-2,7-dimethyl-6-morpholino-2,3-dihydrobenzofuran-5-yl)pyrazolo[1,5-a]pyrimidine-3-carboxamide (80 mg, 41%) as a yellow solid. The product was resolved by chiral pre-SFC(Column: AD 20*250 mm, 5um (Dacel), Mobile phase: CO$_2$/methanol {0.5% Ammonia (7 m methanol)}=70/30) to obtain (R)—N-(2-(hydroxymethyl)-2,7-dimethyl-6-morpholino-2,3-dihydrobenzofuran-5-yl)pyrazolo[1,5-a]pyrimidine-3-carboxamide and (S)—N-(2-(hydroxymethyl)-2,7-dimethyl-6-morpholino-2,3-dihydrobenzofuran-5-yl)pyrazolo[1,5-a]pyrimidine-3-carboxamide (30 mg, 37%) (35 mg, 44%) as a yellow solids with absolute stereochemistry assigned arbitrarily.

Example 83, Peak 1: $^1$H NMR (400 MHz, CDCl$_3$) δ 10.62 (s, 1H), 8.83 (dd, J=1.8, 7.2 Hz, 1H), 8.79 (s, 1H), 8.77 (dd, J=1.8, 4.0 Hz, 1H), 8.36 (s, 1H), 7.07 (dd, J=4.4, 7.2 Hz, 1H), 4.08-4.12 (m, 2H), 3.89-3.91 (m, 2H), 3.64-3.67 (m, 2H), 3.52-3.57 (m, 2H), 3.26 (d, J=15.6 Hz, 1H), 2.94 (d, J=15.6 Hz, 1H), 2.84 (d, J=11.6 Hz, 2H), 2.30 (s, 3H), 2.06 (br, 1H), 1.45 (s, 3H). MS (ESI): m/z=424.1[M+1]$^+$.

Example 84, Peak 2: $^1$H NMR (400 MHz, CDCl$_3$) δ 10.62 (s, 1H), 8.83 (dd, J=1.8, 7.2 Hz, 1H), 8.79 (s, 1H), 8.77 (dd, J=1.8, 4.0 Hz, 1H), 8.36 (s, 1H), 7.07 (dd, J=4.4, 7.2 Hz, 1H), 4.08-4.12 (m, 2H), 3.89-3.91 (m, 2H), 3.64-3.67 (m, 2H), 3.52-3.57 (m, 2H), 3.26 (d, J=15.6 Hz, 1H), 2.94 (d, J=15.6 Hz, 1H), 2.84 (d, J=11.6 Hz, 2H), 2.30 (s, 3H), 2.06 (br, 1H), 1.45 (s, 3H). MS (ESI): m/z=424.1[M+1]$^+$.

Examples 85 and 86. (R)-6-Acetyl-N-(2-(hydroxymethyl)-2-methyl-6-morpholino-2,3-dihydrobenzofuran-5-yl)pyrazolo[1,5-a]pyrimidine-3-carboxamide and (S)-6-Acetyl-N-(2-(hydroxymethyl)-2-methyl-6-morpholino-2,3-dihydrobenzofuran-5-yl)pyrazolo[1,5-a]pyrimidine-3-carboxamide

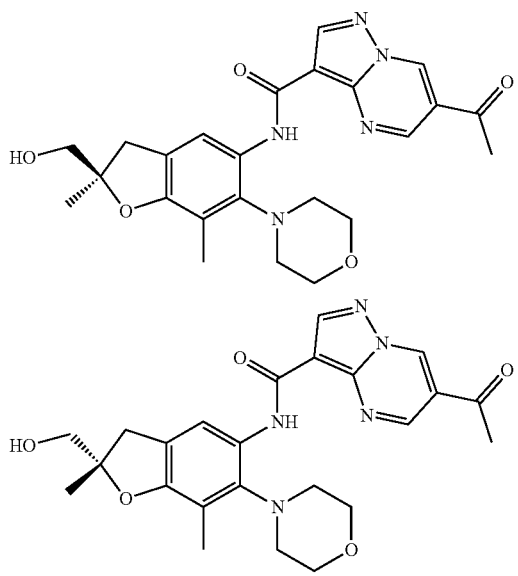

Step A. 6-Bromopyrazolo[1,5-a]pyrimidine-3-carboxylicacid

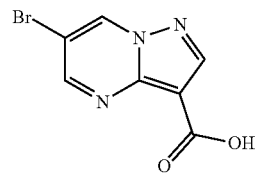 [SMILES: O=C(O)c1cnn2cc(Br)cnc12]

The mixture of 2-bromomalonaldehyde (754.8 mg, 5 mmol) and 5-amino-1H-pyrazole-4-carboxylic acid (635.5 mg, 5 mmol) was stirred at 90° C. in acetic acid (6 mL) and ethanol (2 mL) for 4h. After cooling to room temperature and concentration, the residue was filtered and solid was washed with water and ethyl acetate to afford 6-bromopyrazolo[1,5-a]pyrimidine-3-carboxylic acid (680 mg, 52.1%) as pale brown solid. MS (ESI): m/z=244.0[M+1]$^+$.

Step B. 6-Bromo-N-(2-(hydroxymethyl)-2-methyl-6-morpholino-2,3-dihydrobenzofuran-5-yl)pyrazolo[1,5-a]pyrimidine-3-carboxamide

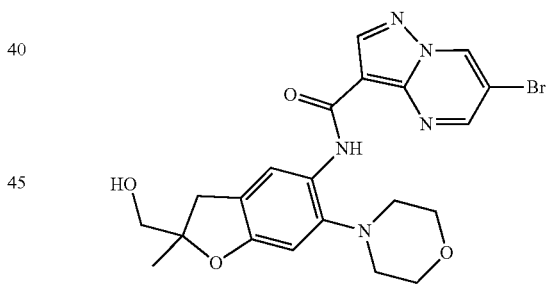

A mixture of 6-bromopyrazolo[1,5-a]pyrimidine-3-carboxylic acid (88 mg, 0.36 mmol), (7-azabenzotriazol-1-yloxy)tripyrrolidinophosphoniumhexafluorophosphate (237 mg, 0.45 mmol), N-ethyl-N-isopropylpropan-2-amine (110 mg, 0.91 mmol) and (5-amino-2-methyl-6-morpholino-2,3-dihydrobenzofuran-2-yl)methanol (Example 6, Step B) (80 mg, 0.30 mmol) in DMF (10 mL) was stirred at room temperature for 18h. Water was added and the mixture was extracted with ethyl acetate (20 mL). The organic phase was washed with brine and dried over sodium sulfate and concentration. The residue was purified by silica gel chromatography using ethyl acetate:petroleum ether (9:1) as eluting solvents to afford 6-bromo-N-(2-(hydroxymethyl)-2-methyl-6-morpholino-2,3-dihydrobenzofuran-5-yl)pyrazolo[1,5-a]pyrimidine-3-carboxamide (66 mg, 45%) as a yellow solid. MS (ESI): m/z=488.1[M+1]$^+$.

Step C. (R)-6-Acetyl-N-(2-(hydroxymethyl)-2-methyl-6-morpholino-2,3-dihydrobenzofuran-5-yl)pyrazolo[1,5-a]pyrimidine-3-carboxamide and (S)-6-Acetyl-N-(2-(hydroxymethyl)-2-methyl-6-morpholino-2,3-dihydrobenzofuran-5-yl)pyrazolo[1,5-a]pyrimidine-3-carboxamide

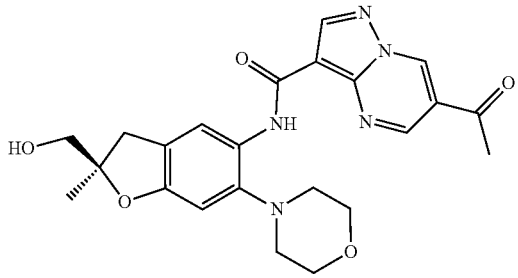

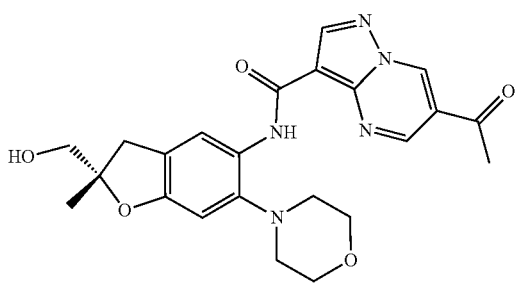

A mixture of tributyl(1-ethoxyvinyl)stannane (98 mg, 0.27 mmol), 6-bromo-N-[2-(hydroxymethyl)-2-methyl-6-morpholino-3H-benzofuran-5-yl]pyrazolo[1,5-a]pyrimidine-3-carboxamide (66 mg, 0.14 mmol) and tetrakis(triphenylphosphine)palladium (16 mg, 0.01 mmol) in toluene (15 mL) was stirred at 100° C. under nitrogen atmosphere for 18h. After cooling down to room temperature, the mixture was added hydrochloride solution (6 mL, 4 m in dioxane). The mixture was stirred at room temperature for 1 hs. After concentration under reduced pressure, the residue was purified by preparative HPLC (Gilson 281, Xbridge 21.2*250 mm c18, 10 um, A: acetonitrile, 25-55%; B:10 mM ammonium bicarbonate in water) to afford 6-acetyl-N-[(2R)-2-(hydroxymethyl)-2-methyl-6-morpholino-3H-benzofuran-5-yl]pyrazolo[1,5-a]pyrimidine-3-carboxamide (40 mg, 65%) as a yellow solid. The product was resolved by chiral pre-SFC(Column: OJ 30*250 mm, Sum (Dacel), Mobile phase: CO$_2$/methanol {0.2% Ammonia (7 m methanol)}=75/25) to afford (R)-6-acetyl-N-(2-(hydroxymethyl)-2-methyl-6-morpholino-2,3-dihydrobenzofuran-5-yl)pyrazolo[1,5-a]pyrimidine-3-carboxamide and (S)-6-acetyl-N-(2-(hydroxymethyl)-2-methyl-6-morpholino-2,3-dihydrobenzofuran-5-yl)pyrazolo[1,5-a]pyrimidine-3-carboxamide (5.3 mg, 0.08%) (2.8 mg, 0.04%) as a yellow solid.

Example 85, Peak 1: $^1$H NMR (400 MHz, CDCl$_3$) δ 10.41 (s, 1H), 9.35 (d, J=2.0 Hz, 1H), 9.24 (d, J=2.0 Hz, 1H), 8.90 (s, 1H), 8.42 (s, 1H), 6.68 (s, 1H), 3.94-3.97 (m, 4H), 3.66 (s, 2H), 3.25 (d, J=16.4 Hz, 1H), 2.94 (d, J=16.4 Hz, 1H), 2.90-2.92 (m, 4H), 1.98-2.02 (m, 1H), 1.88-1.92 (m, 1H), 1.46 (s, 3H). MS (ESI): m/z=452.1[M+1]$^+$.

Example 86, Peak 2: $^1$H NMR (400 MHz, CDCl$_3$) δ 10.41 (s, 1H), 9.35 (d, J=2.0 Hz, 1H), 9.24 (d, J=2.0 Hz, 1H), 8.90 (s, 1H), 8.42 (s, 1H), 6.68 (s, 1H), 3.94-3.97 (m, 4H), 3.66 (s, 2H), 3.25 (d, J=16.4 Hz, 1H), 2.94 (d, J=16.4 Hz, 1H), 2.90-2.92 (m, 4H), 1.98-2.02 (m, 1H), 1.88-1.92 (m, 1H), 1.46 (s, 3H). MS (ESI): m/z=452.1[M+1]$^+$.

Examples 87 and 88. N-[(2R)-6-[4-(2-Hydroxyethyl)piperazin-yl]-2-(hydroxymethyl)-2-methyl-3H-benzofuran-5-yl]pyrazolo[1,5-a]pyrimidine-3-carboxamide and N-[(2S)-6-[4-(2-Hydroxyethyl)piperazin-1-yl]-2-(hydroxymethyl)-2-methyl-3H-benzofuran-5-yl]pyrazolo[1,5-a]pyrimidine-3-carboxamide

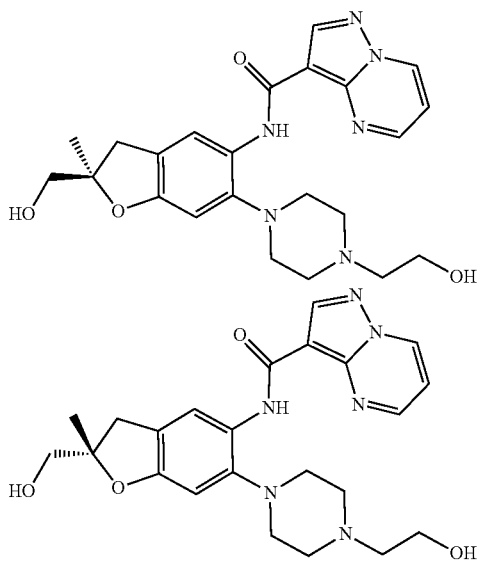

Step A. 2-[4-[2-(Hydroxymethyl)-2-methyl-5-nitro-3H-benzofuran-6-yl]piperazin-1-yl]ethanol

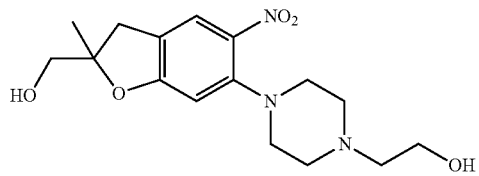 [SMILES: CC1(CO)Cc2cc(N)c(N3CCN(CCO)CC3)cc2O1]

A mixture of (6-chloro-2-methyl-5-nitro-3H-benzofuran-2-yl)methanol (Intermediate 2) (150 mg, 0.62 mmol) and 1-piperazineethanol (320 mg, 2.46 mmol) in DMSO (2 mL) was stirred at 90° C. for 3h. The mixture was purified by silica gel chromatography using methanol: DCM (1:10) as eluting solvents to afford 2-[4-[2-(Hydroxymethyl)-2-methyl-5-nitro-3H-benzofuran-6-yl]piperazin-1-yl]ethanol (110 mg, 49%) as a yellow oil. MS (ESI): m/z=338.2 [M+1]$^+$.

Step B. 2-[4-[5-Amino-2-(hydroxymethyl)-2-methyl-3H-benzofuran-6-yl]piperazin-1-yl]ethanol

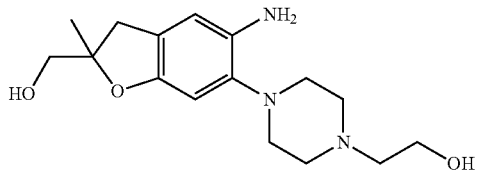

A mixture of 2-[4-[2-(hydroxymethyl)-2-methyl-5-nitro-3H-benzofuran-6-yl]piperazin-1-yl]ethanol (110.0 mg, 0.33 mmol) and 10% palladium on carbon (11 mg) in methanol (10 mL) was stirred at room temperature under hydrogen atmosphere for 1h. The solid was filtered off and the filtrate was concentrated under reduced pressure to afford 2-[4-[5-amino-2-(hydroxymethyl)-2-methyl-3H-benzofuran-6-yl]piperazin-1-yl]ethanol (102 mg) as a yellow oil, which was used directly to next step without further purification. MS (ESI): m/z=308.2 [M+1]⁺.

Step C. N-[(2R)-6-[4-(2-Hydroxyethyl)piperazin-1-yl]-2-(hydroxymethyl)-2-methyl-3H-benzofuran-5-yl]pyrazolo[1,5-a]pyrimidine-3-carboxamide and N-[(2S)-6-[4-(2-Hydroxyethyl)piperazin-1-yl]-2-(hydroxymethyl)-2-methyl-3H-benzofuran-5-yl]pyrazolo[1,5-a]pyrimidine-3-carboxamide

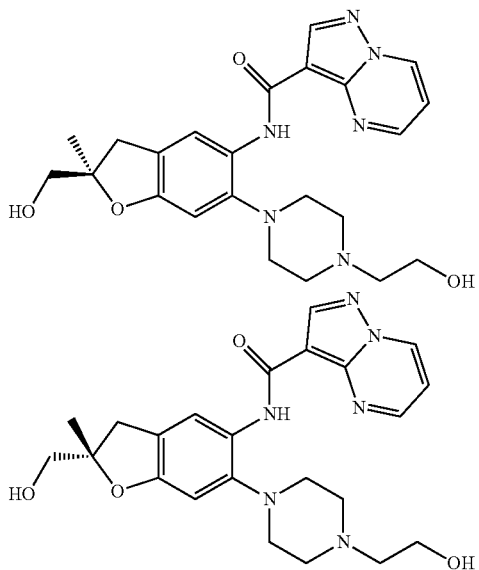

A solution of pyrazolo[1,5-a]pyrimidine-3-carboxylic acid (110 mg, 0.67 mmol), 2-(7-aza-1H-benzotriazole-1-yl)-1,1,3,3-tetramethyluronium hexafluorophosphate (320 mg, 0.84 mmol) and diisopropylethylamine (0.22 mL, 1.34 mmol) was stirred in DMF (3 mL) at room temperature for 10 min. To this mixture was added 2-[4-[5-amino-2-(hydroxymethyl)-2-methyl-3H-benzofuran-6-yl]piperazin-1-yl]ethanol (102 mg, 0.33 mmol) in DMF (2 mL) and the mixture was stirred for an additional 16h. The crude reaction was purified by preparative HPLC (Xbridge 21.2*250 mm c18, 10 um, A: acetonitrile 25-70%; B:10 mM ammonium bicarbonate in water) and then the product was resolved by chiral separation (SFC (OD-H 20*250 mm, Sum, CO₂/methanol (0.2% Ammonia (7 m methanol))=75/25, 35° C.) to afford N-[(2R)-6-[4-(2-hydroxyethyl)piperazin-1-yl]-2-(hydroxymethyl)-2-methyl-3H-benzofuran-5-yl]pyrazolo[1,5-a]pyrimidine-3-carboxamide and N-[(2S)-6-[4-(2-hydroxyethyl)piperazin-1-yl]-2-(hydroxymethyl)-2-methyl-3H-benzofuran-5-yl]pyrazolo[1,5-a]pyrimidine-3-carboxamide (10.1 mg each, 7% each) as a yellow solids with absolute stereochemistry assigned arbitrarily.

Example 87, Peak 1: ¹H NMR (400 MHz, CDCl₃) δ 10.40 (s, 1H), 8.83 (dd, J=1.6, 7.2 Hz, 1H), 8.79 (s, 1H), 8.72 (dd, J=1.6, 4.0 Hz, 1H), 8.42 (s, 1H), 7.06 (dd, J=4.0, 7.2 Hz, 1H), 6.67 (s, 1H), 3.73-3.62 (m, 4H), 3.25 (d, J=15.8 Hz, 1H), 2.99-2.89 (m, 5H), 2.71-2.83 (m, 4H), 2.68-2.61 (m, 2H), 1.46 (s, 3H). MS (ESI): m/z=453.3 [M+1]⁺.

Example 88, Peak 2: ¹H NMR (400 MHz, CDCl₃) δ 10.40 (s, 1H), 8.83 (dd, J=1.6, 7.2 Hz, 1H), 8.79 (s, 1H), 8.72 (dd, J=1.6, 4.0 Hz, 1H), 8.42 (s, 1H), 7.05 (dd, J=4.0, 7.2 Hz, 1H), 6.67 (s, 1H), 3.71-3.64 (m, 4H), 3.25 (d, J=15.7 Hz, 1H), 2.98-2.90 (m, 5H), 2.71-2.83 (m, 4H), 2.68-2.61 (m, 2H), 1.46 (s, 3H). MS (ESI): m/z=453.3 [M+1]⁺.

Example 89. N-[6-[1-(2,2-Difluoroethyl)-4-piperidyl]-2,2-dimethyl-3H-benzofuran-5-yl]pyrazolo[1,5-a]pyrimidine-3-carboxamide

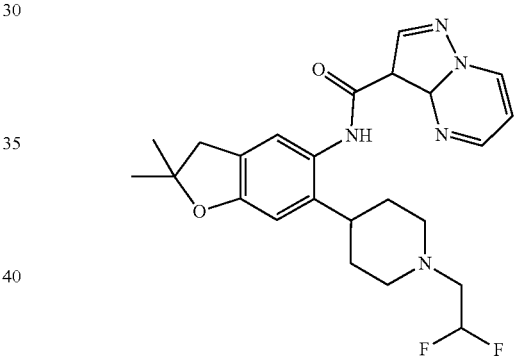

Step A. tert-Butyl 4-(2,2-dimethyl-5-nitro-3H-benzofuran-6-yl)-3,6-dihydro-2H-pyridine-1-carboxylate

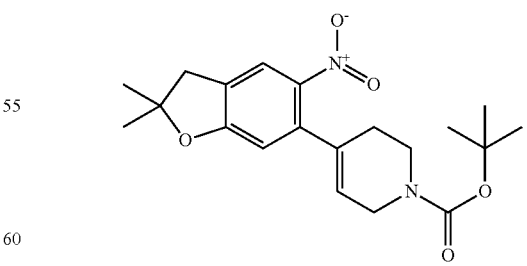

The mixture of tert-butyl 4-(2,2-dimethyl-5-nitro-2,3-dihydrobenzofuran-6-yl)-5,6-dihydropyridine-1(2H)-carboxylate, 6-bromo-2,2-dimethyl-5-nitro-3H-benzofuran (Intermediate 4) (1.0 g, 3.68 mmol), [1,1'-bis(diphenylphosphino)ferrocene] dichloropalladium (II) (135 mg, 0.18 mmol) and cesium carbonate (2.4 g, 7.37 mmol) in 1,4-dioxane (10 mL) and water (1 mL) in sealed tube was stirred at 90° C. under microwave condition for 2h. The mixture was poured into water (30 mL) and extracted with ethyl acetate (100 mL). The organic phases were washed with water and brine and dried over sodium sulfate before concentration to dryness. The residue was purified by preparative TLC using ethyl acetate:petroleum ether (1:4) as eluting solvents to afford tert-butyl 4-(2,2-dimethyl-5-nitro-3H-benzofuran-6-yl)-3,6-dihydro-2H-pyridine-1-carboxylate (1.28 g, 93%) as a yellow solid. MS (ESI): m/z=397.1 [M+Na]$^+$.

Step B. tert-Butyl 4-(5-amino-2,2-dimethyl-3H-benzofuran-6-yl)piperidine-1-carboxylate

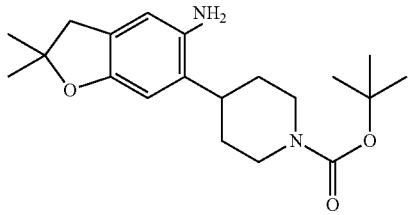 [SMILES: CC(C)(C)OC(=O)N1CCC(c2cc3c(cc2N)CC(C)(C)O3)CC1]

A mixture of tert-butyl 4-(2,2-dimethyl-5-nitro-3H-benzofuran-6-yl)-3,6-dihydro-2H-pyridine-1-carboxylate (50 mg, 0.13 mmol) and 10% palladium on carbon (8 mg) in methanol (10 mL) was stirred at room temperature under a hydrogen atmosphere for 1h. The solid was filtered off and the filtrate was concentrated under reduced pressure to afford tert-butyl 4-(5-amino-2,2-dimethyl-3H-benzofuran-6-yl)piperidine-1-carboxylate (960 mg) as a brown oil, which was used directly to next step without further purification.

Step C. tert-Butyl4-[2,2-dimethyl-5-(pyrazolo[1,5-a]pyrimidine-3-carbonylamino)-3H-benzofuran-6-yl]piperidine-1-carboxylate

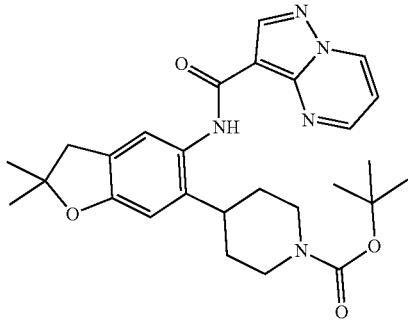 [SMILES: CC(C)(C)OC(=O)N1CCC(c2cc3c(cc2NC(=O)c2cnn4cccnc24)CC(C)(C)O3)CC1]

A solution of pyrazolo[1,5-a]pyrimidine-3-carboxylic acid (860 mg, 5.27 mmol), 2-(7-aza-1H-benzotriazole-1-yl)-1,1,3,3-tetramethyluronium hexafluorophosphate (2.0 g, 5.26 mmol) and diisopropylethylamine (2 mL, 8.13 mmol) was stirred in DMF (10 mL) at room temperature for 10 min. To this mixture [5-tert-butyl 4-(5-amino-2,2-dimethyl-3H-benzofuran-6-yl)piperidine-1-carboxylate (910 mg, 2.63 mmol) in DMF (4 mL) was added and stirred for additional 16h. The mixture was poured into water (50 mL) and extracted with ethyl acetate (100 mL). The organics washed with water, brine and dried over sodium sulfate before concentration to dryness. The residue was purified by silica gel chromatography using ethyl acetate:petroleum ether (1:1) as eluting solvents to afford tert-butyl 4-[2,2-dimethyl-5-(pyrazolo[1,5-a]pyrimidine-3-carbonylamino)-3H-benzofuran-6-yl]piperidine-1-carboxylate (1.2 g, 84%) as a yellow solid. MS (ESI): m/z=492.2[M+1]$^+$.

Step D. N-[2,2-Dimethyl-6-(4-piperidyl)-3H-benzofuran-5-yl]pyrazolo[1,5-a]pyrimidine-3-carboxamide

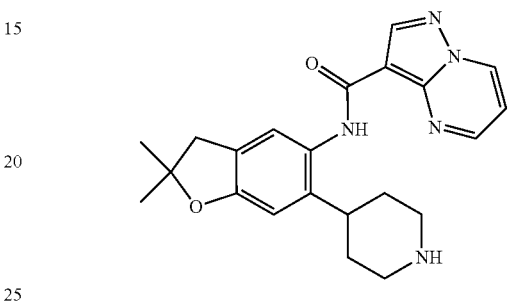

To a solution of tert-butyl 4-[2,2-dimethyl-5-(pyrazolo[1,5-a]pyrimidine-3-carbonylamino)-3H-benzofuran-6-yl]piperidine-carboxylate (1.2 g, 2.20 mmol) in DCM (5 mL) was added trifluoroacetic acid (2.9 mL, 39.5 mmol) and the mixture was stirred at 25° C. for 2h. The mixture was neutralized by triethylamine. After concentration, it was afforded N-[2,2-dimethyl-6-(4-piperidyl)-3H-benzofuran-5-yl]pyrazolo[1,5-a]pyrimidine-3-carboxamide (950 mg) as a yellow solid, which was used directly to next step without further purification. MS (ESI): m/z=392.2[M+1]$^+$.

Step E. N-[6-[1-(2,2-Difluoroethyl)-4-piperidyl]-2,2-dimethyl-3H-benzofuran-5-yl]pyrazolo[1,5-a]pyrimidine-3-carboxamide

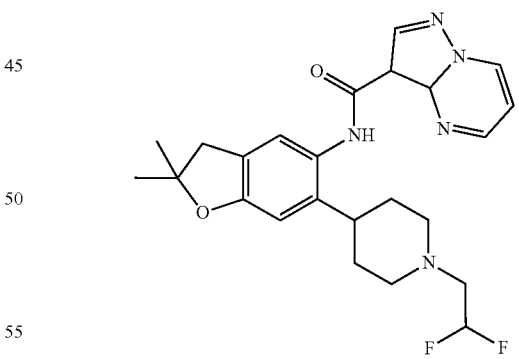

A mixture of N-[2,2-dimethyl-6-(4-piperidyl)-3H-benzofuran-5-yl]pyrazolo[1,5-a]pyrimidine-3-carboxamide (160 mg, 0.41 mmol), 2,2-difluoroethyl trifluoromethanesulfonate (262 mg, 1.22 mmol) and cesium carbonate (400 mg, 1.23 mmol) was stirred in DMF (10 mL) at 25° C. for 15h. The mixture was purified by preparative HPLC(X-bridge 19*250 mm c18, 10 um; A: acetonitrile 30-60%; B: 10 mM ammonium bicarbonate in water) to afford N-[6-[1-(2,2-difluoroethyl)-4-piperidyl]-2,2-dimethyl-3H-benzofuran-5-yl]pyrazolo[1,5-a]pyrimidine-3-carboxamide (25 mg, 14%) as a yellow solid. ¹H NMR (400 MHz, DMSO-d₆) δ 9.60 (s, 1H), 9.39 (dd, J=1.6, 6.8 Hz, 1H), 8.89 (dd, J=1.6, 4.0 Hz 1H), 8.68 (s, 1H), 7.74 (s, 1H), 7.34 (dd, J=4.0, 6.8 Hz, 1H), 6.66 (s, 1H), 6.15 (tt, J=3.6, 56.0 Hz, 1H), 3.12-2.90 (m, 4H), 2.75 (m, 3H), 2.36-2.20 (m, 2H), 1.71 (m, 5H), 1.42 (s, 6H). MS (ESI): m/z=457.3 [M+1].

Example 90. N-[2,2-Dimethyl-6-[1-(2,2,2-trifluoroethyl)-4-piperidyl]-3H-benzofuran-5-yl]pyrazolo[1,5-a]pyrimidine-3-carboxamide

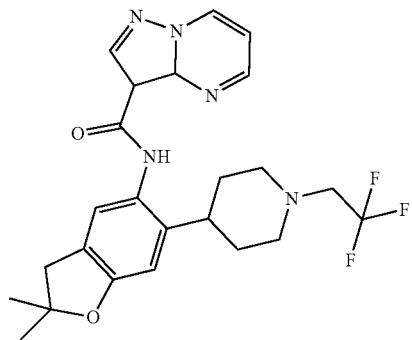 [SMILES: CC1(C)Cc2cc(NC(=O)C3C=NN4C=CC=NC34)c(C3CCN(CC(F)(F)F)CC3)cc2O1]

A mixture of N-[2,2-dimethyl-6-(4-piperidyl)-3H-benzofuran-5-yl]pyrazolo[1,5-a]pyrimidine-3-carboxamide (184 mg, 0.47 mmol), 2,2,2-trifluoroethyl trifluoromethanesulfonate (300 mg, 2.75 mmol) and potassium carbonate (260 mg, 4.0 mmol) was stirred in DMF (10 mL) at 25° C. for 15h. The mixture was purified by preparative HPLC (Xbridge 21.2*250 mm c18, 10 um, A: acetonitrile 25-55%; B: 10 mM ammonium bicarbonate in water) to afford N-[2,2-dimethyl-6-[1-(2,2,2-trifluoroethyl)-4-piperidyl]-3H-benzofuran-5-yl]pyrazolo[1,5-a]pyrimidine-3-carboxamide (42 mg, 19%) as a yellow solid. ¹H NMR (400 MHz, DMSO-d₆) δ 9.60 (s, 1H), 9.39 (dd, J=1.6, 7.0 Hz, 1H), 8.88 (dd, J=1.6, 4.0 Hz, 1H), 8.69 (s, 1H), 7.74 (s, 1H), 7.35 (dd, J=4.0, 7.0 Hz, 1H), 6.67 (s, 1H), 3.19 (q, J=10.3 Hz, 2H), 3.06-2.99 (m, 4H), 2.86-2.78 (m, 1H), 2.50-2.39 (m, 2H), 1.77-1.65 (m, 4H), 1.42 (s, 6H). MS (ESI): m/z=475.3 [M+1].

Example 91. 6-(Difluoromethyl)-N-(2,2-dimethyl-6-morpholino-3H-benzofuran-5-yl)pyrazolo[1,5-a]pyrimidine-3-carboxamide

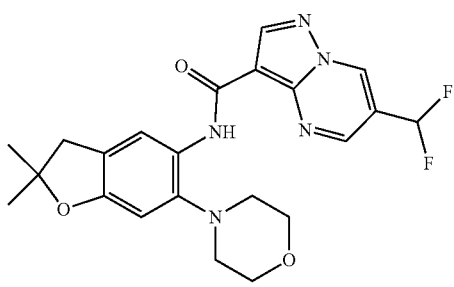 [SMILES: CC1(C)Cc2cc(NC(=O)c3cnn4cc(C(F)F)cnc34)c(N3CCOCC3)cc2O1]

Step A. N-(2,2-Dimethyl-6-morpholino-3H-benzofuran-5-yl)-6-formyl-pyrazolo[1,5-a]pyrimidine-3-carboxamide

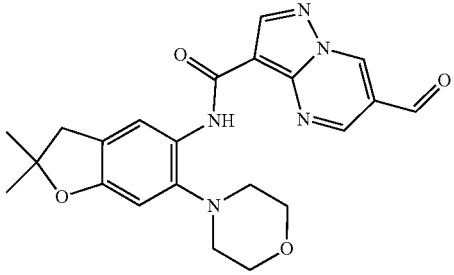 [SMILES: CC1(C)Cc2cc(NC(=O)c3cnn4cc(C=O)cnc34)c(N3CCOCC3)cc2O1]

A solution of 6-formylpyrazolo[1,5-a]pyrimidine-3-carboxylic acid (Example 75, step A) (191 mg, 1.0 mmol), 2-(7-aza-1H-benzotriazole-1-yl)-1,1,3,3-tetramethyluronium hexafluorophosphate (750 mg, 1.97 mmol) and diisopropylethylamine (0.5 mL, 3.0 mmol) was stirred in DMF (2 mL) at room temperature for 10 min. To this mixture was added 2,2-dimethyl-6-morpholino-3H-benzofuran-5-amine (245 mg, 0.98 mmol) in DMF (1 mL) and the reaction was stirred for additional 16h. The mixture was poured into water (20 mL) and extracted with ethyl acetate (50 mL). The organic phase was washed with water, brine and dried over sodium sulfate before concentration to dryness. The residue was purified by silica gel chromatography using ethyl acetate:petroleum ether (1:10) as eluting solvents to afford N-(2,2-dimethyl-6-morpholino-3H-benzofuran-5-yl)-6-formyl-pyrazolo[1,5-a]pyrimidine-3-carboxamide (283 mg, 61%) as a yellow solid. MS (ESI): m/z=422.2[M+1]⁺.

Step B. 6-(Difluoromethyl)-N-(2,2-dimethyl-6-morpholino-3H-benzofuran-5-yl)pyrazolo[1,5-a]pyrimidine-3-carboxamide

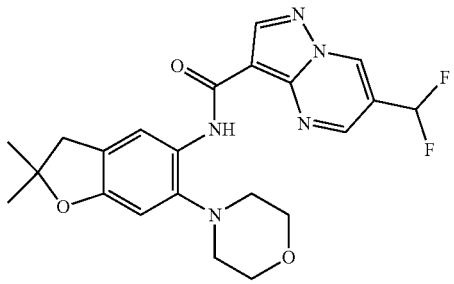 [SMILES: CC1(C)Cc2cc(NC(=O)c3cnn4cc(C(F)F)cnc34)c(N3CCOCC3)cc2O1]

To a solution of N-(2,2-dimethyl-6-morpholino-3H-benzofuran-5-yl)-6-formyl-pyrazolo[1,5-a]pyrimidine-3-carboxamide (120 mg, 0.28 mmol) in DCM (8 mL), diethylaminosulfurtrifluoride (0.17 mL, 1.28 mmol) was added at 0° C. The mixture was stirred at 25° C. for 8h. The mixture was purified by preparative HPLC (Xbridge 21.2*250 mm c18, 10 um acetonitrile 30-70% (10 mM ammonium bicarbonate) in water) to afford 6-(difluoromethyl)-N-(2,2-dimethyl-6-morpholino-3H-benzofuran-5-yl)pyrazolo[1,5-a]pyrimidine-3-carboxamide (10.1 mg, 7.4%) as a brown solid. ¹H NMR (400 MHz, DMSO-d₆) δ 10.36 (s, 1H), 9.75 (d, J=1.6 Hz, 1H), 9.12 (d, J=1.6 Hz, 1H), 8.80 (s, 1H), 8.30

(s, 1H), 7.32 (t, J=54.6 Hz, 2H), 6.73 (s, 1H), 3.90-3.78 (m, 4H), 3.01 (s, 2H), 2.87-2.73 (m, 4H), 1.42 (s, 6H). MS (ESI): m/z=444.2 [M+1].

Examples 92 and 93. (S)—N-(2-(hydroxymethyl)-6-(4-(hydroxymethyl)piperidin-1-yl)-2-methyl-2,3-dihydrobenzofuran-5-yl)-6-methylpyrazolo[1,5-a]pyrimidine-3-carboxamide and (R)—N-(2-(hydroxymethyl)-6-(4-(hydroxymethyl)piperidin-1-yl)-2-methyl-2,3-dihydrobenzofuran-5-yl)-6-methylpyrazolo[1,5-a]pyrimidine-3-carboxamide

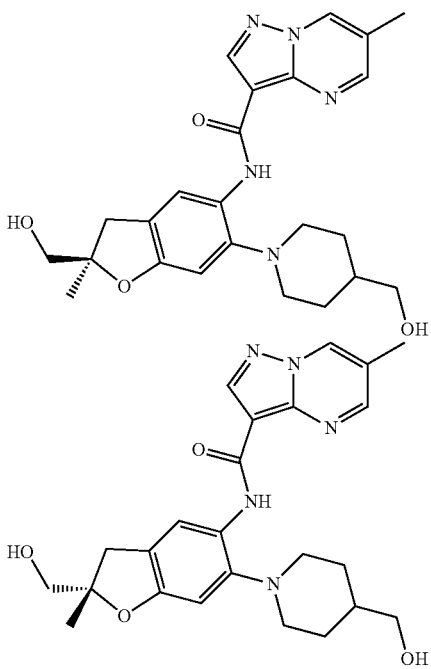

Example 16 was chirally resolved using chiral SFC to provide (S)—N-(2-(hydroxymethyl)-6-(4-(hydroxymethyl)piperidin-1-yl)-2-methyl-2,3-dihydrobenzofuran-5-yl)-6-methylpyrazolo[1,5-a]pyrimidine-3-carboxamide and (R)—N-(2-(hydroxymethyl)-6-(4-(hydroxymethyl)piperidin-1-yl)-2-methyl-2,3-dihydrobenzofuran-5-yl)-6-methylpyrazolo[1,5-a]pyrimidine-3-carboxamide with absolute stereochemistry assigned arbitrarily.

Example 92, Peak 1: $^1$H NMR (400 MHz, DMSO-$d_6$) δ 10.45 (s, 1H), 9.21 (dd, J=2.1, 1.2 Hz, 1H), 8.83 (d, J=2.0 Hz, 1H), 8.58 (s, 1H), 8.33-8.27 (m, 1H), 6.66 (s, 1H), 5.02 (t, J=5.8 Hz, 1H), 4.58 (t, J=5.2 Hz, 1H), 3.49-3.33 (m, 4H), 3.18 (dd, J=15.7, 1.2 Hz, 1H), 2.92 (d, J=11.2 Hz, 2H), 2.86-2.77 (m, 1H), 2.62 (td, J=11.3, 3.1 Hz, 2H), 2.41 (d, J=1.1 Hz, 3H), 1.73-1.57 (m, 4H), 1.50 (dq, J=10.4, 5.3 Hz, 1H), 1.34 (s, 3H). MS (ESI): m/z=452.2 [M+1].

Example 93, Peak 2: $^1$H NMR (400 MHz, DMSO-$d_6$) δ 10.45 (s, 1H), 9.21 (dq, J=1.9, 0.9 Hz, 1H), 8.83 (d, J=2.0 Hz, 1H), 8.58 (s, 1H), 8.30 (d, J=0.9 Hz, 1H), 6.66 (s, 1H), 5.02 (t, J=5.8 Hz, 1H), 4.58 (t, J=5.2 Hz, 1H), 3.49-3.32 (m, 4H), 3.32-3.14 (m, 1H), 2.92 (d, J=11.2 Hz, 2H), 2.81 (dd, J=15.5, 1.2 Hz, 1H), 2.62 (td, J=11.4, 3.2 Hz, 2H), 2.41 (d, J=1.1 Hz, 3H), 1.66 (qd, J=11.8, 10.6, 4.2 Hz, 4H), 1.50 (dq, J=10.6, 5.3 Hz, 1H), 1.34 (s, 3H). MS (ESI): m/z=452.2 [M+1].

Examples 94 and 95. (S)—N-(6-(3-(hydroxymethyl)-3-methylpyrrolidin-1-yl)-2,2-dimethyl-2,3-dihydrobenzofuran-5-yl)pyrazolo[1,5-a]pyrimidine-3-carboxamide and (R)—N-(6-(3-(hydroxymethyl)-3-methylpyrrolidin-1-yl)-2,2-dimethyl-2,3-dihydrobenzofuran-5-yl)pyrazolo[1,5-a]pyrimidine-3-carboxamide

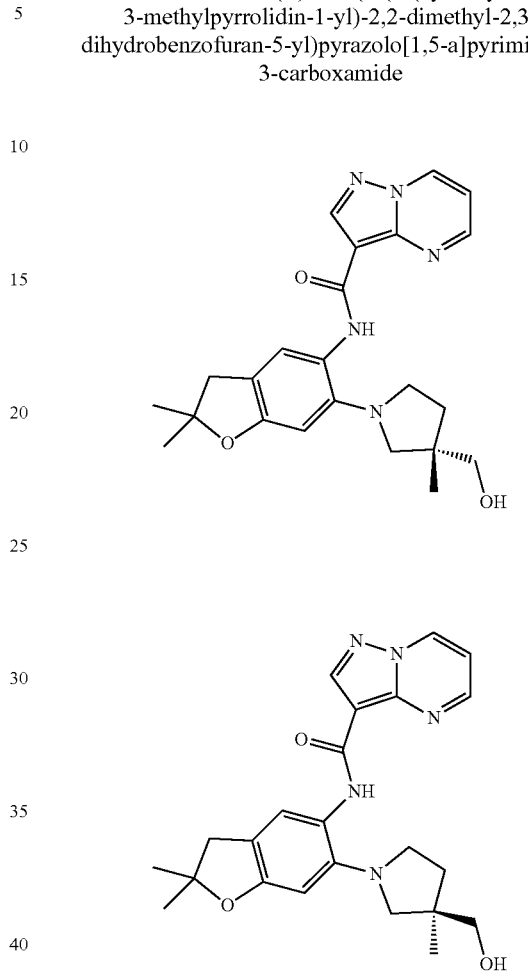

The enantiomers of Example 18 were resolved using chiral SFC to provide (S)—N-(6-(3-(hydroxymethyl)-3-methylpyrrolidin-1-yl)-2,2-dimethyl-2,3-dihydrobenzofuran-5-yl)pyrazolo[1,5-a]pyrimidine-3-carboxamide and (R)—N-(6-(3-(hydroxymethyl)-3-methylpyrrolidin-1-yl)-2,2-dimethyl-2,3-dihydrobenzofuran-5-yl)pyrazolo[1,5-a]pyrimidine-3-carboxamide with absolute stereochemistry assigned arbitrarily.

Example 94, Peak 1: $^1$H NMR (400 MHz, Chloroform-d) δ 9.84 (s, 1H), 9.37 (dd, J=7.0, 1.6 Hz, 1H), 8.87 (dd, J=4.2, 1.6 Hz, 1H), 8.69 (s, 1H), 8.03 (d, J=1.0 Hz, 1H), 7.34 (dd, J=7.0, 4.2 Hz, 1H), 6.54 (s, 1H), 4.70 (t, J=5.3 Hz, 1H), 3.38 (s, 6H), 3.15-3.05 (m, 1H), 3.04-2.95 (m, 5H), 2.74 (d, J=9.0 Hz, 1H), 1.84 (ddd, J=12.1, 8.0, 6.3 Hz, 1H), 1.54 (ddd, J=12.1, 8.0, 5.6 Hz, 1H), 1.42 (s, 7H), 1.14 (s, 3H). MS (ESI): m/z=422.2 [M+1].

Example 95, Peak 2: $^1$H NMR (400 MHz, DMSO-$d_6$) δ 9.83 (s, 1H), 9.36 (dd, J=7.0, 1.6 Hz, 1H), 8.86 (dd, J=4.2, 1.7 Hz, 1H), 8.68 (s, 1H), 8.02 (d, J=1.0 Hz, 1H), 7.33 (dd, J=7.0, 4.2 Hz, 1H), 6.53 (s, 1H), 4.69 (t, J=5.4 Hz, 1H), 3.47-3.32 (m, 2H), 3.14-2.94 (m, 5H), 2.73 (d, J=9.0 Hz, 1H), 1.83 (ddd, J=12.2, 7.9, 6.2 Hz, 1H), 1.53 (ddd, J=12.2, 8.0, 5.6 Hz, 1H), 1.41 (s, 6H), 1.13 (s, 3H). MS (ESI): m/z=422.2 [M+1].

Examples 96 and 97. (S)—N-(2-ethyl-2-methyl-6-morpholino-2,3-dihydrobenzofuran-5-yl)pyrazolo[1,5-a]pyrimidine-3-carboxamide and (R)—N-(2-ethyl-2-methyl-6-morpholino-2,3-dihydrobenzofuran-5-yl)pyrazolo[1,5-a]pyrimidine-3-carboxamide

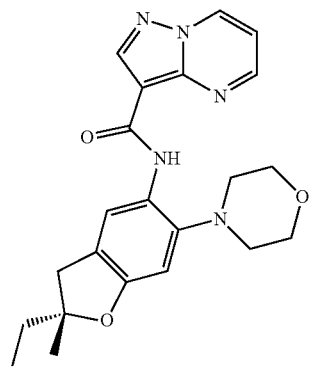

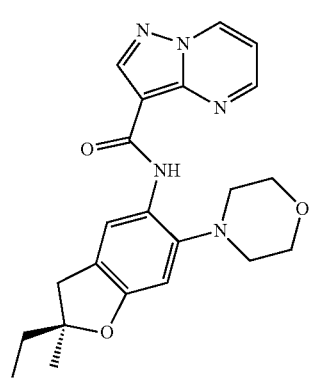

The enantiomers of Example 21 were resolved using chiral SFC to provide (S)—N-(2-ethyl-2-methyl-6-morpholino-2,3-dihydrobenzofuran-5-yl)pyrazolo[1,5-a]pyrimidine-3-carboxamide and (R)—N-(2-ethyl-2-methyl-6-morpholino-2,3-dihydrobenzofuran-5-yl)pyrazolo[1,5-a]pyrimidine-3-carboxamide with absolute stereochemistry assigned arbitrarily.

Example 96, Peak 1: $^1$H NMR (400 MHz, DMSO-d6) δ 10.43 (s, 1H), 9.37 (dd, J=7.0, 1.6 Hz, 1H), 8.94 (dd, J=4.2, 1.7 Hz, 1H), 8.68 (s, 1H), 8.30 (d, J=1.0 Hz, 1H), 7.34 (dd, J=7.0, 4.2 Hz, 1H), 6.72 (s, 1H), 3.88-3.80 (m, 4H), 3.13-3.01 (m, 1H), 2.96-2.86 (m, 1H), 2.86-2.77 (m, 4H), 1.71 (q, J=7.4 Hz, 2H), 1.35 (s, 3H), 0.92 (t, J=7.4 Hz, 3H). MS (ESI): m/z=408.2 [M+1].

Example 97, Peak 2: $^1$H NMR (400 MHz, DMSO-d6) δ 10.43 (s, 1H), 9.37 (dd, J=7.0, 1.6 Hz, 1H), 8.94 (dd, J=4.2, 1.6 Hz, 1H), 8.68 (s, 1H), 8.30 (d, J=1.0 Hz, 1H), 7.34 (dd, J=7.0, 4.2 Hz, 1H), 6.72 (s, 1H), 3.88-3.79 (m, 4H), 3.04 (d, J=1.2 Hz, 1H), 2.97-2.86 (m, 1H), 2.86-2.76 (m, 4H), 1.70 (t, J=7.4 Hz, 2H), 1.35 (s, 3H), 0.92 (t, J=7.4 Hz, 3H). MS (ESI): m/z=408.2 [M+1].

Examples 98 and 99. N-[(2R)-6-[4-(2,2-Difluoroethyl)piperazin-1-yl]-2-(hydroxymethyl)-2-methyl-3H-benzofuran-5-yl]pyrazolo[1,5-a]pyrimidine-3-carboxamide and N-[(2S)-6-[4-(2,2-difluoroethyl)piperazin-1-yl]-2-(hydroxymethyl)-2-methyl-3H-benzofuran-5-yl]pyrazolo[1,5-a]pyrimidine-3-carboxamide

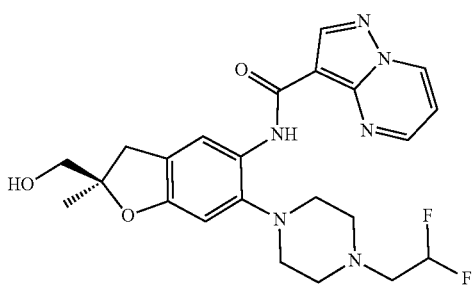

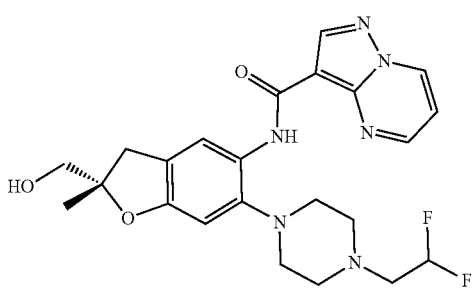

Step A. [6-[4-(2,2-Difluoroethyl)piperazin-1-yl]-2-methyl-5-nitro-3H-benzofuran-2-yl]methanol

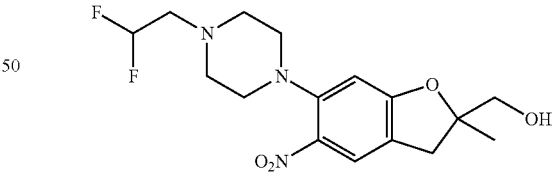

A mixture of (6-chloro-2-methyl-5-nitro-3H-benzofuran-2-yl)methanol (Intermediate 2) (440 mg, 1.81 mmol), 1-(2,2-difluoroethyl)piperazine hydrochloride (3000 mg, 16.1 mmol) and potassium carbonate (1480 mg, 10.72 mmol) in acetonitrile (15 mL) was stirred at 85° C. for 4d. After filtration and concentration under reduced pressure, the residue was purified by silica gel chromatography using ethyl acetate:petroleum ether (1:1) as eluting solvents to afford [6-[4-(2, 2-difluoroethyl)piperazin-1-yl]-2-methyl-5-nitro-3H-benzofuran-2-yl]methanol (486 mg, 75%) as yellow oil. MS (ESI): m/z=358.2 [M+1]$^+$.

521

Step B. [5-Amino-6-[4-(2, 2-difluoroethyl)piper-
azin-1-yl]-2-methyl-3H-benzofuran-2-yl]methanol

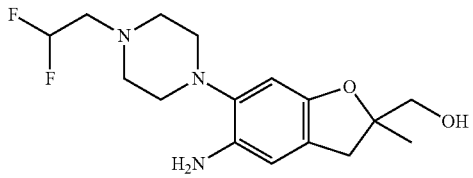 [SMILES: CC1(CO)Cc2cc(N)c(N3CCN(CC(F)F)CC3)cc2O1]

The mixture of [6-[4-(2, 2-difluoroethyl)piperazin-1-yl]-2-methyl-5-nitro-3H-benzofuran-2-yl]methanol (512 mg, 1.43 mmol) and palladium on carbon (150 mg) in methanol (20 mL) was stirred under hydrogen atmosphere at 25° C. for 1h. After filtration and concentration under reduced pressure, it was afforded [5-amino-6-[4-(2, 2-difluoroethyl)piperazin-1-yl]-2-methyl-3H-benzofuran-2-yl]methanol (430 mg, 92%) as a brown oil, which was used directly in the next step without further purification. MS (ESI): m/z=328.1 [M+1]$^+$.

Step C. N-[(2R)-6-[4-(2,2-difluoroethyl)piperazin-1-yl]-2-(hydroxymethyl)-2-methyl-3H-benzofuran-5-yl]pyrazolo[1,5-a]pyrimidine-3-carboxamide and N-[(2S)-6-[4-(2,2-difluoroethyl)piperazin-1-yl]-2-(hydroxymethyl)-2-methyl-3H-benzofuran-5-yl]pyrazolo[1,5-a]pyrimidine-3-carboxamide

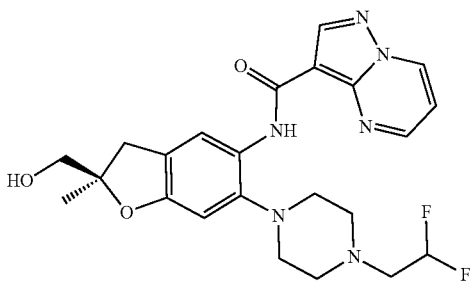

522

-continued

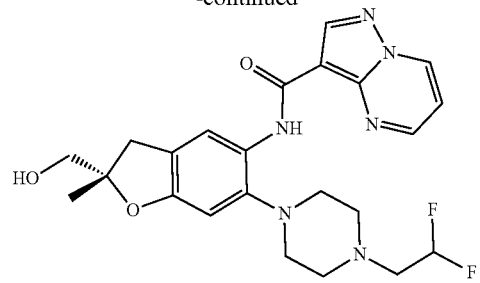

A mixture of pyrazolo[1,5-a]pyrimidine-3-carboxylic acid (344 mg, 2.11 mmol), N,N-diisopropylethylamine (0.66 mL, 3.99 mmol), 2-(7-aza-1H-benzotriazole-1-yl)-1,1,3,3-tetramethyluronium hexafluorophosphate (1016 mg, 2.67 mmol) and [5-amino-6-(difluoromethyl)-2-methyl-3H-benzofuran-2-yl]methanol (430 mg, 1.31 mmol) in DMF (15 mL) was stirred at 25° C. for 16h. The mixture was purified by preparative HPLC (Xbridge 21.2*250 mm c18, 10 um; A: acetonitrile 25-75%; B: 10 mM ammonium bicarbonate in water) and then the product was resolved by Chiral-HPLC [Gilson-281, IA 20*250 mm, 5 um (Dacel), hexane (0.1% n,n-diethylamine)/ethanol (0.1% n,n-diethylamine)=70/30] to afford N-[(2R)-6-[4-(2,2-difluoroethyl)piperazin-1-yl]-2-(hydroxymethyl)-2-methyl-3H-benzofuran-5-yl]pyrazolo[1,5-a]pyrimidine-3-carboxamide and N-[(2S)-6-[4-(2,2-difluoroethyl)piperazin-1-yl]-2-(hydroxymethyl)-2-methyl-3H-benzofuran-5-yl]pyrazolo[1,5-a]pyrimidine-3-carboxamide (121 mg, 20%) (118 mg, 19%) as yellow solids with absolute stereochemistry assigned arbitrarily.

Example 98, Peak 1: $^1$H NMR (400 MHz, DMSO-d$_6$) δ 10.41 (s, 1H), 9.37 (dd, J=1.6, 7.2 Hz, 1H), 8.95 (dd, J=1.6, 4.4 Hz, 1H), 8.68 (s, 1H), 8.31 (s, 1H), 7.35 (dd, J=4.4, 7.2 Hz, 1H), 6.70 (s, 1H), 6.20 (tt, J=4.0, 55.6 Hz, 1H), 5.04 (t, J=6.0 Hz, 1H), 3.48-3.38 (m, 2H), 3.19 (d, J=16 Hz, 1H), 2.93-2.71 (m, 11H), 1.34 (s, 3H). MS (ESI): m/z=473.2 [M+1]$^+$.

Example 99, Peak 2: $^1$H NMR (400 MHz, DMSO-d$_6$) δ 10.41 (s, 1H), 9.37 (dd, J=1.6, 7.2 Hz, 1H), 8.95 (dd, J=1.6, 4.4 Hz, 1H), 8.68 (s, 1H), 8.31 (s, 1H), 7.35 (dd, J=4.4, 7.2 Hz, 1H), 6.70 (s, 1H), 6.20 (tt, J=4.0, 55.6 Hz, 1H), 5.04 (t, J=6.0 Hz, 1H), 3.48-3.38 (m, 2H), 3.19 (d, J=16 Hz, 1H), 2.93-2.71 (m, 11H), 1.34 (s, 3H). MS (ESI): m/z=473.2 [M+1]$^+$.

TABLE 4

The following examples were made in a manner similar to that for Example 4:

| Ex. | Name | Structure | NMR, MS |
|---|---|---|---|
| 100 | N-[6-(6,8-dihydro-5H-imidazo[1,5-a]pyrazin-7-yl)-2,2-dimethyl-3H-benzofuran-5-yl]pyrazolo[1,5-a]pyridine-3-carboxamide | 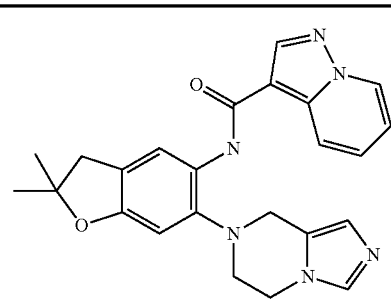 | 1H NMR (400 MHz, DMSO-d6) δ 10.75 (s, 1H), 9.27 (dd, J = 7.0, 1.6 Hz, 1H), 8.64 (s, 1H), 8.41 (d, J = 1.0 Hz, 1H), 7.71 (s, 1H), 7.61 (dd, J = 4.2, 1.7 Hz, 1H), 7.17 (dd, J = 7.0, 4.2 Hz, 1H), 6.83 (s, 1H), 6.63 (s, 1H), 4.27-4.19 (m, 2H), 4.03 (s, 2H), 3.40-3.23 (m, 2H), 3.13-3.00 (m, 2H), 1.43 (s, 6H). MS (ESI): m/z = 430.2 [M + 1]$^+$. |

TABLE 4-continued

*The following examples were made in a manner similar to that for Example 4:*

| Ex. | Name | Structure | NMR, MS |
|---|---|---|---|
| 101 | N-[2,2-dimethyl-6-(5,6,8,9-tetrahydroimidazo[1,5-d][1,4]diazepin-7-yl)-3H-benzofuran-5-yl]pyrazolo[1,5-a]pyrimidine-3-carboxamide | 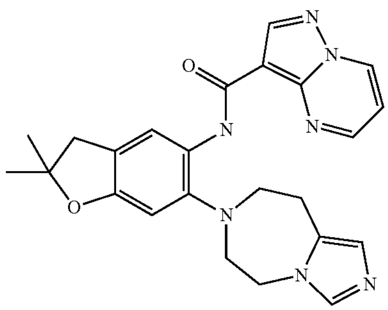 [SMILES: CC1(C)Cc2cc(NC(=O)c3cnn4cccnc34)c(N3CCc4cncn4CC3)cc2O1] | $^1$H NMR (400 MHz, DMSO-d6) δ 10.70 (s, 1H), 9.34 (dd, J = 7.0, 1.6 Hz, 1H), 8.73-8.64 (m, 2H), 8.35 (d, J = 1.0 Hz, 1H), 7.53 (d, J = 1.1 Hz, 1H), 7.26 (dd, J =7.0, 4.2 Hz, 1H), 6.75-6.66 (m, 2H), 4.33 (dd, J = 6.1, 2.5 Hz, 2H), 3.12-3.01 (m, 4H), 2.94 (dd, J = 6.8, 3.2 Hz, 2H), 1.40 (s, 6H). MS (ESI): m/z = 444.2 [M + 1]$^+$. |
| 102 | N-[6-[4-(hydroxymethyl)imidazol-1-yl]-2,2-dimethyl-3H-benzofuran-5-yl]pyrazolo[1,5-a]pyrimidine-3-carboxamide | 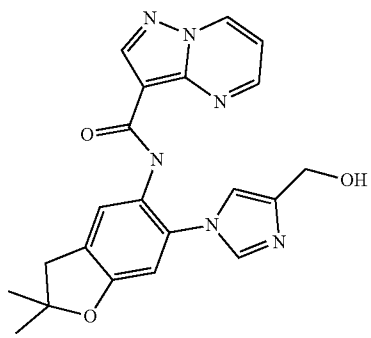 [SMILES: CC1(C)Cc2cc(NC(=O)c3cnn4cccnc34)c(-n3cnc(CO)c3)cc2O1] | $^1$H NMR (400 MHz, DMSO-d6) δ 9.73 (s, 1H), 9.30 (dd, OH J = 7.0, 1.6 Hz, 1H), 8.65-8.55 (m, 2H), 8.29 (t, J = 1.0 Hz, 1H), 7.76 (d, J = 1.4 Hz, 1H), 7.25 (dd, J = 7.0, 4.2 Hz, 1H), 7.18 (dt, J = 1.5, 0.8 Hz, 1H), 6.75 (s, 1H), 4.96 (t, J = 5.5 Hz, 1H), 4.43 (dd, J = 5.5, 0.9 Hz, 2H), 3.12 (d, J = 1.3 Hz, 2H), 1.46 (s, 6H). MS (ESI): m/z = 405.1 [M + 1]$^+$. |
| 103 | N-(6-imidazol-1-yl-2,2-dimethyl-3H-benzofuran-5-yl)pyrazolo[1,5-a]pyrimidine-3-carboxamide | 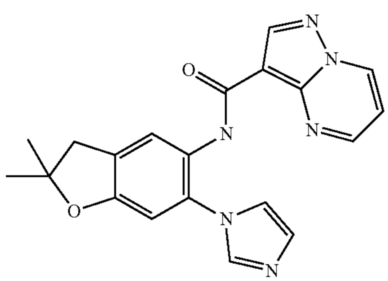 [SMILES: CC1(C)Cc2cc(NC(=O)c3cnn4cccnc34)c(-n3ccnc3)cc2O1] | $^1$H NMR (400 MHz, DMSO-d6) δ 9.64 (s, 1H), 9.30 (dd, J = 7.0, 1.7 Hz, 1H), 8.63 (s, 1H), 8.50 (dd, J = 4.2, 1.7 Hz, 1H), 8.22 (d, J = 1.1 Hz, 1H), 7.85 (t, J = 1.1 Hz, 1H), 7.37 (t, J = 1.3 Hz, 1H), 7.26 (dd, J = 7.0, 4.2 Hz, 1H), 7.14 (t, J = 1.1 Hz, 1H), 6.79 (s, 1H), 3.13 (d, J = 1.3 Hz, 2H), 1.47 (s, 6H). MS (ESI): m/z = 375.1 [M + 1]$^+$. |
| 104 | N-[2,2-dimethyl-6-(2-methylpyrrolidin-1-yl)-3H-benzofuran-5-yl]pyrazolo[1,5-a]pyrimidine-3-carboxamide | 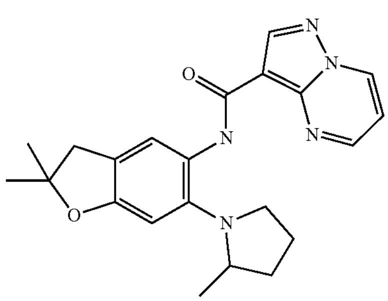 [SMILES: CC1CCCN1c1cc2c(cc1NC(=O)c1cnn3cccnc13)CC(C)(C)O2] | $^1$H NMR (400 MHz, DMSO-d6) δ 10.67 (s, 1H), 9.34 (dd, J = 7.0, 1.6 Hz, 1H), 8.83 (dd, J = 4.2, 1.6 Hz, 1H), 8.66 (s, 1H), 8.31 (d, J = 1.0 Hz, 1H), 7.29 (dd, J = 7.0, 4.1 Hz, 1H), 6.69 (s, 1H), 3.44-3.29 (m, 4H), 3.00 (s, 2H), 2.65 (q, J =8.3 Hz, 1H), 2.20-2.10 (m, 1H), 1.95 (d, J = 7.3 Hz, 2H), 1.86 (td, J = 8.2, 4.1 Hz, 1H), 1.71-1.56 (m, 1H), 1.41 (d, J = 4.7 Hz, 6H), 0.93 (d, J = 6.0 Hz, 3H. MS (ESI): m/z = 392.2 [M + 1]$^+$. |

TABLE 4-continued

The following examples were made in a manner similar to that for Example 4:

| Ex. | Name | Structure | NMR, MS |
|---|---|---|---|
| 105 | N-[6-(3-hydroxy-3-methyl-azetidin-1-yl)-2,2-dimethyl-3H-benzofuran-5-yl)pyrazolo[1,5-a]pyrimidine-3-carboxamide | 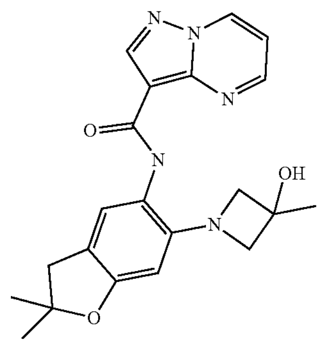 | $^1$H NMR (400 MHz, DMSO-d6) δ 9.37 (dd, J = 7.0, 1.6 Hz, 1H), 9.23 (s, 1H), 8.86 (dd, J = 4.2, 1.7 Hz, 1H), 8.67 (s, 1H), 7.51 (d, J = 0.9 Hz, 1H), 7.33 (dd, J = 7.0, 4.2 Hz, 1H), 6.13 (s, 1H), 5.31 (s, 1H), 3.77-3.70 (m, 2H), 3.55-3.49 (m, 2H), 3.41-3.26 (m, 4H), 2.93 (d, J = 1.3 Hz, 2H), 1.43 (d, J = 19.0 Hz, 10H). MS (ESI): m/z = 394.2 [M + 1]$^+$. |
| 106 | N-(2,2-dimethyl-6-(2-oxa-8-azaspiro[4.5]decan-8-yl)-2,3-dihydrobenzofuran-5-yl)pyrazolo[1,5-a]pyrimidine-3-carboxamide | 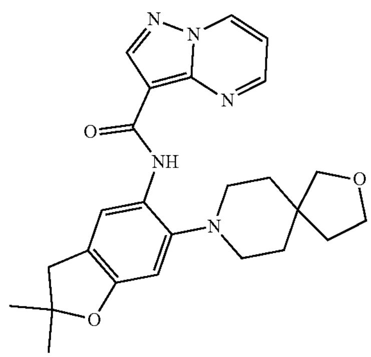 [SMILES: CC1(C)Cc2cc(NC(=O)c3cnn4cccnc34)c(N3CCC4(CCOC4)CC3)cc2O1] | $^1$H NMR (400 MHz, CDCl$_3$) δ 10.44 (s, 1H), 8.82 (dd, J = 1.6, 6.8 Hz, 1H), 8.79 (s, 1H), 8.63 (dd, J = 2.0, 4.4 Hz, 1H), 8.40 (s, 1H), 7.05 (dd, J = 4.0, 7.2 Hz, 1H), 6.63 (s, 1H), 3.90 (t, J = 7.2 Hz, 2H), 3.64 (s, 2H), 3.03 (s, 2H), 2.86-2.84 (m, 4H), 1.89-1.84 (m, 6H), 1.49 (s, 6H). MS (ESI): m/z = 448.3 [M + 1]$^+$. |
| 107 | N-(2,2-dimethyl-6-(2-oxa-6-azaspiro[3.4]octan-6-yl)-2,3-dihydrobenzofuran-5-yl)pyrazolo[1,5-a]pyrimidine-3-carboxamide | 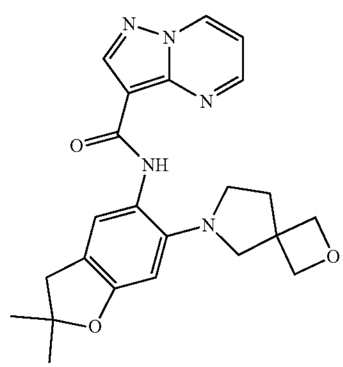 [SMILES: CC1(C)Cc2cc(NC(=O)c3cnn4cccnc34)c(N3CCC4(COC4)C3)cc2O1] | $^1$H NMR (400 MHz, CDCl$_3$) δ 9.77 (s, 1H), 8.81 (dd, J = 1.6, 7.2 Hz, 1H), 8.78 (s, 1H), 8.60 (d, J = 2.8 Hz, 1H), 8.08 (s, 1H), 7.02 (dd, J = 4.0, 6.8 Hz, 1H), 6.52 (s, 1H), 4.68 (s, 4H), 3.39 (s, 2H), 3.11 (t, J = 6.8 Hz, 2H), 3.02 (s, 2H), 2.24 (t, J = 6.8 Hz, 2H), 1.48 (s, 6H). MS (ESI): m/z = 420.2[M + 1]$^+$. |
| 108 | N-(2,2-dimethyl-6-(2-oxa-7-azaspiro[4.4]nonan-7-yl)-2,3-dihydrobenzofuran-5-yl)pyrazolo[1,5-a]pyrimidine-3-carboxamide | 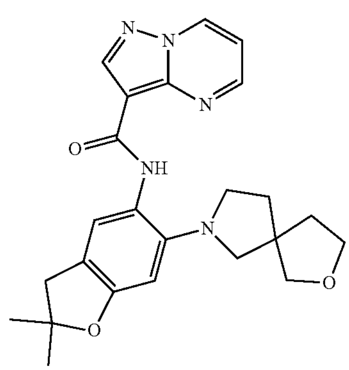 [SMILES: CC1(C)Cc2cc(NC(=O)c3cnn4cccnc34)c(N3CCC4(CCOC4)C3)cc2O1] | $^1$H NMR (400 MHz, DMSO-d6) δ 9.80 (s, 1H), 9.36 (d, J = 6.8 Hz, 1H), 8.83 (d, J = 4.0 Hz, 1H), 8.68 (s, 1H), 7.98 (s, 1H), 7.32 (dd, J = 4.0, 6.8 Hz, 1H), 6.56 (s, 1H), 3.82-3.64 (m, 3H), 3.59 (d, J = 8.4 Hz, 1H), 3.15-3.07 (m, 2H), 3.05 (s, 2H), 2.97 (s, 2H), 2.01-1.91 (m, 4H), 1.41 (s, 6H). MS (ESI): m/z = 434. [M + 1]$^+$. |

TABLE 4-continued

The following examples were made in a manner similar to that for Example 4:

| Ex. | Name | Structure | NMR, MS |
|---|---|---|---|
| 109 | N-(6-(1-hydroxy-8-azaspiro[4.5]decan-8-yl)-2,2-dimethyl-2,3-dihydrobenzofuran-5-yl)pyrazolo[1,5-a]pyrimidine-3-carboxamide | 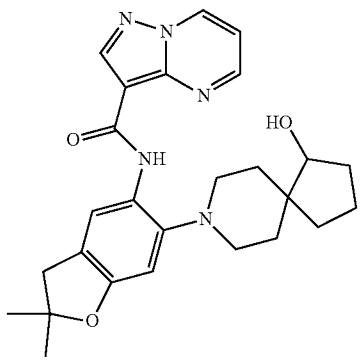 [SMILES: CC1(C)Cc2cc(NC(=O)c3cnn4cccnc34)c(N3CCC4(CCCC4O)CC3)cc2O1] | $^1$H NMR (400 MHz, DMSO-d6) δ 10.55 (s, 1H), 9.35 (dd, J = 1.6, 6.8 Hz, 1H), 9.03 (dd, J = 2.8, 4.4 Hz, 1H), 8.67 (s, 1H), 8.36 (s, 1H), 7.32 (dd, J = 4.4, 6.8 Hz, 1H), 6.70 (s, 1H), 4.63 (s, 1H), 3.67 (d, J = 5.2 Hz, 1H), 3.22 (d, J = 1.2 Hz, 2H), 2.99-2.68 (m, 4H), 2.04-1.99 (m, 1H), 1.89-1.83 (m, 2H), 1.73-1.64 (m, 2H), 1.52-1.46 (m, 2H), 1.41 (s, 7H), 1.30-1.27 (m, 1H). MS (ESI): m/z = 462.3 [M + 1]$^+$. |
| 110 | N-(6-(2-hydroxy-7-azaspiro[3.5]nonan-7-yl)-2,2-dimethyl-2,3-dihydrobenzofuran-5-yl)pyrazolo[1,5-a]pyrimidine-3-carboxamide | 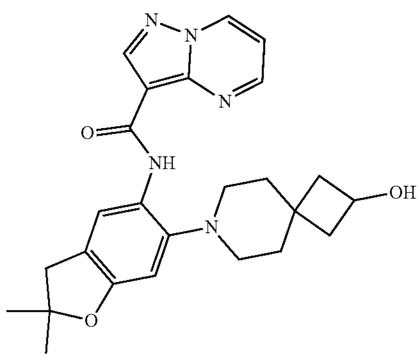 [SMILES: CC1(C)Cc2cc(NC(=O)c3cnn4cccnc34)c(N3CCC4(CC3)CC(O)C4)cc2O1] | $^1$H NMR (400 MHz, DMSO-d6): δ 10.46 (s, 1H), 9.36 (d, J = 6.8 Hz, 1H), 8.74 (d, J = 2.8 Hz, 1H), 8.67 (s, 1H), 8.30 (s, 1H), 7.35 (dd, J = 4.0, 6.8 Hz, 1H), 6.64 (s, 1H), 4.18-4.05 (m, 1H), 2.99 (s, 2H), 2.74-2.58 (m, 4H), 2.29-2.14 (m, 2H), 1.81-1.67 (m, 4H), 1.67-1.54 (m, 2H), 1.41(s, 6H). MS (ESI): m/z = 448.3 [M + 1]$^+$. |
| 111 | N-[2,2-dimethyl-6-(3-oxo-2,7-diazaspiro[3.5]nonan-7-yl)-3H-benzofuran-5-yl]pyrazolo[1,5-a]pyrimidine-3-carboxamide | 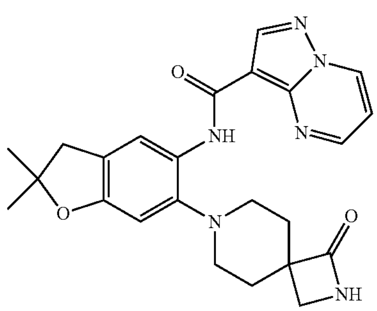 [SMILES: CC1(C)Cc2cc(NC(=O)c3cnn4cccnc34)c(N3CCC4(CC3)CNC4=O)cc2O1] | $^1$H NMR (400 MHz, CDCl$_3$) δ 10.68 (s, 1H), 9.15 (d, J = 2.4 Hz, 1H), 8.79 (dd, J = 1.6, 7.2 Hz, 1H), 8.77 (s, 1H), 8.54 (s, 1H), 7.11 (dd, J = 4.0, 7.2 Hz, 1H), 6.59 (s, 1H), 5.65 (s, 1H), 3.31 (s, 2H), 3.11-3.05 (m, 2H), 3.03 (s, 2H), 2.74-2.64 (m, 2H), 2.56-2.46 (m, 2H), 1.93-1.86 (m, 2H), 1.48(s, 6H). MS (ESI): m/z = 447.3 [M + 1]$^+$. |
| 112 | N-(6-(6,6-difluoro-3-azabicyclo[3.1.0]hexan-3-yl)-2,2-dimethyl-2,3-dihydrobenzofuran-5-yl)pyrazolo[1,5-a]pyrimidine-3-carboxamide | 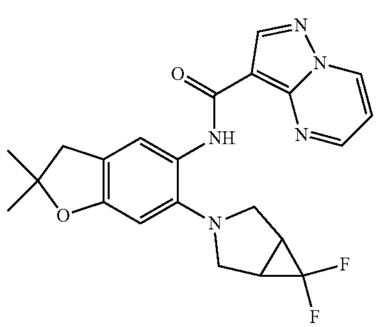 [SMILES: CC1(C)Cc2cc(NC(=O)c3cnn4cccnc34)c(N3CC4C(C3)C4(F)F)cc2O1] | $^1$H NMR (400 MHz, DMSO-d6): δ 9.70 (s, 1H), 9.36 (dd, J = 1.6, 7.2 Hz,1H), 8.82 (dd, J =1.6, 4.0 Hz, 1H), 8.67 (s, 1H), 7.85 (s, 1H), 7.32 (dd, J = 4, 6.8 Hz, 1H), 6.57 (s, 1H), 3.50-3.40 (m, 4H), 2.97 (s, 2H), 2.59-2.52 (m, 2H), 1.41(s, 6H). MS (ESI): m/z = 426.2 [M + 1]$^+$. |

TABLE 4-continued

The following examples were made in a manner similar to that for Example 4:

| Ex. | Name | Structure | NMR, MS |
|---|---|---|---|
| 113 | N-[2,2-Dimethyl-6-(6-oxo-1H-pyridin-3-yl)-3H-benzofuran-5-yl]pyrazolo[1,5-a]pyrimidine-3-carboxamide | 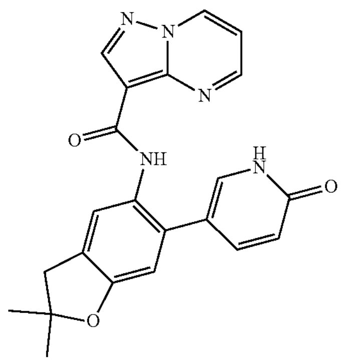 [SMILES: CC1(C)Cc2cc(NC(=O)c3cnn4cccnc34)c(-c3ccc(=O)[nH]c3)cc2O1] | $^1$H NMR (400 MHz, DMSO-d6) δ 9.65 (s, 1H), 9.34 (dd, J = 1.6, 7.0 Hz, 1H), 8.64 (s, 1H), 8.52 (dd, J = 1.6, 4.0 Hz, 1H), 8.13 (s, 1H), 7.47-7.40 (m, 2H), 7.32 (dd, J = 4.0, 7.0 Hz, 1H), 6.65 (s, 1H), 6.39 (d, J = 9.1 Hz, 1H), 3.07 (s, 2H), 1.44 (s, 6H). MS (ESI): m/z = 402.2 [M + 1] |
| 114 | N-(2,2-Dimethyl-6-(2-oxa-7-azaspiro[3.5]nonan-7-yl)-2,3-dihydrobenzofuran-5-yl)pyrazolo[1,5-a]pyrimidine-3-carboxamide | 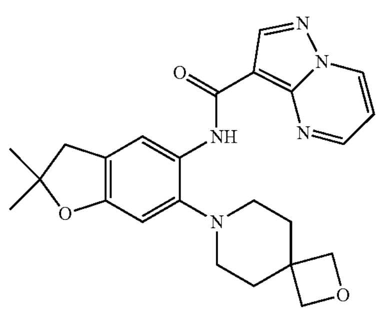 [SMILES: CC1(C)Cc2cc(NC(=O)c3cnn4cccnc34)c(N3CCC4(CC3)COC4)cc2O1] | $^1$H NMR (400 MHz, DMSO-d6): δ 10.44 (s, 1H), 9.35 (d, J = 6.8 Hz, 1H), 8.73 (d, J = 2.0 Hz, 1H), 8.67 (s, 1H), 8.31 (s, 1H), 7.32-7.30 (m, 1H), 6.63 (s, 1H), 4.51-4.29 (m, 4H), 3.08-2.91 (m, 2H), 2.81-2.57 (m, 4H), 2.14-1.89 (m, 4H), 1.40 (s, 6H). MS (ESI): m/z = 434.2 [M + 1]$^+$. |
| 115 | N-(6-(3-Fluoro-4-hydroxypiperidin-1-yl)-2,2-dimethyl-2,3-dihydrobenzofuran-5-yl)pyrazolo[1,5-a]pyrimidine-3-carboxamide | 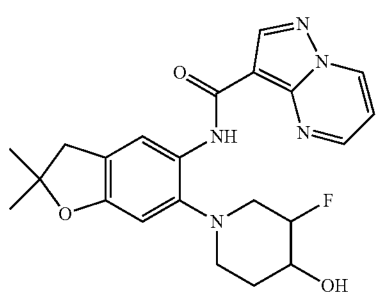 [SMILES: CC1(C)Cc2cc(NC(=O)c3cnn4cccnc34)c(N3CCC(O)C(F)C3)cc2O1] | $^1$H NMR (400 MHz, DMSO-d6): δ 10.39 (s, 1H), 9.36 (dd, J = 1.6, 7.2 Hz, 1H), 8.89 (dd, J = 1.6, 4.0 Hz, 1H), 8.67 (s, 1H), 8.31 (s, 1H), 7.32 (dd, J = 4.0, 7.2 Hz, 1H), 6.68 (s, 1H), 5.08-5.07 (d, J = 6.0 Hz, 1H), 4.86-4.72 (m, 1H), 3.95-3.90 (m, 1H), 3.17-3.11 (m, 1H), 3.03-2.89 (m, 4H), 2.58-2.51 (m, 1H), 2.02-2.00 (m, 1H), 1.99-1.78 (m, 1H), 1.41 (s, 1H). MS (ESI): m/z = 426.2 [M + 1]$^+$. |
| 116 | N-(6-(1,4-diazepan-1-yl)-2,2-dimethyl-2,3-dihydrobenzofuran-5-yl)pyrazolo[1,5-a]pyrimidine-3-carboxamide | 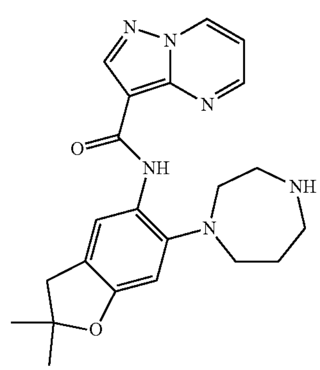 [SMILES: CC1(C)Cc2cc(NC(=O)c3cnn4cccnc34)c(N3CCCNCC3)cc2O1] | $^1$H NMR (400 MHz, DMSO-d$_6$) δ 10.37 (s, 1H), 9.38 (d, J = 6.6 Hz, 1H), 9.00 (d, J = 4.4 Hz, 1H), 8.68 (s, 1H), 8.38 (s, 1H), 8.27 (s, 1H), 7.35 (dd, J = 4.4, 6.6 Hz, 1H), 6.72 (s, 1H), 3.20-3.22 (m, 4H), 3.14-3.15 (m, 2H), 2.99-3.02 (m, 4H), 1.98-1.99 (m, 2H), 1.41 (s, 6H). MS (ESI): m/z = 407.3 [M + 1]$^+$. |

TABLE 4-continued

The following examples were made in a manner similar to that for Example 4:

| Ex. | Name | Structure | NMR, MS |
|---|---|---|---|
| 117 | N-(2,2-dimethyl-6-(1,4-oxazepan-4-yl)-2,3-dihydrobenzofuran-5-yl)pyrazolo[1,5-a]pyrimidine-3-carboxamide | 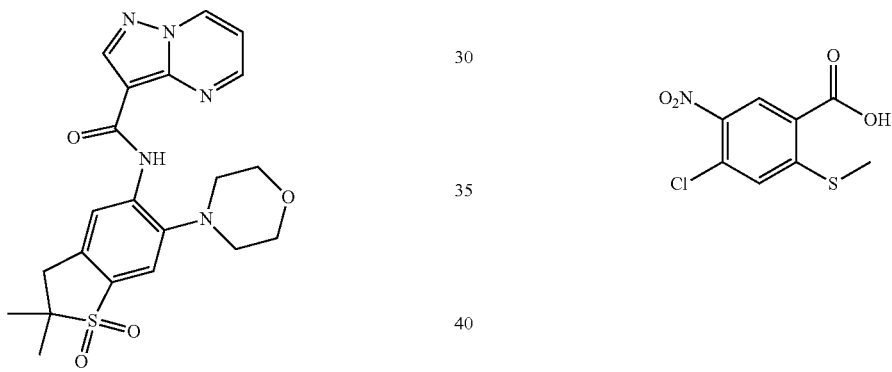 | $^1$H NMR (400 MHz, CDCl$_3$): δ 10.52 (s, 1H), 8.82 (dd, J= 6.8 Hz, 1H), 8.78 (s, 1H),8.75 (dd, J = 4.4 Hz, 1H), 8.37(s, 1H), 7.05 (dd, J = 4.4, 6.8 Hz, 1H), 6.65 (s, 1H), 3.99 (t, J= 7.0 Hz, 2H), 3.91-3.93 (m, 2H), 3.11-3.14 (m, 4H), 3.03 (s, 2H), 2.06-2.12 (m,2H), 1.45 (s, 6H). MS (ESI): m/z = 408.2 [M + 1]$^+$. |

Example 118. N-[2,2-Dimethyl-6-(morpholin-4-yl)-1,1-dioxo-2,3-dihydro-benzothiophen-5-yl]pyrazolo[1,5-a]pyrimidine-3-carboxamide Step A. Methyl 4-chloro-2-fluoro-5-nitro-benzoate

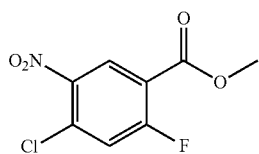

To a mixture of 4-chloro-2-fluoro-5-nitro-benzoic acid (5.06 g, 23.05 mmol) in methyl alcohol (15 mL) was added drop wise sulfurous dichloride (10 mL). The mixture was stirred at 90° C. for 16h. The mixture was concentrated to afford methyl 4-chloro-2-fluoro-5-nitro-benzoate (5.2 g, 92%) as a white solid, which was used directly to next step without further purification. MS (ESI): m/z=234.1[M+1]$^+$.

Step B. 4-Chloro-2-methylsulfanyl-5-nitro-benzoate

A mixture of methyl 4-chloro-2-fluoro-5-nitro-benzoate (800.0 mg, 3.43 mmol) in tetrahydrofuran (20 mL) was added sodium methanethiolate (20% wt in water, 1.2 g, 3.43 mmol). The mixture was stirred at 25° C. for 4h. Water and ethyl acetate (30 mL) was added. The organic layer was separated, dried over sodium sulfate and concentrated to afford methyl 4-chloro-2-methylsulfanyl-5-nitro-benzoate (800 mg) as a yellow solid, which was used directly to next step without further purification. MS (ESI): m/z=262.0[M+1]$^+$.

Step C. Methyl 2-methylsulfanyl-4-morpholino-5-nitro-benzoate

A mixture of methyl 4-chloro-2-methylsulfanyl-5-nitro-benzoate (600.0 mg, 2.29 mmol) in morpholine (3995.15 mg, 45.86 mmol) was stirred at 60° C. overnight. The mixture was concentrated and the residue was purified by silica gel chromatography using ethyl acetate:petroleum ether (1:4) as eluting solvents to afford methyl 2-methylsulfanyl-4-morpholino-5-nitro-benzoate (506 mg, 70%) as yellow solid. MS (ESI): m/z=313.0[M+1]$^+$.

Step D. Methyl 2-methylsulfonyl-4-morpholino-5-nitro-benzoate

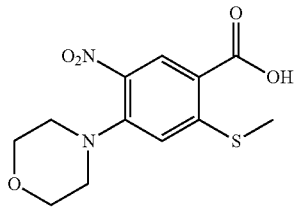 [SMILES: CSc1cc(N2CCOCC2)c([N+](=O)[O-])cc1C(=O)O]

To a mixture of methyl 2-methylsulfanyl-4-morpholino-5-nitro-benzoate (506.0 mg, 1.62 mmol) in methyl alcohol (10 mL) and water (10 mL) was added oxone (1082.16 mg, 6.48 mmol). The mixture was stirred at 50° C. for 5h. Ethyl acetate (30 mL) and water was added and the organic layer was separated, dried over sodium sulfate and concentrated to afford methyl 2-methylsulfonyl-4-morpholino-5-nitro-benzoate (478 mg) as a yellow solid, which was used directly to next step without further purification. MS (ESI): m/z=345.0 [M+1]$^+$.

Step E. 6-Morpholino-5-nitro-1,1-dioxo-benzothiophen-3-one

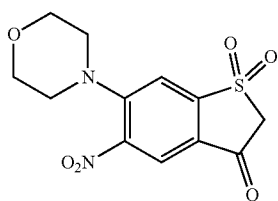 [SMILES: O=C1CS(=O)(=O)c2cc(N3CCOCC3)c([N+](=O)[O-])cc21]

A mixture of methyl 2-methylsulfonyl-4-morpholino-5-nitro-benzoate (574.0 mg, 1.67 mmol) in N,N-Dimethylformamide (15 mL) was treated with sodium hydride (60% wt with mineral oil, 100 mg, 2.5 mmol) at 0° C. The mixture was stirred at 25° C. for 4h. Water was added slowly and the pH was adjusted to 3 using 1N HCl. The aqueous layer was extracted with ethyl acetate (70 mL). The organic layer was concentrated to afford 6-morpholino-5-nitro-1,1-dioxo-benzothiophen-3-one (560 mg) as a yellow solid, which was used directly to next step without further purification. MS (ESI): m/z=313.0[M+1]$^+$.

Step F. 2,2-Dimethyl-6-morpholino-5-nitro-1,1-dioxo-benzothiophen-3-one

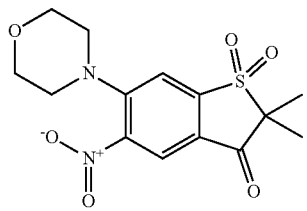

A mixture of 6-morpholino-5-nitro-1,1-dioxo-benzothiophen-3-one (560.0 mg, 1.79 mmol) iodomethane (1272.6 mg, 8.97 mmol) and 1,8-diazabicyclo[5.4.0]undec-7-ene (1362.79 mg, 8.97 mmol) in N,N-dimethylformamide (10 mL) was stirred at 40° C. in a sealed tube for 16h. Water was added and the aqueous layer was extracted with ethyl acetate (70 mL). The organic layer was washed with brine, dried over sodium sulfate and concentrated. The residue was purified by silica gel chromatography using ethyl acetate: petroleum ether (1:5) as eluting solvents to afford 2,2-dimethyl-6-morpholino-5-nitro-1,1-dioxo-benzothiophen-3-one (250 mg, 33%) as yellow solid. MS (ESI): m/z=341.1 [M+1]$^+$.

Step G. 2,2-Dimethyl-6-morpholino-5-nitro-1,1-dioxo-3H-benzothiophen-3-ol

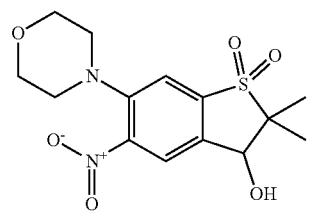 [SMILES: CC1(C)C(O)c2cc([N+](=O)[O-])c(N3CCOCC3)cc2S1(=O)=O]

A mixture of 2,2-dimethyl-6-morpholino-5-nitro-1,1-dioxo-benzothiophen-3-one (200.0 mg, 0.47 mmol) in methyl alcohol (30 mL) was treated with sodium borohydride (53.59 mg, 1.41 mmol) The mixture was stirred at 25° C. for 3h. The mixture was quenched with water and ethyl acetate (30 mL) was added. The organic layer was separated, dried over sodium sulfate and concentrated to afford 2,2-dimethyl-6-morpholino-5-nitro-1,1-dioxo-3H-benzothiophen-3-ol (150 mg) as a brown solid, which was used directly to next step without further purification. MS (ESI): m/z=343.1 [M+1]$^+$.

Step H. 2,2-Dimethyl-6-morpholino-5-nitro-3H-benzothiophene 1,1-dioxide

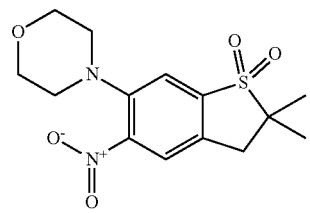 [SMILES: CC1(C)Cc2cc([N+](=O)[O-])c(N3CCOCC3)cc2S1(=O)=O]

A mixture of 2,2-dimethyl-6-morpholino-5-nitro-1,1-dioxo-3H-benzothiophen-3-ol (150.0 mg, 0.44 mmol) triethylsilane (2 mL, 12.52 mmol) in trifluoroacetic acid (8 mL, 107.7 mmol) was stirred at 50° C. for 16h. The mixture was concentrated and purified by silica gel chromatography using ethyl acetate:petroleum ether (1:5 to 1:3) as eluting solvents to afford 2,2-dimethyl-6-morpholino-5-nitro-3H-benzothiophene 1,1-dioxide (88 mg, 62%) as a yellow solid. MS (ESI): m/z=327.0 [M+1]$^+$.

Step I. 2,2-Dimethyl-6-morpholino-1,1-dioxo-3H-benzothiophen-5-amine

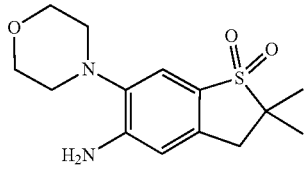

A mixture of 2,2-dimethyl-6-morpholino-5-nitro-3H-benzothiophene 1,1-dioxide (78.0 mg, 0.24 mmol) and 10 wt % palladium on carbon (20.0 mg, 0.24 mmol) in methyl alcohol (20 mL) was stirred at 25° C. under hydrogen atmosphere for 1h. The reaction was filtered through celite and concentrated under reduced pressure to afford 2,2-dimethyl-6-morpholino-1,1-dioxo-3H-benzothiophen-5-amine (60 mg) as a pink solid, which was used directly to next step without further purification. MS (ESI): m/z=297.2 [M+1]$^+$.

Step J. N-[2,2-Dimethyl-6-(morpholin-4-yl)-1,1-dioxo-2,3-dihydro-benzothiophen-5-yl]pyrazolo[1,5-a]pyrimidine-3-carboxamide

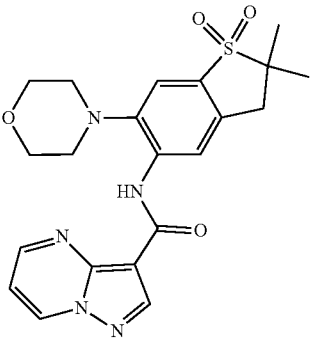 [SMILES: CC1(C)Cc2cc(NC(=O)c3cnn4cccnc34)c(N3CCOCC3)cc2S1(=O)=O]

A mixture of 2,2-dimethyl-6-morpholino-1,1-dioxo-3H-benzothiophen-5-amine (50.0 mg, 0.17 mmol), pyrazolo[1,5-a]pyrimidine-3-carbonyl chloride (Example 3, Step B) (153.16 mg, 0.84 mmol), and potassium carbonate (879.55 mg, 1.69 mmol) in toluene (10 mL) was stirred at 110° C. for 14h. Ethyl acetate (10 mL) and water were added. The organic layer was separated, dried over sodium sulfate and concentrated. The residue was purified by preparative HPLC (Gilson 281, Xbridge 21.2*250 mm c18, 10 um; A: acetonitrile 25-55%; B: 10 M ammonium bicarbonate in water) to afford N-(2,2-dimethyl-6-morpholino-1,1-dioxo-3H-benzothiophen-5-yl)pyrazolo[1,5-a]pyrimidine-3-carboxamide (30 mg, 40%) as a white solid. $^1$H NMR (400 MHz, DMSO-d$_6$) δ 10.88 (s, 1H), 9.42 (dd, J=1.6, 7.2 Hz, 1H), 9.00 (dd, J=1.6, 4.4 Hz, 1H), 8.76 (s, 1H), 8.63 (s, 1H), 7.70 (s, 1H), 7.39 (dd, J=4.4, 7.2 Hz, 1H), 3.88-3.90 (m, 4H), 3.15 (s, 2H), 2.92-2.95 (m, 4H), 1.38 (s, 6H). MS (ESI): m/z=442.1 [M+1]$^+$.

Examples 119 and 120. N—((S)-2-(hydroxymethyl)-2-methyl-6-((1R,4R)-5-(2,2,2-trifluoroethyl)-2,5-diazabicyclo[2.2.1]heptan-2-yl)-2,3-dihydrobenzofuran-5-yl)pyrazolo[1,5-a]pyrimidine-3-carboxamide and N—((R)-2-(hydroxymethyl)-2-methyl-6-((1R,4R)-5-(2,2,2-trifluoroethyl)-2,5-diazabicyclo[2.2.1]heptan-2-yl)-2,3-dihydrobenzofuran-5-yl)pyrazolo[1,5-a]pyrimidine-3-carboxamide

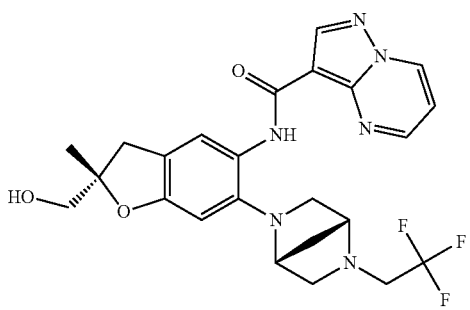

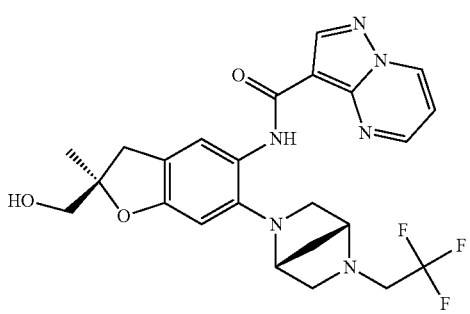

N—((S)-2-(hydroxymethyl)-2-methyl-6-((1R,4R)-5-(2,2,2-trifluoroethyl)-2,5-diazabicyclo[2.2.1]heptan-2-yl)-2,3-dihydrobenzofuran-5-yl)pyrazolo[1,5-a]pyrimidine-3-carboxamide and N—((R)-2-(hydroxymethyl)-2-methyl-6-((1R,4R)-5-(2,2,2-trifluoroethyl)-2,5-diazabicyclo[2.2.1]heptan-2-yl)-2,3-dihydrobenzofuran-5-yl)pyrazolo[1,5-a]pyrimidine-3-carboxamide (3.8 mg, 3%) (4.9 mg, 4%) were isolated as yellow solids with absolute stereochemistry assigned arbitrarily using a method similar to Examples 78 and 79.

Example 119, Peak 1: $^1$H NMR (400 MHz, DMSO-d$_6$): δ9.74 (s, 1H), 9.37 (dd, J=1.6, 6.8 Hz, 1H), 8.85 (dd, J=1.6, 4.0 Hz, 1H), 8.69 (s, 1H), 7.80 (s, 1H), 7.33 (dd, J=4.0, 6.8 Hz, 1H), 6.48 (s, 1H), 5.04 (t, J=6.0 Hz, 1H), 3.93 (s, 1H), 3.51 (s, 1H), 3.45-3.41 (m, 2H), 3.32-3.25 (m, 3H), 3.16 (d, J=16.0 Hz, 1H), 3.07-3.04 (m, 1H), 2.92-2.88 (m, 2H), 2.78 (d, J=15.6 Hz, 1H), 1.89-1.76 (m, 2H), 1.34 (s, 3H). MS (ESI): m/z=503.3 [M+1]$^+$.

Example 120, Peak 2: $^1$H NMR (400 MHz, DMSO-d$_6$): δ 9.72 (s, 1H), 9.37 (dd, J=1.6, 6.8 Hz, 1H), 8.85 (dd, J=1.6, 4.0 Hz, 1H), 8.68 (s, 1H), 7.78 (s, 1H), 7.33 (dd, J=4.0, 6.8 Hz, 1H), 6.47 (s, 1H), 5.04 (t, J=6.0 Hz, 1H), 3.93 (s, 1H), 3.50 (s, 1H), 3.45-3.41 (m, 2H), 3.32-3.25 (m, 3H), 3.16 (d, J=16.0 Hz, 1H), 3.07-3.04 (m, 1H), 2.92-2.88 (m, 2H), 2.78 (d, J=15.6 Hz, 1H), 1.89-1.76 (m, 2H), 1.34 (s, 3H). MS (ESI): m/z=503.3 [M+1]$^+$.

Examples 121 and 122. (S)—N-(6-(4,4-Difluoropiperidin-1-yl)-2-(hydroxymethyl)-2-methyl-2,3-dihydrobenzofuran-5-yl)pyrazolo[1,5-a]pyrimidine-3-carboxamide and (R)—N-(6-(4,4-difluoropiperidin-1-yl)-2-(hydroxymethyl)-2-methyl-2,3-dihydrobenzofuran-5-yl)pyrazolo[1,5-a]pyrimidine-3-carboxamide Examples 123 and 124. N—((S)-6-((1R,4R)-5-(2,2-Difluoroethyl)-2,5-diazabicyclo[2.2.1]heptan-2-yl)-2-(hydroxymethyl)-2-methyl-2,3-dihydrobenzofuran-5-yl)pyrazolo[1,5-a]pyrimidine-3-carboxamide and N—((R)-6-((1R,4R)-5-(2,2-difluoroethyl)-2,5-diazabicyclo[2.2.1]heptan-2-yl)-2-(hydroxymethyl)-2-methyl-2,3-dihydrobenzofuran-5-yl)pyrazolo[1,5-a]pyrimidine-3-carboxamide

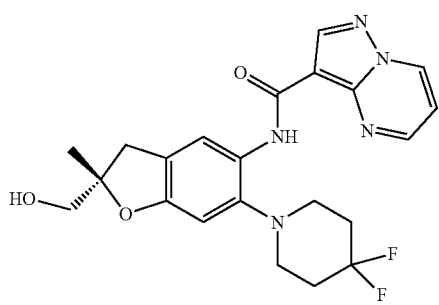

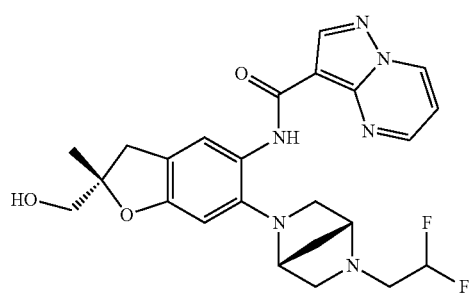

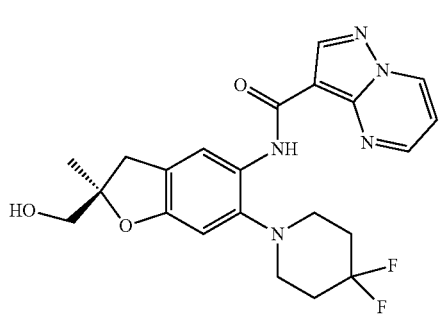

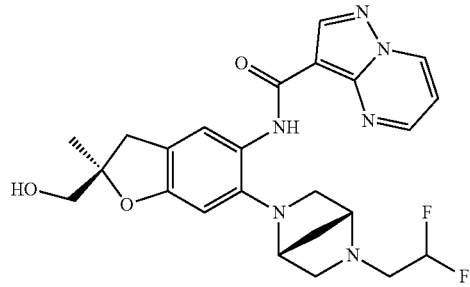

(S)—N-(6-(4,4-Difluoropiperidin-1-yl)-2-(hydroxymethyl)-2-methyl-2,3-dihydrobenzofuran-5-yl)pyrazolo[1,5-a]pyrimidine-3-carboxamide and (R)—N-(6-(4,4-difluoropiperidin-1-yl)-2-(hydroxymethyl)-2-methyl-2,3-dihydrobenzofuran-5-yl)pyrazolo[1,5-a]pyrimidine-3-carboxamide were isolated as white solids with absolute stereochemistry assigned arbitrarily using a method similar to Examples 78 and 79.

Example 121, Peak 1: $^1$H NMR (400 MHz, DMSO-d6) δ 10.42 (s, 1H), 9.38 (dd, J=7.0, 1.6 Hz, 1H), 8.75 (dd, J=4.2, 1.7 Hz, 1H), 8.69 (s, 1H), 8.32 (d, J=1.0 Hz, 1H), 7.37 (dd, J=7.0, 4.2 Hz, 1H), 6.73 (s, 1H), 5.03 (t, J=5.8 Hz, 1H), 3.42 (h, J=5.8 Hz, 2H), 3.20 (dd, J=15.8, 1.2 Hz, 1H), 2.93 (t, J=5.5 Hz, 4H), 2.83 (dd, J=15.6, 1.2 Hz, 1H), 2.31-2.17 (m, 5H), 1.34 (s, 3H). MS (ESI): m/z=444.2 [M+1]$^+$.

Example 122, Peak 2: $^1$H NMR (400 MHz, DMSO-d6) δ 10.42 (s, 1H), 9.38 (dd, J=7.0, 1.6 Hz, 1H), 8.75 (dd, J=4.2, 1.7 Hz, 1H), 8.69 (s, 1H), 8.32 (d, J=1.0 Hz, 1H), 7.37 (dd, J=7.0, 4.2 Hz, 1H), 6.73 (s, 1H), 5.07-5.00 (m, 1H), 3.44 (h, J=5.5 Hz, 7H), 3.39 (d, J=1.2 Hz, OH), 3.24-3.17 (m, 1H), 2.93 (t, J=5.6 Hz, 4H), 2.87-2.78 (m, 1H), 2.32-2.17 (m, 4H), 1.34 (s, 3H). MS (ESI): m/z=444.2 [M+1]$^+$.

N—((S)-6-((1R,4R)-5-(2,2-Difluoroethyl)-2,5-diazabicyclo[2.2.1]heptan-2-yl)-2-(hydroxymethyl)-2-methyl-2,3-dihydrobenzofuran-5-yl)pyrazolo[1,5-a]pyrimidine-3-carboxamide and N—((R)-6-((1R,4R)-5-(2,2-difluoroethyl)-2,5-diazabicyclo[2.2.1]heptan-2-yl)-2-(hydroxymethyl)-2-methyl-2,3-dihydrobenzofuran-5-yl)pyrazolo[1,5-a]pyrimidine-3-carboxamide were isolated as white solids with absolute stereochemistry assigned arbitrarily using a method similar to Examples 78 and 79.

Example 123, Peak 1: $^1$H NMR (400 MHz, DMSO-d$_6$): δ: 9.72 (s, 1H), 9.37 (dd, J=1.6, 7.2 Hz, 1H), 8.86 (dd, J=2.0, 4.4 Hz, 1H), 8.68 (s, 1H), 7.78 (s, 1H), 7.33 (dd, J=4.4, 6.8 Hz, 1H), 6.45 (s, 1H), 5.99 (tt, J=4.4, 56.0 Hz, 1H), 5.04 (t, J=6.0 Hz, 1H), 3.90 (s, 1H), 3.49-3.32 (m, 2H), 3.31-3.26 (m, 1H), 3.16 (d, J=15.6 Hz, 1H), 3.10-3.00 (m, 1H), 2.97-2.81 (m, 4H), 2.78 (d, J=15.6 Hz, 1H), 1.88-1.72 (m, 2H), 1.34 (s, 3H). MS (ESI): m/z=485.2 [M+1]$^+$.

Example 124, Peak 2: $^1$H NMR (400 MHz, DMSO-d$_6$): δ: 9.74 (s, 1H), 9.37 (dd, J=1.6, 7.2 Hz, 1H), 8.86 (dd, J=1.6, 4.0 Hz, 1H), 8.68 (s, 1H), 7.80 (s, 1H), 7.33 (dd, J=4.4, 6.8 Hz, 1H), 6.47 (s, 1H), 6.00 (tt, J=4.0, 56.0 Hz, 1H), 5.04 (t, J=5.6 Hz, 1H), 3.90 (s, 1H), 3.48-3.38 (m, 3H), 3.15 (d, J=15.6 Hz, 1H), 3.06-2.99 (m, 1H), 2.97-2.82 (m, 4H), 2.78 (d, J=15.6 Hz, 1H), 1.88-1.72 (m, 2H), 1.34 (s, 3H). MS (ESI): m/z=485.2 [M+1]$^+$.

Examples 125 and 126. (R)—N-(2-(Hydroxymethyl)-2-methyl-6-(2-oxa-8-azaspiro[4.5]decan-8-yl)-2,3-dihydrobenzofuran-5-yl)pyrazolo[1,5-a]pyrimidine-3-carboxamide and (S)—N-(2-(hydroxymethyl)-2-methyl-6-(2-oxa-8-azaspiro[4.5]decan-8-yl)-2,3-dihydrobenzofuran-5-yl)pyrazolo[1,5-a]pyrimidine-3-carboxamide Examples 127 and 128. (R)—N-(2-(Hydroxymethyl)-2-methyl-6-(4-methylpiperazin-1-yl)-2,3-dihydrobenzofuran-5-yl)pyrazolo[1,5-a]pyrimidine-3-carboxamide and (S)—N-(2-(hydroxymethyl)-2-methyl-6-(4-methylpiperazin-1-yl)-2,3-dihydrobenzofuran-5-yl)pyrazolo[1,5-a]pyrimidine-3-carboxamide

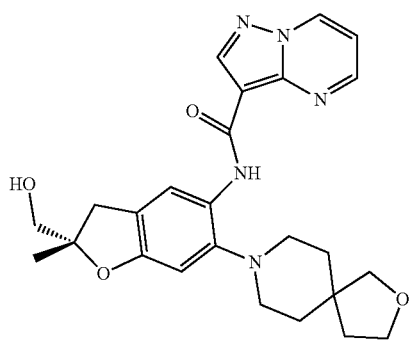

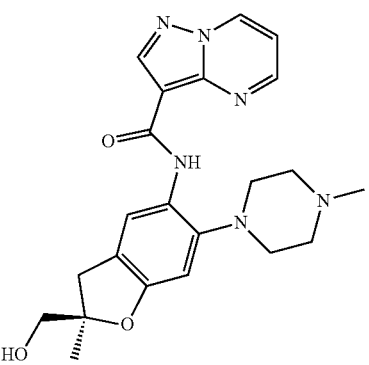

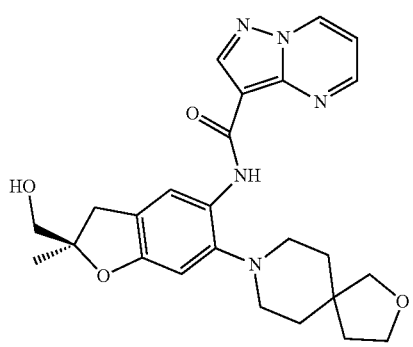

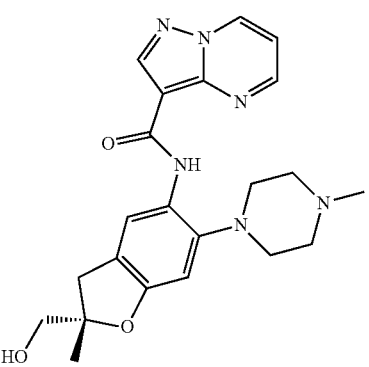

(R)—N-(2-(Hydroxymethyl)-2-methyl-6-(2-oxa-8-azaspiro[4.5]decan-8-yl)-2,3-dihydrobenzofuran-5-yl)pyrazolo[1,5-a]pyrimidine-3-carboxamide and (S)—N-(2-(hydroxymethyl)-2-methyl-6-(2-oxa-8-azaspiro[4.5]decan-8-yl)-2,3-dihydrobenzofuran-5-yl)pyrazolo[1,5-a]pyrimidine-3-carboxamide were isolated as white solids with absolute stereochemistry assigned arbitrarily using a method similar to Examples 78 and 79.

Example 125, Peak 1: $^1$H NMR (400 MHz, DMSO-d$_6$): δ 10.46 (s, 1H), 9.36 (dd, J=1.6, 7.0 Hz, 1H), 8.83 (dd, J=1.6, 4.2 Hz, 1H), 8.68 (s, 1H), 8.30 (s, 1H), 7.34 (dd, J=4.2, 7.0 Hz, 1H), 6.70 (s, 1H), 5.04 (t, J=5.8 Hz, 1H), 3.77 (t, J=7.1 Hz, 2H), 3.57 (s, 2H), 3.43 (t, J=5.6 Hz, 2H), 3.19 (d, J=15.8 Hz, 1H), 2.84-2.72 (m, 5H), 1.84-1.72 (m, 6H), 1.34 (s, 3H). MS (ESI): m/z=464.2 [M+1]$^+$.

Example 126, Peak 2: $^1$H NMR (400 MHz, DMSO-d$_6$): δ 10.46 (s, 1H), 9.36 (dd, J=1.6, 7.0 Hz, 1H), 8.83 (dd, J=1.6, 4.2 Hz, 1H), 8.68 (s, 1H), 8.30 (s, 1H), 7.34 (dd, J=4.2, 7.0 Hz, 1H), 6.70 (s, 1H), 5.04 (t, J=5.8 Hz, 1H), 3.77 (t, J=7.1 Hz, 2H), 3.57 (s, 2H), 3.43 (t, J=5.6 Hz, 2H), 3.19 (d, J=15.8 Hz, 1H), 2.84-2.72 (m, 5H), 1.84-1.72 (m, 6H), 1.34 (s, 3H). MS (ESI): m/z=464.3 [M+1]$^+$.

(R)—N-(2-(Hydroxymethyl)-2-methyl-6-(4-methylpiperazin-1-yl)-2,3-dihydrobenzofuran-5-yl)pyrazolo[1,5-a]pyrimidine-3-carboxamide and (S)—N-(2-(hydroxymethyl)-2-methyl-6-(4-methylpiperazin-1-yl)-2,3-dihydrobenzofuran-5-yl)pyrazolo[1,5-a]pyrimidine-3-carboxamide were isolated as white solids with absolute stereochemistry assigned arbitrarily using a method similar to Examples 78 and 79.

Example 127, Peak 1: $^1$H NMR (400 MHz, CDCl$_3$) δ 10.41 (s, 1H), 8.83 (dd, J=1.2, 6.8 Hz, 1H), 8.80-8.75 (m, 2H), 8.44 (s, 1H), 7.07 (dd, J=4.0, 6.8 Hz, 1H), 6.69 (s, 1H), 3.71-3.61 (m, 2H), 3.25 (d, J=15.6 Hz, 1H), 3.06-2.88 (m, 5H), 2.8-2.63 (m, 4H), 2.44 (s, 3H), 1.46 (s, 3H). MS (ESI): m/z=439.2 [M+1]$^+$.

Example 128, Peak 2: $^1$H NMR (400 MHz, CDCl$_3$) δ 10.44 (s, 1H), 8.83 (d, J=6.8 Hz, 1H), 8.80-8.75 (m, 2H), 8.44 (s, 1H), 7.07 (dd, J=4.0, 7.2 Hz, 1H), 6.70 (s, 1H), 3.71-3.61 (m, 2H), 3.25 (d, J=15.6 Hz, 1H), 3.06-2.88 (m, 5H), 2.8-2.63 (m, 4H), 2.41 (s, 3H), 1.46 (s, 3H). MS (ESI): m/z=439.2 [M+1]$^+$.

Examples 129 and 130. (R)—N-(2-(Hydroxymethyl)-6-(4-(hydroxymethyl)piperidin-1-yl)-2-methyl-2,3-dihydrobenzofuran-5-yl)pyrazolo[1,5-a]pyrimidine-3-carboxamide and (S)—N-(2-(hydroxymethyl)-6-(4-(hydroxymethyl)piperidin-1-yl)-2-methyl-2,3-dihydrobenzofuran-5-yl)pyrazolo[1,5-a]pyrimidine-3-carboxamide

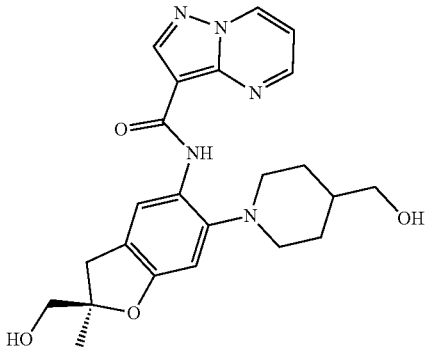

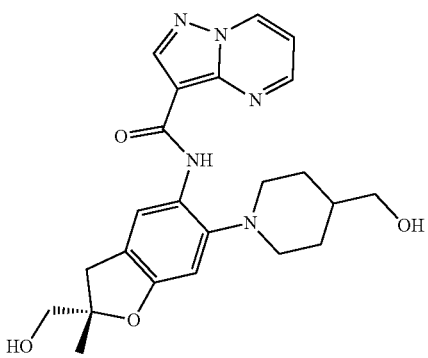

(R)—N-(2-(hydroxymethyl)-6-(4-(hydroxymethyl)piperidin-1-yl)-2-methyl-2,3-dihydrobenzofuran-5-yl)pyrazolo[1,5-a]pyrimidine-3-carboxamide and (S)—N-(2-(hydroxymethyl)-6-(4-(hydroxymethyl)piperidin-1-yl)-2-methyl-2,3-dihydrobenzofuran-5-yl)pyrazolo[1,5-a]pyrimidine-3-carboxamide were isolated as white solids with absolute stereochemistry assigned arbitrarily using a method similar to Examples 78 and 79.

Example 129, Peak 1: $^1$H NMR (400 MHz, CDCl$_3$) δ 10.48 (s, 1H), 8.80 (d, J=7.2 Hz, 1H), 8.79-8.76 (m, 2H), 8.45 (s, 1H), 7.02 (dd, J=4.0, 7.2 Hz, 1H), 6.67 (s, 1H), 3.69-3.60 (m, 4H), 3.23 (d, J=15.6 Hz, 1H), 3.10 (d, J=11.6 Hz, 2H), 2.94 (d, J=15.6 Hz, 1H), 2.68 (t, J=10.8 Hz, 2H), 1.91 (t, J=6.4 Hz, 1H), 1.83-1.65 (m, 5H) 1.46 (s, 3H). MS (ESI): m/z=438.2[M+1]$^+$.

Example 130, Peak 2: $^1$H NMR (400 MHz, CDCl$_3$) δ 10.50 (s, 1H), 8.80 (d, J=7.2 Hz, 1H), 8.79-8.75 (m, 2H), 8.45 (s, 1H), 7.02 (dd, J=6.8 Hz, 1H), 6.67 (s, 1H), 3.70-3.66 (m, 4H), 3.23 (d, J=15.6 Hz, 1H), 3.10 (d, J=11.6 Hz, 2H), 2.94 (d, J=15.6 Hz, 1H), 2.68 (t, J=10.8 Hz, 2H), 1.90 (t, J=6.4 Hz, 1H), 1.83-1.65 (m, 5H), 1.46 (s, 3H). MS (ESI): m/z=438.2 [M+1]$^+$.

Example 131. N-[6-[4-(2, 2-Difluoroethyl) piperazin-1-yl]-2-(hydroxymethyl)-2-methyl-3H-benzofuran-5-yl]-6-fluoro-pyrazolo[1,5-a]pyrimidine-3-carboxamide

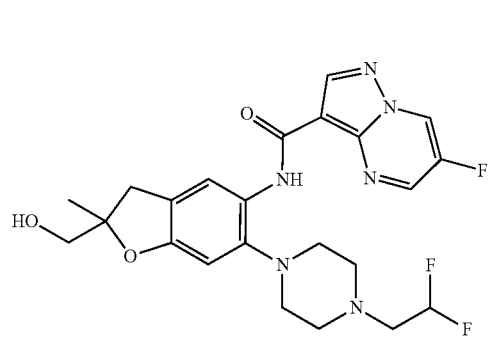 [SMILES: CC1(CO)Cc2cc(NC(=O)c3cnn4cc(F)cnc34)c(N3CCN(CC(F)F)CC3)cc2O1]

The title compound was made in a manner analogous to Examples 54 and 55 to give N-[6-[4-(2, 2-difluoroethyl)piperazin-1-yl]-2-(hydroxymethyl)-2-methyl-3H-benzofuran-5-yl]-6-fluoro-pyrazolo[l, 5-a] pyrimidine-3-carboxamide. $^1$H NMR (400 MHz, dimethyl sulfoxide-d$_6$) δ 10.24 (s, 1H), 9.83 (dd, J=4.8, 2.4 Hz, 1H), 9.15 (d, J=2.4 Hz, 1H), 8.70 (s, 1H), 8.27 (s, 1H), 6.70 (s, 1H), 6.20 (tt, J=56, 4.0 Hz, 1H), 5.04 (t, J=5.6 Hz, 1H), 3.44-3.41 (m, 2H), 3.19 (d, J=15.2 Hz, 1H), 2.89-2.78 (m, 11H), 1.34 (s, 3H). LCMS (ESI): m/z=491.1 [M+H]$^+$.

Examples 132 and 133. (S)—N-(6-(4-(2,2-Difluoroethyl)piperazin-1-yl)-2-(hydroxymethyl)-2-methyl-2,3-dihydrobenzofuran-5-yl)-6-fluoropyrazolo[1,5-a]pyrimidine-3-carboxamide and (R)—N-(6-(4-(2,2-Difluoroethyl)piperazin-1-yl)-2-(hydroxymethyl)-2-methyl-2,3-dihydrobenzofuran-5-yl)-6-fluoropyrazolo[1,5-a]pyrimidine-3-carboxamide

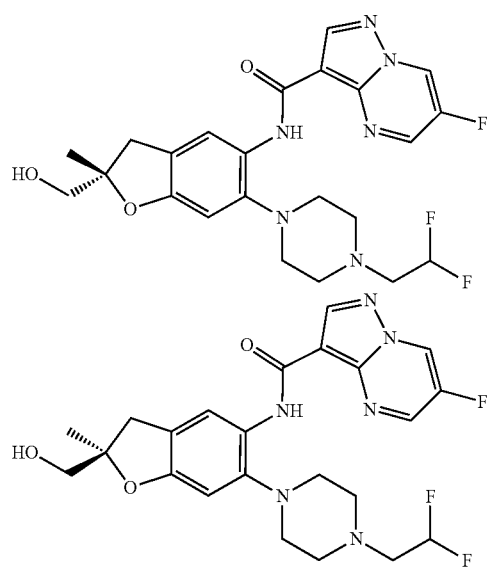

(S)—N-(6-(4-(2,2-Difluoroethyl)piperazin-1-yl)-2-(hydroxymethyl)-2-methyl-2,3-dihydrobenzofuran-5-yl)-6-fluoropyrazolo[1,5-a]pyrimidine-3-carboxamide and (R)—N-(6-(4-(2,2-Difluoroethyl)piperazin-1-yl)-2-

(hydroxymethyl)-2-methyl-2,3-dihydrobenzofuran-5-yl)-6-fluoropyrazolo[1,5-a]pyrimidine-3-carboxamide were resolved in a manner analogous to Examples 163 and 164 with absolute stereochemistry assigned arbitrarily.

Example 132. Peak 1: ¹H NMR (400 MHz, DMSO-d6) δ 10.24 (s, 1H), 9.83 (dd, J=4.4, 2.4 Hz, 1H), 9.16 (d, J=2.4 Hz, 1H), 8.71 (s, 1H), 8.27 (s, 1H), 6.70 (s, 1H), 6.35-6.05 (m, 1H), 5.06 (br s, 1H), 3.50-3.40 (m, 2H), 3.19 (d, J=15.6 Hz, 1H), 2.95-2.70 (m, 11H), 1.34 (s, 3H). MS (ESI): m/z=491.2 [M+1]⁺.

Example 133. Peak 2: ¹H NMR (400 MHz, DMSO-d6) δ 10.24 (s, 1H), 9.83 (dd, J=4.4, 2.4 Hz, 1H), 9.16 (d, J=2.8 Hz, 1H), 8.71 (s, 1H), 8.27 (s, 1H), 6.70 (s, 1H), 6.34-6.06 (m, 1H), 5.05 (t, J=5.6 Hz, 1H), 3.50-3.40 (m, 2H), 3.25-3.10 (m, 1H), 3.00-2.70 (m, 11H), 1.34 (s, 3H). MS (ESI): m/z=491.2 [M+1]⁺.

Examples 134 and 135. (R)—N-(2-isopropyl-2-methyl-6-morpholino-2,3-dihydrobenzofuran-5-yl)pyrazolo[1,5-a]pyrimidine-3-carboxamide and (S)—N-(2-isopropyl-2-methyl-6-morpholino-2,3-dihydrobenzofuran-5-yl)pyrazolo[1,5-a]pyrimidine-3-carboxamide

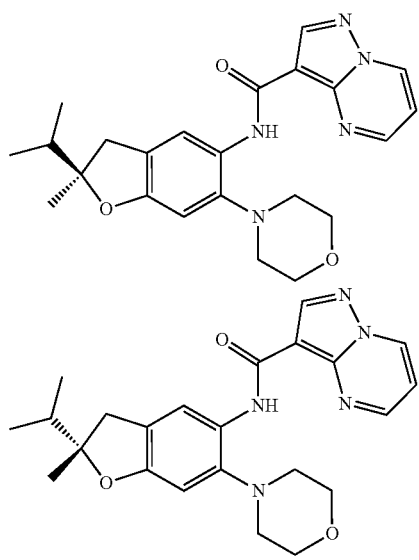

N-(2-isopropyl-2-methyl-6-morpholino-2,3-dihydrobenzofuran-5-yl)pyrazolo[1,5-a]pyrimidine-3-carboxamide (Example 150), 116.3 mg, 0.276 mmol) was resolved by chiral preparatory SFC to afford (R)—N-(2-isopropyl-2-methyl-6-morpholino-2,3-dihydrobenzofuran-5-yl)pyrazolo[1,5-a]pyrimidine-3-carboxamide (35.3 mg, 30%) and (S)—N-(2-isopropyl-2-methyl-6-morpholino-2,3-dihydrobenzofuran-5-yl)pyrazolo[1,5-a]pyrimidine-3-carboxamide (42.0 mg, 36%) as light yellow solids with absolute stereochemistry assigned arbitrarily.

Example 134 Peak 1: ¹H NMR (400 MHz, DMSO-d₆) δ 10.42 (s, 1H), 9.37 (dd, J=7.0, 1.7 Hz, 1H), 8.94 (dd, J=4.2, 1.7 Hz, 1H), 8.68 (s, 1H), 8.30 (s, 1H), 7.34 (dd, J=7.0, 4.2 Hz, 1H), 6.72 (s, 1H), 3.87-3.79 (m, 4H), 3.13 (dd, J=15.9, 1.3 Hz, 1H), 2.86-2.77 (m, 5H), 1.94 (h, J=6.8 Hz, 1H), 1.28 (s, 3H), 0.93 (dd, J=20.3, 6.8 Hz, 6H). MS (ESI): m/z=422.2 [M+1]⁺.

Example 135 Peak 2: ¹H NMR (400 MHz, DMSO-d₆) δ 10.42 (s, 1H), 9.37 (dd, J=7.0, 1.6 Hz, 1H), 8.94 (dd, J=4.2, 1.7 Hz, 1H), 8.68 (s, 1H), 8.30 (s, 1H), 7.34 (dd, J=7.0, 4.1 Hz, 1H), 6.72 (s, 1H), 3.87-3.80 (m, 4H), 3.13 (dd, J=15.7, 1.4 Hz, 1H), 2.86-2.77 (m, 5H), 1.94 (h, J=6.8 Hz, 1H), 1.28 (s, 3H), 0.93 (dd, J=20.3, 6.8 Hz, 6H). MS (ESI): m/z=422.2 [M+1]⁺.

Example 136. N-(6-Methyl-2-morpholino-7-oxo-6,7-dihydro-5H-pyrrolo[3,4-b]pyridin-3-yl)pyrazolo[1,5-a]pyrimidine-3-carboxamide

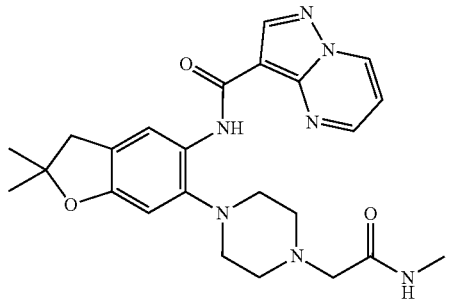

Step A. Ethyl 2-[4-[2,2-dimethyl-5-(pyrazolo[1,5-a]pyrimidine-3-carbonylamino)-3H-benzofuran-6-yl]piperazin-1-yl]acetate

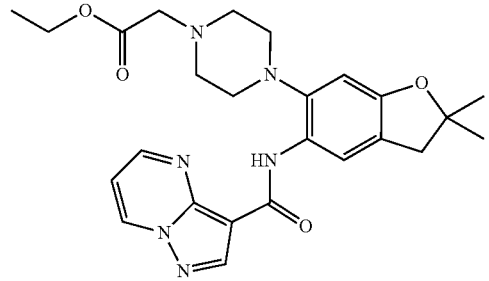

Ethyl 2-[4-(5-amino-2,2-dimethyl-3H-benzofuran-6-yl)piperazin-1-yl]acetate (Example 134 Step C; 200 mg, 0.60 mmol) in pyridine (10 ml) was treated with pyrazolo[1,5-a]pyrimidine-3-carbonyl chloride (120 mg, 0.66 mmol) and stirred at 25° C. for 4h. The reaction was concentrated and purified by silica gel chromatography (eluting gradient 0-10% methanol: dichloromethane) to afford ethyl 2-[4-[2,2-dimethyl-5-(pyrazolo[1,5-a]pyrimidine-3-carbonylamino)-3H-benzofuran-6-yl]piperazin-1-yl]acetate (280 mg, 98% yield) as a brown solid. LCMS (ESI): m/z=479.0 [M+H]+

Step B. N-[2,2-Dimethyl-6-[4-[2-(methylamino)-2-oxo-ethyl]piperazin-1-yl]-3H-benzofuran-5-yl]pyrazolo[1,5-a]pyrimidine-3-carboxamide

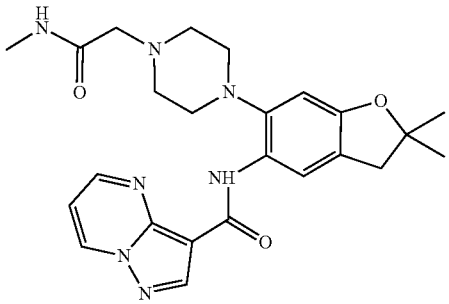

Ethyl 2-[4-[2,2-Dimethyl-5-(pyrazolo[1,5-a]pyrimidine-3-carbonylamino)-3H-benzofuran-6-yl]piperazin-1-yl]acetate (280 mg, 0.59 mmol) was treated with 2M methylamine in tetrahydrofuran (10 ml, 20 mmol) was stirred at 100° C. for 36h under autoclave, concentrated and purified by preparatory TLC (eluent: 10% methanol in dichloromethane) to afford N-[2,2-dimethyl-6-[4-[2-(methylamino)-2-oxo-ethyl]piperazin-1-yl]-3H-benzofuran-5-yl]pyrazolo[1,5-a]pyrimidine-3-carboxamide (93.6 mg, 33% yield) as a brown solid. $^1$H NMR (400 MHz, DMSO-$d_6$) 10.42 (s, 1H), 9.40-9.35 (m, 1H), 8.97-8.95 (m, 1H), 8.67 (s, 1H), 8.33 (s, 1H), 7.75-7.74 (m, 1H), 7.36 (dd, J=7.2, 4.4 Hz, 1H), 6.67 (s, 1H), 3.04 (s, 2H), 3.00 (s, 2H), 2.85-2.84 (m, 4H), 2.72-2.68 (m, 4H), 2.64 (d, J=4.8 Hz, 3H), 1.41 (s, 6H). LCMS (ESI) m/z: 464.1 [M+H]$^+$.

Example 137. N-[6-[4-(2-Hydroxy-1,1-dimethyl-ethyl)piperazin-1-yl]-2,2-dimethyl-3H-benzofuran-5-yl]pyrazolo[1,5-a]pyrimidine-3-carboxamide

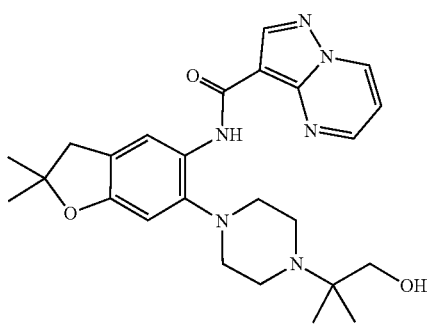 [SMILES: CC1(C)Cc2cc(NC(=O)c3cnn4cccnc34)c(N3CCN(C(C)(C)CO)CC3)cc2O1]

Step A. tert-Butyl4-(2-ethoxy-1,1-dimethyl-2-oxo-ethyl)piperazine-1-carboxylate

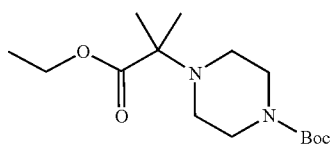 [SMILES: CCOC(=O)C(C)(C)N1CCN(C(=O)OC(C)(C)C)CC1]

A mixture of tert-butyl 1-piperazinecarboxylate (3.0 g, 20.08 mmol), ethyl 2-bromoisobutyrate (5.9 g, 30.12 mmol) and potassium carbonate (5.6 g, 40.16 mmol) in acetonitrile (40 ml) was stirred at 80° C. for 15h under nitrogen. The mixture was filtered, the filtrate was concentrated and the residue was purified by silica gel chromatography (eluent 15% ethyl acetate:petroleum ether) to give tert-butyl 4-(2-ethoxy-1,1-dimethyl-2-oxo-ethyl)piperazine-1-carboxylate (2.8 g, 47% yield) as a colorless oil. $^1$H NMR (400 MHz, CDCl$_3$): δ 4.20-4.16 (m, 2H), 3.43-3.41 (m, 4H), 2.55-2.53 (m, 4H), 1.46 (s, 9H), 1.45-1.26 (m, 9H).

Step B. Ethyl 2-methyl-2-piperazin-1-yl-propanoate dihydrochloride

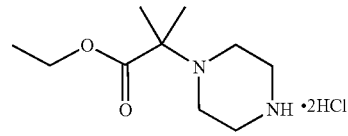

tert-Butyl 4-(2-ethoxy-1,1-dimethyl-2-oxo-ethyl)piperazine-1-carboxylate (1.0 g, 3.33 mmol) in 1,4-dioxane (10 ml) was treated with hydrochloric acid (0.83 ml, 3.32 mmol), stirred at 15° C. for 15h and concentrated to afford ethyl 2-methyl-2-piperazin-1-yl-propanoate dihydrochloride (700 mg, 77% yield) as a yellow oil which was use directly without further purification. $^1$H NMR (400 MHz, DMSO-$d_6$) δ 9.62 (s, 2H), 4.20 (q, J=7.2 Hz, 2H), 3.50-3.25 (m, 8H), 1.52 (s, 6H), 1.26 (t, J=7.2 Hz, 3H).

Step C. Ethyl 2-[4-(2,2-dimethyl-5-nitro-3H-benzofuran-6-yl)piperazin-1-yl]-2-methyl-propanoate

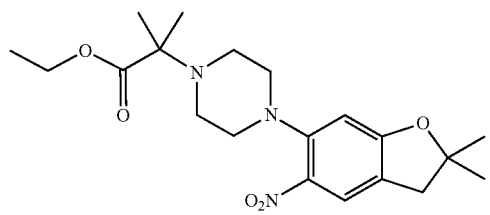 [SMILES: CCOC(=O)C(C)(C)N1CCN(c2cc3c(cc2[N+](=O)[O-])CC(C)(C)O3)CC1]

6-Chloro-2,2-dimethyl-5-nitro-3H-benzofuran (100 mg, 0.44 mmol) in acetonitrile (10 ml) was treated with potassium carbonate (182 mg, 1.32 mmol) and ethyl 2-methyl-2-piperazin-1-yl-propanoate dihydrochloride (180 mg, 0.66 mmol) and stirred at 100° C. for 16h. The mixture was filtered, concentrated and purified by silica gel chromatography (eluting gradient 0-20% ethyl acetate:petroleum ether) to afford ethyl 2-[4-(2,2-dimethyl-5-nitro-3H-benzofuran-6-yl)piperazin-1-yl]-2-methyl-propanoate (150 mg, 87% yield) as a yellow oil. LCMS (ESI): m/z=392.1 [M+H]$^+$.

Step D. 2-[4-(2,2-Dimethyl-5-nitro-3H-benzofuran-6-yl)piperazin-1-yl]-2-methyl-propan-1-ol

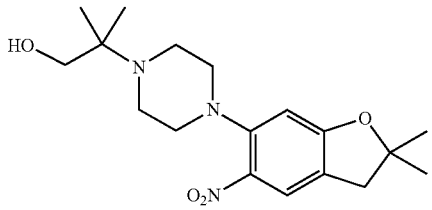 [SMILES: CC1(C)Cc2cc([N+](=O)[O-])c(N3CCN(C(C)(C)CO)CC3)cc2O1]

To a solution of ethyl 2-[4-(2,2-dimethyl-5-nitro-3H-benzofuran-6-yl)piperazin-1-yl]-2-methyl-propanoate (150 mg, 0.38 mmol) in methyl alcohol (5 ml) and tetrahydrofuran (10 ml) was added lithium borohydride (17 mg, 0.77 mmol). After being stirred at 40° C. for 16h, the reaction was diluted with water (1 ml) and extracted with dichloromethane (20 ml×3). The combined organic phases were washed with brine (20 ml×2), dried over sodium sulfate, filtered and concentrated. The residue was purified by silica gel chromatography (eluting gradient 0-50% ethyl acetate: petroleum ether) to afford 2-[4-(2,2-dimethyl-5-nitro-3H-benzofuran-6-yl)piperazin-1-yl]-2-methyl-propan-1-ol (80 mg, 60% yield) as a yellow oil. LCMS (ESI): m/z=350.3 [M+H]$^+$.

Step E. 2-[4-(5-Amino-2,2-dimethyl-3H-benzofuran-6-yl)piperazin-1-yl]-2-methyl-propan-1-ol

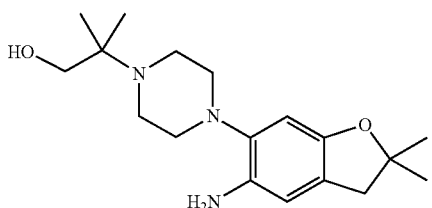

2-[4-(2,2-Dimethyl-5-nitro-3H-benzofuran-6-yl)piperazin-1-yl]-2-methyl-propan-1-ol (80 mg, 0.23 mmol) in methanol (10 ml) was treated with 10% of palladium on carbon (24 mg, 0.02 mmol) and stirred at 25° C. for 2h under hydrogen (15 psi). The reaction was filtered and the filtrate was concentrated to afford 2-[4-(5-amino-2,2-dimethyl-3H-benzofuran-6-yl)piperazin-1-yl]-2-methyl-propan-1-ol (53 mg, 73% yield) as a yellow oil, which was used directly without further purification.

Step F. N-[6-[4-(2-Hydroxy-1,1-dimethyl-ethyl)piperazin-1-yl]-2,2-dimethyl-3H-benzofuran-5-yl]pyrazolo[1,5-a]pyrimidine-3-carboxamide

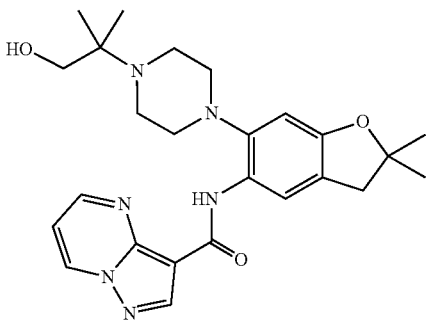

N-[6-[4-(2-Hydroxy-1,1-dimethyl-ethyl)piperazin-1-yl]-2,2-dimethyl-3H-benzofuran-5-yl]pyrazolo[1,5-a]pyrimidine-3-carboxamide (30 mg, 39% yield) was made in a manner analogous to Example 136 and isolated as a yellow solid. $^1$H NMR (400 MHz, CDCl$_3$) δ 10.32 (s, 1H), 8.84-8.80 (m, 2H), 8.69 (dd, J=4.0, 1.6 Hz, 1H), 8.36 (s, 1H), 7.05 (dd, J=6.8, 4.0 Hz, 1H), 6.64 (s, 1H), 3.38 (s, 2H), 3.04 (s, 2H), 3.00-2.90 (m, 4H), 2.85-2.75 (m, 4H), 1.49 (s, 6H), 1.10 (s, 6H). LCMS (ESI) m/z: 465.1 [M+H]$^+$.

Example 138. N-(2-Isopropyl-6-morpholino-1-oxoisoindolin-5-yl)pyrazolo[1,5-a]pyrimidine-3-carboxamide

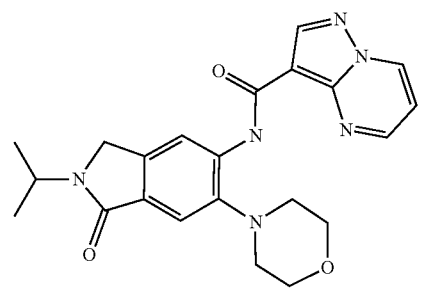

Step A. 6-Chloro-2-isopropyl-5-nitroisoindolin-1-one

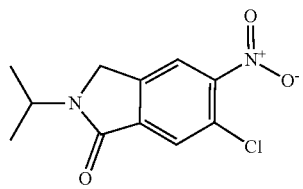 [SMILES: CC(C)N1Cc2cc([N+](=O)[O-])c(Cl)cc2C1=O]

To a solution of methyl 2-(bromomethyl)-5-chloro-4-nitrobenzoate (prepared following protocol from WO 2013/079505) (130 mg, 0.42 mmol) in methanol (4.2 mL) was added trimethylamine (0.071 mL, 0.51 mmol) and isopropylamine (0.043 mL, 0.51 mmol). The reaction mixture was heated at 70° C. for 6h, cooled to ambient temperature, and diluted with isopropyl acetate and 1N HCl. The layers were separated and the aqueous layer was washed with isopropyl acetate (2×). The combined organic layers were dried over sodium sulfate and carried on without further purification.

Step B.
2-Isopropyl-6-morpholino-5-nitroisoindolin-1-one

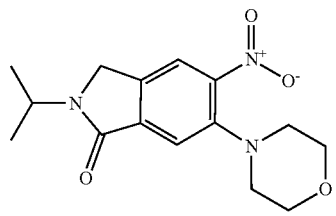 [SMILES: CC(C)N1Cc2cc([N+](=O)[O-])c(N3CCOCC3)cc2C1=O]

A solution of 6-chloro-2-isopropyl-5-nitroisoindolin-1-one (88 mg, 0.35 mmol), morpholine (0.036 mL, 0.42 mmol), diisopropylamine (0.12 mL, 0.69 mmol) in DMSO (1 mL) was heated at 90° C. for 18h. The reaction mixture was cooled to ambient temperature, diluted with water and extracted with isopropyl acetate. The combined organic layers were washed with brine, dried over sodium sulfate, filtered and absorbed onto celite to be purified by silica gel chromatography (0% to 100% isopropyl acetate in heptanes) to afford 2-isopropyl-6-morpholino-5-nitroisoindolin-1-one (17 mg, 16%) as an orange oil. $^1$H NMR (400 MHz, Chloroform-d) δ 7.80 (s, 1H), 7.64 (s, 1H), 4.67 (p, J=6.8 Hz, 1H), 4.36 (s, 2H), 3.88-3.79 (m, 4H), 3.12-3.02 (m, 4H), 1.31 (d, J=6.8 Hz, 6H).

Step C.
5-Amino-2-isopropyl-6-morpholinoisoindolin-1-one

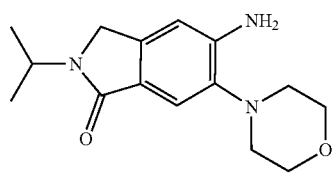 [SMILES: CC(C)N1Cc2cc(N)c(N3CCOCC3)cc2C1=O]

2-Isopropyl-6-morpholino-5-nitroisoindolin-1-one (17 mg, 0.056 mmol) was brought up in ethanol (0.35 mL) and water (0.035 mL) and treated with tin(II) chloride dehydrate (42 mg, 0.22 mmol) and heated to 65° C. for 5h. DCM (0.75 mL) and 2M NaOH (aq) (0.37 mL) were added and the mixture was passed through a hydrophobic frit. The solvent was removed in vacuo to give the desired product as a yellow solid. The crude material was carried on without further purification. MS (ESI): m/z=276.1 [M+1]$^+$.

Step D. N-(2-Isopropyl-6-morpholino-1-oxoisoindolin-5-yl)pyrazolo[1,5-a]pyrimidine-3-carboxamide

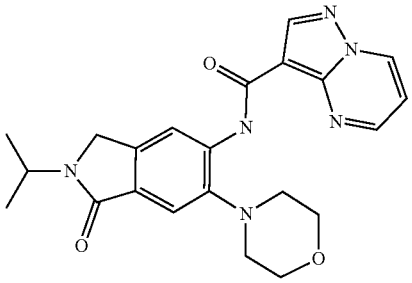

A solution of 5-amino-2-isopropyl-6-morpholino-isoindolin-1-one (19 mg, 0.069 mmol), pyrazolo[1,5-a]pyrimidine-3-carbonyl chloride (19 mg, 0.10 mmol), 4-dimethylaminopyridine (2 mg, 0.014 mmol), and diisopropylethylamine (0.036 mL, 0.21 mmol) in DCE (1 mL) was stirred at ambient temperature for 18h. The reaction was concentrated under reduced pressure and purified by reverse phase HPLC to afford N-(2-isopropyl-6-morpholino-1-oxoisoindolin-5-yl)pyrazolo[1,5-a]pyrimidine-3-carboxamide (6.8 mg, 24%). $^1$H NMR (400 MHz, DMSO-d6) δ 10.90 (s, 1H), 9.41 (dd, J=7.0, 1.6 Hz, 1H), 9.00 (dd, J=4.2, 1.6 Hz, 1H), 8.76 (d, J=3.8 Hz, 2H), 7.56 (s, 1H), 7.39 (dd, J=7.0, 4.2 Hz, 1H), 4.42 (d, J=5.3 Hz, 3H), 3.94-3.83 (m, 4H), 2.96-2.85 (m, 4H), 1.23 (d, J=6.8 Hz, 6H). MS (ESI): m/z=421.2 [M+1]$^+$.

Example 139. (R)—N-(2-(2-Fluoro-3-hydroxy-3-methylbutyl)-6-morpholino-1-oxoisoindolin-5-yl)pyrazolo[1,5-a]pyrimidine-3-carboxamide

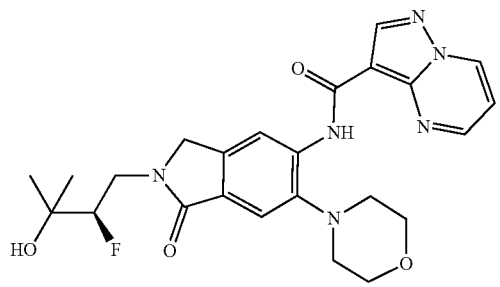 [SMILES: CC(C)(O)[C@H](F)CN1Cc2cc(NC(=O)c3cnn4cccnc34)c(N3CCOCC3)cc2C1=O]

(R)—N-(2-(2-Fluoro-3-hydroxy-3-methylbutyl)-6-morpholino-1-oxoisoindolin-5-yl)pyrazolo[1,5-a]pyrimidine-3-carboxamide (44 mg, 32%) was prepared following the procedure described for Example 138 using (R)-4-amino-3-fluoro-2-methylbutan-2-ol (WO 2014/074675). $^1$H NMR (400 MHz, DMSO-d6) δ 10.90 (s, 1H), 9.41 (dd, J=7.0, 1.6 Hz, 1H), 9.00 (dd, J=4.2, 1.6 Hz, 1H), 8.76 (d, J=2.4 Hz, 2H), 7.59 (s, 1H), 7.39 (dd, J=7.0, 4.2 Hz, 1H), 4.90 (s, 1H), 4.55 (s, 3H), 4.05-3.85 (m, 5H), 3.70 (td, J=15.9, 9.3 Hz, 1H), 2.99-2.85 (m, 4H), 1.24-1.12 (m, 6H). MS (ESI): m/z=483.2 [M+1]$^+$.

Example 140. N-(2-Methyl-6-morpholino-1-oxoisoindolin-5-yl)pyrazolo[1,5-a]pyrimidine-3-carboxamide

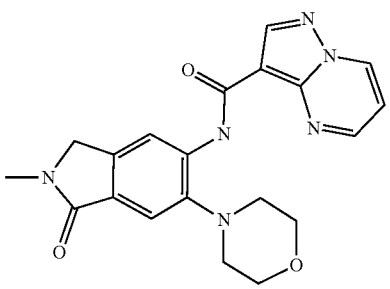 [SMILES: CN1Cc2cc(NC(=O)c3cnn4cccnc34)c(N3CCOCC3)cc2C1=O]

N-(2-Methyl-6-morpholino-1-oxoisoindolin-5-yl)pyrazolo[1,5-a]pyrimidine-3-carboxamide (55 mg, 17%) was prepared following the procedure described for Example 138. $^1$H NMR (400 MHz, DMSO-d6) δ 10.88 (s, 1H), 9.40 (dd, J=7.0, 1.6 Hz, 1H), 8.99 (dd, J=4.2, 1.6 Hz, 1H), 8.74 (d, J=4.6 Hz, 2H), 7.56 (s, 1H), 7.38 (dd, J=7.0, 4.2 Hz, 1H), 4.45 (s, 2H), 3.94-3.84 (m, 4H), 3.07 (s, 3H), 2.97-2.86 (m, 4H). MS (ESI): m/z=393.1 [M+1]$^+$.

Example 141. N-(2-(Hydroxymethyl)-2-methyl-7-morpholinochroman-6-yl)pyrazolo[1,5-a]pyrimidine-3-carboxamide

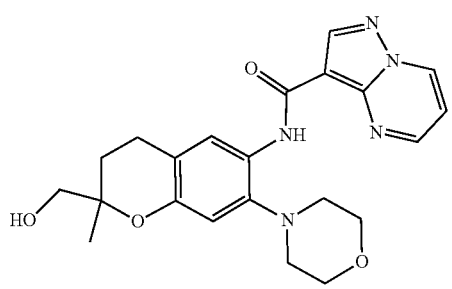 [SMILES: CC1(CO)CCc2cc(NC(=O)c3cnn4cccnc34)c(N3CCOCC3)cc2O1]

Step A. 2-((tert-Butyldimethylsilyloxy)methyl)-7-chloro-2-methylchroman-4-one

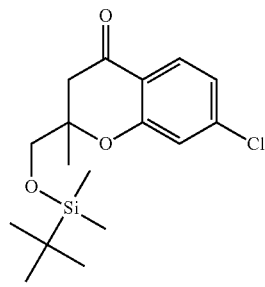 [SMILES: CC1(CO[Si](C)(C)C(C)(C)C)CC(=O)c2ccc(Cl)cc2O1]

A mixture of 1-(4-chloro-2-hydroxyphenyl)ethanone (513.0 mg, 3.01 mmol) pyrrolidine (0.5 mL, 6.01 mmol) and 1-(tert-butyldimethylsilyloxy)propan-2-one (849.56 mg, 4.51 mmol) in methyl alcohol (10 mL) was stirred at reflux for 16h. After concentration, the residue was purified on silica gel chromatography using ethyl acetate:petroleum ether (5:95) as eluting solvents to afford 2-[[tert-butyl(dimethyl)silyl]oxymethyl]-7-chloro-2-methyl-chroman-4-one (685 mg, 57%) as an orange oil. MS (ESI): m/z=341.1 [M+1]$^+$.

Step B. 2-((tert-Butyldimethylsilyloxy)methyl)-7-chloro-2-methylchroman-4-ol

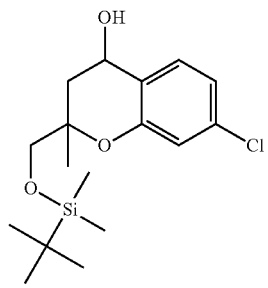 [SMILES: CC1(CO[Si](C)(C)C(C)(C)C)CC(O)c2ccc(Cl)cc2O1]

To a solution of 2-[[tert-butyl(dimethyl)silyl]oxymethyl]-7-chloro-2-methyl-chroman-4-one (102.0 mg, 0.30 mmol) in methyl alcohol (15 mL) was added sodium borohydride (34.11 mg, 0.90 mmol). The mixture was stirred at 25° C. for 3h. Water and ethyl acetate (30 mL) was added. The organic layer was separated, dried sodium sulfate and concentrated to afford 2-[[tert-butyl(dimethyl)silyl]oxymethyl]-7-chloro-2-methyl-chroman-4-ol (101 mg, crude) as a yellow oil, which was used directly to next step without further purification. MS (ESI): m/z=365.2 [M+23]$^+$.

Step C. (7-Chloro-2-methylchroman-2-yl)methanol

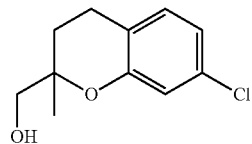

A mixture of 2-[[tert-butyl(dimethyl)silyl]oxymethyl]-7-chloro-2-methyl-chroman-4-ol (513 mg, 1.5 mmol) and triethylsilane (6.85 mL, 42.75 mmol) in trifluoroacetic acid (25 mL) was stirred at 50° C. overnight. Saturated sodium bicarbonate solution was added until pH=7.0. The aqueous phase was extracted with ethyl acetate (20 mL). The organic layer was dried over sodium sulfate and concentrated in vacuo to afford (7-chloro-2-methyl-chroman-2-yl)methanol (115 mg, crude) as a yellow oil, which was used directly to next step without further purification. $^1$H NMR (400 MHz, CDCl$_3$): δ 6.98 (d, J=8.0 Hz, 1H), 8.87-8.80 (m, 2H), 4.43-4.32 (m, 2H), 2.82-2.70 (m, 2H), 2.02-1.92 (m, 1H), 1.87-1.79 (m, 1H), 1.36 (s, 3H).

Step D. (7-Chloro-2-methylchroman-2-yl)methyl benzoate

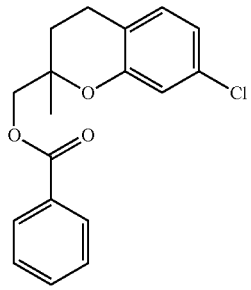 [SMILES: CC1(COC(=O)c2ccccc2)CCc2ccc(Cl)cc2O1]

A mixture of (7-chloro-2-methyl-chroman-2-yl)methanol (115 mg, 0.54 mmol), benzoyl chloride (91 mg, 0.65 mmol) and triethylamine (164 mg, 1.62 mmol) in dichloromethane (10 mL) was stirred overnight. After concentration, the residue was purified by silica gel chromatography using ethyl acetate:petroleum ether (1:20 to 1:10) as eluting solvents to afford (7-chloro-2-methylchroman-2-yl)methyl benzoate (130 mg, 76%) as a yellow oil. MS (ESI): m/z=317.2 [M+1]$^+$.

Step E. (7-Chloro-2-methyl-6-nitrochroman-2-yl)methyl benzoate

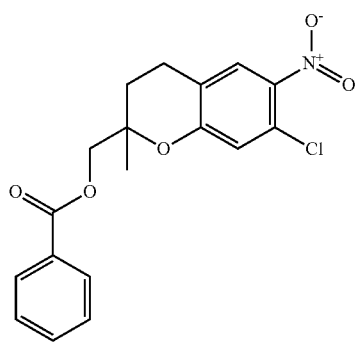 [SMILES: CC1(COC(=O)c2ccccc2)CCc2cc([N+](=O)[O-])c(Cl)cc2O1]

To a solution of (7-Chloro-2-methylchroman-2-yl)methyl benzoate (130 mg, 0.41 mmol) in dichloromethane (5 mL) was added fuming nitric acid (1 mL) drop wise. Water and ethyl acetate (20 mL) was added. The organic layer was dried over sodium sulfate and concentrated under reduced pressure to afford (7-Chloro-2-methyl-6-nitrochroman-2-yl)methyl benzoate (110 mg, crude) as a yellow solid, which was used directly to next step without further purification. MS (ESI): m/z=362.1 [M+1]$^+$.

Step F. (2-Methyl-7-morpholino-6-nitro-chroman-2-yl)methyl benzoate

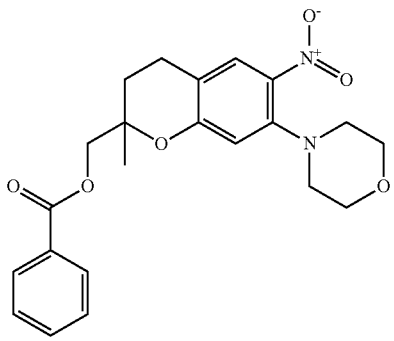 [SMILES: CC1(COC(=O)c2ccccc2)CCc2cc([N+](=O)[O-])c(N3CCOCC3)cc2O1]

A mixture of morpholine (5 mL, 57.16 mmol) and (7-chloro-2-methyl-6-nitro-chroman-2-yl)methylbenzoate (110.0 mg, 0.3 mmol) was stirred at 100° C. overnight. The reaction was concentrated to dryness to afford (2-methyl-7-morpholino-6-nitro-chroman-2-yl)methyl benzoate (115 mg, crude) as a yellow solid, which was used directly to next step without further purification. MS (ESI): m/z=413.2 [M+1]$^+$.

Step G. (2-Methyl-7-morpholino-6-nitro-chroman-2-yl)methanol

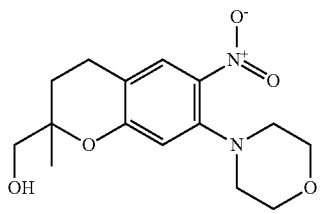 [SMILES: CC1(CO)CCc2cc([N+](=O)[O-])c(N3CCOCC3)cc2O1]

A solution of (2-methyl-7-morpholino-6-nitro-chroman-2-yl)methyl benzoate (94.0 mg, 0.23 mmol) in methyl alcohol (10 mL) at 0° C. was added sodium methanolate (36.92 mg, 0.68 mmol). The mixture was stirred for 1h at room temperature. The solvent was removed under reduced pressure. The residue was dissolved by dichloromethane (25 mL) and saturated ammonium chloride solution was added. The organic layer was washed with water, brine, dried over sodium sulfate and concentrated to afford (2-methyl-7-morpholino-6-nitro-chroman-2-yl)methanol (137 mg, crude) as a yellow solid, which was used directly to next step without further purification. MS (ESI): m/z=309.1 [M+1]$^+$.

Step H. (6-Amino-2-methyl-7-morpholino-chroman-2-yl)methanol

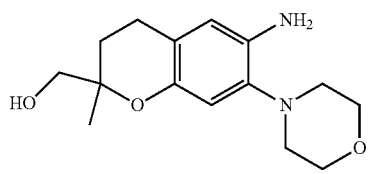 [SMILES: CC1(CO)CCc2cc(N)c(N3CCOCC3)cc2O1]

A mixture of palladium on carbon (20 mg) and (2-methyl-7-morpholino-6-nitro-chroman-2-yl)methanol (131.19 mg, 0.43 mmol) in methyl alcohol (10 mL) was stirred at room temperature under hydrogen atmosphere for 30 min. After filtration and concentration, it was afforded (6-amino-2-methyl-7-morpholino-chroman-2-yl)methanol (79 mg, 60%) as a light yellow solid, which was used directly to next step without further purification. MS (ESI): m/z=279.1 [M+1]$^+$.

Step L. N-[2-(Hydroxymethyl)-2-methyl-7-morpholino-chroman-6-yl]pyrazolo[1,5-a]pyrimidine-3-carboxamide

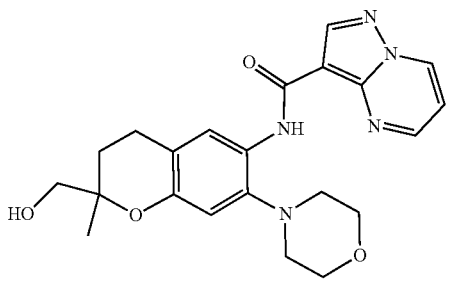 [SMILES: CC1(CO)CCc2cc(NC(=O)c3cnn4cccnc34)c(N3CCOCC3)cc2O1]

A mixture of pyrazolo[1,5-a]pyrimidine-3-carboxylic acid (46.3 mg, 0.28 mmol), diisopropylethylamine (73.36 mg, 0.57 mmol) and (7-azabenzotriazol-1-yloxy)tripyrrolidino-phosphonium hexafluorophosphate (162.77 mg, 0.31 mmol) in N,N-dimethylformamide (2 mL) was stirred at 0° C. Then (6-amino-2-methyl-7-morpholino-chroman-2-yl) methanol (79.0 mg, 0.28 mmol) in N,N-dimethylformamide (1 mL) was added. The mixture was stirred at room temperature for 2h. The crude was purified by reverse phase chromatography (Xbridge 21.2*250 mm c18, 10 um; A: acetonitrile, 25-75%; B: 10 mM ammonium bicarbonate in water) to afford N-[2-(hydroxymethyl)-2-methyl-7-morpholino-chroman-6-yl]pyrazolo[1,5-a]pyrimidine-3-carboxamide (55 mg, 46%) as an off-white solid. $^1$H NMR (400 MHz, CDCl$_3$): δ 10.41 (s, 1H), 8.83 (dd, J=1.6, 6.8 Hz, 1H), 8.79-8.76 (m, 2H), 8.37 (s, 1H), 7.06 (dd, J=4.0, 7.2 Hz, 1H), 6.68 (s, 1H), 3.98-3.92 (m, 4H), 3.69-3.60 (m, 2H), 2.96-2.89 (m, 4H), 2.89-2.76 (m, 2H), 2.08-1.98 (m, 1H), 1.89 (t, J=6.4 Hz, 1H), 1.77-1.70 (m, 1H), 1.29 (s, 3H). MS (ESI): m/z=424.2 [M+1]$^+$.

Example 142. N-(6-Morpholinospiro[3H-benzofuran-2,4'-piperidine]-5-yl)pyrazolo[1,5-a]pyrimidine-3-carboxamide

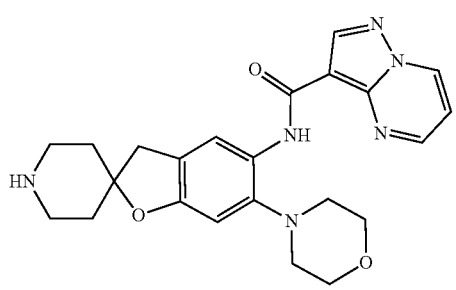 [SMILES: O=C(Nc1cc2c(cc1N1CCOCC1)OC1(CCNCC1)C2)c1cnn2cccnc12]

Step A. tert-Butyl 4-[(2,4-difluorophenyl)methyl]-4-hydroxy-piperidine-1-carboxylate

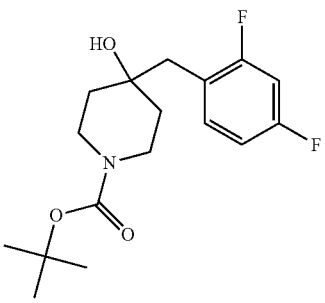 [SMILES: CC(C)(C)OC(=O)N1CCC(O)(Cc2ccc(F)cc2F)CC1]

To a solution of magnesium (2400 mg, 100 mmol) and iodine (180 mg, 0.71 mmol) in diethyl ether (25 mL) at reflux was added 1-(bromomethyl)-2,4-difluorobenzene (8200.0 mg, 39.61 mmol) slowly and stirred for 30 min. To a solution of tert-butyl 4-oxopiperidine-1-carboxylate (6500.0 mg, 32.62 mmol) in diethyl ether (200 mL) was added Grignard reagent at −78° C. and the reaction was stirred room temperature for 2h. Water and EtOAc (200 mL) was added. The organic layer was separated and dried over sodium sulfate. After concentration under reduced pressure, the residue was purified by silica gel chromatography using ethyl acetate:petroleum ether (from 1:4 to 1:2) to afford tert-butyl 4-[(2,4-difluorophenyl)methyl]-4-hydroxy-piperidine-1-carboxylate (9500 mg, 730%) as a white solid. MS (ESI): m/z=350.1 [M+23].

Step B. tert-Butyl 6-fluorospiro[3H-benzofuran-2,4'-piperidine]-1'-carboxylate

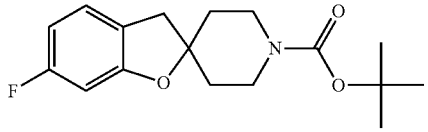 [SMILES: CC(C)(C)OC(=O)N1CCC2(CC1)Cc1ccc(F)cc1O2]

A mixture of tert-butyl 4-[(2,4-difluorophenyl)methyl]-4-hydroxy-piperidine-1-carboxylate (491.0 mg, 1.5 mmol) and potassium tert-butanolate (420.74 mg, 3.75 mmol) in tetrahydrofuran (30 mL) was stirred at 65° C. for 3h. Water was added. The aqueous layer was extracted with ethylacetate (60 mL). The organic layer was dried over sodium sulfate and concentrated to afford tert-butyl 6-fluorospiro[3H-benzofuran-2,4'-piperidine]-1'-carboxylate (409 mg, crude) as a yellow solid, which was used directly to next step without further purification. MS(ESI): m/z=252.2 [M-55]$^+$.

Step C. 6-Fluorospiro[3H-benzofuran-2,4'-piperidine]

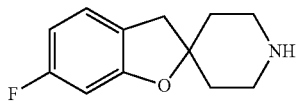 [SMILES: Fc1ccc2c(c1)OC1(CCNCC1)C2]

To a solution of tert-butyl 6-fluorospiro[3H-benzofuran-2,4'-piperidine]-1'-carboxylate (270.0 mg, 0.88 mmol) in dichloromethane (9 mL), was added trifluoroacetic acid (1 mL). The reaction solution was stirred for 2h at room temperature. Saturated sodium bicarbonate solution was added until pH=7.0. The aqueous layer was extracted twice with 20 mL of dichloromethane. The combined organic layer was washed with saturated brine and dried over anhydrous magnesium sulfate. After removal of the solvent, it was afforded 6-fluorospiro[3H-benzofuran-2,4'-piperidine] (189 mg, crude) as a yellow solid, which was used directly to next step without further purification. MS (ESI): m/z=208.2 [M+1]+.

Step D. 6-Fluoro-5-nitro-spiro[3H-benzofuran-2,4'-piperidine]

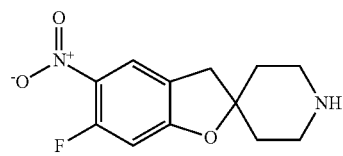

To a solution of 6-fluorospiro[3H-benzofuran-2,4'-piperidine] (171.0 mg, 0.8300 mmol) in dichloromethane (10 ml) was added concentrated nitric acid (0.5 mL, 8 mmol). The reaction was stirred at 25° C. for 1h. Water was added. Then saturated sodium bicarbonate was added until pH=7.0. The aqueous was extracted with dichloromethane (50 mL). The organic layer was dried over sodium sulfate and concentrated in vacuo to afford 6-fluoro-5-nitro-spiro[3H-benzofuran-2,4'-piperidine] (135 mg, crude) as a yellow solid, which was used directly to next step without further purification. MS (ESI): m/z=253.2 [M+1]+.

Step E. tert-Butyl 6-fluoro-5-nitro-spiro[3H-benzofuran-2,4'-piperidine]-1'-carboxylate

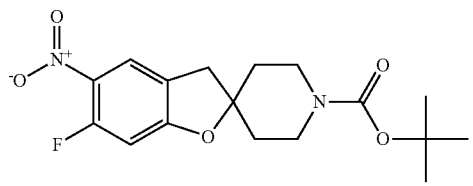

A mixture of 6-fluoro-5-nitro-spiro[3H-benzofuran-2,4'-piperidine] (135.0 mg, 0.54 mmol), triethylamine (108.31 mg, 1.07 mmol) and di-tert-butyl dicarbonate (80.28 mg, 0.80 mmol) was stirred at room temperature for 2h. Then the reaction was concentrated in vacuo to obtained tert-butyl 6-fluoro-5-nitro-spiro[3H-benzofuran-2,4'-piperidine]-1'-carboxylate (with 7a impurity) (270 mg, crude) as a yellow solid, which was used directly to next step without further purification. MS (ESI): m/z=297.1 [M-55]+.

Step F. tert-Butyl 6-morpholino-5-nitro-3H-spiro[benzofuran-2,4'-piperidine]-1'-carboxylate

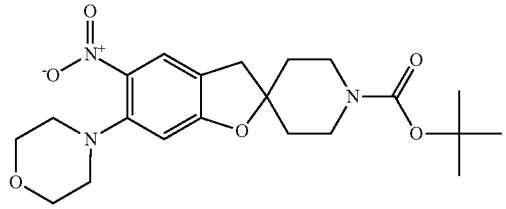

A mixture of tert-butyl 6-fluoro-5-nitro-3H-spiro[benzofuran-2,4'-piperidine]-1'-carboxylate (270.0 mg, 0.38 mmol), morpholine (66.76 mg, 0.77 mmol) and potassium carbonate (132.09 mg, 0.96 mmol) in acetonitrile (6 mL) was stirred at room temperature overnight. Then to the reaction was added water and the aqueous layer was extracted twice with 20 mL of ethyl acetate. The combined organic layer was washed with saturated brine and then dried over anhydrous magnesium sulfate. After removal of solvents, the residue was purified on silica gel chromatography using ethyl acetate:petroleum ether (1:1) as eluting solvents to afford tert-butyl 6-morpholino-5-nitro-3H-spiro[benzofuran-2,4'-piperidine]-1'-carboxylate (73 mg, 42%) as a yellow oil. MS (ESI): m/z=420.3 [M+1]+.

Step G. tert-Butyl 5-amino-6-morpholino-spiro[3H-benzofuran-2,4'-piperidine]-1'-carboxylate

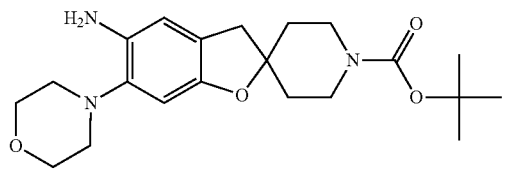 [SMILES: CC(C)(C)OC(=O)N1CCC2(CC1)Cc1cc(N)c(N3CCOCC3)cc1O2]

A mixture of palladium on carbon (20.0 mg, 10% wt) and tert-butyl 6-morpholino-5-nitro-spiro[3H-benzofuran-2,4'-piperidine]-1'-carboxylate (73.0 mg, 0.17 mmol) in methylalcohol (10 mL) was stirred at room temperature under hydrogen atmosphere for 2h. After filtration and concentration under reduced pressure, it was afforded tert-butyl 5-amino-6-morpholino-spiro[3H-benzofuran-2,4'-piperidine]-1'-carboxylate (61 mg, 79%) as a yellow solid. MS (ESI): m/z=390.2 [M+1]+.

Step H. tert-Butyl 5-amino-6-morpholino-spiro[3H-benzofuran-2,4'-piperidine]-1'-carboxylate

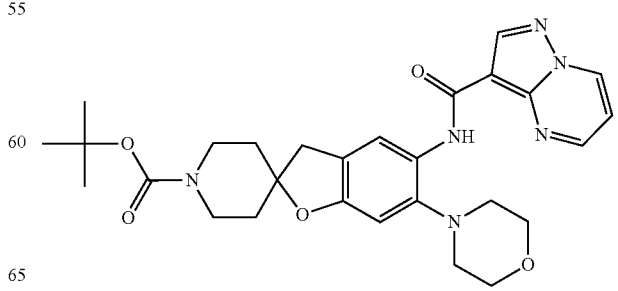

A mixture of pyrazolo[1,5-a]pyrimidine-3-carboxylic acid (25.55 mg, 0.16 mmol), (7-azabenzotriazol-1-yloxy)tripyrrolidino-phosphonium hexafluorophosphate (89.82 mg, 0.17 mmol) and N-ethyl-N-isopropylpropan-2-amine (60.72 mg, 0.47 mmol) in N,N-dimethylformanide (2 mL) was stirred at 0° C. Then tert-butyl 5-amino-6-morpholino-spiro[3H-benzofuran-2,4'-piperidine]-1'-carboxylate (61.0 mg, 0.16 mmol) in N,N-dimethylformanide (1 mL) was added and the reaction was stirred at room temperature for 2h. The crude was purified by reverse phase chromatography (Gilson 281-G, Phenomenex, Gemini C18, 21.2×100 mm. 5 um, 110A, A: acetonitrile 55-70%; B: 0.05% formic acid in water) to afford tert-butyl 6-morpholino-5-(pyrazolo[1,5-a]pyrimidine-3-carbonylamino)spiro[3H-benzofuran-2,4'-piperidine]-1'-carboxylate (73 mg, 87%) as a yellow solid. MS (ESI): m/z=535.3 [M+1]+.

Step L. N-(6-morpholinospiro[3H-benzofuran-2,4'-piperidine]-5-yl)pyrazolo[1,5-a]pyrimidine-3-carboxamide

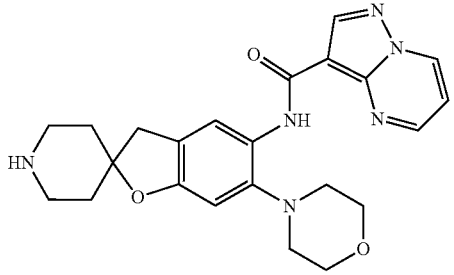

To a solution of tert-butyl 6-morpholino-5-(pyrazolo[1,5-a]pyrimidine-3-carbonylamino)spiro[3H-benzofuran-2,4'-piperidine]-1'-carboxylate (73.0 mg, 0.14 mmol) in dichloromethane (5 mL) was added trifluoroacetic acid (0.5 mL). The reaction solution was stirred for 2h at room temperature. To the reaction solution, an aqueous saturated sodium bicarbonate was added until pH=7.0. The aqueous layer was extracted twice with 20 mL of dichloromethane. The combined organic layer was washed with saturated brine and then dried over anhydrous magnesium sulfate. After concentration, the residue was purified by reverse phase chromatography (Gilson 281-G, Phenomenex, Gemini C18, 21.2×100 mm. 5 um, 110A, A: acetonitrile, 55-70%; B: 0.05% formic acid in water) to afford N-(6-morpholinospiro[3H-benzofuran-2,4'-piperidine]-5-yl)pyrazolo[1,5-a]pyrimidine-3-carboxamide (29 mg, 49%) as a yellow solid. $^1$H NMR (400 MHz, MeOD-d$_4$) δ 9.03 (dd, J=1.6, 7.2 Hz, 1H), 8.82 (dd, J=1.6, 4.0 Hz, 1H), 8.56 (s, 1H), 8.41 (s, 1H), 8.20 (s, 1H), 7.19 (dd, J=4.0, 7.2 Hz, 1H), 6.69 (s, 1H), 3.87-3.80 (m, 4H), 3.31-3.20 (m, 4H), 3.04 (s, 1H), 2.82-2.76 (m, 4H), 2.10-2.02 (m, 2H), 1.98-1.88 (m, 2H). MS (ESI): m/z=435.3 [M+1]+.

Example 143. N-(7-Cyano-2,2-dimethyl-6-morpholino-2,3-dihydrobenzofuran-5-yl)pyrazolo[1,5-a]pyrimidine-3-carboxamide

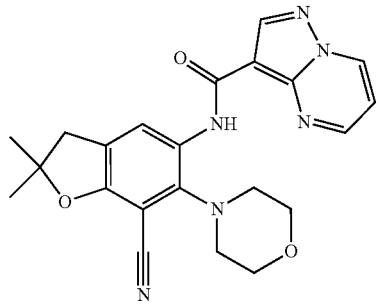 [SMILES: CC1(C)Cc2cc(NC(=O)c3cnn4cccnc34)c(N3CCOCC3)c(C#N)c2O1]

Step A. 2-Chloro-6-(2-methylallyloxy)benzonitrile

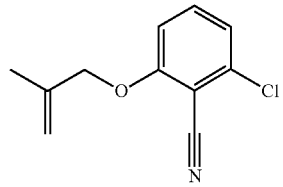

A mixture of 2-chloro-6-hydroxy-benzonitrile (500.0 mg, 3.26 mmol), 3-bromo-2-methylpropene (0.39 mL, 3.91 mmol) and potassium carbonate (898.6 mg, 6.51 mmol) in acetonitrile (10 mL) was stirred at 25° C. overnight. The solid was filtered off, the filtrate was concentrated and purified by silica gel chromatography using petroleum ether:ethyl acetate (100:1) to afford 2-chloro-6-(2-methylallyloxy)benzonitrile (699.0 mg, 98%) as a light oil. MS (ESI): m/z=208.1 [M+1]+.

Step B. 6-Chloro-2-hydroxy-3-(2-methylallyl)benzonitrile

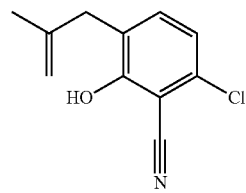

A mixture of 2-chloro-6-(2-methylallyloxy)benzonitrile (100.0 mg, 0.48 mmol) in N,N-dimethylformamide (3 mL) was stirred at 220° C. under microwave condition for 2h. Water was added. The aqueous phase was extracted with ethyl acetate (20 mL). The organic layer was washed with brine and dried over sodium sulfate. The organic layer was concentrated to afford 6-chloro-2-hydroxy-3-(2-methylallyl)benzonitrile (70 mg, 70%) as a light oil. (ESI): m/z=208.2 [M+1]+.

Step C. 6-Chloro-2,2-dimethyl-2,3-dihydrobenzofuran-7-carbonitrile

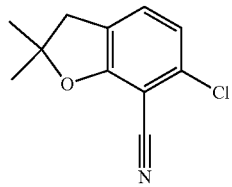

To a mixture of 6-chloro-2-hydroxy-3-(2-methylallyl)benzonitrile (200.0 mg, 0.96 mmol) in dichloromethane (10 mL) was added 3-chloroperoxybenzoic acid (292.3 mg, 1.44 mmol) at 0° C. The mixture was stirred at 25° C. overnight. Water and dichloromethane (20 mL) was added. The organic layer was washed by saturated sodium bicarbonate, brine and dried over sodium sulfate. After concentration, it was afforded 6-chloro-2,2-dimethyl-3H-benzofuran-7-carbonitrile (200.0 mg, crude) as a colorless oil, which was used to next step without further purification. MS (ESI): m/z=208.1 [M+1]$^+$.

Step D. 6-Chloro-2,2-dimethyl-5-nitro-2,3-dihydrobenzofuran-7-carbonitrile

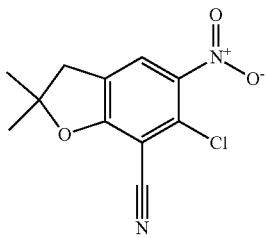 [SMILES: CC1(C)Cc2cc([N+](=O)[O-])c(Cl)c(C#N)c2O1]

A mixture of 6-chloro-2,2-dimethyl-3H-benzofuran-7-carbonitrile (200.0 mg, 0.96 mmol) in dichloromethane (10 mL) was added fuming nitric acid (0.5 mL) drop wise at 25° C. The mixture was stirred at 25° C. for 30 min. The mixture was poured into ice water. The aqueous layer was extracted with ethyl acetate (30 mL). The organic layer was dried over sodium sulfate. After concentration, the residue was purified by silica gel chromatography using ethyl acetate:petroleum ether (1:9) to afford 6-chloro-2,2-dimethyl-5-nitro-3H-benzofuran-7-carbonitrile (200.0 mg, 74%) as a light grey solid. MS (ESI): m/z=253.1 [M+1]$^+$.

Step E. 2,2-Dimethyl-6-morpholino-5-nitro-2,3-dihydrobenzofuran-7-carbonitrile

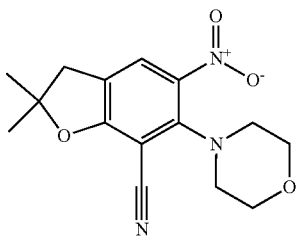 [SMILES: CC1(C)Cc2cc([N+](=O)[O-])c(N3CCOCC3)c(C#N)c2O1]

A mixture of 6-chloro-2,2-dimethyl-5-nitro-3H-benzofuran-7-carbonitrile (100.0 mg, 0.40 mmol) in morpholine (2 mL) in a sealed vial was stirred at 110° C. overnight. The mixture was concentrated and the residue was purified by silica gel chromatography using ethyl acetate:petroleum ether (1:2) to afford 2,2-dimethyl-6-morpholino-5-nitro-3H-benzofuran-7-carbonitrile (100 mg, 79%) as a yellow oil. MS (ESI): m/z=304.2 [M+1]$^+$.

Step F. 5-Amino-2,2-dimethyl-6-morpholino-2,3-dihydrobenzofuran-7-carbonitrile

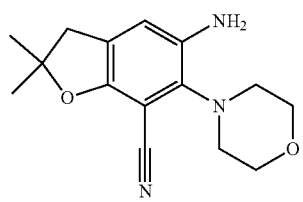 [SMILES: CC1(C)Cc2cc(N)c(N3CCOCC3)c(C#N)c2O1]

A mixture of 2,2-dimethyl-6-morpholino-5-nitro-3H-benzofuran-7-carbonitrile (80.0 mg, 0.26 mmol) and palladium on carbon (8 mg, 10% wt) in methanol (10 mL) was stirred at 25° C. under hydrogen atmosphere for 1h. After filtration and concentration under reduced pressure, it was afforded 5-amino-2,2-dimethyl-6-morpholino-3H-benzofuran-7-carbonitrile (70.0 mg, crude) as a green oil, which was used directly to next step without further purification. MS (ESI): m/z=274.1[M+1]$^+$.

Step G. N-(7-Cyano-2,2-dimethyl-6-morpholino-2,3-dihydrobenzofuran-5-yl)pyrazolo[1,5-a]pyrimidine-3-carboxamide

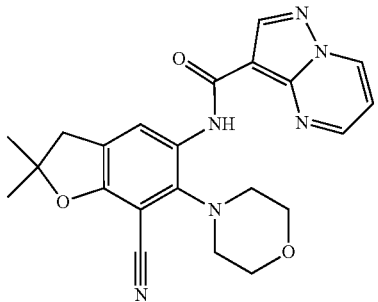 [SMILES: CC1(C)Cc2cc(NC(=O)c3cnn4cccnc34)c(N3CCOCC3)c(C#N)c2O1]

A mixture of pyrazolo[1,5-a]pyrimidine-3-carboxylic acid (41.8 mg, 0.26 mmol), (7-azabenzotriazol-1-yloxy)tripyrrolidinophoshoniumhexafluorophosphate (133.4 mg, 0.26 mmol) and N-ethyl-N-isopropylpropan-2-amine (99.1 mg, 0.77 mmol) in N,N-dimethylformamide (5 mL) was stirred at room temperature for 30 min. 5-Amino-2,2-dimethyl-6-morpholino-3H-benzofuran-7-carbonitrile (70.0 mg, 0.26 mmol) was added. The resulting mixture was stirred at room temperature overnight. Water and ethyl acetate (30 mL) was added. The organic layer was separated the organic layer was washed with brine and dried over sodium sulfate. After concentration, the residue was purified by silica gel chromatography using ethyl acetate:petroleum ether (10:1) and then further purified by preparative HPLC(Column: Xbridge 21.2*250 mm c18, 10 um; A: acetonitrile, 25-75%;

B:10 mM ammonium bicarbonatein water) to afford N-(7-cyano-2,2-dimethyl-6-morpholino-3H-benzofuran-5-yl)pyrazolo[1,5-a]pyrimidine-3-carboxamide (28 mg, 26%) as a yellow solid. $^1$H NMR (400 MHz, CDCl$_3$): δ 10.65 (s, 1H), 8.85 (d, J=7.2 Hz, 1H), 8.82-8.77 (m, 2H), 8.73 (s, 1H), 7.13-7.08 (m, 1H), 4.05-3.95 (m, 4H), 3.73-2.70 (m, 6H), 1.54 (s, 6H). MS (ESI): m/z=419.2[M+1]$^+$.

Example 144. N-(2-(Difluoromethyl)-2-methyl-6-morpholino-2,3-dihydrobenzofuran-5-yl)-6-methylpyrazolo[1,5-a]pyrimidine-3-carboxamide

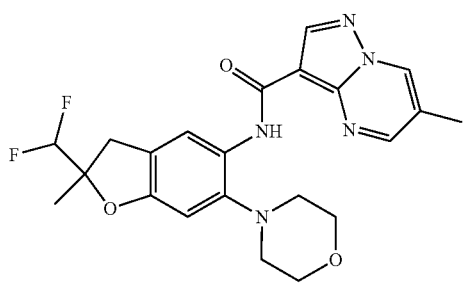

Step A. Methyl 2-methyl-6-morpholino-5-nitro-2,3-dihydrobenzofuran-2-carboxylate

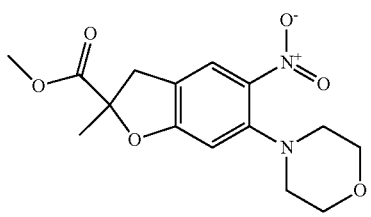 [SMILES: COC(=O)C1(C)Cc2cc([N+](=O)[O-])c(N3CCOCC3)cc2O1]

A mixture of 6-fluoro-2-methyl-5-nitro-3H-benzofuran-2-carboxylate (Intermediate 3, step D) (300.0 mg, 1.18 mmol) in morpholine (2 mL) in a sealed tube was stirred at 80° C. overnight. The mixture was concentrated and the residue was purified by silica gel chromatography using ethyl acetate:petroleum ether (1:6) as eluting solvents to afford methyl 2-methyl-6-morpholino-5-nitro-3H-benzofuran-2-carboxylate (329.0 mg, 83%) as yellow oil. MS (ESI): m/z=323.1 [M+1]$^+$.

Step B. 2-Methyl-6-morpholino-5-nitro-2,3-dihydrobenzofuran-2-carbaldehyde

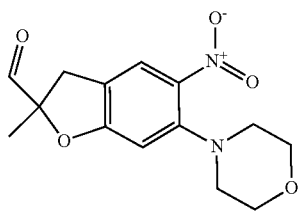 [SMILES: CC1(C=O)Cc2cc([N+](=O)[O-])c(N3CCOCC3)cc2O1]

To a mixture of methyl 2-methyl-6-morpholino-5-nitro-3H-benzofuran-2-carboxylate (315.0 mg, 0.89 mmol) in dichloromethane (10 mL) was added diisobutyl aluminium hydride (1.33 mL, 1.33 mmol) drop wise at -78° C. over 5 min. Then the mixture was stirred at -78° C. for 2h. The mixture was quenched with sodium sulfate decahydrate. The reaction was filtered and the filtrate was concentrated and the residue was purified by silica gel chromatography using ethyl acetate:petroleum ether (1:6) as eluting solvents to afford 2-methyl-6-morpholino-5-nitro-3H-benzofuran-2-carbaldehyde (163.0 mg, 56%) as a yellow solid. (ESI): m/z=293.1 [M+1]$^+$.

Step C. 4-(2-(Difluoromethyl)-2-methyl-5-nitro-2,3-dihydrobenzofuran-6-yl)morpholine

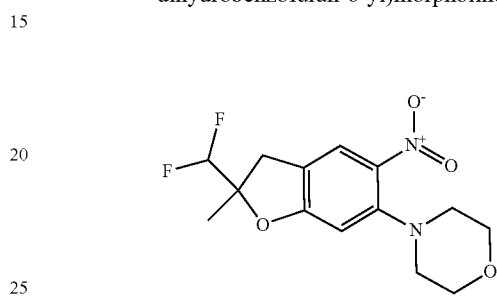

To a mixture of 2-methyl-6-morpholino-5-nitro-3H-benzofuran-2-carbaldehyde (163.0 mg, 0.56 mmol) in dichloromethane (10 mL) was added drop wise diethylaminosulfurtrifluoride (561.8 mg, 2.79 mmol) at -78° C. The mixture was stirred at -78° C. overnight, concentrated and purified by silica gel chromatography using ethyl acetate:petroleum ether (1:9) as eluting solvents to afford 4-[2-(difluoromethyl)-2-methyl-5-nitro-3H-benzofuran-6-yl]morpholine (77.0 mg, 42%) as a yellow solid. (ESI): m/z=315.1 [M+1]$^+$.

Step D. 2-(Difluoromethyl)-2-methyl-6-morpholino-2,3-dihydrobenzofuran-5-amine

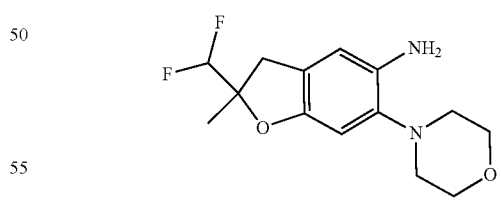

A mixture of 4-[2-(difluoromethyl)-2-methyl-5-nitro-3H-benzofuran-6-yl]morpholine (77.0 mg, 0.25 mmol) and palladium on carbon (15 mg, 15% wt) in methyl alcohol (5 mL) was stirred at 25° C. under hydrogen atmosphere for 1h. After filtration, the filtrate was concentrated under reduced pressure to afford 2-(difluoromethyl)-2-methyl-6-morpholino-3H-benzofuran-5-amine (55.0 mg, crude) as a colorless oil, which was used to next step without purification further. (ESI): m/z=285.1 [M+1]$^+$.

Step E. N-(2-(Difluoromethyl)-2-methyl-6-morpholino-2,3-dihydrobenzofuran-5-yl)-6-methylpyrazolo[1,5-a]pyrimidine-3-carboxamide

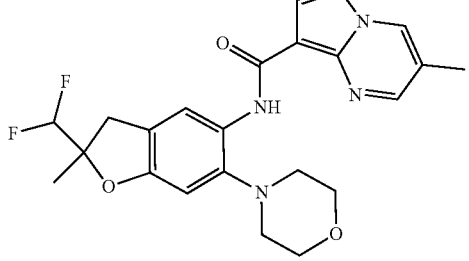

A mixture of 2-(difluoromethyl)-2-methyl-6-morpholino-3H-benzofuran-5-amine (55.0 mg, 0.19 mmol), 6-methylpyrazolo[1,5-a]pyrimidine-3-carboxylic acid (Example 7, step A) (34.27 mg, 0.19 mmol), (7-azabenzotriazol-1-yloxy)tripyrrolidinophosphoniumhexafluorophosphate (100.9 mg, 0.19 mmol) and N-ethyl-N-isopropylpropan-2-amine (75.0 mg, 0.58 mmol) in N,N-dimethylformamide (5 mL) was stirred at room temperature overnight. Water and ethyl acetate (30 mL) were added and the organic layer was separated. The organic layer was washed with brine and dried over sodium sulfate. After concentration, the residue was purified by silica gel chromatography using ethyl acetate:petroleum ether (10:1) as eluting solvents to afford N-[2-(difluoromethyl)-2-methyl-6-morpholino-3H-benzofuran-5-yl]-6-methyl-pyrazolo[1,5-a]pyrimidine-3-carboxamide (38.0 mg, 44%) as a yellow solid. $^1$H NMR (400 MHz, DMSO-d$_6$): δ 10.40 (s, 1H), 9.24 (s, 1H), 8.87 (s, 1H) 8.60 (s, 1H), 8.36 (s, 1H), 6.85 (s, 1H), 6.18 (t, J=54.8 Hz, 1H), 3.88-3.82 (m, 4H), 3.36 (d, J=17.2 Hz, 1H), 3.06 (d, J=16.4 Hz, 1H), 2.86-2.79 (m, 4H), 2.44 (s, 3H) 1.46 (s, 3H). MS (ESI): m/z=444.1[M+1]$^+$.

Example 145. [1-[2,2-Dimethyl-5-(pyrazolo[1,5-a]pyrimidine-3-carbonylamino)-3H-benzofuran-6-yl]-4-piperidyl]methyl diethyl phosphate

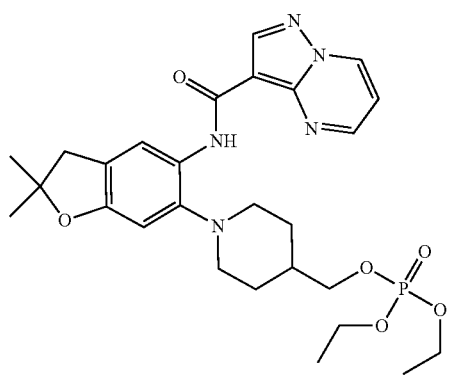 [SMILES: CCOP(=O)(OCC)OCC1CCN(c2cc3c(cc2NC(=O)c2cnn4cccnc24)CC(C)(C)O3)CC1]

Step A. [1-(2,2-Dimethyl-5-nitro-3H-benzofuran-6-yl)-4-piperidyl]methyl diethyl phosphate

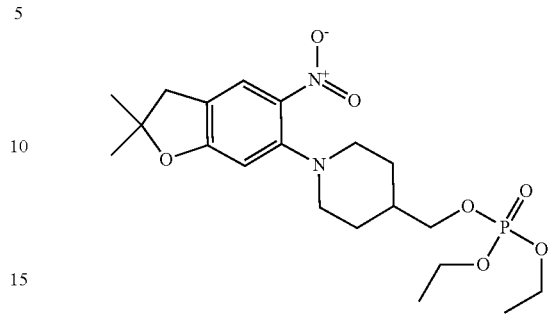

To a solution of [1-(2,2-dimethyl-5-nitro-3H-benzofuran-6-yl)-4-piperidyl]methanol (Example 4, Step A) (270 mg, 0.85 mmol), iodine (22 mg, 0.09 mmol) and diethyl phosphate (141 mg, 1.02 mmol) in dichloromethane (10 mL) was added hydrogen peroxide (0.31 mL, 4.26 mmol) then the mixture was stirred at 20° C. for 20h. Water and dichloromethane (50 mL) was added and the aqueous phase was extracted with dichloromethane (2×50 mL). The combined organic phases were washed with brine, dried over sodium sulfate and concentrated under reduced pressure. The residue was purified by silica gel chromatography using ethyl acetate:petroleum ether (1:1 to 2:1) as eluting solvents to afford [1-(2,2-dimethyl-5-nitro-3H-benzofuran-6-yl)-4-piperidyl]methyl diethyl phosphate (113 mg, 23%) as a yellow solid. MS (ESI): m/z=443.1 [M+1]$^+$.

Step B. [1-(5-Amino-2,2-dimethyl-3H-benzofuran-6-yl)-4-piperidyl]methyl diethyl phosphate

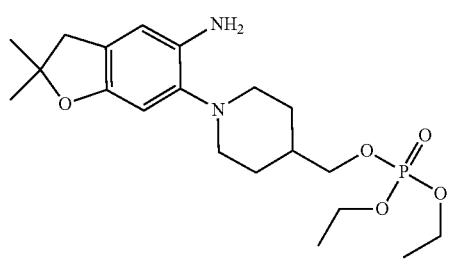 [SMILES: CCOP(=O)(OCC)OCC1CCN(c2cc3c(cc2N)CC(C)(C)O3)CC1]

A mixture of [1-(2,2-dimethyl-5-nitro-3H-benzofuran-6-yl)-4-piperidyl]methyl diethyl phosphate (113 mg, 0.19 mmol), iron powder (54 mg, 0.96 mmol) and ammonium chloride (52 mg, 0.96 mmol) in ethanol (5 mL) and water (0.5 mL), was heated at 60° C. for 2h. After filtration, water and dichloromethane (50 mL) was added. The aqueous phase was extracted with dichloromethane (2×50 mL). The combined organic phases were washed with brine, dried over sodium sulfate and concentrated under reduced pressure to afford [1-(5-amino-2,2-dimethyl-3H-benzofuran-6-yl)-4-piperidyl]methyl diethyl phosphate (79 mg, crude) as a brown solid, which was used directly to next step without further purification. MS (ESI): m/z=413.3 [M+1]$^+$.

Step C. [1-[2,2-Dimethyl-5-(pyrazolo[1,5-a]pyrimidine-3-carbonylamino)-3H-benzofuran-6-yl]-4-piperidyl]methyl diethyl phosphate

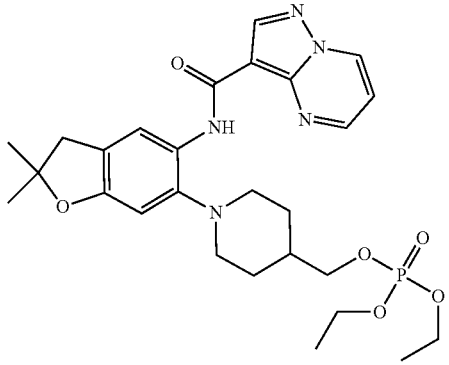 [SMILES: CCOP(=O)(OCC)OCC1CCN(c2cc3c(cc2NC(=O)c2cnn4cccnc24)CC(C)(C)O3)CC1]

A mixture of [1-(5-amino-2,2-dimethyl-3H-benzofuran-6-yl)-4-piperidyl]methyl diethyl phosphate (79 mg, 0.14 mmol), pyrazolo[1,5-a]pyrimidine-3-carboxylic acid (27 mg, 0.17 mmol), 2-(7-aza-1H-benzotriazole-1-yl)-1,1,3,3-tetramethyluronium hexafluorophosphate (78 mg, 0.21 mmol) and diisopropylethylamine (53 mg, 0.41 mmol) in N,N-dimethylformamide (5 mL) was stirred at 20° C. for 1h. The mixture was purified by preparative HPLC (Xbridge 21.2*250 mm c18, 10 um; A: acetonitrile 25-55%; B: 10 mM ammonium bicarbonate in water) to afford [1-[2,2-dimethyl-5-(pyrazolo[1,5-a]pyrimidine-3-carbonylamino)-3H-benzofuran-6-yl]-4-piperidyl]methyl diethyl phosphate (7 mg, 9%) as yellow solid. $^1$H NMR (400 MHz, CDCl$_3$): δ 10.51 (s, 1H), 8.85 (dd, J=1.6, 4.0 Hz, 1H), 8.79-8.76 (m, 2H), 8.44 (s, 1H), 7.10 (dd, J=1.6, 7.2 Hz, 1H), 6.63 (s, 1H), 4.14 (q, J=7.2 Hz, 4H), 4.01-4.00 (m, 2H), 3.11 (d, J=11.6 Hz, 2H), 3.03 (s, 2H), 2.69-2.64 (m, 2H), 1.87-1.77 (m, 5H), 1.48 (s, 6H), 1.35 (t, J=6.8 Hz, 6H). MS (ESI): m/z=558.3 [M+1]$^+$.

Example 146. N-(1-methyl-6'-morpholino-3'H-spiro[azetidine-3,2'-benzofuran]-5'-yl)pyrazolo[1,5-a]pyrimidine-3-carboxamide

Step A. tert-Butyl 3-[(2,4-Difluorophenyl)methyl]-3-hydroxy-azetidine-1-carboxylate

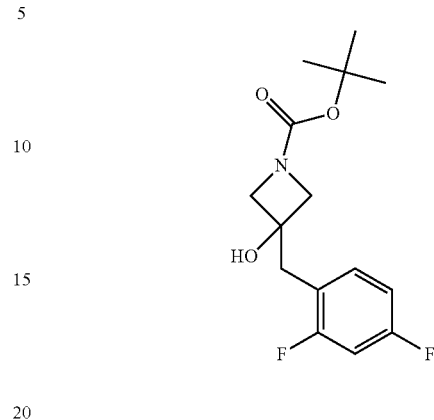

To the mixture of magnesium powder (2.0 g, 81.51 mmol) and iodine (6.1 g, 24.15 mmol) in diethyl ether (40 mL) at 40° C. was added 2,4-difluorobenzylbromide (5.0 g, 24.15 mmol) dropwise. The reaction was stirred for 30 min. To a solution of 1-Boc-3-azetidinoe (4.1 g, 24.15 mmol) in diethyl ether (40 mL) was added Grignard reagent at −78° C. and the reaction was stirred at room temperature for 2h. Saturated ammonium chloride solution was added. The aqueous layer was extracted with ethyl acetate (40 mL) twice. The combined organic layer was dried over anhydrous sodium sulfate, concentrated under reduced pressure to afford tert-butyl 3-[(2,4-difluorophenyl)methyl]-3-hydroxy-azetidine-1-carboxylate (4 g, crude) as a colorless oil, which was used directly to next step without further purification. MS (ESI): m/z=244.1 [M-56]$^+$.

Step B. tert-Butyl 6-fluorospiro[3H-benzofuran-2,3'-azetidine]-1'-carboxylate

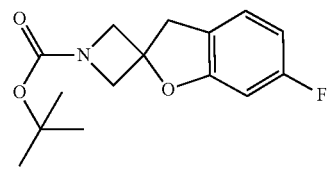 [SMILES: CC(C)(C)OC(=O)N1CC2(Cc3ccc(F)cc3O2)C1]

The mixture of potassium tert-butylate (3.7 g, 33.41 mmol) and tert-butyl 3-[(2,4-difluorophenyl)methyl]-3-hydroxy-azetidine-1-carboxylate (4.0 g, 13.36 mmol) in tetrahydrofuran (75 mL) was stirred at 65° C. overnight. After cooling to room temperature, water was added. The aqueous layer was extracted with ethyl acetate (100 mL). The organic layer was washed with water, brine, dried over anhydrous sodium sulfate and concentrated. The residue was purified by reverse phase Combiflash (A: acetonitrile 30%-50%; B: 0.1% wt ammonium bicarbonate in water) to afford tert-butyl 6-fluorospiro[3H-benzofuran-2,3'-azetidine]-1'-carboxylate (350 mg, 19%) as an orange oil. MS (ESI): m/z=224.1 [M-56]$^+$.

Step C. 6-Fluorospiro[3H-benzofuran-2,3'-azetidine]

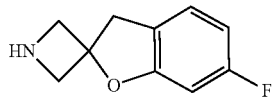

A mixture of tert-butyl 6-fluorospiro[3H-benzofuran-2,3'-azetidine]-1'-carboxylate (350 mg, 1.25 mmol) and trifluoroacetic acid (2 mL) in dichloromethane (40 mL) at room temperature was stirred overnight. Ammonia (30% wt in methanol, 10 mL) was slowly added. After concentration under reduced pressure, it was afforded 6-fluorospiro[3H-benzofuran-2,3'-azetidine] (400.0 mg, crude) as a yellow solid, which was used directly to next step without further purification. MS (ESI): m/z=180.1 [M+1]$^+$.

Step D. 6-Fluoro-1'-methyl-spiro[3H-benzofuran-2,3'-azetidine]

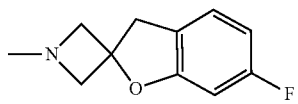

To a solution of 6-fluorospiro[3H-benzofuran-2,3'-azetidine] (100.0 mg, 0.56 mmol) in methyl alcohol (4 mL) was added formaldehyde (30% wt in water, 1.1 g, 13.8 mmol) then the mixture was stirred at 25° C. for 30 min. To the mixture was added sodium cyanoborohydride (70.0 mg, 1.12 mmol). The reaction was stirred at 25° C. for 1h. Water was added and the crude was purified by reverse phase combiflash (A: acetonitrile 23%-30%; B: 0.1% wt ammonium bicarbonate in water) to afford 6-fluoro-1'-methyl-spiro[3H-benzofuran-2,3'-azetidine] (108 mg, 99%) as a yellow solid. MS (ESI): m/z=194.1 [M+1]$^+$.

Step E. 6-Fluoro-1'-methyl-5-nitro-spiro[3H-benzofuran-2,3'-azetidine]

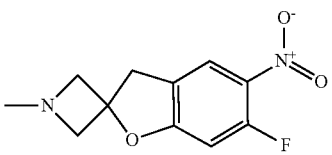 [SMILES: CN1CC2(Cc3cc([N+](=O)[O-])c(F)cc3O2)C1]

A mixture of 6-fluoro-1'-methyl-spiro[3H-benzofuran-2,3'-azetidine] (90.0 mg, 0.4700 mmol) in dichloromethane (10 mL) was added drop wise fuming nitric acid (0.3 mL, 4.66 mmol) at 25° C. The mixture was stirred at 25° C. for 30 min and poured into ice water. 5M Sodium hydroxide was added until pH=10.0. The organic layer was dried over anhydrous sodium sulfate and concentrated under reduced pressure to afford 6-fluoro-1'-methyl-5-nitro-spiro[3H-benzofuran-2,3'-azetidine] (85 mg, 77%) as a yellow solid. $^1$H NMR (400 MHz, MeOD-d$_4$): 7.90-7.88 (d, J=8.0 Hz, 1H), 6.70-6.67 (d, J=11.6 Hz, 1H), 3.52-3.46 (m, 4H), 3.39 (s, 2H), 2.35 (s, 3H). MS (ESI): m/z=239.1 [M+1]$^+$.

Step F. 1'-Methyl-6-morpholino-5-nitro-spiro[3H-benzofuran-2,3'-azetidine]

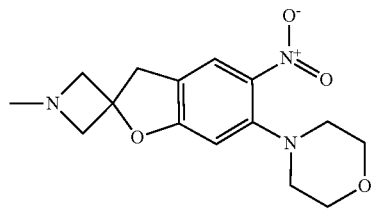 [SMILES: CN1CC2(Cc3cc([N+](=O)[O-])c(N4CCOCC4)cc3O2)C1]

A solution of 6-fluoro-1'-methyl-5-nitro-spiro[3H-benzofuran-2,3'-azetidine] (116.0 mg, 0.49 mmol) in morpholine (426.0 mg, 4.9 mmol), was stirred at 110° C. for 3h, then removed the solvents under reduced pressure to get the residue and used in next step directly without further purification. MS (ESI): m/z=306.1 [M+1]$^+$.

Step G. 1'-Methyl-6-morpholino-spiro[3H-benzofuran-2,3'-azetidine]-5-amine

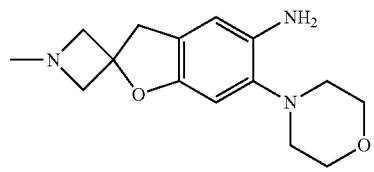 [SMILES: CN1CC2(Cc3cc(N)c(N4CCOCC4)cc3O2)C1]

To a solution of 1'-methyl-6-morpholino-5-nitro-spiro[3H-benzofuran-2,3'-azetidine] (90.0 mg, 0.29 mmol) in methyl alcohol (10 mL) was added palladium on carbon (20.0 mg, 10% wt). The mixture was stirred at 25° C. for 2h under hydrogen atmosphere. After filtration and concentration, it was afforded 1'-methyl-6-morpholino-spiro[3H-benzofuran-2,3'-azetidine]-5-amine (65 mg, 82%) as a brown oil. MS (ESI): m/z=276.2 [M+1]$^+$.

Step H. N-(1'-Methyl-6-morpholino-spiro[3H-benzofuran-2,3'-azetidine]-5-yl)pyrazolo[1,5-a]pyrimidine-3-carboxamide

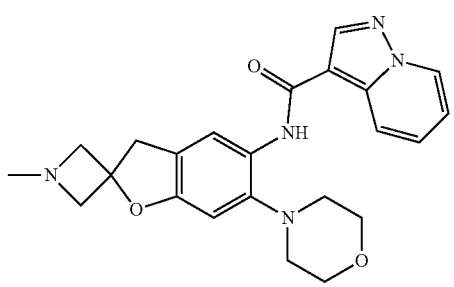

To a solution of 1'-methyl-6-morpholino-spiro[3H-benzofuran-2,3'-azetidine]-5-amine (30.0 mg, 0.11 mmol) in N,N-dimethylformamide (3 mL) was added pyrazolo[1,5-a]pyrimidine-3-carboxylic acid (23.0 mg, 0.14 mmol), N,N-diisopropylethylamine (42.0 mg, 0.33 mmol) and o-(7-azabenzotriazol-1-yl)-N,N,N',N'-te-tramethyluronium hexafluorophosphate (83.0 mg, 0.22 mmol). The mixture was stirred at 25° C. for 3h. Water was added. The aqueous layer was extracted with ethyl acetate (20 mL). The organic layer was washed with water, brine, dried over sodium sulfate and concentrated. The residue was purified by preparative HPLC (A: acetonitrile 25-55%; B: 0.05% wt formic acid in water) to afford N-(1'-methyl-6-morpholino-spiro[3H-benzofuran-2,3'-azetidine]-5-yl)pyrazolo[1,5-a]pyrimidine-3-carboxamide (20 mg, 44%) as a yellow solid. $^1$H NMR (400 MHz, DMSO-d$_6$): δ 10.46 (s, 1H), 9.37 (dd, J=1.6, 6.8 Hz, 1H), 8.95 (dd, J=1.6, 4.0 Hz, 1H), 8.68 (s, 1H), 8.34 (s, 1H), 7.35 (dd, J=4.0, 6.8 Hz, 1H), 6.80 (s, 1H), 3.84 (t, J=8.8 Hz, 4H), 3.46-3.42 (m, 4H), 3.27-3.25 (m, 2H), 2.86-2.76 (m, 4H), 2.31 (s, 3H). MS (ESI): m/z=421.3 [M+1]$^+$.

Example 147. N-(1-(2,2-Difluoroethyl)-6'-morpholino-3'H-spiro[azetidine-3,2'-benzofuran]-5'-yl)pyrazolo[1,5-a]pyrimidine-3-carboxamide

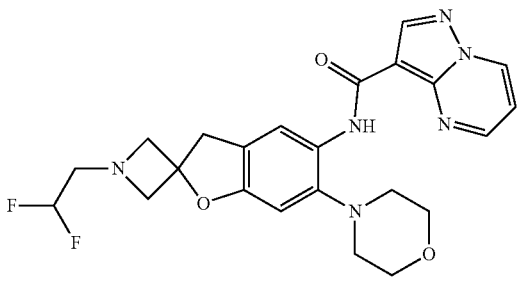

Step A. 1'-(2,2-Difluoroethyl)-6-fluoro-spiro[3H-benzofuran-2,3'-azetidine]

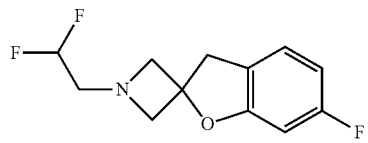 [SMILES: Fc1ccc2c(c1)OC1(C2)CN(CC(F)F)C1]

A mixture of 6-fluorospiro[3H-benzofuran-2,3'-azetidine] (Example 146, Step C) (185.0 mg, 1.03 mmol), 2,2-difluoroethyl trifluoromethanesulfonate (265.0 mg, 1.24 mmol) and potassium carbonate (442.0 mg, 3.2 mmol) in acetonitrile (10 mL) was stirred at 25° C. overnight. After filtration and concentration, it was afforded 1'-(2,2-difluoroethyl)-6-fluoro-spiro[3H-benzofuran-2,3'-azetidine] (170 mg, crude) as white solid, which was used directly to next step without further purification. MS (ESI): m/z=244.1 [M+1]$^+$.

Step B. 1'-(2,2-Difluoroethyl)-6-fluoro-5-nitro-spiro[3H-benzofuran-2,3'-azetidine]

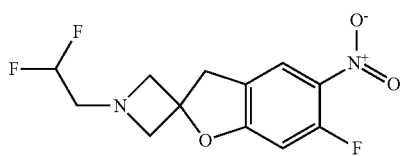 [SMILES: O=[N+]([O-])c1cc2c(cc1F)OC1(C2)CN(CC(F)F)C1]

A mixture of 1'-(2,2-difluoroethyl)-6-fluoro-spiro[3H-benzofuran-2,3'-azetidine] (113.0 mg, 0.47 mmol) in dichloromethane (10 mL) was added drop wise fuming nitric acid (0.3 mL, 4.66 mmol) at 25° C. The mixture was stirred at 25° C. for 30 min. The mixture was poured into ice water. 5N sodium hydroxide was added until pH=10.0. The aqueous layer was extracted with dichloromethane (40 mL). The organic layer was dried over anhydrous sodium sulfate and concentrated under reduced pressure to afford 1'-(2,2-difluoroethyl)-6-fluoro-5-nitro-spiro[3H-benzofuran-2,3'-azetidine] (165 mg crude) as a yellow solid, which was used directly to next step without further purification. MS (ESI): m/z=289.1 [M+1]$^+$.

Step C. 1-(2,2-Difluoroethyl)-6'-morpholino-5'-nitro-3'H-spiro[azetidine-3,2'-benzofuran]

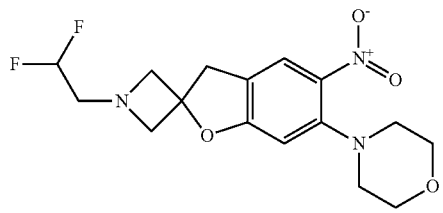 [SMILES: O=[N+]([O-])c1cc2c(cc1N1CCOCC1)OC1(C2)CN(CC(F)F)C1]

A solution of 1'-(2,2-difluoroethyl)-6-fluoro-5-nitro-spiro[3H-benzofuran-2,3'-azetidine](120.0 mg, 0.42 mmol) in morpholine (426.0 mg, 4.9 mmol) was stirred at 110° C. for 3h. After concentration, it was afforded 1-(2,2-difluoroethyl)-6'-morpholino-5'-nitro-3'H-spiro[azetidine-3,2'-benzofuran] (90 mg, crude) as a yellow oil, which was used to the next step directly without further purification. MS (ESI): m/z=356.2 [M+1]$^+$.

Step D. 1'-(2,2-Difluoroethyl)-6-morpholino-spiro[3H-benzofuran-2,3'-azetidine]-5-amine

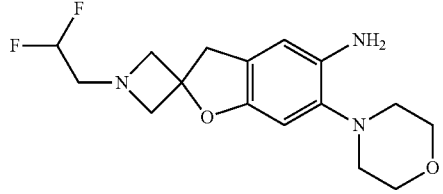 [SMILES: Nc1cc2c(cc1N1CCOCC1)OC1(C2)CN(CC(F)F)C1]

To a solution of 1'-(2,2-difluoroethyl)-6-morpholino-5-nitro-spiro[3H-benzofuran-2,3'-azetidine](90.0 mg, 0.25 mmol) in methyl alcohol (10 mL) was added palladium on carbon (20.0 mg, 10% wt). The mixture was stirred at 25° C. for 2h under hydrogen atmosphere. After filtration and concentration, it was afforded 1'-(2,2-difluoroethyl)-6-morpholino-spiro[3H-benzofuran-2,3'-azetidine]-5-amine (50 mg, crude) as a brown oil, which was used to the next step directly without further purification. MS (ESI): m/z=326.2 [M+1]$^+$.

Step E. N-[1'-(2,2-Difluoroethyl)-6-morpholino-spiro[3H-benzofuran-2,3'-azetidine]-5-yl]pyrazolo[1,5-a]pyrimidine-3-carboxamide

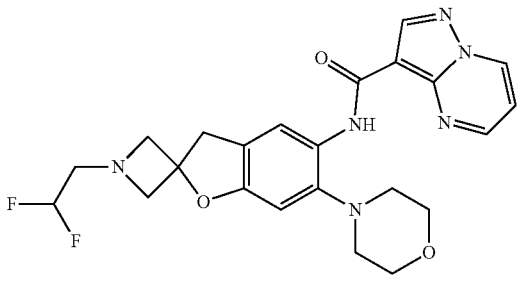

To a solution of pyrazolo[1,5-a]pyrimidine-3-carboxylic acid (26.0 mg, 0.16 mmol) in N,N-dimethylformamide (3 mL) was added 1'-(2,2-difluoroethyl)-6-morpholino-spiro[3H-benzofuran-2,3'-azetidine]-5-amine (40.0 mg, 0.1200 mmol), N,N-diisopropylethylamine (47.0 mg, 0.37 mmol) and o-(7-azabenzotriazol-1-yl)-N,N,N',N'-tetramethyluronium hexafluorophosphate (93.0 mg, 0.25 mmol). The mixture was stirred at 25° C. for 3h. Water and ethyl acetate (20 mL) was added and the organic layer was washed with water, brine and concentrated. The residue was purified by preparative HPLC (A: acetonitrile 25-55%; B: 0.05% wt formic acid in water) to afford N-[1'-(2,2-difluoroethyl)-6-morpholino-spiro[3H-benzofuran-2,3'-azetidine]-5-yl]pyrazolo[1,5-a]pyrimidine-3-carboxamide (16.0 mg, 0.034 mmol, 28%) as a yellow solid. $^1$H NMR (400 MHz, DMSO-d$_6$): δ 10.45 (s, 1H), 9.37 (dd, J=1.6, 6.8 Hz, 1H), 8.95 (dd, J=1.6, 4.4 Hz, 1H), 8.68 (s, 1H), 8.35 (s, 1H), 7.34 (dd, J=4.4, 6.8 Hz, 1H), 6.80 (s, 1H), 6.15-5.87 (m, 1H), 3.85-3.83 (m, 4H), 3.57-3.44 (m, 6H), 2.95-2.86 (m, 2H), 2.82-2.80 (m, 4H). MS (ESI): m/z=471.1 [M+1]$^+$.

Example 148. N-[6-Morpholino-1'-(2,2,2-trifluoroethyl)spiro[3H-benzofuran-2,3'-azetidine]-5-yl]pyrazolo[1,5-a]pyrimidine-3-carboxamide

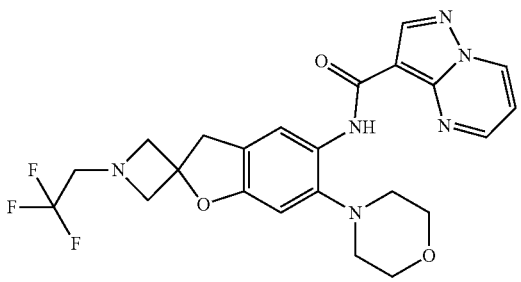

The title compound was made in a manner analogous to Example 147 to give N-[6-Morpholino-1'-(2,2,2-trifluoroethyl)spiro[3H-benzofuran-2,3'-azetidine]-5-yl]pyrazolo[1,5-a]pyrimidine-3-carboxamide (72 mg, 25%) as a yellow solid. $^1$H NMR (400 MHz, DMSO-d$_6$): δ 10.46 (s, 1H), 9.37 (dd, J=1.6, 6.8 Hz, 1H), 8.95 (dd, J=1.6, 4.4 Hz, 1H), 8.68 (s, 1H), 7.34 (dd, J=4.4, 6.8 Hz, 1H), 6.81 (s, 1H), 3.85-3.83 (m, 4H), 3.64-3.57 (m, 6H), 3.16 (s, 2H), 2.82-2.80 (m, 4H). MS (ESI): m/z=489.2 [M+1]$^+$.

Example 149. N-(6-(4-(2,2-difluoroethyl)-1,4-diazepan-1-yl)-2,2-dimethyl-2,3-dihydrobenzofuran-5-yl)pyrazolo[1,5-a]pyrimidine-3-carboxamide

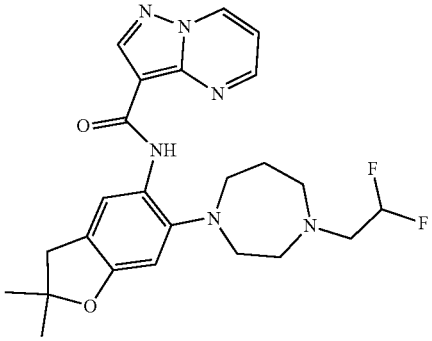 [SMILES: CC1(C)Cc2cc(NC(=O)c3cnn4cccnc34)c(N3CCCN(CC(F)F)CC3)cc2O1]

Step A. tert-Butyl 4-(2,2-dimethyl-5-nitro-2,3-dihydrobenzofuran-6-yl)-1,4-diazepane-1-carboxylate

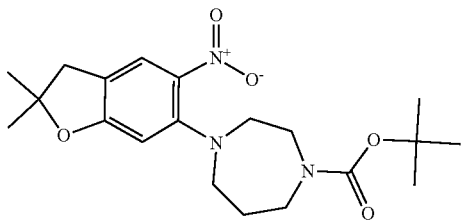 [SMILES: CC(C)(C)OC(=O)N1CCCN(c2cc3c(cc2[N+](=O)[O-])CC(C)(C)O3)CC1]

A mixture of 6-fluoro-2,2-dimethyl-5-nitro-2,3-dihydrobenzofuran (Example 3, Step F) (210 mg, 0.99 mmol), tert-butyl 1,4-diazepane-1-carboxylate (219 mg, 1.09 mmol) and potassium carbonate (412 mg, 2.98 mmol) in acetonitrile (10 mL) was stirred at 80° C. for 2h. After removal of the solvents under reduced pressure, the residue was purified by silica gel chromatography using ethyl acetate:petroleum ether (from 1:9 to 1:1) as eluting solvents to afford tert-butyl 4-(2,2-dimethyl-5-nitro-2,3-dihydrobenzofuran-6-yl)-1,4-diazepane-1-carboxylate (260 mg, 63%) as a yellow solid. MS (ESI): m/z=392.2 [M+1]$^+$.

Step B. 1-(2,2-Dimethyl-5-nitro-2,3-dihydrobenzofuran-6-yl)-1,4-diazepane

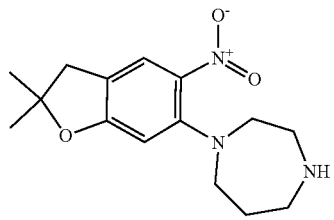 [SMILES: CC1(C)Cc2cc([N+](=O)[O-])c(N3CCCNCC3)cc2O1]

A mixture of tert-butyl 4-(2,2-dimethyl-5-nitro-2,3-dihydrobenzofuran-6-yl)-1,4-diazepane-1-carboxylate (260 mg, 0.66 mmol) and trifluoroacetic acid (1 mL) in dichloromethane (3 mL), was stirred at 25° C. for 2h. After removal of solvents under reduced pressure, it was afforded 1-(2,2- dimethyl-5-nitro-2,3-dihydrobenzofuran-6-yl)-1,4-diazepane trifluoroacetic acid salt (180 mg, crude) as a yellow solid, which was used directly to next step without further purification. MS (ESI): m/z=291.2 [M+1]⁺.

Step C. 1-(2,2-Difluoroethyl)-4-(2,2-dimethyl-5-nitro-2,3-dihydrobenzofuran-6-yl)-1,4-diazepane

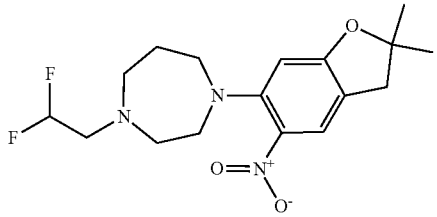 [SMILES: CC1(C)Cc2cc([N+](=O)[O-])c(N3CCCN(CC(F)F)CC3)cc2O1]

A mixture of 1-(2,2-dimethyl-5-nitro-2,3-dihydrobenzofuran-6-yl)-1,4-diazepane trifluoroacetic acid salt (180 mg, 0.61 mmol), 2,2-difluoroethyl trifluoromethanesulfonate (132 mg, 0.61 mmol) and potassium carbonate (257 mg, 1.85 mmol) in acetonitrile (10 mL) was stirred at 80° C. for 16h. After filtration and removal of the solvents under reduced pressure, the residue was purified by silica gel chromatography using ethyl acetate:petroleum ether (from 1:9 to 1:1) as eluting solvents to afford 1-(2,2-difluoroethyl)-4-(2,2-dimethyl-5-nitro-2,3-dihydrobenzofuran-6-yl)-1,4-diazepane (150 mg, 64%) as a yellow solid. MS (ESI): m/z=356.2 [M+1]⁺.

Step D. 6-(4-(2,2-Difluoroethyl)-1,4-diazepan-1-yl)-2,2-dimethyl-2,3-dihydrobenzofuran-5-amine

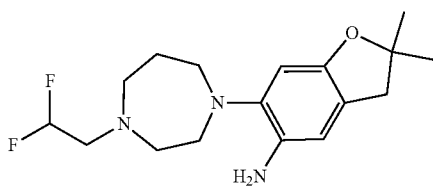 [SMILES: CC1(C)Cc2cc(N)c(N3CCCN(CC(F)F)CC3)cc2O1]

A mixture of 1-(2,2-difluoroethyl)-4-(2,2-dimethyl-5-nitro-2,3-dihydrobenzofuran-6-yl)-1,4-diazepane (150 mg, 0.42 mmol) and palladium on carbon (20 mg, 10% wt) in methanol (3 mL) was stirred at 25° C. under hydrogen atmosphere for 2 hours. After filtration and concentration, it was afforded 6-(4-(2,2-difluoroethyl)-1,4-diazepan-1-yl)-2,2-dimethyl-2,3-dihydrobenzofuran-5-amine (120 mg, crude) as a brown oil, which was used directly to next step without further purification. MS (ESI): m/z=326.3 [M+1]⁺.

Step E. N-(6-(4-(2,2-Difluoroethyl)-1,4-diazepan-1-yl)-2,2-dimethyl-2,3-dihydrobenzofuran-5-yl)pyrazolo[1,5-a]pyrimidine-3-carboxamide

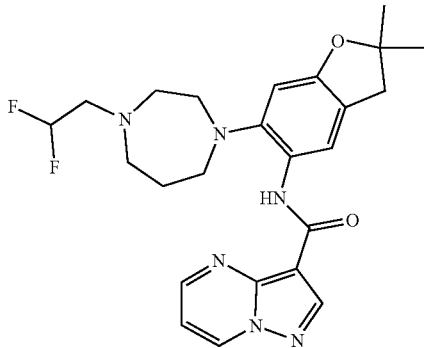 [SMILES: CC1(C)Cc2cc(NC(=O)c3cnn4cccnc34)c(N3CCCN(CC(F)F)CC3)cc2O1]

A mixture of 6-(4-(2,2-difluoroethyl)-1,4-diazepan-1-yl)-2,2-dimethyl-2,3-dihydrobenzofuran-5-amine (120 mg, 0.36 mmol), pyrazolo[1,5-a]pyrimidine-3-carboxylic acid (60 mg, 0.36 mmol), 2-(7-aza-1H-benzotriazole-1-yl)-1,1,3,3-tetramethyluronium hexafluorophosphate (210 mg, 0.55 mmol) and diisopropylethylamine (95 mg, 0.73 mmol) in N,N-dimethylformamide (3 mL) was stirred at 60° C. for 3h. The crude was purified by preparative HPLC (Xbridge 21.2*250 mm c18, 10 um; A: acetonitrile 25-55%; B: 10 mM ammonium bicarbonate in water) to afford N-(6-(4-(2,2-difluoroethyl)-1,4-diazepan-1-yl)-2,2-dimethyl-2,3-dihydrobenzofuran-5-yl)pyrazolo[1,5-a]pyrimidine-3-carboxamide (22 mg, 12%) as a yellow solid. ¹H NMR (400 MHz, MeOD-d₄): δ 9.17 (d, J=6.0 Hz, 1H), 8.95 (d, J=2.8 Hz, 1H), 8.70 (s, 1H), 8.06 (s, 1H), 7.31 (dd, J=6.0, 2.8 Hz, 1H), 6.73 (s, 1H), 6.27-6.54 (tt, J=1.2, 53.2 Hz 1H), 3.77-3.89 (m, 6H), 3.45 (s, 2H), 3.23 (t, J=5.6 Hz 2H), 3.05 (s, 2H), 2.21-2.27 (m, 2H), 1.48 (s, 6H). MS (ESI): m/z=471.3 [M+1]⁺.

Example 150. N-(2-Isopropyl-2-methyl-6-morpholino-2,3-dihydrobenzofuran-5-yl)pyrazolo[1,5-a]pyrimidine-3-carboxamide

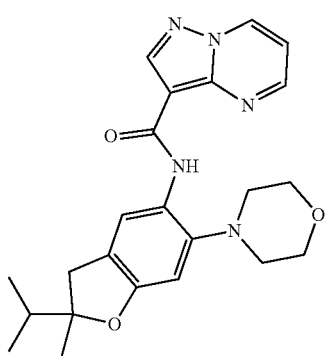 [SMILES: CC(C)C1(C)Cc2cc(NC(=O)c3cnn4cccnc34)c(N3CCOCC3)cc2O1]

Step A.
1-(2,4-Difluorophenyl)-2,3-dimethylbutan-2-ol

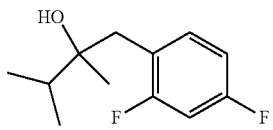

A mixture of magnesium (2.2 g, 92.88 mmol) and iodine (59 mg, 0.23 mmol) in diethyl ether (80 mL) at 40° C. under nitrogen atmosphere was slowly added 2,4-difluorobenenzyl bromide (4.2 g, 20.31 mmol) and stirred for 2h. To a solution of 3-methyl-2-butanone (2 g, 23.22 mmol) in diethyl ether (100 mL) at −78° C. under nitrogen atmosphere was added Grignard reagent and the reaction was stirred at room temperature for 2h. Saturated ammonium chloride solution and ethyl acetate (200 mL) was added. The organic layer was separated, washed with water, brine and dried over sodium sulfate. After concentration, the residue was purified by silica gel chromatography using ethyl acetate:petroleum ether (1:10) as eluting solvents to afford 1-(2,4-difluorophenyl)-2,3-dimethyl-butan-2-ol (3.4 g, 65%) as a yellow oil. MS (ESI): m/z=197.2 [M-17]$^+$.

Step B. 6-Fluoro-2-isopropyl-2-methyl-2,3-dihydrobenzofuran

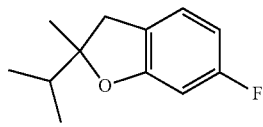

A mixture of 1-(2,4-difluorophenyl)-2,3-dimethyl-butan-2-ol (428 mg, 2 mmol) and tetrahydrofuran (50 mL) at 0° C. was added potassium tert-butylate (1.12 g, 9.99 mmol). The reaction was stirred for 16h. The aqueous layer was extracted with ethyl acetate (100 mL) and the organics were washed with saturated brine solution. The organics were then separated and dried over sodium sulfate before concentration to dryness. The residue was purified by silica gel chromatography using ethyl acetate:petroleum ether (1:20) as eluting solvents to afford 6-fluoro-2-isopropyl-2-methyl-3H-benzofuran (350 mg, 90%) as a yellow oil. MS (ESI): m/z=217.1 [M+23]$^+$.

Step C. 6-Fluoro-2-isopropyl-2-methyl-5-nitro-2,3-dihydrobenzofuran

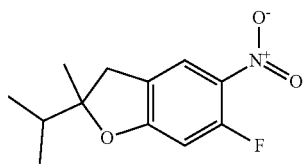 [SMILES: CC(C)C1(C)Cc2cc([N+](=O)[O-])c(F)cc2O1]

To a solution of 6-fluoro-2-isopropyl-2-methyl-3H-benzofuran (350 mg, 1.8 mmol) in dichloromethane (30 mL) at 0° C. was added fuming nitric acid (2 mL). Water and dichloromethane (30 mL) were added and the organics were then separated and dried over sodium sulfate before concentration to dryness. The residue was purified by silica gel chromatography using ethyl acetate:petroleum ether (1:5) as eluting solvents to afford 6-fluoro-2-isopropyl-2-methyl-5-nitro-2,3-dihydrobenzofuran (220 mg, 51%) as a yellow oil. MS (ESI): m/z=240.1 [M+1]$^+$.

Step D. 4-(2-Isopropyl-2-methyl-5-nitro-2,3-dihydrobenzofuran-6-yl)morpholine

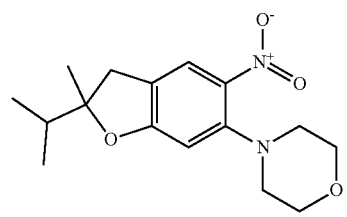 [SMILES: CC(C)C1(C)Cc2cc([N+](=O)[O-])c(N3CCOCC3)cc2O1]

A mixture of 6-fluoro-2-isopropyl-2-methyl-5-nitro-3H-benzofuran (220 mg, 0.92 mmol), morphline (88 mg, 1.01 mmol) and potassium carbonate (254 mg, 1.84 mmol) in acetonitrile (15 mL) was stirred at 25° C. for 16h. Water was added and the aqueous layer was extracted with ethyl acetate (30 mL). The organic layer was washed with brine and dried over sodium sulfate before concentration to dryness. The residue was purified by silica gel chromatography using ethyl acetate:petroleum ether (1:1) as eluting solvents to afford 4-(2-isopropyl-2-methyl-5-nitro-2,3-dihydrobenzofuran-6-yl)morpholine (250 mg, 85%) as a yellow solid. MS (ESI): m/z=307.2 [M+1]$^+$.

Step E. 2-Isopropyl-2-methyl-6-morpholino-2,3-dihydrobenzofuran-5-amine

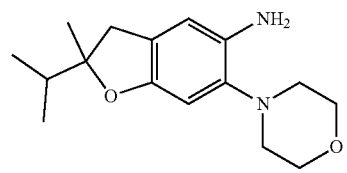 [SMILES: CC(C)C1(C)Cc2cc(N)c(N3CCOCC3)cc2O1]

A mixture of palladium on carbon (80.0 mg, 10% wt) and 4-(2-isopropyl-2-methyl-5-nitro-2,3-dihydrobenzofuran-6-yl)morpholine (250 mg, 0.78 mmol) in methanol (15 mL) was stirred at 25° C. under hydrogen atmosphere for 2h. After filtration and concentration under reduced pressure, it was afforded 2-isopropyl-2-methyl-6-morpholino-2,3-dihydrobenzofuran-5-amine (200 mg, 89%) as a white oil. MS (ESI): m/z=277.3 [M+1]$^+$.

579

Step F. N-(2-Isopropyl-2-methyl-6-morpholino-2,3-dihydrobenzofuran-5-yl)pyrazolo[1,5-a]pyrimidine-3-carboxamide

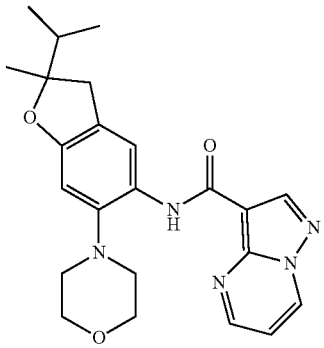 [SMILES: CC(C)C1(C)Cc2cc(NC(=O)c3cnn4cccnc34)c(N3CCOCC3)cc2O1]

A mixture of pyrazolo[1,5-a]pyrimidine-3-carboxylic acid (130 mg, 0.80 mmol), (7-azabenzotriazol-1-yloxy)tripyrrolidinophosphonium hexafluorophosphate (464 mg, 0.87 mmol), ethyldiisopropylamine (347 mg, 2.16 mmol) 2-isopropyl-2-methyl-6-morpholino-2,3-dihydrobenzofuran-5-amine (200 mg, 0.72 mmol) in N,N-dimethylformamide (10 mL) was stirred at room temperature overnight. After concentration, the residue was purified by preparative HPLC (A: acetonitrile 25-45%; 0.05% wt formic acid in water) to afford N-(2-isopropyl-2-methyl-6-morpholino-2,3-dihydrobenzofuran-5-yl)pyrazolo[1,5-a]pyrimidine-3-carboxamide (125 mg, 41%) as a yellow solid. $^1$H NMR (400 MHz, CDCl$_3$) δ 10.46 (s, 1H), 8.83 (dd, J=1.6, 7.2 Hz, 1H), 8.79 (s, 1H), 8.76 (dd, J=1.6, 4.0 Hz, 1H), 8.40 (s, 1H), 7.06 (dd, J=4.0, 7.2 Hz, 1H), 6.65 (s, 1H), 4.00-3.89 (m, 4H), 3.16 (d, J=11.6 Hz, 1H), 2.93-2.87 (m, 4H), 2.83 (d, J=11.6 Hz, 1H), 2.08-1.95 (m, 2H), 1.01 (d, J=6.8, 3H), 0.96 (d, J=6.8 Hz, 6H). MS (ESI): m/z=422.2 [M+1]$^+$.

Example 151. N-(6-(4-(2-Hydroxy-2-methylpropyl)piperazin-1-yl)-2-(hydroxymethyl)-2-methyl-2,3-dihydrobenzofuran-5-yl)pyrazolo[1,5-a]pyrimidine-3-carboxamide

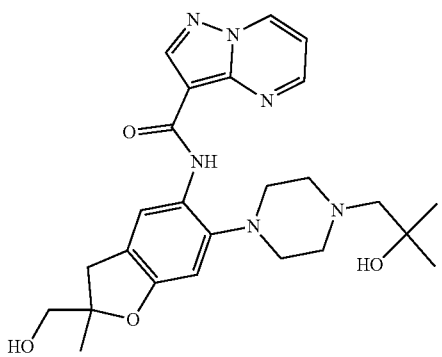 [SMILES: CC(C)(O)CN1CCN(c2cc3c(cc2NC(=O)c2cnn4cccnc24)CC(C)(CO)O3)CC1]

580

Step A. 2-Methyl-1-(piperazin-1-yl)propan-2-ol

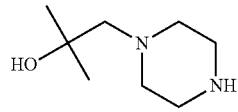

Piperazine (6.88 g, 80 mmol) was dissolved in ethanol (40 mL). 1-Chloro-2-methyl-2-propanol (2.18 g, 20 mmol) was added. The mixture was stirred at 110° C. for 6h. After the mixture was left to cool to room temperature, the solvent was evaporated. Ethyl acetate (40 mL) was added and the precipitated solid was removed by filtration. The filtrate was concentrated under reduced pressure to afford 2-methyl-1-piperazin-1-yl-propan-2-ol (4.1 g, crude) as a white solid, which was used directly to the next step without purification. MS (ESI): m/z=159.3 [M+1]$^+$.

Step B. 1-(4-(2-(Hydroxymethyl)-2-methyl-5-nitro-2,3-dihydrobenzofuran-6-yl)piperazin-1-yl)-2-methylpropan-2-ol

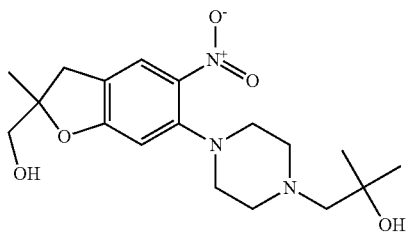 [SMILES: CC(C)(O)CN1CCN(c2cc3c(cc2[N+](=O)[O-])CC(C)(CO)O3)CC1]

A mixture of (6-fluoro-2-methyl-5-nitro-2,3-dihydrobenzofuran-2-yl)methanol (Intermediate 3) (300 mg, 1.32 mmol), 2-methyl-1-(piperazin-1-yl)propan-2-ol (1.44 g, 6.6 mmol) and potassium carbonate (365 mg, 2.64 mmol) in acetonitrile (10 mL) was stirred at 25° C. for 16h. Water was added and the aqueous layer was extracted with ethyl acetate (20 mL) and the organic was washed with brine and dried over sodium sulfate before concentration to dryness. The residue was purified by silica gel chromatography using ethyl acetate:petroleum ether (1:2) as eluting solvents to afford 1-(4-(2-(hydroxymethyl)-2-methyl-5-nitro-2,3-dihydrobenzofuran-6-yl)piperazin-1-yl)-2-methylpropan-2-ol (100 mg, 18%) as a yellow solid. MS (ESI): m/z=366.3 [M+1]$^+$.

Step C. 1-(4-(5-Amino-2-(hydroxymethyl)-2-methyl-2,3-dihydrobenzofuran-6-yl)piperazin-1-yl)-2-methylpropan-2-ol

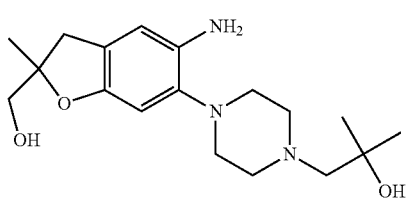 [SMILES: CC(C)(O)CN1CCN(c2cc3c(cc2N)CC(C)(CO)O3)CC1]

A mixture of palladium on carbon (30 mg, 10% wt) and 1-(4-(2-(hydroxymethyl)-2-methyl-5-nitro-2,3-dihydrobenzofuran-6-yl)piperazin-1-yl)-2-methylpropan-2-ol (100 mg, 0.27 mmol) in methanol (10 mL) was stirred at 25° C. under hydrogen atmosphere for 2h. After filtration and concentration under reduced pressure, it was afforded 1-(4-(5-amino-2-(hydroxymethyl)-2-methyl-2,3-dihydrobenzofuran-6-yl)piperazin-1-yl)-2-methylpropan-2-ol (60 mg, crude) as a white oil, which was used directly to next step without further purification. MS (ESI): m/z=336.1 [M+1]$^+$.

Step D. N-(6-(4-(2-Hydroxy-2-methylpropyl)piperazin-1-yl)-2-(hydroxymethyl)-2-methyl-2,3-dihydrobenzofuran-5-yl)pyrazolo[1,5-a]pyrimidine-3-carboxamide

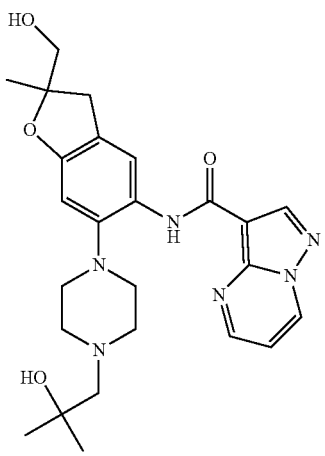 [SMILES: CC(C)(O)CN1CCN(c2cc3c(cc2NC(=O)c2cnn4cccnc24)CC(C)(CO)O3)CC1]

A mixture of 1-(4-(5-amino-2-(hydroxymethyl)-2-methyl-2,3-dihydrobenzofuran-6-yl)piperazin-1-yl)-2-methylpropan-2-ol (60 mg, 0.18 mmol), (7-azabenzotriazol-1-yloxy)tripyrrolidinophosphonium hexafluorophosphate (113 mg, 0.21 mmol), ethyldiisopropylamine (68 mg, 0.54 mmol) and pyrazolo[1,5-a]pyrimidine-3-carboxylic acid (32 mg, 0.21 mmol) in N,N-dimethylformamide (10 mL) was stirred at room temperature overnight. After concentration, the residue was purified by preparative HPLC (A: acetonitrile 25-45%; B: 0.05% wt formic acid in water) to afford N-(6-(4-(2-hydroxy-2-methylpropyl)piperazin-1-yl)-2-(hydroxymethyl)-2-methyl-2,3-dihydrobenzofuran-5-yl)pyrazolo[1,5-a]pyrimidine-3-carboxamide (50 mg, 58%) as a yellow solid. $^1$H NMR (400 MHz, CDCl$_3$) δ 10.39 (s, 1H), 8.86-8.75 (m, 3H), 8.43 (s, 1H), 8.17 (s, 1H), 7.08 (dd, J=4.0, 6.8 Hz, 1H), 6.68 (s, 1H), 5.33 (s, 1H), 3.69-3.61 (m, 2H), 3.25 (d, J=16.0 Hz, 1H), 3.08-2.90 (m, 8H), 2.58-2.50 (m, 2H), 1.46 (s, 3H), 1.26 (s, 6H). MS (ESI): m/z=481.2 [M+1]$^+$.

Example 152. N-(1'-Methyl-6-morpholino-3H-spiro[benzofuran-2,4'-piperidine]-5-yl)pyrazolo[1,5-a]pyrimidine-3-carboxamide

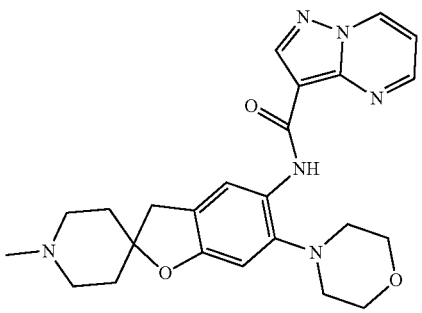 [SMILES: CN1CCC2(CC1)Cc1cc(NC(=O)c3cnn4cccnc34)c(N3CCOCC3)cc1O2]

Step A. tert-Butyl 4-[(2,4-difluorophenyl)methyl]-4-hydroxy-piperidine-1-carboxylate

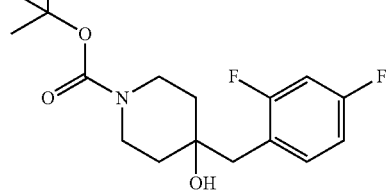

To a solution of magnesium (2400 mg, 100 mmol) and iodine (180 mg, 0.71 mmol) in diethyl ether (25 mL) at reflux was added 1-(bromomethyl)-2,4-difluorobenzene (8200.0 mg, 39.61 mmol) slowly and stirred for 30 min. To a solution of tert-butyl 4-oxopiperidine-1-carboxylate (6500.0 mg, 32.62 mmol) in diethyl ether (200 mL) was added Grignard reagent and stirred at −78° C. then room temperature for 2h. Water and EtOAc (200 mL) was added. The organic layer was separated and dried over sodium sulfate. After concentration, the residue was purified by silica gel chromatography using petroleum ether: ethyl acetate (4:1 to 2:1) as eluting solvents to afford tert-butyl 4-[(2,4-difluorophenyl)methyl]-4-hydroxy-piperidine-1-carboxylate (9500 mg, 73%) as a white solid. MS (ESI): m/z=350.1[M+23]$^+$.

Step B. tert-Butyl 6-fluoro-3H-spiro[benzofuran-2,4'-piperidine]-1'-carboxylate

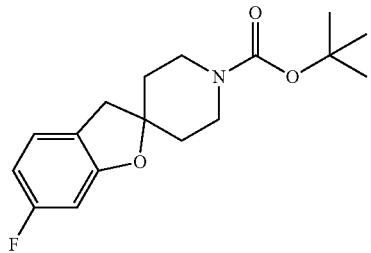 [SMILES: CC(C)(C)OC(=O)N1CCC2(CC1)Cc1ccc(F)cc1O2]

A mixture of tert-butyl 4-[(2,4-difluorophenyl)methyl]-4-hydroxy-piperidine-1-(818.0 mg, 2.5 mmol) and potassium tert-butanolate (700.95 mg, 6.25 mmol) in tetrahydrofuran (50 mL) was stirred at 65° C. for 3h. To the reaction mixture was added water and the aqueous layer was extracted with ethyl acetate (100 mL). The organic layer was dried over sodium sulfate and concentrated to dryness to afford tert-butyl 6-fluorospiro[3H-benzofuran-2,4'-piperidine]-1'-carboxylate (644 mg, crude) as a yellow solid, which was used directly to next step without further purification. MS (ESI): m/z=252.2 [M-55]$^+$.

Step C. 6-Fluorospiro[3H-benzofuran-2,4'-piperidine]

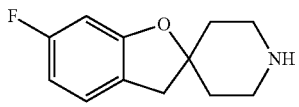

To a solution of tert-butyl 6-fluorospiro[3H-benzofuran-2,4'-piperidine]-1'-carboxylate (644.0 mg, 2.1 mmol) in dichloromethane (20 mL), was added trifluoroacetic acid (2 mL). The reaction solution was stirred for 2h at room temperature. To the reaction was added saturated sodium hydrogen carbonate (20 mL). The aqueous layer was extracted twice with 20 mL of dichloromethane. The combined organic layer was washed with brine and dried over anhydrous magnesium sulfate. After removal of the solvent, it was afforded 6-fluorospiro[3H-benzofuran-2,4'-piperidine] (429 mg, crude) as a yellow solid, which was used directly to next step without further purification. MS (ESI): m/z=208.2 [M+1]$^+$.

Step D. 6-Fluoro-1'-methyl-3H-spiro[benzofuran-2,4'-piperidine]

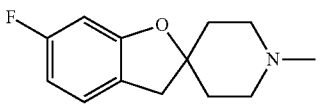 [SMILES: CN1CCC2(CC1)Cc1ccc(F)cc1O2]

To a solution of 6-fluorospiro[3H-benzofuran-2,4'-piperidine] (429.0 mg, 1.51 mmol) in methyl alcohol (40 mL) was added formaldehyde (28% wt in water, 1.5 mL) at room temperature. The reaction solution was stirred for 30 min at room temperature. Sodium borohydride (574.22 mg, 15.11 mmol) was added slowly and the reaction was stirred for 2h at room temperature. To the reaction solution saturated ammonium chloride (200 mL) was added and the aqueous layer was extracted twice with 200 mL of ethyl acetate. The combined organic layers were washed with brine and dried over anhydrous magnesium sulfate. After concentration, it was afforded 6-fluoro-1'-methyl-spiro[3H-benzofuran-2,4'-piperidine] (402 mg, crude) as a yellow oil, which was used directly to next step without further purification. MS (ESI): m/z=222.2 [M+1]$^+$.

Step E. 6-Fluoro-1'-methyl-5-nitro-3H-spiro[benzofuran-2,4'-piperidine]

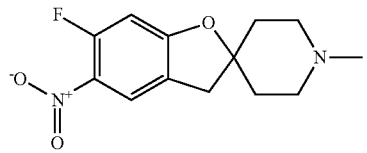

To a solution of 6-fluoro-1'-methyl-spiro[3H-benzofuran-2,4'-piperidine] (402.0 mg, 1.82 mmol) in dichloromethane (30 mL) was added fuming nitric acid (1.7 mL, 27.25 mmol) slowly. The mixture was stirred at room temperature for 30 min. Water (50 mL) was added. Sodium bicarbonate was added until pH=7 was reached and the aqueous layer was extracted with dichloromethane (50 mL). The organic layer was dried over sodium sulfate and concentrated to afford 6-fluoro-1'-methyl-5-nitro-3H-spiro[benzofuran-2,4'-piperidine] (399 mg, crude) as a yellow solid, which was used directly to next step without further purification. MS (ESI): m/z=267.1 [M-55]$^+$.

Step F. 1'-Methyl-6-morpholino-5-nitro-3H-spiro[benzofuran-2,4'-piperidine]

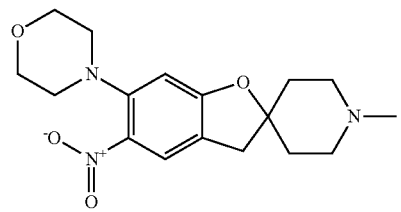

A mixture of 6-fluoro-1'-methyl-5-nitro-spiro[3H-benzofuran-2,4'-piperidine] (399.0 mg, 1.5 mmol), morpholine (195.82 mg, 2.25 mmol) and potassium carbonate (516.64 mg, 3.75 mmol) in acetonitrile (10 mL) was stirred at 25° C. overnight. Water was added and the aqueous layer was extracted twice with 20 mL of ethyl acetate. The combined organic layer was washed with saturated brine and dried over anhydrous magnesium sulfate. After concentration, it was afforded 1'-methyl-6-morpholino-5-nitro-3H-spiro[benzofuran-2,4'-piperidine] (467 mg, crude) as a yellow solid, which was used directly to next step without further purification. MS (ESI): m/z=334.2 [M+1]$^+$.

Step G. 1'-Methyl-6-morpholino-3H-spiro[benzofuran-2,4'-piperidin]-5-amine

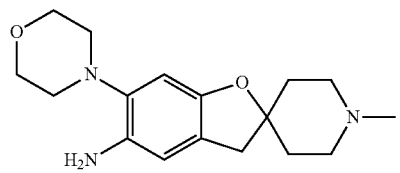 [SMILES: CN1CCC2(CC1)Cc1cc(N)c(N3CCOCC3)cc1O2]

A mixture of 10 wt % palladium on carbon (70.0 mg) and 1'-methyl-6-morpholino-5-nitro-3H-spiro[benzofuran-2,4'- piperidine] (467.0 mg, 1.4 mmol) in methyl alcohol (40 mL) was stirred at room temperature under a hydrogen atmosphere for 2h. After filtration and concentration under reduced pressure, it was afforded 1'-methyl-6-morpholino-3H-spiro[benzofuran-2,4'-piperidin]-5-amine (419 mg, crude) as a brown solid, which was used directly to next step without further purification. MS (ESI): m/z=304.3 [M+1]$^+$.

Step H. N-(1'-Methyl-6-morpholino-3H-spiro[benzofuran-2,4'-piperidine]-5-yl)pyrazolo[1,5-a]pyrimidine-3-carboxamide

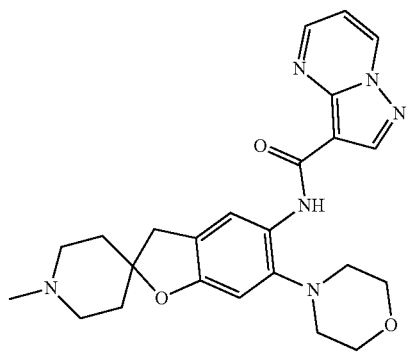 [SMILES: CN1CCC2(CC1)Cc1cc(NC(=O)c3cnn4cccnc34)c(N3CCOCC3)cc1O2]

To a mixture of pyrazolo[1,5-a]pyrimidine-3-carboxylic acid (109.69 mg, 0.6700 mmol), (3-hydroxy-3H-1,2,3-triazolo[4,5-b]pyridinato-O)tri-1-pyrrolidinylphosphonium hexafluorophosphate (385.62 mg, 0.74 mmol) and N-ethyl-N-isopropylpropan-2-amine (260.7 mg, 2.02 mmol) in N,N-dimethylformanide (5 mL) at 0° C. was added 1'-methyl-6-morpholino-spiro[3H-benzofuran-2,4'-piperidine]-5-amine (204.0 mg, 0.6700 mmol) in N,N-dimethylformanide (2 mL) and the reaction was stirred at room temperature overnight. The crude was purified by reverse phase chromatography (Xbridge Prep C18 10 um OBD, 19*250 mm, A: acetonitrile 30-60%; B: 0.01% wt ammonium hydroxide and 10 mM ammonium carbonate in water) to afford N-(1'-methyl-6-morpholino-3H-spiro[benzofuran-2,4'-piperidine]-5-yl)pyrazolo[1,5-a]pyrimidine-3-carboxamide (121 mg, 40%) as a yellow solid. $^1$H NMR (400 MHz, CDCl$_3$) δ 10.46 (s, 1H), 8.83 (dd, J=1.6, 6.8 Hz, 1H), 8.78 (s, 1H), 8.77 (dd, J=1.6, 4.4 Hz, 1H), 8.43 (s, 1H), 7.06 (dd, J=4.4, 7.2 Hz, 1H), 6.69 (s, 1H), 3.99-3.91 (m, 4H), 3.02 (s, 2H), 2.94-2.88 (m, 4H), 2.66-2.44 (m, 4H), 2.35 (s, 3H), 2.05-1.95 (m, 2H), 1.89-1.79 (m, 2H). MS (ESI): m/z=449.3 [M+1]$^+$.

Example 153 and 154. (R)—N-(2-(hydroxymethyl)-6-morpholino-2-(trifluoromethyl)-2,3-dihydrobenzofuran-5-yl)pyrazolo[1,5-a]pyrimidine-3-carboxamide and (S)—N-(2-(hydroxymethyl)-6-morpholino-2-(trifluoromethyl)-2,3-dihydrobenzofuran-5-yl)pyrazolo[1,5-a]pyrimidine-3-carboxamide

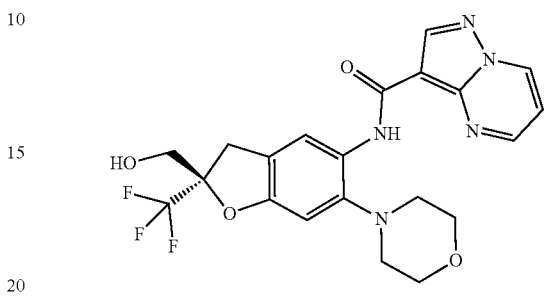

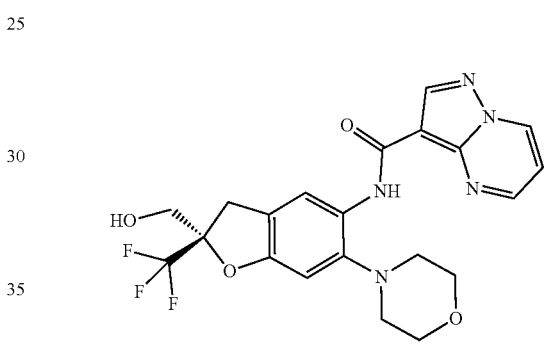

Step A. Methyl 2-(2,4-difluorobenzyl)-3,3,3-trifluoro-2-hydroxypropanoate

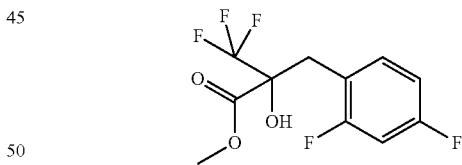

To a solution of magnesium powder (3290.81 mg, 137.12 mmol) and iodine (243.76 mg, 0.96 mmol) in diethyl ether (50 mL) at reflux was added 2,4-difluorobenzyl bromide (11291.0 mg, 54.54 mmol) drop wise and stirred for 30 min. This Grignard solution was then added to a solution of methyl 3,3,3-trifluoro-2-oxopropanoate (8567.5 mg, 54.92 mmol) in diethyl ether (200 mL) at −78° C. and stirred for 30 min followed by room temperature for 2h. Saturated ammonium chloride solution and ethyl acetate (200 mL) was added. The organic phase was separated and dried over sodium sulfate. After concentration, the residue was purified by silica gel chromatography using ethyl acetate:petroleum ether (from 1:20 to 1:10) as eluting solvents to afford methyl 3-(2,4-difluorophenyl)-2-hydroxy-2-methyl-propanoate (9.7 g, 63%) as a yellow oil. MS (ESI): m/z=307.1 [M+23]$^+$.

Step B. 2-(2,4-Difluorobenzyl)-3,3,3-trifluoro-2-hydroxypropanoic acid

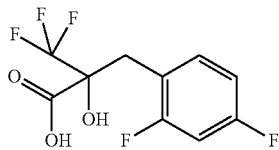 [SMILES: O=C(O)C(O)(Cc1ccc(F)cc1F)C(F)(F)F]

A mixture of methyl methyl 2-(2,4-difluorobenzyl)-3,3,3-trifluoro-2-hydroxypropanoate (9.7 g, 34.13 mmol) and potassium hydroxide (5.73 g, 102.4 mmol) in methyl alcohol (100 mL) and water (50 mL) was stirred at 50° C. for 2h. After cooling to room temperature, 1N hydrochloric acid was added until pH=3.0. The aqueous phase was extracted with ethyl acetate (200 mL). The organic layer was separated, dried over sodium sulfate and concentrated to afford 2-(2,4-difluorobenzyl)-3,3,3-trifluoro-2-hydroxypropanoic acid (9.2 g, crude) as a white solid, which was used directly to next step without further purification. $^1$H NMR (400 MHz, CDCl$_3$) δ 7.35-7.29 (m, 1H), 6.85-6.77 (m, 2H), 3.45 (d, J=16.0 Hz, 1H), 3.20 (d, J=16.0 Hz, 1H).

Step C. 6-Fluoro-2-(trifluoromethyl)-2,3-dihydrobenzofuran-2-carboxylicacid

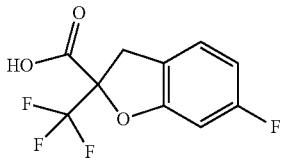 [SMILES: O=C(O)C1(C(F)(F)F)Cc2ccc(F)cc2O1]

To a mixture of 2-(2,4-difluorobenzyl)-3,3,3-trifluoro-2-hydroxypropanoic acid (3.6 g, 13.33 mmol) in N,N-dimethylformamide (5 mL) and toluene (20 mL) was added sodium hydride (1.06 g, 26.65 mmol) at room temperature. The mixture was stirred at 110° C. overnight. After cooling to room temperature, 1N hydrochloric acid was added until pH=3.0. The aqueous phase was extracted with ethyl acetate (50 mL). The organic layer was separated, dried over sodium sulfate and concentrated to afford 6-fluoro-2-(trifluoromethyl)-2,3-dihydrobenzofuran-2-carboxylic acid (3.3 g, crude) as a brown solid, which was used directly to next step without further purification. MS (ESI): m/z=273.1 [M+23]$^+$.

Step D. Methyl 6-fluoro-2-(trifluoromethyl)-2,3-dihydrobenzofuran-2-carboxylate

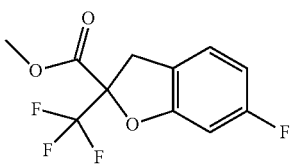 [SMILES: COC(=O)C1(C(F)(F)F)Cc2ccc(F)cc2O1]

To a mixture of 6-fluoro-2-(trifluoromethyl)-2,3-dihydrobenzofuran-2-carboxylic acid (500 mg, 2.0 mmol) and cesium carbonate (1.3 g, 4.0 mmol) in N,N-dimethylformamide (10 mL) was added methyl iodide (570 mg, 4.0 mmol). The mixture was stirred at room temperature overnight. Water was added and the aqueous phase was extracted with ethyl acetate (50 mL). The organic layer was washed with brine, dried over sodium sulfate and concentrated to afford methyl 6-fluoro-2-(trifluoromethyl)-2,3-dihydrobenzofuran-2-carboxylate (500 mg, crude), which was used directly to next step without further purification. $^1$H NMR (400 MHz, CDCl$_3$) δ 7.12-7.09 (m, 1H), 6.70-6.66 (m, 2H), 3.89 (s, 3H), 3.68 (d, J=16.0 Hz, 1H), 3.62 (d, J=16.0 Hz, 1H).

Step E. Methyl 6-fluoro-5-nitro-2-(trifluoromethyl)-2,3-dihydrobenzofuran-2-carboxylate

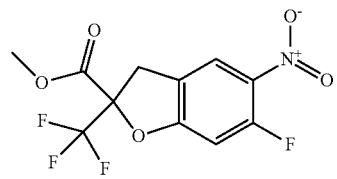 [SMILES: COC(=O)C1(C(F)(F)F)Cc2cc([N+](=O)[O-])c(F)cc2O1]

To a mixture of methyl methyl 6-fluoro-2-(trifluoromethyl)-2,3-dihydrobenzofuran-2-carboxylate (3.8 g, 8.77 mmol) in dichloromethane (20 mL) was added fuming nitric acid (4.0 mL). The mixture was stirred at room temperature for 1h. The mixture was poured into ice water and the aqueous phase was extracted with ethyl acetate (50 mL). The organic phase was separated, dried over sodium sulfate and concentrated. The residue was purified by silica gel chromatography using ethyl acetate:petroleum ether from 1:20 to 1:5 as eluting solvents to afford methyl 6-fluoro-5-nitro-2-(trifluoromethyl)-2,3-dihydrobenzofuran-2-carboxylate (2.6 g, 96%) as a light yellow solid. $^1$H NMR (400 MHz, CDCl$_3$) δ 8.00 (d, J=7.2 Hz, 1H), 6.86 (d, J=10.4 Hz, 1H), 3.93 (s, 3H), 3.76 (d, J=15.6 Hz, 1H), 3.70 (d, J=15.6 Hz, 1H). MS (ESI): m/z=310.0 [M+1]$^+$.

Step F. Methyl 6-morpholino-5-nitro-2-(trifluoromethyl)-2,3-dihydrobenzofuran-2-carboxylate

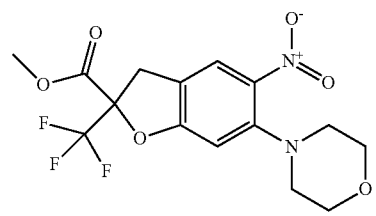 [SMILES: COC(=O)C1(C(F)(F)F)Cc2cc([N+](=O)[O-])c(N3CCOCC3)cc2O1]

A mixture of morpholine (108 mg, 1.25 mmol), 6-fluoro-5-nitro-2-(trifluoromethyl)-2,3-dihydrobenzofuran-2-carboxylate (350 mg, 1.13 mmol) and cesium carbonate (738 mg, 2.26 mmol) in acetonitrile (20 mL) was stirred at room temperature for 3h. Water was added and the aqueous phase was extracted with ethyl acetate (40 mL). The organic layer was separated, dried over sodium sulfate and concentrated to afford methyl 6-morpholino-5-nitro-2-(trifluoromethyl)-2,3-dihydrobenzofuran-2-carboxylate (400 mg, 84%) as a yellow oil. MS (ESI): m/z=377.1 [M+I]$^+$.

Step G. (6-Morpholino-5-nitro-2-(trifluoromethyl)-2,3-Dihydrobenzofuran-2-yl)methanol

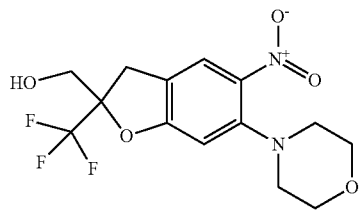 [SMILES: O=[N+]([O-])c1cc2c(cc1N1CCOCC1)OC(CO)(C(F)(F)F)C2]

To a mixture of methyl 6-morpholino-5-nitro-2-(trifluoromethyl)-2,3-dihydrobenzofuran-2-carboxylate (400 mg, 1.06 mmol) in tetrahydrofuran (20 mL) and ethanol (5 mL) was added sodium borohydride (121.19 mg, 3.19 mmol) and lithium chloride (134 mg, 3.19 mmol) at 0° C. The mixture was stirred at room temperature for 2h. Saturated ammonium chloride solution and ethyl acetate (50 mL) was added. The organic layer was separated, dried over sodium sulfate and concentrated to afford (6-morpholino-5-nitro-2-(trifluoromethyl)-2,3-dihydrobenzofuran-2-yl)methanol (370 mg, crude) as a yellow solid, which was used directly to next step without further purification. MS (ESI): m/z=349.1 [M+1]$^+$.

Step H. (5-Amino-6-morpholino-2-(trifluoromethyl)-2,3-Dihydrobenzofuran-2-yl)methanol

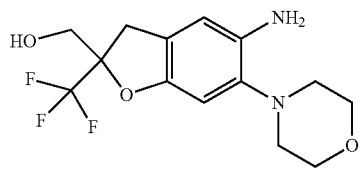 [SMILES: Nc1cc2c(cc1N1CCOCC1)OC(CO)(C(F)(F)F)C2]

A mixture of palladium on carbon (60 mg, 10% wt) and (6-morpholino-5-nitro-2-(trifluoromethyl)-2,3-dihydrobenzofuran-2-yl)methanol (370 mg, 1.06 mmol) in methyl alcohol (30 mL) was stirred at room temperature under hydrogen atmosphere for 2h. After filtration and concentration under reduced pressure, it was afforded (5-amino-6-morpholino-2-(trifluoromethyl)-2,3-dihydrobenzofuran-2-yl)methanol (50 mg, crude) as a dark solid, which was used directly to next step without further purification. MS (ESI): m/z=319.1 [M+1]$^+$.

Step I. (R)—N-(2-(hydroxymethyl)-6-morpholino-2-(trifluoromethyl)-2,3-dihydrobenzofuran-5-yl)pyrazolo[1,5-a]pyrimidine-3-carboxamide and (S)—N-(2-(hydroxymethyl)-6-morpholino-2-(trifluoromethyl)-2,3-dihydrobenzofuran-5-yl)pyrazolo[1,5-a]pyrimidine-3-carboxamide

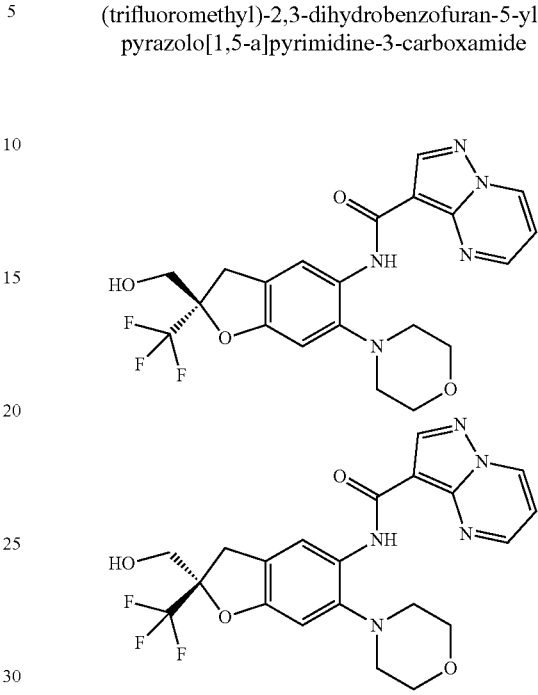

A mixture of [5-amino-6-morpholino-2-(trifluoromethyl)-3H-benzofuran-2-yl]methanol (310 mg, 0.97 mmol), pyrazolo[1,5-a]pyrimidine-3-carboxylic acid (167 mg, 1.02 mmol), (7-azabenzotriazol-1-yloxy)tripyrrolidinophosphoniumhexafluorophosphate (558 mg, 1.07 mmol) and N-ethyl-N-isopropylpropan-2-amine (354 mg, 2.92 mmol) in N,N-dimethylformamide (10 mL) was stirred at room temperature for 2h. Water was added and the aqueous phase was extracted with ethyl acetate (20 mL). The organic layer was separated, washed with brine, dried over sodium sulfate and concentrated under reduced pressure. The residue was purified by silica gel chromatography using ethyl acetate: petroleum ether (9:1) to afford 250 mg racemic product as a yellow solid. The product was resolved by chiral preparatory SFC (Column: OJ 4.6*250 mm, Sum (Decial), Mobile phase: CO$_2$/MeOH (0.2% Methanol Ammonia)=65/35) to afford N-[(2R)-2-(hydroxymethyl)-6-morpholino-2-(trifluoromethyl)-3H-benzofuran-5-yl]pyrazolo[1,5-a]pyrimidine-3-carboxamide and N-[(2S)-2-(Hydroxymethyl)-6-morpholino-2-(trifluoromethyl)-3H-benzofuran-5-yl]pyrazolo[1,5-a]pyrimidine-3-carboxamide (105 mg, 22%) (100 mg, 21%) as light yellow solids with absolute stereochemistry assigned arbitrarily.

Example 153, Peak 1: $^1$H NMR (400 MHz, CDCl$_3$) δ 10.49 (s, 1H), 8.84 (dd, J=1.6, 7.2 Hz, 1H), 8.78 (s, 1H), 8.76 (dd, J=4.0, 6.4 Hz, 1H), 8.49 (s, 1H), 7.08 (dd, J=1.6, 4.0 Hz, 1H), 6.77 (s, 1H), 4.07 (d, J=12.4 Hz, 1H), 3.96-3.93 (m, 4H), 3.86 (d, J=12.4 Hz, 1H), 3.53 (d, J=16.4 Hz, 1H), 3.42 (d, J=16.4 Hz, 1H), 2.92-2.89 (m, 4H). MS (ESI): m/z=464.2 [M+1]$^+$.

Example 154, Peak 2: $^1$H NMR (400 MHz, CDCl$_3$) δ 10.49 (s, 1H), 8.84 (dd, J=1.6, 7.2 Hz, 1H), 8.78 (s, 1H), 8.76 (dd, J=4.0, 6.4 Hz, 1H), 8.49 (s, 1H), 7.08 (dd, J=1.6, 4.0 Hz, 1H), 6.77 (s, 1H), 4.07 (d, J=12.4 Hz, 1H), 3.96-3.93 (m, 4H), 3.86 (d, J=12.4 Hz, 1H), 3.53 (d, J=16.4 Hz, 1H), 3.42 (d, J=16.4 Hz, 1H), 2.92-2.89 (m, 4H). MS (ESI): m/z=464.2 [M+1]⁺.

Examples 155 and 156. (R)—N-(2-((difluoromethoxy)methyl)-2-Methyl-6-morpholino-2,3-dihydrobenzofuran-5-yl)pyrazolo[1,5-a]pyrimidine-3-carboxamide and (S)—N-(2-((difluoromethoxy)methyl)-2-Methyl-6-morpholino-2,3-dihydrobenzofuran-5-yl)pyrazolo[1,5-a]pyrimidine-3-carboxamide

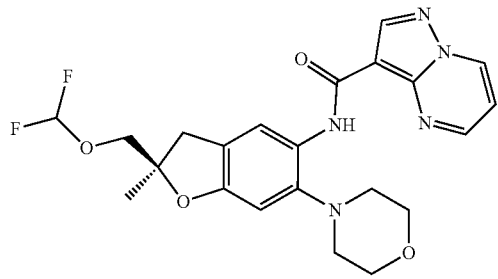

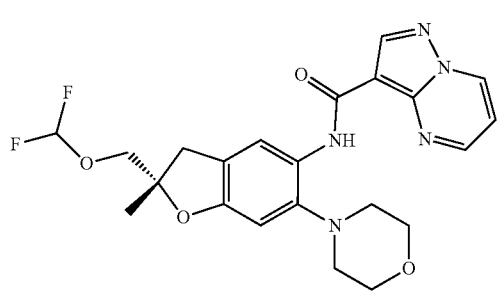

Step A. (2-Methyl-6-morpholino-5-nitro-2,3-dihydrobenzofuran-2-yl)methanol

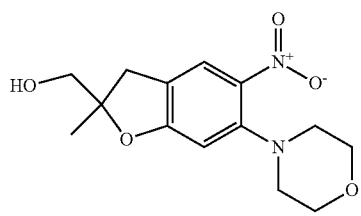 [SMILES: CC1(CO)Cc2cc([N+](=O)[O-])c(N3CCOCC3)cc2O1]

A mixture of morpholine (230 mg, 2.64 mmol), (6-fluoro-2-methyl-5-nitro-3H-benzofuran-2-yl)methanol (Intermediate 3) (300 mg, 1.32 mmol) and potassium carbonate (364 mg, 2.64 mmol) in acetonitrile (20 mL) was stirred at room temperature for 3h. Water was added and the mixture was extracted with ethyl acetate (40 mL). The organic layer was concentrated to afford (2-methyl-6-morpholino-5-nitro-2,3-dihydrobenzofuran-2-yl)methanol (420 mg, crude) as a yellow oil, which was used directly to next step without further purification. MS (ESI): m/z=295.1 [M+1]⁺.

Step B. 4-(2-((Difluoromethoxy)methyl)-2-Methyl-5-nitro-2,3-dihydrobenzofuran-6-yl)morpholine

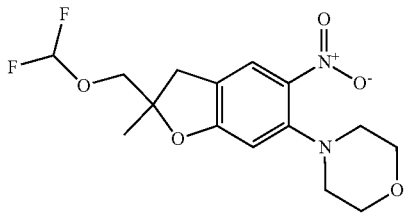 [SMILES: CC1(COC(F)F)Cc2cc([N+](=O)[O-])c(N3CCOCC3)cc2O1]

To a mixture of (2-methyl-6-morpholino-5-nitro-2,3-dihydrobenzofuran-2-yl)methanol (180 mg, 0.61 mmol) and copper iodide (34 mg, 0.24 mmol) in acetonitrile (20 mL) was added difluoro(fluorosulfonyl)acetic acid (218 mg, 1.22 mmol) at 50° C. The mixture was stirred 50° C. for 1h. The mixture was concentrated and purified by silica gel chromatography using ethyl acetate:petroleum ether (3:20) to afford 4-(2-((difluoromethoxy)methyl)-2-methyl-5-nitro-2,3-dihydrobenzofuran-6-yl)morpholine (70 mg, 31%) as a yellow oil. MS (ESI): m/z=345.1 [M+1]⁺.

Step C. 2-((Difluoromethoxy)methyl)-2-methyl-6-morpholino-2,3-dihydrobenzofuran-5-amine

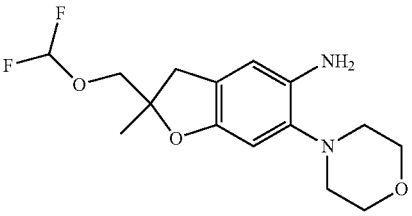 [SMILES: CC1(COC(F)F)Cc2cc(N)c(N3CCOCC3)cc2O1]

A mixture of palladium on carbon (20 mg, 10% wt) and 4-(2-((difluoromethoxy)methyl)-2-methyl-5-nitro-2,3-dihydrobenzofuran-6-yl)morpholine (70 mg, 0.2 mmol) in methanol (15 mL) was stirred at room temperature under hydrogen atmosphere for 1h. After filtration and concentration under reduced pressure, it was afforded 2-((difluoromethoxy)methyl)-2-methyl-6-morpholino-2,3-dihydrobenzofuran-5-amine (60 mg, crude) as a green oil, which was used directly to next step without further purification. MS (ESI): m/z=315.1[M+1]⁺.

Step D. (R)—N-(2-((difluoromethoxy)methyl)-2-Methyl-6-morpholino-2,3-dihydrobenzofuran-5-yl)pyrazolo[1,5-a]pyrimidine-3-carboxamide and (S)—N-(2-((difluoromethoxy)methyl)-2-Methyl-6-morpholino-2,3-dihydrobenzofuran-5-yl)pyrazolo[1,5-a]pyrimidine-3-carboxamide

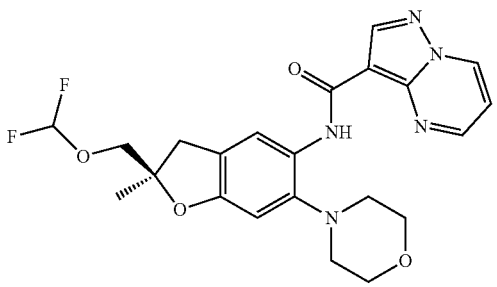

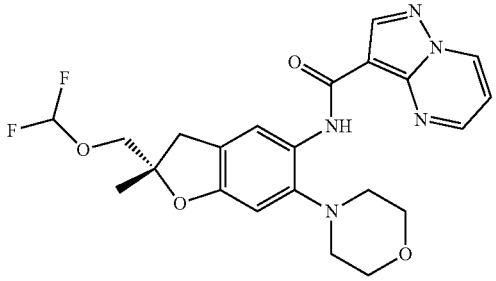

A mixture of pyrazolo[1,5-a]pyrimidine-3-carboxylic acid (80 mg, 0.5 mmol), (7-azabenzotriazol-1-yloxy)tripyrrolidinophosphoniumhexafluorophosphate (324 mg, 0.62 mmol), N-ethyl-N-isopropylpropan-2-amine (150 mg, 1.24 mmol) and 2-((difluoromethoxy)methyl)-2-methyl-6-morpholino-2,3-dihydrobenzofuran-5-amine (140 mg, 0.42 mmol) in N,N-dimethylformamide (10 mL) was stirred at room temperature for 2h. Water was added and the aqueous phase was extracted with ethyl acetate (20 mL). The organic layer was washed with brine, dried over sodium sulfate and concentrated. The residue was purified by silica gel chromatography using ethyl acetate:petroleum ether (3:1) as eluting solvents to afford N-(2-(hydroxymethyl)-2,7-dimethyl-6-morpholino-2,3-dihydrobenzofuran-5-yl)pyrazolo[1,5-a]pyrimidine-3-carboxamide (140 mg, 73%) as a yellow solid. The product was resolved by chiral preparatory SFC (Column: AD 20*250 mm, Sum (Dacel), Mobile phase: CO2/MEOH {0.5% Ammonia (7M methanol)}=70/30) to afford N-[(2R)-2-(difluoromethoxymethyl)-2-methyl-6-morpholino-3H-benzofuran-5-yl]pyrazolo[1,5-a]pyrimidine-3-carboxamide and N-[(2S)-2-(difluoromethoxymethyl)-2-methyl-6-morpholino-3H-benzofuran-5-yl]pyrazolo[1,5-a]pyrimidine-3-carboxamide (50 mg, 53%) (45 mg, 47%) as yellow solids with absolute stereochemistry assigned arbitrarily.

Example 155, Peak 1: $^1$H NMR (400 MHz, DMSO-d$_6$) δ 10.45 (s, 1H), 9.36 (dd, J=1.5, 6.8 Hz, 1H), 8.94 (dd, J=1.6, 4.0 Hz, 1H), 8.68 (s, 1H), 8.32 (s, 1H), 7.35 (dd, J=4.0, 7.2 Hz, 1H), 6.73 (t, J=75.2 Hz, 1H), 6.77 (s, 1H), 3.94 (s, 2H), 3.85-3.83 (m, 4H), 3.18 (d, J=15.6 Hz, 1H), 2.97 (d, J=15.6 Hz, 1H), 2.83-2.81 (m, 4H), 1.42 (s, 3H). MS (ESI): m/z=460.2[M+1]$^+$.

Example 156, Peak 2: $^1$H NMR (400 MHz, DMSO-d$_6$) δ 10.45 (s, 1H), 9.36 (dd, J=1.5, 6.8 Hz, 1H), 8.94 (dd, J=1.6, 4.0 Hz, 1H), 8.68 (s, 1H), 8.32 (s, 1H), 7.35 (dd, J=4.0, 7.2 Hz, 1H), 6.73 (t, J=75.2 Hz, 1H), 6.77 (s, 1H), 3.94 (s, 2H), 3.85-3.83 (m, 4H), 3.18 (d, J=15.6 Hz, 1H), 2.97 (d, J=15.6 Hz, 1H), 2.83-2.81 (m, 4H), 1.42 (s, 3H). MS (ESI): m/z=460.2[M+1]$^+$.

Examples 157 and 158. (R)—N-(2-(2-Hydroxypropan-2-yl)-2-methyl-6-morpholino-2,3-dihydrobenzofuran-5-yl)pyrazolo[1,5-a]pyrimidine-3-carboxamide and (S)—N-(2-(2-Hydroxypropan-2-yl)-2-methyl-6-morpholino-2,3-dihydrobenzofuran-5-yl)pyrazolo[1,5-a]pyrimidine-3-carboxamide

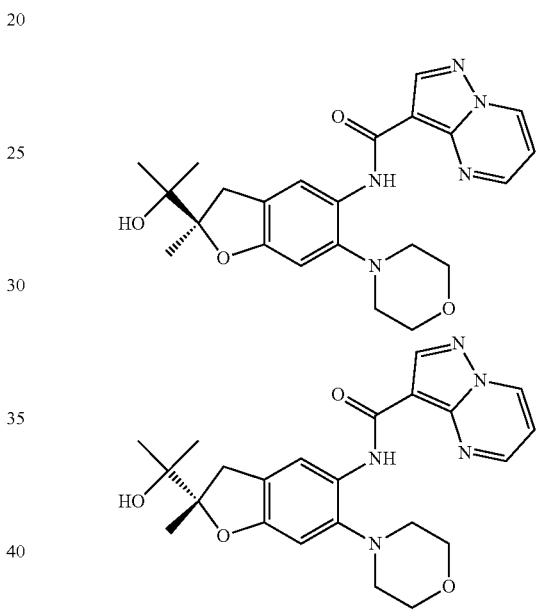

Step A. 2-(6-Fluoro-2-methyl-2,3-dihydrobenzofuran-2-yl)propan-2-ol

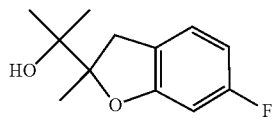

To a solution of methyl 6-fluoro-2-methyl-3H-benzofuran-2-carboxylate (877 mg, 4.17 mmol) in anhydrous tetrahydrofuran (20 mL) was added drop-wise methylmagnesium bromide (3 M in ditheyl ether, 4.17 mL, 12.52 mmol) under N$_2$ atmosphere at −78° C. The mixture was stirred at −78° C. for 1h. The mixture was quenched with saturated ammonium chloride solution. Ethyl acetate (50 mL) was added. The organic layer was separated, dried over sodium sulfate and concentrated to afford 2-(6-fluoro-2-methyl-2,3-dihydrobenzofuran-2-yl)propan-2-ol (800 mg, crude) as a colorless oil, which was used directly to next step without further purification. MS (ESI): m/z=193.1 [M-17]$^+$.

Step B. 2-(6-Fluoro-2-methyl-5-nitro-2,3-dihydrobenzofuran-2-yl)propan-2-ol

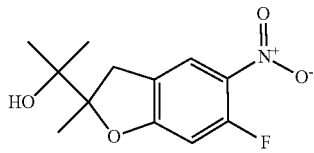 [SMILES: CC(C)(O)C1(C)Cc2cc([N+](=O)[O-])c(F)cc2O1]

A mixture of 2-(6-fluoro-2-methyl-2,3-dihydrobenzofuran-2-yl)propan-2-ol (400 mg, 1.9 mmol) in dichloromethane (15 mL) was added concentrated nitric acid (60-70% wt, 0.5 mL). The mixture was stirred at room temperature for 1h. The mixture was poured into ice water and extracted with dichloromethane (30 mL). The organic layer was separated, dried over sodium sulfate and concentrated. The residue was purified by silica gel chromatography ethyl acetate:petroleum ether (1:4) as eluting solvents to afford 2-(6-fluoro-2-methyl-5-nitro-2,3-dihydrobenzofuran-2-yl)propan-2-ol (320 mg, 59%) as a brown oil. $^1$H NMR (400 MHz, CDCl$_3$) δ 7.94 (d, J=7.8 Hz, 1H), 6.61 (d, J=12.8 Hz, 1H), 3.54 (d, J=15.6 Hz, 1H), 2.82 (d, J=15.6 Hz, 1H), 1.38 (s, 3H), 1.24 (s, 6H).

Step C. 2-(2-Methyl-6-morpholino-5-nitro-2,3-dihydrobenzofuran-2-yl)propan-2-ol

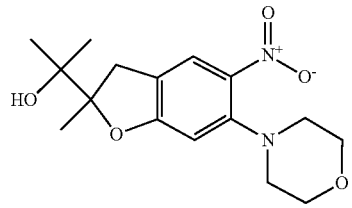 [SMILES: CC(C)(O)C1(C)Cc2cc([N+](=O)[O-])c(N3CCOCC3)cc2O1]

A mixture of morpholine (218 mg, 2.51 mmol), 2-(6-fluoro-2-methyl-5-nitro-2,3-dihydrobenzofuran-2-yl)propan-2-ol (320 mg, 1.25 mmol) and potassium carbonate (346 mg, 2.51 mmol) in acetonitrile (20 mL) was stirred at room temperature for 3h. Water was added and the aqueous phase was extracted with ethyl acetate (50 mL). The organic layer was dried over sodium sulfate and concentrated to afford 2-(2-methyl-6-morpholino-5-nitro-2,3-dihydrobenzofuran-2-yl)propan-2-ol (318 mg, crude) as a yellow oil, which was used directly to next step without further purification. MS (ESI): m/z=323.2 [M+1]$^+$.

Step D. 2-(5-Amino-2-methyl-6-morpholino-2,3-dihydrobenzofuran-2-yl)propan-2-ol

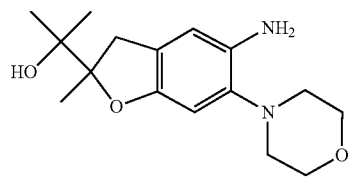 [SMILES: CC(C)(O)C1(C)Cc2cc(N)c(N3CCOCC3)cc2O1]

A mixture of palladium on carbon (100 mg, 10% wt) and 2-(2-methyl-6-morpholino-5-nitro-2,3-dihydrobenzofuran-2-yl)propan-2-ol (300 mg, 0.93 mmol) in methanol (30 mL) was stirred at room temperature under hydrogen atmosphere for 1h. After filtration and concentration under reduced pressure, it was afforded 2-(5-amino-2-methyl-6-morpholino-2,3-dihydrobenzofuran-2-yl)propan-2-ol (280 mg, crude) as a green oil, which was used directly to next step without further purification. MS (ESI): m/z=293.2[M+1]$^+$.

Step E. (R)—N-(2-(2-Hydroxypropan-2-yl)-2-methyl-6-morpholino-2,3-dihydrobenzofuran-5-yl)pyrazolo[1,5-a]pyrimidine-3-carboxamide and (S)—N-(2-(2-Hydroxypropan-2-yl)-2-methyl-6-morpholino-2,3-dihydrobenzofuran-5-yl)pyrazolo[1,5-a]pyrimidine-3-carboxamide

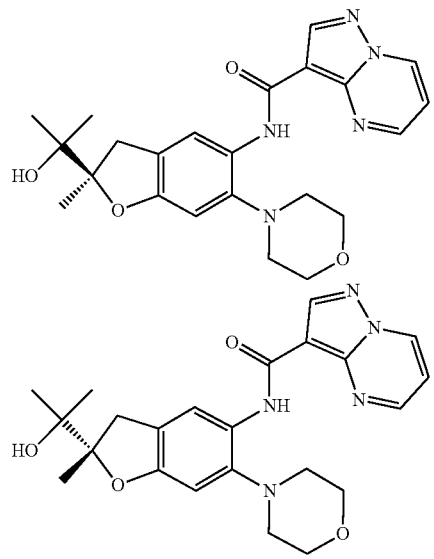

A mixture of pyrazolo[1,5-a]pyrimidine-3-carboxylic acid (174 mg, 1.07 mmol), (7-azabenzotriazol-1-yloxy)tripyrrolidinophosphoniumhexafluorophosphate (695 mg, 1.33 mmol), N-ethyl-N-isopropylpropan-2-amine (323 mg, 2.67 mmol) and 2-(5-amino-2-methyl-6-morpholino-2,3-dihydrobenzofuran-2-yl)propan-2-ol (260 mg, 0.89 mmol) in N,N-dimethylformamide (10 mL) was stirred at room temperature for 2h. The crude reaction was purified by preparative HPLC (Gilson 281, Xbridge 21.2*250 mm c18, 10 um; A: acetonitrile, 25-55%, B: 10 M ammonium bicarbonatein water) to afford N-(2-(2-hydroxypropan-2-yl)-2-methyl-6-morpholino-2,3-dihydrobenzofuran-5-yl)pyrazolo[1,5-a]pyrimidine-3-carboxamide (100 mg) as a yellow solid. The product was resolved by chiral preparatory SFC (Column: AD 20*250 mm, Sum (Dacel), Mobile phase: CO2/MEOH{0.5% Ammonia (7M methanol)}=70/30) to afford N-[(2R)-2-(1-hydroxy-1-methyl-ethyl)-2-methyl-6-morpholino-3H-benzofuran-5-yl]pyrazolo[1,5-a]pyrimidine-3-carboxamide and N-[(2S)-2-(1-hydroxy-1-methyl-ethyl)-2-methyl-6-morpholino-3H-benzofuran-5-yl]pyrazolo[1,5-a]pyrimidine-3-carboxamide (45 mg, 45%) (50 mg, 50%) as yellow solids with absolute stereochemistry assigned arbitrarily.

Example 157, Peak 1: $^1$H NMR (400 MHz, DMSO-d$_6$) δ 10.43 (s, 1H), 9.37 (dd, J=7.2, 1.6 Hz, 1H), 8.94 (dd, J=4.0, 1.6 Hz, 1H), 8.68 (s. 1H), 8.29 (s, 1H), 7.34 (dd, J=7.2, 4.0 Hz, 1H), 6.71 (s, 1H), 4.53 (s, 1H), 3.85-3.83 (m, 4H), 3.46 (d, J=16.0 Hz, 1H), 2.83-2.81 (m, 4H), 2.73 (d, J=16.0 Hz, 1H), 1.32 (s, 3H), 1.17 (d, J=5.2 Hz, 6H). MS (ESI): m/z=438.3[M+1]⁺.

Example 158, Peak 2: ¹H NMR (400 MHz, DMSO-$d_6$) δ 10.43 (s, 1H), 9.37 (dd, J=7.2, 1.6 Hz, 1H), 8.94 (dd, J=4.0, 1.6 Hz, 1H), 8.68 (s. 1H), 8.29 (s, 1H), 7.34 (dd, J=7.2, 4.0 Hz, 1H), 6.71 (s, 1H), 4.53 (s, 1H), 3.85-3.83 (m, 4H), 3.46 (d, J=16.0 Hz, 1H), 2.83-2.81 (m, 4H), 2.73 (d, J=16.0 Hz, 1H), 1.32 (s, 3H), 1.17 (d, J=5.2 Hz, 6H). MS (ESI): m/z=438.3[M+1]⁺.

Examples 159 and 160. (R)—N-(2-Cyclopropyl-6-(4-(2,2-difluoroethyl)piperazin-1-yl)-2-methyl-2,3-dihydrobenzofuran-5-yl)pyrazolo[1,5-a]pyrimidine-3-carboxamide and (S)—N-(2-Cyclopropyl-6-(4-(2,2-difluoroethyl)piperazin-1-yl)-2-methyl-2,3-dihydrobenzofuran-5-yl)pyrazolo[1,5-a]pyrimidine-3-carboxamide

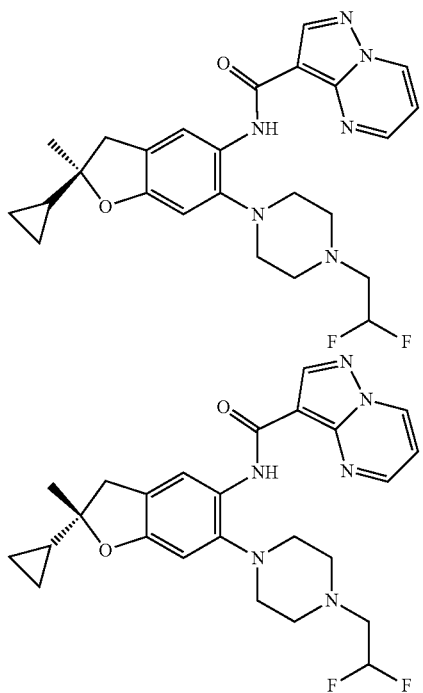

Step A.
2-Cyclopropyl-1-(2,4-difluorophenyl)propan-2-ol

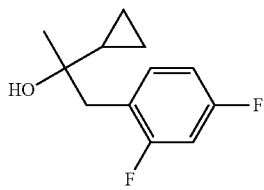

To a mixture of 1-(2,4-difluorophenyl)propan-2-one (prepared by similar method as Example 14, step B) (900.0 mg, 5.29 mmol) in tetrahydrofuran (20 mL) was added dropwise cyclopropylmagnesium bromide (0.5 M in tetrahydrofuran, 10.58 mL, 5.29 mmol) at −78° C. under nitrogen atmosphere. The mixture was stirred at room temperature for 1h. The reaction was quenched by addition of saturated ammonium chloride (20 mL). The mixture was extracted with ethyl acetate (50 mL) twice. The combined organic layers were washed with water, dried over anhydrous sodium sulfate and concentrated under reduced pressure. The residue was purified on silica gel chromatography using ethyl acetate:petroleum ether (1:10) as eluting solvents to afford 2-cyclopropyl-1-(2,4-difluorophenyl)propan-2-ol (800.0 mg, 68%) as a light yellow foam. MS (ESI): m/z=195.1 [M-17]⁺.

Step B. 2-Cyclopropyl-6-fluoro-2-methyl-2,3-dihydrobenzofuran

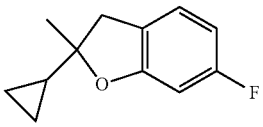

A mixture of 2-cyclopropyl-1-(2,4-difluorophenyl)propan-2-ol (600.0 mg, 2.83 mmol) and tert-butoxypotassium (1268.9 mg, 11.31 mmol) in tetrahydrofuran (10 mL) was stirred at 65° C. for 3h. After cooling to room temperature, water and ethyl acetate (20 mL) was added. The organic layer was separated and dried over sodium sulfate. After concentration, the residue was purified by silica gel chromatography using ethyl acetate:petroleum ether (1:10) as eluting solvents to afford 2-cyclopropyl-6-fluoro-2-methyl-3H-benzofuran (460.0 mg, 80%) as a colorless oil. MS (ESI): m/z=193.1 [M+H]⁺.

Step C. 2-Cyclopropyl-6-fluoro-2-methyl-5-nitro-2,3-dihydrobenzofuran

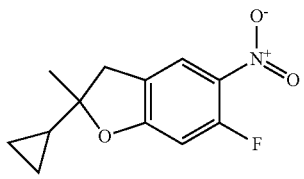 [SMILES: CC1(C2CC2)Cc2cc([N+](=O)[O-])c(F)cc2O1]

To a solution of 2-cyclopropyl-6-fluoro-2-methyl-3H-benzofuran (460.0 mg, 2.39 mmol) in dichloromethane (20 mL) at 0° C. was slowly added fuming nitric acid (0.5 mL) and stirred for 15 min. The mixture was poured into ice water and the organic layer was separated and dried over hydrous sodium sulfate. After concentration, the residue was purified by silica gel chromatography using ethyl acetate:petroleum ether (1:15) as eluting solvents to afford 2-cyclopropyl-6-fluoro-2-methyl-5-nitro-3H-benzofuran (450.0 mg, 75%) as an orange solid. MS (ESI): m/z=238.1 [M+1]⁺.

Step D. 1-(2-Cyclopropyl-2-methyl-5-nitro-2,3-dihydrobenzofuran-6-yl)-4-(2,2-difluoroethyl)piperazine

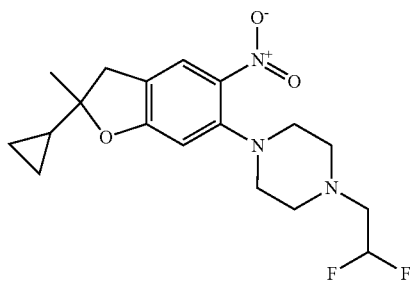 [SMILES: CC1(C2CC2)Cc2cc([N+](=O)[O-])c(N3CCN(CC(F)F)CC3)cc2O1]

A mixture of 2-cyclopropyl-6-fluoro-2-methyl-5-nitro-3H-benzofuran (220.0 mg, 0.93 mmol), 1-(2,2-difluoroethyl)piperazine dihydrochloride (310.3 mg, 1.39 mmol) and cesium carbonate (906.5 mg, 2.78 mmol) in acetonitrile (5 mL) was stirred at 60° C. overnight. The reaction mixture was filtered and the filtrate was concentrated under reduced pressure. The residue was purified by silica gel chromatography using ethyl acetate:petroleum ether (1:2) to afford 1-(2-cyclopropyl-2-methyl-5-nitro-3H-benzofuran-6-yl)-4-(2,2-difluoroethyl)piperazine (300.0 mg, 84%) as a yellow solid. MS (ESI): m/z=368.2 [M+1]$^+$.

Step E. 2-Cyclopropyl-6-(4-(2,2-difluoroethyl)piperazin-1-yl)-2-methyl-2,3-dihydrobenzofuran-5-amine

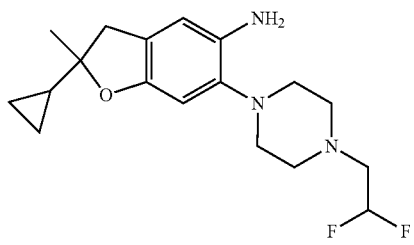 [SMILES: CC1(C2CC2)Cc2cc(N)c(N3CCN(CC(F)F)CC3)cc2O1]

A mixture of 1-(2-cyclopropyl-2-methyl-5-nitro-3H-benzofuran-6-yl)-4-(2,2-difluoroethyl)piperazine (150.0 mg, 0.41 mmol) and palladium on carbon (15.0 mg, 10% wt) in methanol (5 mL) was stirred at 25° C. under hydrogen atmosphere for 2h. After filtration, the filtrate was concentrated under reduced pressure to afford 2-cyclopropyl-6-[4-(2,2-difluoroethyl)piperazin-1-yl]-2-methyl-3H-benzofuran-5-amine (100.0 mg, crude) as a colorless oil, which was used directly to next step without further purification. MS (ESI): m/z=338.3 [M+1]$^+$.

Step F. (R)—N-(2-Cyclopropyl-6-(4-(2,2-difluoroethyl)piperazin-1-yl)-2-methyl-2,3-dihydrobenzofuran-5-yl)pyrazolo[1,5-a]pyrimidine-3-carboxamide and (S)—N-(2-Cyclopropyl-6-(4-(2,2-difluoroethyl) piperazin-1-yl)-2-methyl-2,3-dihydrobenzofuran-5-yl)pyrazolo[1,5-a]pyrimidine-3-carboxamide

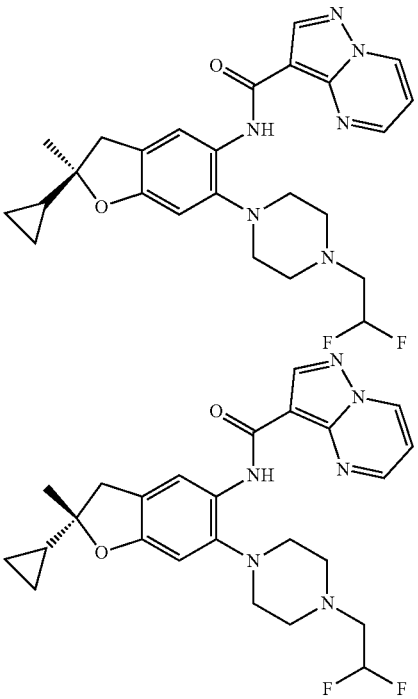

A mixture of 2-cyclopropyl-6-[4-(2,2-difluoroethyl)piperazin-1-yl]-2-methyl-3H-benzofuran-5-amine (240.0 mg, 0.71 mmol), (7-azabenzotriazol-1-yloxy)tripyrrolidinophosphoniumhexafluorophosphate (370.9 mg, 0.71 mmol) and N-ethyl-N-isopropylpropan-2-amine (275.8 mg, 2.13 mmol) in N,N-dimethylformamide (5 mL) was stirred at room temperature for 30 min. Pyrazolo[1,5-a]pyrimidine-3-carboxylic acid (116.0 mg, 0.71 mmol) was then added. The resulting mixture was stirred at room temperature overnight. Water and ethyl acetate (30 mL) was added and the organic layer was separated and dried over sodium sulfate. After filtration and concentration under reduced pressure, the residue was purified by silica gel chromatography using ethyl acetate:petroleum ether (10:1) and then resolved by chiral pre-HPLC(Column: AS-H 20*250 mm, 5 um (Dacel), Mobile phase: Hexane (0.1% DEA)/Ethanol (0.1% DEA)=80/20) to afford N-[(2R)-2-cyclopropyl-6-[4-(2,2-difluoroethyl)piperazin-1-yl]-2-methyl-3H-benzofuran-5-yl]pyrazolo[1,5-a]pyrimidine-3-carboxamide and N-[(2S)-2-cyclopropyl-6-[4-(2,2-difluoroethyl)piperazin-1-yl]-2-methyl-3H-benzofuran-5-yl]pyrazolo[1,5-a]pyrimidine-3-carboxamide (40 mg, 12%) (55 mg, 16%) as yellow solids with absolute stereochemistry assigned arbitrarily.

Example 159, Peak 1: $^1$HNMR (400 MHz, DMSO-d$_6$): δ 10.38 (s, 1H), 9.35 (d, J=6.8 Hz, 1H), 8.94 (d, J=2.8 Hz, 1H), 8.67 (s, 1H), 8.29 (s, 1H), 7.35 (dd, J=4.0, 6.8 Hz, 1H), 6.68 (s, 1H), 6.19 (tt, J=4.0, 56.0 Hz, 1H), 2.98 (q, J=15.6, 32.0 Hz, 2H), 2.91-2.73 (m, 1OH), 1.36 (s, 3H), 1.25-1.16 (m, 1H), 0.46-0.40 (m, 3H) 0.31-0.27 (m, 1H). MS (ESI): m/z=483.3[M+1]$^+$.

Example 160, Peak 2: ¹H NMR (400 MHz, DMSO-d₆): δ 10.38 (s, 1H), 9.35 (d, J=6.8 Hz, 1H), 8.94 (d, J=2.8 Hz, 1H), 8.67 (s, 1H), 8.29 (s, 1H), 7.35 (dd, J=4.0, 6.8 Hz, 1H), 6.68 (s, 1H), 6.19 (tt, J=4.0, 56.0 Hz, 1H), 2.98 (q, J=15.6, 32.0 Hz, 2H), 2.91-2.73 (m, 1OH), 1.36 (s, 3H), 1.25-1.16 (m, 1H), 0.46-0.40 (m, 3H) 0.31-0.27 (m, 1H). MS (ESI): m/z=483.3[M+1]⁺.

Examples 161 and 162. (R)—N-(2-Cyclopropyl-6-(4-fluoro-4-(hydroxymethyl)piperidin-1-yl)-2-methyl-2,3-dihydrobenzofuran-5-yl)pyrazolo[1,5-a]pyrimidine-3-carboxamide and (S)—N-(2-Cyclopropyl-6-(4-fluoro-4-(hydroxymethyl)piperidin-1-yl)-2-methyl-2,3-dihydrobenzofuran-5-yl)pyrazolo[1,5-a]pyrimidine-3-carboxamide

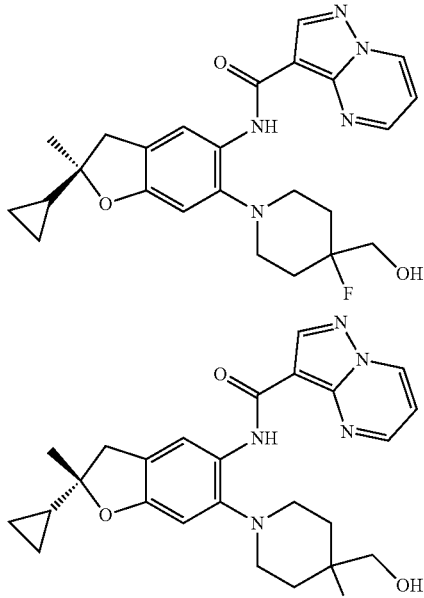

Step A. (1-(2,2-Dimethyl-5-nitro-2,3-dihydrobenzofuran-6-yl)-4-fluoropiperidin-4-yl)methanol 2,2,2-trifluoroacetic acid salt

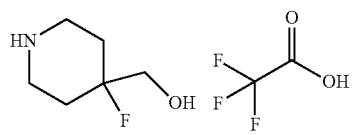

A mixture of tert-butyl 4-fluoro-4-(hydroxymethyl)piperidine-1-carboxylate (300 mg, 1.29 mmol in trifluoroacetic acid (1 mL) and dichloromethane (2 mL) was stirred 20° C. for 1h. The mixture was concentration under reduced pressure to afford (4-fluoropiperidin-4-yl)methanol 2,2,2-trifluoroacetic acid salt (300 mg, 1.21 mmol, crude) as a colorless oil, which was used directly to the next step without purification. MS (ESI): m/z=134.1 [M+1]⁺.

Step B. (1-(2-Cyclopropyl-2-methyl-5-nitro-2,3-dihydrobenzofuran-6-yl)-4-fluoropiperidin-4-yl)methanol

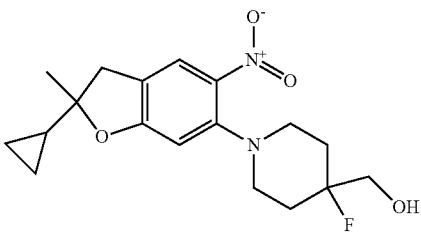 [SMILES: CC1(C2CC2)Cc2cc([N+](=O)[O-])c(N3CCC(F)(CO)CC3)cc2O1]

A mixture of 2-cyclopropyl-6-fluoro-2-methyl-5-nitro-3H-benzofuran (Examples 159 and 160, step C) (110.0 mg, 0.46 mmol), (4-fluoro-4-piperidyl)methanol and potassium carbonate (192.3 mg, 1.39 mmol) in acetonitrile (5 mL) was stirred at room temperature overnight. The reaction mixture was filtered and the filtrate was concentrated under vacuum and the residue was purified on silica gel chromatography using ethyl acetate:petroleum ether (1:5) as eluting solvents to afford [1-(2-cyclopropyl-2-methyl-5-nitro-3H-benzofuran-6-yl)-4-fluoro-4-piperidyl]methanol (130.0 mg, 76%) as a yellow solid. MS (ESI): m/z=351.2 [M+1]⁺.

Step F. (1-(5-Amino-2-cyclopropyl-2-methyl-2,3-dihydrobenzofuran-6-yl)-4-fluoropiperidin-4-yl)methanol

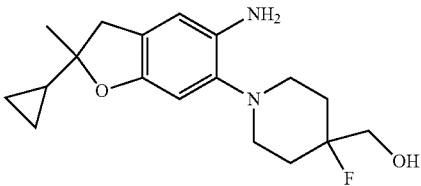 [SMILES: CC1(C2CC2)Cc2cc(N)c(N3CCC(F)(CO)CC3)cc2O1]

A mixture of [1-(2-cyclopropyl-2-methyl-5-nitro-3H-benzofuran-6-yl)-4-fluoro-4-piperidyl]methanol (130.0 mg, 0.37 mmol) and palladium on carbon (13 mg, 10% wt) in methyl alcohol (5 mL) was stirred at 25° C. under hydrogen atmosphere for 1h. After filtration, the filtrate was concentrated under reduced pressure to afford [1-(5-amino-2-cyclopropyl-2-methyl-3H-benzofuran-6-yl)-4-fluoro-4-piperidyl]methanol (100.0 mg, crude) as a colorless oil, which was used in the next step without further purification. MS (ESI): m/z=321.2 [M+1]⁺.

Step G. (R)—N-(2-Cyclopropyl-6-(4-fluoro-4-(hydroxymethyl)piperidin-1-yl)-2-methyl-2,3-dihydrobenzofuran-5-yl)pyrazolo[1,5-a]pyrimidine-3-carboxamide and (S)—N-(2-Cyclopropyl-6-(4-fluoro-4-(hydroxymethyl)piperidin-1-yl)-2-methyl-2,3-dihydrobenzofuran-5-yl)pyrazolo[1,5-a]pyrimidine-3-carboxamide

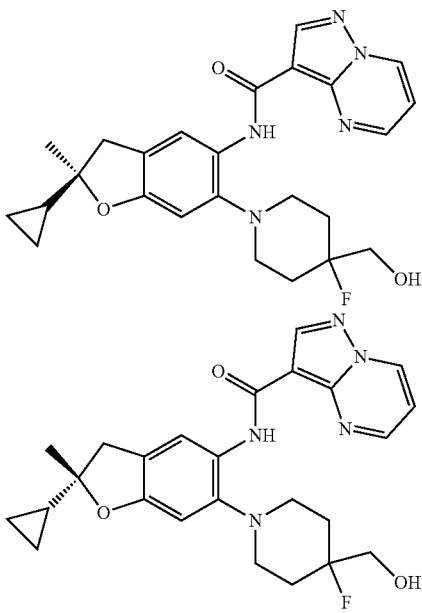

A mixture of [1-(5-amino-2-cyclopropyl-2-methyl-3H-benzofuran-6-yl)-4-fluoro-4-piperidyl]methanol (100.0 mg, 0.3100 mmol), pyrazolo[1,5-a]pyrimidine-3-carbonyl chloride (56.7 mg, 0.31 mmol), (7-azabenzotriazol-1-yloxy)tripyrrolidinophosphoniumhexafluorophosphate (162.7 mg, 0.31 mmol) and N-ethyl-N-isopropylpropan-2-amine (121.0 mg, 0.94 mmol) in N,N-dimethylformamide (5 mL) was stirred at room temperature overnight. Water and ethyl acetate (30 mL) were added and the organic layer was separated. The organic layer was washed with brine and dried over sodium sulfate.

After filtration, the mixture was concentrated and purified by silica gel chromatography using ethyl acetate:petroleum ether (10:1) and resolved by chiral preparative HPLC(Column CE-4, Mobile Phase: n-Hexane (0.1% DEA): EtOH (0.1% DEA)=70:30, Flow rate: 50 mL/min) to afford N-[(2S)-2-cyclopropyl-6-[4-fluoro-4-(hydroxymethyl)-1-piperidyl]-2-methyl-3H-benzofuran-5-yl]pyrazolo[1,5-a]pyrimidine-3-carboxamide and N-[(2R)-2-cyclopropyl-6-[4-fluoro-4-(hydroxymethyl)-1-piperidyl]-2-methyl-3H-benzofuran-5-yl]pyrazolo[1,5-a]pyrimidine-3-carboxamide (36.0 mg, 25%; 25.0 mg, 17%) as yellow solids with absolute stereochemistry assigned arbitrarily.

Example 161, Peak 1: $^1$H NMR (400 MHz, DMSO-d$_6$): δ 10.41 (s, 1H), 9.36 (dd, J=1.6, 7.2 Hz, 1H), 8.88 (dd, J=1.2, 4.0 Hz, 1H), 8.68 (s, 1H), 8.32 (s, 1H), 7.33 (dd, J=4.0, 7.2 Hz, 1H), 6.68 (s, 1H), 5.15 (t, J=6.0 Hz, 1H), 3.53 (dd, J=6.0, 18.0 Hz, 2H), 2.99 (q, J=16.0, 31.6 Hz, 2H), 2.92-2.78 (m, 4H), 2.15-1.95 (m, 2H), 1.91-1.75 (m, 2H), 1.37 (s, 3H), 1.27-1.16 (m, 1H), 0.46-0.36 (m, 3H) 0.33-0.26 (m, 1H). MS (ESI): m/z=466.2[M+1]$^+$.

Example 162, Peak 2: $^1$H NMR (400 MHz, DMSO-d$_6$):4 10.41 (s, 1H), 9.36 (dd, J=1.6, 7.2 Hz, 1H), 8.88 (dd, J=1.2, 4.0 Hz, 1H), 8.68 (s, 1H), 8.32 (s, 1H), 7.33 (dd, J=4.4, 7.2 Hz, 1H), 6.68 (s, 1H), 5.15 (t, J=6.0 Hz, 1H), 3.52 (dd, J=6.0, 18.0 Hz, 2H), 2.99 (q, J=16.0, 31.6 Hz, 2H), 2.92-2.78 (m, 4H), 2.14-1.94 (m, 2H), 1.91-1.79 (m, 2H), 1.36 (s, 3H), 1.27-1.17 (m, 1H), 0.46-0.36 (m, 3H) 0.33-0.26 (m, 1H). MS (ESI): m/z=466.2[M+1]$^+$.

Examples 163 and 164. (R)-6-Chloro-N-(2-(hydroxymethyl)-6-(4-(hydroxymethyl)piperidin-1-yl)-2-methyl-2,3-dihydrobenzofuran-5-yl)pyrazolo[1,5-a]pyrimidine-3-carboxamide and (S)-6-Chloro-N-(2-(hydroxymethyl)-6-(4-(hydroxymethyl)piperidin-1-yl)-2-methyl-2,3-dihydrobenzofuran-5-yl)pyrazolo[1,5-a]pyrimidine-3-carboxamide

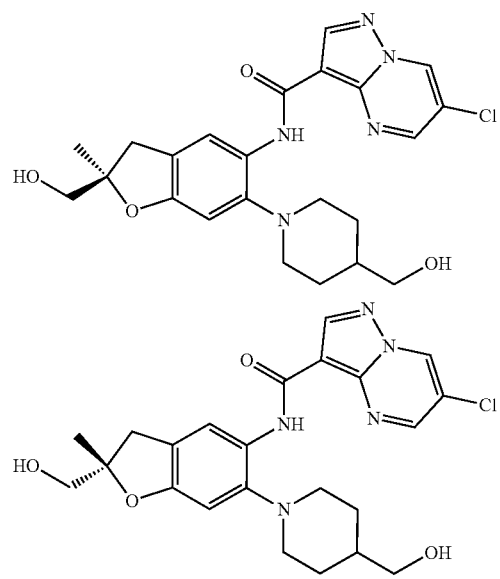

Step A. 6-Chloropyrazolo[1,5-a]pyrimidine-3-carboxylic acid

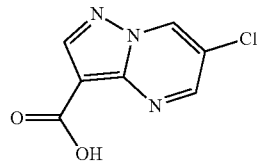 [SMILES: O=C(O)c1cnn2cc(Cl)cnc12]

A mixture of 5-amino-1H-pyrazole-4-carboxylic acid (100.0 mg, 0.79 mmol) and 2-chloromalonaldehyde (84.0 mg, 0.79 mmol) in acetic acid (1 mL) and 0.3 mL ethanol was stirred for 2h at 60° C. After filtration, the wet cake was washed with methanol and dried in vacuo to afford 6-chloropyrazolo[1,5-a]pyrimidine-3-carboxylic acid (80 mg, crude) as a white solid, which was used directly to next step without further purification. MS (ESI): m/z=179.9 [M-17]$^+$.

Step B. [1-[2-(Hydroxymethyl)-2-methyl-5-nitro-3H-benzofuran-6-yl]-4-piperidyl]methanol

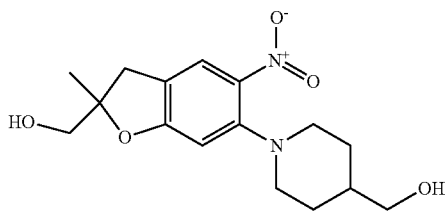 [SMILES: CC1(CO)Cc2cc([N+](=O)[O-])c(N3CCC(CO)CC3)cc2O1]

A mixture of (6-fluoro-2-methyl-5-nitro-3H-benzofuran-2-yl)methanol (Intermediate 3) (285 mg, 1.22 mmol) and 4-piperidinylmethanol (211 mg, 1.83 mmol) in acetonitrile (5 mL), was stirred at 20° C. for 2h. The solvent was removed under reduced pressure and the residue was purified by silica gel chromatography using ethyl acetate:petroleum ether (from 1:1 to 2:1) as eluting solvents to afford [1-[2-(hydroxymethyl)-2-methyl-5-nitro-3H-benzofuran-6-yl]-4-piperidyl]methanol (360 mg, 91%) as a yellow oil. MS (ESI): m/z=323.1 [M+1]$^+$.

Step C. [1-[5-Amino-2-(hydroxymethyl)-2-methyl-3H-benzofuran-6-yl]-4-piperidyl]methanol

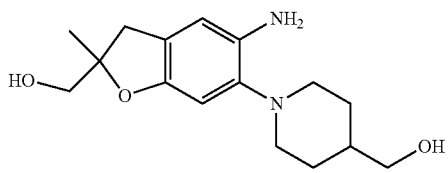 [SMILES: CC1(CO)Cc2cc(N)c(N3CCC(CO)CC3)cc2O1]

A mixture of [1-[2-(hydroxymethyl)-2-methyl-5-nitro-3H-benzofuran-6-yl]-4-piperidyl]methanol (120 mg, 0.37 mmol) and palladium on carbon (20 mg, 10% wt) in methanol (10 mL) was stirred at 20° C. under hydrogen atmosphere for 2 hours. After filtration and concentration under reduced pressure, [1-[5-amino-2-(hydroxymethyl)-2-methyl-3H-benzofuran-6-yl]-4-piperidyl]methanol (87 mg) was afforded as a brown solid, which was used directly to next step without further purification. MS (ESI): m/z=293.2 [M+1]$^+$.

Step D. (R)-6-Chloro-N-(2-(hydroxymethyl)-6-(4-(hydroxymethyl)piperidin-1-yl)-2-methyl-2,3-dihydrobenzofuran-5-yl)pyrazolo[1,5-a]pyrimidine-3-carboxamide and (S)-6-Chloro-N-(2-(hydroxymethyl)-6-(4-(hydroxymethyl)piperidin-1-yl)-2-methyl-2,3-dihydrobenzofuran-5-yl)pyrazolo[1,5-a]pyrimidine-3-carboxamide

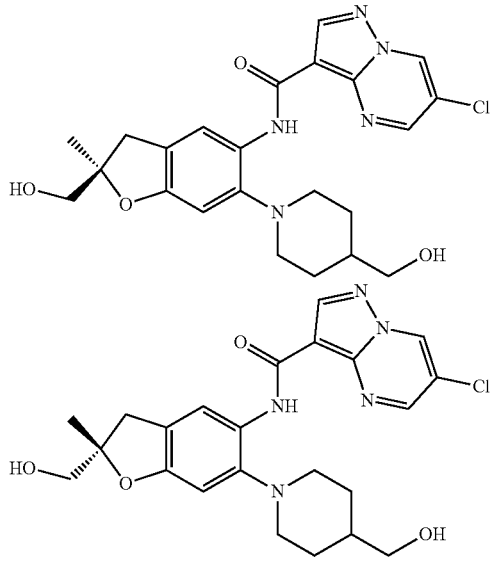

A mixture of [1-[5-amino-2-(hydroxymethyl)-2-methyl-3H-benzofuran-6-yl]-4-piperidyl]methanol (87 mg, 0.30 mmol), 6-chloropyrazolo[1,5-a]pyrimidine-3-carboxylic acid (70 mg, 0.36 mmol), 2-(7-aza-1H-benzotriazole-1-yl)-1,1,3,3-tetramethyluronium hexafluorophosphate (170 mg, 0.45 mmol) and diisopropylethylamine (115 mg, 0.89 mmol) in N,N-dimethylformamide (5 mL) was stirred at 20° C. for 2h. The mixture was purified by silica gel chromatography using ethyl acetate:petroleum ether (1:1 to 2:1) as eluting solvents to afford 6-chloro-N-(2-(hydroxymethyl)-6-(4-(hydroxymethyl)piperidin-1-yl)-2-methyl-2,3-dihydrobenzofuran-5-yl)pyrazolo[1,5-a]pyrimidine-3-carboxamide (120 mg, 81%) as a yellow solid. The product was resolved by chiral SFC (SFC-80 (Thar, Waters), AD 20*250 mm, Sum (Dacel), mobile phase: CO2/MEOH{0.5% Ammonia (7M methanol)}=60/40) to afford (S)-6-chloro-N-(2-(hydroxymethyl)-6-(4-(hydroxymethyl)piperidin-1-yl)-2-methyl-2,3-dihydrobenzofuran-5-yl)pyrazolo[1,5-a]pyrimidine-3-carboxamide and (R)-6-chloro-N-(2-(hydroxymethyl)-6-(4-(hydroxymethyl)piperidin-1-yl)-2-methyl-2,3-dihydrobenzofuran-5-yl)pyrazolo[1,5-a]pyrimidine-3-carboxamide (43.1 mg, 72%) (28.9 mg, 48%) as yellow solids with absolute stereochemistry assigned arbitrarily.

Example 163, Peak 1: $^1$H NMR (400 MHz, DMSO-d$_6$): δ 10.39 (s, 1H), 9.81-9.80 (m, 1H), 8.98-8.97 (m, 1H), 8.69 (s, 1H), 8.31 (s, 1H), 6.67 (s, 1H), 5.02 (t, J=5.6 Hz, 1H), 4.64 (t, J=4.8 Hz, 1H), 3.45-3.39 (m, 4H), 3.20-3.17 (m, 1H), 2.91-2.89 (m, 2H), 2.83-2.79 (m, 1H), 2.66-2.60 (m, 2H), 1.67-1.63 (m, 4H), 1.51-1.48 (m, 1H), 1.33 (s, 3H). MS (ESI): m/z=472.2 [M+1]$^+$.

Example 164, Peak 2: $^1$H NMR (400 MHz, DMSO-d$_6$): δ 10.39 (s, 1H), 9.81 (d, J=2.0 Hz, 1H), 8.98 (d, J=2.0 Hz, 1H), 8.69 (s, 1H), 8.31 (s, 1H), 6.67 (s, 1H), 5.02 (t, J=5.6 Hz, 1H), 4.64 (t, J=4.8 Hz, 1H), 3.45-3.39 (m, 4H), 3.20-3.17 (m, 1H), 2.91-2.89 (m, 2H), 2.83-2.79 (m, 1H), 2.66-2.60 (m, 2H), 1.67-1.63 (m, 4H), 1.51-1.48 (m, 1H), 1.33 (s, 3H). MS (ESI): m/z=472.2 [M+1]$^+$.

TABLE 5

The following examples were made in a manner similar to that for Examples 163 and 164.

| Ex. | Name | Structure | NMR, MS |
|---|---|---|---|
| 165, 166 | (S)-6-Chloro-N-(2-(hydroxymethyl)-2-methyl-6-morpholino-2,3-dihydrobenzofuran-5-yl)pyrazolo[1,5-a]pyrimidine-3-carboxamide and (R)-6-Chloro-N-(2-(hydroxymethyl)-2-methyl-6-morpholino-2,3-dihydrobenzofuran-5-yl)pyrazolo[1,5-a]pyrimidine-3-carboxamide (absolute stereochemistry assigned arbitrarily) | | Example 165, Peak 1: $^1$H NMR (400 MHz, CDCl$_3$) δ 10.33 (s, 1H), 8.87 (d, J = 2.4 Hz, 1H), 8.77 (s, 1H), 8.70 (d, J = 2.0 Hz, 1H), 8.43 (s, 1H), 6.68 (s, 1H), 3.97-3.94 (m, 4H), 3.67 (s, 2H), 3.25 (d, J = 16.0 Hz, 1H), 2.94 (d, J = 15.6 Hz, 1H), 2.92-2.89 (m, 4H), 1.46 (s, 3H). MS (ESI): m/z = 444.1 [M + 1]$^+$. Example 166, Peak 2: $^1$H NMR (400 MHz, CDCl$_3$) δ 10.33 (s, 1H), 8.87 (d, J = 2.4 Hz, 1H), 8.77 (s, 1H), 8.70 (d, J = 2.0 Hz, 1H), 8.43 (s, 1H), 6.68 (s, 1H), 3.95-3.93 (m, 4H), 3.67 (s, 2H), 3.25 (d, J = 16.0 Hz, 1H), 2.94 (d, J =15.2 Hz, 1H), 2.92-2.89 (m, 4H), 1.46 (s, 3H). MS (ESI): m/z = 444.1 [M + 1]$^+$. |
| 167 | 6-Chloro-N-(2,2-dimethyl-6-(2-oxa-8-azaspiro[4.5]decan-8-yl)-2,3-dihydrobenzofuran-5-yl)pyrazolo[1,5-a]pyrimidine-3-carboxamide | 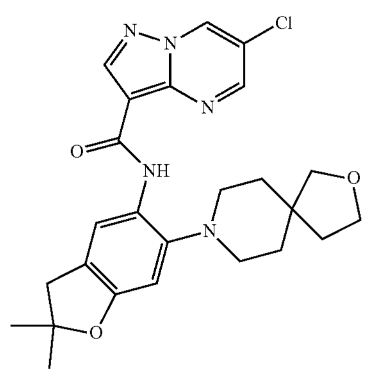 [SMILES: CC1(C)Cc2cc(NC(=O)c3cnn4cc(Cl)cnc34)c(N3CCC4(CCOC4)CC3)cc2O1] | $^1$H NMR (400 MHz, CDCl$_3$) δ 10.30 (s, 1H), 8.86 (d, J = 2.0 Hz, 1H), 8.77 (s, 1H), 8.54 (d, J = 2.4 Hz, 1H), 8.38 (s, 1H), 6.64 (s, 1H), 3.91 (t, J = 7.2 Hz, 2H), 3.65 (s, 2H), 3.03 (s, 2H), 2.86-2.84 (m, 4H), 1.85 (t , J = 7.2 Hz, 2H), 1.85-1.81 (m, 4H), 1.48 (s, 6H). MS (ESI): m/z = 482.1 [M + 1]$^+$. |
| 168 | N-(6-(4-(2,2-Difluoroethyl)piperazin-1-yl)-2-(hydroxymethyl)-2-methyl-2,3-dihydrobenzofuran-5-yl)-6-methylpyrazolo[1,5-a]pyrimidine-3-carboxamide | 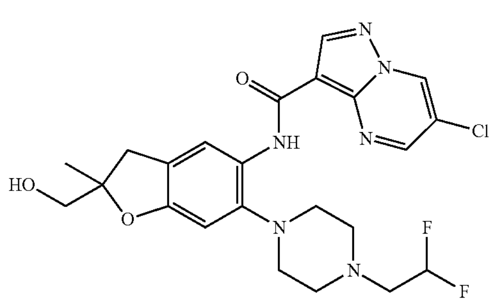 [SMILES: CC1(CO)Cc2cc(NC(=O)c3cnn4cc(Cl)cnc34)c(N3CCN(CC(F)F)CC3)cc2O1] | $^1$H NMR (400 MHz, dimethyl sulfoxide-d$_6$) δ 10.18 (s, 1H), 9.82 (d, J = 2.0 Hz, 1H), 8.96 (d, J= 2.0 Hz, 1H), 8.70 (s, 1H), 8.26 (s, 1H), 6.70 (s, 1H), 6.20 (tt, J = 56.0, 4.4 Hz, 1H) , 5.05 (t, J = 5.6 Hz, 1H), 3.45-3.41 (m, 2H), 3.20 (d, J = 16.4 Hz, 1H), 2.88-2.78 (m, 11H), 1.33 (s, 3H). LCMS (ESI): m/z = 507.0 [M + H]$^+$. |

TABLE 5-continued

The following examples were made in a manner similar to that for Examples 163 and 164.

| Ex. | Name | Structure | NMR, MS |
|---|---|---|---|
| 169 and 170 | (S)-6-Chloro-N-(6-(4-(2,2-difluoroethyl)piperazin-1-yl)-2-(hydroxymethyl)-2-methyl-2,3-dihydrobenzofuran-5-yl)pyrazolo[1,5-a]pyrimidine-3-carboxamide and (R)-6-Chloro-N-(6-(4-(2,2-difluoroethyl)piperazin-1-yl)-2-(hydroxymethyl)-2-methyl-2,3-dihydrobenzofuran-5-yl)pyrazolo[1,5-a]pyrimidine-3-carboxamide (absolute stereochemistry assigned arbitrarily) | | Example 169 Peak 1: $^1$H NMR (400 MHz, CDCl$_3$) δ 10.22 (s, 1H), 8.88 (d, J = 2.0 Hz, 1H), 8.78 (s, 1H), 8.65 (d, J = 2.0 Hz, 1H), 8.40 (s, 1H), 6.68 (s, 1H), 6.15-5.80 (m, 1H), 3.68-3.67 (m, 2H), 3.25-3.23 (m, 1H), 2.95 -2.84 (m, 11H), 1.92 (t, J = 6.4 Hz, 1H), 1.47 (s, 3H). LCMS (ESI): m/z = 507.2 [M + H]$^+$. Example 170 Peak 2: $^1$H NMR (400 MHz, CDCl$_3$) δ 10.22 (s, 1H), 8.88 (d, J = 2.0 Hz, 1H), 8.78 (s, 1H), 8.65 (d, J = 2.0 Hz, 1H), 8.40 (s, 1H), 6.68 (s, 1H), 6.15-5.80 (m, 1H), 3.69-3.66 (m, 2H), 3.25-3.23 (m, 1H), 2.95-2.84 (m, 11H), 2.00 (t, J = 6.4 Hz, 1H), 1.47 (s, 3H). LCMS (ESI): m/z = 507.2 [M + H]$^+$. |

Examples 171 and 172. (R)—N-(2-(Hydroxymethyl)-2-methyl-6-(trifluoromethoxy)-2,3-dihydrobenzofuran-5-yl)pyrazolo[1,5-a]pyrimidine-3-carboxamide and (S)—N-(2-(hydroxymethyl)-2-methyl-6-(trifluoromethoxy)-2,3-dihydrobenzofuran-5-yl)pyrazolo[1,5-a]pyrimidine-3-carboxamide

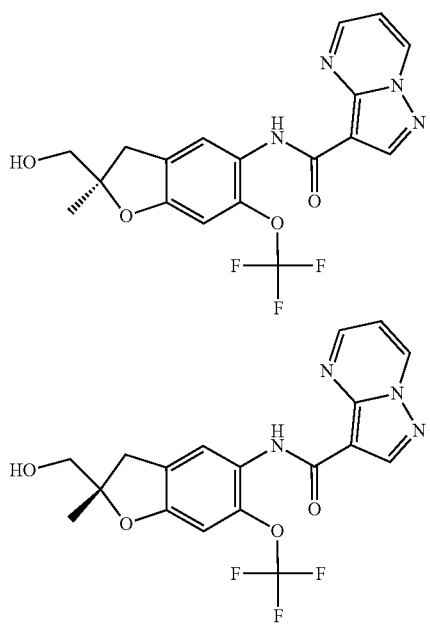

The title compounds were made in a manner analogous to Example 70 to give N-(2-(hydroxymethyl)-2-methyl-6-(trifluoromethoxy)-2,3-dihydrobenzofuran-5-yl)pyrazolo[1,5-a]pyrimidine-3-carboxamide which was resolved via Chiral SFC to afford N-[(2R)-2-(hydroxymethyl)-2-methyl-6-(trifluoromethoxy)-3H-benzofuran-5-yl]pyrazolo[1,5-a]pyrimidine-3-carboxamide (73.9 mg, 38.1% yield) and N-[(2S)-2-(hydroxymethyl)-2-methyl-6-(trifluoromethoxy)-3H-benzofuran-5-yl]pyrazolo[1,5-a]pyrimidine-3-carboxamide (73.4 mg, 37.9% yield) as light yellow solids. Stereochemistry was arbitrarily assigned based on peak elution.

Example 171 peak 1: $^1$H NMR (400 MHz, dimethyl sulfoxide-d$_6$): δ 10.23 (s, 1H), 9.40 (dd, J=1.6, 7.2 Hz, 1H), 8.83 (dd, J=1.6, 4.4 Hz, 1H), 8.72 (s, 1H), 8.28 (s, 1H), 7.34 (dd, J=4.4, 7.2 Hz, 1H), 6.86 (s, 1H), 5.11 (t, J=5.6 Hz, 1H), 3.53-3.40 (m, 2H), 3.28 (d, J=16.4 Hz, 1H), 2.92 (d, J=16.4 Hz, 1H), 1.37 (s, 3H). $^{19}$F NMR (400 MHz, DMSO-d6) δ -57.24 (s, 3F). MS (ESI): m/z=409.1 [M+1]$^+$.

Example 172 peak 2: $^1$H NMR (400 MHz, dimethyl sulfoxide-d$_6$): δ 10.23 (s, 1H), 9.40 (dd, J=1.6, 6.8 Hz, 1H), 8.83 (dd, J=1.6, 4.0 Hz, 1H), 8.72 (s, 1H), 8.28 (s, 1H), 7.34 (dd, J=4.0, 6.8 Hz, 1H), 6.85 (s, 1H), 5.11 (t, J=5.6 Hz, 1H), 3.53-3.40 (m, 2H), 3.28 (d, J=16.4 Hz, 1H), 2.92 (d, J=16.4 Hz, 1H), 1.37 (s, 3H). $^{19}$F NMR (400 MHz, DMSO-d$_6$) δ -57.24 (s, 3F). MS (ESI): m/z=409.1 [M+1]$^+$.

Example 173. N-[6-Morpholino-1-oxo-2-(2,2,2-trifluoroethyl)isoindolin-5-yl]pyrazolo[1,5-a]pyrimidine-3-carboxamide

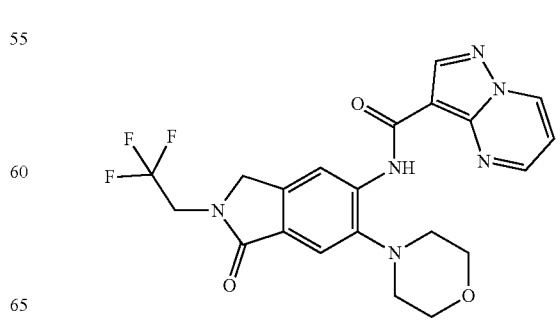

Step A. 6-Chloro-5-nitro-2-(2,2,2-trifluoroethyl)isoindolin-1-one

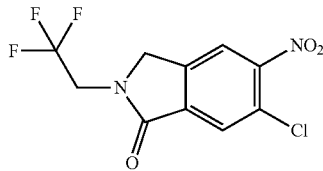 [SMILES: O=C1c2cc(Cl)c([N+](=O)[O-])cc2CN1CC(F)(F)F]

To methyl 2-(bromomethyl)-5-chloro-4-nitro-benzoate (preparation 5, WO 2013079505 (150 mg, 0.49 mmol) in methanol (5 ml) was added triethylamine (0.081 ml, 0.58 mmol) and 2,2,2-trifluoroethylamine (0.047 ml, 0.58 mmol). The reaction was heated to 70° C. for 18 h, concentrated and purified by silica gel chromatography (eluting gradient 0-20% methanol: dichloromethane) to afford 6-chloro-5-nitro-2-(2,2,2-trifluoroethyl)isoindolin-1-one (90 mg, 63%). LCMS (ESI) m/z: 295.0 [M+H]$^+$.

Step B. 6-Morpholino-5-nitro-2-(2,2,2-trifluoroethyl)isoindolin-1-one

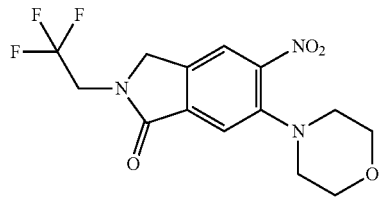

A solution of 6-chloro-5-nitro-2-(2,2,2-trifluoroethyl)isoindolin-1-one (90 mg, 0.31 mmol), morpholine (0.032 ml, 0.37 mmol), N,N-diisopropylethylamine (0.100 ml, 0.61 mmol) in dimethyl sulfoxide (1.5 ml) was heated at 80° C. for 18 h. The reaction was cooled to rt then diluted with water and extracted with isopropyl acetate (3×). The combined organic layers were washed with brine, dried over sodium sulfate, filtered and concentrated. The crude product purified by silica gel chromatography (eluting gradient 0-20% methanol: dichloromethane) to afford 6-morpholino-5-nitro-2-(2,2,2-trifluoroethyl)isoindolin-1-one (87 mg, 82%). LCMS (ESI) m/z: 346.0 [M+H]$^+$.

Step C. 5-Amino-6-morpholino-2-(2,2,2-trifluoroethyl)isoindolin-1-one

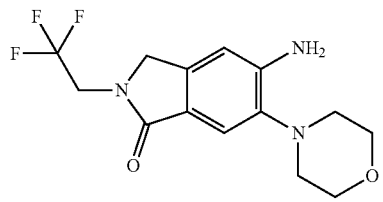 [SMILES: O=C1c2cc(N3CCOCC3)c([N+](=O)[O-])cc2CN1CC(F)(F)F]

To solution of 6-morpholino-5-nitro-2-(2,2,2-trifluoroethyl)isoindolin-1-one (60 mg, 0.17 mmol) in ethanol (3.5 ml) and water (1.0 ml) was added iron (48 mg, 0.87 mmol) and ammonium chloride (37 mg, 0.69 mmol). The reaction mixture was heated to 50° C. for 6 h. The reaction mixture was cooled to rt then filtered through celite and concentrated. The crude product was purified by silica gel chromatography (eluting gradient 0-20% methanol: dichloromethane) to afford 5-amino-6-morpholino-2-(2,2,2-trifluoroethyl)isoindolin-1-one (40 mg, 73%). LCMS (ESI) m/z: 316.0 [M+H]$^+$.

Step D. N-[6-morpholino-1-oxo-2-(2,2,2-trifluoroethyl)isoindolin-5-yl]pyrazolo[1,5-a]pyrimidine-3-carboxamide

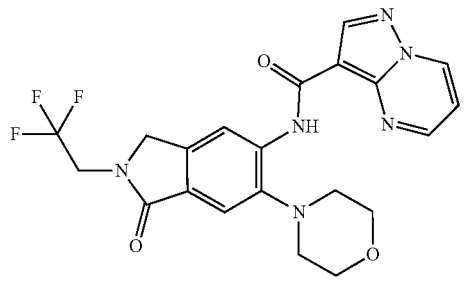 [SMILES: O=C(Nc1cc2c(cc1N1CCOCC1)C(=O)N(CC(F)(F)F)C2)c1cnn2cccnc12]

To a solution of 5-amino-6-morpholino-2-(2,2,2-trifluoroethyl)isoindolin-1-one (50 mg, 0.16 mmol) and pyrazolo[1,5-a]pyrimidine-3-carbonyl chloride (60 mg, 0.32 mmol) in 1,2-dichloroethane (2.00 ml) was added triethylamine (0.090 ml, 0.63 mmol). The reaction mixture was stirred at 70° C. for 18 h. The reaction was quenched with water and extracted with ethyl acetate. The organic phase was dried with sodium sulfate, filtered, and concentrated. The crude product was purified by silica gel chromatography (eluting gradient 0-20% methanol: dichloromethane) followed by reverse-phase HPLC to afford N-[6-morpholino-1-oxo-2-(2,2,2-trifluoroethyl)isoindolin-5-yl]pyrazolo[1,5-a]pyrimidine-3-carboxamide (14 mg, 19%). $^1$H NMR (400 MHz, dimethyl sulfoxide-d$_6$) δ 10.94 (s, 1H), 9.43 (dd, J=7.0, 1.5 Hz, 1H), 9.01 (dd, J=4.3, 1.6 Hz, 1H), 8.80 (s, 1H), 8.77 (s, 1H), 7.66 (s, 1H), 7.40 (dd, J=7.0, 4.2 Hz, 1H), 4.62 (s, 2H), 4.38 (q, J=9.7 Hz, 2H), 3.90 (t, J=4.4 Hz, 4H), 2.93 (t, J=4.5 Hz, 4H). LCMS(ESI) m/z: 461.1 [M+H]$^+$.

TABLE 6

The following examples were made in a manner similar to that for Example 173:

| Ex. | Name | Structure | NMR, MS |
|---|---|---|---|
| 174 | N-[2-(2,2-difluoroethyl)-6-morpholino-1-oxo-isoindolin-5-yl]pyrazolo[1,5-a]pyrimidine-3-carboxamide | 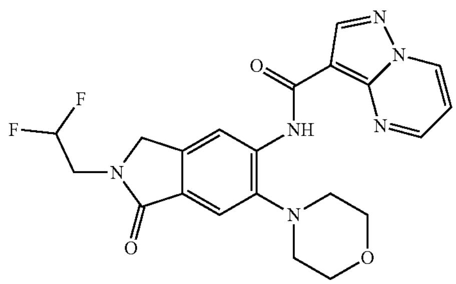 [SMILES: O=C(Nc1cc2c(cc1N1CCOCC1)C(=O)N(CC(F)F)C2)c1cnn2cccnc12] | $^1$H NMR (400 MHz, dimethyl sulfoxide-d$_6$) δ 10.93 (s, 1H), 9.43 (dd, J = 7.0, 1.6 Hz, 1H), 9.01 (dd, J = 4.2, 1.6 Hz, 1H), 8.77 (d, J = 2.9 Hz, 2H), 7.63 (s, 1H), 7.40 (dd, J = 7.0, 4.2 Hz, 1H), 6.29 (tt, J = 55.2, 3.6 Hz, 1H), 4.58 (s, 2H), 4.09-3.76 (m, 6H), 3.01-2.84 (m, 4H). LCMS (ESI) m/z: 443.1 [M + H]+. |
| 175 | N-[2-(3-hydroxy-3-methyl-butyl)-6-morpholino-1-oxo-isoindolin-5-yl]pyrazolo[1,5-a]pyrimidine-3-carboxamide | 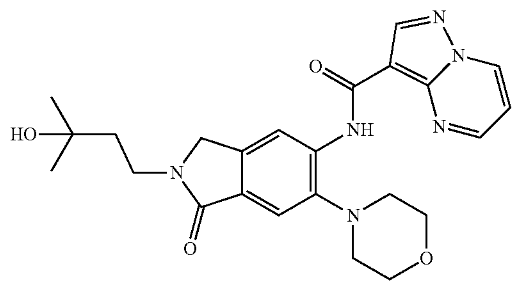 [SMILES: CC(C)(O)CCN1Cc2cc(NC(=O)c3cnn4cccnc34)c(N3CCOCC3)cc2C1=O] | $^1$H NMR (400 MHz, dimethyl sulfoxide-d$_6$) δ 10.89 (s, 1H), 9.41 (dd, J = 7.0, 1.6 Hz, 1H), 9.00 (dd, J = 4.2, 1.6 Hz, 1H), 8.75 (d, J = 2.4 Hz, 2H), 7.56 (s, 1H), 7.39 (dd, J = 7.0, 4.2 Hz, 1H), 4.46 (s, 2H), 4.34 (s, 1H), 3.94-3.86 (m, 4H), 3.64-3.54 (m, 2H), 2.96-2.87 (m, 4H), 1.73-1.63 (m, 2H), 1.15 (s, 6H). LCMS (ESI) m/z: 465.2 [M + H]$^+$. |
| 176 | N-[2-(2-hydroxy-2-methyl-propyl)-6-morpholino-1-oxo-isoindolin-5-yl]pyrazolo[1,5-a]pyrimidine-3-carboxamide | 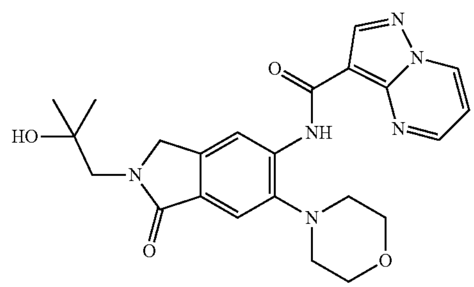 [SMILES: CC(C)(O)CN1Cc2cc(NC(=O)c3cnn4cccnc34)c(N3CCOCC3)cc2C1=O] | $^1$H NMR (400 MHz, dimethyl sulfoxide-d$_6$) δ 10.90 (s, 1H), 9.42 (dd, J = 7.0, 1.6 Hz, 1H), 9.01 (dd, J = 4.2, 1.6 Hz, 1H), 8.77 (s, 1H), 8.74 (s, 1H), 7.59 (s, 1H), 7.39 (dd, J = 7.0, 4.2 Hz, 1H), 4.69 (s, 1H), 4.64 (s, 2H), 3.94-3.85 (m, 4H), 3.47-3.41 (m, 2H), 2.96-2.86 (m, 4H), 1.11 (s, 6H). LCMS (ESI) m/z: 451.2 [M + H]+ |
| 177 | N-[6-[4-(2-amino-2-oxo-ethyl)piperazin-1-yl]-1-oxo-2-tetrahydropyran-4-yl-isoindolin-5-yl]pyrazolo[1,5-a]pyrimidine-3-carboxamide | 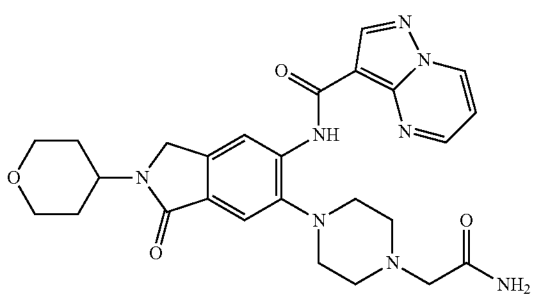 [SMILES: NC(=O)CN1CCN(c2cc3c(cc2NC(=O)c2cnn4cccnc24)CN(C2CCOCC2)C3=O)CC1] | $^1$H NMR (400 MHz, DMSO-d$_6$) δ 10.89 (s, 1H), 9.40 (dd, J = 7.0, 1.6 Hz, 1H), 9.03 (dd, J = 4.2, 1.6 Hz, 1H), 8.78 (s, 1H), 8.75 (s, 1H), 7.58 (s, 1H), 7.39 (dd, J = 7.0, 4.2 Hz, 1H), 7.29 (s, 1H), 7.19 (s, 1H), 4.47 (s, 2H), 4.32 ? 4.19 (m, 1H), 4.01-3.91 (m, 2H), 3.50-3.41 (m, 2H), 3.06 (s, 2H), 2.95 (dd, J = 5.5, 3.5 Hz, 4H), 2.83-2.75 (m, 4H), 1.83 (qd, J = 12.3, 4.5 Hz, 2H), 1.71-1.61 (m, 2H). LCMS (ESI) m/z: 519.2 [M + H]+ |
| 178 | N-[2-(2-methoxyethyl)-6-morpholino-1-oxo-isoindolin-5-yl]pyrazolo[1,5-a]pyrimidine-3-carboxamide | 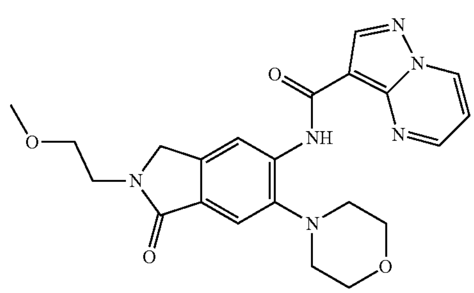 [SMILES: COCCN1Cc2cc(NC(=O)c3cnn4cccnc34)c(N3CCOCC3)cc2C1=O] | $^1$H NMR (400 MHz, DMSO-d6) δ 10.89 (s, 1H), 9.41 (dd, J = 7.0, 1.6 Hz, 1H), 9.00 (dd, J = 4.2, 1.6 Hz, 1H), 8.75 (d, J = 3.3 Hz, 2H), 7.58 (d, J = 0.5 Hz, 1H), 7.39 (dd, J = 7.0, 4.2 Hz, 1H), 4.53-4.47 (m, 2H), 3.93-3.87 (m, 4H), 3.70-3.64 (m, 2H), 3.56 (td, J = 5.4, 0.7 Hz, 2H), 3.27 (s, 3H), 2.95-2.88 (m, 4H). LCMS (ESI) m/z: 437.2 [M + H]+ |

TABLE 6-continued

The following examples were made in a manner similar to that for Example 173:

| Ex. | Name | Structure | NMR, MS |
|---|---|---|---|
| 179 | N-[2-(2-hydroxyethyl)-6-morpholino-1-oxo-isoindolin-5-yl]pyrazolo[1,5-a]pyrimidine-3-carboxamide | 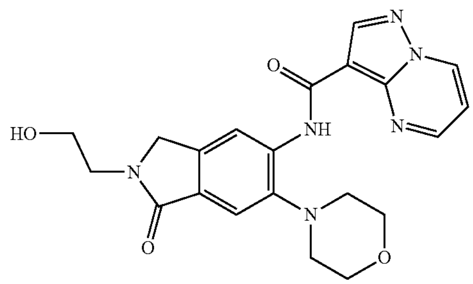 [SMILES: O=C(Nc1cc2c(cc1N1CCOCC1)C(=O)N(CCO)C2)c1cnn2cccnc12] | LCMS (ESI) m/z: 423.1 [M + H]+ |
| 180 | N-[2-(1-methyl-4-piperidyl)-6-morpholino-1-oxo-isoindolin-5-yl]pyrazolo[1,5-a]pyrimidine-3-carboxamide | 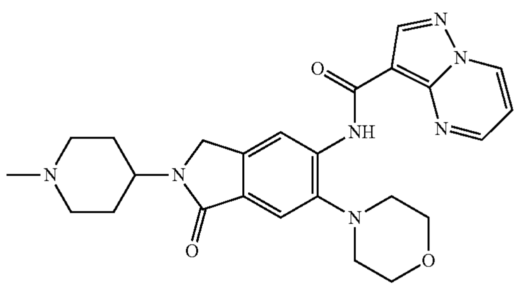 [SMILES: CN1CCC(N2Cc3cc(NC(=O)c4cnn5cccnc45)c(N4CCOCC4)cc3C2=O)CC1] | $^1$H NMR (400 MHz, DMSO-d$_6$) δ 10.90 (s, 1H), 9.41 (dd, J = 7.0, 1.6 Hz, 1H), 9.00 (dd, J = 4.2, 1.6 Hz, 1H), 8.76 (d, J = 2.8 Hz, 2H), 7.57 (s, 1H), 7.39 (dd, J = 7.0, 4.3 Hz, 1H), 4.45 (s, 2H), 4.03-3.86 (m, 5H), 2.96-2.82 (m, 6H), 2.19 (s, 3H), 2.00 (td, J = 11.9, 2.3 Hz, 2H), 1.81 (qd, J = 12.2, 3.8 Hz, 2H), 1.72-1.60 (m, 2H). LCMS (ESI) m/z: 476.2 [M + H]+ |
| 181 | N-[2-(4-hydroxycyclohexyl)-6-morpholino-1-oxo-isoindolin-5-yl]pyrazolo[1,5-a]pyrimidine-3-carboxamide | 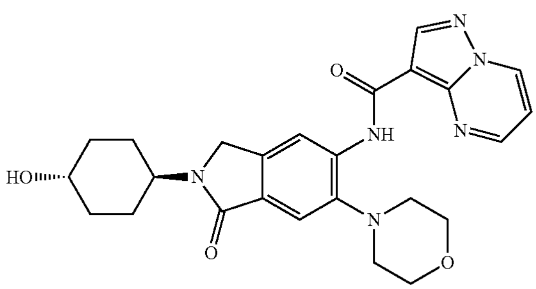 [SMILES: O=C(Nc1cc2c(cc1N1CCOCC1)C(=O)N([C@H]1CC[C@H](O)CC1)C2)c1cnn2cccnc12] | $^1$H NMR (400 MHz, DMSO-d$_6$) δ 10.89 (s, 1H), 9.41 (dd, J = 7.0, 1.6 Hz, 1H), 8.99 (dd, J = 4.3, 1.7 Hz, 1H), 8.75 (d, J = 1.3 Hz, 2H), 7.56 (s, 1H), 7.38 (dd, J = 7.0, 4.2 Hz, 1H), 4.62 (d, J = 4.4 Hz, 1H), 4.41 (s, 2H), 4.03-3.85 (m, 5H), 3.42 (dd, J = 10.5, 4.7 Hz, 1H), 2.94-2.86 (m, 4H), 1.91 (d, J = 13.5 Hz, 2H), 1.77-1.55 (m, 4H), 1.39-1.25 (m, 2H). LCMS (ESI) m/z: 477.2 [M + H]+ |

TABLE 7

The following examples were made in a manner similar to that for Example 4:

| Ex. | Name | Structure | NMR, MS |
|---|---|---|---|
| 182 | N-[2,2-dimethyl-6-[(1S,5R)-6-(methylcarbamoyl)-3-azabicyclo[3.1.0]hexan-3-yl]-3H-benzofuran-5-yl]pyrazolo[1,5-a]pyrimidine-3-carboxamide | 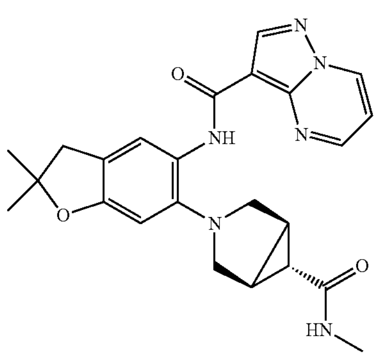 [SMILES: CNC(=O)[C@H]1[C@@H]2CN(c3cc4c(cc3NC(=O)c3cnn5cccnc35)CC(C)(C)O4)C[C@@H]21] | $^1$H NMR (400 MHz, dimethyl sulfoxide-d$_6$) δ 9.58 (s, 1H), 9.36 (dd, J = 7.0, 1.7 Hz, 1H), 8.90 (dd, J = 4.3, 1.7 Hz, 1H), 8.67 (s, 1H), 8.01 (d, J = 0.9 Hz, 1H), 7.73 (d, J = 4.7 Hz, 1H), 7.34 (dd, J = 7.0, 4.3 Hz, 1H), 6.60 (s, 1H), 3.43-3.38 (m, 2H), 3.12-3.05 (m, 2H), 3.00-2H), 2.58 (d, J = 4.6 Hz, 3H), 2.17 (t, J = 3.0 Hz, 1H), 1.94-1.87 (m, 2H), 1.40 (s, 6H). LCMS (ESI) m/z: 447.2 [M + H]+. |

TABLE 7-continued

The following examples were made in a manner similar to that for Example 4:

| Ex. | Name | Structure | NMR, MS |
|---|---|---|---|
| 183 | N-[2,2-dimethyl-6-[4-[2-(methylamino)-2-oxo-ethyl]-1-piperidyl]-3H-benzofuran-5-yl]pyrazolo[1,5-a]pyrimidine-3-carboxamide | 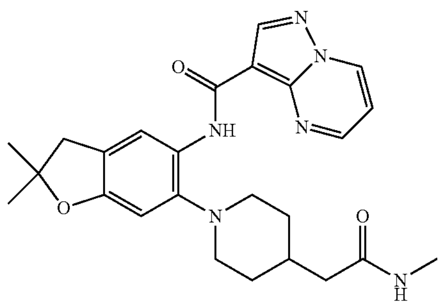 | $^1$H NMR (400 MHz, dimethyl sulfoxide-d$_6$) δ 10.44 (s, 1H), 9.37 (dd, J = 7.0, 1.6 Hz, 1H), 8.88 (dd, J = 4.2, 1.7 Hz, 1H), 8.68 (s, 1H), 8.32 (d, J = 1.0 Hz, 1H), 7.78 (d, J = 4.8 Hz, 1H), 7.33 (dd, J = 7.0, 4.2 Hz, 1H), 6.68 (s, 1H), 3.02-2.96 (m, 2H), 2.94-2.84 (m, 2H), 2.69-2.56 (m, 5H), 2.11 (d, J = 6.9 Hz, 2H), 1.81 (s, 1H), 1.69 (d, J = 12.1 Hz, 2H), 1.62-1.48 (m, 2H), 1.41 (s, 6H). LCMS (ESI) m/z: 463.3 [M + H]+. |
| 184 | N-[6-(4-carbamoyl-4-methyl-1-piperidyl)-2,2-dimethyl-3H-benzofuran-5-yl]pyrazolo[1,5-a]pyrimidine-3-carboxamide | 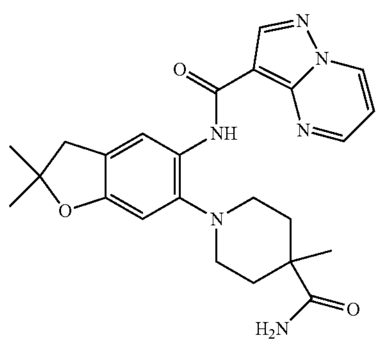 [SMILES: CC1(C)Cc2cc(NC(=O)c3cnn4cccnc34)c(N3CCC(C)(C(N)=O)CC3)cc2O1] | $^1$H NMR (400 MHz, dimethyl sulfoxide-d$_6$) δ 10.43 (s, 1H), 9.36 (dd, J = 7.0, 1.7 Hz, 1H), 8.90 (dd, J = 4.2, 1.7 Hz, 1H), 8.68 (s, 1H), 8.32 (d, J= 1.0 Hz, 1H), 7.33 (dd, J = 7.0, 4.2 Hz, 1H), 7.18 (s, 1H), 6.90 (s, 1H), 6.63 (s, 1H), 3.02-2.96 (m, 2H), 2.87-2.76 (m, 2H), 2.73-2.62 (m, 2H), 2.21 (m, 2H), 1.67-1.56 (m, 2H), 1.41 (s, 6H), 1.21 (s, 3H). LCMS (ESI) m/z: 449.2 [M + H]+. |
| 185 | N-[6-(4-hydroxyazepan-1-yl)-2,2-dimethyl-3H-benzofuran-5-yl]pyrazolo[1,5-a]pyrimidine-3-carboxamide | 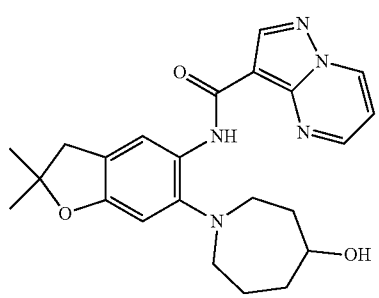 [SMILES: CC1(C)Cc2cc(NC(=O)c3cnn4cccnc34)c(N3CCCC(O)CC3)cc2O1] | $^1$H NMR (400 MHz, dimethyl sulfoxide-d$_6$) δ 10.45 (s, 1H), 9.36 (dd, J = 7.0, 1.6 Hz, 1H), 8.93 (dd, J = 4.2, 1.7 Hz, 1H), 8.67 (s, 1H), 8.26 (d, J = 1.0 Hz, 1H), 7.34 (dd, J = 7.0, 4.2 Hz, 1H), 6.64 (s, 1H), 4.54 (d, J = 3.7 Hz, 1H), 3.98-3.87 (m, 1H), 3.03-2.80 (m, 6H), 2.04 (m, 1H), 1.99-1.80 (m, 3H), 1.80-1.57 (m, 2H), 1.40 (s, 6H). LCMS (ESI) m/z: 422.2 [M + H]+. |
| 186 | N-[6-[(1S,5R)-6-carbamoyl-3-azabicyclo[3.1.0]hexan-3-yl]-2,2-dimethyl-3H-benzofuran-5-yl]pyrazolo[1,5-a]pyrimidine-3-carboxamide | 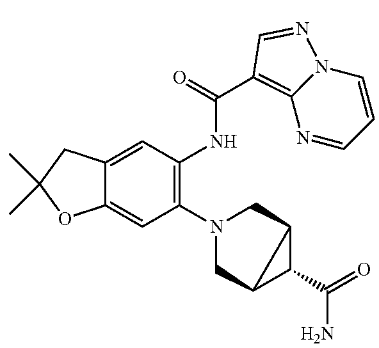 [SMILES: CC1(C)Cc2cc(NC(=O)c3cnn4cccnc34)c(N3C[C@@H]4[C@H](C3)[C@H]4C(N)=O)cc2O1] | $^1$H NMR (400 MHz, dimethyl sulfoxide-d$_6$) δ 9.58 (s, 1H), 9.36 (dd, J = 7.0, 1.6 Hz, 1H), 8.98 (dd, J = 4.3, 1.7 Hz, 1H), 8.68 (s, 1H), 8.01 (d, J = 1.0 Hz, 1H), 7.39-7.29 (m, 2H), 6.78 (s, 1H), 6.60 (s, 1H), 3.44-3.38 (m, 2H), 3.11-3.03 (m, 2H), 2.97 (d, J = 1.1 Hz, 2H), 2.20 (t, J = 3.0 Hz, 1H), 1.90 m, 2H), 1.41 (s, 6H). LCMS (ESI) m/z: 433.2 [M + H]+. |

TABLE 7-continued

The following examples were made in a manner similar to that for Example 4:

| Ex. | Name | Structure | NMR, MS |
|---|---|---|---|
| 187 | N-[6-[4-(2-amino-2-oxo-ethyl)piperazin-1-yl]-2,2-dimethyl-3H-benzofuran-5-yl]pyrazolo[1,5-a]pyrimidine-3-carboxamide | 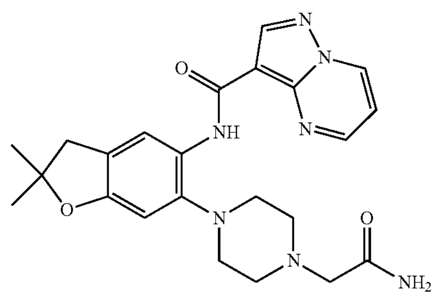 [SMILES: CC1(C)Cc2cc(NC(=O)c3cnn4cccnc34)c(N3CCN(CC(N)=O)CC3)cc2O1] | $^1$H NMR (400 MHz, dimethyl sulfoxide-d$_6$) δ 10.42 (s, 1H), 9.36 (dd, J = 7.0, 1.6 Hz, 1H), 8.97 (dd, J = 4.2, 1.7 Hz, 1H), 8.67 (s, 1H), 8.33 (s, 1H), 7.35 (dd, J = 7.0, 4.2 Hz, 1H), 7.19 (d, J = 29.3 Hz, 2H), 6.68 (s, 1H), 3.01 (m, 4H), 2.85 (m, 4H), 2.73 (m, 4H), 1.41 (s, 6H). LCMS (ESI) m/z: 450.2 [M + H]+. |
| 188 | N-[2,2-dimethyl-6-[3-(3-methylimidazol-4-yl)pyrrolidin-1-yl]-3H-benzofuran-5-yl]pyrazolo[1,5-a]pyrimidine-3-carboxamide | 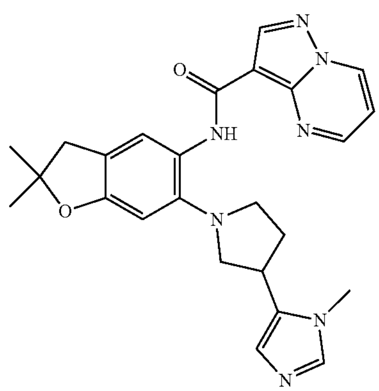 [SMILES: Cn1cncc1C1CCN(c2cc3c(cc2NC(=O)c2cnn4cccnc24)CC(C)(C)O3)C1] | $^1$H NMR (400 MHz, dimethyl sulfoxide-d$_6$) δ 10.00 (s, 1H), 9.35 (dd, J = 7.0, 1.6 Hz, 1H), 8.82 (dd, J = 4.2, 1.6 Hz, 1H), 8.67 (s, 1H), 8.00 (d, J = 1.0 Hz, 1H), 7.48 (dd, J = 1.1, 0.5 Hz, 1H), 7.30 (dd, J = 7.0, 4.2 Hz, 1H), 6.74 (t, J = 0.9 Hz, 1H), 6.63 (s, 1H), 3.55 (s, 3H), 3.53-3.43 (m, 2H), 3.16-3.05 (m, 2H), 3.03-2.94 (m, 2H), 2.39 (m, 1H), 2.02-1.89 (m, 1H), 1.41 (s, 6H). LCMS (ESI) m/z: 458.2 [M + H]+. |
| 189 | N-[6-(5,7-dihydropyrrolo[3,4-b]pyridin-6-yl)-2,2-dimethyl-3H-benzofuran-5-yl]pyrazolo[1,5-a]pyrimidine-3-carboxamide | 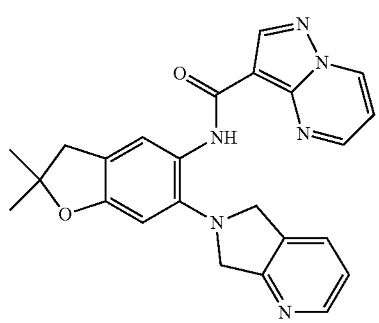 [SMILES: CC1(C)Cc2cc(NC(=O)c3cnn4cccnc34)c(N3Cc4cccnc4C3)cc2O1] | $^1$H NMR (400 MHz, dimethyl sulfoxide-d$_6$) δ 10.38 (s, 1H), 9.29 (dd, J = 7.0, 1.6 Hz, 1H), 8.67(s, 1H), 8.45 (ddt, J = 5.0, 1.4, 0.7 Hz, 1H), 8.14 (d, J = 1.0 Hz, 1H), 7.83 (dd, J = 4.2, 1.7 Hz, 1H), 7.76-7.72 (m, 1H), 7.36-7.27 (m, 1H), 7.16 (dd, J = 7.0, 4.2 Hz, 1H), 6.91 (s, 1H), 4.52 (s, 2H), 4.48 (s, 2H), 3.02 (s, 2H), 1.43 (s, 6H). LCMS (ESI) m/z: 427.2 [M + H]+. |
| 190 | N-[2,2-dimethyl-6-[3-(1H-pyrazol-5-yl)-1-piperidyl]-3H-benzofuran-5-yl]pyrazolo[1,5-a]pyrimidine-3-carboxamide | 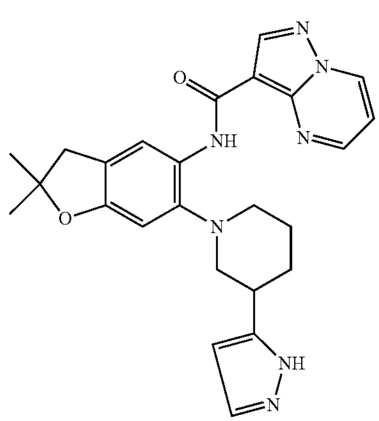 [SMILES: CC1(C)Cc2cc(NC(=O)c3cnn4cccnc34)c(N3CCCC(c4ccn[nH]4)C3)cc2O1] | $^1$H NMR (400 MHz, dimethyl sulfoxide-d$_6$) δ 12.40 (s, 1H), 10.53 (s, 1H), 9.37 (dd, J = 7.0, 1.6 Hz, 1H), 8.89 (dd, J = 4.2, 1.6 Hz, 1H), 8.68 (s, 1H), 8.33 (s, 1H), 7.33 (dd, J = 7.0, 4.2 Hz, 1H), 6.70 (s, 1H), 6.04 (s, 1H), 3.12 (m, 1H), 3.00 (s, 2H), 2.93 (m, 1H), 2.67 (s, 2H), 2.16 (m, 1H), 2.05-1.89 (m, 1H), 1.87-1.76 (m, 1H), 1.52(m, 1H), 1.41 (d, J = 3.2 Hz, 6H). LCMS (ESI) m/z: 458.2 [M + H]+. |

TABLE 7-continued

The following examples were made in a manner similar to that for Example 4:

| Ex. | Name | Structure | NMR, MS |
|---|---|---|---|
| 191 | N-[6-(1,3,3a,4,6,6a-hexahydrofuro[3,4-c]pyrrol-5-yl)-2,2-dimethyl-3H-benzofuran-5-yl]pyrazolo[1,5-a]pyrimidine-3-carboxamide | 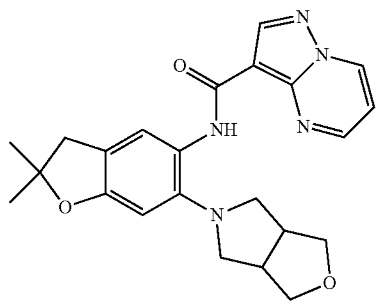 [SMILES: CC1(C)Cc2cc(NC(=O)c3cnn4cccnc34)c(N3CC4COCC4C3)cc2O1] | $^1$H NMR (400 MHz, dimethyl sulfoxide-d$_6$) δ 10.02 (s, 1H), 9.37 (dd, J = 7.0, 1.6 Hz, 1H), 8.85 (dd, J = 4.2, 1.6 Hz, 1H), 8.69 (s, 1H), 8.15 (d, J = 1.0 Hz, 1H), 7.34 (dd, J = 7.0, 4.2 Hz, 1H), 6.67 (s, 1H), 3.83-3.76 (m, 2H), 3.60-3.53 (m, 2H), 3.15-3.08 (m, 2H), 3.02-2.98 (m, 2H), 2.96-2.87 (m, 2H),2.73 (dd, J = 9.2, 3.1 Hz, 2H), 1.42 (s, 6H). LCMS (ESI) m/z: 420.2 [M + H]+. |
| 192 | N-[2,2-dimethyl-6-[3-(1H-pyrazol-3-yl)pyrrolidin-1-yl]-3H-benzofuran-5-yl]pyrazolo[1,5-a]pyrimidine-3-carboxamide | 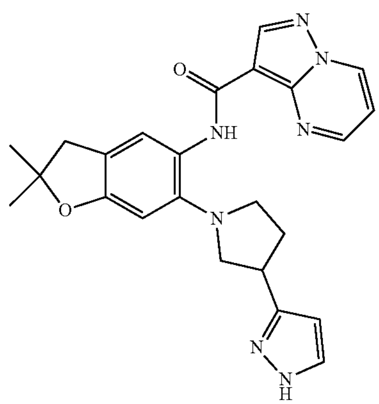 [SMILES: CC1(C)Cc2cc(NC(=O)c3cnn4cccnc34)c(N3CCC(c4cc[nH]n4)C3)cc2O1] | $^1$H NMR (400 MHz, dimethyl sulfoxide-d$_6$) δ 12.52 (d, J = 70.2 Hz, 1H), 10.04 (s, 1H), 9.35 (dd, J = 7.0, 1.6 Hz, 1H), 8.77 (s, 1H), 8.67 (s, 1H), 8.01 (s, 1H), 7.58 (s, 1H), 7.30 (dd, J = 7.0, 4.2 Hz, 1H), 6.60 (s, 1H), 6.13 (s, 1H), 3.68-3.51 (m, 1H), 3.48-3.40 (m, 1H), 3.30-3.22 (m, 1H), 3.20-3.07 (m, 2H), 2.98 (s, 2H), 2.35 (m, 1H), 2.07 (m, 1H), 1.41 (s, 6H). LCMS (ESI) m/z: 444.2 [M + H]+. |
| 193 | N-[6-(5,5-difluoro-2-azabicyclo[2.2.1]heptan-2-yl)-2,2-dimethyl-3H-benzofuran-5-yl]pyrazolo[1,5-a]pyrimidine-3-carboxamide | 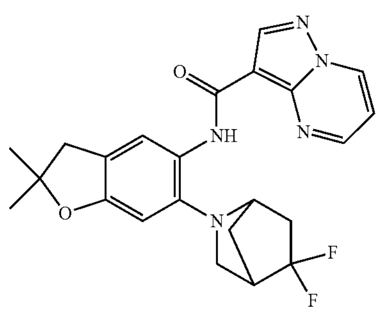 [SMILES: CC1(C)Cc2cc(NC(=O)c3cnn4cccnc34)c(N3CC4CC3CC4(F)F)cc2O1] | $^1$H NMR (400 MHz, dimethyl sulfoxide-d$_6$) δ 9.82 (s, 1H), 9.36 (dd, J = 7.0, 1.6 Hz, 1H), 8.84 (dd,J = 4.2, 1.6 Hz, 1H), 8.67 (s, 1H), 7.91 (d, J = 1.1 Hz, 1H), 7.32 (dd, J = 7.0, 4.2 Hz, 1H), 6.48 (s, 1H), 3.93 (s, 1H), 3.39-3.34 (m, 1H), 3.17-3.08 (m, 1H), 2.97 (d, J= 1.1 Hz, 2H), 2.81 (s, 1H), 2.35-2.19 (m, 1H), 2.06 (d, J = 11.4 Hz, 2H), 1.88 (d, J = 10.5 Hz, 1H), 1.41 (s, 6H). LCMS (ESI) m/z: 440.2 [M + H]+. |
| 194 | N-[2,2-dimethyl-6-(6-oxa-2-azaspiro[3.5]nonan-2-yl)-3H-benzofuran-5-yl]pyrazolo[1,5-a]pyrimidine-3-carboxamide | 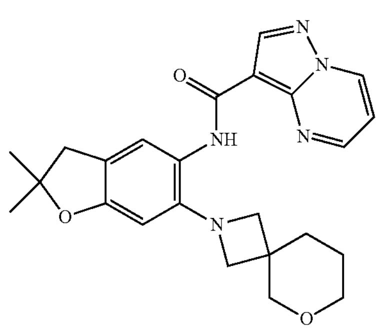 [SMILES: CC1(C)Cc2cc(NC(=O)c3cnn4cccnc34)c(N3CC4(CCCOC4)C3)cc2O1] | $^1$H NMR (400 MHz, dimethyl sulfoxide-d$_6$) δ 9.37 (dd, J = 7.0, 1.6Hz, 1H), 9.25 (s, 1H), 8.87 (dd, J = 4.2, 1.6 Hz, 1H), 8.67 (s, 1H), 7.58 (d, J = 1.0 Hz, 1H), 7.34 (dd, J = 7.0, 4.2 Hz, 1H), 6.15 (s, 1H), 3.67 (s, 2H), 3.60 (d, J = 7.1 Hz, 2H), 3.49-3.40 (m, 4H), 2.93 (d, J = 1.0 Hz, 2H), 1.74 (t, J = 6.0 Hz, 2H), 1.40 (s, 8H). LCMS (ESI) m/z: 434.2 [M + H]+. |

TABLE 7-continued

The following examples were made in a manner similar to that for Example 4:

| Ex. | Name | Structure | NMR, MS |
|---|---|---|---|
| 195 | N-[2,2-dimethyl-6-[3-(trifluoromethyl)pyrrolidin-1-yl]-3H-benzofuran-5-yl]pyrazolo[1,5-a]pyrimidine-3-carboxamide | 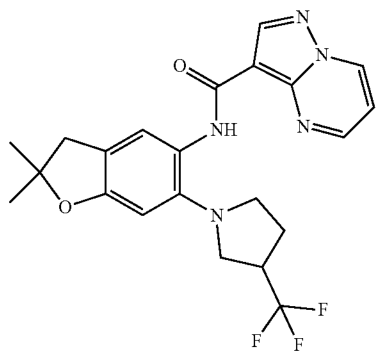 [SMILES: CC1(C)Cc2cc(NC(=O)c3cnn4cccnc34)c(N3CCC(C(F)(F)F)C3)cc2O1] | $^1$H NMR (400 MHz, dimethyl sulfoxide-$d_6$) δ 10.03 (s, 1H), 9.36 (dd, J = 7.0, 1.6 Hz, 1H), 8.83 (dd, J = 4.2, 1.7 Hz, 1H), 8.68 (s, 1H), 8.12 (d, J = 1.0 Hz, 1H), 7.33 (dd, J = 7.0, 4.2 Hz, 1H), 6.66 (s, 1H), 3.42-3.34 (m, 1H), 3.14-3.01 (m, 3H), 2.99 (d, J = 1.1 Hz, 2H), 2.24 (m, 1H), 2.02 (m, 1H), 1.41 (d, J = 1.0 Hz, 6H). LCMS (ESI) m/z: 446.2 [M + H]+. |
| 196 | N-(6-(3,3-difluoropiperidin-1-yl)-2,2-dimethyl-2,3-dihydrobenzofuran-5-yl)pyrazolo[1,5-a]pyrimidine-3-carboxamide | 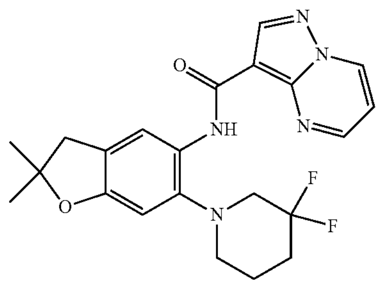 [SMILES: CC1(C)Cc2cc(NC(=O)c3cnn4cccnc34)c(N3CCCC(F)(F)C3)cc2O1] | $^1$H NMR (400 MHz, dimethyl sulfoxide-$d_6$) δ 10.35 (s, 1H), 9.35 (dd, J = 7.0, 1.6 Hz, 1H), 8.78 (dd, J = 4.2, 1.7 Hz, 1H), 8.67 (s, 1H), 8.39-8.18 (m, 1H), 7.32 (dd, J = 7.0, 4.2 Hz, 1H), 6.73 (s, 1H), 3.23-3.09 (m, 2H), 3.06-2.88 (m, 2H), 2.80-2.66 (m, 2H), 2.17-1.95 (m, 2H), 1.95-1.79 (m, 2H), 1.41 (s, 6H). (ESI): m/z = 428.2 [M + 1]$^+$. |
| 197 | N-(6-((3aR,6aS)-5,5-difluorohexahydrocyclopenta[c]pyrrol-2(1H)-yl)-2,2-dimethyl-2,3-dihydrobenzofuran-5-yl)pyrazolo[1,5-a]pyrimidine-3-carboxamide | 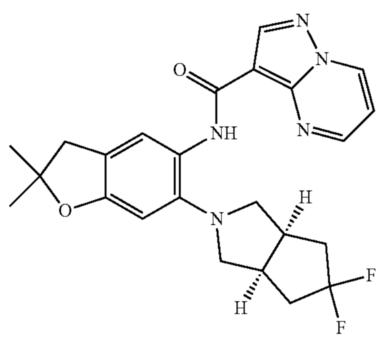 [SMILES: CC1(C)Cc2cc(NC(=O)c3cnn4cccnc34)c(N3C[C@@H]4CC(F)(F)C[C@@H]4C3)cc2O1] | $^1$H NMR (400 MHz, dimethyl sulfoxide-$d_6$) δ 9.83 (s, 1H), 9.37 (dd, J = 7.0, 1.6 Hz, 1H), 8.78 (dd, J = 4.2, 1.5 Hz, 1H), 8.69 (s, 1H), 7.95 (s, 1H), 7.33 (dd, J = 7.0, 4.2 Hz, 1H), 6.62 (s, 1H), 3.12-3.01 (m, 2H), 2.99 (s, 2H), 2.84 (d, J = 7.8 Hz, 4H), 2.32-2.14 (m, 2H), 2.10-1.83 (m, 2H), 1.42 (s, 6H). (ESI): m/z = 454.2 [M + 1]$^+$. |
| 198 | N-(6-(2-(methoxymethyl)morpholino)-2,2-dimethyl-2,3-dihydrobenzofuran-5-yl)pyrazolo[1,5-a]pyrimidine-3-carboxamide | 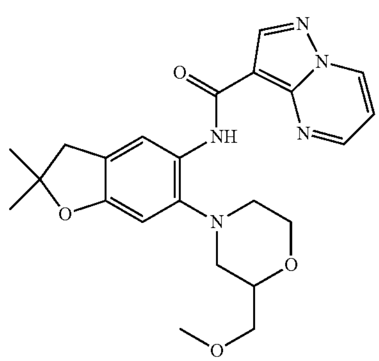 [SMILES: COCC1CN(c2cc3c(cc2NC(=O)c2cnn4cccnc24)CC(C)(C)O3)CCO1] | $^1$H NMR (400 MHz, dimethyl sulfoxide-$d_6$) δ 10.41 (s, 1H), 9.36 (dd, J = 7.0, 1.6 Hz, 1H), 8.89 (dd, J = 4.2, 1.6 Hz, 1H), 8.67 (s, 1H), 8.30 (s, 1H), 7.34 (dd, J = 7.0, 4.2 Hz, 1H), 6.69 (s, 1H), 4.02-3.77 (m, 3H), 3.45-3.27 (m, 2H), 3.17 (s, 3H), 3.00 (s, 2H), 2.91-2.70 (m, 3H), 2.60-2.51 (m, 1H), 1.41 (s, 6H). (ESI): m/z = 438.2 [M + 1]$^+$. |

TABLE 7-continued

The following examples were made in a manner similar to that for Example 4:

| Ex. | Name | Structure | NMR, MS |
|---|---|---|---|
| 199 | N-(6-(6,6-difluoro-3-azabicyclo[3.2.0]heptan-3-yl)-2,2-dimethyl-2,3-dihydrobenzofuran-5-yl)pyrazolo[1,5-a]pyrimidine-3-carboxamide | 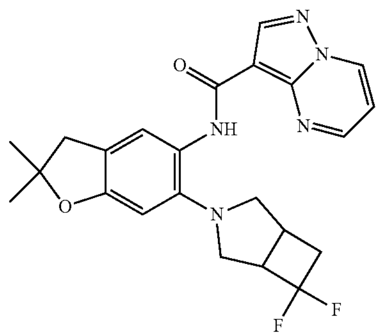 [SMILES: CC1(C)Cc2cc(NC(=O)c3cnn4cccnc34)c(N3CC4CC(F)(F)C4C3)cc2O1] | $^1$H NMR (400 MHz, dimethyl sulfoxide-d$_6$) δ 9.58 (s, 1H), 9.35 (dd, J = 7.0, 1.7 Hz, 1H), 8.75 (dd, J = 4.2, 1.6 Hz, 1H), 8.68 (s, 1H), 7.83 (s, 1H), 7.31 (dd, J = 7.0, 4.2 Hz, 1H), 6.67 (s, 1H), 3.44-3.20 (m, 3H), 3.17 (d, J = 9.0 Hz, 1H), 2.99 (s, 2H), 2.84 (dd, J = 10.4, 7.6 Hz, 1H), 2.79-2.53 (m, 3H), 1.42 (s, 6H). (ESI): m/z = 440.2 [M + 1]$^+$. |
| 200 | N-(6-((3aR,6aS)-4,4-difluorohexahydrocyclopenta[c]pyrrol-2(1H)-yl)-2,2-dimethyl-2,3-dihydrobenzofuran-5-yl)pyrazolo[1,5-a]pyrimidine-3-carboxamide | 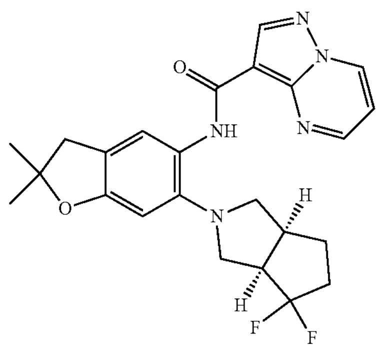 [SMILES: CC1(C)Cc2cc(NC(=O)c3cnn4cccnc34)c(N3C[C@H]4CCC(F)(F)[C@H]4C3)cc2O1] | $^1$H NMR (400 MHz, dimethyl sulfoxide-d$_6$) δ 9.78 (s, 1H), 9.36 (dd, J = 7.0, 1.6 Hz, 1H), 8.83 (dd, J = 4.3, 1.6 Hz, 1H), 8.68 (s, 1H), 7.93 (s, 1H), 7.31 (dd, J = 7.0, 4.2 Hz, 1H), 6.64 (s, 1H), 3.14 (t, J = 8.0 Hz, 1H), 3.10-3.01 (m, 2H), 2.99 (s, 2H), 2.95-2.77 (m, 4H), 2.47-2.20 (m, 1H), 2.10-1.91 (m, 1H), 1.91-1.75 (m, 1H), 1.68-1.50 (m, 1H), 1.41 (s, 6H). (ESI) : m/z = 454.2 [M + 1]$^+$. |
| 201 | N-(6-(2-(hydroxymethyl)pyrrolidin-1-yl)-2,2-dimethyl-2,3-dihydrobenzofuran-5-yl)pyrazolo[1,5-a]pyrimidine-3-carboxamide | 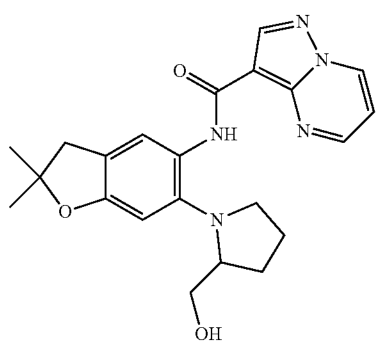 [SMILES: CC1(C)Cc2cc(NC(=O)c3cnn4cccnc34)c(N3CCCC3CO)cc2O1] | $^1$H NMR (400 MHz, dimethyl sulfoxide-d$_6$) δ 10.54 (s, 1H), 9.35 (dd, J = 7.0, 1.6 Hz, 1H), 8.82 (dd, J = 4.2, 1.7 Hz, 1H), 8.66 (s, 1H), 8.27 (d, J = 1.0 Hz, 1H), 7.30 (dd, J = 7.0, 4.2 Hz, 1H), 6.76 (s, 1H), 4.33 (t, J = 5.5 Hz, 1H), 3.55-3.39 (m, 1H), 3.39-3.10 (m, 3H), 3.00 (s, 2H), 2.77-2.60 (m, 1H), 2.26-2.05 (m, 1H), 2.05-1.74 (m, 2H), 1.41 (s, 6H). (ESI): m/z = 408.2 [M + 1]$^+$. |
| 202 | N-(6-(3-(1H-imidazol-2-yl)piperidin-1-yl)-2,2-dimethyl-2,3-dihydrobenzofuran-5-yl)pyrazolo[1,5-a]pyrimidine-3-carboxamide | 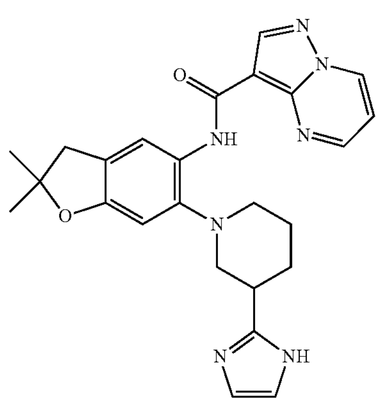 [SMILES: CC1(C)Cc2cc(NC(=O)c3cnn4cccnc34)c(N3CCCC(c4ncc[nH]4)C3)cc2O1] | $^1$H NMR (400 MHz, dimethyl sulfoxide-d$_6$) δ 11.67 (s, 1H), 10.56 (s, 1H), 9.36 (dd, J = 7.0, 1.6 Hz, 1H), 8.90 (dd, J = 4.2, 1.7 Hz, 1H), 8.68 (s, 1H), 8.36 (s, 1H), 7.33 (dd, J = 7.0, 4.2 Hz, 1H), 6.92 (s, 1H), 6.70 (s, 1H), 3.36-3.23 (m, 1H), 3.16 (d, J = 11.7 Hz, 1H), 3.00 (s, 2H), 2.92 (d, J = 11.3 Hz, 1H), 2.78 (t, J = 11.0 Hz, 1H), 2.65 (td, J = 11.4, 2.6 Hz, 1H), 2.18 (d, J = 11.9 Hz, 1H), 1.96 (d, J = 11.9 Hz, 1H), 1.83 (s, 1H), 1.72-1.57 (m, 1H), 1.41 (d, J = 3.7 Hz, 6H). (ESI) : m/z = 458.2 [M + 1]$^+$. |

TABLE 7-continued

The following examples were made in a manner similar to that for Example 4:

| Ex. | Name | Structure | NMR, MS |
|---|---|---|---|
| 203 | N-(6-((3R,4S)-3,4-difluoro-pyrrolidin-1-yl)-2,2-dimethyl-2,3-dihydrobenzo-furan-5-yl)pyrazolo[1,5-a]pyrimidine-3-carboxamide | 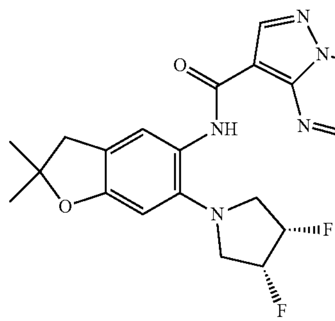 | $^1$H NMR (400 MHz, dimethyl sulfoxide-d$_6$) δ 9.92 (s, 1H), 9.36 (dd, J = 7.0, 1.7 Hz, 1H), 8.84 (dd, J = 4.2, 1.7 Hz, 1H), 8.67 (s, 1H), 7.95 (s, 1H), 7.32 (dd, J = 7.0, 4.2 Hz, 1H), 6.59 (s, 1H), 5.52-5.36 (m, 1H), 5.36-5.18 (m, 1H), 3.67-3.46 (m, 2H), 3.31 (s, 2H), 2.98 (s, 2H), 1.41 (s, 6H). (ESI): m/z = 414.2 [M + 1]$^+$. |
| 204 | N-(6-(5,5-difluoro-2-azaspiro[3.3]heptan-2-yl)-2,2-dimethyl-2,3-dihydrobenzo-furan-5-yl)pyrazolo[1,5-a]pyrimidine-3-carboxamide | 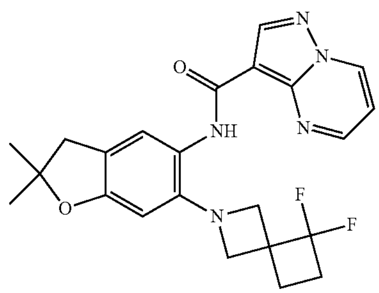 [SMILES: CC1(C)Cc2cc(NC(=O)c3cnn4cccnc34)c(N3CC4(CCC4(F)F)C3)cc2O1] | $^1$H NMR (400 MHz, dimethyl sulfoxide- d$_6$) δ 9.37 (dd, J = 7.0, 1.6 Hz, 1H), 9.22(s, 1H), 8.83 (dd, J = 4.2, 1.6 Hz, 1H), 8.68 (s, 1H), 7.46 (s, 1H), 7.34 (dd, J = 7.0, 4.2 Hz, 1H), 6.15 (s, 1H), 4.07 (d, J = 8.1 Hz, 2H), 3.68 (d, J = 8.0 Hz, 2H), 2.93 (s, 2H), 2.48-2.31 (m, 2H), 1.93 (t, J = 8.5 Hz, 2H). (ESI): m/z = 440.2 [M + 1]$^+$. |
| 205 | N-(6-((4-cyanobenzyl)(methyl)amino)-2,2-dimethyl-2,3-dihydrobenzo-furan-5-yl)pyrazolo[1,5-a]pyrimidine-3-carboxamide | 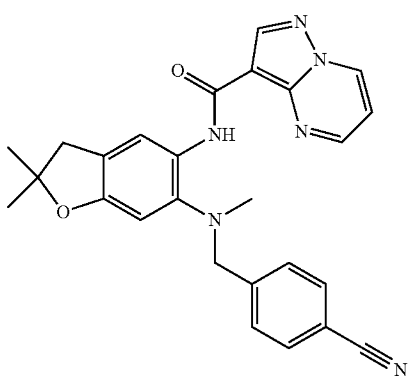 [SMILES: CN(Cc1ccc(C#N)cc1)c1cc2c(cc1NC(=O)c1cnn3cccnc13)CC(C)(C)O2] | $^1$H NMR (400 MHz, dimethyl sulfoxide-d$_6$) δ 10.47 (s, 1H), 9.37 (dd, J = 7.0, 1.7 Hz, 1H), 8.77 (dd, J = 4.2, 1.6 Hz, 1H), 8.67 (s, 1H), 8.30-8.14 (m, 1H), 7.87-7.70 (m, 2H), 7.67 (d, J = 8.3 Hz, 2H), 7.34 (dd, J = 7.0, 4.2 Hz, 1H), 6.77 (s, 1H), 4.23 (s, 2H), 2.98 (s, 2H), 2.56 (s, 3H), 1.40 (s, 6H). (ESI): m/z = 453.2 [M + 1]$^+$. |
| 206 | N-(6-(4-(1H-imidazol-1-yl)piperidin-1-yl)-2,2-dimethyl-2,3-dihydrobenzo-furan-5-yl)pyrazolo[1,5-a]pyrimidine-3-carboxamide | 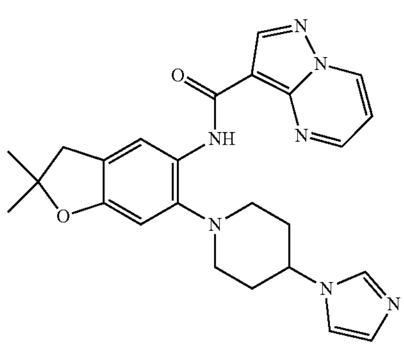 [SMILES: CC1(C)Cc2cc(NC(=O)c3cnn4cccnc34)c(N3CCC(n4ccnc4)CC3)cc2O1] | $^1$H NMR (400 MHz, dimethyl sulfoxide-d$_6$) δ 10.30 (s, 1H), 9.36 (dd, J = 7.0, 1.6 Hz, 1H), 8.81 (dd, J = 4.2, 1.7 Hz, 1H), 8.68 (s, 1H), 8.24 (s, 1H), 7.85-7.66 (m, 1H), 7.34 (dd, J = 7.0, 4.2 Hz, 1H), 7.28 (t, J = 1.3 Hz, 1H), 6.95 (t, J = 1.1 Hz, 1H), 6.71 (s, 1H), 4.33-4.11 (m, 1H), 3.07 (d, J = 11.8 Hz, 2H), 3.01 (s, 2H), 2.93-2.74 (m, 2H), 2.25-2.04 (m, 4H), 1.42 (s, 6H). (ESI): m/z = 458.2 [M + 1]$^+$. |

TABLE 7-continued

The following examples were made in a manner similar to that for Example 4:

| Ex. | Name | Structure | NMR, MS |
|---|---|---|---|
| 207 | N-(6-(4,4-difluoroazepan-1-yl)-2,2-dimethyl-2,3-dihydrobenzofuran-5-yl)pyrazolo[1,5-a]pyrimidine-3-carboxamide | 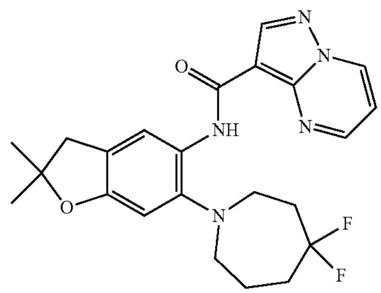 [SMILES: CC1(C)Cc2cc(NC(=O)c3cnn4cccnc34)c(N3CCCC(F)(F)CC3)cc2O1] | $^1$H NMR (400 MHz, dimethyl sulfoxide-d$_6$) δ 10.42 (s, 1H), 9.38 (dd, J = 7.0, 1.6 Hz, 1H), 8.75 (dd, J = 4.2, 1.6 Hz, 1H), 8.68 (s, 1H), 8.29 (s, 1H), 7.37 (dd, J = 7.0, 4.2 Hz, 1H), 6.73 (s, 1H), 3.11-3.02 (m, 2H), 2.99 (s, 2H), 2.97-2.90 (m, 2H), 2.55-2.40 (m, 2H), 2.39-2.20 (m, 2H), 1.90-1.78 (m, 2H), 1.41 (s, 6H). (ESI): m/z = 442.2 [M + 1]$^+$. |
| 208 | N-(6-((1R,5S,6r)-6-carbamoyl-3-azabicyclo[3.1.0]hexan-3-yl)-2,2-dimethyl-2,3-dihydrobenzofuran-5-yl)pyrazolo[1,5-a]pyrimidine-3-carboxamide | 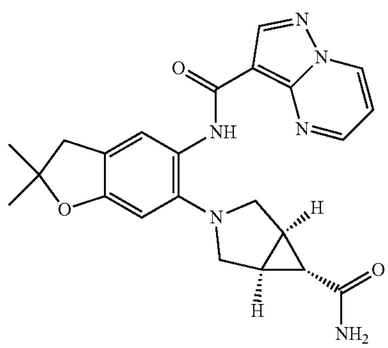 [SMILES: CC1(C)Cc2cc(NC(=O)c3cnn4cccnc34)c(N3C[C@@H]4[C@H](C3)[C@H]4C(N)=O)cc2O1] | $^1$H NMR (400 MHz, dimethyl sulfoxide-d$_6$) δ 9.58 (s, 1H), 9.36 (dd, J = 7.0, 1.6 Hz, 1H), 8.98 (dd, J = 4.2, 1.7 Hz, 1H), 8.68 (s, 1H), 8.01 (s, 1H), 7.37-7.29 (m, 2H), 6.78 (s, 1H), 6.60 (s, 1H), 3.41 (d, J = 9.3 Hz, 2H), 3.08 (d, J = 9.3 Hz, 1H), 2.97 (s, 2H), 2.20 (t, J = 3.0 Hz, 1H), 1.92-1.87 (m, 2H), 1.41 (s, 6H). (ESI): m/z = 433.2 [M + 1]$^+$. |
| 209 | N-(6-(4-hydroxyazepan-1-yl)-2,2-dimethyl-2,3-dihydrobenzofuran-5-yl)pyrazolo[1,5-a]pyrimidine-3-carboxamide | 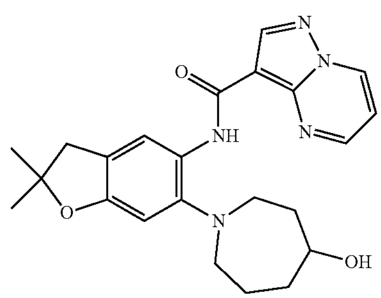 [SMILES: CC1(C)Cc2cc(NC(=O)c3cnn4cccnc34)c(N3CCCC(O)CC3)cc2O1] | $^1$H NMR (400 MHz, dimethyl sulfoxide-d$_6$) δ 10.45 (s, 1H), 9.36 (dd, J = 7.0, 1.7 Hz, 1H), 8.93 (dd, J = 4.2, 1.7 Hz, 1H), 8.67 (s, 1H), 8.26 (s, 1H), 7.34 (dd, J = 7.0, 4.2 Hz, 1H), 6.64 (s, 1H), 4.54 (d, J = 3.7 Hz, 1H), 3.98-3.86 (m, 1H), 3.05-2.89 (m, 4H), 2.89-2.78 (m, 1H), 2.10-1.99 (m, 1H), 1.98-1.81 (m, 2H), 1.81-1.65 (m, 1H), 1.64 (s, 1H), 1.40 (d, J = 1.5 Hz, 6H). (ESI): m/z = 422.2 [M + 1]$^+$. |
| 210 | N-(6-(4-carbamoyl-4-methylpiperidin-1-yl)-2,2-dimethyl-2,3-dihydrobenzofuran-5-yl)pyrazolo[1,5-a]pyrimidine-3-carboxamide | 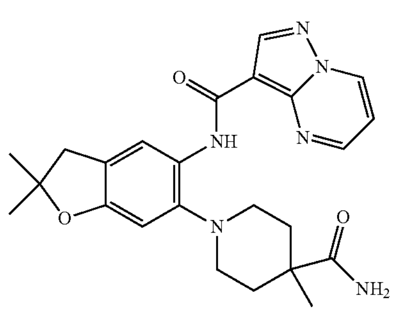 [SMILES: CC1(C)Cc2cc(NC(=O)c3cnn4cccnc34)c(N3CCC(C)(C(N)=O)CC3)cc2O1] | $^1$H NMR (400 MHz, dimethyl sulfoxide-d$_6$) δ 10.43 (s, 1H), 9.36 (dd, J = 7.0, 1.7 Hz, 1H), 8.89 (dd, J = 4.2, 1.7 Hz, 1H), 8.67 (s, 1H), 8.32 (s, 1H), 7.33 (dd, J = 7.0, 4.1 Hz, 1H), 7.18 (s, 1H), 6.89 (s, 1H), 6.63 (s, 1H), 2.99 (s, 2H), 2.87-2.76 (m, 2H), 2.72-2.62 (m, 2H), 2.26-2.16 (m, 2H), 1.6-1.56 (m, 2H), 1.41 (s, 6H), 1.21 (s, 3H). (ESI): m/z = 449.2 [M + 1]$^+$. |

TABLE 7-continued

The following examples were made in a manner similar to that for Example 4:

| Ex. | Name | Structure | NMR, MS |
|---|---|---|---|
| 211 | N-(2,2-dimethyl-6-(4-(2-(methylamino)-2-oxoethyl)piperidin-1-yl)-2,3-dihydrobenzofuran-5-yl)pyrazolo[1,5-a]pyrimidine-3-carboxamide | 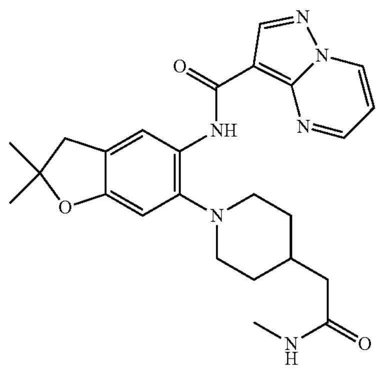 [SMILES: CNC(=O)CC1CCN(c2cc3c(cc2NC(=O)c2cnn4cccnc24)CC(C)(C)O3)CC1] | $^1$H NMR (400 MHz, dimethyl sulfoxide-d$_6$) δ 10.43 (s, 1H), 9.37 (dd, J = 7.0, 1.7 Hz, 1H), 8.88 (dd, J = 4.2, 1.7 Hz, 1H), 8.68 (s, 1H), 8.38-8.26 (m, 1H), 7.78 (q, J = 5.5, 5.0 Hz, 1H), 7.33 (dd, J = 7.0, 4.2 Hz, 1H), 6.68 (s, 1H), 2.99 (s, 2H), 2.93-2.84 (m, 2H), 2.69-2.60 (m, 2H), 2.58 (d, J = 4.6 Hz, 3H), 2.11 (d, J = 7.0 Hz, 2H), 1.88-1.73 (m, 1H), 1.69 (d, J = 12.6 Hz, 2H), 1.62-1.48 (m, 2H), 1.40 (s, 6H). (ESI): m/z = 463.3 [M + 1]$^+$. |
| 212 | N-(2,2-dimethyl-6-((1R,5S,6r)-6-(methylcarbamoyl)-3-azabicyclo[3.1.0]hexan-3-yl)-2,3-dihydrobenzofuran-5-yl)pyrazolo[1,5-a]pyrimidine-3-carboxamide | 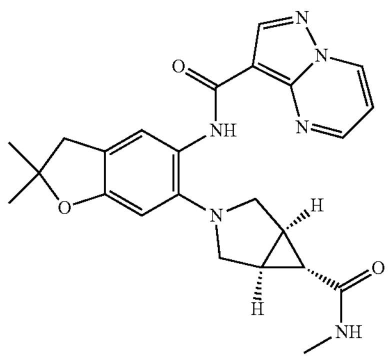 [SMILES: CNC(=O)[C@H]1[C@@H]2CN(c3cc4c(cc3NC(=O)c3cnn5cccnc35)CC(C)(C)O4)C[C@@H]21] | $^1$H NMR (400 MHz, dimethyl sulfoxide-d$_6$) δ 9.58 (s, 1H), 9.36 (dd, J = 7.0, 1.6 Hz, 1H), 8.90 (dd, J = 4.3, 1.7 Hz, 1H), 8.67 (s, 1H), 8.08-7.90 (m, 1H), 7.73 (q, J = 4.5 Hz, 1H), 7.34 (dd, J = 7.0, 4.2 Hz, 1H), 6.60 (s, 1H), 3.40 (d, J = 9.2 Hz, 2H), 3.08 (d, J = 9.1 Hz, 2H), 2.97 (s, 2H), 2.58 (d, J = 4.6 Hz, 3H), 2.17 (t, J = 3.0 Hz, 1H), 1.97-1.84 (m, 2H), 1.40 (s, 6H). (ESI): m/z = 447.2 [M + 1]$^+$. |
| 213 | N-(2,2-dimethyl-6-(3-oxo-2,8-diazaspiro[4.5]decan-8-yl)-2,3-dihydrobenzofuran-5-yl)pyrazolo[1,5-a]pyrimidine-3- | 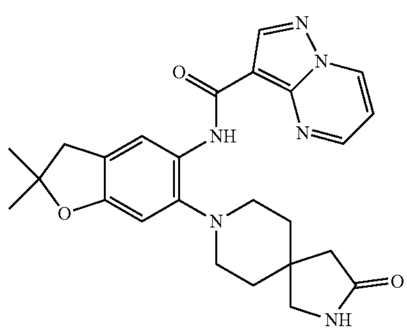 [SMILES: CC1(C)Cc2cc(NC(=O)c3cnn4cccnc34)c(N3CCC4(CC3)CNC(=O)C4)cc2O1] | $^1$H NMR (400 MHz, dimethyl sulfoxide-d$_6$) δ 10.46 (s, 1H), 9.35 (dd, J = 7.0, 1.6 Hz, 1H), 8.84 (dd, J = 4.2, 1.6 Hz, 1H), 8.67 (s, 1H), 8.34-8.28 (m, 1H), 7.58 (s, 1H), 7.33 (dd, J = 7.0, 4.2 Hz, 1H), 6.73 (s, 1H), 3.21-3.12 (m, 2H), 3.04-2.95 (m, 2H), 2.84-2.70 (m, 4H), 2.17 (s, 2H), 1.80 (d, J= 6.4 Hz, 4H), 1.41 (s, 6H). (ESI): m/z = 461.2 [M + 1]$_+$. |
| 214 | N-(2,2-dimethyl-6-(pyrrolidin-1-yl)-2,3-dihydrobenzofuran-5-yl)pyrazolo[1,5-a]pyrimidine-3-carboxamide | 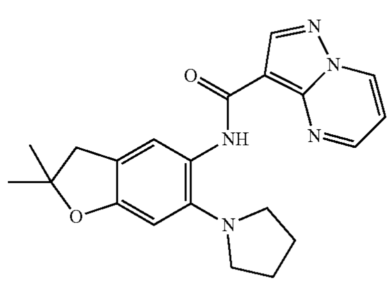 [SMILES: CC1(C)Cc2cc(NC(=O)c3cnn4cccnc34)c(N3CCCC3)cc2O1] | $^1$H NMR (400 MHz, dimethyl sulfoxide-d$_6$) δ 10.13 (s, 1H), 9.37 (dd, J = 7.0, 1.6 Hz, 1H), 8.85 (dd, J = 4.2, 1.6 Hz, 1H), 8.68 (s, 1H), 8.08 (s, 1H), 7.31 (dd, J = 7.0, 4.2 Hz, 1H), 6.59 (s, 1H), 3.00 (m, 4H), 2.98 (s, 2H), 1.98-1.86 (m, 4H), 1.41 (s, 6H). MS (ESI): m/z = 378.2 [M + 1]$^+$. |

TABLE 7-continued

The following examples were made in a manner similar to that for Example 4:

| Ex. | Name | Structure | NMR, MS |
|---|---|---|---|
| 215 | N-(6-(6-(hydroxymethyl)-3-azabicyclo[3.1.0]hexan-3-yl)-2,2-dimethyl-2,3-dihydrobenzofuran-5-yl)pyrazolo[1,5-a]pyrimidine-3-carboxamide | 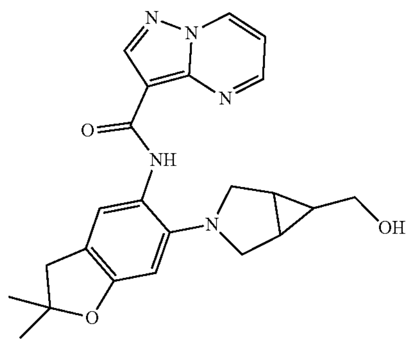 [SMILES: CC1(C)Cc2cc(NC(=O)c3cnn4cccnc34)c(N3CC4C(CO)C4C3)cc2O1] | $^1$H NMR (400 MHz, dimethyl sulfoxide-d$_6$) δ 9.69 (s, 1H), 9.36 (dd, J = 7.0, 1.7 Hz, 1H), 8.98 (dd, J = 4.2, 1.7 Hz, 1H), 8.68 (s, 1H), 8.12 (d, J = 1.0 Hz, 1H), 7.33 (dd, J = 7.0, 4.2 Hz, 1H), 6.63 (s, 1H), 4.54 (s, 1H), 3.33 (m, 2H), 3.26 (d, J = 8.7 Hz, 2H), 2.99-2.95 (m, 2H), 2.97 (s, 2H), 1.92 (m, 1H), 1.42 (m, 2H), 1.40 (s, 6H). MS (ESI): m/z = 420.2 [M + 1]$^+$. |
| 216 | N-(6-(4-cyanopiperidin-1-yl)-2,2-dimethyl-2,3-dihydrobenzofuran-5-yl)pyrazolo[1,5-a]pyrimidine-3-carboxamide | 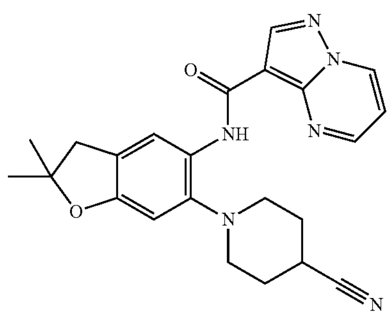 [SMILES: CC1(C)Cc2cc(NC(=O)c3cnn4cccnc34)c(N3CCC(C#N)CC3)cc2O1] | $^1$H NMR (400 MHz, dimethyl sulfoxide-d$_6$) δ 10.37 (s, 1H), 9.38 (dd, J = 7.0, 1.6 Hz, 1H), 8.86 (dd, J = 4.2, 1.6 Hz, 1H), 8.69 (s, 1H), 8.32 (d, J = 1.2 Hz, 1H), 7.38 (dd, J = 7.0, 4.2 Hz, 1H), 6.66 (s, 1H), 3.09 (m, 1H), 3.00 (s, 2H), 2.90 (m, 2H), 2.77 (m, 2H), 2.12 (m, 2H), 1.99 (m, 2H), 1.41 (s, 6H). MS (ESI): m/z = 417.2 [M + 1]$^+$. |
| 217 | N-(6-(3,3-difluoropyrrolidin-1-yl)-2,2-dimethyl-2,3-dihydrobenzofuran-5-yl)pyrazolo[1,5-a]pyrimidine-3-carboxamide | 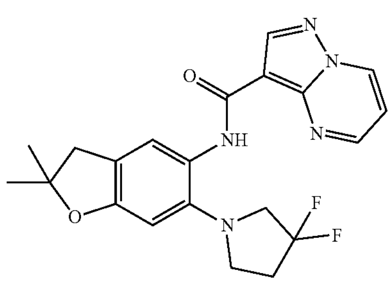 [SMILES: CC1(C)Cc2cc(NC(=O)c3cnn4cccnc34)c(N3CCC(F)(F)C3)cc2O1] | $^1$H NMR (400 MHz, dimethyl sulfoxide-d$_6$) δ 10.24 (s, 1H), 9.36 (dd, J = 7.0, 1.6 Hz, 1H), 8.79 (dd, J = 4.2, 1.7 Hz, 1H), 8.68 (s, 1H), 8.22 (d, J = 1.0 Hz, 1H), 7.33 (dd, J = 7.0, 4.2 Hz, 1H), 6.73 (s, 1H), 3.48 (t, J = 13.1 Hz, 2H), 3.25-3.14 (m, 2H), 3.00 (s, 2H), 2.49 (m, 2H), 1.41 (s, 6H). MS (ESI): m/z = 414.1 [M + 1]$^+$. |
| 218 | N-(2,2-dimethyl-6-(4-(trifluoromethyl)piperidin-1-yl)-2,3-dihydrobenzofuran-5-yl)pyrazolo[1,5-a]pyrimidine-3-carboxamide | 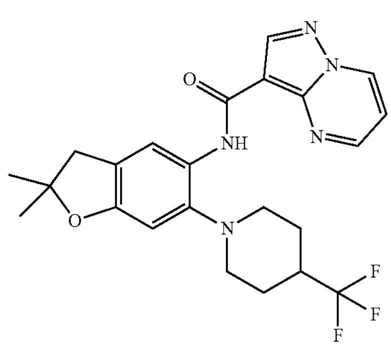 [SMILES: CC1(C)Cc2cc(NC(=O)c3cnn4cccnc34)c(N3CCC(C(F)(F)F)CC3)cc2O1] | $^1$H NMR (400 MHz, dimethyl sulfoxide-d$_6$) δ 10.34 (s, 1H), 9.37 (dd, J = 7.0, 1.6 Hz, 1H), 8.72 (dd, J = 4.2, 1.7 Hz, 1H), 8.68 (s, 1H), 8.31 (d, J = 1.0 Hz, 1H), 7.38 (dd, J = 7.0, 4.2 Hz, 1H), 6.66 (s, 1H), 3.05-2.95 (m, 5H), 2.72 (m, 2H), 1.98-1.77 (m, 4H), 1.41 (s, 6H). MS (ESI): m/z = 460.2 [M + 1]$^+$. |

TABLE 7-continued

The following examples were made in a manner similar to that for Example 4:

| Ex. | Name | Structure | NMR, MS |
|---|---|---|---|
| 219 | N-(6-(4-isobutyryl-piperazin-1-yl)-2,2-dimethyl-2,3-dihydrobenzo-furan-5-yl)pyrazolo[1,5-a]pyrimidine-3-carboxamide | 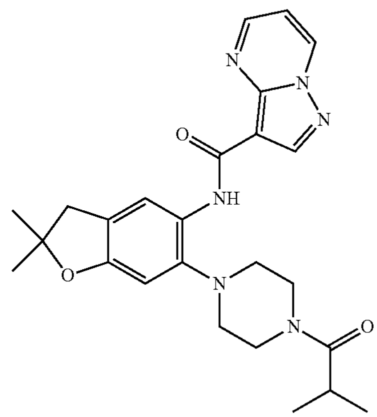 [SMILES: CC(C)C(=O)N1CCN(c2cc3c(cc2NC(=O)c2cnn4cccnc24)CC(C)(C)O3)CC1] | $^1$H NMR (400 MHz, dimethyl sulfoxide-d$_6$) δ 10.48 (s, 1H), 9.36 (dd, J = 7.0, 1.6 Hz, 1H), 8.87 (dd, J = 4.2, 1.7 Hz, 1H), 8.68 (s, 1H), 8.32 (d, J = 1.0 Hz, 1H), 7.32 (dd, J = 7.0, 4.2 Hz, 1H), 6.70 (s, 1H), 3.73 (s, 4H), 3.00 (s, 2H), 2.91 (p, J = 6.7 Hz, 1H), 2.78 (m, 4H), 1.41 (s, 6H), 1.03 (d, J = 6.7 Hz, 6H). MS (ESI): m/z = 463.2 [M + 1]$^+$. |
| 220 | N-(6-(4-acetyl-1,4-diazepan-1-yl)-2,2-dimethyl-2,3-dihydrobenzo-furan-5-yl)pyrazolo[1,5-a]pyrimidine-3-carboxamide | 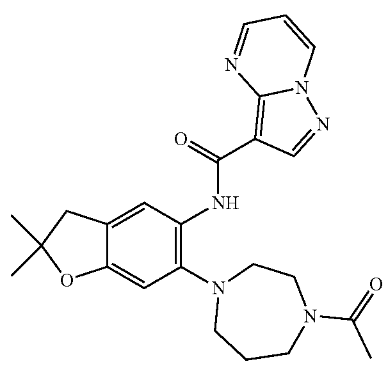 [SMILES: CC(=O)N1CCCN(c2cc3c(cc2NC(=O)c2cnn4cccnc24)CC(C)(C)O3)CC1] | $^1$H NMR (400 MHz, dimethyl sulfoxide-d$_6$) δ 10.39 (s, 1H), 9.36 (dt, J = 7.0, 1.5 Hz, 1H), 8.87 (dd, J = 4.2, 1.6 Hz, 1H), 8.68 (d, J = 1.5 Hz, 1H), 8.33-8.19 (m, 1H), 7.32 (ddd, J = 7.0, 4.2, 1.1 Hz, 1H), 6.67 (d, J = 20.9 Hz, 1H), 3.76-3.59 (m, 4H), 3.06-2.98 (m, 3H), 2.94 (m, 3H), 1.99 (m, 5H), 1.41 (s, 6H). MS (ESI): m/z = 449.2 [M + 1]$^+$. |
| 221 | N-(2,2-dimethyl-6-(3-oxo-2,8-diazaspiro[4.5]decan-8-yl)-2,3-dihydrobenzo-furan-5-yl)pyrazolo[1,5-a]pyrimidine-3-carboxamide | 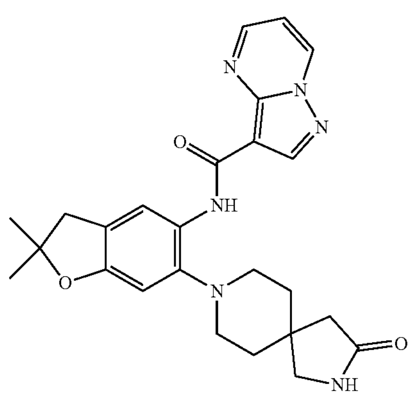 [SMILES: CC1(C)Cc2cc(NC(=O)c3cnn4cccnc34)c(N3CCC4(CC3)CNC(=O)C4)cc2O1] | $^1$H NMR (400 MHz, dimethyl sulfoxide-d$_6$) δ 10.46 (s, 1H), 9.36 (dd, J = 7.0, 1.6 Hz, 1H), 8.84 (dd, J = 4.2, 1.7 Hz, 1H), 8.67 (s, 1H), 8.32 (s, 1H), 7.67-7.51 (m, 1H), 7.34 (dd, J = 7.0, 4.2 Hz, 1H), 6.73 (s, 1H), 3.17 (s, 2H), 3.05-2.95 (s, 2H), 2.84-2.70 (m, 4H), 2.18 (s, 2H), 1.80 (m, 4H), 1.41 (s, 6H). MS (ESI): m/z = 461.2 [M + 1]$^+$. |

TABLE 7-continued

The following examples were made in a manner similar to that for Example 4:

| Ex. | Name | Structure | NMR, MS |
|---|---|---|---|
| 222 and 223 | (R)-N-(2,2-dimethyl-6-(2-oxa-7-azaspiro[4.4]nonan-7-yl)-2,3-dihydrobenzofuran-5-yl)pyrazolo[1,5-a]pyrimidine-3-carboxamide and (S)-N-(2,2-dimethyl-6-(2-oxa-7-azaspiro[4.4]nonan-7-yl)-2,3-dihydrobenzofuran-5-yl)pyrazolo[1,5-a]pyrimidine-3-carboxamide (stereochemistry assigned arbitrarily) | | Example 222 Peak 1: $^1$H NMR (400 MHz, dimethyl sulfoxide-d$_6$) δ 9.80 (s, 1H), 9.36 (dd, J = 7.0, 1.6 Hz, 1H), 8.83 (dd, J = 4.2, 1.7 Hz, 1H), 8.68 (s, 1H), 7.98 (d, J = 1.1 Hz, 1H), 7.32 (dd, J = 7.0, 4.2 Hz, 1H), 6.56 (s, 1H), 3.82-3.70 (m, 2H), 3.70-3.57 (m, 2H), 3.19-3.06 (m, 2H), 3.05 (s, 2H), 2.97 (d, J = 1.3 Hz, 2H), 2.05-1.87 (m, 4H), 1.41 (s, 6H). MS (ESI): m/z = 434 [M + 1]$^+$.<br>Example 223, Peak 2: $^1$H NMR (400 MHz, dimethyl sulfoxide-d$_6$) δ 9.80 (s, 1H), 9.36 (dd, J = 7.0, 1.6 Hz, 1H), 8.83 (dd, J = 4.2, 1.7 Hz, 1H), 8.68 (s, 1H), 7.98 (t, J = 0.9 Hz, 1H), 7.32 (dd, J = 7.0, 4.2 Hz, 1H), 6.56 (s, 1H), 3.82-3.70 (m, 2H), 3.70-3.57 (m, 2H), 3.19-3.06 (m, 2H), 3.05 (s, 2H), 2.97 (d, J = 1.1 Hz, 2H), 2.03-1.87 (m, 4H), 1.41 (s, 6H). MS (ESI): m/z = 434 [M + 1]$^+$. |
| 224 | N-[6-(6-hydroxy-4-methyl-1,4-diazepan-1-yl)-2,2-dimethyl-3H-benzofuran-5-yl]pyrazolo[1,5-a]pyrimidine-3-carboxamide | 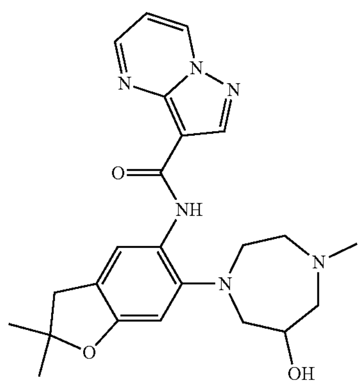 | $^1$H NMR (400 MHz, Methanol-d$_4$) δ 9.05 (d, J = 6.6 Hz, 1H), 8.83 (d, J= 3.7 Hz, 1H), 8.57 (s, 1H), 8.43 (d, J = 30.3 Hz, 1H), 7.86 (s, 1H), 7.23-7.15 (m, 1H), 6.61 (s, 1H), 4.22-4.15 (m, 1H), 3.63 (d, J = 12.7 Hz, 1H), 3.41 (td, J = 14.8, 14.4, 6.1 Hz, 3H), 3.29 (dd, J = 13.3, 3.9 Hz, 1H), 3.18 (m, 2H), 3.11 (dd, J = 13.4, 3.5 Hz, 1H), 2.93 (s, 2H), 2.77 (s, 3H), 1.35 (s, 6H). MS (ESI): m/z = 437.3 [M + 1]$^+$. |
| 225 | N-(6-(4-(2-(Isopropylamino)-2-oxoethyl)piperazin-1-yl)-2,2-dimethyl-2,3-dihydrobenzofuran-5-yl)pyrazolo[1,5-a]pyrimidine-3-carboxamide | 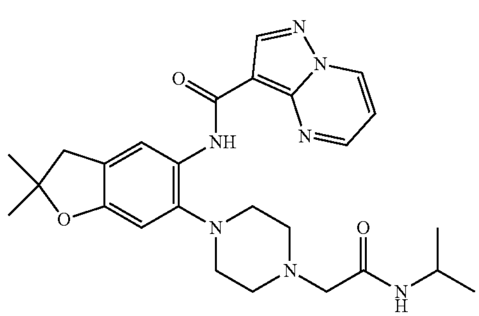 [SMILES: CC(C)NC(=O)CN1CCN(c2cc3c(cc2NC(=O)c2cnn4cccnc24)CC(C)(C)O3)CC1] | $^1$H NMR (400 MHz, dimethyl sulfoxide-d$_6$) δ 10.41 (s, 1H), 9.36 (dd, J = 7.0, 1.6 Hz, 1H), 8.98 (dd, J = 4.2, 1.6 Hz, 1H), 8.67 (s, 1H), 8.33 (d, J = 0.9 Hz, 1H), 7.52 (d, J = 8.1 Hz, 1H), 7.35 (dd, J = 7.0, 4.2 Hz, 1H), 6.71 (s, 1H), 3.99-3.81 (m, 1H), 3.05-2.95 (m, 4H), 2.90-2.81 (m, 4H), 2.72 (d, J= 5.1 Hz, 4H), 1.41 (s, 6H), 1.08 (d, J = 6.6 Hz, 6H). (ESI): m/z = 492.2 [M + 1]$^+$. |

TABLE 7-continued

The following examples were made in a manner similar to that for Example 4:

| Ex. | Name | Structure | NMR, MS |
|---|---|---|---|
| 226 | N-(6-(4-(1-Amino-2-methyl-1-oxopropan-2-yl)piperazin-1-yl)-2,2-dimethyl-2,3-dihydrobenzofuran-5-yl)pyrazolo[1,5-a]pyrimidine-3-carboxamide | 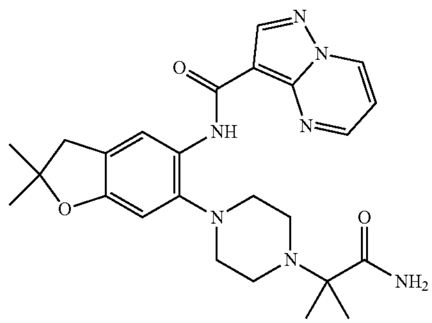 [SMILES: CC1(C)Cc2cc(NC(=O)c3cnn4cccnc34)c(N3CCN(C(C)(C)C(N)=O)CC3)cc2O1] | $^1$H NMR (400 MHz, dimethyl sulfoxide-d6) δ 10.34 (s, 1H), 9.36 (dd, J = 7.0, 1.6 Hz, 1H), 8.86 (dd, J = 4.2, 1.6 Hz, 1H), 8.67 (s, 1H), 8.26 (s, 1H), 7.37 (dd, J = 7.1, 4.2 Hz, 1H), 7.16 (d, J = 3.4 Hz, 1H), 7.02 (d, J = 3.0 Hz, 1H), 6.66 (s, 1H), 3.00 (s, 2H), 2.86 (t, J = 4.6 Hz, 4H), 2.67 (d, J = 4.7 Hz, 4H), 1.41 (s, 6H), 1.15 (s, 6H). (ESI): m/z = 478.2 [M + 1]$^+$. |
| 227 | N-(6-((3R,5S)-4-(2-Amino-2-oxoethyl)-3,5-dimethyl-piperazin-1-yl)-2,2-dimethyl-2,3-dihydrobenzofuran-5-yl)pyrazolo[1,5-a]pyrimidine-3-carboxamide | 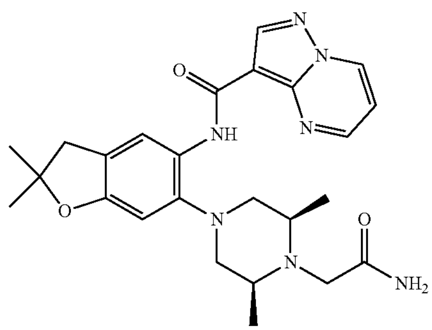 [SMILES: C[C@@H]1CN(c2cc3c(cc2NC(=O)c2cnn4cccnc24)CC(C)(C)O3)C[C@H](C)N1CC(N)=O] | (ESI): m/z = 478.2 [M + 1]$^+$. |
| 228 | N-(2,2-Dimethyl-6-(4-(2-morpholino-2-oxoethyl)piperazin-1-yl)-2,3-dihydrobenzofuran-5-yl)pyrazolo[1,5-a]pyrimidine-3-carboxamide | 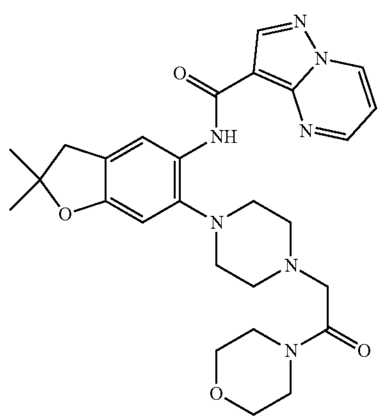 [SMILES: CC1(C)Cc2cc(NC(=O)c3cnn4cccnc34)c(N3CCN(CC(=O)N4CCOCC4)CC3)cc2O1] | $^1$H NMR (400 MHz, dimethyl sulfoxide-d$_6$) δ 10.38 (s, 1H), 9.37 (dd, J = 6.9, 1.6 Hz, 1H), 8.97 (dd, J = 4.3, 1.7 Hz, 1H), 8.67 (s, 1H), 8.31 (s, 1H), 7.37 (dd, J = 7.0, 4.2 Hz, 1H), 6.69 (s, 1H), 3.57 (d, J = 22.3 Hz, 7H), 3.45 (t, J = 4.7 Hz, 2H), 3.29 (s, 2H), 3.00 (s, 2H), 2.82 (t, J = 4.7 Hz, 4H), 2.70 (d, J = 4.9 Hz, 5H), 2.54 (dd, J = 8.1, 4.2 Hz, 1H), 1.41 (s, 6H). (ESI): m/z = 520.2 [M + 1]$^+$. |
| 229 | N-(2,2-Dimethyl-6-(3-(2-methylpyrimidin-4-yl)pyrrolidin-1-yl)-2,3-dihydrobenzofuran-5-yl)pyrazolo[1,5-a]pyrimidine-3-carboxamide | 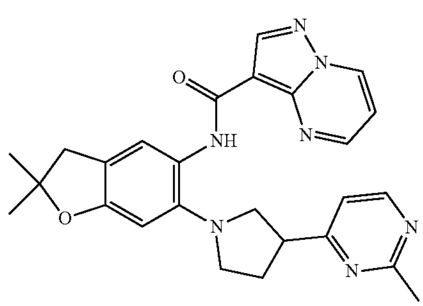 | $^1$H NMR (400 MHz, dimethyl sulfoxide-d$_6$) δ 10.05 (s, 1H), 9.35 (dd, J = 7.0, 1.5 Hz, 1H), 8.73 (dd, J = 4.2, 1.6 Hz, 1H), 8.67 (s, 1H), 8.52 (d, J = 5.2 Hz, 1H), 8.03 (s, 1H), 7.34-7.24 (m, 2H), 6.64 (s, 1H), 3.64 (p, J = 7.9 Hz, 1H), 3.47-3.32 (m, 2H), 3.36-3.13 (m, 3H), 2.99 (s, 2H), 2.47-2.34 (m, 1H), 2.27-2.13 (m, 1H), 1.42 (s, 6H). (ESI): m/z = 470.2 [M + 1]$^+$. |

TABLE 7-continued

The following examples were made in a manner similar to that for Example 4:

| Ex. | Name | Structure | NMR, MS |
|---|---|---|---|
| 230 | N-(2,2-Dimethyl-6-(4-((tetrahydrofuran-2-yl)methyl)piperazin-1-yl)-2,3-dihydrobenzofuran-5-yl)pyrazolo[1,5-a]pyrimidine-3-carboxamide | 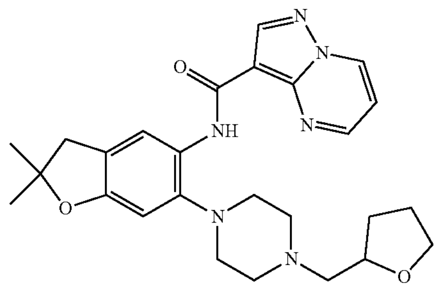 [SMILES: CC1(C)Cc2cc(NC(=O)c3cnn4cccnc34)c(N3CCN(CC4CCCO4)CC3)cc2O1] | $^1$H NMR (400 MHz, dimethyl sulfoxide-d$_6$) δ 10.41 (s, 1H), 9.36 (dd, J = 7.0, 1.6 Hz, 1H), 8.91 (dd, J = 4.1, 1.6 Hz, 1H), 8.67 (s, 1H), 8.31 (s, 1H), 7.37 (dd, J = 7.0, 4.1 Hz, 1H), 6.69 (s, 1H), 4.02-3.91 (m, 1H), 3.81-3.70 (m, 1H), 3.61 (td, J = 7.8, 6.3 Hz, 1H), 2.99 (s, 2H), 2.84-2.73 (m, 6H), 2.66 (s, 2H), 2.0 1.79 (m, 2H), 1.84-1.70 (m, 2H), 1.57-1.43 (m, 1H), 1.41 (s, 6H). MS (ESI): m/z = 477.2 [M + 1]$^+$. |
| 231 | N-(6-(4-(2-(1H-Imidazol-1-yl)ethyl)piperazin-1-yl)-2,2-dimethyl-2,3-dihydrobenzofuran-5-yl)pyrazolo[1,5-a]pyrimidine-3-carboxamide | 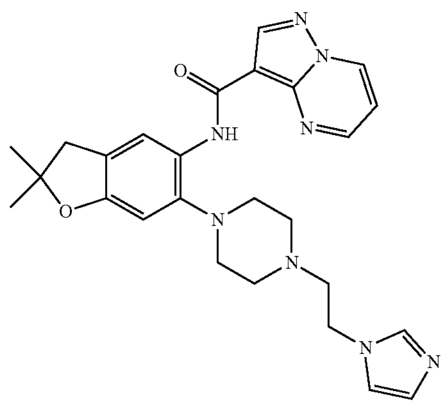 [SMILES: CC1(C)Cc2cc(NC(=O)c3cnn4cccnc34)c(N3CCN(CCn4ccnc4)CC3)cc2O1] | $^1$H NMR (400 MHz, dimethyl sulfoxide-d$_6$) δ 10.39 (s, 1H), 9.36 (dd, J = 7.0, 1.7 Hz, 1H), 8.92 (dd, J = 4.3, 1.7 Hz, 1H), 8.68 (s, 1H), 8.30 (s, 1H), 7.65 (s, 1H), 7.35 (dd, J = 7.0, 4.2 Hz, 1H), 7.21 (d, J = 1.2 Hz, 1H), 6.87 (d, J = 1.0 Hz, 1H), 6.70 (s, 1H), 4.11 (t, J = 6.6 Hz, 2H), 3.00 (s, 2H), 2.82 (t, J = 4.7 Hz, 4H), 2.74 (t, J = 6.6 Hz, 2H), 2.70 (s, 5H), 1.41 (s, 6H). MS (ESI): m/z = 487.2 [M + 1]$^+$. |
| 232 | N-(6-(4-(2-(Dimethylamino)-2-oxoethyl)piperazin-1-yl)-2,2-dimethyl-2,3-dihydrobenzofuran-5-yl)pyrazolo[1,5-a]pyrimidine-3-carboxamide | 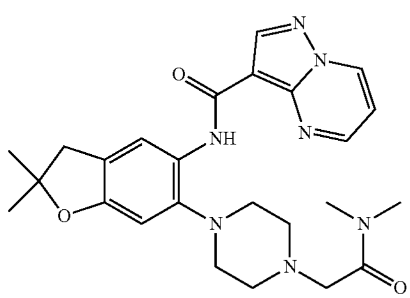 | $^1$H NMR (400 MHz, dimethyl sulfoxide-d$_6$) δ 10.39 (s, 1H), 9.36 (dd, J = 7.0, 1.7 Hz, 1H), 8.99 (dd, J = 4.2, 1.7 Hz, 1H), 8.67 (s, 1H), 8.32 (s, 1H), 7.37 (dd, J = 7.0, 4.2 Hz, 1H), 6.69 (s, 1H), 5.75 (s, 2H), 3.28 (d, J = 9.9 Hz, 3H), 3.06 (s, 3H), 3.00 (s, 2H), 2.82 (d, J = 4.9 Hz, 7H), 2.72 (d, J = 4.5 Hz, 4H), 1.41 (s, 6H). MS (ESI): m/z = 478.2 [M + 1]$^+$. |
| 233 | N-(6-(5,6-Dihydroimidazo 1,2-a]pyrazin-7(8H)-yl)-2,2-dimethyl-2,3-dihydrobenzofuran-5-yl)pyrazolo[1,5-a]pyrimidine-3-carboxamide | 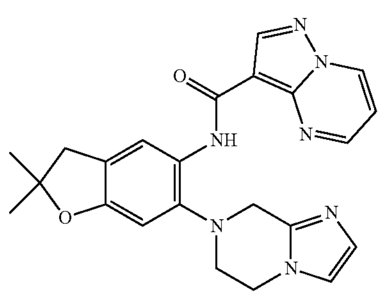 [SMILES: CC1(C)Cc2cc(NC(=O)c3cnn4cccnc34)c(N3CCn4ccnc4C3)cc2O1] | $^1$H NMR (400 MHz, dimethyl sulfoxide-d$_6$) δ 10.73 (s, 1H), 9.28 (dd, J = 7.0, 1.6 Hz, 1H), 8.65 (s, 1H), 8.40 (s, 1H), 7.70 (dd, J = 4.1, 1.6 Hz, 1H), 7.25 (d, J = 1.2 Hz, 1H), 7.17 (dd, J = 7.0, 4.1 Hz, 1H), 6.92 (d, J = 1.2 Hz, 1H), 6.84 (s, 1H), 4.19 (t, J = 5.3 Hz, 2H), 4.00 (s, 2H), 3.43-3.35 (m, 2H), 3.04 (s, 2H), 1.43 (s, 6H). MS (ESI): m/z = 430.2 [M + 1]$^+$. |

TABLE 7-continued

The following examples were made in a manner similar to that for Example 4:

| Ex. | Name | Structure | NMR, MS |
|---|---|---|---|
| 234 | N-(6-(Hexahydro-5H-furo[2,3-c]pyrrol-5-yl)-2,2-dimethyl-2,3-dihydrobenzofuran-5-yl)pyrazolo[1,5-a]pyrimidine-3-carboxamide | 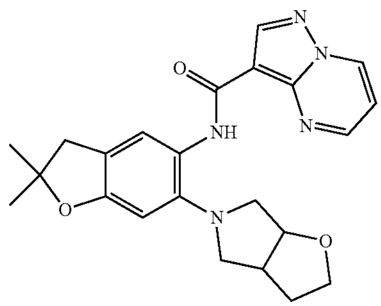 [SMILES: CC1(C)Cc2cc(NC(=O)c3cnn4cccnc34)c(N3CC4CCOC4C3)cc2O1] | $^1$H NMR (400 MHz, dimethyl sulfoxide-d$_6$) δ 9.80 (s, 1H), 9.36 (dd, J = 7.0, 1.6 Hz, 1H), 8.85 (dd, J = 4.2, 1.6 Hz, 1H), 8.68 (s, 1H), 7.95 (s, 1H), 7.31 (dd, J = 7.0, 4.2 Hz, 1H), 6.58 (s, 1H), 4.57 (ddd, J = 8.0, 5.9, 2.9 Hz, 1H), 3.87 (q, J = 7.5 Hz, 1H), 3.72-3.57 (m, 1H), 3.13-3.02 (m, 2H), 3.00-2.81 (m, 3H), 2.07 (s, 2H), 1.90 (dq, J = 12.2, 7.6 Hz, 1H), 1.74-1.62 (m, 1H), 1.41 (s, 6H). MS (ESI): m/z = 420.2 [M + 1]$^+$. |
| 235 | N-(6-(4-(1,3,4-Oxadiazol-2-yl)piperidin-1-yl)-2,2-dimethyl-2,3-dihydrobenzofuran-5-yl)pyrazolo[1,5-a]pyrimidine-3-carboxamide | 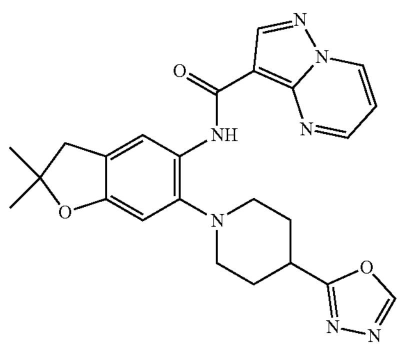 [SMILES: CC1(C)Cc2cc(NC(=O)c3cnn4cccnc34)c(N3CCC(c4nnco4)CC3)cc2O1] | $^1$H NMR (400 MHz, dimethyl sulfoxide-d$_6$) δ 10.49 (s, 1H), 9.36 (dd, J = 7.0, 1.7 Hz, 1H), 9.20 (s, 1H), 8.85 (dd, J = 4.2, 1.7 Hz, 1H), 8.68 (s, 1H), 8.36 (s, 1H), 7.34 (dd, J = 7.0, 4.2 Hz, 1H), 6.70 (s, 1H), 3.27-3.15 (m, 1H), 3.01 (s, 3H), 3.01-2.95 (m, 1H), 2.84 (td, J= 11.2, 3.1 Hz, 2H), 2.25-2.05 (m, 4H), 1.42 (s, 6H). MS (ESI): m/z = 460.2 [M + 1]$^+$. |
| 236 | N-(6-(3-Carbamoyl-pyrrolidin-1-yl)-2,2-dimethyl-2,3-dihydrobenzofuran-5-yl)pyrazolo[1,5-a]pyrimidine-3-carboxamide | 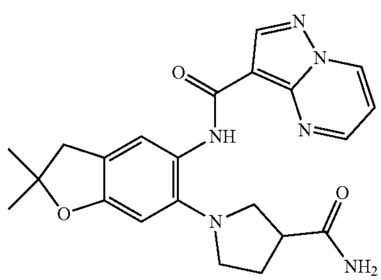 [SMILES: CC1(C)Cc2cc(NC(=O)c3cnn4cccnc34)c(N3CCC(C(N)=O)C3)cc2O1] | $^1$H NMR (400 MHz, dimethyl sulfoxide-d$_6$) δ 10.16 (s, 1H), 9.36 (dd, J = 7.0, 1.7 Hz, 1H), 8.90 (dd, J = 4.2, 1.7 Hz, 1H), 8.67 (s, 1H), 8.11 (s, 1H), 7.37-7.28 (m, 2H), 6.85 (s, 1H), 6.59 (s, 1H), 3.28 (d, J = 7.7 Hz, 1H), 3.16-2.93 (m, 3H), 2.98 (s, 2H), 2.11 (q, J = 7.1 Hz, 2H), 1.41 (s, 6H). MS (ESI): m/z = 421.2 [M + 1]$^+$. |
| 237 | N-(6-(9-Hydroxy-3-oxa-7-azabicyclo[3.3.1]nonan-7-yl)-2,2-dimethyl-2,3-dihydrobenzofuran-5-yl)pyrazolo[1,5-a]pyrimidine-3-carboxamide | 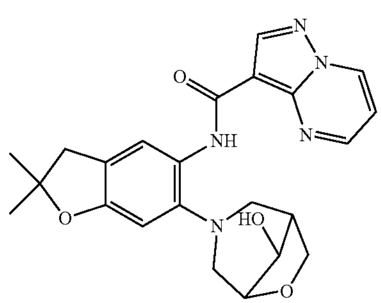 | 1:0.38 diastereomeric ratio. Resonances from the minor diastereomer are indicated with partial integrals. $^1$H NMR (400 MHz, dimethyl sulfoxide-d$_6$) δ 9.52 (s, 1H), 9.43 (s, 0.35H), 9.31-9.23 (m, 1.47H), 8.80-8.71 (m, 1.45H), 8.68 (m, J = 2.7 Hz, 1.38H), 7.92 (s, 1H), 7.83 (s, 0.33H), 7.30-7.21 (m, 1.46H), 6.64 (s, 1H), 6.59 (s, 0.36H), 5.07-4.99 (m, 1.44H), 3.95-3.88 (m, 3H), 3.81-3.73 (m, 1H), 3.52 (d, J = 11.3 Hz, 1H), 3.44 (s, 1H), 3.42 (s, 1H), 3.15-3.01 (m, 5H), 2.98 (s, 3H), 2.78 (d, J = 10.5 Hz, 1H), 1.65-1.55 (m, 3H), 1.41 (s, 8H). MS (ESI): m/z = 450.2 [M + 1]$^+$. |

TABLE 7-continued

The following examples were made in a manner similar to that for Example 4:

| Ex. | Name | Structure | NMR, MS |
|---|---|---|---|
| 238 | N-(2,2-Dimethyl-6-(1,4,6,7-tetrahydro-5H-imidazo[4,5-c]pyridin-5-yl)-2,3-dihydrobenzofuran-5-yl)pyrazolo[1,5-a]pyrimidine-3-carboxamide | 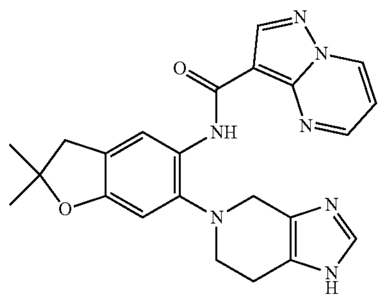 [SMILES: CC1(C)Cc2cc(NC(=O)c3cnn4cccnc34)c(N3CCc4[nH]cnc4C3)cc2O1] | $^1$H NMR (400 MHz, dimethyl sulfoxide-d$_6$) δ 11.99-11.57 (m, 1H), 11.00-10.63 (m, 1H), 9.27 (d, J = 7.0 Hz, 1H), 8.64 (s, 1H), 8.44-8.33 (m, 1H), 7.84-7.61 (m, 1H), 7.50 (s, 1H), 7.17 (dd, J = 7.0, 4.2 Hz, 1H), 6.88-6.62 (m, 1H), 3.83 (d, J = 24.2 Hz, 2H), 3.27-3.13 (m, 2H), 3.02 (s, 2H), 2.86-2.68 (m, 2H), 1.42 (s, 6H). MS (ESI): m/z = 430.2 [M + 1]$^+$. |
| 239 | N-(6-(7-Methoxy-2-azabicyclo[2.2.1]heptan-2-yl)-2,2-dimethyl-2,3-dihydrobenzofuran-5-yl)pyrazolo[1,5-a]pyrimidine-3-carboxamide | 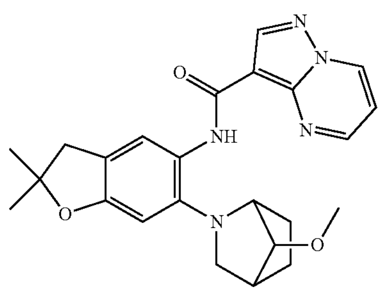 [SMILES: COC1C2CCC1N(c1cc3c(cc1NC(=O)c1cnn4cccnc14)CC(C)(C)O3)C2] | 1:0.39 diastereomeric ratio. Resonances from the minor diastereomer are indicated with partial integrals. $^1$H NMR (400 MHz, dimethyl sulfoxide-d$_6$) δ 10.06 (s, 0.39 H), 9.73 (s, 1H), 9.37 (m, 1.38 H), 8.94-8.87 (m, 1.43 H), 8.71 (s, 0.30H), 8.67 (s, 1H), 8.18 (s, 0.4H), 7.82 (s, 1H), 7.38-7.29 (m, 1.39 H), 6.94 (s, 0.33H), 6.48 (s, 1H), 3.99 (s, 1H), 3.74-3.68 (m, 1H), 3.23 (s, 5H), 3.05 (s, 1H), 3.03 (s, 1H), 2.95 (s, 2H), 2.34 (s, 1H), 1.81-1.62 (m, 3H), 1.48-1.38 (m, 10H). MS (ESI): m/z = 434.2 [M + 1]$^+$. |
| 240 | N-(6-(2-Azabicyclo[3.1.0]hexan-2-yl)-2,2-dimethyl-2,3-dihydrobenzofuran-5-yl)pyrazolo[1,5-a]pyrimidine-3-carboxamide | 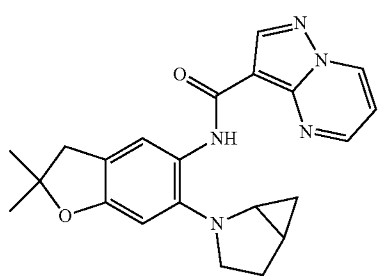 [SMILES: CC1(C)Cc2cc(NC(=O)c3cnn4cccnc34)c(N3CCC4CC43)cc2O1] | 1:0.12 diastereomeric ratio. Resonances from the minor diastereomer are indicated with partial integrals. $^1$H NMR (400 MHz, dimethyl sulfoxide-d$_6$) δ 10.06 (s, 0.12 H), 10.01 (s, 1H), 9.39 (dd, J = 6.9, 1.5 Hz, 0.12 H), 9.35 (dd, J = 7.0, 1.7 Hz, 1H), 8.91 (dd, J = 4.3, 1.6 Hz, 0.12 H), 8.87 (dd, J = 4.3, 1.6 Hz, 1H), 8.71 (s, 0.12 H), 8.67 (s, 1H), 8.18 (s, 0.12 H), 8.13 (s, 1H), 7.34 (dd, J = 7.0, 4.2 Hz, 0.12 H), 7.30 (dd, J = 7.0, 4.2 Hz, 1H), 6.94 (s, 0.12 H), 6.87 (s, 1H), 3.45 (t, J = 8.9 Hz, 1H), 3.30 (t, J= 13.1 Hz, 1H), 3.05 (s, 0H), 2.99 (s, 2H), 2.93 (td, J = 5.8, 2.6 Hz, 1H), 2.34-2.24 (m, 1H), 2.19-2.05 (m, 1H), 1.94 (dd, J = 11.8, 6.8 Hz, 1H), 1.60-1.50 (m, 1H), 1.41 (d, J = 4.7 Hz, 7H), 1.01 - 0.92 (m, 1H), 0.48 (dt, J = 8.3, 5.6 Hz, 1H). MS (ESI): m/z = 390.2 [M + 1]$^+$. |

TABLE 7-continued

The following examples were made in a manner similar to that for Example 4:

| Ex. | Name | Structure | NMR, MS |
|---|---|---|---|
| 241 | N-(2,2-Dimethyl-6-(3-sulfamoyl-pyrrolidin-1-yl)-2,3-dihydrobenzo-furan-5-yl)pyrazolo[1,5-a]pyrimidine-3-carboxamide | 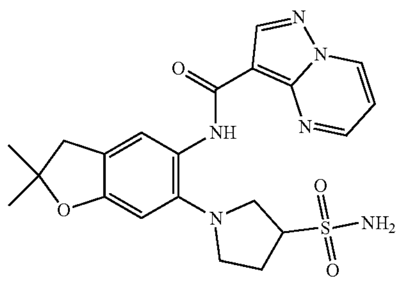 [SMILES: CC1(C)Cc2cc(NC(=O)c3cnn4cccnc34)c(N3CCC(S(N)(=O)=O)C3)cc2O1] | $^1$H NMR (400 MHz, dimethyl sulfoxide-d$_6$) δ 10.17 (s, 1H), 9.36 (dd, J = 7.0, 1.7 Hz, 1H), 8.90 (dd, J = 4.2, 1.6 Hz, 1H), 8.67 (s, 1H), 8.18 (s, 1H), 7.33 (dd, J = 7.0, 4.3 Hz, 1H), 6.94 (s, 2H), 6.69 (s, 1H), 3.92-3.80 (m, 1H), 3.52 (dd, J = 10.1, 8.4 Hz, 1H), 3.33-3.03 (m, 4H), 3.00 (s, 2H), 2.37-2.27 (m, 2H), 1.42 (s, 6H). MS (ESI): m/z = 457.1 [M + 1]$^+$. |
| 242 | N-(6-(4-(2-(Cyclopropyl-amino)-2-oxoethyl)piperazin-1-yl)-2,2-dimethyl-2,3-dihydrobenzo-furan-5-yl)pyrazolo[1,5-a]pyrimidine-3-carboxamide | 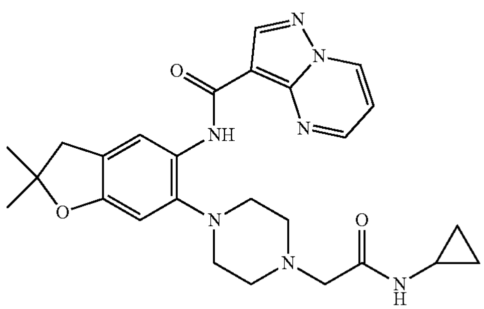 [SMILES: CC1(C)Cc2cc(NC(=O)c3cnn4cccnc34)c(N3CCN(CC(=O)NC4CC4)CC3)cc2O1] | MS (ESI): m/z = 490.2 [M + 1]$^+$. |
| 243 | N-(2,2-Dimethyl-6-(4-(2-oxo-2-(pyrrolidin-1-yl)ethyl)piperazin-1-yl)-2,3-dihydrobenzo-furan-5-yl)pyrazolo[1,5-a]pyrimidine-3-carboxamide | 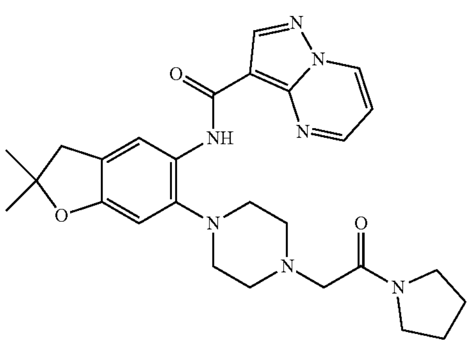 [SMILES: CC1(C)Cc2cc(NC(=O)c3cnn4cccnc34)c(N3CCN(CC(=O)N4CCCC4)CC3)cc2O1] | $^1$H NMR (400 MHz, dimethyl sulfoxide-d$_6$) δ 10.41 (s, 1H), 9.36 (dd, J = 7.0, 1.7 Hz, 1H), 9.02 (dd, J = 4.3, 1.7 Hz, 1H), 8.68 (s, 1H), 8.32 (s, 1H), 7.36 (dd, J = 7.0, 4.2 Hz, 1H), 6.70 (s, 1H), 3.52 (t, J = 6.7 Hz, 2H), 3.44-3.26 (m, 2H, buried under H$_2$O peak), 3.23 (s, 2H), 3.00 (s, 2H), 2.86-2.72 (m, 8H), 1.94-1.82 (m, 2H), 1.83-1.71 (m, 2H), 1.42 (s, 6H). MS (ESI): m/z = 504.2 [M + 1]$^+$. |
| 244 | N-(6-(4-(1-(Cyclopropyl-amino)-1-oxopropan-2-yl)piperazin-1-yl)-2,2-dimethyl-2,3-dihydrobenzo-furan-5-yl)pyrazolo[1,5-a]pyrimidine-3-carboxamide | 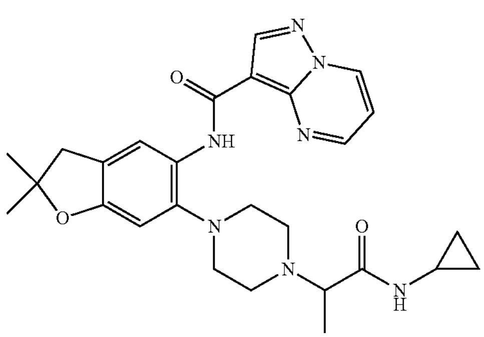 [SMILES: CC(C(=O)NC1CC1)N1CCN(c2cc3c(cc2NC(=O)c2cnn4cccnc24)CC(C)(C)O3)CC1] | $^1$H NMR (400 MHz, dimethyl sulfoxide-d$_6$) δ 10.41 (s, 1H), 9.36 (dd, J = 7.0, 1.7 Hz, 1H), 9.00 (dd, J = 4.2, 1.7 Hz, 1H), 8.67 (s, 1H), 8.33 (s, 1H), 7.85 (d, J = 4.6 Hz, 1H), 7.37 (dd, J = 7.0, 4.2 Hz, 1H), 6.69 (s, 1H), 3.08 (q, J = 6.8 Hz, 1H), 2.99 (s, 2H), 2.84-2.66 (m, 9H), 1.41 (s, 6H), 1.14 (d, J = 6.9 Hz, 3H), 0.69-0.58 (m, 2H), 0.49-0.34 (m, 2H). MS (ESI): m/z = 504.2 [M + 1]$^+$. |

TABLE 7-continued

The following examples were made in a manner similar to that for Example 4:

| Ex. | Name | Structure | NMR, MS |
|---|---|---|---|
| 245 | N-(2,2-Dimethyl-6-(4-(2,2,2-trifluoro-1-hydroxyethyl)piperidin-1-yl)-2,3-dihydrobenzofuran-5-yl)pyrazolo[1,5-a]pyrimidine-3-carboxamide | 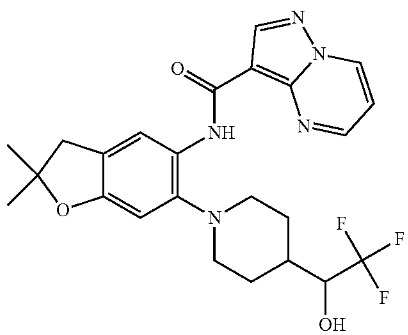 [SMILES: CC1(C)Cc2cc(NC(=O)c3cnn4cccnc34)c(N3CCC(C(O)C(F)(F)F)CC3)cc2O1] | $^1$H NMR (400 MHz, dimethyl sulfoxide-d$_6$) δ 10.51 (s, 1H), 9.35 (dd, J = 7.0, 1.7 Hz, 1H), 8.99 (dd, J = 4.2, 1.7 Hz, 1H), 8.67 (s, 1H), 8.37 (s, 1H), 7.33 (dd, J = 7.0, 4.2 Hz, 1H), 6.69 (s, 1H), 6.38 (d, J = 2.6 Hz, 1H), 3.94 (s, 1H), 2.99 (s, 2H), 2.95 (d, J = 11.4 Hz, 2H), 2.74-2.59 (m, 2H), 1.98-1.83 (m, 2H), 1.80-1.72 (m, 2H), 1.66 (d, J = 12.3 Hz, 1H), 1.41 (s, 6H). MS (ESI): m/z = 490.2 [M + 1]$^+$. |
| 246 | N-(6-(4,6-dihydropyrrolo[3,4-c]pyrazol-5(1H)-yl)-2,2-dimethyl-2,3-dihydrobenzofuran-5-yl)pyrazolo[1,5-a]pyrimidine-3-carboxamide | 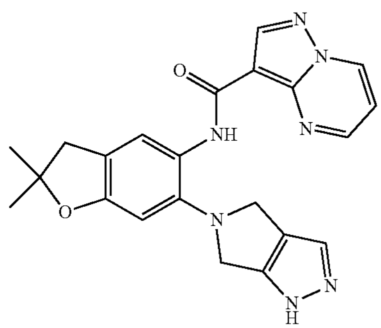 [SMILES: CC1(C)Cc2cc(NC(=O)c3cnn4cccnc34)c(N3Cc4cn[nH]c4C3)cc2O1] | $^1$H NMR (400 MHz, dimethyl sulfoxide-d6) δ 12.54 (s, 1H), 10.45 (s, 1H), 9.31 (dd, J = 7.0, 1.7 Hz, 1H), 8.66 (s, 1H), 8.10 (dd, J = 4.1, 1.5 Hz, 1H), 8.06 (s, 1H), 7.51 (s, 1H), 7.21 (dd, J = 7.0, 4.2 Hz, 1H), 6.85 (s, 1H), 4.27 (s, 4H), 3.00 (s, 2H), 1.43 (s, 6H). MS (ESI): m/z = 416.2 [M + 1]$^+$. |
| 247 | N-(2,2-dimethyl-6-(3-methyl-4,6-dihydropyrrolo]3,4-c]pyrazol-5(1H)-yl)-2,3-dihydrobenzofuran-5-yl)pyrazolo[1,5-a]pyrimidine-3-carboxamide | 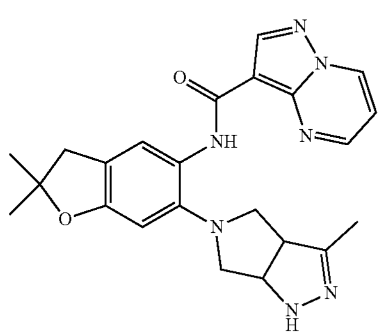 [SMILES: CC1=NNC2CN(c3cc4c(cc3NC(=O)c3cnn5cccnc35)CC(C)(C)O4)CC12] | $^1$H NMR (400 MHz, dimethyl sulfoxide-d6) δ 12.19 (s, 1H), 10.43 (s, 1H), 9.31 (dd, J = 7.0, 1.7 Hz, 1H), 8.66 (s, 1H), 8.13 (dd, J = 4.2, 1.7 Hz, 1H), 8.08 (s, 1H), 7.23 (dd, J = 7.0, 4.2 Hz, 1H), 6.82 (s, 1H), 4.20 (d, J = 12.3 Hz, 4H), 3.00 (s, 2H), 2.19 (s, 3H), 1.42 (s, 6H). MS (ESI): m/z = 430.2 [M + 1]$^+$. |

Example 248. N-(6-(2-(2,2-Difluoroethyl)-2,7-diazaspiro[3.5]nonan-7-yl)-2,2-dimethyl-2,3-dihydrobenzofuran-5-yl)pyrazolo[1,5-a]pyrimidine-3-carboxamide

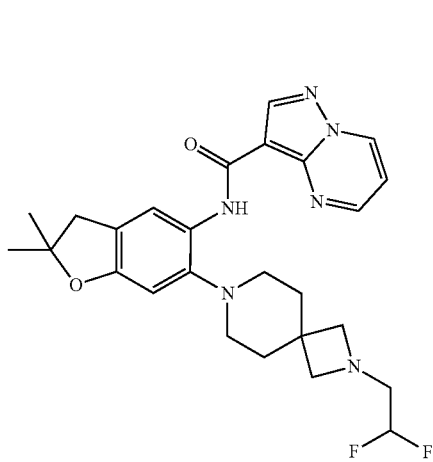 [SMILES: CC1(C)Cc2cc(NC(=O)c3cnn4cccnc34)c(N3CCC4(CC3)CN(CC(F)F)C4)cc2O1]

Step A. tert-Butyl 7-(2,2-dimethyl-5-nitro-2,3-dihydrobenzofuran-6-yl)-2,7-diazaspiro[3.5]nonane-2-carboxylate

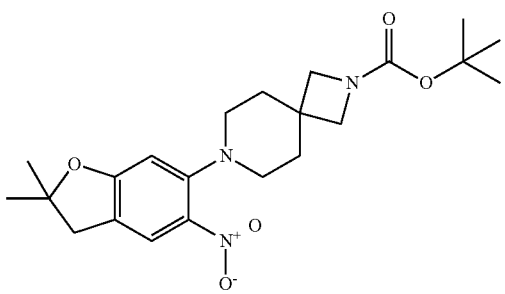

To a mixture of 6-bromo-2,2-dimethyl-5-nitro-3H-benzofuran (Intermediate 4; 200 mg, 0.74 mmol), and cesium carbonate (790 mg, 2.43 mmol) in acetonitrile (2.23 ml) was added tert-butyl 2,7-diazaspiro[3.5]nonane-2-carboxylate and oxalic acid (256 mg, 0.809 mmol). The mixture was heated at 60° C. for 16h, cooled to room temperature, and diluted with water and isopropyl acetate. The aqueous phase was isolated and extracted with isopropyl acetate (3×). The combined organic phases were dried over anhydrous sodium sulfate, filtered and purified by flash column chromatography (eluting gradient 0-100% isopropyl acetate: heptanes) to afford the title compound (177 mg, 0.424 mmol, 58% yield) as a bright yellow solid. $^1$H NMR (400 MHz, dimethyl sulfoxide-d6) δ 7.82 (s, 1H), 6.54 (s, 1H), 3.58 (s, 5H), 2.99 (s, 2H), 2.90-2.82 (m, 4H), 1.82-1.73 (m, 4H), 1.43 (s, 6H), 1.38 (s, 9H).

Step B. 7-(2,2-Dimethyl-5-nitro-2,3-dihydrobenzofuran-6-yl)-2,7-diazaspiro[3.5]nonane

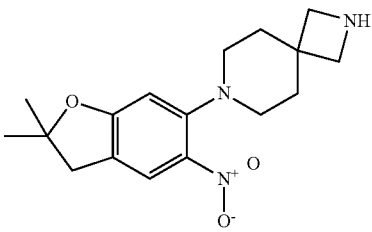

tert-butyl 7-(2,2-Dimethyl-5-nitro-2,3-dihydrobenzofuran-6-yl)-2,7-diazaspiro[3.5]nonane-2-carboxylate (176 mg, 0.422 mmol) was dissolved in dichloromethane (3.3 ml) and treated with trifluoroacetic acid (1.3 ml). After 10 min, the solvent was removed under reduced pressure. The product was taken on without further purification.

Step C. 2-(2,2-Difluoroethyl)-7-(2,2-dimethyl-5-nitro-2,3-dihydrobenzofuran-6-yl)-2,7-diazaspiro[3.5]nonane

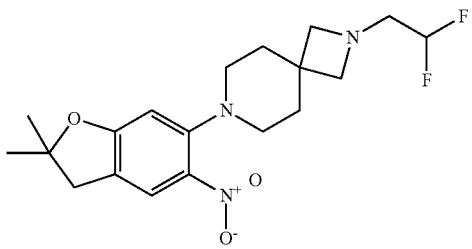

7-(2,2-Dimethyl-5-nitro-2,3-dihydrobenzofuran-6-yl)-2,7-diazaspiro[3.5]nonane (67 mg, 0.21 mmol) was dissolved in dichloromethane (8 ml) and slowly treated with collidine (0.61 ml, 4.6 mmol) followed by 2,2-difluoroethyl trifluoromethanesulfonate (0.044 ml, 0.32 mmol). After 18h, methanol (5 ml) and potassium carbonate were added. The reaction mixture stirred vigorously for 4h at ambient temperature and then was diluted with water and isopropyl acetate. The aqueous phase was isolated and extracted with isopropyl acetate (3×). The combined organic phases were dried over anhydrous sodium sulfate, filtered and purified by column chromatography (eluting gradient 0-100% isopropyl acetate: heptanes) to afford 2-(2,2-difluoroethyl)-7-(2,2-dimethyl-5-nitro-2,3-dihydrobenzofuran-6-yl)-2,7-diazaspiro[3.5]nonane (61 mg, 0.16 mmol) as a yellow solid. $^1$H NMR (400 MHz, dimethyl sulfoxide-d$_6$) δ 7.81 (s, 1H), 6.54 (s, 1H), 5.93 (tt, J=55.9, 4.3 Hz, 1H), 3.08 (s, 4H), 2.98 (s, 2H), 2.85 (m, 4H), 2.82 (d, J=4.3 Hz, 2H), 1.82-1.72 (m, 4H), 1.43 (s, 6H).

Step D. 6-(2-(2,2-Difluoroethyl)-2,7-diazaspiro[3.5]nonan-7-yl)-2,2-dimethyl-2,3-dihydrobenzofuran-5-amine

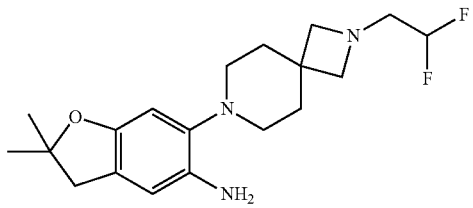 [SMILES: CC1(C)Cc2cc(N)c(N3CCC4(CC3)CN(CC(F)F)C4)cc2O1]

A mixture of 2-(2,2-difluoroethyl)-7-(2,2-dimethyl-5-nitro-2,3-dihydrobenzofuran-6-yl)-2,7-diazaspiro[3.5]nonane (61 mg, 0.16 mmol), iron (77 mg, 1.4 mmol), and ammonium chloride (74 mg, 1.4 mmol) in ethanol (6 ml) and water (2m) was stirred at 80° C. for 30 min. The mixture was filtered through celite and a small plug of silica to afford 6-(2-(2,2-difluoroethyl)-2,7-diazaspiro[3.5]nonan-7-yl)-2,2-dimethyl-2,3-dihydrobenzofuran-5-amine (0.16 mmol) which was used without further purification. $^1$H NMR (400 MHz, dimethyl sulfoxide-$d_6$) δ 6.50 (s, 1H), 6.28 (s, 1H), 4.16 (s, 2H), 3.32-3.15 (m, 254H), 3.08 (s, 4H), 2.82 (s, 5H), 2.69-2.65 (m, 1H), 2.61 (s, 4H), 1.78 (t, J=5.3 Hz, 4H), 1.33 (s, 6H).

Step E. N-(6-(2-(2,2-Difluoroethyl)-2,7-diazaspiro[3.5]nonan-7-yl)-2,2-dimethyl-2,3-dihydrobenzofuran-5-yl)pyrazolo[1,5-a]pyrimidine-3-carboxamide

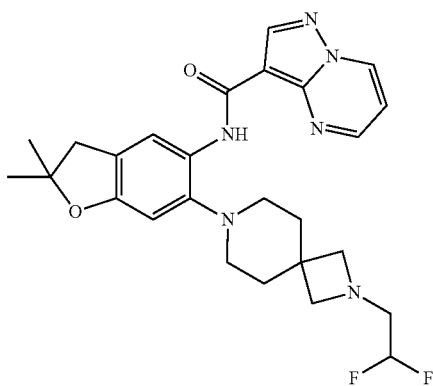 [SMILES: CC1(C)Cc2cc(NC(=O)c3cnn4cccnc34)c(N3CCC4(CC3)CN(CC(F)F)C4)cc2O1]

To a solution of pyrazolo[1,5-a]pyrimidine-3-carboxylic acid (20.3 mg, 0.124 mmol) in dimethylformamide (2 ml) at 0° C. under a nitrogen atmosphere was added (7-azabenzotriazol-1-yloxy)tripyrrolidinophosphonium hexafluorophosphate (62 mg, 0.119 mmol) followed by 2,4,6-trimethylpyridine (0.119 mmol). 6-[2-(2,2-Difluoroethyl)-2,7-diazaspiro[3.5]nonan-7-yl]-2,2-dimethyl-3-benzofuran-5-amine (38 mg, 0.11 mmol) was then introduced and the reaction mixture was warmed to room temperature. After 16h, the mixture was filtered through a plug of silica and concentrated in vacuo. The residue was purified by reverse phase HPLC to afford the title compound (23 mg, 0.047 mmol, 44% yield). $^1$H NMR (400 MHz, dimethyl sulfoxide-$d_6$) δ 10.46 (s, 1H), 9.35 (dd, J=7.0, 1.6 Hz, 1H), 8.74 (dd, J=4.2, 1.7 Hz, 1H), 8.67 (s, 1H), 8.32 (d, J=1.0 Hz, 1H), 7.32 (dd, J=7.0, 4.2 Hz, 1H), 6.65 (s, 1H), 5.95 (tt, J=55.9, 4.2 Hz, 1H), 3.15 (s, 4H), 2.99 (s, 2H), 2.84 (td, J=16.1, 4.3 Hz, 2H), 2.75-2.63 (m, 4H), 1.92 (m, 4H), 1.40 (s, 6H). MS (ESI): m/z=497.2 [M+1]$^+$.

Example 249. N-(2,2-dimethyl-6-(2-(2,2,2-trifluoroethyl)-2,7-diazaspiro[3.5]nonan-7-yl)-2,3-dihydrobenzofuran-5-yl)pyrazolo[1,5-a]pyrimidine-3-carboxamide

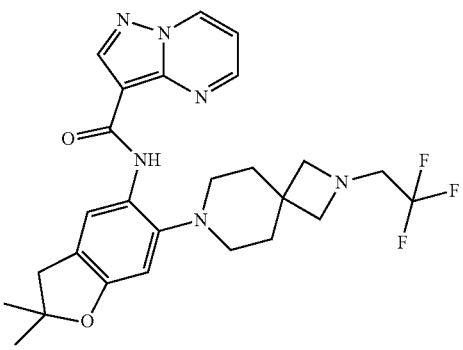 [SMILES: CC1(C)Cc2cc(NC(=O)c3cnn4cccnc34)c(N3CCC4(CC3)CN(CC(F)(F)F)C4)cc2O1]

The title compound was made in a manner analogous to Example 248, replacing 2,2-difluoroethyl trifluoromethanesulfonate with 2,2,2-trifluoroethyl trifluoromethanesulfonate (Step C), to give N-(2,2-dimethyl-6-(2-(2,2,2-trifluoroethyl)-2,7-diazaspiro[3.5]nonan-7-yl)-2,3-dihydrobenzofuran-5-yl)pyrazolo[1,5-a]pyrimidine-3-carboxamide (26 mg, 62% yield) as an orange crystalline solid. $^1$H NMR (400 MHz, dimethyl sulfoxide-$d_6$) δ 10.46 (s, 1H), 9.35 (dd, J=7.0, 1.6 Hz, 1H), 8.75 (dd, J=4.2, 1.7 Hz, 1H), 8.67 (s, 1H), 8.32 (d, J=0.9 Hz, 1H), 7.32 (dd, J=7.0, 4.2 Hz, 1H), 6.65 (s, 1H), 3.26-3.16 (m, 6H), 2.99 (s, 2H), 2.77-2.63 (m, 4H), 1.98-1.88 (m, 4H), 1.40 (s, 6H). MS (ESI): m/z=515.2 [M+1]$^+$.

Example 250. N-[2-(2-Hydroxy-1,1-dimethylethyl)-6-morpholino-1-oxo-isoindolin-5-yl]pyrazolo[1,5-a]pyrimidine-3-carboxamide

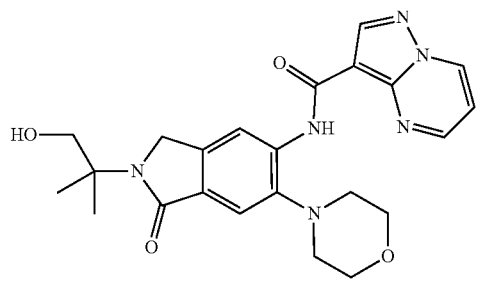 [SMILES: CC(C)(CO)N1Cc2cc(NC(=O)c3cnn4cccnc34)c(N3CCOCC3)cc2C1=O]

Step 1: Ethyl 5-fluoro-2-methyl-4-nitro-benzoate

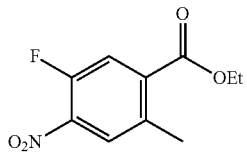 [SMILES: CCOC(=O)c1cc(F)c([N+](=O)[O-])cc1C]

To a solution of 1-bromo-5-fluoro-2-methyl-4-nitrobenzene (5.0 g, 21.36 mmol) and triethylamine (50 ml, 360.71 mmol) in ethanol (100 ml) was added bis(triphenylphosphine) palladium(II) dichloride (1.5 g, 2.14 mmol). The reaction was stirred at 70° C. for 16h under carbon monoxide (50 psi). The reaction was filtered through celite and the filtrate was concentrated to dryness. The residue was purified by flash column chromatography (eluent 10% ethyl acetate:petroleum ether) to give ethyl 5-fluoro-2-methyl-4-nitro-benzoate (2.0 g, 41% yield) as a yellow solid. $^1$H NMR (400 MHz, CDCl$_3$) δ 7.92 (d, J=7.2 Hz, 1H), 7.82 (d, J=11.6 Hz, 1H), 4.42 (q, J=7.2 Hz, 2H), 2.63 (s, 3H), 1.42 (t, J=7.2 Hz, 3H).

Step 2: Ethyl 2-(bromomethyl)-5-fluoro-4-nitro-benzoate

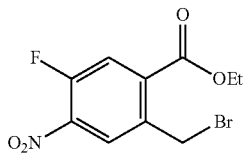 [SMILES: CCOC(=O)c1cc(F)c([N+](=O)[O-])cc1CBr]

To a solution of ethyl 5-fluoro-2-methyl-4-nitro-benzoate (200 mg, 0.88 mmol) in carbon tetrachloride (5 ml) was added benzoyl peroxide (43 mg, 0.18 mmol) and N-bromosuccinimide (313 mg, 1.76 mmol). The mixture was stirred at 100° C. for 16h under nitrogen. The reaction was concentrated to dryness and the crude reaction was purified by flash column chromatography (eluent 20% ethyl acetate:petroleum ether) to afford ethyl 2-(bromomethyl)-5-fluoro-4-nitro-benzoate (110 mg, 41% yield) as a yellow oil. $^1$HNMR (400 MHz, CDCl$_3$) δ 8.18 (d, J=6.4 Hz, 1H), 7.90 (d, J=10.8 Hz, 1H), 4.92 (s, 2H), 4.50 (q, J=7.2 Hz, 2H), 1.49 (t, J=7.2 Hz, 3H).

Step 3: 6-Fluoro-2-(2-hydroxy-1,1-dimethyl-ethyl)-5-nitro-isoindolin-1-one

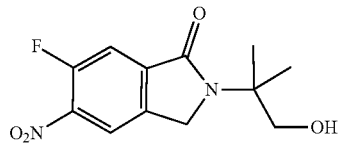 [SMILES: CC(C)(CO)N1Cc2cc([N+](=O)[O-])c(F)cc2C1=O]

To a solution of ethyl 2-(bromomethyl)-5-fluoro-4-nitro-benzoate (110 mg, 0.36 mmol) in methanol (3 ml) was added 2-amino-2-methyl-1-propanol (64 mg, 0.72 mmol) and triethylamine (73 mg, 0.72 mmol). The mixture was stirred at 70° C. for 6h. The mixture was concentrated and purified by preparatory TLC (50% ethyl acetate in petroleum ether) to afford 6-fluoro-2-(2-hydroxy-1,1-dimethyl-ethyl)-5-nitro-isoindolin-1-one (60 mg, 62% yield) as a yellow solid. $^1$HNMR (400 MHz, CDCl$_3$) δ 8.12 (d, J=6.4 Hz, 1H), 7.70 (d, J=9.2 Hz, 1H), 4.58 (s, 2H), 4.17 (t, J=6.8 Hz, 1H), 3.94 (d, J=6.8 Hz, 2H), 1.49 (s, 6H).

Step 4: 2-(2-Hydroxy-1,1-dimethyl-ethyl)-6-morpholino-5-nitro-isoindolin-1-one

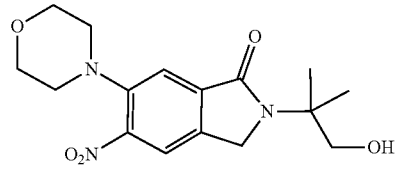 [SMILES: CC(C)(CO)N1Cc2cc([N+](=O)[O-])c(N3CCOCC3)cc2C1=O]

To a solution of 6-fluoro-2-(2-hydroxy-1,1-dimethylethyl)-5-nitro-isoindolin-1-one (240 mg, 0.89 mmol) in dimethyl sulfoxide (4 ml) was added morpholine (156 mg, 1.79 mmol) and N,N-diisopropylethylamine (231 mg, 1.79 mmol). The mixture was stirred at 90° C. for 3h. The mixture was concentrated and purified by preparatory TLC (50% ethyl acetate in petroleum ether) to afford 2-(2-hydroxy-1,1-dimethyl-ethyl)-6-morpholino-5-nitro-isoindolin-1-one (245 mg, 82% yield) as a yellow solid. $^1$H NMR (400 MHz, CDCl$_3$) δ 7.77 (s, 1H), 7.60 (s, 1H), 4.59 (t, J=6.8 Hz, 1H), 4.51 (s, 2H), 3.91 (d, J=6.8 Hz, 2H), 3.87 (t, J=4.4 Hz, 4H), 3.10 (t, J=4.4 Hz, 4H), 1.47 (s, 6H). LCMS (ESI): m/z=336.1 [M+H]$^+$.

Step 5: 5-Amino-2-(2-hydroxy-1,1-dimethyl-ethyl)-6-morpholino-isoindolin-1-one

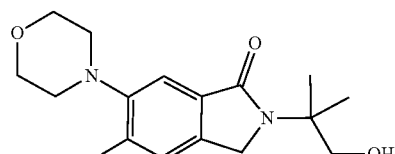

To a solution of 2-(2-hydroxy-1,1-dimethyl-ethyl)-6-morpholino-5-nitro-isoindolin-1-one (245 mg, 0.73 mmol) in ethanol (5 ml) and water (1 ml) was added iron (204 mg, 3.65 mmol) and ammonium chloride (195 mg, 3.65 mmol). The reaction was stirred at 80° C. for 2h. The reaction was filtered and the filtrate was concentrated. The crude material was diluted with water (10 ml) and extracted with ethyl acetate (20 ml×3). The combined organic phases were washed with brine (20 ml), dried over sodium sulfate and concentrated to give 5-amino-2-(2-hydroxy-1,1-dimethylethyl)-6-morpholino-isoindolin-1-one (210 mg, 94% yield) as a pale yellow solid. LCMS (ESI): m/z=305.9 [M+H]$^+$.

Step 6: N-[2-(2-Hydroxy-1,1-dimethyl-ethyl)-6-morpholino-1-oxo-isoindolin-5-yl]pyrazolo [1,5-a]pyrimidine-3-carboxamide

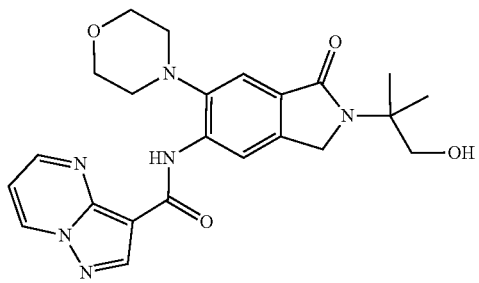

To a solution of 5-amino-2-(2-hydroxy-1,1-dimethyl-ethyl)-6-morpholino-isoindolin-1-one (210 mg, 0.69 mmol), N,N-diisopropylethylamine (267 mg, 2.06 mmol) and 4-dimethyl aminopyridine (17 mg, 0.14 mmol) in 1,2-dichloroethane (8 ml) was added pyrazolo[1,5-a] pyrimidine-3-carbonyl chloride (200 mg, 1.10 mmol). The reaction mixture was stirred at 35° C. for 16h. The reaction was concentrated and purified by reverse phase HPLC (20-50% acetonitrile in water with 0.05% ammonia hydroxide) to give N-[2-(2-hydroxy-1,1-dimethyl-ethyl)-6-morpholino-1-oxo-isoindolin-5-yl]pyrazolo[1,5-a]pyrimidine-3-carboxamide (60.8 mg, 19% yield) as pale yellow solid. $^1$H NMR (400 MHz, dimethyl sulfoxide-d$_6$) δ10.89 (s, 1H), 9.41 (d, J=5.6 Hz, 1H), 9.00 (d, J=2.8 Hz, 1H), 8.76 (s, 1H), 8.70 (s, 1H), 7.50 (s, 1H), 7.40 (dd, J=7.2, 4.0 Hz, 1H), 4.95 (t, J=5.6 Hz, 1H), 4.57 (s, 2H), 3.92-3.86 (m, 4H), 3.69 (d, J=6.0 Hz, 2H), 2.92-2.85 (m, 4H), 1.43 (s, 6H). LCMS (ESI): m/z=451.1 [M+H]$^+$.

TABLE 8

The following examples were made in a manner similar to that for Example 250.

| Ex. | Name | Structure | NMR, MS |
| --- | --- | --- | --- |
| 251 | N-[6-Morpholino-2-(oxetan-3-yl)-1-oxo-isoindolin-5-yl]pyrazolo[1,5-a]pyrimidine-3-carboxamide | 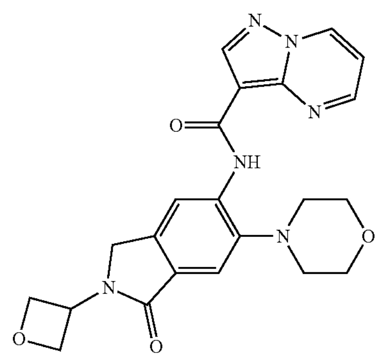 [SMILES: O=C(Nc1cc2c(cc1N1CCOCC1)C(=O)N(C1COC1)C2)c1cnn2cccnc12] | $^1$H NMR (400 MHz, dimethyl sulfoxide-d6) δ 10.92 (s, 1H), 9.41 (d, J = 6.4 Hz, 1H), 8.99 (s, 1H), 8.81-8.72 (m, 2H), 7.59 (s, 1H), 7.39 (m, 1H), 5.41 (t, J = 6.8 Hz, 1H), 4.92-4.84 (m, 2H), 4.83-4.73 (m, 4H), 3.95-3.85 (m, 4H), 2.96-2.86 (m, 4H). LCMS (ESI): m/z = 435.2 [M + H]$^+$. |
| 252 | N-[6-Morpholino-2-[2-(oxetan-3-yl)ethyl]-1-oxo-isoindolin-5-yl]pyrazolo[1,5-a]pyrimidine-3-carboxamide | 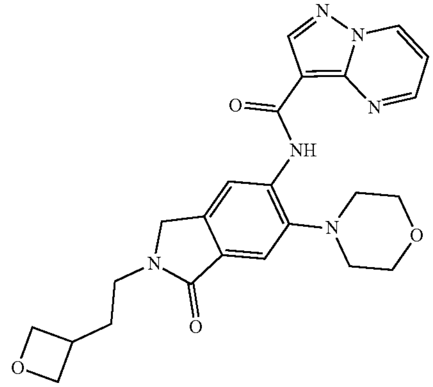 [SMILES: O=C(Nc1cc2c(cc1N1CCOCC1)C(=O)N(CCC1COC1)C2)c1cnn2cccnc12] | $^1$H NMR (400 MHz, CDCl$_3$) δ 10.93 (s, 1H), 8.81-8.82 (m, 4H), 7.72 (s, 1H), 7.17-7.09 (m, 1H), 4.82 (t, J = 6.8 Hz, 2H), 4.43 (t, J = 6.4 Hz, 2H), 4.37 (s, 2H), 4.08-4.96 (m, 4H), 3.58 (t, J = 7.2 Hz, 2H), 3.18-2.91 (m, 5H), 2.13-2.03 (m, 2H). LCMS (ESI): m/z = 463.1 [M + H]$^+$. |

TABLE 8-continued

The following examples were made in a manner similar to that for Example 250.

| Ex. | Name | Structure | NMR, MS |
|---|---|---|---|
| 253 | N-(2-(Cyanomethyl)-6-morpholino-1-oxoisoindolin-5-yl)pyrazolo[1,5-a]pyrimidine-3-carboxamide | 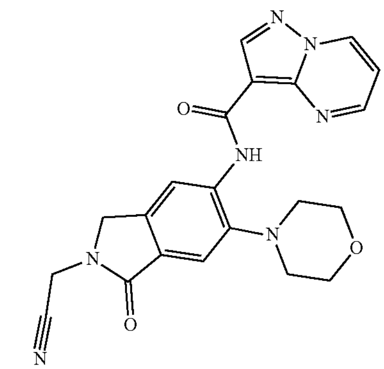 [SMILES: N#CCN1Cc2cc(NC(=O)c3cnn4cccnc34)c(N3CCOCC3)cc2C1=O] | $^1$H NMR (400 MHz, dimethyl sulfoxide-d$_6$):δ 10.92 (s, 1H), 9.42-9.40 (m, 1H), 9.00-8.99 (m, 1H), 8.80 (s, 1H), 8.76 (s, 1H), 7.64 (s, 1H), 7.40-7.38 (m, 1H), 4.71 (s, 2H), 4.57 (s, 2H), 3.90 (t, J = 4.4 Hz, 4H), 2.92 (t, J = 4.4 Hz, 4H). LCMS (ESI): m/z = 417.9 [M + H]$^+$. |
| 254 | N-(6-Morpholino-1-oxo-2-tetrahydrofuran-3-yl-isoindolin-5-yl)pyrazolo[1,5-a]pyrimidine-3-carboxamide | 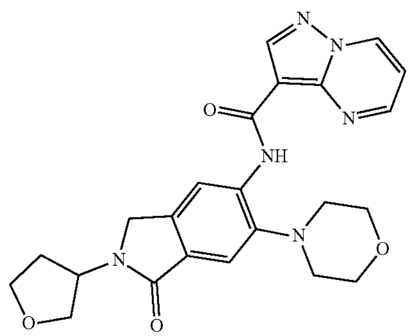 [SMILES: O=C(Nc1cc2c(cc1N1CCOCC1)C(=O)N(C1CCOC1)C2)c1cnn2cccnc12] | $^1$H NMR (400 MHz, CDCl$_3$) δ 10.92 (s, 1H), 8.87-8.81 (m, 4H), 7.72 (s, 1H), 7.11 (dd, J = 6.8, 4.0 Hz, 1H), 5.15 (d, J = 4.0 Hz, 1H), 4.49-4.37 (m, 2H), 4.16-4.12 (m, 1H), 4.00 (s, 4H), 3.89-3.83 (m, 3H), 2.99 (s, 4H), 2.43-2.34 (m, 1H), 2.04-2.02 (m, 1H). LCMS (ESI): m/z = 448.9 [M + H]$^+$. |
| 255 | N-(6-Morpholino-1-oxo-2-tetrahydropyran-4-yl-isoindolin-5-yl)pyrazolo[1,5-a]pyrimidine-3-carboxamide | 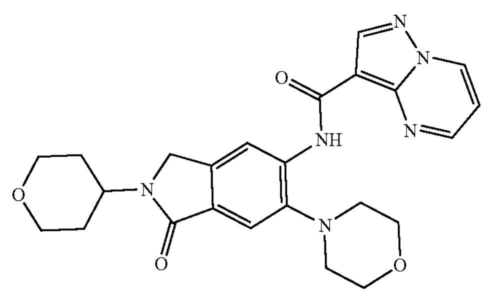 [SMILES: O=C(Nc1cc2c(cc1N1CCOCC1)C(=O)N(C1CCOCC1)C2)c1cnn2cccnc12] | $^1$H NMR (400 MHz, CDCl$_3$) δ 10.93 (s, 1H), 8.88-8.83 (m, 4H), 7.74 (s, 1H), 7.13 (dd, J = 6.4, 4.0 Hz, 1H), 4.55-4.46 (m, 1H), 4.38 (s, 2H), 4.15-4.05 (m, 2H), 4.06-3.96 (m, 4H), 3.59 (t, J = 11.2 Hz, 2H), 3.05-2.95 (m, 4H), 1.94-1.77 (m, 4H). LCMS (ESI): m/z = 463.0 [M + H]$^+$. |
| 256 | N-(6-Methyl-2-morpholino-7-oxo-6,7-dihydro-5H-pyrrolo[3,4-b]pyridin-3-yl)pyrazolo[1,5-a]pyrimidine-3-carboxamide | 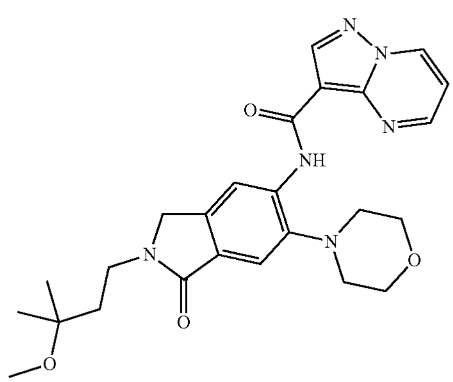 [SMILES: COC(C)(C)CCN1Cc2cc(NC(=O)c3cnn4cccnc34)c(N3CCOCC3)cc2C1=O] | $^1$H NMR (400 MHz, CDCl$_3$) δ 10.92 (s, 1H), 8.88-8.82 (m, 4H), 7.72 (s, 1H), 7.12 (dd, J = 6.8, 4.0 Hz, 1H), 4.40 (s, 2H), 4.02 (t, J = 4.4 Hz, 4H), 3.71-3.67 (m, 2H), 3.25 (s, 3H), 3.01 (t, J = 4.4 Hz, 4H), 1.87-1.83 (m, 4H), 1.25 (s, 6H). LCMS (ESI): m/z = 479.2 [M + H]$^+$. |

TABLE 8-continued

The following examples were made in a manner similar to that for Example 250.

| Ex. | Name | Structure | NMR, MS |
|---|---|---|---|
| 257 | N-[6-Morpholino-1-oxo-2-(tetrahydropyran-2-ylmethyl)isoindolin-5-yl]pyrazolo[1,5-a]pyrimidine-3-carboxamide | 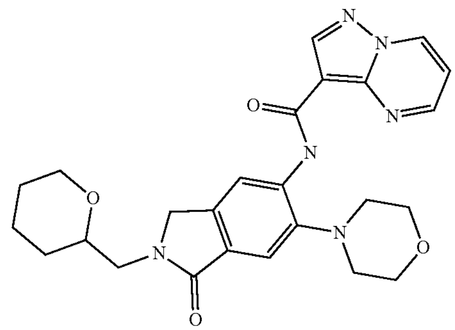 [SMILES: O=C(Nc1cc2c(cc1N1CCOCC1)C(=O)N(CC1CCCCO1)C2)c1cnn2cccnc12] | $^1$H NMR (400 MHz, CDCl$_3$) δ 10.92 (s, 1H), 8.88-8.82 (m, 4H), 7.74 (s, 1H), 7.14 (dd, J = 6.8, 4.0 Hz, 1H), 4.66-4.47 (m, 2H), 4.01-3.97 (m, 5H), 3.81-3.39 (m, 4H), 3.00-2.99 (m, 4H), 1.86-1.67 (m, 2H), 1.55-1.49 (m, 3H), 1.37-1.31 (m, 1H). LCMS (ESI): m/z = 477.3 [M + H]$^+$. |
| 258 | N-[6-[4-(2,2-Difluoroethyl)piperazin-1-yl]-2-[(2R)-2-fluoro-3-hydroxy-3-methyl-butyl]-1-oxo-isoindolin-5-yl]pyrazolo[1,5-a]pyrimidine-3-carboxamide | 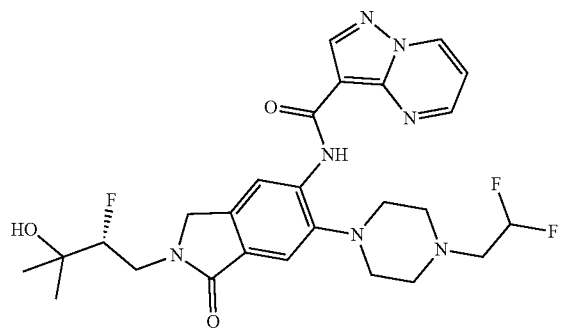 [SMILES: CC(C)(O)[C@H](F)CN1Cc2cc(NC(=O)c3cnn4cccnc34)c(N3CCN(CC(F)F)CC3)cc2C1=O] | $^1$H NMR (400 MHz, CDCl$_3$) δ 10.82 (s, 1H), 8.90-8.75 (m, 4H), 7.73 (s, 1H), 7.14 (s, 1H), 6.14-5.83 (m, 1H), 4.65-4.42 (m, 3H), 4.28-4.10 (m, 1H), 3.75-3.60 (m, 1H), 3.12-2.84 (m, 9H), 2.48-2.40 (m, 1H), 1.34 (s, 6H). LCMS (ESI): m/z = 546.2 [M + H]+. |
| 259 and 260 | N-[2-[(2R)-2-Fluoro-3-hydroxy-3-methyl-butyl]-1-oxo-6-[4-[(1S)-2,2,2-trifluoro-1-hydroxy-ethyl]-1-piperidyl]isoindolin-5-yl]pyrazolo[1,5-a]pyrimidine-3-carboxamide and N-[2-[(2R)-2-fluoro-3-hydroxy-3-methyl-butyl]-1-oxo-6-[4-[(1R)-2,2,2-trifluoro-1-hydroxy-ethyl]-1-piperidyl]isoindolin-5-yl]pyrazolo[1,5-c]pyrimidine-3-carboxamide (absolute stereochemistry assigned arbitrarily) | | Example 259, Peak 1: $^1$H NMR (400 MHz, dimethyl sulfoxide-d$_6$) δ 10.95 (s, 1H), 9.39 (d, J = 6.8 Hz, 1H), 9.06 (d, J = 3.6 Hz, 1H), 8.79 (s, 1H), 8.74 (s, 1H), 7.58 (s, 1H), 7.37 (dd, J = 6.8, 4.0 Hz, 1H), 6.43 (s, 1H), 4.89 (s, 1H), 4.59-4.35 (m, 3H), 4.05-3.85 (m, 2H), 3.73-3.65 (m, 1H), 3.08-2.96 (m, 2H), 2.88-2.73 (m, 2H), 2.03-1.69 (m, 5H), 1.25-1.10 (m, 6H). LCMS (ESI): m/z = 579.1 [M + H]$^+$. Example 260, Peak 2: $^1$H NMR (400 MHz, dimethyl sulfoxide-d$_6$) δ 10.95 (s, 1H), 9.39 (d, J = 6.8 Hz, 1H), 9.06 (d, J = 3.6 Hz, 1H), 8.79 (s, 1H), 8.74 (s, 1H), 7.59 (s, 1H), 7.37 (dd, J = 6.8, 4.4 Hz, 1H), 6.43 (s, 1H), 4.89 (s, 1H), 4.61-4.31 (m, 3H), 4.05-3.83 (m, 2H), 3.73-3.65 (m, 1H), 3.08-2.96 (m, 2H), 2.88-2.73 (m, 2H), 2.03-1.69 (m, 5H), 1.25-1.10 (m, 6H). LCMS (ESI): m/z = 579.1 [M + H]$^+$. |

TABLE 8-continued

The following examples were made in a manner similar to that for Example 250.

| Ex. | Name | Structure | NMR, MS |
|---|---|---|---|
| 261 | N-[6-(3,3-Difluoropyrrolidin-1-yl)-2-[(2R)-2-fluoro-3-hydroxy-3-methyl-butyl]-1-oxo-isoindolin-5-yl]pyrazolo[1,5-a]pyrimidine-3-carboxamide | 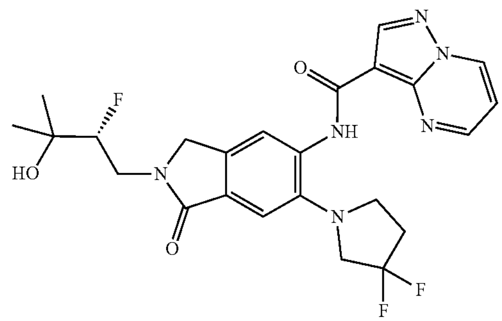 [SMILES: CC(C)(O)[C@H](F)CN1Cc2cc(NC(=O)c3cnn4cccnc34)c(N3CCC(F)(F)C3)cc2C1=O] | $^1$H NMR (400 MHz, dimethyl sulfoxide-d6) δ 10.77 (s, 1H), 9.40 (dd, J = 7.0, 1.6 Hz, 1H), 8.84 (dd, J = 4.3, 1.6 Hz, 1H), 8.75 (s, 1H), 8.74 (s, 1H), 7.65 (s, 1H), 7.38 (dd, J = 7.0, 4.2 Hz, 1H), 4.90 (s, 1H), 4.61-4.34 (m, 3H), 3.94 (ddd, J = 38.5, 15.0, 1.9 Hz, 1H), 3.78-3.66 (m, 1H), 3.61 (t, J = 12.9 Hz, 2H), 2.59 (dq, J = 15.3, 8.0, 7.4 Hz, 2H), 1.18 (dd, J = 4.4, 1.6 Hz, 6H). LCMS (ESI): m/z = 503.2 [M + H]+. |
| 262 | N-[2-[(3-Hydroxycyclobutyl)methyl]-6-morpholino-1-oxo-isoindolin-5-yl]pyrazolo[1,5-a]pyrimidine-3-carboxamide | 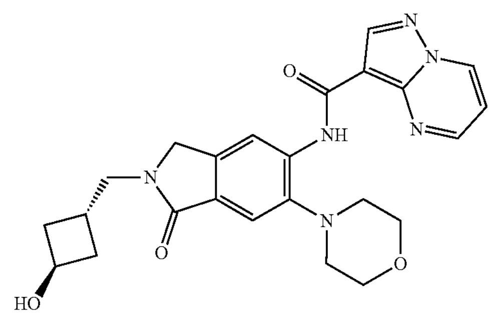 [SMILES: O=C(Nc1cc2c(cc1N1CCOCC1)C(=O)N(C[C@H]1C[C@H](O)C1)C2)c1cnn2cccnc12] | $^1$H NMR (400 MHz, dimethyl sulfoxide-d6) δ 10.89 (s, 1H), 9.41 (dd, J = 7.0, 1.6 Hz, 1H), 9.00 (dd, J = 4.3, 1.6 Hz, 1H), 8.75 (d, J = 4.6 Hz, 2H), 7.57 (s, 1H), 7.39 (dd, J = 7.0, 4.2 Hz, 1H), 4.99 (d, J = 6.1 Hz, 1H), 4.44 (s, 2H), 4.33-4.21 (m, 1H), 3.95-3.85 (m, 4H), 3.55 (d, J = 8.0 Hz, 2H), 2.95-2.87 (m, 4H), 2.08-1.87 (m, 4H). LCMS (ESI): m/z = 463.2 [M + H]+. |
| 263 | N-[6-[4-(Hydroxymethyl)-1-piperidyl]-1-oxo-2-(2,2,2-trifluoroethyl)isoindolin-5-yl]pyrazolo[1,5-a]pyrazine-3-carboxamide | 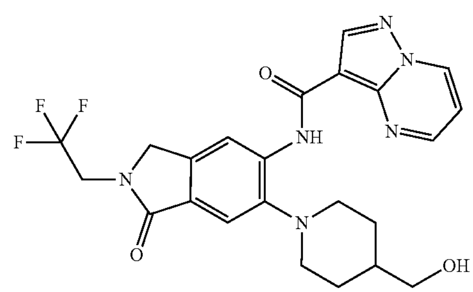 [SMILES: O=C(Nc1cc2c(cc1N1CCC(CO)CC1)C(=O)N(CC(F)(F)F)C2)c1cnn2cccnc12] | $^1$H NMR (400 MHz, dimethyl sulfoxide-d6) δ 10.98 (s, 1H), 9.40 (dd, J = 7.0, 1.6 Hz, 1H), 8.96 (dd, J = 4.2, 1.6 Hz, 1H), 8.81 (s, 1H), 8.76 (s, 1H), 7.64 (s, 1H), 7.38 (dd, J = 7.0, 4.2 Hz, 1H), 4.60 (s, 3H), 4.36 (q, J = 9.7 Hz, 2H), 3.44 (t, J = 5.3 Hz, 2H), 3.01 (d, J = 11.3 Hz, 2H), 2.77 (dd, J = 12.1, 9.9 Hz, 2H), 1.83-1.73 (m, 2H), 1.66 (m, 3H). LCMS (ESI): m/z = 489.1 [M + H]+. |
| 264 | N-[2-[(2R)-2-Fluoro-3-hydroxy-3-methyl-butyl]-6-morpholino-1-oxo-isoindolin-5-yl]-6-methyl-pyrazolo[1,5-a]pyrimidine-3-carboxamide | 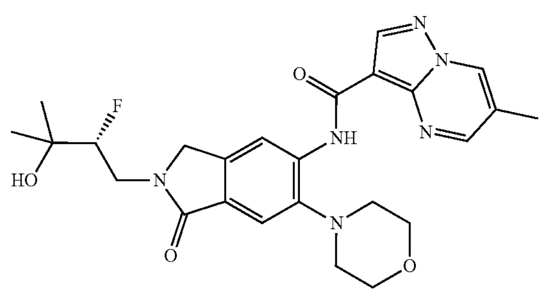 [SMILES: Cc1cnc2c(C(=O)Nc3cc4c(cc3N3CCOCC3)C(=O)N(C[C@@H](F)C(C)(C)O)C4)cnn2c1] | $^1$H NMR (400 MHz, dimethyl sulfoxide-d6) δ 10.84 (s, 1H), 9.27 (dd, J = 2.1, 1.1 Hz, 1H), 8.92 (d, J = 2.0 Hz, 1H), 8.76 (s, 1H), 8.67 (s, 1H), 7.58 (s, 1H), 4.90 (s, 1H), 4.63-4.35 (m, 3H), 3.91 (dd, J = 5.8, 3.2 Hz, 5H), 3.70 (td, J = 15.6, 9.4 Hz, 1H), 2.97-2.85 (m, 4H), 2.46 (d, J = 1.1 Hz, 3H), 1.22-1.13. LCMS (ESI): m/z = 497.2 [M + H]+. (m, 6H). |
| 265 | N-[6-[4-(2-Amino-2-oxo-ethyl)piperazin-1-yl]-1-oxo-2-(2,2,2-trifluoroethyl)isoindolin-5-yl]pyrazolo[1,5-a]pyrimidine-3-carboxamide | 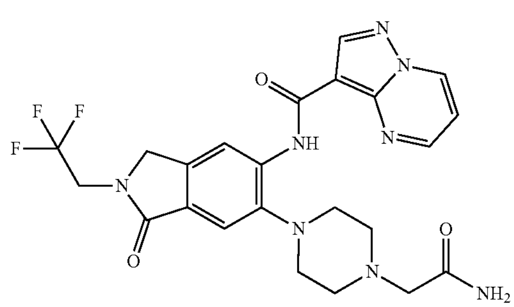 [SMILES: NC(=O)CN1CCN(c2cc3c(cc2NC(=O)c2cnn4cccnc24)CN(CC(F)(F)F)C3=O)CC1] | $^1$H NMR (400 MHz, dimethyl sulfoxide-d6) δ 10.92 (s, 1H), 9.44-9.33 (m, 1H), 9.04 (dd, J = 4.3, 1.6 Hz, 1H), 8.82 (s, 1H), 8.76 (s, 1H), 7.64 (s, 1H), 7.40 (dd, J = 7.0, 4.2 Hz, 1H), 7.24 (d, J = 43.2 Hz, 2H), 4.61 (s, 2H), 4.37 (q, J = 9.6 Hz, 2H), 3.06 (s, 2H), 2.96 (t, J = 4.7 Hz, 4H), 2.80 (t, J = 4.4 Hz, 4H). LCMS (ESI): m/z = 517.1 [M + H]+. |

TABLE 8-continued

The following examples were made in a manner similar to that for Example 250.

| Ex. | Name | Structure | NMR, MS |
|---|---|---|---|
| 266 | N-[6-[4-(2,2-Difluoroethyl)piperazin-1-yl]-1-oxo-2-(2,2,2-trifluoroethyl)isoindolin-5-yl]pyrazolo[1,5-a]pyrimidine-3-carboxamide | 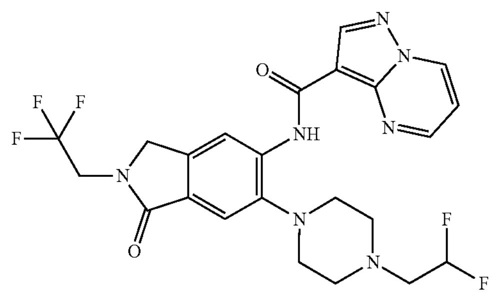 [SMILES: O=C(Nc1cc2c(cc1N1CCN(CC(F)F)CC1)C(=O)N(CC(F)(F)F)C2)c1cnn2cccnc12] | ¹H NMR (400 MHz, dimethyl sulfoxide-d6) δ 10.86 (s, 1H), 9.41 (dd, J = 7.0, 1.6 Hz, 1H), 9.01 (dd, J = 4.2, 1.6 Hz, 1H), 8.80 (s, 1H), 8.76 (s, 1H), 7.62 (s, 1H), 7.40 (dd, J = 7.0, 4.2 Hz, 1H), 6.22 (t, J = 4.4 Hz, 1H), 4.60 (s, 2H), 4.37 (q, J = 9.6 Hz, 2H), 2.99-2.81 (m, 10H). LCMS (ESI): m/z = 524.1 [M + H]+. |
| 267 | N-[2-(3-hydroxy-2,2-Dimethyl-propyl)-6-morpholino-1-oxo-isoindolin-5-yl]pyrazolo[1,5-a]pyrimidine-3-carboxamide | 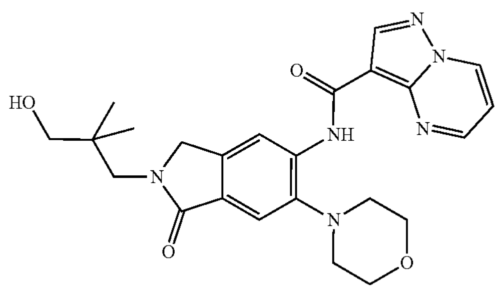 [SMILES: CC(C)(CO)CN1Cc2cc(NC(=O)c3cnn4cccnc34)c(N3CCOCC3)cc2C1=O] | ¹H NMR (400 MHz, dimethyl sulfoxide-d6) δ 10.90 (s, 1H), 9.41 (ddd, J = 7.0, 1.7, 0.8 Hz, 1H), 9.00 (dt, J = 4.2, 1.1 Hz, 1H), 8.79-8.71 (m, 2H), 7.59 (s, 1H), 7.39 (dd, J = 7.0, 4.2 Hz, 1H), 4.75 (t, J = 5.8 Hz, 1H), 4.57 (s, 2H), 3.90 (t, J = 4.4 Hz, 4H), 3.36 (tdd, J = 2.5, 1.6, 0.9 Hz, 2H), 3.16 (d, J = 5.8 Hz, 2H), 2.96-2.87 (m, 4H). LCMS (ESI): m/z = 465.2 [M + H]+. |
| 268 | N-[2-[[3-(Hydroxymethyl)oxetan-3-yl]methyl]-6-morpholino-1-oxo-isoindolin-5-yl]pyrazolo[1,5-a]pyrimidine-3-carboxamide | 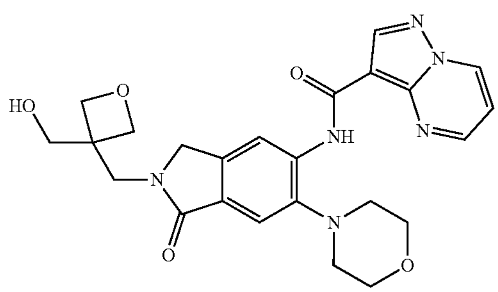 [SMILES: O=C(Nc1cc2c(cc1N1CCOCC1)C(=O)N(CC1(CO)COC1)C2)c1cnn2cccnc12] | ¹H NMR (400 MHz, dimethyl sulfoxide-d6) δ 10.91 (s, 1H), 9.41 (dd, J = 7.0, 1.6 Hz, 1H), 9.00 (dd, J = 4.3, 1.6 Hz, 1H), 8.75 (d, J = 5.8 Hz, 2H), 7.59 (s, 1H), 7.39 (dd, J = 7.0, 4.2 Hz, 1H), 4.94 (t, J = 5.3 Hz, 1H), 4.52 (s, 2H), 4.49 (d, J = 6.0 Hz, 2H), 4.35 (d, J = 6.0 Hz, 2H), 3.90 (t, J = 4.5 Hz, 4H), 3.80 (s, 2H), 3.57 (d, J = 5.3 Hz, 2H), 2.95-2.88 (m, 4H). LCMS (ESI): m/z = 479.2 [M + H]+. |
| 269 | 6-Bromo-N-[2-[(2R)-2-fluoro-3-hydroxy-3-methyl-butyl]-6-morpholino-1-oxo-isoindolin-5-yl]pyrazolo[1,5-a]pyrimidine-3-carboxamide | 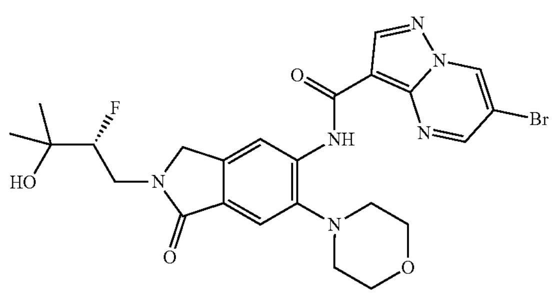 [SMILES: CC(C)(O)[C@H](F)CN1Cc2cc(NC(=O)c3cnn4cc(Br)cnc34)c(N3CCOCC3)cc2C1=O] | ¹H NMR (400 MHz, dimethyl sulfoxide-d6) δ 10.69 (s, 1H), 9.91 (d, J = 2.0 Hz, 1H), 9.06 (d, J = 2.1 Hz, 1H), 8.75 (s, 1H), 8.73 (s, 1H), 7.59 (s, 1H), 4.90 (s, 1H), 4.62-4.51 (m, 2H), 4.51-4.34 (m, 1H), 3.88 (m, 5H), 3.70 (m, 1H), 2.91 (m, 4H), 1.18 (dd, J = 4.6, 1.6 Hz, 6H). LCMS (ESI): m/z = 561.1 [M + H]+. |
| 270 | N-[2-(2,2-Difluoro-3-hydroxy-3-methyl-butyl)-6-morpholino-1-oxo-isoindolin-5-yl]pyrazolo[1,5-a]pyrimidine-3-carboxamide | 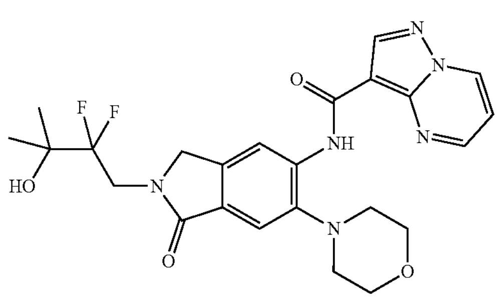 [SMILES: CC(C)(O)C(F)(F)CN1Cc2cc(NC(=O)c3cnn4cccnc34)c(N3CCOCC3)cc2C1=O] | ¹H NMR (400 MHz, dimethyl sulfoxide-d6) δ 10.91 (s, 1H), 9.41 (dt, J = 7.0, 1.2 Hz, 1H), 9.00 (dd, J = 4.3, 1.6 Hz, 1H), 8.77 (d, J = 6.8 Hz, 2H), 7.62 (s, 1H), 7.39 (dd, J = 7.0, 4.2 Hz, 1H), 5.43 (s, 1H), 4.59 (s, 2H), 4.12 (t, J = 17.0 Hz, 2H), 3.95-3.85 (m, 4H), 2.93 (m, 4H), 1.25 (s, 6H). LCMS (ESI): m/z = 501.2 [M + H]+. |

TABLE 8-continued

The following examples were made in a manner similar to that for Example 250.

| Ex. | Name | Structure | NMR, MS |
|---|---|---|---|
| 271 | 6-Chloro-N-[2-[(2R)-2-fluoro-3-hydroxy-3-methyl-butyl]-6-morpholino-1-oxo-isoindolin-5-yl]pyrazolo[1,5-a]pyrimidine-3-carboxamide | 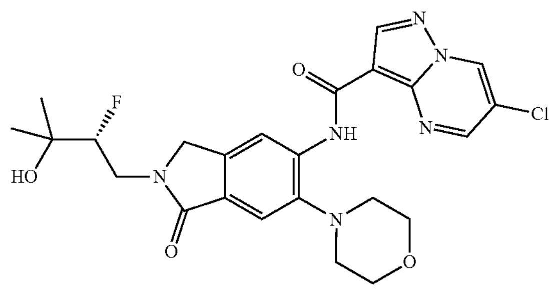 [SMILES: CC(C)(O)[C@H](F)CN1Cc2cc(NC(=O)c3cnn4cc(Cl)cnc34)c(N3CCOCC3)cc2C1=O] | $^1$H NMR (400 MHz, dimethyl sulfoxide-d6) δ 10.70 (s, 1H), 9.86 (d, J = 2.3 Hz, 1H), 9.05 (d, J = 2.2 Hz, 1H), 8.78 (s, 1H), 8.73 (s, 1H), 7.59 (s, 1H), 4.90 (s, 1H), 4.58-4.35 (m, 3H), 3.93-3.84 (m, 5H), 3.70 (m, 1H), 2.95-2.88 (m, 4H), 1.18 (dd, J = 4.4, 1.6 Hz, 6H). LCMS (ESI): m/z = 517.1 [M + H]+. |
| 272 | N-[6-[4-(2-Amino-2-oxo-ethyl)piperazin-1-yl]-2-isopropyl-1-oxo-isoindolin-5-yl]pyrazolo[1,5-a]pyrimidine-3-carboxamide | 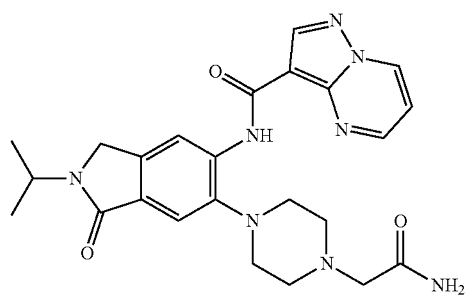 [SMILES: CC(C)N1Cc2cc(NC(=O)c3cnn4cccnc34)c(N3CCN(CC(N)=O)CC3)cc2C1=O] | $^1$H NMR (400 MHz, dimethyl sulfoxide-d6) δ 10.89 (s, 1H), 9.43-9.35 (m, 1H), 9.03 (dd, J = 4.3, 1.6 Hz, 1H), 8.78 (s, 1H), 8.75 (s, 1H), 7.56 (s, 1H), 7.39 (dd, J = 7.0, 4.2 Hz, 1H), 7.30 (s, 1H), 7.18 (s, 1H), 4.48-4.35 (m, 3H), 3.06 (s, 2H), 2.98-2.90 (m, 4H), 2.85-2.80 (m, 4H), 1.23 (d, J = 6.7 Hz, 6H). LCMS (ESI): m/z = 477.2 [M + H]+. |
| 273 | N-[2-(2,2-Difluoro-3-hydroxy-propyl)-6-morpholino-1-oxo-isoindolin-5-yl]pyrazolo[1,5-a]pyrimidine-3-carboxamide | 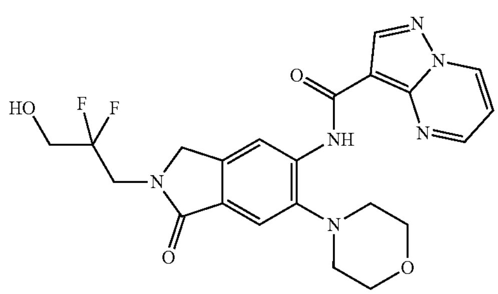 [SMILES: O=C(Nc1cc2c(cc1N1CCOCC1)C(=O)N(CC(F)(F)CO)C2)c1cnn2cccnc12] | $^1$H NMR (400 MHz, dimethyl sulfoxide-d6) δ 10.92 (s, 1H), 9.41 (dd, J = 7.0, 1.6 Hz, 1H), 9.00 (dd, J = 4.2, 1.6 Hz, 1H), 8.77 (d, J = 6.5 Hz, 2H), 7.63 (s, 1H), 7.39 (dd, J = 7.0, 4.2 Hz, 1H), 5.61 (t, J = 6.2 Hz, 1H), 4.59 (s, 2H), 4.02 (t, J = 15.5 Hz, 2H), 3.92-3.88 (m, 4H), 3.68 (td, J = 13.6, 6.3 Hz, 2H), 2.97-2.88 (m, 4H). LCMS (ESI): m/z = 473.1 [M + H]+. |
| 274 | (R)-N-(6-(4-cyanopiperidin-1-yl)-2-(2-fluoro-3-hydroxy-3-methylbutyl)-1-oxoisoindolin-5-yl)pyrazolo[1,5-a]pyrimidine-3-carboxamide | 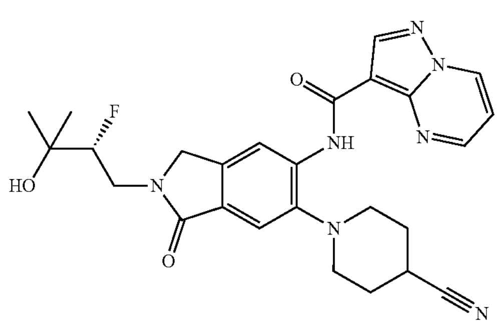 [SMILES: CC(C)(O)[C@H](F)CN1Cc2cc(NC(=O)c3cnn4cccnc34)c(N3CCC(C#N)CC3)cc2C1=O] | $^1$H NMR (400 MHz, dimethyl sulfoxide-d6) δ 10.86 (s, 1H), 9.43 (dd, J = 7.0, 1.6 Hz, 1H), 8.91 (dd, J = 4.2, 1.6 Hz, 1H), 8.77 (d, J = 1.7 Hz, 2H), 7.56 (s, 1H), 7.44 (dd, J = 7.0, 4.2 Hz, 1H), 4.90 (s, 1H), 4.63-4.46 (m, 2H), 4.50-4.39 (m, 2H), 3.99 (m, 1H), 3.70 (m, 1H), 3.16 (s, 1H), 3.04-2.94 (m, 2H), 2.90 (m, 2H), 2.17 (m, 2H), 2.07 (m, 2H), 1.22-1.13 (m, 6H). LCMS (ESI) m/z:506.2 [M + H]+. |

TABLE 8-continued

The following examples were made in a manner similar to that for Example 250.

| Ex. | Name | Structure | NMR, MS |
|---|---|---|---|
| 275 and 276 | N-(6-morpholino-1-oxo-2-(tetrahydrofuran-3-yl)isoindolin-5-yl)pyrazolo[1,5-a]pyrimidine-3-carboxamide (absolute stereochemistry assigned arbitrarily) | | Example 276, Peak 1: $^1$H NMR (400 MHz, dimethyl sulfoxide-d6) δ 10.90 (s, 1H), 9.41 (dd, J = 7.0, 1.6 Hz, 1H), 9.00 (dd, J = 4.2, 1.6 Hz, 1H), 8.76 (s, 2H), 7.58 (s, 1H), 7.39 (dd, J = 7.0, 4.2 Hz, 1H), 4.90 (m, 1H), 4.50 (s, 2H), 3.99 (m, 1H), 3.94-3.85 (m, 4H), 3.87-3.66 (m, 3H), 2.96-2.87 (m, 4H), 2.24 (m, 1H), 2.14-1.92 (m, 1H).MS (ESI): m/z = 449.2 [M + 1]$^+$.<br>Example 275, Peak 2: $^1$H NMR (400 MHz, dimethyl sulfoxide-d6) δ 10.90 (s, 1H), 9.41 (dd, J = 7.0, 1.6 Hz, 1H), 9.00 (dd, J = 4.2, 1.6 Hz, 1H), 8.76 (s, 2H), 7.58 (s, 1H), 7.39 (dd, J = 7.0, 4.2 Hz, 1H), 4.90 (m, 1H), 4.50 (s, 2H), 3.99 (m, 1H), 3.94-3.86 (m, 4H), 3.84-3.67 (m, 3H), 2.96-2.85 (m, 4H), 2.30-2.17 (m, 1H), 2.11-1.95 (m, 1H). MS (ESI): m/z = 449.2 [M + 1]$^+$. |
| 277 and 278 | N-(6-morpholino-1-oxo-2-((tetrahydro-2H-pyran-2-yl)methyl)isoindolin-5-yl)pyrazolo[1,5-a]pyrimidine-3-carboxamide (absolute stereochemistry assigned arbitrarily) | | Example 278, Peak 1: $^1$H NMR (400 MHz, dimethyl sulfoxide-d$_6$) δ 10.88 (s, 1H), 9.40 (dd, J = 7.0, 1.6 Hz, 1H), 8.99 (dd, J = 4.2, 1.6 Hz, 1H), 8.75 (s, 1H), 8.73 (s, 1H), 7.57 (s, 1H), 7.38 (dd, J = 7.0, 4.2 Hz, 1H), 4.52 (s, 2H), 3.97-3.80 (m, 5H), 3.61-3.45 (m, 3H), 3.35 (m, 1H), 2.97-2.84 (m, 4H), 1.84-1.71 (m, 1H), 1.57 (m, 1H), 1.45 (m, 3H), 1.20 (m, 1H). MS (ESI): m/z = 477.2 [M + 1]$^+$.<br>Example 277, Peak 2: $^1$H NMR (400 MHz, dimethyl sulfoxide-d$_6$) δ 10.89 (s, 1H), 9.40 (dd, J = 7.0, 1.6 Hz, 1H), 9.00 (dd, J = 4.2, 1.6 Hz, 1H), 8.75 (s, 1H), 8.73 (s, 1H), 7.57 (s, 1H), 7.39 (dd, J = 7.0, 4.2 Hz, 1H), 4.52 (s, 2H), 3.97-3.81 (m, 5H), 3.62-3.47 (m, 3H), 3.35 (m, 1H), 2.97-2.82 (m, 4H), 1.77 (m, 1H), 1.63-1.52 (m, 1H), 1.52-1.38 (m, 3H), 1.28-1.10 (m, 1H). MS (ESI): m/z = 477.2 [M + 1]$^+$. |
| 279 | N-[6-[4-(2,2-Difluoroethyl)piperazin-1-yl]-2-(3-hydroxy-3-methyl-butyl)-1-oxo-isoindolin-5-yl]pyrazolo[1,5-a]pyrimidine-3-carboxamide | 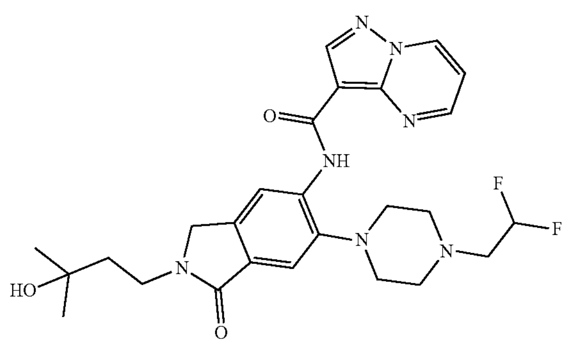 [SMILES: CC(C)(O)CCN1Cc2cc(NC(=O)c3cnn4cccnc34)c(N3CCN(CC(F)F)CC3)cc2C1=O] | $^1$H NMR (400 MHz, CDCl$_3$) δ 10.82 (s, 1H), 8.88-8.86 (m, 1H), 8.83-8.82 (m, 2H), 8.80-8.78 (m, 1H), 7.71 (s, 1H), 7.13 (dd, J = 6.8, 4.0 Hz, 1H), 6.12-5.83 (m, 1H), 4.41 (s, 2H), 3.78 (t, J = 7.2 Hz, 2H), 3.03-3.01 (m, 4H), 2.93-2.87 (m, 6H), 1.84 (t, J = 7.2 Hz, 2H), 1.30 (s, 6H). LCMS (ESI): m/z = 528.3 [M + H]$^+$. |

TABLE 8-continued

The following examples were made in a manner similar to that for Example 250.

| Ex. | Name | Structure | NMR, MS |
|---|---|---|---|
| 280 | N-[6-[4-(2-Amino-2-oxo-ethyl)piperazin-1-yl]-2-(3-hydroxy-3-methyl-butyl)-1-oxo-isoindolin-5-yl]pyrazolo[1,5-a]pyrimidine-3-carboxamide | 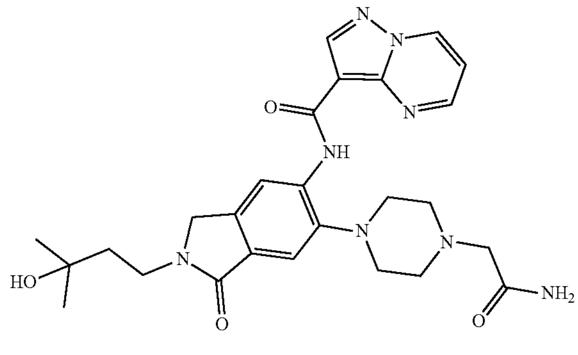 [SMILES: CC(C)(O)CCN1Cc2cc(NC(=O)c3cnn4cccnc34)c(N3CCN(CC(N)=O)CC3)cc2C1=O] | $^1$H NMR (400 MHz, DMSO-d6) δ 10.87 (s, 1H), 9.39 (dd, J = 7.2, 2.0 Hz, 1H), 9.03-9.01 (m, 1H), 8.75 (s, 1H), 8.74 (s, 1H), 7.54 (s, 1H), 7.39 (dd, J = 7.2, 4.4 Hz, 1H), 7.30 (s, 1H), 7.20 (s, 1H), 4.45 (s, 2H), 4.35 (s, 1H), 3.58 (t, J = 8.0 Hz, 2H), 3.05 (s, 2H), 2.99-2.89 (m, 4H), 2.84-2.74 (m, 4H), 1.68 (t, J = 8.0 Hz, 2H), 1.15 (s, 6H). LCMS (ESI): m/z = 521.3 [M + H]$^+$. |
| 281 | N-[6-[4-(2-Amino-2-oxo-ethyl)piperazin-1-yl]-2-(1-methyl-4-piperidyl)-1-oxo-isoindolin-5-yl]pyrazolo[1,5-a]pyrimidine-3-carboxamide | 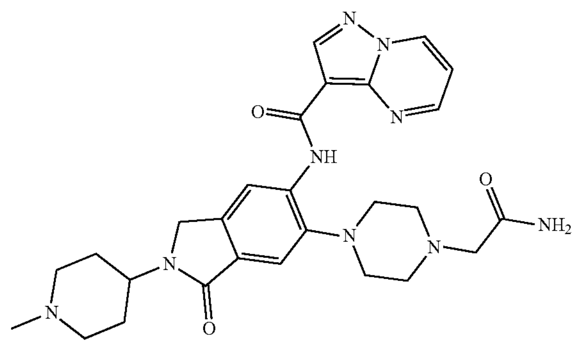 [SMILES: CN1CCC(N2Cc3cc(NC(=O)c4cnn5cccnc45)c(N4CCN(CC(N)=O)CC4)cc3C2=O)CC1] | $^1$H NMR (400 MHz, DMSO-d6) δ 10.89 (s, 1H), 9.40 (d, J = 7.2 Hz, 1H), 9.05-9.00 (m, 1H), 8.78 (s, 1H), 8.75 (s, 1H), 7.56 (s, 1H), 7.39 (dd, J = 7.2, 4.0 Hz, 1H), 7.31 (s, 1H), 7.21 (s, 1H), 4.44 (s, 2H), 3.99-3.90 (m, 1H), 3.06 (s, 2H), 2.96-2.92 (m, 2H), 2.90-2.82 (m, 2H), 2.81-2.75 (m, 2H), 2.69-2.65 (m, 2H), 2.34-2.31 (m, 2H), 2.19 (s, 3H), 2.02-1.95 (m, 2H), 1.85-1.75 (m, 2H), 1.70-1.65 (m, 2H). LCMS (ESI): m/z = 532.3 [M + H]$^+$. |
| 282 and 283 | N-[6-[4-[(1S)-2,2-Difluoro-1-hydroxy-ethyl]-1-piperidyl]-2-[(2R)-2-fluoro-3-hydroxy-3-methyl-butyl]-1-oxo-isoindolin-5-yl]pyrazolo[1,5-a]pyrimidine-3-carboxamide and N-[6-[4-[(1R)-2,2-difluoro-1-hydroxy-ethyl]-1-piperidyl]-2-[(2R)-2-fluoro-3-hydroxy-3-methyl-butyl]-1-oxo-isoindolin-5-yl]pyrazolo[1,5-a]pyrimidine-3-carboxamide (absolute stereochemistry assigned arbitrarily) | | Example 282, Peak 1: $^1$H NMR (400 MHz, DMSO-d$_6$) δ 10.97 (s, 1H), 9.40-9.35 (m, 1H), 9.10-9.05 (m, 1H), 8.78 (s, 1H), 8.74 (s, 1H), 7.58 (s, 1H), 7.36 (dd, J = 6.8, 4.4 Hz, 1H), 6.00 (td, J = 55.6, 4.4 Hz, 1H), 4.91 (br s, 1H), 4.65-4.29 (m, 3H), 4.04-3.55 (m, 3H), 3.07-2.95 (m, 2H), 2.86-2.70 (m, 2H), 2.04-1.86 (m, 2H), 1.84-1.63 (m, 3H), 1.18 (s, 3H), 1.17 (s, 3H). LCMS (ESI): m/z = 561.1 [M + H]$^+$. Example 283, Peak 2: $^1$H NMR (400 MHz, DMSO-d$_6$) δ 10.97 (s, 1H), 9.40-9.35 (m, 1H), 9.10-9.05 (m, 1H), 8.78 (s, 1H), 8.74 (s, 1H), 7.58 (s, 1H), 7.36 (dd, J = 6.8, 4.4 Hz, 1H), 6.00 (td, J = 55.6, 4.4 Hz, 1H), 4.93 (br s, 1H), 4.65-4.29 (m, 3H), 4.04-3.55 (m, 3H), 3.07-2.95 (m, 2H), 2.86-2.70 (m, 2H), 2.04-1.86 (m, 2H), 1.84-1.63 (m, 3H), 1.18 (s, 3H), 1.17 (s, 3H). LCMS (ESI): m/z = 561.1 [M + H]$^+$. |

TABLE 8-continued

The following examples were made in a manner similar to that for Example 250.

| Ex. | Name | Structure | NMR, MS |
|---|---|---|---|
| 284 | N-[6-[4-(2,2-Difluoroethyl)piperazin-1-yl]-2-[(2R)-2-fluoro-3-hydroxy-3-methyl-butyl]-1-oxo-isoindolin-5-yl]-6-methyl-pyrazolo[1,5-a]pyrimidine-3-carboxamide | 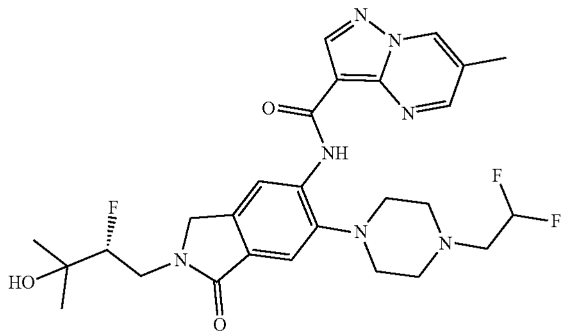 [SMILES: Cc1cnc2c(C(=O)Nc3cc4c(cc3N3CCN(CC(F)F)CC3)C(=O)N(C[C@@H](F)C(C)(C)O)C4)cnn2c1] | $^1$H NMR (400 MHz, DMSO-$d_6$) δ 10.75 (s, 1H), 9.27 (s, 1H), 8.88 (d, J = 2.4 Hz, 1H), 8.74 (s, 1H), 8.66 (s, 1H), 7.55 (s, 1H), 6.38-6.08 (m, 1H), 4.91 (s, 1H), 4.54-4.37 (m, 3H), 4.00-3.87 (m, 1H), 3.74-3.64 (m, 1H), 2.98-2.86 (m, 10H), 2.46 (s, 3H), 1.18 (s, 3H), 1.17 (s, 3H). LCMS (ESI): m/z = 560.1 [M + H]$^+$. |
| 285 | 6-Chloro-N-[6-[4-(2,2-difluoroethyl)piperazin-1-yl]-2-[(2R)-2-fluoro-3-hydroxy-3-methyl-butyl]-1-oxo-isoindolin-5-yl]pyrazolo[1,5-a]pyrimidine-3-carboxamide | 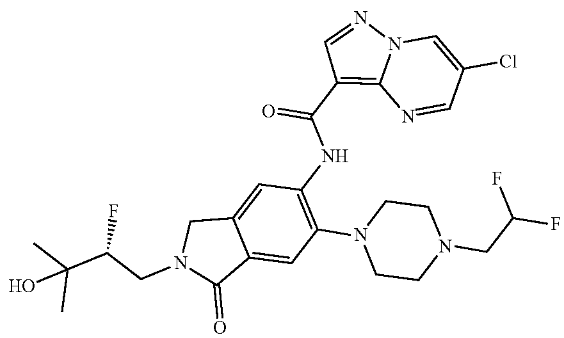 | $^1$H NMR (400 MHz, DMSO-$d_6$) δ 10.61 (s, 1H), 9.87 (d, J = 2.0 Hz, 1H), 9.01 (d, J = 2.4 Hz, 1H), 8.78 (s, 1H), 8.71 (s, 1H), 7.56 (s, 1H), 6.37-6.09 (m, 1H), 4.91 (s, 1H), 4.54-4.52 (m, 2H), 4.39-4.32 (m, 1H), 4.00-3.86 (m, 1H), 3.75-3.65 (m, 1H), 2.94-2.85 (m, 10H), 1.18 (s, 3H), 1.17 (s, 3H). LCMS (ESI): m/z = 580.1 [M + H]$^+$. |

Example 286. N3-[2-[(2R)-2-Fluoro-3-hydroxy-3-methyl-butyl]-6-morpholino-1-oxo-isoindolin-5-yl]pyrazolo[1,5-a]pyrimidine-3,6-dicarboxamide

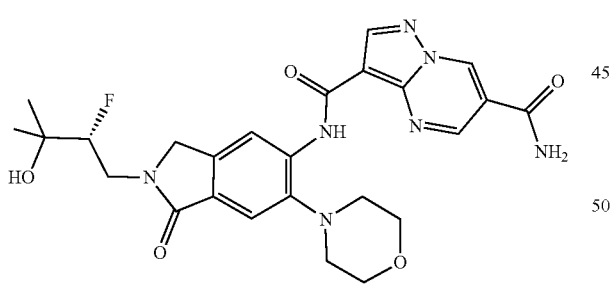

A solution of 6-bromo-N-[2-[(2R)-2-fluoro-3-hydroxy-3-methyl-butyl]-6-morpholino-1-oxo-isoindolin-5-yl]pyrazolo[1,5-a]pyrimidine-3-carboxamide (Example 269; 80 mg, 0.14 mmol), tris(dibenzylideneacetone)dipalladium(0) (13.5 mg, 0.014 mmol), 1,1'-bis(diphenylphosphino)ferrocene (16.0 mg, 0.029 mmol) and zinc cyanide (37 mg, 0.31 mmol) in N,N-dimethylformamide (1.5 ml) was purged with nitrogen and stirred at 120° C. for 30 min. The reaction was quenched with water and extracted with ethyl acetate. The organic phase was isolated, dried with sodium sulfate, filtered, concentrated and purified by silica gel chromatography (eluting gradient 0%-20% methanol:dichloromethane) followed by reverse-phase HPLC to afford N3-[2-[(2R)-2-fluoro-3-hydroxy-3-methyl-butyl]-6-morpholino-1-oxo-isoindolin-5-yl]pyrazolo[1,5-a]pyrimidine-3,6-dicarboxamide (2.6 mg, 4%). $^1$H NMR (400 MHz, dimethyl sulfoxide-d6) δ 11.00 (s, 1H), 10.09 (s 1H), 8.96 (1H), 8.76 (s, 1H), 8.71 (s, 1H), 4.90 (s, 1H), 4.61-4.46 (m, 3H), 4.34-4.40 (m, 1H), 4.04-3.86 (m, 5H), 2.96-2.89 (m, 4H), 1.39-1.18 (m, 6H). LCMS (ESI) m/z: 526.2 [M+H]$^+$.

Example 287. N-(2-Isopropyl-6-morpholino-1,1-dioxo-3H-1,2-benzothiazol-5-yl)pyrazolo[1,5-a]pyrimidine-3-carboxamide

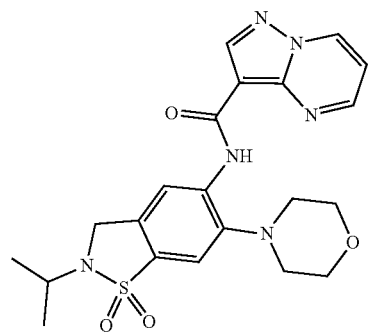 [SMILES: CC(C)N1Cc2cc(NC(=O)c3cnn4cccnc34)c(N3CCOCC3)cc2S1(=O)=O]

Step A. 5-Chloro-2-methyl-4-nitro-benzenesulfonyl chloride

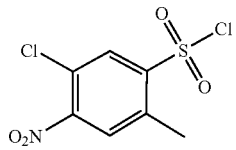

To a chilled and well-stirred solution of acetic acid (1.84 ml, 32.15 mmol) and hydrochloric acid (10 ml, 120 mmol) was added 5-chloro-2-methyl-4-nitrophenylamine (6.0 g, 32.15 mmol) in small portions at −5° C., then sodium nitrite (2.9 g, 41.80 mmol) in water (6 ml) was added drop-wise to the mixture and stirred for 3h at −5° C. to afford the solution of diazonium salt. In a separate vessel, concentrated hydrochloric acid (10 ml) was added drop-wise to sodium sulfite (18.7 g, 180.06 mmol) to afford sulfur dioxide which was bubbled into acetic acid (10 ml) to afford the solution of sulfur dioxide in acetic acid. Cuprous chloride (637 mg, 6.43 mmol) was added to the resulting solution. The solution of diazonium salt was added drop-wise to the solution of sulfur dioxide in acetic acid at −5° C. After the addition, the mixture was stirred at −5° C. for further 3h. Water (50 ml) was added to the mixture which was extracted with dichloromethane (150 ml×3). The combined organic phases were washed with brine (150 ml×3), dried over anhydrous sodium sulfate, filtered and concentrated. The crude material was purified by flash column (eluent 0-10% ethyl acetate:petroleum ether) to afford 5-chloro-2-methyl-4-nitro-benzenesulfonyl chloride (4.5 g, 52% yield) as yellow solid. $^1$H NMR (400 MHz, dimethyl sulfoxide-$d_6$) δ 7.92 (s, 1H), 7.90 (s, 1H), 2.57 (s, 3H).

Step B. 5-Chloro-N-isopropyl-2-methyl-4-nitro-benzenesulfonamide

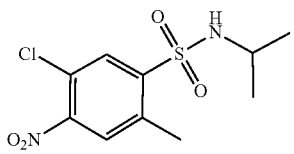 [SMILES: Cc1cc([N+](=O)[O-])c(Cl)cc1S(=O)(=O)NC(C)C]

To a solution of 5-chloro-2-methyl-4-nitro-benzenesulfonyl chloride (2.0 g, 7.4 mmol) and N,N-diisopropylethylamine (1.9 g, 14.8 mmol) in N,N-dimethylformamide (10 ml) was added isopropylamine (525 mg, 8.88 mmol). The mixture was stirred at 20° C. for 30 min, poured into water (50 ml) and extracted with ethyl acetate (150 ml×3). The combined organic phases were washed with brine (150 ml×3), dried over anhydrous sodium sulfate and concentrated to dryness. The residual was purified by flash column (eluting gradient 0-20% ethyl acetate:petroleum ether) to afford 5-chloro-N-isopropyl-2-methyl-4-nitro-benzenesulfonamide (1.8 g, 83% yield) as yellow solid. $^1$H NMR (400 MHz, dimethyl sulfoxide-$d_6$) δ 8.18-8.15 (m, 2H), 8.06 (s, 1H), 3.34-3.31 (m, 1H), 2.67 (s, 3H), 0.99-0.98 (d, J=6.0 Hz, 6H).

Step C. 2-(Bromomethyl)-5-chloro-N-isopropyl-4-nitro-benzenesulfonamide

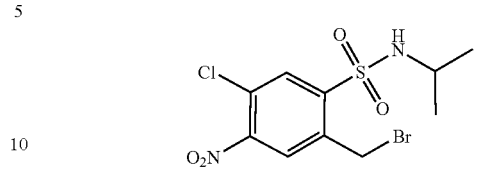

To a solution of 5-chloro-N-isopropyl-2-methyl-4-nitro-benzenesulfonamide (350 mg, 1.20 mmol) in acetonitrile (10 ml) was added azobisisobutyronitrile (20 mg, 0.12 mmol) and N-bromosuccinimide (234 mg, 1.32 mmol) under nitrogen atmosphere. The mixture was stirred at 70° C. for 16h and then concentrated. The crude product was purified by flash column (eluting gradient 0-20% ethyl acetate:petroleum ether) to afford 2-(bromomethyl)-5-chloro-N-isopropyl-4-nitro-benzenesulfonamide (80 mg, 18% yield) as white solid. $^1$H NMR (400 MHz, CDCl$_3$) δ 8.23 (s, 1H), 8.05 (s, 1H), 4.97 (s, 2H), 3.63-3.50 (m, 1H), 1.18 (d, J=6.4 Hz, 6H).

Step D. 6-Chloro-2-isopropyl-5-nitro-3H-1,2-benzothiazole 1,1-dioxide

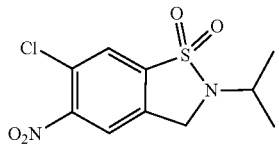 [SMILES: CC(C)N1Cc2cc([N+](=O)[O-])c(Cl)cc2S1(=O)=O]

To a solution of 2-(bromomethyl)-5-chloro-N-isopropyl-4-nitro-benzenesulfonamide (240 mg, 0.64 mmol) in N,N-dimethylformamide (10 ml) were added cesium carbonate (420 mg, 1.30 mmol) at 0° C. The reaction mixture was stirred at 25° C. for 30 min. The reaction mixture was poured into ice water (20 ml) and extracted with dichloromethane (20 ml×3). The combined organic phases were dried over anhydrous sodium sulfate, filtered and concentrated. The crude material was purified by flash column (eluting gradient 0-10% methanol: dichloromethane) to afford 6-chloro-2-isopropyl-5-nitro-3H-1,2-benzothiazole 1,1-dioxide (160 mg, 85% yield) as white solid. $^1$H NMR (400 MHz, CDCl$_3$) δ 7.97 (s, 1H), 7.88 (s, 1H), 4.43 (s, 2H), 4.18-4.09 (m, 1H), 1.41 (d, J=6.4 Hz, 6H).

Step E. 2-Isopropyl-6-morpholino-5-nitro-3H-1,2-benzothiazole 1,1-dioxide

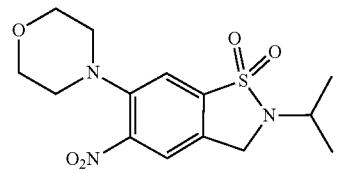 [SMILES: CC(C)N1Cc2cc([N+](=O)[O-])c(N3CCOCC3)cc2S1(=O)=O]

To a solution of 6-chloro-2-isopropyl-5-nitro-3H-1,2-benzothiazole 1,1-dioxide (160 mg, 0.56 mmol) in dimethyl sulfoxide (4 ml) was added N,N-diisopropylethylamine (72 mg, 0.56 mmol) was added morpholine (72 mg, 0.82 mmol). The mixture was stirred at 90° C. for 1h. The reaction mixture was concentrated and purified by preparatory TLC (eluent: 20% ethyl acetate:petroleum ether) to afford 2-isopropyl-6-morpholino-5-nitro-3H-1,2-benzothiazole 1,1-dioxide (160 mg, 85% yield) as white solid. $^1$H NMR (400 MHz, CDCl$_3$) δ 7.75 (s, 1H), 7.53 (s, 1H), 4.36 (s, 2H), 4.10-4.07 (m, 1H), 3.86 (t, J=4.4 Hz, 4H), 3.10-3.08 (t, J=4.4 Hz, 4H), 1.40 (d, J=6.4 Hz, 6H).

Step F. 2-Isopropyl-6-morpholino-1,1-dioxo-3H-1,2-benzothiazol-5-amine

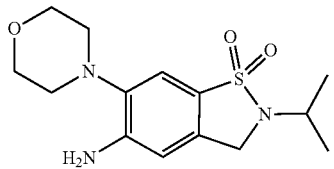

To a solution of 2-isopropyl-6-morpholino-5-nitro-3H-1,2-benzothiazole 1,1-dioxide (160 mg, 0.46 mmol) in ethanol (5 ml) and water (1 ml) was added iron (130 mg, 2.34 mmol) and ammonium chloride (63 mg, 1.17 mmol). The mixture was stirred at 80° C. for 2h. The mixture was filtered and the filtrate was concentrated. The residue was diluted with water (20 ml) and extracted with ethyl acetate (20 ml×3). The combined organic phases were dried over anhydrous sodium sulfate, filtered and concentrated to afford 2-isopropyl-6-morpholino-1,1-dioxo-3H-1,2-benzothiazol-5-amine (140 mg) as a yellow solid, which was used without further purification. LCMS (ESI): m/z=312.1 [M+H]$^+$.

Step G. N-(2-Isopropyl-6-morpholino-1,1-dioxo-3H-1,2-benzothiazol-5-yl)pyrazolo[1,5-a]pyrimidine-3-carboxamide

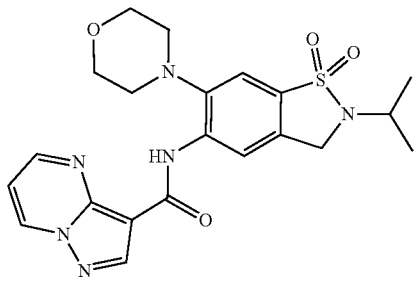

To a solution of 2-isopropyl-6-morpholino-1,1-dioxo-3H-1,2-benzothiazol-5-amine (124 mg, 0.40 mmol) and pyrazolo[1,5-a]pyrimidine-3-carboxylic acid (65 mg, 0.40 mmol) in pyridine (4 ml) was added phosphorus oxychloride (0.18 ml, 1.99 mmol). The reaction was stirred at 25° C. for 5 min. The reaction mixture was quenched with saturated sodium bicarbonate solution (10 ml) at 0° C. and extracted with ethyl acetate (20 ml×3). The combined organic phases were dried over anhydrous sodium sulfate, filtered and concentrated. The residue was purified by reverse phase HPLC (23-53% acetonitrile in water with 0.225% formic acid) to give N-(2-isopropyl-6-morpholino-1,1-dioxo-3H-1,2-benzothiazol-5-yl)pyrazolo[1,5-a]pyrimidine-3-carboxamide (71.3 mg, 39% yield) as white solid. $^1$H NMR (400 MHz, dimethyl sulfoxide-d$_6$) δ 10.91 (s, 1H), 9.42-9.40 (m, 1H), 9.01-9.00 (m, 1H), 8.76-8.74 (m, 2H), 7.78 (s, 1H), 7.41-7.38 (dd, J=7.2, 4.4 Hz, 1H), 4.45 (s, 2H), 3.90 (t, J=6.4 Hz, 4H), 3.60-3.30 (m, 1H), 2.94-2.92 (m, 4H), 1.29 (d, J=6.8 Hz, 6H). LCMS (ESI): m/z=457.0 [M+H]$^+$.

Example 288. N-[2-(2-Hydroxy-2-methyl-propyl)-6-morpholino-1,1-dioxo-3H-1,2-benzothiazol-5-yl]pyrazolo[1,5-a]pyrimidine-3-carboxamide

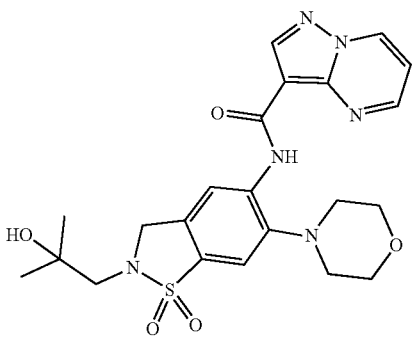 [SMILES: CC(C)(O)CN1Cc2cc(NC(=O)c3cnn4cccnc34)c(N3CCOCC3)cc2S1(=O)=O]

The title compound was made in a manner analogous to Example 287 to give N-[2-(2-hydroxy-2-methyl-propyl)-6-morpholino-1,1-dioxo-3H-1,2-benzothiazol-5-yl]pyrazolo[1,5-a]pyrimidine-3-carboxamide (67 mg, 19% yield) as a white solid. $^1$H NMR (400 MHz, dimethyl sulfoxide-d$_6$) δ 10.90 (s, 1H), 9.43-9.41 (m, 1H), 9.01-8.99 (m, 1H), 8.77-8.75 (m, 1H), 8.70-8.69 (m, 1H), 7.83 (s, 1H), 7.41-7.38 (m, 1H), 4.65 (s, 1H), 4.58 (s, 2H), 3.95-3.85 (m, 4H), 3.07 (s, 2H), 2.95-2.90 (m, 4H), 1.19 (s, 6H). LCMS (ESI): m/z=487.1 [M+H]$^+$.

Example 289. N-[2-[(2R)-2-Fluoro-3-hydroxy-3-methyl-butyl]-6-morpholino-1,1-dioxo-3H-1,2-benzothiazol-5-yl]pyrazolo[1,5-a]pyrimidine-3-carboxamide

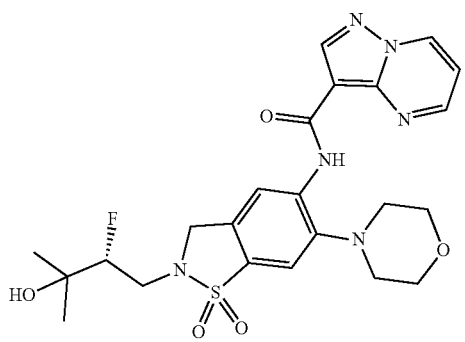 [SMILES: CC(C)(O)[C@H](F)CN1Cc2cc(NC(=O)c3cnn4cccnc34)c(N3CCOCC3)cc2S1(=O)=O]

The title compound was made in a manner analogous to Example 287 to give N-[2-[(2R)-2-fluoro-3-hydroxy-3-methyl-butyl]-6-morpholino-1,1-dioxo-3H-1,2-benzothiazol-5-yl]pyrazolo[1,5-a]pyrimidine-3-carboxamide as a white solid. $^1$H NMR (400 MHz, CDCl$_3$) δ 10.88 (s, 1H), 8.89-8.81 (m, 4H), 7.66 (s, 1H), 7.15 (dd, J=7.2, 4.4 Hz, 1H), 4.72-4.58 (m, 2H), 4.44-4.40 (m, 1H), 4.03 (t, J=4.4 Hz, 4H), 3.92-3.80 (m, 1H), 3.48-3.42 (m, 1H), 3.01 (t, J=4.4 Hz, 4H), 1.35 (s, 6H). LCMS (ESI): m/z=519.2 [M+H]⁺.

Example 290. Diethyl ((2-methyl-6-morpholino-5-(pyrazolo[1,5-a]pyrimidine-3-carboxamido)-2,3-dihydrobenzofuran-2-yl)methyl) phosphate

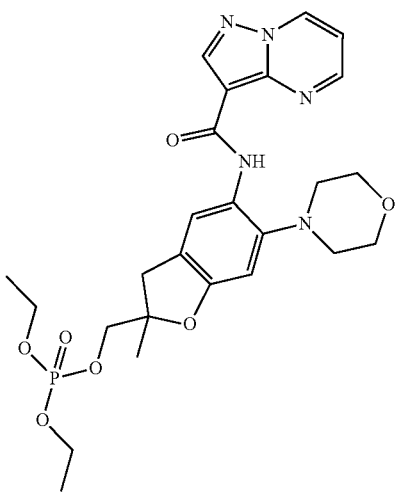 [SMILES: CCOP(=O)(OCC)OCC1(C)Cc2cc(NC(=O)c3cnn4cccnc34)c(N3CCOCC3)cc2O1]

N-[2-(hydroxymethyl)-2-methyl-6-morpholino-3H-benzofuran-5-yl]pyrazolo[1,5-a]pyrimidine-3-carboxamide (142 mg, 0.35 mmol) was dissolved in tetrahydrofuran (2.6 ml) and treated with trimethylamine (0.07 ml, 0.52 mmol), diethyl chlorophosphate (0.06 ml, 0.38 mmol), and 4-dimethylaminopyridine (47 mg, 0.38 mmol). Dichloromethane (2 ml) was added and the reaction mixture was heated at 50° C. Additional diethyl chlorophosphate (0.55 ml, 3.82 mmol) and trimethylamine (0.73 ml, 5.22 mmol) were added and the reaction was allowed to stir at 50° C. for 2 wk. The reaction mixture was cooled to ambient temperature and diluted with dichloromethane, water, and brine. The aqueous phase was isolated and extracted into dichloromethane (3×). The combined organic phases were dried over anhydrous sodium sulfate, filtered and concentrated. The crude residue was purified via HPLC to afford the title compound (29 mg, 0.053 mmol). ¹H NMR (400 MHz, dimethyl sulfoxide-d₆) δ 10.44 (s, 1H), 9.37 (dd, J=7.0, 1.6 Hz, 1H), 8.95 (dd, J=4.2, 1.7 Hz, 1H), 8.68 (s, 1H), 8.33 (d, J=1.0 Hz, 1H), 7.34 (dd, J=7.0, 4.2 Hz, 1H), 6.76 (s, 1H), 4.03 (d, J=5.7 Hz, 2H), 4.01-3.93 (m, 4H), 3.84 (m, 4H), 3.26-3.16 (m, 1H), 3.05-2.92 (m, 1H), 2.86-2.75 (m, 4H), 1.42 (s, 3H), 1.20 (tdd, J=7.1, 2.8, 0.9 Hz, 6H). MS (ESI): m/z=546.2 [M+1]⁺.

Example 291. (R)—N-(2,2-Dimethyl-6-(pyrrolidin-2-ylmethoxy)-2,3-dihydrobenzofuran-5-yl)pyrazolo[1,5-a]pyrimidine-3-carboxamide

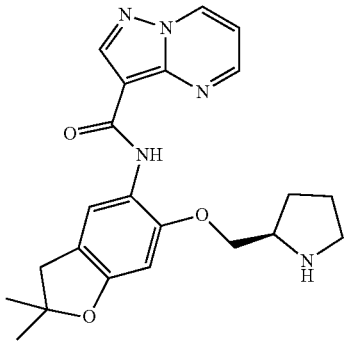 [SMILES: CC1(C)Cc2cc(NC(=O)c3cnn4cccnc34)c(OC[C@H]3CCCN3)cc2O1]

Step A. tert-Butyl 2-(((2,2-dimethyl-5-nitro-2,3-dihydrobenzofuran-6-yl)oxy)methyl)pyrrolidine-1-carboxylate

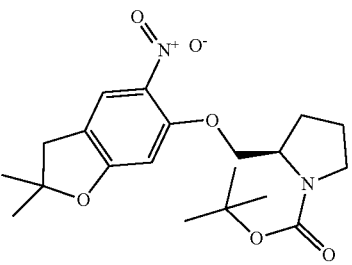

A mixture of tert-butyl (2R)-2-(hydroxymethyl)pyrrolidine-1-carboxylate (395 mg, 1.92 mmol), potassium tert-butoxide (249 mg, 2.20 mmol), and 6-chloro-2,2-dimethyl-5-nitro-3H-benzofuran (250 mg, 1.10 mmol) in dioxane (6.1 ml) was stirred at 40° C. for 36h. The reaction mixture was diluted with water and isopropyl acetate. The aqueous phase was isolated and extracted with isopropyl acetate (3×). The combined organic phases were dried over anhydrous sodium sulfate, filtered and purified by flash column chromatography (eluting gradient 0-50% isopropyl acetate: heptanes) to afford the title compound (196 mg, 0.498 mmol, 45% yield) as an orange-yellow viscous oil. ¹H NMR (400 MHz, dimethyl sulfoxide-d₆) δ 7.84 (s, 1H), 6.75 (s, 1H), 4.13 (d, J=4.0 Hz, 2H), 4.08-3.94 (m, 2H), 3.27 (m, 2H), 3.00 (d, J=0.9 Hz, 2H), 2.02-1.85 (m, 2H), 1.76 (s, 1H), 1.45 (s, 6H), 1.39 (s, 9H).

Step B. tert-Butyl (R)-2-(((5-amino-2,2-dimethyl-2,3-dihydrobenzofuran-6-yl)oxy)methyl)pyrrolidine-1-carboxylate

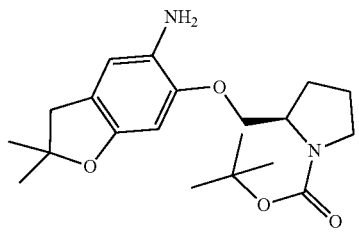 [SMILES: CC(C)(C)OC(=O)N1CCC[C@@H]1COc1cc2c(cc1N)CC(C)(C)O2]

A mixture of tert-butyl (R)-2-(((2,2-dimethyl-5-nitro-2,3-dihydrobenzofuran-6-yl)oxy)methyl)pyrrolidine-1-carboxylate (180 mg, 0.456 mmol), iron (535 mg, 9.58 mmol), and ammonium chloride (512 mg, 9.58 mmol) in ethanol (13 ml) and water (2.5 ml) was stirred at 80° C. for 30 min. The mixture was filtered through celite and a small plug of silica to afford tert-butyl (R)-2-(((5-amino-2,2-dimethyl-2,3-dihydrobenzofuran-6-yl)oxy)methyl)pyrrolidine-1-carboxylate (139 mg, 0.385 mmol) which was carried on without further purification.

Step C. tert-Butyl 2-(((2,2-dimethyl-5-(pyrazolo[1,5-a]pyrimidine-3-carboxamido)-2,3-dihydrobenzofuran-6-yl)oxy)methyl)pyrrolidine-1-carboxylate

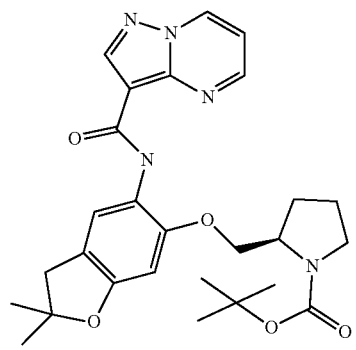

tert-Butyl (R)-2-(((5-amino-2,2-dimethyl-2,3-dihydrobenzofuran-6-yl)oxy)methyl)pyrrolidine-1-carboxylate (139 mg, 0.385 mmol), pyrazolo[1,5-a]pyrimidine-3-carbonyl chloride (105 mg, 0.578 mmol), and dimethylaminopyridine (9.5 mg, 0.077 mmol) were dissolved in dichloroethane (3 ml) and treated with N,N-diisopropylethylamine (0.20 ml, 1.16 mmol) and stirred for 16h at room temperature. The reaction mixture was absorbed onto celite and purified via flash column chromatography (eluting gradient 0-100% isopropyl acetate: heptanes) to provide tert-butyl (R)-2-(((2,2-dimethyl-5-(pyrazolo[1,5-a]pyrimidine-3-carboxamido)-2,3-dihydrobenzofuran-6-yl)oxy)methyl)pyrrolidine-1-carboxylate (130 mg, 0.257 mmol, 67% yield).

Step D. (R)—N-(2,2-Dimethyl-6-(pyrrolidin-2-ylmethoxy)-2,3-dihydrobenzofuran-5-yl)pyrazolo[1,5-a]pyrimidine-3-carboxamide

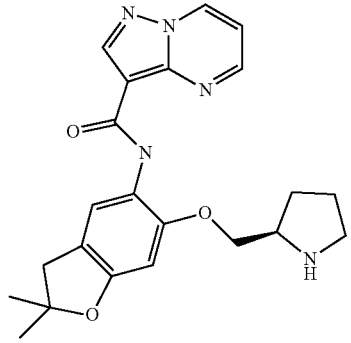

tert-Butyl (R)-2-(((2,2-dimethyl-5-(pyrazolo[1,5-a]pyrimidine-3-carboxamido)-2,3-dihydrobenzofuran-6-yl)oxy)methyl)pyrrolidine-1-carboxylate (130 mg, 0.256 mmol) was dissolved in dichloromethane (2 ml) and treated with trifluoroacetic acid (0.25 ml). After 90 min, the solvent was removed and the material was purified by reverse phase HPLC to afford (R)—N-(2,2-dimethyl-6-(pyrrolidin-2-ylmethoxy)-2,3-dihydrobenzofuran-5-yl)pyrazolo[1,5-a]pyrimidine-3-carboxamide (45 mg, 0.11 mmol). $^1$H NMR (400 MHz, dimethyl sulfoxide-$d_6$) δ 10.12 (s, 1H), 9.37 (dd, J=7.0, 1.6 Hz, 1H), 8.81 (dd, J=4.2, 1.7 Hz, 1H), 8.67 (s, 1H), 8.25 (s, 1H), 7.34 (dd, J=7.0, 4.2 Hz, 1H), 6.54 (s, 1H), 3.88 (d, J=6.4 Hz, 2H), 3.65-3.51 (m, 1H), 2.97 (s, 2H), 2.85 (t, J=6.7 Hz, 2H), 2.03-1.86 (m, 1H), 1.79-1.61 (m, 2H), 1.61-1.46 (m, 1H), 1.41 (s, 6H). MS (ESI): m/z=408.2 [M+1]$^+$

Example 292. (R)—N-(6-((1-(2,2-Difluoroethyl)pyrrolidin-2-yl)methoxy)-2,2-dimethyl-2,3-dihydrobenzofuran-5-yl)pyrazolo[1,5-a]pyrimidine-3-carboxamide

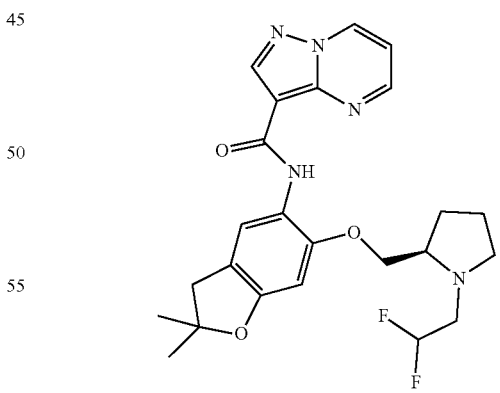

(R)—N-(2,2-Dimethyl-6-(pyrrolidin-2-ylmethoxy)-2,3-dihydrobenzofuran-5-yl)pyrazolo[1,5-a]pyrimidine-3-carboxamide (Example 291, 52 mg, 0.128 mmol) was dissolved in dimethylformamide (2 ml) and treated with triethylamine (0.45 ml, 3.20 mmol) followed by 2,2-difluoroethyl trifluoromethanesulfonate (0.021 ml, 0.154 mmol) and heated at 60° C. for 16h. Additional triethylamine (0.45 ml, 3.20 mmol) and 2,2-difluoroethyl trifluoromethanesulfonate (0.021 ml, 0.154 mmol) were added and continued to stir at 60° C. for 4h. The reaction mixture was concentrated in vacuo and purified by reverse phase HPLC to afford the title compound (24 mg, 0.05 mmol, 60% yield) as a solid. $^1$H NMR (400 MHz, dimethyl sulfoxide-d$_6$) δ 10.02 (s, 1H), 9.37 (dd, J=7.0, 1.6 Hz, 1H), 8.85 (dd, J=4.3, 1.6 Hz, 1H), 8.67 (s, 1H), 8.23 (s, 1H), 7.34 (dd, J=7.0, 4.2 Hz, 1H), 6.58 (s, 1H), 5.99 (tt, J=56.2, 4.4 Hz, 1H), 4.08 (dd, J=9.4, 5.1 Hz, 1H), 3.81 (dd, J=9.3, 7.2 Hz, 1H), 3.18 (m, 1H), 3.11 (m, 1H), 2.98 (s, 2H), 2.82 (qd, J=14.3, 4.8 Hz, 1H), 2.47 (m, 1H), 2.11-2.00 (m, 1H), 1.74 (m, 3H), 1.42 (s, 6H), 1.24 (s, 1H). MS (ESI): m/z=472.2 [M+1]$^+$.

TABLE 9

The following examples were made in a manner similar to that for Example 64:

| Ex. | Name | Structure | NMR, MS |
|---|---|---|---|
| 293 | N-(6-(((1S,3S,5S)-2-(2,2-difluoroethyl)-2-azabicyclo[3.1.0]hexan-3-yl)methoxy)-2,2-dimethyl-2,3-dihydrobenzofuran-5-yl)pyrazolo[1,5-a]pyrimidine-3-carboxamide | 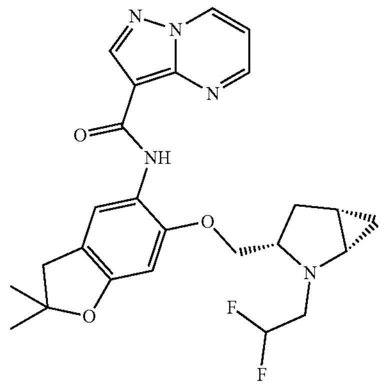 [SMILES: CC1(C)Cc2cc(NC(=O)c3cnn4cccnc34)c(OC[C@@H]3C[C@@H]4C[C@@H]4N3CC(F)F)cc2O1] | 1H NMR (400 MHz, dimethyl sulfoxide-d$_6$) δ 9.98 (s, 1H), 9.37 (dd, J = 7.0, 1.6 Hz, 1H), 8.86 (dd, J = 4.2, 1.6 Hz, 1H), 8.67 (s, 1H), 8.19 (d, J = 1.1 Hz, 1H), 7.35 (dd, J = 7.0, 4.2 Hz, 1H), 6.57 (s, 1H), 5.97 (tt, J = 56.2, 4.3 Hz, 1H), 4.00 (dd, J = 9.3, 5.9 Hz, 1H), 3.89-3.80 (m, 1H), 3.70 (dd, J = 9.4, 6.6 Hz, 1H), 3.23-3.11 (m, 2H), 2.97 (s, 2H), 2.67 (td, J = 6.3, 2.4 Hz, 1H), 2.42 (m, 1H), 1.66-1.60 (m, 1H), 1.51-1.43 (m, 1H), 1.41 (s, 6H), 0.57 (m, 1H), 0.32 (m, 1H). MS (ESI): m/z = 484.2 [M + 1]+. |
| 294 | N-(6-(((1R,5S,6R)-3-(2,2-difluoroethyl)-3-azabicyclo[3.1.0]hexan-6-yl)methoxy)-2,2-dimethyl-2,3-dihydrobenzofuran-5-yl)pyrazolo[1,5-a]pyrimidine-3-carboxamide | 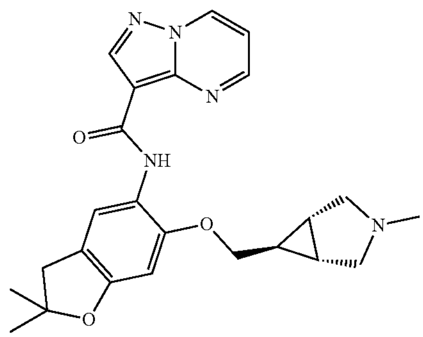 | 1H NMR (400 MHz, dimethyl sulfoxide-d$_6$) δ 10.27 (s, 1H), 9.36 (dd, J = 7.0, 1.6 Hz ,1H), 8.75 (dd, J = 4.2, 1.6 Hz, 1H), 8.67 (s, 1H), 8.27 (d, J = 1.1 Hz, 1H), 7.26 (dd, J = 7.0, 4.1 Hz, 1H), 6.50 (s, 1H), 6.12 (tt, J = 55.8, 4.2 Hz, 1H), 3.90 (d, J = 6.9 Hz, 2H), 3.05 (d, J = 8.7 Hz, 2H), 2.97 (s, 2H), 2.86 (td, J = 16.2, 4.2 Hz, 2H), 2.49-2.45 (m, 2H), 1.71 (m, 1H), 1.52 (m, 2H), 1.41 (s, 6H). MS (ESI): m/z = 484.2 [M + 1]+. |
| 295 | N-(6-(((1R,5S,6R)-3-azabicyclo[3.1.0]hexan-6-yl)methoxy)-2,2-dimethyl-2,3-dihydrobenzofuran-5-yl)pyrazolo[1,5-a]pyrimidine-3-carboxamide | 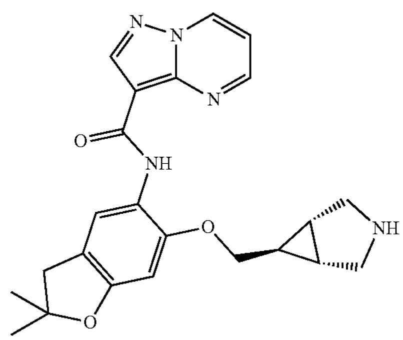 [SMILES: CC1(C)Cc2cc(NC(=O)c3cnn4cccnc34)c(OC[C@H]3[C@@H]4CNC[C@@H]43)cc2O1] | 1H NMR (400 MHz, dimethyl sulfoxide-d$_6$) δ 10.13 (s, 1H), 9.37 (dd, J = 7.0, 1.6 Hz, 1H), 8.88 (dd, J = 4.2, 1.6 Hz, 1H), 8.67 (s, 1H), 8.23 (s, 1H), 7.34 (dd, J = 7.0, 4.2 Hz, 1H), 6.52 (s, 1H), 3.96 (d, J = 6.9 Hz, 2H), 2.97 (s, 2H), 2.85 (d, J = 11.1 Hz, 2H), 2.78-2.66 (m, 2H), 1.49 (m, 2H), 1.41 (s, 6H), 1.29 (m, 1H). MS (ESI): m/z = 420.2 [M + 1]+. |
| 296 | N-(2,2-Dimethyl-6-((tetrahydrofuran-3-yl)methoxy)-2,3-dihydrobenzofuran-5-yl)pyrazolo[1,5-α]pyrimidine-3-carboxamide | 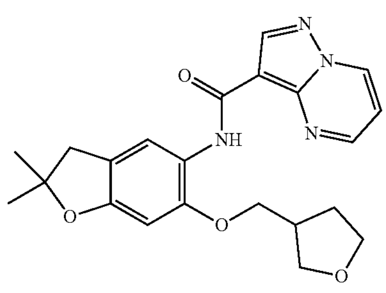 [SMILES: CC1(C)Cc2cc(NC(=O)c3cnn4cccnc34)c(OCC3CCOC3)cc2O1] | MS (ESI): m/z = 409.2 [M + 1]$^+$. |

TABLE 9-continued

The following examples were made in a manner similar to that for Example 64:

| Ex. | Name | Structure | NMR, MS |
|---|---|---|---|
| 297 | N-(2,2-Dimethyl-6-(pyridin-3-ylmethoxy)-2,3-dihydrobenzofuran-5-yl)pyrazolo[1,5-α]pyrimidine-3-carboxamide | 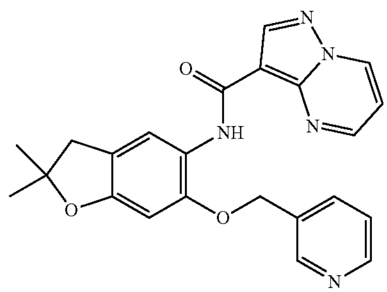 [SMILES: CC1(C)Cc2cc(NC(=O)c3cnn4cccnc34)c(OCc3cccnc3)cc2O1] | $^1$H NMR (400 MHz, dimethyl sulfoxide-$d_6$) δ 10.09 (s, 1H), 9.35 (dd, J = 7.0, 1.6 Hz, 1H), 8.91 (d, J = 2.5 Hz, 1H), 8.66 (s, 1H), 8.62 (dd, J = 4.9, 1.6 Hz, 1H), 8.40 (dd, J = 4.3, 1.6 Hz, 1H), 8.31 (s, 1H), 7.99 (dt, J = 8.0, 2.1 Hz, 1H), 7.49 (dd, J = 7.7, 4.8 Hz, 1H), 7.30 (dd, J = 7.0, 4.3 Hz, 1H), 6.77 (s, 1H), 5.25 (s, 2H), 3.00 (s, 2H), 1.43 (s, 6H). MS (ESI): m/z = 416.1 [M + 1]$^+$. |
| 298 | N-(6-(Cyclopropylmethoxy)-2,2-dimethyl-2,3-dihydrobenzofuran-5-yl)pyrazolo[1,5-α]pyrimidine-3-carboxamide | 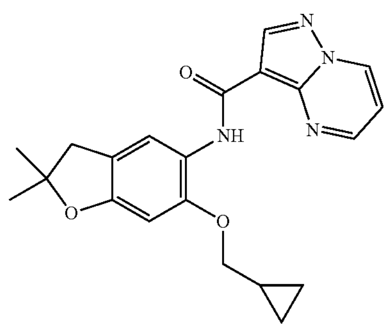 [SMILES: CC1(C)Cc2cc(NC(=O)c3cnn4cccnc34)c(OCC3CC3)cc2O1] | $^1$H NMR (400 MHz, dimethyl sulfoxide-$d_6$) δ 10.31 (s, 1H), 9.37 (dd, J = 7.1, 1.6 Hz, 1H), 8.85 (dd, J = 4.2, 1.6 Hz, 1H), 8.67 (s, 1H), 8.29 (s, 1H), 7.31 (dd, J = 7.0, 4.2 Hz, 1H), 6.52 (s, 1H), 3.91 (d, J = 6.8 Hz, 2H), 2.97 (s, 2H), 1.41 (s, 6H), 1.37 (dd, J = 8.2, 4.3 Hz, 1H), 0.64 (dt, J = 8.0, 2.9 Hz, 2H), 0.47-0.35 (m, 2H). MS (ESI): m/z = 379.1 [M + 1]$^+$. |
| 299 | N-(2,2-Dimethyl-6-((3-methyloxetan-3-yl)methoxy)-2,3-dihydrobenzofuran-5-yl)pyrazolo[1,5-α]pyrimidine-3-carboxamide | 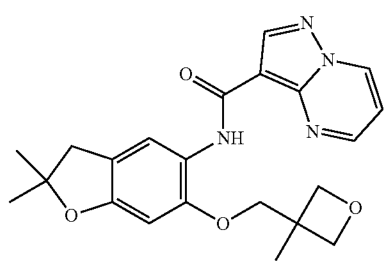 [SMILES: CC1(COc2cc3c(cc2NC(=O)c2cnn4cccnc24)CC(C)(C)O3)COC1] | $^1$H NMR (400 MHz, dimethyl sulfoxide-$d_6$) δ 9.89 (s, 1H), 9.37 (dd, J = 7.0, 1.5 Hz, 1H), 8.83 (dd, J = 4.3, 1.7 Hz, 1H), 8.68 (s, 1H), 8.31 (s, 1H), 7.32 (dd, J = 7.0, 4.2 Hz, 1H), 6.63 (s, 1H), 4.56 (d, J = 5.8 Hz, 2H), 4.39 (d, J = 5.8 Hz, 2H), 4.17 (s, 2H), 2.98 (s, 2H), 1.53 (s, 3H), 1.42 (s, 6H). MS (ESI): m/z = 409.1 [M + 1]$^+$. |
| 300 | N-(2,2-Dimethyl-6-((1-methyl-1H-pyrazol-4-yl)methoxy)-2,3-dihydrobenzofuran-5-yl)pyrazolo[1,5-α]pyrimidine-3-carboxamide | 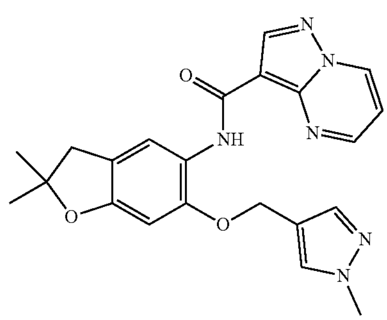 [SMILES: Cn1cc(COc2cc3c(cc2NC(=O)c2cnn4cccnc24)CC(C)(C)O3)cn1] | $^1$H NMR (400 MHz, dimethyl sulfoxide-$d_6$) δ 10.16 (s, 1H), 9.35 (dd, J = 7.0, 1.7 Hz, 1H), 8.65 (s, 1H), 8.32-8.25 (m, 2H), 7.85 (s, 1H), 7.64 (s, 1H), 7.33 (dd, J = 7.0, 4.2 Hz, 1H), 6.71 (s, 1H), 5.02 (s, 2H), 3.87 (s, 3H), 2.98 (s, 2H), 1.42 (s, 6H). MS (ESI): m/z = 419.1 [M + 1]$^+$. |
| 301 | N-(2,2-Dimethyl-6-(pyridin-4-ylmethoxy)-2,3-dihydrobenzofuran-5-yl)pyrazolo[1,5-α]pyrimidine-3-carboxamide | 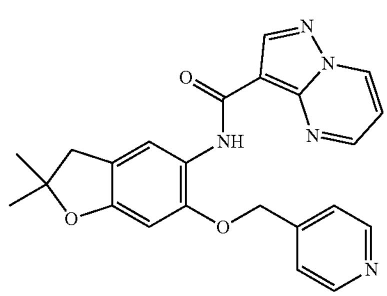 [SMILES: CC1(C)Cc2cc(NC(=O)c3cnn4cccnc34)c(OCc3ccncc3)cc2O1] | MS (ESI): m/z = 416.1 [M + 1]$^+$. |

TABLE 9-continued

The following examples were made in a manner similar to that for Example 64:

| Ex. | Name | Structure | NMR, MS |
|---|---|---|---|
| 302 | N-(6-(2,2-Difluoroethoxy)-2,2-dimethyl-2,3-dihydrobenzofuran-5-yl)pyrazolo[1,5-α]pyrimidine-3-carboxamide | 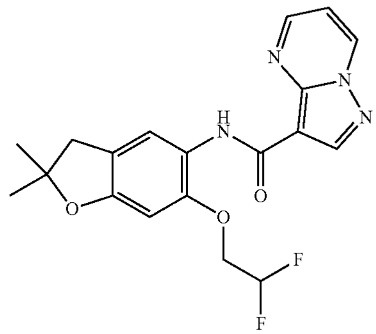 [SMILES: CC1(C)Cc2cc(NC(=O)c3cnn4cccnc34)c(OCC(F)F)cc2O1] | $^1$H NMR (400 MHz, dimethyl sulfoxide-d$_6$) δ 10.30 (s, 1H), 9.38 (dd, J = 7.0, 1.7 Hz, 1H), 8.83 (dd, J = 4.2, 1.6 Hz, 1H), 8.68 (s, 1H), 8.31 (s, 1H), 7.34 (dd, J = 7.0, 4.2 Hz, 1H), 6.66 (s, 1H), 6.54 (t, J = 3.7 Hz, 1H), 4.41 (td, J = 14.2, 3.7 Hz, 2H), 2.99 (s, 2H), 1.42 (s, 6H). MS (ESI): m/z = 389.1 [M + 1]$^+$. |
| 303 | 2,2-Dimethyl-6-[1-(1-methylpyrazol-4-yl)ethoxy]-3H-benzofuran-5-amine | 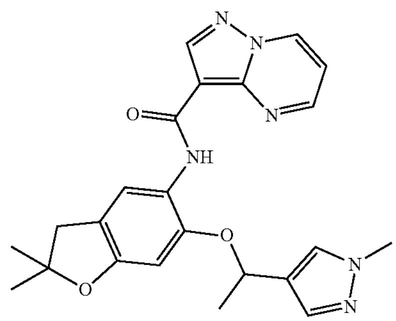 | $^1$H NMR (400 MHz, CDCl$_3$) δ 10.22 (s, 1H), 8.80 (dd, J = 6.8, 1.6 Hz, 1H), 8.75 (s, 1H), 8.54 (dd, J = 4.4, 1.6 Hz, 1H), 8.40 (s, 1H), 7.57 (s, 1H), 7.34 (s, 1H), 7.01 (dd, J = 6.8, 4.0 Hz, 1H), 6.45 (s, 1H), 5.41 (q, J = 6.4 Hz, 1H), 3.84 (s, 3H), 3.01 (s, 2H), 1.75 (d, J = 6.4 Hz, 3H), 1.47 (s, 6H). LCMS (ESI): m/z = 455.0 [M + H]$^+$. |
| 304 | N-(2,2-Dimethyl-6-((1-methylpiperidin-3-yl)oxy)-2,3-dihydrobenzofuran-5-yl)pyrazolo[1,5-α]pyrimidine-3-carboxamide | 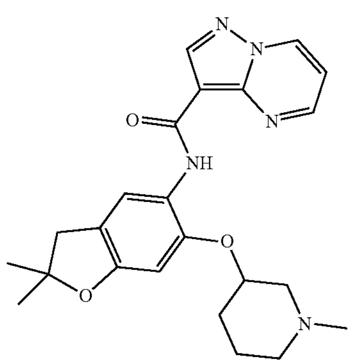 | $^1$H NMR (400 MHz, CDCl$_3$) δ 10.17 (s., 1H), 8.82 (d, J = 7.2 Hz, 1H), 8.76 (s, 1H), 8.68 (s., 1H), 8.41 (s, 1H), 7.04 (dd, J = 6.8, 4.0 Hz, 1H), 6.49 (s, 1H), 4.38 (m, 1H), 3.16-3.14 (m 1H), 3.02 (s, 2H), 2.74-2.72 (m, 1H), 2.32 (s, 3H), 2.28-2.23 (m, 2H), 2.05-2.01 (m, 1H), 1.87-1.85 (m, 1H), 1.78-1.55 (m, 2H), 1.49 (s, 6H). LCMS (ESI): m/z = 422.1 [M + H]$^+$. |

TABLE 9-continued

The following examples were made in a manner similar to that for Example 64:

| Ex. | Name | Structure | NMR, MS |
|---|---|---|---|
| 305 and 306 | R)-N-(2,2-Dimethyl-6-((2-oxo piperidin-4-yl)methoxy)-2,3-dihydrobenzofuran-5-yl)pyrazolo[1,5-α]pyrimidine-3-carboxamide and (S)-N-(2,2-Dimethyl-6-((2-oxo piperidin-4-yl)methoxy)-2,3-dihydrobenzofuran-5-yl)pyrazolo[1,5-α]pyrimidine-3-carboxamide (absolute stereochemistry assigned arbitrarily) | | Example 305, Peak 1: $^1$HNMR (400 MHz, CDCl$_3$) δ 9.85 (s, 1H), 8.86-8.77 (m, 3H), 8.36 (s, 1H), 7.04 (dd, J = 6.4, 4.0 Hz, 1H), 6.40 (s, 1H), 5.76 (s, 1H), 4.07-4.04 (m, 1H), 3.92 (dd, J = 8.8, 6.4 Hz, 1H), 3.44-3.40 (m, 2H), 3.03 (s, 2H), 2.95-2.91 (m, 1H), 2.61-2.50 (m, 2 H), 2.06-1.94 (m, 1H), 1.91-1.80 (m, 1H), 1.49 (s, 6H). LCMS (ESI): m/z = 436.2 [M + H]$^+$. Example 306, Peak 1: $^1$HNMR (400 MHz, CDCl$_3$) δ 9.84 (s, 1H), 8.85-8.77 (m, 3H), 8.36 (s, 1H), 7.04 (dd, J = 6.8, 4.0 Hz, 1H), 6.40 (s, 1H), 5.76 (s, 1H), 4.07-4.04 (m, 1H), 3.92 (dd, J = 8.8, 6.4 Hz, 1H), 3.44-3.40 (m, 2H), 3.03 (s, 2H), 2.95-2.91 (m, 1H), 2.61-2.50 (m, 2 H), 2.06-1.94 (m, 1H), 1.91-1.80 (m, 1H), 1.49 (s, 6H). LCMS (ESI): m/z = 436.2 [M + H]$^+$. |
| 307 and 308 | N-[2,2-Dimethyl-6-[[(3R)-5-oxopyrrolidin-3-yl]methoxy]-3H-benzofuran-5-yl]pyrazolo[1,5-a]pyrimidine-3-carboxamide and N-[2,2-Dimethyl-6-[[(3S)-5-oxo pyrrolidin-3-yl]methoxy]-3H-benzofuran-5-yl]pyrazolo[1,5-a]pyrimidine-3-carboxamide (absolute stereochemistry assigned arbitrarily) | | Example 308, Peak 1: $^1$H NMR (400 MHz, CDCl$_3$) δ 9.85 (s, 1H), 8.82-8.71 (m, 3H), 8.32 (s, 1H), 7.05 (dd, J = 7.2, 4.8 Hz, 1H), 6.41 (s, 1 H), 5.53 (s, 1H), 4.11-4.06 (m, 2H), 3.64-3.59 (m, 1H), 3.43-3.39 (m, 1H), 3.06-3.04 (m, 1H), 3.03 (s, 2H), 2.58 (d, J = 8..8 Hz, 2H), 1.49 (s, 6 H). LCMS (ESI): m/z = 422.2 [M + H]$^+$. Example 307, Peak 2: $^1$H NMR (400 MHz, CDCl$_3$) δ 9.85 (s, 1H), 8.82-8.71 (m, 3H), 8.31 (s, 1H), 7.05 (dd, J = 6.8, 4.4 Hz, 1H), 6.41 (s, 1 H), 5.54 (s, 1H), 4.10-4.05 (m, 2H), 3.64-3.59 (m, 1H), 3.43-3.39 (m, 1H), 3.06-3.04 (m, 1H), 3.03 (s, 2H), 2.58 (d, J = 8.8 Hz, 2H), 1.49 (s, 6H). LCMS (ESI): m/z = 422.2 [M + H]$^+$. |

TABLE 9-continued

The following examples were made in a manner similar to that for Example 64:

| Ex. | Name | Structure | NMR, MS |
|---|---|---|---|
| 309 | N-(2,2-Dimethyl-6-(piperidin-4-ylmethoxy)-2,3-dihydrobenzofuran-5-yl)pyrazolo[1,5-α]pyrimidine-3-carboxamide | 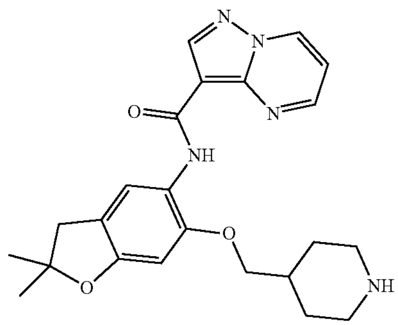 [SMILES: CC1(C)Cc2cc(NC(=O)c3cnn4cccnc34)c(OCC3CCNCC3)cc2O1] | $^1$H NMR (400 MHz, dimethyl sulfoxide-d$_6$) δ 10.03 (s, 1 H), 9.40 (d, J = 6.0 Hz, 1 H), 8.85-8.75 (m, 2 H), 8.65 (s, 1 H), 8.23 (s, 1 H), 7.40 (dd, J = 7.2, 4.0 Hz, 1 H), 6.60 (s, 1 H), 3.96 (d, J = 6.8 Hz, 2 H), 3.30-3.25 (m, 2 H), 2.97-2.92 (m, 4 H), 2.30-2.15 (m, 2H), 2.10-2.00 (m, 2 H), 1.55-1.45 (m, 2 H), 1.41 (s, 6 H). LCMS (ESI): m/z = 422.3 [M + H]$^+$. |
| 310 and 311 | (S)-N-(6-(2,2-difluoroethoxy)-2-(hydroxymethyl)-2-methyl-2,3-dihydrobenzofuran-5-yl)pyrazolo[1,5-a]pyrimidine-3-carboxamide and (R)-N-(6-(2,2-difluoroethoxy)-2-(hydroxymethyl)-2-methyl-2,3-dihydrobenzofuran-5-yl)pyrazolo[1,5-a]pyrimidine-3-carboxamide (absolute stereochemistry assigned arbitrarily) | | Example 310, Peak 1: $^1$H NMR (400 MHz, dimethyl sulfoxide-d6) δ 10.27 (s, 1H), 9.36 (dd, J = 7.0, 1.5 Hz, 1H), 8.83 (dd, J = 4.2, 1.5 Hz, 1H), 8.67 (s, 1H), 8.28 (s, 1H), 7.33 (dd, J = 7.0, 4.2 Hz, 1H), 6.70-6.33 (m, 2H), 5.04 (t, J = 5.8 Hz, 1H), 4.40 (td, J = 14.5, 3.2 Hz, 2H), 3.43 (m, 2H), 3.19 (d, J = 15.6 Hz, 1H), 2.82 (d, J = 15.5 Hz, 1H), 1.35 (s, 3H). MS (ESI): m/z = 405.1 [M + 1]$^+$. Example 311, Peak 2: $^1$H NMR (400 MHz, dimethyl sulfoxide-d6) δ 10.27 (s, 1H), 9.36 (dd, J = 7.0, 1.6 Hz, 1H), 8.83 (dd, J = 4.2, 1.6 Hz, 1H), 8.67 (s, 1H), 8.28 (s, 1H), 7.33 (dd, J = 7.0, 4.2 Hz, 1H), 6.70-6.31 (m, 2H), 5.04 (t, J = 5.7 Hz, 1H), 4.40 (td, J = 14.2, 3.0 Hz, 2H), 3.44 (m, 2H), 3.19 (d, J = 15.7 Hz, 1H), 2.82 (d, J = 15.6 Hz, 1H), 1.35 (s, 3H). MS (ESI): m/z = 405.1 [M + 1]$^+$. |

TABLE 9-continued

The following examples were made in a manner similar to that for Example 64:

| Ex. | Name | Structure | NMR, MS |
|---|---|---|---|
| 312 and 313 | N-[(2S)-6-(cis-4-Hydroxycyclohexoxy)-2-(1-hydroxy-1-methyl-ethyl)-2-methyl-3H-benzofuran-5-yl]pyrazolo[1,5-a]pyrimidine-3-carboxamide and N-[(2R)-6-(cis-4-Hydroxycyclohexoxy)-2-(1-hydroxy-1-methyl-ethyl)-2-methyl-3H-benzofuran-5-yl]pyrazolo[1,5-a]pyrimidine-3-carboxamide (absolute stereochemistry assigned arbitrarily) | | Example 312, Peak 1: $^1$H NMR (400 MHz, DMSO-d$_6$) δ 10.10 (s, 1H), 9.40-9.35 (m, 1H), 9.00-8.95 (m, 1H), 8.67 (s, 1H), 8.14 (s, 1H), 7.35-7.32 (m, 1H), 6.50 (s, 1H), 4.67 (s, 1H), 4.63 (d, J = 3.2 Hz, 1H), 4.55-4.50 (m, 1H), 3.65-3.60 (m, 1H), 2.67-2.66 (m, 1H), 2.52-2.51 (m, 1H), 1.99-1.96 (m, 2H), 1.81-1.73 (m, 2H), 1.69-1.59 (m, 4H), 1.24 (s, 3H), 1.23 (s, 3H), 1.16 (s, 3H). LCMS (ESI): m/z = 467.0 [M + H]$^+$. Example 313, Peak 2: $^1$H NMR (400 MHz, DMSO-d$_6$) δ 10.10 (s, 1H), 9.40-9.35 (m, 1H), 9.00-8.95 (m, 1H), 8.67 (s, 1H), 8.14 (s, 1H), 7.35-7.32 (m, 1H), 6.50 (s, 1H), 4.67 (s, 1H), 4.63 (d, J = 3.2 Hz, 1H), 4.55-4.50 (m, 1H), 3.65-3.60 (m, 1H), 2.67-2.66 (m, 1H), 2.52-2.51 (m, 1H), 1.99-1.96 (m, 2H), 1.78-1.64 (m, 6H), 1.24 (s, 3H), 1.23 (s. 3H), 1.16 (s, 3H). LCMS (ESI): m/z = 467.0 [M + H]$^+$. |
| 314 and 315 | N-[(2S)-6-(trans-4-Hydroxycyclohexoxy)-2-(1-hydroxy-1-methyl-ethyl)-2-methyl-3H-benzofuran-5-yl]pyrazolo[1,5-a]pyrimidine-3-carboxamide and N-[(2R)-6-(trans-4-Hydroxycyclohexoxy)-2-(1-hydroxy-1-methyl-ethyl)-2-methyl-3H-benzofuran-5-yl]pyrazolo[1,5-a]pyrimidine-3-carboxamide (absolute stereochemistry assigned arbitrarily) | | Example 314, Peak 1: $^1$H NMR (400 MHz, DMSO-d$_6$) δ 10.18 (s, 1H), 9.36 (d, J = 6.8 Hz, 1H), 8.82 (dd, J = 4.0, 1.6 Hz, 1H), 8.65 (s, 1H), 8.14 (s, 1H), 7.33-7.30 (m, 1H), 6.52 (s, 1H), 4.67 (s, 1H), 4.58 (d, J = 4.0 Hz, 1H), 4.39-4.36 (m, 1H), 3.60-3.58 (m, 1H), 2.67-2.66 (m, 1H), 2.52-2.51 (m, 1H), 2.07-2.04 (m, 2H), 1.93-1.86 (m, 2H), 1.58-1.53 (m, 2H), 1.41-1.35 (m, 2H), 1.24 (s, 3H), 1.23 (s, 3H), 1.16 (s, 3H). LCMS (ESI): m/z = 467.0 [M + H]$^+$. Example 315, Peak 2: $^1$H NMR (400 MHz, DMSO-d6) δ 10.18 (s, 1H), 9.40-9.35 (m, 1H), 8.82 (dd, J = 4.4, 2.0 Hz, 1H), 8.65 (s, 1H), 8.14 (s, 1H), 7.33-7.30 (m, 1H), 6.52 (s, 1H), 4.67 (s, 1H), 4.58 (s, 1H), 4.39-4.36 (m, 1H), 3.60-3.50 (m, 1H), 2.67-2.66 (m, 1H), 2.52-2.51 (m, 1H), 2.07-2.04 (m, 2H), 1.92-1.88 (m, 2H), 1.57-1.56 (m, 2H), 1.38-1.35 (m, 2H), 1.24 (s, 3H), 1.23 (s, 3H), 1.16 (s, 3H). LCMS (ESI): m/z = 467.2 [M + H]$^+$. |

TABLE 10

The following examples were made in a manner similar to that for Example 6:

| Ex. | Name | Structure | NMR, MS |
|---|---|---|---|
| 316 and 317 | (R)-N-(2-(hydroxymethyl)-6-(4-(hydroxymethyl)piperidin-1-yl)-2-(trifluoromethyl)-2,3-dihydrobenzofuran-5-yl)pyrazolo[1,5-a]pyrimidine-3-carboxamide and (S)-N-(2-(hydroxymethyl)-6-(4-(hydroxymethyl)piperidin-1-yl)-2-(trifluoromethyl)-2,3-dihydrobenzofuran-5-yl)pyrazolo[1,5-a]pyrimidine-3-carboxamide (absolute stereochemistry assigned arbitrarily) |  | Example 316, Peak 1: $^1$H NMR (400 MHz, Chloroform-d) δ 10.44 (s, 1H), 8.77-8.66 (m, 3H), 8.41 (s, 1H), 6.96 (dd, J = 7.0, 4.1 Hz, 1H), 6.69 (s, 1H), 3.99 (d, J = 12.3 Hz, 1H), 3.79 (d, J = 12.4 Hz, 1H), 3.56 (d, J = 4.9 Hz, 2H), 3.38 (q, J = 16.2 Hz, 2H), 3.02 (t, J = 10.6 Hz, 2H), 2.60 (dd, J = 11.7, 9.2 Hz, 2H), 2.34-1.90 (m, 1H), 1.79-1.62 (m, 4H), 1.30-1.11 (m, 2H). (ESI): m/z = 492.2 [M + 1]$^+$. Example 317, Peak 2: $^1$H NMR (400 MHz, Chloroform-d) δ 10.52 (s, 1H), 8.86-8.75 (m, 3H), 8.50 (s, 1H), 7.03 (dd, J = 7.0, 4.2 Hz, 1H), 6.77 (s, 1H), 4.07 (d, J = 12.4 Hz, 1H), 3.85 (d, J = 12.4 Hz, 1H), 3.64 (d, J = 4.9 Hz, 2H), 3.55-3.37 (m, 2H), 3.21-2.97 (m, 2H), 2.67 (q, J = 10.0 Hz, 2H), 2.29-1.87 (m, 2H), 1.75 (d, J = 29.5 Hz, 3H), 1.37-1.20 (m, 2H). (ESI): m/z = 492.2 [M + 1]$^+$. |
| 318 and 319 | (R)-N-(6-(4-fluoro-4-(hydroxymethyl)piperidin-1-yl)-2-(hydroxymethyl)-2-(trifluoromethyl)-2,3-dihydrobenzofuran-5-yl)pyrazolo[1,5-a]pyrimidine-3-carboxamide and (S)-N-(6-(4-fluoro-4-(hydroxymethyl)piperidin-1-yl)-2-(hydroxymethyl)-2-(trifluoromethyl)-2,3-dihydrobenzofuran-5-yl)pyrazolo[1,5-a]pyrimidine-3-carboxamide (absolute stereochemistry assigned arbitrarily) |  | Example 318, Peak 1: $^1$H NMR (400 MHz, dimethyl sulfoxide-d$_6$) δ 10.46 (s, 1H), 9.37 (dt, J = 7.0, 1.0 Hz, 1H), 8.89 (dd, J = 4.3, 1.5 Hz, 1H), 8.70 (s, 1H), 8.42 (s, 1H), 7.34 (dd, J = 7.0, 4.2 Hz, 1H), 6.92 (s, 1H), 5.57 (t, J = 6.1 Hz, 1H), 5.16 (t, J = 5.9 Hz, 1H), 3.76 (qd, J = 12.1, 6.1 Hz, 2H), 3.60-3.45 (m, 3H), 3.37 (s, 1H), 2.87 (q, J = 9.4, 8.8 Hz, 4H), 2.06 (dt, J = 35.2, 11.3 Hz, 2H), 1.86 (t, J = 12.3 Hz, 2H). (ESI): m/z = 510.2 [M + 1]$^+$. Example 319, Peak 2: $^1$H NMR (400 MHz, dimethyl sulfoxide-d$_6$) δ 10.44 (s, 1H), 9.34 (d, J = 7.0 Hz, 1H), 8.88 (dd, J = 4.2, 1.5 Hz, 1H), 8.68 (s, 1H), 8.40 (s, 1H), 7.32 (dd, J = 7.0, 4.2 Hz, 1H), 6.90 (s, 1H), 5.66-5.56 (m, 1H), 5.22-5.10 (m, 1H), 3.76 (qd, J = 12.1, 6.1 Hz, 2H), 3.53 (dd, J = 17.6, 6.2 Hz, 3H), 3.34 (d, J = 16.6 Hz, 1H), 2.94-2.79 (m, 4H), 2.15-1.95 (m, 2H), 1.90-1.81 (m, 2H). (ESI): m/z = 510.2 [M + 1]$^+$. |

TABLE 10-continued

The following examples were made in a manner similar to that for Example 6:

| Ex. | Name | Structure | NMR, MS |
|---|---|---|---|
| 320 and 321 | (R)-N-(2-(hydroxymethyl)-2-methyl-6-(1-oxo-2,7-diazaspiro[3.5]nonan-7-yl)-2,3-dihydrobenzofuran-5-yl)pyrazolo[1,5-a]pyrimidine-3-carboxamide and (S)-N-(2-(hydroxymethyl)-2-methyl-6-(1-oxo-2,7-diazaspiro[3.5]nonan-7-yl)-2,3-dihydrobenzofuran-5-yl)pyrazolo[1,5-a]pyrimidine-3-carboxamide (absolute stereochemistry assigned arbitrarily) | | Example 320, Peak 1: $^1$H NMR (400 MHz, Chloroform-d) δ 10.69 (s, 1H), 9.15 (s, 1H), 8.80 (dd, J = 7.1, 1.7 Hz, 1H), 8.77 (s, 1H), 8.56 (s, 1H), 7.11 (dd, J = 7.0, 4.1 Hz, 1H), 6.62 (s, 1H), 5.68 (s, 1H), 3.66 (d, J = 6.3 Hz, 2H), 3.33 (s, 2H), 3.24 (d, J = 15.6 Hz, 1H), 3.13-3.04 (m, 2H), 2.94 (d, J = 15.5 Hz, 1H), 2.69 (t, J = 11.6 Hz, 2H), 2.52 (td, J = 12.6, 4.1 Hz, 2H), 1.92 (dd, J = 9.5, 5.0 Hz, 3H), 1.46 (s, 3H). (ESI): m/z = 463.2 [M + 1]$^+$. Example 321, Peak 2: $^1$H NMR (400 MHz, Chloroform-d) δ 10.69 (s, 1H), 9.14 (s, 1H), 8.84-8.73 (m, 2H), 8.56 (s, 1H), 7.11 (dd, J = 7.0, 4.1 Hz, 1H), 6.62 (s, 1H), 5.68 (s, 1H), 3.66 (d, J = 6.0 Hz, 2H), 3.34 (s, 2H), 3.24 (d, J = 15.6 Hz, 1H), 3.08 (d, J = 11.8 Hz, 2H), 2.94 (d, J = 15.6 Hz, 1H), 2.70 (dd, J = 12.8, 10.5 Hz, 2H), 2.57-2.45 (m, 2H), 1.91 (d, J = 13.5 Hz, 3H), 1.46 (s, 3H). (ESI): m/z = 463.2 [M + 1]$^+$. |
| 322 | N-(2-(hydroxymethyl)-6-(6-(hydroxymethyl)-3-azabicyclo[3.1.0]hexan-3-yl)-2-methyl-2,3-dihydrobenzofuran-5-yl)pyrazolo[1,5-a]pyrimidine-3-carboxamide | 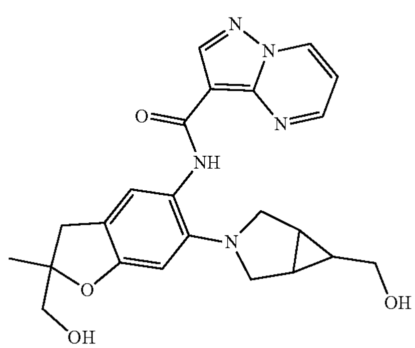 [SMILES: CC1(CO)Cc2cc(NC(=O)c3cnn4cccnc34)c(N3CC4C(CO)C4C3)cc2O1] | $^1$H NMR (400 MHz, Chloroform-d) δ 9.67 (s, 1H), 8.85 (d, J = 4.1 Hz, 1H), 8.76-8.68 (m, 2H), 8.17 (s, 1H) 6.99 (dd, J = 7.0, 4.2 Hz, 1H), 6.55 (s, 1H), 3.59 (s, 2H), 3.46 (d, J = 7.3 Hz, 2H), 3.34 (t, J = 8.1 Hz, 2H), 3.15 (d, J = 15.5 Hz, 1H), 2.96 (t, J = 8.9 Hz, 2H), 2.85 (d, J = 15.4 Hz, 1H), 1.38 (s, 5H), 1.31-1.15 (m, 3H). (ESI): m/z = 436.2 [M + 1]$^+$. |

TABLE 10-continued

The following examples were made in a manner similar to that for Example 6:

| Ex. | Name | Structure | NMR, MS |
|---|---|---|---|
| 323 and 324 | N-[(2S)-2-(Hydroxymethyl)-6-[4-(1-hydroxy-1-methyl-ethyl)-1-piperidyl]-2-methyl-3H-benzofuran-5-yl]pyrazolo[1,5-α]pyrimidine-3-carboxamide and N-[(2R)-2-(Hydroxymethyl)-6-[4-(1-hydroxy-1-methyl-ethyl)-1-piperidyl]-2-methyl-3H-benzofuran-5-yl]pyrazolo[1,5-α]pyrimidine-3-carboxamide (absolute stereochemistry assigned arbitrarily) | | Example 323, Peak 1: $^1$HNMR (400 MHz, CDCl$_3$) δ 10.45 (s, 1H), 8.85-8.75 (m, 3H), 8.43 (s, 1H), 7.00 (dd, J = 7.2, 4.0 Hz, 1H), 6.66 (s, 1H), 3.75-3.65 (m, 2H), 3.24 (d, J = 16.0 Hz, 1H), 3.20-3.10 (m, 1H), 2.94 (d, J = 16.0 Hz, 1 H), 2.66-2.60 (m, 2 H), 1.90-1.70 (m, 5 H), 1.47 (s, 3 H), 1.27 (s, 6H). LCMS (ESI): m/z = 466.2 [M + H]$^+$. Example 324, Peak 2: $^1$HNMR (400 MHz, CDCl$_3$) δ 10.44 (s, 1H), 8.84-8.77 (m, 3H), 8.42 (s, 1H), 7.00 (dd, J = 7.2, 4.0 Hz, 1H), 6.66 (s, 1H), 3.67 (s, 2H), 3.24 (d, J = 16.0 Hz, 1H), 3.20-3.10 (m, 1H), 2.94 (d, J = 16.0 Hz, 1 H), 2.65-2.62 (m, 2 H), 1.90-1.70 (m, 5 H), 1.47 (s, 3 H), 1.26 (s, 6H). LCMS (ESI): m/z = 466.2 [M + H]$^+$. |
| 325 | N-(6-(4-(2,2-Difluoroethyl)piperazin-1-yl)-2-(hydroxymethyl)-2-methyl-2,3-dihydrobenzofuran-5-yl)-6-methylpyrazolo[1,5-a]pyrimidine-3-carboxamide | 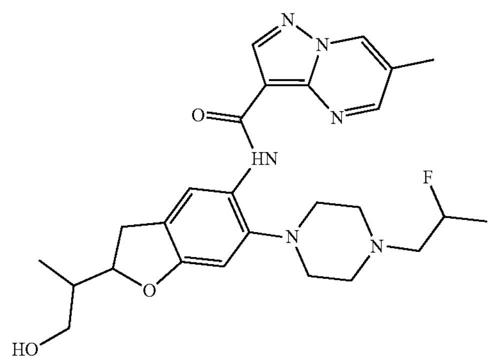 | $^1$H NMR (400 MHz, dimethyl sulfoxide-d$_6$) δ 10.31 (s, 1H), 9.22 (s, 1H), 8.82 (d, J = 1.6 Hz, 1H), 8.59 (s, 1H), 8.27 (s, 1H), 6.69 (s, 1H), 6.33-6.06 (m, 1H), 5.04 (t, J = 6.0 Hz, 1H), 3.42 (t, J = 5.2 Hz, 1H), 3.32-3.17 (m, 2H), 2.88-2.84 (m, 2H), 2.84-2.79 (m, 8H), 2.44 (s, 3H), 1.33 (s, 3H). LCMS (ESI): m/z = 487.5 [M + H]$^+$ |
| 326 and 327 | (S)-N-(6-(4-(2,2-Difluoroethyl)piperazin-1-yl)-2-(hydroxymethyl)-2-methyl-2,3-dihydrobenzofuran-5-yl)-6-methylpyrazolo[1,5-a]pyrimidine-3-carboxamide and (R)-N-(6-(4-(2,2-Difluoroethyl)piperazin-1-yl)-2-(hydroxymethyl)-2-methyl-2,3-dihydrobenzofuran-5-yl)-6-methylpyrazolo[1,5-a]pyrimidine-3-carboxamide (absolute stereochemistry assigned arbitrarily) | | Example 326, Peak 1: $^1$H NMR (400 MHz, CD$_3$OD) δ 8.93 (s, 1H), 8.79 (d, J = 1.6 Hz, 1H), 8.57 (s, 1H), 8.18 (s, 1H), 6.69 (s, 1H), 6.18-5.88 (m, 1H), 3.62-3.57 (m, 2H), 3.24 (d, J = 16.0 Hz, 1H), 2.93-2.85 (m, 11H), 2.50 (s, 3H), 1.42 (s, 3H). MS (ESI): m/z = 487.1 [M + 1]$^+$. Example 327, Peak 2: $^1$H NMR (400 MHz, CD$_3$OD) δ 8.92 (s, 1H), 8.78 (s, 1H), 8.56 (s, 1H), 8.18 (s, 1H), 6.68 (s, 1H), 6.17-5.87 (m, 1H), 3.62-3.57 (m, 2H), 3.24 (d, J = 16.0 Hz, 1H), 2.93-2.85 (m, 11H), 2.50 (s, 3H), 1.42 (s, 3H). MS (ESI): m/z = 487.1 [M + 1]$^+$. |

TABLE 10-continued

The following examples were made in a manner similar to that for Example 6:

| Ex. | Name | Structure | NMR, MS |
|---|---|---|---|
| 328 | N-(6-(4-Fluoro-4-(hydroxymethyl)-piperidin-1-yl)-2-(hydroxymethyl)-2-methyl-2,3-dihydrobenzofuran-5-yl)-6-methylpyrazolo[1,5-α]pyrimidine-3-carboxamide | 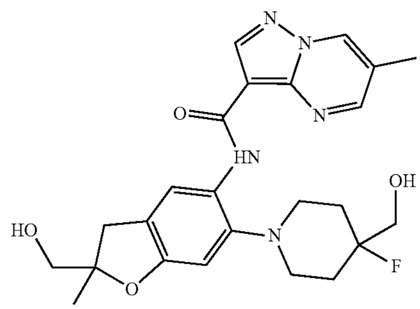 [SMILES: Cc1cnc2c(C(=O)Nc3cc4c(cc3N3CCC(F)(CO)CC3)OC(C)(CO)C4)cnn2c1] | $^1$H NMR (400 MHz, dimethyl sulfoxide-$d_6$) 10.41 (s, 1H), 9.22 (s, 1H), 8.81 (d, J = 2.0 Hz, 1H), 8.59 (s, 1H), 8.31 (s, 1H), 6.68 (s, 1H), 5.22 (t, J = 6.4 Hz, 1H), 5.04 (t, J = 6.4 Hz, 1H), 3.55-3.50 (m, 2H), 3.44-3.41 (m, 2H), 3.19 (d, J = 16.0 Hz, 1H), 2.87-2.80 (m, 5H), 2.40 (s, 3H), 2.17-2.02 (m, 2H), 1.82 (t, J = 5.2 Hz, 2H), 1.34 (s, 3H). LCMS (ESI): m/z = 470.1 [M + H]$^+$. |
| 329, 330, 331 and 332 | N-((R)-6-((R)-4-hydroxy-4-methylazepan-1-yl)-2-(hydroxymethyl)-2-methyl-2,3-dihydrobenzofuran-5-yl)pyrazolo[1,5-a]pyrimidine-3-carboxamide, N-((R)-6-((S)-4-hydroxy-4-methylazepan-1-yl)-2-(hydroxymethyl)-2-methyl-2,3-dihydrobenzofuran-5-yl)pyrazolo[1,5-a]pyrimidine-3-carboxamide, N-((S)-6-((R)-4-hydroxy-4-methylazepan-1-yl)-2-(hydroxymethyl)-2-methyl-2,3-dihydrobenzofuran-5-yl)pyrazolo[1,5- | | Example 329, Peak 4: 1H NMR (400 MHz, dimethyl sulfoxide-d6) δ 10.50 (s, 1H), 9.36 (dd, J = 7.0, 1.6 Hz, 1H), 8.95 (dd, J = 4.2, 1.7 Hz, 1H), 8.67 (s, 1H), 8.24 (s, 1H), 7.35 (dd, J = 7.0, 4.2 Hz, 1H), 6.64 (s, 1H), 5.02 (t, J = 5.8 Hz, 1H), 4.29 (s, 1H), 3.42 (m, 2H), 3.22-3.14 (m, 1H), 3.13-3.03 (m, 1H), 2.94-2.75 (m, 4H), 2.07-1.86 (m, 3H), 1.85-1.69 (m, 2H), 1.62-1.49 (m, 1H), 1.33 (s, 3H), 1.18 (s, 3H). MS (ESI): m/z = 452.2 [M + 1]$^+$. Example 330, Peak 3: $^1$H NMR (400 MHz, dimethyl sulfoxide-d6) δ 10.50 (s, 1H), 9.36 (dd, J = 7.0, 1.6 Hz, 1H), 8.95 (dd, J = 4.2, 1.6 Hz, 1H), 8.67 (s, 1H), 8.24 (s, 1H), 7.35 (dd, J = 7.0, 4.2 Hz, 1H), 6.64 (s, 1H), 5.02 (t, J = 5.8 Hz, 1H), 4.29 (s, 1H), 3.42 (m, 2H), 3.18 (d, J = 15.9 Hz, 1H), 3.07 (m, 1H), 2.95-2.73 (m, 4H), 2.09-1.86 (m, |

TABLE 10-continued

The following examples were made in a manner similar to that for Example 6:

| Ex. | Name | Structure | NMR, MS |
|---|---|---|---|
| | a]pyrimidine-3-carboxamide and N-((S)-6-((S)-4-hydroxy-4-methylazepan-1-yl)-2-(hydroxymethyl)-2-methyl-2,3-dihydrobenzofuran-5-yl)pyrazolo[1,5-a]pyrimidine-3-carboxamide (absolute and relative stereochemistry assigned arbitrarily) | 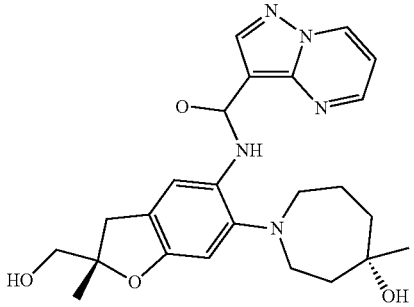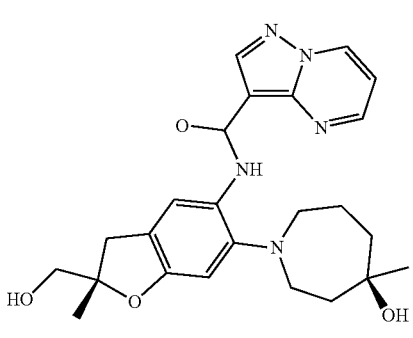 | 3H), 1.85-1.70 (m, 2H), 1.63-1.47 (m, 1H), 1.34 (s, 3H), 1.18 (s, 3H). MS (ESI): m/z = 452.2 [M + 1]$^+$. Example 331, Peak 2: 1H NMR (400 MHz, dimethyl sulfoxide-d6) δ 10.50 (s, 1H), 9.36 (dd, J = 7.0, 1.6 Hz, 1H), 8.95 (dd, J = 4.2, 1.7 Hz, 1H), 8.67 (s, 1H), 8.24 (s, 1H), 7.35 (dd, J = 7.0, 4.2 Hz, 1H), 6.64 (s, H), 5.02 (t, J = 5.8 Hz, 1H), 4.29 (s, 1H), 3.49-3.35 (m, 2H), 3.18 (d, J = 16.1 Hz, 1H), 3.07 (m, 1H), 2.95-2.73 (m, 4H), 2.06-1.87 (m, 3H), 1.85-1.70 (m, 2H), 1.60-1.48 (m, 1H), 1.34 (s, 3H), 1.18 (s, 3H). MS (ESI): m/z = 452.2 [M + 1]$^+$. Example 332, Peak 1: $^1$H NMR (400 MHz, dimethyl sulfoxide-d6) δ 10.50 (s, 1H), 9.36 (dd, J = 7.0, 1.6 Hz, 1H), 8.95 (dd, J = 4.2, 1.7 Hz, 1H), 8.67 (s, 1H), 8.24 (s, 1H), 7.35 (dd, J = 7.0, 4.2 Hz, 1H), 6.64 (s, 1H), 5.02 (t, J = 5.8 Hz, 1H), 4.29 (s, 1H), 3.42 (m, 2H), 3.18 (d, J = 16.2 Hz, 1H), 3.14-2.98 (m, 1H), 2.95-2.73 (m, 4H), 2.10-1.85 (m, 3H), 1.85-1.68 (m, 2H), 1.62-1.47 (m, 1H), 1.33 (s, 3H), 1.18 (s, 3H). MS (ESI): m/z = 452.2 [M + 1]$^+$. |

TABLE 10-continued

The following examples were made in a manner similar to that for Example 6:

| Ex. | Name | Structure | NMR, MS |
|---|---|---|---|
| 333 and 334 | (R)-N-(6-(4-(2-amino-2-oxoethyl)piperidin-1-yl)-2-(hydroxymethyl)-2-methyl-2,3-dihydrobenzofuran-5-yl)pyrazolo[1,5-a]pyrimidine-3-carboxamide and (S)-N-(6-(4-(2-amino-2-oxoethyl)piperidin-1-yl)-2-(hydroxymethyl)-2-methyl-2,3-dihydrobenzofuran-5-yl)pyrazolo[1,5-a]pyrimidine-3-carboxamide (absolute stereochemistry assigned arbitrarily) | | Example 333, Peak 1: $^1$H NMR (400 MHz, dimethyl sulfoxide-d6) δ 10.43 (s, 1H), 9.36 (dd, J = 7.0, 1.6 Hz, 1H), 8.88 (dd, J = 4.2, 1.6 Hz, 1H), 8.68 (s, 1H), 8.31 (s, 1H), 7.33 (m, 2H), 6.79 (s, 1H), 6.67 (s, 1H), 5.02 (t, J = 5.8 Hz, 1H), 3.42 (m, 2H), 3.19 (d, J = 16.0 Hz, 1H), 2.90 (d, J = 11.1 Hz, 2H), 2.82 (d, J = 15.9 Hz, 1H), 2.64 (t, J = 11.3 Hz, 2H), 2.14-2.04 (m, 2H), 1.89-1.77 (m, 1H), 1.73 (m, 2H), 1.64-1.49 (m, 2H), 1.34 (s, 3H). MS (ESI): m/z = 465.2 [M + 1]$^+$. Example 334, Peak 2: $^1$H NMR (400 MHz, dimethyl sulfoxide-d6) δ 10.43 (s, 1H), 9.36 (dd, J = 7.0, 1.6 Hz, 1H), 8.88 (dd, J = 4.2, 1.6 Hz, 1H), 8.68 (s, 1H), 8.31 (s, 1H), 7.33 (m, 2H), 6.79 (s, 1H), 6.67 (s, 1H), 5.02 (t, J = 5.8 Hz, 1H), 3.42 (m, 2H), 3.19 (d, J = 16.0 Hz, 1H), 2.90 (d, J = 11.1 Hz, 2H), 2.82 (d, J = 15.9 Hz, 1H), 2.64 (t, J = 11.3 Hz, 2H), 2.10 (m, 2H), 1.87-1.77 (m, 1H), 1.73 (m, 2H), 1.67-1.46 (m, 2H), 1.34 (s, 3H). MS (ESI): m/z = 465.2 [M + 1]$^+$. |
| 335 and 336 | (R)-N-(6-(4-cyanopiperidin-1-yl)-2-(hydroxymethyl)-2-methyl-2,3-dihydrobenzofuran-5-yl)pyrazolo[1,5-a]pyrimidine-3-carboxamide and (S)-N-(6-(4-cyanopiperidin-1-yl)-2-(hydroxymethyl)-2-methyl-2,3-dihydrobenzofuran-5-yl)pyrazolo[1,5-a]pyrimidine-3-carboxamide (absolute stereochemistry assigned arbitrarily) | | Example 336, Peak 1: $^1$H NMR (400 MHz, dimethyl sulfoxide-d$_6$) δ 10.37 (s, 1H), 9.38 (dd, J = 7.0, 1.6 Hz, 1H), 8.86 (dd, J = 4.2, 1.7 Hz, 1H), 8.69 (s, 1H), 8.30 (d, J = 1.0 Hz, 1H), 7.38 (dd, J = 7.0, 4.2 Hz, 1H), 6.65 (s, 1H), 5.09-4.96 (m, 1H), 3.49-3.36 (m, 2H), 3.20 (d, J = 16.8 Hz, 1H), 3.09 (m, 1H), 2.96-2.86 (m, 2H), 2.86-2.79 (m, 1H), 2.76 (m, 2H), 2.17-2.07 (m, 2H), 2.00 (m, 2H), 1.34 (s, 3H). MS (ESI): m/z = 433.2 [M + 1]$^+$. Example 335, Peak 2: $^1$H NMR (400 MHz, dimethyl sulfoxide-d6) δ 10.37 (s, 1H), 9.38 (dd, J = 7.0, 1.7 Hz, 1H), 8.86 (dd, J = 4.2, 1.6 Hz, 1H), 8.69 (s, 1H), 8.30 (s, 1H), 7.38 (dd, J = 7.0, 4.2 Hz, 1H), 6.65 (s, 1H), 5.07-4.98 (m, 1H), 3.42 (m, 2H), 3.20 (d, J = 16.8 Hz, 1H), 3.09 (m, 1H), 2.97-2.87 (m, 2H), 2.87-2.71 (m, 3H), 2.18-2.06 (m, 2H), 2.00 (m, 2H), 1.34 (s, 3H). MS (ESI): m/z = 433.2 [M + 1]$^+$. |

TABLE 10-continued

The following examples were made in a manner similar to that for Example 6:

| Ex. | Name | Structure | NMR, MS |
|---|---|---|---|
| 337, 338, 339 and 340 | N-((R)-6-((R)-4-hydroxyazepan-1-yl)-2-(hydroxymethyl)-2-methyl-2,3-dihydrobenzofuran-5-yl)pyrazolo[1,5-a]pyrimidine-3-carboxamide, N-((R)-6-((S)-4-hydroxyazepan-1-yl)-2-(hydroxymethyl)-2-methyl-2,3-dihydrobenzofuran-5-yl)pyrazolo[1,5-a]pyrimidine-3-carboxamide, N-((S)-6-((R)-4-hydroxyazepan-1-yl)-2-(hydroxymethyl)-2-methyl-2,3-dihydrobenzofuran-5-yl)pyrazolo[1,5-a]pyrimidine-3-carboxamide and N-((S)-6-((S)-4-hydroxyazepan-1-yl)-2-(hydroxymethyl)-2-methyl-2,3-dihydrobenzofuran-5-yl)pyrazolo[1,5-a]pyrimidine-3-carboxamide (absolute and relative stereochemistry assigned arbitrarily) | (four structures shown) | Example 337, Peak 1: $^1$H NMR (400 MHz, dimethyl sulfoxide-d6) δ 10.45 (s, 1H), 9.36 (dd, J = 7.0, 1.7 Hz, 1H), 8.93 (dd, J = 4.2, 1.7 Hz, 1H), 8.67 (s, 1H), 8.24 (s, 1H), 7.34 (dd, J = 7.0, 4.2 Hz, 1H), 6.63 (s, 1H), 5.06-4.97 (m, 1H), 4.54 (d, J = 3.7 Hz, 1H), 3.92 (m, 1H), 3.52-3.37 (m, 2H), 3.18 (d, J = 16.5 Hz, 1H), 3.03-2.75 (m, 5H), 2.10-2.00 (m, 1H), 1.99-1.79 (m, 3H), 1.81-1.70 (m, H), 1.69-1.58 (m, 1H), 1.34 (s, 3H). MS (ESI): m/z = 438.2 [M + 1]$^+$.<br>Example 338, Peak 2: $^1$H NMR (400 MHz, dimethyl sulfoxide-d6) δ 10.45 (s, 1H), 9.36 (dd, J = 7.0, 1.7 Hz, 1H), 8.93 (dd, J = 4.2, 1.7 Hz, 1H), 8.67 (s, 1H), 8.24 (s, 1H), 7.34 (dd, J = 7.0, 4.2 Hz, 1H), 6.63 (s, 1H), 5.06-4.96 (m, 1H), 4.54 (d, J = 3.7 Hz, 1H), 4.00-3.85 (m, 1H), 3.48-3.36 (m, 2H), 3.23-3.13 (m, 1H), 3.04-2.77 (m, 5H), 2.05 (m, 1H), 1.98-1.81 (m, 3H), 1.81-1.71 (m, 1H), 1.72-1.58 (m, 1H), 1.33 (s, 3H). MS (ESI): m/z = 433.2 [M + 1]$^+$.<br>Example 339, Peak 3: $^1$H NMR (400 MHz, DMSO-d6) δ 10.45 (s, 1H), 9.36 (dd, J = 7.0, 1.7 Hz, 1H), 8.93 (dd, J = 4.2, 1.7 Hz, 1H), 8.67 (s, 1H), 8.24 (s, 1H), 7.34 (dd, J = 7.0, 4.2 Hz, 1H), 6.63 (s, 1H), 5.02 (t, J = 5.8 Hz, 1H), 4.54 (d, J = 3.7 Hz, 1H), 3.92 (m, 1H), 3.51-3.37 (m, 2H), 3.18 (d, J = 16.2 Hz, 1H), 3.06-2.90 (m, 3H), 2.87 (m, 1H), 2.85-2.75 (m, 1H), 2.12-1.99 (m, 1H), 1.99-1.81 (m, 3H), 1.81-1.69 (m, 1H), 1.69-1.57 (m, 1H), 1.34 (s, 3H). MS (ESI): m/z = 438.2 [M + 1]$^+$.<br>Example 340, Peak 4: $^1$H NMR (400 MHz, DMSO-d6) δ 10.45 (s, 1H), 9.36 (dd, J = 7.0, 1.6 Hz, 1H), 8.93 (dd, J = 4.2, 1.6 Hz, 1H), 8.67 (s, 1H), 8.24 (s, 1H), 7.34 (dd, J = 7.0, 4.2 Hz, 1H), 6.63 (s, 1H), 5.02 (t, J = 5.8 Hz, 1H), 4.54 (d, J = 3.6 Hz, 1H), 3.92 (m, 1H), 3.42 (m, 2H), 3.18 (d, J = 16.1 Hz, 1H), 3.05-2.85 (m, 3H), 2.85-2.75 (m, 1H), 2.11-1.99 (m, 1H), 1.99-1.81 (m, 3H), 1.81-1.55 (m, 2H), 1.33 (s, 3H). MS (ESI): m/z = 438.2 [M + 1]$^+$. |

TABLE 10-continued

The following examples were made in a manner similar to that for Example 6:

| Ex. | Name | Structure | NMR, MS |
|---|---|---|---|
| 341 and 342 | N-[(2R)-6-[4-(1-hydroxycyclopropyl)-1-piperidyl]-2-(hydroxymethyl)-2-methyl-3H-benzofuran-5-yl]pyrazolo[1,5-a]pyrimidine-3-carboxamide and N-[(2S)-6-[4-(1-hydroxycyclopropyl)-1-piperidyl]-2-(hydroxymethyl)-2-methyl-3H-benzofuran-5-yl]pyrazolo[1,5-a]pyrimidine-3-carboxamide (absolute stereochemistry assigned arbitrarily) |  | Example 341, Peak 1: $^1$H NMR (400 MHz, CDCl$_3$) δ 10.57 (s, 1H), 8.95-8.90 (m, 1H), 8.78-8.77 (m, 2H), 8.48 (s, 1H), 6.99 (dd, J = 6.8, 4.0 Hz, 1H), 6.65 (s, 1H), 3.66 (d, J = 6.0 Hz, 2H), 3.22 (d, J = 16.0 Hz, 1H), 3.15-3.12 (m, 2H), 2.93 (d, J = 16.0 Hz, 1H), 2.66-2.60 (m, 2H), 2.08-2.06 (m, 2H), 1.88 (t, J = 6.0 Hz, 1H), 1.80-1.78 (m, 3H), 1.46 (s, 3H), 1.02-0.99 (m, 1H), 0.79 (t, J = 6.0 Hz, 2H), 0.53 (t, J = 5.6 Hz, 2H). LCMS (ESI): m/z = 464.0 [M + H]$^+$. Example 342, Peak 2: $^1$HNMR (400 MHz, CDCl$_3$) δ 10.50 (s, 1H), 8.90-8.85 (m, 1H), 8.75-8.65 (m, 2H), 8.41 (s, 1H), 6.92 (dd, J = 6.8, 4.0 Hz, 1H), 6.58 (s, 1H), 3.60-3.55 (m, 2H), 3.16 (d, J = 15.6 Hz, 1H), 3.10-3.00 (m, 2H), 2.86 (d, J = 15.6 Hz, 1H), 2.60-2.54 (m, 2H), 2.02-1.98 (m, 2H), 1.90-1.70 (m, 4H), 1.39 (s, 3H), 0.95-0.85 (m, 1H), 0.73 (t, J = 6.0 Hz, 2H), 0.46 (t, J = 5.6 Hz, 2H). LCMS (ESI): m/z = 464.1 [M + H]$^+$. |
| 343 | N-[2-(Hydroxymethyl)-2-methyl-6-(4-propanoyl-1-piperidyl)-3H-benzofuran-5-yl]pyrazolo[1,5-a]pyrimidine-3-carboxamide | 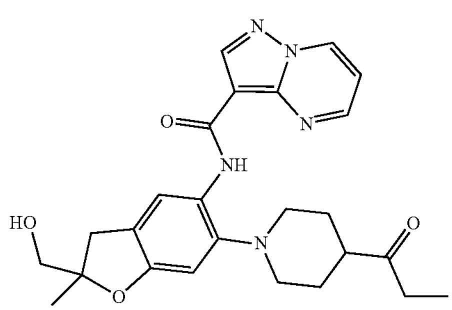 [SMILES: CCC(=O)C1CCN(c2cc3c(cc2NC(=O)c2cnn4cccnc24)CC(C)(CO)O3)CC1] | $^1$H NMR (400 MHz, CDCl$_3$): δ 10.62 (s, 1H), 9.05-9.00 (m, 1H), 8.80-8.75 (m, 2H), 8.53 (s, 1H), 7.10 (dd, J = 7.2, 4.0 Hz, 1H), 6.64 (s, 1H), 3.66 (s, 2H), 3.23 (d, J = 15.2 Hz, 1H), 3.12-3.09 (m, 2H), 2.93 (d, J = 15.6 Hz, 1H), 2.69-2.61 (m, 2H), 2.56 (q, J = 7.2 Hz, 2H), 2.12-2.09 (m, 2H), 1.87-1.83 (m, 2H), 1.46 (s, 3H), 1.10 (t, J = 7.2 Hz, 3H). LCMS (ESI): m/z = 486.2 [M + Na]$^+$. |

TABLE 10-continued

The following examples were made in a manner similar to that for Example 6:

| Ex. | Name | Structure | NMR, MS |
|---|---|---|---|
| 344 and 345 | N-(6-(4-(1H-imidazol-1-yl)piperidin-1-yl)-2-(hydroxymethyl)-2-methyl-2,3-dihydrobenzofuran-5-yl)pyrazolo[1,5-a]pyrimidine-3-carboxamide (absolute stereochemistry assigned arbitrarily) |  | Example 344, Peak 1: $^1$H NMR (400 MHz, dimethyl sulfoxide-d6) δ 10.30 (s, 1H), 9.36 (dd, J = 7.0, 1.7 Hz, 1H), 8.82 (dd, J = 4.2, 1.7 Hz, 1H), 8.68 (s, 1H), 8.23 (s, 1H), 7.77 (s, 1H), 7.35 (dd, J = 7.0, 4.2 Hz, 1H), 7.28 (t, J = 1.2 Hz, 1H), 6.95 (s, 1H), 6.70 (s, 1H), 5.11-4.94 (m, 1H), 4.22 (m, 1H), 3.51-3.39 (m, 2H), 3.25-3.16 (m, 1H), 3.11-3.00 (m, 2H), 2.93-2.77 (m, 3H), 2.21-2.10 (m, 4H), 1.35 (s, 3H). MS (ESI): m/z = 474.2 [M + 1]$^+$.<br>Example 345, Peak 2: $^1$H NMR (400 MHz, dimethyl sulfoxide-d6) δ 10.30 (s, 1H), 9.36 (dd, J = 7.0, 1.7 Hz, 1H), 8.82 (dt, J = 4.2, 1.4 Hz, 1H), 8.68 (s, 1H), 8.23 (s, 1H), 7.77 (s, 1H), 7.39-7.31 (m, 1H), 7.28 (q, J = 1.4 Hz, 1H), 6.95 (t, J = 1.0 Hz, 1H), 6.70 (s, 1H), 5.09-4.95 (m, 1H), 4.30-4.17 (m, 1H), 3.52-3.39 (m, 2H), 3.25-3.17 (m, 1H), 3.14-3.00 (m, 2H), 2.92-2.77 (m, 3H), 2.23-2.07 (m, 4H), 1.35 (s, 3H). MS (ESI): m/z = 474.1 [M + 1]$^+$. |
| 346 and 347 | (S)-N-(6-(4-fluoro-4-(hydroxymethyl)piperidin-1-yl)-2-(hydroxymethyl)-2-methyl-2,3-dihydrobenzofuran-5-yl)pyrazolo[1,5-a]pyrimidine-3-carboxamide and (R)-N-(6-(4-fluoro-4-(hydroxymethyl)piperidin-1-yl)-2-(hydroxymethyl)-2-methyl-2,3-dihydrobenzofuran-5-yl)pyrazolo[1,5-a]pyrimidine-3-carboxamide (absolute stereochemistry assigned arbitrarily) |  | Example 346, Peak 1: $^1$H NMR (400 MHz, DMSO-d6) δ 10.41 (s, 1H), 9.22 (dd, J = 2.1, 1.2 Hz, 1H), 8.82 (d, J = 2.0 Hz, 1H), 8.59 (s, 1H), 8.31 (s, 1H), 6.68 (s, 1H), 5.20 (t, J = 5.8 Hz, 1H), 5.09-4.96 (m, 1H), 3.53 (dd, J = 15.8, 5.8 Hz, 2H), 3.42 (m, 2H), 3.24-3.15 (m, 1H), 2.95-2.76 (m, 5H), 2.40 (d, J = 1.1 Hz, 3H), 2.20-1.99 (m, 2H), 1.82 (t, J = 12.1 Hz, 2H), 1.34 (s, 3H). LCMS (ESI): m/z = 470.2 [M + H]$^+$.<br>Example 347, Peak 2: $^1$H NMR (400 MHz, DMSO-d$_6$) δ 10.41 (s, 1H), 9.22 (dt, J = 2.1, 1.1 Hz, 1H), 8.82 (dd, J = 2.1, 0.5 Hz, 1H), 8.59 (s, 1H), 8.31 (d, J = 0.9 Hz, 1H), 6.68 (s, 1H), 5.20 (t, J = 5.8 Hz, 1H), 5.07-4.98 (m, 1H), 3.53 (dd, J = 15.8, 5.9 Hz, 2H), 3.48-3.36 (m, 2H), 3.24-3.14 (m, 1H), 2.94-2.76 (m, 5H), 2.44-2.36 (m, 3H), 2.09 (m, 2H), 1.82 (t, J = 12.1 Hz, 2H), 1.34 (s, 3H). LCMS (ESI): m/z = 470.2 [M + H]$^+$. |

TABLE 10-continued

The following examples were made in a manner similar to that for Example 6:

| Ex. | Name | Structure | NMR, MS |
|---|---|---|---|
| 348 and 349 | N-((R)-6-((1R,5S,6S)-6-carbamoyl-3-azabicyclo[3.1.0]hexan-3-yl)-2-(hydroxymethyl)-2-methyl-2,3-dihydrobenzofuran-5-yl)pyrazolo[1,5-a]pyrimidine-3-carboxamide and N-((S)-6-((1R,5S,6R)-6-carbamoyl-3-azabicyclo[3.1.0]hexan-3-yl)-2-(hydroxymethyl)-2-methyl-2,3-dihydrobenzofuran-5-yl)pyrazolo[1,5-a]pyrimidine-3-carboxamide (absolute stereochemistry assigned arbitrarily) | 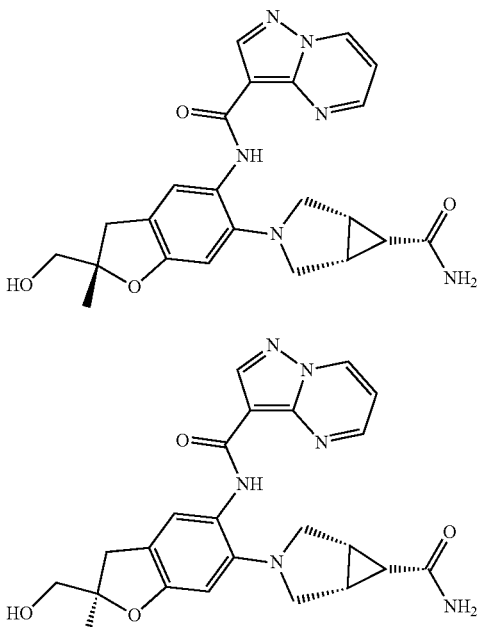 | Example 348, Peak 1: $^1$H NMR (400 MHz, dimethyl sulfoxide-d6) δ 9.32-9.28 (m, 2H), 8.84-8.80 (m, 1H), 8.77 (s, 1H), 7.44 (s, 1H), 7.32 (s, 1H), 7.26 (dd, J = 7.0, 4.2 Hz, 1H), 6.69 (s, 1H), 6.41 (s, 1H), 5.04-4.98 (m, 1H), 3.57 (d, J = 8.6 Hz, 2H), 3.46-3.38 (m, 2H), 3.20 (d, J = 8.6 Hz, 2H), 3.12 (d, J = 16.2 Hz, 1H), 2.74 (d, J = 16.0 Hz, 1H), 1.85-1.78 (m, 2H), 1.58 (t, J = 8.0 Hz, 1H), 1.33 (s, 3H). MS (ESI): m/z = 449.1 [M + 1]$^+$. Example 349, Peak 2: $^1$H NMR (400 MHz, dimethyl sulfoxide-d6) δ 9.32-9.28 (m, 2H), 8.83 (d, J = 1.7 Hz, 1H), 8.77 (s, 1H), 7.44 (s, 1H), 7.32 (s, 1H), 7.26 (dd, J = 7.0, 4.2 Hz, 1H), 6.69 (s, 1H), 6.41 (s, 1H), 5.04-4.98 (m, 1H), 3.57 (d, J = 9.1 Hz, 2H), 3.47-3.37 (m, 2H), 3.24-3.16 (m, 3H), 3.12 (d, J = 16.2 Hz, 1H), 2.74 (d, J = 16.1 Hz, 1H), 1.85-1.78 (m, 2H), 1.58 (t, J = 8.0 Hz, 1H), 1.33 (s, 3H). MS (ESI): m/z = 449.1 [M + 1]$^+$. |
| 350 and 351 | N-(2-(hydroxymethyl)-2-methyl-6-((1-methyl-1H-pyrazol-4-yl)methoxy)-2,3-dihydrobenzofuran-5-yl)pyrazolo[1,5-a]pyrimidine-3-carboxamide and N-(3-hydroxy-3-methyl-7-((1-methyl-1H-pyrazol-4-yl)methoxy)chroman-6-yl)pyrazolo[1,5-a]pyrimidine-3-carboxamide (absolute stereochemistry assigned arbitrarily) | 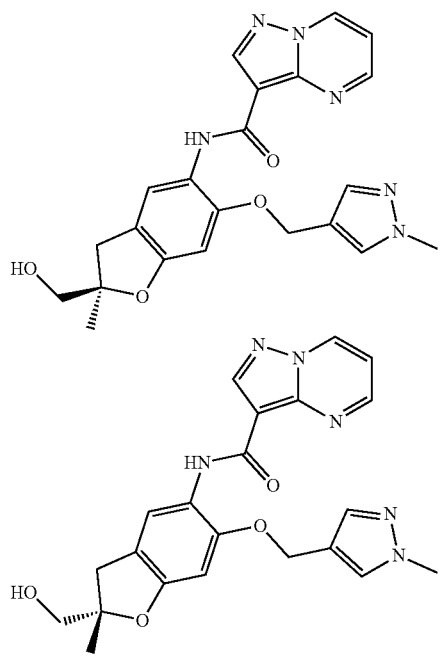 [SMILES: Cn1cc(COc2cc3c(cc2NC(=O)c2cnn4cccnc24)C[C@](C)(CO)O3)cn1 ; Cn1cc(COc2cc3c(cc2NC(=O)c2cnn4cccnc24)C[C@@](C)(CO)O3)cn1] | Example 350, Peak 2: $^1$H NMR (400 MHz, DMSO-d6) δ 10.13 (s, 1H), 9.33 (dd, J = 7.0, 1.7 Hz, 1H), 8.64 (s, 1H), 8.32 (dd, J = 4.2, 1.7 Hz, 1H), 8.25 (s, 1H), 7.84 (s, 1H), 7.62 (d, J = 0.6 Hz, 1H), 7.32 (dd, J = 7.0, 4.2 Hz, 1H), 6.68 (s, 1H), 5.06-5.00 (m, 3H), 3.86 (s, 3H), 3.50-3.39 (m, 2H), 3.17 (d, J = 15.7 Hz, 1H), 2.80 (d, J = 15.8 Hz, 1H), 1.35 (s, 3H). MS (ESI): m/z = 435.1 [M + 1]$^+$. Example 351, Peak 1: $^1$H NMR (400 MHz, DMSO-d6) δ 10.13 (s, 1H), 9.33 (dd, J = 7.0, 1.7 Hz, 1H), 8.64 (s, 1H), 8.32 (dd, J = 4.2, 1.7 Hz, 1H), 8.25 (s, 1H), 7.84 (s, 1H), 7.68-7.52 (m, 1H), 7.32 (dd, J = 7.0, 4.2 Hz, 1H), 6.68 (s, 1H), 5.03 (m, 3H), 3.86 (s, 3H), 3.52-3.39 (m, 2H), 3.17 (d, J = 16.0 Hz, 1H), 2.80 (d, J = 15.9 Hz, 1H), 1.35 (s, 3H). MS (ESI): m/z = 435.1 [M + 1]$^+$. |

Example 352. N-(6-(4-(2,2-Difluoro-1-hydroxy-ethyl)piperidin-1-yl)-2-(hydroxymethyl)-2-methyl-2,3-dihydrobenzofuran-5-yl)pyrazolo[1,5-a]pyrimidine-3-carboxamide

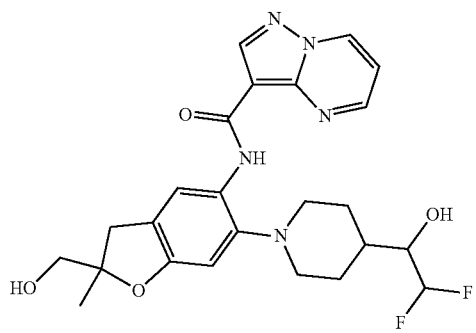 [SMILES: CC1(CO)Cc2cc(NC(=O)c3cnn4cccnc34)c(N3CCC(C(O)C(F)F)CC3)cc2O1]

Step A. tert-Butyl 4-(2,2-difluoro-1-hydroxyethyl)piperidine-1-carboxylate

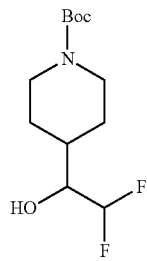

To a solution of tert-butyl 4-formyl-1-piperidinecarboxylate (1 g, 4.69 mmol) in tetrahydrofuran (20 ml) was added difluoromethyl trimethylsilane (0.82 g, 6.56 mmol) and 1M tetrabutyl ammoniumfluoride (0.47 ml, 0.47 mmol) in tetrahydrofuran. The mixture was stirred at 17° C. for 15h under nitrogen atmosphere. The reaction was concentrated under reduced pressure to give tert-butyl 4-(2,2-difluoro-1-hydroxy-ethyl)piperidine-1-carboxylate (1.4 g, 100% yield) as a light yellow oil, which was used directly without further purification. $^1$H NMR (400 MHz, CDCl$_3$): δ 5.76 (td, J=50.8, 4.4 Hz, 1H), 4.25-4.10 (m, 2H), 3.61-3.52 (m, 1H), 2.75-2.60 (m, 2H), 1.81-1.74 (m, 2H), 1.65-1.62 (m, 2H), 1.46 (s, 9H), 1.41-1.37 (m, 1H), Step B. 2,2-Difluoro-1-(piperidin-4-yl)ethanol hydrochloride

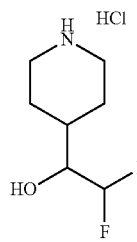

To a solution of tert-butyl 4-(2,2-difluoro-1-hydroxyethyl)piperidine-1-carboxylate (1.19 g, 4.49 mmol) in ethyl acetate (10 ml) was added hydrochloric acid (11 ml, 4 M, 45.33 mmol) in ethyl acetate. The mixture was stirred at 17° C. for 40 min and concentrated under reduced pressure to give 2,2-difluoro-1-(4-piperidyl)ethanol hydrochloride (900 mg, 99% yield) as a colorless oil, which used directly without further purification.

Step C. N-(6-(4-(2,2-Difluoro-1-hydroxyethyl)piperidin-1-yl)-2-(hydroxymethyl)-2-methyl-2,3-dihydrobenzofuran-5-yl)pyrazolo[1,5-a]pyrimidine-3-carboxamide

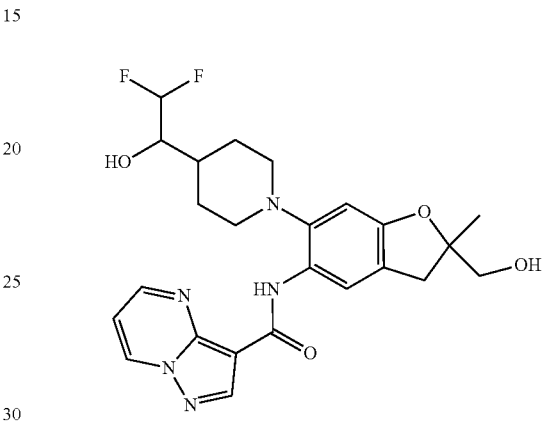

The title compound was made in a manner analogous to Example 6, Step s A through C to afford N-(6-(4-(2,2-Difluoro-1-hydroxyethyl)piperidin-1-yl)-2-(hydroxymethyl)-2-methyl-2,3-dihydrobenzofuran-5-yl)pyrazolo[1,5-a]pyrimidine-3-carboxamide (0.12 g, 53% yield over 3 steps). $^1$H NMR (400 MHz, CD$_3$OD): δ 9.08-9.04 (m, 2H), 8.63 (s, 1H), 8.27 (s, 1H), 7.22-7.20 (dd, J=7.6, 4.4 Hz, 1H), 6.68 (s, 1H), 5.95 (td, J=41.6, 4.8 Hz, 1H), 3.62-3.58 (m, 3H), 3.23 (d, J=16.0 Hz, 1H), 3.04-3.01 (m, 2H), 2.90 (d, J=16.0 Hz, 1H), 2.71-2.67 (m, 2H), 2.10-1.95 (m, 2H), 1.78-1.63 (m, 3H), 1.42 (s, 3H). LCMS (ESI): m/z=488.1 [M+H]$^+$.

Example 353. N-[6-[4-Fluoro-4-(hydroxymethyl)-1-piperidyl]-2-(1-hydroxy-1-methyl-ethyl)-2-methyl-3H-benzofuran-5-yl]pyrazolo[1,5-a]pyrimidine-3-carboxamide (308303452)

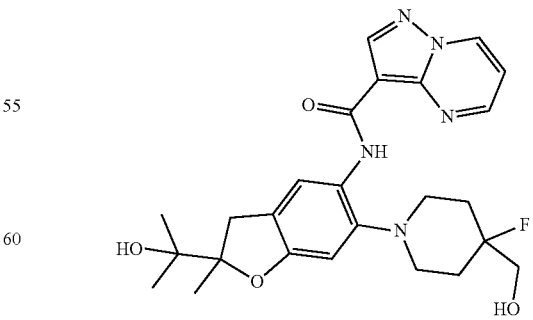

The title compound was made in a manner analogous to Examples 157 and 158 to afford N-[6-[4-fluoro-4-(hydroxymethyl)-1-piperidyl]-2-(1-hydroxy-1-methyl-ethyl)-2- methyl-3H-benzofuran-5-yl]pyrazolo[1,5-a]pyrimidine-3-carboxamide (63 mg, 29% yield) as a yellow solid. ¹H NMR (400 MHz, CDCl₃) δ 10.43 (s, 1H), 8.87-8.74 (m, 2H), 8.68 (m, 1H), 8.44 (s, 1H), 7.03 (m, 1H), 6.71 (s, 1H), 3.73 (d, J=18.8 Hz, 2H), 3.51 (d, J=15.6 Hz, 1H), 3.07-2.90 (m, 4H), 2.80 (d, J=15.2 Hz, 1H), 2.17-1.97 (m, 4H), 1.42 (s, 3H), 1.37 (s, 3H), 1.26 (s, 3H). LCMS (ESI): m/z=484.0 [M+H]⁺.

Example 354 and 355. (S)—N-(6-(4-(Hydroxymethyl)piperidin-1-yl)-2-(2-hydroxypropan-2-yl)-2-methyl-2,3-dihydrobenzofuran-5-yl)pyrazolo[1,5-a]pyrimidine-3-carboxamide and (R)—N-(6-(4-(Hydroxymethyl)piperidin-1-yl)-2-(2-hydroxypropan-2-yl)-2-methyl-2,3-dihydrobenzofuran-5-yl)pyrazolo[1,5-a]pyrimidine-3-carboxamide

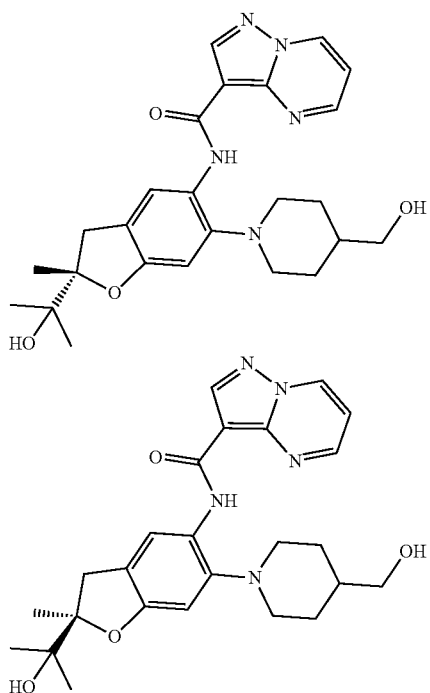

The title compounds were made in a manner analogous to Examples 157 and 158 to afford (S)—N-(6-(4-(Hydroxymethyl)piperidin-1-yl)-2-(2-hydroxypropan-2-yl)-2-methyl-2,3-dihydrobenzofuran-5-yl)pyrazolo[1,5-a]pyrimidine-3-carboxamide and (R)—N-(6-(4-(Hydroxymethyl)piperidin-1-yl)-2-(2-hydroxypropan-2-yl)-2-methyl-2,3-dihydrobenzofuran-5-yl)pyrazolo[1,5-a]pyrimidine-3-carboxamide (absolute stereochemistry assigned arbitrarily).

Example 354, Peak 1: ¹H NMR (400 MHz, dimethyl sulfoxide-d₆) δ 10.47 (s, 1H), 9.36-9.35 (d, J=5.2 Hz, 1H), 8.90-8.88 (m, 1H), 8.67 (s, 1H), 8.30 (s, 1H), 7.34-7.31 (dd J=4.4, 7.2 Hz, 1H), 6.68 (s, 1H), 4.55 (t, J=5.6 Hz, 1H), 4.50 (s, 1H), 3.44 (d, J=16.0 Hz, 1H), 3.40-3.38 (m, 2H), 2.94-2.91 (m, 2H), 2.71 (d, J=16.0 Hz, 1H), 2.66-2.60 (m, 2H), 1.72-1.70 (m, 2H), 1.59-1.56 (m, 3H), 1.31 (s, 3H), 1.16 (d, J=4.0 Hz, 6H). LCMS (ESI): m/z=466.1 [M+H]⁺.

Example 355, Peak 2: ¹H NMR (400 MHz, dimethyl sulfoxide-d₆) δ 10.48 (s, 1H), 9.37-9.35 (d, J=6.8 Hz, 1H), 8.90-8.89 (m, 1H), 8.68 (s, 1H), 8.31 (s, 1H), 7.35-7.32 (m, 1H), 6.69 (s, 1H), 4.56 (t, J=5.6 Hz, 1H), 4.51 (s, 1H), 3.45 (d, J=16.0 Hz, 1H), 3.40-3.38 (m, 2H), 2.94-2.92 (m, 2H), 2.71 (d, J=16.0 Hz, 1H), 2.66-2.61 (m, 2H), 1.73-1.70 (m, 2H), 1.59-1.53 (m, 3H), 1.32 (s, 3H), 1.16 (d, J=3.2 Hz, 6H). LCMS (ESI): m/z=466.1 [M+H]⁺.

Example 356. N-(6-Methyl-2-morpholino-7-oxo-6,7-dihydro-5H-pyrrolo[3,4-b]pyridin-3-yl)pyrazolo[1,5-a]pyrimidine-3-carboxamide

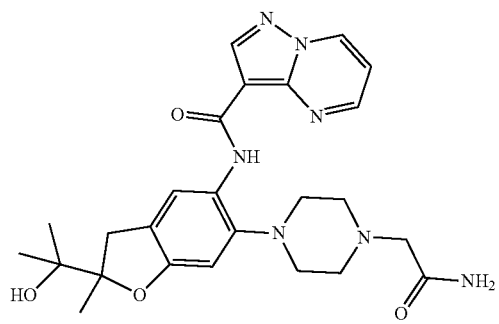 [SMILES: CC(C)(O)C1(C)Cc2cc(NC(=O)c3cnn4cccnc34)c(N3CCN(CC(N)=O)CC3)cc2O1]

The title compound was made in a manner analogous to Examples 157 and 158 to afford N-[6-[4-(2-amino-2-oxoethyl) piperazin-1-yl]-2-(1-hydroxy-1-methyl-ethyl)-2-methyl-3H-benzofuran-5-yl]pyrazolo[1,5-a]pyrimidine-3-carboxamide (64.5 mg, 27% yield) as a yellow solid. ¹H NMR (400 MHz, CDCl₃): 10.37 (s, 1H), 8.85 (dd, J=7.2, 2.0 Hz, 1H), 8.79 (s, 1H), 8.73-8.71 (m, 1H), 8.42 (s, 1H), 7.09-7.07 (m, 2H), 6.67 (s, 1H), 5.48 (s, 1H), 3.51 (d, J=15.6 Hz, 1H), 3.13 (s, 2H), 2.97-2.96 (m, 4H), 2.83-2.79 (m, 5H), 1.43 (s, 3H), 1.37 (s, 3H), 1.26 (s, 3H). LCMS (ESI): m/z=494.0 [M+H]⁺.

Example 357. N-(6-(1-(2-Hydroxyethyl)piperidin-4-yl)-2,2-dimethyl-2,3-dihydrobenzofuran-5-yl)pyrazolo[1,5-a]pyrimidine-3-carboxamide

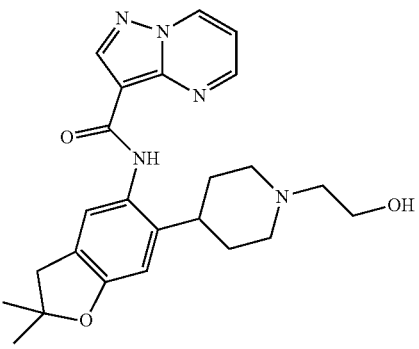 [SMILES: CC1(C)Cc2cc(NC(=O)c3cnn4cccnc34)c(C3CCN(CCO)CC3)cc2O1]

N-[2,2-Dimethyl-6-(4-piperidyl)-3H-benzofuran-5-yl] pyrazolo[1,5-a]pyrimidine-3-carboxamide (Example 62, Step D, 50.8 mg, 0.13 mmol) was brought up in acetonitrile (1.3 ml, 24.7 mmol) and treated with trimethylamine (0.45 ml, 3.24 mmol) followed by iodoethanol (29 mg, 0.169 mmol) and heated at 60° C. for 72h. The reaction mixture was then concentrated and purified by reverse phase HPLC to give N-[6-[1-(2-hydroxyethyl)-4-piperidyl]-2,2-dimethyl-3H-benzofuran-5-yl]pyrazolo[1,5-a]pyrimidine-3-carboxamide (13.8 mg, 24% yield) as a solid. ¹H NMR (400

MHz, dimethyl sulfoxide-d$_6$) δ 9.61 (s, 1H), 9.39 (dd, J=7.0, 1.6 Hz, 1H), 8.87 (dd, J=4.3, 1.6 Hz, 1H), 8.68 (s, 1H), 7.74 (s, 1H), 6.65 (s, 1H), 4.36 (s, 1H), 3.51 (t, J=6.4 Hz, 2H), 3.00 (s, 2H), 2.98 (m, 2H), 2.88-2.75 (m, 1H), 2.40 (t, J=6.4 Hz, 2H), 2.15-2.00 (m, 2H), 1.82-1.57 (m, 4H), 1.42 (s, 6H). MS (ESI): m/z=436.2 [M+1]$^+$.

Example 358. N-(3-Hydroxy-2,2-dimethyl-5-morpholino-2,3-dihydrobenzofuran-6-yl)pyrazolo[1,5-a]pyrimidine-3-carboxamide

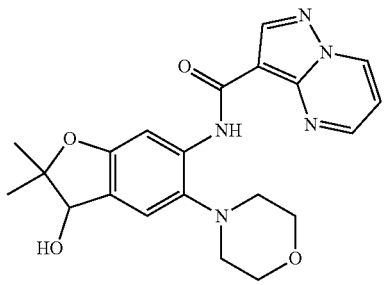 [SMILES: CC1(C)Oc2cc(NC(=O)c3cnn4cccnc34)c(N3CCOCC3)cc2C1O]

Step A.
1-Chloro-4-((2-methylallyl)oxy)-2-nitrobenzene

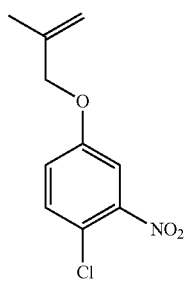

Cesium carbonate (3.58 g, 11.0 mmol) was added portion-wise to a solution of 4-chloro-3-nitrophenol (1.74 g, 10.0 mmol) in N,N-dimethylformamide (25 ml) followed by addition of 3-bromo-2-methyl-prop-1-ene (1.62 g, 12.0 mmol). The mixture was stirred for 3h and filtered. The filtrate was concentrated in vacuo and the residue partitioned between water and ethyl acetate. The organic phase was isolated, washed with water and brine, dried over magnesium sulfate and concentrated. The residue was purified by silica gel chromatography (eluting gradient 0-20% isopropyl acetate: heptane) to afford 1-chloro-4-((2-methylallyl)oxy)-2-nitrobenzene (2.00 g, 88% yield) as a light yellow oil. MS (ESI): m/z=226[M−1]$^-$.

Step B. 4-(4-((2-Methylallyl)oxy)-2-nitrophenyl)morpholine

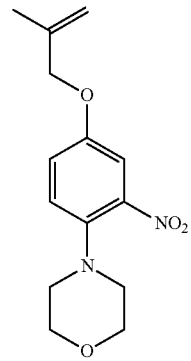 [SMILES: C=C(C)COc1ccc(N2CCOCC2)c(N)c1]

A mixture of 1-chloro-4-(2-methylallyloxy)-2-nitro-benzene (2.00 g, 8.8 mmol) and morpholine (23 ml, 263 mmol) was heated in a sealed vial at 100° C. for 36h. The mixture was concentrated in vacuo and the residue was partitioned between ethyl ether and 5% aqueous citric acid. The organic phase was isolated, washed with water and brine, dried over magnesium sulfate and concentrated. The residue was purified by silica gel chromatography (eluting gradient 0-20% isopropyl acetate: heptane) to afford 4-(4-((2-methylallyl)oxy)-2-nitrophenyl)morpholine (2.11 g, 78% yield) as a yellow oil. MS (ESI): m/z=279[M+1]$^+$.

Step C. 5-((2-Methylallyl)oxy)-2-morpholinoaniline

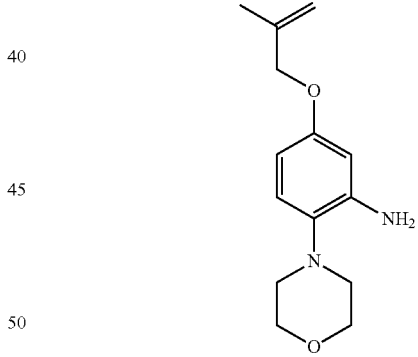

Iron (7.62 g, 136.5 mmol) was added portion-wise over a period of 1h to a mixture of 4-[4-(2-methylallyloxy)-2-nitrophenyl]morpholine (2.11 g, 6.82 mmol) and saturated aqueous ammonium chloride (12 ml) in methanol (40 ml) at 65° C. After 30 min, the reaction was cooled to room temperature, filtered through Celite and the precipitate was washed with methanol. The filtrate was concentrated and the residue partitioned between water and ethyl acetate. The organic phase was isolated, washed with water and brine, dried over magnesium sulfate and concentrated. The residue was purified by silica gel chromatography (eluting gradient 04% methanol: dichloromethane) to afford 5-((2-methylallyl)oxy)-2-morpholinoaniline (1.06 g, 62% yield) as a light red oil. MS (ESI): m/z=249[M+1]$^+$.

Step D.
5-Amino-2-(2-methylallyl)-4-morpholinophenol

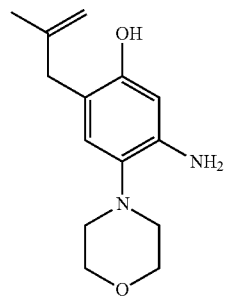 [SMILES: C=C(C)Cc1cc(N2CCOCC2)c(N)cc1O]

A mixture of 5-(2-methylallyloxy)-2-morpholino-aniline (500 mg, 2.01 mmol) in dimethylformamide (6 ml) was subjected to a microwave heating at 180° C. for 12h. The mixture was concentrated in vacuo and the residue partitioned between ethyl ether and water. The organic phase was isolated, washed with water (3*20 ml) and brine, dried over magnesium sulfate and concentrated to afford 5-amino-2-(2-methylallyl)-4-morpholinophenol (498 mg, 100% yield) MS (ESI): m/z=249[M+1]$^+$.

Step E. 2,2-Dimethyl-5-morpholino-2,3-dihydrobenzofuran-6-amine

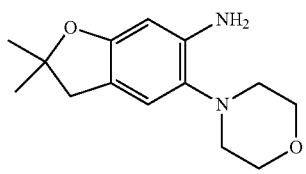 [SMILES: CC1(C)Cc2cc(N3CCOCC3)c(N)cc2O1]

Potassium tert-butoxide (450 mg, 4.0 mmol) was added portion-wise to a solution of 5-amino-2-(2-methylallyl)-4-morpholino-phenol in tetrahydrofuran (25 ml) at 5° C. The mixture was then heated in a sealed vial at 60° C. for 2h. The mixture was concentrated in vacuo and the residue partitioned between ethyl acetate and 1% aqueous citric acid. The organic phase was isolated, washed with water and brine, dried over magnesium sulfate and concentrated. The residue was purified by silica gel chromatography (eluting gradient 04% methanol: dichloromethane) to afford 2,2-dimethyl-5-morpholino-2,3-dihydrobenzofuran-6-amine (234 mg, 45%) as a colorless solid. $^1$H NMR (400 MHz, Chloroform-d) δ 6.83 (t, J=1.0 Hz, 1H), 6.17 (s, 1H), 4.02 (s, 2H), 3.82 (dd, J=5.7, 3.4 Hz, 4H), 2.92-2.88 (m, 2H), 2.86-2.80 (m, 4H), 1.44 (s, 6H). MS (ESI): m/z=249[M+1]$^+$.

Step F. N-(2,2-Dimethyl-5-morpholino-2,3-dihydrobenzofuran-6-yl)pyrazolo[1,5-a]pyrimidine-3-carboxamide

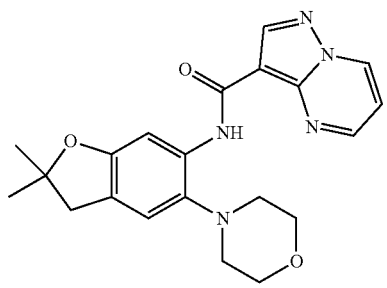 [SMILES: CC1(C)Cc2cc(N3CCOCC3)c(NC(=O)c3cnn4cccnc34)cc2O1]

A mixture of 2,2-dimethyl-5-morpholino-3H-benzofuran-6-amine (234 mg, 0.90 mmol), pyrazolo[1,5-a]pyrimidine-3-carbonyl chloride hydrochloride (254 mg, 1.17 mmol), N,N-diisopropylethylamine (0.47 ml, 2.68 mmol) and 4-dimethylaminopyridine (22 mg, 0.18 mmol) in pyridine (6 ml) was subjected to a microwave heating at 110° C. for 30 min. The mixture was concentrated in vacuo and the residue partitioned between ethyl acetate and water. The organic phase was isolated, washed with aqueous saturated citric acid, aqueous saturated sodium bicarbonate and brine, dried over magnesium sulfate and concentrated. The residue was purified by silica gel chromatography (eluting gradient 0-100% isopropyl acetate: heptane) to afford N-(2,2-dimethyl-5-morpholino-2,3-dihydrobenzofuran-6-yl)pyrazolo[1,5-a]pyrimidine-3-carboxamide (309 mg, 88%) as a light yellow solid. MS (ESI): m/z=394[M+1]$^+$.

Step G. 2,2-Dimethyl-5-morpholino-6-(pyrazolo[1,5-a]pyrimidine-3-carboxamido)-2,3-dihydrobenzofuran-3-yl acetate

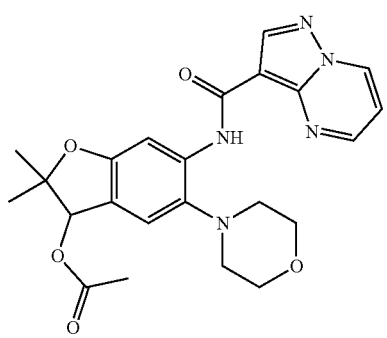 [SMILES: CC(=O)OC1c2cc(N3CCOCC3)c(NC(=O)c3cnn4cccnc34)cc2OC1(C)C]

2,3-Dichloro-5,6-dicyano-1,4-benzoquinone (196 mg, 0.86 mmol) was added portion-wise to a solution of N-(2,2-dimethyl-5-morpholino-3H-benzofuran-6-yl)pyrazolo[1,5-a]pyrimidine-3-carboxamide (309 mg, 0.786 mmol) in acetic acid (12 ml). The mixture was stirred for 3h, concentrated in vacuo and the residue partitioned between ethyl acetate and 1 M aqueous sodium carbonate. The organic phase was isolated, washed with aqueous sodium carbonate, water and brine, dried over magnesium sulfate and concentrated. The residue was purified by silica gel chromatography (eluting gradient 0-60% isopropyl acetate: heptane) to afford 2,2-dimethyl-5-morpholino-6-(pyrazolo[1,5-a]pyrimidine-3-carboxamido)-2,3-dihydrobenzofuran-3-yl acetate (290 mg, 82%). MS (ESI): m/z=452[M+1]⁺.

Step H. N-(3-Hydroxy-2,2-dimethyl-5-morpholino-2,3-dihydrobenzofuran-6-yl)pyrazolo[1,5-a]pyrimidine-3-carboxamide

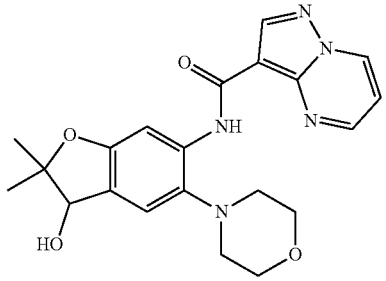 [SMILES: CC1(C)Oc2cc(NC(=O)c3cnn4cccnc34)c(N3CCOCC3)cc2C1O]

A mixture of [2,2-dimethyl-5-morpholino-6-(pyrazolo[1,5-a]pyrimidine-3-carbonylamino)-3H-benzofuran-3-yl] acetate (280 mg, 0.62 mmol) and lithium hydroxide (1M in water, 1.55 mmol) was stirred in a mixture of methanol and tetrahydrofuran (4:1) for 4h. The mixture was concentrated and the residue partitioned between ethyl acetate and 1% aqueous citric acid. The organic phase was isolated and concentrated to afford N-(3-hydroxy-2,2-dimethyl-5-morpholino-2,3-dihydrobenzofuran-6-yl)pyrazolo[1,5-a]pyrimidine-3-carboxamide (162 mg, 62%) as a colorless solid. ¹H NMR (400 MHz, dimethyl sulfoxide-d₆) δ 10.83 (s, 1H), 9.38 (dd, J=7.0, 1.6 Hz, 1H), 8.96 (dd, J=4.3, 1.6 Hz, 1H), 8.72 (s, 1H), 7.98 (s, 1H), 7.38-7.35 (m, 1H), 7.34 (s, 1H), 5.41 (d, J=6.7 Hz, 1H), 4.66 (d, J=6.7 Hz, 1H), 3.88 (t, J=4.7 Hz, 4H), 2.90-2.77 (m, 4H), 1.35 (s, 3H), 1.28 (s, 3H). MS (ESI): m/z=410[M+1]⁺.

Example 359. N-(2,2-dimethyl-5-morpholino-3-oxo-2,3-dihydrobenzofuran-6-yl)pyrazolo[1,5-a]pyrimidine-3-carboxamide

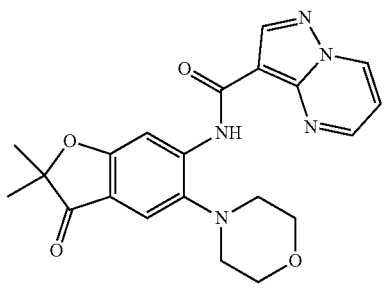 [SMILES: CC1(C)Oc2cc(NC(=O)c3cnn4cccnc34)c(N3CCOCC3)cc2C1=O]

Dess-Martin periodinane (179 mg, 0.42 mmol) was added portion-wise to a solution of N-(3-hydroxy-2,2-dimethyl-5-morpholino-3H-benzofuran-6-yl)pyrazolo[1,5-a]pyrimidine-3-carboxamide (115 mg, 0.28 mmol) in dichloromethane (30 ml). The mixture was stirred for 3h. The mixture was filtered through celite, the filtrate concentrated and the residue partitioned between ethyl acetate and saturated aqueous sodium bicarbonate. The organic phase was isolated, washed with water and brine, dried over magnesium sulfate and concentrated. The residue was purified by silica gel chromatography (eluent 100% isopropyl acetate) followed by recrystallisation from acetonitrile to afford N-(2,2-dimethyl-5-morpholino-3-oxo-2,3-dihydrobenzofuran-6-yl)pyrazolo[1,5-a]pyrimidine-3-carboxamide (26 mg, 22%) as a colorless solid. ¹H NMR (400 MHz, dimethyl sulfoxide-d₆) δ 11.17 (s, 1H), 9.42 (dd, J=7.0, 1.6 Hz, 1H), 9.00 (dd, J=4.2, 1.6 Hz, 1H), 8.79 (s, 1H), 8.38 (s, 1H), 7.59 (s, 1H), 7.40 (dd, J=7.0, 4.2 Hz, 1H), 3.90 (t, J=4.5 Hz, 4H), 2.95-2.83 (m, 4H), 1.40 (s, 6H). MS (ESI): m/z=408[M+1]⁺.

Examples 360 and 361. (R)—N-(6-(4-(2,2-Difluoroethyl)piperazin-1-yl)-2-(2-hydroxypropan-2-yl)-2-methyl-2,3-dihydrobenzofuran-5-yl)pyrazolo[1,5-a]pyrimidine-3-carboxamide and (S)—N-(6-(4-(2,2-Difluoroethyl)piperazin-1-yl)-2-(2-hydroxypropan-2-yl)-2-methyl-2,3-dihydrobenzofuran-5-yl)pyrazolo[1,5-a]pyrimidine-3-carboxamide

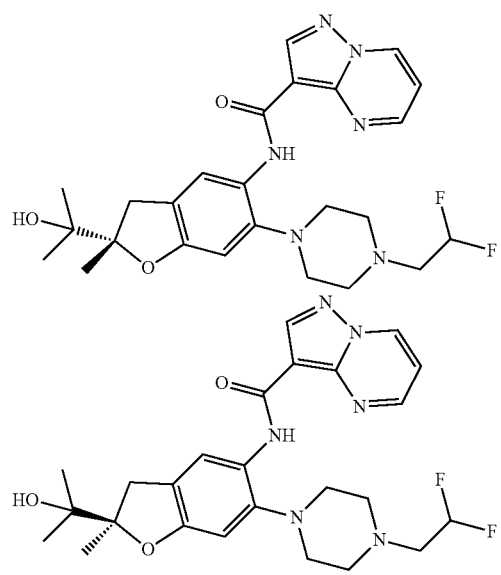

The title compounds were made in a manner analogous to Example 157 and 158 to give (R)—N-(6-(4-(2,2-difluoroethyl)piperazin-1-yl)-2-(2-hydroxypropan-2-yl)-2-methyl-2,3-dihydrobenzofuran-5-yl)pyrazolo[1,5-a]pyrimidine-3-carboxamide and (S)—N-(6-(4-(2,2-difluoroethyl)piperazin-1-yl)-2-(2-hydroxypropan-2-yl)-2-methyl-2,3-dihydrobenzofuran-5-yl)pyrazolo[1,5-a]pyrimidine-3-carboxamide with absolute stereochemistry assigned arbitrarily.

Example 360, Peak 1: ¹H NMR (400 MHz, Chloroform-d) δ 10.37 (s, 1H), 8.87-8.81 (m, 1H), 8.79 (s, 1H), 8.74-8.69 (m, 1H), 8.40 (s, 1H), 7.08 (dd, J=7.0, 4.2 Hz, 1H), 6.67 (s, 1H), 5.96 (tt, J=55.9, 4.3 Hz, 1H), 3.50 (d, J=15.5 Hz, 1H), 3.01-2.78 (m, 11H), 2.01 (s, 1H), 1.41 (s, 3H), 1.37 (s, 3H), 1.25 (s, 3H). (ESI): m/z=501.2 [M+1]⁺.

Example 361, Peak 2: ¹H NMR (400 MHz, Chloroform-d) δ 10.37 (s, 1H), 8.87-8.81 (m, 1H), 8.79 (s, 1H), 8.75-8.70 (m, 1H), 8.40 (s, 1H), 7.08 (dd, J=7.0, 4.2 Hz, 1H), 6.67 (s, 1H), 5.96 (tt, J=55.9, 4.3 Hz, 1H), 3.50 (d, J=15.5 Hz, 1H), 2.99-2.76 (m, 12H), 1.41 (s, 3H), 1.37 (s, 3H), 1.25 (s, 3H). (ESI): m/z=501.2 [M+1]⁺.

Example 362. N-(6-(4-(2,2-difluoroethyl)piperazin-1-yl)-2-((difluoromethoxy)methyl)-2-methyl-2,3-dihydrobenzofuran-5-yl)pyrazolo[1,5-a]pyrimidine-3-carboxamide

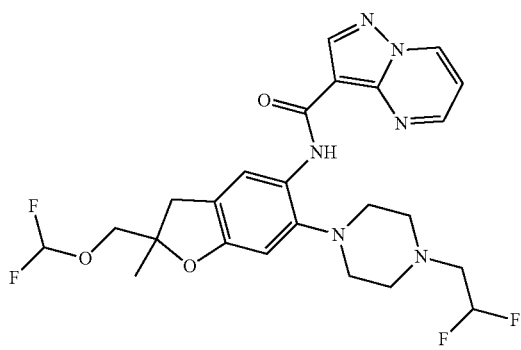 [SMILES: CC1(COC(F)F)Cc2cc(NC(=O)c3cnn4cccnc34)c(N3CCN(CC(F)F)CC3)cc2O1]

The title compound was made in a manner analogous to Example 155 and 156 to give N-(6-(4-(2,2-difluoroethyl)piperazin-1-yl)-2-((difluoromethoxy)methyl)-2-methyl-2,3-dihydrobenzofuran-5-yl)pyrazolo[1,5-a]pyrimidine-3-carboxamide. $^1$H NMR (400 MHz, Methanol-$d_4$) δ 9.15 (d, J=7.0 Hz, 1H), 8.95 (d, J=4.1 Hz, 1H), 8.67 (s, 1H), 8.24 (s, 1H), 8.10 (s, 1H), 7.31 (dd, J=7.0, 4.2 Hz, 1H), 6.74 (s, 1H), 3.94 (s, 2H), 3.34-3.19 (m, 2H), 3.18 (d, J=3.5 Hz, 1H), 3.12 (s, 5H), 3.07-2.97 (m, 5H), 1.50 (s, 3H), 1.31 (s, 1H). (ESI): m/z=523.2 [M+1]$^+$.

Example 363. N-(6-(4-(hydroxymethyl)piperidin-1-yl)-2-(2-hydroxypropan-2-yl)-2-methyl-2,3-dihydrobenzofuran-5-yl)pyrazolo[1,5-a]pyrimidine-3-carboxamide

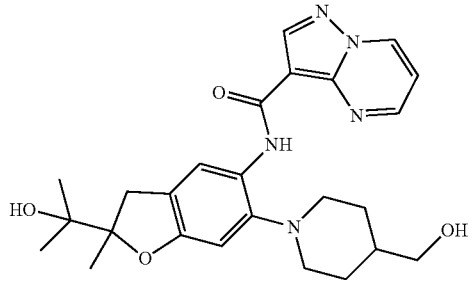 [SMILES: CC(C)(O)C1(C)Cc2cc(NC(=O)c3cnn4cccnc34)c(N3CCC(CO)CC3)cc2O1]

The title compound was made in a manner analogous to Example 157 and 158 to give N-(6-(4-(hydroxymethyl)piperidin-1-yl)-2-(2-hydroxypropan-2-yl)-2-methyl-2,3-dihydrobenzofuran-5-yl)pyrazolo[1,5-a]pyrimidine-3-carboxamide. $^1$H NMR (400 MHz, Chloroform-d) δ 10.50 (s, 1H), 8.84-8.73 (m, 3H), 8.44 (s, 1H), 7.02 (dd, J=7.0, 4.1 Hz, 1H), 6.67 (s, 1H), 3.63 (t, J=4.9 Hz, 2H), 3.50 (d, J=15.4 Hz, 1H), 3.11 (d, J=11.4 Hz, 2H), 2.79 (d, J=15.4 Hz, 1H), 2.68 (dt, J=11.4, 8.4 Hz, 2H), 2.06 (s, 1H), 1.79 (s, 3H), 1.51 (t, J=5.4 Hz, 1H), 1.41 (s, 3H), 1.36 (s, 3H), 1.25 (s, 3H). (ESI): m/z=466.2 [M+1]$^+$.

Example 364. N-(6-(4-(2,2-Difluoroethyl)piperazin-1-yl)-2-(difluoromethyl)-2-methyl-2,3-dihydrobenzofuran-5-yl)pyrazolo[1,5-a]pyrimidine-3-carboxamide

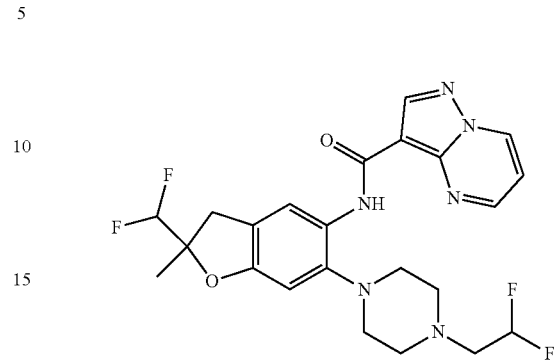

The title compound was made in a manner analogous to Examples 50 and 51 to give N-(6-(4-(2,2-difluoroethyl)piperazin-1-yl)-2-(difluoromethyl)-2-methyl-2,3-dihydrobenzofuran-5-yl)pyrazolo[1,5-a]pyrimidine-3-carboxamide. $^1$H NMR (400 MHz, Chloroform-d) δ 10.38 (s, 1H), 8.84 (d, J=7.0 Hz, 1H), 8.79 (s, 1H), 8.73 (d, J=4.1 Hz, 1H), 8.43 (s, 1H), 7.08 (dd, J=7.0, 4.1 Hz, 1H), 6.71 (s, 1H), 5.85 (dt, J=82.7, 55.8 Hz, 2H), 3.43 (d, J=16.2 Hz, 1H), 3.08-2.80 (m, 11H), 1.54 (s, 3H). (ESI): m/z=493.2 [M+1]$^+$.

Examples 365 and 366. (R)—N-(6-(4-(2,2-Difluoroethyl)piperazin-1-yl)-2-(hydroxymethyl)-2-(trifluoromethyl)-2,3-dihydrobenzofuran-5-yl)pyrazolo[1,5-a]pyrimidine-3-carboxamide and (S)—N-(6-(4-(2,2-Difluoroethyl)piperazin-1-yl)-2-(hydroxymethyl)-2-(trifluoromethyl)-2,3-dihydrobenzofuran-5-yl)pyrazolo[1,5-a]pyrimidine-3-carboxamide

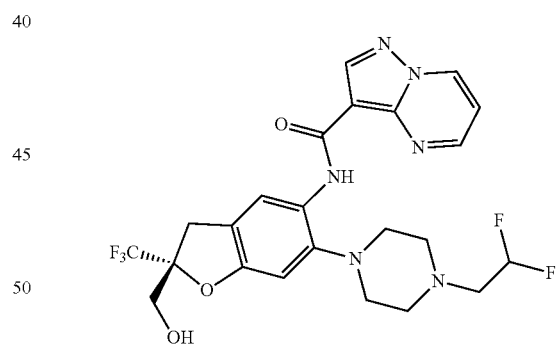

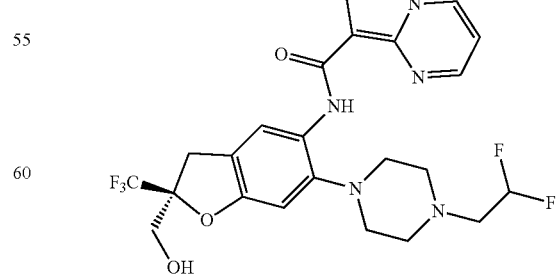

The title compounds were made in a manner analogous to Example 153 and 154 to give (R)—N-(6-(4-(2,2-difluoroethyl)piperazin-1-yl)-2-(hydroxymethyl)-2-(trifluoromethyl)-2,3-dihydrobenzofuran-5-yl)pyrazolo[1,5-a]pyrimidine-3-carboxamide and (S)—N-(6-(4-(2,2-difluoroethyl)piperazin-1-yl)-2-(hydroxymethyl)-2-(trifluoromethyl)-2,3-dihydrobenzofuran-5-yl)pyrazolo[1,5-a]pyrimidine-3-carboxamide with absolute stereochemistry assigned arbitrarily.

Example 365, Peak 1: $^1$H NMR (400 MHz, dimethyl sulfoxide-d$_6$) δ 10.43 (s, 1H), 9.36 (d, J=7.0 Hz, 1H), 8.94 (d, J=4.1 Hz, 1H), 8.68 (s, 1H), 8.39 (s, 1H), 7.35 (dd, J=7.0, 4.2 Hz, 1H), 6.92 (s, 1H), 6.19 (tt, J=55.7, 4.4 Hz, 1H), 5.59 (t, J=6.0 Hz, 1H), 3.76 (qd, J=12.1, 6.0 Hz, 2H), 3.49 (d, J=16.6 Hz, 1H), 3.32 (s, 1H), 2.89-2.72 (m, 1OH). (ESI): m/z=527.2 [M+1]$^+$.

Example 366, Peak 2: $^1$H NMR (400 MHz, dimethyl sulfoxide-d$_6$) δ 10.43 (s, 1H), 9.35 (d, J=7.0 Hz, 1H), 8.94 (d, J=4.1 Hz, 1H), 8.67 (s, 1H), 8.39 (s, 1H), 7.34 (dd, J=7.0, 4.1 Hz, 1H), 6.91 (s, 1H), 6.19 (tt, J=55.6, 4.2 Hz, 1H), 5.59 (t, J=6.1 Hz, 1H), 3.75 (qd, J=12.1, 5.8 Hz, 2H), 3.49 (d, J=16.6 Hz, 1H), 3.32 (s, 1H), 2.94-2.72 (m, 1OH). (ESI): m/z=527.2 [M+1]$^+$.

Example 367 and 368. N-[(2R)-2-(2,2-difluoroethyl)-2-methyl-6-morpholino-3H-benzofuran-5-yl]pyrazolo[1,5-a]pyrimidine-3-carboxamide and N-[(2S)-2-(2,2-difluoroethyl)-2-methyl-6-morpholino-3H-benzofuran-5-yl]pyrazolo[1,5-a]pyrimidine-3-carboxamide

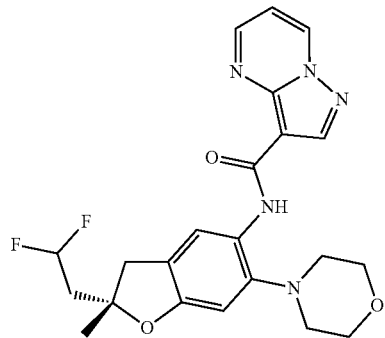

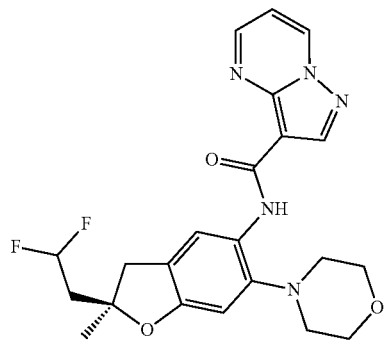

Step A.
2-Fluoro-4-(2-methylallyloxy)-1-nitro-benzene

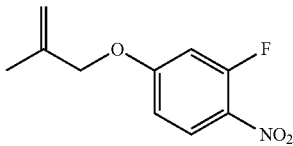

To a solution of 3-fluoro-4-nitrophenol (20.6 g, 131.2 mmol) in acetonitrile was added 3-bromo-2-methylpropene (15.6 ml, 183.7 mmol) and potassium carbonate (25.4 g, 183.7 mmol). The reaction mixture was stirred at 55° C. for 13h and then cooled to room temperature and maintained there with stirring overnight. The mixture was diluted with isopropyl acetate and washed with water. The aqueous phase was isolated and extracted with isopropyl acetate. The combined organic phases were dried over sodium sulfate, filtered and purified by column chromatography (eluting gradient 0-25% isopropyl acetate: heptanes) to give the title compound as a white crystalline solid (26.0 g, 94% yield). $^1$H NMR (400 MHz, dimethyl sulfoxide-d$_6$) δ 8.15 (t, J=9.2 Hz, 1H), 7.20 (dd, J=13.7, 2.7 Hz, 1H), 7.00 (ddd, J=9.3, 2.7, 1.1 Hz, 1H), 5.11-5.04 (m, 1H), 5.01 (d, J=1.5 Hz, 1H), 4.66 (s, 2H), 1.81-1.73 (m, 3H).

Step B. 4-[5-(2-Methylallyloxy)-2-nitro-phenyl]morpholine

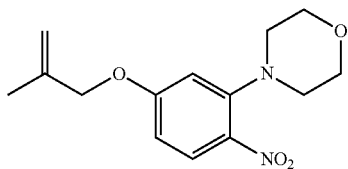 [SMILES: C=C(C)COc1ccc([N+](=O)[O-])c(N2CCOCC2)c1]

To a mixture of 2-fluoro-4-(2-methylallyloxy)-1-nitrobenzene (26.0 g, 123.2 mmol), and potassium carbonate (56.2 g, 406.6 mmol) in dimethyl sulfoxide (186.7 ml, 2600 mmol) was added morpholine (10.7 ml, 123.20 mmol) and the mixture was heated to 100° C. After 40 min, the reaction was cooled to room temperature and diluted with water and ethyl acetate. The organic phase was isolated and washed with saturated aqueous sodium bicarbonate. The aqueous phase was then extracted with ethyl acetate (3×). The combined organic phases were washed brine, dried over sodium sulfate, filtered, concentrated and purified by column chromatography (eluting gradient 0-50% isopropyl acetate: heptanes) to give the title product as a bright yellow-orange crystalline solid (32.3 g, 94% yield). $^1$H NMR (400 MHz, dimethyl sulfoxide-d$_6$) δ 7.92 (d, J=9.0 Hz, 1H), 6.72-6.66 (m, 2H), 5.13-5.04 (m, 1H), 5.00 (s, 1H), 4.60 (s, 2H), 3.77-3.64 (m, 4H), 3.07-2.91 (m, 4H), 1.78 (s, 3H).

Step C. 2-(2-Methylallyl)-5-morpholino-4-nitro-phenol

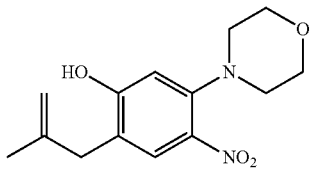

A solution of 4-[5-(2-methylallyloxy)-2-nitro-phenyl]morpholine (375 mg, 1.35 mmol) was heated in dimethylformamide (2 ml) at 220° C. for 60 min. The reaction was cooled to room temperature and diluted with isopropyl acetate and brine. The aqueous phase was isolated and extracted with isopropyl acetate (3×). The combined organic phases were dried over sodium sulfate, filtered and purified by column chromatography (eluting gradient 0-50% isopropyl acetate: heptanes) to give the desired product (44.1 mg, 11.8% yield) along with recovered starting material and undesired regioisomers. $^1$H NMR (400 MHz, dimethyl sulfoxide-$d_6$) δ 10.73 (s, 1H), 7.74 (s, 1H), 6.59 (s, 1H), 4.84-4.73 (m, 1H), 4.64 (dd, J=2.2, 0.9 Hz, 1H), 3.79-3.64 (m, 5H), 3.20 (s, 2H), 2.97-2.88 (m, 5H), 1.66 (s, 3H).

Step D. 1-(2-Hydroxy-4-morpholino-5-nitro-phenyl)propan-2-one

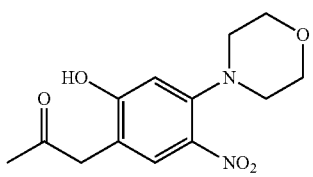 [SMILES: CC(=O)Cc1cc([N+](=O)[O-])c(N2CCOCC2)cc1O]

To a solution of 2-(2-Methylallyl)-5-morpholino-4-nitro-phenol (283.5 mg, 1.02 mmol) in water (0.08 M) and dioxane (0.03 M) was added osmium tetroxide (0.08 M in tert-butyl alcohol, 0.6 ml, 0.05 mmol) followed by sodium periodate (435.8 mg, 2.04 mmol). The suspension was stirred overnight at room temperature, poured into water and extracted with dichloromethane. The organic phase was isolated, dried over sodium sulfate, concentrated and purified by column chromatography (eluting gradient 0-100% isopropyl acetate: heptanes) to give the desired product (135.2 mg, 47% yield). $^1$H NMR (400 MHz, Chloroform-d) δ 8.26 (s, 1H), 7.78 (s, 1H), 6.60 (s, 1H), 3.88-3.81 (m, 4H), 3.73 (s, 2H), 3.08-2.97 (m, 4H), 2.35 (s, 3H).

Step E. Methyl 2-(2-methyl-6-morpholino-5-nitro-3H-benzofuran-2-yl)acetate

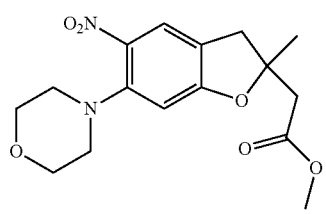 [SMILES: COC(=O)CC1(C)Cc2cc([N+](=O)[O-])c(N3CCOCC3)cc2O1]

A mixture of 1-(2-hydroxy-4-morpholino-5-nitro-phenyl)propan-2-one (1.7 g, 6.07 mmol) methyl(triphenylphosphoranylidine)acetate (2.13 g, 6.37 mmol) in chloroform (100 ml) was stirred at 60° C. for 2h. Triethylamine (6 ml) was added and the mixture was stirred at 60° C. for 12h. The reaction was then concentrated and purified by column chromatography (eluent 3% ethyl acetate:petroleum ether) to afford methyl 2-(2-methyl-6-morpholino-5-nitro-3H-benzofuran-2-yl)acetate (1.6 g, 78% yield) as a yellow solid. (ESI): m/z=337.1 [M+1]$^+$.

Step F. 2-(2-Methyl-6-morpholino-5-nitro-3H-benzofuran-2-yl)acetaldehyde

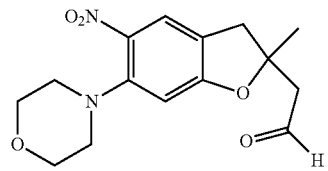 [SMILES: CC1(CC=O)Cc2cc([N+](=O)[O-])c(N3CCOCC3)cc2O1]

To a mixture of diisobutylaluminium hydride (2.01 ml, 2.01 mmol) in dichloromethane (10 ml) was added methyl 2-(2-methyl-6-morpholino-5-nitro-3H-benzofuran-2-yl)acetate (450.0 mg, 1.34 mmol) drop-wise at −78° C. over 5 min and the reaction was maintained there for 2h. The mixture was quenched with sodium sulfate decahydrate, filtered, concentrated and purified by column chromatography (eluent 15% ethyl acetate:petroleum ether) to afford 2-(2-methyl-6-morpholino-5-nitro-3H-benzofuran-2-yl)acetaldehyde (450 mg, 99% yield) as a yellow solid. (ESI): m/z=307.1 [M+1]$^+$.

Step G. 4-[2-(2,2-Difluoroethyl)-2-methyl-5-nitro-3H-benzofuran-6-yl]morpholine

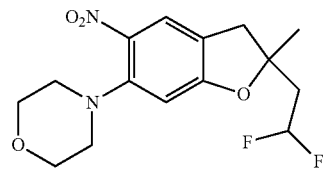 [SMILES: CC1(CC(F)F)Cc2cc(N)c(N3CCOCC3)cc2O1]

A mixture of diethylaminosulfur trifluoride (1.48 g, 7.35 mmol) in dichloromethane (30 ml) was added drop-wise to 2-(2-methyl-6-morpholino-5-nitro-3H-benzofuran-2-yl)acetaldehyde (450.0 mg, 1.47 mmol) at −78° C. and the reaction was maintained there for 30 min followed by room temperature for 12h. The mixture was concentrated and purified by column chromatography (eluent 15% ethyl acetate:petroleum ether) to afford 4-[2-(2,2-difluoroethyl)-2-methyl-5-nitro-3H-benzofuran-6-yl]morpholine (320 mg, 63% yield) as a yellow solid. (ESI): m/z=329.1 [M+1]$^+$.

731

Step H. 2-(2,2-Difluoroethyl)-2-methyl-6-morpholino-3H-benzofuran-5-amine

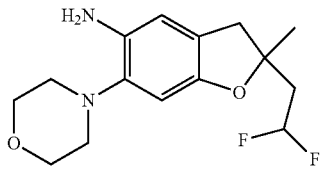

The title compound was made in a manner analogous to Example 2, Step B to afford 2-(2,2-difluoroethyl)-2-methyl-6-morpholino-3H-benzofuran-5-amine (245 mg, 84% yield) as a colorless oil. (ESI): m/z=299.1 [M+1]$^+$.

Examples 367 and 368. N-[(2R)-2-(2,2-difluoroethyl)-2-methyl-6-morpholino-3H-benzofuran-5-yl]pyrazolo[1,5-a]pyrimidine-3-carboxamide and N-[(2S)-2-(2,2-difluoroethyl)-2-methyl-6-morpholino-3H-benzofuran-5-yl]pyrazolo[1,5-a]pyrimidine-3-carboxamide

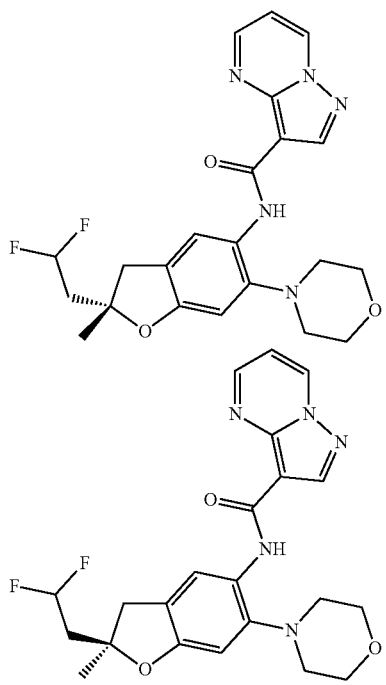

The title compounds were made in a manner analogous to Examples 29 and 30 to give N-[(2R)-2-(2,2-difluoroethyl)-2-methyl-6-morpholino-3H-benzofuran-5-yl]pyrazolo[1,5-a]pyrimidine-3-carboxamide (130 mg, 36% yield) and N-[(2S)-2-(2,2-difluoroethyl)-2-methyl-6-morpholino-3H-benzofuran-5-yl]pyrazolo[1,5-a]pyrimidine-3-carboxamide (120 mg, 33% yield) as yellow solids.

Example 367, Peak 1: $^1$H NMR (400 MHz, dimethyl sulfoxide-d$_6$) δ 10.44 (s, 1H), 9.36 (d, J=7.0 Hz, 1H), 8.93 (d, J=4.1 Hz, 1H), 8.67 (s, 1H), 8.32 (s, 1H), 7.34 (dd, J=7.0, 4.2 Hz, 1H), 6.76 (s, 1H), 3.83 (t, J=4.2 Hz, 4H), 3.20 (d, J=15.8 Hz, 1H), 3.00 (d, J=15.8 Hz, 1H), 2.81 (t, J=4.3 Hz, 4H), 2.50 (s, 1H), 2.35 (td, J=17.4, 4.6 Hz, 2H), 1.44 (s, 3H). MS (ESI): m/z=444.2 [M+1]$^+$. MS (ESI): m/z=299.1 [M+1]$^+$.

Example 368, Peak 2: $^1$H NMR (400 MHz, dimethyl sulfoxide-d$_6$) δ 10.45 (s, 1H), 9.38 (dd, J=7.0, 1.4 Hz, 1H), 8.95 (dd, J=4.2, 1.4 Hz, 1H), 8.69 (s, 1H), 8.33 (s, 1H), 7.35 (dd, J=7.0, 4.2 Hz, 1H), 6.77 (s, 1H), 3.83 (t, J=4.2 Hz, 4H), 3.34 (s, 2H), 3.21 (d, J=15.8 Hz, 1H), 3.01 (d, J=15.8 Hz, 1H), 2.82 (t, J=4.5 Hz, 4H), 2.36 (td, J=17.4, 4.7 Hz, 1H), 1.45 (s, 3H). MS (ESI): m/z=299.1 [M+1]$^+$.

Example 369. N-[1'-(2-Hydroxyethyl)-6-morpholino-spiro[3H-benzofuran-2,4'-piperidine]-5-yl]pyrazolo[1,5-a]pyrimidine-3-carboxamide

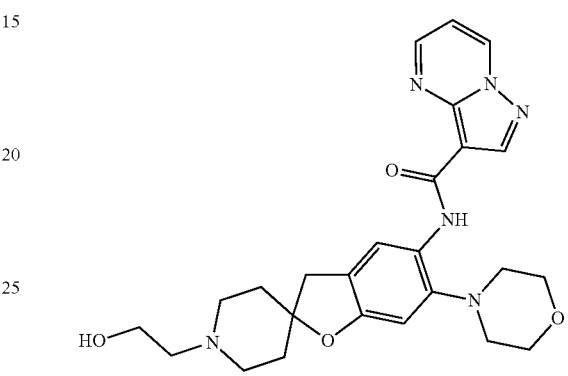

Step A. 2-(6-Fluorospiro[3H-benzofuran-2,4'-piperidine]-1'-yl)ethanol

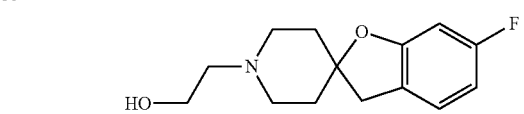 [SMILES: OCCN1CCC2(CC1)Cc1ccc(F)cc1O2]

To a solution of 6-fluorospiro[3H-benzofuran-2,4'-piperidine (Example 142, Step C; 414.0 mg, 2 mmol) in acetonitrile (15 ml) was added potassium carbonate (689.2 mg, 4.99 mmol) and 2-bromoethanol (374.5 mg, 3 mmol). The reaction was stirred at 45° C. for 12h, cooled to room temperature, filtered and concentrated to give 2-(6-fluorospiro[3H-benzofuran-2,4'-piperidine]-1'-yl)ethanol (561 mg, quant.) as a yellow solid. MS (ESI): m/z=252.1 [M+1]$^+$.

Step B. 2-(6-Fluoro-5-nitro-spiro[3H-benzofuran-2,4'-piperidine]-1'-yl)ethanol

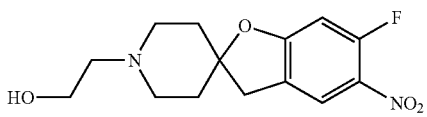 [SMILES: O=[N+]([O-])c1cc2c(cc1F)OC1(CCN(CCO)CC1)C2]

To a solution of 2-(6-fluorospiro[3H-benzofuran-2,4'-piperidine]-1'-yl)ethanol (510.0 mg, 2 mmol) in dichloromethane (9 ml) was added fuming nitric acid (1 ml, 16 mmol) and the reaction was stirred for 2h. The reaction was quenched with saturated aqueous sodium bicarbonate and extracted with dichloromethane (2×). The combined organic phases were isolated, washed with brine, dried over magnesium sulfate and concentrated to give 2-(6-fluoro-5-nitro-spiro[3H-benzofuran-2,4'-piperidine]-1'-yl)ethanol (374 mg, 35% yield) as a yellow oil. MS (ESI): m/z=297.1 [M+1]$^+$.

Step C. 2-(6-Morpholino-5-nitro-spiro[3H-benzofuran-2,4'-piperidine]-1'-yl)ethanol

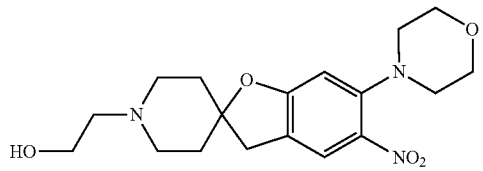 [SMILES: O=[N+]([O-])c1cc2c(cc1N1CCOCC1)OC1(CCN(CCO)CC1)C2]

A mixture of potassium carbonate (435.2 mg, 3.16 mmol), morpholine (0.33 ml, 3.79 mmol) and 2-(6-fluoro-5-nitro-spiro[3H-benzofuran-2,4'-piperidine]-1'-yl)ethanol (374.0 mg, 1.26 mmol) in acetonitrile (10 ml) was stirred for 2h. The reaction was diluted with water and extracted with ethyl acetate (2×). The combined organic phases were isolated, washed with saturated brine, dried over anhydrous magnesium sulfate and concentrated. The residue was purified by column chromatography (eluent 1:10 methanol: dichloromethane) to afford 2-(6-morpholino-5-nitro-spiro[3H-benzofuran-2,4'-piperidine]-1'-yl)ethanol (214 mg, 47% yield) as an orange solid. MS (ESI): m/z=364.2 [M+1]$^+$.

Step D. 2-(5-Amino-6-morpholino-spiro[3H-benzofuran-2,4'-piperidine]-1'-yl)ethanol

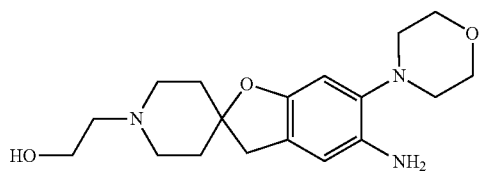

The title compound was made in a manner analogous to Example 2, Step B to afford 2-(5-amino-6-morpholino-spiro[3H-benzofuran-2,4'-piperidine]-1'-yl)ethanol (160 mg, 64% yield) as a yellow oil. (ESI): m/z=334.2 [M+1]$^+$.

Step E. 2-(5-Amino-6-morpholino-spiro[3H-benzofuran-2,4'-piperidine]-1'-yl)ethanol

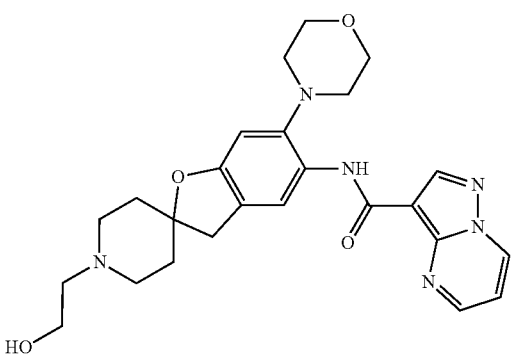 [SMILES: O=C(Nc1cc2c(cc1N1CCOCC1)OC1(CCN(CCO)CC1)C2)c1cnn2cccnc12]

The title compound was made in a manner analogous to Example 1, Step C to afford 2 N-[1'-(2-hydroxyethyl)-6-morpholino-spiro[3H-benzofuran-2,4'-piperidine]-5-yl]pyrazolo[1,5-a]pyrimidine-3-carboxamide (91 mg, 40% yield) as a yellow solid. 1H NMR (400 MHz, Chloroform-d) 610.47 (s, 1H), 8.87-8.74 (m, 3H), 8.43 (s, 1H), 7.07 (dd, J=7.0, 4.1 Hz, 1H), 6.69 (s, 1H), 3.95 (t, J=4.5 Hz, 4H), 3.64 (t, J=5.4 Hz, 2H), 3.02 (s, 2H), 2.92 (t, J=4.6 Hz, 4H), 2.74-2.57 (m, 4H), 2.00 (dt, J=13.3, 4.3 Hz, 2H), 1.83 (ddd, J=13.2, 8.8, 4.7 Hz, 2H), 1.61 (s, 2H). (ESI): m/z=479.2 [M+1]$^+$.

TABLE 11

The following examples were made in a manner similar to that for Example 152:

| Ex. | Name | Structure | NMR, MS |
|---|---|---|---|
| 370 | N-[1'-(2,2-difluoroethyl)-6-morpholino-spiro[3H-benzofuran-2,4'-piperidine]-5-yl]pyrazolo[1,5-a]pyrimidine-3-carboxamide | 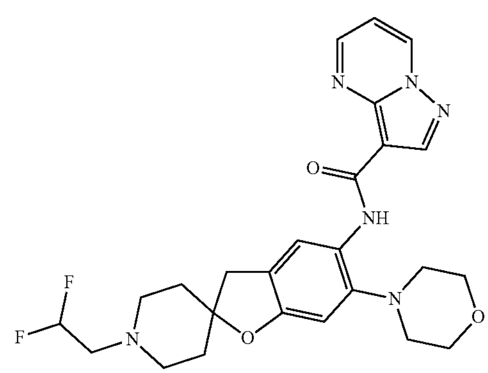 [SMILES: O=C(Nc1cc2c(cc1N1CCOCC1)OC1(CCN(CC(F)F)CC1)C2)c1cnn2cccnc12] | $^1$H NMR (400 MHz, Chloroform-d) δ 10.47 (s, 1H), 8.87-8.74 (m, 3H), 8.43 (s, 1H), 7.07 (dd, J = 7.0, 4.1 Hz, 1H), 6.68 (s, 1H), 5.91 (tt, J = 56.1, 4.3 Hz, 1H), 3.95 (t, J = 4.5 Hz, 4H), 3.01 (s, 2H), 2.92 (t, J = 4.5 Hz, 4H), 2.88-2.65 (m, 6H), 1.99 (dt, J = 13.1, 3.7 Hz, 2H), 1.84 (ddd, J = 13.5, 9.3, 4.2 Hz, 2H). MS (ESI): m/z = 499.2 [M + 1]$^+$. |

TABLE 11-continued

The following examples were made in a manner similar to that for Example 152:

| Ex. | Name | Structure | NMR, MS |
|---|---|---|---|
| 371 | N-(6-(4-(Hydroxymethyl)piperidin-1-yl)-1'-methyl-3H-spiro[benzofuran-2,4'-piperidin]-5-yl)pyrazolo[1,5-a]pyrimidine-3-carboxamide | 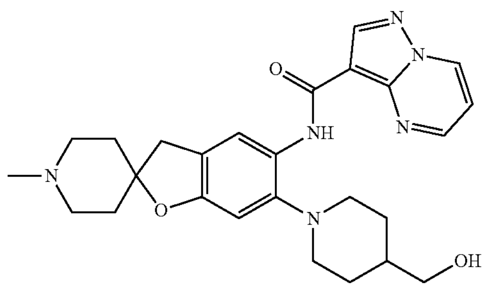 [SMILES: CN1CCC2(CC1)Cc1cc(NC(=O)c3cnn4cccnc34)c(N3CCC(CO)CC3)cc1O2] | $^1$H NMR (400 MHz, Chloroform-d) δ 10.51 (s, 1H), 8.88-8.73 (m, 3H), 8.43 (s, 1H), 7.02 (dd, J = 7.0, 4.3 Hz, 1H), 6.69 (s, 1H), 3.71-3.56 (m, 2H), 3.10 (d, J = 11.4 Hz, 2H), 3.01 (s, 2H), 2.76-2.42 (m, 6H), 2.34 (s, 3H), 2.00 (d, J = 13.2 Hz, 3H), 1.90-1.67 (m, 6H). (ESI): m/z = 477.2 [M + 1]$^+$. |
| 372 | N-(1'-isopropyl-6-morpholino-spiro[3H-benzofuran-2,4'-piperidine]-5-yl)pyrazolo[1,5-a]pyrimidine-3-carboxamide | 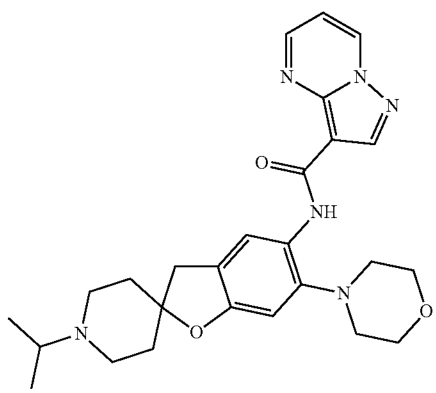 [SMILES: CC(C)N1CCC2(CC1)Cc1cc(NC(=O)c3cnn4cccnc34)c(N3CCOCC3)cc1O2] | $^1$H NMR (400 MHz, dimethyl sulfoxide-d$_6$) δ 10.47 (d, J = 4.8 Hz, 1H), 9.39 (dd, J = 7.0, 1.6 Hz, 1H), 8.95 (dd, J = 4.1, 1.7 Hz, 1H), 8.69 (d, J = 2.1 Hz, 1H), 8.37 (s, 1H), 7.36 (dd, J = 7.0, 4.2 Hz, 1H), 6.81 (d, J = 2.6 Hz, 1H), 3.84 (t, J = 4.4 Hz, 4H), 3.50-3.36 (m, 4H), 3.21-3.06 (m, 3H), 2.82 (t, J = 4.5 Hz, 4H), 2.08 (dt, J = 50.5, 14.3 Hz, 4H), 1.30 (dd, J = 6.6, 3.6 Hz, 6H). (ESI): m/z = 477.3 [M + 1]$^+$. |
| 373 | N-(6-(4-(2-Amino-2-oxoethyl)piperazin-1-yl)-1'-methyl-3H-spiro[benzofuran-2,4'-piperidin]-5-yl)pyrazolo[1,5-a]pyrimidine-3-carboxamide | 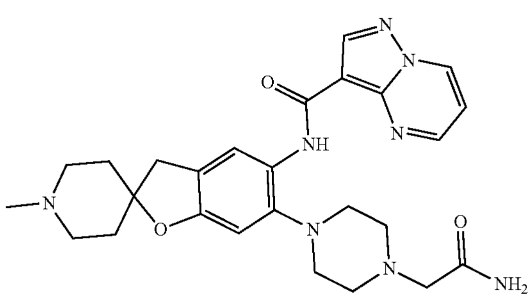 [SMILES: CN1CCC2(CC1)Cc1cc(NC(=O)c3cnn4cccnc34)c(N3CCN(CC(N)=O)CC3)cc1O2] | $^1$H NMR (400 MHz, DMSO-d$_6$) δ 10.42 (s, 1H), 9.40-9.35 (m, 1H), 9.00-8.95 (m, 1H), 8.67 (s, 1H), 8.34 (s, 1H), 7.35 (dd, J = 6.8, 4.0 Hz, 1H), 7.23 (s, 1H), 7.17 (s, 1H), 6.72 (s, 1H), 3.03-3.00 (m, 4H), 2.84-2.83 (m, 4H), 2.74-2.72 (m, 4H), 2.69-2.60 (m, 4H), 2.32 (s, 3H), 1.86-1.78 (m, 4H). LCMS (ESI) m/z: 505.2 [M + H]$^+$. |
| 374 | N-(1'-Acetyl-6-(4-(2-amino-2-oxoethyl)piperazin-1-yl)-3H-spiro[benzofuran-2,4'-piperidin]-5-yl)pyrazolo[1,5-a]pyrimidine-3-carboxamide | 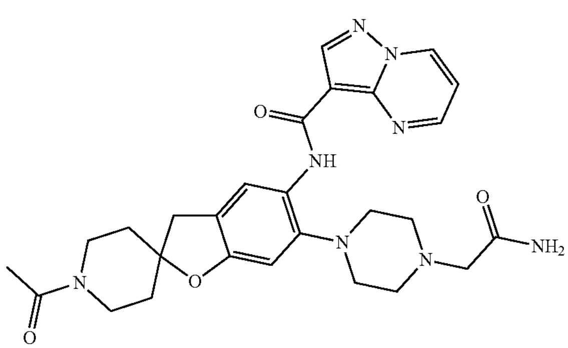 [SMILES: CC(=O)N1CCC2(CC1)Cc1cc(NC(=O)c3cnn4cccnc34)c(N3CCN(CC(N)=O)CC3)cc1O2] | $^1$H NMR (400 MHz, DMSO-d$_6$) δ 10.43 (s, 1H), 9.40-9.35 (m, 1H), 9.00-8.95 (m, 1H), 8.68 (s, 1H), 8.36 (s, 1H), 7.35 (dd, J = 6.8, 4.0 Hz, 1H), 7.22 (s, 1H), 7.17 (s, 1H), 6.75 (s, 1H), 3.78-3.73 (m, 1H), 3.54-3.41 (m, 2H), 3.38-3.32 (m, 1H), 3.04-3.01 (m, 4H), 2.85 (s, 4H), 2.74-2.72 (m, 4H), 2.03 (s, 3H), 1.86-1.66 (m, 4H). LCMS (ESI): m/z = 533.2 [M + H]$^+$. |

TABLE 11-continued

The following examples were made in a manner similar to that for Example 152:

| Ex. | Name | Structure | NMR, MS |
|---|---|---|---|
| 375 | N-(6-(4-(2-(Cyclopropylamino)-2-oxoethyl)piperazin-1-yl)-3H-spiro[benzofuran-2,4'-piperidin]-5-yl)pyrazolo[1,5-a]pyrimidine-3-carboxamide | 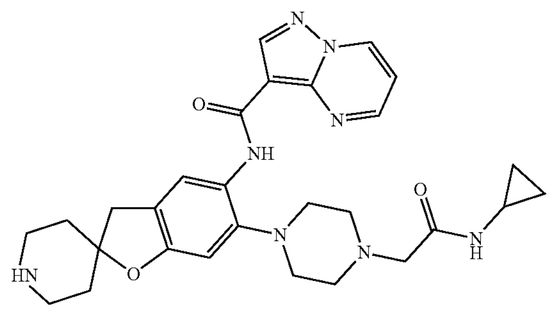 [SMILES: O=C(CN1CCN(c2cc3c(cc2NC(=O)c2cnn4cccnc24)CC2(CCNCC2)O3)CC1)NC1CC1] | $^1$H NMR (400 MHz, CDCl$_3$) δ 10.36 (s, 1H), 8.90-8.85 (m, 1H), 8.78 (s, 1H), 8.75-8.70 (m, 1H), 8.41 (s, 1H), 7.17 (s, 1H), 7.07 (dd, J = 6.8, 4.0 Hz, 1H), 6.68 (s, 1H), 3.17-3.12 (m, 4H), 3.08 (s, 2H), 3.03-2.94 (m, 6H), 2.78-2.74 (m, 5H), 1.93-1.92 (m, 2H), 1.83-1.80 (m, 2H), 0.84-0.81 (m, 2H), 0.55-0.50 (m, 2H). LCMS (ESI): m/z = 531.3 [M + H]$^+$. |
| 376 | N-(6-(4-(2-(Cyclopropylamino)-2-oxoethyl)piperazin-1-yl)-1'-methyl-3H-spiro[benzofuran-2,4'-piperidin]-5-yl)pyrazolo[1,5-a]pyrimidine-3-carboxamide | 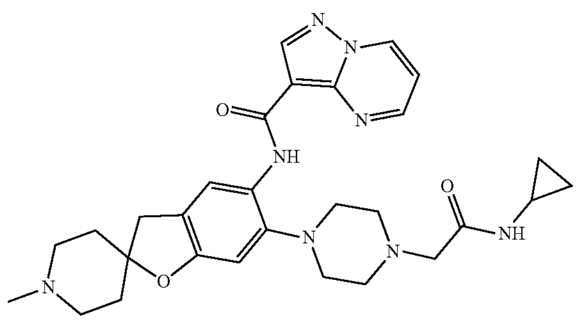 [SMILES: CN1CCC2(CC1)Cc1cc(NC(=O)c3cnn4cccnc34)c(N3CCN(CC(=O)NC4CC4)CC3)cc1O2] | $^1$H NMR (400 MHz, CDCl$_3$) δ 10.36 (s, 1H), 8.84-8.82 (m, 1H), 8.78 (s, 1H), 8.72-8.70 (m, 1H), 8.41 (s, 1H), 7.17 (s, 1H), 7.01 (dd, J = 6.4, 4.0 Hz, 1H), 6.68 (s, 1H), 3.08 (s, 2H), 3.02 (s, 2H), 2.94-2.92 (m, 4H), 2.76-2.74 (m, 5H), 2.65-2.61 (m, 3H), 2.37 (s, 3H), 2.04-2.02 (m, 2H), 2.00-1.98 (m, 2H), 0.84-0.82 (m, 2H), 0.55-0.50 (m, 2H). LCMS (ESI): m/z = 545.3 [M + H]$^+$. |
| 377 | N-(6-(2,2-Difluoroethoxy)-3H-spiro[benzofuran-2,4'-piperidin]-5-yl)pyrazolo[1,5-a]pyrimidine-3-carboxamide | 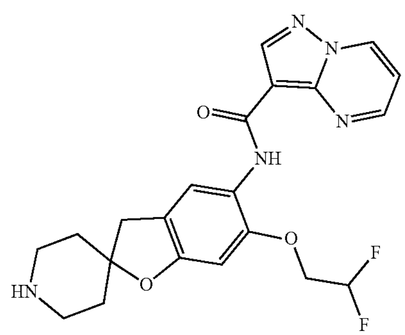 [SMILES: O=C(Nc1cc2c(cc1OCC(F)F)OC1(CCNCC1)C2)c1cnn2cccnc12] | $^1$H NMR (400 MHz, DMSO-d$_6$) δ 10.32 (s, 1H), 9.40-9.35 (m, 1H), 8.85-8.75 (m, 2H), 8.67 (s, 1H), 8.35 (s, 1H), 7.34 (dd, J = 7.2, 4.0 Hz, 1H), 6.75 (s, 1H), 6.67-6.40 (m, 1H), 4.46-4.37 (m, 2H), 3.32-3.15 (m, 4H), 3.11 (s, 2H), 2.05-1.95 (m, 4H). LCMS (ESI): m/z = 430.1 [M + H]$^+$. |
| 378 | N-(6-(2,2-difluoroethoxy)-1'-methyl-3H-spiro[benzofuran-2,4'-piperidin]-5-yl)pyrazolo[1,5-a]pyrimidine-3-carboxamide | 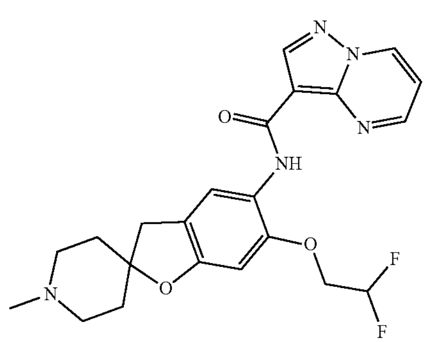 [SMILES: CN1CCC2(CC1)Cc1cc(NC(=O)c3cnn4cccnc34)c(OCC(F)F)cc1O2] | $^1$H NMR (400 MHz, CDCl$_3$) δ 10.24 (s, 1H), 8.84-8.80 (m, 1H), 8.75 (s, 1H), 8.70 (dd, J = 4.0, 1.6 Hz, 1H), 8.42 (s, 1H), 7.04 (dd, J = 6.8, 4.0 Hz, 1H), 6.42 (s, 1H), 6.40-6.10 (m, 1H), 4.30-4.22 (m, 2H), 3.01 (s, 2H), 2.58-2.53 (m, 4H), 2.35 (s, 3H), 2.02-2.00 (m, 2H), 1.99-1.68 (m, 2H). LCMS (ESI): m/z = 444.2 [M + H]$^+$. |

Example 379. N-[6-[4-(2,2-difluoroethyl)piperazin-yl]-2,2-dimethyl-3H-benzofuran-5-yl]-6-(methylamino)pyrazolo[1,5-a]pyrimidine-3-carboxamide

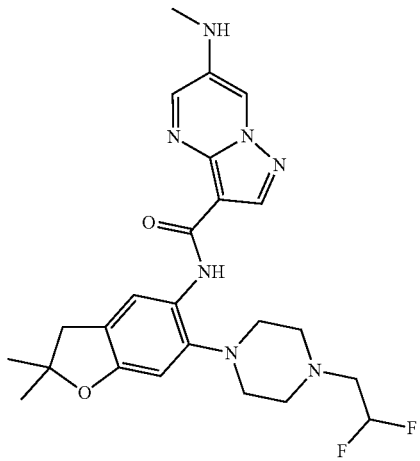 [SMILES: CNc1cnc2c(C(=O)Nc3cc4c(cc3N3CCN(CC(F)F)CC3)OC(C)(C)C4)cnn2c1]

Step A. Ethyl 6-[(4-methoxyphenyl)methyl-methyl-amino]pyrazolo[1,5-a]pyrimidine-3-carboxylate

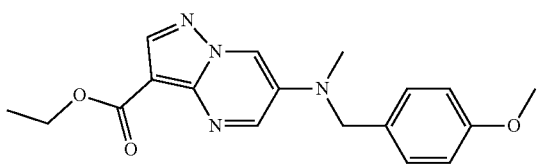 [SMILES: CCOC(=O)c1cnn2cc(N(C)Cc3ccc(OC)cc3)cnc12]

A mixture of ethyl 6-bromopyrazolo[1,5-a]pyrimidine-3-carboxylate (1.5 g, 5.55 mmol), N-(4-methoxybenzyl)-N-methylamine (1.67 g, 11.04 mmol) and N,N-diisopropylethylamine (2.75 ml, 16.63 mmol) in ethanol (25 ml) was stirred at 85° C. for 96h. The mixture was concentrated to dryness and the residue was purified by column chromatography (eluent 50% ethyl acetate: petroleum ether) to afford ethyl 6-[(4-methoxyphenyl)methyl-methyl-amino]pyrazolo[1,5-a]pyrimidine-3-carboxylate (1120 mg, 57.5% yield) as a yellow solid. (ESI): m/z=341.2 [M+1]$^+$.

Step B. 6-[(4-Methoxyphenyl)methyl-methyl-amino]pyrazolo[1,5-a]pyrimidine-3-carboxylic acid

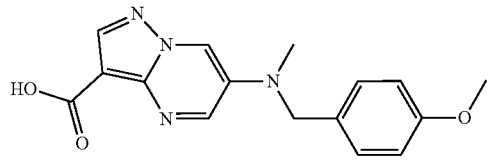 [SMILES: COc1ccc(CN(C)c2cnc3c(C(=O)O)cnn3c2)cc1]

A mixture of ethyl 6-[(4-methoxyphenyl)methyl-methyl-amino]pyrazolo[1,5-a]pyrimidine-3-carboxylate (50 mg, 0.15 mmol) and lithium hydroxide hydrate (7.0 mg, 0.17 mmol) in tetrahydrofuran (1 ml), methanol (1 ml) and water (1 ml) was stirred in a sealed tube at 100° C. under microwave irradiation for 45 min. The mixture will neutralized with 2N HCl and concentrated to dryness to afford 6-[(4-methoxyphenyl)methyl-methyl-amino]pyrazolo[1,5-a]pyrimidine-3-carboxylic acid (50 mg, 98% yield) as a yellow solid. (ESI): m/z=313.1 [M+1]$^+$.

Step C. N-[6-[4-(2,2-Difluoroethyl)piperazin-1-yl]-2,2-dimethyl-3H-benzofuran-5-yl]-6-[(4-methoxyphenyl)methyl-methyl-amino]pyrazolo[1,5-a]pyrimidine-3-carboxamide

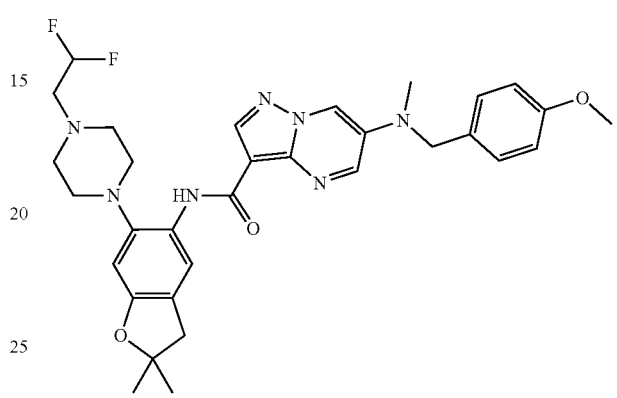

A mixture of 6-[4-(2,2-difluoroethyl)piperazin-1-yl]-2,2-dimethyl-3H-benzofuran-5-amine (120.0 mg, 0.39 mmol), 6-[(4-methoxyphenyl)methyl-methyl-amino]pyrazolo[1,5-a]pyrimidine-3-carboxylic acid (150.0 mg, 0.48 mmol), HATU (300.0 mg, 0.79 mmol) and N,N-diisopropylethylamine (0.3 ml, 1.72 mmol) in N,N-dimethylformamide (2 ml) was stirred for 12h. The reaction was then purified by preparative HPLC (Xbridge 21.2*250 mm c18, 10 um acetonitrile 50-70% (10 mM ammonium bicarbonate) in water) to afford N-[6-[4-(2,2-difluoroethyl)piperazin-1-yl]-2,2-dimethyl-3H-benzofuran-5-yl]-6-[(4-methoxyphenyl)methyl-methyl-amino]pyrazolo[1,5-a]pyrimidine-3-carboxamide (96 mg, 41% yield).

Step D. N-[6-[4-(2,2-difluoroethyl)piperazin-1-yl]-2,2-dimethyl-3H-benzofuran-5-yl]-6-(methylamino)pyrazolo[1,5-a]pyrimidine-3-carboxamide

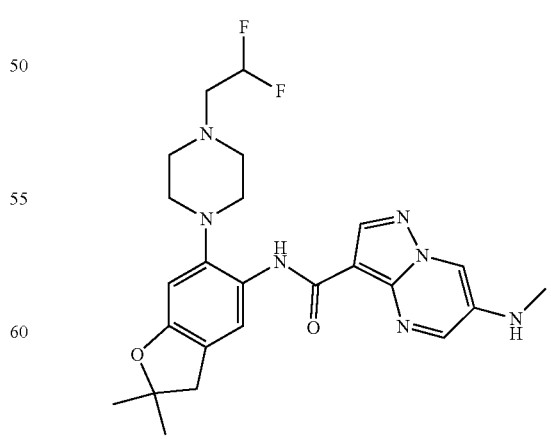

N-[6-[4-(2,2-difluoroethyl)piperazin-1-yl]-2,2-dimethyl-3H-benzofuran-5-yl]-6-[(4-methoxyphenyl)methyl-methylamino]pyrazolo[1,5-a]pyrimidine-3-carboxamide (120 mg, 0.2 mmol) and trifluoroacetic acid (2 ml, 0.2000 mmol) in dichloromethane (6 ml) was stirred for 3h. The reaction was then purified by preparative HPLC (Xbridge 21.2*250 mm c18, 10 um acetonitrile 50-70% (10 mM ammonium bicarbonate) in water) to afford N-[6-[4-(2,2-difluoroethyl)piperazin-1-yl]-2,2-dimethyl-3H-benzofuran-5-yl]-6-(methylamino)pyrazolo[1,5-a]pyrimidine-3-carboxamide (60 mg, 62% yield). $^1$H NMR (400 MHz, dimethyl sulfoxide-d$_6$) δ 10.30 (s, 1H), 8.61 (d, J=2.6 Hz, 1H), 8.38-8.27 (m, 3H), 6.70 (s, 1H), 2.99 (s, 2H), 2.93-2.73 (m, 14H), 1.41 (s, 6H). (ESI): m/z=502.2 [M+1]$^+$.

TABLE 12

The following examples were made in a manner similar to that for Example 64:

| Ex. | Name | Structure | NMR, MS |
|---|---|---|---|
| 380 | N-(1'-methyl-6-morpholino-3H-spiro[benzofuran-2,4'-piperidin]-5-yl)-6-(methylamino)pyrazolo[1,5-a]pyrimidine-3-carboxamide | 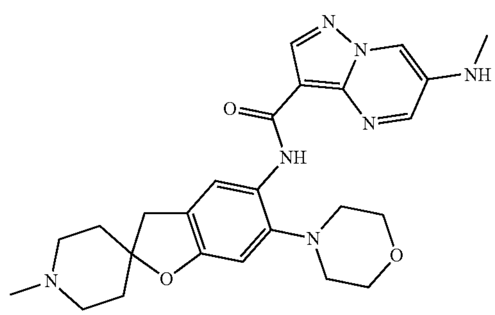 | $^1$H NMR (400 MHz, dimethyl sulfoxide-d$_6$) δ 10.33 (s, 1H), 8.64 (d, J = 2.6 Hz, 1H), 8.38-8.29 (m, 3H), 6.75 (s, 1H), 6.31 (q, J = 4.9 Hz, 1H), 3.83 (t, J = 4.5 Hz, 4H), 2.98 (s, 2H), 2.84-2.73 (m, 8H), 2.45 (s, 3H), 2.20 (s, 3H), 1.87-1.70 (m, 4H). (ESI): m/z = 478.3 [M + 1]$^+$. |
| 381 and 382 | (S)-N-(6-(4-(2,2-difluoroethyl)piperazin-1-yl)-2-(hydroxymethyl)-2-methyl-2,3-dihydrobenzofuran-5-yl)-6-(methylamino)pyrazolo[1,5-a]pyrimidine-3-carboxamide and (R)-N-(6-(4-(2,2-difluoroethyl)piperazin-1-yl)-2-(hydroxymethyl)-2-methyl-2,3-dihydrobenzofuran-5-yl)-6-(methylamino)pyrazolo[1,5-a]pyrimidine-3-carboxamide (absolute stereochemistry assigned arbitrarily) | | Example 381, Peak 1: $^1$H NMR (400 MHz, dimethyl sulfoxide-d$_6$) δ 10.30 (s, 1H), 8.61 (d, J = 2.5 Hz, 1H), 8.35 (s, 1H), 8.33-8.26 (m, 2H), 6.69 (s, 1H), 6.44-6.32 (m, 1H), 6.26-6.01 (m, 1H), 5.05 (t, J = 5.8 Hz, 1H), 3.42 (t, J = 5.5 Hz, 2H), 3.18 (d, J = 15.7 Hz, 1H), 2.93-2.66 (m, 14H), 1.33 (s, 3H). (ESI): m/z = 502.2 [M + 1]$^+$. Example 382, Peak 2: $^1$H NMR (400 MHz, dimethyl sulfoxide-d$_6$) δ 10.30 (s, 1H), 8.61 (d, J = 2.4 Hz, 1H), 8.35 (s, 1H), 8.33-8.28 (m, 2H), 6.69 (s, 1H), 6.48-6.30 (m, 1H), 5.05 (t, J = 5.8 Hz, 1H), 3.42 (t, J = 5.4 Hz, 2H), 3.18 (d, J = 15.7 Hz, 1H), 2.88 (dd, J = 15.6, 4.3 Hz, 1H), 2.84-2.74 (m, 14H), 1.33 (s, 3H). (ESI): m/z = 502.2 [M + 1]$^+$. |
| 383 | N-(6-(4-(2,2-difluoroethyl)piperazin-1-yl)-2',3',5',6'-tetrahydro-3H-spiro[benzofuran-2,4'-pyran]-5-yl)-6-(methylamino)pyrazolo[1,5-a]pyrimidine-3-carboxamide | 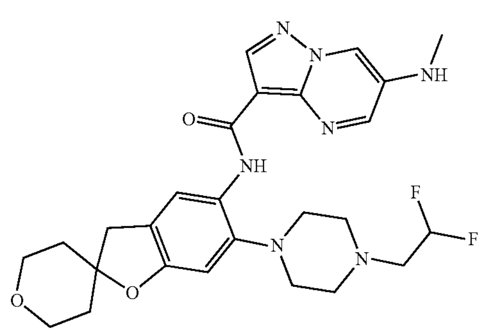 [SMILES: CNc1cnc2c(C(=O)Nc3cc4c(cc3N3CCN(CC(F)F)CC3)OC3(CCOCC3)C4)cnn2c1] | $^1$H NNMR (400 MHz, dimethyl sulfoxide-d$_6$) δ 10.29 (s, 1H), 8.61 (d, J = 2.6 Hz, 1H), 8.33 (dd, J = 20.7, 3.1 Hz, 3H), 6.76 (s, 1H), 6.44-6.31 (m, 1H), 3.77 (dt, J = 11.6, 5.5 Hz, 2H), 3.63 (dt, J = 10.9, 4.9 Hz, 2H), 3.33 (s, 2H), 3.05 (s, 2H), 2.92-2.73 (m, 12H), 1.79 (t, J = 5.6 Hz, 4H). $^{19}$F NMR (376 MHz, dimethyl sulfoxide-d$_6$) δ -118.43. (ESI): m/z = 528.3 [M + 1]$^+$. |

Example 384. N-(6-Cyclopropyl-2,2-dimethyl-3I-benzofuran-5-yl)pyrazolo[1,5-a]pyrimidine-3-carboxamide

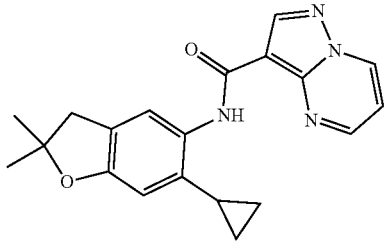

Step A.
6-Cyclopropyl-2,2-dimethyl-5-nitro-3H-benzofuran

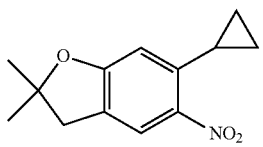 [SMILES: CC1(C)Cc2cc([N+](=O)[O-])c(C3CC3)cc2O1]

A mixture of 6-bromo-2,2-dimethyl-5-nitro-3H-benzofuran (300.0 mg, 1.1 mmol), cyclopropylboronic acid (142.1 mg, 1.65 mmol), tricyclohexylphosphine (61.84 mg, 0.22 mmol), palladium acetate (24.75 mg, 0.11 mmol) and potassium phosphate tribasic (819.12 mg, 3.86 mmol) in toluene (8 ml) and water (1 ml) was stirred under nitrogen at 110° C. for 2h under microwave conditions. The reaction was concentrated to dryness and the residue was taken up in ethyl acetate (20 ml) and the resulting organic phase was washed with water (2×) and brine, dried over magnesium sulfate, concentrated to dryness and purified by column chromatography (eluent 25% ethyl acetate: isohexane) to afford 6-cyclopropyl-2,2-dimethyl-5-nitro-3H-benzofuran (220 mg, 86% yield) as a yellow oil. MS (ESI): m/z=234.2 [M+1]$^+$.

Step B.
6-Cyclopropyl-2,2-dimethyl-3H-benzofuran-5-amine

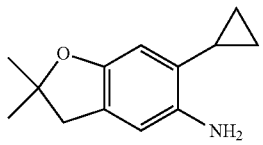

The title compound was made in a manner analogous to Example 2, Step B to afford 6-cyclopropyl-2,2-dimethyl-3H-benzofuran-5-amine (100 mg, 96% yield). $^1$H NMR (400 MHz, CDCl$_3$) δ=6.54 (s, 1H), 6.46 (s, 1H), 2.93 (s, 2H), 1.75-1.60 (m, 1H), 1.44 (s, 6H), 0.96-0.82 (m, 2H), 0.65-0.53 (m, 2H).

Step C. N-(6-Cyclopropyl-2,2-dimethyl-3H-benzofuran-5-yl)pyrazolo[1,5-a]pyrimidine-3-carboxamide

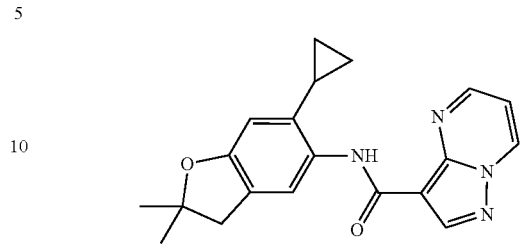

The title compound was made in a manner analogous to Example 378, Step C to afford N-(6-cyclopropyl-2,2-dimethyl-3H-benzofuran-5-yl)pyrazolo[1,5-a]pyrimidine-3-carboxamide (120 mg, 47% yield). $^1$H NMR (400 MHz, dimethyl sulfoxide-d$_6$) δ 10.04 (s, 1H), 9.38 (dd, J=7.0, 1.6 Hz, 1H), 8.89 (dd, J=4.3, 1.6 Hz, 1H), 8.69 (s, 1H), 8.02 (s, 1H), 7.32 (dd, J=7.0, 4.2 Hz, 1H), 6.49 (s, 1H), 3.00 (s, 2H), 1.92 (td, J=8.4, 4.4 Hz, 1H), 1.40 (s, 6H), 1.10-0.99 (m, 2H), 0.73-0.62 (m, 2H). MS (ESI): m/z=349.2 [M+1]$^+$.

Example 385. N-(2-methyl-6-morpholino-1,1-dioxo-3H-1,2-benzothiazol-5-yl)pyrazolo[1,5-a]pyrimidine-3-carboxamide

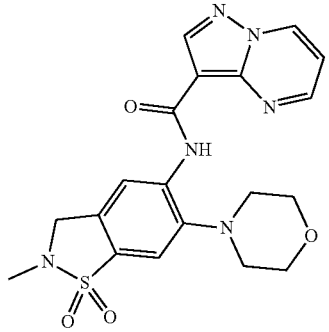 [SMILES: CN1Cc2cc(NC(=O)c3cnn4cccnc34)c(N3CCOCC3)cc2S1(=O)=O]

Step A. 6-Chloro-1,1-dioxo-1,2-benzothiazol-3-one

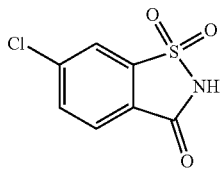 [SMILES: O=C1NS(=O)(=O)c2cc(Cl)ccc21]

To a mixture of methyl 4-chloro-2-(chlorosulfonyl)benzoate (500 mg, 1.86 mmol) in tetrahydrofuran (10 ml) was added ammonium hydroxide (2 ml, 28%). The mixture was stirred at room temperature for 1h and then concentrated to afford 6-chloro-1,1-dioxo-1,2-benzothiazol-3-one (400 mg) as a white solid, which was used without further purification. MS (ESI): m/z=218.1 [M+1]$^+$.

Step B. 6-Chloro-2-methyl-1,1-dioxo-1,2-benzothiazol-3-one

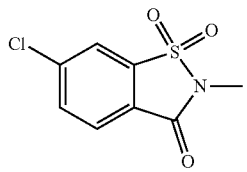

A mixture of 6-chloro-1,1-dioxo-1,2-benzothiazol-3-one (400 mg, 1.84 mmol), iodomethane (391 mg, 2.76 mmol) and cesium carbonate (898 mg, 2.76 mmol) in N,N-dimethylformamide (6 ml) was stirred at 80° C. in a sealed tube for 12h. Water was added and the reaction was extracted with ethyl acetate (20 ml). The organic phase was isolated, washed with brine, dried over sodium sulfate and concentrated to afford 6-chloro-2-methyl-1,1-dioxo-1,2-benzothiazol-3-one (340 mg) as a brown solid, which was used without further purification. MS (ESI): m/z=232.1 [M+1]$^+$.

Step C. 1 6-Chloro-2-methyl-5-nitro-1,1-dioxo-1,2-benzothiazol-3-one

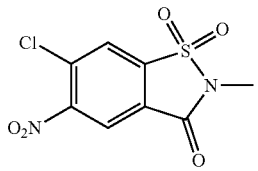 [SMILES: CN1C(=O)c2cc([N+](=O)[O-])c(Cl)cc2S1(=O)=O]

To a mixture of 6-chloro-2-methyl-1,1-dioxo-1,2-benzothiazol-3-one (500 mg, 2.16 mmol) in fuming sulfuric acid (6 ml) was added drop-wise fuming nitric acid (2 ml). The mixture was stirred at 70° C. for 12h. The reaction was cooled to room temperature and poured into ice water. The reaction was extracted with ethyl acetate (2×20 ml). The organic phases were combined, dried over sodium sulfate and concentrated. The residue was purified by column chromatography (eluent 1:5 ethyl acetate:petroleum ether) to afford 6-chloro-2-methyl-5-nitro-1,1-dioxo-1,2-benzothiazol-3-one (52 mg, 9% yield over 3 steps) as a white solid. $^1$H NMR (400 MHz, CDCl$_3$) δ 8.44 (s, 1H), 8.14 (s, 1H), 3.32 (s, 3H).

Step D. 2-Methyl-6-morpholino-5-nitro-1,1-dioxo-1,2-benzothiazol-3-one

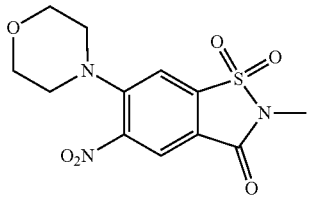 [SMILES: CN1C(=O)c2cc([N+](=O)[O-])c(N3CCOCC3)cc2S1(=O)=O]

A mixture of 6-chloro-2-methyl-5-nitro-1,1-dioxo-1,2-benzothiazol-3-one (38 mg, 0.14 mmol) in acetonitrile (3 ml) was treated with morphine (20 mg, 0.21 mmol) and stirred for 2h at ambient temperature. Water was added and the reaction was washed with ethyl acetate. The organic phase was isolated, dried over sodium sulfate and concentrated to afford 2-methyl-6-morpholino-5-nitro-1,1-dioxo-1,2-benzothiazol-3-one (43 mg, 96%) as a yellow solid. MS (ESI): m/z=328.1 [M+1]$^+$.

Step E. 2-Methyl-6-morpholino-1,1-dioxo-3H-1,2-benzothiazol-5-amine

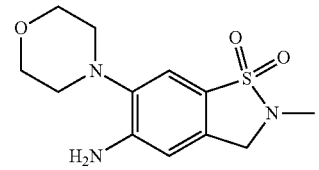 [SMILES: CN1Cc2cc(N)c(N3CCOCC3)cc2S1(=O)=O]

To a mixture of 2-methyl-6-morpholino-5-nitro-1,1-dioxo-1,2-benzothiazol-3-one (43 mg, 0.13 mmol) in tetrahydrofuran (8 ml) was added drop-wise borane-tetrahydrofuran complex (1 M in tetrhydrofuran, 3 ml, 3 mmol). The mixture was stirred at 65° C. for 12h. Methanol was added and the mixture was stirred at room temperature for 30 min. The mixture was concentrated to afford 2-methyl-6-morpholino-1,1-dioxo-3H-1,2-benzothiazol-5-amine (35 mg) as a colorless oil, which was used without further purification. MS (ESI): m/z=284.1 [M+1]$^+$.

Step F. N-(2-Methyl-6-morpholino-1,1-dioxo-3H-1,2-benzothiazol-5-yl)pyrazolo[1,5-a]pyrimidine-3-carboxamide

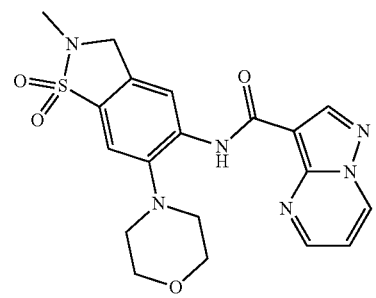 [SMILES: CN1Cc2cc(NC(=O)c3cnn4cccnc34)c(N3CCOCC3)cc2S1(=O)=O]

To a mixture of potassium carbonate (30 mg, 0.21 mmol), 2-methyl-6-morpholino-1,1-dioxo-3H-1,2-benzothiazol-5-amine (35 mg, 0.12 mmol) in toluene (10 ml) was added pyrazolo[1,5-a]pyrimidine-3-carbonyl chloride (24 mg, 0.13 mmol, Example 3, Step B). The mixture was stirred at 110° C. for 4h, concentrated and purified by preparative HPLC (Waters, XBridge C18, 4.6×150 mm, 3.5 m, A: acetonitrile, 30%-45%; B: 10 mM ammonium hydrogen carbonate in water) to afford N-(2-methyl-6-morpholino-1,1-dioxo-3H-1,2-benzothiazol-5-yl)pyrazolo[1,5-a]pyrimidine-3-carboxamide (15 mg, 28%) as a white solid. $^1$H NMR (400 MHz, dimethyl sulfoxide-d$_6$) δ 10.91 (s, 1H), 9.41 (dd, J=1.2, 6.8 Hz, 1H), 9.00 (dd, J=1.2, 4.0 Hz, 1H), 8.76 (s, 1H), 8.71 (s, 1H), 7.40 (dd, J=4.0, 6.8 Hz, 1H), 4.39 (s, 2H), 3.91-3.88 (m, 4H), 2.95-2.93 (m, 4H), 2.81 (s, 3H). MS (ESI): m/z=429.2 [M+1]$^+$.

Example 386. N-[2-(Cyanomethyl)-2-methyl-6-morpholino-3H-benzofuran-5-yl]pyrazolo[1,5-a]pyrimidine-3-carboxamide

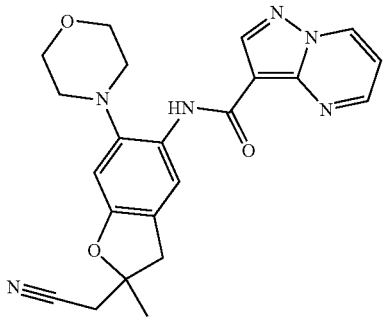 [SMILES: CC1(CC#N)Cc2cc(NC(=O)c3cnn4cccnc34)c(N3CCOCC3)cc2O1]

Step A. 2-(2,4-Difluoro-5-nitrophenyl)acetic acid

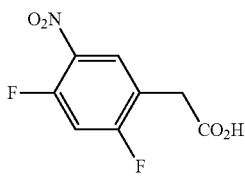

To a solution of (2,4-difluoro-phenyl)acetic acid (200.0 g, 1.16 mol) in sulfuric acid (825 ml) was added dropwise nitric acid (69%, 82.5 ml) at 0° C. The reaction mixture was stirred at 0° C. for 45 min and then poured into ice water. The resulting precipitate was collected by filtration, washed with water and dried to afford 2-(2,4-difluoro-5-nitrophenyl)acetic acid (216.0 g, 85% yield) as a white solid. $^1$H NMR (400 MHz, CDCl$_3$): δ 8.13 (t, J=8.0 Hz, 1H), 7.08 (dd, J=8.8, 10.0 Hz, 1H), 3.78 (s, 2H). $^{19}$F NMR (376 MHz, CDCl$_3$): δ −100.6 (d, J=15.0 Hz, 1F), −111.9 (d, J=15.0 Hz, 1F).

Step B. 1-(2,4-Difluoro-5-nitrophenyl)propan-2-one

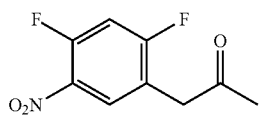

To a solution of 2-(2,4-difluoro-5-nitrophenyl)acetic acid (216.0 g, 996 mmol) in acetic anhydride (562 ml) was added 1-methylimidazole (79.4 ml, 996 mmol) dropwise at 0° C. The reaction mixture was stirred at 0° C. for 90 min. The reaction was quenched with ice water and then adjusted to pH=7-8 with saturated aqueous sodium bicarbonate. The resulting mixture was extracted with ethyl acetate (500 ml×4) and the combined organic phases were isolated and dried over anhydrous sodium sulfate and concentrated to a small volume under reduced pressure and purified by column chromatography to give compound 1-(2,4-difluoro-5-nitrophenyl)propan-2-one (34 g, 64% yield). $^1$H NMR (400 MHz, CDCl$_3$): δ 8.00 (t, J=8.0 Hz, 1H), 7.05 (dd, J=8.8, 10.4 Hz, 1H), 3.83 (s, 2H), 2.31 (s, 3H).

Step C. 1-(2-Fluoro-4-morpholino-5-nitrophenyl)propan-2-one

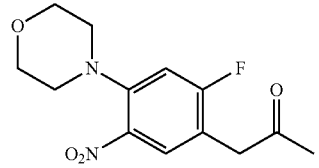 [SMILES: CC(=O)Cc1cc([N+](=O)[O-])c(N2CCOCC2)cc1F]

To a solution of 1-(2,4-difluoro-5-nitrophenyl)propan-2-one (105.0 g, 0.49 mol) in dimethylformamide (1.0 L) were added potassium carbonate (135 g, 0.98 mol) and morpholine (51.0 g, 0.59 mol) at room temperature. The reaction mixture was stirred at room temperature for 1.5 h and water (5 L) was added. The resulting mixture was extracted with ethyl acetate (1 L×3). The combined organic phases were isolated, washed with brine (1 L), dried over anhydrous sodium sulfate and concentrated under reduced pressure. The resulting semi-solid was suspended in a mixture of ethyl acetate:petroleum ether (1:2, 300 ml) and stirred for 30 min. 1-(2-Fluoro-4-morpholino-5-nitrophenyl)propan-2-one (105 g, 76% yield) was obtained after filtration as a yellow solid. $^1$H NMR (400 MHz, CDCl$_3$): δ 7.77 (d, J=8.0 Hz, 1H), 6.80 (d, J=11.2 Hz, 1H), 3.86 (t, J=4.8 Hz, 4H), 3.74 (s, 2H), 3.06 (t, J=4.8 Hz, 4H), 2.27 (s, 3H).

Step D. 4-(5-Fluoro-4-((2-methyl-1,3-dioxolan-2-yl)methyl)-2-nitrophenyl)morpholine

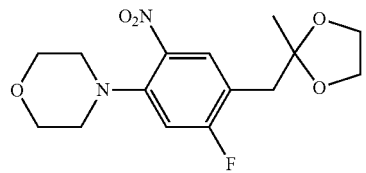 [SMILES: CC1(Cc2cc([N+](=O)[O-])c(N3CCOCC3)cc2F)OCCO1]

A mixture of 1-(2-fluoro-4-morpholino-5-nitrophenyl)propan-2-one (132.0 g, 0.468 mol), ethan-1,2-diol (86.8 g, 1.404 mol) and p-toluenesulphonic acid (8.8 g, 46.8 mmol) in toluene (1 L) was refluxed under a Dean-Stark apparatus to remove water overnight. The reaction mixture was cooled to room temperature and aqueous sodium bicarbonate (500 ml) was added. The resulting mixture was extracted with ethyl acetate (500 ml×3). The combined organic layers were dried over anhydrous sodium sulfate and concentrated under reduced pressure to afford 4-(5-fluoro-4-((2-methyl-1,3-dioxolan-2-yl)methyl)-2-nitrophenyl)morpholine (150 g, 98% yield) as a yellow solid. $^1$H NMR (400 MHz, CDCl$_3$): δ 7.90 (d, J=7.6 Hz, 1H), 6.77 (d, J=11.2 Hz, 1H), 3.92-3.97 (m, 2H), 3.80-3.87 (m, 6H), 3.04 (t, J=4.8 Hz, 4H), 2.94 (s, 2H), 1.34 (s, 3H).

749

Step E. 2-((2-Methyl-1,3-dioxolan-2-yl)methyl)-5-morpholino-4-nitrophenol

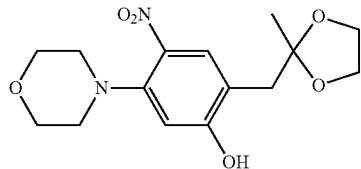 [SMILES: CC1(Cc2cc([N+](=O)[O-])c(N3CCOCC3)cc2O)OCCO1]

To a solution of 4-(5-fluoro-4-((2-methyl-1,3-dioxolan-2-yl)methyl)-2-nitrophenyl)morpholine (15 g, 46 mmol) in dimethyl sulfoxide (100 ml) was added potassium hydroxide (5.1 g, 92 mmol) under an atmosphere of nitrogen. The reaction mixture was stirred at 100° C. for 4 h and then cooled to room temperature. The mixture was poured into ice water (1000 ml) and the pH was adjusted to pH=5-6 with 4N aqueous HCl. The resulting mixture was extracted with ethyl acetate (200 ml×4) and the combined organic layers were dried over anhydrous sodium sulfate and concentrated under reduced pressure to give 2-((2-methyl-1,3-dioxolan-2-yl)methyl)-5-morpholino-4-nitrophenol (15 g), which was used without further purification.

Step F. 1-(2-Hydroxy-4-morpholino-5-nitrophenyl)propan-2-one

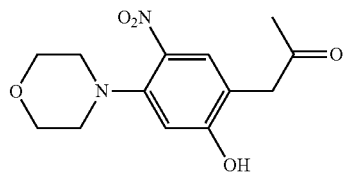 [SMILES: CC(=O)Cc1cc([N+](=O)[O-])c(N2CCOCC2)cc1O]

To a solution of 2-((2-methyl-1,3-dioxolan-2-yl)methyl)-5-morpholino-4-nitrophenol (15.0 g, 46 mmol) in tetrahydrofuran (100 ml) and water (100 ml) was added p-toluenesulphonic acid (8.4 g, 49 mmol). The reaction mixture was stirred at 50° C. for 4 h and then cooled to room temperature. Saturated aqueous sodium bicarbonate (200 ml) was added and the resulting mixture was extracted with ethyl acetate (200 ml×3). The combined organic layers were isolated, dried over anhydrous sodium sulfate and concentrated under reduced pressure. The residue was purified by column chromatography (eluent 1:2 ethyl acetate:petroleum ether) to afford 1-(2-hydroxy-4-morpholino-5-nitrophenyl)propan-2-one (4.8 g, 37% yield over two steps) as a yellow solid. $^1$H NMR (400 MHz, CDCl$_3$): δ 8.57 (br s, 1H), 7.83 (s, 1H), 6.63 (s, 1H), 3.87 (t, J=4.8 Hz, 4H), 3.75 (s, 2H), 3.05 (t, J=4.8 Hz, 4H), 2.39 (s, 3H).

750

Step G. 2-(2-Methyl-5-morpholino-6-nitro-3H-benzofuran-2-yl)acetonitrile

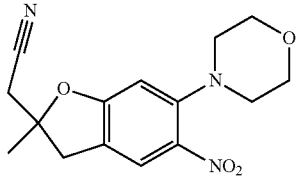

A mixture of 1-(2-hydroxy-5-morpholino-4-nitro-phenyl)propan-2-one (300.0 mg, 1.07 mmol) (triphenylphosphoranylidene)acetonitrile (338.7 mg, 1.12 mmol) in chloroform (15 ml) was stirred at 60° C. for 3h. triethylamine (4 ml) was added and the mixture was stirred at 60° C. for 12h. The reaction was then concentrated and purified by column chromatography (eluent 33% ethyl acetate: petroleum ether) to afford 2-(2-methyl-5-morpholino-6-nitro-3H-benzofuran-2-yl)acetonitrile (71 mg, 18% yield) as a yellow solid. MS (ESI): m/z=304.1 [M+1]$^+$.

Step H. 2-(5-Amino-2-methyl-6-morpholino-3H-benzofuran-2-yl)acetonitrile

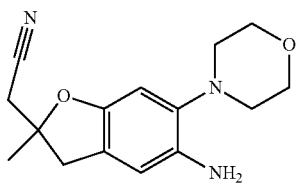 [SMILES: CC1(CC#N)Cc2cc([N+](=O)[O-])c(N3CCOCC3)cc2O1]

The title compound was made in a manner analogous to Example 2, Step B to afford 2-(5-amino-2-methyl-6-morpholino-3H-benzofuran-2-yl)acetonitrile (70 mg, 90% yield) as a brown oil. (ESI): m/z=274.2 [M+1]$^+$.

Step I. N-[2-(Cyanomethyl)-2-methyl-6-morpholino-3H-benzofuran-5-yl]pyrazolo[1,5-a]pyrimidine-3-carboxamide

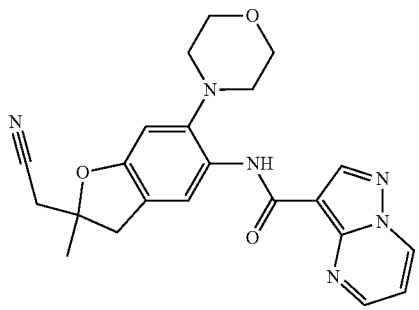 [SMILES: CC1(CC#N)Cc2cc(NC(=O)c3cnn4cccnc34)c(N3CCOCC3)cc2O1]

The title compound was made in a manner analogous to Example 1, Step C to afford 2 N-[1'-(2-hydroxyethyl)-6-morpholino-spiro[3H-benzofuran-2,4'-piperidine]-5-yl]pyrazolo[1,5-a]pyrimidine-3-carboxamide (91 mg, 40% yield) as a yellow solid. $^1$H NMR (400 MHz, CDCl$_3$) δ 10.49 (s, 1H), 8.84 (d, J=6.8 Hz, 1H), 8.77-8.78 (m, 2H), 8.47 (s, 1H), 7.08 (dd, J=4.0, 6.8 Hz, 1H), 6.70 (s, 1H), 3.94-3.97 (m, 4H), 3.22 (d, J=16.0 Hz, 1H), 3.16 (d, J=15.6 Hz, 1H), 2.91-2.93 (m, 4H), 2.79 (d, J=16.8 Hz, 1H), 2.73 (d, J=16.4 Hz, 1H), 1.68 (s, 3H). (ESI): m/z=419.1 [M+1]$^+$.

Examples 387 and 388. (S)—N-(2-(2-hydroxyethyl)-2-methyl-6-morpholino-2,3-dihydrobenzofuran-5-yl)pyrazolo[1,5-a]pyrimidine-3-carboxamide and (R)—N-(2-(2-hydroxyethyl)-2-methyl-6-morpholino-2,3-dihydrobenzofuran-5-yl)pyrazolo[1,5-a]pyrimidine-3-carboxamide

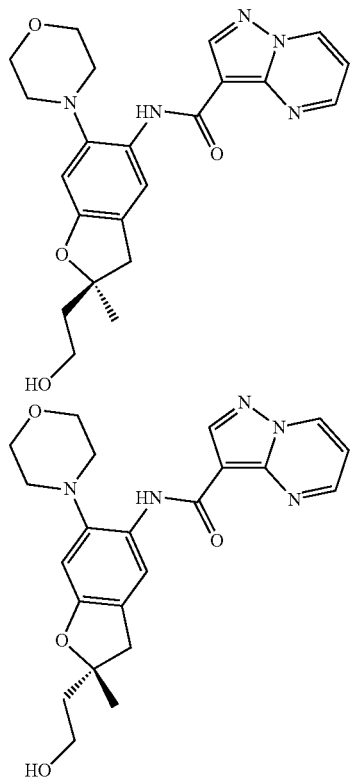

Step A. 2-(2-Methyl-6-morpholino-5-nitro-3H-benzofuran-2-yl)ethanol

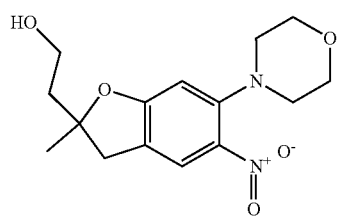

To sodium borohydride (113.0 mg, 2.97 mmol) in a mixture of tetrahydrofuran (12 ml) and ethanol (3 ml) was added lithium chloride (124.9 mg, 2.97 mmol) followed by methyl 2-(2-methyl-6-morpholino-5-nitro-3H-benzofuran-2-yl)acetate (Examples 367 and 368, Step E; 200.0 mg, 0.59 mmol) at 0° C. The mixture was stirred at 25° C. for 2h and quenched with aqueous ammonium chloride (20 ml). The organic phase was isolated, dried over magnesium sulfate, filtered and concentrated to afford 2-(2-methyl-6-morpholino-5-nitro-3H-benzofuran-2-yl)ethanol (180 mg, 82% yield) as a yellow solid. (ESI): m/z=309.2.

Step B. 2-(5-Amino-2-methyl-6-morpholino-3H-benzofuran-2-yl)ethanol

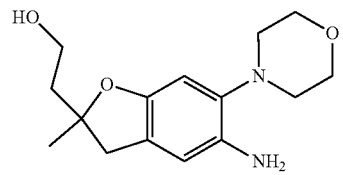 [SMILES: CC1(CCO)Cc2cc(N)c(N3CCOCC3)cc2O1]

The title compound was made in a manner analogous to Example 2, Step B to afford 2-(5-amino-2-methyl-6-morpholino-3H-benzofuran-2-yl)ethanol (130 mg, 70% yield) as a white oil. (ESI): m/z=279.3 [M+1]$^+$.

Step C. (R)—N-(2-(2-hydroxyethyl)-2-methyl-6-morpholino-2,3-dihydrobenzofuran-5-yl)pyrazolo[1,5-a]pyrimidine-3-carboxamide and (S)—N-(2-(2-hydroxyethyl)-2-methyl-6-morpholino-2,3-dihydrobenzofuran-5-yl)pyrazolo[1,5-a]pyrimidine-3-carboxamide

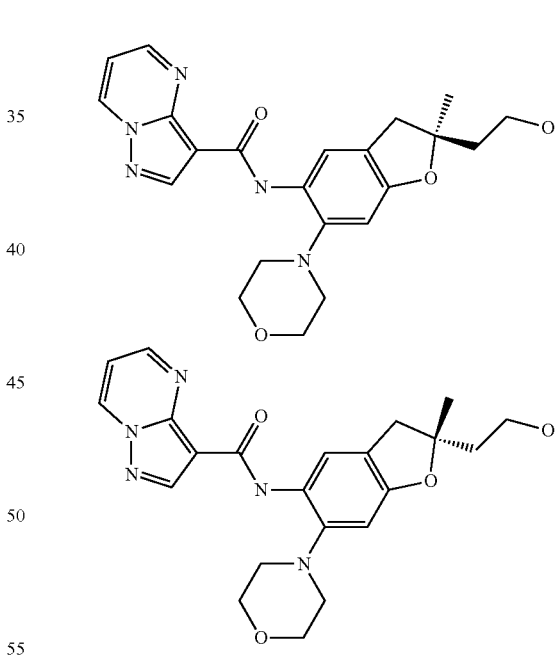

The title compounds were made in a manner analogous to Example 1, Step C to afford (R)—N-(2-(2-hydroxyethyl)-2-methyl-6-morpholino-2,3-dihydrobenzofuran-5-yl)pyrazolo[1,5-a]pyrimidine-3-carboxamide and (S)—N-(2-(2-hydroxyethyl)-2-methyl-6-morpholino-2,3-dihydrobenzofuran-5-yl)pyrazolo[1,5-a]pyrimidine-3-carboxamide (91 mg, 40% yield) as yellow solids with stereochemistry assigned arbitrarily.

Example 387, Peak 1: $^1$H NMR (400 MHz, CDCl$_3$) δ 10.48 (s, 1H), 8.90-8.70 (m, 3H), 8.45 (s, 1H), 7.07 (dd, J=7.0, 4.1 Hz, 1H), 6.65 (s, 1H), 5.35 (s, 1H), 3.98-3.80 (m, 6H), 3.18 (d, J=15.5 Hz, 1H), 3.02 (d, J=15.6 Hz, 1H), 2.94-2.90 (m, 4H), 1.99 (dt, J=14.6, 5.6 Hz, 1H), 1.50 (s, 3H), 1.26 (s, 2H). (ESI): m/z=424.2 [M+1]+.

Example 388, Peak 2: ¹H NMR (400 MHz, CDCl₃) δ 10.48 (s, 1H), 8.98-8.70 (m, 3H), 8.45 (s, 1H), 7.07 (dd, J=7.0, 4.1 Hz, 1H), 6.65 (s, 1H), 5.35 (s, 1H), 3.92 (dd, J=26.9, 22.3 Hz, 6H), 3.18 (d, J=15.7 Hz, 1H), 3.02 (d, J=15.5 Hz, 1H), 2.94-2.90 (m, 4H), 2.07-1.95 (m, 1H), 1.50 (s, 3H), 1.25 (s, 2H). (ESI): m/z=424.2 [M+1]+.

Example 389. N-[6-[4-(Aminomethyl)-4-fluoro-1-piperidyl]-2,2-dimethyl-3H-benzofuran-5-yl]pyrazolo[1,5-a]pyrimidine-3-carboxamide

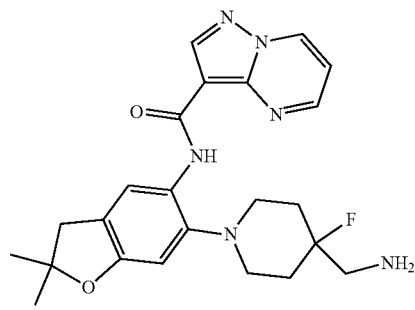 [SMILES: CC1(C)Cc2cc(NC(=O)c3cnn4cccnc34)c(N3CCC(F)(CN)CC3)cc2O1]

Step A. tert-Butyl N-[[1-(2,2-dimethyl-5-nitro-3H-benzofuran-6-yl)-4-fluoro-4-piperidyl]methyl]carbamate

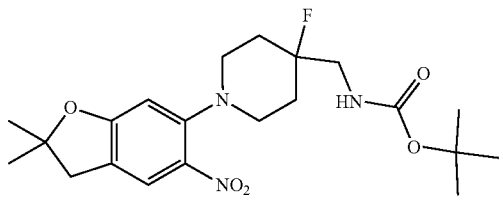 [SMILES: CC(C)(C)OC(=O)NCC1(F)CCN(c2cc3c(cc2[N+](=O)[O-])CC(C)(C)O3)CC1]

The title compound was made in a manner analogous to Example 13, Step A to afford tert-butyl N-[[1-(2,2-dimethyl-5-nitro-3H-benzofuran-6-yl)-4-fluoro-4-piperidyl]methyl] carbamate (416 mg, 94% yield) as a yellow solid. (ESI): m/z=424.2 [M+1]+.

Step B. tert-Butyl N-[[1-(5-amino-2,2-dimethyl-3H-benzofuran-6-yl)-4-fluoro-4-piperidyl]methyl]carbamate

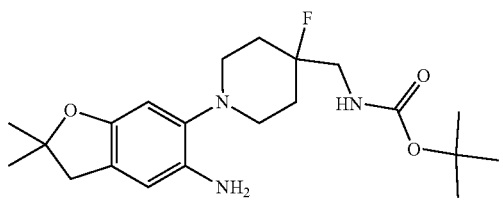 [SMILES: CC(C)(C)OC(=O)NCC1(F)CCN(c2cc3c(cc2N)CC(C)(C)O3)CC1]

The title compound was made in a manner analogous to Example 2, Step B to afford tert-butyl N-[[1-(5-amino-2,2-dimethyl-3H-benzofuran-6-yl)-4-fluoro-4-piperidyl] methyl]carbamate (370 mg, 80% yield) as a yellow oil. (ESI): m/z=394.3 [M+1]+.

Step C. tert-Butyl N-[[1-[2,2-dimethyl-5-(pyrazolo[1,5-a]pyrimidine-3-carbonylamino)-3H-benzofuran-6-yl]-4-fluoro-4-piperidyl]methyl]carbamate

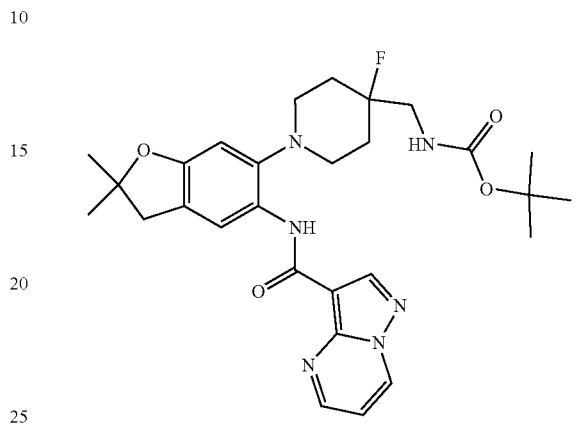

The title compound was made in a manner analogous to Example 1, Step C to afford tert-butyl N-[[1-[2,2-dimethyl-5-(pyrazolo[1,5-a]pyrimidine-3-carbonylamino)-3H-benzofuran-6-yl]-4-fluoro-4-piperidyl]methyl]carbamate (487 mg, 96% yield) as a yellow solid. (ESI): m/z=539.3 [M+1]+.

Step D. N-[6-[4-(Aminomethyl)-4-fluoro-1-piperidyl]-2,2-dimethyl-3H-benzofuran-5-yl]pyrazolo[1,5-a]pyrimidine-3-carboxamide

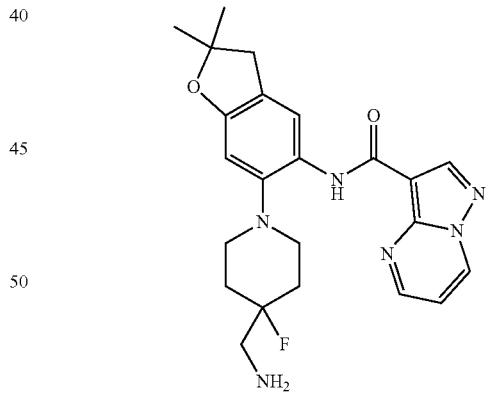

The title compound was made in a manner analogous to Example 3, Step M to afford N-[6-[4-(aminomethyl)-4-fluoro-1-piperidyl]-2,2-dimethyl-3H-benzofuran-5-yl]pyrazolo[1,5-a]pyrimidine-3-carboxamide (300 mg, 76% yield) as a light yellow foam. ¹H NMR (400 MHz, Chloroform-d) δ 10.42 (s, 1H), 8.86-8.76 (m, 2H), 8.68 (dt, J=3.4, 1.5 Hz, 1H), 8.40 (s, 1H), 7.07-6.99 (m, 1H), 6.67 (s, 1H), 3.07-2.85 (m, 8H), 2.11-1.87 (m, 4H), 1.48 (d, J=1.2 Hz, 6H). (ESI): m/z=439.3 [M+1]+.

Examples 390 and 391. (R)—N-(1'-methyl-6-morpholino-3H-spiro[benzofuran-2,3'-pyrrolidin]-5-yl)pyrazolo[1,5-a]pyrimidine-3-carboxamide and (S)—N-(1'-methyl-6-morpholino-3H-spiro[benzofuran-2,3'-pyrrolidin]-5-yl)pyrazolo[1,5-a]pyrimidine-3-carboxamide

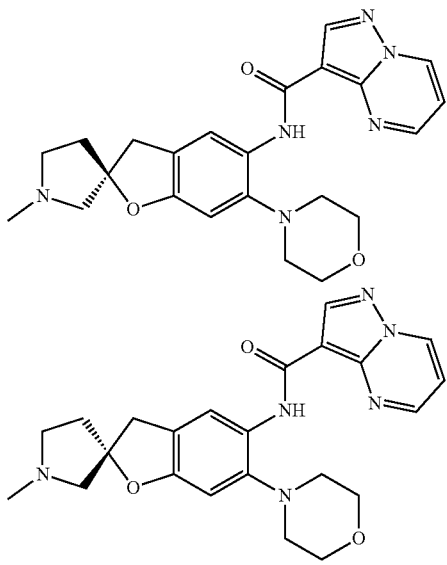

Step A. 1'-Methyl-6-morpholino-5-nitro-spiro[3H-benzofuran-2,3'-pyrrolidine]

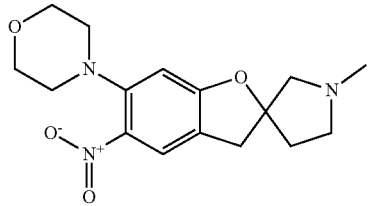 [SMILES: CN1CCC2(Cc3cc([N+](=O)[O-])c(N4CCOCC4)cc3O2)C1]

A mixture of 6-fluoro-1'-methyl-5-nitro-spiro[3H-benzofuran-2,3'-pyrrolidine] (304.0 mg, 1.21 mmol), morpholine (0.31 ml, 3.62 mmol) and potassium carbonate (415.5 mg, 3.0 mmol) in acetonitrile (15 ml) was stirred 25° C. overnight. The reaction was filtered and dried under reduced pressure to afford 1'-methyl-6-morpholino-5-nitro-spiro[3H-benzofuran-2,3'-pyrrolidine] (323 mg, 80% yield) as a yellow oil. MS-ES: [M+H]⁺ 320.2.

Step B. 1'-Methyl-6-morpholino-spiro[3H-benzofuran-2,3'-pyrrolidine]-5-amine

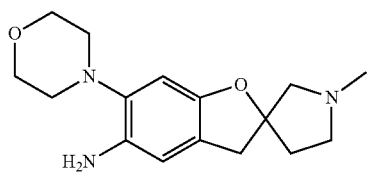 [SMILES: CN1CCC2(Cc3cc(N)c(N4CCOCC4)cc3O2)C1]

The title compound was made in a manner analogous to Example 2, Step B to afford 1'-methyl-6-morpholino-spiro[3H-benzofuran-2,3'-pyrrolidine]-5-amine (310 mg, 76% yield) as a yellow oil. MS-ES: [M+H]⁺ 290.2.

Step C. (R)—N-(1'-Methyl-6-morpholino-3H-spiro[benzofuran-2,3'-pyrrolidin]-5-yl)pyrazolo[1,5-a]pyrimidine-3-carboxamide and (S)—N-(1'-Methyl-6-morpholino-3H-spiro[benzofuran-2,3'-pyrrolidin]-5-yl)pyrazolo[1,5-a]pyrimidine-3-carboxamide

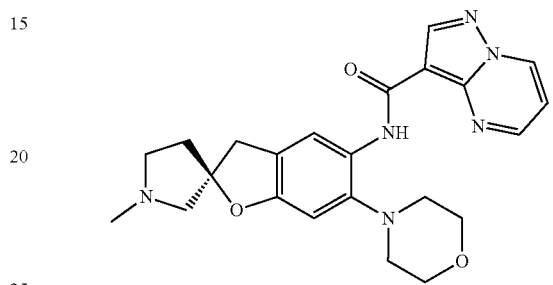

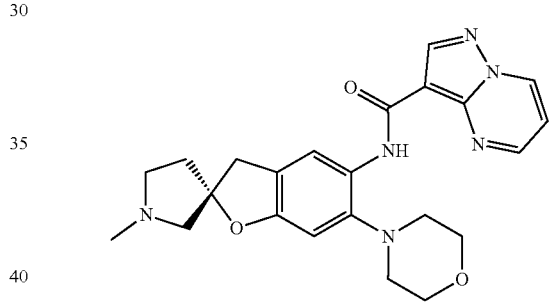

The title compounds were made in a manner analogous to Example 1, Step C to afford (R)—N-(1'-methyl-6-morpholino-3H-spiro[benzofuran-2,3'-pyrrolidin]-5-yl)pyrazolo[1,5-a]pyrimidine-3-carboxamide (98.8 mg, 21% yield) and (S)—N-(1'-methyl-6-morpholino-3H-spiro[benzofuran-2,3'-pyrrolidin]-5-yl)pyrazolo[1,5-a]pyrimidine-3-carboxamide (108.5 mg, 23% yield) as yellow solids upon resolution via chiral HPLC with stereochemistry assigned arbitrarily.

Example 390, Peak 1: $^1$H NMR (400 MHz, Chloroform-d) δ 10.48 (s, 1H), 8.84 (dd, J=7.0, 1.7 Hz, 1H), 8.79-8.72 (m, 2H), 8.45 (s, 1H), 7.07 (dd, J=7.0, 4.1 Hz, 1H), 6.69 (s, 1H), 4.01-3.90 (m, 4H), 3.34-3.20 (m, 2H), 3.09 (d, J=10.6 Hz, 1H), 3.02 (q, J=8.0 Hz, 1H), 2.91 (t, J=4.5 Hz, 4H), 2.77 (s, 2H), 2.51 (s, 3H), 2.41 (dt, J=13.3, 6.5 Hz, 1H), 2.13 (dt, J=14.0, 7.7 Hz, 1H). MS-ES: [M+H]⁺ 435.3.

Example 391, Peak 2: $^1$H NMR (400 MHz, Chloroform-d) δ 10.48 (s, 1H), 8.83 (dd, J=7.0, 1.7 Hz, 1H), 8.80-8.75 (m, 2H), 8.44 (s, 1H), 7.07 (dd, J=7.0, 4.1 Hz, 1H), 6.69 (s, 1H), 3.95 (t, J=4.5 Hz, 4H), 3.33-3.18 (m, 2H), 3.05 (d, J=10.4 Hz, 1H), 2.97 (q, J=8.3 Hz, 1H), 2.91 (dd, J=5.6, 3.5 Hz, 4H), 2.60 (d, J=10.5 Hz, 2H), 2.43 (s, 3H), 2.41-2.35 (m, 1H), 2.10 (ddd, J=14.2, 8.6, 6.0 Hz, 1H). MS-ES: [M+H]⁺ 435.3.

Example 392. N-[2-(1-fluoro-2-hydroxy-2-methyl-propyl)-2-methyl-6-morpholino-3H-benzofuran-5-yl]pyrazolo[1,5-a]pyrimidine-3-carboxamide

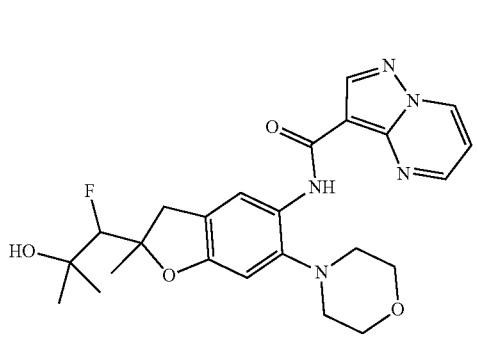 [SMILES: CC(C)(O)C(F)C1(C)Cc2cc(NC(=O)c3cnn4cccnc34)c(N3CCOCC3)cc2O1]

Step A. 1-(2,4-Difluorophenyl)-3-fluoro-2,4-dimethyl-pentane-2,4-diol

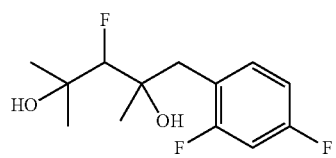 [SMILES: CC(C)(O)C(F)C(C)(O)Cc1ccc(F)cc1F]

To a solution of ethyl 4-(2,4-difluorophenyl)-2-fluoro-3-hydroxy-3-methyl-butanoate (1000 mg, 3.62 mmol) in tetrahydrofuran (36 ml) at −78° C. was added methyl lithium (6.03 ml, 18.1 mmol) and the reaction was stirred for 3h at room temperature. Saturated aqueous ammonium chloride and ethyl acetate were added. The organic phase was separated, dried over sodium sulfate and concentrated. The residue was purified by column chromatography (eluent 25% ethyl acetate: petroleum ether) to afford 1-(2,4-difluorophenyl)-3-fluoro-2,4-dimethyl-pentane-2,4-diol (310 mg, 33% yield) as a colorless oil.

Step B. 1-Fluoro-1-(6-fluoro-2-methyl-3H-benzofuran-2-yl)-2-methyl-propan-2-ol

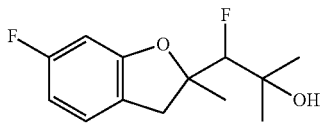

1-(2,4-Difluorophenyl)-3-fluoro-2,4-dimethyl-pentane-2,4-diol (310 mg, 1.2 mmol) in tetrahydrofuran (20 ml) was treated with potassium tert-butoxide (331 mg, 3.0 mmol) at 0° C. and warmed to 60° C. with stirring for 24 h. After cooling to room temperature, the mixture was diluted with water. The organic phase was isolated and concentrated to afford 1-fluoro-1-(6-fluoro-2-methyl-3H-benzofuran-2-yl)-2-methyl-propan-2-ol (210 mg, 65% yield) which was used directly without further purification. MS-ES: [M−H$_2$O+H]$^+$ 225.2.

Step C. 1-Fluoro-1-(6-fluoro-2-methyl-5-nitro-3H-benzofuran-2-yl)-2-methyl-propan-2-ol

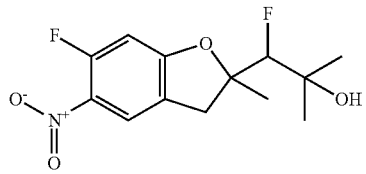 [SMILES: CC(C)(O)C(F)C1(C)Cc2cc([N+](=O)[O-])c(F)cc2O1]

The title compound was made in a manner analogous to Intermediate 1, Step D to afford 1-fluoro-1-(6-fluoro-2-methyl-5-nitro-3H-benzofuran-2-yl)-2-methyl-propan-2-ol (200 mg, 21% yield) as a brown oil. MS-ESI: [M+H]$^+$ 288.

Step D. 1-Fluoro-2-methyl-1-(2-methyl-6-morpholino-5-nitro-3H-benzofuran-2-yl)propan-2-ol

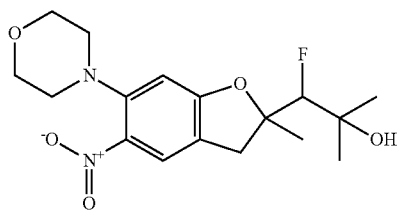

The title compound was made in a manner analogous to Example 50, Step A to afford 1-fluoro-2-methyl-1-(2-methyl-6-morpholino-5-nitro-3H-benzofuran-2-yl)propan-2-ol (59 mg, 60% yield) as a yellow oil. MS-ESI: [M+H]$^+$ 355.1.

Step E. 1-(5-Amino-2-methyl-6-morpholino-3H-benzofuran-2-yl)-1-fluoro-2-methyl-propan-2-ol

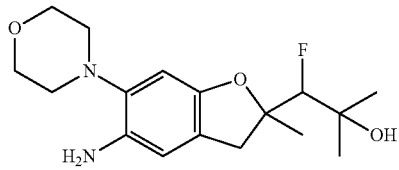 [SMILES: CC(C)(O)C(F)C1(C)Cc2cc(N)c(N3CCOCC3)cc2O1]

The title compound was made in a manner analogous to Example 2, Step B to afford 1-(5-amino-2-methyl-6-morpholino-3H-benzofuran-2-yl)-1-fluoro-2-methyl-propan-2-ol (39 mg, 72% yield) as a brown oil. MS-ESI: [M+H]$^+$ 325.1.

Step F. N-[2-(1-Fluoro-2-hydroxy-2-methyl-propyl)-2-methyl-6-morpholino-3H-benzofuran-5-yl]pyrazolo[1,5-a]pyrimidine-3-carboxamide

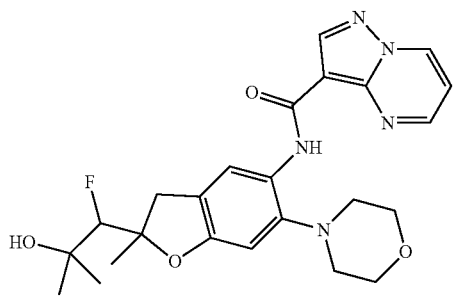 [SMILES: CC(C)(O)C(F)C1(C)Cc2cc(NC(=O)c3cnn4cccnc34)c(N3CCOCC3)cc2O1]

The title compound was made in a manner analogous to Example 1, Step C to afford N-(2-(1-fluoro-2-hydroxy-2-methylpropyl)-2-methyl-6-morpholino-2,3-dihydrobenzofuran-5-yl)pyrazolo[1,5-a]pyrimidine-3-carboxamide (10 mg, 18%) as a light yellow solid. $^1$H NMR (400 MHz, CDCl$_3$): 10.48 (s, 1H), 8.83 (dd, J=1.2, 6.8 Hz, 1H), 8.79 (s, 1H), 8.77 (dd, J=1.2, 4.4 Hz, 1H), 8.47 (s, 1H), 7.07 (dd, J=4.4, 6.8 Hz, 1H), 6.69 (s, 1H), 4.37 (d, J=44.4 Hz, 1H), 3.96-3.94 (m, 4H), 3.68-3.65 (m, 2H), 2.93-2.83 (m, 4H), 2.64 (s, 1H), 1.57 (s, 3H), 1.35-1.32 (m, 6H). MS-ES: [M+H]$^+$ 470.

Example 393. N-(6-Morpholinospiro[3H-benzofuran-2,3'-pyrrolidine]-5-yl)pyrazolo[1,5-a]pyrimidine-3-carboxamide

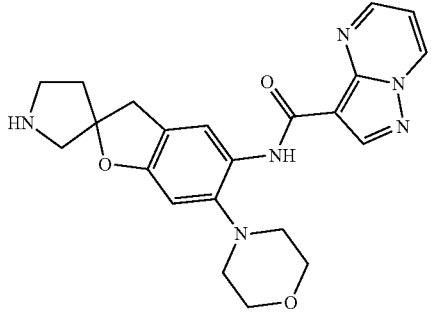 [SMILES: O=C(Nc1cc2c(cc1N1CCOCC1)OC1(CCNC1)C2)c1cnn2cccnc12]

Step A. tert-Butyl 3-[(2,4-difluorophenyl)methyl]-3-hydroxy-pyrrolidine-1-carboxylate

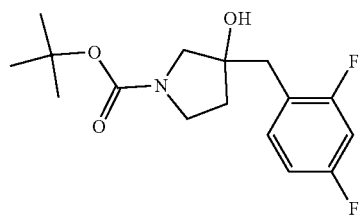 [SMILES: CC(C)(C)OC(=O)N1CCC(O)(Cc2ccc(F)cc2F)C1]

To a solution of magnesium (2.90 g, 120.8 mmol) and iodine (80 mg, 0.31 mmol) in ether (25 ml) was added 2,4-difluorobenzyl bromide (9.94 g, 48 mmol) dropwise at reflux and the resulting mixture was stirred for 30 min. This mixture was then added to a solution of N-boc-3-pyrrolidone (7.41 g, 40 mmol) in ether (100 ml) at −78° C. and the reaction was stirred at room temperature for 2h. Saturated aqueous ammonium chloride and ethyl acetate (200 ml) were added and the organic phase was isolated, dried over sodium sulfate and concentrated. The residue was purified by column chromatography (eluting gradient 1:10 to 1:5 ethyl acetate:petroleum ether) to afford tert-butyl 3-[(2,4-difluorophenyl)methyl]-3-hydroxy-pyrrolidine-1-carboxylate (2.30 g, 15% yield) as a yellow oil. MS-ES: [M+H]$^+$258.

Step B. tert-Butyl 6-fluorospiro[3H-benzofuran-2,3'-pyrrolidine]-1'-carboxylate

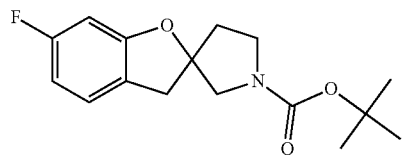 [SMILES: CC(C)(C)OC(=O)N1CCC2(Cc3ccc(F)cc3O2)C1]

The title compound was made in a manner analogous to Example 3, Step E to afford tert-butyl 6-fluorospiro[3H-benzofuran-2,3'-pyrrolidine]-1'-carboxylate (552 mg, 71% yield) as an off-white solid.

Step C. 6-Fluorospiro[3H-benzofuran-2,3'-pyrrolidine]

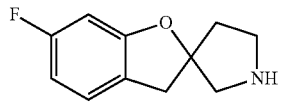

To tert-butyl 6-fluorospiro[3H-benzofuran-2,3'-pyrrolidine]-1'-carboxylate (552.0 mg, 1.9 mmol) in dichloromethane (11 ml) was added trifluoroacetic acid (2 ml) and the mixture was stirred at 25° C. for 4h. To the reaction was added aqueous saturated sodium bicarbonate (20 ml) and the aqueous layer was isolated and extracted with dichloromethane (2×). The combined organic phases were washed with saturated brine, dried over anhydrous magnesium sulfate, filtered and concentrated to afford 6-fluorospiro[3H-benzofuran-2,3'-pyrrolidine] (303 mg, 1.5 mmol) as a yellow oil. MS-ES: [M+H]$^+$194.1.

Step D. Benzyl 6-fluorospiro[3H-benzofuran-2,3'-pyrrolidine]-1'-carboxylate

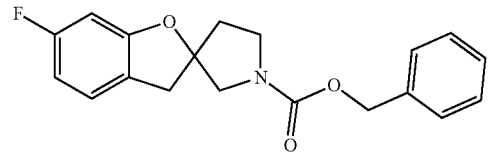 [SMILES: O=C(OCc1ccccc1)N1CCC2(Cc3ccc(F)cc3O2)C1]

To a mixture of benzyl chloroformate (469.4 mg, 2.8 mmol) and 6-fluorospiro[3H-benzofuran-2,3'-pyrrolidine]

(409 mg, 2.1 mmol) in dichloromethane (15 ml) was added trimethylamine (4.23 mmol) and the reaction was stirred at Then stirred at 25° C. for 2h. The reaction was concentrated and purified by column chromatography (eluent 1:1 ethyl acetate:petroleum ether) to afford benzyl 6-fluorospiro[3H-benzofuran-2,3'-pyrrolidine]-1'-carboxylate (739 mg, 78% yield) as a yellow oil. MS-ES: [M+Na]$^+$328.2.

Step E. Benzyl 6-morpholino-5-nitro-spiro[3H-benzofuran-2,3'-pyrrolidine]-1'-carboxylate

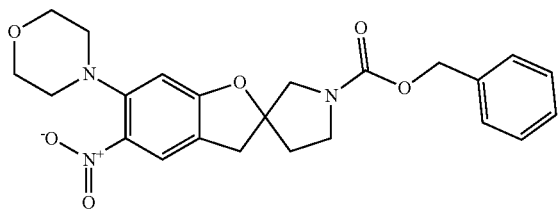

A mixture of benzyl 6-fluoro-5-nitro-spiro[3H-benzofuran-2,3'-pyrrolidine]-1'-carboxylate (589 mg, 1.6 mmol), morpholine (0.41 ml, 4.75 mmol) and potassium carbonate (545.4 mg, 3.95 mmol) in acetonitrile (18 ml) was stirred at 25° C. overnight. The reaction was filtered and dried under reduced pressure to afford benzyl 6-morpholino-5-nitro-spiro[3H-benzofuran-2,3'-pyrrolidine]-1'-carboxylate (451 mg, 56% yield) as a yellow oil. MS-ES: [M+H]$^+$ 440.2.

Step F. Benzyl 5-amino-6-morpholino-spiro[3H-benzofuran-2,3'-pyrrolidine]-1'-carboxylate

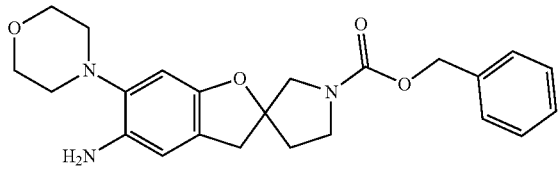 [SMILES: Nc1cc2c(cc1N1CCOCC1)OC1(CCN(C(=O)OCc3ccccc3)C1)C2]

A solution of benzyl 6-morpholino-5-nitro-spiro[3H-benzofuran-2,3'-pyrrolidine]-1'-carboxylate (451.0 mg, 1.0 mmol), ammonium chloride (549 mg, 10.3 mmol), iron (574.7 mg, 10.3 mmol) and ammonium chloride (549 mg, 10.3 mmol) in ethanol (40 ml) and water (8 ml) was stirred for 2h at 78° C. The reaction mixture was filtered and the precipitate was washed with dichloromethane. The filtrate was extracted with dichloromethane, the organic phase was isolated and dried under reduced pressure to afford benzyl 5-amino-6-morpholino-spiro[3H-benzofuran-2,3'-pyrrolidine]-1'-carboxylate (421 mg, 95% yield) as a brown solid.

Step G. Benzyl 6-morpholino-5-(pyrazolo[1,5-a]pyrimidine-3-carbonylamino)spiro[3H-benzofuran-2,3'-pyrrolidine]-1'-carboxylate

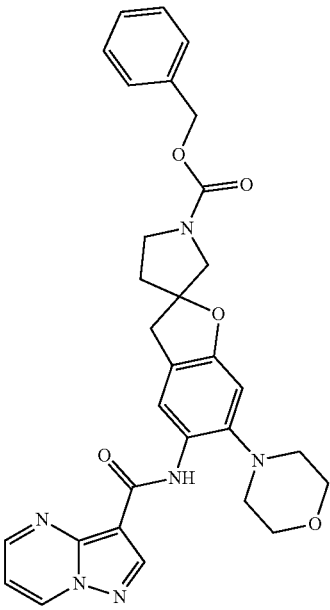 [SMILES: O=C(Nc1cc2c(cc1N1CCOCC1)OC1(CCN(C(=O)OCc3ccccc3)C1)C2)c1cnn2cccnc12]

The title compound was made in a manner analogous to Example 1, Step C to afford benzyl 6-morpholino-5-(pyrazolo[1,5-a]pyrimidine-3-carbonylamino)spiro[3H-benzofuran-2,3'-pyrrolidine]-1'-carboxylate (464 mg). MS-ES: [M+H]$^+$555.3.

Step H. N-(6-Morpholinospiro[3H-benzofuran-2,3'-pyrrolidine]-5-yl)pyrazolo[1,5-a]pyrimidine-3-carboxamide

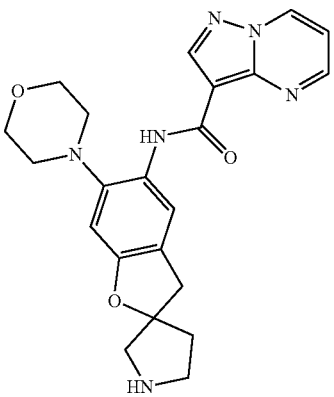 [SMILES: O=C(Nc1cc2c(cc1N1CCOCC1)OC1(CCNC1)C2)c1cnn2cccnc12]

A mixture of benzyl 6-morpholino-5-(pyrazolo[1,5-a]pyrimidine-3-carbonylamino)spiro[3H-benzofuran-2,3'-pyrrolidine]-1'-carboxylate (434 mg, 0.8 mmol) and trifluoroacetic acid (3 ml) was stirred at 50° C. for 2h. The reaction was concentrated and purified by HPLC (Xbridge 21.2*250 mm c18, 10 um, A: 10 mM aqueous ammonium bicarbonate, B: acetonitrile) to afford N-(6-morpholino-3H-spiro[benzofuran-2,3'-pyrrolidine]-5-yl)pyrazolo[1,5-a]pyrimidine-3- carboxamide (59.4 mg, 18%) as a yellow solid. ¹H NMR (400 MHz, CDCl₃): 10.48 (s, 1H), 8.84 (d, J=3.4 Hz, 1H), 8.79 (s, 1H), 8.78 (d, J=6.6 Hz, 1H), 8.45 (s, 1H), 7.08 (s, J=4.4, 6.6 Hz, 1H), 7.35 (dd, J=4.4, 6.6 Hz, 1H), 6.65 (s, 1H), 3.94-3.95 (m, 4H), 3.21-3.33 (m, 4H), 3.12-3.13 (m, 1H), 2.90-2.92 (m, 4H), 2.84 (d, J=12 Hz, 1H), 1.26 (s, 2H).

Example 394. N-(2,2-bis(hydroxymethyl)-6-morpholino-2,3-dihydrobenzofuran-5-yl)pyrazolo[1,5-a]pyrimidine-3-carboxamide

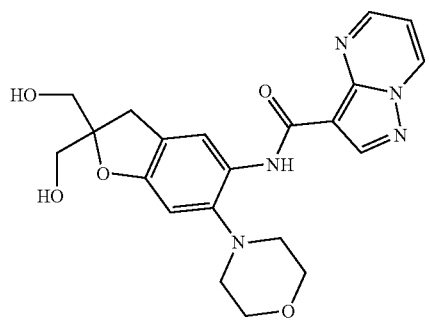 [SMILES: O=C(Nc1cc2c(cc1N1CCOCC1)OC(CO)(CO)C2)c1cnn2cccnc12]

Step A. 5-[(4-Chloro-2-fluoro-phenyl)methyl]-2,2-dimethyl-1,3-dioxan-5-ol

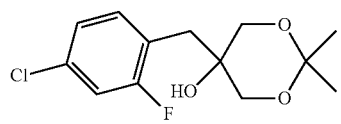 [SMILES: CC1(C)OCC(O)(Cc2ccc(Cl)cc2F)CO1]

A mixture of potassium tert-butoxide (2700.0 mg, 24.11 mmol) and 5-[(4-chloro-2-fluoro-phenyl)methyl]-2,2-dimethyl-1,3-dioxan-5-ol (3000.0 mg, 10.92 mmol) in tetrahydrofuran (60 mL) was stirred at 50° C. for 12h. Upon cooling to room temperature and concentration, the residue was purified by silica gel chromatography (eluent: 1:1 ethyl acetate:petroleum ether) to afford 6'-chloro-2,2-dimethyl-spiro[1,3-dioxane-5,2'-3H-benzofuran] (930 mg, 3.6512 mmol, 33.4% yield) as a colorless oil.

Step B. 6'-Chloro-2,2-dimethyl-spiro[1,3-dioxane-5, 2'-3H-benzofuran]

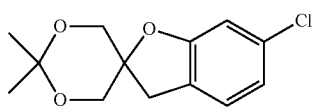 [SMILES: CC1(C)OCC2(CO1)Cc1ccc(Cl)cc1O2]

The title compound was made in a manner analogous to Example 3, Step E to afford 6'-chloro-2,2-dimethyl-spiro[1,3-dioxane-5,2'-3H-benzofuran] (930 mg, 33% yield) as a colorless oil. MS-ES: [M+H]⁺ 255.1.

Step C. 6'-Chloro-2,2-dimethyl-5'-nitro-spiro[1,3-dioxane-5,2'-3H-benzofuran]

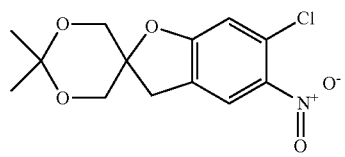

A mixture of 6'-chloro-2,2-dimethyl-spiro[1,3-dioxane-5, 2'-3H-benzofuran] (930 mg, 3.7 mmol) and copper(II) nitrate (2200 mg, 11.7 mmol) in acetic acid (5 ml) and acetic anhydride (5 ml) was stirred at room temperature. Upon concentration, the residue was purified by column chromatography (eluent 50% ethyl acetate:petroleum ether) to afford 6'-chloro-2,2-dimethyl-5'-nitro-spiro[1,3-dioxane-5, 2'-3H-benzofuran] (900 mg, 82% yield) as a yellow oil.

Step D. 4-(2,2-Dimethyl-5'-nitro-spiro[1,3-dioxane-5,2'-3H-benzofuran]-6'-yl)morpholine

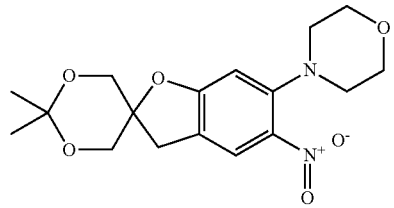

6'-Chloro-2,2-dimethyl-5'-nitro-spiro[1,3-dioxane-5,2'-3H-benzofuran] (600 mg, 2 mmol) and morpholine (3 ml, 35 mmol) was stirred at 90° C. for 12h. The reaction was concentrated and purified by column chromatography (eluent 30% ethyl acetate:petroleum ether) to afford 4-(2, 2-dimethyl-5'-nitro-spiro[1,3-dioxane-5,2'-3H-benzofuran]-6'-yl)morpholine (65 mg, 9% yield). MS-ES: [M+H]⁺ 351.

Step E. 2, 2-dimethyl-6'-morpholino-spiro[1,3-dioxane-5,2'-3H-benzofuran]-5'-amine

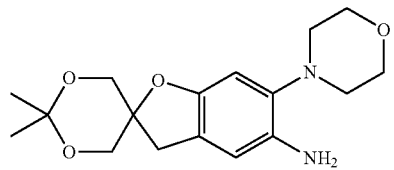 [SMILES: CC1(C)OCC2(CO1)Cc1cc(N)c(N3CCOCC3)cc1O2]

The title compound was made in a manner analogous to Example 2, Step B to afford 2, 2-dimethyl-6'-morpholino-spiro[1,3-dioxane-5,2'-3H-benzofuran]-5'-amine (90 mg) which was used directly without further purification.

Step F. N-(2',2'-Dimethyl-6-morpholino-3H-spiro[benzofuran-2,5'-[1,3]dioxan]-5-yl)pyrazolo[1,5-a]pyrimidine-3-carboxamide

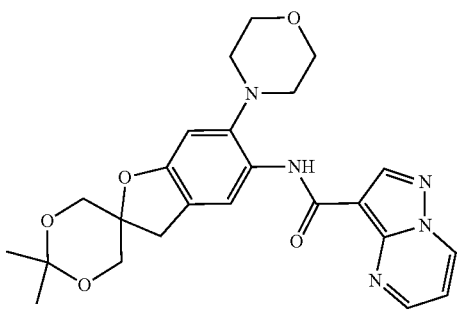 [SMILES: CC1(C)OCC2(CO1)Cc1cc(NC(=O)c3cnn4cccnc34)c(N3CCOCC3)cc1O2]

2,2-Dimethyl-6'-morpholino-spiro[1,3-dioxane-5,2'-3H-benzofuran]-5'-amine (90 mg, 0.28 mmol), pyrazolo[1,5-a]pyrimidine-3-carboxylic acid (100 mg, 0.61 mmol), HATU (180 mg, 0.47 mmol) and N,N-diisopropylamine (0.2 ml, 1.22 mmol) was stirred in N,N-dimethylformamide (5 ml) at 25° C. for 12h. The mixture was concentrated and purified by column chromatography (eluent 40% ethyl acetate:petroleum ether) to afford N-(2,2-dimethyl-6'-morpholino-spiro[1,3-dioxane-5,2'-3H-benzofuran]-5'-yl)pyrazolo[1,5-a]pyrimidine-3-carboxamide (110 mg, 84% yield).

Step G. N-(2,2-Bis(hydroxymethyl)-6-morpholino-2,3-dihydrobenzofuran-5-yl)pyrazolo[1,5-a]pyrimidine-3-carboxamide

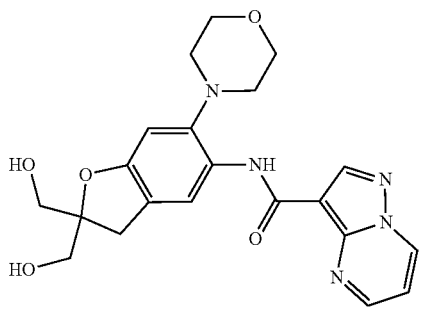 [SMILES: O=C(Nc1cc2c(cc1N1CCOCC1)OC(CO)(CO)C2)c1cnn2cccnc12]

A mixture of N-(2,2-dimethyl-6'-morpholino-spiro[1,3-dioxane-5,2'-3H-benzofuran]-5'-yl)pyrazolo[1,5-a]pyrimidine-3-carboxamide (90 mg, 0.19 mmol) and concentrated hydrochloric acid (2 ml) in methanol (10 ml) was stirred at 25° C. for 3h, concentrated and purified by HPLC (Xbridge 21.2*250 mm c18, 10 um 20-30% 10 mM aqueous ammonium bicarbonate in acetonitrile) to afford N-[2,2-bis(hydroxymethyl)-6-morpholino-3H-benzofuran-5-yl]pyrazolo[1,5-a]pyrimidine-3-carboxamide (41.5 mg, 51% yield). $^1$H NMR (400 MHz, dimethyl sulfoxide-$d_6$) δ 10.39 (s, 1H), 9.38 (dd, J=7.1, 1.6 Hz, 1H), 8.96 (dd, J=4.3, 1.6 Hz, 1H), 8.68 (s, 1H), 8.19 (s, 1H), 7.35 (dd, J=7.0, 4.2 Hz, 1H), 6.70 (s, 1H), 4.85 (t, J=5.8 Hz, 1H), 4.77 (s, 1H), 3.92 (d, J=10.8 Hz, 1H), 3.87-3.77 (m, 5H), 3.35 (d, J=6.5 Hz, 3H), 2.92-2.78 (m, 5H).

Example 395. N-(2,2-dimethyl-6-(2-(methylcarbamoyl)cyclopropyl)-2,3-dihydrobenzofuran-5-yl)pyrazolo[1,5-a]pyrimidine-3-carboxamide

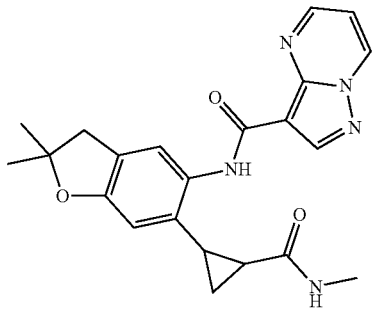 [SMILES: CNC(=O)C1CC1c1cc2c(cc1NC(=O)c1cnn3cccnc13)CC(C)(C)O2]

Step A. 2,2-Dimethyl-5-nitro-6-vinyl-3H-benzofuran

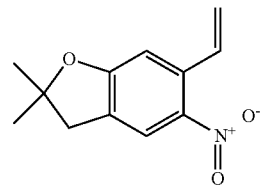

6-Bromo-2,2-dimethyl-5-nitro-2,3-dihydrobenzofuran (Intermediate 4, 200 mg, 0.74 mmol), vinylboronicacid pinacol ester (0.38 ml, 2.24 mmol), [1,1'-bis(diphenylphosphino)ferrocene]dichloropalladium(II) (270 mg, 0.37 mmol) and potassium phosphate (314.0 mg, 1.48 mmol) in 1,4-dioxane (5 ml) and water (2 ml) was heated at 110° C. under microwave conditions for 2h. The solvent was removed and the crude reaction was purified by preparatory TLC (eluent 1:3 ethyl acetate:petroleum ether) to afford 2,2-dimethyl-5-nitro-6-vinyl-3H-benzofuran (81 mg, 45% yield) as a yellow solid. MS-ES: [M+H]$^+$ 220.1.

Step B. Ethyl 2-(2,2-dimethyl-5-nitro-3H-benzofuran-6-yl)cyclopropanecarboxylate

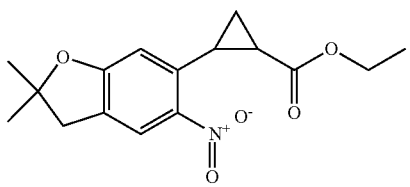

To a mixture of rhodium(II) acetate dimer (163.3 mg, 0.37 mmol) and 2,2-dimethyl-5-nitro-6-vinyl-3H-benzofuran (1.62 g, 7.4 mmol) in dichloromethane (60 ml) under nitrogen was added ethyl diazoacetate (1.2 ml, 11.1 mmol) dropwise. The mixture was stirred for 12h, concentrated to dryness and purified by column chromatography (eluent 20% ethyl acetate:petroleum ether) to afford ethyl 2-(2,2- dimethyl-5-nitro-3H-benzofuran-6-yl)cyclopropanecarboxylate (480 mg, 21% yield) as a white solid. MS-ES: [M+H]⁺ 306.2.

Step C. 2-(2,2-Dimethyl-5-nitro-3H-benzofuran-6-yl)cyclopropanecarboxylic acid

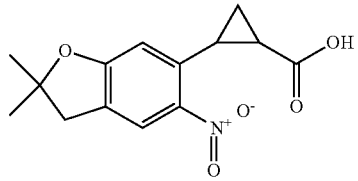

A solution of ethyl 2-(2,2-dimethyl-5-nitro-3H-benzofuran-6-yl)cyclopropanecarboxylate (60 mg, 0.2 mmol) and lithium hydroxide (23.5 mg, 0.98 mmol) in methanol (5 ml) was stirred for 16h, diluted with water, acidified with 1M hydrochloric acid, and extracted with ethyl acetate. The organic phase was isolated, washed with saturated brine, dried over anhydrous sodium sulfate, filtered and concentrated under reduced pressure to give 2-(2,2-dimethyl-5-nitro-3H-benzofuran-6-yl)cyclopropanecarboxylic acid (50 mg, 92% yield) as a colorless oil.

Step D. 2-(2,2-Dimethyl-5-nitro-2,3-dihydrobenzofuran-6-yl)cyclopropane-1-carboxylic acid

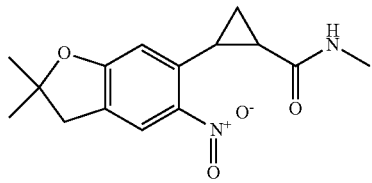

The title compound was made in a manner analogous to Example 394, Step F to afford 2-(2,2-dimethyl-5-nitro-3H-benzofuran-6-yl)-N-methyl-cyclopropanecarboxamide (45 mg, 86% yield) as a yellow solid. MS-ESI [M+H]⁺ 291.1.

Step E. 2-(2,2-Dimethyl-5-nitro-2,3-dihydrobenzofuran-6-yl)-N-methylcyclopropane-1-carboxamide

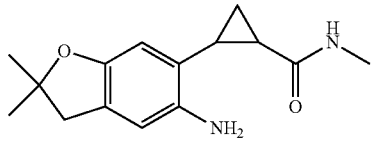

The title compound was made in a manner analogous to Example 2, Step B to afford 2-(5-amino-2,2-dimethyl-3H-benzofuran-6-yl)-N-methyl-cyclopropanecarboxamide (35 mg, 87% yield) as a yellow solid.

Step F. N-(2,2-Dimethyl-6-(2-(methylcarbamoyl)cyclopropyl)-2,3-dihydrobenzofuran-5-yl)pyrazolo[1,5-a]pyrimidine-3-carboxamide

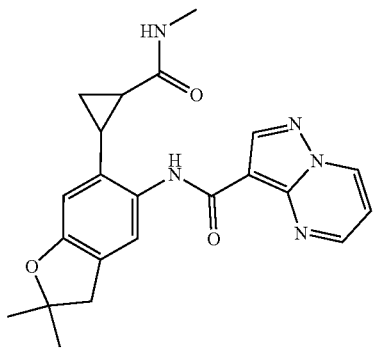

The title compound was made in a manner analogous to Example 394, Step F to afford N-[2,2-dimethyl-6-[2-(methylcarbamoyl)cyclopropyl]-3H-benzofuran-5-yl]pyrazolo[1,5-a]pyrimidine-3-carboxamide (10 mg, 18% yield) as a light yellow solid. ¹H NMR (400 MHz, dimethyl sulfoxide-d₆) δ 9.96 (s, 1H), 9.38 (d, J=6.8 Hz, 1H), 8.86-8.76 (m, 1H), 8.68 (s, 1H), 7.97 (d, J=4.4 Hz, 2H), 7.35 (dd, J=7.0, 4.2 Hz, 1H), 6.50 (s, 1H), 3.00 (s, 2H), 2.42 (d, J=4.6 Hz, 3H), 2.40-2.31 (m, 1H), 1.79 (dt, J=8.8, 4.7 Hz, 1H), 1.40 (s, 7H), 1.17 (d, J=9.5 Hz, 1H). MS-ESI [M+H]⁺406.3.

Example 396. N-(6-((1R,2R)-2-Carbamoylcyclopropyl)-2,2-dimethyl-2,3-dihydrobenzofuran-5-yl)pyrazolo[1,5-a]pyrimidine-3-carboxamide

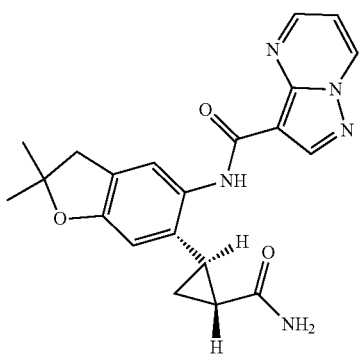

Step A. (1R,2R)-2-(2,2-dimethyl-5-nitro-3H-benzofuran-6-yl)cyclopropanecarboxylic acid

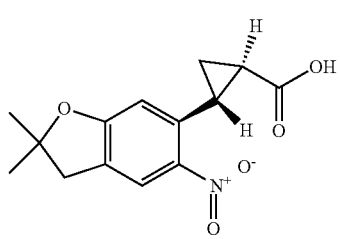

The title compound was made in a manner analogous to Example 395, Step C to afford (1R,2R)-2-(2,2-dimethyl-5-nitro-3H-benzofuran-6-yl)cyclopropanecarboxylic acid as a white solid. (140 mg, quantitative) as a white solid. MS-ES: [M+H]⁺278.1.

Step B. (1R,2R)-2-(2,2-Dimethyl-5-nitro-3H-benzofuran-6-yl)cyclopropanecarbonyl chloride

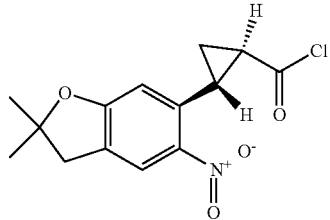

A mixture of (1R,2R)-2-(2,2-dimethyl-5-nitro-3H-benzofuran-6-yl)cyclopropanecarboxylic acid (45 mg, 0.16 mmol) and thionyl chloride (10 ml, 0.16 mmol) was heated to 80° C. and stirred for 3h. The reaction was then concentrated to afford (1R,2R)-2-(2,2-dimethyl-5-nitro-3H-benzofuran-6-yl)cyclopropanecarbonyl chloride (50 mg, quantitative). MS-ESI: [M+H]⁺ 292.2.

Step C. (1R,2R)-2-(2,2-dimethyl-5-nitro-2,3-dihydrobenzofuran-6-yl)cyclopropane-1-carboxamide

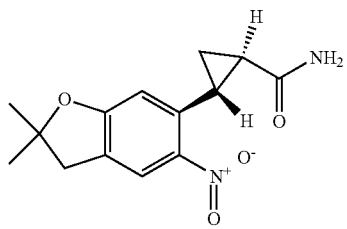

A solution of (1R,2R)-2-(2,2-dimethyl-5-nitro-3H-benzofuran-6-yl)cyclopropanecarbonyl chloride (45 mg, 0.15 mmol) and ammonium hydroxide (5 ml) was stirred for 12h and concentrated to afford (1R,2R)-2-(2,2-dimethyl-5-nitro-3H-benzofuran-6-yl)cyclopropanecarboxamide (40 mg, 95% yield) as a white solid. MS-ES: [M+H]⁺ 277.2

Step D. (1R,2R)-2-(5-Amino-2,2-dimethyl-2,3-dihydrobenzofuran-6-yl)cyclopropane-1-carboxamide

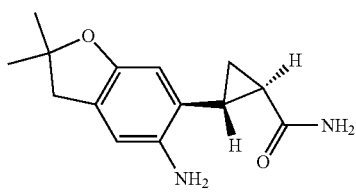

The title compound was made in a manner analogous to Example 2, Step B to afford (1R,2R)-2-(5-amino-2,2-dimethyl-3H-benzofuran-6-yl)cyclopropanecarboxamide (10 mg, 28% yield), which was used directly without further purification. MS-ES: [M+H]⁺247.3.

Step E. N-(6-((1R,2R)-2-Carbamoylcyclopropyl)-2,2-dimethyl-2,3-dihydrobenzofuran-5-yl)pyrazolo[1,5-a]pyrimidine-3-carboxamide

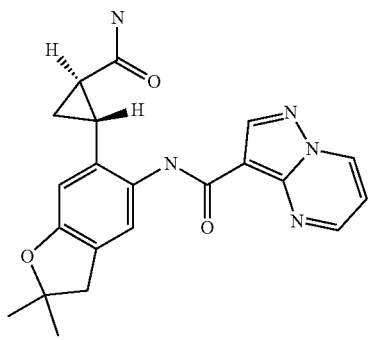 [SMILES: CC1(C)Cc2cc(NC(=O)c3cnn4cccnc34)c([C@@H]3C[C@H]3C(N)=O)cc2O1]

The title compound was made in a manner analogous to Example 395, Step C to afford N-[6-[(1R,2R)-2-carbamoylcyclopropyl]-2,2-dimethyl-3H-benzofuran-5-yl]pyrazolo[1,5-a]pyrimidine-3-carboxamide (3 mg, 19% yield) as a yellow solid. ¹H NMR (400 MHz, dimethyl sulfoxide-d₆) δ 9.96 (s, 1H), 9.38 (d, J=6.9 Hz, 1H), 8.86 (d, J=4.2 Hz, 1H), 8.68 (s, 1H), 7.97 (s, 1H), 7.58 (s, 1H), 7.33 (dd, J=7.0, 4.3 Hz, 1H), 6.87 (s, 1H), 6.50 (s, 1H), 3.00 (s, 2H), 2.33 (s, 1H), 1.91-1.75 (m, 1H), 1.41 (d, J=2.9 Hz, 6H), 1.38-1.12 (m, 2H). MS-ES: [M+H]⁺ 392.3.

Example 397. N-(6-((1R,2R)-2-(Hydroxymethyl)cyclopropyl)-2,2-dimethyl-2,3-dihydrobenzofuran-5-yl)pyrazolo[1,5-a]pyrimidine-3-carboxamide

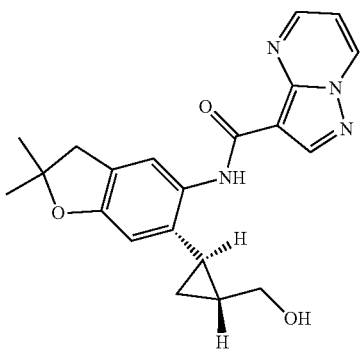

Step A. ((1R,2R)-2-(2,2-Dimethyl-5-nitro-2,3-dihydrobenzofuran-6-yl)cyclopropyl)methanol

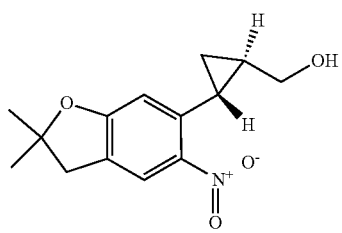

A mixture of (1R,2R)-2-(2,2-dimethyl-5-nitro-3H-benzofuran-6-yl)cyclopropanecarboxylic acid (Example 396, Step A; 50 mg, 0.18 mmol) in borane-tetrahydrofuran complex (5 ml, 10 mmol) was stirred for 2h at 25° C. Methanol (20 ml) was added and the reaction was concentrated to afford [(1R,2R)-2-(2,2-dimethyl-5-nitro-3H-benzofuran-6-yl)cyclopropyl]methanol (40 mg, 84% yield) as a yellow solid. MS-ES: [M+H]⁺ 264.1.

Step B. ((1R, 2R)-2-(5-Amino-2, 2-dimethyl-2, 3-dihydrobenzofuran-6-yl) cyclopropyl)methanol

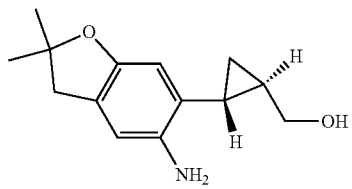 [SMILES: CC1(C)Cc2cc(N)c([C@@H]3C[C@H]3CO)cc2O1]

The title compound was made in a manner analogous to Example 2, Step B to afford [(R, 2R)-2-(5-amino-2,2-dimethyl-3H-benzofuran-6-yl)cyclopropyl]methanol (36 mg, 100% yield), which was used directly without further purification. MS-ESI: [M+H]⁺ 234.2.

Step C. N-(6-((1R,2R)-2-(Hydroxymethyl)cyclopropyl)-2,2-dimethyl-2,3-dihydrobenzofuran-5-yl)pyrazolo[1,5-a]pyrimidine-3-carboxamide

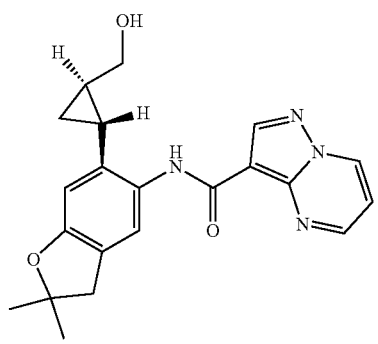

The title compound was made in a manner analogous to Example 395, Step C to afford N-[6-[(1R,2R)-2-(hydroxymethyl)cyclopropyl]-2,2-dimethyl-3H-benzofuran-5-yl]pyrazolo[1,5-a]pyrimidine-3-carboxamide (38.2 mg, 65% yield) as a yellow solid. ¹HNMR (400 MHz, dimethyl sulfoxide-d₆) δ 9.91 (s, 1H), 9.43-9.32 (m, 1H), 8.86 (dd, J=4.3, 1.6 Hz, 1H), 8.69 (s, 1H), 7.90 (s, 1H), 7.33 (dd, J=7.1, 4.2 Hz, 1H), 6.46 (s, 1H), 3.55-3.36 (m, 2H), 2.99 (s, 2H), 1.86 (dt, J=9.7, 4.9 Hz, 1H), 1.40 (s, 6H), 1.32 (q, J=6.1 Hz, 1H), 1.00 (dt, J=9.1, 4.7 Hz, 1H), 0.78 (dt, J=9.2, 4.9 Hz, 1H). MS-ES: [M+H]⁺379.2.

Example 398. N-(2-Isopropyl-6-morpholino-1-oxoisoindolin-5-yl)-6-(methylamino)pyrazolo[1,5-a]-pyrimidine-3-carboxamide

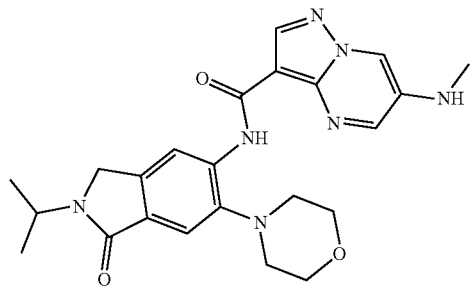 [SMILES: CNc1cnc2c(C(=O)Nc3cc4c(cc3N3CCOCC3)C(=O)N(C(C)C)C4)cnn2c1]

The title compound was made in a manner analogous to Example 381 using 5-amino-2-isopropyl-6-morpholinoisoindolin-1-one (Example 138, Step C) to afford N-(2-isopropyl-6-morpholino-1-oxoisoindolin-5-yl)-6-(methylamino)pyrazolo[1,5-a]-pyrimidine-3-carboxamide (15 mg, 26% yield) as a yellow solid. ¹H NMR (400 MHz, dimethyl sulfoxide-d₆) δ 10.78 (s, 1H), 8.76 (s, 1H), 8.68 (s, 1H), 8.43 (s, 1H), 8.34 (s, 1H), 7.55 (s, 1H), 6.37 (s, 1H), 4.41 (s, 3H), 3.89 (m, 4H), 2.89 (m, 4H), 2.76 (m, 3H), 1.22 (s, 6H). LCMS (ESI): m/z=450.0 [M+H]⁺.

Examples 399 and 400. N-[2-[(3R,4S)-3-Fluorotetrahydropyran-4-yl]-6-morpholino-1-oxo-isoindolin-5-yl]pyrazolo[1,5-a]pyrimidine-3-carboxamide and N-[2-[(3S,4R)-3-fluorotetrahydro pyran-4-yl]-6-morpholino-1-oxo-isoindolin-5-yl]pyrazolo[1,5-a] pyrimidine-3-carboxamide

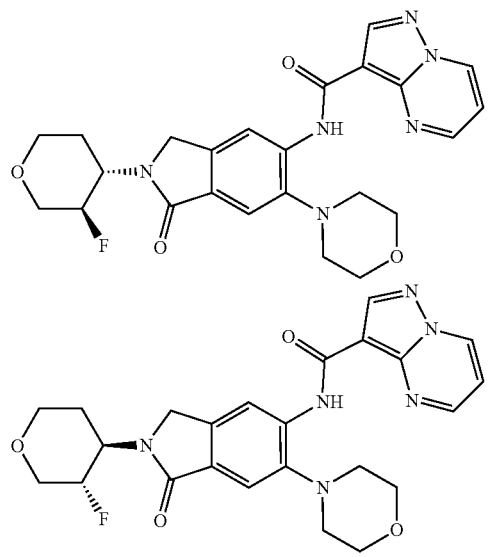

Step A. Ethyl 2-(dibromomethyl)-5-fluoro-4-nitro-benzoate

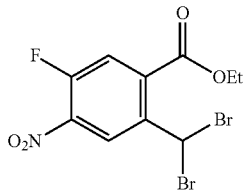 [SMILES: CCOC(=O)c1cc(F)c([N+](=O)[O-])cc1C(Br)Br]

To a solution of 1-bromo-2,5-pyrrolidinedione (7.83 g, 44.02 mmol) in carbon tetrachloride (100 ml) was added benzoyl peroxide (0.43 mg, 1.76 mmol) and ethyl 5-fluoro-2-methyl-4-nitro-benzoate (2.0 g, 8.8 mmol). The mixture was stirred at 100° C. for 16h, concentrated and purified by silica gel column chromatography (eluent 5% ethyl acetate:petroleum ether) to afford ethyl 2-(dibromomethyl)-5-fluoro-4-nitro-benzoate (2.80 g, 82% yield) as a yellow oil. $^1$H NMR (400 MHz, CDCl$_3$) δ 8.84 (d, J=7.2 Hz, 1H), 7.92 (s, 1H), 7.83 (d, J=10.4 Hz, 1H), 4.48 (q, J=7.2 Hz, 1H), 1.46 (t, J=7.2 Hz, 3H).

Step B. Ethyl 5-fluoro-2-formyl-4-nitro-benzoate

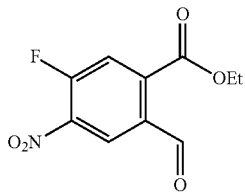 [SMILES: CCOC(=O)c1cc(F)c([N+](=O)[O-])cc1C=O]

To a solution of ethyl 2-(dibromomethyl)-5-fluoro-4-nitro-benzoate (2.50 g, 6.49 mmol) in tetrahydrofuran (30 ml) was added silver nitrate (4.41 g, 25.98 mmol) in water (30 ml) and the mixture was stirred at 25° C. for 16h. Sodium bicarbonate (1.0 g) was added in portions to the reaction and the reaction was stirred for 48h. The reaction was filtered and diluted with ethyl acetate (200 ml). The organic phase was separated and the aqueous phase was extracted with ethyl acetate (100 ml). The combined organic phases were washed with saturated sodium bicarbonate solution and brine, and dried over sodium sulfate. After concentration, the crude oil was purified by silica gel column chromatography (eluent 10% ethyl acetate:petroleum ether) to give ethyl 5-fluoro-2-formyl-4-nitro-benzoate (0.85 g, 54% yield) as a yellow oil. $^1$H NMR (400 MHz, CDCl$_3$) δ 10.59 (s, 1H), 8.63 (d, J=7.2 Hz, 1H), 7.91 (d, J=10.8 Hz, 1H), 4.51 (q, J=7.2 Hz, 1H), 1.46 (t, J=7.2 Hz, 3H).

Step C. Ethyl 2-formyl-5-morpholino-4-nitro-benzoate

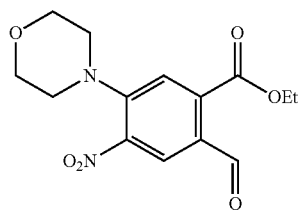 [SMILES: CCOC(=O)c1cc(N2CCOCC2)c([N+](=O)[O-])cc1C=O]

To a solution of ethyl 5-fluoro-2-formyl-4-nitro-benzoate (850 mg, 3.52 mmol) in dichloromethane (5 ml) was added N,N-diisopropylethylamine (911 mg, 7.05 mmol) and morpholine (399 mg, 4.58 mmol) at 0° C. and stirred for 2h. Upon reaction completion, the mixture was diluted with water (20 ml) and extracted with dichloromethane (80 ml×2). The organic phases were combined and washed with brine (50 ml), dried over sodium sulfate, and concentrated under reduced pressure. The residue was purified on silica gel column (eluent 30% ethyl acetate:petroleum ether) to obtain ethyl 2-formyl-5-morpholino-4-nitro-benzoate (540 mg, 49% yield) as a yellow solid. $^1$H NMR (400 MHz, CDCl$_3$) δ 10.38 (s, 1H), 8.37 (s, 1H), 7.50 (s, 1H), 4.48 (q, J=7.2 Hz, 2H), 3.86 (t, J=4.4 Hz, 4H), 3.26 (t, J=4.4 Hz, 4H), 1.44 (t, J=7.2 Hz, 3H). LCMS (ESI): m/z=308.9 [M+H]$^+$.

Step D. Ethyl 4-amino-2-formyl-5-morpholino-benzoate

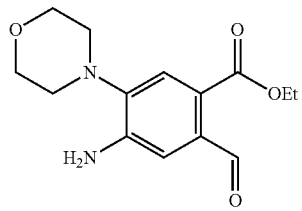 [SMILES: CCOC(=O)c1cc(N2CCOCC2)c(N)cc1C=O]

To a solution of ethyl 2-formyl-5-morpholino-4-nitro-benzoate (0.5 g, 1.6 mmol) in ethanol (10 ml) and water (2 ml) was added iron (0.45 g, 8.1 mmol) and ammonium chloride (0.43 g, 8.1 mmol). The reaction was stirred at 80° C. for 1h, filtered and the filtrate was concentrated. The residue was dissolved in dichloromethane (90 ml) and washed with water (50 ml) and brine (50 ml). The organic phase was dried over sodium sulfate and concentrated to dryness to give ethyl 4-amino-2-formyl-5-morpholino-benzoate (0.42 g, 93% yield) as a yellow solid. LCMS (ESI): m/z=278.9 [M+H]$^+$.

Step E. trans-Ethyl 4-amino-2-(((3-fluorotetrahydro-2H-pyran-4-yl)amino)methyl)-5-morpholinobenzoate

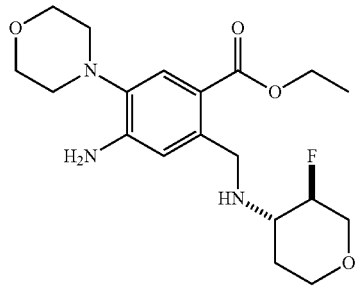 [SMILES: CCOC(=O)c1cc(N2CCOCC2)c(N)cc1CN[C@H]1CCOC[C@@H]1F]

To a solution of trans-3-fluorotetrahydropyran-4-amine (77 mg, 0.65 mmol) in methanol (5 ml) was added ethyl 4-amino-2-formyl-5-morpholino-benzoate (150 mg, 0.54 mmol). The mixture was stirred at 20° C. for 1h. Sodium cyanoborohydride (67 mg, 1.08 mmol) was added and the reaction was stirred at 20° C. for 16h. The reaction was concentrated and purified by preparatory TLC (eluent: 100% ethyl acetate) to afford trans-ethyl 4-amino-2-(((3-fluoro tetrahydro-2H-pyran-4-yl)amino)methyl)-5-morpholino-benzoate (100 mg, 48% yield) as a yellow solid. LCMS (ESI): m/z=382.0 [M+H]⁺.

Step F. trans-5-Amino-2-(3-fluorotetrahydro-2H-pyran-4-yl)-6-morpholino isoindolin-1-one

To a solution of triethylamine (53 mg, 0.52 mmol) in toluene (5 ml) under nitrogen was added trans-ethyl 4-amino-2-(((3-fluorotetrahydro-2H-pyran-4-yl)amino) methyl)-5-morpholinobenzoate (100 mg, 0.26 mmol). The mixture was stirred at 110° C. for 24h, concentrated and purified by preparatory TLC (eluent: 100% ethyl acetate) to afford trans-5-amino-2-(3-fluorotetrahydro-2H-pyran-4-yl)-6-morpholino isoindolin-1-one (75 mg, 85% yield) as a yellow solid. LCMS (ESI): m/z=358.0 [M+Na]⁺.

Step G. trans-N-(2-(3-Fluorotetrahydro-2H-pyran-4-yl)-6-morpholino-1-oxoisoindolin-5-yl)pyrazolo[1,5-a]pyrimidine-3-carboxamide

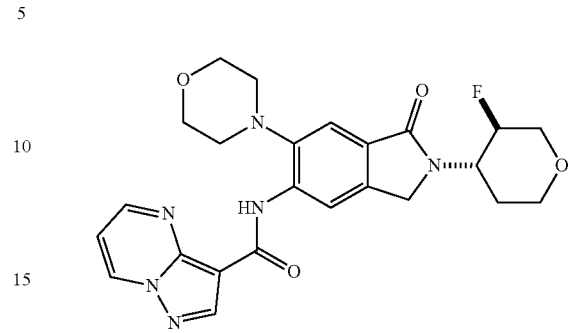

To a solution of pyrazolo[1,5-a]pyrimidine-3-carbonyl chloride (48 mg, 0.27 mmol) in dichloromethane (10 ml) was added trans-5-amino-2-(3-fluorotetrahydro-2H-pyran-4-yl)-6-morpholino isoindolin-1-one (75 mg, 0.22 mmol) and N,N-diisopropylethyl amine (86 mg, 0.67 mmol). The reaction was stirred at 40° C. for 12h, concentrated and purified by preparatory TLC (eluent 10% methanol: dichloromethane) to give trans-N-(2-(3-fluorotetrahydro-2H-pyran-4-yl)-6-morpholino-1-oxoisoindolin-5-yl)pyrazolo[1,5-a]pyrimidine-3-carboxamide (35 mg, 32% yield) as a white solid. LCMS (ESI): m/z=481.1 [M+H]⁺.

Step H. N-(2-((3R,4S)-3-Fluorotetrahydro-2H-pyran-4-yl)-6-morpholino-1-oxo isoindolin-5-yl)pyrazolo[1,5-a]pyrimidine-3-carboxamide and N-(2-((3S,4R)-3-fluorotetrahydro-2H-pyran-4-yl)-6-morpholino-1-oxoisoindolin-5-yl)pyrazolo[1,5-a]pyrimidine-3-carboxamide

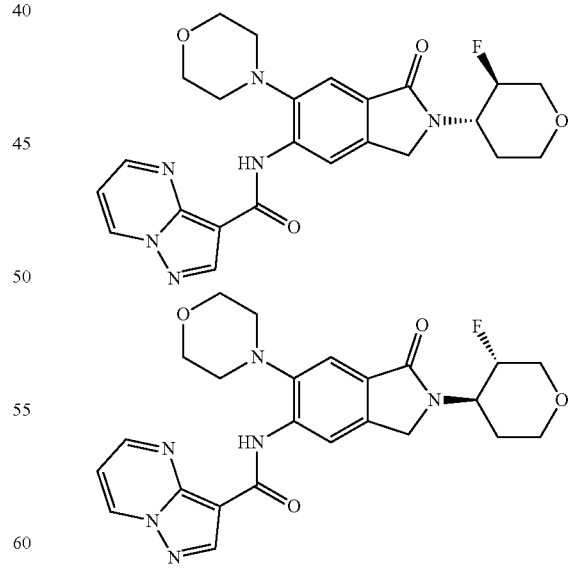

trans-N-(2-(3-Fluorotetrahydro-2H-pyran-4-yl)-6-morpholino-1-oxoisoindolin-5-yl)pyrazolo[1,5-a]pyrimidine-3-carboxamide (35 mg, 0.07 mmol) was separated by preparatory SFC (AD (250 mm*30 mm, 10 um), 55%, 0.1% ammonium hydroxide in methanol) to give N-(2-((3R,4S)-

3-Fluorotetrahydro-2H-pyran-4-yl)-6-morpholino-1-oxo isoindolin-5-yl)pyrazolo[1,5-a]pyrimidine-3-carboxamide (10 mg, 30% yield) and N-(2-((3S,4R)-3-fluorotetrahydro-2H-pyran-4-yl)-6-morpholino-1-oxoisoindolin-5-yl) pyrazolo[1,5-a]pyrimidine-3-carboxamide (11 mg, 31% yield) as white solids with absolute stereochemistry assigned arbitrarily.

Example 399, Peak 1: $^1$H NMR (400 MHz, CDCl$_3$) δ 10.94 (s, 1H), 8.96-8.69 (m, 4H), 7.76 (s, 1H), 7.13 (dd, J=6.8, 4.4 Hz, 1H), 4.88-4.66 (m, 1H), 4.56-4.44 (m, 2H), 4.30-4.22 (m, 1H), 4.02 (t, J=4.4 Hz, 4H), 3.59-3.39 (m, 2H), 3.00 (t, J=4.4 Hz, 4H), 2.04-1.96 (m, 2H). LCMS (ESI): m/z=481.1 [M+H]$^+$.

Example 400, Peak 2: $^1$H NMR (400 MHz, CDCl$_3$) δ 10.94 (s, 1H), 8.97-8.73 (m, 4H), 7.76 (s, 1H), 7.13 (dd, J=6.8, 4.4 Hz, 1H), 4.86-4.65 (m, 1H), 4.55-4.44 (m, 2H), 4.30-4.22 (m, 1H), 4.03-4.01 (m, 4H), 3.59-3.39 (m, 2H), 3.05-2.90 (m, 4H), 2.04-1.96 (m, 2H). LCMS (ESI): m/z=481.1 [M+H]$^+$.

Example 401. N-(2-Methyl-7-morpholino-1-oxo-1,2,3,4-tetrahydroisoquinolin-6-yl)pyrazolo[1,5-a]pyrimidine-3-carboxamide

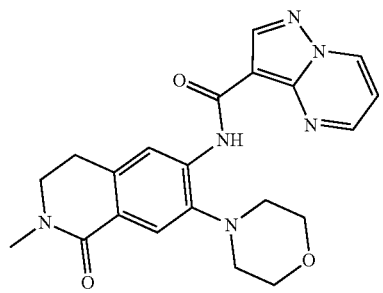 [SMILES: CN1CCc2cc(NC(=O)c3cnn4cccnc34)c(N3CCOCC3)cc2C1=O]

Step A. Ethyl 2-methyl-5-morpholino-4-nitro-benzoate

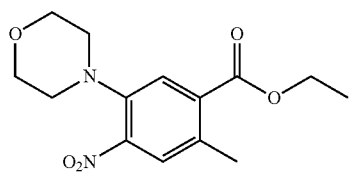

A mixture of ethyl 5-fluoro-2-methyl-4-nitro-benzoate (1.4 g, 6.16 mmol) and morpholine (2.15 g, 24.65 mmol) was stirred at 110° C. for 2h. The reaction mixture was concentrated to dryness and purified by silica gel column chromatography (eluting gradient 10-50% ethyl acetate: petroleum ether) to afford ethyl 2-methyl-5-morpholino-4-nitro-benzoate (1.6 g, 88% yield) as a red oil.

Step B. Ethyl 5-morpholino-4-nitro-2-(2-oxoethyl)benzoate

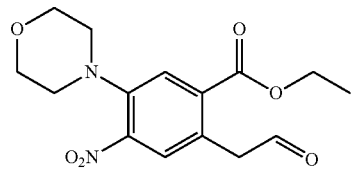 [SMILES: CCOC(=O)c1cc(N2CCOCC2)c([N+](=O)[O-])cc1CC=O]

To a solution of ethyl 2-methyl-5-morpholino-4-nitrobenzoate (0.5 g, 1.70 mmol) in N,N-dimethylformamide (5 ml) was added Bredereck's reagent (0.3 g, 1.70 mmol). The mixture was at 140° C. for 3h, cooled to room temperature, concentrated to dryness and purified by silica gel column chromatography (eluting gradient 1$_0$-5$_0$% ethyl acetate:petroleum ether) to afford ethyl 5-morpholino-4-nitro-2-(2-oxoethyl)benzoate (0.2 g, 36% yield) as a red oil. $^1$HNMR (400 MHz, CDCl$_3$) δ 9.80 (s, 1H), 7.80 (s, 1H), 7.61 (s, 1H), 4.37 (q, J=6.8 Hz, 2H), 4.08 (s, 2H), 3.85 (t, J=4.4 Hz, 4H), 3.10 (t, J=4.4 Hz, 4H), 1.40 (t, J=7.2 Hz, 3H).

Step C. 2-Methyl-7-morpholino-6-nitro-isoquinolin-1-one

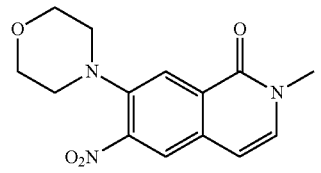

To a solution of methylamine (135 mg, 4.34 mmol) in N,N-dimethylformamide (5 ml) was added ethyl 5-morpholino-4-nitro-2-(2-oxoethyl)benzoate (200 mg, 0.62 mmol) and the reaction was irradiated under microwave conditions at 140° C. for 30 min. The reaction mixture was concentrated to dryness and purified by preparatory TLC (eluent 50% ethyl acetate:petroleum ether) to afford 2-methyl-7-morpholino-6-nitro-isoquinolin-1-one (60 mg, 33% yield) as a red oil. $^1$HNMR (400 MHz, CDCl$_3$) δ 8.15 (s, 1H), 7.83 (s, 1H), 7.09 (d, J=7.6 Hz, 1H), 6.47 (d, J=7.6 Hz, 1H), 3.86 (t, J=4.4 Hz, 4H), 3.63 (s, 3H), 3.12 (t, J=4.4 Hz, 4H).

Step D. 6-Amino-2-methyl-7-morpholino-3,4-dihydroisoquinolin-1-one

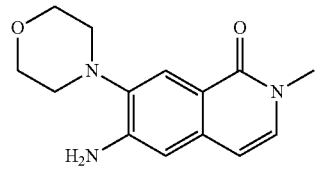 [SMILES: Cn1ccc2cc(N)c(N3CCOCC3)cc2c1=O]

To a solution of 2-methyl-7-morpholino-6-nitro-isoquinolin-1-one (150 mg, 0.52 mmol) in methanol (5 ml) was added 10% palladium on carbon (55 mg, 0.05 mmol). The reaction mixture was stirred at 65° C. for 1h under hydrogen gas (15 psi), filtered and the filtrate was concentrated to obtain 6-amino-2-methyl-7-morpholino-3,4-dihydroisoquinolin-1-one (120 mg, 88% yield) as a white solid. The crude was used directly without further purification. LCMS (ESI): m/z=262.0 [M+H]+.

Step E. 6-Amino-2-methyl-7-morpholino-3,4-dihydroisoquinolin-1-one

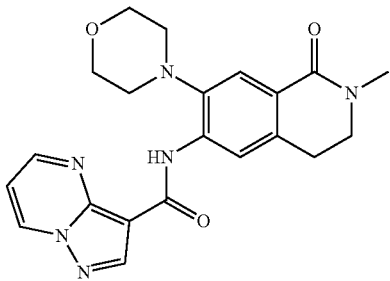

To a solution of pyrazolo[1,5-a]pyrimidine-3-carboxylic acid (82 mg, 0.51 mmol) and 6-amino-2-methyl-7-morpholino-3,4-dihydroisoquinolin-1-one (120 mg, 0.46 mmol) in pyridine (6 ml) was added phosphorus oxychloride (0.21 ml, 2.3 mmol) and the reaction was stirred at 25° C. for 2h. The reaction mixture was quenched with aqueous 10% sodium bicarbonate (5 ml) solution at 0° C. and extracted with ethyl acetate (10 ml*2). The organic phases were isolated, dried over anhydrous sodium sulfate, filtered and concentrated. The residue was purified by reverse phase chromatography (acetonitrile 45-75% 0.05% ammonia in water) to give N-(2-methyl-7-morpholino-1-oxo-3,4-dihydroisoquinolin-6-yl)pyrazolo[1,5-a]pyrimidine-3-carboxamide (17 mg, 9% yield) as a white solid. $^1$HNMR (400 MHz, CDCl$_3$) δ 10.86 (s, 1H), 8.87-8.70 (m, 3H), 8.56 (s, 1H), 7.98 (s, 1H), 7.12 (s, 1H), 4.03-3.95 (m, 4H), 3.59-3.56 (m, 2H), 3.16 (s, 3H), 3.04-2.99 (m, 6H). LCMS (ESI): m/z=407.0 [M+H]+.

Example 402. N-(7-Morpholino-1,1-dioxido-3,4-dihydro-2H-benzo[b][1,4]thiazin-6-yl)pyrazolo[1,5-a]pyrimidine-3-carboxamide

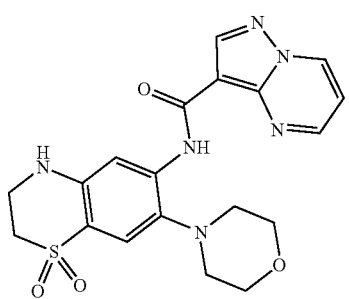 [SMILES: O=C(Nc1cc2c(cc1N1CCOCC1)S(=O)(=O)CCN2)c1cnn2cccnc12]

Step A. 2-Amino-5-chloro-4-nitrobenzene-1-sulfonyl chloride

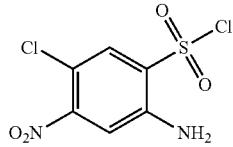 [SMILES: Nc1cc([N+](=O)[O-])c(Cl)cc1S(=O)(=O)Cl]

4-Chloro-3-nitroaniline (10.0 g, 57.95 mmol) was added in small portions to a well-stirred solution of chlorosulfonic acid (28 ml, 406.3 mmol) maintained at 10° C., and then raised to 150° C. for 1h. The reaction was cooled to room temperature, thionyl chloride (7.5 ml, 102.41 mmol) was added dropwise, and the reaction was returned to 150° C. for 1h. The reaction was cooled to room temperature, poured onto chopped ice (50 g) and extracted with ethyl acetate (150 ml×3). The organic phases were combined, dried over sodium sulfate, concentrated and purified by column chromatography (eluting gradient 15-20% ethyl acetate:petroleum ether) to afford 2-amino-5-chloro-4-nitro-benzene-sulfonyl chloride (6.0 g, 38% yield) as a brown solid. $^1$H NMR (400 MHz, CDCl$_3$) δ 7.97 (s, 1H), 7.27 (s, 1H), 5.57 (s, 2H).

Step B. 2-Amino-5-chloro-4-nitrobenzenethiol

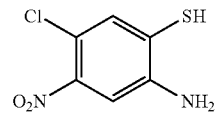

To a solution of triphenyl phosphine (8.7 g, 33.20 mmol) in toluene (60 ml) in a 100 ml three-neck round-bottom flask with a nitrogen inlet, reflux condenser, and calcium chloride guard tube, was added 2-amino-5-chloro-4-nitro-benzene-sulfonyl chloride (3.0 g, 11.07 mmol) in portions. The reaction was stirred at 15° C. for 1h, water (50 ml) was added, and the reaction was stirred for 30 min. Upon completion, the organic phase was isolated and washed with 10% aqueous sodium hydroxide (15 ml×2). The alkaline aqueous extracts were washed with ethyl acetate (30 ml×2), acidified with 2M hydrogen chloride and extracted with dichloromethane (30 ml×2). The combined organic extracts were then washed with brine (15 ml), dried over sodium sulfate and concentrated to dryness to afford 2-amino-5-chloro-4-nitro-benzenethiol (1.7 g, 75% yield) as an orange solid which was used directly without further purification. $^1$H NMR (400 MHz, DMSO-d$_6$) δ 8.19 (s, 1H), 7.81 (s, 1H).

Step C. 7-Chloro-6-nitro-2H-benzo[b][1,4]thiazin-3(4H)-one

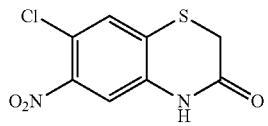 [SMILES: O=C1CSc2cc(Cl)c([N+](=O)[O-])cc2N1]

To the solution of 2-amino-5-chloro-4-nitro-benzenethiol (1.7 g, 8.31 mmol), ethanethiol (1.8 ml, 24.92 mmol) and ethyl bromoacetate (4.2 g, 24.92 mmol) in tetrahydrofuran (30 ml) was added 1,8-diazabicyclo[5.4.0]undec-7-ene (3.8 g, 24.92 mmol). The reaction was stirred at 20° C. for 2 min, concentrated to dryness, taken up in ethyl acetate (30 ml) and washed with water (30 ml×2) and brine (30 ml). The organic phase was then dried over sodium sulfate and concentrated. The material was then brought up in acetic acid (10 ml), stirred at 100° C. for 10 min, concentrated, and purified by flash column chromatography (eluent 60% ethyl acetate:petroleum ether) to afford 7-chloro-6-nitro-4H-1,4-benzothiazin-3-one (1.3 g, 64% yield) as a yellow solid. $^1$H NMR (400 MHz, dimethyl sulfoxide-$d_6$) δ 10.98 (s, 1H), 7.83 (s, 1H), 7.63 (s, 1H), 3.63 (s, 2H).

Step D. 7-Morpholino-6-nitro-2H-benzo[b][1,4]thiazin-3-one

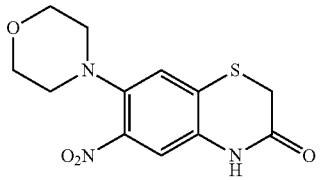 [SMILES: O=C1CSc2cc(N3CCOCC3)c([N+](=O)[O-])cc2N1]

A mixture of 7-chloro-6-nitro-4H-1,4-benzothiazin-3-one (1.2 g, 4.90 mmol) in morpholine (17 ml, 198.17 mmol) was stirred at 120° C. for 18h. The reaction was extracted with ethyl acetate (40 ml×3) and the organic phases were combined, washed with water (40 ml×2) and brine (40 ml), dried over sodium sulfate, concentrated and purified by silica gel column chromatography (eluent 50% ethyl acetate in petroleum ether) to afford 7-morpholino-1-nitro-4H-1,4-benzothiazin-3-one (700 mg, 48% yield) as a yellow solid. $^1$H NMR (400 MHz, CDCl$_3$) δ 8.19 (s, 1H), 7.42 (s, 1H), 7.11 (s, 1H), 3.87-3.85 (m, 4H), 3.50 (s, 2H), 3.04-3.03 (m, 4H).

Step E. 7-Morpholino-6-nitro-2H-benzo[b][1,4]thiazin-3-one 1,1-dioxide

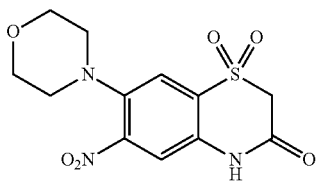 [SMILES: O=C1CS(=O)(=O)c2cc(N3CCOCC3)c([N+](=O)[O-])cc2N1]

7-Morpholino-6-nitro-4H-1,4-benzothiazin-3-one (700 mg, 2.37 mmol) in 1,4-dioxane (10 ml) was treated with 3-chloroperoxybenzoicacid (1.4 g, 7.11 mmol) and stirred at 40° C. for 12h. The reaction was concentrated to dryness and the residue was brought up in ethyl acetate (30 ml) and water (30 ml). The organic phase was isolated, washed with water (30 ml) and brine (30 ml), dried over sodium sulfate, concentrated, and purified by silica gel column chromatography (eluting gradient 0-33% ethyl acetate:petroleum ether) to afford 7-morpholino-6-nitro-2H-benzo[b][1,4]thiazin-3-one 1,1-dioxide (500 mg, 64% yield) as a yellow solid. $^1$H NMR (400 MHz, dimethyl sulfoxide-$d_6$) δ 7.71 (s, 1H), 7.63 (s, 1H), 5.75 (s, 1H), 4.83 (s, 2H), 3.67 (t, J=4.4 Hz, 4H), 2.99 (t, J=4.4 Hz, 4H).

Step F. 7-Morpholino-6-nitro-3,4-dihydro-2H-benzo[b][1,4]thiazine 1,1-dioxide

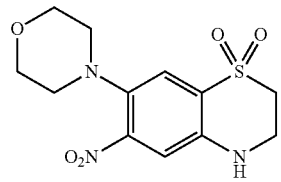 [SMILES: O=[N+]([O-])c1cc2c(cc1N1CCOCC1)S(=O)(=O)CCN2]

To a solution of 7-morpholino-6-nitro-2H-benzo[b][1,4]thiazin-3-one 1,1-dioxide (500 mg, 1.53 mmol) in tetrahydrofuran (60 ml) was added borane (1M in tetrahydrofuran, 7.64 ml, 7.64 mmol) at 20° C. The mixture was stirred at 65° C. for 2h, cooled to 0° C., treated with methanol (10 ml) dropwise and stirred at 65° C. for 1h. After concentration, it was afforded 7-morpholino-6-nitro-3,4-dihydro-2H-benzo[b][1,4]thiazine 1,1-dioxide (400 mg, 84% yield) as a red oil, which was used to next step without further purification. $^1$H NMR (400 MHz, dimethyl sulfoxide-$d_6$) δ 7.56 (s, 1H), 7.37 (s, 1H), 7.14 (s, 1H), 3.75-3.74 (m, 2H), 3.63-3.60 (m, 4H), 3.49-3.46 (m, 2H), 2.83-2.80 (m, 4H).

Step G. 6-Amino-7-morpholino-3,4-dihydro-2H-benzo[b][1,4]thiazine 1,1-dioxide

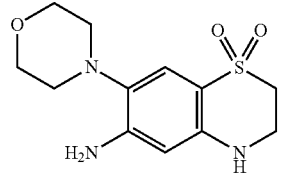 [SMILES: Nc1cc2c(cc1N1CCOCC1)S(=O)(=O)CCN2]

To the solution of 7-morpholino-6-nitro-3,4-dihydro-2H-benzo[b][1,4]thiazine 1,1-dioxide (400 mg, 1.28 mmol) in methanol (50 ml) was added 10% palladium on carbon (1.4 g, 1.28 mmol). The mixture was stirred at 25° C. for 2h under hydrogen (15 psi). The reaction was filtered and the filtrate was concentrated to afford 6-amino-7-morpholino-3,4-dihydro-2H-benzo[b][1,4]thiazine 1,1-dioxide (350 mg, 97% yield) as a white solid. LCMS (ESI): m/z=283.8 [M+H]$^+$.

Step H. N-(7-Morpholino-1,1-dioxido-3,4-dihydro-2H-benzo[b][1,4]thiazin-6-yl) pyrazolo[1,5-a]pyrimidine-3-carboxamide

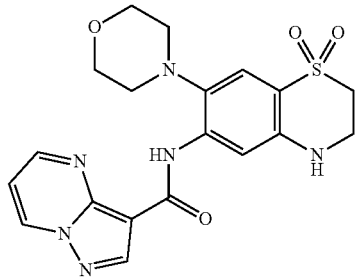

To a solution of 6-amino-7-morpholino-3,4-dihydro-2H-benzo[b][1,4]thiazine 1,1-dioxide (260 mg, 0.92 mmol), pyrazolo[1,5-a]pyrimidine-3-carboxylic acid (150 mg, 0.92 mmol), and ((3H-[1,2,3]triazolo[4,5-b]pyridin-3-yl)oxy)tri(pyrrolidin-1-yl) phosphonium hexafluorophosphate (574 mg, 1.1 mmol) in N,N-dimethylformamide (5 ml) was added N,N-diisopropylethylamine (237 mg, 1.84 mmol). The mixture was stirred at 90° C. for 48h, concentrated to dryness and residue was brought up in ethyl acetate (30 ml) and water (30 ml). The organic phase was isolated, washed with water (30 ml) and brine (30 ml), dried over sodium sulfate, concentrated, and purified by silica gel column chromatography (eluting gradient 0-60% ethyl acetate in petroleum ether). The crude solid was washed with methanol (10 ml) and dried in vacuum to afford N-(7-morpholino-1,1-dioxido-3,4-dihydro-2H-benzo[b][1,4]thiazin-6-yl)pyrazolo[1,5-a]pyrimidine-3-carboxamide (104 mg, 25% yield) as a yellow solid. $^1$H NMR (400 MHz, dimethyl sulfoxide-$d_6$) δ 10.83 (s, 1H), 9.40-9.38 (m, 1H), 8.96 (m, 1H), 8.72 (s, 1H), 8.10 (s, 1H), 7.38-7.36 (m, 2H), 7.10 (s, 1H), 3.87-3.85 (m, 4H), 3.71-3.69 (m, 2H), 3.33-3.31 (m, 2H), 2.80-2.78 (m, 4H). LCMS (ESI): m/z=428.9 [M+H]$^+$.

Example 403. N-(3,3-Dimethyl-7-morpholino-1,1-dioxido-3,4-dihydro-2H-benzo[b][1,4]thiazin-6-yl) pyrazolo[1,5-a]pyrimidine-3-carboxamide

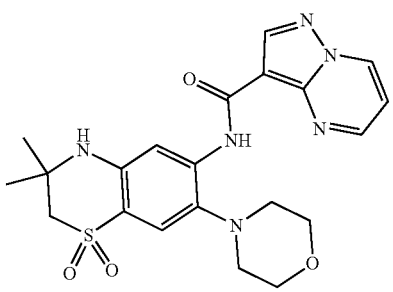 [SMILES: CC1(C)CS(=O)(=O)c2cc(N3CCOCC3)c(NC(=O)c3cnn4cccnc34)cc2N1]

Step A. 1-(2-Amino-5-fluoro-4-nitro-phenyl)sulfanyl-2-methyl-propan-2-ol

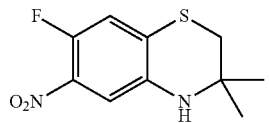 [SMILES: CC1(C)CSc2cc(F)c([N+](=O)[O-])cc2N1]

To 2-amino-5-fluoro-4-nitro-benzenethiolate (Example 402, Step B; 1.82 g, 8.6 mmol) in water (10 ml) was added 1,2-epoxy-2-methylpropane (6.2 g, 86.0 mmol) and dichloromethane (10 ml) and the mixture was stirred vigorously at 10° C. for 2 h. The organic layer was then isolated, washed with brine (5 ml×2), and concentrated to afford 1-(2-amino-5-fluoro-4-nitro-phenyl)sulfanyl-2-methyl-propan-2-ol (0.86 g, 38% yield) as an orange solid. $^1$H NMR (400 MHz, CDCl$_3$) δ 7.37-7.35 (m, 1H), 7.30-7.27 (m, 1H), 4.33 (s, 2H), 3.09 (s, 2H), 1.99 (s, 1H), 1.37 (s, 6H).

Step B. 7-Fluoro-3,3-dimethyl-6-nitro-2,4-dihydro-1,4-benzothiazine

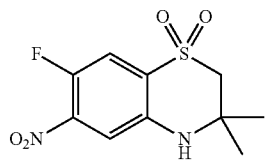 [SMILES: CC1(C)CS(=O)(=O)c2cc(F)c([N+](=O)[O-])cc2N1]

1-(2-Amino-5-fluoro-4-nitro-phenyl)sulfanyl-2-methyl-propan-2-ol (0.76 g, 2.9 mmol) in xylene (10 ml) was treated with phosphoric acid (5.69 g, 58.09 mmol) and heated to 120° C. for 1h under nitrogen atmosphere. The mixture was diluted with 1:1 ethyl acetate:water (10 ml) and the organic phase was isolated, washed with water (5 ml×2), concentrated and purified by silica gel column (eluent 20% ethyl acetate:petroleum ether) to afford 7-fluoro-3,3-dimethyl-6-nitro-2,4-dihydro-1,4-benzothiazine (0.53 g, 75% yield) as an orange solid. $^1$H NMR (400 MHz, CDCl$_3$) δ 7.16 (d, J=6.4, 1H), 6.95 (d, J=10.8, 1H), 3.94 (s, 1H), 2.83 (s, 2H), 1.38 (s, 6H).

Step C. 7-Fluoro-3,3-dimethyl-6-nitro-3,4-dihydro-2H-benzo[b][1,4]thiazine 1,1-dioxide To a solution of 7-fluoro-3,3-dimethyl-6-nitro-2,4-dihydro-1,4-benzothiazine (0.5 g, 2.06 mmol) in dichloromethane (20 ml) was added 3-chloroperoxybenzoic acid (2.09 g, 10.32 mmol) and the mixture was stirred at 10° C. for 1 h. The reaction was quenched with a saturated solution of 1:1 sodium bicarbonate:sodium sulfite (30 ml) and the organic phase was isolated. The organic phase was washed with brine (20 ml×2), filtered and the filtrate was concentrated under reduced pressure to afford 7-fluoro-3,3-dimethyl-6-nitro-3,4-dihydro-2H-benzo[b][1,4] thiazine 1,1-dioxide (0.5 g, 88% yield) as a yellow solid.

Step D. 3,3-Dimethyl-7-morpholino-6-nitro-3,4-dihydro-2H-benzo[b][1,4]thiazine 1,1-dioxide

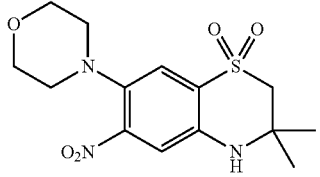

To a solution of 7-fluoro-3,3-dimethyl-6-nitro-3,4-dihydro-2H-benzo[b][1,4]thiazine 1,1-dioxide (0.4 g, 1.46 mmol) in dimethyl sulfoxide (10 ml) was added morpholine (1.27 g, 14.58 mmol) and N,N-diiso propylethylamine (0.95 g, 7.29 mmol) and the mixture was stirred at 90° C. for 2 h. Upon cooling to 20° C., the reaction was diluted with 3:2 ethyl acetate:water (25 ml). The organic phase was isolated, washed with brine (5 ml×2), dried over sodium sulfate, and concentrated under reduced pressure to give the crude residue, which was purified by silica gel column (eluent 5% methanol: dichloromethane) to afford 3,3-dimethyl-7-morpholino-6-nitro-3,4-dihydro-2H-benzo[b][1,4]thiazine 1,1-dioxide (160 mg, 32% yield) as an orange solid. $^1$H NMR (400 MHz, CDCl$_3$) δ 7.59 (s, 1H), 6.91 (s, 1H), 4.36 (s, 1H), 3.76 (t, J=4.4 Hz, 4H), 3.33 (s, 2H), 2.94 (t, J=4.4 Hz, 4H), 1.53 (s, 6H). LCMS (ESI): m/z=341.9 [M+H]$^+$.

Step E. 6-Amino-3,3-dimethyl-7-morpholino-3,4-dihydro-2H-benzo[b][1,4]thiazine 1,1-dioxide

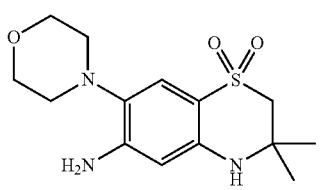 [SMILES: CC1(C)CS(=O)(=O)c2cc(N3CCOCC3)c(N)cc2N1]

The title compound was made in a manner analogous to Example 402, Step G to afford 6-amino-3,3-dimethyl-7-morpholino-3,4-dihydro-2H-benzo[b][1,4]thiazine 1,1-dioxide (0.14 g, 100% yield) as a white solid. $^1$H NMR (400 MHz, dimethyl sulfoxide-d$_6$) δ 6.94 (s, 1H), 6.26 (s, 1H), 5.94 (s, 1H), 5.44 (s, 2H), 3.72 (t, J=4.4 Hz, 4H), 3.26 (s, 2H), 2.68 (t, J=4.4 Hz, 4H), 1.33 (s, 6H).

Step F. N-(3,3-Dimethyl-7-morpholino-1,1-dioxido-3,4-dihydro-2H-benzo[b][1,4] thiazin-6-yl)pyrazolo[1,5-a]pyrimidine-3-carboxamide

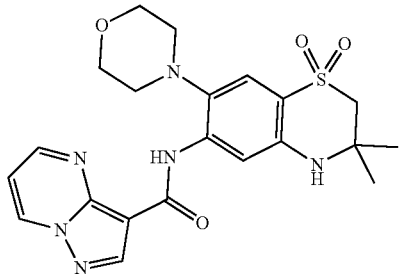

The title compound was made in a manner analogous to Example 287, Step G to afford N-(3,3-dimethyl-7-morpholino-1,1-dioxido-3,4-dihydro-2H-benzo[b][1,4]thiazin-6-yl) pyrazolo[1,5-a]pyrimidine-3-carboxamide (50 mg, 28% yield) as a pale solid. $^1$H NMR (400 MHz, CDCl$_3$) δ 10.83 (s, 1H), 9.40-9.39 (m, 1H), 8.98-8.97 (m, 1H), 8.73 (s, 1H), 8.11 (s, 1H), 7.39-7.37 (m, 1H), 7.37 (s, 1H), 6.94 (s, 1H), 3.88-3.86 (m, 4H), 3.43 (s, 2H), 2.82-2.80 (m, 4H), 1.40 (s, 6H). LCMS (ESI): m/z=457 [M+H]$^+$.

Example 404. N-(2,2-Dimethyl-6-(1-methyl-1H-pyrazol-4-yl)-2,3-dihydrobenzofuran-5-yl)pyrazolo[1,5-a]pyrimidine-3-carboxamide

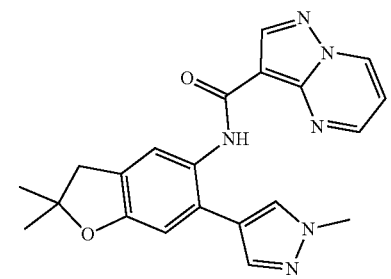 [SMILES: Cn1cc(-c2cc3c(cc2NC(=O)c2cnn4cccnc24)CC(C)(C)O3)cn1]

Step A. 4-(2,2-Dimethyl-5-nitro-2,3-dihydrobenzofuran-6-yl)-1-methyl-1H-pyrazole

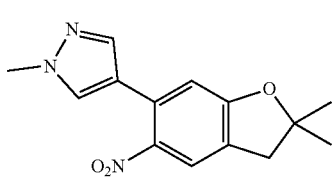

To a mixture of 6-chloro-2,2-dimethyl-5-nitro-3H-benzofuran (0.2 g, 0.88 mmol), 1,1'-bis (diphenylphosphino)ferrocene palladium dichloride (64.3 mg, 0.09 mmol) and cesium carbonate (0.57 g, 1.76 mmol) in 1,4-dioxane (2 ml) and water (0.2 ml) was added 1-methyl-4-(4,4,5,5-tetramethyl-1,3,2-dioxaborolan-2-yl)-H-pyrazole (0.37 g, 1.76 mmol). The mixture was purged with nitrogen (3×) and stirred at 120° C. for 24 h. After being cooled to 20° C., the mixture was filtered through celite and purified by preparatory TLC (eluent 50% ethyl acetate:petroleum ether) to afford 4-(2,2-dimethyl-5-nitro-2,3-dihydrobenzofuran-6-yl)-1-methyl-1H-pyrazole (0.2 g, 83% yield) as a yellow solid. LCMS (ESI): m/z=273.9 [M+H]⁺.

Step B. 2,2-Dimethyl-6-(1-methyl-1H-pyrazol-4-yl)-2,3-dihydrobenzofuran-5-amine

The title compound was made in a manner analogous to Example 402, Step G to afford 2,2-dimethyl-6-(1-methyl-1H-pyrazol-4-yl)-2,3-dihydrobenzofuran-5-amine (0.16 g, 90% yield) as a dark-green oil. LCMS (ESI): m/z=244.0 [M+H]⁺

Step C. N-(2,2-Dimethyl-6-(1-methyl-1H-pyrazol-4-yl)-2,3-dihydrobenzofuran-5-yl) pyrazolo [1,5-a] pyrimidine-3-carboxamide

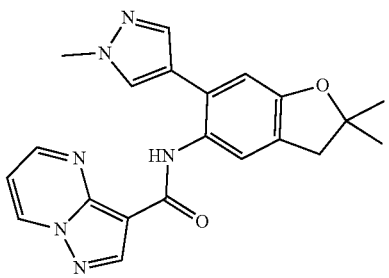

The title compound was made in a manner analogous to Example 138, Step D to afford N-(2,2-dimethyl-6-(1-methyl-1H-pyrazol-4-yl)-2,3-dihydrobenzofuran-5-yl)pyrazolo[1,5-a]pyrimidine-3-carboxamide (180 mg, 81% yield) as a green solid. ¹H NMR (400 MHz, dimethyl sulfoxide-d₆) δ 9.68 (s, 1H), 9.33 (m, 1H), 8.65 (s, 1H), 8.63-8.62 (m, 1H), 7.94 (s, 1H), 7.91 (s, 1H), 7.62 (s, 1H), 7.28-7.25 (m, 1H), 6.72 (s, 1H), 3.84 (s, 3H), 3.04 (s, 2H), 1.44 (s, 6H).

Example 405. N-(6-(5-Cyanopyridin-3-yl)-2,2-dimethyl-2,3-dihydrobenzofuran-5-yl)pyrazolo[1,5-a]pyrimidine-3-carboxamide

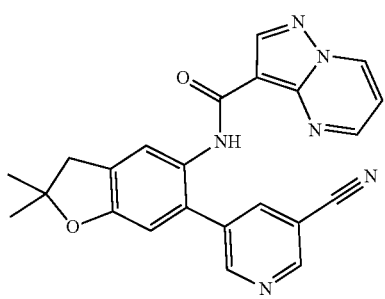 [SMILES: CC1(C)Cc2cc(NC(=O)c3cnn4cccnc34)c(-c3cncc(C#N)c3)cc2O1]

The title compound was made in a manner analogous to Example 404 to afford N-(6-(5-cyanopyridin-3-yl)-2,2-dimethyl-2,3-dihydrobenzofuran-5-yl)pyrazolo[1,5-a]pyrimidine-3-carboxamide. ¹H NMR (400 MHz, CDCl₃): 9.40 (s, 1H), 8.92-8.88 (m, 2H), 8.77 (d, J=6.4 Hz, 1H), 8.70 (s, 1H), 8.35 (s, 1H), 8.15-8.05 (m, 2H), 7.01-6.97 (m, 1H), 6.64 (s, 1H), 3.13 (s, 2H), 1.54 (s, 6H). LCMS (ESI): m/z=411.2 [M+H]⁺.

Example 406. N-[2,2-Dimethyl-6-(1-methylimidazol-2-yl)-3H-benzofuran-5-yl]pyrazolo[1,5-a]pyrimidine-3-carboxamide

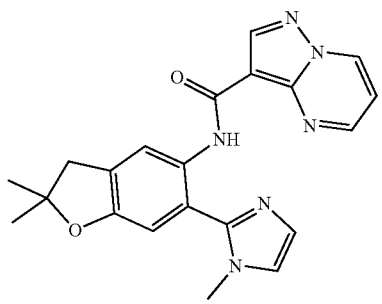 [SMILES: Cn1ccnc1-c1cc2c(cc1NC(=O)c1cnn3cccnc13)CC(C)(C)O2]

Step A. 2-(2, 2-Dimethyl-5-nitro-3H-benzofuran-6-yl)-1-methyl-imidazole

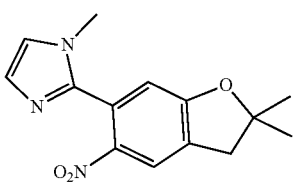 [SMILES: Cn1ccnc1-c1cc2c(cc1[N+](=O)[O-])CC(C)(C)O2]

A solution of 6-chloro-2,2-dimethyl-5-nitro-3H-benzofuran (100.0 mg, 0.44 mmol) and 1-methyl-2-(tributylstannyl)imidazole (245 mg, 0.66 mmol) in N,N-dimethyl formamide (4 ml) was purged with nitrogen for 15 min at 20° C. Tetrakis(triphenylphosphine)palladium(0) (51 mg, 0.04 mmol) was added and the mixture was stirred at 55° C. for 16h. Acetic acid (0.6 ml) was added followed by water (20 ml) and the reaction mixture was extracted with ethyl acetate (20 ml×2). The combined organic phases were isolated, washed with water (40 ml×4) and brine (40 ml), dried over anhydrous sodium sulfate and concentrated in vacuum to give 2-(2,2-dimethyl-5-nitro-3H-benzofuran-6-yl)-1-methyl-imidazole (34 mg, 28% yield) as a yellow solid. ¹H NMR (400 MHz, CDCl₃) δ 8.02 (s, 1H), 7.55 (s, 1H), 6.97 (s, 1H), 6.67 (s, 1H), 3.45 (s, 3H), 3.13 (s, 2H), 1.56 (s, 6H). LCMS (ESI): m/z=273.9 [M+H]⁺.

Step B. N-[2, 2-Dimethyl-6-(1-methylimidazol-2-yl)-3H-benzofuran-5-yl]pyrazolo [1, 5-a]pyrimidine-3-carboxamide

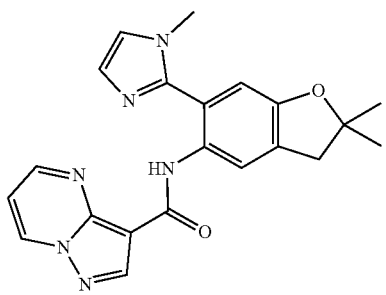

N-[2,2-Dimethyl-6-(1-methylimidazol-2-yl)-3H-benzofuran-5-yl]pyrazolo[1,5-a] pyrimidine-3-carboxamide was prepared following the procedure described for Example 404, Step B-C from 2-(2,2-dimethyl-5-nitro-3H-benzofuran-6-yl)-1-methyl-imidazole as a yellow solid. $^1$H NMR (400 MHz, CDCl$_3$) δ 9.68 (s, 1H), 8.73-8.68 (m, 2H), 8.48-8.45 (m, 2H), 7.56 (s, 1H), 7.18 (s, 1H), 6.95-6.92 (m, 1H), 6.65 (s, 1H), 3.40 (s, 3H), 3.12 (s, 2H), 1.52 (s, 6H). LCMS (ESI): m/z=389.2 [M+H]$^+$.

Example 407. 6-Cyano-N-(2,2-dimethyl-6-morpholino-2,3-dihydrobenzofuran-5-yl)pyrazolo[1,5-a]pyrimidine-3-carboxamide

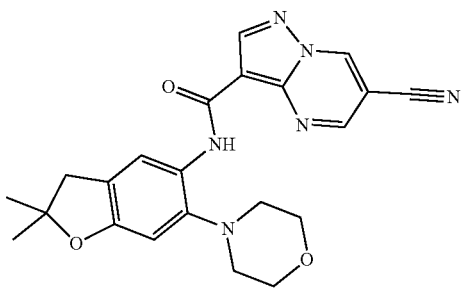

Step A. 6-Formylpyrazolo[1,5-a]pyrimidine-3-carboxylic acid

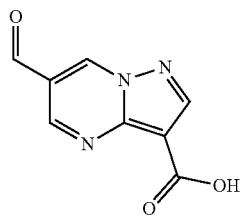 [SMILES: O=Cc1cnc2c(C(=O)O)cnn2c1]

A mixture of 5-amino-1H-pyrazole-4-carboxylic acid (0.5 g, 3.93 mmol), methane tricarbaldehyde (0.47 g, 4.7 mmol) and acetic acid (1 ml) in ethanol (6 ml) was stirred under an atmosphere of nitrogen at 15° C. for 1h followed by 70° C. for 15h. The suspension was filtered and the precipitate was washed with ethanol (10 ml). The solid was collected and dried to give 6-formylpyrazolo [1, 5-a] pyrimidine-3-carboxylic acid (0.47 g, 63% yield) as a white solid. $^1$H NMR (400 MHz, dimethyl sulfoxide-d$_6$): δ 12.68 (s, 1H), 10.06 (s, 1H), 9.92 (s, 1H), 9.11 (d, J=2.4 Hz, 1H), 8.78 (s, 1H).

Step B. N-(2,2-Dimethyl-6-morpholino-2,3-dihydrobenzofuran-5-yl)-6-formyl pyrazolo[1,5-a]pyrimidine-3-carboxamide

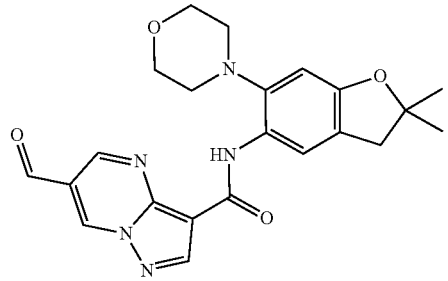

The title compound was made in a manner analogous to Example 1, Step C to afford to afford N-(2,2-dimethyl-6-morpholino-2,3-dihydrobenzofuran-5-yl)-6-formylpyrazolo [1,5-a]pyrimidine-3-carboxamide (0.21 g, 62% yield) as a yellow solid. LCMS (ESI): m/z=421.9 [M+H]$^+$.

Step C. N-(2,2-Dimethyl-6-morpholino-2,3-dihydrobenzofuran-5-yl)-6-((hydroxyl imino)methyl)pyrazolo[1,5-a]pyrimidine-3-carboxamide

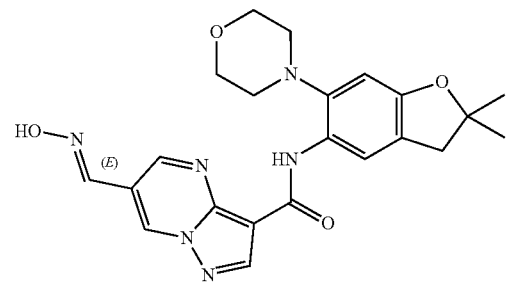

To a stirred solution of N-(2,2-dimethyl-6-morpholino-2, 3-dihydrobenzofuran-5-yl)-6-formylpyrazolo[1,5-a]pyrimidine-3-carboxamide (0.15 g, 0.35 mmol) in ethanol (5 ml) was added hydroxylamine hydrochloride (97 mg, 1.4 mmol) and sodium acetate (0.11 g, 1.4 mmol). The mixture was stirred at 20° C. for 2h under an atmosphere of nitrogen. Water (10 ml) was added and the mixture was extracted with dichloromethane (50 ml×4), dried over sodium sulfate and concentrated under reduced pressure to give N-(2,2-dimethyl-6-morpholino-2,3-dihydrobenzofuran-5-yl)-6-((hydroxyimino)methyl)pyrazolo[1,5-a]pyrimidine-3-carboxamide (155 mg, 99% yield) as a yellow solid. LCMS (ESI): m/z=437.0 [M+H]$^+$.

Step D. 6-Cyano-N-(2,2-dimethyl-6-morpholino-2,3-dihydrobenzofuran-5-yl) pyrazolo[1,5-a]pyrimidine-3-carboxamide

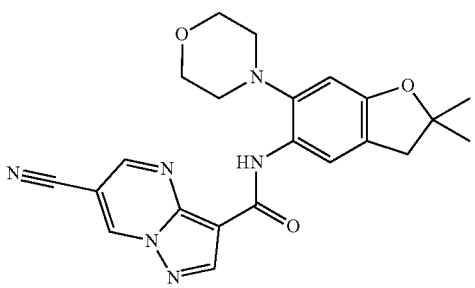 [SMILES: CC1(C)Cc2cc(NC(=O)c3cnn4cc(C#N)cnc34)c(N3CCOCC3)cc2O1]

To a stirred solution of N-(2,2-dimethyl-6-morpholino-2,3-dihydrobenzofuran-5-yl)-6-((hydroxyimino)methyl)pyrazolo[1,5-a]pyrimidine-3-carboxamide (180 mg, 0.41 mmol) in carbon tetrachloride (5 ml) was added thionylchloride (0.15 ml, 2.06 mmol). The mixture was stirred at 65° C. for 2h under an atmosphere of nitrogen. Water (10 ml) was added and the mixture was extracted with dichloromethane (20 ml×3). The combined organic phases were washed with saturated sodium bicarbonate (20 ml), dried over sodium sulfate and concentrated to dryness. The residue was purified by column chromatography (eluent 3% methanol: dichloromethane) followed by recrystallization in methanol to give 6-cyano-N-(2,2-dimethyl-6-morpholino-2,3-dihydrobenzofuran-5-yl)pyrazolo[1,5-a]pyrimidine-3-carboxamide (53 mg, 29% yield) as a yellow solid. $^1$H NMR (400 MHz, CDCl$_3$): δ 10.33 (s, 1H), 9.20 (d, J=2.0 Hz, 1H), 8.95 (s, 1H), 8.85 (d, J=2.0 Hz, 1H), 8.40 (s, 1H), 6.68 (s, 1H), 3.94 (t, J=4.0 Hz, 4H), 3.05 (s, 2H), 2.91 (t, J=4.0 Hz, 4H), 1.50 (s, 6H). LCMS (ESI): m/z=419.1 [M+H]$^+$.

Example 408. 1-(2-Amino-2-oxoethyl)-4-(2,2-dimethyl-5-(pyrazolo[1,5-a]pyrimidine-3-carboxamido)-2,3-dihydrobenzofuran-6-yl)-1-methylpiperazin-1-ium

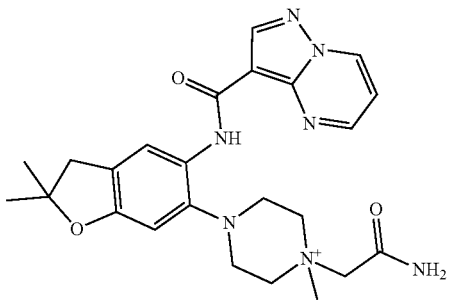 [SMILES: CC1(C)Cc2cc(NC(=O)c3cnn4cccnc34)c(N3CC[N+](C)(CC(N)=O)CC3)cc2O1]

A solution of N-(6-(4-(2-amino-2-oxoethyl)piperazin-1-yl)-2,2-dimethyl-2,3-dihydrobenzofuran-5-yl)pyrazolo[1,5-a]pyrimidine-3-carboxamide (27 mg, 0.06 mmol) in tetrahydrofuran (1 ml) was added to a solution of sodium hydride (60 mass % in oil, 2.8 mg, 0.069 mmol) in tetrahydrofuran (0.3 ml) at ambient temperature and then heated at 60° C. for 2h. The mixture was cooled to room temperature and treated with a solution of iodomethane (4.3 ml, 0.069 mmol) in dimethylformamide N,N-dimethylformamide (0.5 ml). After 12 h at 40° C., the reaction was quenched with water (1 ml). The reaction mixture was concentrated under reduced pressure and purified in a manner similar to Example 145 to obtain the title compound as a solid (7.6 mg, 27% yield). $^1$H NMR (400 MHz, dimethyl sulfoxide-d6) δ 10.05 (s, 1H), 9.39 (dd, J=7.0, 1.3 Hz, 1H), 9.10 (d, J=2.9 Hz, 1H), 8.69 (s, 1H), 8.48 (s, 1H), 8.29 (s, 1H), 7.80 (s, 1H), 7.36 (dd, J=6.9, 4.2 Hz, 1H), 6.95 (s, 1H), 4.38 (s, 2H), 3.88 (d, J=12.6 Hz, 2H), 3.74 (d, J=12.4 Hz, 3H), 3.42 (s, 3H), 3.27 (m, 4H), 3.02 (s, 2H), 1.43 (s, 6H). LCMS (ESI) m/z: 464.2 [M+H]$^+$.

Examples 409, 410, 411 and 412. N—((R)-2-(hydroxymethyl)-2-methyl-6-(4-((R)-1,1,1-trifluoro-2-hydroxypropan-2-yl)piperidin-1-yl)-2,3-dihydrobenzofuran-5-yl)pyrazolo[1,5-a]pyrimidine-3-carboxamide; N—((R)-2-(hydroxymethyl)-2-methyl-6-(4-((S)-1,1,1-trifluoro-2-hydroxypropan-2-yl)piperidin-1-yl)-2,3-dihydrobenzofuran-5-yl) pyrazolo[1,5-a]pyrimidine-3-carboxamide; N—((S)-2-(hydroxymethyl)-2-methyl-6-(4-((R)-1,1,1-trifluoro-2-hydroxypropan-2-yl)piperidin-1-yl)-2,3-dihydrobenzofuran-5-yl)pyrazolo[1,5-a]pyrimidine-3-carboxamide; and N—((S)-2-(hydroxymethyl)-2-methyl-6-(4-((S)-1,1,1-trifluoro-2-hydroxypropan-2-yl)piperidin-1-yl)-2,3-dihydrobenzofuran-5-yl) pyrazolo[1,5-a]pyrimidine-3-carboxamide

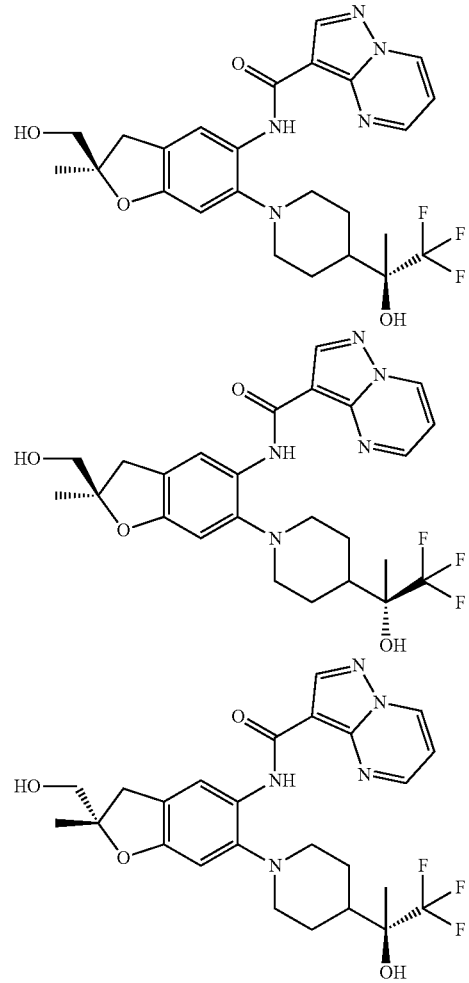

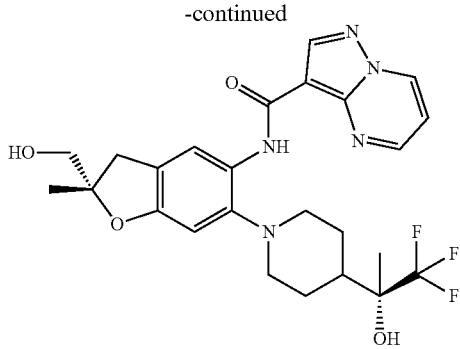

Step A. 1,1,1-trifluoro-2-(1-(2-(hydroxymethyl)-2-methyl-5-nitro-2,3-dihydrobenzofuran-6-yl)piperidin-4-yl)propan-2-ol

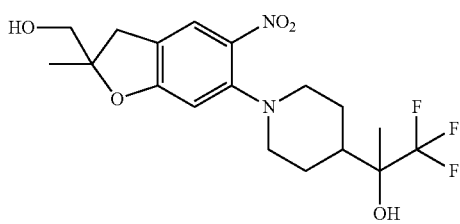

A mixture of (6-fluoro-2-methyl-5-nitro-2,3-dihydrobenzofuran-2-yl)methanol (Intermediate 3) (250 mg, 1.10 mmol), 1,1,1-trifluoro-2-(4-piperidyl)propan-2-ol (250 mg, 1.27 mmol) and cesium carbonate (1.18 g, 3.63 mmol) in acetonitrile (5 ml) was stirred at 80° C. for 18h. Isopropyl acetate, water, and brine were added and the organic phase was separated and dried over sodium sulfate. After filtration and concentration under reduced pressure, the residue was purified by silica gel chromatography (eluting gradient 0%-100% isopropyl acetate: heptane) to afford 1,1,1-trifluoro-2-(1-(2-(hydroxymethyl)-2-methyl-5-nitro-2,3-dihydrobenzofuran-6-yl)piperidin-4-yl)propan-2-ol compound with 3-methyl-6-nitro-7-(4-(1,1,1-trifluoro-2-hydroxypropan-2-yl)piperidin-1-yl)chroman-3-ol (359 mg, 81% yield) as an orange oil. MS (ESI): m/z=405.1 [M+1]$^+$.

Step B. 2-(1-(5-amino-2-(hydroxymethyl)-2-methyl-2,3-dihydrobenzofuran-6-yl)piperidin-4-yl)-1,1,1-trifluoropropan-2-ol

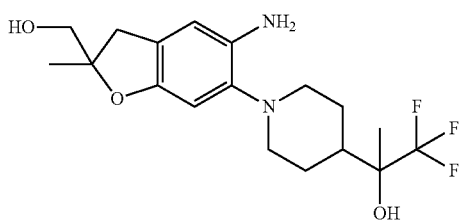 [SMILES: CC1(CO)Cc2cc(N)c(N3CCC(C(C)(O)C(F)(F)F)CC3)cc2O1]

A mixture of 1,1,1-trifluoro-2-(1-(2-(hydroxymethyl)-2-methyl-5-nitro-2,3-dihydrobenzofuran-6-yl)piperidin-4-yl)propan-2-ol (357 mg, 0.883 mmol), iron powder (247 mg, 4.41 mmol) and ammonium chloride (236 mg, 4.41 mmol) in ethanol (18 ml) and water (6 ml) was stirred at 50° C. for 3h. The reaction was filtered, the filtrate was concentrated under reduced pressure and the residue was purified by silica gel column chromatography (eluting gradient 0%-20% methanol: dichloromethane) to afford 2-(1-(5-amino-2-(hydroxymethyl)-2-methyl-2,3-dihydrobenzofuran-6-yl)piperidin-4-yl)-1,1,1-trifluoropropan-2-ol compound with 6-amino-3-methyl-7-(4-(1,1,1-trifluoro-2-hydroxypropan-2-yl)piperidin-1-yl)chroman-3-ol (253 mg, 77% yield). MS (ESI): m/z=375.1 [M+1]$^+$.

Step C. N-(2-(hydroxymethyl)-2-methyl-6-(4-(1,1,1-trifluoro-2-hydroxypropan-2-yl)piperidin-1-yl)-2,3-dihydrobenzofuran-5-yl)pyrazolo[1,5-a]pyrimidine-3-carboxamide

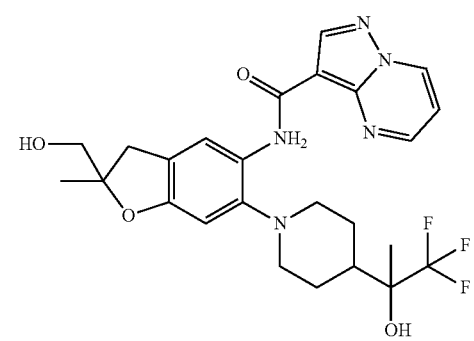 [SMILES: CC1(CO)Cc2cc(NC(=O)c3cnn4cccnc34)c(N3CCC(C(C)(O)C(F)(F)F)CC3)cc2O1]

A mixture 2-(1-(5-amino-2-(hydroxymethyl)-2-methyl-2,3-dihydrobenzofuran-6-yl)piperidin-4-yl)-1,1,1-trifluoropropan-2-ol (253 mg, 0.676 mmol), pyrazolo[1,5-a]pyrimidine-3-carbonyl chloride (135 mg, 0.744 mmol), 4-dimethylaminopyridine (16.7 mg, 0.135 mmol) and diisopropylethylamine (0.35 ml, 2.03 mmol) in 1,2-dichloroethane (5.00 ml) was stirred at 25° C. for 18h. The crude reaction was concentrated under reduced pressure to afford N-(2-(hydroxymethyl)-2-methyl-6-(4-(1,1,1-trifluoro-2-hydroxypropan-2-yl)piperidin-1-yl)-2,3-dihydrobenzofuran-5-yl)pyrazolo[1,5-a]pyrimidine-3-carboxamide and N-(3-hydroxy-3-methyl-7-(4-(1,1,1-trifluoro-2-hydroxypropan-2-yl)piperidin-1-yl)chroman-6-yl)pyrazolo[1,5-a]pyrimidine-3-carboxamide. MS (ESI): m/z=520.2 [M+1]$^+$.

Step D. N—((R)-2-(hydroxymethyl)-2-methyl-6-(4-((R)-1,1,1-trifluoro-2-hydroxypropan-2-yl)piperidin-1-yl)-2,3-dihydrobenzofuran-5-yl)pyrazolo[1,5-a]pyrimidine-3-carboxamide; N—((R)-2-(hydroxymethyl)-2-methyl-6-(4-((S)-1,1,1-trifluoro-2-hydroxypropan-2-yl)piperidin-1-yl)-2,3-dihydrobenzofuran-5-yl)pyrazolo[1,5-a]pyrimidine-3-carboxamide; N—((S)-2-(hydroxymethyl)-2-methyl-6-(4-((R)-1,1,1-trifluoro-2-hydroxypropan-2-yl)piperidin-1-yl)-2,3-dihydrobenzofuran-5-yl)pyrazolo[1,5-a]pyrimidine-3-carboxamide; and N—((S)-2-(hydroxymethyl)-2-methyl-6-(4-((S)-1,1,1-trifluoro-2-hydroxypropan-2-yl)piperidin-1-yl)-2,3-dihydrobenzofuran-5-yl)pyrazolo[1,5-a]pyrimidine-3-carboxamide

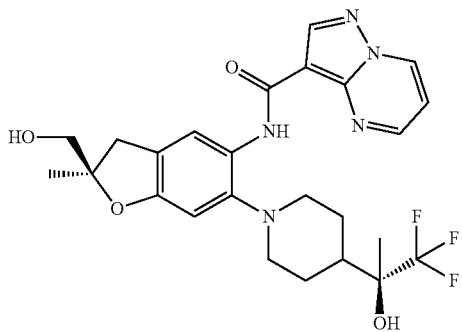

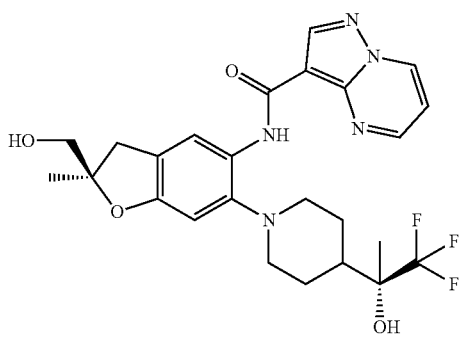

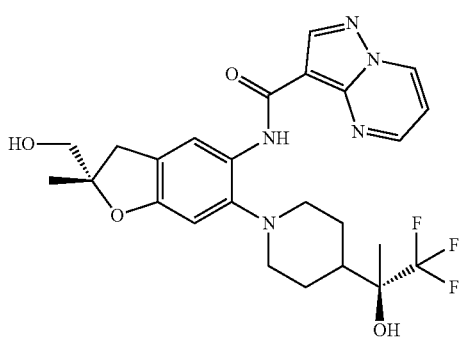

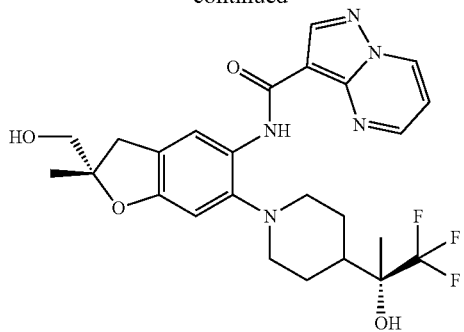

N-(2-(hydroxymethyl)-2-methyl-6-(4-(1,1,1-trifluoro-2-hydroxypropan-2-yl)piperidin-1-yl)-2,3-dihydrobenzofuran-5-yl)pyrazolo[1,5-a]pyrimidine-3-carboxamide and N-(3-hydroxy-3-methyl-7-(4-(1,1,1-trifluoro-2-hydroxypropan-2-yl)piperidin-1-yl)chroman-6-yl)pyrazolo[1,5-a]pyrimidine-3-carboxamide (Example X) were resolved via chiral SFC: (Jasco 2088 SFC (ChiralpakAD, 250*21.2 mm, 5um) at 25% Methanol with/0.1% ammonium hydroxide at 70 ml/min, 100 bar, 40 deg C., 220 nm) followed by (Jasco 2088 SFC (Whelk-O1, 150*21.2 mm, 5um) at 35% Methanol with 0.1% ammonium hydroxide at 70m/min, 100 bar, 40 deg C., 220 nm); (PIC 100 SFC (Chiralpak AD, 250*21.2 mm, 5um), 25% IPA 2 with 0.1% ammonium hydroxide at 70 mil/min, 100 bar, 40 deg C., 220 nm. Absolute and relative stereochemistry arbitrarily assigned Example 409, Peak 5: $^1$H NMR (400 MHz, DMSO-d6) δ 10.33 (s, 1H), 9.36 (dd, J=7.0, 1.6 Hz, 1H), 8.90 (dd, J=4.3, 1.6 Hz, 1H), 8.68 (s, 1H), 8.24 (s, 1H), 7.33 (dd, J=7.0, 4.2 Hz, 1H), 6.65 (s, 1H), 5.85 (s, 1H), 5.03 (t, J=5.8 Hz, 1H), 3.49-3.38 (m, 2H), 3.26-3.15 (m, 2H), 3.00 (d, J=11.6 Hz, 2H), 2.82 (d, J=15.7 Hz, 1H), 2.64 (d, J=24.0 Hz, 2H), 1.88-1.60 (m, 6H), 1.34 (s, 3H), 1.27 (s, 4H). MS (ESI): m/z=520.2 [M+1]$^+$.

Example 410, Peak 4: 1H NMR (400 MHz, DMSO-d6) δ 10.33 (s, 1H), 9.36 (dd, J=7.0, 1.6 Hz, 1H), 8.90 (dd, J=4.2, 1.6 Hz, 1H), 8.68 (s, 1H), 8.24 (s, 1H), 7.33 (dd, J=7.0, 4.2 Hz, 1H), 6.65 (s, 1H), 5.85 (s, 1H), 5.03 (t, J=5.8 Hz, 1H), 3.50-3.37 (m, 2H), 3.25-3.10 (d, J=15.7 Hz, 1H), 2.99 (m, 2H), 2.82 (d, J=15.7 Hz, 1H), 2.73-2.56 (m, 2H), 1.91-1.63 (m, 5H), 1.34 (s, 3H), 1.27 (s, 3H). MS (ESI): m/z=520.2 [M+1]$^+$.

Example 411, Peak 1: $^1$H NMR (400 MHz, DMSO-d6) δ 10.33 (s, 1H), 9.36 (dd, J=7.0, 1.6 Hz, 1H), 8.90 (dd, J=4.2, 1.6 Hz, 1H), 8.68 (s, 1H), 8.24 (s, 1H), 7.33 (dd, J=7.0, 4.2 Hz, 1H), 6.65 (s, 1H), 5.85 (s, 1H), 5.03 (t, J=5.8 Hz, 1H), 3.43 (p, J=5.5 Hz, 2H), 3.19 (d, J=15.7 Hz, 1H), 3.00 (m, 2H), 2.82 (d, J=15.7 Hz, 1H), 2.64 (m 2H), 1.86-1.65 (m, 5H), 1.34 (s, 3H), 1.27 (s, 3H). MS (ESI): m/z=520.2 [M+1]$^+$.

Example 412, Peak 3: $^1$H NMR (400 MHz, DMSO-d6) δ 10.33 (s, 1H), 9.36 (dd, J=7.0, 1.6 Hz, 1H), 8.90 (dd, J=4.2, 1.6 Hz, 1H), 8.68 (s, 1H), 8.24 (s, 1H), 7.33 (dd, J=7.0, 4.2 Hz, 1H), 6.65 (s, 1H), 5.86 (s, 1H), 5.03 (t, J=5.8 Hz, 1H), 3.47-3.38 (m, 2H), 3.19 (d, J=16.1 Hz, 1H), 3.11-2.88 (m, 2H), 2.82 (d, J=16.0 Hz, 1H), 2.62 (m, 2H), 1.92-1.59 (m, 5H), 1.34 (s, 3H), 1.27 (s, 3H). MS (ESI): m/z=520.2 [M+1]$^+$.

TABLE 13

The following examples were made in a manner similar to that for Examples 409-412

| Ex. | Name | Structure | NMR, MS |
|---|---|---|---|
| 413 and 414 | N-((R)-6-((1R,5S,6R)-6-carbamoyl-3-azabicyclo[3.1.0]hexan-3-yl)-2-(hydroxymethyl)-2-methyl-2,3-dihydrobenzofuran-5-yl)pyrazolo[1,5-a]pyrimidine-3-carboxamide and N-((S)-6-((1R,5S,6S)-6-carbamoyl-3-azabicyclo[3.1.0]hexan-3-yl)-2-(hydroxymethyl)-2-methyl-2,3-dihydrobenzofuran-5-yl)pyrazolo[1,5-a]pyrimidine-3-carboxamide (absolute stereochemistry assigned arbitrarily) | | Example 414, Peak 1: $^1$H NMR (400 MHz, DMSO-d6) δ 9.58 (s, 1H), 9.36 (dd, J = 7.0, 1.6 Hz, 1H), 8.97 (dd, J = 4.3, 1.6 Hz, 1H), 8.68 (s, 1H), 8.00 (s, 1H), 7.33 (dd, J = 7.0, 4.2 Hz, 2H), 6.77 (s, 1H), 6.59 (s, 1H), 5.03 (t, J = 5.8 Hz, 1H), 3.42 (m, 4H), 3.17 (d, J = 15.9 Hz, 1H), 3.07 (m, 2H), 2.79 (d, J = 15.8 Hz, 1H), 2.21 (t, J = 2.9 Hz, 1H), 1.90 (s, 2H), 1.33 (s, 3H). MS (ESI): m/z = 449.2 [M + 1]$^+$.<br>Example 413, Peak 2: $^1$H NMR (400 MHz, DMSO-d6) δ 9.58 (s, 1H), 9.36 (dd, J = 7.0, 1.6 Hz, 1H), 8.97 (dd, J = 4.2, 1.6 Hz, 1H), 8.68 (s, 1H), 8.00 (s, 1H), 7.33 (dd, J = 7.0, 4.2 Hz, 2H), 6.77 (s, 1H), 6.59 (s, 1H), 5.03 (t, J = 5.8 Hz, 1H), 3.42 (m, 4H), 3.17 (d, J = 16.1 Hz, 1H), 3.07 (m, 2H), 2.79 (d, J = 15.8 Hz, 1H), 2.21 (t, J = 2.9 Hz, 1H), 1.90 (s, 2H), 1.33 (s, 3H). MS (ESI): m/z = 449.2 [M + 1]$^+$. |
| 415 and 416 | (R)-N-(6-(4-(2-amino-2-oxoethyl)piperazin-1-yl)-2-(hydroxymethyl)-2-methyl-2,3-dihydrobenzofuran-5-yl)pyrazolo[1,5-a]pyrimidine-3-carboxamide and (S)-N-(6-(4-(2-amino-2-oxoethyl)piperazin-1-yl)-2-(hydroxymethyl)-2-methyl-2,3-dihydrobenzofuran-5-yl)pyrazolo[1,5-a]pyrimidine-3-carboxamide (absolute stereochemistry assigned arbitrarily) | | Example 416, Peak 1: $^1$H NMR (400 MHz, DMSO-d6) δ 10.42 (s, 1H), 9.36 (dd, J = 7.0, 1.6 Hz, 1H), 8.97 (dd, J = 4.2, 1.6 Hz, 1H), 8.67 (s, 1H), 8.32 (s, 1H), 7.35 (dd, J = 7.0, 4.2 Hz, 1H), 7.19 (d, J = 28.2 Hz, 2H), 6.67 (s, 1H), 5.03 (t, J = 5.8 Hz, 1H), 3.42 (m, 2H), 3.19 (d, J = 16.2 Hz, 1H), 3.01 (s, 2H), 2.93-2.78 (m, 5H), 2.73 (s, 4H), 1.34 (s, 3H). MS (ESI): m/z = 466.2 [M + 1]$^+$.<br>Example 415, Peak 2: $^1$H NMR (400 MHz, DMSO-d6) δ 10.42 (s, 1H), 9.36 (dd, J = 7.0, 1.6 Hz, 1H), 8.97 (dd, J = 4.2, 1.6 Hz, 1H), 8.67 (s, 1H), 8.32 (s, 1H), 7.35 (dd, J = 7.0, 4.2 Hz, 1H), 7.23 (s, 1H), 7.16 (s, 1H), 6.67 (s, 1H), 5.03 (t, J = 5.8 Hz, 1H), 3.49-3.37 (m, 2H), 3.19 (d, J = 15.7 Hz, 1H), 3.01 (s, 2H), 2.84 (m, 5H), 2.73 (s, 4H), 1.34 (s, 3H). MS (ESI): m/z = 466.2 [M + 1]$^+$. |

TABLE 13-continued

The following examples were made in a manner similar to that for Examples 409-412

| Ex. | Name | Structure | NMR, MS |
|---|---|---|---|
| 417 and 418 | (R)-N-(2-(hydroxymethyl)-2-methyl-6-(3-oxo-2,8-diazaspiro[4.5]decan-8-yl)-2,3-dihydrobenzofuran-5-yl)pyrazolo[1,5-a]pyrimidine-3-carboxamide and (S)-N-(2-(hydroxymethyl)-2-methyl-6-(3-oxo-2,8-diazaspiro[4.5]decan-8-yl)-2,3-dihydrobenzofuran-5-yl)pyrazolo[1,5-a]pyrimidine-3-carboxamide (absolute stereochemistry assigned arbitrarily) | | Example 417, Peak 2: $^1$H NMR (400 MHz, DMSO-d6) δ 10.46 (s, 1H), 9.36 (dd, J = 7.0, 1.6 Hz, 1H), 8.84 (dd, J = 4.2, 1.6 Hz, 1H), 8.67 (s, 1H), 8.30 (s, 1H), 7.58 (s, 1H), 7.34 (dd, J = 7.0, 4.2 Hz, 1H), 6.72 (s, 1H), 5.02 (t, J = 5.8 Hz, 1H), 3.42 (m, 2H), 3.17 (m, 3H), 2.82 (d, J = 16.0 Hz, 1H), 2.77 (m, 4H), 2.18 (s, 2H), 1.80 (m, 4H), 1.34 (s, 3H). MS (ESI): m/z = 477.2 [M + 1]$^+$. Example 418 Peak 1: $^1$H NMR (400 MHz, DMSO-d6) δ 10.46 (s, 1H), 9.36 (dd, J = 7.0, 1.6 Hz, 1H), 8.84 (dd, J = 4.2, 1.6 Hz, 1H), 8.67 (s, 1H), 8.30 (s, 1H), 7.58 (s, 1H), 7.34 (dd, J = 7.0, 4.2 Hz, 1H), 6.72 (s, 1H), 5.02 (t, J = 5.8 Hz, 1H), 3.43 (m, 2H), 3.19 (m, 3H), 2.82 (d, J = 16.1 Hz, 1H), 2.79-2.73 (m, 4H), 2.18 (s, 2H), 1.80 (m, 4H), 1.34 (s, 3H). MS (ESI): m/z = 477.2 [M + 1]$^+$. |
| 419 and 420 | (R)-N-(6-(5,7-dihydro-6H-pyrrolo[3,4-b]pyridin-6-yl)-2-(hydroxymethyl)-2-methyl-2,3-dihydrobenzofuran-5-yl)pyrazolo[1,5-a]pyrimidine-3-carboxamide and (S)-N-(6-(5,7-dihydro-6H-pyrrolo[3,4-b]pyridin-6-yl)-2-(hydroxymethyl)-2-methyl-2,3-dihydrobenzofuran-5-yl)pyrazolo[1,5-a]pyrimidine-3-carboxamide (absolute stereochemistry assigned arbitrarily) | | Example 419, Peak 1: $^1$H NMR (400 MHz, DMSO-d6) δ 10.39 (s, 1H), 9.29 (dd, J = 7.0, 1.7 Hz, 1H), 8.67 (s, 1H), 8.45 (d, J = 4.9 Hz, 1H), 8.13 (s, 1H), 7.82 (dd, J = 4.2, 1.7 Hz, 1H), 7.75 (d, J = 6.3 Hz, 1H), 7.32 (dd, J = 7.6, 5.0 Hz, 1H), 7.16 (dd, J = 7.0, 4.2 Hz, 1H), 6.90 (s, 1H), 5.05 (t, J = 5.8 Hz, 1H), 4.51 (s, 2H), 4.47 (s, 2H), 3.44 (m, 2H), 3.25-3.18 (m, 1H), 2.84 (d, J = 16.1 Hz, 1H), 1.36 (s, 3H). MS (ESI): m/z = 443.1 [M + 1]$^+$. Example 420, Peak 2: $^1$H NMR (400 MHz, DMSO-d6) δ 10.39 (s, 1H), 9.29 (dd, J = 7.0, 1.7 Hz, 1H), 8.67 (s, 1H), 8.45 (dd, J = 5.0, 1.4 Hz, 1H), 8.13 (s, 1H), 7.82 (dd, J = 4.2, 1.7 Hz, 1H), 7.75 (d, J = 6.4 Hz, 1H), 7.32 (dd, J = 7.6, 5.0 Hz, 1H), 7.16 (dd, J = 7.0, 4.2 Hz, 1H), 6.90 (s, 1H), 5.05 (t, J = 5.8 Hz, 1H), 4.51 (s, 2H), 4.47 (s, 2H), 3.45 (m, 2H), 3.26-3.16 (m, 1H), 2.84 (d, J = 16.1 Hz, 1H), 1.36 (s, 3H). MS (ESI): m/z = 443.1 [M + 1]$^+$. |

Examples 421, 422 and 423. N—((S)-3-hydroxy-3-methyl-7-(4-((S)-1,1,1-trifluoro-2-hydroxypropan-2-yl)piperidin-1-yl)chroman-6-yl)pyrazolo[1,5-a]pyrimidine-3-carboxamide; N—((R)-3-hydroxy-3-methyl-7-(4-((R)-1,1,1-trifluoro-2-hydroxypropan-2-yl)piperidin-1-yl)chroman-6-yl)pyrazolo[1,5-a]pyrimidine-3-carboxamide and N-(3-hydroxy-3-methyl-7-(4-(1,1,1-trifluoro-2-hydroxypropan-2-yl)piperidin-1-yl)chroman-6-yl)pyrazolo[1,5-a]pyrimidine-3-carboxamide

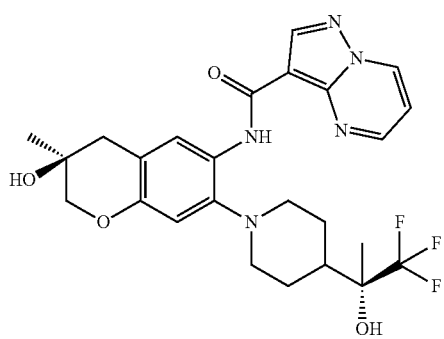

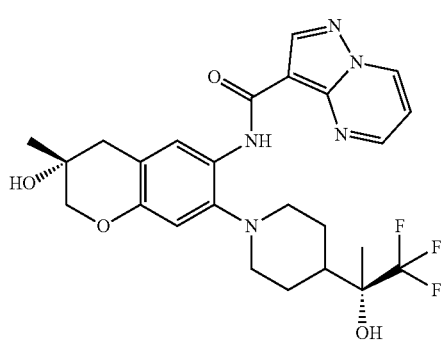

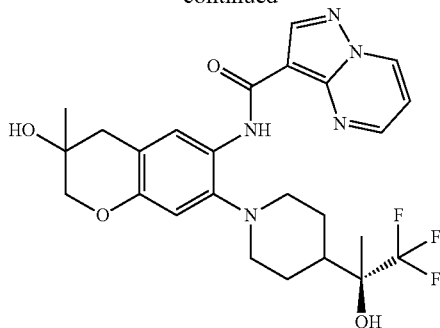

The title compounds were made in the process of generating Examples 409-412, Step A and isolated during Examples 409-412, Step D. Absolute and relative stereochemistry arbitrarily assigned.

Example 421, Peak 3: $^1$H NMR (400 MHz, DMSO-d6) δ 10.29 (s, 1H), 9.41-9.31 (m, 1H), 8.90 (d, J=2.7 Hz, 1H), 8.68 (s, 1H), 8.12 (s, 1H), 7.34 (dd, J=7.0, 4.2 Hz, 1H), 6.66 (s, 1H), 5.86 (s, 1H), 4.82 (s, 1H), 3.75 (s, 2H), 3.03 (m, 2H), 2.68 (d, J=7.7 Hz, 2H), 2.65-2.55 (m, 2H), 1.77 (m, 5H), 1.28 (s, 3H), 1.19 (s, 3H). MS (ESI): m/z=520.2 [M+1]$^+$.

Example 422, Peak 2: $^1$H NMR (400 MHz, DMSO-d6) δ 10.29 (s, 1H), 9.36 (dd, J=7.0, 1.6 Hz, 1H), 8.90 (dd, J=4.2, 1.6 Hz, 1H), 8.68 (s, 1H), 8.12 (s, 1H), 7.34 (dd, J=7.0, 4.2 Hz, 1H), 6.66 (s, 1H), 5.87 (s, 1H), 4.82 (s, 1H), 3.74 (s, 2H), 3.02 (m, 2H), 2.76-2.65 (m, 2H), 2.66-2.54 (m, 2H), 1.78 (m, 5H), 1.28 (s, 3H), 1.19 (s, 3H). MS (ESI): m/z=520.2 [M+1]$^+$.

Example 423, Peak 1: $^1$H NMR (400 MHz, DMSO-d6) δ 10.29 (s, 1H), 9.36 (dd, J=7.0, 1.6 Hz, 1H), 8.90 (dd, J=4.2, 1.6 Hz, 1H), 8.68 (s, 1H), 8.12 (s, 1H), 7.34 (dd, J=7.0, 4.2 Hz, 1H), 6.66 (s, 1H), 5.87 (s, 1H), 4.82 (s, 1H), 3.74 (s, 2H), 3.01 (m, 2H), 2.78-2.53 (m, 2H), 2.66-2.54 (m, 2H), 1.78 (m, 5H), 1.28 (s, 3H), 1.19 (s, 3H). MS (ESI): m/z=520.2 [M+1]$^+$.

TABLE 14

The following examples were made in a manner similar to that for Examples 423-425

| Ex. | Name | Structure | NMR, MS |
|---|---|---|---|
| 424 and 425 | (R)-N-(7-(4-(2-amino-2-oxoethyl)piperazin-1-yl)-3-hydroxy-3-methylchroman-6-yl)pyrazolo[1,5-a]pyrimidine-3-carboxamide and (S)-N-(7-(4-(2-amino-2-oxoethyl)piperazin-1-yl)-3-hydroxy-3-methylchroman-6-yl)pyrazolo[1,5-a]pyrimidine-3-carboxamide (absolute stereochemistry assigned arbitrarily) | | Example 424, Peak 1: $^1$H NMR (400 MHz, DMSO-d6) δ 10.37 (s, 1H), 9.36 (dd, J = 7.0, 1.6 Hz, 1H), 8.97 (dd, J = 4.2, 1.7 Hz, 1H), 8.67 (s, 1H), 8.19 (s, 1H), 7.35 (dd, J = 7.0, 4.2 Hz, 1H), 7.24 (s, 1H), 7.16 (s, 1H), 6.68 (s, 1H), 4.83 (s, 1H), 3.75 (s, 2H), 3.02 (s, 2H), 2.90-2.82 (m, 4H), 2.79-2.63 (m, 6H), 1.20 (s, 3H). MS (ESI): m/z = 466.2 [M + 1]$^+$. Example 425, Peak 2: $^1$H NMR (400 MHz, DMSO-d6) δ 10.37 (s, 1H), 9.36 (dd, J = 7.0, 1.6 Hz, 1H), 8.97 (dd, J = 4.2, 1.6 Hz, 1H), 8.67 (s, 1H), 8.19 (s, 1H), 7.35 (dd, J = 7.0, 4.2 Hz, 1H), 7.24 (s, 1H), 7.16 (s, 1H), 6.68 (s, 1H), 4.83 (s, 1H), 3.75 (s, 2H), 3.02 (s, 2H), 2.92-2.79 (m, 4H), 2.69 (m, 6H), 1.20 (s, 3H). MS (ESI): m/z = 466.2 [M + 1]$^+$. |
| 426 and 427 | (R)-N-(7-(4-cyanopiperidin-1-yl)-3-hydroxy-3-methylchroman-6-yl)pyrazolo[1,5-a]pyrimidine-3-carboxamide and (S)-N-(7-(4-cyanopiperidin-1-yl)-3-hydroxy-3-methylchroman-6-yl)pyrazolo[1,5-a]pyrimidine-3-carboxamide (absolute stereochemistry assigned arbitrarily) | | Example 426, Peak 1: $^1$H NMR (400 MHz, DMSO-d6) δ 10.33 (s, 1H), 9.39 (dd, J = 7.0, 1.6 Hz, 1H), 8.87 (dd, J = 4.2, 1.6 Hz, 1H), 8.68 (s, 1H), 8.17 (s, 1H), 7.39 (dd, J = 7.0, 4.2 Hz, 1H), 6.66 (s, 1H), 4.83 (s, 1H), 3.75 (s, 2H), 3.10 (m, 1H), 2.97-2.86 (m, 2H), 2.85-2.73 (m, 2H), 2.72-2.62 (m, 2H), 2.10 (m, 2H), 2.06-1.95 (m, 2H), 1.19 (s, 3H). MS (ESI): m/z = 433.1 [M + 1]$^+$. Example 427, Peak 2: $^1$H NMR (400 MHz, DMSO-d6) δ 10.33 (s, 1H), 9.39 (dd, J = 7.0, 1.6 Hz, 1H), 8.87 (dd, J = 4.2, 1.6 Hz, 1H), 8.68 (s, 1H), 8.17 (s, 1H), 7.39 (dd, J = 7.0, 4.2 Hz, 1H), 6.66 (s, 1H), 4.83 (s, 1H), 3.75 (s, 2H), 3.10 (m, 1H), 2.97-2.86 (m, 2H), 2.85-2.73 (m, 2H), 2.72-2.62 (m, 2H), 2.10 (m, 2H), 2.06-1.95 (m, 2H), 1.19 (s, 3H). MS (ESI): m/z = 433.1 [M + 1]$^+$. |

TABLE 14-continued

The following examples were made in a manner similar to that for Examples 423-425

| Ex. | Name | Structure | NMR, MS |
| --- | --- | --- | --- |
| 428 and 429 | (R)-N-(7-(4-(1H-imidazol-1-yl)piperidin-1-yl)-3-hydroxy-3-methylchroman-6-yl)pyrazolo[1,5-a]pyrimidine-3-carboxamide and (S)-N-(7-(4-(1H-imidazol-1-yl)piperidin-1-yl)-3-hydroxy-3-methylchroman-6-yl)pyrazolo[1,5-a]pyrimidine-3-carboxamide (absolute stereochemistry assigned arbitrarily) | | Example 428, Peak 2: $^1$H NMR (400 MHz, DMSO-d6) δ 10.26 (s, 1H), 9.36 (dd, J = 7.0, 1.6 Hz, 1H), 8.82 (dd, J = 4.2, 1.6 Hz, 1H), 8.68 (s, 1H), 8.11 (s, 1H), 7.78 (s, 1H), 7.35 (dd, J = 7.0, 4.2 Hz, 1H), 7.30 (s, 1H), 6.95 (s, 1H), 6.71 (s, 1H), 4.84 (s, 1H), 4.24 (dt, J = 11.0, 6.1 Hz, 1H), 3.76 (s, 2H), 3.09 (d, J = 11.7 Hz, 2H), 2.90-2.77 (m, 2H), 2.77-2.62 (m, 2H), 2.27-2.08 (m, 4H), 1.20 (s, 3H). MS (ESI): m/z = 474.2 [M + 1]$^+$. Example 429, Peak 1: $^1$H NMR (400 MHz, DMSO-d6) δ 10.26 (s, 1H), 9.36 (dd, J = 7.0, 1.6 Hz, 1H), 8.82 (dd, J = 4.2, 1.6 Hz, 1H), 8.68 (s, 1H), 8.11 (s, 1H), 7.35 (dd, J = 7.0, 4.2 Hz, 1H), 7.30 (s, 1H), 6.95 (s, 1H), 6.71 (s, 1H), 4.84 (s, 1H), 4.24 (dt, J = 10.9, 6.1 Hz, 1H), 3.76 (s, 2H), 3.09 (d, J = 11.8 Hz, 2H), 2.91-2.77 (m, 2H), 2.77-2.60 (m, 2H), 2.28-2.05 (m, 4H), 1.20 (s, 3H). MS (ESI): m/z = 474.2 [M + 1]$^+$. |
| 430 and 431 | (R)-N-(3-hydroxy-3-methyl-7-((1-methyl-1H-pyrazol-4-yl)methoxy)chroman-6-yl)pyrazolo[1,5-a]pyrimidine-3-carboxamide and (S)-N-(3-hydroxy-3-methyl-7-((1-methyl-1H-pyrazol-4-yl)methoxy)chroman-6-yl)pyrazolo[1,5-a]pyrimidine-3-carboxamide (absolute stereochemistry assigned arbitrarily) | | Example 430, Peak 3: $^1$H NMR (400 MHz, DMSO-d6) δ 10.15 (s, 1H), 9.34 (dd, J = 7.0, 1.7 Hz, 1H), 8.64 (s, 1H), 8.33 (dd, J = 4.2, 1.7 Hz, 1H), 8.13 (s, 1H), 7.84 (s, 1H), 7.66-7.59 (m, 1H), 7.38-7.29 (m, 1H), 6.66 (s, 1H), 5.02 (s, 2H), 4.82 (s, 1H), 3.87 (s, 3H), 3.76 (s, 2H), 2.66 (d, J = 3.9 Hz, 2H), 1.20 (s, 3H). MS (ESI): m/z = 435.1 [M + 1]$^+$. Example 431, Peak 1: $^1$H NMR (400 MHz, DMSO-d6) δ 10.15 (s, 1H), 9.34 (dd, J = 7.0, 1.7 Hz, 1H), 8.64 (s, 1H), 8.33 (dd, J = 4.2, 1.7 Hz, 1H), 8.13 (s, 1H), 7.84 (s, 1H), 7.63 (d, J = 0.6 Hz, 1H), 7.33 (dd, J = 7.0, 4.2 Hz, 1H), 6.66 (s, 1H), 5.02 (s, 2H), 4.82 (s, 1H), 3.87 (s, 3H), 3.76 (s, 2H), 2.66 (d, J = 4.0 Hz, 2H), 1.20 (s, 3H). MS (ESI): m/z = 435.1 [M + 1]$^+$. |

TABLE 14-continued

The following examples were made in a manner similar to that for Examples 423-425

| Ex. | Name | Structure | NMR, MS |
|---|---|---|---|
| 432 and 433 | (R)-N-(2-(hydroxymethyl)-2-methyl-7-morpholinochroman-6-yl)pyrazolo[1,5-a]pyrimidine-3-carboxamide and (S)-N-(2-(hydroxymethyl)-2-methyl-7-morpholinochroman-6-yl)pyrazolo[1,5-a]pyrimidine-3-carboxamide (absolute stereochemistry assigned arbitrarily) | | Example 433, Peak 1: $^1$H NMR (400 MHz, DMSO-d6) δ 10.35 (s, 1H), 9.37 (dd, J = 7.0, 1.6 Hz, 1H), 8.95 (dd, J = 4.2, 1.6 Hz, 1H), 8.67 (s, 1H), 8.21 (s, 1H), 7.34 (dd, J = 7.0, 4.2 Hz, 1H), 6.62 (s, 1H), 4.90 (t, J = 5.8 Hz, 1H), 3.90-3.73 (m, 4H), 3.49-3.35 (m, 2H), 2.87-2.76 (m, 4H), 2.76-2.65 (m, 2H), 1.89 (dt, J = 14.0, 7.2 Hz, 1H), 1.68 (dt, J = 12.9, 6.1 Hz, 1H), 1.20 (s, 3H). MS (ESI): m/z = 424.1 [M + 1]$^+$. Example 432, Peak 2: $^1$H NMR (400 MHz, DMSO-d6) δ 10.35 (s, 1H), 9.37 (dd, J = 7.0, 1.6 Hz, 1H), 8.95 (dd, J = 4.2, 1.7 Hz, 1H), 8.67 (s, 1H), 8.21 (s, 1H), 7.34 (dd, J = 7.0, 4.2 Hz, 1H), 6.62 (s, 1H), 4.97-4.82 (m, 1H), 3.83 (m, 4H), 3.48-3.36 (m, 2H), 2.89-2.75 (m, 4H), 2.70 (m, 2H), 1.89 (dt, J = 14.0, 7.2 Hz, 1H), 1.68 (dt, J = 12.9, 6.1 Hz, 1H), 1.20 (s, 3H). MS (ESI): m/z = 424.2 [M + 1]$^+$. |

Example 434. N-(6-(4-(2-hydroxy-2-methylpropyl)piperazin-1-yl)-2,2-dimethyl-2,3-dihydrobenzofuran-5-yl)pyrazolo[1,5-a]pyrimidine-3-carboxamide

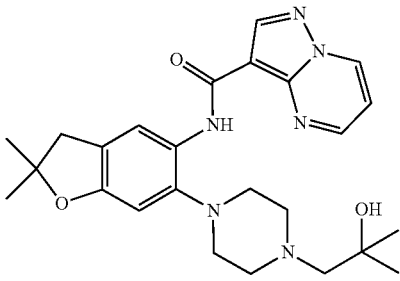 [SMILES: CC(C)(O)CN1CCN(c2cc3c(cc2NC(=O)c2cnn4cccnc24)CC(C)(C)O3)CC1]

Step A. 1-(2,2-Dimethyl-5-nitro-2,3-dihydrobenzofuran-6-yl)piperazine

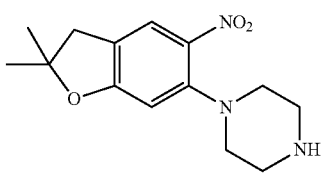 [SMILES: CC1(C)Cc2cc([N+](=O)[O-])c(N3CCNCC3)cc2O1]

A mixture of 6-chloro-2,2-dimethyl-5-nitro-3H-benzofuran (10.0 g, 43.9 mmol), piperazine (4.16 g, 48.3 mmol) and N,N-diisopropylethylamine (25.4 ml, 154 mmol) in dimethylsulfoxide (133 mL) was heated at 45° C. for 12 h. The mixture was diluted with water, brine, and dichloromethane. The phases were separated and the aqueous phase was extracted into dichloromethane. The combined organic phases were dried over sodium sulfate, concentrated under reduced pressure and purified by silica gel chromatography (eluting gradient 0%-20% methanol: dichloromethane) to afford 1-(2,2-dimethyl-5-nitro-2,3-dihydrobenzofuran-6-yl)piperazine (5.96 g, 49% yield) as a bright orange foam. $^1$H NMR (400 MHz, DMSO-d6) δ 7.83 (s, 1H), 6.57 (s, 1H), 3.00 (d, J=1.1 Hz, 2H), 2.91 (d, J=10.5 Hz, 8H), 1.44 (s, 6H).

Step B. Ethyl 2-(4-(2,2-dimethyl-5-nitro-2,3-dihydrobenzofuran-6-yl)piperazin-1-yl)acetate

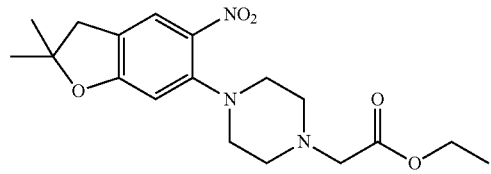 [SMILES: CCOC(=O)CN1CCN(c2cc3c(cc2[N+](=O)[O-])CC(C)(C)O3)CC1]

A mixture of 1-(2,2-dimethyl-5-nitro-2,3-dihydrobenzofuran-6-yl)piperazine (5.96 g, 21.5 mmol), potassium carbonate (4.46 g, 32.3 mmol) and ethyl 2-bromoacetate (2.55 ml, 22.6 mmol) in dimethylformamide (100 ml) was stirred at ambient temperature for 18h. The mixture was diluted with water, brine, and isopropyl acetate. The layers were separated and the aqueous phase was extracted with isopropyl acetate. The combined organic phases were dried over sodium sulfate, concentrated under reduced pressure and purified by silica gel chromatography (eluting gradient 0%-100% isopropyl acetate: heptane) to afford ethyl 2-(4-(2,2-dimethyl-5-nitro-2,3-dihydrobenzofuran-6-yl)piperazin-1-yl)acetate (7.74 g, 99% yield) as an orange oil. $^1$H NMR (400 MHz, DMSO-d6) δ 7.82 (t, J=1.2 Hz, 1H), 6.59

(s, 1H), 4.09 (q, J=7.1 Hz, 2H), 3.27 (s, 2H), 3.00 (d, J=1.0 Hz, 2H), 2.99-2.93 (m, 4H), 2.68-2.58 (m, 4H), 1.44 (s, 6H), 1.24-1.14 (m, 4H).

Step C. Ethyl 2-(4-(5-amino-2,2-dimethyl-2,3-dihydrobenzofuran-6-yl)piperazin-1-yl)acetate

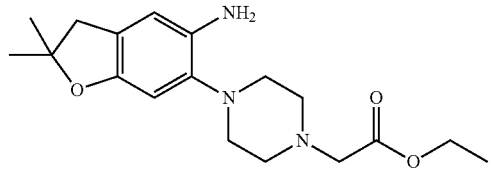 [SMILES: CCOC(=O)CN1CCN(c2cc3c(cc2N)CC(C)(C)O3)CC1]

A mixture of ethyl 2-(4-(2,2-dimethyl-5-nitro-2,3-dihydrobenzofuran-6-yl)piperazin-1-yl)acetate (7.74 g, 21.3 mmol) and 10% palladium on carbon (2.27 g, 2.13 mmol) in ethanol (100 ml) was stirred for 18h under an atmosphere of hydrogen. The mixture was filtered and the filtrate was concentrated under reduced pressure and purified by silica gel chromatography (eluting gradient 0%-5% methanol: dichloromethane) to afford ethyl 2-(4-(5-amino-2,2-dimethyl-2,3-dihydrobenzofuran-6-yl)piperazin-1-yl)acetate (6.36 g, 90% yield). $^1$H NMR (400 MHz, DMSO-d6) δ 6.52 (s, 1H), 6.34 (s, 1H), 4.17 (s, 2H), 4.10 (q, J=7.1 Hz, 2H), 3.25 (s, 2H), 2.83 (s, 2H), 2.74 (d, J=4.4 Hz, 4H), 2.63 (s, 4H), 1.34 (s, 6H), 1.24-1.14 (m, 3H).

Step D. Ethyl 2-(4-(5-(bis(4-methoxybenzyl)amino)-2,2-dimethyl-2,3-dihydrobenzofuran-6-yl)piperazin-1-yl)acetate

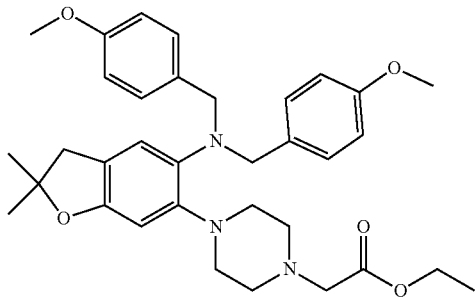 [SMILES: CCOC(=O)CN1CCN(c2cc3c(cc2N(Cc2ccc(OC)cc2)Cc2ccc(OC)cc2)CC(C)(C)O3)CC1]

A mixture of ethyl 2-(4-(5-amino-2,2-dimethyl-2,3-dihydrobenzofuran-6-yl)piperazin-1-yl)acetate (6.36 g, 19.1 mmol), potassium carbonate (5.28 g, 38.2 mmol), potassium iodide (634 mg, 3.82 mmol) and 4-methoxybenxyl chloride (2.64 ml, 20.0 mmol) in dimethylformamide (38 ml) was stirred at ambient temperature for 18h. Additional potassium carbonate (5.28 g, 38.2 mmol) and 4-methoxybenxyl chloride (2.64 ml, 20.0 mmol) were added. After 18h, the reaction was filtered and the filtrate was concentrated in vacuo. The residue was purified by silica gel chromatography (eluting gradient 0%-50% isopropyl acetate: heptane) to afford ethyl 2-(4-(5-(bis(4-methoxybenzyl)amino)-2,2-dimethyl-2,3-dihydrobenzofuran-6-yl)piperazin-1-yl)acetate (4.66 g, 47% yield) as a tan solid. $^1$H NMR (400 MHz, DMSO-d6) δ 7.04 (d, J=8.7 Hz, 4H), 6.82 (d, J=8.7 Hz, 4H), 6.62 (s, 1H), 6.36 (s, 1H), 4.09 (q, J=7.1 Hz, 2H), 4.05 (s, 4H), 3.71 (s, 6H), 3.29-3.25 (m, 2H), 3.07 (s, 4H), 2.80 (s, 2H), 2.72 (d, J=12.1 Hz, 4H), 1.35 (s, 6H), 1.24-1.13 (m, 3H).

Step E. 1-(4-(5-(Bis(4-methoxybenzyl)amino)-2,2-dimethyl-2,3-dihydrobenzofuran-6-yl)piperazin-1-yl)-2-methylpropan-2-ol

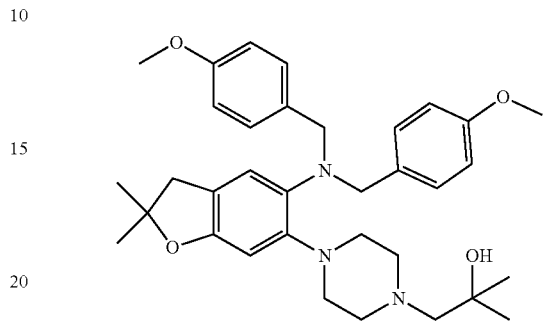

Methylmagnesium bromide in diethyl ether (3M, 0.150 ml, 0.442 mmol) was added to ethyl 2-(4-(5-(bis(4-methoxybenzyl)amino)-2,2-dimethyl-2,3-dihydrobenzofuran-6-yl)piperazin-1-yl)acetate (102 mg, 0.177 mmol) in tetrahydrofuran (2.1 ml) at ambient temperature and the reaction was stirred for 18h. The mixture was diluted with water, saturated ammonium chloride, and isopropyl acetate. The layers were separated and the aqueous phase was extracted into isopropyl acetate. The combined organic phases were dried over sodium sulfate, concentrated under reduced pressure and purified by silica gel chromatography (eluting gradient 0%-100% isopropyl acetate: heptane) to afford 1-(4-(5-(bis(4-methoxybenzyl)amino)-2,2-dimethyl-2,3-dihydrobenzofuran-6-yl)piperazin-1-yl)-2-methylpropan-2-ol (90 mg, 91% yield). $^1$H NMR (400 MHz, Chloroform-d) δ 6.99 (d, J=8.7 Hz, 4H), 6.83-6.77 (m, 4H), 6.51 (s, 1H), 6.44 (s, 1H), 4.99 (p, J=6.3 Hz, OH), 4.08 (s, 4H), 3.79 (s, 7H), 3.23 (s, 5H), 2.86 (s, 2H), 2.82 (t, J=4.2 Hz, 4H), 2.39 (s, 2H), 1.45 (s, 7H), 1.21 (s, 6H).

Step F. 1-(4-(5-Amino-2,2-dimethyl-2,3-dihydrobenzofuran-6-yl)piperazin-1-yl)-2-methylpropan-2-ol

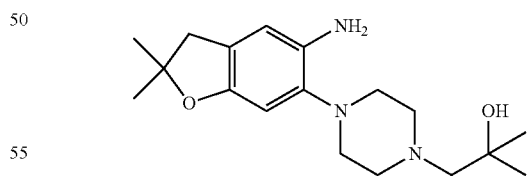

A mixture of 1-(4-(5-(bis(4-methoxybenzyl)amino)-2,2-dimethyl-2,3-dihydrobenzofuran-6-yl)piperazin-1-yl)-2-methylpropan-2-ol (90 mg, 0.161 mmol) and 10% palladium on carbon (17.1 mg, 0.0161 mmol) in ethanol (5 ml) was stirred for 18h under an atmosphere of hydrogen. The mixture was filtered through a pad of celite and the filtrate was concentrated under reduced pressure to afford 1-(4-(5-amino-2,2-dimethyl-2,3-dihydrobenzofuran-6-yl)piperazin-1-yl)-2-methylpropan-2-ol (37.4 mg, 73% yield) which was used without further purification.

Step G. N-(6-(4-(2-Hydroxy-2-methylpropyl)piperazin-1-yl)-2,2-dimethyl-2,3-dihydrobenzofuran-5-yl)pyrazolo[1,5-a]pyrimidine-3-carboxamide

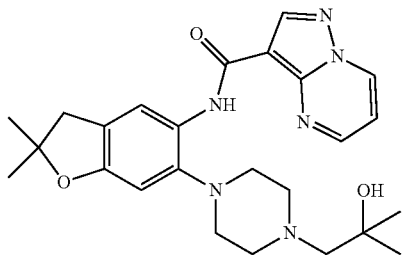 [SMILES: CC(C)(O)CN1CCN(c2cc3c(cc2NC(=O)c2cnn4cccnc24)CC(C)(C)O3)CC1]

A mixture of 1-(4-(5-amino-2,2-dimethyl-2,3-dihydrobenzofuran-6-yl)piperazin-1-yl)-2-methylpropan-2-ol (37.4 mg, 0.117 mmol), pyrazolo[1,5-a]pyrimidine-3-carbonyl chloride (31.9 mg, 0.176 mmol), and 4-dimethylaminopyridine (2.86 mg, 0.0234 mmol) in pyridine (5 ml) was stirred at ambient temperature for 36h. The reaction was then concentrated under reduced pressure and purified by preparative HPLC ((Xbridge 21.2*250 mm c18, 10 um; A: acetonitrile 10-20%; B: 10 mM ammonium bicarbonate in water) to afford the title compound (33.6 mg, 62% yield) as a solid. $^1$H NMR (400 MHz, DMSO-$d_6$) δ 10.42 (s, 1H), 9.37 (dd, J=7.0, 1.6 Hz, 1H), 8.91 (dd, J=4.2, 1.6 Hz, 1H), 8.68 (s, 1H), 8.31 (s, 1H), 7.39 (dd, J=7.0, 4.2 Hz, 1H), 6.68 (s, 1H), 4.10 (s, 1H), 3.00 (s, 2H), 2.79 (m, 8H), 2.32 (s, 2H), 1.42 (s, 6H), 1.13 (s, 6H). MS (ESI): m/z=465.3 [M+1]$^+$.

Example 435. N-(6-(4-(2-Ethyl-2-hydroxybutyl)piperazin-1-yl)-2,2-dimethyl-2,3-dihydrobenzofuran-5-yl)pyrazolo[1,5-a]pyrimidine-3-carboxamide

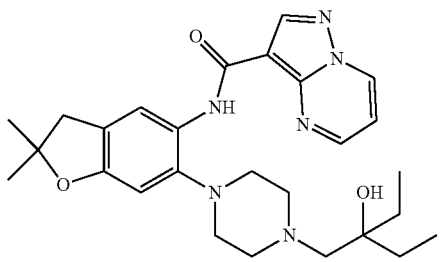 [SMILES: CCC(O)(CC)CN1CCN(c2cc3c(cc2NC(=O)c2cnn4cccnc24)CC(C)(C)O3)CC1]

The title compound was made in a manner analogous to Example 434 to give N-(6-(4-(2-ethyl-2-hydroxybutyl)piperazin-1-yl)-2,2-dimethyl-2,3-dihydrobenzofuran-5-yl)pyrazolo[1,5-a]pyrimidine-3-carboxamide (70.4 mg, 33% yield) as a solid. $^1$H NMR (400 MHz, DMSO-$d_6$) δ 10.41 (s, 1H), 9.37 (dd, J=7.0, 1.6 Hz, 1H), 8.91 (dd, J=4.3, 1.6 Hz, 1H), 8.68 (s, 1H), 8.31 (s, 1H), 7.39 (dd, J=7.0, 4.2 Hz, 1H), 6.68 (s, 1H), 3.79 (s, 1H), 3.00 (s, 2H), 2.79 (m, 8H), 2.32 (s, 2H), 1.54-1.29 (m, 10H), 0.80 (t, J=7.4 Hz, 6H). MS (ESI): m/z=493.3 [M+1]$^+$.

Examples 436 and 437. (S)—N-(2-(hydroxymethyl)-2-methyl-7-morpholinochroman-6-yl)pyrazolo[1,5-a]pyrimidine-3-carboxamide and (R)—N-(2-(hydroxymethyl)-2-methyl-7-morpholinochroman-6-yl)pyrazolo[1,5-a]pyrimidine-3-carboxamide were generated upon chiral resolution of Example 141

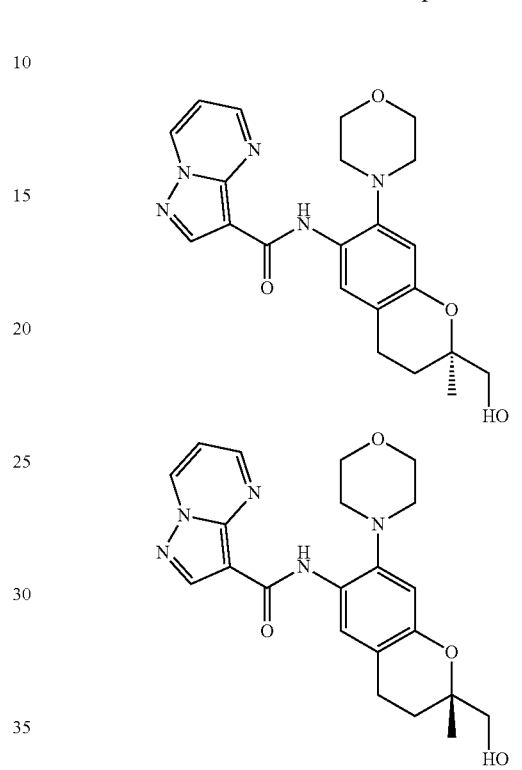

A mixture of N-(2-(hydroxymethyl)-2-methyl-7-morpholinochroman-6-yl)pyrazolo[1,5-a]pyrimidine-3-carboxamide was resolved by chiral SFC (Amylose-1 15*2.1 cm, Sum (PIC), A=CO$_2$, B=methanol{0.1% ammonium hydroxide} 40% isocratic) to obtain (R)—N-(2-(hydroxymethyl)-2-methyl-7-morpholinochroman-6-yl)pyrazolo[1,5-a]pyrimidine-3-carboxamide and (S)—N-(2-(hydroxymethyl)-2-methyl-7-morpholinochroman-6-yl)pyrazolo[1,5-a]pyrimidine-3-carboxamide (16 mg, 38%) (16 mg, 38%) as off white solids with absolute stereochemistry assigned arbitrarily.

Example 436 (S), Peak 2: $^1$H NMR (400 MHz, DMSO-d6) δ 10.35 (s, 1H), 9.37 (dd, J=7.0, 1.6 Hz, 1H), 8.95 (dd, J=4.2, 1.7 Hz, 1H), 8.67 (s, 1H), 8.21 (s, 1H), 7.34 (dd, J=7.0, 4.2 Hz, 1H), 6.62 (s, 1H), 4.97-4.82 (m, 1H), 3.83 (m, 4H), 3.48-3.36 (m, 2H), 2.89-2.75 (m, 4H), 2.70 (m, 2H), 1.89 (dt, J=14.0, 7.2 Hz, 1H), 1.68 (dt, J=12.9, 6.1 Hz, 1H), 1.20 (s, 3H). MS (ESI): m/z=424.2 [M+1].

Example 437 (R), Peak 1: $^1$H NMR (400 MHz, DMSO-d6) δ 10.35 (s, 1H), 9.37 (dd, J=7.0, 1.6 Hz, 1H), 8.95 (dd, J=4.2, 1.6 Hz, 1H), 8.67 (s, 1H), 8.21 (s, 1H), 7.34 (dd, J=7.0, 4.2 Hz, 1H), 6.62 (s, 1H), 4.90 (t, J=5.8 Hz, 1H), 3.90-3.73 (m, 4H), 3.49-3.35 (m, 2H), 2.87-2.76 (m, 4H), 2.76-2.65 (m, 2H), 1.89 (dt, J=14.0, 7.2 Hz, 1H), 1.68 (dt, J=12.9, 6.1 Hz, 1H), 1.20 (s, 3H). MS (ESI): m/z=424.1 [M+1]$^+$.

Examples 438 and 439. (S)—N-(2-(dimethylcarbamoyl)-2-methyl-6-morpholino-2,3-dihydrobenzofuran-5-yl)pyrazolo[1,5-a]pyrimidine-3-carboxamide and (R)—N-(2-(dimethylcarbamoyl)-2-methyl-6-morpholino-2,3-dihydrobenzofuran-5-yl)pyrazolo[1,5-a]pyrimidine-3-carboxamide were generated upon chiral resolution of Example 23

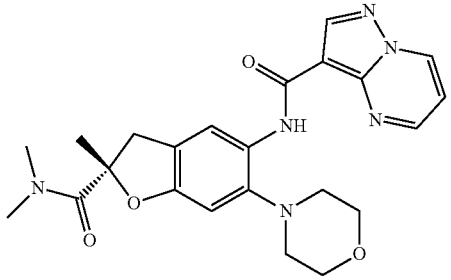

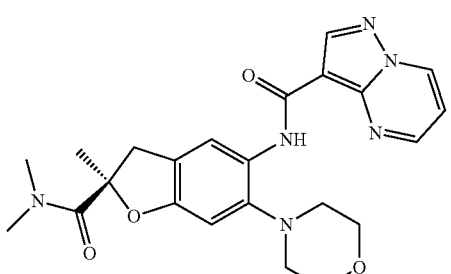

A mixture of N-(2-(dimethylcarbamoyl)-2-methyl-6-morpholino-2,3-dihydrobenzofuran-5-yl)pyrazolo[1,5-a]pyrimidine-3-carboxamide was resolved by chiral SFC (Amylose-1 15*2.1 cm, Sum (PIC), A=CO₂, B=methanol{0.1% ammonium hydroxide} 40% isocratic) to obtain (R)—N-(2-(dimethylcarbamoyl)-2-methyl-6-morpholino-2,3-dihydrobenzofuran-5-yl)pyrazolo[1,5-a]pyrimidine-3-carboxamide and (S)—N-(2-(dimethylcarbamoyl)-2-methyl-6-morpholino-2,3-dihydrobenzofuran-5-yl)pyrazolo[1,5-a]pyrimidine-3-carboxamide (14 mg, 34%) (15 mg, 34%) as yellow solids with absolute stereochemistry assigned arbitrarily.

Example 438, Peak 1: ¹H NMR (400 MHz, DMSO-d₆) δ 10.45 (s, 1H), 9.37 (dd, J=7.0, 1.6 Hz, 1H), 8.95 (dd, J=4.2, 1.7 Hz, 1H), 8.69 (s, 1H), 8.35 (d, J=1.0 Hz, 1H), 7.35 (dd, J=7.0, 4.2 Hz, 1H), 6.84 (s, 1H), 3.84 (m, 5H), 3.16 (m, 3H), 3.09-3.01 (m, 1H), 2.90-2.86 (m, 3H), 2.85-2.79 (m, 4H), 1.58 (s, 3H). MS (ESI): m/z=451.2 [M+1]⁺.

Example 439, Peak 2: 1H NMR (400 MHz, DMSO-d6) δ 10.45 (s, 1H), 9.37 (dd, J=7.0, 1.6 Hz, 1H), 8.95 (dd, J=4.2, 1.7 Hz, 1H), 8.69 (s, 1H), 8.35 (s, 1H), 7.35 (dd, J=7.0, 4.2 Hz, 1H), 6.84 (s, 1H), 3.91-3.76 (m, 5H), 3.20-3.12 (m, 3H), 3.10-2.98 (m, 1H), 2.88 (s, 3H), 2.85-2.80 (m, 4H), 1.57 (d, J=2.0 Hz, 3H). MS (ESI): m/z=451.1 [M+1]⁺.

Example 440. N-(2,2-dimethyl-6-(4-(2-oxo-2-(((tetrahydrofuran-2-yl)methyl)amino)ethyl)piperazin-1-yl)-2,3-dihydrobenzofuran-5-yl)pyrazolo[1,5-a]pyrimidine-3-carboxamide

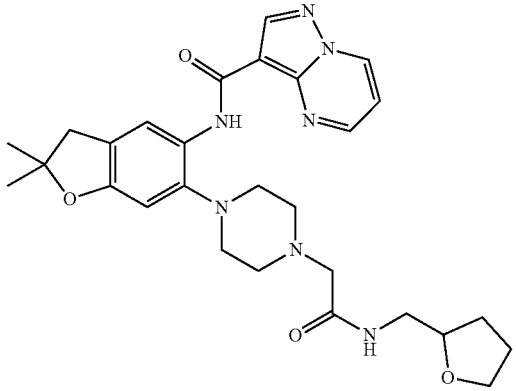

Step A. 2-(4-(2,2-dimethyl-5-nitro-2,3-dihydrobenzofuran-6-yl)piperazin-1-yl)-N-(tetrahydrofuran-2-yl)acetamide

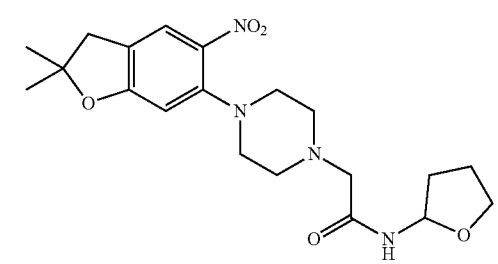 [SMILES: CC1(C)Cc2cc([N+](=O)[O-])c(N3CCN(CC(=O)NC4CCCO4)CC3)cc2O1]

A mixture of 6-chloro-2,2-dimethyl-5-nitro-3H-benzofuran (Intermediate 1) (200 mg, 0.88 mmol) and 2-piperazin-1-yl-N-(tetrahydrofuran-2-ylmethyl)acetamide (220 mg, 0.97 mmol) in dimethyl sulfoxide (1.3 ml) was treated with N,N-diisopropylethylamine (0.17 ml, 0.97 mmol) and stirred at 60° C. for 24h. The mixture was poured into water and the reaction was extracted by ethyl acetate (100 ml). The organic phase was washed with water and brine, dried over sodium sulfate and filtered before concentration to dryness. The residue was purified by purified by silica gel chromatography (eluting gradient 0-100% IPAC in heptanes) to afford 2-(4-(2,2-dimethyl-5-nitro-2,3-dihydrobenzofuran-6-yl)piperazin-1-yl)-N-(tetrahydrofuran-2-yl)acetamide (347 mg, 94%) as a solid. 1H NMR (400 MHz, DMSO-d6) δ 7.82 (s, 1H), 7.72 (t, J=6.0 Hz, 1H), 6.59 (s, 1H), 4.08 (q, J=5.3 Hz, 1H), 3.86 (p, J=6.5 Hz, 1H), 3.80-3.70 (m, 1H), 3.66-3.56 (m, 1H), 3.17 (dd, J=5.5, 2.2 Hz, 4H), 3.05-2.93 (m, 8H), 2.56 (dtdt, J=4.5, 2.0, 1.0, 0.5 Hz, 4H), 1.93-1.73 (m, 3H), 1.50 (ddd, J=10.1, 7.8, 5.4 Hz, 1H), 1.44 (s, 6H). LCMS (ESI): m/z=419.2 [M+H]⁺.

815
Step B. 2-(4-(5-amino-2,2-dimethyl-2,3-dihydrobenzofuran-6-yl)piperazin-1-yl)-N-(tetrahydrofuran-2-yl)acetamide

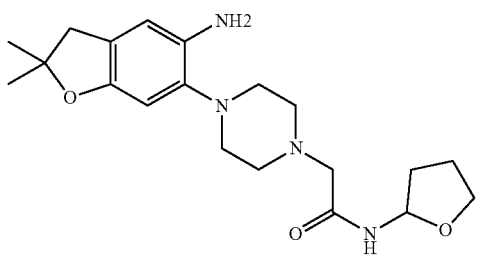 [SMILES: CC1(C)Cc2cc(N)c(N3CCN(CC(=O)NC4CCCO4)CC3)cc2O1]

A mixture of 2-(4-(2,2-dimethyl-5-nitro-2,3-dihydrobenzofuran-6-yl)piperazin-1-yl)-N-(tetrahydrofuran-2-yl)acetamide (342 mg, 0.82 mmol), iron powder (245 mg, 4.39 mmol) and ammonium chloride (235 mg, 4.39 mmol) in ethanol (25 ml) and water (5 ml), was heated at 60° C. for 2h. The reaction mixture was cooled to room temperature then filtered through celite and concentrated. The crude product was purified by silica gel chromatography (eluting gradient 0-20% methanol: dichloromethane) to afford 2-(4-(5-amino-2,2-dimethyl-2,3-dihydrobenzofuran-6-yl)piperazin-1-yl)-N-(tetrahydrofuran-2-yl)acetamide (210 mg, 0.54 mmol, 62% yield) as a solid, which was used without further purification. MS (ESI): m/z=389.2 [M+1]$^+$.

816
Step C. Example X. N-(2,2-dimethyl-6-(4-(2-oxo-2-(((tetrahydrofuran-2-yl)methyl)amino)ethyl)piperazin-1-yl)-2,3-dihydrobenzofuran-5-yl)pyrazolo[1,5-a]pyrimidine-3-carboxamide

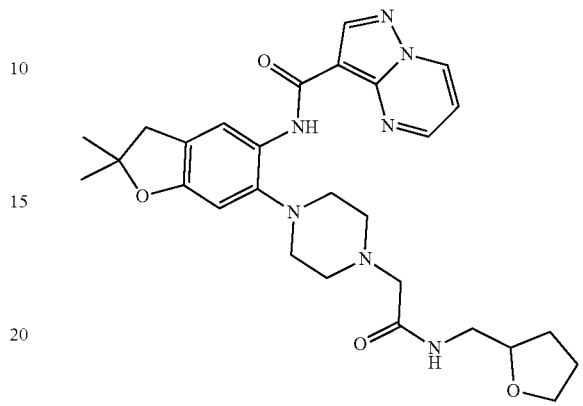

A mixture of 2-(4-(5-amino-2,2-dimethyl-2,3-dihydrobenzofuran-6-yl)piperazin-1-yl)-N-(tetrahydrofuran-2-yl)acetamide (210 mg, 0.54 mmol), pyrazolo[1,5-a]pyrimidine-3-carbonyl chloride (240 mg, 1.32 mmol), and 4-dimethylaminopyridine (21.5 mg, 0.175 mmol) in pyridine (5 ml) was stirred at ambient temperature for 36h. The reaction was then concentrated under reduced pressure and purified by preparative HPLC ((Gemini NX, 5*3 cm c18, 5um; A: acetonitrile 20-60%; B: 0.1% ammonium hydroxide in water) to afford the title compound (108 mg, 0.202 mmol, 23% yield) as a solid. H NMR (400 MHz, DMSO-d6) δ 10.41 (s, 1H), 9.36 (dd, J=7.0, 1.6 Hz, 1H), 8.97 (dd, J=4.2, 1.7 Hz, 1H), 8.67 (s, 1H), 8.33 (s, 1H), 7.74 (t, J=6.0 Hz, 1H), 7.35 (dd, J=7.0, 4.2 Hz, 1H), 6.69 (s, 1H), 3.92-3.80 (m, 1H), 3.80-3.69 (m, 1H), 3.68-3.54 (m, 1H), 3.26-3.13 (m, 2H), 3.08 (d, J=3.2 Hz, 2H), 3.00 (s, 2H), 2.89-2.80 (m, 4H), 2.72 (s, 4H), 1.92-1.73 (m, 3H), 1.56-1.45 (m, 1H), 1.41 (s, 6H). MS (ESI): m/z=534.2 [M+1]$^+$.

TABLE 15

The following examples were made in a manner similar to that for Example 440:

| Ex. | Name | Structure | NMR, MS |
|---|---|---|---|
| 441. | N-(2,2-dimethyl-6-(4-(2-oxo-2-(thiazol-2-ylamino)ethyl)piperazin-1-yl)-2,3-dihydrobenzofuran-5-yl)pyrazolo[1,5-a]pyridine-3-carboxamide | 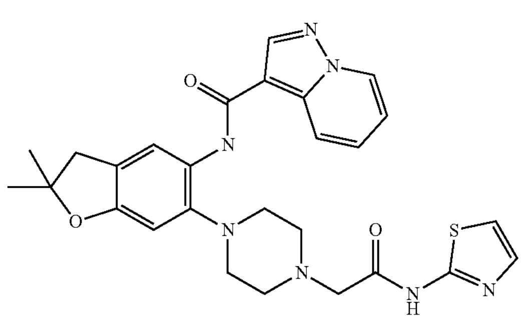 [SMILES: CC1(C)Cc2cc(NC(=O)c3cnn4ccccc34)c(N3CCN(CC(=O)Nc4nccs4)CC3)cc2O1] | $^1$H NMR (400 MHz, dimethyl sulfoxide-d$_6$) δ 11.94 (s, 1H), 10.42 (s, 1H), 9.45-9.26 (m, 1H), 8.98 (dd, J = 4.2, 1.7 Hz, 1H), 8.67 (s, 1H), 8.34 (s, 1H), 7.50 (d, J = 3.6 Hz, 1H), 7.32-7.21 (m, 2H), 6.72 (s, 1H), 3.52-3.38 (m, 2H), 3.00 (s, 2H), 2.85 (s, 8H), 1.41 (s, 6H). MS (ESI): m/z = 533.2 [M + 1]$^+$. |

TABLE 15-continued

The following examples were made in a manner similar to that for Example 440:

| Ex. | Name | Structure | NMR, MS |
|---|---|---|---|
| 442. and 443. | (S)-N-(6-(hexahydropyrrolo[1,2-a]pyrazin-2(1H)-yl)-2,2-dimethyl-2,3-dihydrobenzofuran-5-yl)pyrazolo[1,5-a]pyrimidine-3-carboxamide and (R)-N-(6-(hexahydropyrrolo[1,2-a]pyrazin-2(1H)-yl)-2,2-dimethyl-2,3-dihydrobenzofuran-5-yl)pyrazolo[1,5-a]pyrimidine-3-carboxamide (absolute stereochemistry assigned arbitrarily) | | Example 442, Peak 2: $^1$H NMR (400 MHz, dimethyl sulfoxide-d$_6$) δ 10.44 (s, 1H), 9.35 (dd, J = 7.0, 1.6 Hz, 1H), 8.84 (dd, J = 4.2, 1.7 Hz, 1H), 8.67 (s, 1H), 8.34 (s, 1H), 7.34 (dd, J = 7.0, 4.2 Hz, 1H), 6.71 (s, 1H), 3.09-2.91 (m, 5H), 2.88-2.73 (m, 2H), 2.63-2.53 (m, 1H), 2.45-2.35 (m, 1H), 2.20 (d, J = 8.3 Hz, 1H), 1.80-1.65 (m, 3H), 1.41 (s, 6H), 1.39-1.23 (m, 1H). MS (ESI): m/z = 433.2 [M + 1]$^+$. Example 443, Peak 1: $^1$H NMR (400 MHz, dimethyl sulfoxide-d$_6$) δ 10.44 (s, 1H), 9.35 (dd, J = 7.0, 1.7 Hz, 1H), 8.84 (dd, J = 4.2, 1.7 Hz, 1H), 8.67 (s, 1H), 8.34 (s, 1H), 7.34 (dd, J = 7.0, 4.2 Hz, 1H), 6.71 (s, 1H), 3.09-2.91 (m, 5H), 2.88-2.73 (m, 2H), 2.63-2.53 (m, 1H), 2.45-2.35 (m, 1H), 2.20 (d, J = 8.3 Hz, 1H), 1.80-1.65 (m, 3H), 1.41 (s, 6H), 1.39-1.23 (m, 1H). MS (ESI): m/z = 433.2 [M + 1]$^+$. |

Example 444. (R)—N-(2-methyl-2-(2-(methylthio)ethyl)-6-morpholino-2,3-dihydrobenzofuran-5-yl)pyrazolo[1,5-a]pyrimidine-3-carboxamide

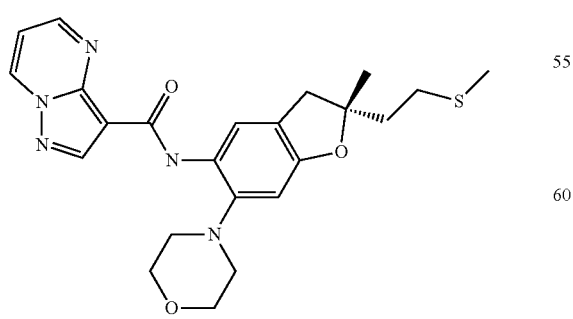

Step A. (R)-2-(2-methyl-6-morpholino-5-(pyrazolo[1,5-a]pyrimidine-3-carboxamido)-2,3-dihydrobenzofuran-2-yl)ethyl methanesulfonate

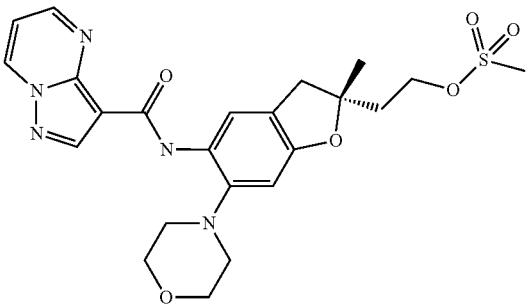

To a mixture of (R)—N-(2-(2-hydroxyethyl)-2-methyl-6-morpholino-2,3-dihydrobenzofuran-5-yl)pyrazolo[1,5-a]pyrimidine-3-carboxamide (Example 388) (32 mg, 0.076 mmol) and triethylamine (0.016 ml, 0.11 mmol) in dichloromethane (1.0 ml) at 0° C. was added methanesulfonyl chloride (0.0070 ml, 0.091 mmol). After 15 min, the mixture was diluted with water and extracted with dichloromethane. The combined organics were dried over sodium sulfate, filtered, and concentrated in vacuo to afford (R)-2-(2-methyl-6-morpholino-5-(pyrazolo[1,5-a]pyrimidine-3-carboxamido)-2,3-dihydrobenzofuran-2-yl)ethyl methanesulfonate (38 mg, 0.076 mmol), which was used crude without further purification. MS (ESI): m/z=502.2 [M+1]$^+$.

Step B. (R)—S-(2-(2-methyl-6-morpholino-5-(pyrazolo[1,5-a]pyrimidine-3-carboxamido)-2,3-dihydrobenzofuran-2-yl)ethyl) ethanethioate

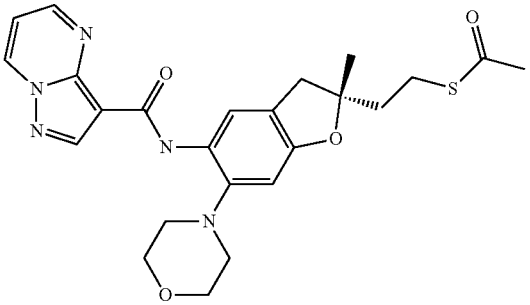

A solution of (R)-2-(2-methyl-6-morpholino-5-(pyrazolo[1,5-a]pyrimidine-3-carboxamido)-2,3-dihydrobenzofuran-2-yl)ethyl methanesulfonate (38 mg, 0.076 mmol) in N,N-dimethylformamide (5 ml) was treated with sodium thiomethoxide (8.4 mg, 0.11 mmol) and heated to 60° C. fo 4 h. Potassium carbonate (52 mg, 0.38 mmol) was added to the mixture at 60° C. After 2h, potassium thioacetate (43 mg, 0.38 mmol) was added and heated at 90° C. for 18h. The mixture was diluted with water and extracted with isopropyl acetate. The combined organic layers were washed with brine, dried over sodium sulfate, and concentrated. The residue was purified by silica gel chromatography (eluting gradient 0-100% isopropyl acetate in heptanes) to afford (R)—S-(2-(2-methyl-6-morpholino-5-(pyrazolo[1,5-a]pyrimidine-3-carboxamido)-2,3-dihydrobenzofuran-2-yl) ethyl) ethanethioate (24 mg, 0.050 mmol, 66% yield) as a solid. MS (ESI): m/z=482 [M+1]$^+$.

Step C. (R)—N-(2-methyl-2-(2-(methylthio)ethyl)-6-morpholino-2,3-dihydrobenzofuran-5-yl)pyrazolo[1,5-a]pyrimidine-3-carboxamide

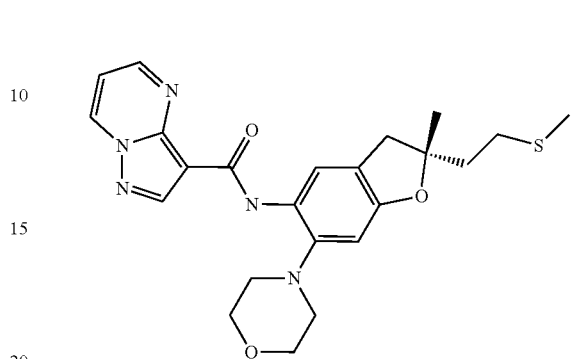

A solution of (R)—S-(2-(2-methyl-6-morpholino-5-(pyrazolo[1,5-a]pyrimidine-3-carboxamido)-2,3-dihydrobenzofuran-2-yl) ethyl) ethanethioate (24 mg, 0.050 mmol) in methanol (3 ml) was treated with sodium hydroxide (3.0 mg, 0.075 mmol) at ambient temperature for 1h. Iodomethane (4.0 ul, 0.061 mmol) was added and the reaction mixture continued to stir for 2h at this temperature. The mixture was diluted with water and extracted with dichloromethane. The combined organic layers were washed with brine, dried over sodium sulfate and concentrated. The residue was purified by preparative HPLC ((Gemini NX, 5*3 cm c18, 5 um; A: acetonitrile 30-70%; B: 0.1% ammonium hydroxide in water) to afford (R)—N-(2-methyl-2-(2-(methylthio)ethyl)-6-morpholino-2,3-dihydrobenzofuran-5-yl)pyrazolo[1,5-a]pyrimidine-3-carboxamide (2.6 mg, 0.0057 mmol, 11% yield) as a solid. $^1$H NMR (400 MHz, DMSO-d$_6$) δ 10.43 (s, 1H), 9.37 (dd, J=7.0, 1.6 Hz, 1H), 8.94 (dd, J=4.2, 1.6 Hz, 1H), 8.68 (s, 1H), 8.31 (s, 1H), 7.34 (dd, J=7.0, 4.2 Hz, 1H), 6.73 (s, 1H), 3.88-3.78 (m, 4H), 3.14 (d, J=16.6 Hz, 1H), 2.94 (d, J=16.6 Hz, 1H), 2.85-2.77 (m, 4H), 2.57-2.52 (m, 2H), 2.07 (s, 3H), 2.00-1.90 (m, 2H), 1.39 (s, 3H). MS (ESI): m/z=454.1 [M+1]$^+$.

Example 445. (R)—N-(6-((1-(2-amino-2-oxoethyl)pyrrolidin-3-yl)oxy)-2,2-dimethyl-2,3-dihydrobenzofuran-5-yl)pyrazolo[1,5-a]pyrimidine-3-carboxamide

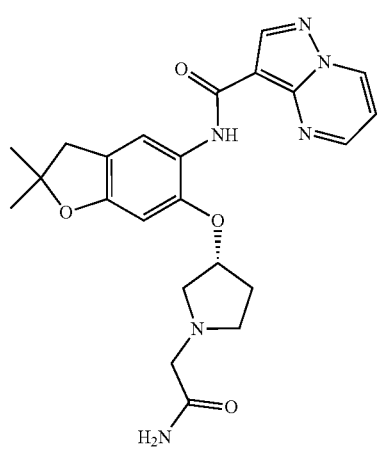

821

Step A. tert-butyl (R)-3-((2,2-dimethyl-5-nitro-2,3-dihydrobenzofuran-6-yl)oxy)pyrrolidine-1-carboxylate

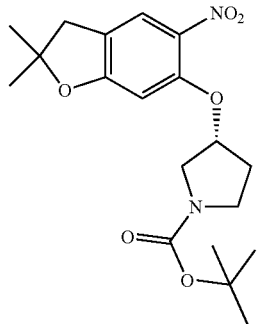 [SMILES: CC(C)(C)OC(=O)N1CC[C@@H](Oc2cc3c(cc2[N+](=O)[O-])CC(C)(C)O3)C1]

A mixture of 6-chloro-2,2-dimethyl-5-nitro-3H-benzofuran (50 mg, 0.22 mmol) and tert-butyl (R)-3-hydroxypyrrolidine-1l-carboxylate (82 mg, 0.44 mmol) in DMSO (1.7 ml) was treated with sodium hydride (60% in oil, 18 mg, 0.44 mmol) at room temperature for 1h. The reaction mixture was diluted with saturated sodium bicarbonate solution, brine, and isopropyl acetate. The layers were separated and the aqueous phase extracted into isopropyl acetate (3×). The combined organic layers were dried over sodium sulfate, filtered and absorbed under reduced pressure onto celite. The crude product was purified by silica gel chromatography (eluting gradient 0-100% isopropyl acetate in heptanes) to afford tert-butyl (R)-3-((2,2-dimethyl-5-nitro-2,3-dihydrobenzofuran-6-yl)oxy)pyrrolidine-1-carboxylate (64 mg, 0.17 mmol, 77% yield) as a solid.

Step B. (R)-3-((2,2-dimethyl-5-nitro-2,3-dihydrobenzofuran-6-yl)oxy)pyrrolidine

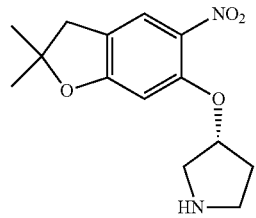 [SMILES: CC1(C)Cc2cc([N+](=O)[O-])c(O[C@@H]3CCNC3)cc2O1]

A solution of tert-butyl (R)-3-((2,2-dimethyl-5-nitro-2,3-dihydrobenzofuran-6-yl)oxy)pyrrolidine-1-carboxylate (64 mg, 0.17 mmol) in dichloromethane (6 ml) was treated with trifluoroacetic acid (0.50 ml) at room temperature. After 30 minutes the solvent was removed in vacuo to afford the crude residue (R)-3-((2,2-dimethyl-5-nitro-2,3-dihydrobenzofuran-6-yl)oxy)pyrrolidine, which was carried on without further purification.

822

Step C. (R)-2-(3-((2,2-dimethyl-5-nitro-2,3-dihydrobenzofuran-6-yl)oxy)pyrrolidin-1-yl)acetamide

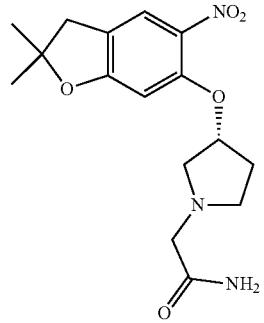 [SMILES: CC1(C)Cc2cc([N+](=O)[O-])c(O[C@@H]3CCN(CC(N)=O)C3)cc2O1]

A mixture of (R)-3-((2,2-dimethyl-5-nitro-2,3-dihydrobenzofuran-6-yl)oxy)pyrrolidine (47 mg, 0.17 mmol) in 1,4-dioxane (13 ml, 0.013M) was treated with N,N-diisopropylethylamine (0.088 ml, 0.50 mmol) and 2-bromoacetamide (26 mg, 0.19 mmol) and heated at 60° C. for 18h. The reaction mixture was absorbed onto celite and the crude product was purified by silica gel chromatography (eluting gradient 0-100% isopropyl acetate in heptanes) to afford (R)-2-(3-((2,2-dimethyl-5-nitro-2,3-dihydrobenzofuran-6-yl)oxy)pyrrolidin-1-yl)acetamide (82 mg, 0.17 mmol).

Step D. (R)-2-(3-((5-amino-2,2-dimethyl-2,3-dihydrobenzofuran-6-yl)oxy)pyrrolidin-1-yl)acetamide

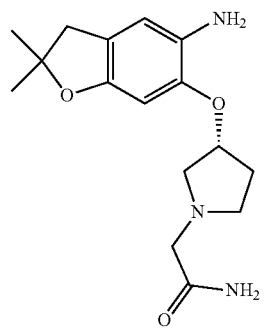

A mixture of (R)-2-(3-((2,2-dimethyl-5-nitro-2,3-dihydrobenzofuran-6-yl)oxy)pyrrolidin-1-yl)acetamide (82 mg, 0.17 mmol), iron powder (68 mg, 1.22 mmol) and ammonium chloride (65 mg, 1.22 mmol) in ethanol (5 ml) and water (1.5 ml), was heated at 60° C. for 4h. The reaction mixture was cooled to room temperature then filtered through celite and concentrated. The crude product was purified by silica gel chromatography (eluting gradient 0-20% methanol: dichloromethane) to afford (R)-2-(3-((5-amino-2,2-dimethyl-2,3-dihydrobenzofuran-6-yl)oxy)pyrrolidin-1-yl)acetamide (52 mg, 0.17 mmol) as a solid, which was used without further purification. MS (ESI): m/z=306.1 [M+1]$^+$.

Step E. (R)—N-(6-((1-(2-amino-2-oxoethyl)pyrrolidin-3-yl)oxy)-2,2-dimethyl-2,3-dihydrobenzofuran-5-yl)pyrazolo[1,5-a]pyrimidine-3-carboxamide

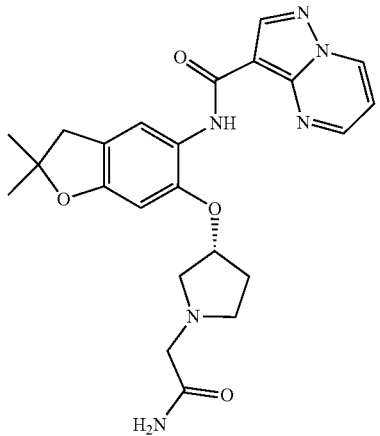

A mixture of pyrazolo[1,5-a]pyrimidine-3-carboxylic acid (31 mg, 0.19 mmol), (R)-2-(3-((5-amino-2,2-dimethyl-2,3-dihydrobenzofuran-6-yl)oxy)pyrrolidin-yl)acetamide (52 mg, 0.17 mmol), and (7-azabenzotriazol-1-yloxy)tripyrrolidinophosphoniumhexafluorophosphate (98 mg, 0.19 mmol) in dimethylformamide (5 ml) was treated with collidine (0.025 ml, 0.19 mmol) and the resulting mixture was stirred at room temperature for 18h. The reaction was concentrated under reduced pressure and the residue was purified by preparative ((Gemini NX, 5*3 cm c18, 5 um; A: acetonitrile 5-50%; B: 0.1% formic acid in water) to afford N-(6-(2,2-dimethylmorpholino)-2-(hydroxymethyl)-2-methyl-2,3-dihydrobenzofuran-5-yl)pyrazolo[1,5-a]pyrimidine-3-carboxamide as a solid (12 mg, 0.026 mmol, 15%).
$^1$H NMR (400 MHz, dimethyl sulfoxide-d6) δ 10.20 (s, 1H), 9.36 (dd, J=7.0, 1.6 Hz, 1H), 8.85 (dd, J=4.2, 1.6 Hz, 1H), 8.66 (s, 1H), 8.30 (s, 1H), 7.32 (dd, J=7.0, 4.2 Hz, 1H), 7.15 (s, 1H), 7.03 (s, 1H), 6.49 (s, 1H), 5.04-4.89 (m, 1H), 3.13 (dd, J=10.5, 6.1 Hz, 1H), 3.05 (s, 2H), 2.97 (s, 2H), 2.87-2.77 (m, 2H), 2.72-2.61 (m, 1H), 2.41-2.27 (m, 1H), 2.03 (dd, J=8.0, 5.7 Hz, 1H), 1.41 (s, 6H). MS (ESI): m/z=451.2 [M+1]$^+$.

TABLE 16

The following examples were made in a manner similar to that for Example 445:

| Ex. | Name | Structure | NMR, MS |
|---|---|---|---|
| 446. | N-(6-((1-(2-hydroxyethyl)azetidin-3-yl)oxy)-2,2-dimethyl-2,3-dihydrobenzofuran-5-yl)pyrazolo[1,5-a]pyrimidine-3-carboxamide | 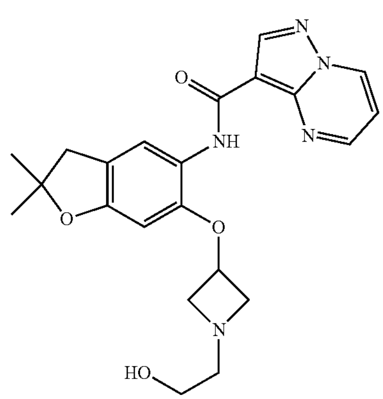 [SMILES: CC1(C)Cc2cc(NC(=O)c3cnn4cccnc34)c(OC3CN(CCO)C3)cc2O1] | $^1$H NMR (400 MHz, dimethyl sulfoxide-d$_6$) δ 10.26 (s, 1H), 9.38 (dd, J = 7.0, 1.6 Hz, 1H), 8.87 (dd, J = 4.2, 1.6 Hz, 1H), 8.67 (s, 1H), 8.29 (d, J = 1.0 Hz, 1H), 7.34 (dd, J = 7.0, 4.2 Hz, 1H), 6.33 (s, 1H), 4.86 (q, J = 5.6 Hz, 1H), 4.48-4.35 (m, 1H), 3.90-3.76 (m, 2H), 3.46-3.39 (m, 2H), 3.20-3.12 (m, 2H), 2.97 (d, J = 1.1 Hz, 2H), 2.61-2.52 (m, 2H), 1.41 (s, 6H). MS (ESI): mz = 424.1 [M + 1]$^+$. |
| 447. | (S)-N-(6-((1-(2-amino-2-oxoethyl)pyrrolidin-3-yl)oxy)-2,2-dimethyl-2,3-dihydrobenzofuran-5-yl)pyrazolo[1,5-a]pyrimidine-3-carboxamide | 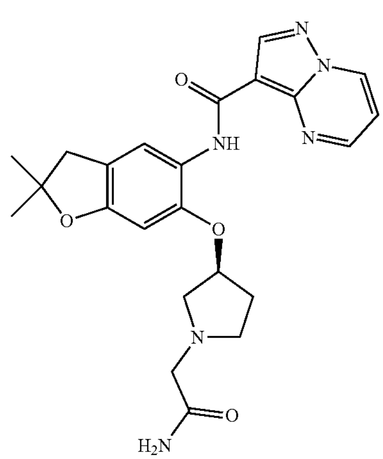 [SMILES: CC1(C)Cc2cc(NC(=O)c3cnn4cccnc34)c(O[C@H]3CCN(CC(N)=O)C3)cc2O1] | $^1$H NMR (400 MHz, dimethyl sulfoxide-d$_6$) δ 10.20 (s, 1H), 9.36 (dd, J = 7.0, 1.6 Hz, 1H), 8.85 (dd, J = 4.2, 1.6 Hz, 1H), 8.66 (s, 1H), 8.30 (s, 1H), 7.32 (dd, J = 7.0, 4.2 Hz, 1H), 7.14 (s, 1H), 7.03 (s, 1H), 6.49 (s, 1H), 5.02-4.90 (m, 1H), 3.13 (dd, J = 10.5, 6.2 Hz, 1H), 3.05 (s, 2H), 2.97 (s, 2H), 2.89-2.77 (m, 2H), 2.71-2.62 (m, 1H), 2.40-2.29 (m, 1H), 2.03 (dd, J = 8.1, 5.6 Hz, 1H), 1.41 (s, 6H). MS (ESI): m/z = 451.2 [M + 1]$^+$. |

Example 448. N-(6-((1-ethyl-1H-pyrazol-4-yl)methoxy)-2,2-dimethyl-2,3-dihydrobenzofuran-5-yl)pyrazolo[1,5-a]pyrimidine-3-carboxamide

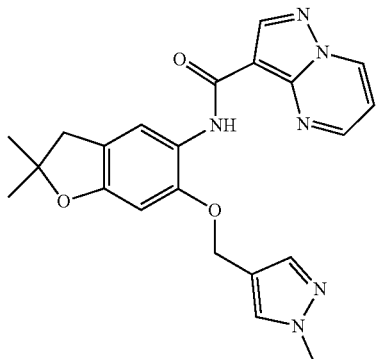

Step A. (1-ethyl-1H-pyrazol-4-yl)methanol

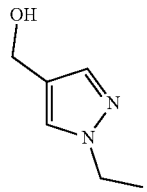

A mixture of 1-ethylpyrazole-4-carboxylic acid (200 mg, 1.43 mmol) was dissolved in tetrahydrofuran (20 ml, 0.07M) and treated with borane-tetrahydrofuran complex (4.4 ml, 4.4 mmol) for 4h at 25° C. Methanol was added and the mixture was stirred at room temperature for 30 min. The mixture was concentrated to afford (1-ethyl-1H-pyrazol-4-yl)methanol (180 mg, 1.43 mmol), which was used without further purification. $^1$H NMR (400 MHz, dimethyl sulfoxide-d$_6$) δ 8.00 (s, 1H), 7.67 (s, 1H), 5.06 (t, J=5.5 Hz, 1H), 4.38-4.28 (m, 4H), 1.34 (m, 3H) MS (ESI): m/z=127 [M+1]$^+$.

Step B. 2,2-dimethyl-5-nitro-2,3-dihydrobenzofuran-6-ol

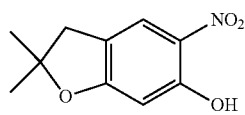

6-chloro-2,2-dimethyl-5-nitro-3H-benzofuran (2.00 g, 8.79 mmol) was dissolved in tert-butanol (67.6 ml) and treated with potassium hydroxide (567 mg, 10.1 mmol). The reaction mixture was heated at 80° C. for 24h. Potassium hydroxide was added (1.13 g, 20.2 mmol) and the reaction was stirred at 85° C. for an additional 24h. After cooling to room temperature, the pH was adjusted to 6 with 5% aqueous potassium bisulfate solution. The mixture was diluted with water (100 mL) and extracted with ethyl acetate (200 mL×3). The combined organic layers were washed with brine (300 mL), dried over sodium sulfate and concentrated. The residue was purified by silica gel chromatography (eluting gradient 0-100% isopropyl acetate in heptanes) to afford 2,2-dimethyl-5-nitro-3H-benzofuran-6-ol (1.54 g, 7.36 mmol, 84% yield) as a yellow solid. $^1$H NMR (400 MHz, dimethyl sulfoxide-d6) 6 10.96 (s, 1H), 7.89 (t, J=1.3 Hz, 1H), 6.44 (s, 1H), 2.99 (d, J=1.2 Hz, 2H), 1.44 (s, 6H).

Step C. 4-(((2,2-dimethyl-5-nitro-2,3-dihydrobenzofuran-6-yl)oxy)methyl)-1-ethyl-1H-pyrazole

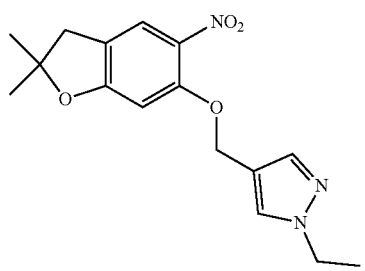 [SMILES: CCn1cc(COc2cc3c(cc2[N+](=O)[O-])CC(C)(C)O3)cn1]

To a mixture of 2,2-dimethyl-5-nitro-3H-benzofuran-6-ol (200 mg, 0956 mmol), (1-ethyl-1H-pyrazol-4-yl)methanol (180 mg, 1.43 mmol), and triphenylphosphine (326 mg, 1.24 mmol) in tetrohydrofuran (7.35 ml) was added diisopropylazodicarboxylate (0.25 ml, 1.2 mmol) dropwise. The reaction mixture was stirred at ambient temperature for an overnight period. The reaction was quenched with 1 N HCl and extracted with isopropyl acetate. The combined organics were dried over sodium sulfate, filtered and concentrated. The crude product was purified by silica gel chromatography (eluting gradient 0-100% methanol: dichloromethane) to afford 4-(((2,2-dimethyl-5-nitro-2,3-dihydrobenzofuran-6-yl)oxy)methyl)-1-ethyl-H-pyrazole (45 mg, 0.142 mmol, 15% yield). MS (ESI): m/z=318 [M+1]$^+$.

Step D. 6-((1-ethyl-1H-pyrazol-4-yl)methoxy)-2,2-dimethyl-2,3-dihydrobenzofuran-5-amine

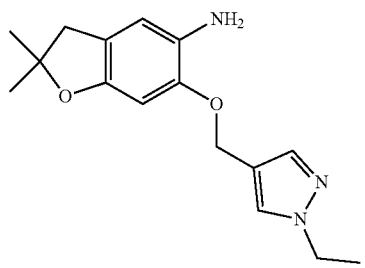 [SMILES: CCn1cc(COc2cc3c(cc2N)CC(C)(C)O3)cn1]

6-((1-ethyl-1H-pyrazol-4-yl)methoxy)-2,2-dimethyl-2,3-dihydrobenzofuran-5-amine was made in a manner analogous to Example 445, Step D to give the desired product (41 mg, quant.) which was used without further purification. MS (ESI): m/z=288 [M+1]$^+$.

827

Step E. N-(6-((1-ethyl-1H-pyrazol-4-yl)methoxy)-2,2-dimethyl-2,3-dihydrobenzofuran-5-yl)pyrazolo[1,5-a]pyrimidine-3-carboxamide

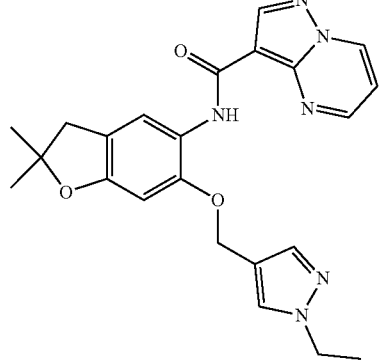

The title compound was made in a manner analogous to Example 445, Step E to give N-(6-((1-ethyl-1H-pyrazol-4-yl)methoxy)-2,2-dimethyl-2,3-dihydrobenzofuran-5-yl)pyrazolo[1,5-a]pyrimidine-3-carboxamide (19 mg, 31% yield). $^1$H NMR (400 MHz, dimethyl sulfoxide-$d_6$) δ 10.16 (s, 1H), 9.33 (dd, J=7.1, 1.4 Hz, 1H), 8.63 (s, 1H), 8.27 (t, J=2.8 Hz, 2H), 7.88 (s, 1H), 7.64 (s, 1H), 7.30 (dd, J=7.0, 4.2 Hz, 1H), 6.70 (s, 1H), 5.02 (s, 2H), 4.15 (q, J=7.3 Hz, 2H), 2.98 (s, 2H), 1.42 (s, 6H), 1.36 (t, J=7.3 Hz, 3H). MS (ESI): m/z=433.2 [M+1]$^+$.

Example 449. N-(2-(((2R,5R)-5-amino-1,3-dioxan-2-yl)methyl)-6-morpholino-1-oxoisoindolin-5-yl)pyrazolo[1,5-a]pyrimidine-3-carboxamide

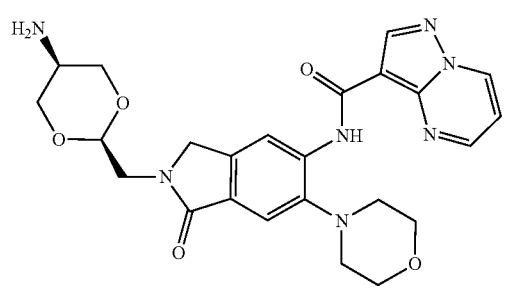 [SMILES: N[C@H]1CO[C@@H](CN2Cc3cc(NC(=O)c4cnn5cccnc45)c(N4CCOCC4)cc3C2=O)OC1]

828

Step A. 2-((2R,5R)-2-((6-chloro-5-nitro-1-oxoisoindolin-2-yl)methyl)-1,3-dioxan-5-yl)isoindoline-1,3-dione

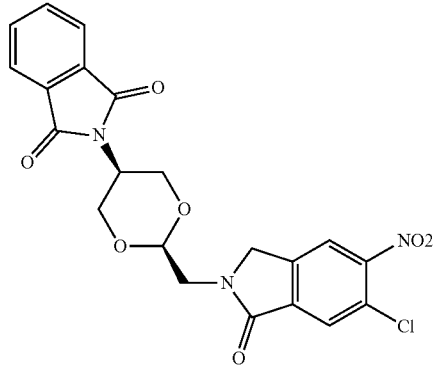 [SMILES: O=C1c2cc(Cl)c([N+](=O)[O-])cc2CN1C[C@H]1OC[C@@H](N2C(=O)c3ccccc3C2=O)CO1]

To methyl 2-(bromomethyl)-5-chloro-4-nitro-benzoate (preparation 5, WO 2013079505 (300 mg, 0.97 mmol) in methanol (10 ml) was added triethylamine (0.16 ml, 1.2 mmol) and 2-[2-(aminomethyl)-1,3-dioxan-5-yl]isoindoline-1,3-dione (306 mg, 1.2 mmol). The reaction was heated to 70° C. for 18 h, concentrated and purified by silica gel chromatography (eluting gradient 0-20% methanol: dichloromethane) to afford 2-((2r, 5r)-2-((6-chloro-5-nitro-1-oxoisoindolin-2-yl)methyl)-1,3-dioxan-5-yl)isoindoline-1,3-dione (301 mg, 68%). $^1$H NMR (400 MHz, DMSO-d6) δ 8.36 (s, 1H), 8.05 (s, 1H), 7.85 (td, J=4.3, 2.5 Hz, 4H), 4.91 (t, J=4.3 Hz, 1H), 4.70 (s, 2H), 4.29 (d, J=8.4 Hz, 3H), 4.11-4.06 (m, 2H), 3.74 (d, J=4.5 Hz, 2H). LCMS (ESI) m/z: 458.0 [M+H]$^+$.

Step B. 2-(((2R,5R)-2-((6-chloro-5-nitro-1-oxoisoindolin-2-yl)methyl)-1,3-dioxan-5-yl)carbamoyl)benzoic acid

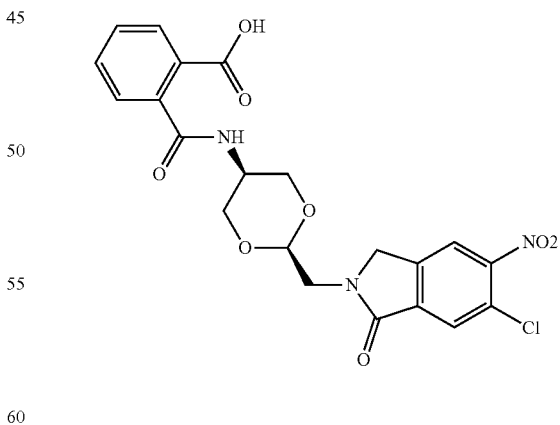

The title compound was made in a manner analogous to Example 173, Step B to give the desired product 2-(((2r,5r)-2-((6-chloro-5-nitro-1-oxoisoindolin-2-yl)methyl)-1,3-dioxan-5-yl)carbamoyl)benzoic acid (390 mg, quant) which was used without further purification. MS (ESI): m/z=596.1 [M+1]$^+$.

Step C. 2-(((2R,5R)-5-amino-1,3-dioxan-2-yl)methyl)-6-chloro-5-nitroisoindolin-1-one

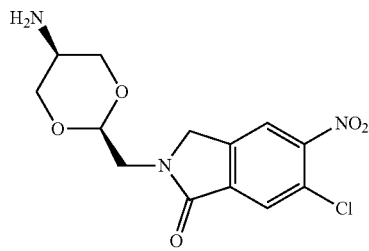 [SMILES: N[C@H]1CO[C@@H](CN2Cc3cc([N+](=O)[O-])c(Cl)cc3C2=O)OC1]

2-(((2r, 5r)-2-((6-chloro-5-nitro-1-oxoisoindolin-2-yl)methyl)-1,3-dioxan-5-yl)carbamoyl)benzoic acid (390 mg, 0.66 mmol) was dissolved in methanol (20 ml) and treated with hydrazine (5 ml) and stirred at ambient temperature for 1 week. The reaction mixture was concentrated in vacuo and the crude product purified by by silica gel chromatography (eluting gradient 0-20% methanol: dichloromethane) to afford 2-(((2r, 5r)-5-amino-1,3-dioxan-2-yl)methyl)-6-chloro-5-nitroisoindolin-1-one (164 mg, 0.432 mmol, 66% yield). $^1$H NMR (400 MHz, DMSO-d6) δ 8.06 (s, 1H), 7.58 (s, 1H), 4.61 (t, J=4.7 Hz, 1H), 4.55 (s, 2H), 3.94 (dd, J=11.2, 5.0 Hz, 2H), 3.72-3.66 (m, 4H), 3.63 (d, J=4.7 Hz, 2H), 3.18 (t, J=10.9 Hz, 2H), 3.03-2.97 (m, 4H), 2.78 (dt, J=10.4, 5.1 Hz, 1H), 1.40 (s, 2H).

Step D. tert-butyl((2R,5R)-2-((6-chloro-5-nitro-1-oxoisoindolin-2-yl)methyl)-1,3-dioxan-5-yl)carbamate

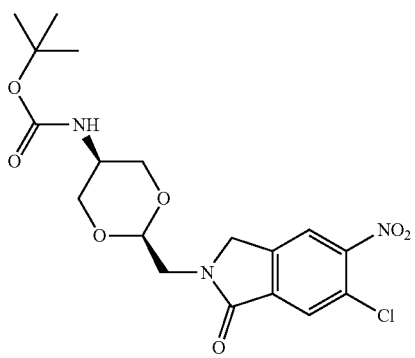 [SMILES: CC(C)(C)OC(=O)N[C@H]1CO[C@@H](CN2Cc3cc([N+](=O)[O-])c(Cl)cc3C2=O)OC1]

To a mixture of 2-(((2r, 5r)-5-amino-1,3-dioxan-2-yl)methyl)-6-chloro-5-nitroisoindolin-1-one (163 mg, 0.43 mmol), 4-dimethylaminopyridine (10 mg, 0.086 mmol), and trimethylamine (0.090 ml, 0.644 mmol) in tetrahydrofuran (3 ml) was added di-tert-butyl dicarbonate (145 mg, 0.644 mmol) at ambient temperature. After 16h, the mixture was diluted with water and extracted with isopropyl acetate. The combined organics were dried over sodium sulfate, filtered and concentrated. The crude product was purified by silica gel chromatography (eluting gradient 0-100% methanol: dichloromethane) to afford tert-butyl ((2r, 5r)-2-((6-chloro-5-nitro-1-oxoisoindolin-2-yl)methyl)-1,3-dioxan-5-yl)carbamate (33 mg, 0.069 mmol, 16% yield). (ESI): m/z=479.1 [M+1]$^+$.

Step E. tert-butyl ((2R,5R)-2-((5-amino-6-chloro-1-oxoisoindolin-2-yl)methyl)-1,3-dioxan-5-yl)carbamate

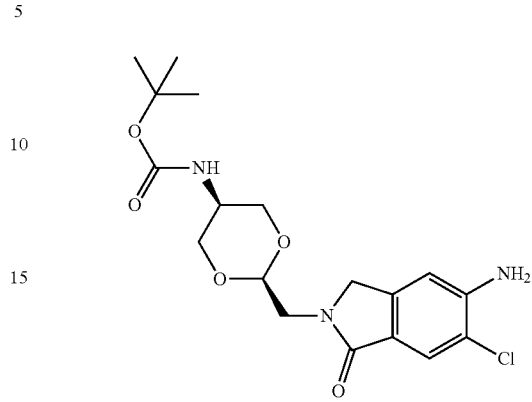

A mixture of tert-butyl ((2r, 5r)-2-((6-chloro-5-nitro-1-oxoisoindolin-2-yl)methyl)-1,3-dioxan-5-yl)carbamate (33 mg, 0.069 mmol) and 10% palladium on carbon (1.5 mg) in methanol (5.3 ml) was stirred at 25° C. under a hydrogen atmosphere for 3h. The reaction was filtered through a pad pf celite and concentrated under reduced pressure to afford tert-butyl ((2r, 5r)-2-((5-amino-6-chloro-1-oxoisoindolin-2-yl)methyl)-1,3-dioxan-5-yl)carbamate (31 mg), which was used without further purification. MS (ESI): m/z=449 [M+1]$^+$.

Step F. tert-butyl ((2R,5R)-2-((6-morpholino-1-oxo-5-(pyrazolo[1,5-a]pyrimidine-3-carboxamido)isoindolin-2-yl)methyl)-1,3-dioxan-5-yl)carbamate

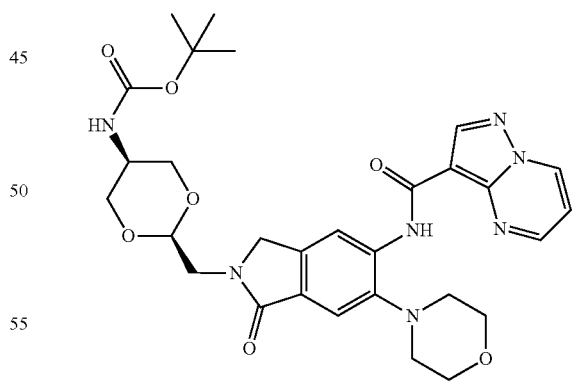

The title compound was made in a manner analogous to Example 173, Step D using tert-butyl ((2r, 5r)-2-((5-amino-6-chloro-1-oxoisoindolin-2-yl)methyl)-1,3-dioxan-5-yl)carbamate, Step E) to give the desired product tert-butyl ((2r, 5r)-2-((6-morpholino-1-oxo-5-(pyrazolo[1,5-a]pyrimidine-3-carboxamido)isoindolin-2-yl)methyl)-1,3-dioxan-5-yl)carbamate, which was used crude without further purification. MS (ESI): m/z=594 [M+1]$^+$.

Step G. N-(2-(((2R,5R)-5-amino-1,3-dioxan-2-yl)methyl)-6-morpholino-1-oxoisoindolin-5-yl)pyrazolo[1,5-a]pyrimidine-3-carboxamide

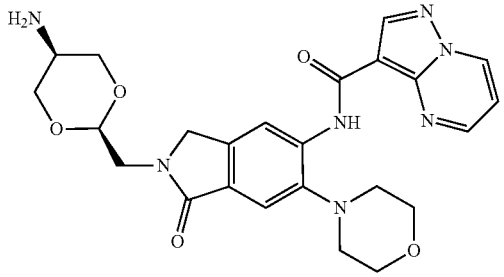 [SMILES: N[C@H]1CO[C@@H](CN2Cc3cc(NC(=O)c4cnn5cccnc45)c(N4CCOCC4)cc3C2=O)OC1]

A mixture of tert-butyl ((2R,5R)-2-((6-morpholino-1-oxo-5-(pyrazolo[1,5-a]pyrimidine-3-carboxamido)isoindolin-2-yl)methyl)-1,3-dioxan-5-yl)carbamate (40 mg, 0.067 mmol) in dichloromethane (5 ml) was treated with trifluoroacetic acid (0.5 ml) at ambient temperature. After 72h, the mixture was concentrated and the crude residue purified by preparative HPLC ((Gemini NX, 5*3 cm c18, Sum; A: acetonitrile 5-50%; B: 0.1% ammonium hydroxide in water) to afford N-(2-(((2r, 5r)-5-amino-1,3-dioxan-2-yl)methyl)-6-morpholino-1-oxoisoindolin-5-yl)pyrazolo[1,5-a]pyrimidine-3-carboxamide (3 mg, 0.0061 mmol, 9% yield) as a solid: $^1$H NMR (400 MHz, DMSO-d6) δ 10.90 (s, 1H), 9.41 (dd, J=7.0, 1.6 Hz, 1H), 9.00 (dd, J=4.2, 1.6 Hz, 1H), 8.76 (s, 1H), 8.74 (s, 1H), 7.58 (s, 1H), 7.39 (dd, J=7.0, 4.2 Hz, 1H), 4.60 (t, J=4.8 Hz, 1H), 4.52 (s, 2H), 3.95 (dd, J=11.2, 4.8 Hz, 2H), 3.92-3.88 (m, 4H), 3.60 (d, J=4.8 Hz, 2H), 3.18 (t, J=10.9 Hz, 2H), 2.95-2.88 (m, 4H), 2.80 (dt, J=10.4, 5.2 Hz, 1H). MS (ESI): m/z=494.2 [M+1]$^+$.

Example 450. N-(2,2-dimethyl-6-(4-(2-(methylsulfonyl)ethyl)piperazin-1-yl)-2,3-dihydrobenzofuran-5-yl)pyrazolo[1,5-a]pyrimidine-3-carboxamide

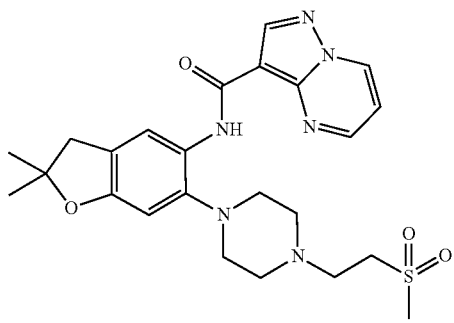

Potassium peroxymonosulfate (81 mg, 0.13 mmol) was added to a solution of N-[2,2-dimethyl-6-[4-(2-methylsulfanylethyl)piperazin-1-yl]-3H-benzofuran-5-yl]pyrazolo[1,5-a]pyrimidine-3-carboxamide (30.8 mg, 0.066 mmol) in N,N-dimethylformamide (2.2 ml) at 0° C. for 2h. The reaction mixture was warmed to room temperature and stirred overnight. The crude reside was purified by preparative HPLC ((Gemini NX, 5*3 cm c18, Sum; A: acetonitrile 30-70%; B: 0.1% ammonium hydroxide in water) to afford N-(2,2-dimethyl-6-(4-(2-(methylsulfonyl)ethyl)piperazin-1-yl)-2,3-dihydrobenzofuran-5-yl)pyrazolo[1,5-a]pyrimidine-3-carboxamide (1.3 mg, 0.0026 mmol, 4% yield). MS (ESI): m/z=499.2 [M+1]$^+$.

Example 451. S-[[(1R,2S)-2-aminocyclohexyl]amino]-N-(6-methoxy-2,2-dimethyl-3H-benzofuran-5-yl)pyrazolo[1,5-a]pyrimidine-3-carboxamide

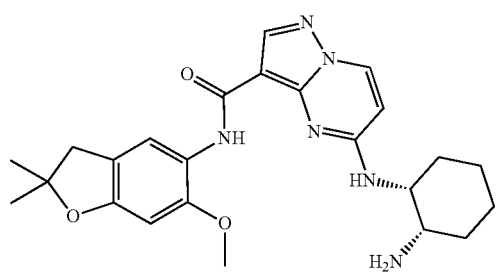 [SMILES: COc1cc2c(cc1NC(=O)c1cnn3ccc(N[C@@H]4CCCC[C@@H]4N)nc13)CC(C)(C)O2]

Step A. methyl 5-[[(1R,2S)-2-(tert-butoxycarbonylamino)cyclohexyl]amino]pyrazolo[1,5-a]pyrimidine-3-carboxylate

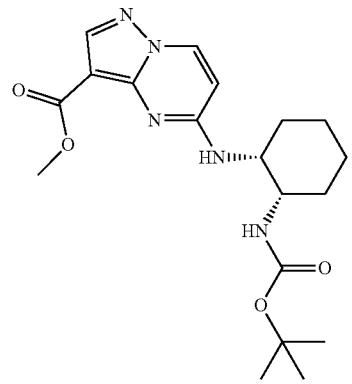 [SMILES: COC(=O)c1cnn2ccc(N[C@@H]3CCCC[C@@H]3NC(=O)OC(C)(C)C)nc12]

A microwave vial was charged with methyl 5-chloropyrazolo[1,5-a]pyrimidine-3-carboxylate (500 mg, 2.36 mmol), tert-butyl N-[(1S,2R)-2-aminocyclohexyl]carbamate (506 mg, 2.36 mmol), and methanol (4.7 mL). The vial was sealed and stirred at 90° C. for 30 min in the microwave, resulting in a suspension. The reaction mixture was concentrated in vacuo and the crude product was purified by column chromatography (0-100% isopropyl acetate/heptane) to afford methyl 5-[[(1R,2S)-2-(tert-butoxycarbonylamino)cyclohexyl]amino]pyrazolo[1,5-a]pyrimidine-3-carboxylate (420.2 mg, 1.08 mmol, 46% yield) as a white solid. MS: m/z=390 (M+1).

833

Step B. 5-[[(1R,2S)-2-(tert-butoxycarbonylamino)cyclohexyl]amino]pyrazolo[1,5-a]pyrimidine-3-carboxylic acid

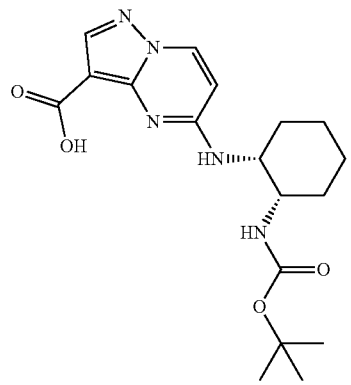 [SMILES: CC(C)(C)OC(=O)N[C@H]1CCCC[C@H]1Nc1ccn2ncc(C(=O)O)c2n1]

To a mixture of methyl 5-[[(1R,2S)-2-(tert-butoxycarbonylamino)cyclohexyl]amino]pyrazolo[1,5-a]pyrimidine-3-carboxylate (330 mg, 0.85 mmol) in tetrahydrofuran (1.7 mL) and water (3.40 mL) was added lithium hydroxide (61 mg, 2.54 mmol). The mixture was stirred at reflux for 2 days, after which a second portion of lithium hydroxide (61 mg, 2.54 mmol) was added. After an additional 3 h, the reaction was brought to room temperature and partitioned between dichloromethane and water. The aqueous phase was acidified to pH 2 with 1 N hydrochloric acid and extracted with dichloromethane (3×). The combined organic phase was dried over sodium sulfate, filtered, and concentrated in vacuo to afford 5-[[(1R,2S)-2-(tert-butoxycarbonylamino)cyclohexyl]amino]pyrazolo[1,5-a]pyrimidine-3-carboxylic acid (196.4 mg, 0.5232 mmol) as a white solid. MS: m/z=376 (M+1).

Step C. tert-butyl N-[(1S,2R)-2-[[3-[(6-methoxy-2,2-dimethyl-3H-benzofuran-5-yl)carbamoyl]pyrazolo[1,5-a]pyrimidin-5-yl]amino]cyclohexyl]carbamate

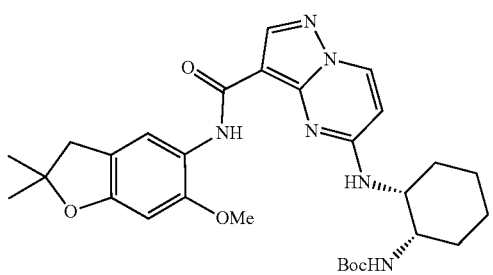 [SMILES: COc1cc2c(cc1NC(=O)c1cnn3ccc(N[C@@H]4CCCC[C@@H]4NC(=O)OC(C)(C)C)nc13)CC(C)(C)O2]

The title compound was made in a manner analogous to Example 12 from 6-methoxy-2,2-dimethyl-3H-benzofuran-5-amine (Example 34, Step B) to afford tert-butyl N-[(1S,2R)-2-[[3-[(6-methoxy-2,2-dimethyl-3H-benzofuran-5-yl)carbamoyl]pyrazolo[1,5-a]pyrimidin-5-yl]amino]cyclohexyl]carbamate (97.3 mg, 0.177 mmol, 68.3% yield). MS: m/z=551 (M+1).

834

Step D. 5-[[(1R,2S)-2-aminocyclohexyl]amino]-N-(6-methoxy-2,2-dimethyl-3H-benzofuran-5-yl)pyrazolo[1,5-a]pyrimidine-3-carboxamide

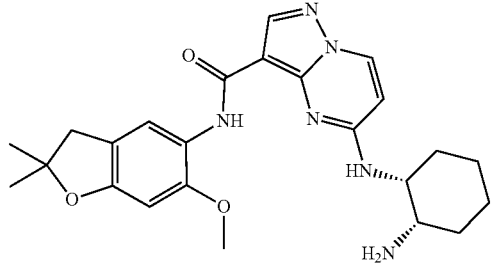 [SMILES: COc1cc2c(cc1NC(=O)c1cnn3ccc(N[C@@H]4CCCC[C@@H]4N)nc13)CC(C)(C)O2]

To a solution of tert-butyl N-[(1S,2R)-2-[[3-[(6-methoxy-2,2-dimethyl-3H-benzofuran-5-yl)carbamoyl]pyrazolo[1,5-a]pyrimidin-5-yl]amino]cyclohexyl]carbamate (97.3 mg, 0.177 mmol) in dichloromethane (1.77 mL) at 0° C. was added trifluoroacetic acid (0.442 mL, 5.84 mmol). The resulting solution was brought to room temperature and stirred for 3 h. The reaction mixture was concentrated in vacuo and purified by HPLC to afford 5-[[(1R,2S)-2-aminocyclohexyl]amino]-N-(6-methoxy-2,2-dimethyl-3H-benzofuran-5-yl)pyrazolo[1,5-a]pyrimidine-3-carboxamide (37 mg, 0.082 mmol, 46.5% yield) as a white solid. $^1$HNMR (400 MHz, DMSO-$d_6$) δ 9.64 (s, 1H), 8.55 (d, J=7.6 Hz, 1H), 8.14 (s, 1H), 7.94 (s, 1H), 7.71 (s, 1H), 6.63-6.53 (m, 2H), 4.22 (s, 1H), 3.83 (s, 3H), 3.09 (s, 1H), 2.96 (s, 2H), 1.78 (s, 1H), 1.62-1.49 (m, 7H), 1.41 (s, 6H), 1.31 (s, 3H). MS: m/z=451.2 (M+1).

Example 452. N-(6-carbamoyl-2,2-dimethyl-3H-benzofuran-5-yl)pyrazolo[1,5-a]pyrimidine-3-carboxamide

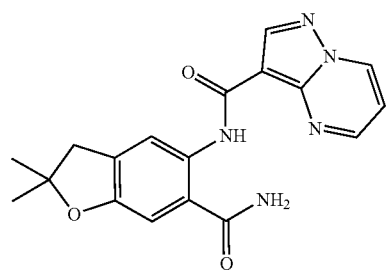

Step A. 2,2-dimethyl-5-nitro-3H-benzofuran-6-carbonitrile

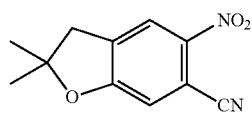 [SMILES: CC1(C)Cc2cc([N+](=O)[O-])c(C#N)cc2O1]

To a microwave vial containing 6-chloro-2,2-dimethyl-5-nitro-3H-benzofuran (100 mg, 0.44 mmol), tris(dibenzylideneacetone)dipalladium(0) (20.1 mg, 0.022 mmol), S-Phos (18.6 mg, 0.044 mmol), and zinc cyanide (56.7 mg, 0.48 mmol) were added N,N-dimethylformamide (2.2 mL) and water (0.021 mL). The mixture was sparged with nitrogen for 5 min, after which the vial was sealed and stirred in the microwave at 150° C. for 30 min. The crude reaction mixture was partitioned between 1 N sodium hydroxide and dichloromethane. The aqueous phase was extracted with dichloromethane (2×). The combined organic phase was dried over sodium sulfate, filtered, and concentrated to afford an orange solid. The crude residue was purified on silica (0-70% isopropyl acetate/heptane) to afford 2,2-dimethyl-5-nitro-3H-benzofuran-6-carbonitrile (75 mg, 0.34 mmol, 95% yield) as a yellow solid. $^1$H NMR (400 MHz, CDCl$_3$) δ 8.14 (t, J=1.2 Hz, 1H), 7.10 (s, 1H), 3.16 (d, J=1.2 Hz, 2H), 1.56 (s, 6H).

Step B.
2,2-dimethyl-5-nitro-3H-benzofuran-6-carboxamide

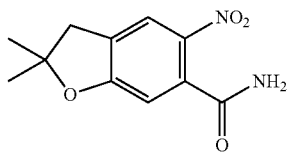 [SMILES: CC1(C)Cc2cc([N+](=O)[O-])c(C(N)=O)cc2O1]

A mixture of 2,2-dimethyl-5-nitro-3H-benzofuran-6-carbonitrile (41.4 mg, 0.190 mmol) and potassium hydroxide (11.7 mg, 0.209 mmol) in tert-butanol (0.632 mL) was stirred at 60° C. Upon completion of the hydrolysis (2h), the mixture was diluted with water and extracted with dichloromethane. The aqueous layer was extracted with dichloromethane (2×). The combined organic phase was dried over sodium sulfate, filtered, and concentrated to afford the crude product as an orange solid (45 mg, 0.19 mmol, quantitative yield). MS: m/z=237 [M+1]$^+$.

Step C.
5-amino-2,2-dimethyl-3H-benzofuran-6-carboxamide

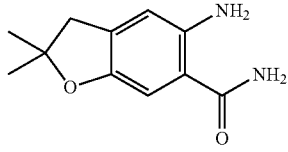

2,2-dimethyl-5-nitro-3H-benzofuran-6-carboxamide (45 mg, 0.195 mmol) was suspended in ethanol (1.9 mL). N,N-dimethylformamide (0.3 mL) was added to solubilize the substrate. 10% palladium on carbon (2 mg, 0.0019 mmol) was added, and the atmosphere was exchanged for hydrogen through 3 cycles of vacuum/H$_2$. The mixture was stirred under H$_2$ (1 atm) overnight. The contents were filtered through a 0.45 um syringe filter, and the filtrate was concentrated in vacuo. Flash column chromatography (0-100% isopropyl acetate/heptane) gave 5-amino-2,2-dimethyl-3H-benzofuran-6-carboxamide (22.6 mg, 0.110 mmol, 57% yield) as a white solid. MS: m/z=207 [M+1]$^+$.

Step D. N-(6-carbamoyl-2,2-dimethyl-3H-benzofuran-5-yl)pyrazolo[1,5-a]pyrimidine-3-carboxamide

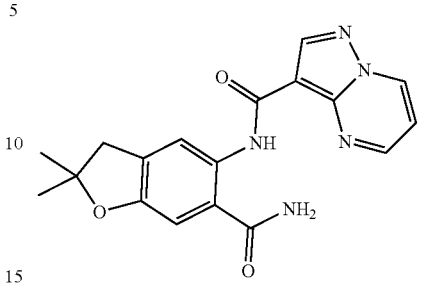

The title compound was made in a manner analogous to Example 4, Step C to afford N-(6-carbamoyl-2,2-dimethyl-3H-benzofuran-5-yl)pyrazolo[1,5-a]pyrimidine-3-carboxamide (5 mg, 4.5% yield). $^1$H NMR (400 MHz, DMSO-d$_6$) δ 11.60 (s, 1H), 9.31 (dd, J=7.0, 1.7 Hz, 1H), 8.81 (dd, J=4.1, 1.7 Hz, 1H), 8.63 (s, 1H), 8.18 (s, 1H), 7.97 (s, 1H), 7.47 (s, 1H), 7.27 (dd, J=7.0, 4.2 Hz, 1H), 7.02 (s, 1H), 3.08 (d, J=1.2 Hz, 2H), 2.62 (s, 1H), 1.44 (s, 6H). MS: m/z=352.1 [M+1]$^+$.

Example 453. N-(6-(4-ethylpiperazin-1-yl)-2,2-dimethyl-2,3-dihydrobenzofuran-5-yl)pyrazolo[1,5-a]pyrimidine-3-carboxamide

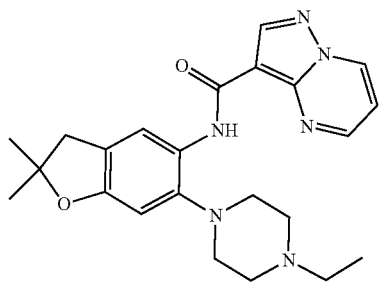 [SMILES: CCN1CCN(c2cc3c(cc2NC(=O)c2cnn4cccnc24)CC(C)(C)O3)CC1]

N-(2,2-dimethyl-6-piperazin-1-yl-3H-benzofuran-5-yl)pyrazolo[1,5-a]pyrimidine-3-carboxamide (Example 533) (50 mg, 0.127 mmol) and bromoethane (0.255 mmol) were dissolved in 1,4-dioxane (1.27 ml, 0.1M) and treated with N,N-diisopropylethylamine (0.067 ml, 0.382 mmol). The reaction mixture was stirred for 16 h at 100° C., concentrated under reduced pressure and the crude residue purified by preparative HPLC to afford N-(6-(4-ethylpiperazin-1-yl)-2,2-dimethyl-2,3-dihydrobenzofuran-5-yl)pyrazolo[1,5-a]pyrimidine-3-carboxamide (7.7 mg, 0.018 mmol, 14% yield) as a solid. $^1$H NMR (400 MHz, DMSO-d$_6$) δ 10.41 (s, 1H), 9.36 (dd, J=7.0, 1.7 Hz, 1H), 8.89 (dd, J=4.2, 1.7 Hz, 1H), 8.67 (s, 1H), 8.30 (d, J=1.0 Hz, 1H), 7.35 (dd, J=7.0, 4.2 Hz, 1H), 6.69 (s, 1H), 3.17 (d, J=5.2 Hz, 2H), 3.00 (dq, J=1.0, 0.5 Hz, 2H), 2.82 (m, 4H), 2.61 (m, 2H), 2.45 (m, 2H), 1.41 (s, 6H), 1.04 (t, J=7.2 Hz, 3H). MS (ESI). m/z=421.2 [M+1]$^+$.

TABLE 17

The following examples were made in a manner similar to that for Example 453:

| Ex. | Name | Structure | NMR, MS |
|---|---|---|---|
| 454. | N-(2,2-dimethyl-6-(4-(2-(methylthio)ethyl)piperazin-1-yl)-2,3-dihydrobenzofuran-5-yl)pyrazolo[1,5-a]pyrimidine-3-carboxamide | 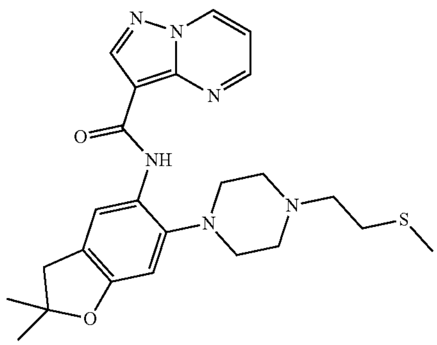 | $^1$H NMR (400 MHz, dimethyl sulfoxide-d$_6$) δ 10.39 (s, 1H), 9.36 (ddd, J = 7.0, 1.6, 0.5 Hz, 1H), 8.91 (ddd, J = 4.2, 1.7, 0.5 Hz, 1H), 8.67 (s, 1H), 8.30 (d, J = 1.0 Hz, 1H), 7.36 (dd, J = 7.0, 4.2 Hz, 1H), 6.69 (s, 1H), 3.00 (s, 2H), 2.81 (t, J = 4.7 Hz, 4H), 2.69-2.64 (m, 6H), 2.09 (d, J = 0.5 Hz, 3H), 2.07 (d, J = 0.5 Hz, 2H), 1.41 (s, 6H). MS (ESI): m/z = 467.2 [M + 1]$^+$. |
| 455. | N-(6-(4-(3-amino-3-oxopropyl)piperazin-1-yl)-2,2-dimethyl-2,3-dihydrobenzofuran-5-yl)pyrazolo[1,5-a]pyrimidine-3-carboxamide | 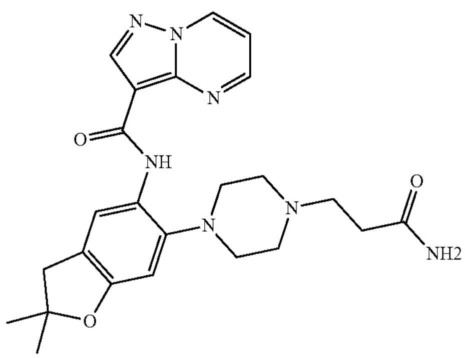 [SMILES: CC1(C)Cc2cc(NC(=O)c3cnn4cccnc34)c(N3CCN(CCC(N)=O)CC3)cc2O1] | $^1$H NMR (400 MHz, DMSO-d$_6$) δ 10.40 (s, 1H), 9.36 (dd, J = 7.0, 1.6 Hz, 1H), 8.91 (dd, J = 4.2, 1.7 Hz, 1H), 8.67 (s, 1H), 8.31 (d, J = 1.0 Hz, 1H), 7.36 (m, 2H), 6.77 (s, 1H), 6.69 (s, 1H), 3.29-3.22 (m, 2H), 2.99 (s, 2H), 2.81 (m, 4H), 2.63 (m, 4H), 2.26 (t, J = 7.2 Hz, 2H), 1.41 (s, 6H). MS (ESI): m/z = 464.2 [M + 1]$^+$. |
| 456. | N-(6-(4-(cyanomethyl)piperazin-1-yl)-2,2-dimethyl-2,3-dihydrobenzofuran-5-yl)pyrazolo[1,5-a]pyrimidine-3-carboxamide | 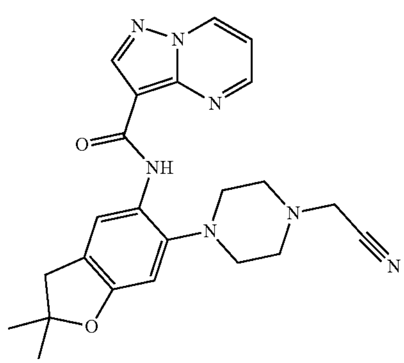 [SMILES: CC1(C)Cc2cc(NC(=O)c3cnn4cccnc34)c(N3CCN(CC#N)CC3)cc2O1] | $^1$H NMR (400 MHz, DMSO-d$_6$) δ 10.29 (s, 1H), 9.35 (dd, J = 7.0, 1.6 Hz, 1H), 9.06 (dd, J = 4.2, 1.7 Hz, 1H), 8.68 (s, 1H), 8.30 (d, J = 1.1 Hz, 1H), 7.29 (dd, J = 7.0, 4.2 Hz, 1H), 6.71 (s, 1H), 3.84 (s, 2H), 3.00 (d, J = 1.1 Hz, 2H), 2.87 (dd, J = 5.8, 3.6 Hz, 4H), 2.75 (dd, J = 6.0, 3.4 Hz, 4H), 1.41 (s, 6H). MS (ESI): m/z = 432.2 [M + 1]$^+$. |
| 457. | N-(6-(4-(2-cyanoethyl)piperazin-1-yl)-2,2-dimethyl-2,3-dihydrobenzofuran-5-yl)pyrazolo[1,5-a]pyrimidine-3-carboxamide | 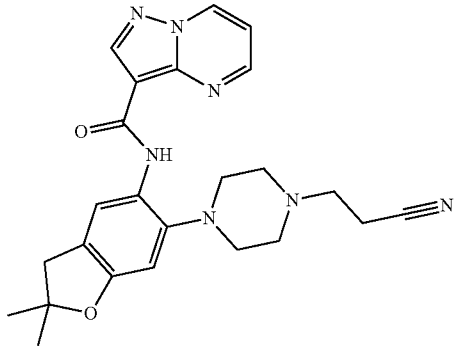 [SMILES: CC1(C)Cc2cc(NC(=O)c3cnn4cccnc34)c(N3CCN(CCC#N)CC3)cc2O1] | $^1$H NMR (400 MHz, DMSO-d$_6$) δ 10.38 (s, 1H), 9.36 (dd, J = 7.0, 1.6 Hz, 1H), 8.92 (dd, J = 4.2, 1.6 Hz, 1H), 8.68 (s, 1H), 8.30 (d, J = 1.1 Hz, 1H), 7.34 (dd, J = 7.0, 4.2 Hz, 1H), 6.71 (s, 1H), 3.00 (d, J = 1.1 Hz, 2H), 2.83 (t, J = 4.7 Hz, 4H), 2.75-2.63 (m, 8H), 1.41 (s, 6H). MS (ESI): m/z = 446.2 [M + 1]$^+$. |

TABLE 17-continued

The following examples were made in a manner similar to that for Example 453:

| Ex. | Name | Structure | NMR, MS |
|---|---|---|---|
| 458. | N-(6-(4-(cyclopropylmethyl)piperazin-1-yl)-2,2-dimethyl-2,3-dihydrobenzofuran-5-yl)pyrazolo[1,5-a]pyrimidine-3-carboxamide | 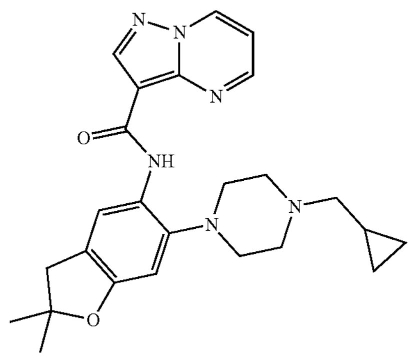 [SMILES: CC1(C)Cc2cc(NC(=O)c3cnn4cccnc34)c(N3CCN(CC4CC4)CC3)cc2O1] | $^1$H NMR (400 MHz, DMSO-$d_6$) δ 10.41 (s, 1H), 9.35 (dd, J = 7.0, 1.6 Hz, 1H), 8.87 (dd, J = 4.2, 1.7 Hz, 1H), 8.67 (s, 1H), 8.31 (d, J = 1.0 Hz, 1H), 7.35 (dd, J = 7.0, 4.2 Hz, 1H), 6.71 (s, 1H), 3.00 (s, 2H), 2.83 (m, 4H), 2.75-2.62 (m, 4H), 2.29 (d, J = 6.6 Hz, 2H), 1.41 (s, 6H), 0.93-0.82 (m, 1H), 0.51-0.43 (m, 2H), 0.16-0.07 (m, 2H). MS (ESI): m/z = 447.2 [M + 1]$^+$. |
| 459. | N-(2,2-dimethyl-6-(4-((3-methyl-1,2,4-oxadiazol-5-yl)methyl)piperazin-1-yl)-2,3-dihydrobenzofuran-5-yl)pyrazolo[1,5-a]pyrimidine-3-carboxamide | 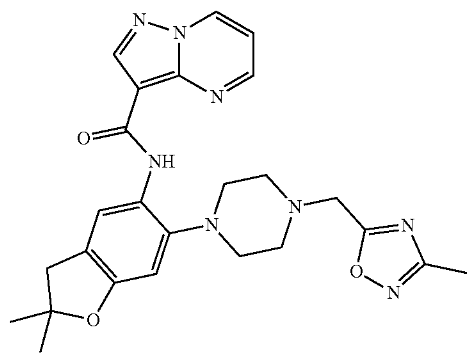 | $^1$H NMR (400 MHz, DMSO-$d_6$) δ 10.35 (s, 1H), 9.36 (dd, J = 7.0, 1.6 Hz, 1H), 8.81 (dd, J = 4.2, 1.7 Hz, 1H), 8.67 (s, 1H), 8.29 (d, J = 1.0 Hz, 1H), 7.33 (dd, J = 7.0, 4.2 Hz, 1H), 6.71 (s, 1H), 3.99 (s, 2H), 3.01-2.98 (s, 2H), 2.86-2.80 (m, 4H), 2.81-2.73 (m, 4H), 2.38 (s, 3H), 1.41 (s, 6H). MS (ESI): m/z = 489.2 [M + 1]$^+$. |
| 460. | N-(2,2-dimethyl-6-(4-((1-methyl-1H-pyrazol-4-yl)methyl)piperazin-1-yl)-2,3-dihydrobenzofuran-5-yl)pyrazolo[1,5-a]pyrimidine-3-carboxamide | 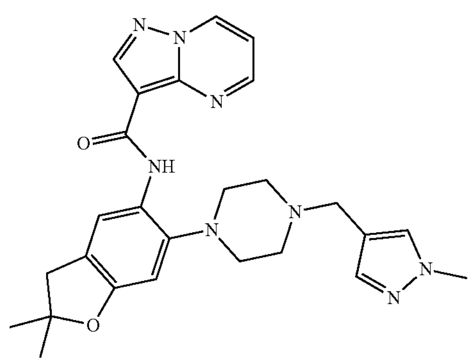 | $^1$H NMR (400 MHz, DMSO-$d_6$) δ 10.41 (s, 1H), 9.35 (dd, J = 7.0, 1.6 Hz, 1H), 8.66 (s, 1H), 8.47 (dd, J = 4.2, 1.6 Hz, 1H), 8.31 (d, J = 1.0 Hz, 1H), 7.60 (d, J = 0.8 Hz, 1H), 7.33 (d, J = 0.8 Hz, 1H), 7.30 (dd, J = 7.0, 4.2 Hz, 1H), 6.69 (s, 1H), 3.83 (s, 3H), 3.49 (s, 2H), 2.99 (s, 2H), 2.80 (m, 4H), 2.60 (m, 4H), 1.40 (s, 6H). MS (ESI): m/z = 487.2 [M + 1]$^+$. |
| 461. | N-(2,2-dimethyl-6-(4-((5-methyl-1,2,4-oxadiazol-3-yl)methyl)piperazin-1-yl)-2,3-dihydrobenzofuran-5-yl)pyrazolo[1,5-a]pyrimidine-3-carboxamide | 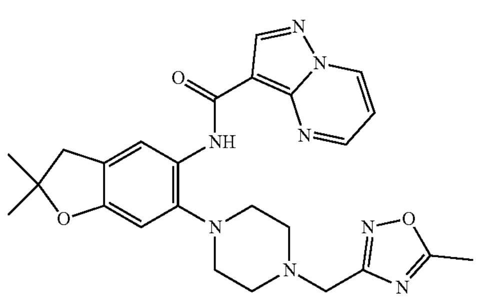 | $^1$H NMR (400 MHz, DMSO-$d_6$) δ 10.36 (s, 1H), 9.37 (dd, J = 7.0, 1.6 Hz, 1H), 8.83 (dd, J = 4.2, 1.7 Hz, 1H), 8.67 (s, 1H), 8.30 (s, 1H), 7.36 (dd, J = 7.0, 4.2 Hz, 1H), 6.70 (s, 1H), 3.74 (s, 2H), 2.99 (m, 2H), 2.83 (m, 3H), 2.77-2.69 (m, 3H), 2.60 (s, 2H), 1.41 (s, 6H). MS (ESI): m/z = 489.2 [M + 1]$^+$. |

TABLE 17-continued

The following examples were made in a manner similar to that for Example 453:

| Ex. | Name | Structure | NMR, MS |
|---|---|---|---|
| 462. | N-(6-(4-(2-(1H-pyrazol-1-yl)ethyl)piperazin-1-yl)-2,2-dimethyl-2,3-dihydrobenzofuran-5-yl)pyrazolo[1,5-a]pyrimidine-3-carboxamide | 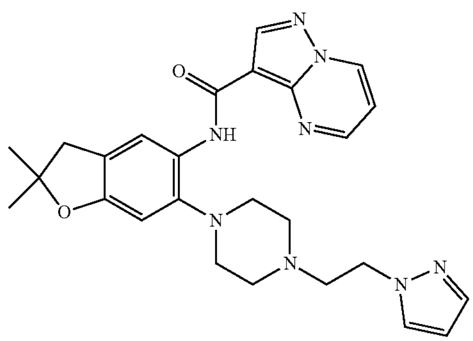 [SMILES: CC1(C)Cc2cc(NC(=O)c3cnn4cccnc34)c(N3CCN(CCn4cccn4)CC3)cc2O1] | $^1$H NMR (400 MHz, DMSO-$d_6$) δ 10.38 (s, 1H), 9.36 (dd, J = 7.0, 1.6 Hz, 1H), 8.91 (dd, J = 4.2, 1.7 Hz, 1H), 8.67 (s, 1H), 8.30 (d, J = 1.1 Hz, 1H), 7.75 (dd, J = 2.2, 0.7 Hz, 1H), 7.42 (dd, J = 1.8, 0.7 Hz, 1H), 7.35 (dd, J = 7.0, 4.2 Hz, 1H), 6.68 (s, 1H), 6.22 (t, J = 2.0 Hz, 1H), 4.26 (t, J = 6.8 Hz, 2H), 3.00 (s, 2H), 2.87-2.78 (m, 6H), 2.73-2.63 (m, 4H), 1.41 (s, 6H). MS (ESI): m/z = 487.2 [M + 1]$^+$. |
| 463. | N-(2,2-dimethyl-6-(4-((5-methyl-1,3,4-oxadiazol-2-yl)methyl)piperazin-1-yl)-2,3-dihydrobenzofuran-5-yl)pyrazolo[1,5-a]pyrimidine-3-carboxamide | 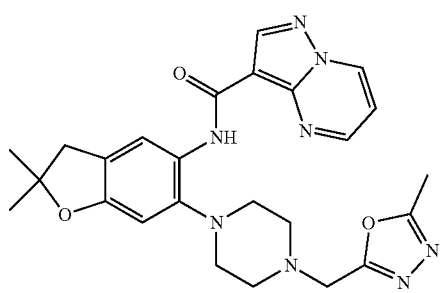 [SMILES: Cc1nnc(CN2CCN(c3cc4c(cc3NC(=O)c3cnn5cccnc35)CC(C)(C)O4)CC2)o1] | $^1$H NMR (400 MHz, DMSO-$d_6$) δ 10.36 (s, 1H), 9.36 (dd, J = 7.0, 1.6 Hz, 1H), 8.81 (dd, J = 4.2, 1.7 Hz, 1H), 8.67 (s, 1H), 8.30 (d, J = 0.9 Hz, 1H), 7.33 (dd, J = 7.0, 4.2 Hz, 1H), 6.70 (s, 1H), 3.88 (s, 2H), 2.99 (d, J = 1.1 Hz, 2H), 2.84 (d, J = 4.8 Hz, 3H), 2.73 (s, 4H), 1.41 (s, 7H). MS (ESI): m/z = 489.2 [M + 1]$^+$. |
| 464. | N-(2,2-dimethyl-6-(4-((tetrahydro-2H-pyran-4-yl)methyl)piperazin-1-yl)-2,3-dihydrobenzofuran-5-yl)pyrazolo[1,5-a]pyrimidine-3-carboxamide | 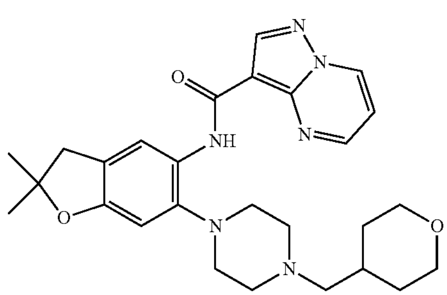 [SMILES: CC1(C)Cc2cc(NC(=O)c3cnn4cccnc34)c(N3CCN(CC4CCOCC4)CC3)cc2O1] | $^1$H NMR (400 MHz, DMSO-$d_6$) δ 10.39 (s, 1H), 9.36 (dd, J = 7.0, 1.6 Hz, 1H), 8.90 (dd, J = 4.2, 1.7 Hz, 1H), 8.67 (s, 1H), 8.30 (d, J = 0.9 Hz, 1H), 7.36 (dd, J = 7.0, 4.2 Hz, 1H), 6.68 (s, 1H), 3.88-3.79 (m, 2H), 3.02-2.97 (m, 2H), 2.81 (t, J = 4.7 Hz, 4H), 2.60 (s, 4H), 2.25 (d, J = 7.3 Hz, 2H), 1.77 (m, 1H), 1.69-1.60 (m, 2H), 1.41 (s, 6H), 1.21-1.07 (m, 2H). MS (ESI): m/z = 491.2 [M + 1]$^+$. |
| 465. | N-(6-(4-(3-methoxypropyl)piperazin-1-yl)-2,2-dimethyl-2,3-dihydrobenzofuran-5-yl)pyrazolo[1,5-a]pyrimidine-3-carboxamide | 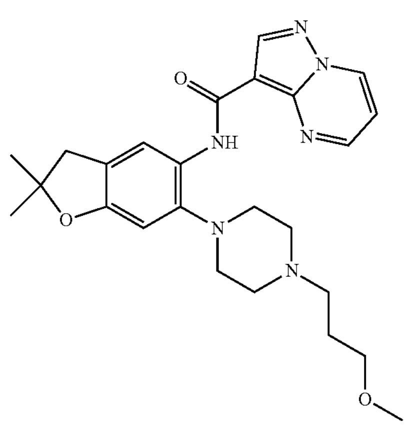 | $^1$H NMR (400 MHz, DMSO-$d_6$) δ 10.39 (s, 1H), 9.36 (dd, J = 7.0, 1.6 Hz, 1H), 8.89 (dd, J = 4.2, 1.7 Hz, 1H), 8.67 (s, 1H), 8.30 (d, J = 1.0 Hz, 1H), 7.36 (dd, J = 7.0, 4.2 Hz, 1H), 6.69 (s, 1H), 3.41-3.34 (m, 2H), 3.23 (s, 3H), 3.03-2.95 (m, 2H), 2.81 (t, J = 4.7 Hz, 4H), 2.66-2.56 (m, 4H), 2.42 (dd, J = 8.0, 6.7 Hz, 2H), 1.75-1.64 (m, 2H), 1.41 (s, 6H). MS (ESI): m/z = 465.2 [M + 1]$^+$. |

TABLE 17-continued

The following examples were made in a manner similar to that for Example 453:

| Ex. | Name | Structure | NMR, MS |
|---|---|---|---|
| 466. | N-(6-(4-(cyclobutylmethyl)piperazin-1-yl)-2,2-dimethyl-2,3-dihydrobenzofuran-5-yl)pyrazolo[1,5-a]pyrimidine-3-carboxamide | 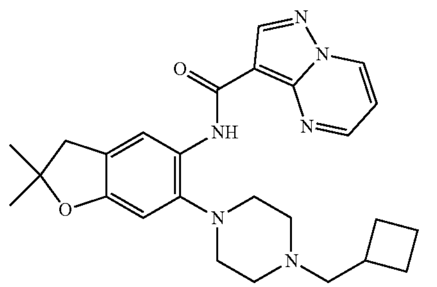 [SMILES: CC1(C)Cc2cc(NC(=O)c3cnn4cccnc34)c(N3CCN(CC4CCC4)CC3)cc2O1] | $^1$H NMR (400 MHz, DMSO-d$_6$) δ 10.39 (s, 1H), 9.36 (dd, J = 7.0, 1.6 Hz, 1H), 8.90 (dd, J = 4.2, 1.7 Hz, 1H), 8.67 (s, 1H), 8.30 (d, J = 0.9 Hz, 1H), 7.38 (dd, J = 7.0, 4.2 Hz, 1H), 6.69 (s, 1H), 3.02-2.97 (m, 2H), 2.79 (ddt, J = 5,3, 4.4, 0.9 Hz, 4H), 2.62-2.54 (m, 4H), 2.44 (d, J = 6.7 Hz, 2H), 2.02 (dddd, J = 9.8, 8.6, 5.0, 2.7 Hz, 2H), 1.95-1.75 (m, 2H), 1.73-1.61 (m, 2H), 1.41 (s, 6H). MS (ESI): m/z = 461.2 [M + 1]$^+$. |
| 467. | N-(2,2-dimethyl-6-(4-(2-oxopyrrolidin-3-yl)piperazin-1-yl)-2,3-dihydrobenzofuran-5-yl)pyrazolo[1,5-a]pyrimidine-3-carboxamide | 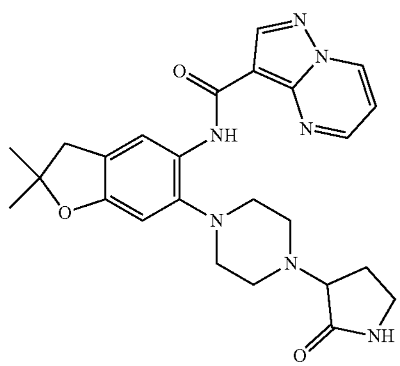 [SMILES: CC1(C)Cc2cc(NC(=O)c3cnn4cccnc34)c(N3CCN(C4CCNC4=O)CC3)cc2O1] | $^1$H NMR (400 MHz, DMSO-d$_6$) δ 10.41 (s, 1H), 9.34 (dd, J = 7.0, 1.6 Hz, 1H), 9.19 (dd, J = 4.2, 1.7 Hz, 1H), 8.66 (s, 1H), 8.36 (d, J = 1.0 Hz, 1H), 7.76 (s, 1H), 7.31 (dd, J = 7.0, 4.2 Hz, 1H), 6.69 (s, 1H), 3.22-3.06 (m, 5H), 3.03-2.98 (m, 2H), 2.89-2.70 (m, 6H), 2.27-2.14 (m, 1H), 1.95 (m, 1H), 1.41 (s, 6H), 1.24 (s, 1H). MS (ESI): m/z = 476.2 [M + 1]$^+$. |
| 468. | N-(2,2-dimethyl-6-(4-((5-oxopyrrolidin-2-yl)methyl)piperazin-1-yl)-2,3-dihydrobenzofuran-5-yl)pyrazolo[1,5-a]pyrimidine-3-carboxamide | 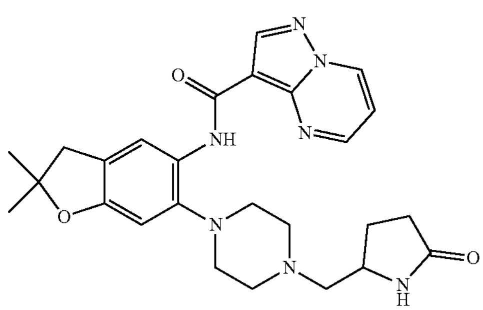 [SMILES: CC1(C)Cc2cc(NC(=O)c3cnn4cccnc34)c(N3CCN(CC4CCC(=O)N4)CC3)cc2O1] | $^1$H NMR (400 MHz, DMSO-d$_6$) δ 10.38 (s, 1H), 9.37 (dd, J = 7.0, 1.6 Hz, 1H), 8.89 (dd, J = 4.2, 1.7 Hz, 1H), 8.68 (s, 1H), 8.30-8.26 (m, 1H), 7.53 (s, 1H), 7.35 (dd, J = 7.0, 4.2 Hz, 1H), 6.67 (s, 1H), 3.79-3.69 (m, 1H), 3.02-2.97 (m, 2H), 2.82 (m, 4H), 2.75-2.59 (m, 4H), 2,41 (m, 2H), 2.24-2.03 (m, 3H), 1.78-1.66 (m, 1H), 1.41 (s, 7H). MS (ESI): m/z = 490.2 [M + 1]$^+$. |
| 469. | N-(6-(4-(2,3-dihydroxypropyl)piperazin-1-yl)-2,2-dimethyl-2,3-dihydrobenzofuran-5-yl)pyrazolo[1,5-a]pyrimidine-3-carboxamide | 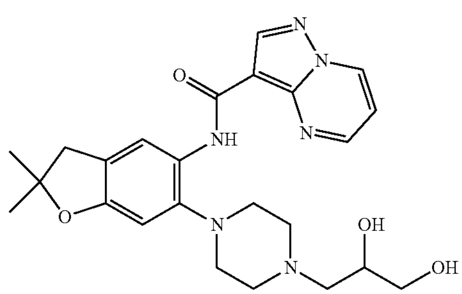 [SMILES: CC1(C)Cc2cc(NC(=O)c3cnn4cccnc34)c(N3CCN(CC(O)CO)CC3)cc2O1] | $^1$H NMR (400 MHz, DMSO-d$_6$) δ 10.38 (s, 1H), 9.37 (dd, J = 7.0, 1.6 Hz, 1H), 8.92 (s, 1H), 8.68 (s, 1H), 8.31 (d, J = 1.0 Hz, 1H), 7.37 (dd, J = 7.0, 4.2 Hz, 1H), 6.69 (s, 1H), 4.40 (d, J = 25.2 Hz, 1H), 3.67 (s, 1H), 3.46-3.34 (m, 2H), 3.29-3.14 (m, 2H), 3.00 (d, J = 1.0 Hz, 2H), 2.95-2.60 (m, 5H), 1.41 (s, 6H). MS (ESI): m/z = 467.2 [M + 1]$^+$. |

TABLE 17-continued

The following examples were made in a manner similar to that for Example 453:

| Ex. | Name | Structure | NMR, MS |
|---|---|---|---|
| 470. | N-(2,2-dimethyl-6-(4-(2-(2-oxopyrrolidin-1-yl)ethyl)piperazin-1-yl)-2,3-dihydrobenzofuran-5-yl)pyrazolo[1,5-a]pyrimidine-3-carboxamide | 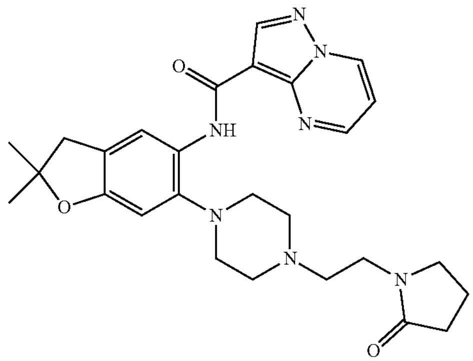 [SMILES: CC1(C)Cc2cc(NC(=O)c3cnn4cccnc34)c(N3CCN(CCN4CCCC4=O)CC3)cc2O1] | $^1$H NMR (400 MHz, DMSO-$d_6$) δ 10.38 (s, 1H), 9.36 (dd, J = 7.0, 1.6 Hz, 1H), 8.91 (dd, J = 4.2, 1.7 Hz, 1H), 8.67 (s, 1H), 8.30 (d, J = 1.0 Hz, 1H), 7.35 (dd, J = 7.0, 4.2 Hz, 1H), 6.68 (s, 1H), 3.49-3.36 (m, 4H), 3.17 (d, J = 5.2 Hz, 1H), 3.03-2.95 (m, 2H), 2.85-2.78 (m, 4H), 2.70-2.61 (m, 3H), 2.21 (dd, J = 8.8, 7.6 Hz, 2H), 2.01-1.85 (m, 2H), 1.41 (s, 7H). MS (ESI): m/z = 504.2 [M + 1]$^+$. |

Example 471. N-(2,2-dimethyl-6-morpholino-3H-benzofuran-5-yl)-6-(hydroxymethyl)pyrazolo[1,5-a]pyrimidine-3-carboxamide

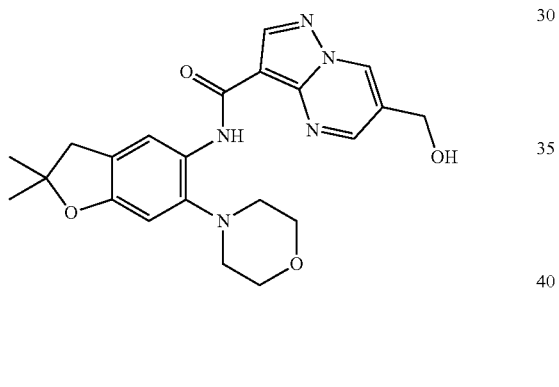

To a solution of 6-bromo-N-(2,2-dimethyl-6-morpholino-3H-benzofuran-5-yl)pyrazolo[, 5-a]pyrimidine-3-carboxamide (100 mg, 0.21 mmol) in 1,4-dioxane (3 ml) and water (0.30 ml) was added potassium acetoxymethyl(trifluoro)boron (115 mg, 0.64 mmol), sodium carbonate (68 mg, 0.64 mmol), 2-dicyclohexylphosphino-2',6'-di-i-propoxy-1,1'-biphenyl (60 mg, 0.13 mmol) and Ruphos-Pd-G2 (44 mg, 0.06 mmol). The reaction mixture was stirred at 120° C. for 0.5 h under microwave irradiation. The reaction mixture was filtered and concentrated. The residue was purified by prep-TLC (5% methanol in dichloromethane) to afford N-(2,2-dimethyl-6-morpholino-3H-benzofuran-5-yl)-6-(hydroxymethyl)pyrazolo[1,5-a]pyrimidine-3-carboxamide (48 mg, 53%) as a yellow solid. $^1$H NMR (400 MHz, DMSO-$d_6$) 10.42 (s, 1H), 9.22 (s, 1H), 8.95 (s, 1H), 8.65 (s, 1H), 8.32 (s, 1H), 6.72 (s, 1H), 5.64 (t, J=5.6 Hz, 1H), 4.70 (d, J=5.6 Hz, 2H), 3.90-3.80 (m, 4H), 3.00 (s, 2H), 2.90-2.80 (m, 4H), 1.41 (s, 6H). LCMS (ESI): m/z=424.1 [M+H]$^+$.

Examples 472 and 473. N-[6-[4-[(1R)-2-amino-1-methyl-2-oxo-ethyl]piperazin-1-yl]-2,2-dimethyl-3H-benzofuran-5-yl]pyrazolo[1,5-a]pyrimidine-3-carboxamide and N-[6-[4-[(1S)-2-amino-1-methyl-2-oxo-ethyl]piperazin-1-yl]-2,2-dimethyl-3H-benzofuran-5-yl]pyrazolo[1,5-a]pyrimidine-3-carboxamide

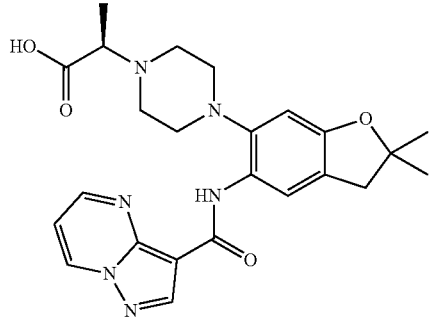

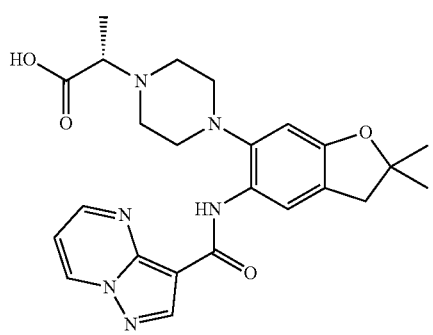

847

Step A: N-[6-[4-(2-amino-1-methyl-2-oxo-ethyl) piperazin-1-yl]-2,2-dimethyl-3H-benzofuran-5-yl] pyrazolo[1,5-a]pyrimidine-3-carboxamide

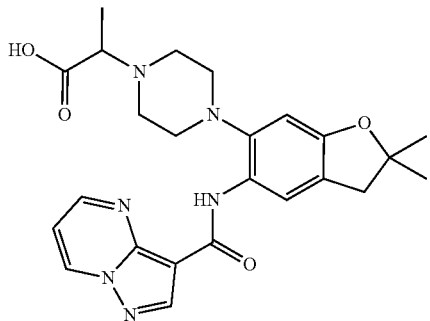 [SMILES: CC(C(=O)O)N1CCN(c2cc3c(cc2NC(=O)c2cnn4cccnc24)CC(C)(C)O3)CC1]

To a solution of N-(2,2-dimethyl-6-piperazin-1-yl-3H-benzofuran-5-yl) pyrazolo[1,5-a]pyrimidine-3-carboxamide (Example 533) (200 mg, 0.51 mmol) in 1,4-dioxane (5 ml) was added N,N-diisopropylethylamine (197.6 mg, 1.53 mmol) and 2-bromopropanamide (85.2 mg, 0.56 mmol). The reaction was stirred at 100° C. for 16 h. The reaction was concentrated and purified by pre-TLC (10% methanol in dichloromethane) to afford N-[6-[4-(2-amino-1-methyl-2-oxo-ethyl)piperazin-1-yl]-2,2-dimethyl-3H-benzofuran-5-yl]pyrazolo[1,5-a]pyrimidine-3-carboxamide (162.0 mg, 68.6% yield) as a yellow solid. LCMS (ESI): m/z=464.2 [M+H]$^+$ Step B: N-[6-[4-[(1R)-2-amino-1-methyl-2-oxo-ethyl]piperazin-1-yl]-2,2-dimethyl-3H-benzofuran-5-yl]pyrazolo[1,5-a]pyrimidine-3-carboxamide and N-[6-[4-[(1S)-2-amino-1-methyl-2-oxo-ethyl]piperazin-1-yl]-2,2-dimethyl-3H-benzofuran-5-yl]pyrazolo[1,5-a]pyrimidine-3-carboxamide

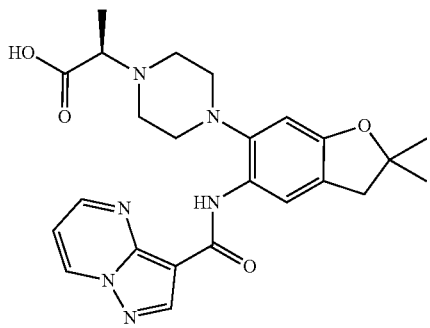

848

-continued

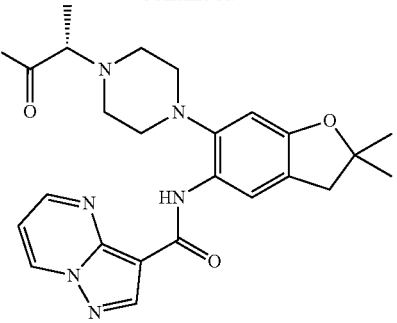

N-[6-[4-(2-amino-1-methyl-2-oxo-ethyl)piperazin-1-yl]-2,2-dimethyl-3H-benzofuran-5-yl]pyrazolo[1,5-a]pyrimidine-3-carboxamide (162 mg, 0.35 mmol) was resolved by chiral SFC to afford N-[6-[4-[(1R)-2-amino-1-methyl-2-oxo-ethyl]piperazin-1-yl]-2,2-dimethyl-3H-benzofuran-5-yl]pyrazolo[1,5-a]pyrimidine-3-carboxamide (45 mg, 27%; RT=2.97 min) and N-[6-[4-[(1S)-2-amino-1-methyl-2-oxo-ethyl]piperazin-1-yl]-2,2-dimethyl-3H-benzofuran-5-yl]pyrazolo[1,5-a]pyrimidine-3-carboxamide (35 mg, 21%; RT=3.45 min) as yellow solids with absolute stereochemistry assigned arbitrarily.

Example 472, Peak 1: $^1$H NMR (400 MHz, DMSO-d$_6$) δ 10.38 (s, 1H), 9.34-9.33 (m, 1H), 8.94-8.93 (m, 1H), 8.65 (s, 1H), 8.31 (s, 1H), 7.33 (dd, J=7.2, 4.4 Hz, 1H), 7.28 (s, 1H), 7.06 (s, 1H), 6.66 (s, 1H), 3.09-3.07 (m, 1H), 2.98 (s, 2H), 2.81-2.80 (m, 4H), 2.79-2.73 (m, 4H), 1.39 (s, 6H), 1.13 (d, J=6.8 Hz, 3H). LCMS (ESI): m/z=464.2 [M+H]$^+$ Example 473, Peak 2: ¹H NMR (400 MHz, DMSO-d₆) δ 10.40 (s, 1H), 9.37-9.35 (m, 1H), 8.96-8.95 (m, 1H), 8.67 (s, 1H), 8.33 (s, 1H), 7.35 (dd, J=7.2, 4.4 Hz, 1H), 7.30 (s, 1H), 7.10 (s, 1H), 6.68 (s, 1H), 3.12-3.07 (m, 1H), 2.99 (s, 2H), 2.82 (s, 4H), 2.75 (s, 4H), 1.40 (s, 6H), 1.15 (d, J=6.8 Hz, 3H). LCMS (ESI): m/z=464.3 [M+H]+

TABLE 18

The following examples were made in a manner similar to that for Example 472:

| Ex. | Name | Structure | NMR, MS |
|---|---|---|---|
| 474 | (S)-N-(6-(4-(2-hydroxypropyl)piperazin-1-yl)-2,2-dimethyl-2,3-dihydrobenzofuran-5-yl)pyrazolo[1,5-a]pyrimidine-3-carboxamide | 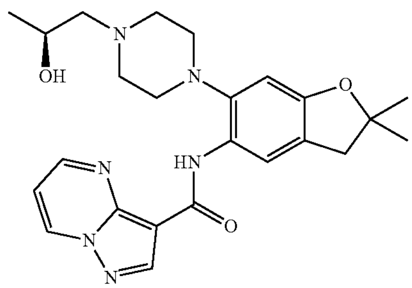 [SMILES: C[C@H](O)CN1CCN(c2cc3c(cc2NC(=O)c2cnn4cccnc24)CC(C)(C)O3)CC1] | ¹H NMR (400 MHz, DMSO-d₆) δ 10.40 (s, 1H), 9.36-9.34 (m, 1H), 8.90-8.88 (m, 1H), 8.67 (s, 1H), 8.29 (s, 1H), 7.36-7.34 (m, 1H), 6.68 (s, 1H), 4.37-4.35 (m, 1H), 3.80-3.78 (m, 1H), 2.98 (s, 2H), 2.81-2.79 (m, 4H), 2.68-2.66 (m, 4H), 2.36-2.34 (m, 1H), 1.40 (s, 6H), 1.09-1.05 (m, 3H). LCMS (ESI): m/z = 451.3 [M + 1]⁺. |
| 475 | (R)-N-(6-(4-(2-hydroxypropyl)piperazin-1-yl)-2,2-dimethyl-2,3-dihydrobenzofuran-5-yl)pyrazolo[1,5-a]pyrimidine-3-carboxamide | 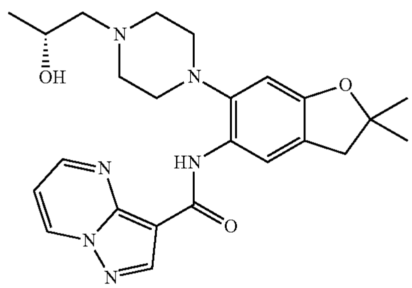 [SMILES: C[C@@H](O)CN1CCN(c2cc3c(cc2NC(=O)c2cnn4cccnc24)CC(C)(C)O3)CC1] | ¹H NMR (400 MHz, DMSO-d₆) δ 10.40 (s, 1H), 9.36-9.34 (m, 1H), 8.90-8.88 (m, 1H), 8.67 (s, 1H), 8.29 (s, 1H), 7.36-7.34 (m, 1H), 6.68 (s, 1H), 4.37-4.35 (m, 1H), 3.80-3.78 (m, 1H), 2.98 (s, 2H), 2.81-2.79 (m, 4H), 2.68-2.66 (m, 4H), 2.36-2.34 (m, 1H), 1.40 (s, 6H), 1.09-1.05 (m, 3H). LCMS (ESI): m/z = 451.3 [M + 1]⁺. |
| 476 | N-(6-(4-(2-amino-2-methylpropyl)piperazin-1-yl)-2,2-dimethyl-2,3-dihydrobenzofuran-5-yl)pyrazolo[1,5-a]pyrimidine-3-carboxamide | 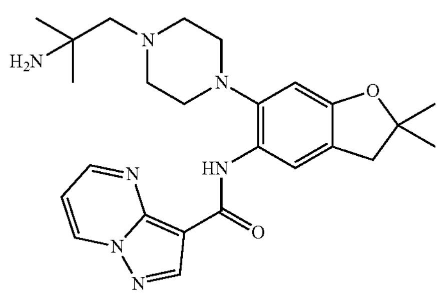 [SMILES: CC(C)(N)CN1CCN(c2cc3c(cc2NC(=O)c2cnn4cccnc24)CC(C)(C)O3)CC1] | ¹H NMR (400 MHz, DMSO-d₆) δ 10.39 (s, 1H), 9.39-9.34 (m, 1H), 8.91-8.80 (m, 1H), 8.68 (s, 1H), 8.29 (s, 1H), 7.38-7.35 (m, 1H), 6.65 (s, 1H), 2.99 (s, 2H), 2.85-2.80 (m, 8H), 2.40 (s, 2H), 1.41 (s, 6H), 1.13 (s, 6H). LCMS (ESI): m/z = 486.2 [M + Na]⁺. |
| 477 | N-[6-[4-[(2R)-2-Aminopropyl]piperazin-1-yl]-2,2-dimethyl-3H-benzofuran-5-yl]pyrazolo[1,5-a]pyrimidine-3-carboxamide | 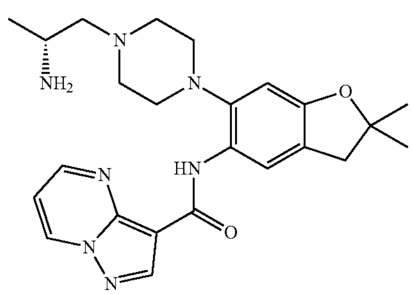 [SMILES: C[C@@H](N)CN1CCN(c2cc3c(cc2NC(=O)c2cnn4cccnc24)CC(C)(C)O3)CC1] | ¹H NMR (400 MHz, CD₃OD) δ 9.11-9.10 (m, 1H), 8.88-8.87 (m, 1H), 8.64 (s, 1H), 8.19 (s, 1H), 7.27 (dd, J = 6.0, 4.4 Hz, 1H), 6.65 (s, 1H), 3.15-3.10 (m, 1H), 3.03 (s, 2H), 2.95-2.85 (m, 4H), 2.85-2.75 (m, 2H), 2.70-2.60 (m, 2H), 2.45-2.30 (m, 2H), 1.46 (s, 6H), 1.10 (d, J = 6.0, 3H). LCMS (ESI): m/z = 472.1 [M + Na]⁺. |

TABLE 18-continued

The following examples were made in a manner similar to that for Example 472:

| Ex. | Name | Structure | NMR, MS |
|---|---|---|---|
| 478 | N-[6-[4-[(2S)-2-Aminopropyl]piperazin-1-yl]-2,2-dimethyl-3H-benzofuran-5-yl]pyrazolo[1,5-a]pyrimidine-3-carboxamide | 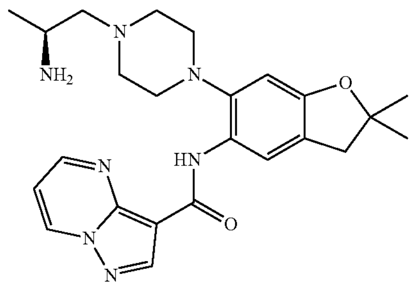 [SMILES: C[C@H](N)CN1CCN(c2cc3c(cc2NC(=O)c2cnn4cccnc24)CC(C)(C)O3)CC1] | $^1$H NMR (400 MHz, CD$_3$OD) δ 9.12 (dd, J = 6.8, 1.6 Hz, 1H), 8.90 (dd, J = 4.0, 1.6 Hz, 1H), 8.66 (s, 1H), 8.19 (s, 1H), 7.27 (dd, J = 6.8, 4.0 Hz, 1H), 6.66 (s, 1H), 3.15-3.10 (m, 1H), 3.03 (s, 2H), 2.95-2.85 (m, 4H), 2.85-2.75 (m, 2H), 2.70-2.60 (m, 2H), 2.45-2.30 (m, 2H), 1.56 (s, 6H), 1.14 (d, J = 6.4, 3H). LCMS (ESI): m/z = 472.1 [M + Na]$^+$. |
| 479 | N-[2,2-Dimethyl-6-[4-[(5-methyl-2-oxo-3H-oxazol-4-yl)methyl]piperazin-1-yl]-3H-benzofuran-5-yl]pyrazolo[1,5-a]pyrimidine-3-carboxamide | 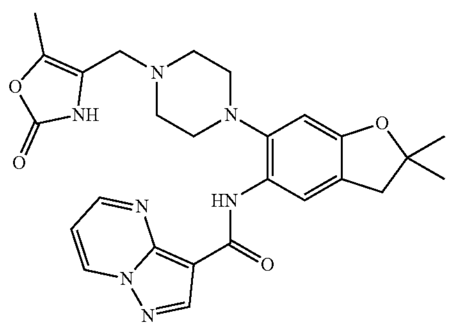 [SMILES: Cc1oc(=O)[nH]c1CN1CCN(c2cc3c(cc2NC(=O)c2cnn4cccnc24)CC(C)(C)O3)CC1] | $^1$H NMR (400 MHz, CDCl$_3$) δ 10.31 (s, 1H), 8.85 (dd, J = 7.2, 2.0 Hz, 1H), 8.79 (s, 1H), 8.65 (dd, J = 4.0, 1.6 Hz, 1H), 8.35 (s, 1H). 7.10 (dd, J = 6.8, 4.0 Hz, 1H), 6.64 (s, 1H), 3.32 (s, 2H), 3.04 (s, 2H), 2.99-2.89 (m, 4H), 2.74-2.64 (m, 4H), 2.07 (s, 3H), 1.49 (s, 6H). LCMS (ESI): m/z = 504.2 [M + H]$^+$ |
| 480 and 481 | (S)-N-(2,2-dimethyl-6-(4-(1-(methylamino)-1-oxopropan-2-yl)piperazin-1-yl)-2,3-dihydrobenzofuran-5-yl)pyrazolo[1,5-a]pyrimidine-3-carboxamide (R)-N-(2,2-dimethyl-6-(4-(1-(methylamino)-1-oxopropan-2-yl)piperazin-1-yl)-2,3-dihydrobenzofuran-5-yl)pyrazolo[1,5-a]pyrimidine-3-carboxamide (absolute stereochemistry assigned arbitrarily) | | Example 480, Peak 1: $^1$H NMR (400 MHz, CDCl$_3$): 10.32 (s, 1H), 8.83-8.82 (m, 1H), 8.77 (s, 1H), 8.71-8.70 (m, 1H), 8.38 (s, 1H), 7.15-7.03 (m, 2H), 6.64 (s, 1H), 3.12-3.06 (m, 1H), 3.03 (s, 2H), 2.94-2.93 (m, 4H), 2.85 (d, J = 4.8 Hz, 3H), 2.83-2.75 (m, 2H), 2.70-2.69 (m, 2H), 1.49 (s, 6H), 1.31 (d, J = 7.2 Hz, 3H). LCMS (ESI): m/z = 478.1 [M + H]$^+$ Example 481, Peak 2: $^1$H NMR (400 MHz, CDCl$_3$): 10.32 (s, 1H), 8.83-8.82 (m, 1H), 8.77 (s, 1H), 8.71-8.70 (m, 1H), 8.38 (s, 1H), 7.15-7.03 (m, 2H), 6.64 (s, 1H), 3.12-3.06 (m, 1H), 3.03 (s, 2H), 2.94-2.93 (m, 4H), 2.85 (d, J = 4.4 Hz, 3H), 2.83-2.75 (m, 2H), 2.70-2.69 (m, 2H), 1.49 (s, 6H), 1.31 (d, J = 6.8 Hz, 3H). LCMS (ESI): m/z = 478.1 [M + H]$^+$ |

TABLE 18-continued

The following examples were made in a manner similar to that for Example 472:

| Ex. | Name | Structure | NMR, MS |
|---|---|---|---|
| 482 and 483 | N-[6-[4-[(1S)-1-carbamoyl-3-hydroxy-propyl]piperazin-1-yl]-2,2-dimethyl-3H-benzofuran-5-yl]pyrazolo[1,5-a]pyrimidine-3-carboxamide and N-[6-[4-[(1R)-1-carbamoyl-3-hydroxy-propyl]piperazin-1-yl]-2,2-dimethyl-3H-benzofuran-5-yl]pyrazolo[1,5-a]pyrimidine-3-carboxamide (absolute stereochemistry assigned arbitrarily) | | Example 482, Peak 1: $^1$H NMR (400 MHz, DMSO-$d_6$) δ 10.41 (s, 1H), 9.35-9.33 (m, 1H), 8.99 (dd, J = 4.0, 1.6 Hz, 1H), 8.66 (s, 1H), 8.36 (s, 1H), 7.41 (s, 1H), 7.34 (dd, J = 7.2, 4.4 Hz, 1H), 7.14 (s, 1H), 6.67 (s, 1H), 4.47 (t, J = 5.2 Hz, 1H). 3.51-3.38 (m, 2H), 3.23 (t, J = 7.2 Hz, 1H), 2.99 (s, 2H), 2.83-2.75 (m, 8H), 1.79-1.68 (m, 2H), 1.41 (s, 6H). LCMS (ESI): m/z = 494.2 [M + H]$^+$. Example 483, Peak 2: $^1$H NMR (400 MHz, DMSO-$d_6$) δ 10.41 (s, 1H), 9.36-9.34 (m, 1H), 8.99-8.98 (m, 1H), 8.66 (s, 1H), 8.36 (s, 1H), 7.41 (s, 1H), 7.34 (dd, J = 6.8, 4.0 Hz, 1H), 7.14 (s, 1H), 6.67 (s, 1H), 4.47 (t, J = 5.2 Hz, 1H), 3.52-3.40 (m, 2H), 3.23 (t, J = 7.2 Hz, 1H), 2.99 (s, 2H), 2.85-2.74 (m, 8H), 1.80-1.67 (m, 2H), 1.41 (s, 6H). LCMS (ESI): m/z = 494.2 [M + H]$^+$ |

Example 484. 5-(Difluoromethyl)-N-(2-isopropyl-6-morpholino-1-oxo-isoindolin-5-yl)pyrazolo[1,5-a]pyrimidine-3-carboxamide

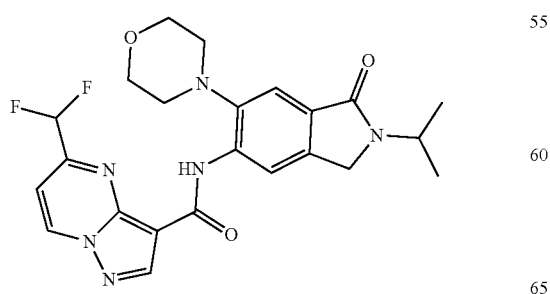

Step A: Methyl 5-[(E)-2-(dimethylamino)vinyl]
pyrazolo[1,5-a]pyrimidine-3-carboxylate

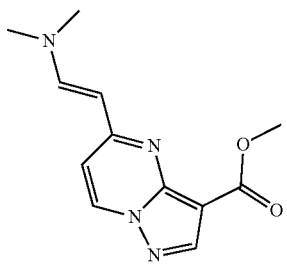

To a solution of ethyl 5-methylpyrazolo[1,5-a]pyrimidine-3-carboxylate (1.30 g, 6.33 mmol) in N,N-dimethylformamide (20 ml) was added lithium hydroxide (75 mg, 3.17 mmol) and N,N-dimethylformamide dimethyl acetal (2.26 g, 19 mmol). The mixture was stirred at 120° C. for 16 h. The reaction was concentrated and purified by flash column chromatography (ethyl acetate) to afford methyl 5-[(E)-2-(dimethylamino)vinyl]pyrazolo[1,5-a]pyrimidine-3-carboxylate (950 mg, 60% yield) as a dark yellow solid. $^1$H NMR (400 MHz, CDCl$_3$) δ 8.32 (s, 1H), 8.23 (d, J=7.6 Hz, 1H), 7.90 (d, J=12.8 Hz, 1H), 6.53 (d, J=7.6 Hz, 1H), 5.18 (d, J=12.8 Hz, 1H), 3.91 (s, 3H), 3.04 (br s, 6H).

Step B: Methyl 5-formylpyrazolo[1,5-a]pyrimidine-3-carboxylate

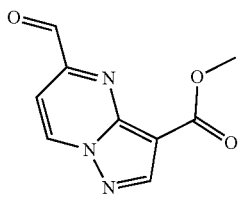

To a solution of methyl 5-[(E)-2-(dimethylamino)vinyl]pyrazolo[1,5-a]pyrimidine-3-carboxylate (950.0 mg, 3.86 mmol) in methyl alcohol (20 ml) was added sodium periodate (1.65 g, 7.72 mmol) in water (20 ml). The mixture was stirred at 60° C. for 16 h. Methyl alcohol was removed and the aqueous solution was extracted with ethyl acetate (150 ml×2). The combined organic phase was washed with saturated sodium bicarbonate solution (100 ml) and brine (150 mL), dried over sodium sulfate and concentrated. The crude product was purified by flash column chromatography (ethyl acetate) to give methyl 5-formylpyrazolo[1,5-a]pyrimidine-3-carboxylate (630 mg, 79% yield) as a yellow solid.
$^1$H NMR (400 MHz, CDCl$_3$) δ 10.17 (s, 1H), 8.92 (d, J=6.4 Hz, 1H), 8.73 (s, 1H), 7.62 (d, J=7.2 Hz, 1H), 4.02 (s, 3H).

Step C: Methyl 5-(difluoromethyl)pyrazolo[1,5-a]pyrimidine-3-carboxylate

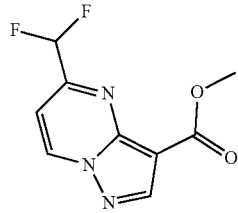

To a solution of methyl 5-formylpyrazolo[1,5-a]pyrimidine-3-carboxylate (600 mg, 2.92 mmol) in dichloromethane (10 ml) was added diethylaminosulfur trifluoride (943 mg, 5.85 mmol) dropwise at 0° C. The reaction was stirred at 25° C. for 16 h. The reaction was concentrated and purified by flash column chromatography (33% ethyl acetate in petroleum ether) to afford methyl 5-(difluoromethyl)pyrazolo[1,5-a]pyrimidine-3-carboxylate (430 mg, 64% yield) as a yellow solid. $^1$H NMR (400 MHz, CDCl$_3$) δ 8.91 (d, J=7.2 Hz, 1H), 8.67 (s, 1H), 7.35 (d, J=7.2 Hz, 1H), 6.76 (t, J=54.4 Hz, 1H), 3.98 (s, 3H).

Step D: 5-(Difluoromethyl)pyrazolo[1,5-a]pyrimidine-3-carboxylic acid

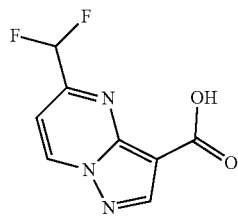

A mixture of methyl 5-(difluoromethyl)pyrazolo[1,5-a]pyrimidine-3-carboxylate (100 mg, 0.44 mmol) and lithium hydroxide monohydrate (24 mg, 0.57 mmol) in tetrahydrofuran (1 ml) and methyl alcohol (1 ml) was stirred at 100° C. under microwave irradiation for 100 min. The reaction was acidified with hydrochloric acid (1 M, 0.6 mL) and concentrated to afford 5-(difluoromethyl) pyrazolo[1,5-a]pyrimidine-3-carboxylic acid (90 mg, 95% yield) as a red solid, which was directly used in the next step without further purification. $^1$H NMR (400 MHz, DMSO-d$_6$) δ 9.31 (d, J=7.2 Hz, 1H), 8.40 (s, 1H), 7.27 (d, J=7.2 Hz, 1H), 7.02 (t, J=54.4 Hz, 1H).

Step E: 5-(Difluoromethyl)pyrazolo[1,5-a]pyrimidine-3-carbonyl chloride

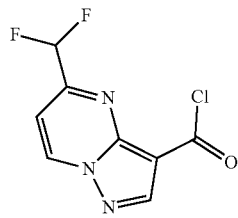

To a solution of 5-(difluoromethyl)pyrazolo[1,5-a]pyrimidine-3-carboxylic acid (70 mg, 0.33 mmol) in oxalyl chloride (2.8 ml, 32 mmol) was added N,N-dimethylformamide (24 mg, 0.33 mmol). The mixture was stirred at 25° C. for 1 h. The reaction mixture was concentrated to obtain 5-(difluoromethyl)pyrazolo[1,5-a]pyrimidine-3-carbonyl chloride (70 mg, 92% yield) as a yellow solid, which was used directly.

Step F: 5-(Difluoromethyl)-N-(2-isopropyl-6-morpholino-1-oxo-isoindolin-5-yl)pyrazolo[1,5-a]pyrimidine-3-carboxamide

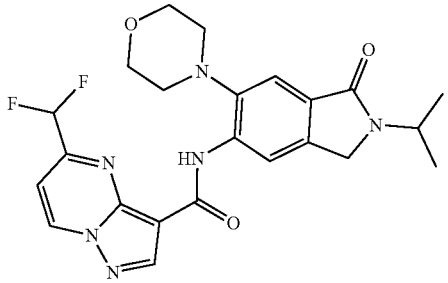 [SMILES: CC(C)N1Cc2cc(NC(=O)c3cnn4ccc(C(F)F)nc34)c(N3CCOCC3)cc2C1=O]

To a solution of 5-(difluoromethyl)pyrazolo[1,5-a]pyrimidine-3-carbonyl chloride (70 mg, 0.30 mmol) in pyridine (5 ml) was added 5-amino-2-isopropyl-6-morpholino-isoindolin-1-one (65 mg, 0.24 mmol). The reaction mixture was stirred at 50° C. for 6h. The reaction was concentrated and purified by prep-TLC (10% methanol in dichloromethane) to give the crude product, which was triturated with methanol (5 mL) to give 5-(difluoromethyl)-N-(2-isopropyl-6-morpholino-1-oxo-isoindolin-5-yl)pyrazolo[1,5-a]pyrimidine-3-carboxamide (39 mg, 35 yield) as yellow solid. $^1$H NMR (400 MHz, CDCl$_3$) δ 10.04 (s, 1H), 9.01 (d, J=7.2 Hz, 8.92 (s, 1H), 8.60 (s, 1H), 7.69 (s, 1H), 7.41 (d, J=7.6 Hz, 1H), 6.84 (t, J=54.4 Hz, 1H), 4.72-4.64 (m, 1H), 4.35 (s, 2H), 3.92-3.83 (m, 4H), 3.04-2.954 (m, 4H), 1.31 (d, J=6.4 Hz, 6H). LCMS (ESI): m/z=471.2 [M+H]$^+$.

TABLE 19

The following examples were made in a manner similar to that for Example 484:

| Ex. | Name | Structure | NMR, MS |
|---|---|---|---|
| 485 | 6-cyano-N-(2-isopropyl-6-morpholino-1-oxo-isoindolin-5-yl)pyrazolo[1,5-a]pyrimidine-3-carboxamide | 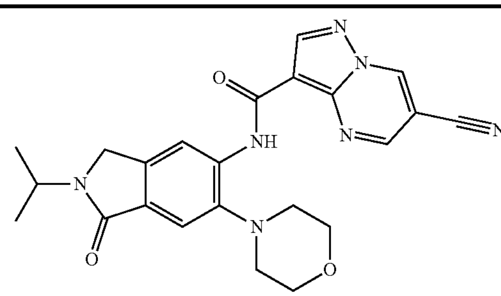 | $^1$H NMR (400 MHz, DMSO-d$_6$) δ 10.74 (s, 1H), 10.28-10.24 (m, 1H), 9.32 (d, J = 1.9 Hz, 1H), 8.95 (s, 1H), 8.73 (s, 1H), 7.58 (s, 1H), 4.48-4.32 (m, 3H), 3.92-3.82 (m, 4H), 2.93-2.86 (m, 4H), 1.22 (d, J = 6.8 Hz, 6H). MS: m/z = 446.2 [M + H]$^+$. |
| 486 | N3-(2-isopropyl-6-morpholino-1-oxo-isoindolin-5-yl)pyrazolo[1,5-a]pyrimidine-3,6-dicarboxamide | 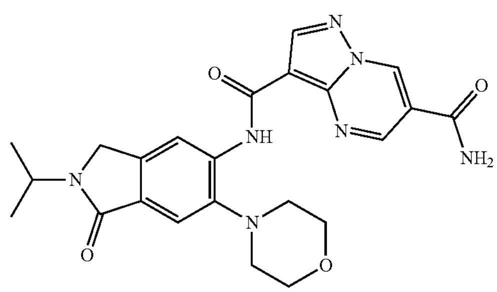 [SMILES: CC(C)N1Cc2cc(NC(=O)c3cnn4cc(C(N)=O)cnc34)c(N3CCOCC3)cc2C1=O] | $^1$H NMR (400 MHz, DMSO-d$_6$) δ 10.74 (s, 1H), 10.28-10.24 (m, 1H), 9.32 (d, J = 1.9 Hz, 1H), 8.95 (s, 1H), 8.73 (s, 1H), 7.58 (s, 1H), 4.48-4.32 (m, 3H), 3.92-3.82 (m, 4H), 2.93-2.86 (m, 4H), 1.22 (d, J = 6.8 Hz, 6H). MS: m/z = 464.2 [M + H]$^+$. |

Example 487. N-[6-Cyclopropyl-2-[(2R)-2-fluoro-3-hydroxy-3-methyl-butyl]-1-oxo-isoindolin-5-yl]pyrazolo[1,5-a]pyrimidine-3-carboxamide

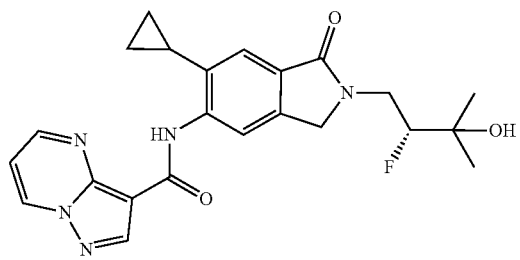 [SMILES: CC(C)(O)[C@H](F)CN1Cc2cc(NC(=O)c3cnn4cccnc34)c(C3CC3)cc2C1=O]

Step A: 6-Cyclopropyl-2-[(2R)-2-fluoro-3-hydroxy-3-methyl-butyl]-5-nitro-isoindolin-1-one

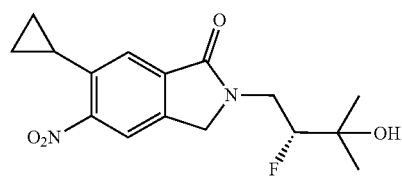 [SMILES: CC(C)(O)[C@H](F)CN1Cc2cc([N+](=O)[O-])c(C3CC3)cc2C1=O]

To a solution of 6-chloro-2-[(2R)-2-fluoro-3-hydroxy-3-methyl-butyl]-5-nitro-isoindolin-1-one (200 mg, 0.63 mmol), cyclopropyl boronic acid (82 mg, 0.95 mmol), potassium phosphate, tribasic (536 mg, 2.53 mmol) and triphenylphosphine (50 mg, 0.19 mmol) in toluene (5 ml) and water (1 ml) was added palladium(II) acetate (21 mg, 0.09 mmol) under the protection of nitrogen. The reaction was stirred at 120° C. for 2 h with microwave irradiation. The reaction was diluted with water (5 ml) and extracted with dichloromethane (50 ml×3). The combined organic phase was washed with brine (50 ml×2), dried over sodium sulfate, filtered and concentrated. The residue was purified by prep-TLC (50% ethyl acetate in petroleum ether) to afford 6-cyclopropyl-2-[(2R)-2-fluoro-3-hydroxy-3-methyl-butyl]-5-nitro-isoindolin-1-one (with some triphenylphosphine oxide; 200 mg, 98% yield) as a yellow solid.

Step B: 5-Amino-6-cyclopropyl-2-[(2R)-2-fluoro-3-hydroxy-3-methyl-butyl]isoindolin-1-one

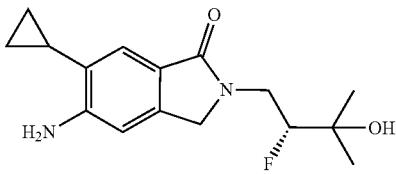 [SMILES: CC(C)(O)[C@H](F)CN1Cc2cc(N)c(C3CC3)cc2C1=O]

To a solution of 6-cyclopropyl-2-[(2R)-2-fluoro-3-hydroxy-3-methyl-butyl]-5-nitro-isoindolin-1-one (200 mg, 0.62 mmol) and iron (173 mg, 3.1 mmol) in ethanol (5 ml) and water (1 ml) was added ammonium chloride (166 mg, 3.1 mmol). The reaction was stirred at 80° C. for 2 h. The reaction was filtered and concentrated. The residue was dissolved in ethyl acetate (20 ml), diluted with water (20 ml) and extracted with ethyl acetate (100 ml×3). The combined organic phase was washed with brine (100 ml×2), dried over sodium sulfate, filtered and concentrated to afford 5-amino-6-cyclopropyl-2-[(2R)-2-fluoro-3-hydroxy-3-methyl-butyl]isoindolin-1-one (110 mg, 61% yield) as a yellow solid.

Step C: N-[6-Cyclopropyl-2-[(2R)-2-fluoro-3-hydroxy-3-methyl-butyl]-1-oxo-isoindolin-5-yl]pyrazolo[1,5-a]pyrimidine-3-carboxamide

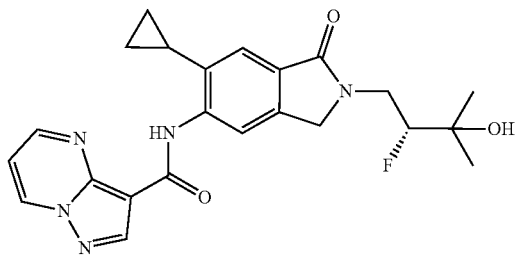 [SMILES: CC(C)(O)[C@H](F)CN1Cc2cc(NC(=O)c3cnn4cccnc34)c(C3CC3)cc2C1=O]

To a solution of 5-amino-6-cyclopropyl-2-[(2R)-2-fluoro-3-hydroxy-3-methyl-butyl]isoindolin-1-one (100 mg, 0.34 mmol) in pyridine (10 ml) was added pyrazolo[1,5-a]pyrimidine-3-carbonyl chloride (75 mg, 0.41 mmol). The reaction was stirred at 25° C. for 2 h and concentrated. The residue was purified by prep-TLC (10% methanol in dichloromethane) to afford N-[6-cyclopropyl-2-[(2R)-2-fluoro-3-hydroxy-3-methyl-butyl]-1-oxo-isoindolin-5-yl]pyrazolo[1,5-a]pyrimidine-3-carboxamide (92.2 mg, 59% yield) as a yellow solid. $^1$H NMR (400 MHz, DMSO-$d_6$) δ 10.58 (s, 1H), 9.40 (dd, J=6.8, 1.6 Hz, 1H), 8.94 (dd, J=4.0, 1.2 Hz, 1H), 8.76 (s, 1H), 8.68 (s, 1H), 7.46 (s, 1H), 7.36 (dd, J=6.8, 4.0 Hz, 1H), 4.87 (s, 1H), 4.59-4.37 (m, 3H), 4.01-3.88 (m, 1H), 3.74-3.64 (m, 1H), 2.12-2.04 (m, 1H), 1.24-1.15 (m, 8H), 0.79-0.75 (m, 2H). LCMS (ESI): m/z=438.1 [M+H]$^+$.

Example 488. N-[2,2-Dimethyl-6-(1-methylimidazol-4-yl)-3H-benzofuran-5-yl]pyrazolo[1,5-a]pyrimidine-3-carboxamide

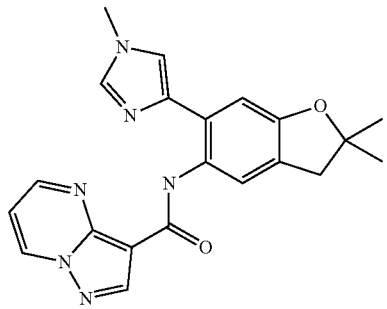

Step A: 4-(2,2-Dimethyl-5-nitro-3H-benzofuran-6-yl)-1-methyl-imidazole

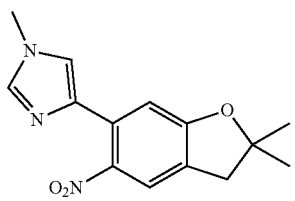 [SMILES: Cn1cnc(-c2cc3c(cc2N)CC(C)(C)O3)c1]

To a solution of 6-bromo-2,2-dimethyl-5-nitro-3H-benzofuran (200 mg, 0.74 mmol) bis(triphenylphosphine)palladium(II) dichloride (103 mg, 0.15 mmol) in N,N-dimethylformamide (5 ml) was added tributyl-(1-methylimidazol-4-yl)stannane (382 mg, 1.03 mmol) under nitrogen. The mixture was stirred at 100° C. for 16 h. The reaction mixture was filtered, diluted with water (20 ml) and extracted with ethyl acetate (20 ml×2). The organic phase was washed with brine (10 ml×2), dried over sodium sulfate, filtered and concentrated. The residue was purified by flash chromatography (5-10% ethyl acetate in petroleum ether) to afford 4-(2,2-dimethyl-5-nitro-3H-benzofuran-6-yl)-1-methyl-imidazole (113 mg, 56%) as a yellow solid. $^1$H NMR (400 MHz, CDCl$_3$) δ 7.62 (s, 1H), 7.47 (s, 1H), 7.13 (s, 1H), 7.07 (s, 1H), 3.73 (s, 3H), 3.06 (s, 2H), 1.52 (s, 6H). LCMS (ESI): m/z=274.0 [M+H]$^+$.

Step B: 2,2-Dimethyl-6-(1-methylimidazol-4-yl)-3H-benzofuran-5-amine

To a solution of 4-(2,2-dimethyl-5-nitro-3H-benzofuran-6-yl)-1-methyl-imidazole (120 mg, 0.44 mmol) in methanol (4 ml) was added 10% palladium on carbon (46 mg, 0.22 mmol). The reaction mixture was stirred under hydrogen atmosphere (15 psi) at 25° C. for 2 h. The reaction was filtered, and the filtrate was concentrated. The residue was purified by prep-TLC (5% methanol in dichloromethane) to afford 2,2-dimethyl-6-(1-methylimidazol-4-yl)-3H-benzofuran-5-amine (85 mg, 80%) as a yellow solid. LCMS (ESI): m/z=243.9 [M+H]$^+$.

Step C: N-[2,2-Dimethyl-6-(1-methylimidazol-4-yl)-3H-benzofuran-5-yl]pyrazolo[1,5-a]pyrimidine-3-carboxamide

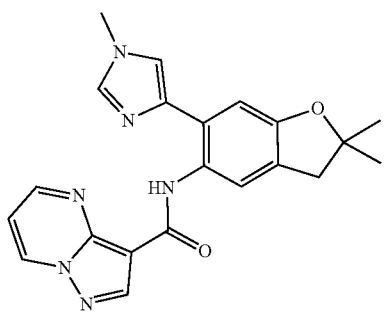

To a solution of 2,2-dimethyl-6-(1-methylimidazol-4-yl)-3H-benzofuran-5-amine (85 mg, 0.35 mmol) in pyridine (2 ml) was added pyrazolo[1,5-a]pyrimidine-3-carbonyl chloride (95 mg, 0.52 mmol). The reaction mixture was stirred at 25° C. for 2 h. The reaction was concentrated and the residue was purified by prep-TLC (10% ethyl acetate in petroleum ether) to give N-[2,2-dimethyl-6-(1-methylimidazol-4-yl)-3H-benzofuran-5-yl]pyrazolo[1,5-a]pyrimidine-3-carboxamide (45 mg, 33.2%) as a yellow solid. $^1$H NMR (400 MHz, CDCl$_3$) δ 11.45 (s, 1H), 8.78-8.76 (m, 2H), 8.67-8.65 (m, 1H), 8.28 (s, 1H), 7.48 (s, 1H), 7.11 (s, 1H), 6.98 (dd, J=7.2, 4.0 Hz, 1H), 6.92 (s, 1H), 3.71 (s, 3H), 3.08 (s, 2H), 1.51 (s, 6H). LCMS (ESI): m/z=389.0 [M+H]$^+$.

TABLE 20

The following examples were made in a manner similar to that for Example 488:

| Ex. | Name | Structure | NMR, MS |
|---|---|---|---|
| 489 | N-[2,2-dimethyl-6-(1-methylpyrazol-3-yl)-3H-benzofuran-5-yl]pyrazolo[1,5-a]pyrimidine-3-carboxamide | 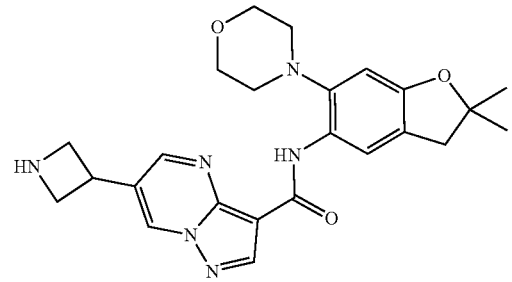 | $^1$H NMR (400 MHz, CDCl$_3$) δ 11.10 (s, 1H), 8.78 (dd, J = 7.2, 1.6 Hz, 1H), 8.76 (s, 1H), 8.66-8.65 (m, 1H), 8.27 (s, 1H), 7.37 (d, J = 2.4 Hz, 1H), 6.99 (dd, J = 7.2, 4.0 Hz, 1H), 6.96 (s, 1H), 6.48 (d, J = 2.0 Hz, 1H), 3.90 (s, 3H), 3.09 (s, 2H), 1.51 (s, 6H). LCMS (ESI): m/z = 389.0 [M + H]$^+$. |

Example 490. 6-(Azetidin-3-yl)-N-(2,2-dimethyl-6-morpholino-3H-benzofuran-5-yl)pyrazolo[1,5-a]pyrimidine-3-carboxamide

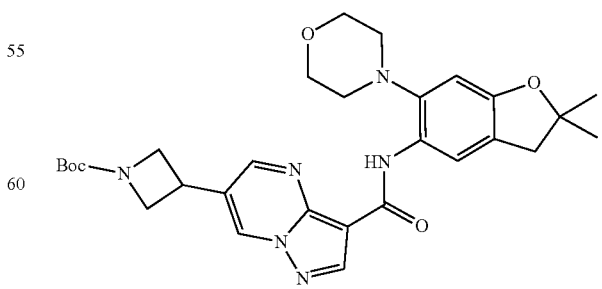

Step A: tert-Butyl 3-[3-[(2,2-dimethyl-6-morpholino-3H-benzofuran-5-yl)carbamoyl]pyrazolo[1,5-a]pyrimidin-6-yl]azetidine-1-carboxylate To a mixture of zinc (211 mg, 3.23 mmol) in N, N-dimethylacetamide (2.5 ml) was added chlorotrimethylsilane (0.03 ml, 0.40 mmol) and 1, 2-dibromoethane (0.03 ml, 0.40 mmol) at 20° C. under nitrogen. The resulting mixture was stirred for 15 min. A solution of 1-Boc-3-iodoazetidine (700 mg, 2.47 mmol) in N, N-dimethylacetamide (1 ml) was added portion wise. The reaction mixture was stirred for 30 min to give a solution of zinc reagent.

In another reaction vessel, to a solution of 6-bromo-N-(2,2-dimethyl-6-morpholino-3H-benzofuran-5-yl)pyrazolo[1,5-a] pyrimidine-3-carboxamide (200 mg, 0.42 mmol) in N, N-dimethylacetamide (2 ml) was added 1,1'-bis(diphenylphosphino)ferrocene palladium dichloride (75 mg, 0.10 mmol), cuprous iodide (39 mg, 0.20 mmol) and the freshly prepared (1-tert-butoxycarbonylazetidin-3-yl)-iodo-zinc (3.03 ml, 2.12 mmol). The reaction mixture was stirred at 80° C. for 16 h under nitrogen. The reaction mixture was quenched by water (50 ml) and extracted with dichloromethane (50 ml×3). The combined organic layers were washed with water (150 ml×3), brine (150 ml), dried over anhydrous sodium sulfate, filtered and concentrated. The residue was purified by flash column chromatography on silica gel (eluting with 0-20-50-100% ethyl acetate in petroleum ether) to afford a crude product which was further purified by prep-TLC (5% methanol in dichloromethane) twice to afford tert-butyl 3-[3-[(2,2-dimethyl-6-morpholino-3H-benzofuran-5-yl)carbamoyl]pyrazolo[1,5-a] pyrimidin-6-yl]azetidine-1-carboxylate (100 mg, 43%) as a yellow solid. LCMS (ESI): m/z=549.3[M+H]$^+$.

Step B: 6-(azetidin-3-yl)-N-(2,2-dimethyl-6-morpholino-3H-benzofuran-5-yl)pyrazolo[1,5-a]pyrimidine-3-carboxamide hydrochloride

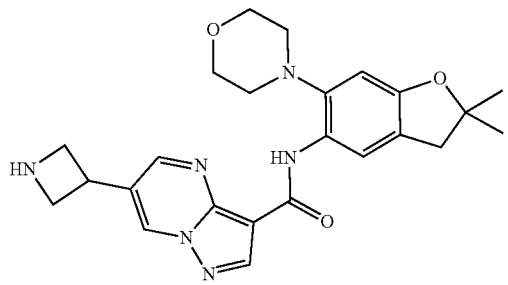

A mixture of tert-butyl 3-[3-[(2,2-dimethyl-6-morpholino-3H-benzofuran-5-yl)carbamoyl]pyrazolo[1,5-a]pyrimidin-6-yl]azetidine-1-carboxylate (90 mg, 0.16 mmol) in 4 M hydrochloric acid in methanol (2 ml, 8 mmol) was stirred at 28° C. for 30 min. The reaction mixture was concentrated to obtain a residue which was triturated with methanol to afford 6-(azetidin-3-yl)-N-(2,2-dimethyl-6-morpholino-3H-benzofuran-5-yl) pyrazolo[1,5-a]pyrimidine-3-carboxamide (35 mg, 42%, HCl salt) as a yellow solid. $^1$H NMR (400 MHz, DMSO-$d_6$) 10.34 (s, 1H), 9.60-9.50 (m, 1H), 9.05-8.95 (m, 1H), 8.70 (s, 1H), 8.31 (s, 1H), 6.72 (s, 1H), 4.50-4.25 (m, 5H), 3.95-3.75 (m, 4H), 3.00 (s, 2H), 2.95-2.75 (m, 4H), 1.42 (s, 6H). LCMS (ESI): m/z=449.1 [M+H]$^+$.

Example 491. N$^3$-(2,2-dimethyl-6-morpholino-2,3-dihydrobenzofuran-5-yl)pyrazolo[1,5-a]pyrimidine-3,6-dicarboxamide

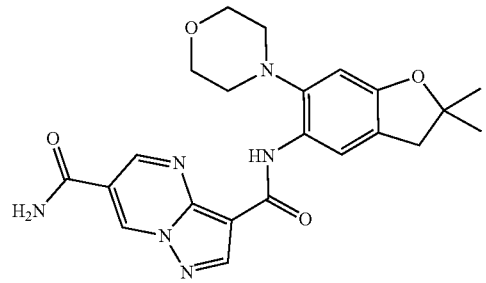

Step A: ethyl 3-((2,2-dimethyl-6-morpholino-2,3-dihydrobenzofuran-5-yl)carbamoyl) pyrazolo[1,5-a]pyrimidine-6-carboxylate

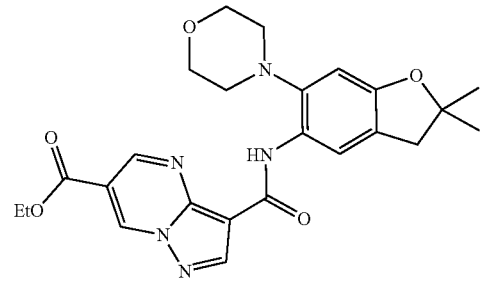

A solution of 6-bromo-N-(2,2-dimethyl-6-morpholino-3H-benzofuran-5-yl)pyrazolo[1,5-a]pyrimidine-3-carboxamide (150 mg, 0.3 mmol), triethylamine (96 mg, 1.0 mmol) and 1,1'-bis(diphenylphosphino) ferrocene palladium dichloride (23 mg, 0.03 mmol) in anhydrous ethanol (25 ml) was stirred at 80° C. for 20 h under CO atmosphere (40 psi). The reaction mixture was concentrated and the residue was purified by prep-TLC (4% methanol in dichloromethane) to afford ethyl 3-[(2,2-dimethyl-6-morpholino-3H-benzofuran-5-yl)carbamoyl]pyrazolo[1,5-a]pyrimidine-6-carboxylate (120.0 mg, 81%) as a yellow solid. LCMS (ESI): m/z=466.1 [M+H]$^+$.

Step B: N$^3$-(2,2-dimethyl-6-morpholino-2,3-dihydrobenzofuran-5-yl)pyrazolo[1,5-a]pyrimidine-3,6-dicarboxamide

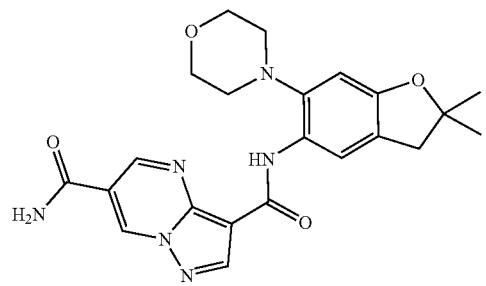

To ethyl 3-[(2,2-dimethyl-6-morpholino-3H-benzofuran-5-yl)carbamoyl]pyrazolo[1,5-a]pyrimidine-6-carboxylate (120.0 mg, 0.3 mmol) was added anhydrous ethanol (30 ml) saturated with ammonia (22.0 mg, 1.3 mmol). The mixture was stirred at 100° C. for 48 h and concentrated. The crude product was triturated with 10% methanol in dichloromethane twice to give N-3-(2,2-dimethyl-6-morpholino-3H-benzofuran-5-yl)pyrazolo[1,5-a]pyrimidine-3,6-dicarboxamide (37.1 mg, 32%) as a reddish purple solid. $^1$H NMR (400 MHz, DMSO-d6) δ 10.42 (s, 1H), 9.76 (d, J=2.0 Hz, 1H), 9.26 (d, J=2.0 Hz, 1H), 8.79 (s, 1H), 8.41 (s, 1H), 8.32 (s, 1H), 7.92 (s, 1H), 6.73 (s, 1H), 3.87-3.84 (m, 4H), 3.01 (s, 2H), 2.83-2.81 (m, 4H), 1.41 (s, 6H). LCMS (ESI): m/z=437.2 [M+H]$^+$.

Example 492. N3-[2-[(2R)-2-Fluoro-3-hydroxy-3-methyl-butyl]-6-morpholino-1-oxo-isoindolin-5-yl]-N$^6$-methyl-pyrazolo[1,5-a]pyrimidine-3,6-dicarboxamide

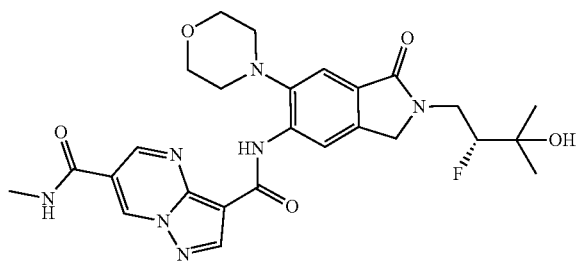

Step A: Methyl 3-[[2-[(2R)-2-fluoro-3-hydroxy-3-methyl-butyl]-6-morpholino-1-oxo-isoindolin-5-yl]carbamoyl]pyrazolo[1,5-a]pyrimidine-6-carboxylate

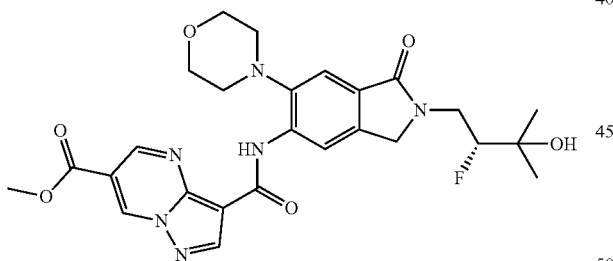

To a solution of 6-bromo-N-[2-[(2R)-2-fluoro-3-hydroxy-3-methyl-butyl]-6-morpholino-1-oxo-isoindolin-5-yl]pyrazolo[1,5-a]pyrimidine-3-carboxamide (Example 269 (100 mg, 0.18 mmol) in methanol (15 ml) was added triethylamine (54 mg, 0.53 mmol) and 1,1'-bis(diphenylphosphino)ferrocene palladium dichloride (7 mg, 0.01 mmol). The reaction was stirred at 80° C. for 16 h under CO (50 psi). The reaction was diluted with water (50 ml) and extracted with dichloromethane (100 ml×3). The organic phase was washed with brine (100 ml×2), dried over sodium sulfate, filtered and concentrated. The residue was purified by prep-TLC (10% methanol in dichloromethane) to afford methyl 3-[[2-[(2R)-2-fluoro-3-hydroxy-3-methyl-butyl]-6-morpholino-1-oxo-isoindolin-5-yl]carbamoyl]pyrazolo[1,5-a]pyrimidine-6-carboxylate (90 mg, 94% yield) as a brown solid. LCMS (ESI): m/z=541.1 [M+H]$^+$.

Step B: 3-[[2-[(2R)-2-Fluoro-3-hydroxy-3-methyl-butyl]-6-morpholino-1-oxo-isoindolin-5-yl]carbamoyl]pyrazolo[1,5-a]pyrimidine-6-carboxylic acid

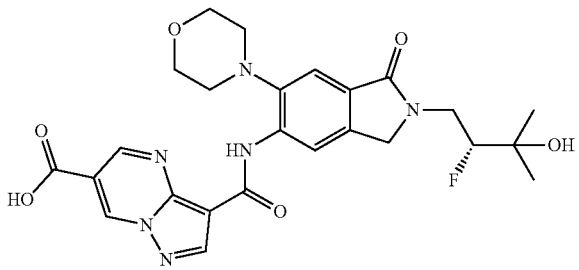 [SMILES: CC(C)(O)[C@H](F)CN1Cc2cc(NC(=O)c3cnn4cc(C(=O)O)cnc34)c(N3CCOCC3)cc2C1=O]

To a solution of methyl 3-[[2-[(2R)-2-fluoro-3-methyl-butyl]-6-morpholino-1-oxo-isoindolin-5-yl]carbamoyl]pyrazolo[1,5-a]pyrimidine-6-carboxylate (80 mg, 0.15 mmol) in methanol (2 ml) and water (1 ml) was added lithium hydroxide (18 mg, 0.74 mmol). The reaction was stirred at 30° C. for 2 h. The reaction was diluted with water (10 ml) and washed with ethyl acetate (50 ml×3). The aqueous phase was adjusted to pH 5 with hydrochloric acid (2 M) and extracted with dichloromethane (50 ml×3). The organic phase was washed with brine (50 ml×2), dried over sodium sulfate, filtered and concentrated to afford 3-[[2-[(2R)-2-fluoro-3-hydroxy-3-methyl-butyl]-6-morpholino-1-oxo-isoindolin-5-yl]carbamoyl]pyrazolo[1,5-a]pyrimidine-6-carboxylic acid (72 mg, 92%) as a brown solid. LCMS (ESI): m/z=527.1 [M+H]$^+$.

Step C: N3-[2-[(2R)-2-Fluoro-3-hydroxy-3-methyl-butyl]-6-morpholino-1-oxo-isoindolin-5-yl]-N$^6$-methyl-pyrazolo[1,5-a]pyrimidine-3,6-dicarboxamide

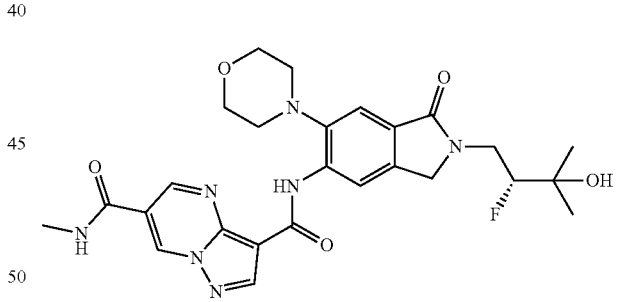

To a solution of 3-[[2-[(2R)-2-fluoro-3-hydroxy-3-methyl-butyl]-6-morpholino-1-oxo-isoindolin-5-yl]carbamoyl]pyrazolo[1,5-a]pyrimidine-6-carboxylic acid (72.0 mg, 0.14 mmol), methanamine hydrochloride (19 mg, 0.27 mmol) and HATU (78 mg, 0.21 mmol) in N,N-dimethylformamide (5 ml) was added N,N-diisopropylethylamine (0.05 ml, 0.27 mmol). The reaction was stirred at 30° C. for 30 min. The reaction was filtered and purified by reverse phase chromatography (Waters Xbridge Prep OBD C18 150 mm*30 mm, 5 m, acetonitrile 20-50%/0.05% ammonia hydroxide in water) to afford N$^3$-[2-[(2R)-2-fluoro-3-hydroxy-3-methyl-butyl]-6-morpholino-1-oxo-isoindolin-5-yl]-N$^6$-methyl-pyrazolo[1,5-a]pyrimidine-3,6-dicarboxamide (14.1 mg, 18.5% yield) as a yellow solid. $^1$H NMR (400 MHz, DMSO-d$_6$) δ 10.85 (s, 1H), 9.71 (d, J=2.0 Hz, 1H), 9.29 (d, J=2.0 Hz, 1H), 8.96-8.95 (m, 1H), 8.86 (s, 1H), 8.76 (s, 1H), 7.61 (s, 1H), 4.92 (s, 1H), 4.56-4.37 (m, 3H), 3.97-3.86 (m, 5H), 3.76-3.66 (m, 1H), 2.94-2.88 (m, 7H), 1.18 (s, 6H).

LCMS (ESI): m/z=540.1 [M+H]$^+$.

Example 493. 6-(difluoromethoxy)-N-(2,2-dimethyl-6-morpholino-2,3-dihydrobenzofuran-5-yl)pyrazolo[1,5-a]pyrimidine-3-carboxamide

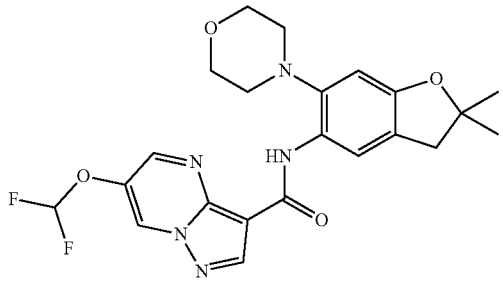 [SMILES: CC1(C)Cc2cc(NC(=O)c3cnn4cc(OC(F)F)cnc34)c(N3CCOCC3)cc2O1]

To a solution of N-(2,2-dimethyl-6-morpholino-2,3-dihydrobenzofuran-5-yl)-6-hydroxypyrazolo [1,5-a]pyrimidine-3-carboxamide (Example 530) (180 mg, 0.44 mmol) in DMF (8 ml) and water (0.8 ml) was added cesium carbonate (172 mg, 0.53 mmol) and sodium chlorodifluoroacetate (134 mg, 0.88 mmol). The mixture was heated at 100° C. for 16 h. The reaction mixture was cooled to room temperature, diluted with ethyl acetate (50 ml), and washed with H$_2$O (20 ml×2). The organic phase was dried over anhydrous sodium sulfate, filtered and concentrated. The residue was purified by prep-TLC (2% methanol in dichloromethane) to afford 6-(difluoromethoxy)-N-(2,2-dimethyl-6-morpholino-2,3-dihydrobenzofuran-5-yl)pyrazolo[1,5-a]pyrimidine-3-carboxamide (26 mg, 12%) as a yellow solid. $^1$H NMR (400 MHz, CDCl$_3$) δ 10.37 (s, 1H), 8.82-8.81 (m, 2H), 8.72 (d, J=2.4 Hz, 1H), 8.43 (s, 1H), 6.90-6.43 (m, 2H), 4.09-3.88 (m, 4H), 3.05 (s, 2H), 2.99-2.86 (m, 4H), 1.49 (s, 6H). LCMS (ESI): m/z=460.0 [M+H]$^+$.

Examples 494 and 495. N-[(2R)-6-[4-(2,2-difluoroethyl)piperazin-1-yl]-2-(hydroxymethyl)-2-methyl-3H-benzofuran-5-yl]-6-fluoro-pyrazolo[1,5-a]pyrimidine-3-carboxamide and N-[(2S)-6-[4-(2,2-difluoroethyl)piperazin-1-yl]-2-(hydroxymethyl)-2-methyl-3H-benzofuran-5-yl]-6-fluoro-pyrazolo[1,5-a]pyrimidine-3-carboxamide

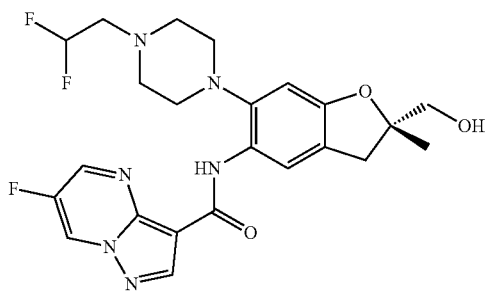

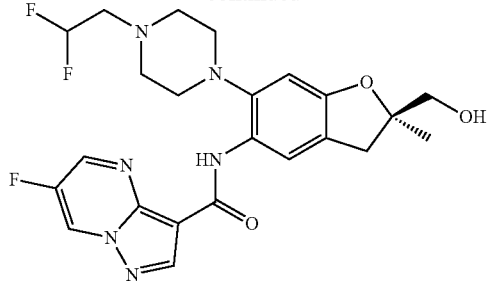

N-[6-[4-(2,2-difluoroethyl)piperazin-1-yl]-2-(hydroxymethyl)-2-methyl-3H-benzofuran-5-yl]-6-fluoro-pyrazolo[1,5-a]pyrimidine-3-carboxamide (Example 131, 155 mg, 0.32 mmol) was resolved by chiral SFC to afford N-[(2S)-6-[4-(2,2-difluoroethyl)piperazin-1-yl]-2-(hydroxymethyl)-2-methyl-3H-benzofuran-5-yl]-6-fluoro-pyrazolo[1,5-a]pyrimidine-3-carboxamide (70.44 mg, 44.1%) and N-[(2R)-6-[4-(2,2-difluoroethyl)piperazin-1-yl]-2-(hydroxymethyl)-2-methyl-3H-benzofuran-5-yl]-6-fluoro-pyrazolo[1,5-a]pyrimidine-3-carboxamide (71.18 mg, 44.5%) as yellow solids with absolute stereochemistry assigned arbitrarily.

Example 494, Peak 2: $^1$H NMR (400 MHz, DMSO-d$_6$) δ 10.24 (s, 1H), 9.85-9.75 (m, 1H), 9.20-9.10 (m, 1H), 8.71 (s, 1H), 8.27 (s, 1H), 6.70 (s, 1H), 6.40-6.05 (m, 1H), 5.10-4.95 (m, 1H), 3.50-3.40 (m, 2H), 3.25-3.10 (m, 1H), 3.00-2.70 (m, 11H), 1.34 (s, 3H). LCMS (ESI): m/z=491.2 [M+H]$^+$.

Example 495, Peak 1: $^1$H NMR (400 MHz, DMSO-d$_6$) δ 10.24 (s, 1H), 9.85-9.75 (m, 1H), 9.20-9.10 (m, 1H), 8.71 (s, 1H), 8.27 (s, 1H), 6.70 (s, 1H), 6.40-6.05 (m, 1H), 5.06 (s, 1H), 3.50-3.40 (m, 2H), 3.25-3.10 (m, 1H), 3.00-2.70 (m, 11H), 1.34 (s, 3H). LCMS (ESI): m/z=491.2 [M+H]$^+$.

Example 496. N-[6-(Cyclopropylmethoxy)-2-[(2R)-2-fluoro-3-hydroxy-3-methyl-butyl]-1-oxo-isoindolin-5-yl]pyrazolo[1,5-a]pyrimidine-3-carboxamide

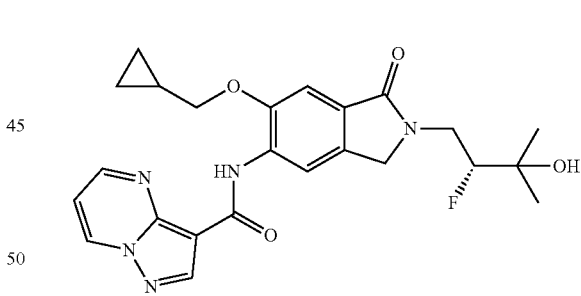

Step A: 1-Bromo-5-(cyclopropylmethoxy)-2-methyl-4-nitro-benzene

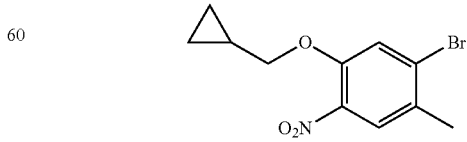

To a solution of cyclopropanemethanol (0.92 g, 12.82 mmol) and 1-bromo-5-fluoro-2-methyl-4-nitrobenzene (1.5 g, 6.41 mmol) in tetrahydrofuran (50 ml) was added sodium tert-butoxide (0.74 g, 7.69 mmol). The mixture was stirred at 50° C. for 16 h. The mixture was filtered and concentrated. The crude product was purified by flash column chromatography (5% ethyl acetate in petroleum ether) to give 1-bromo-5-(cyclopropylmethoxy)-2-methyl-4-nitro-benzene (1.1 g, 60% yield) as a white solid.

$^1$H NMR (400 MHz, CDCl$_3$) δ 7.74 (s, 1H), 7.25 (s, 1H), 3.95 (d, J=6.4 Hz, 2H), 2.38 (s, 3H), 1.32-1.26 (m, 1H), 0.71-0.64 (m, 2H), 0.42-0.38 (m, 2H).

Step B: Ethyl 5-(cyclopropylmethoxy)-2-methyl-4-nitro-benzoate

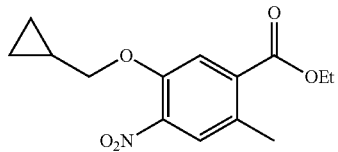 [SMILES: CCOC(=O)c1cc(OCC2CC2)c([N+](=O)[O-])cc1C]

To a solution of 1-bromo-5-(cyclopropylmethoxy)-2-methyl-4-nitro-benzene (500 mg, 1.75 mmol) in triethylamine (10 ml, 72 mmol) and ethanol (20 ml) was added bis(triphenylphosphine)palladium(II) dichloride (122 mg, 0.17 mmol). The reaction was stirred at 80° C. for 16 h under CO (40-50 psi). The reaction was filtered and concentrated. The crude product was purified by flash column chromatography (3% ethyl acetate in petroleum ether) to give ethyl 5-(cyclopropylmethoxy)-2-methyl-4-nitro-benzoate (340 mg, 69% yield) as a yellow solid. $^1$H NMR (400 MHz, CDCl$_3$) δ 7.65 (s, 1H), 7.57 (s, 1H), 4.40 (q, J=7.2 Hz, 2H), 4.00 (d, J=6.8 Hz, 2H), 2.55 (s, 3H), 1.42 (t, J=7.2 Hz, 3H), 1.31-1.27 (m, 1H), 0.70-0.62 (m, 2H), 0.43-0.36 (m, 2H).

Step C: Ethyl 2-(bromomethyl)-5-(cyclopropylmethoxy)-4-nitro-benzoate

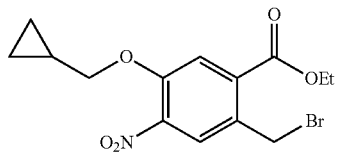 [SMILES: CCOC(=O)c1cc(OCC2CC2)c([N+](=O)[O-])cc1CBr]

To a solution of ethyl 5-(cyclopropylmethoxy)-2-methyl-4-nitro-benzoate (400 mg, 1.43 mmol) in acetonitrile (10 ml) was added 1-bromo-2,5-pyrrolidinedione (305 mg, 1.72 mmol) and 2,2'-azobis(2-methylpropionitrile) (35 mg, 0.21 mmol). The mixture was stirred at 80° C. for 16 h under nitrogen and concentrated. The crude product was purified by flash column chromatography (2% ethyl acetate in petroleum ether) to afford ethyl 2-(bromomethyl)-5-(cyclopropylmethoxy)-4-nitro-benzoate (260 mg, 50% yield) as a yellow solid. $^1$H NMR (400 MHz, CDCl$_3$) δ 7.88 (s, 1H), 7.61 (s, 1H), 4.87 (s, 2H), 4.46 (q, J=7.2 Hz, 2H), 4.04 (d, J=6.8 Hz, 2H), 1.46 (t, J=7.2 Hz, 3H), 1.34-1.29 (m, 1H), 0.73-0.64 (m, 2H), 0.45-0.37 (m, 2H).

Step D: 6-(Cyclopropylmethoxy)-2-[(2R)-2-fluoro-3-hydroxy-3-methyl-butyl]-5-nitro-isoindolin-1-one

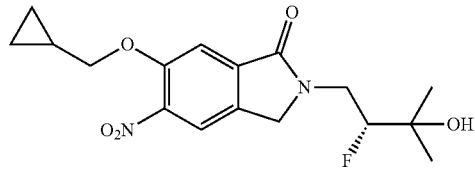 [SMILES: CC(C)(O)[C@H](F)CN1Cc2cc([N+](=O)[O-])c(OCC3CC3)cc2C1=O]

To a solution of ethyl 2-(bromomethyl)-5-(cyclopropylmethoxy)-4-nitro-benzoate (370 mg, 1.03 mmol) in methyl alcohol (15 ml) was added (3R)-4-amino-3-fluoro-2-methyl-butan-2-ol (187 mg, 1.55 mmol) and triethylamine (209 mg, 2.07 mmol). The reaction was stirred at 60° C. for 5 h. The reaction was concentrated and purified by flash chromatography (70% ethyl acetate in petroleum ether) to afford 6-(cyclopropylmethoxy)-2-[(2R)-2-fluoro-3-hydroxy-3-methyl-butyl]-5-nitro-isoindolin-1-one (190 mg, 52% yield) as a yellow solid. $^1$H NMR (400 MHz, CDCl$_3$) δ 7.84 (s, 1H), 7.51 (s, 1H), 4.69-4.42 (m, 3H), 4.35-4.15 (m, 1H), 4.05 (d, J=6.4 Hz, 2H), 3.73-3.63 (m, 1H), 2.31-2.15 (m, 1H), 1.36-1.32 (m, 6H), 1.31-1.28 (m, 1H), 0.71-0.63 (m, 2H), 0.45-0.35 (m, 2H).

Step E: 5-Amino-6-(cyclopropylmethoxy)-2-[(2R)-2-fluoro-3-hydroxy-3-methyl-butyl]isoindolin-1-one

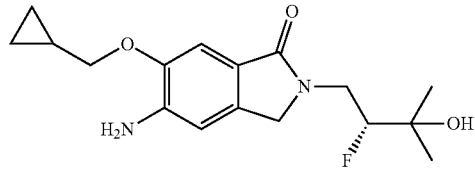

To a solution of 6-(cyclopropylmethoxy)-2-[(2R)-2-fluoro-3-hydroxy-3-methyl-butyl]-5-nitro-isoindolin-1-one (190 mg, 0.54 mmol) in ethanol (10 ml) and water (2 ml) was added iron (150 mg, 2.7 mmol) and ammonium chloride (144 mg, 2.7 mmol). The reaction was stirred at 80° C. for 2 h. The reaction was filtered, then concentrated. The reaction was taken up in dichloromethane (80 ml×2), washed with brine (80 ml), dried over sodium sulfate, and concentrated to give 5-amino-6-(cyclopropylmethoxy)-2-[(2R)-2-fluoro-3-hydroxy-3-methyl-butyl]isoindolin-1-one (170 mg, 97% yield) as a yellow solids. LCMS (ESI): m/z=323.0 [M+H]$^+$.

Step F: N-[6-(Cyclopropylmethoxy)-2-[(2R)-2-fluoro-3-hydroxy-3-methyl-butyl]-1-oxo-isoindolin-5-yl]pyrazolo[1,5-a]pyrimidine-3-carboxamide

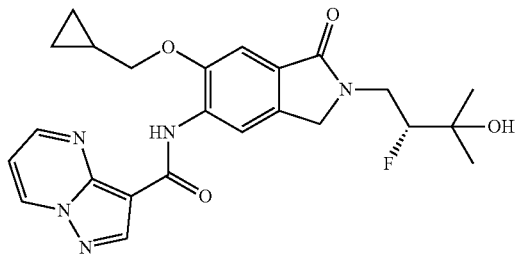 [SMILES: CC(C)(O)[C@H](F)CN1Cc2cc(NC(=O)c3cnn4cccnc34)c(OCC3CC3)cc2C1=O]

To a solution of pyrazolo[1,5-a]pyrimidine-3-carbonyl chloride (148 mg, 0.82 mmol) in pyridine (5 ml) was added 5-amino-6-(cyclopropylmethoxy)-2-[(2R)-2-fluoro-3-hydroxy-3-methyl-butyl]isoindolin-1-one (220 mg, 0.68 mmol). The reaction mixture was stirred at 50° C. for 16 h. The reaction was concentrated and purified by flash column chromatography (75% ethyl acetate in dichloromethane) to give N-[6-(cyclopropylmethoxy)-2-[(2R)-2-fluoro-3-hydroxy-3-methyl-butyl]-1-oxo-isoindolin-5-yl]pyrazolo[1,5-a]pyrimidine-3-carboxamide (252 mg, 77% yield) as a yellow solid. $^1$H NMR (400 MHz, DMSO-$d_6$) δ 10.80 (s, 1H), 9.38 (d, J=7.2 Hz, 1H), 8.87 (d, J=3.2 Hz, 1H), 8.76-8.68 (m, 2H), 7.35-7.30 (m, 1H), 7.25 (s, 1H), 4.91 (s, 1H), 4.55-4.35 (m, 3H), 4.09-3.84 (m, 3H), 3.75-3.61 (m, 1H), 1.49-1.43 (m, 1H), 1.23-1.13 (m, 6H), 0.73-0.65 (m, 2H), 0.49-0.41 (m, 2H). LCMS (ESI): m/z=468.1 [M+H]$^+$.

Examples 497 and 498. N-((2R,3'S)-1',3'-dimethyl-6-morpholino-3H-spiro[benzofuran-2,4'-piperidin]-5-yl)pyrazolo[1,5-a]pyrimidine-3-carboxamide and N-((2R,3'R)-1',3'-dimethyl-6-morpholino-3H-spiro[benzofuran-2,4'-piperidin]-5-yl)pyrazolo[1,5-a]pyrimidine-3-carboxamide

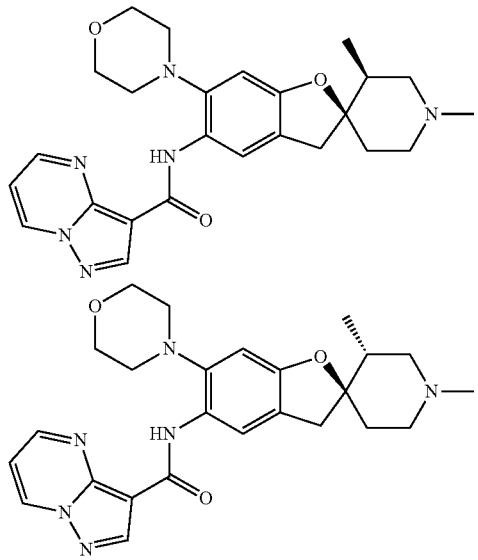

To a solution of 1',3'-dimethyl-6-morpholino-spiro[3H-benzofuran-2,4'-piperidine]-5-amine (900 mg, 2.84 mmol; prepared following the procedure described for Example 152 from 1,3-dimethylpiperidin-4-one) in pyridine (50 ml) was added pyrazolo[1,5-a]pyrimidine-3-carbonyl chloride (669 mg, 3.69 mmol). The mixture was stirred at 60° C. for 3 h. The reaction was concentrated, and the residue was triturated with methanol (5 ml) to afford N-(1',3'-dimethyl-6-morpholino-spiro[3H-benzofuran-2,4'-piperidine]-5-yl)pyrazolo[1,5-a] pyrimidine-3-carboxamide (1.0 g, 76% yield) as a yellow solid. It was resolved by chiral preparatory SFC to afford N-[(2R,3'S)-1',3'-dimethyl-6-morpholino-spiro[3H-benzofuran-2,4'-piperidine]-5-yl]pyrazolo[1,5-a] pyrimidine-3-carboxamide (325 mg, 25%; RT=2.105 min) and N-[(2R,3'R)-1',3'-dimethyl-6-morpholino-spiro[3H-benzofuran-2,4'-piperidine]-5-yl]pyrazolo[1,5-a]pyrimidine-3-carboxamide (350 mg, 26.4%; RT=2.822 min) as yellow solids with absolute stereochemistry assigned arbitrarily.

Example 497, Peak 1: $^1$H NMR (400 MHz, CDCl$_3$) δ 10.46 (s, 1H), 8.89-8.81 (m, 1H), 8.79 (s, 1H), 8.78-8.76 (m, 1H), 8.41 (s, 1H), 7.07 (dd, J=6.8, 4.0 Hz, 1H), 6.68 (s, 1H), 3.96-3.94 (m, 4H), 3.22 (d, J=15.6 Hz, 1H), 2.93-2.89 (m, 5H), 2.70-2.63 (m, 2H), 2.42-2.39 (m, 1H), 2.34 (s, 3H), 2.22-2.18 (m, 1H), 2.05-2.01 (m, 1H), 1.93-1.84 (m, 1H), 1.82-1.81 (m, 1H), 0.87 (d, J=6.4 Hz, 3H). LCMS (ESI): m/z=463.3 [M+H]$^+$.

Example 498, Peak 2: $^1$H NMR (400 MHz, CDCl$_3$) δ 10.44 (s, 1H), 8.85 (dd, J=6.8, 1.6 Hz, 1H), 8.79 (s, 1H), 8.77 (dd, J=4.0, 1.6 Hz, 1H), 8.45 (s, 1H), 7.08 (dd, J=6.8, 4.0 Hz, 1H), 6.64 (s, 1H), 3.96-3.94 (m, 4H), 3.42-3.37 (m, 1H), 3.30 (d, J=16.8 Hz, 1H), 3.27-3.22 (m, 1H), 3.20-3.12 (m, 1H), 2.94 (d, J=16.8 Hz, 1H), 2.93-2.90 (m, 5H), 2.82 (s, 3H), 2.68-2.62 (m, 1H), 2.61-2.55 (m, 1H), 2.17-2.13 (m, 1H), 0.92 (d, J=6.8 Hz, 3H). LCMS (ESI): m/z=463.1 [M+H]$^+$.

Example 499. N-(2,2-Dimethyl-6-morpholino-1-oxo-2,3-dihydro-1H-inden-5-yl)pyrazolo[1,5-a]pyrimidine-3-carboxamide

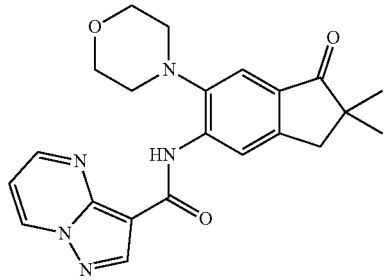 [SMILES: CC1(C)Cc2cc(NC(=O)c3cnn4cccnc34)c(N3CCOCC3)cc2C1=O]

Step A: N-(2,3-Dihydro-1H-inden-5-yl)acetamide

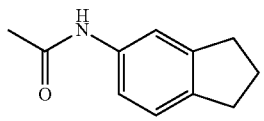

To a stirred solution of 2,3-dihydro-1H-inden-5-ylamine (15.0 g, 112.6 mmol) and triethylamine (17.1 g, 168.9 mmol) in dichloromethane (300 ml) was added acetyl chloride (26.5 g, 337.9 mmol) dropwise. The mixture was stirred at 26° C. for 2.5 h, quenched with methanol (20 ml) and water (100 ml), and extracted with dichloromethane (150 mL×3). The combined organic phase was dried over anhydrous sodium sulfate, filtered and concentrated. The residue was purified by flash column chromatography (20-45% ethyl acetate in petroleum ether) to afford N-(2,3-dihydro-1H-inden-5-yl)acetamide (19.0 g, 96%) as a light brown solid. $^1$H NMR (400 MHz, CDCl$_3$) δ 7.65 (s, 1H), 7.43 (s, 1H), 7.17-7.12 (m, 2H), 2.89-2.83 (m, 4H), 2.14 (s, 3H), 2.06 (quint, J=7.2 Hz, 2H).

Step B: N-(6-bromoindan-5-yl)acetamide

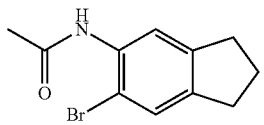

To a stirred solution of N-(2,3-dihydro-1H-inden-5-yl)acetamide (19.0 g, 108.4 mmol) in acetic acid (350 ml) was added bromine (6.83 ml, 133.4 mmol) in acetic acid (3 ml) at 0° C. over a period of 20 min. The mixture was stirred at 26° C. for 1 h under nitrogen, and diluted with water until no more precipitate formed. The precipitate was collected, washed with water, and dried under vacuum to give N-(6-bromoindan-5-yl)acetamide (27.0 g, 98%) as a light yellow solid. LCMS (ESI): m/z=255.8 [M+H]$^+$.

Step C: N-(6-bromo-1-oxo-indan-5-yl)acetamide

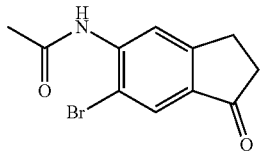

To a stirred solution of N-(6-bromoindan-5-yl)acetamide (27.0 g, 106.3 mmol) in acetic acid (300 ml) was added dropwise chromium trioxide (44.0 g, 439.9 mmol) in 50% aqueous acetic acid (34 ml) at 50° C. and stirred for another 20 min. Then it was cooled to 0° C. when the reaction was quenched with 2-propanol (10 ml). The solvent was removed in vacuo, and the residue was diluted with water (100 ml) and extracted with ethyl acetate (100 ml×3). The combined organic phase was washed with 0.5 M aqueous NaOH (50 ml) and brine, dried over anhydrous sodium sulfate, and concentrated. The residue was purified by flash column chromatography (0-4% methanol in dichloromethane) to afford N-(6-bromo-1-oxo-indan-5-yl)acetamide (13.1 g, 46%) as a light yellow solid. $^1$H NMR (400 MHz, CDCl$_3$) δ 8.59 (s, 1H), 7.94 (s, 1H), 7.91 (br s, 1H), 3.11 (t, J=6.0 Hz, 2H), 2.71 (t, J=6.0 Hz, 2H), 2.30 (s, 3H).

Step D: 5-Amino-6-bromo-indan-1-one

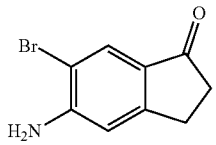

A mixture of N-(6-bromo-1-oxo-indan-5-yl)acetamide (13.1 g, 48.9 mmol) and 6 M aqueous hydrochloric acid (260 ml, 1.560 mol) was stirred at 100° C. for 1 h under nitrogen. The solution was cooled to 0° C. and adjusted to pH=8 with 10 M aqueous sodium hydroxide solution. The precipitate formed was collected, washed with water, and dried under vacuum to afford 5-amino-6-bromo-indan-1-one (10.8 g, 98%) as a light brown powder. $^1$H NMR (400 MHz, CDCl$_3$) δ 7.86 (s, 1H), 6.74 (s, 1H), 4.68 (s, 2H), 2.98 (t, J=6.0 Hz, 2H), 2.64 (t, J=6.0 Hz, 2H).

Step E: 6-Bromo-5-nitro-indan-1-one

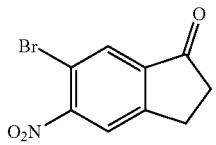

To a suspension of 5-amino-6-bromo-indan-1-one (4.0 g, 17.7 mmol) in 20% aqueous HBF$_4$ (16 ml) at 0° C. was added 4 M aqueous sodium nitrite (1.9 g, 27.3 mmol) drop wise over a period of 5 min. The mixture was stirred for 50 min after the addition was completed. The resulting foamy suspension was added portion wise to a vigorously stirred mixture of copper (5.3 g, 83.2 mmol) and sodium nitrite (16.3 g, 236.7 mmol) in water (32 ml) at 26° C. over a period of 30 min. During the addition, excessive foaming was broken up by the addition of small amounts of diethyl ether. After the mixture was stirred for a further 50 min, it was filtered through Celite pad and washed with ethyl acetate (300 ml). The organic phase was separated, washed with brine, dried over anhydrous sodium sulfate, filtered and concentrated. The residue was purified by flash column chromatography (10-20% ethyl acetate in petroleum ether) to afford 6-bromo-5-nitro-indan-1-one (2.1 g, 47%) as a yellow solid. $^1$H NMR (400 MHz, CDCl$_3$) δ 8.08 (s, 1H), 7.85 (s, 1H), 3.21 (t, J=6.0 Hz, 2H), 2.83 (t, J=6.0 Hz, 2H).

Step F: 6-Bromo-2,2-dimethyl-5-nitro-indan-1-one

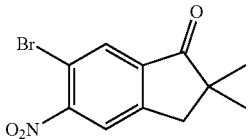 [SMILES: CC1(C)Cc2cc([N+](=O)[O-])c(Br)cc2C1=O]

To a mixture of 6-bromo-5-nitro-indan-1-one (1.2 g, 4.5 mmol) and iodomethane (1.4 ml, 22.9 mmol) in N, N-dimethylformamide (40 ml) was added 60% sodium hydride mineral oil (544 mg, 13.6 mmol) in batches at 0° C. The mixture was stirred at 0° C. for 10 min, quenched by saturated ammonium chloride solution (10 mL) and extracted with ethyl acetate (100 ml×3). The combined organic phase was dried over sodium sulfate, filtered and concentrated. The residue was purified by flash column chromatography (2-5% ethyl acetate in petroleum ether) to afford 6-bromo-2,2-dimethyl-5-nitro-indan-1-one (450 mg, 35%) as a yellow solid. LCMS (ESI): m/z=284.1 [M+H]$^+$.

Step G:
2,2-Dimethyl-6-morpholino-5-nitro-indan-1-one

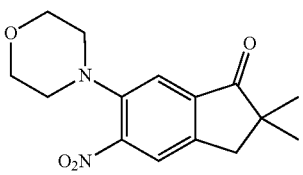 [SMILES: CC1(C)Cc2cc([N+](=O)[O-])c(N3CCOCC3)cc2C1=O]

To a stirred solution of 6-bromo-2,2-dimethyl-5-nitro-indan-1-one (450 mg, 1.6 mmol) in dimethyl sulfoxide (18 ml) was added morpholine (276 mg, 3.2 mmol) and N,N-diisopropylethylamine (614 mg, 4.8 mmol). The mixture was stirred at 110° C. for 16 h, diluted with water (50 ml), and extracted with ethyl acetate (100 ml×3). The combined organic phase was washed with brine (30 ml), dried over sodium sulfate, filtered and concentrated. The residue was purified by flash column chromatography (10% ethyl acetate in petroleum ether) to give the mixture of 2,2-dimethyl-6-morpholino-5-nitro-indan-1-one and 6-bromo-2,2-dimethyl-5-morpholino-indan-1-one (340 mg, 74%) as a yellow solid which was used directly for next step. LCMS (ESI): m/z=290.9 [M+H]$^+$.

Step H:
5-Amino-2,2-dimethyl-6-morpholino-indan-1-one

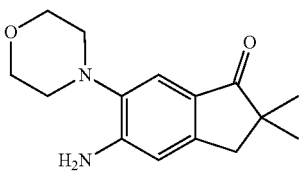

To a stirred mixture of 2,2-dimethyl-6-morpholino-5-nitro-indan-1-one and 6-bromo-2,2-dimethyl-5-morpholino-indan-1-one (340 mg) in ethanol (25 ml) and water (5 ml) was added iron (327 mg, 5.9 mmol) and ammonium chloride (313 mg, 5.9 mmol). The mixture was stirred at 80° C. for 2 h under nitrogen. The reaction mixture was filtered and concentrated. The residue was purified by flash column chromatography (20-60% ethyl acetate in petroleum ether) to afford 5-amino-2,2-dimethyl-6-morpholino-indan-1-one (190 mg, 62%) as light a yellow solid. LCMS (ESI): m/z=261.0 [M+H]$^+$.

Step I: N-(2,2-dimethyl-6-morpholino-1-oxo-2,3-dihydro-1H-inden-5-yl)pyrazolo[1,5-a]pyrimidine-3-carboxamide

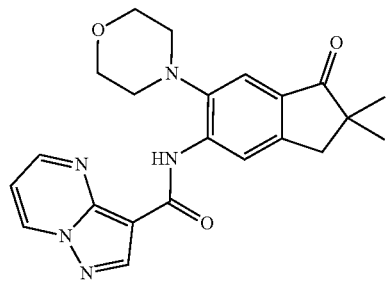

A mixture of 5-amino-2,2-dimethyl-6-morpholino-indan-1-one (50 mg, 0.2 mmol) and pyrazolo[1,5-a]pyrimidine-3-carbonyl chloride (52 mg, 0.3 mmol) in pyridine (5 ml) was stirred at 28° C. for 20 h and concentrated. The residue was purified by flash column chromatography (eluting 0-1% methanol in dichloromethane) followed by prep-TLC (100% ethyl acetate). The crude product was further triturated with methanol to afford N-(2,2-dimethyl-6-morpholino-1-oxo-indan-5-yl)pyrazolo[1,5-a]pyrimidine-3-carboxamide (54 mg, 68%) as a white solid. 1H NMR (400 MHz, DMSO-d$_6$): δ 10.94 (s, 1H), 9.40 (d, J=6.8 Hz, 1H), 8.98 (d, J=4.4 Hz, 1H), 8.75 (s, 1H), 8.68 (s, 1H), 7.53 (s, 1H), 7.38 (dd, J=6.8, 4.4 Hz, 1H), 3.91-3.85 (m, 4H), 2.98 (s, 2H), 2.91-2.86 (m, 4H), 1.14 (s, 6H). LCMS (ESI): m/z=406.1 [M+H]$^+$.

Example 500. N-[2-[(2R)-2-Fluoro-3-hydroxy-3-methyl-butyl]-1-oxo-isoindolin-5-yl]pyrazolo[1,5-a]pyrimidine-3-carboxamide

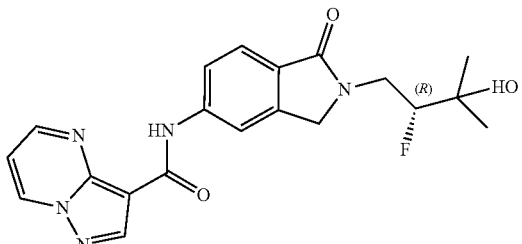

Step A: 5-amino-2-[(2R)-2-fluoro-3-hydroxy-3-methyl-butyl]isoindolin-1-one

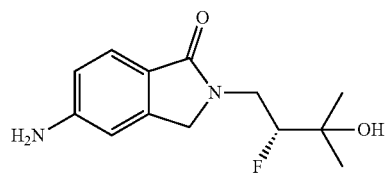 [SMILES: CC(C)(O)[C@H](F)CN1Cc2cc(N)ccc2C1=O]

To a solution of 6-chloro-2-[(2R)-2-fluoro-3-hydroxy-3-methyl-butyl]-5-nitro-isoindolin-1-one (100 mg, 0.32 mmol) in methanol (30 ml) was added 10% palladium on carbon (7 mg, 0.06 mmol). The reaction mixture was stirred at 25° C. for 6 h under a hydrogen atmosphere (15 psi). The mixture was filtered and the filtrate was concentrated. The residue was purified by flash chromatography (0-50% ethyl acetate in petroleum ether) to afford 5-amino-2-[(2R)-2-fluoro-3-hydroxy-3-methyl-butyl]isoindolin-1-one (50 mg, 63%) as a white solid. LCMS (ESI): m/z=253.1 [M+H]$^+$.

Step B: N-[2-[(2R)-2-Fluoro-3-hydroxy-3-methyl-butyl]-1-oxo-isoindolin-5-yl]pyrazolo[1,5-a]pyrimidine-3-carboxamide

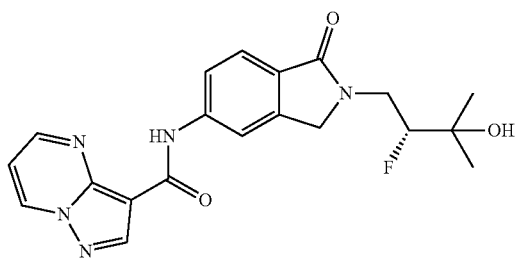 [SMILES: CC(C)(O)[C@H](F)CN1Cc2cc(NC(=O)c3cnn4cccnc34)ccc2C1=O]

To a solution of pyrazolo[1,5-a]pyrimidine-3-carbonyl chloride (47 mg, 0.26 mmol) in pyridine (2 ml) was added 5-amino-2-[(2R)-2-fluoro-3-hydroxy-3-methyl-butyl]isoindolin-1-one (55 mg, 0.22 mmol). The reaction mixture was stirred at 50° C. for 16 h and concentrated. The residue was purified by flash column chromatography (3% methyl alcohol in dichloromethane) to give N-[2-[(2R)-2-fluoro-3-hydroxy-3-methyl-butyl]-1-oxo-isoindolin-5-yl]pyrazolo[1,5-a]pyrimidine-3-carboxamide (29 mg, 32%) as a white solid. $^1$H NMR (400 MHz, CDCl$_3$) δ 10.13 (s, 1H), 8.88-8.85 (m, 1H), 8.79 (s, 1H), 8.77-8.75 (m, 1H), 8.33 (s, 1H), 7.84 (d, J=8.0 Hz, 1H), 7.53-7.50 (m, 1H), 7.11 (dd, J=6.8, 4.0 Hz, 1H), 4.69-4.45 (m, 3H), 4.25-4.15 (m, 1H), 3.68-3.64 (m, 1H), 2.42 (s, 1H), 1.35 (s, 3H), 1.33 (s, 3H). LCMS (ESI): m/z=398.2 [M+H]$^+$.

Example 501. N-(1'-(2-fluoroethyl)-6-morpholino-3H-spiro[benzofuran-2,4'-piperidin]-5-yl)pyrazolo[1,5-a]pyrimidine-3-carboxamide

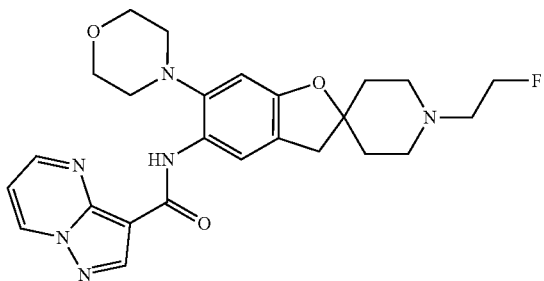

To a solution of N-(6-morpholinospiro[3H-benzofuran-2,4'-piperidine]-5-yl)pyrazolo[1,5-a]pyrimidine-3-carboxamide (80 mg, 0.18 mmol), 1-bromo-2-fluoroethane (70 mg, 0.55 mmol) in acetonitrile (10 ml) was added N,N-diisopropylethylamine (71 mg, 0.55 mmol). The reaction was stirred at 60° C. for 16 h. The reaction was diluted with water (10 ml) and extracted with dichloromethane (20 ml×3). The combined organic phase was washed with brine (20 ml×2), dried over sodium sulfate, filtered and concentrated. The residue was triturated with acetonitrile (3 ml) to afford N-[1'-(2-fluoroethyl)-6-morpholino-spiro[3H-benzofuran-2,4'-piperidine]-5-yl]pyrazolo[1,5-a] pyrimidine-3-carboxamide (48 mg, 54% yield) as a yellow solid. $^1$H NMR (400 MHz, CDCl$_3$) δ 10.48 (s, 1H), 8.84 (dd, J=6.8 Hz, 1.6 Hz, 1H), 8.79 (s, 1H), 8.78 (dd, J=4.0 Hz, 1.6 Hz, 1H), 8.43 (s, 1H), 7.07 (dd, J=6.8 Hz, 4.0 Hz, 1H), 6.69 (s, 1H), 4.71-4.68 (m, 1H), 4.60-4.57 (m, 1H), 3.97-3.94 (m, 4H), 3.03 (s, 2H), 2.94-2.90 (m, 4H), 2.86-2.83 (m, 1H), 2.80-2.70 (m, 5H), 2.05-2.01 (m, 2H), 2.00-1.91 (m, 2H). LCMS (ESI): m/z=481.3 [M+H]$^+$.

Example 502. N-(1'-ethyl-6-morpholino-3H-spiro[benzofuran-2,4'-piperidin]-5-yl)pyrazolo[1,5-a]pyrimidine-3-carboxamide

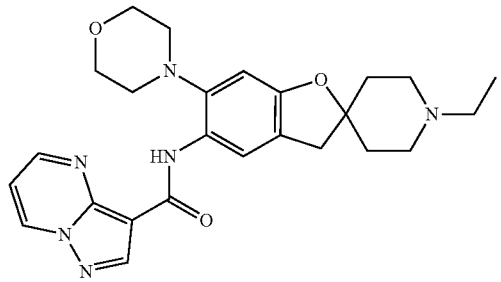

To a solution of N-(6-morpholinospiro[3H-benzofuran-2,4'-piperidine]-5-yl)pyrazolo[1,5-a]pyrimidine-3-carboxamide (200 mg, 0.46 mmol), acetaldehyde (61 mg, 1.38 mmol) and acetic acid (0.6 ml) in methanol (20 ml) was added sodium cyanoborohydride (34.7 mg, 0.55 mmol). The solution was stirred at 20° C. for 3 h. The reaction was concentrated. The residue was taken up in ethyl acetate (20 ml) and washed with water (20 ml×2) and brine (20 ml). The organic phase was dried over sodium sulfate, filtered and concentrated. The crude product was purified by prep-TLC (5% methanol in dichloromethane) to afford N-(1'-ethyl-6-morpholino-spiro[3H-benzofuran-2,4'-piperidine]-5-yl) pyrazolo[1,5-a]pyrimidine-3-carboxamide (32 mg, 15% yield) as a white solid. $^1$H NMR (400 MHz, DMSO-d$_6$) δ 10.43 (s, 1H), 9.36 (d, J=6.0 Hz, 1H), 8.96-8.91 (m, 1H), 8.67 (s, 1H), 8.30 (s, 1H), 7.34 (dd, J=6.8, 4.0 Hz, 1H), 6.75 (s, 1H), 3.90-3.81 (m, 4H), 2.98 (s, 2H), 2.81-2.79 (m, 4H), 2.60-2.55 (m, 2H), 2.40-2.37 (m, 4H), 1.84-1.74 (m, 4H), 1.01 (t, J=6.8 Hz, 3H). LCMS (ESI): m/z=463.3 [M+H]$^+$.

TABLE 21

The following examples were made in a manner similar to that for Example 502:

| Ex. | Name | Structure | NMR, MS |
|---|---|---|---|
| 503. | N-(6-(4-((1H-imidazol-2-yl)methyl)piperazin-1-yl)-2,2-dimethyl-2,3-dihydrobenzofuran-5-yl)pyrazolo[1,5-a]pyrimidine-3-carboxamide | 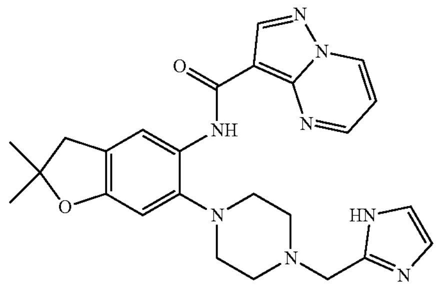 [SMILES: CC1(C)Cc2cc(NC(=O)c3cnn4cccnc34)c(N3CCN(Cc4ncc[nH]4)CC3)cc2O1] | $^1$H NMR (400 MHz, DMSO-$d_6$) δ 11.91 (s, 1H), 10.41 (s, 1H), 9.36 (dd, J = 7.0, 1.6 Hz, 1H), 8.66 (s, 1H), 8.61 (dd, J = 4.2, 1.7 Hz, 1H), 8.32 (d, J = 1.0 Hz, 1H), 7.95 (s, 0H), 7.36 (dd, J = 7.0, 4.2 Hz, 1H), 7.09 (s, 1H), 6.89 (s, 1H), 6.68 (s, 1H), 3.66 (s, 2H), 3.17 (d, J = 5.2 Hz, 1H), 2.99 (d, J = 1.1 Hz, 2H), 2.85-2.79 (m, 4H), 2.70-2.61 (m, 4H), 1.41 (s, 6H). MS (ESI): m/z = 473.2 [M + H]$^+$. |
| 504. | N-(6-(4-(isoxazol-4-ylmethyl)piperazin-1-yl)-2,2-dimethyl-2,3-dihydrobenzofuran-5-yl)pyrazolo[1,5-a]pyrimidine-3-carboxamide | 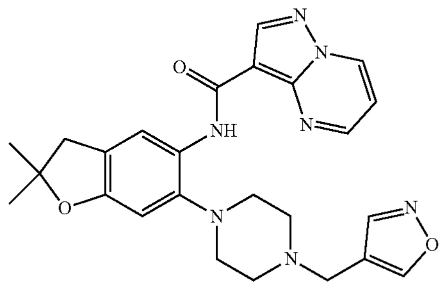 [SMILES: CC1(C)Cc2cc(NC(=O)c3cnn4cccnc34)c(N3CCN(Cc4cnoc4)CC3)cc2O1] | $^1$H NMR (400 MHz, DMSO-$d_6$) δ 10.38 (s, 1H), 9.36 (dd, J = 7.0, 1.6 Hz, 1H), 8.88 (s, 1H), 8.67 (s, 1H), 8.63 (dd, J = 4.2, 1.7 Hz, 1H), 8.59 (s, 1H), 8.29 (d, J = 1.0 Hz, 1H), 7.30 (dd, J = 7.0, 4.2 Hz, 1H), 6.69 (s, 1H), 3.55 (d, J = 0.8 Hz, 2H), 3.04-2.93 (m, 2H), 2.82 (t, J = 4.6 Hz, 4H), 2.62 (d, J = 5.9 Hz, 4H), 1.41 (s, 6H). MS (ESI): m/z = 474.2 [M + H]$^+$. |
| 505. | N-(6-(4-((1H-pyrazol-5-yl)methyl)piperazin-1-yl)-2,2-dimethyl-2,3-dihydrobenzofuran-5-yl)pyrazolo[1,5-a]pyrimidine-3-carboxamide | 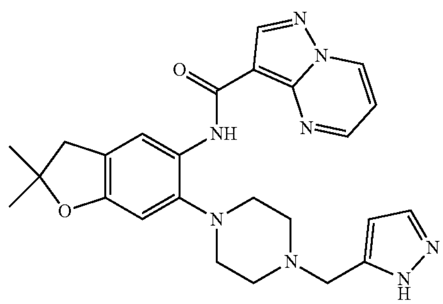 [SMILES: CC1(C)Cc2cc(NC(=O)c3cnn4cccnc34)c(N3CCN(Cc4ccn[nH]4)CC3)cc2O1] | $^1$H NMR (400 MHz, DMSO-$d_6$) δ 10.41 (s, 1H), 9.36 (dd, J = 7.3, 1.6 Hz, 1H), 8.66 (s, 1H), 8.42 (d, J = 33.5 Hz, 1H), 8.32 (d, J = 1.0 Hz, 1H), 7.80-7.19 (m, 2H), 6.69 (s, 1H), 6.19 (s, 1H), 3.66 (d, J = 22.3 Hz, 2H), 3.17 (d, J = 5.3 Hz, 1H), 2.99 (d, J = 1.1 Hz, 2H), 2.81 (t, J = 4.7 Hz, 4H), 2.71-2.60 (m, 4H), 1.41 (s, 6H). MS (ESI): m/z = 73.2 [M + H]$^+$. |
| 506. | N-(2,2-dimethyl-6-(4-((1-methyl-1H-imidazol-5-yl)methyl)piperazin-1-yl)-2,3-dihydrobenzofuran-5-yl)pyrazolo[1,5-a]pyrimidine-3-carboxamide | 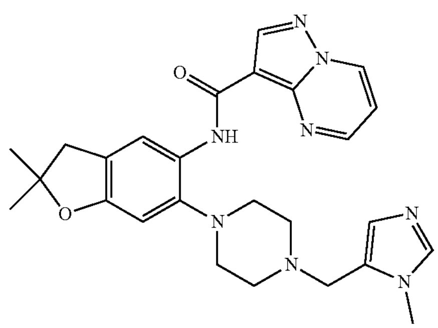 [SMILES: Cn1cncc1CN1CCN(c2cc3c(cc2NC(=O)c2cnn4cccnc24)CC(C)(C)O3)CC1] | $^1$H NMR (400 MHz, DMSO-$d_6$) δ 10.39 (s, 1H), 9.37 (dd, J = 7.0, 1.6 Hz, 1H), 8.80 (dd, J = 4.2, 1.6 Hz, 1H), 8.67 (s, 1H), 8.31 (d, J = 1.0 Hz, 1H), 7.57 (dd, J = 1.1, 0.5 Hz, 1H), 7.36 (dd, J = 7.0, 4.2 Hz, 1H), 6.80 (d, J = 1.1 Hz, 1H), 6.67 (s, 1H), 3.64 (d, J = 0.5 Hz, 3H), 3.58 (d, J = 0.8 Hz, 2H), 2.99 (dd, J = 1.1, 0.6 Hz, 2H), 2.84-2.75 (m, 4H), 2.69-2.57 (m, 3H), 1.40 (s, 6H). MS (ESI): m/z = 487.2 [M + H]$^+$. |
| 507. | N-(2,2-dimethyl-6-(4-((2-methyl-1H-imidazol-4-yl)methyl)piperazin-1-yl)-2,3-dihydrobenzofuran-5-yl)pyrazolo[1,5-a]pyrimidine-3-carboxamide | 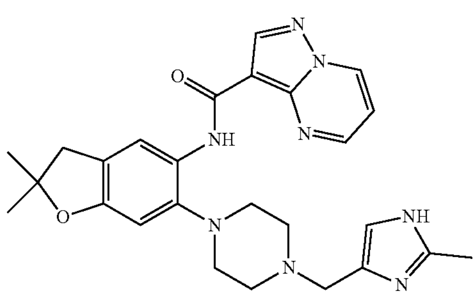 | $^1$H NMR (400 MHz, DMSO-$d_6$) δ 10.44 (s, 1H), 9.36 (dd, J = 7.0, 1.6 Hz, 1H), 8.66 (s, 1H), 8.46 (dd, J = 4.2, 1.6 Hz, 1H), 8.32 (d, J = 1.1 Hz, 1H), 7.30 (dd, J = 7.0, 4.2 Hz, 1H), 6.69 (s, 1H), 4.09 (m, 2H), 3.49 (s, 2H), 3.17 (d, J = 4.9 Hz, 3H), 2.79 (t, J = 4.5 Hz, 4H), 2.64 (s, 4H), 2.25 (s, 3H), 1.41 (s, 6H). MS (ESI): m/z = 487.2 [M + H]$^+$. |

TABLE 21-continued

The following examples were made in a manner similar to that for Example 502:

| Ex. | Name | Structure | NMR, MS |
|---|---|---|---|
| 508. | N-(6-(4-isopropylpiperazin-1-yl)-2,2-dimethyl-2,3-dihydrobenzofuran-5-yl)pyrazolo[1,5-a]pyrimidine-3-carboxamide | 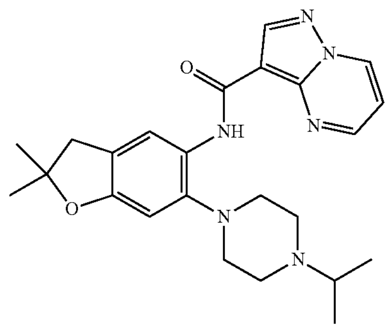 [SMILES: CC(C)N1CCN(c2cc3c(cc2NC(=O)c2cnn4cccnc24)CC(C)(C)O3)CC1] | $^1$H NMR (400 MHz, DMSO-$d_6$) δ 10.33 (s, 1H), 9.36 (dd, J = 7.0, 1.6 Hz, 1H), 8.85 (dd, J = 4.2, 1.7 Hz, 1H), 8.67 (s, 1H), 8.25 (s, 1H), 7.36 (dd, J = 7.0, 4.2 Hz, 1H), 6.67 (s, 1H), 3.04-2.96 (m, 2H), 2.85-2.75 (m, 3H), 2.72-2.61 (m, 5H), 1.41 (s, 6H), 1.02 (d, J = 6.5 Hz, 6H). MS (ESI): m/z = 435.2 [M + H]$^+$. |
| 509. | N-(6-(4-((1H-imidazol-4-yl)methyl)piperazin-1-yl)-2,2-dimethyl-2,3-dihydrobenzofuran-5-yl)pyrazolo[1,5-a]pyrimidine-3-carboxamide | 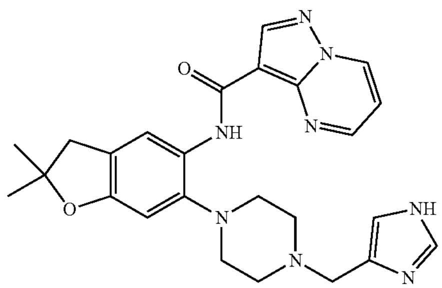 [SMILES: CC1(C)Cc2cc(NC(=O)c3cnn4cccnc34)c(N3CCN(Cc4c[nH]cn4)CC3)cc2O1] | $^1$H NMR (400 MHz, DMSO-$d_6$) δ 10.43 (s, 1H), 9.36 (dd, J = 7.0, 1.6 Hz, 1H), 8.66 (s, 1H), 8.43 (dd, J = 4.2, 1.6 Hz, 1H), 8.34-8.26 (m, 1H), 7.62 (d, J = 1.1 Hz, 1H), 7.32 (dd, J = 7.0, 4.2 Hz, 1H), 6.68 (s, 1H), 4.08 (s, 1H), 3.58 (s, 2H), 3.17 (d, J = 2.7 Hz, 2H), 2.99 (s, 2H), 2.84-2.71 (m, 4H), 2.70-2.59 (m, 4H), 1.40 (s, 6H). MS (ESI): m/z = 473.2 [M + H]$^+$. |

Examples 510 and 511. (R)—N-(7-(4-(2,2-difluoroethyl)piperazin-1-yl)-3-hydroxy-3-methylchroman-6-yl)pyrazolo[1,5-a]pyrimidine-3-carboxamide and (S)—N-(7-(4-(2,2-difluoroethyl)piperazin-1-yl)-3-hydroxy-3-methylchroman-6-yl)pyrazolo[1,5-a]pyrimidine-3-carboxamide

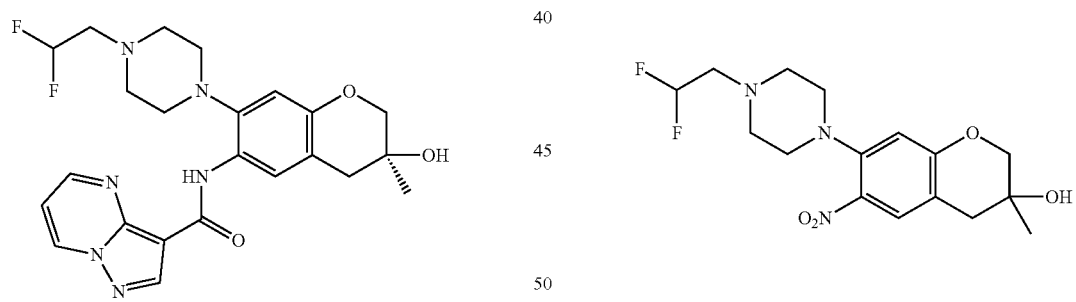

Step A: 7-(4-(2,2-difluoroethyl)piperazin-1-yl)-3-methyl-6-nitrochroman-3-ol

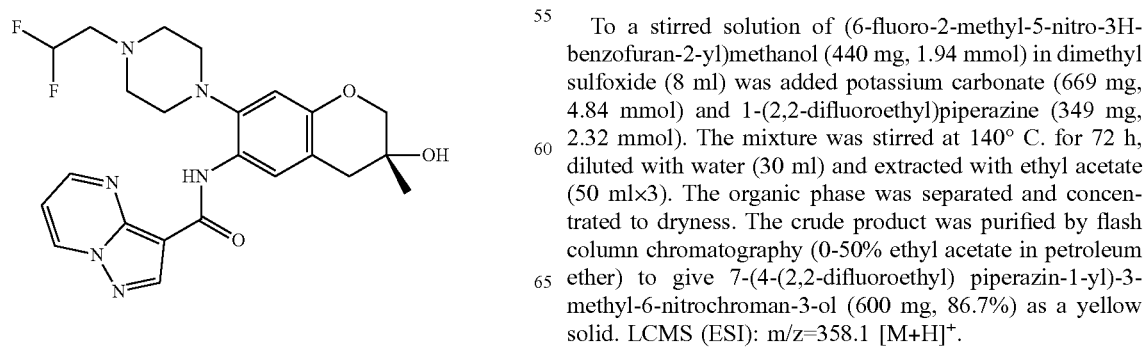

To a stirred solution of (6-fluoro-2-methyl-5-nitro-3H-benzofuran-2-yl)methanol (440 mg, 1.94 mmol) in dimethyl sulfoxide (8 ml) was added potassium carbonate (669 mg, 4.84 mmol) and 1-(2,2-difluoroethyl)piperazine (349 mg, 2.32 mmol). The mixture was stirred at 140° C. for 72 h, diluted with water (30 ml) and extracted with ethyl acetate (50 ml×3). The organic phase was separated and concentrated to dryness. The crude product was purified by flash column chromatography (0-50% ethyl acetate in petroleum ether) to give 7-(4-(2,2-difluoroethyl) piperazin-1-yl)-3-methyl-6-nitrochroman-3-ol (600 mg, 86.7%) as a yellow solid. LCMS (ESI): m/z=358.1 [M+H]$^+$.

Step B: 6-amino-7-(4-(2,2-difluoroethyl)piperazin-1-yl)-3-methylchroman-3-ol

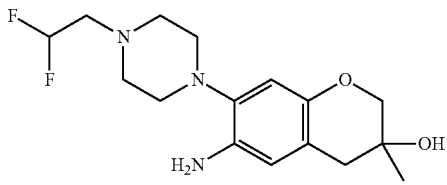 [SMILES: CC1(O)COc2cc(N3CCN(CC(F)F)CC3)c(N)cc2C1]

To a solution of 7-(4-(2,2-difluoroethyl)piperazin-1-yl)-3-methyl-6-nitrochroman-3-ol (600 mg, 1.68 mmol) in methanol (20 ml) was added 10% palladium on carbon (268 mg, 0.25 mmol) at 25° C. under $H_2$ (15 psi). The mixture was stirred for 12 h. The solution was filtered and concentrated to afford 6-amino-7-(4-(2,2-difluoroethyl)piperazin-1-yl)-3-methylchroman-3-ol (320 mg, 58%) as a white solid. LCMS (ESI): m/z=328.1 $[M+H]^+$.

Step C: (S)—N-(7-(4-(2,2-difluoroethyl)piperazin-1-yl)-3-hydroxy-3-methylchroman-6-yl)pyrazolo[1,5-a]pyrimidine-3-carboxamide and (R)—N-(7-(4-(2,2-difluoroethyl)piperazin-1-yl)-3-hydroxy-3-methylchroman-6-yl)pyrazolo[1,5-a]pyrimidine-3-carboxamide

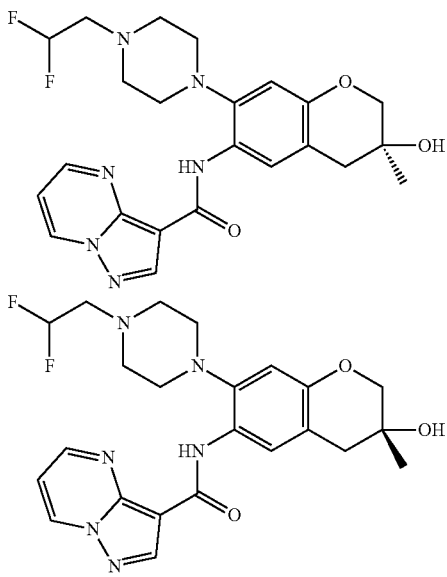

To a solution of 6-amino-7-(4-(2,2-difluoroethyl)piperazin-1-yl)-3-methylchroman-3-ol (270 mg, 0.82 mmol) in pyridine (2 ml) was added pyrazolo[1,5-a]pyrimidine-3-carbonyl chloride (173 mg, 0.95 mmol). The mixture was stirred at 28° C. for 16 h. The solution was concentrated and purified by chromatography on silica (solvent gradient: 0-50% ethyl acetate in petroleum ether) and was further resolved by chiral preparatory SFC to afford (S)—N-(7-(4-(2,2-difluoroethyl)piperazin-1-yl)-3-hydroxy-3-methylchroman-6-yl)pyrazolo[1,5-a]pyrimidine-3-carboxamide (98 mg, 22.1%; RT=4.715 min) and (R)—N-(7-(4-(2,2-difluoroethyl)piperazin-1-yl)-3-hydroxy-3-methylchroman-6-yl)pyrazolo[1,5-a]pyrimidine-3-carboxamide (100 mg, 24%; RT=5.362 min) as yellow solids with absolute stereochemistry assigned arbitrarily.

Example 510, Peak 2: $^1$H NMR (400 MHz, CDCl$_3$) δ 10.35 (s, 1H), 8.84 (dd, J=7.2, 1.6 Hz, 1H), 8.78 (s, 1H), 8.73 (dd, J=4.0, 2.0 Hz, 1H), 8.32 (s, 1H), 7.08 (dd, J=6.8, 4.4 Hz, 1H), 6.75 (s, 1H), 5.96 (tt, J=56.0, 4.4 Hz, 1H), 3.94 (d, J=12.8 Hz, 1H), 3.83 (d, J=11.2 Hz, 1H), 3.00-2.80 (m, 12H), 2.18 (br s, 1H), 1.37 (s, 3H). LCMS (ESI): m/z=473.1 $[M+H]^+$.

Example 511, Peak 1: $^1$H NMR (400 MHz, CDCl$_3$) δ 10.35 (s, 1H), 8.85 (dd, J=7.2, 1.6 Hz, 1H), 8.79 (s, 1H), 8.74 (dd, J=4.4, 2.0 Hz, 1H), 8.33 (s, 1H), 7.09 (dd, J=7.2, 4.8 Hz, 1H), 6.76 (s, 1H), 5.98 (tt, J=52.0, 4.4 Hz, 1H), 3.95 (d, J=10.4 Hz, 1H), 3.84 (d, J=10.4 Hz, 1H), 3.00-2.80 (m, 12H), 2.13 (s, 1H), 1.38 (s, 3H). LCMS (ESI): m/z=473.1 $[M+H]^+$.

Examples 512 and 513. (S)—N-(6-Cyclopropyl-2,2-dimethyl-2,3-dihydrobenzofuran-5-yl)-5-((5-oxopyrrolidin-3-yl)methyl)pyrazolo[1,5-a]pyrimidine-3-carboxamide and (R)—N-(6-cyclopropyl-2,2-dimethyl-2,3-dihydrobenzofuran-5-yl)-5-((5-oxopyrrolidin-3-yl)methyl)pyrazolo[1,5-a]pyrimidine-3-carboxamide

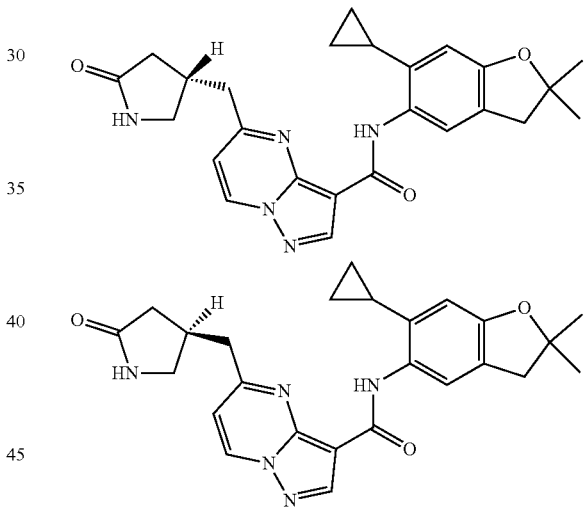

Step A: Methyl 1-(2,4-dimethoxybenzyl)-5-oxopyrrolidine-3-carboxylate

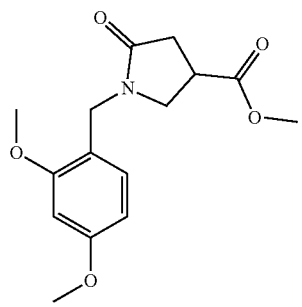 [SMILES: COC(=O)C1CC(=O)N(Cc2ccc(OC)cc2OC)C1]

A solution of 2,4-dimethoxybenzylamine (7.0 g, 41.86 mmol) and dimethyl itaconate (7.94 g, 50.24 mmol) in methanol (100 ml) was stirred at 28° C. for 14 h. The reaction mixture was concentrated and the residue was purified by silica gel column (10-20% ethyl acetate in petroleum ether) to afford methyl 1-(2,4-dimethoxybenzyl)-5-oxopyrrolidine-3-carboxylate (8 g, 65%) as a colorless oil. $^1$H NMR (400 MHz, CDCl$_3$): 7.12 (d, J=8.8 Hz, 1H), 6.45-6.42 (m, 2H), 4.45-4.40 (m, 2H), 3.79 (s, 6H), 3.69 (s, 3H), 3.46 (d, J=8.0 Hz, 2H), 3.18-3.14 (m, 1H), 2.70-2.63 (m, 2H).

Step B: 1-(2,4-Dimethoxybenzyl)-4-(hydroxymethyl)pyrrolidin-2-one

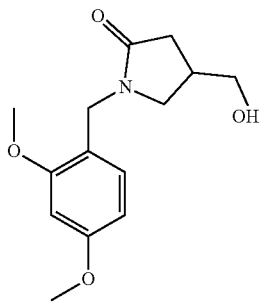 [SMILES: COc1ccc(CN2CC(CO)CC2=O)c(OC)c1]

To a solution of methyl 1-(2,4-dimethoxybenzyl)-5-oxopyrrolidine-3-carboxylate (5.0 g, 17.05 mmol) in tetrahydrofuran (60 ml) and methanol (30 ml) was added lithium borohydride (928 mg, 42.62 mmol). The reaction was stirred at 25° C. for 2.5 h. The reaction was quenched with water (50 ml) and extracted with ethyl acetate (150 ml×3). The combined organic phase was washed with brine (60 ml×2), dried over anhydrous sodium sulfate, filtered and concentrated to afford 1-(2,4-dimethoxybenzyl)-4-(hydroxymethyl)pyrrolidin-2-one (4.1 g, 91%) as a white solid. LCMS (ESI): m/z=266.2 [M+H]$^+$.

Step C: 1-(2,4-Dimethoxybenzyl)-4-(iodomethyl)pyrrolidin-2-one

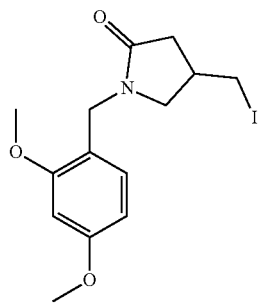 [SMILES: COc1ccc(CN2CC(CI)CC2=O)c(OC)c1]

To a solution of 1-(2,4-dimethoxybenzyl)-4-(hydroxymethyl)pyrrolidin-2-one (4.1 g, 15.45 mmol), triphenylphosphine (6.1 g, 23.18 mmol) and imidazole (3.16 g, 46.36 mmol) in dichloromethane (50 ml) was added iodine (5.9 g, 23.18 mmol) at 26° C. The mixture was stirred at 26° C. under nitrogen for 16 h. The reaction was quenched with saturated sodium sulfite solution (20 ml) and extracted with dichloromethane (50 ml×3). The combined organic phase was dried over anhydrous sodium sulfate, filtered and concentrated. The residue was purified by flash column chromatography (0-5% Ethyl acetate in dichloromethane) to afford 1-(2,4-dimethoxybenzyl)-4-(iodomethyl)pyrrolidin-2-one (1.6 g, 27.6%) as a yellow oil. $^1$H NMR (400 MHz, CDCl$_3$) δ 7.13 (d, J=9.2 Hz, 1H), 6.46-6.43 (m, 2H), 4.41 (s, 2H), 3.81 (s, 3H), 3.80 (s, 3H), 3.42-3.38 (m, 1H), 3.22-3.14 (m, 2H), 3.02-2.98 (m, 1H), 2.62-2.57 (m, 2H), 2.24-2.18 (m, 1H).

Step D: Ethyl 5-((1-(2,4-Dimethoxybenzyl)-5-oxopyrrolidin-3-yl)methyl)pyrazolo[1,5-a]pyrimidine-3-carboxylate

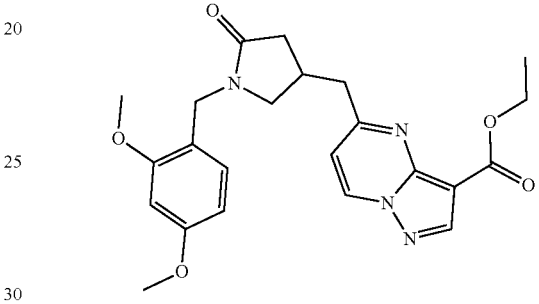

To a solution of zinc (362 mg, 5.54 mmol) in N,N-dimethylacetamide (10 ml) was added chlorotrimethylsilane (0.11 ml, 0.85 mmol) and 1,2-dibromoethane (0.06 ml, 0.85 mmol) at 20° C. under nitrogen. The resulting mixture was stirred at 20° C. for 15 min. A solution of 1-[(2,4-dimethoxyphenyl)methyl]-4-(iodomethyl)pyrrolidin-2-one (1.6 g, 4.26 mmol) in N,N-dimethylacetamide (12 ml) was added portionwise. The reaction mixture was stirred for 30 min to give a solution of zinc reagent.

In another reaction vessel, to a solution of ethyl 5-bromopyrazolo[1,5-a]pyrimidine-3-carboxylate (520 mg, 1.94 mmol) in N,N-dimethylacetamide (10 ml) was added cuprous iodide (74 mg, 0.39 mmol), 1,1'-Bis(diphenylphosphino)ferrocene palladium dichloride (142 mg, 0.19 mmol). The mixture was purged with nitrogen atmosphere three times and the freshly prepared (1-(2,4-dimethoxybenzyl)-5-oxopyrrolidin-3-yl)zinc(II) iodide solution was added dropwise. The reaction mixture was stirred at 80° C. for 16 h under nitrogen. The reaction was quenched with water (20 ml) and extracted with dichloromethane (20 ml×3). The combined organic phase was dried over anhydrous sodium sulfate, filtered and concentrated. The residue was purified by flash column chromatography (0-2% methanol in dichloromethane) to afford ethyl 5-((1-(2,4-dimethoxybenzyl)-5-oxopyrrolidin-3-yl)methyl)pyrazolo[1,5-a]pyrimidine-3-carboxylate (800 mg, 94%) as a brown solid. LCMS (ESI): m/z=439.0 [M+H]$^+$.

Step E: Ethyl 5-((5-Oxopyrrolidin-3-yl)methyl)pyrazolo[1,5-a]pyrimidine-3-carboxylate

Step G: N-(6-cyclopropyl-2,2-dimethyl-3H-benzofuran-5-yl)-5-[(5-oxopyrrolidin-3-yl)methyl]pyrazolo[1,5-a]pyrimidine-3-carboxamide

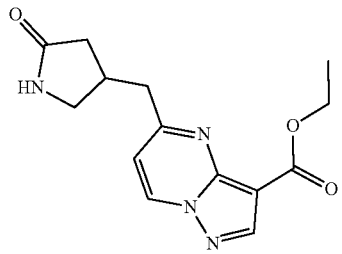 [SMILES: CCOC(=O)c1cnn2ccc(CC3CNC(=O)C3)nc12]

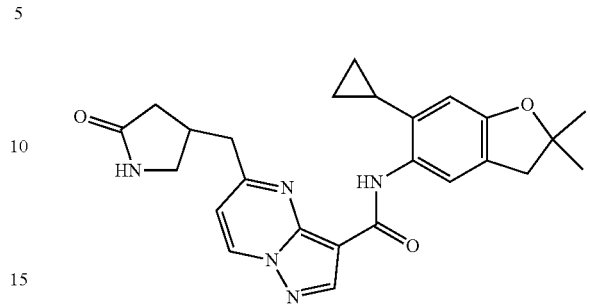

To a solution of 5-((5-oxopyrrolidin-3-yl)methyl)pyrazolo[1,5-a]pyrimidine-3-carboxylic acid (200 mg, 0.77 mmol), 6-cyclopropyl-2,2-dimethyl-3H-benzofuran-5-amine (234 mg, 1.15 mmol) and (7-azabenzotriazol-1-yloxy)tripyrrolidinophosphoniumhexafluorophosphate (481 mg, 0.92 mmol) in N,N-dimethylformamide (5 ml) was added N,N-diisopropylethylamine (0.27 ml, 1.54 mmol). The mixture was stirred at 25° C. for 12 h. The reaction mixture was concentrated and the residue was purified by flash column chromatography (0-9% methanol in dichloromethane) to afford N-(6-cyclopropyl-2,2-dimethyl-3H-benzofuran-5-yl)-5-[(5-oxopyrrolidin-3-yl)methyl]pyrazolo[1,5-a]pyrimidine-3-carboxamide (130 mg, 38%) as a colorless oil.

To ethyl 5-((1-(2,4-dimethoxybenzyl)-5-oxopyrrolidin-3-yl)methyl)pyrazolo[1,5-a]pyrimidine-3-carboxylate (400 mg, 0.91 mmol) was added trifluoroacetic acid (8.0 ml, 107.70 mmol). The mixture was stirred at 50° C. for 16 h. The reaction was quenched with saturated sodium bicarbonate solution to adjust pH to 7 and extracted with dichloromethane (30 ml×3). The combined organic phase was dried over anhydrous sodium sulfate, filtered and concentrated. The residue was purified by flash column chromatography (0-10% methanol in dichloromethane) to afford ethyl 5-((5-oxopyrrolidin-3-yl)methyl)pyrazolo[1,5-a]pyrimidine-3-carboxylate (330 mg, 99%) as a white solid. LCMS (ESI): m/z=289.0 [M+H]$^+$.

Step F: 5-((5-Oxopyrrolidin-3-yl)methyl)pyrazolo[1,5-a]pyrimidine-3-carboxylic acid

Step H: (S)—N-(6-cyclopropyl-2,2-dimethyl-2,3-dihydrobenzofuran-5-yl)-5-((5-oxopyrrolidin-3-yl)methyl)pyrazolo[1,5-a]pyrimidine-3-carboxamide and (R)—N-(6-cyclopropyl-2,2-dimethyl-2,3-dihydrobenzofuran-5-yl)-5-((5-oxopyrrolidin-3-yl)methyl)pyrazolo[1,5-a]pyrimidine-3-carboxamide

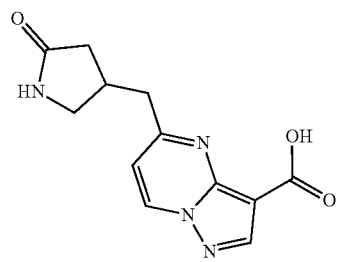 [SMILES: O=C1CC(Cc2ccn3ncc(C(=O)O)c3n2)CN1]

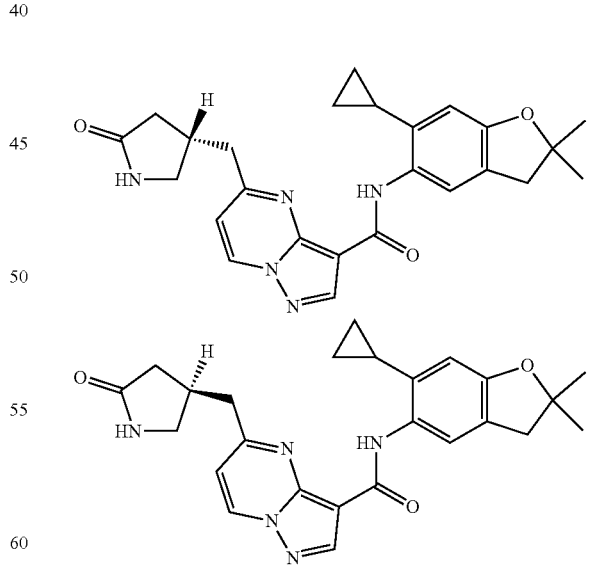

A mixture of lithium hydroxide hydrate (67 mg, 1.60 mmol) and ethyl 5-((5-oxopyrrolidin-3-yl)methyl)pyrazolo[1,5-a]pyrimidine-3-carboxylate (230 mg, 0.80 mmol) in tetrahydrofuran (6 ml), water (6 ml) and methanol (3 ml) was stirred at 30° C. for 1 h. The solution was concentrated in vacuo to afford 5-((5-oxopyrrolidin-3-yl)methyl)pyrazolo[1,5-a]pyrimidine-3-carboxylic acid (200 mg, 96%) as a yellow solid which was used directly for the next step without further purification. LCMS (ESI): m/z=261.0 [M+H]$^+$.

N-(6-cyclopropyl-2,2-dimethyl-3H-benzofuran-5-yl)-5-[(5-oxopyrrolidin-3-yl)methyl]pyrazolo[1,5-a]pyrimidine-3-carboxamide (130 mg, 0.29 mmol) was separated by chiral SFC (Chiralpak OJ 250 mm×30 mm×5 m; Supercritical CO$_2$/MeOH+NH$_3$.H$_2$O=30/30; 50 ml/min) to afford (S)—

N-(6-cyclopropyl-2,2-dimethyl-2,3-dihydrobenzofuran-5-yl)-5-((5-oxopyrrolidin-3-yl)methyl)pyrazolo[1,5-a]pyrimidine-3-carboxamide (19 mg, 14%, RT=5.15 min) and (R)—N-(6-cyclopropyl-2,2-dimethyl-2,3-dihydrobenzofuran-5-yl)-5-((5-oxopyrrolidin-3-yl)methyl)pyrazolo[1,5-a]pyrimidine-3-carboxamide (15 mg, 11%, RT=5.58 min) as white solids with absolute stereochemistry assigned arbitrarily.

Example 512, Peak 1: $^1$H NMR (400 MHz, CDCl$_3$) δ 9.60 (s, 1H), 8.78-8.70 (m, 2H), 7.84 (s, 1H), 6.89 (d, J=7.2 Hz, 1H), 6.48 (s, 1H), 5.58 (br s, 1H), 3.59-3.51 (m, 1H), 3.24-3.17 (m, 1H), 3.12-3.01 (m, 5H), 2.56-2.52 (m, 1H), 2.20-2.11 (m, 1H), 2.03-1.93 (m, 1H), 1.48 (s, 6H), 0.98-0.90 (m, 2H), 0.76-0.69 (m, 2H). LCMS (ESI): m/z=446.2 [M+H]$^+$.

Example 513, Peak 2: $^1$H NMR (400 MHz, CDCl$_3$) δ 9.60 (s, 1H), 8.80-8.70 (m, 2H), 7.84 (s, 1H), 6.89 (d, J=7.2 Hz, 1H), 6.48 (s, 1H), 5.48 (br s, 1H), 3.57-3.50 (m, 1H), 3.20-3.15 (m, 1H), 3.12-3.00 (m, 5H), 2.59-2.48 (m, 1H), 2.22-2.12 (m, 1H), 2.00-1.91 (m, 1H), 1.48 (s, 6H), 0.96-0.92 (m, 2H), 0.74-0.70 (m, 2H). LCMS (ESI): m/z=446.3 [M+H]$^+$.

Examples 514 and 515. (R)—N-(6-cyclopropyl-2,2-dimethyl-2,3-dihydrobenzofuran-5-yl)-5-((2-oxopyrrolidin-3-yl)methyl)pyrazolo[1,5-a]pyrimidine-3-carboxamide and (S)—N-(6-cyclopropyl-2,2-dimethyl-2,3-dihydrobenzofuran-5-yl)-5-((2-oxopyrrolidin-3-yl)methyl)pyrazolo[1,5-a]pyrimidine-3-carboxamide

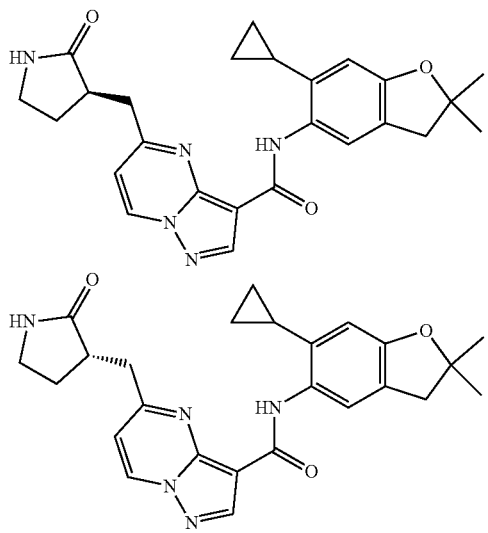

Step A: 1-tert-Butyl 3-methyl 2-oxopyrrolidine-1,3-dicarboxylate

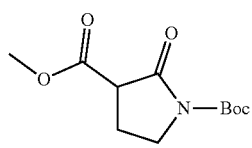 [SMILES: COC(=O)C1CCN(C(=O)OC(C)(C)C)C1=O]

To a solution of 1-(tert-butoxycarbonyl)-2-pyrrolidinone (2.3 g, 12.4 mmol) in tetrahydrofuran (100 ml) was added lithium bis(trimethylsilyl)amide (1.0 M in THF, 16.1 ml, 16.14 mmol) at −78° C. dropwise under nitrogen. The reaction was stirred at −78° C. for 30 min. To the above solution was added methyl chloroformate (1.72 ml, 22.22 mmol) dropwise. The mixture was stirred at −78° C. for 1 h, quenched with saturated ammonium chloride solution (40 ml), and extracted with ethyl acetate (100 ml×3). The combined organic phase was washed with brine (100 ml×2), dried over sodium sulfate, filtered and concentrated. The residue was purified by flash column chromatography (eluting 0-30% ethyl acetate in petroleum ether) to afford 1-tert-butyl 3-methyl 2-oxopyrrolidine-1,3-dicarboxylate (1.9 g, 63%). $^1$H NMR (400 MHz, CDCl$_3$) δ 3.89-3.78 (m, 1H), 3.74 (s, 3H), 3.72-3.69 (m, 1H), 3.56-3.53 (m, 1H), 2.41-2.37 (m, 1H), 2.26-2.21 (m, 1H), 1.53 (s, 9H).

Step B: Ethyl 5-(bromomethyl)pyrazolo[1,5-a]pyrimidine-3-carboxylate

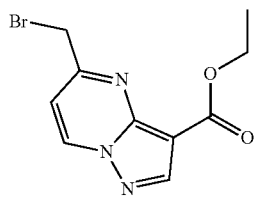 [SMILES: CCOC(=O)c1cnn2ccc(CBr)nc12]

To a solution of ethyl 5-methylpyrazolo[1,5-a]pyrimidine-3-carboxylate (1.0 g, 4.87 mmol) in carbon tetrachloride (20 ml) was added benzoylperoxide (118 mg, 0.49 mmol) and 1-bromo-2,5-pyrrolidinedione (954 mg, 5.36 mmol). The mixture was stirred at 80° C. for 16 h under nitrogen protection and concentrated. The crude product was purified by flash column chromatography (eluting 0-10% ethyl acetate in petroleum ether) to afford ethyl 5-(bromomethyl)pyrazolo[1,5-a]pyrimidine-3-carboxylate (580 mg, 42%) as a yellow solid. $^1$H NMR (400 MHz, CDCl$_3$) δ 8.72 (d, J=7.2 Hz, 1H), 8.57 (s, 1H), 7.21 (d, J=7.2 Hz, 1H), 4.65 (s, 2H), 4.42 (q, J=7.2 Hz, 2H), 1.42 (t, J=7.2 Hz, 3H).

Step C: 1-tert-Butyl 3-methyl 3-((3-(ethoxycarbonyl)pyrazolo[1,5-a]pyrimidin-5-yl)methyl)-2-oxopyrrolidine-1,3-dicarboxylate

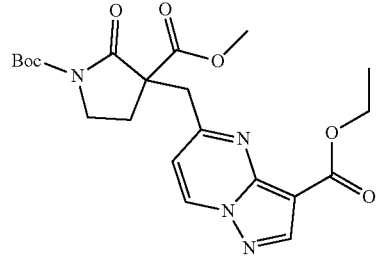 [SMILES: CCOC(=O)c1cnn2ccc(CC3(C(=O)OC)CCN(C(=O)OC(C)(C)C)C3=O)nc12]

To the solution of 1-tert-butyl 3-methyl 2-oxopyrrolidine-1,3-dicarboxylate (1.0 g, 4.12 mmol) and ethyl 5-(bromomethyl)pyrazolo[1,5-a]pyrimidine-3-carboxylate (780 mg, 2.75 mmol) in acetonitrile (50 ml) was added potassium carbonate (759 mg, 5.49 mmol). The mixture was stirred at 100° C. for 2 h, diluted with water (150 ml) and extracted with dichloromethane (50 ml×3). The combined organic phase was washed with brine (50 ml×2), dried over anhydrous sodium sulfate, filtered and concentrated. The residue was purified by flash column chromatography (eluting 0-50% ethyl acetate in petroleum ether) to afford 1-tert-butyl 3-methyl 3-((3-(ethoxycarbonyl)pyrazolo[1,5-a]pyrimidin-5-yl)methyl)-2-oxopyrrolidine-1,3-dicarboxylate (750 mg, 61%) as a yellow solid. $^1$H NMR (400 MHz, CDCl$_3$) δ 8.59 (d, J=6.8 Hz, 1H), 8.49 (s, 1H), 6.94 (d, J=7.6 Hz, 1H), 4.38 (q, J=6.8 Hz, 2H), 3.91-3.80 (m, 3H), 3.72 (s, 3H), 3.32 (d, J=16.8 Hz, 1H), 2.93-2.89 (m, 1H), 2.42-2.36 (m, 1H), 1.52 (s, 9H), 1.39 (d, J=7.2 Hz, 3H).

Step D: Ethyl 5-((2-oxopyrrolidin-3-yl)methyl)pyrazolo[1,5-a]pyrimidine-3-carboxylate

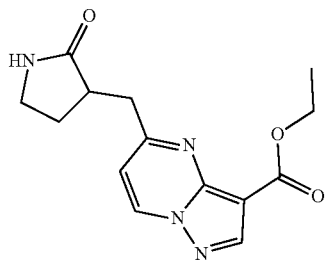 [SMILES: CCOC(=O)c1cnn2ccc(CC3CCNC3=O)nc12]

To a solution of 1-tert-butyl 3-methyl 3-((3-(ethoxycarbonyl)pyrazolo[1,5-a]pyrimidin-5-yl)methyl)-2-oxopyrrolidine-1,3-dicarboxylate (500.0 mg, 1.12 mmol) in N,N-dimethylformamide (5 ml) was added lithium iodide (1.5 g, 11.2 mmol). The mixture was stirred at 150° C. for 3 h, diluted with water (30 ml) and extracted with dichloromethane (30 ml×3). The combined organic phase was washed with brine (30 ml×2), dried over sodium sulfate, filtered and concentrated. The residue was purified by flash column chromatography (eluting 5% methanol in dichloromethane) to afford ethyl 5-[(2-oxopyrrolidin-3-yl)methyl]pyrazolo[1,5-a]pyrimidine-3-carboxylate (300 mg, 93%) as a white solid. $^1$H NMR (400 MHz, CDCl$_3$) δ 8.61 (d, J=6.8 Hz, 1H), 8.53 (s, 1H), 6.99 (d, J=7.2 Hz, 1H), 5.58 (br s, 1H), 4.40 (q, J=6.8 Hz, 2H), 3.53-3.50 (m, 1H), 3.41-3.38 (m, 2H), 3.11-3.06 (m, 2H), 2.61-2.58 (m, 1H), 2.09-2.03 (m, 1H), 1.42 (t, J=6.8 Hz, 3H).

Step E: 5-((2-Oxopyrrolidin-3-yl)methyl)pyrazolo[1,5-a]pyrimidine-3-carboxylic acid

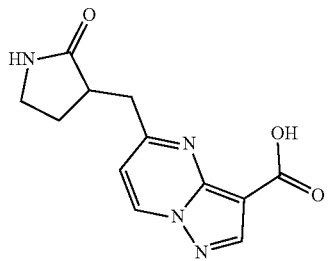 [SMILES: O=C(O)c1cnn2ccc(CC3CCNC3=O)nc12]

To a solution of ethyl 5-[(2-oxopyrrolidin-3-yl)methyl]pyrazolo[1,5-a]pyrimidine-3-carboxylate (300 mg, 1.04 mmol) in ethanol (2 ml), water (2 ml) and tetrahydrofuran (2 ml) was added lithium hydroxide monohydrate (131 mg, 3.12 mmol). The mixture was stirred at 30° C. for 1 h and concentrated in vacuo to afford 5-[(2-oxopyrrolidin-3-yl)methyl]pyrazolo[1,5-a]pyrimidine-3-carboxylic acid (230 mg, 85%) as a white solid.

Step F: N-(6-Cyclopropyl-2,2-dimethyl-3H-benzofuran-5-yl)-5-[(2-oxopyrrolidin-3-yl)methyl]pyrazolo[1,5-a]pyrimidine-3-carboxamide

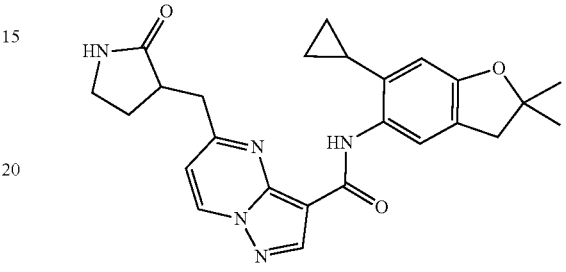

To a solution of 5-[(2-oxopyrrolidin-3-yl)methyl]pyrazolo[1,5-a]pyrimidine-3-carboxylic acid (200.0 mg, 0.77 mmol), 6-cyclopropyl-2,2-dimethyl-3H-benzofuran-5-amine (187.46 mg, 0.92 mmol), and PyAOP (480.81 mg, 0.92 mmol) in N,N-dimethylformamide (10 ml) was added N,N-diisopropylethylamine (198.64 mg, 1.54 mmol). The mixture was stirred at 20° C. for 12 h, diluted with water (30 ml) and extracted with dichloromethane (30 ml×3). The combined organic phase was washed with brine (30 ml×2), dried over sodium sulfate, filtered and concentrated. The residue was purified by flash column chromatography (eluting 0-10% methanol in dichloromethane) to afford N-(6-cyclopropyl-2,2-dimethyl-3H-benzofuran-5-yl)-5-[(2-oxopyrrolidin-3-yl)methyl]pyrazolo[1,5-a]pyrimidine-3-carboxamide (220 mg, 64%) as a white solid. LCMS (ESI): m/z=446.3 [M+H]$^+$.

Step G: (R)—N-(6-cyclopropyl-2,2-dimethyl-2,3-dihydrobenzofuran-5-yl)-5-((2-oxopyrrolidin-3-yl)methyl)pyrazolo[1,5-a]pyrimidine-3-carboxamide and (S)—N-(6-cyclopropyl-2,2-dimethyl-2,3-dihydrobenzofuran-5-yl)-5-((2-oxopyrrolidin-3-yl)methyl)pyrazolo[1,5-a]pyrimidine-3-carboxamide

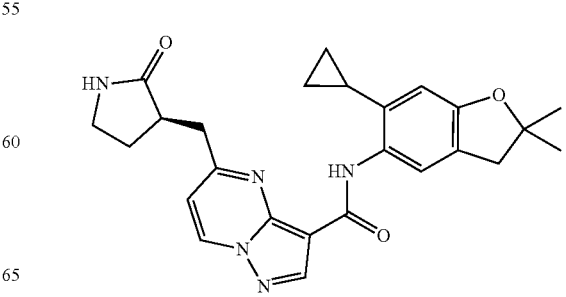

893
-continued

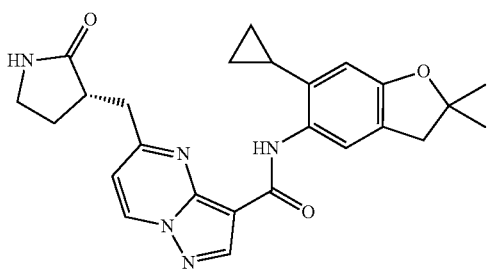

N-(6-cyclopropyl-2,2-dimethyl-3H-benzofuran-5-yl)-5-[(2-oxopyrrolidin-3-yl)methyl]pyrazolo[1,5-a]pyrimidine-3-carboxamide (220 mg, 0.49 mmol) was resolved by chiral SFC (AD, 250 mm×30 mm, 10 m, supercritical $CO_2$/ ammonium hydroxide in ethanol=40/40, 60 ml/min) to give N-(6-cyclopropyl-2,2-dimethyl-3H-benzofuran-5-yl)-5-[[(3S)-2-oxopyrrolidin-3-yl]methyl]pyrazolo[1,5-a]pyrimidine-3-carboxamide (38.34 mg, 17%; RT=4.633 min) and N-(6-cyclopropyl-2,2-dimethyl-3H-benzofuran-5-yl)-5-[[(3R)-2-oxopyrrolidin-3-yl]methyl]pyrazolo[1,5-a]pyrimidine-3-carboxamide (36.75 mg, 17%; RT=5.202 min) as yellow solids with absolute stereochemistry assigned arbitrarily.

Example 514, Peak 1: $^1$H NMR (400 MHz, $CDCl_3$) δ 9.69 (s, 1H), 8.74 (s, 1H), 8.70 (d, J=7.2 Hz, 1H), 7.88 (s, 1H), 7.01 (d, J=7.2 Hz, 1H), 6.48 (s, 1H), 5.55 (s, 1H), 3.43-3.38 (m, 1H), 3.35-3.31 (m, 2H), 3.06-3.05 (m, 3H), 3.04-3.02 (m, 1H), 2.30-2.24 (m, 1H), 2.01-1.95 (m, 2H), 1.48 (s, 6H), 0.98-0.95 (m, 2H), 0.73-0.70 (m, 2H). LCMS (ESI): m/z=446.3 [M+H]$^+$.

Example 515, Peak 2: $^1$H NMR (400 MHz, $CDCl_3$) δ 9.69 (s, 1H), 8.74 (s, 1H), 8.70 (d, J=7.2 Hz, 1H), 7.88 (s, 1H), 7.01 (d, J=7.2 Hz, 1H), 6.48 (s, 1H), 5.53 (s, 1H), 3.43-3.38 (m, 1H), 3.35-3.31 (m, 2H), 3.06-3.05 (m, 3H), 3.04-3.02 (m, 1H), 2.30-2.24 (m, 1H), 2.01-1.95 (m, 2H), 1.48 (s, 6H), 0.98-0.94 (m, 2H), 0.73-0.70 (m, 2H). LCMS (ESI): m/z=446.3 [M+H]$^+$.

Examples 516 and 517. N-[(1S)-1-Hydroxy-2,2-dimethyl-6-morpholino-indan-5-yl]pyrazolo[1,5-a]pyrimidine-3-carboxamide and N-[(1R)-1-Hydroxy-2,2-dimethyl-6-morpholino-indan-5-yl]pyrazolo[1,5-a]pyrimidine-3-carboxamide

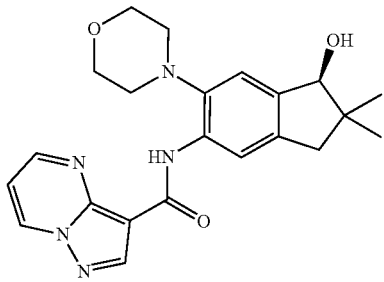

894
-continued

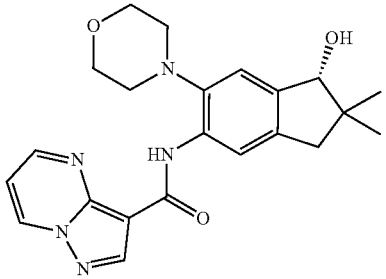

Step A:
5-Amino-2,2-dimethyl-6-morpholino-indan-1-ol

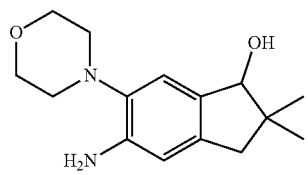

To a stirred solution of 5-amino-2,2-dimethyl-6-morpholino-indan-1-one (150 mg, 0.6 mmol) (Example 499, Step H) in tetrahydrofuran (9 ml) and methanol (3 ml) was added sodium borohydride (65 mg, 1.7 mmol) at 0° C. The mixture was stirred under nitrogen at 0° C. for 10 min, then at 28° C. for 8.5 h. The reaction mixture was quenched with water (15 ml) and extracted with dichloromethane (50 ml×3). The combined organic phase was dried over sodium sulfate, filtered and concentrated to afford crude 5-amino-2,2-dimethyl-6-morpholino-indan-1-ol (150 mg, 99%) as a light brown solid, which was used for the next step directly without further purification. LCMS (ESI): m/z=263.1 [M+H]$^+$.

Step B: N-(1-Hydroxy-2,2-dimethyl-6-morpholino-2,3-dihydro-1H-inden-5-yl)pyrazolo[1,5-a]pyrimidine-3-carboxamide

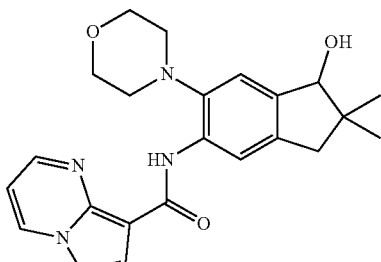

A mixture of 5-amino-2,2-dimethyl-6-morpholino-indan-1-ol (150.0 mg, 0.6 mmol) and pyrazolo[1,5-a]pyrimidine-3-carbonyl chloride (135.0 mg, 0.7 mmol) in pyridine (15 ml) was stirred at 28° C. for 18 h and concentrated. The residue was purified by flash column chromatography (0-2% methanol in dichloromethane) to afford N-(1-hydroxy-2,2-dimethyl-6-morpholino-indan-5-yl)pyrazolo[1,5-a]pyrimidine-3-carboxamide (220.0 mg, 94%) as alight yellow solid. LCMS (ESI): m/z=408.1 [M+H]⁺.

Step C: N-[(1S)-1-Hydroxy-2,2-dimethyl-6-morpholino-indan-5-yl]pyrazolo[1,5-a]pyrimidine-3-carboxamide and N-[(1R)-1-Hydroxy-2,2-dimethyl-6-morpholino-indan-5-yl]pyrazolo[1,5-a]pyrimidine-3-carboxamide

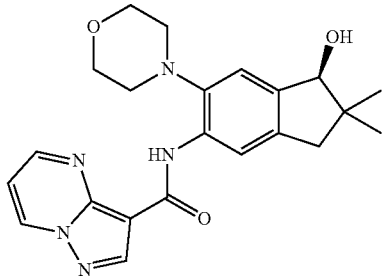

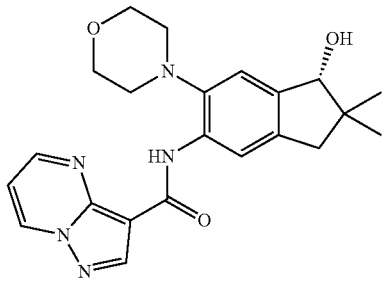 [SMILES: CC1(C)Cc2cc(NC(=O)c3cnn4cccnc34)c(N3CCOCC3)cc2C1O]

N-(1-hydroxy-2,2-dimethyl-6-morpholino-indan-5-yl) pyrazolo[1,5-a]pyrimidine-3-carboxamide (220 mg, 0.5 mmol) was resolved by chiral SFC (AD (250 mm×30 mm, 10 m); supercritical CO₂ 35%/0.1% ammonium hydroxide in ethanol) to afford N-[(1S)-1-hydroxy-2,2-dimethyl-6-morpholino-indan-5-yl]pyrazolo[1,5-a]pyrimidine-3-carboxamide (59.4 mg, 27%; RT=4.667 min) and N-[(1R)-1-hydroxy-2,2-dimethyl-6-morpholino-indan-5-yl]pyrazolo[1,5-a]pyrimidine-3-carboxamide (56.6 mg, 26%; RT=4.955 min) as light yellow solids with absolute stereochemistry assigned arbitrarily.

Example 516, Peak 1: ¹H NMR (400 MHz, CD₃OD) δ 9.13 (dd, J=7.2, 1.6 Hz, 1H), 8.93 (dd, J=4.0, 1.6 Hz, 1H), 8.66 (s, 1H), 8.31 (s, 1H), 7.31-7.27 (m, 2H), 4.61 (s, 1H), 3.99-3.95 (m, 4H), 2.95-2.90 (m, 4H), 2.77 (d, J=15.2 Hz, 1H), 2.64 (d, J=15.2 Hz, 1H), 1.18 (s, 3H), 1.03 (s, 3H). LCMS (ESI): m/z=408.2 [M+H]⁺.

Example 517, Peak 2: ¹H NMR (400 MHz, CD₃OD) δ 9.13 (dd, J=7.2, 1.6 Hz, 1H), 8.94 (dd, J=4.0, 1.6 Hz, 1H), 8.67 (s, 1H), 8.32 (s, 1H), 7.32-7.28 (m, 2H), 4.61 (s, 1H), 3.99-3.95 (m, 4H), 2.95-2.90 (m, 4H), 2.77 (d, J=15.6 Hz, 1H), 2.64 (d, J=15.2 Hz, 1H), 1.18 (s, 3H), 1.03 (s, 3H). LCMS (ESI): m/z=408.2 [M+H]⁺.

Example 518. N-(4-dimethylphosphoryl-2-morpholino-phenyl)pyrazolo[1,5-a] pyrimidine-3-carboxamide

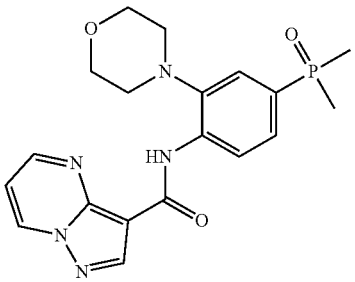 [SMILES: CP(C)(=O)c1ccc(NC(=O)c2cnn3cccnc23)c(N2CCOCC2)c1]

Step A: 4-(5-chloro-2-nitro-phenyl)morpholine

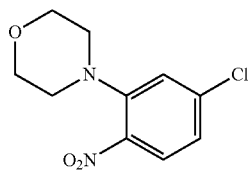 [SMILES: O=[N+]([O-])c1ccc(Cl)cc1N1CCOCC1]

To a solution of 4-chloro-2-fluoronitrobenzene (3.0 g, 17.09 mmol) in toluene (40 ml) was added potassium carbonate (2.36 g, 17.09 mmol) and morpholine (1.50 ml, 17.09 mmol). The reaction mixture was stirred at 30° C. for 16 h. The reaction was quenched with water (200 ml) and extracted with ethyl acetate (200 ml×2). The combined organic phase was washed with water (400 ml×3) and brine (400 ml). The organic layer was separated, dried over anhydrous sodium sulfate, filtered and concentrated. The residue was purified by flash column chromatography on silica gel (eluting with 0-9% ethyl acetate in petroleum ether) to afford 4-(5-chloro-2-nitro-phenyl) morpholine (3.9 g, 94%) as a red solid. LCMS (ESI): m/z=242.9 [M+H]⁺.

Step B: 4-(5-dimethylphosphoryl-2-nitro-phenyl)morpholine

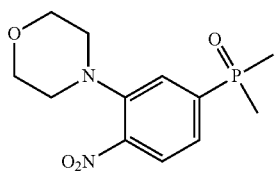

To a solution of 4-(5-chloro-2-nitro-phenyl)morpholine (500 mg, 2.06 mmol) in N,N-dimethyl formamide (5 ml) was added methyl phosphonoylmethane (193 mg, 2.47 mmol), potassium phosphate tribasic (481 mg, 2.27 mmol), 4,5-bis(diphenylphosphino)-9,9-dimethylxanthene (60 mg, 0.10 mmol) and palladium(II) acetate (23 mg, 0.10 mmol). The reaction mixture was stirred at 120° C. for 16 h under nitrogen. The reaction mixture was filtered and the filtrate was diluted with water (50 ml). The mixture was extracted with ethyl acetate (50 ml×3). The combined organic phase was dried over anhydrous sodium sulfate, filtered and concentrated. The residue was purified by flash column chromatography (eluting with 0-100% ethyl acetate in petroleum ether, then 0-10% methanol in dichloromethane) to afford 4-(5-dimethylphosphoryl-2-nitro-phenyl) morpholine (150 mg, 26%) as a yellow solid. LCMS (ESI): m/z=285.0 [M+H].

Step C: 4-dimethylphosphoryl-2-morpholino-aniline

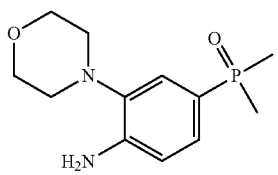 [SMILES: CP(C)(=O)c1ccc([N+](=O)[O-])c(N2CCOCC2)c1]

To a solution of 4-(5-dimethylphosphoryl-2-nitro-phenyl) morpholine (250 mg, 0.88 mmol) in ethanol (10 ml) and water (2 ml) was added iron (246 mg, 4.4 mmol) and ammonium chloride (0.15 mL, 4.4 mmol). The reaction mixture was stirred at 80° C. for 16 h under nitrogen. The mixture was filtered and the filtrate was concentrated. The residue was purified by prep-TLC (10% methanol in dichloromethane) to afford 4-dimethylphosphoryl-2-morpholino-aniline (160 mg, 72%) as a yellow solid. 1H NMR (400 MHz, CDCl$_3$) δ 7.50-7.40 (m, 1H), 7.25-7.10 (m, 1H), 6.85-6.75 (m, 1H), 4.30 (s, 2H), 3.95-3.75 (m, 4H), 3.00-2.85 (m, 4H), 1.70 (s, 3H), 1.66 (s, 3H).

Step D: N-(4-dimethylphosphoryl-2-morpholino-phenyl)pyrazolo[1,5-a]pyrimidine-3-carboxamide

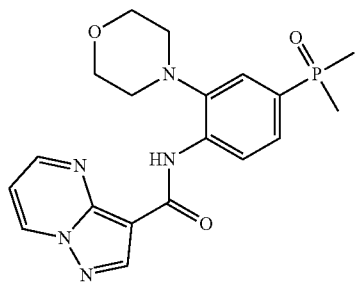 [SMILES: CP(C)(=O)c1ccc(NC(=O)c2cnn3cccnc23)c(N2CCOCC2)c1]

A mixture of pyrazolo[1,5-a] pyrimidine-3-carbonyl chloride (120 mg, 0.66 mmol) and 4-dimethylphosphoryl-2-morpholino-aniline (120 mg, 0.47 mmol) in pyridine (2 ml) was stirred at 28° C. for 16 h. The reaction was concentrated and the residue was purified by prep-TLC (10% methanol in dichloromethane) to obtain a crude product which was triturated with methanol (5 ml) to afford N-(4-dimethylphosphoryl-2-morpholino-phenyl)pyrazolo[1,5-a] pyrimidine-3-carboxamide (97 mg, 51%) as a white solid. $^1$H NMR (400 MHz, CDCl$_3$) 10.81 (s, 1H), 8.95-8.60 (m, 4H), 7.85-7.70 (m, 1H), 7.45-7.30 (m, 1H), 7.20-7.05 (m, 1H), 4.05-3.95 (m, 4H), 3.05-3.95 (m, 4H), 1.76 (s, 3H), 1.73 (s, 3H). LCMS (ESI): m/z=400.1 [M+H]$^+$.

Examples 519 and 520. N-[(3R)-3-(cyanomethyl)-3-methyl-7-morpholino-chroman-6-yl]pyrazolo[1,5-a]pyrimidine-3-carboxamide and N-[(3S)-3-(cyanomethyl)-3-methyl-7-morpholino-chroman-6-yl]pyrazolo[1,5-a]pyrimidine-3-carboxamide

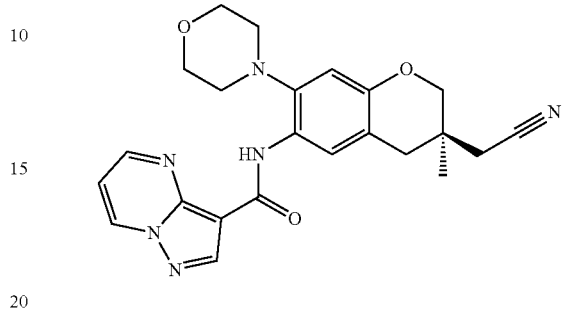

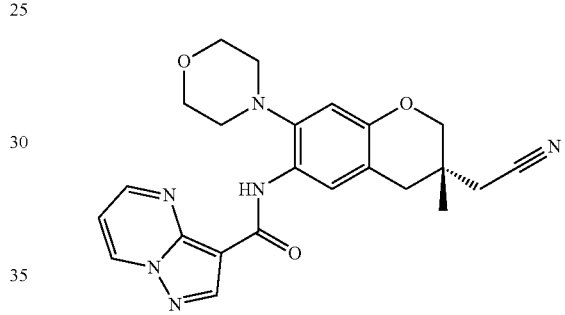

Step A: diethyl 2-(2,4-difluorobenzyl)-2-methylmalonate

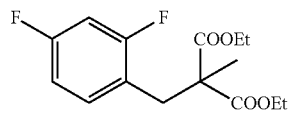 [SMILES: CCOC(=O)C(C)(Cc1ccc(F)cc1F)C(=O)OCC]

To a suspension of 60% sodium hydride (1.4 g, 34.5 mmol) in N,N-dimethylformamide (100 ml) was added diethyl methyl malonate (5.0 g, 28.7 mmol) dropwise at 0° C. The mixture was stirred at 0° C. for 30 min, then 2,4-difluorobenzyl bromide (6.5 g, 31.6 mmol) in N, N-dimethylformamide (6 ml) was added dropwise. The mixture was stirred from 0° C. to 28° C. for 2.5 h. The reaction was quenched with saturated ammonium chloride solution (10 ml) and extracted with ethyl acetate (100 ml×3). The combined organic phase was dried over sodium sulfate, filtered and concentrated. The residue was purified by flash column chromatography (eluting 3-7% ethyl acetate in petroleum ether) to give diethyl 2-[(2,4-difluorophenyl)methyl]-2-methyl-propanedioate (8.4 g, 97%) as a colorless oil. $^1$H NMR (400 MHz, CDCl$_3$): δ 7.14-7.09 (m, 1H), 6.80-6.74 (m, 2H), 4.23-4.17 (m, 4H), 3.25 (s, 2H), 1.34 (s, 3H), 1.26 (t, J=7.2 Hz 6H).

Step B: 2-(2,4-difluorobenzyl)-2-methylpropane-1,3-diol

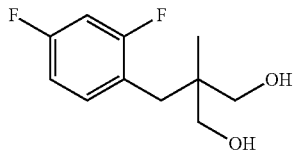

To a stirred solution of diethyl 2-[(2,4-difluorophenyl)methyl]-2-methyl-propanedioate (6.4 g, 21.2 mmol) in tetrahydrofuran (70 ml) was added lithium aluminum hydride (2.0 g, 53.0 mmol) in batches at −10° C. The mixture was stirred from −10° C. to 25° C. for 3.5 h. The reaction was quenched with water (30 ml) and extracted with ethyl acetate (100 ml×3). The combined organic phase was dried over sodium sulfate, filtered and concentrated. The residue was purified by flash column chromatography (eluting 20-60% ethyl acetate in petroleum ether) to give 2-[(2,4-difluorophenyl)methyl]-2-methyl-propane-1,3-diol (4.5 g, 97%) as a colorless oil. $^1$H NMR (400 MHz, CDCl$_3$) δ 7.31-7.25 (m, 1H), 6.87-6.80 (m, 2H), 3.61-3.54 (m, 4H), 2.77 (s, 2H), 2.56 (s, 2H), 0.77 (s, 3H).

Step C: (7-fluoro-3-methylchroman-3-yl)methanol

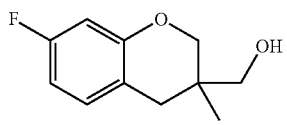

To a stirred solution of 2-[(2,4-difluorophenyl)methyl]-2-methyl-propane-1,3-diol (4.7 g, 21.6 mmol) in N,N-dimethylformamide (20 ml) and toluene (80 ml) was added 60% sodium hydride in mineral oil (1.9 g, 47.6 mmol) at 0° C. The reaction was heated at 100° C. for 2 h under nitrogen. The reaction was quenched with a saturated ammonium chloride solution (25 ml) and extracted with dichloromethane (100 ml×3). The combined organic phase was dried over sodium sulfate, filtered and concentrated. The residue was purified by flash column chromatography (eluting 0-15% ethyl acetate in petroleum ether) to afford (7-fluoro-3-methyl-chroman-3-yl)methanol (3.9 g, 92%) as a light yellow solid. $^1$H NMR (400 MHz, CDCl$_3$) δ 6.98-6.94 (m, 1H), 6.61-6.53 (m, 2H), 4.06-4.03 (m, 1H), 3.80-3.77 (m, 1H), 3.55 (d, J=10.8 Hz, 1H), 3.46 (d, J=10.8 Hz, 1H), 2.64 (d, J=16.8 Hz, 1H), 2.48 (d, J=16.0 Hz, 1H), 1.65 (s, 1H), 1.05 (s, 3H).

Step D: (7-fluoro-3-methylchroman-3-yl)methyl methanesulfonate

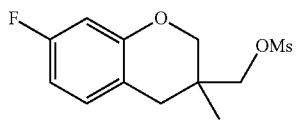

To a stirred solution of (7-fluoro-3-methyl-chroman-3-yl)methanol (3.4 g, 17.3 mmol) in dichloromethane (60 ml) was added triethylamine (4.4 g, 43.3 mmol) and methanesulfonyl chloride (3.2 g, 28.3 mmol) at 0° C. The mixture was stirred at 28° C. for 2 h. The reaction was quenched with water (50 ml) and extracted with dichloromethane (100 ml×3). The combined organic phases was dried over sodium sulfate, filtered and concentrated to afford crude (7-fluoro-3-methyl-chroman-3-yl)methyl methanesulfonate (4.9 g, 99%) as an orange oil. $^1$H NMR (400 MHz, CDCl$_3$) δ 6.99-6.96 (m, 1H), 6.65-6.55 (m, 2H), 4.10 (d, J=10.4 Hz, 1H), 4.07-4.01 (m, 2H), 3.79 (d, J=10.8 Hz, 1H), 3.00 (s, 3H), 2.68 (d, J=16.4 Hz, 1H), 2.61 (d, J=16.4 Hz, 1H), 1.14 (s, 3H).

Step E: 2-(7-fluoro-3-methylchroman-3-yl)acetonitrile

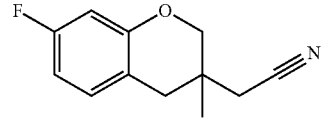

To a stirred solution of (7-fluoro-3-methyl-chroman-3-yl)methyl methanesulfonate (4.9 g, 17.9 mmol) in dimethyl sulfoxide (80 ml) was added potassium cyanide (3.5 g, 53.4 mmol). The mixture was stirred at 110° C. for 17 h under nitrogen. The reaction was quenched with water (100 ml) and extracted with ethyl acetate (100 ml×3). The combined organic phase was dried over sodium sulfate, filtered and concentrated. The residue was purified by flash column chromatography (eluting 0-10% ethyl acetate in petroleum ether) to afford 2-(7-fluoro-3-methyl-chroman-3-yl)acetonitrile (3.3 g, 90%) as a colorless oil. $^1$H NMR (400 MHz, CDCl$_3$) δ 7.00-6.97 (m, 1H), 6.66-6.56 (m, 2H), 3.99-3.96 (m, 1H), 3.81 (d, J=11.2 Hz, 1H), 2.70 (s, 2H), 2.40 (s, 2H), 1.24 (s, 3H).

Step F: 2-(7-fluoro-3-methyl-6-nitrochroman-3-yl)acetonitrile

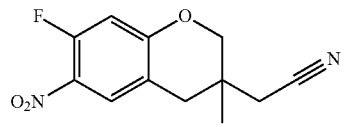 [SMILES: CC1(CC#N)COc2cc(F)c([N+](=O)[O-])cc2C1]

To a stirred solution of 2-(7-fluoro-3-methyl-chroman-3-yl)acetonitrile (1.5 g, 7.31 mmol) in acetic acid (5 ml) and acetic anhydride (10 ml) was added copper(II) nitrate (4.1 g, 21.9 mmol) at 0° C. The mixture was stirred at 0° C. for 15 min and at 28° C. for 0.5 h. Water (100 ml) was added and extracted with ethyl acetate (100 ml×3). The combined organic phase was washed with saturated sodium bicarbonate solution (100 ml×3), dried over sodium sulfate, filtered and concentrated. The residue was purified by flash column chromatography (eluting 15-30% ethyl acetate in petroleum ether) to give 2-(7-fluoro-3-methyl-6-nitro-chroman-3-yl)acetonitrile (1.8 g, 98%) as a light yellow solid.

Step G: 2-(3-methyl-7-morpholino-6-nitrochroman-3-yl)acetonitrile

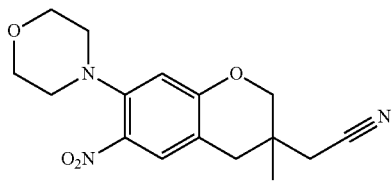 [SMILES: CC1(CC#N)COc2cc(N3CCOCC3)c([N+](=O)[O-])cc2C1]

To a stirred solution of 2-(7-fluoro-3-methyl-6-nitro-chroman-3-yl)acetonitrile (1.5 g, 6.1 mmol) in dimethyl sulfoxide (30 ml) was added N,N-diisopropylethylamine (2.4 g, 18.4 mmol) and morpholine (1.1 g, 12.3 mmol). The mixture was stirred at 90° C. for 16 h under nitrogen. Water (100 ml) was added, and the mixture was extracted with ethyl acetate (200 ml×3), dried over sodium sulfate, filtered and concentrated. The residue was purified by flash column chromatography (10-20% ethyl acetate in petroleum ether) to give 2-(3-methyl-7-morpholino-6-nitro-chroman-3-yl)acetonitrile (640 mg, 33%) as a yellow oil. $^1$H NMR (400 MHz, CDl$_3$) δ 7.75 (s, 1H), 6.53 (s, 1H), 4.07 (d, J=11.2 Hz, 1H), 3.87 (d, J=12.4 Hz, 1H), 3.86-3.83 (m, 4H), 3.02-2.99 (m, 4H), 2.71 (s, 2H), 2.45-2.33 (m, 2H), 1.25 (s, 3H).

Step H: 2-(6-amino-3-methyl-7-morpholinochroman-3-yl)acetonitrile

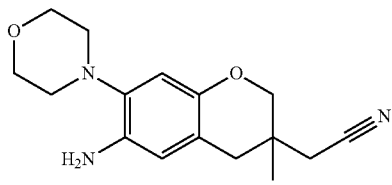 [SMILES: CC1(CC#N)COc2cc(N3CCOCC3)c(N)cc2C1]

To a stirred solution of 2-(3-methyl-7-morpholino-6-nitro-chroman-3-yl)acetonitrile (300 mg, 1.0 mmol) in ethanol (20 ml) and water (4 ml) was added iron (264 mg, 4.7 mmol) and ammonium chloride (253 mg, 4.7 mmol). The mixture was stirred at 80° C. for 2 h under nitrogen. The mixture was filtered and the filtrate was concentrated. The residue was purified by column chromatography (eluting 20-70% ethyl acetate in petroleum ether) to afford 2-(6-amino-3-methyl-7-morpholino-chroman-3-yl)acetonitrile (270 mg, 99%) as a reddish purple solid. LCMS (ESI): m/z=288.0 [M+H]$^+$.

Step I: 2-(3-methyl-7-morpholino-6-nitrochroman-3-yl)acetonitrile

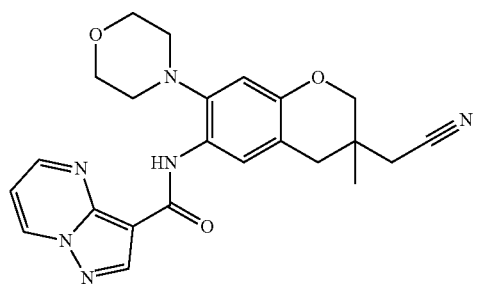 [SMILES: CC1(CC#N)COc2cc(N3CCOCC3)c(NC(=O)c3cnn4cccnc34)cc2C1]

To a stirred solution of 2-(6-amino-3-methyl-7-morpholino-chroman-3-yl)acetonitrile (220.0 mg, 0.8 mmol) in pyridine (25 ml) was added pyrazolo[1,5-a]pyrimidine-3-carbonyl chloride (167 mg, 0.9 mmol). The mixture was stirred at 25° C. for 2 h and concentrated. The residue was purified by column chromatography (eluting 0-1% methanol in dichloromethane) to give N-[3-(cyanomethyl)-3-methyl-7-morpholino-chroman-6-yl]pyrazolo[1,5-a]pyrimidine-3-carboxamide (340.0 mg, 99%) as a yellow solid. LCMS (ESI): m/z=433.2 [M+H]$^+$.

Step J: N-[(3R)-3-(cyanomethyl)-3-methyl-7-morpholino-chroman-6-yl]pyrazolo[1,5-a]pyrimidine-3-carboxamide and N-[(3S)-3-(cyanomethyl)-3-methyl-7-morpholino-chroman-6-yl]pyrazolo[1,5-a]pyrimidine-3-carboxamide

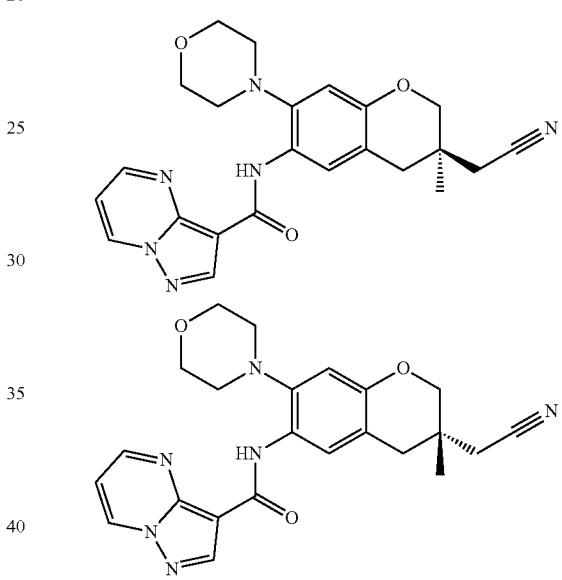

N-[3-(cyanomethyl)-3-methyl-7-morpholino-chroman-6-yl]pyrazolo[1,5-a]pyrimidine-3-carboxamide (340 mg, 0.8 mmol) was resolved by chiral preparatory SFC to afford N-[(3R)-3-(cyanomethyl)-3-methyl-7-morpholino-chroman-6-yl]pyrazolo[1,5-a]pyrimidine-3-carboxamide (124.8 mg, 36%; RT=3.341 min) and N-[(3S)-3-(cyanomethyl)-3-methyl-7-morpholino-chroman-6-yl]pyrazolo[1,5-a]pyrimidine-3-carboxamide (113.1 mg, 33%; RT=4.977 min) as light yellow solids with absolute stereochemistry assigned arbitrarily.

Example 519, Peak 1: $^1$H NMR (400 MHz, CD$_3$OD) δ 9.14 (d, J=6.8 Hz, 1H), 8.93 (s, 1H), 8.67 (s, 1H), 8.17 (s, 1H), 7.29 (s, 1H), 6.77 (s, 1H), 4.05-3.91 (m, 5H), 3.83 (d, J=10.8 Hz, 1H), 3.00-2.84 (m, 4H), 2.77 (d, J=16.4 Hz, 1H), 2.71 (d, J=17.6 Hz, 1H), 2.54 (s, 2H), 1.21 (s, 3H). LCMS (ESI): m/z=433.2 [M+H]$^+$.

Example 520, Peak 2: $^1$H NMR (400 MHz, CD$_3$OD) for second peak on SFC: 9.14 (d, J=5.6 Hz, 1H), 8.92 (s, 1H), 8.67 (s, 1H), 8.17 (s, 1H), 7.29 (s, 1H), 6.77 (s, 1H), 4.00-3.91 (m, 5H), 3.84 (d, J=11.2 Hz, 1H), 2.96-2.86 (m, 4H), 2.77 (d, J=17.2 Hz, 1H), 2.71 (d, J=17.2 Hz, 1H), 2.54 (s, 2H), 1.21 (s, 3H). LCMS (ESI): m/z=433.2 [M+H]$^+$.

Example 521. N-[6-chloro-2-[(2R)-2-fluoro-3-hydroxy-3-methyl-butyl]-1-oxo-isoindolin-5-yl]pyrazolo[1,5-a]pyrimidine-3-carboxamide

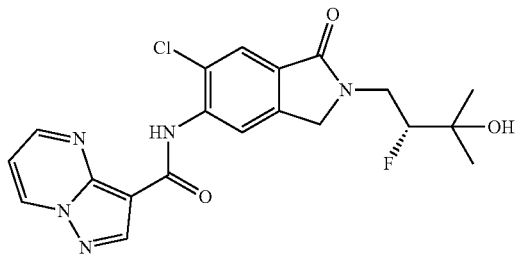 [SMILES: CC(C)(O)[C@H](F)CN1Cc2cc(NC(=O)c3cnn4cccnc34)c(Cl)cc2C1=O]

Step A: Methyl 4-amino-5-chloro-2-methyl-benzoate

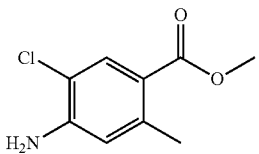

To a solution of methyl 5-chloro-2-methyl-4-nitro-benzoate (600 mg, 2.61 mmol) in ethanol (10 ml) and water (2 ml) was added iron (729.7 mg, 13.07 mmol) and ammonium chloride (699 mg, 13.07 mmol). The mixture was stirred at 80° C. for 2 h. The reaction mixture was filtered and concentrated. The residue was purified by flash column chromatography (0-10% ethyl acetate in petroleum ether) to afford methyl 4-amino-5-chloro-2-methyl-benzoate (450 mg, 86%) as a white solid. LCMS (ESI): m/z=199.8 [M+H]$^+$.

Step B: Methyl 5-chloro-2-methyl-4-(pyrazolo[1,5-a]pyrimidine-3-carbonylamino)benzoate

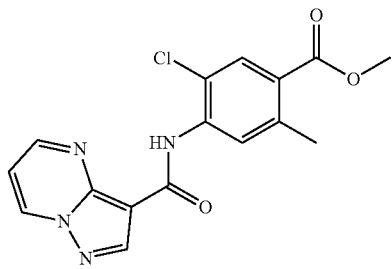 [SMILES: COC(=O)c1cc(Cl)c(NC(=O)c2cnn3cccnc23)cc1C]

To a solution of methyl 4-amino-5-chloro-2-methyl-benzoate (400 mg, 2.0 mmol) in tetrahydrofuran (20 ml) was added sodium hydride (60% in mineral oil, 160 mg, 4.0 mmol) at 25° C. After stirring at 25° C. for 30 min, pyrazolo[1,5-a]pyrimidine-3-carbonyl chloride (546 mg, 3.0 mmol) was added to the solution. The reaction mixture was stirred at 25° C. for 4 h. The reaction was diluted with water (10 ml) and extracted with dichloromethane (20 ml×3). The combined organic phase was washed with brine (20 ml×3), dried over anhydrous sodium sulfate, filtered and concentrated. The residue was triturated with methanol to afford methyl 5-chloro-2-methyl-4-(pyrazolo[1,5-a]pyrimidine-3-carbonylamino)benzoate (77 mg, 11%) as a yellow solid. LCMS (ESI): m/z=345.0 [M+H]$^+$.

Step C: Methyl 2-(bromomethyl)-5-chloro-4-(pyrazolo[1,5-a]pyrimidine-3-carbonylamino)benzoate

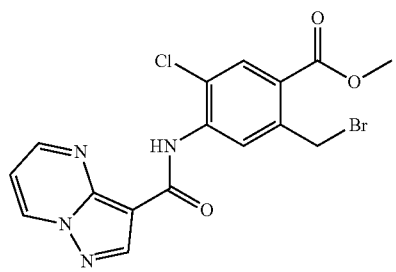 [SMILES: COC(=O)c1cc(Cl)c(NC(=O)c2cnn3cccnc23)cc1CBr]

To a solution of methyl 5-chloro-2-methyl-4-(pyrazolo[1,5-a]pyrimidine-3-carbonylamino)benzoate (77 mg, 0.22 mmol) in acetonitrile (10 ml) was added 2,2'-azobis(2-methylpropionitrile) (4 mg, 0.02 mmol) and 1-bromo-2,5-pyrrolidinedione (44 mg, 0.25 mmol) under nitrogen. The mixture was stirred at 80° C. for 16 h and concentrated. The residue was purified by flash column chromatography (0-10% methanol in dichloromethane) to afford methyl 2-(bromomethyl)-5-chloro-4-(pyrazolo[1,5-a]pyrimidine-3-carbonylamino)benzoate (40 mg, 42% yield) as a white solid. LCMS (ESI): m/z=424.8 [M+H]$^+$.

Step D: N-[6-chloro-2-[(2R)-2-fluoro-3-hydroxy-3-methyl-butyl]-1-oxo-isoindolin-5-yl]pyrazolo[1,5-a]pyrimidine-3-carboxamide

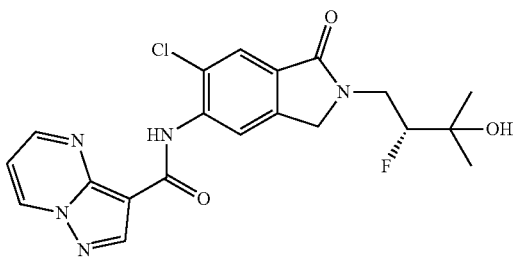 [SMILES: CC(C)(O)[C@H](F)CN1Cc2cc(NC(=O)c3cnn4cccnc34)c(Cl)cc2C1=O]

To a solution of methyl 2-(bromomethyl)-5-chloro-4-(pyrazolo[1,5-a]pyrimidine-3-carbonylamino)benzoate (40 mg, 0.09 mmol) and (3R)-4-amino-3-fluoro-2-methyl-butan-2-ol (14 mg, 0.11 mmol) in methanol (10 ml) was added triethylamine (0.04 ml, 0.28 mmol). The reaction was stirred at 70° C. for 2 h and concentrated. The residue was purified by prep-TLC (10% methanol in dichloromethane) to afford N-[6-chloro-2-[(2R)-2-fluoro-3-hydroxy-3-methyl-butyl]-1-oxo-isoindolin-5-yl]pyrazolo[1,5-a]pyrimidine-3-carboxamide (20 mg, 47%) as a white solid. $^1$H NMR (400 MHz, CDCl$_3$) δ 10.63 (s, 1H), 8.88-8.85 (m, 2H), 8.79-8.77 (m, 2H), 7.91 (s, 1H), 7.13-7.09 (m, 1H), 4.67-4.46 (m, 3H), 4.28-4.15 (m, 1H), 3.71-3.60 (m, 1H), 2.44 (s, 1H), 1.35 (s, 3H), 1.33 (s, 3H). LCMS (ESI): m/z=432.0 [M+H]$^+$.

Examples 522 and 523. N-[(2R)-2-(1-Hydroxy-1-methyl-ethyl)-6-[4-(1H-imidazol-4-ylmethyl)piperazin-1-yl]-2-methyl-3H-benzofuran-5-yl]pyrazolo[1,5-a]pyrimidine-3-carboxamide and N-[(2S)-2-(1-hydroxy-1-methyl-ethyl)-6-[4-(1H-imidazol-4-ylmethyl)piperazin-1-yl]-2-methyl-3H-benzofuran-5-yl]pyrazolo[1,5-a]pyrimidine-3-carboxamide

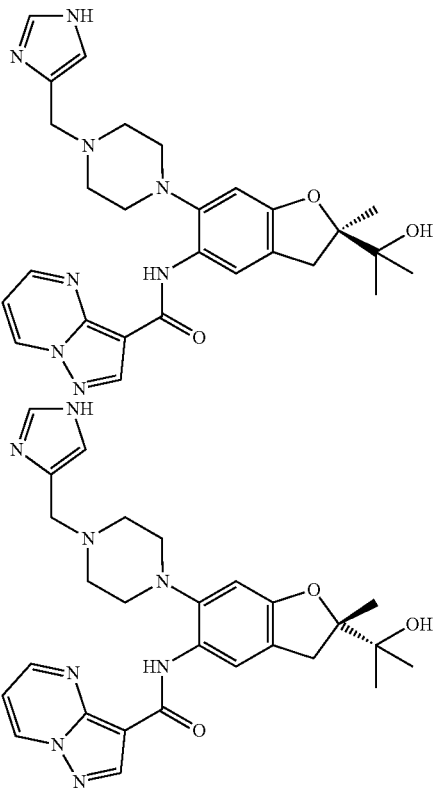

Step A: 2-[6-[4-(1H-Imidazol-4-ylmethyl)piperazin-1-yl]-2-methyl-5-nitro-3H-benzofuran-2-yl]propan-2-ol

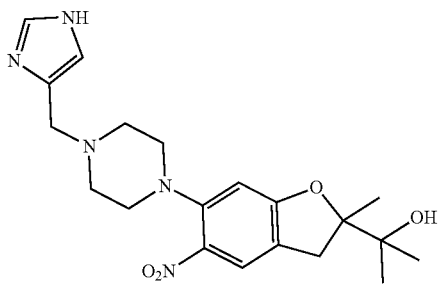 [SMILES: CC(C)(O)C1(C)Cc2cc([N+](=O)[O-])c(N3CCN(Cc4c[nH]cn4)CC3)cc2O1]

To a solution of 1H-imidazole-4-carbaldehyde (44 mg, 0.47 mmol) in methanol (5 ml), acetic acid (0.25 ml) and dichloromethane (5 ml) was added 2-(2-methyl-5-nitro-6-piperazin-1-yl-3H-benzofuran-2-yl)propan-2-ol (100 mg, 0.31 mmol). The mixture was stirred at 25° C. for 1 h when sodium cyanoborohydride (29 mg, 0.47 mmol) was added. The reaction was stirred at 25° C. for 16 h. The reaction was diluted with water (20 ml) and extracted with dichloromethane (50 ml×2). The organic phase was washed with brine (50 ml×2), dried over sodium sulfate, filtered and concentrated. The residue was purified by flash column chromatography (10% methanol in dichloromethane) to afford 2-[6-[4-(1H-imidazol-4-ylmethyl) piperazin-1-yl]-2-methyl-5-nitro-3H-benzofuran-2-yl]propan-2-ol (100 mg, 80% yield) as a yellow solid. LCMS (ESI): m/z=402.3 [M+H]$^+$.

Step B: 2-[5-Amino-6-[4-(1H-imidazol-4-ylmethyl)piperazin-1-yl]-2-methyl-3H-benzofuran-2-yl]propan-2-ol

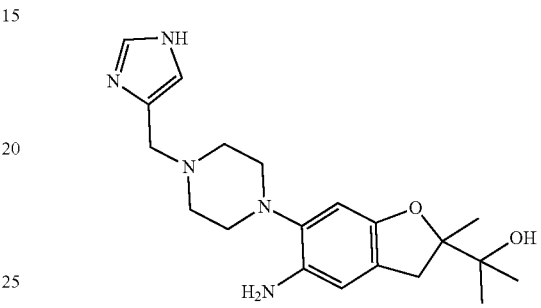

To a solution of 2-[6-[4-(1H-imidazol-4-ylmethyl)piperazin-1-yl]-2-methyl-5-nitro-3H-benzofuran-2-yl]propan-2-ol (510 mg, 1.27 mmol) in ethanol (10 ml) and water (2 ml) was added iron (354 mg, 6.35 mmol) and ammonium chloride (339 mg, 6.35 mmol). The reaction was stirred at 80° C. for 2 h. The reaction was filtered and concentrated. The residue was taken up in dichloromethane (80 ml×2), washed with saturated brine solution (80 ml), dried over sodium sulfate and concentrated to give 2-[5-amino-6-[4-(1H-imidazol-4-ylmethyl)piperazin-1-yl]-2-methyl-3H-benzofuran-2-yl]propan-2-ol (450 mg, 95% yield) as a yellow solid. LCMS (ESI): m/z=372.0 [M+H]$^+$.

Step C: N-[2-(1-hydroxy-1-methyl-ethyl)-6-[4-(1H-imidazol-4-ylmethyl)piperazin-1-yl]-2-methyl-3H-benzofuran-5-yl]pyrazolo[1,5-a]pyrimidine-3-carboxamide

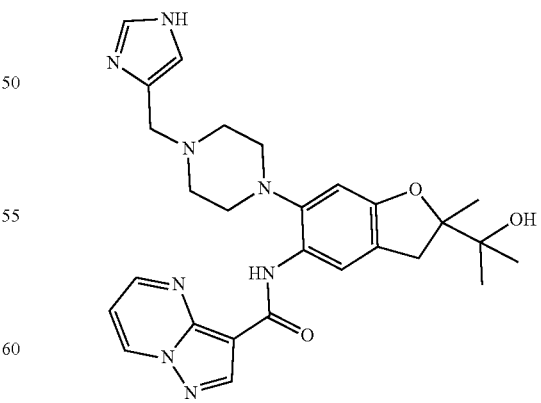

To a solution of pyrazolo[1,5-a]pyrimidine-3-carbonyl chloride (263 mg, 1.45 mmol) in pyridine (10 ml) was added 2-[5-amino-6-[4-(1H-imidazol-4-ylmethyl)piperazin-1-yl]-2-methyl-3H-benzofuran-2-yl]propan-2-ol (450 mg, 1.21 mmol). The reaction mixture was stirred at 50° C. for 16h. The reaction were concentrated and purified by flash column chromatography (10% methanol in dichloromethane) to give N-[2-(1-hydroxy-1-methyl-ethyl)-6-[4-(1H-imidazol-4-yl methyl)piperazin-1-yl]-2-methyl-3H-benzofuran-5-yl]pyrazolo[1,5-a]pyrimidine-3-carboxamide (480 mg, 76% yield) as a yellow solid. LCMS (ESI): m/z=517.3 [M+H]+.

Step D: N-[(2R)-2-(1-hydroxy-1-methyl-ethyl)-6-[4-(1H-imidazol-4-ylmethyl)piperazin-1-yl]-2-methyl-3H-benzofuran-5-yl]pyrazolo[1,5-a]pyrimidine-3-carboxamide and N-[(2S)-2-(1-hydroxy-1-methyl-ethyl)-6-[4-(1H-imidazol-4-ylmethyl)piperazin-1-yl]-2-methyl-3H-benzofuran-5-yl]pyrazolo[1,5-a]pyrimidine-3-carboxamide

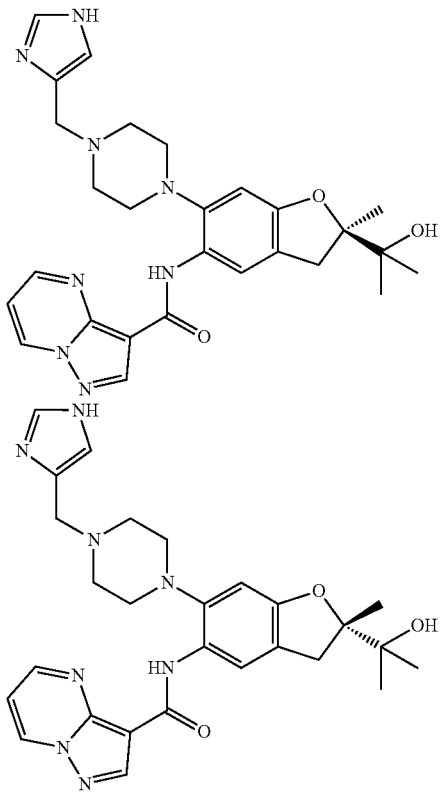

N-[2-(1-hydroxy-1-methyl-ethyl)-6-[4-(1H-imidazol-4-ylmethyl)piperazin-1-yl]-2-methyl-3H-benzofuran-5-yl]pyrazolo[1,5-a]pyrimidine-3-carboxamide (480 mg, 0.93 mmol) was resolved by chiral preparatory SFC to afford N-[(2R)-2-(1-hydroxy-1-methyl-ethyl)-6-[4-(1H-imidazol-4-ylmethyl)piperazin-1-yl]-2-methyl-3H-benzofuran-5-yl]pyrazolo[1,5-a]pyrimidine-3-carboxamide (121 mg, 25%) and N-[(2S)-2-(1-hydroxy-1-methyl-ethyl)-6-[4-(1H-imidazol-4-ylmethyl)piperazin-1-yl]-2-methyl-3H-benzofuran-5-yl]pyrazolo[1,5-a]pyrimidine-3-carboxamide (161 mg, 33%) as yellow solids with absolute stereochemistry assigned arbitrarily.

Example 522, Peak 1: $^1$H NMR (400 MHz, CDCl$_3$) δ 10.37 (s, 1H), 8.78 (d, J=6.8 Hz, 1H), 8.71 (s, 1H), 8.49-8.44 (m, 1H), 8.35 (s, 1H), 7.60 (s, 1H), 7.11-7.01 (m, 1H), 6.93 (s, 1H), 6.60 (s, 1H), 3.63 (s, 2H), 3.51 (d, J=15.6 Hz, 1H), 2.97-2.59 (m, 10H), 1.40 (s, 3H), 1.38 (s, 3H), 1.25 (s, 3H). LCMS (ESI): m/z=517.2 [M+H]+.

Example 523, Peak 2: $^1$H NMR (400 MHz, CDCl$_3$) δ 10.40 (s, 1H), 8.80 (d, J=6.8 Hz, 1H), 8.75 (s, 1H), 8.57-8.51 (m, 1H), 8.38 (s, 1H), 7.62 (s, 1H), 7.11-7.02 (m, 1H), 6.97 (s, 1H), 6.64 (s, 1H), 3.65 (s, 2H), 3.51 (d, J=15.6 Hz, 1H), 2.98-2.58 (m, 10H), 1.41 (s, 3H), 1.38 (s, 3H), 1.26 (s, 3H). LCMS (ESI): m/z=517.1 [M+H]+.

Examples 524 and 525. N-[(2S)-6-[4-(2-amino-2-oxo-ethyl)piperazin-1-yl]-2-(1-hydroxy-1-methyl-ethyl)-2-methyl-3H-benzofuran-5-yl]pyrazolo[1,5-a]pyrimidine-3-carboxamide and N-[(2R)-6-[4-(2-amino-2-oxo-ethyl)piperazin-1-yl]-2-(1-hydroxy-1-methyl-ethyl)-2-methyl-3H-benzofuran-5-yl]pyrazolo[1,5-a]pyrimidine-3-carboxamide

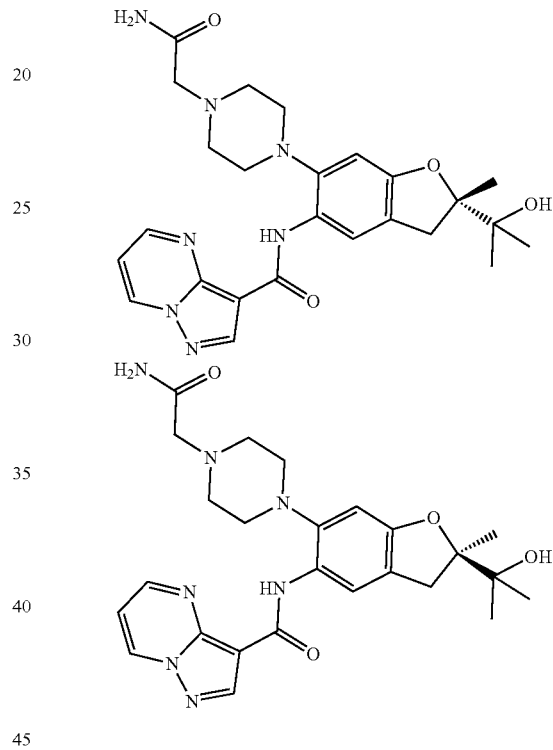

N-[6-[4-(2-amino-2-oxo-ethyl)piperazin-1-yl]-2-(1-hydroxy-1-methyl-ethyl)-2-methyl-3H-benzofuran-5-yl]pyrazolo[1,5-a]pyrimidine-3-carboxamide (Example 356) (650 mg, 1.32 mmol) was resolved by chiral SFC (OD (250 mm×30 mm, 5 m), 45%/0.1% NH$_3$H$_2$O in MeOH) to afford N-[(2S)-6-[4-(2-amino-2-oxo-ethyl)piperazin-1-yl]-2-(1-hydroxy-1-methyl-ethyl)-2-methyl-3H-benzofuran-5-yl]pyrazolo[1,5-a]pyrimidine-3-carboxamide (271.7 mg, 41.4%; RT=5.11 min) and N-[(2R)-6-[4-(2-amino-2-oxo-ethyl)piperazin-1-yl]-2-(1-hydroxy-1-methyl-ethyl)-2-methyl-3H-benzofuran-5-yl]pyrazolo[1,5-a]pyrimidine-3-carboxamide (278.4 mg, 42.4%; RT=5.99 min) as yellow solids with absolute stereochemistry assigned arbitrarily.

Example 524, Peak 1: $^1$H NMR (400 MHz, DMSO-d$_6$) δ 10.40 (s, 1H), 9.36 (dd, J=6.8, 1.6 Hz, 1H), 8.97 (dd, J=4.0, 1.6 Hz, 1H), 8.67 (s, 1H), 8.31 (s, 1H), 7.35 (dd, J=6.8, 4.0 Hz, 1H), 7.23 (s, 1H), 7.17 (s, 1H), 6.68 (s, 1H), 4.52 (s, 1H), 3.45 (d, J=15.6 Hz, 1H), 3.01 (s, 2H), 2.90-2.80 (m, 4H), 2.75-2.65 (m, 5H), 1.32 (s, 3H), 1.17 (s, 3H), 1.15 (s, 3H). LCMS (ESI): m/z=494.2 [M+H]+.

Example 525, Peak 2: $^1$H NMR (400 MHz, DMSO-d6) δ 10.38 (s, 1H), 9.34 (dd, J=7.2, 1.6 Hz, 1H), 8.95 (dd, J=4.4, 1.6 Hz, 1H), 8.65 (s, 1H), 8.29 (s, 1H), 7.33 (dd, J=7.2, 4.4 Hz, 1H), 7.21 (s, 1H), 7.15 (s, 1H), 6.66 (s, 1H), 4.50 (s, 1H), 3.43 (d, J=16.0 Hz, 1H), 2.99 (s, 2H), 2.90-2.80 (m, 4H), 2.75-2.65 (m, 5H), 1.30 (s, 3H), 1.15 (s, 3H), 1.14 (s, 3H). LCMS (ESI): m/z=494.2 [M+H]+.

Examples 526 and 527. (N-[(2R)-2-(2-hydroxy-2-methyl-propyl)-2-methyl-6-morpholino-3H-benzofuran-5-yl]pyrazolo[1,5-a]pyrimidine-3-carboxamide and (N-[(2S)-2-(2-hydroxy-2-methyl-propyl)-2-methyl-6-morpholino-3H-benzofuran-5-yl]pyrazolo[1,5-a]pyrimidine-3-carboxamide

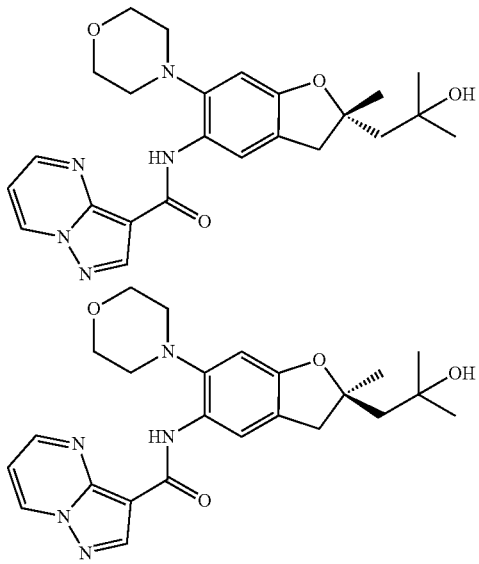

N-[2-(2-hydroxy-2-methyl-propyl)-2-methyl-6-morpholino-3H-benzofuran-5-yl]pyrazolo[1,5-a]pyrimidine-3-carboxamide (180 mg, 0.40 mmol) was prepared following the procedure described for Example 6, from 1-(2,4-difluorophenyl)-2,4-dimethyl-pentane-2,4-diol. It was resolved by chiral SFC (Chiralpak AD 100×4.6 mm×3 m; 40%/0.05% DEA in ethanol) to afford N-[(2R)-2-(2-hydroxy-2-methyl-propyl)-2-methyl-6-morpholino-3H-benzofuran-5-yl]pyrazolo[1,5-a]pyrimidine-3-carboxamide (60 mg, 33.3%; RT=4.731 min) and N-[(2S)-2-(2-hydroxy-2-methyl-propyl)-2-methyl-6-morpholino-3H-benzofuran-5-yl]pyrazolo[1,5-a]pyrimidine-3-carboxamide (50 mg, 27.8%; RT=5.207 min) as light yellow solids with absolute stereochemistry assigned arbitrarily.

Example 526, Peak 1: 1H NMR (400 MHz, CDCl3) δ 10.46 (s, 1H), 8.85-8.81 (m, 1H), 8.80-8.76 (m, 2H), 8.42 (s, 1H), 7.06 (dd, J=6.8, 4.4 Hz, 1H), 6.66 (s, 1H), 3.99-3.88 (m, 4H), 3.31 (d, J=15.6 Hz, 1H), 3.05 (br s, 1H), 2.98 (d, J=15.6 Hz, 1H), 2.92-2.90 (m, 4H), 2.05 (s, 2H), 1.52 (s, 3H), 1.32 (s, 3H), 1.27 (s, 3H). LCMS (ESI): m/z=452.1 [M+H]+.

Example 527, Peak 2: 1H NMR (400 MHz, CDCl3) δ 10.46 (s, 1H), 8.83 (dd, J=6.8, 2.0 Hz, 1H), 8.80-8.76 (m, 2H), 8.42 (s, 1H), 7.06 (dd, J=7.2, 4.0 Hz, 1H), 6.66 (s, 1H), 3.98-3.90 (m, 4H), 3.31 (d, J=15.6 Hz, 1H), 3.04 (s, 1H), 2.98 (d, J=15.6 Hz, 1H), 2.92-2.90 (m, 4H), 2.06 (s, 2H), 1.52 (s, 3H), 1.33 (s, 3H), 1.27 (s, 3H). LCMS (ESI): m/z=452.1 [M+H]+.

Example 528. (R)—N-(6-ethyl-2-(2-fluoro-3-hydroxy-3-methylbutyl)-1-oxoisoindolin-5-yl)pyrazolo[1,5-a]pyrimidine-3-carboxamide

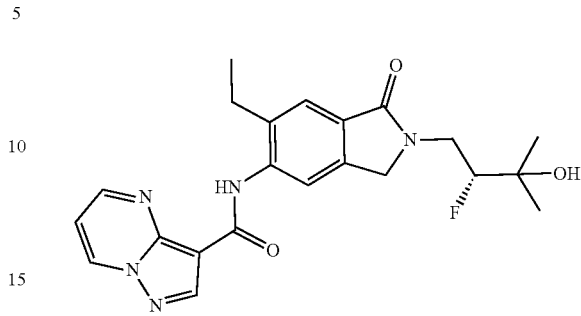

Step A: (R)-2-(2-fluoro-3-hydroxy-3-methylbutyl)-5-nitro-6-vinylisoindolin-1-one

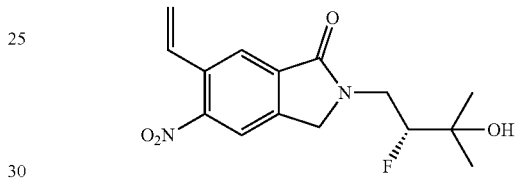

To a solution of 6-chloro-2-[(2R)-2-fluoro-3-hydroxy-3-methyl-butyl]-5-nitro-isoindolin-1-one (100 mg, 0.32 mmol) in 1,4-dioxane (3 ml) and water (0.5 ml) was added 4,4,5,5-tetramethyl-2-vinyl-1,3,2-dioxaborolane (80 mg, 0.47 mmol), palladium(II) acetate (7 mg, 0.03 mmol), 2-dicyclohexylphosphino-2',6'-dimethoxybiphenyl (26 mg, 0.06 mmol) and potassium phosphate (201 mg, 0.95 mmol). The mixture was stirred at 90° C. for 30 min under microwave condition and concentrated. The residue was dissolved in ethyl acetate (50 ml), and washed with water (40 ml) and brine (40 ml). The organic phase was dried over anhydrous sodium sulfate, filtered and concentrated. The residue was purified by flash column chromatography (50% ethyl acetate in petroleum ether) to afford (R)-2-(2-fluoro-3-hydroxy-3-methylbutyl)-5-nitro-6-vinylisoindolin-1-one (90 mg, 93%) as colorless oil. 1H NMR (400 MHz, CDCl3) δ 8.11 (s, 1H), 7.98 (s, 1H), 7.13 (dd, J=17.6, 11.2 Hz, 1H), 5.89 (d, J=16.8 Hz, 1H), 5.58 (d, J=11.2 Hz, 1H), 4.74 (d, J=18.0 Hz, 1H), 4.63-4.45 (m, 2H), 4.35-4.21 (m, 1H), 3.72-3.64 (m, 1H), 2.15 (s, 1H), 1.35 (s, 6H). LCMS (ESI): m/z=309 [M+H]+.

Step B: (R)-5-amino-6-ethyl-2-(2-fluoro-3-hydroxy-3-methylbutyl)isoindolin-1-one

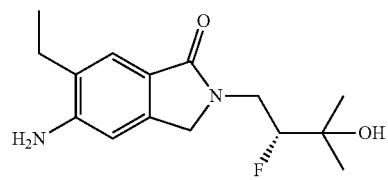 [SMILES: C=Cc1cc2c(cc1[N+](=O)[O-])CN(C[C@@H](F)C(C)(C)O)C2=O]

To a stirred solution of (R)-5-amino-2-(2-fluoro-3-hydroxy-3-methylbutyl)-6-vinylisoindolin-1-one (90 mg, 0.29 mmol) in methanol (10 ml) was added 10% palladium on carbon (31 mg, 0.029 mmol). The mixture was stirred at 26° C. under hydrogen atmosphere (15 psi) for 2 h. The mixture was filtered and the filtrate was concentrated to afford (R)-5-amino-6-ethyl-2-(2-fluoro-3-hydroxy-3-methylbutyl) isoindolin-1-one (75 mg, 92%) as colorless oil. LCMS (ESI): m/z=281 [M+H]$^+$.

Step C: (R)—N-(6-ethyl-2-(2-fluoro-3-hydroxy-3-methylbutyl)-1-oxoisoindolin-5-yl)pyrazolo[1,5-a]pyrimidine-3-carboxamide

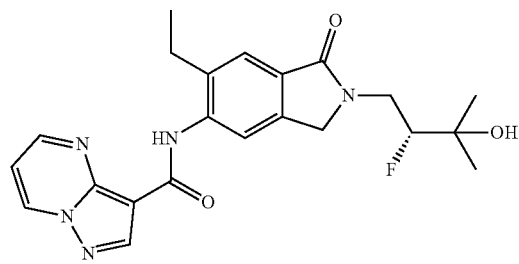 [SMILES: CCc1cc2c(cc1NC(=O)c1cnn3cccnc13)CN(C[C@@H](F)C(C)(C)O)C2=O]

To a solution of (R)-5-amino-6-ethyl-2-(2-fluoro-3-hydroxy-3-methylbutyl) isoindolin-1-one (75 mg, 0.27 mmol) in pyridine (2 ml) was added pyrazolo[1,5-a]pyrimidine-3-carbonyl chloride (63 mg, 0.35 mmol). The mixture was stirred at 26° C. for 16 h and concentrated. The residue was purified by prep-TLC (9% methanol in dichloromethane) to afford (R)—N-(6-ethyl-2-(2-fluoro-3-hydroxy-3-methylbutyl)-1-oxoisoindolin-5-yl)pyrazolo[1,5-a]pyrimidine-3-carboxamide (54 mg, 46%) as a white solid. $^1$H NMR (400 MHz, CDCl$_3$) δ 10.11 (s, 1H), 8.87 (dd, J=7.2, 1.6 Hz, 1H), 8.79 (s, 1H), 8.74 (dd, J=4.4, 2.0 Hz, 1H), 8.64 (s, 1H), 7.72 (s, 1H), 7.10 (dd, J=7.2, 4.4 Hz, 1H), 4.67-4.44 (m, 3H), 4.28-4.12 (m, 1H), 3.73-3.63 (m, 1H), 2.95 (q, J=7.2 Hz, 2H), 2.61 (s, 1H), 1.39 (t, J=7.2 Hz, 3H), 1.34 (s, 3H), 1.32 (s, 3H). LCMS (ESI): m/z=426.1 [M+H]$^+$.

Example 529. (R)—N-(2-(2-fluoro-3-hydroxy-3-methylbutyl)-6-isopropyl-1-oxoisoindolin-5-yl)pyrazolo[1,5-a]pyrimidine-3-carboxamide

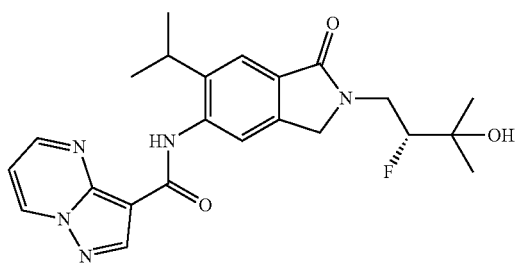 [SMILES: CC(C)c1cc2c(cc1NC(=O)c1cnn3cccnc13)CN(C[C@@H](F)C(C)(C)O)C2=O]

Step A: (R)-2-(2-fluoro-3-hydroxy-3-methylbutyl)-5-nitro-6-(prop-1-en-2-yl) isoindolin-1-one

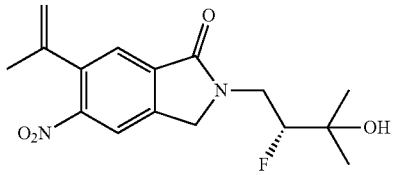 [SMILES: C=C(C)c1cc2c(cc1[N+](=O)[O-])CN(C[C@@H](F)C(C)(C)O)C2=O]

To a solution of (R)-6-chloro-2-(2-fluoro-3-hydroxy-3-methylbutyl)-5-nitroisoindolin-1-one (100 mg, 0.32 mmol) in 1,4-dioxane (3 ml) and water (0.5 ml) was added 4,4,5,5-tetramethyl-2-(prop-1-en-2-yl)-1,3,2-dioxaborolane (80 mg, 0.47 mmol), palladium(II) acetate (7 mg, 0.03 mmol), 2-dicyclohexylphosphino-2',6'-dimethoxybiphenyl (26 mg, 0.06 mmol) and potassium phosphate (201 mg, 0.95 mmol). The mixture was stirred at 90° C. for 30 min under microwave condition and concentrated. The residue was dissolved in ethyl acetate (50 ml), washed with water (40 ml) and brine (40 ml). The organic phase was dried over anhydrous sodium sulfate, filtered and concentrated. The residue was purified by flash column chromatography (50% ethyl acetate in petroleum ether) to afford (R)-2-(2-fluoro-3-hydroxy-3-methylbutyl)-5-nitro-6-(prop-1-en-2-yl)isoindolin-1-one (80 mg, 78%) as a colorless oil. $^1$H NMR (400 MHz, CDCl$_3$) δ 7.91 (s, 1H), 7.82 (s, 1H), 5.24 (s, 1H), 4.99 (s, 1H), 4.73 (d, J=17.6 Hz, 1H), 4.65-4.45 (m, 2H), 4.37-4.21 (m, 1H), 3.72-3.65 (m, 1H), 2.13 (s, 3H), 1.35 (s, 6H). LCMS (ESI): m/z=323.0 [M+H]$^+$.

Step B: (R)-5-amino-2-(2-fluoro-3-hydroxy-3-methylbutyl)-6-isopropylisoindolin-1-one

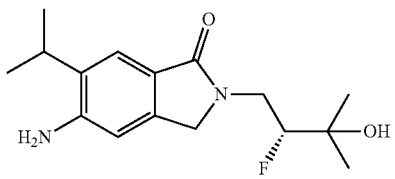 [SMILES: CC(C)c1cc2c(cc1N)CN(C[C@@H](F)C(C)(C)O)C2=O]

To a stirred solution of (R)-2-(2-fluoro-3-hydroxy-3-methylbutyl)-5-nitro-6-(prop-1-en-2-yl)isoindolin-1-one (120 mg, 0.37 mmol) in methanol (10 ml) was added 10% palladium on carbon (40 mg, 0.029 mmol). The mixture was stirred at 26° C. under hydrogen atmosphere (15 psi) for 2 h. The reaction mixture was filtered and the filtrate was concentrated to afford (R)-5-amino-2-(2-fluoro-3-hydroxy-3-methylbutyl)-6-isopropylisoindolin-1-one (96 mg, 88%) as a colorless oil. $^1$H NMR (400 MHz, CDCl$_3$) δ 7.64 (s, 1H), 6.69 (s, 1H), 4.60-4.29 (m, 3H), 4.24-3.98 (m, 3H), 3.70-3.55 (m, 1H), 3.94-2.83 (m, 1H), 2.62 (s, 1H), 1.32-1.29 (m, 12H).

913

Step C: (R)—N-(2-(2-fluoro-3-hydroxy-3-methyl-butyl)-6-isopropyl-1-oxoisoindolin-5-yl)pyrazolo[1,5-a]pyrimidine-3-carboxamide

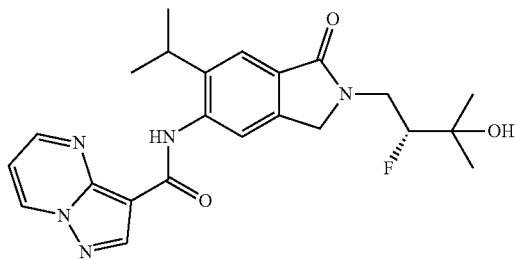

To a solution of (R)-5-amino-2-(2-fluoro-3-hydroxy-3-methylbutyl)-6-isopropylisoindolin-1-one (96 mg, 0.33 mmol) in pyridine (2 ml) was added pyrazolo[1,5-a]pyrimidine-3-carbonyl chloride (77 mg, 0.42 mmol). The mixture was stirred at 26° C. for 16 h and concentrated. The residue was purified by prep-TLC (9% methanol in dichloromethane) to afford (R)—N-(2-(2-fluoro-3-hydroxy-3-methyl-butyl)-6-isopropyl-1-oxoisoindolin-5-yl)pyrazolo[1,5-a]pyrimidine-3-carboxamide (57 mg, 39%) as a white solid. $^1$H NMR (400 MHz, CDCl$_3$) δ 10.14 (s, 1H), 8.88 (dd, J=6.8, 1.6 Hz, 1H), 8.80 (s, 1H), 8.74 (dd, J=4.4, 2.0 Hz, 1H), 8.56 (s, 1H), 7.84 (s, 1H), 7.10 (dd, J=7.2, 4.4 Hz, 1H), 4.68-4.43 (m, 3H), 4.27-4.10 (m, 1H), 3.76-3.65 (m, 1H), 3.51-3.42 (m, 1H), 2.47 (s, 1H), 1.47 (d, J=6.8 Hz, 6H), 1.34 (s, 3H), 1.32 (s, 3H). LCMS (ESI): m/z=440.1 [M+H]$^+$.

914

Example 530. N-(2,2-dimethyl-6-morpholino-2,3-dihydrobenzofuran-5-yl)-6-hydroxypyrazolo[1,5-a]pyrimidine-3-carboxamide

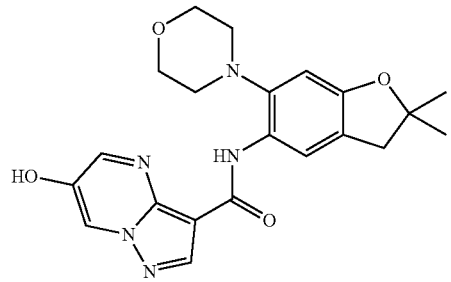 [SMILES: CC1(C)Cc2cc(NC(=O)c3cnn4cc(O)cnc34)c(N3CCOCC3)cc2O1]

To a solution of 6-bromo-N-(2,2-dimethyl-6-morpholino-2,3-dihydrobenzofuran-5-yl)pyrazolo [1,5-a]pyrimidine-3-carboxamide (200 mg, 0.42 mmol) in methanol (10 ml) was added potassium hydroxide (143 mg, 2.54 mmol). The mixture was stirred at 65° C. for 72 h and concentrated. The residue was dissolved in water (20 ml) and washed with dichloromethane (30 ml×3). The aqueous phase was acidified to pH=3 with 2N HCl aqueous solution, and extracted with 20% methanol in dichloromethane (20 ml×3). The combined organic phase was dried over anhydrous sodium sulfate, filtered and concentrated to afford N-(2,2-dimethyl-6-morpholino-2,3-dihydrobenzofuran-5-yl)-6-hydroxypyrazolo[1,5-a]pyrimidine-3-carboxamide (40 mg, 22%) as a yellow solid. $^1$H NMR (400 MHz, DMSO-d$_6$) δ 10.33 (s, 1H), 8.76-8.72 (m, 2H), 8.49 (s, 1H), 8.29 (s, 1H), 6.70 (s, 1H), 3.82 (s, 4H), 2.99 (s, 2H), 2.80 (s, 4H), 1.41 (s, 6H). LCMS (ESI): m/z=410.0 [M+H]$^+$.

TABLE 22

| Ex. | Name | Structure | NMR, MS |
|---|---|---|---|
| | The following examples were made in a manner similar to that for Example 4: | | |
| 531 | N-[6-(4-carbamoyl-1-piperidyl)-2,2-dimethyl-3H-benzofuran-5-yl]pyrazolo[1,5-a]pyrimidine-3-carboxamide | 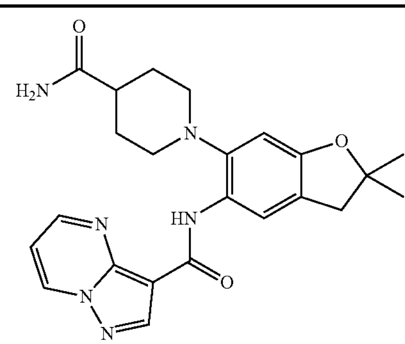 | $^1$H NMR (400 MHz, CDCl$_3$) δ 10.71 (s, 1H), 9.19 (dd, J = 4.0, 1.6 Hz, 1H), 8.79 - 8.77 (m, 2H), 8.55 (s, 1H), 7.08 (dd, J = 7.2, 4.4 Hz, 1H), 6.63 (s, 1H), 5.54-5.52 (m, 1H), 5.31-5.29 (m, 1H), 3.14-3.11 (m, 2H), 3.04 (s, 2H), 2.73-2.67 (m, 2H), 2.35-2.30 (m, 3H), 1.92-1.90 (m, 2H), 1 49 (s, 6H). LCMS (ESI): m/z = 435.1 [M + H]$^+$. |
| 532 | N-[6-[4-(dimethylamino)-1-piperidyl]-2,2-dimethyl-3H-benzofuran-5-yl]pyrazolo[1,5-a]pyrimidine-3-carboxamide | 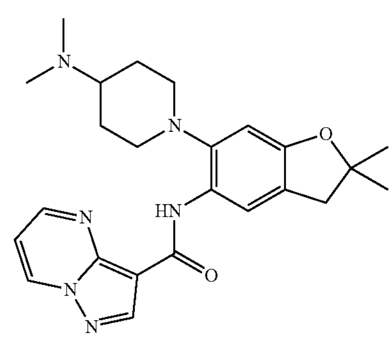 [SMILES: CN(C)C1CCN(c2cc3c(cc2NC(=O)c2cnn4cccnc24)CC(C)(C)O3)CC1] | $^1$H NMR (400 MHz, CDCl$_3$) δ 10.43 (s, 1H), 8.83-8.78 (m, 3H), 8.38 (s, 1H), 7.04 (dd, J = 7.2, 4.4 Hz, 1H), 6.64 (s, 1H), 3.16-3.12 (m, 2H), 3.03 (s, 2H), 2.70-2.64 (m, 2H), 2.34 (s, 6H), 2.25-2.18 (m, 1H), 1.98-1.95 (m, 2H), 1.86-1.83 (m, 2H), 1.49 (s, 6H). LCMS (ESI): m/z = 435.2 [M + H]$^+$. |

TABLE 22-continued

The following examples were made in a manner similar to that for Example 4:

| Ex. | Name | Structure | NMR, MS |
|---|---|---|---|
| 533 | N-(2,2-dimethyl-6-(piperazin-1-yl)-2,3-dihydrobenzofuran-5-yl)pyrazolo[1,5-a]pyrimidine-3-carboxamide | 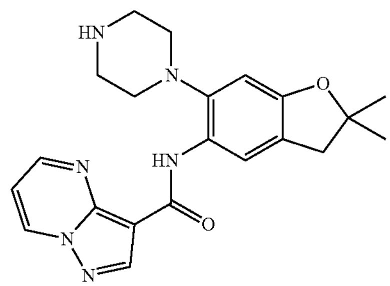 [SMILES: CC1(C)Cc2cc(NC(=O)c3cnn4cccnc34)c(N3CCNCC3)cc2O1] | $^1$H NMR (400 MHz, DMSO-d$_6$) δ 10.34 (s, 1H), 9.39 (dd, J = 6.8 Hz, 1.6 Hz, 1H), 9.02 (dd, J = 4.0 Hz, 1.2 Hz, 1H), 8.70 (s, 1H), 8.34 (s, 1H), 7.39 (dd, J = 6.8 Hz, 4.4 Hz, 1H), 6.70 (s, 1H), 4.17-4.13 (m, 1H), 3.32-3.28 (m, 2H), 3.16 (d, J = 5.6 Hz, 2H), 3.07-3.00 (m, 6H), 1.41 (s, 6H). LCMS (ESI): m/z = 393.0 [M + H]$^+$. |
| 534 | N-[6-(4-carbamoyl-4-fluoro-1-piperidyl)-2,2-dimethyl-3H-benzofuran-5-yl]pyrazolo[1,5-a]pyrimidine-3-carboxamide | 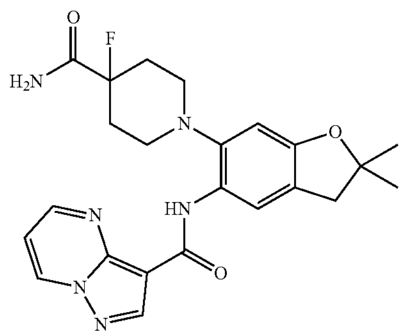 [SMILES: CC1(C)Cc2cc(NC(=O)c3cnn4cccnc34)c(N3CCC(F)(C(N)=O)CC3)cc2O1] | $^1$H NMR (400 MHz, DMSO-d$_6$) δ 10.57 (s, 1H), 9.37 (d, J = 7.2 Hz, 1H), 9.27 (s, 1H), 8.67 (s, 1H), 8.46 (s, 1H), 7.72 (s, 1H), 7 49 (s, 1H), 7.40-7.30 (m, 1H), 6.74 (s, 1H), 3.10-2.75 (m, 6H), 2.65-2.55 (m, 2H), 1.95-1.75 (m, 2H), 1.41 (s, 6H). LCMS (ESI): m/z = 453.3 [M + H]$^+$. |
| 535 | N-[6-[4-(2-Amino-2-oxo-ethyl)-4-methyl-1-piperidyl]-2,2-dimethyl-3H-benzofuran-5-yl]pyrazolo[1,5-a]pyrimidine-3-carboxamide | 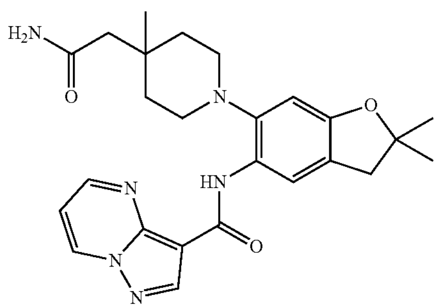 [SMILES: CC1(CC(N)=O)CCN(c2cc3c(cc2NC(=O)c2cnn4cccnc24)CC(C)(C)O3)CC1] | $^1$H NMR (400 MHz, DMSO-d$_6$) δ 10.37 (s, 1H). 9.35 (dd, J = 6.8, 1.6 Hz, 1H), 8.92 (dd, J = 4.0, 1.2 Hz, 1H), 8.67 (s, 1H), 8.29 (s, 1H), 7.38-7.30 (m, 2H), 6.78 (s, 2H), 2.99 (s, 2H), 2.83-2.72 (m, 4H), 2.13 (s, 2H), 1.83-1.75 (m, 2H), 1.61-1.54 (m, 2H), 1.41 (s, 6H), 1.12 (s, 3H). LCMS (ESI): m/z = 463.2 [M + H]$^+$. |
| 536 | N-[6-[4-(2-amino-2-oxo ethyl)-4-hydroxy-1-piperidyl]-2,2-dimethyl-3H-benzofuran-5-yl]pyrazolo[1,5-a]pyrimidine-3-carboxamide | 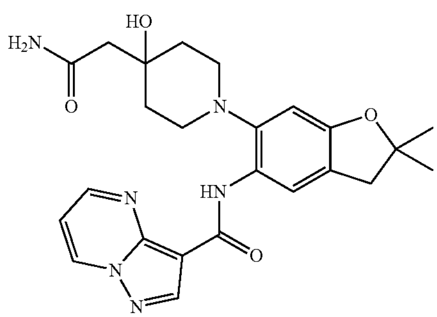 [SMILES: CC1(C)Cc2cc(NC(=O)c3cnn4cccnc34)c(N3CCC(O)(CC(N)=O)CC3)cc2O1] | $^1$HNMR (400 MHz, CDCl$_3$) δ 10.44 (s, 1H), 8.83-8.78 (m, 3H), 8.42 (s, 1H), 7.06 (dd, J = 6.8 Hz, 4.0 Hz, 1H), 6.67 (s, 1H), 5.94 (s, 1H), 5.46 (s, 1H), 4.00 (br s, 1H), 3.07-3.04 (m, 4H), 2.87-2.83 (m, 2H), 2.53 (s, 2H), 2.02-1.91 (m, 4H), 1.49 (s, 6H). LCMS (ESI): m/z = 465.1 [M + H]$^+$. |
| 537 | N-(6-(dimethylamino)-2,2-dimethyl-2,3-dihydrobenzofuran-5-yl)pyrazolo[1,5-a]pyrimidine-3-carboxamide | 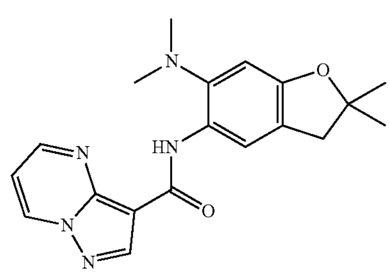 [SMILES: CN(C)c1cc2c(cc1NC(=O)c1cnn3cccnc13)CC(C)(C)O2] | $^1$H NMR (400 MHz, CDCl$_3$) δ 10.48 (s, 1H), 8.81 (dd, J = 7.2, 1.6 Hz, 1H), 8.77 (s, 1H), 8.71-8.70 (m, 1H), 8.36 (s, 1H), 7.02 (dd, J = 7.2, 4.0 Hz, 1H), 6.64 (s, 1H), 3.04 (s, 2H), 2.72 (s, 6H), 1.49 (s, 6H). LCMS (ESI): m/z = 352.1 [M + H]$^+$. |

TABLE 23

The following examples were made in a manner similar to that for Example 64:

| Ex. | Name | Structure | NMR, MS |
|---|---|---|---|
| 538 | N-(2,2-dimethyl-6-((1-methyl-1H-imidazol-4-yl)methoxy)-2,3-dihydrobenzofuran-5-yl)pyrazolo[1,5-a]pyrimidine-3-carboxamide | 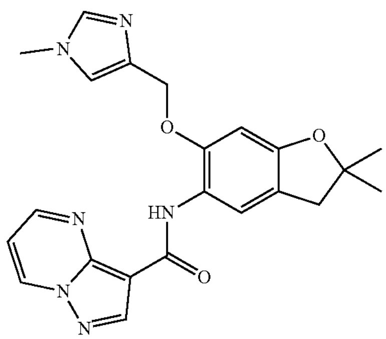 [SMILES: Cn1cnc(COc2cc3c(cc2NC(=O)c2cnn4cccnc24)CC(C)(C)O3)c1] | $^1$H NMR (400 MHz, CDCl$_3$) δ 10.20 (s, 1H), 8.79-8.77 (m, 1H), 8.74 (s, 1H), 8.49-8.47 (m, 1H), 8.35 (s, 1H), 7.45 (s, 1H), 7.00-6.96 (m, 2H), 6.56 (s, 1H), 5.12 (s, 2H), 3.68 (s, 3H), 3.02 (s, 2H), 1.49 (s, 6H). LCMS (ESI): m/z = 419.0 [M + H]$^+$ |
| 539 | N-[6-(1H-Imidazol-4-ylmethoxy)-2,2-dimethyl-3H-benzofuran-5-yl]pyrazolo[1,5-a]pyrimidine-3-carboxamide | 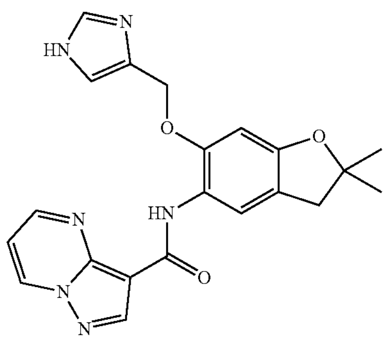 [SMILES: CC1(C)Cc2cc(NC(=O)c3cnn4cccnc34)c(OCc3c[nH]cn3)cc2O1] | $^1$H NMR (400 MHz, DMSO-d$_6$) δ 10.19 (s, 1H), 9.31(d, J = 6.0 Hz, 1H), 8.64 (s, 1H), 8.33 (br s, 1H), 8.26 (s, 1H), 7.73 (s, 1H), 7.29 (s, 1H), 7.26-7.24 (m, 1H), 6.75 (s, 1H), 5.05 (s, 2H), 2.98 (s, 2H), 1.42 (s, 6H). LCMS (ESI): m/z = 405.2 [M + H]$^+$ |
| 540 and 541 | N-[2,2-dimethyl-6-[[(2R)-5-oxopyrrolidin-2-yl]methoxy]-3H-benzofuran-5-yl]pyrazolo[1,5-a]pyrimidine-3-carboxamide and N-[2,2-dimethyl-6-[[(2S)-5-oxopyrrolidin-2-yl]methoxy]-3H-benzofuran-5-yl]pyrazolo[1,5-a]pyrimidine-3-carboxamide (absolute stereochemistry assigned arbitrarily) | | Example 540, Peak 1: $^1$H NMR (400 MHz, DMSO-d$_6$) δ 9.99 (s, 1H), 9.33 (dd, J = 6.8, 1.6 Hz, 1H), 8.86 (dd, J = 4.0, 1.6 Hz, 1H), 8.65 (s, 1H), 8.20 (s, 1H), 7.72 (s, 1H), 7.31 (dd, J = 6.8, 4.0 Hz, 1H), 6.56 (s, 1H), 4.05-4.01 (m, 2H), 3.96-3.94 (m, 1H), 2.97 (s, 2H), 2.27-2.17 (m, 3H), 1.94-1.91 (m, 1H), 1.41 (s, 6H). LCMS (ESI): m/z = 422.2 [M + H]$^+$.<br>Example 541, Peak 2: $^1$H NMR (400 MHz, DMSO-d$_6$) δ 10.01 (s, 1H), 9.37-9.36 (m, 1H), 8.88-8.87 (m, 1H), 8.67 (s, 1H), 8.22 (s, 1H), 7.73 (s, 1H), 7.33 (dd, J = 7.2, 4.4 Hz, 1H), 6.58 (s, 1H), 4.08-4.02 (m, 2H), 3.97-3.95 (m, 1H), 2.98 (s, 2H), 2.28-2.17 (m, 3H), 1.94-1.93 (m, 1H), 1.42 (s, 6H). LCMS (ESI): m/z = 422.2 [M + H]$^+$. |

TABLE 23-continued

The following examples were made in a manner similar to that for Example 64:

| Ex. | Name | Structure | NMR, MS |
|---|---|---|---|
| 542 | N-[2,2-Dimethyl-6-[(5-methyl-1H-pyrazol-3-yl)methoxy]-3H-benzofuran-5-yl]pyrazolo[1,5-a]pyrimidine-3-carboxamide | 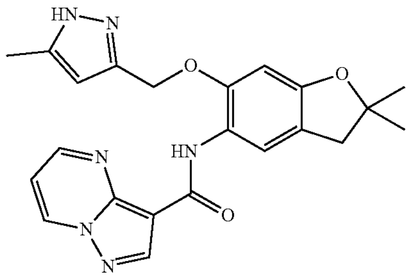 | $^1$H NMR (400 MHz, CDCl$_3$) δ 9.95 (s, 1H), 8.82-8.74 (m, 3H), 8.41 (s, 1H), 7.04 (dd, J = 6.8, 4.8 Hz, 1H), 6.49 (s, 1H), 6.16 (s, 1H), 5.16 (s, 2H), 3.03 (s, 2H), 2.35 (s, 3H), 1.50 (s, 6H). LCMS (ESI): m/z = 441.0 [M + Na]$^+$ |
| 543 | N-[2,2-Dimethyl-6-[(5-methyl-1H-pyrazol-3-yl)methoxy]-3H-benzofuran-5-yl]pyrazolo[1,5-a]pyrimidine-3-carboxamide | 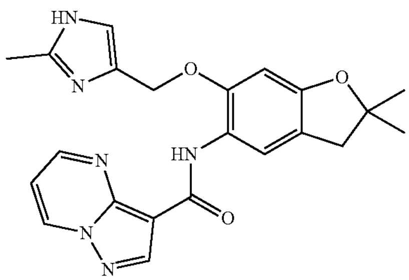 | $^1$H NMR (400 MHz, CD$_3$OD) δ 9.13 (dd, J = 6.8, 1.6 Hz, 1H), 8.64 (s, 1H), 8.47 (dd, J = 4.0, 1.6 Hz, 1H), 8.03 (s, 1H), 7.57 (s, 1H), 7.24 (dd, J = 7.2, 4.0 Hz, 1H), 6.63 (s, 1H), 5.21 (s, 2H), 3.03 (s, 2H), 2.59 (s, 3H), 1.47 (s, 6H). LCMS (ESI): m/z = 419.1 [M + H]$^+$ |

TABLE 24

The following examples were made in a manner similar to that for Example 173:

| Ex. | Name | Structure | NMR, MS |
|---|---|---|---|
| 544 and 545 | N-[2-[(1S)-3-hydroxy-1,3-dimethyl-butyl]-6-morpholino-1-oxo-isoindolin-5-yl]pyrazolo[1,5-a]pyrimidine-3-carboxamide N-[2-[(1R)-3-hydroxy-1,3-dimethyl-butyl]-6-morpholino-1-oxo-isoindolin-5-yl]pyrazolo[1,5-a]pyrimidine-3-carboxamide (absolute stereochemistry assigned arbitrarily) | | Example 544, Peak 1: $^1$H NMR (400 MHz, CDCl$_3$) δ 10.93 (s, 1H), 8.92-8.75 (m, 4H), 7.71 (s, 1H), 7.13 (dd, J = 6.0, 4.4 Hz, 1H), 4.83-4.72 (m, 1H), 4.38 (s, 2H), 4.05-3.95 (m, 4H), 3.04-2.88 (m, 5H), 1.92-1.86 (m, 1H), 1.70-1.64 (m, 1H), 1.35 (d, J = 6.8 Hz, 3H), 1.29 (s, 3H), 1.13 (s, 3H). LCMS (ESI): m/z = 479.2 [M + H]$^+$. Example 545, Peak 2: $^1$H NMR (400 MHz, CDCl$_3$) δ 10.93 (s, 1H), 8.94-8.74 (m, 4H), 7.72 (s, 1H), 7.13 (dd, J = 6.8, 4.4 Hz, 1H), 4.84-4.73 (m, 1H), 4.38 (s, 2H), 4.06-3.96 (m, 4H), 3.03-2.85 (m, 5H), 1.93-1.87 (m, 1H), 1.69-1.63 (m, 1H), 1.36 (d, J= 6.8 Hz, 3H), 1.30 (s, 3H), 1.13 (s, 3H). LCMS (ESI): m/z = 479.2 [M + H]$^+$ |

TABLE 24-continued

The following examples were made in a manner similar to that for Example 173:

| Ex. | Name | Structure | NMR, MS |
|---|---|---|---|
| 546 | N-[2-(1-methylazetidin-3-yl)-6-morpholino-1-oxo-isoindolin-5-yl]pyrazolo[1,5-a]pyrimidine-3-carboxamide | 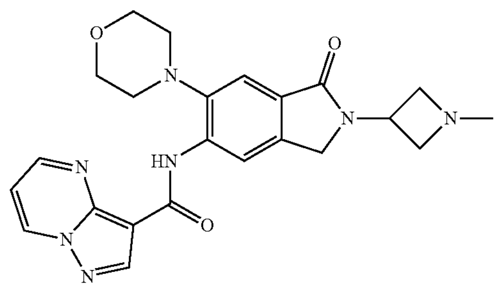 | $^1$HNMR (400 MHz, CDCl$_3$) δ 10.93 (s, 1H), 8.88-8.82 (m, 4H), 7.70 (s, 1H), 7.12 (dd, J = 7.2, 4.4 Hz, 1H), 5.02-4.99 (m, 1H), 4.57 (s, 2H), 4.01-3.99 (m, 4H), 3.85-3.72 (m, 2H), 3.50-3.40 (m, 2H), 3.00-2.97 (m, 4H), 2.48 (s, 3H). LCMS (ESI): m/z = 479.2 [M + H]$^+$. |
| 547 and 548 | Cis-N-[2-[4-(1-Hydroxy-1-methyl-ethyl)cyclohexyl]-6-morpholino-1-oxo-isoindolin-5-yl]pyrazolo[1,5-a]pyrimidine-3-carboxamide trans-N-[2-[4-(1-Hydroxy-1-methyl-ethyl)cyclohexyl]6-morpholino-1-oxo-isoindolin-5-yl]pyrazolo[1,5-a]pyrimidine-3-carboxamide (absolute stereochemistry assigned arbitrarily) | | Example 547, Peak 1: $^1$H NMR (400 MHz, CDCl$_3$) δ 10.92 (s, 1H), 8.88-8.82 (m, 4H), 7.74 (s, 1H), 7.13 (dd, J = 6.8, 4.0 Hz, 1H), 4.59 (s, 2H), 4.48-4.47 (m, 1H), 4.03-4.00 (m, 4H), 3.01-2.99 (m, 4H), 2.19-2.16 (m, 2H), 1.85-1.76 (m, 4H), 1.53-1.50 (m, 3H), 1.25 (s, 6H). LCMS (ESI): m/z = 519.2 [M + H]$^+$. Example 548, Peak 2: $^1$H NMR (400 MHz, DMSO-d$_6$) δ 10.89 (s, 1H), 9.40 (dd, J = 7.2, 1.6 Hz, 1H), 8.99 (dd, J = 4.0, 1 6 Hz, 1H), 8.75 (s, 2H), 7.56 (s, 1H), 7.38 (dd, J = 6.8, 4.4 Hz, 1H), 4.42 (s, 2H), 4.08 (s, 1H), 3.98-3.88 (m, 5H), 2.90-2.89 (m, 4H), 1.91-1.88 (m, 2H), 1.82-1.74 (m, 2H), 1.60-1.50 (m, 2H), 1.25-1.14 (m, 3H), 1.06 (s, 6H). LCMS (ESI): m/z = 519.2 [M + H]$^+$ |
| 549 and 550 | N-[2-[[(1S,2R)-2-hydroxycyclopentyl]-methyl]-6-morpholino-1-oxo-isoindolin-5-yl]pyrazolo[1,5-a]pyrimidine-3-carboxamide W-[2-[[(1R,2S)-2-hydroxycyclopentyl]-methyl]-6-morpholino-1-oxo-isoindolin-5-yl]pyrazolo[1,5-a]pyrimidine-3-carboxamide (absolute stereochemistry assigned arbitrarily) | | Example 549, Peak 1: $^1$H NMR (400 MHz, CDCl$_3$) δ 10.92 (s, 1H), 8.87-8.81 (m, 4H), 7.72 (s, 1H), 7.12 (dd, J = 7.2, 4.0 Hz, 1H), 4.51-4.41 (m, 2H), 4.02-4.00 (m, 4H), 3.98-3.97 (m, 1H), 3.64 (d, J = 6.8 Hz, 2H), 3.00-2.98 (m, 4H), 2.66-2.65 (m, 1H), 2.14-1.61 (m, 6H), 1.41-1.34 (m, 1H). LCMS (ESI): m/z = 477.2 [M + H]$^+$. Example 550, Peak 2: $^1$H NMR (400 MHz, CDCl$_3$) δ 10.92 (s, 1H), 8.87-8.81 (m, 4H), 7.72 (s, 1H), 7.12 (dd, J= 7.2, 4.4 Hz, 1H), 4.52-4.41 (m, 2H), 4.02-4.00 (m, 4H), 3.98-3.97 (m, 1H), 3.64 (d, J = 6.4 Hz, 2H), 3.00-2.98 (m, 4H), 2.66-2.64 (m, 1H), 2.12-1.66 (m, 6H), 1.41-1.33 (m, 1H). LCMS (ESI): m/z = 477.2 [M + H]$^+$. |

TABLE 24-continued

The following examples were made in a manner similar to that for Example 173:

| Ex. | Name | Structure | NMR, MS |
|---|---|---|---|
| 551 and 552 | N-[6-morpholino-2-[(2S)-2-morpholinopropyl]-1-oxo-isoindolin-5-yl]pyrazolo[1,5-a]pyrimidine-3-carboxamide; and N-[6-morpholino-2-[(2R)-2-morpholinopropyl]-1-oxo-isoindolin-5-yl]pyrazolo[1,5-a]pyrimidine-3-carboxamide (absolute stereochemistry assigned arbitrarily) | 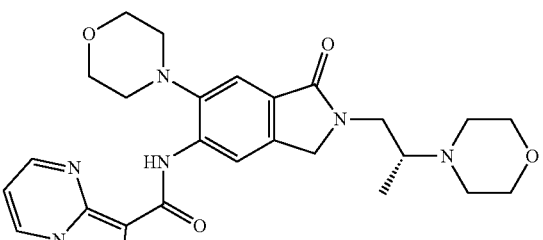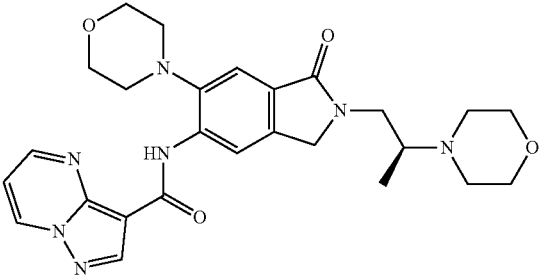 | Example 551, Peak 1: $^1$HNMR (400 MHz, DMSO-$d_6$) δ 10.90 (s, 1H), 9.42-9.40 (m, 1H), 8.99 (s, 1H), 8.78-8.73 (m, 2H), 7.57 (s, 1H), 7.42-7.36 (m, 1H), 4.61-4.48 (m, 2H), 3.95-3.85 (m, 4H), 3.61-3.45 (m, 6H), 2.95-2.85 (m, 5H), 2.65-2.53 (m, 2H), 2.48-2.35 (m, 2H), 0.93 (d, J = 6.4 Hz, 3H). LCMS (ESI): m/z = 506.2 $[M + H]^+$. Example 552, Peak 2: $^1$HNMR (400 MHz, DMSO-$d_6$) δ 10.90 (s, 1H), 9.42-9.40 (m, 1H), 9.00 (s, 1H), 8.78-8.73 (m, 2H), 7.57 (s, 1H), 7.42-7.36 (m, 1H), 4.61-4.48 (m, 2H), 3.95-3.85 (m, 4H), 3.61-3.45 (m, 6H), 2.95-2.85 (m, 5H), 2.65-2.53 (m, 2H), 2.48-2.35 (m, 2H), 0.93 (d, J = 6.4 Hz, 3H). LCMS (ESI): m/z = 506.2 $[M + H]^+$. |
| 553 and 554 | N-[2-[(3R)-1-methyl-2-oxo pyrrolidin-3-yl]-6-morpholino-1-oxo-isoindolin-5-yl]pyrazolo[1,5-a]pyrimidine-3-carboxamide; and N-[2-[(3S)-1-methyl-2-oxo-pyrrolidin-3-yl]-6-morpholino-1-oxo-isoindolin-5-yl]pyrazolo[1,5-a]pyrimidine-3-carboxamide (absolute stereochemistry assigned arbitrarily) | 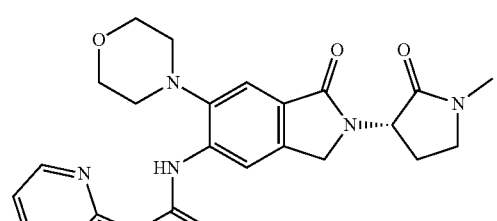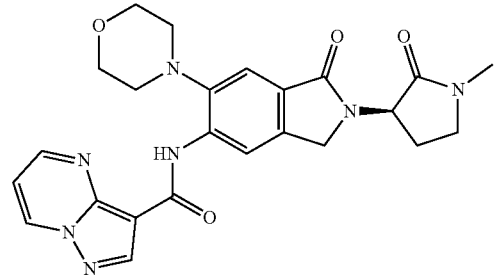 | Example 553, Peak 1: $^1$H NMR (400 MHz, CD$_3$OD) δ 9.14 (dd, J = 6.8, 1.6 Hz, 1H), δ 93 (dd, J = 4.0, 1.6 Hz, 1H), 8.73 (s, 1H), 8.67 (s, 1H), 7.70 (s, 1H), 7.29 (dd, J = 6.8, 4.4 Hz, 1H), 5.09 (t, J = 9.6 Hz, 1H), 4.54 (d, J = 17.2 Hz, 1H), 4.38 (d, J = 17.2 Hz, 1H), 4.03-3.97 (m, 4H), 3.56-3.53 (m, 2H), 2.99-2.96 (m, 4H), 2.95 (s, 3H), 2.52-2.44 (m, 1H), 2.34-2.24 (m, 1H). LCMS (ESI): m/z = 476.2 $[M + H]^+$. Example 554, Peak 2: $^1$H NMR (400 MHz, CD$_3$OD) δ 9.15 (dd, J = 7.2, 1.6 Hz, 1H), 8.95 (dd, J = 4.4, 2.0 Hz, 1H), 8.75 (s, 1H), 8.69 (s, 1H), 7.71 (s, 1H), 7.30 (dd, J = 6.8, 4.4 Hz, 1H), 5.09 (t, J = 9.6 Hz, 1H), 4.55 (d, J = 17.2 Hz, 1H), 4.38 (d, J = 17.2 Hz, 1H), 4.03-3.97 (m, 4H), 3.56-3.53 (m, 2H), 2.99-2.96 (m, 4H), 2.95 (s, 3H), 2.52-2.45 (m, 1H), 2.34-2.26 (m, 1H). LCMS (ESI): m/z = 476.2 $[M + H]^+$. |

TABLE 24-continued

The following examples were made in a manner similar to that for Example 173:

| Ex. | Name | Structure | NMR, MS |
|---|---|---|---|
| 555 and 556 | N-[6-morpholino-1-oxo-2-[[(3S)-tetrahydrofuran-3-yl]methyl]-isoindolin-5-yl]pyrazolo[1,5-a]pyrimidine-3-carboxamide N-[6-morpholino-1-oxo-2-[[(3R)-tetrahydrofuran-3-yl]methyl]-isoindolin-5-yl]pyrazolo[1,5-a]pyrimidine-3-carboxamide (absolute stereochemistry assigned arbitrarily) | | Example 555, Peak 1: $^1$H NMR (400 MHz, DMSO-d$_6$) δ 10.90 (s, 1H), 9.41 (d, J = 6.8 Hz, 1H), 8.99 (s, 1H), 8.75 (s, 2H), 7.57 (s, 1H), 7.40-7.37 (m, 1H), 4.50 (s, 2H), 3.89 (s, 4H), 3.80-3.69 (m, 2H), 3.66-3.60 (m, 1H), 3.51-3.50 (m, 2H), 3.46-3.42 (m, 1H), 2.91 (s, 4H), 2.66-2.58 (m, 1H), 1.97-1.93 (m, 1H), 1.60-1.56 (m, 1H). LCMS (ESI): m/z = 463.1 [M + H]$^+$. Example 556, Peak 2: $^1$H NMR (400 MHz, DMSO-d$_6$) δ 10.90 (s, 1H), 9.41 (d, J = 6.8 Hz, 1H), 8.99 (s, 1H), 8.76 (s, 2H), 7.58 (s, 1H), 7.41-7.37 (m, 1H), 4.50 (s, 2H), 3.90 (s, 4H), 3.80-3.69 (m, 2H), 3.66-3.60 (m, 1H), 3.52-3.50 (m, 2H), 3.47-3.43 (m, 1H), 2.91 (s, 4H), 2.66-2.58 (m, 1H), 2.00-1.91 (m, 1H), 1.62-1.54 (m, 1H). LCMS (ESI): m/z = 463.1 [M + H]$^+$. |
| 557 and 558 | N-[2-[(2R,2S)-2-fluoro-3-hydroxy-butyl]-6-morpholino-1-oxo-isoindolin-5-yl]pyrazolo[1,5-a]pyrimidine-3-carboxamide; and N-[2-[(2S,3R)-2-fluoro-3-hydroxy-butyl]-6-morpholino-1-oxo-isoindolin-5-yl]pyrazolo[1,5-a]pyrimidine-3-carboxamide (absolute stereochemistry assigned arbitrarily) | | Example 557, Peak 1: $^1$H NMR (400 MHz, DMSO-d$_6$) δ 10.90 (s, 1H), 9.39 (d, J = 6.4 Hz, 1H), 8.98 (s, 1H), 8.74 (s, 2H), 7.59 (s, 1H), 7.40-7.37 (m, 1H), 5.17-5.16 (m, 1H), 4.60-4.41 (m, 3H), 3.97-3.73 (m, 7H), 2.91 (s, 4H), 1.15 (d, J = 6.0 Hz, 3H). LCMS (ESI): m/z = 469.2 [M + H]$^+$. Example 558, Peak 2: $^1$H NMR (400 MHz, DMSO-d$_6$) δ 10.99 (s, 1H), 9.48 (d, J = 6.8 Hz, 1H), 9.08 (s, 1H), 8.83 (s, 2H), 7.67 (s, 1H), 7.50-7.45 (m, 1H), 5.23 (d, J = 5.6 Hz, 1H), 4.62-4.52 (m, 3H), 4.03-3.81 (m, 7H), 2.99 (s, 4H), 1.23 (d, J = 5.6 Hz, 3H). LCMS (ESI): m/z = 469.2 [M + H]$^+$. |

TABLE 24-continued

The following examples were made in a manner similar to that for Example 173:

| Ex. | Name | Structure | NMR, MS |
|---|---|---|---|
| 559 and 560 | N-[2-[[(1S,2S)-2-hydroxycyclopentyl]-methyl]-6-morpholino-1-oxo-isoindolin-5-yl]pyrazolo[1,5-a]pyrimidine-3-carboxamide N-[2-[[(1R,2R)-2-hydroxycyclopentyl]-methyl]-6-morpholino-1-oxo-isoindolin-5-yl]pyrazolo[1,5-a]pyrimidine-3-carboxamide (absolute stereochemistry assigned arbitrarily) | | Example 559, Peak 1: $^1$H NMR (400 MHz, CDCl$_3$) δ 10.95 (s, 1H), 8.89-8.82 (m, 4H), 7.73 (s, 1H), 7.14 (dd, J = 6,8, 4.0 Hz, 1H), 4.69 (s, 1H), 4.56 (d, J = 17.2 Hz, 1H), 4.36 (d, J = 17.2 Hz, 1H), 4.16-4.09 (m, 1H), 4.03-4.01 (m, 4H), 3.99-3.90 (m, 1H), 3.27-3.22 (m, 1H), 3.00-2.99 (m, 4H), 2.03-1.57 (m, 7H). LCMS (ESI): m/z = 477.2 [M + H]$^+$. Example 560, Peak 2: $^1$H NMR (400 MHz, CDCl$_3$) δ 10.95 (s, 1H), 8.89-8.82 (m, 4H), 7.73 (s, 1H), 7.14 (dd, J = 6.8, 4.0 Hz, 1H), 4.69 (s, 1H), 4.56 (d, J = 17.6 Hz, 1H), 4.36 (d, J = 16.8 Hz, 1H), 4.16-4.09 (m, 1H), 4.03-4.01 (m, 4H), 3.99-3.96 (m, 1H), 3.27-3.22 (m, 1H), 3.01-2.99 (m, 4H), 2.03-1.55 (m, 7H). LCMS (ESI): m/z = 477.2 [M + H]$^+$. |
| 561 and 562 | N-(2-((2S,3S)-2-fluoro-3-hydroxybutyl)-6-morpholino-1-oxoisoindolin-5-yl)pyrazolo[1,5-a]pyrimidine-3-carboxamide; and N-(2-((2R,3R)-2-fluoro-3-hydroxybutyl)-6-morpholino-1-oxoisoindolin-5-yl)pyrazolo[1,5-a]pyrimidine-3-carboxamide (absolute stereochemistry assigned arbitrarily) | | Example 561, Peak 1: $^1$H NMR (400 MHz, DMSO-d$_6$) δ 10.89 (s, 1H), 9.39-9.37 (m, 1H), 8.99-8.98 (m, 1H), 8.74-8.73 (m, 2H), 7.58 (s, 1H), 7.38 (dd, J = 6.8, 4.4 Hz, 1H), 5.09-5.08 (m, 1H), 4.63-4.47 (m, 3H), 3.89-3.81 (m, 7H), 2.95-2.85 (m, 4H), 115 (d, J = 6.4 Hz, 3H). LCMS (ESI): m/z = 469.2 [M + H]$^+$ Example 562, Peak 2: $^1$H NMR (400 MHz, DMSO-d$_6$) δ 10.90 (s, 1H), 9.42-9.40 (m, 1H), 9.00-8.99 (m, 1H), 8.75 (s, 2H), 7.59 (s, 1H), 7.40-7.37 (m, 1H), 5.01 (d, J = 5.60, 1H), 4.63-4.48 (m, 3H), 3.90-3.66 (m, 7H), 2.92 (s, 4H), 1.16 (d, J = 6.4 Hz, 3H). LCMS (ESI): m/z = 469.2 [M + H]$^+$. |
| 563 | N-[6-(azetidin-1-yl)-2-[(2R)-2-fluoro-3-hydroxy-3-methyl-butyl]-1-oxo-isoindolin-5-yl]pyrazolo[1,5-a]pyrimidine-3-carboxamide | 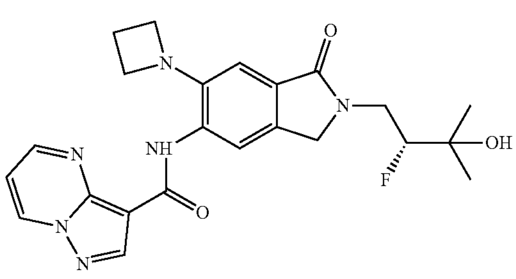 [SMILES: CC(C)(O)[C@H](F)CN1Cc2cc(NC(=O)c3cnn4cccnc34)c(N3CCC3)cc2C1=O] | $^1$H NMR (400 MHz, CDCl$_3$) δ 9.86 (s, 1H), 8.96-8.73 (m, 3H), 8.33 (s, 1H), 7.27 (s, 1H), 7.12 (br s, 1H), 4.64-4.35 (m, 3H), 4.29-4.09 (m, 1H), 4.05-3.89 (m, 4H), 3.78-3.60 (m, IH), 2.75 (s, 1H), 2.35-2.25 (m, 2H), 1.34 (s, 3H), 1.32 (s, 3H). LCMS (ESI): m/z = 453.1 [M + H]$^+$. |

TABLE 24-continued

The following examples were made in a manner similar to that for Example 173:

| Ex. | Name | Structure | NMR, MS |
|---|---|---|---|
| 564 and 565 | N-(2-((1S,2R)-2-(hydroxymethyl)cyclopentyl)-6-morpholino-1-oxoisoindolin-5-yl)pyrazolo[1,5-a]pyrimidine-3-carboxamide; and N-(2-((1R,2S)-2-(hydroxymethyl)cyclopentyl)-6-morpholino-1-oxoisoindolin-5-yl)pyrazolo[1,5-a]pyrimidine-3-carboxamide (absolute stereochemistry assigned arbitrarily) | | Example 564, Peak 1: $^1$H NMR (400 MHz, CDCl$_3$) δ 10.95 (s, 1H), 8.89-8.82 (m, 4H), 7.74 (s, 1H), 7.14 (dd, J = 6.4, 4.0 Hz, 1H), 4.81 (br s, 1H), 4.58 (d, J = M2 Hz, 1H) , 4.31 (d, J = 16.8 Hz, 1H), 4.21-4.18 (m, 1H), 4.02 (s, 4H), 3.63-3.58 (m, 1H), 3.20 (t, J = 10.8 Hz, 1H), 3.00 (s, 4H), 2.45-2.35 (m, 1H), 2.11-1.89 (m, 4H), 1.29-1.26 (m, 2H). LCMS (ESI): m/z = 477.3 [M + H]$^+$. Example 565, Peak 2: $^1$H NMR (400 MHz, CDCl$_3$) δ 10.95 (s, 1H), 8 89-8.82 (m, 4H), 7.74 (s, 1H), 7.14 (dd, ,/= 6.4, 4.4 Hz, 1H), 4.81 (br s, 1H), 4.58 (d, J = 17.2 Hz, 1H) , 4.31 (d, J = 17.2 Hz, 1H), 4.21-4.18 (m, 1H), 4.02 (s, 4H), 3.63-3.58 (m, 1H), 3.20 (t, J = 10.8 Hz, 1H), 3.00 (s, 4H), 2.45-2.35 (m, 1H), 2.16-1.84 (m, 4H), 1.29-1.26 (m, 2H). LCMS (ESI): m/z = 477.3 [M + H]$^+$. |
| 566 and 567 | N-(2-((1S,2S)-2-(hydroxymethyl)cyclopentyl)-6-morpholino-1-oxoisoindolin-5-yl)pyrazolo[1,5-a]pyrimidine-3-carboxamide; and N-(2-((1R,2R)-2-(hydroxymethyl)cyclopentyl)-6-morpholino-1-oxoisoindolin-5-yl)pyrazolo[1,5-a]pyrimidine-3-carboxamide (absolute stereochemistry assigned arbitrarily) | | Example 566, Peak 1: $^1$H NMR (400 MHz, DMSO-d$_6$) δ 10.89 (s, 1H), 9.40 (dd, J = 7.2, 1.6 Hz, 1H), 9.02-8.96 (m, 1H), 8.75 (s, 2H), 7.55 (s, 1H), 7.38 (dd, J = 7.2, 4.4 Hz, 1H), 4.51-4.41 (m, 3H), 4.29-4.25 (m, 1H), 3.93-3.86 (m, 4H), 3.45-3.36 (m, 2H), 2.90 (s, 4H), 2.22-2.09 (m, 1H), 1.93-1.38 (m, 6H). LCMS (ESI): m/z = 477.3 [M + H]$^+$. Example 567, Peak 2: $^1$H NMR (400 MHz, DMSO-d$_6$) δ 10.89 (s, 1H), 9.41-9.40 (m, 1H), 9.00-8.99 (m, 1H), 8.75 (s, 2H), 7.55 (s, 1H), 7.38 (dd, J = 7.2, 4.0 Hz, 1H), 4.52-4.40 (m, 3H), 4.33-4.22 (m, 1H), 3.90 (s, 4H), 3.46-3.38 (m, 2H), 2.91 (s, 4H), 2.15-1.85 (m, 1H), 1.92-1.38 (m, 6H). LCMS (ESI): m/z = 477.3 [M + H]$^+$. |
| 568 | N-[2-[(2R)-2-Fluoro-3-hydroxy-3-methyl-butyl]-6-[2-hydroxyethyl(methyl)amino]-1-oxo-isoindolin-5-yl]pyrazolo[1,5-a]pyrimidine-3-carboxamide | 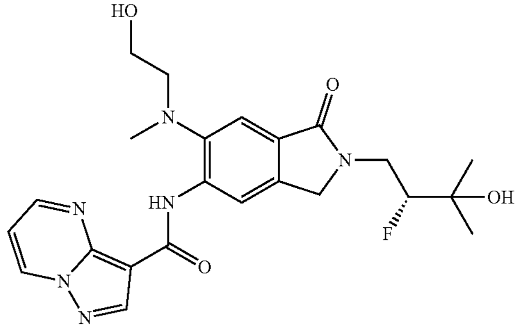 [SMILES: CN(CCO)c1cc2c(cc1NC(=O)c1cnn3cccnc13)CN(C[C@@H](F)C(C)(C)O)C2=O] | $^1$H NMR (400 MHz, CDCl$_3$) δ 10.91 (s, 1H), 8.85-8.81 (m, 4H), 7.72 (s, 1H), 7.12-7.06 (m, 1H), 4.65-4.46 (m, 3H), 4.25-4.12 (m, 1H), 3.81-3.67 (m, 5H), 3.33-3.27 (m, 2H), 2.67 (s, 3H), 1.36-1.30 (m, 6H). LCMS (ESI): m/z = 471.2 [M + H]$^+$ |

TABLE 25

The following examples were made in a manner similar to that for Example 250:

| Ex. | Name | Structure | NMR, MS |
|---|---|---|---|
| 569 | N-[6-(4-Cyano-4-methyl-1-piperidyl)-2-[(2R)-2-fluoro-3-hydroxy-3-methyl-butyl]-1-oxo-isoindolin-5-yl]pyrazolo[1,5-a]pyrimidine-3-carboxamide | 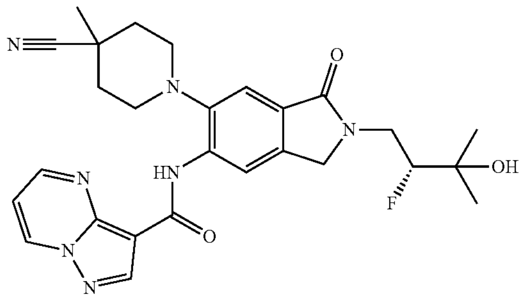 [SMILES: CC1(C#N)CCN(c2cc3c(cc2NC(=O)c2cnn4cccnc24)CN(C[C@@H](F)C(C)(C)O)C3=O)CC1] | $^1$H NMR (400 MHz, CDCl$_3$) δ 10.75 (s, 1H), 8.98-8.60 (m, 4H), 7.77 (s, 1H), 7.17-7.09 (m, 1H), 4.71-4.36 (m, 3H), 4.29-4.09 (m, 1H), 3.72-3.64 (m, 1H), 3.15-3.05 (m, 4H), 2.53 (s, 1H), 2.25-2.17 (m, 2H), 2.01-1.93 (m, 2H), 1.55 (s, 3H), 1.40-1.28 (m, 6H). LCMS (ESI): m/z = 520.2 [M + H]$^+$. |
| 570 | N-[6-(dimethylamino)-2-[(2R)-2-fluoro-3-hydroxy-3-methyl-butyl]-1-oxo-isoindolin-5-yl]pyrazolo[1,5-a]pyrimidine-3-carboxamide | 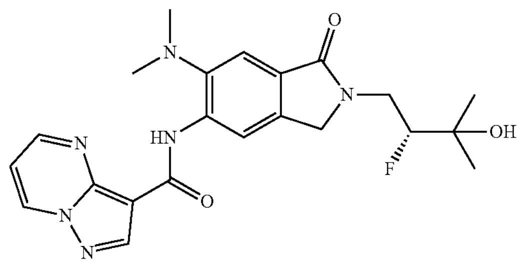 | $^1$H NMR (400 MHz, CDCl$_3$) δ 11.03 (s, 1H), 8.86-8.75 (m, 4H), 7.70 (s, 1H), 7.08 (dd, J = 7.2, 4.0 Hz, 1H), 4.64-4.48 (m, 3H), 4.25-4.12 (m, 1H), 3.75-3.66 (m, 1H), 2.81 (s, 6H), 1.34 (s, 3H), 1.32 (s, 3H). LCMS (ESI): m/z = 441.1 [M + H]$^+$. |

BIOLOGICAL EXAMPLES

Compounds were assayed for inhibition of human IRAK4 and IRAK1 catalytic activity using recombinant enzyme produced from insect cells. Full-length IRAK4 protein, carrying an N-terminal His6-Tag, was obtained from Life Technologies (Carlsbad, Calif., USA). The IRAK1 construct was produced internally and was comprised of IRAK1 residues Arg194 to Ser712, preceded by an NH$_2$-terminal His6 tag and the coding sequence for glutathione-S-transferase.

Kinase activities were assayed using the Transcreener-Fluorecescence polarization platform (BelBrook Labs, Madison, Wis., USA) that measures amounts of the reaction product, ADP. The IRAK4 reaction conditions were optimized using an IRAK1-derived peptide (sequence H-KKARFSRFAGSSPSQSSMVAR) to provide a linear reaction rate over the course of a 90 min incubation, which resulted in 10-12% conversion of the starting ATP to ADP. Final IRAK4 assay conditions were 1.25 nM IRAK4; 125 uM ATP; 10 uM MgCl2; 125 uM peptide in reaction buffer (25 mM HEPES (pH7.4); 2 mM Dithiothreitol; 0.015% Brij-35; and 0.5% dimethyl sulfoxide. The IRAK1 activity was optimized similarly, yielding final assay conditions of 3 mM IRAK1; 62.5 uM ATP; 5 uM MgCl$_2$, and 62.5 uM IRAK1 peptide in reaction buffer for 60 min.

Assays of compounds for kinase inhibition were performed using inhibitors serially-diluted in dimethyl sulfoxide, which was accomplished with a LabCyte Echo 555 liquid dispenser. 384 well assay plates spotted with compound received 4 ul of a 2× substrate (ATP+peptide) mix in reaction buffer, followed by 4 ul of 2× enzyme diluted in reaction buffer. Reactions were halted at 60 (IRAK1) or 90 (IRAK4) min by addition of 6 ul of detection buffer, containing EDTA (40 nM final concentration), 0.95 ug of the ADP-binding antibody ADP2, ADP tracer (3 nM final concentration), and 25 uM HEPES. Following a 1 hr incubation, fluorescence polarization of the ADP2-antibody::TRACER complex was read on a Tecan M1000 plate reader using a 635/20 excitation filter in combination with a 670/20 emission filter. Delta milli-P values were analyzed using Genedata software to fit dose-response curves and compute compound Ki values, using ATP Km values of 642 um and 83.2 uM for IRAK4 and IRAK1, respectively. Tables 15, 16 and 17 provide IRAK4 Ki values for representative compounds of the present invention.

TABLE 26

IRAK4 Ki values of representative compounds of the present invention.

| Example | IRAK4 Ki (uM) |
|---|---|
| 1 | 0.0047 |
| 2 | 0.026 |
| 3 | 0.15 |
| 4 | 0.0015 |
| 5 | 0.054 |
| 6 | 0.014 |
| 7 | 0.0039 |
| 8 | 0.0023 |
| 9 | 0.098 |
| 10 | 0.27 |
| 11 | 0.072 |
| 12 | 0.002 |
| 13 | 0.0067 |
| 14 | 0.019 |
| 15 | 0.012 |
| 16 | 0.0019 |
| 17 | 0.18 |
| 18 | 0.021 |
| 19 | 0.0033 |
| 20 | 0.78 |
| 21 | 0.0064 |
| 22 | |
| 23 | 0.031 |
| 24 | 0.0029 |
| 25 | 0.01 |
| 26 | 0.0051 |
| 27 | 0.26 |
| 28 | 0.027 |

TABLE 26-continued

IRAK4 Ki values of representative compounds of the present invention.

| Example | IRAK4 Ki (uM) |
|---|---|
| 29 | 0.009 |
| 30 | 0.032 |
| 31 | 0.0054 |
| 32 | 0.015 |
| 33 | 0.005 |
| 34 | 0.038 |
| 35 | 0.69 |
| 36 | 0.15 |
| 37 | 0.37 |
| 38 | 0.36 |
| 39 | 0.011 |
| 40 | 0.001 |
| 41 | 0.084 |
| 42 | 0.2 |
| 43 | 0.13 |
| 44 | 0.0017 |
| 45 | 0.0019 |
| 46 | 0.54 |
| 47 | 0.18 |
| 48 | 0.19 |
| 49 | 0.022 |
| 50 | 0.0062 |
| 51 | 0.0096 |
| 52 | 0.0038 |
| 53 | 0.0027 |
| 54 | 0.016 |
| 55 | 0.034 |
| 56 | 0.021 |
| 57 | 0.06 |
| 58 | 0.036 |
| 59 | 0.0096 |
| 60 | 0.0066 |
| 61 | 0.035 |
| 62 | 0.26 |
| 63 | 0.39 |
| 64 | 0.0087 |
| 65 | 0.0092 |
| 66 | 0.024 |
| 67 | 0.0044 |
| 68 | 0.0098 |
| 69 | 0.027 |
| 70 | 0.028 |
| 71 | 0.92 |
| 72 | 0.45 |
| 73 | 0.36 |
| 74 | 0.75 |
| 75 | 0.065 |
| 76 | 0.025 |
| 77 | 0.013 |
| 78 | 0.84 |
| 79 | 1.5 |
| 80 | 0.034 |
| 81 | 0.1 |
| 82 | 0.19 |
| 83 | 0.062 |
| 84 | 0.024 |
| 85 | 0.017 |
| 86 | 0.049 |
| 87 | 0.019 |
| 88 | 0.0076 |
| 89 | 0.026 |
| 90 | 0.043 |
| 91 | 0.039 |
| 92 | 0.0023 |
| 93 | 0.0018 |
| 94 | 0.029 |
| 95 | 0.025 |
| 96 | 0.014 |
| 97 | 0.0072 |
| 98 | 0.0028 |
| 99 | 0.0033 |
| 100 | 0.021 |
| 101 | 0.032 |
| 102 | 0.19 |
| 103 | 0.088 |
| 104 | 0.022 |
| 105 | 0.72 |
| 106 | 0.0024 |
| 107 | 0.079 |
| 108 | 0.079 |
| 109 | 0.0042 |
| 110 | 0.0025 |
| 111 | 0.0048 |
| 112 | 0.078 |
| 113 | 0.32 |
| 114 | 0.017 |
| 115 | 0.0095 |
| 116 | 0.018 |
| 117 | 0.017 |
| 118 | 0.014 |
| 119 | 0.79 |
| 120 | 0.001 |
| 121 | 0.016 |
| 122 | 0.006 |
| 123 | 1.1 |
| 124 | 0.49 |
| 125 | 0.005 |
| 126 | 0.0057 |
| 127 | 0.026 |
| 128 | 0.034 |
| 129 | 0.0032 |
| 130 | 0.0033 |
| 131 | |
| 132 | 0.0048 |
| 133 | 0.0041 |
| 134 | |
| 135 | |
| 136 | 0.0035 |
| 137 | 0.17 |
| 138 | 0.0068 |
| 139 | 0.0015 |
| 140 | 0.026 |
| 141 | 0.016 |
| 142 | 0.02 |
| 143 | 0.74 |
| 144 | 0.013 |
| 145 | 0.13 |
| 146 | 0.027 |
| 147 | 0.023 |
| 148 | 0.0061 |
| 149 | 0.025 |
| 150 | 0.089 |
| 151 | 0.072 |
| 152 | 0.012 |
| 153 | 0.014 |
| 154 | 0.0093 |
| 155 | 0.022 |
| 156 | 0.027 |
| 157 | 0.0088 |
| 158 | 0.027 |
| 159 | 0.0044 |
| 160 | 0.0048 |
| 161 | 0.0038 |
| 162 | 0.0045 |
| 163 | 0.0039 |
| 164 | 0.0028 |
| 165 | 0.0056 |
| 166 | 0.018 |
| 167 | 0.0028 |

Blank = not determined

TABLE 27

IRAK4 Ki values of representative compounds of the present invention.

| Example | IRAK4 Ki (uM) |
|---|---|
| 168 | 0.0036 |
| 169 | 0.0025 |
| 170 | 0.003 |
| 171 | 0.038 |
| 172 | 0.016 |
| 173 | 0.029 |
| 174 | 0.02 |
| 175 | 0.0022 |
| 176 | 0.051 |
| 177 | 0.002 |
| 178 | 0.015 |
| 179 | 0.031 |
| 180 | 0.0038 |
| 181 | 0.002 |
| 182 | 0.056 |
| 183 | 0.0051 |
| 184 | 0.0031 |
| 185 | 0.0058 |
| 186 | 0.015 |
| 187 | 0.002 |
| 188 | 0.084 |
| 189 | 0.0055 |
| 190 | 0.63 |
| 191 | 0.027 |
| 192 | 0.044 |
| 193 | 0.1 |
| 194 | 0.41 |
| 195 | 0.02 |
| 196 | 0.013 |
| 197 | 0.033 |
| 198 | 0.14 |
| 199 | 0.17 |
| 200 | 0.022 |
| 201 | 0.028 |
| 202 | 0.69 |
| 203 | 0.015 |
| 204 | 0.73 |
| 205 | 0.086 |
| 206 | 0.0034 |
| 207 | 0.017 |
| 208 | 0.015 |
| 209 | 0.0058 |
| 210 | 0.0031 |
| 211 | 0.0051 |
| 212 | 0.056 |
| 213 | 0.003 |
| 214 | 0.012 |
| 215 | 0.0054 |
| 216 | 0.003 |
| 217 | 0.015 |
| 218 | 0.017 |
| 219 | 0.082 |
| 220 | 0.075 |
| 221 | 0.003 |
| 222 | 0.094 |
| 223 | 0.072 |
| 224 | 0.33 |
| 225 | 0.045 |
| 226 | 0.006 |
| 227 | 0.49 |
| 228 | 0.048 |
| 229 | 0.26 |
| 230 | 0.018 |
| 231 | 0.003 |
| 232 | 0.034 |
| 233 | 0.10 |
| 234 | 0.033 |
| 235 | 0.004 |
| 236 | 0.013 |
| 237 | 0.81 |
| 238 | 0.036 |
| 239 | 0.12 |
| 240 | 0.027 |
| 241 | 0.015 |
| 242 | 0.028 |
| 243 | 0.25 |
| 244 | 0.036 |
| 245 | 0.010 |
| 246 | 0.006 |
| 247 | 0.015 |
| 248 | 0.036 |
| 249 | 0.047 |
| 250 | 0.024 |
| 251 | 0.029 |
| 252 | 0.005 |
| 253 | 0.020 |
| 254 | 0.026 |
| 255 | 0.004 |
| 256 | 0.002 |
| 257 | 0.006 |
| 258 | 0.003 |
| 259 | 0.002 |
| 260 | |
| 261 | 0.002 |
| 262 | 0.010 |
| 263 | 0.008 |
| 264 | 0.002 |
| 265 | 0.004 |
| 266 | 0.009 |
| 267 | 0.039 |
| 268 | 0.075 |
| 269 | 0.0015 |
| 270 | 0.0097 |
| 271 | 0.0017 |
| 272 | 0.004 |
| 273 | 0.037 |
| 274 | 0.0014 |
| 275 | 0.034 |
| 276 | 0.026 |
| 277 | 0.016 |
| 278 | 0.004 |
| 279 | 0.0018 |
| 280 | 0.002 |
| 281 | 0.0024 |
| 282 | 0.002 |
| 283 | 0.002 |
| 284 | 0.002 |
| 285 | 0.002 |
| 286 | 0.002 |
| 287 | 0.026 |
| 288 | 0.063 |
| 289 | 0.008 |
| 290 | 0.18 |
| 291 | 0.38 |
| 292 | 0.76 |
| 293 | 0.69 |
| 294 | 0.014 |
| 295 | 0.0082 |
| 296 | 0.018 |
| 297 | 0.023 |
| 298 | 0.007 |
| 299 | 0.031 |
| 300 | 0.007 |
| 301 | 0.017 |
| 302 | 0.011 |
| 303 | 0.97 |
| 304 | 0.72 |
| 305 | 0.029 |
| 306 | 0.052 |
| 307 | 0.032 |
| 308 | 0.009 |
| 309 | 0.015 |
| 310 | 0.023 |
| 311 | 0.010 |
| 312 | 0.073 |
| 313 | 0.49 |
| 314 | 0.065 |
| 315 | 0.52 |
| 316 | 0.0052 |
| 317 | 0.0024 |

TABLE 27-continued

IRAK4 Ki values of representative compounds of the present invention.

| Example | IRAK4 Ki (uM) |
|---|---|
| 318 | 0.0043 |
| 319 | 0.0031 |
| 320 | 0.0046 |
| 321 | 0.011 |
| 322 | 0.035 |
| 323 | 0.0042 |
| 324 | 0.0048 |
| 325 | 0.006 |
| 326 | 0.0032 |
| 327 | 0.0033 |
| 328 | 0.0027 |
| 329 | 0.006 |
| 330 | 0.006 |
| 331 | 0.012 |
| 332 | 0.006 |
| 333 | 0.003 |
| 334 | 0.003 |
| 335 | 0.002 |

Blank = not determined

TABLE 28

IRAK4 Ki values of representative compounds of the present invention.

| Example | IRAK4 Ki (uM) |
|---|---|
| 336 | 0.003 |
| 337 | 0.0045 |
| 338 | 0.0077 |
| 339 | 0.005 |
| 340 | 0.008 |
| 341 | 0.004 |
| 342 | 0.0039 |
| 343 | 0.005 |
| 344 | 0.008 |
| 345 | 0.004 |
| 346 | 0.0029 |
| 347 | 0.0036 |
| 348 | 0.89 |
| 349 | 1.1 |
| 350 | 0.005 |
| 351 |  |
| 352 | 0.002 |
| 353 |  |
| 354 | 0.003 |
| 355 | 0.006 |
| 356 | 0.004 |
| 357 | 0.41 |
| 358 | 0.51 |
| 359 | 0.26 |
| 360 | 0.0063 |
| 361 | 0.0092 |
| 362 | 0.0067 |
| 363 | 0.0053 |
| 364 | 0.0037 |
| 365 | 0.0045 |
| 366 | 0.0075 |
| 367 | 0.0058 |
| 368 | 0.021 |
| 369 | 0.0068 |
| 370 | 0.0058 |
| 371 | 0.0014 |
| 372 | 0.013 |
| 373 | 0.0017 |
| 374 | 0.002 |
| 375 | 0.047 |
| 376 | 0.046 |
| 377 | 0.011 |
| 378 | 0.0073 |
| 379 | 0.0051 |
| 380 | 0.0081 |
| 381 | 0.003 |
| 382 | 0.004 |
| 383 | 0.0076 |
| 384 | 0.037 |
| 385 | 0.019 |
| 386 | 0.016 |
| 387 | 0.015 |
| 388 | 0.012 |
| 389 | 0.0013 |
| 390 | 0.016 |
| 391 | 0.031 |
| 392 | 0.018 |
| 393 | 0.024 |
| 394 | 0.075 |
| 395 | 0.34 |
| 396 | 0.11 |
| 397 | 0.088 |
| 398 | 0.007 |
| 399 | 0.005 |
| 400 | 0.001 |
| 401 | 0.097 |
| 402 | 0.019 |
| 403 | 0.68 |
| 404 | 0.064 |
| 405 | 0.52 |
| 406 | 0.15 |
| 407 | 0.006 |
| 408 | 0.046 |
| 409 | 0.0067 |
| 410 | 0.0062 |
| 411 | 0.0076 |
| 412 | 0.0059 |
| 413 | 0.032 |
| 414 | 0.012 |
| 415 | 0.003 |
| 416 | 0.003 |
| 417 | 0.0036 |
| 418 | 0.0048 |
| 419 | 0.009 |
| 420 | 0.014 |
| 421 | 0.10 |
| 422 | 0.11 |
| 423 | 0.0096 |
| 424 | 0.003 |
| 425 | 0.006 |
| 426 | 0.005 |
| 427 | 0.038 |
| 428 | 0.075 |
| 429 | 0.012 |
| 430 | 0.13 |
| 431 | 0.020 |
| 432 | 0.010 |
| 433 | 0.014 |
| 434 | 0.022 |
| 435 | 0.053 |

TABLE 29

IRAK4 Ki values of representative compounds of the present invention.

| Example | IRAK4 Ki (uM) |
|---|---|
| 436 | 0.01 |
| 437 | 0.014 |
| 438 | 0.055 |
| 439 | 0.034 |
| 440 | 0.053 |
| 441 | 0.006 |
| 442 | 0.096 |
| 443 | 0.038 |
| 444 | 0.0028 |

TABLE 29-continued

IRAK4 Ki values of representative compounds of the present invention.

| Example | IRAK4 Ki (uM) |
|---|---|
| 445 | 0.0033 |
| 446 | 0.052 |
| 447 | 0.006 |
| 448 | 0.024 |
| 449 | 0.08 |
| 450 | |
| 451 | 0.0047 |
| 452 | 0.15 |
| 453 | 0.044 |
| 454 | 0.0088 |
| 455 | 0.0058 |
| 456 | 0.0026 |
| 457 | 0.0044 |
| 458 | 0.037 |
| 459 | 0.016 |
| 460 | 0.0059 |
| 461 | 0.029 |
| 462 | 0.0065 |
| 463 | 0.025 |
| 464 | 0.067 |
| 465 | 0.038 |
| 466 | 0.099 |
| 467 | 0.013 |
| 468 | 0.0051 |
| 469 | 0.0088 |
| 470 | 0.012 |
| 471 | 0.0065 |
| 472 | 0.0025 |
| 473 | 0.005 |
| 474 | 0.02 |
| 475 | 0.0095 |
| 476 | 0.033 |
| 477 | 0.035 |
| 478 | 0.006 |
| 479 | 0.0067 |
| 480 | |
| 481 | |
| 482 | |
| 483 | |
| 484 | 0.35 |
| 485 | 0.066 |
| 486 | 0.037 |
| 487 | 0.00061 |
| 488 | 0.61 |
| 489 | 0.24 |
| 490 | 0.98 |
| 491 | 0.0011 |
| 492 | 0.0091 |
| 493 | 0.043 |
| 494 | 0.04 |
| 495 | 0.017 |
| 496 | 0.00083 |
| 497 | 0.0026 |
| 498 | 0.029 |
| 499 | 0.03 |
| 500 | 0.084 |
| 501 | 0.0069 |
| 502 | 0.0058 |
| 503 | 0.004 |
| 504 | 0.0031 |
| 505 | 0.0052 |
| 506 | 0.0051 |
| 507 | 0.0032 |
| 508 | 0.043 |
| 509 | 0.0011 |
| 510 | 0.044 |
| 511 | |
| 512 | 0.15 |
| 513 | 0.21 |
| 514 | 0.81 |
| 515 | 0.42 |
| 516 | 0.0061 |
| 517 | 0.14 |
| 518 | 0.13 |
| 519 | 0.039 |
| 520 | 0.0011 |
| 521 | 0.004 |
| 522 | 0.0034 |
| 523 | 0.0044 |
| 524 | 0.0041 |
| 525 | 0.0042 |
| 526 | |
| 527 | |
| 528 | |
| 529 | |
| 530 | |
| 531 | 0.0032 |
| 532 | 0.0072 |
| 533 | 0.013 |
| 534 | 0.002 |
| 535 | 0.0031 |
| 536 | 0.0031 |
| 537 | 0.012 |
| 538 | 0.22 |
| 539 | 0.033 |
| 540 | 0.074 |
| 541 | 0.19 |
| 542 | 0.059 |
| 543 | 0.14 |
| 544 | 0.013 |
| 545 | 0.0059 |
| 546 | 0.011 |
| 547 | 0.038 |
| 548 | 0.0029 |
| 549 | 0.0081 |
| 550 | 0.0021 |
| 551 | 0.0029 |
| 552 | 0.012 |
| 553 | 0.058 |
| 554 | 0.014 |
| 555 | 0.0038 |
| 556 | 0.0045 |
| 557 | 0.0073 |
| 558 | 0.0084 |
| 559 | 0.0022 |
| 560 | 0.0016 |
| 561 | 0.011 |
| 562 | 0.0019 |
| 563 | 0.033 |
| 564 | 0.028 |
| 565 | 0.094 |
| 566 | 0.008 |
| 567 | 0.0059 |
| 568 | |
| 569 | 0.0031 |
| 570 | 0.00063 |

Blank = not determined

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims.

Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually.

What is claimed is:

1. A compound of Formula 0:

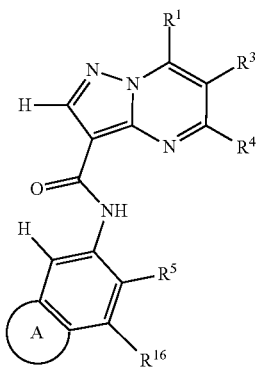

Formula 0 or a stereoisomer or pharmaceutically acceptable salt thereof, wherein:

$R^1$ is hydrogen or halogen;

$R^3$ is halogen, CN, $C_{1-3}$alkyl, $C_{2-3}$alkenyl, $C_{3-7}$cycloalkyl group, $C_1$-$C_3$alkanoyl, —($C_0$-$C_3$alkyl)C(O)NR$^6$R$^7$, —($C_{2-3}$alkenyl)C(O)NR$^6$R$^7$, —S(O)$_{1-2}$NR$^6$R$^7$, —NR$^8$R$^9$, —O—$C_{1-3}$alkyl, a 3-7 membered monocyclic saturated or partially saturated heterocyclic group, a 5-6 membered monocyclic heteroaryl ring, or a 5-6 membered monocyclic aryl ring, Br, Cl, F, OCHF$_2$, CHF$_2$, or CF$_3$, cyclopropyl, azetidinyl, CN, —C(O)CH$_3$, —C(O)NH$_2$, —C(O)NHCH$_3$, —NHCH$_3$, —SO$_2$—NH$_2$, or —SO$_2$—NHCH$_3$;

wherein any alkyl, alkanoyl, or alkenyl is independently optionally substituted by halogen, oxo, CN, OH, $C_{1-3}$alkoxy, or $C_{1-3}$haloalkoxy, and wherein any cycloalkyl group, heterocyclic group, heteroaryl ring, or aryl ring is independently optionally substituted by halogen, oxo, CN, OH, $C_{1-3}$alkyl, or $C_{1-3}$haloalkyl;

$R^4$ is hydrogen, halogen, $C_{1-3}$alkyl, $C_{2-3}$alkenyl, —($C_0$-$C_3$alkyl)C(O)R$^{13}$, —($C_{2-3}$alkenyl)C(O)NR$^{10}$R$^{11}$, —S(O)$_{1-2}$NR$^{10}$R$^{11}$, a 3-7 membered monocyclic saturated or partially saturated heterocyclic group, —C(O)NR$^8$R$^9$, or —NR$^8$R$^9$, wherein any alkyl, alkenyl, or heterocyclic group is independently optionally substituted by halogen, oxo, CN, OH, $C_{1-3}$alkoxy, $C_{1-3}$haloalkoxy, or a 3-7 membered monocyclic saturated or partially saturated heterocyclic group that may be optionally substituted with oxo;

$R^5$ is hydrogen, —CN, $C_{1-6}$alkyl, $C_{1-6}$alkoxy, $C_{3-10}$cycloalkyl group, —NR$^8$R$^9$, —C(O)NR$^8$R$^9$, —O($C_{3-7}$cycloalkyl group), —O($C_{1-3}$alkyl)-3-8 membered cycloalkyl group, —O($C_{0-3}$alkyl)-3-8 membered saturated or partially saturated heterocyclic group, —O($C_{1-3}$alkyl)-phenyl, a —O($C_{1-3}$alkyl)-5-6 membered heteroaryl ring, a 3-11 membered saturated or partially saturated heterocyclic group, or a 5-6 membered monocyclic heteroaryl ring, wherein any alkyl or alkoxy is independently optionally substituted by halogen, oxo, CN, OH, $C_{1-3}$alkoxy, $C_{1-3}$haloalkoxy, or a 3-11 membered saturated or partially saturated heterocyclic group that may be optionally substituted with (i) —C(O)($C_{1-3}$alkyl) optionally substituted with halogen or (ii) with $C_{1-3}$alkyl optionally substituted with halogen, and wherein any cycloalkyl group, heterocyclic group, phenyl, or heteroaryl ring is optionally substituted by halogen; oxo; CN; OH; $C_{1-6}$alkoxy; —NR$^8$R$^9$; —C(O)($C_{1-3}$alkyl); —($C_{0-3}$alkyl)C(O)NR$^{10}$R$^{11}$; —S(O)$_{1-2}$NR$^8$R$^9$; —OP(O)(O$C_{1-3}$alkyl)$_2$; $C_{3-10}$cycloalkyl group optionally substituted with OH or halogen; a 3-11 membered saturated or partially saturated heterocyclic group optionally substituted with oxo or $C_{1-3}$alkyl; a 5-6 membered monocyclic heteroaryl ring optionally substituted by halogen, oxo, CN, OH, $C_{1-3}$alkyl, or $C_{1-3}$haloalkyl; or $C_{1-4}$alkyl optionally substituted by halogen, oxo, CN, OH, O—$C_{1-3}$ alkyl, —S—$C_{1-3}$alkyl, —SO$_2$—$C_{1-3}$alkyl, —NR$^8$R$^9$, —C(O)NR$^8$R$^9$, phenyl, $C_{3-10}$cycloalkyl, a 3-11 membered saturated or partially saturated heterocyclic group optionally substituted with oxo or $C_{1-3}$ alkyl, or a 5-6 membered monocyclic heteroaryl ring optionally substituted with oxo, halogen, or $C_{1-3}$alkyl;

A is a 3-11 membered heterocyclic group optionally substituted by halogen, oxo, CN, OH, $C_{1-6}$alkyl, —($C_{0-3}$alkyl)-$C_{3-6}$cycloalkyl group, a —($C_{0-3}$alkyl)-3-11 membered heterocyclic group, —NR$^8$R$^9$, —NR$^{12}$C(O)R$^{13}$—NR$^{12}$S(O)$_{1-2}$R$^{13}$, —C(O)($C_{1-3}$alkyl), —C(O)NR$^{10}$R$^{11}$, —C(O)OR$^{13}$, —S(O)$_{1-2}$NR$^{10}$R$^{11}$, or —($C_{0-3}$alkyl)-OP(O)(O$C_{1-3}$alkyl)$_2$, wherein any alkyl, cycloalkyl group, or heterocyclic group is independently optionally substituted by halogen; oxo; CN; OR$^{13}$; $C_{1-3}$haloalkoxy; —C(O)($C_{1-3}$alkyl); —S—$C_{1-3}$alkyl; or $C_{1-3}$alkyl optionally substituted with OH, halogen, $C_{1-3}$haloalkyl, $C_{1-3}$alkoxy, $C_{1-3}$haloalkoxy, or a 3-8 membered heterocyclic group, and wherein when A is a 5-membered nitrogen containing heterocyclic group, the nitrogen atom is substituted;

$R^6$ and $R^7$ are, independently at each occurrence, hydrogen, $C_{1-3}$alkyl, or $C_{3-6}$cycloalkyl group, wherein any alkyl or cycloalkyl group is independently optionally substituted by halogen, oxo, CN, OH, $C_{1-3}$alkyl, $C_{1-3}$haloalkyl, $C_{1-3}$alkoxy, or $C_{1-3}$haloalkoxy;

$R^8$, $R^9$, $R^{10}$ and $R^{11}$ are, independently at each occurrence, hydrogen, $C_{1-6}$alkyl, $C_{3-6}$cycloalkyl group, —($C_{0-3}$alkyl)-phenyl, a 3-11 membered saturated heterocyclic group, a 5-6 membered monocyclic heteroaryl ring, —C(O)R$^{13}$, —C(O)OR$^{13}$, —C(O)NR$^6$R$^7$, or —S(O)$_{1-2}$R$^{13}$, or R$^{10}$ and R$^{11}$ are taken together to form a 5-8 membered heterocyclic group, wherein any alkyl, cycloalkyl group, phenyl, heterocyclic group, or heteroaryl ring is independently optionally substituted by halogen, oxo, CN, $C_{1-3}$alkyl, $C_{1-3}$haloalkyl, $C_{1-3}$alkoxy, $C_{1-3}$haloalkoxy, —OR$^{13}$, —NR$^6$R$^7$, or a 5-6 membered monocyclic heteroaryl ring;

$R^{12}$ is, independently at each occurrence, hydrogen, $C_{1-6}$alkyl or $C_{3-6}$cycloalkyl group, wherein any alkyl or cycloalkyl group is independently optionally substituted by halogen, oxo, CN, OH, $C_{1-3}$alkyl, $C_{1-3}$haloalkyl, $C_{1-3}$alkoxy, or $C_{1-3}$haloalkoxy;

$R^{13}$ is, independently at each occurrence, hydrogen, $C_{1-6}$alkyl, $C_{3-10}$cycloalkyl group, or a 3-11 membered saturated heterocyclic group, wherein any alkyl, cycloalkyl group, or heterocyclic group is independently optionally substituted by halogen, oxo, CN, OH, $C_{1-3}$alkyl, $C_{1-3}$haloalkyl, $C_{1-3}$alkoxy, $C_{1-3}$haloalkoxy, —$OR^{12}$, or —$NR^6R^7$; and
$R^{16}$ is hydrogen, halogen, CN, or $C_{1-3}$alkyl optionally substituted with —$NH_2$, halogen, or CN.

2. The compound of claim 1 wherein $R^4$ is hydrogen, halogen, $C_{1-3}$alkyl, $C_{2-3}$alkenyl, —($C_0$-$C_3$alkyl)C(O)$R^{13}$—($C_{2-3}$alkenyl)C(O)$NR^{10}R^{11}$, —$S(O)_{1-2}NR^{10}R^{11}$, or —$NR^8R^9$;
wherein any alkyl or alkenyl is independently optionally substituted by halogen, oxo, CN, OH, $C_{1-3}$alkoxy, or $C_{1-3}$haloalkoxy.

3. The compound of claim 1 wherein A is a 3-11 membered heterocyclic group optionally substituted by halogen, oxo, CN, OH, $C_{1-6}$alkyl, $C_{3-6}$cycloalkyl group, —$NR^8R^9$, —$NR^{12}C(O)R^{13}$, —$NR^{12}S(O)_{1-2}R^{13}$, —$C(O)NR^{10}R^{11}$, —$C(O)OR^{13}$, or —$S(O)_{1-2}NR^{10}R^{11}$;
wherein any alkyl or cycloalkyl group is independently optionally substituted by halogen, oxo, CN, OH, $C_{1-3}$alkyl, $C_{1-3}$haloalkyl, $C_{1-3}$alkoxy, or $C_{1-3}$haloalkoxy;
wherein when A is a 5-membered nitrogen containing heterocyclic group, the nitrogen atom is substituted; and,
$R^8$, $R^9$, $R^{10}$ and $R^{11}$ are, independently at each occurrence, hydrogen, $C_{1-6}$alkyl, $C_{3-6}$cycloalkyl group, a 3-11 membered saturated heterocyclic group, —$C(O)R^{13}$, —$C(O)OR^{13}$, —$C(O)NR^6R^7$, or —$S(O)_{1-2}R^{13}$;
wherein any alkyl, cycloalkyl group or other ring is independently optionally substituted by halogen, oxo, CN, $C_{1-3}$alkyl, $C_{1-3}$haloalkyl, $C_{1-3}$alkoxy, $C_{1-3}$haloalkoxy, —$OR^{13}$, or —$NR^6R^7$.

4. The compound of claim 1, or a stereoisomer or pharmaceutically acceptable salt thereof, wherein $R^1$ and $R^4$ are each hydrogen, and $R^3$ is halogen, $CH_3$, $CH_2OH$, $CH_2F$, $OCHF_2$, $CHF_2$, $CF_3$, cyclopropyl, azetidinyl, CN, —C(O)$CH_3$, —C(O)$NH_2$, —C(O)$NHCH_3$, —$NHCH_3$, —$SO_2$—$NH_2$, or —$SO_2$—$NHCH_3$.

5. The compound of claim 1, or a stereoisomer or pharmaceutically acceptable salt thereof, wherein $R^1$ and $R^4$ are each hydrogen, and $R^3$ is Br, Cl, F, $OCHF_2$, $CHF_2$, $CF_3$, $CH_3$, or $CH_2OH$.

6. The compound of claim 1, or a stereoisomer or pharmaceutically acceptable salt thereof, wherein $R^1$ and $R^4$ are each hydrogen, and $R^3$ is cyclopropyl, azetidinyl, CN, —C(O)$CH_3$, —C(O)$NH_2$, —C(O)$NHCH_3$, —$NHCH_3$, —$SO_2$—$NH_2$, or —$SO_2$—$NHCH_3$.

7. The compound of claim 1, or a stereoisomer or pharmaceutically acceptable salt thereof, wherein $R^5$ is a 3-11 membered saturated or partially saturated heterocyclic group optionally substituted by halogen, oxo, CN, OH, —($C_{0-3}$alkyl)C(O)$NR^{10}R^{11}$, —OP(O)(O$C_{1-3}$alkyl)$_2$, or $C_{1-3}$alkyl optionally substituted by halogen, oxo, CN, OH, or —$NR^8R^9$.

8. The compound of claim 7, or a stereoisomer or pharmaceutically acceptable salt thereof, wherein $R^5$ is an N-linked 3-11 membered saturated heterocyclic group optionally substituted by halogen, oxo, CN, OH, —($C_{0-3}$alkyl)C(O)$NR^{10}R^{11}$, —OP(O)(O$C_{1-3}$alkyl)$_2$, or $C_{1-3}$alkyl optionally substituted by halogen, oxo, CN, OH, or —$NR^8R^9$.

9. The compound of claim 7, or a stereoisomer or pharmaceutically acceptable salt thereof, wherein the ring heteroatoms of the said 3-11 membered saturated or partially saturated heterocyclic group of $R^5$ are selected from nitrogen and oxygen.

10. The compound of claim 9, or a stereoisomer or pharmaceutically acceptable salt thereof, wherein $R^5$ is N-linked piperidinyl, N-linked piperazinyl, or N-linked morpholinyl, wherein any $R^5$ is optionally substituted by halogen, oxo, CN, OH, or $C_{1-3}$alkyl optionally substituted by halogen, oxo, CN, or OH.

11. The compound of claim 1, or a stereoisomer or pharmaceutically acceptable salt thereof, wherein:
$R^5$ is —$CH_2CH_3$, —$C(CH_3)_2$, Cl, CN, cyclopropyl, —C(O)$NH_2$, —$OCH_3$, —$OCH_2CF_3$, —$OCH_2CHF_2$, —$CF_3$, —$CHF_2$, —$OCF_3$, —$OCHF_2$, —$NHCH_3$, —$N(CH_3)_2$,

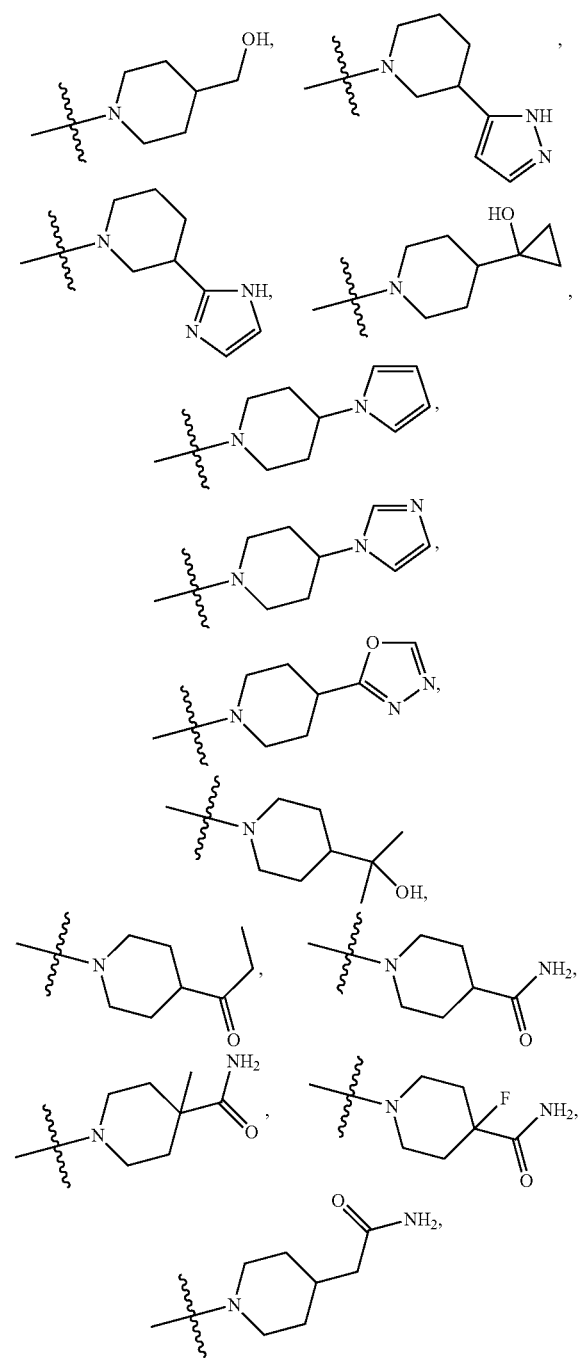

945
-continued
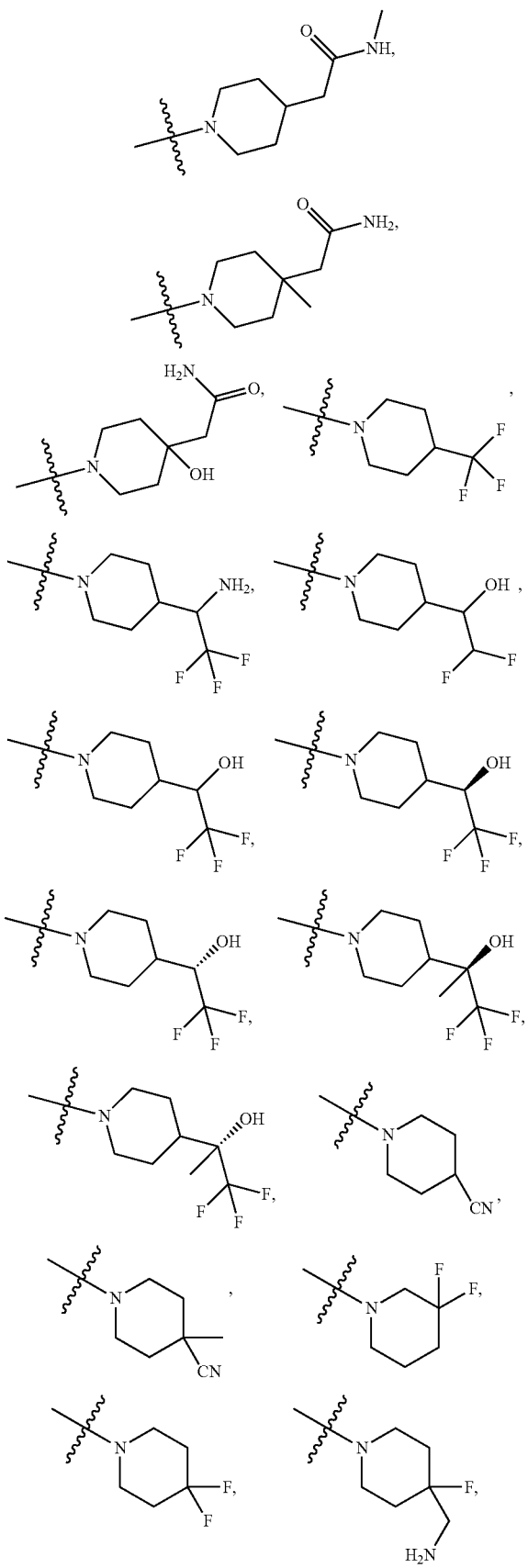
946
-continued
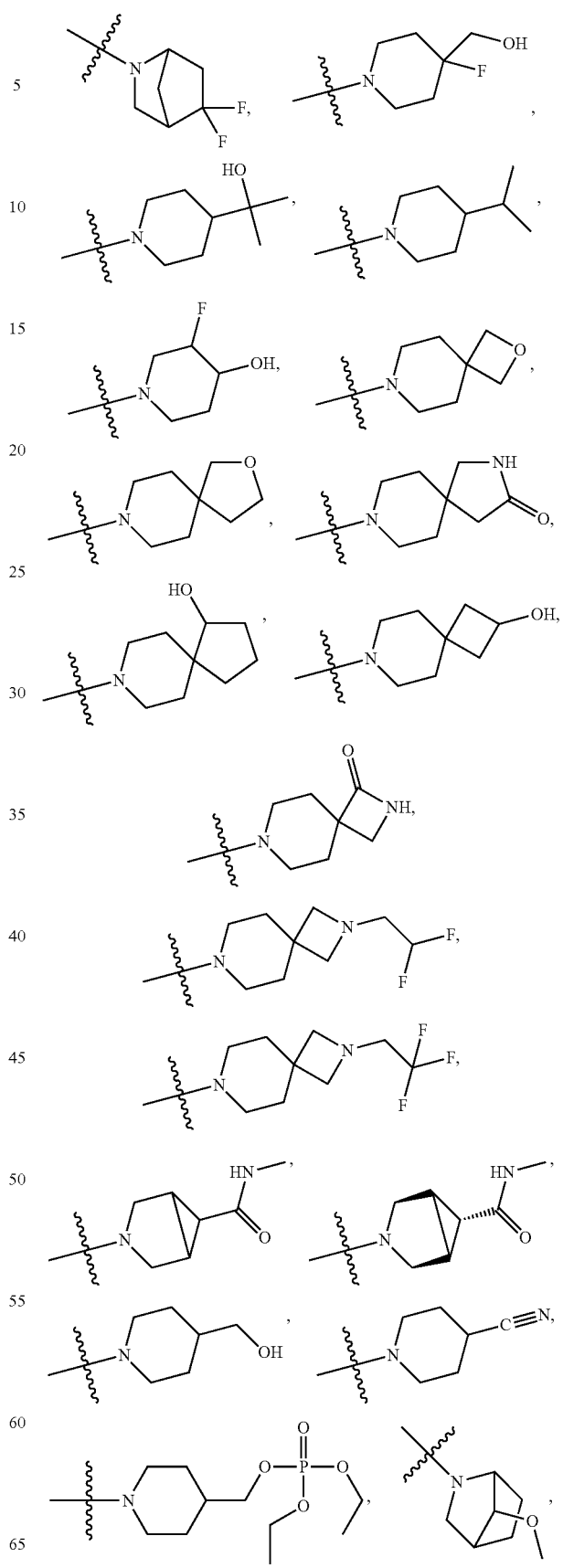

947
-continued
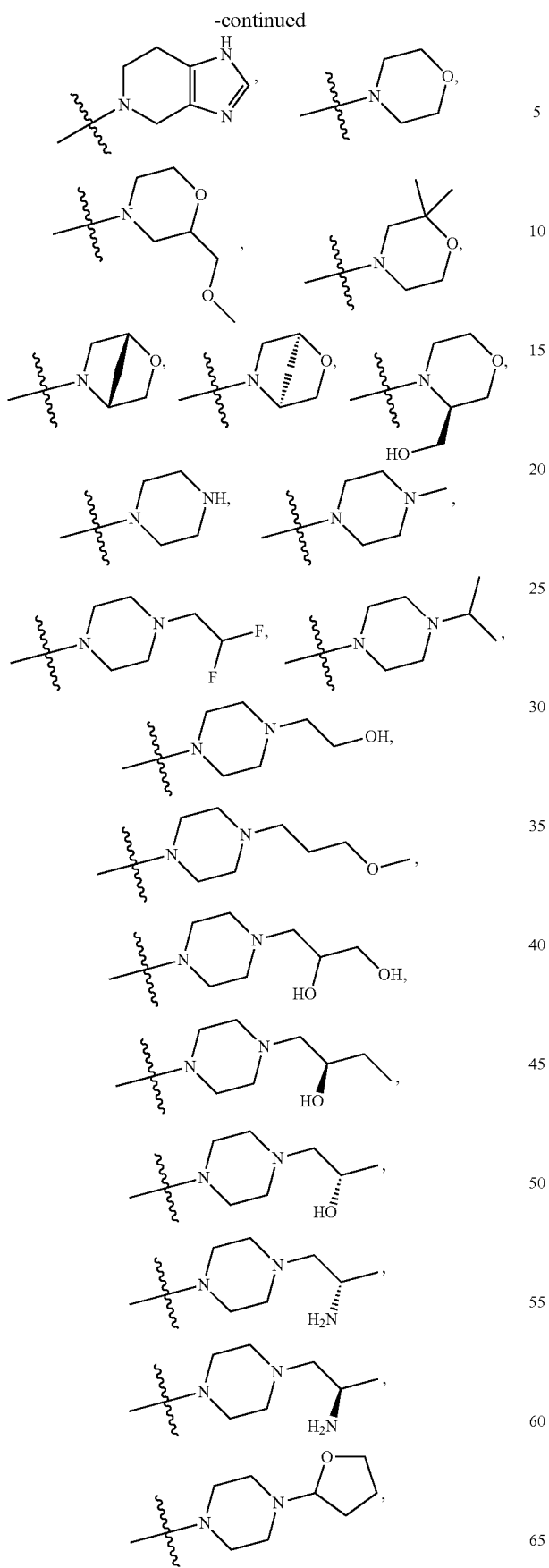
948
-continued
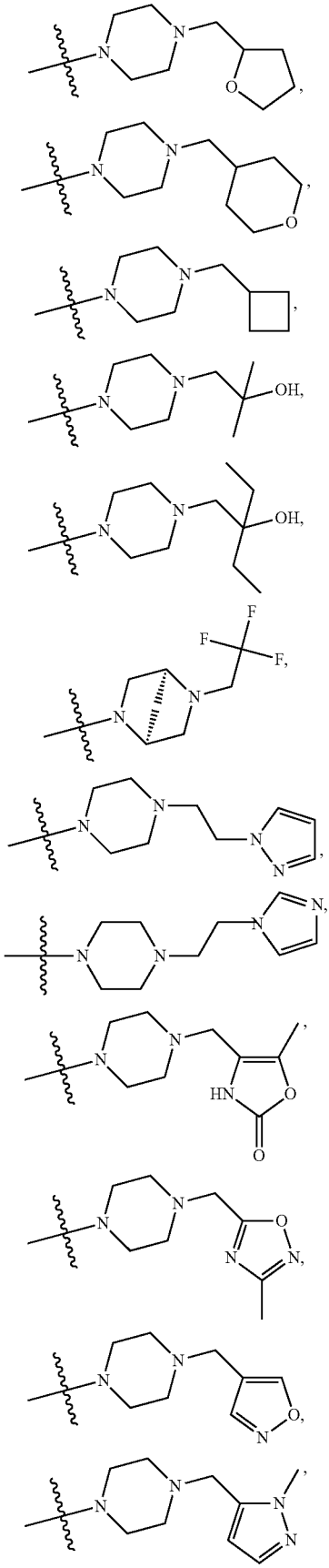

949 950
-continued -continued
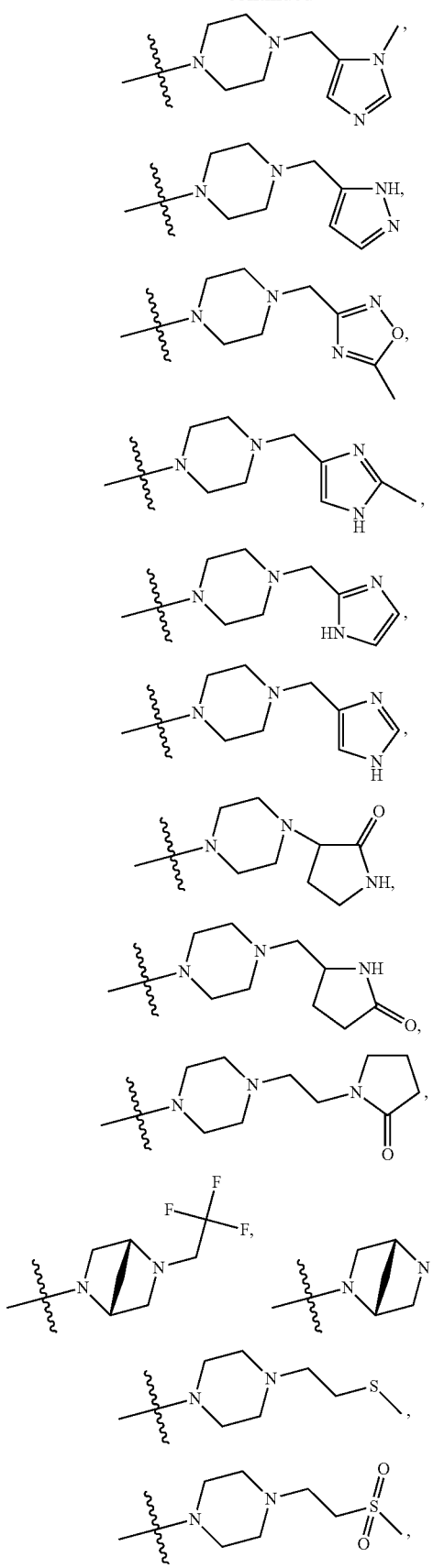
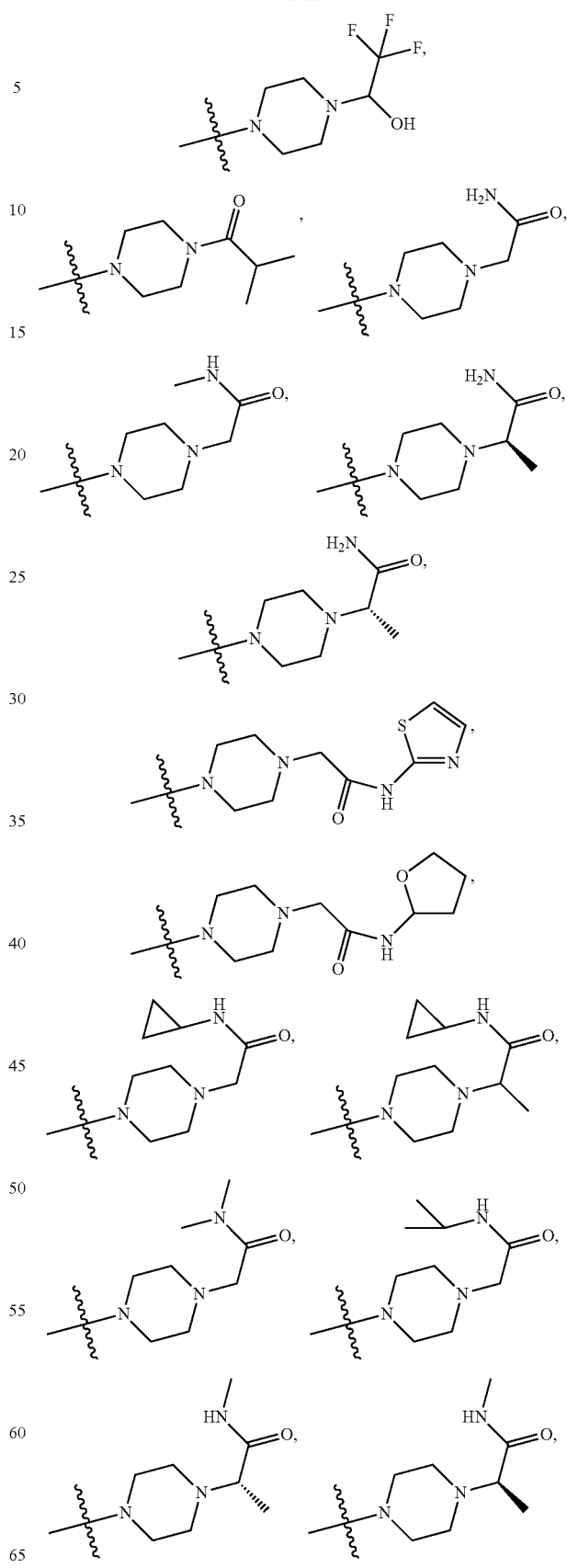

951
-continued
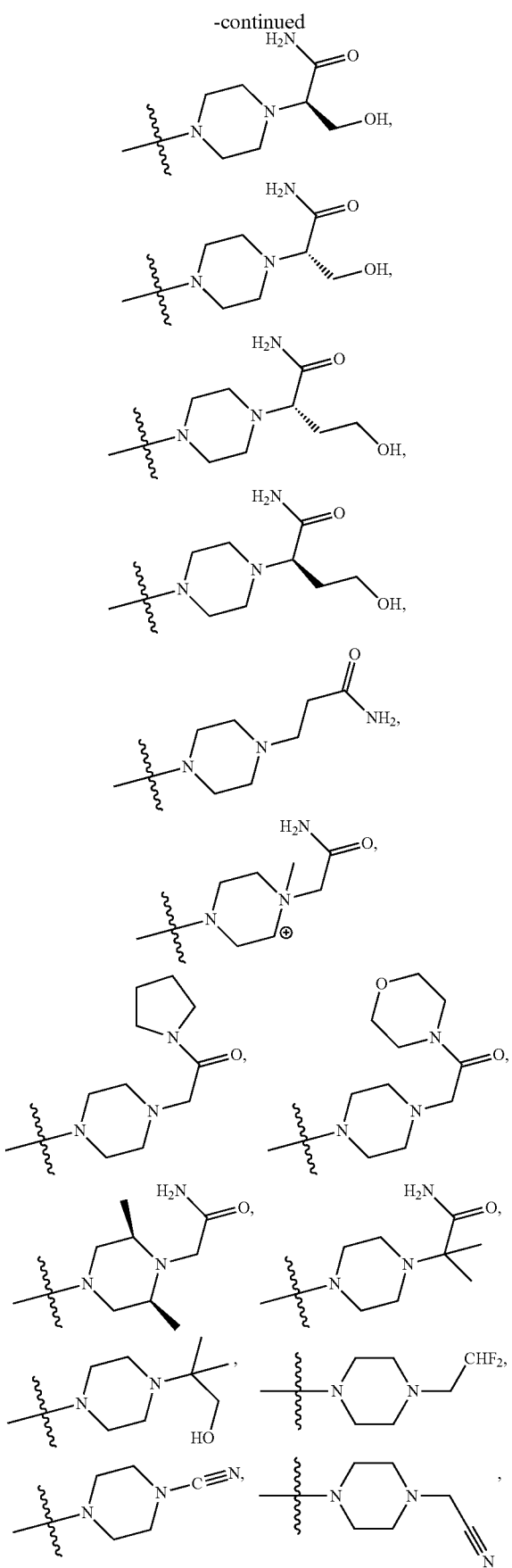
952
-continued
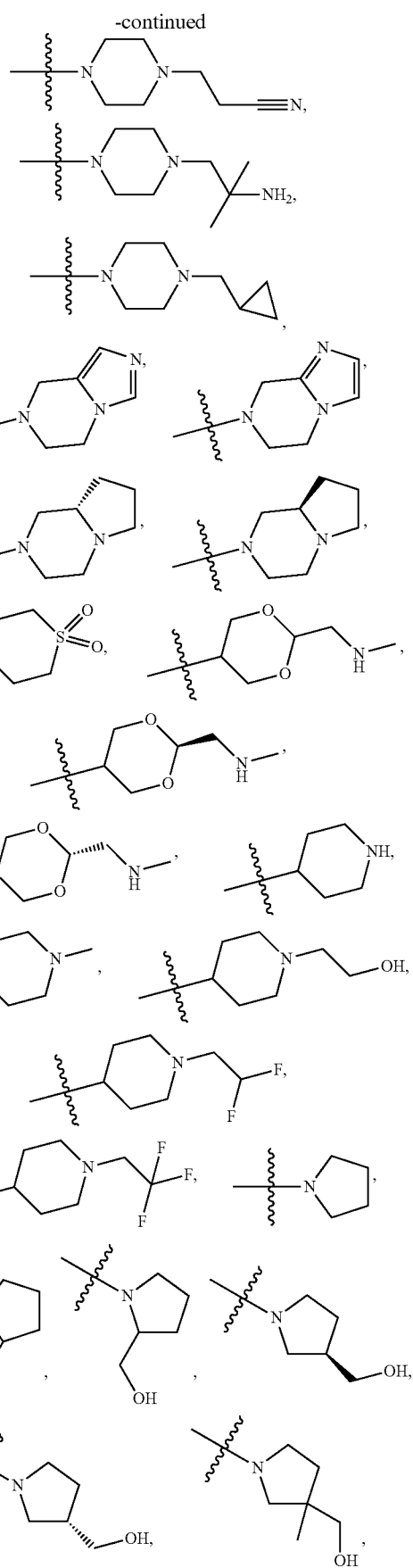

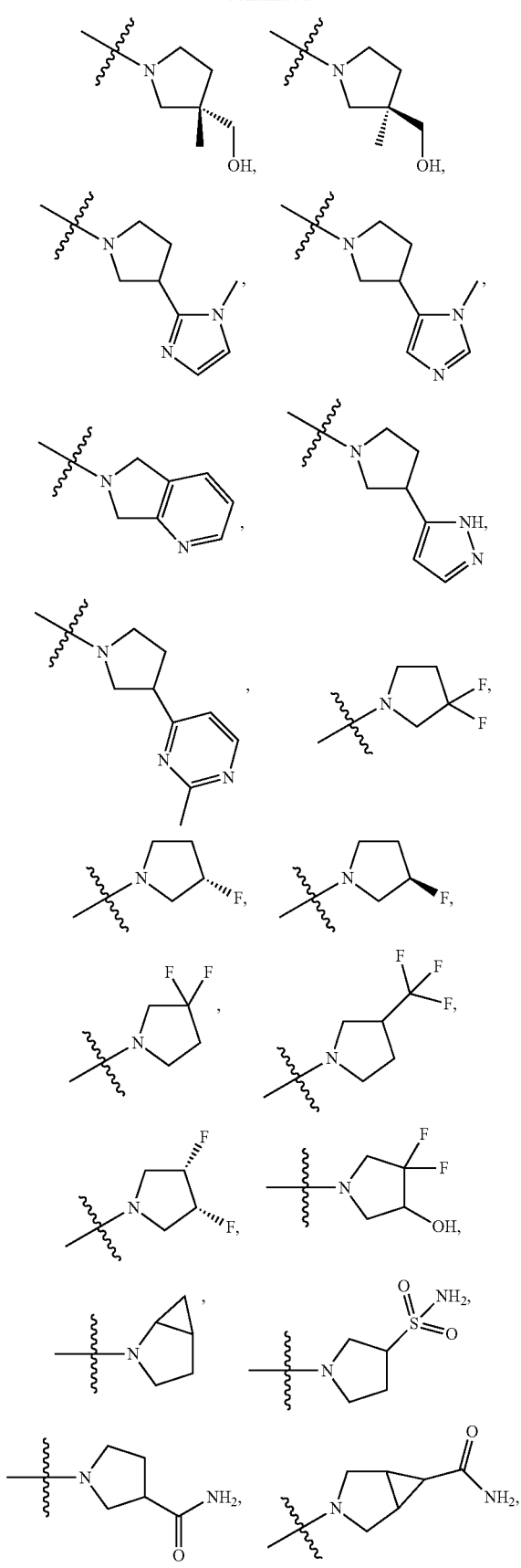
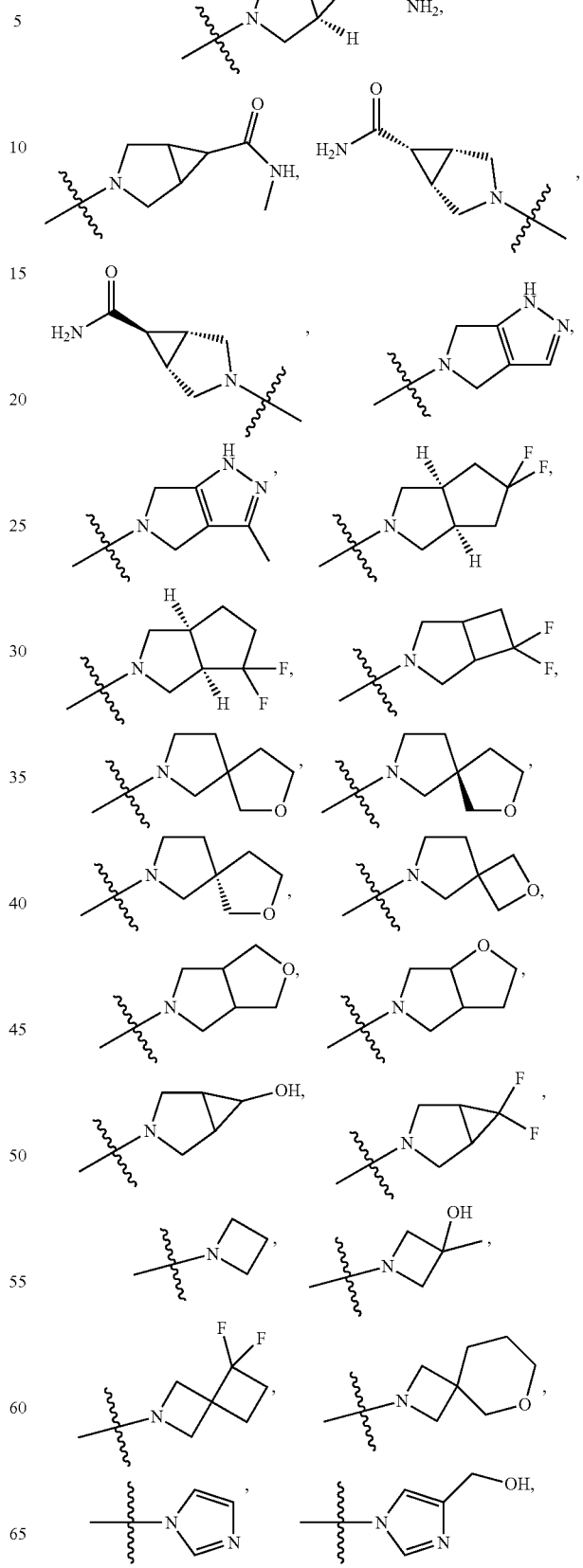

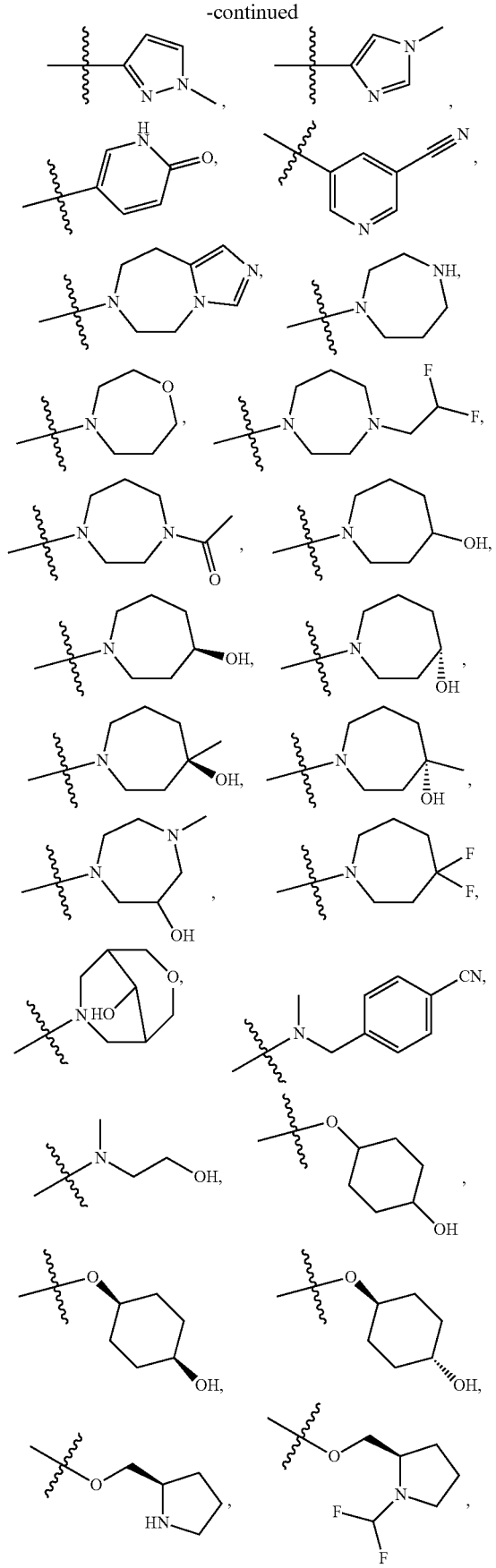
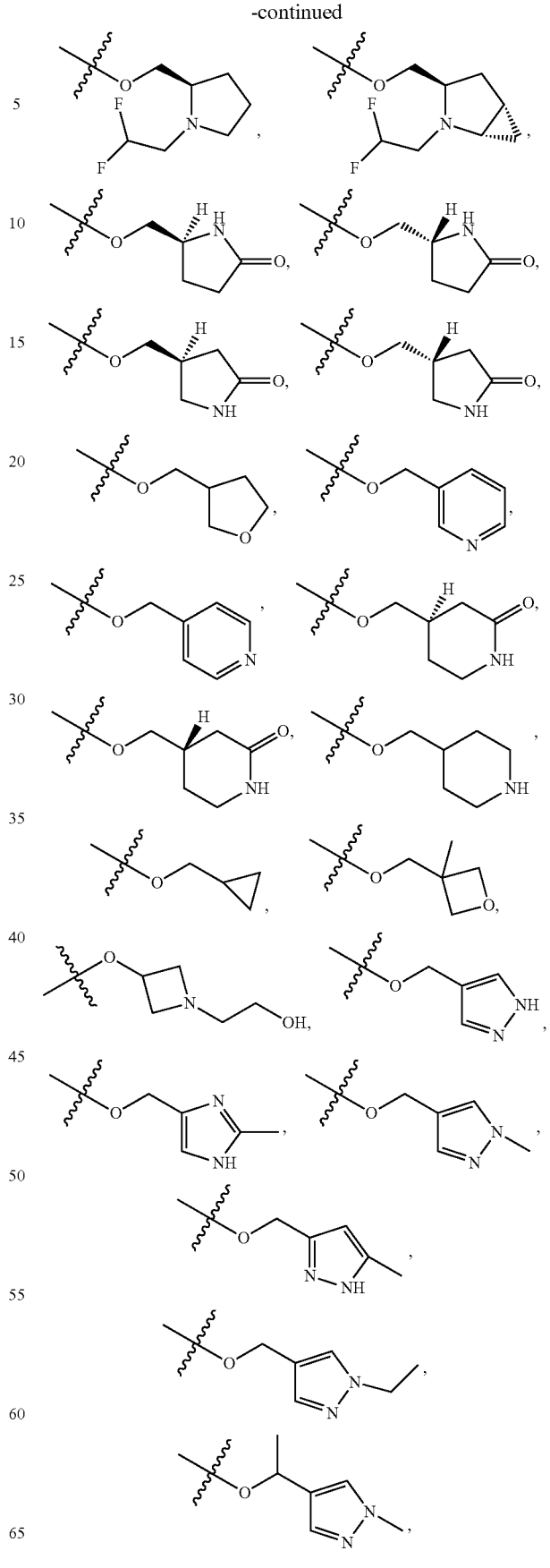

957
-continued
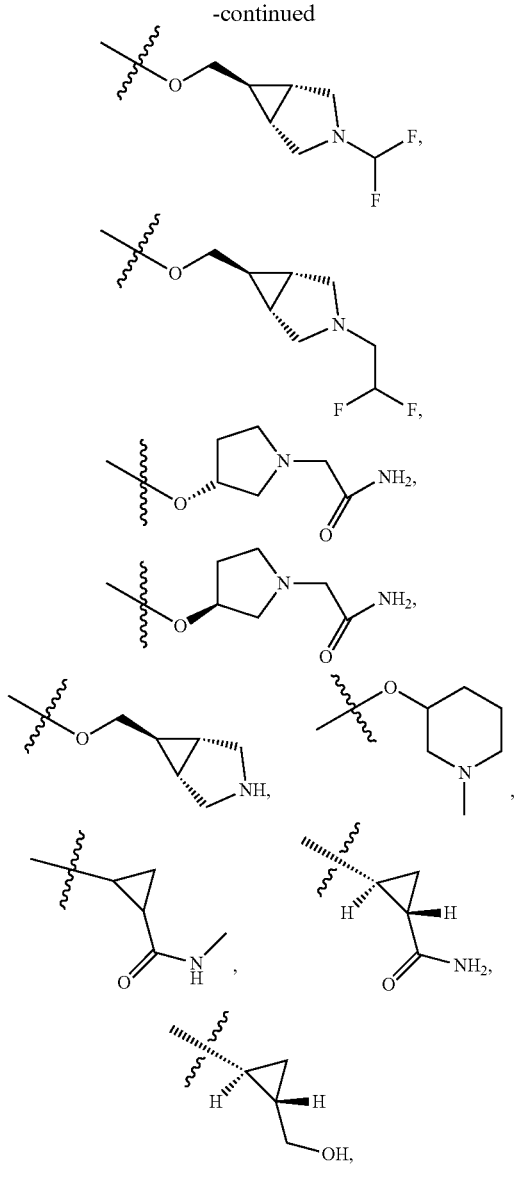
a stereoisomer thereof.
12. The compound of claim 1, or a stereoisomer or pharmaceutically acceptable salt thereof, wherein $R^5$ is
958
-continued
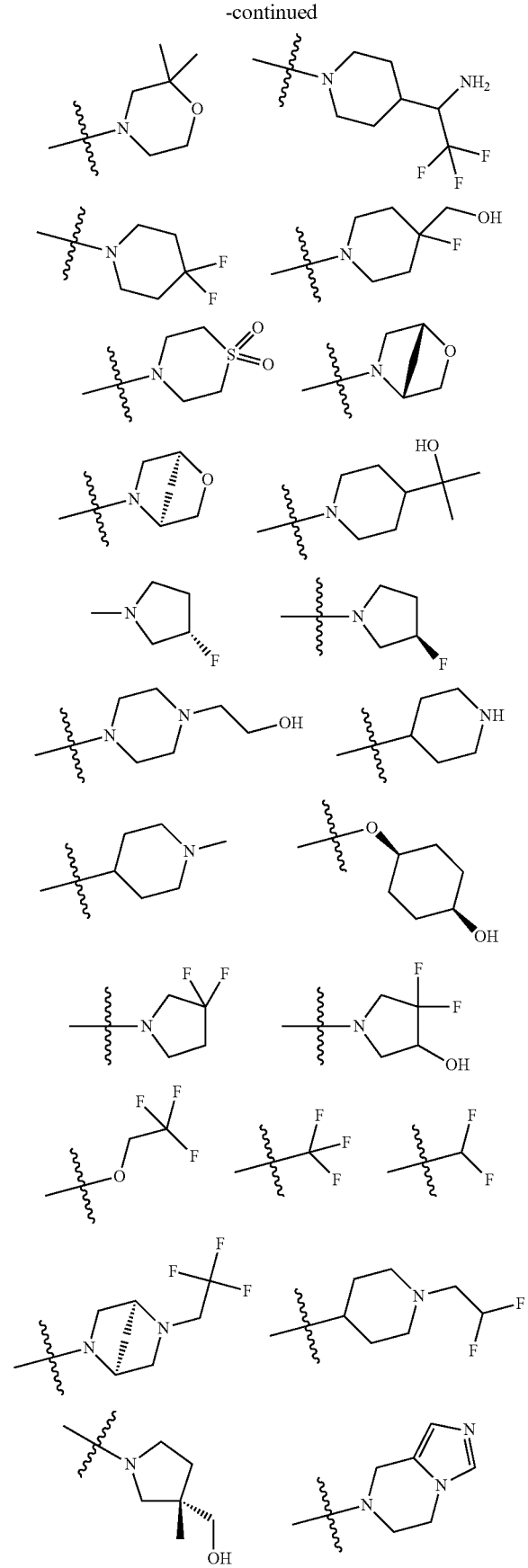

-continued

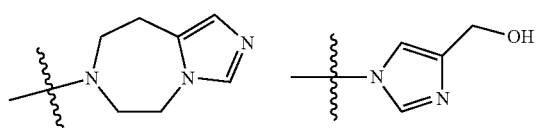
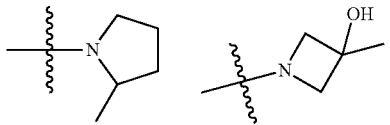
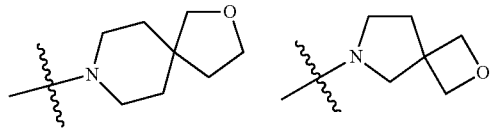
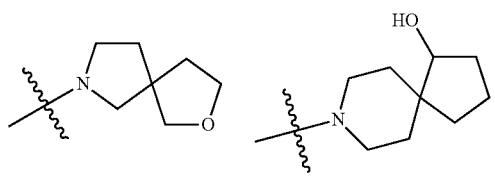
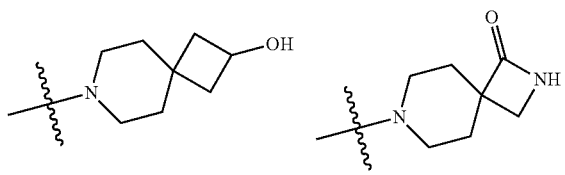
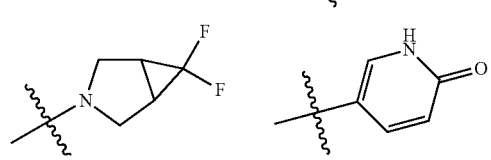
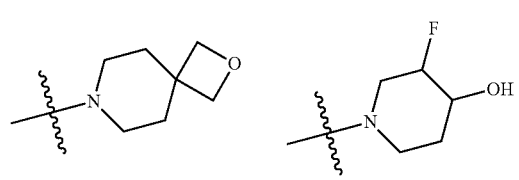
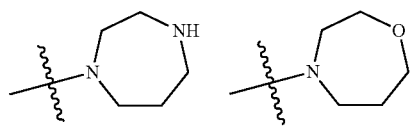
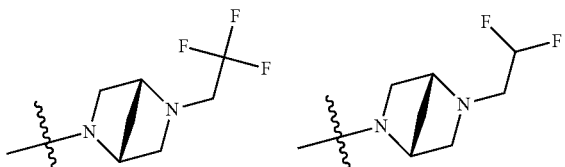
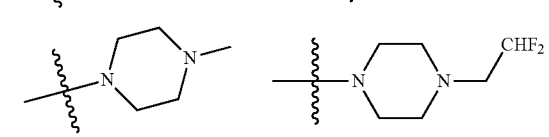
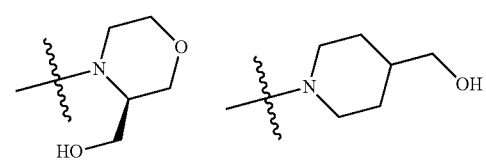

-continued

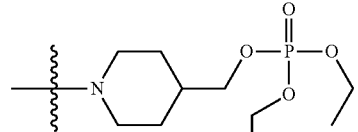
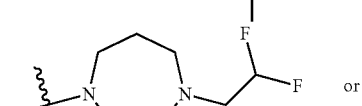
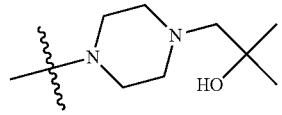

or stereoisomer thereof.

13. The compound of claim 1, or a stereoisomer or pharmaceutically acceptable salt thereof, wherein $R^5$ is

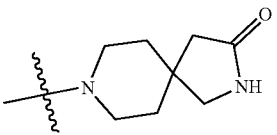
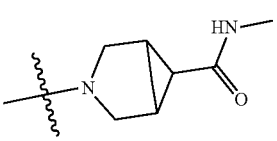
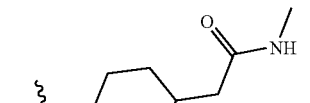
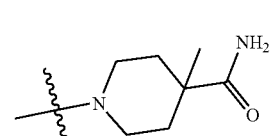

or

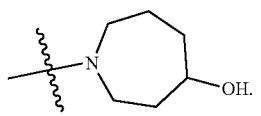

14. The compound of claim 1, or a stereoisomer or pharmaceutically acceptable salt thereof, wherein A is a 3-11 membered, non-aromatic heterocyclic group.

15. The compound of claim 1, or a stereoisomer or pharmaceutically acceptable salt thereof, wherein A is a 3-11 membered heterocyclic group comprising at least one oxygen as a ring atom and is optionally substituted by halogen, oxo, CN, OH, $C_{1-6}$alkyl, $C_{3-6}$cycloalkyl group, —$NR^8R^9$, —$NR^{12}C(O)R^{13}$, —$NR^{12}S(O)_{1-2}R^{13}$, —$C(O)NR^{10}R^{11}$, —$C(O)OR^{13}$, or —$S(O)_{1-2}NR^{10}R^{11}$, wherein any alkyl or cycloalkyl group is independently optionally substituted by halogen, oxo, CN, OH, $C_{1-3}$alkyl, $C_{1-3}$haloalkyl, $C_{1-3}$alkoxy, or $C_{1-3}$haloalkoxy.

16. The compound of claim 1, or a stereoisomer or pharmaceutically acceptable salt thereof, wherein the following portion of Formula 0 is further defined as 0-A:

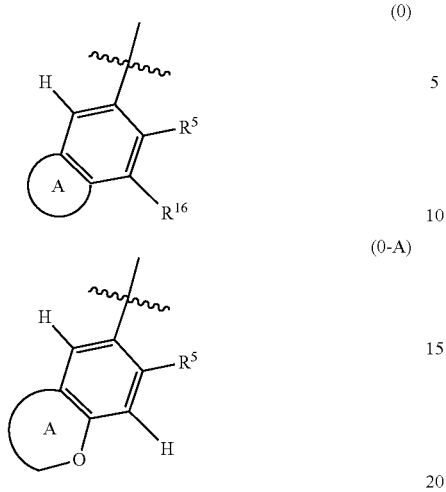

(0)

(0-A)

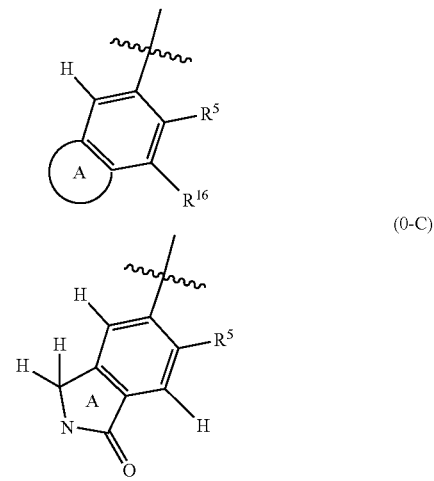

(0-C)

wherein A is a 5 or 6 membered ring optionally containing an additional ring heteroatom and wherein A is optionally substituted by halogen, oxo, CN, OH, $C_{1-6}$alkyl, $C_{3-6}$cycloalkyl group, —$NR^8R^9$, —$NR^{12}C(O)R^{13}$, —$NR^{12}S(O)_{1-2}R^{13}$, —$C(O)NR^{10}R^{11}$, —$C(O)OR^{13}$, or —$S(O)_{1-2}NR^{10}R^{11}$, wherein any alkyl or cycloalkyl group is independently optionally substituted by halogen, oxo, CN, OH, $C_{1-3}$alkyl, $C_{1-3}$haloalkyl, $C_{1-3}$alkoxy, or $C_{1-3}$haloalkoxy.

17. The compound of claim 16 or a stereoisomer or pharmaceutically acceptable salt thereof, wherein 0-A is further defined as 0-B:

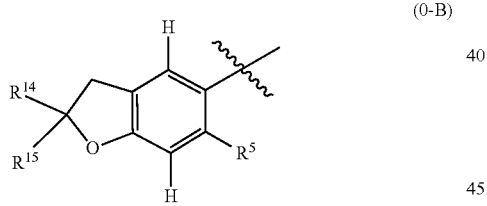

(0-B)

wherein $R^{10}$ and $R^{11}$ are each selected from halogen, oxo, CN, OH, $C_{1-6}$alkyl, $C_{3-6}$cycloalkyl group, —$NR^8R^9$, —$NR^{12}C(O)R^{13}$, —$NR^{12}S(O)_{1-2}R^{13}$, —$C(O)NR^{10}R^{11}$, —$C(O)OR^{13}$, and —$S(O)_{1-2}NR^{10}R^{11}$, wherein any alkyl or cycloalkyl group is independently optionally substituted by halogen, oxo, CN, OH, $C_{1-3}$alkyl, $C_{1-3}$haloalkyl, $C_{1-3}$alkoxy, or $C_{1-3}$haloalkoxy;

or $R^{10}$ and $R^{11}$ together form a $C_{3-6}$cycloalkyl group or saturated or partially saturated 3-6 membered heterocyclic group, wherein any cycloalkyl group or other ring is independently optionally substituted by halogen, oxo, CN, OH, $C_{1-3}$alkyl, $C_{1-3}$haloalkyl, $C_{1-3}$alkoxy, or $C_{1-3}$haloalkoxy.

18. The compound of claim 1, or a stereoisomer or pharmaceutically acceptable salt thereof, wherein the following portion of Formula 0, is further defined as 0-C:

wherein the nitrogen comprises a substituent as defined in claim 1.

19. A compound of Formula 0:

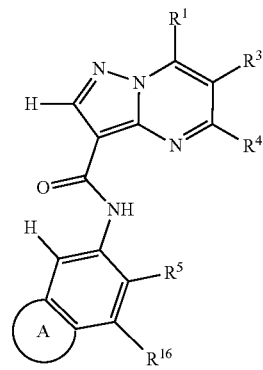

Formula 0 or a stereoisomer or pharmaceutically acceptable salt thereof, wherein:

$R^1$ is hydrogen or halogen;

$R^3$ is hydrogen, halogen, CN, OH, $C_{1-3}$alkyl, $C_{2-3}$alkenyl, $C_{3-7}$cycloalkyl group, $C_1$-$C_3$alkanoyl, —$(C_0$-$C_3$alkyl)C(O)NR^6R^7$, —$(C_{2-3}$alkenyl)C(O)NR^6R^7$, —$S(O)_{1-2}NR^6R^7$, —$NR^8R^9$, —O—$C_{1-3}$alkyl, a 3-7 membered monocyclic saturated or partially saturated heterocyclic group, a 5-6 membered monocyclic heteroaryl ring, or a 5-6 membered monocyclic aryl ring, wherein any alkyl, alkanoyl, or alkenyl is independently optionally substituted by halogen, oxo, CN, OH, $C_{1-3}$alkoxy, or $C_{1-3}$haloalkoxy, and wherein any cycloalkyl group, heterocyclic group, heteroaryl ring, or aryl ring is independently optionally substituted by halogen, oxo, CN, OH, $C_{1-3}$alkyl, or $C_{1-3}$haloalkyl;

$R^4$ is hydrogen, halogen, $C_{1-3}$alkyl, $C_{2-3}$alkenyl, —$(C_0$-$C_3$alkyl)C(O)R^{13}$—$(C_{2-3}$alkenyl)C(O)NR^{10}R^{11}$, —$S(O)_{1-2}NR^{10}R^{11}$, a 3-7 membered monocyclic saturated or partially saturated heterocyclic group, —$C(O)NR^8R^9$, or —$NR^8R^9$, wherein any alkyl, alkenyl, or heterocyclic group is independently optionally substituted by halogen, oxo, CN, OH, C$_{1-3}$alkoxy, C$_{1-3}$haloalkoxy, or a 3-7 membered monocyclic saturated or partially saturated heterocyclic group that may be optionally substituted with oxo;

R$^5$ is hydrogen, —CN, C$_{1-6}$alkyl, C$_{1-6}$alkoxy, C$_{3-10}$cycloalkyl group, —NR$^8$R$^9$, —C(O)NR$^8$R$^9$, —O(C$_{3-7}$cycloalkyl group), —O(C$_{1-3}$alkyl)-3-8 membered cycloalkyl group, —O(C$_{0-3}$alkyl)-3-8 membered saturated or partially saturated heterocyclic group, —O(C$_{1-3}$alkyl)-phenyl, a —O(C$_{1-3}$ alkyl)-5-6 membered heteroaryl ring, a 3-11 membered saturated or partially saturated heterocyclic group, or a 5-6 membered monocyclic heteroaryl ring, wherein any alkyl or alkoxy is independently optionally substituted by halogen, oxo, CN, OH, C$_{1-3}$alkyl, C$_{1-3}$haloalkoxy, or a 3-11 membered saturated or partially saturated heterocyclic group that may be optionally substituted with (i) —C(O)(C$_{1-3}$alkyl) optionally substituted with halogen or (ii) with C$_{1-3}$alkyl optionally substituted with halogen, and wherein any cycloalkyl group, heterocyclic group, phenyl, or heteroaryl ring is optionally substituted by halogen; oxo; CN; OH; C$_{1-6}$alkoxy; —NR$^8$R$^9$; —C(O)(C$_{1-3}$alkyl); —(C$_{0-3}$alkyl)C(O)NR$^{10}$R$^{11}$; —S(O)$_{1-2}$NR$^8$R$^9$; —OP(O)(OC$_{1-3}$alkyl)$_2$; C$_{3-10}$cycloalkyl group optionally substituted with OH or halogen; a 3-11 membered saturated or partially saturated heterocyclic group optionally substituted with oxo or C$_{1-3}$alkyl; a 5-6 membered monocyclic heteroaryl ring optionally substituted by halogen, oxo, CN, OH, C$_{1-3}$alkyl, or C$_{1-3}$haloalkyl; or C$_{1-4}$alkyl optionally substituted by halogen, oxo, CN, OH, —O—C$_{1-3}$ alkyl, —S—C$_{1-3}$alkyl, —SO$_2$—C$_{1-3}$alkyl, —NR$^8$R$^9$, —C(O) NR$^8$R$^9$, phenyl, C$_{3-10}$cycloalkyl, a 3-11 membered saturated or partially saturated heterocyclic group optionally substituted with oxo or C$_{1-3}$ alkyl, or a 5-6 membered monocyclic heteroaryl ring optionally substituted with oxo, halogen, or C$_{1-3}$alkyl;

A is a 3-11 membered heterocyclic group optionally substituted by halogen, oxo, CN, OH, C$_{1-6}$alkyl, —(C$_{0-3}$alkyl)-C$_{3-6}$cycloalkyl group, a —(C$_{0-3}$alkyl)-3-11 membered heterocyclic group, —NR$^8$R$^9$, —NR$^{12}$C(O)R$^{13}$, —NR$^{12}$S(O)$_{1-2}$R$^{13}$, —C(O)(C$_{1-3}$alkyl), —C(O)NR$^{10}$R$^{11}$, —C(O)OR$^{13}$, —S(O)$_{1-2}$NR$^{10}$R$^{11}$, or —(C$_{0-3}$alkyl)-OP(O)(OC$_{1-3}$alkyl)$_2$, wherein any alkyl, cycloalkyl group, or heterocyclic group is independently optionally substituted by halogen; oxo; CN; OR$^{13}$; C$_{1-3}$haloalkoxy; —C(O)(C$_{1-3}$alkyl); —S—C$_{1-3}$alkyl; or C$_{1-3}$alkyl optionally substituted with OH, halogen, C$_{1-3}$haloalkyl, C$_{1-3}$alkoxy, C$_{1-3}$haloalkoxy, or a 3-8 membered heterocyclic group, and wherein when A is a 5-membered nitrogen containing heterocyclic group, the nitrogen atom is substituted;

R$^6$ and R$^7$ are, independently at each occurrence, hydrogen, C$_{1-3}$alkyl, or C$_{3-6}$cycloalkyl group, wherein any alkyl or cycloalkyl group is independently optionally substituted by halogen, oxo, CN, OH, C$_{1-3}$alkyl, C$_{1-3}$haloalkyl, C$_{1-3}$alkoxy, or C$_{1-3}$haloalkoxy;

R$^8$, R$^9$, R$^{10}$ and R$^{11}$ are, independently at each occurrence, hydrogen, C$_{1-6}$alkyl, C$_{3-6}$cycloalkyl group, —(C$_{0-3}$alkyl)-phenyl, a 3-11 membered saturated heterocyclic group, a 5-6 membered monocyclic heteroaryl ring, —C(O)R$^{13}$, —C(O)OR$^{13}$, —C(O)NR$^6$R$^7$, or —S(O)$_{1-2}$R$^{13}$, or R$^{10}$ and R$^{11}$ are taken together to form a 5-8 membered heterocyclic group, wherein any alkyl, cycloalkyl group, phenyl, heterocyclic group, or heteroaryl ring is independently optionally substituted by halogen, oxo, CN, C$_{1-3}$alkyl, C$_{1-3}$haloalkyl, C$_{1-3}$alkoxy, C$_{1-3}$haloalkoxy, —OR$^{13}$, —NR$^6$R$^7$, or a 5-6 membered monocyclic heteroaryl ring;

R$^{12}$ is, independently at each occurrence, hydrogen, C$_{1-6}$alkyl or C$_{3-6}$cycloalkyl group, wherein any alkyl or cycloalkyl group is independently optionally substituted by halogen, oxo, CN, OH, C$_{1-3}$alkyl, C$_{1-3}$haloalkyl, C$_{1-3}$alkoxy, or C$_{1-3}$haloalkoxy;

R$^{13}$ is, independently at each occurrence, hydrogen, C$_{1-6}$alkyl, C$_{3-10}$cycloalkyl group, or a 3-11 membered saturated heterocyclic group, wherein any alkyl, cycloalkyl group, or heterocyclic group is independently optionally substituted by halogen, oxo, CN, OH, C$_{1-3}$alkyl, C$_{1-3}$haloalkyl, C$_{1-3}$alkoxy, C$_{1-3}$haloalkoxy, —OR$^{12}$ or —NR$^6$R$^7$; and R$^{16}$ is hydrogen, halogen, CN, or C$_{1-3}$alkyl optionally substituted with —NH$_2$, halogen, or CN, wherein the following portion of Formula (0)

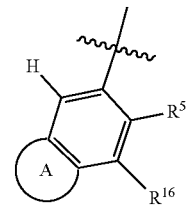

is selected from

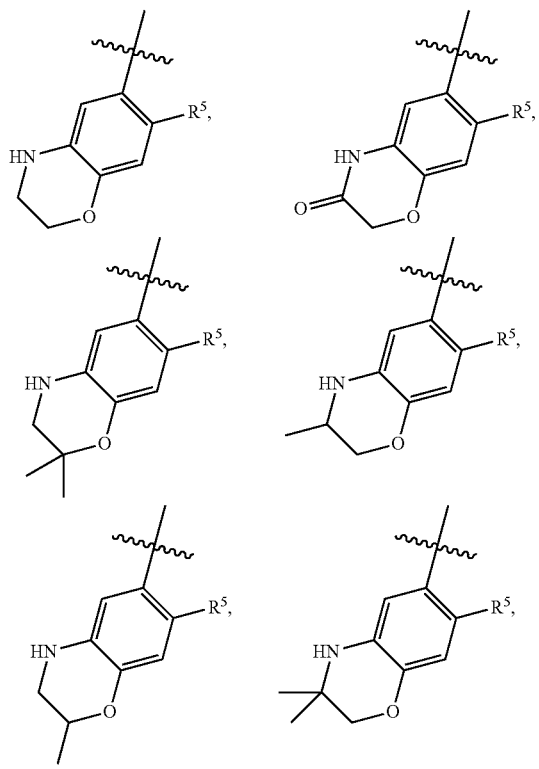

965
-continued
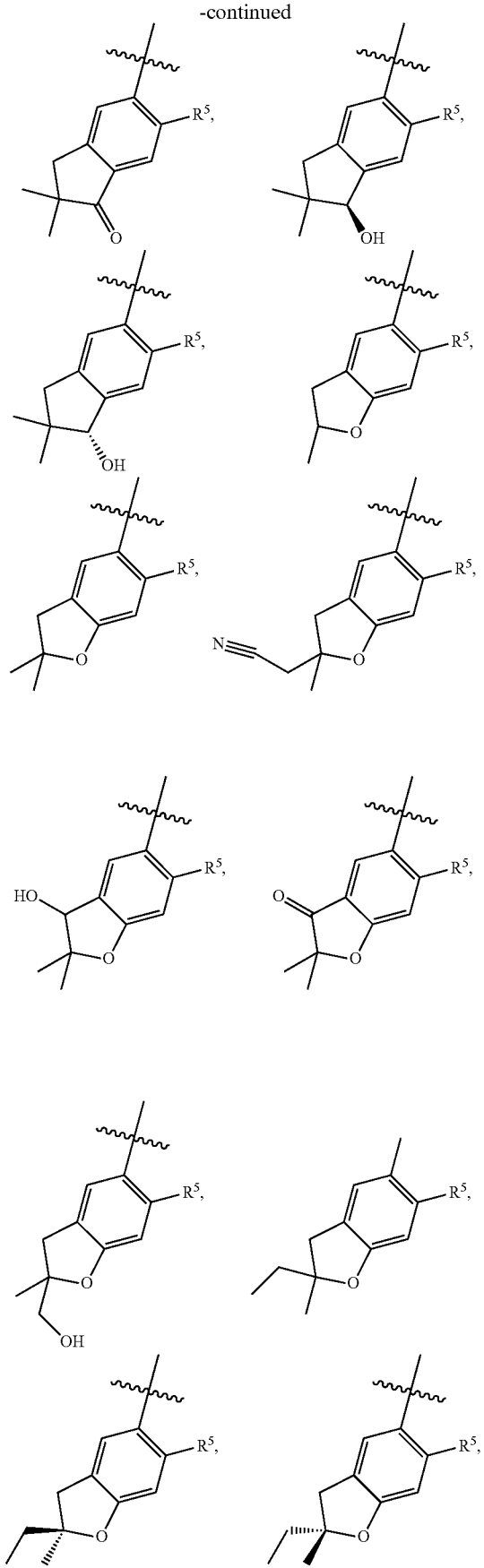
966
-continued
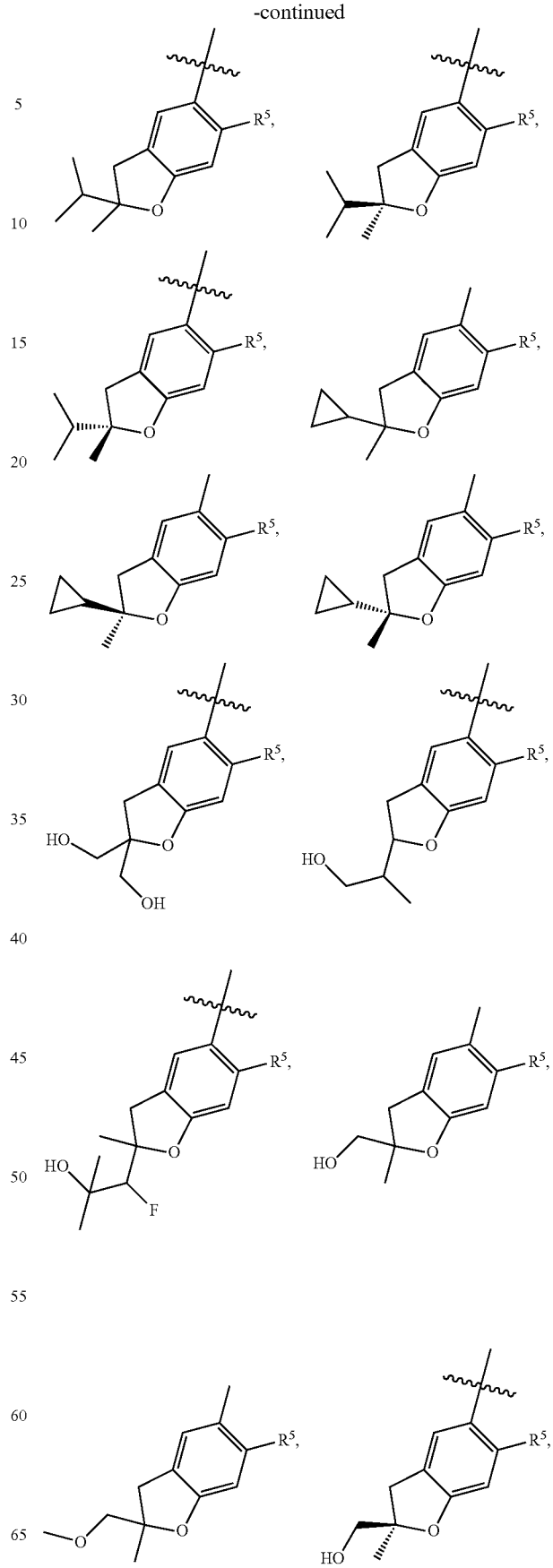

967
-continued
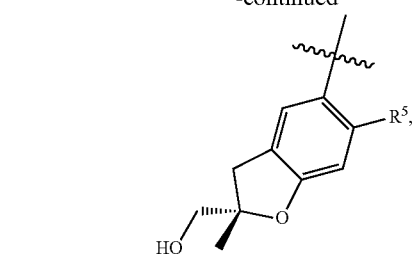
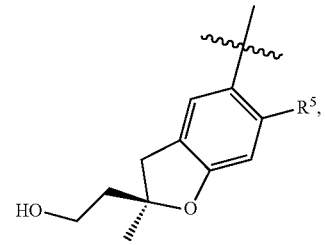
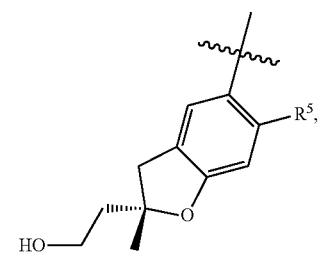
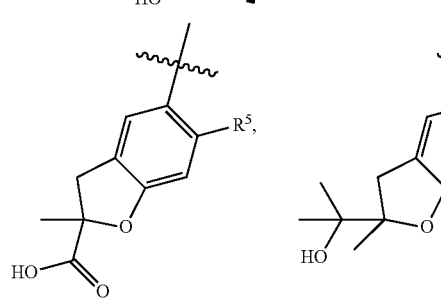
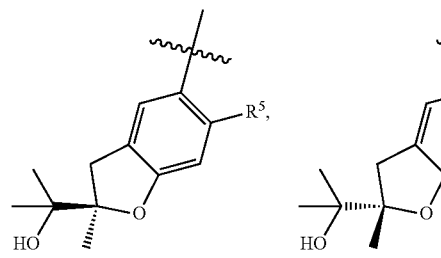
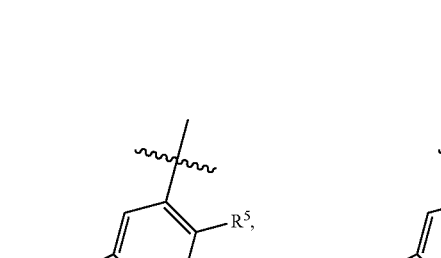
968
-continued
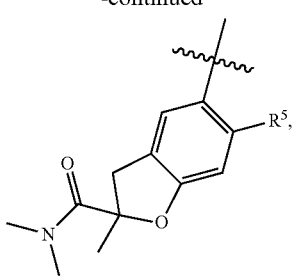
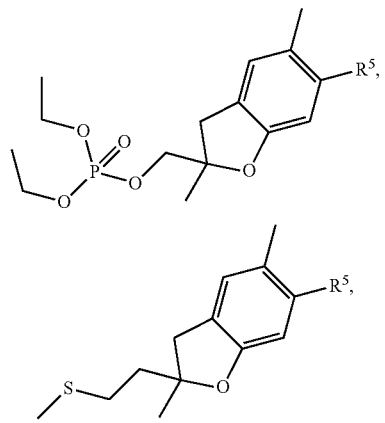
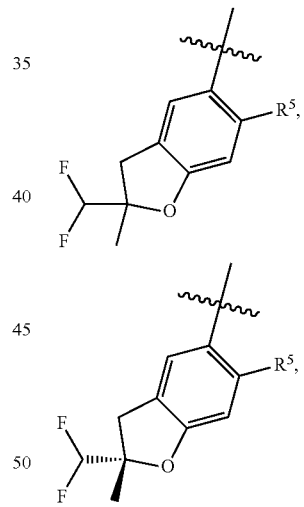
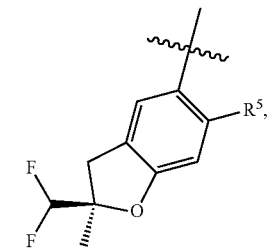
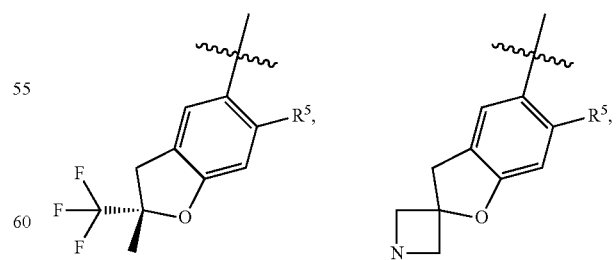
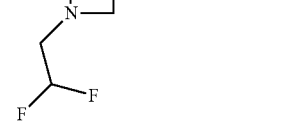

969
-continued
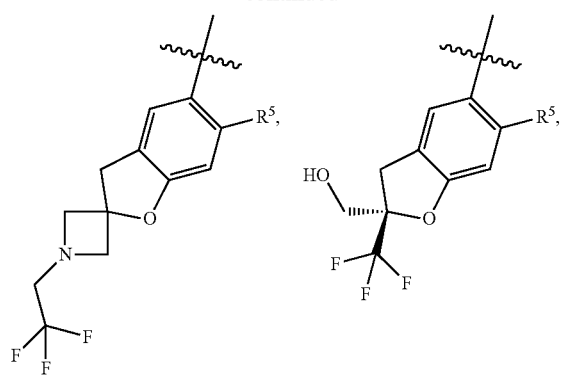
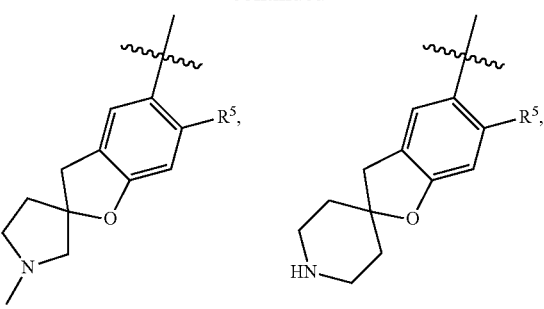
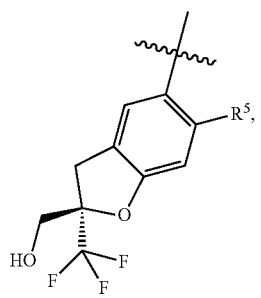
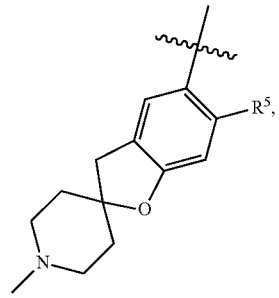
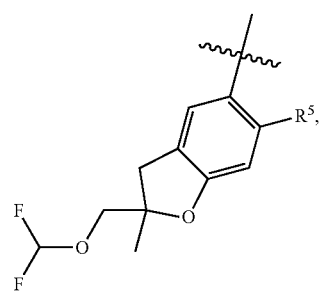
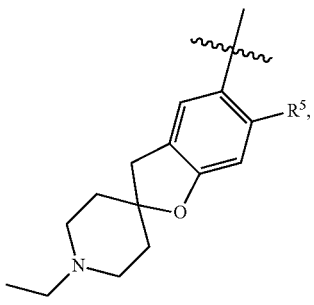
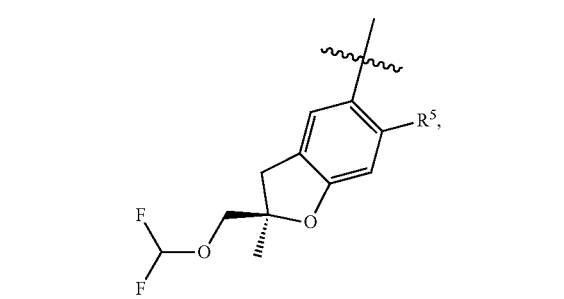
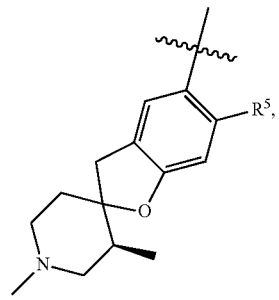
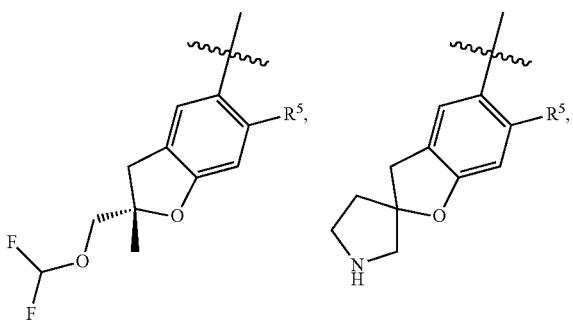
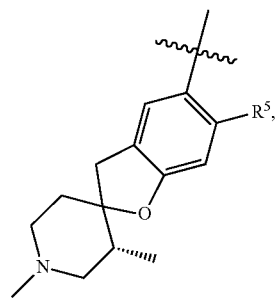

971
-continued
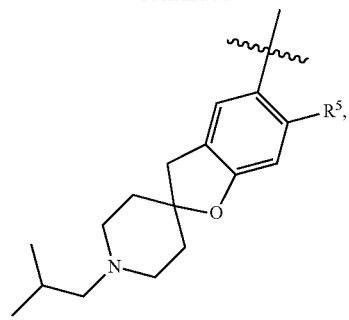
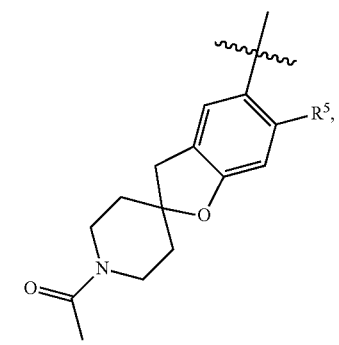
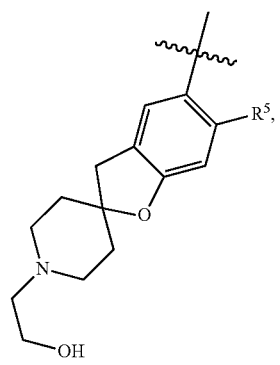
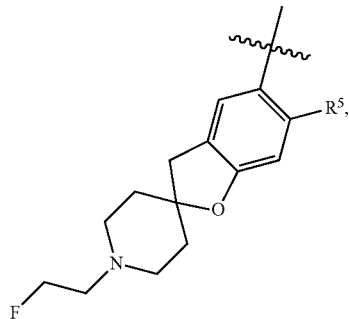
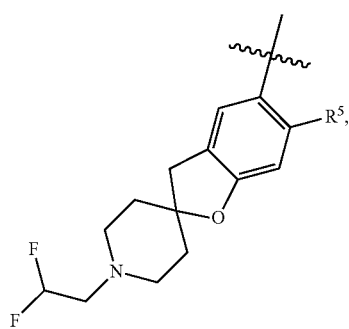
972
-continued
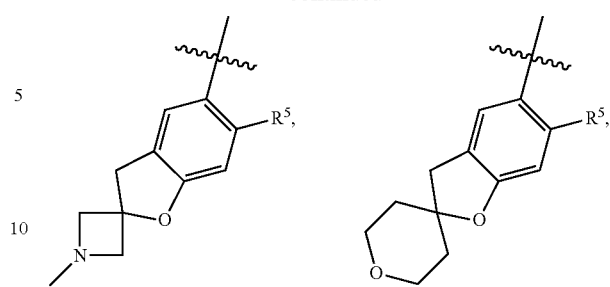
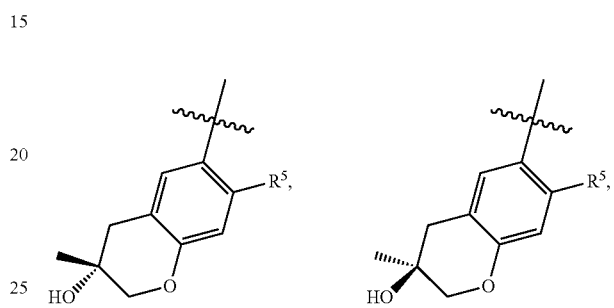
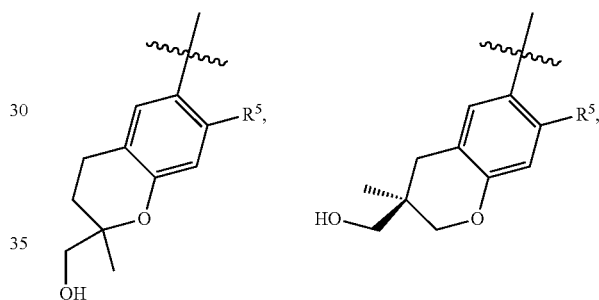
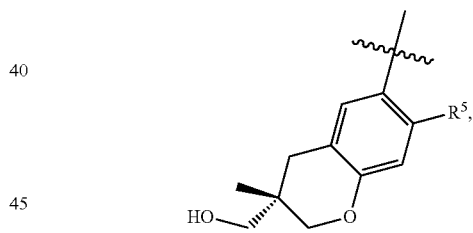
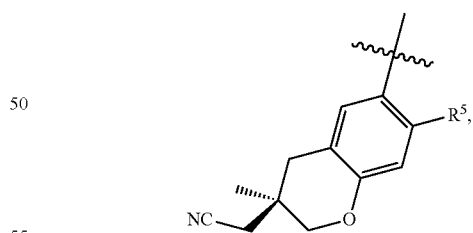
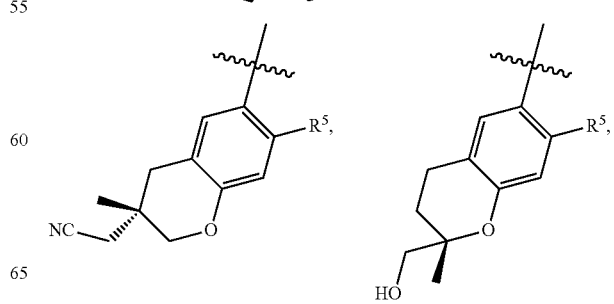

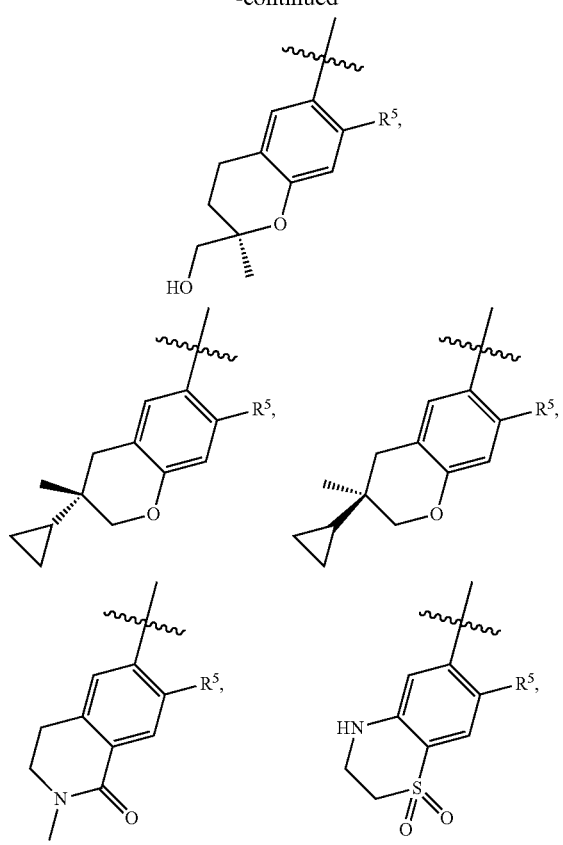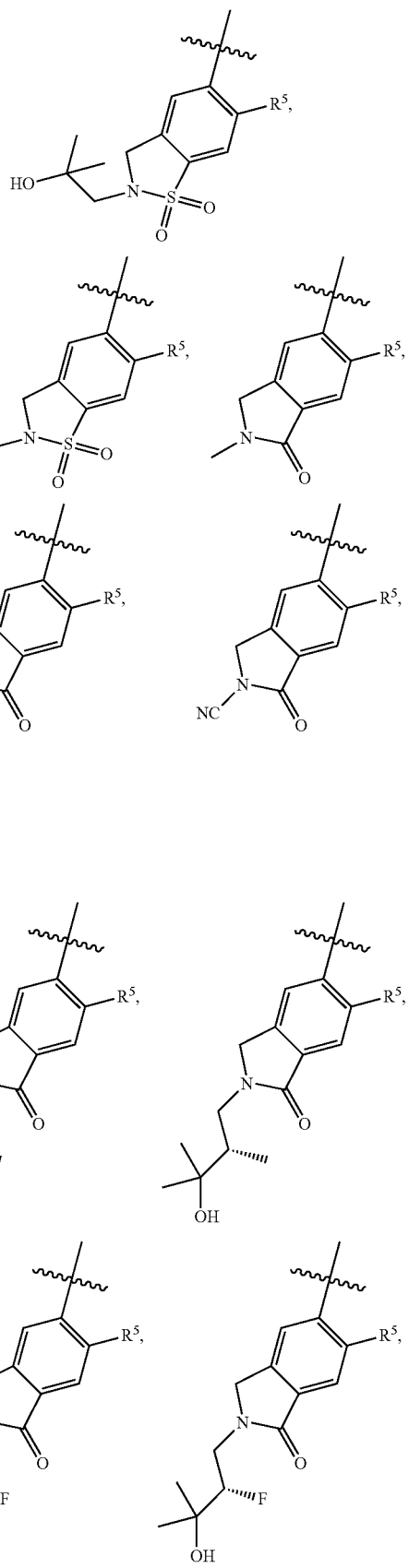

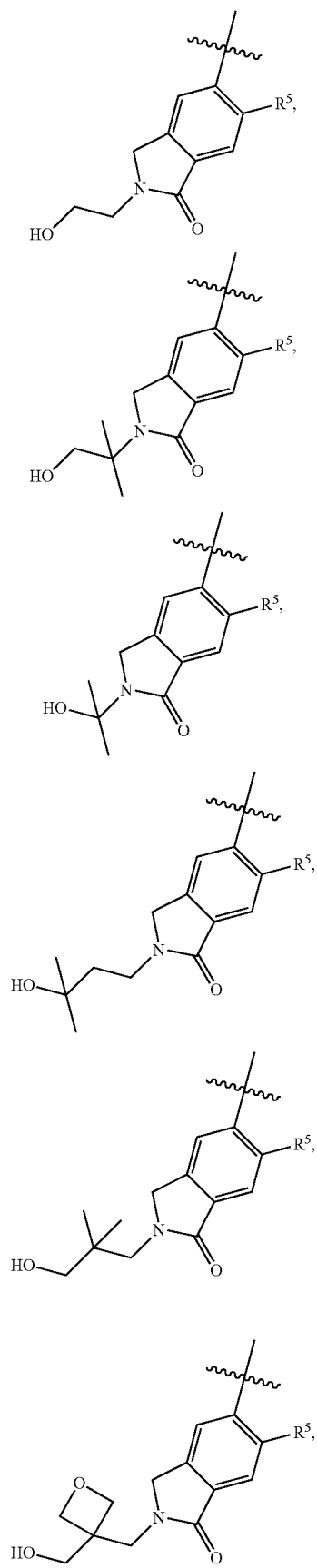
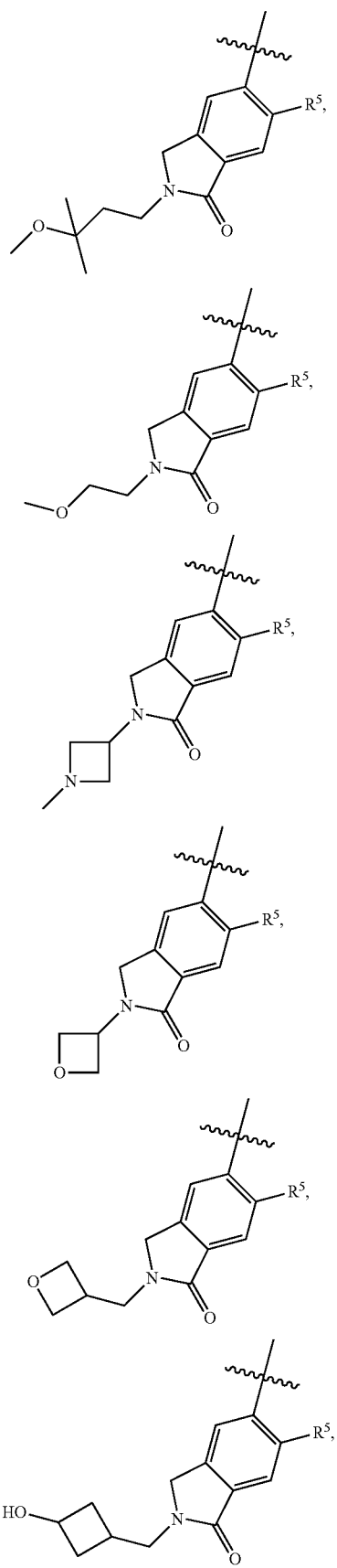

977
-continued
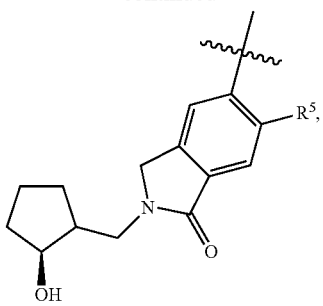
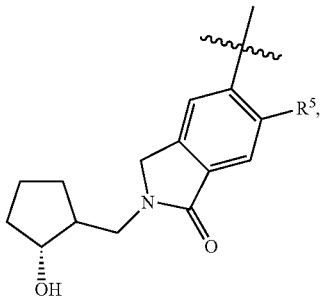
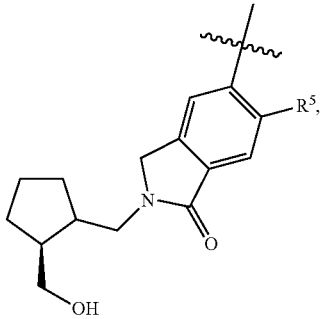
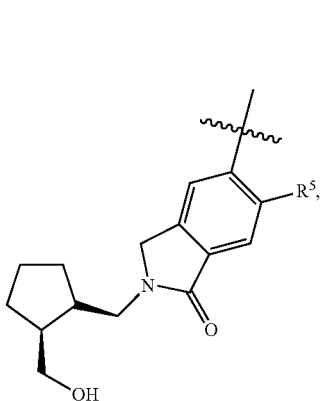
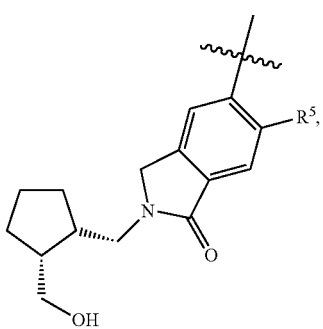
978
-continued
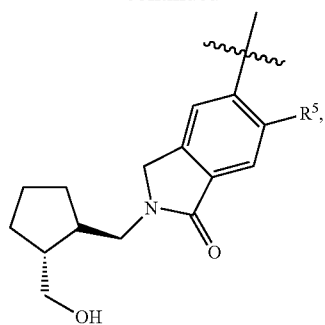
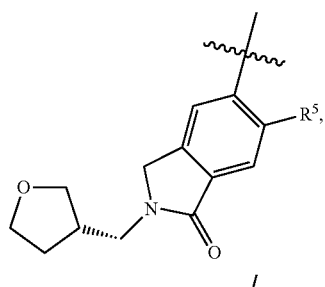
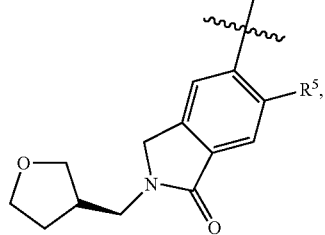
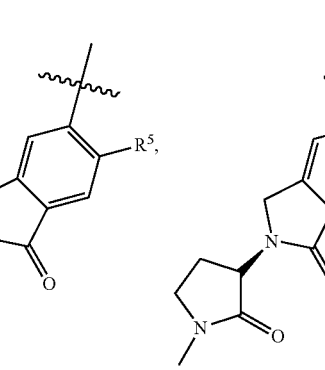
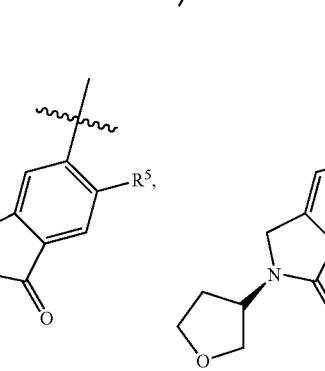

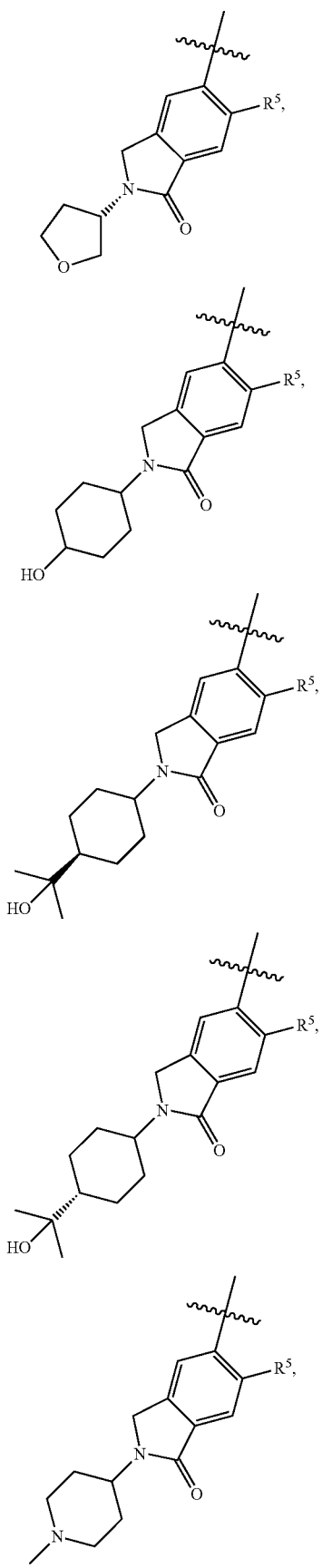
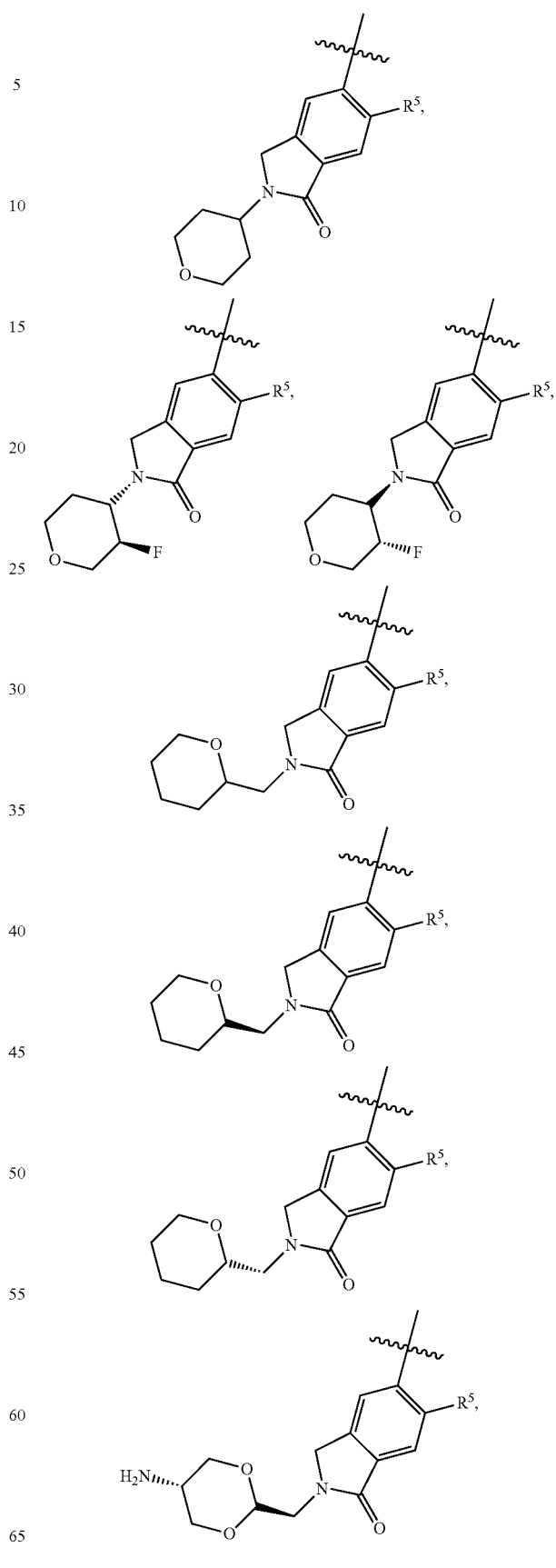

981
-continued
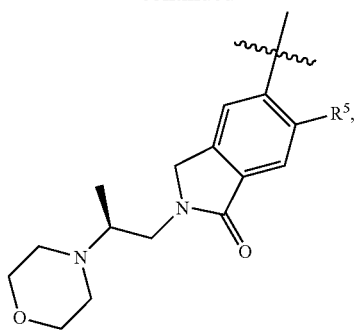
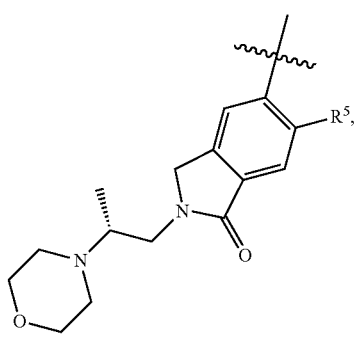
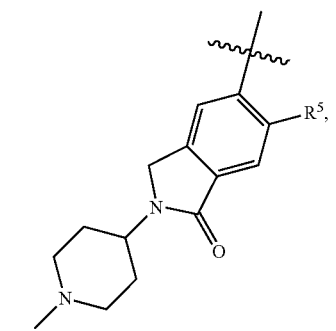
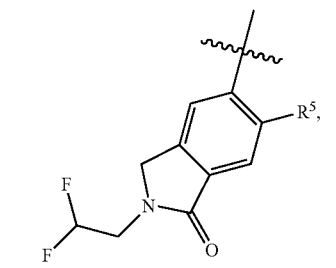
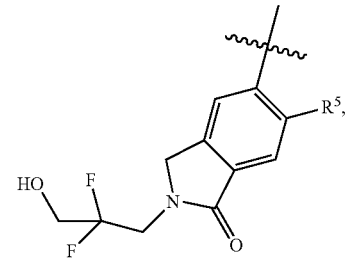
982
-continued
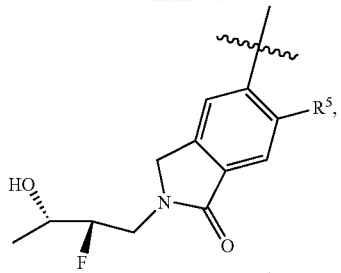
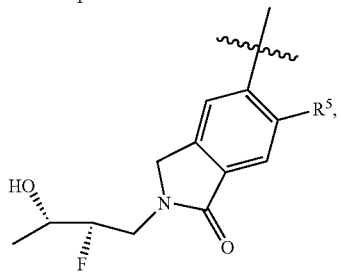
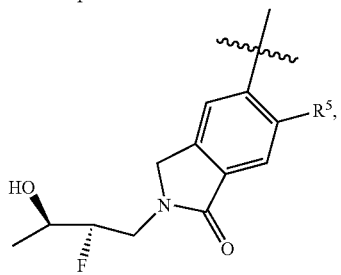
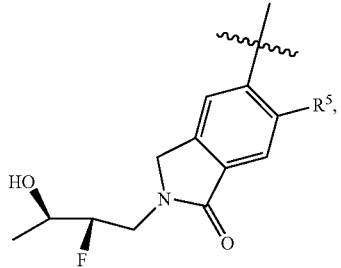
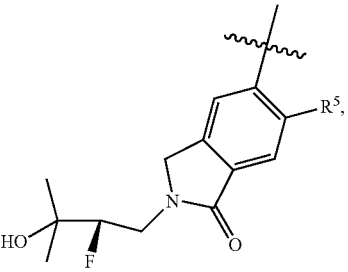
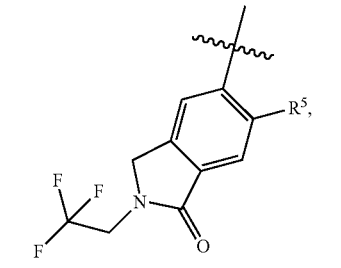
or a stereoisomer thereof.
20. The compound of claim 19, or a stereoisomer or pharmaceutically acceptable salt thereof, wherein the following portion of Formula (0)

983
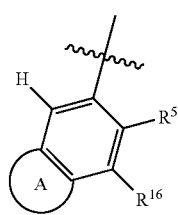
is selected from
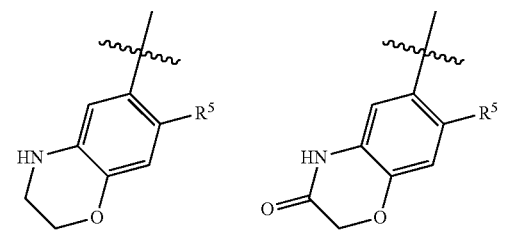
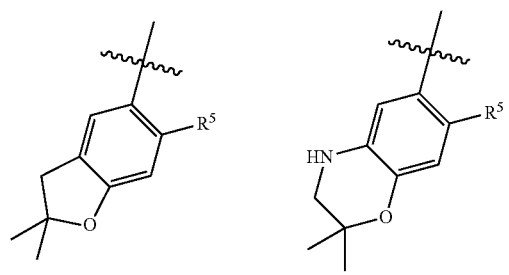
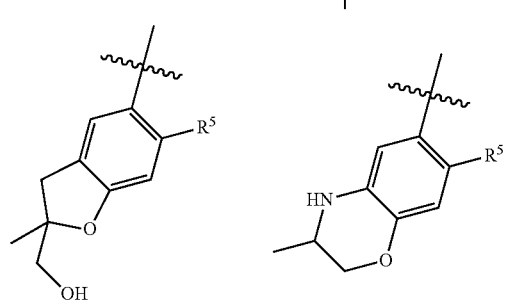
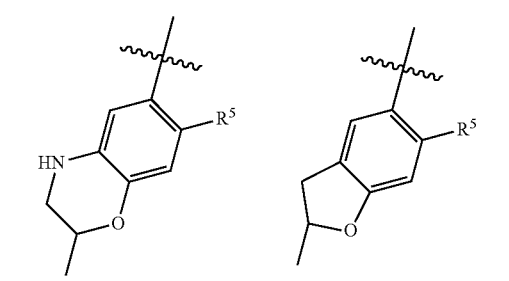
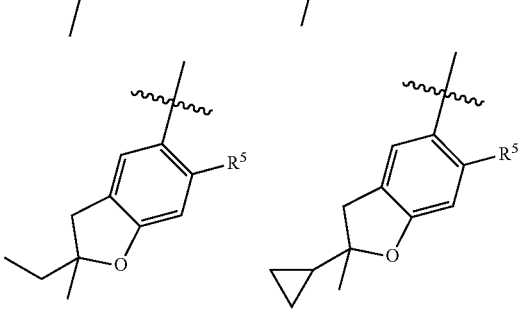
984
-continued
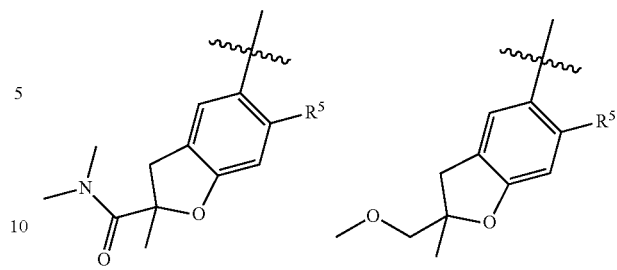
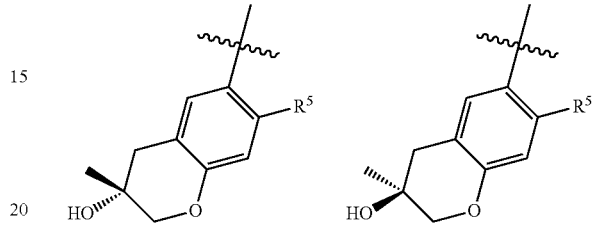
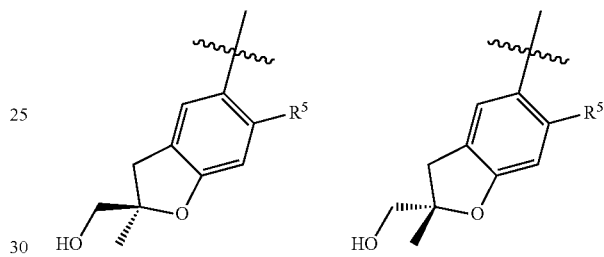
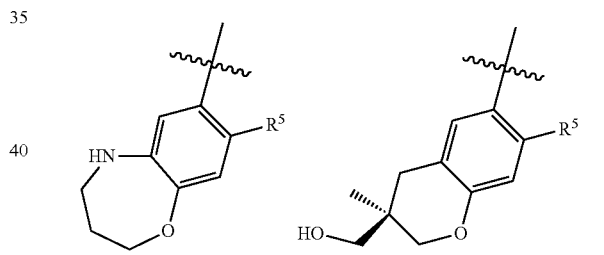
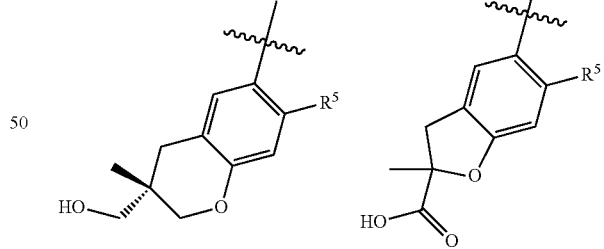
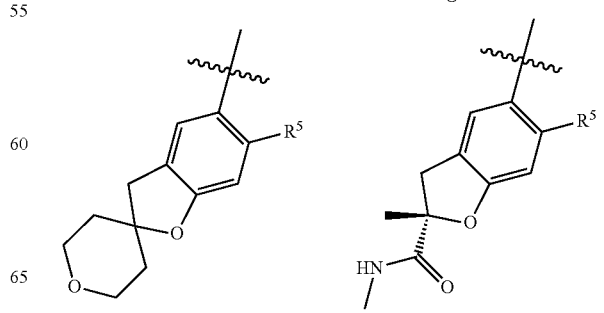

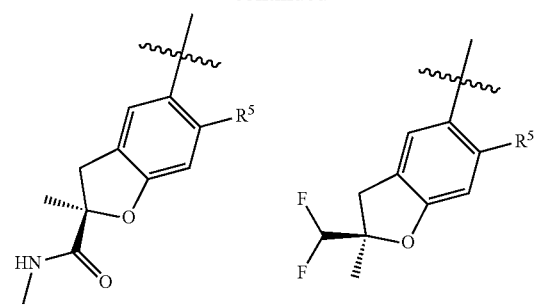
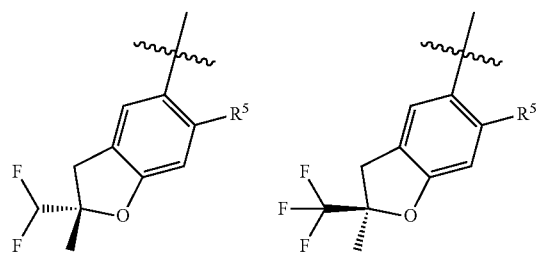
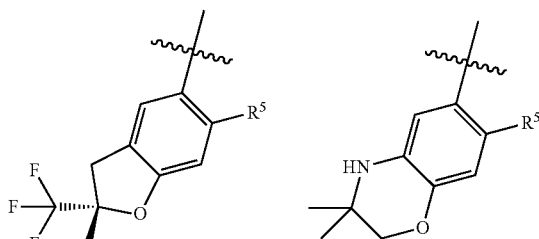
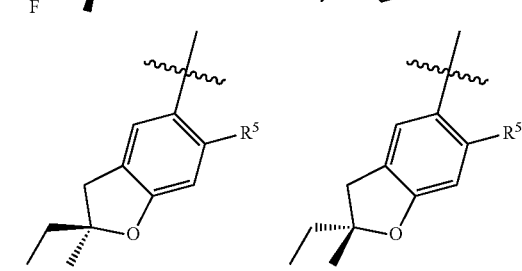
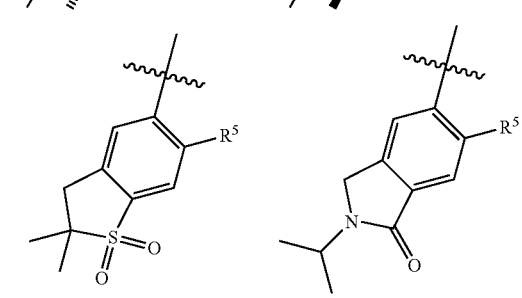
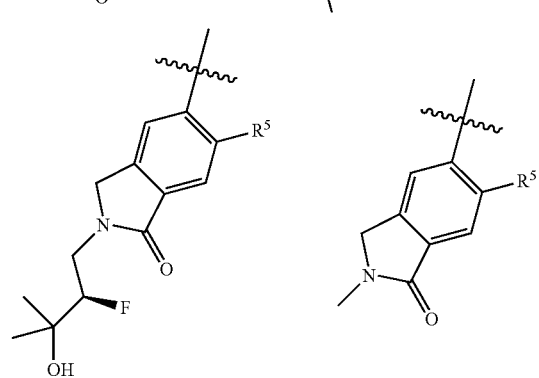
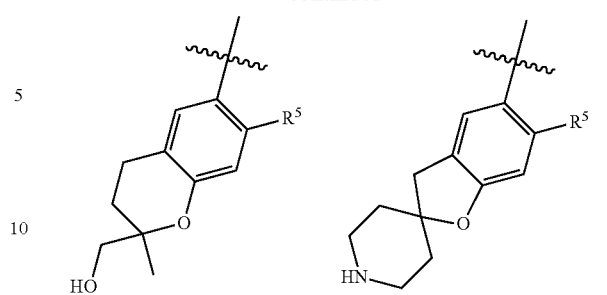
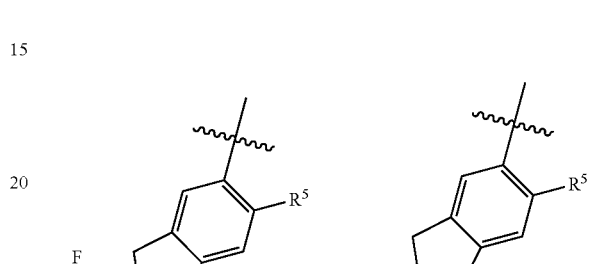
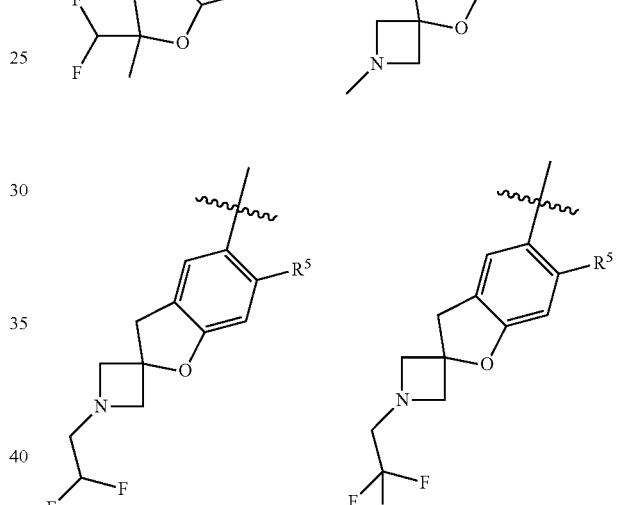
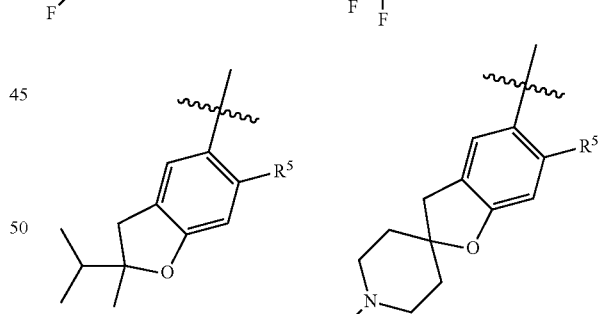
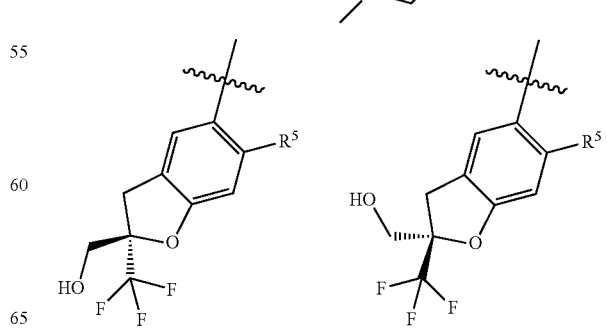

-continued

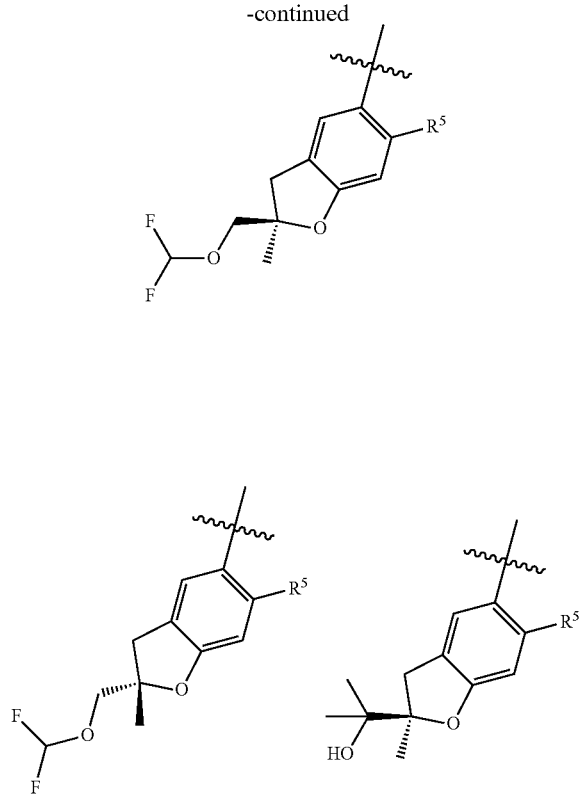

-continued

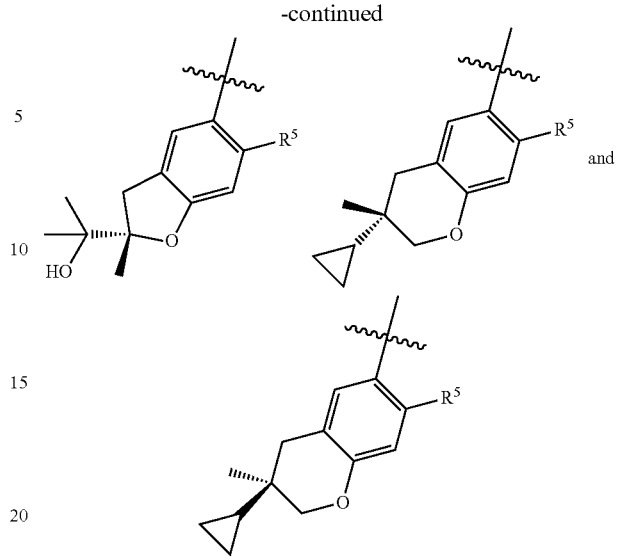

and stereoisomers thereof.

21. The compound of claim 1, selected from the group consisting of the compounds of Tables 1, 2 and 3, or a stereoisomer or pharmaceutically acceptable salt thereof.

22. A pharmaceutical composition comprising a compound of claim 1, or a stereoisomer or pharmaceutically acceptable salt thereof, and a pharmaceutically acceptable excipient, carrier or diluent.

* * * * *